US012128113B2

(12) United States Patent
Benenato et al.

(10) Patent No.: US 12,128,113 B2
(45) **Date of Patent: *Oct. 29, 2024**

(54) POLYNUCLEOTIDES ENCODING JAGGED1 FOR THE TREATMENT OF Alagille SYNDROME

(71) Applicant: ModernaTX, Inc., Cambridge, MA (US)

(72) Inventors: Kerry Benenato, Sudbury, MA (US); Stephen Hoge, Brookline, MA (US); Paolo Martini, Boston, MA (US); Iain Mcfadyen, Arlington, MA (US); Vladimir Presnyak, Manchester, NH (US); Ding An, Waban, MA (US); Ellalahewage Sathyajith Kumarasinghe, Harvard, MA (US)

(73) Assignee: ModernaTX, Inc., Cambridge, MA (US)

( * ) Notice: Subject to any disclaimer, the term of this patent is extended or adjusted under 35 U.S.C. 154(b) by 347 days.

This patent is subject to a terminal disclaimer.

(21) Appl. No.: 16/302,607

(22) PCT Filed: May 18, 2017

(86) PCT No.: PCT/US2017/033413

§ 371 (c)(1),
(2) Date: Nov. 16, 2018

(87) PCT Pub. No.: WO2017/201342

PCT Pub. Date: Nov. 23, 2017

(65) Prior Publication Data

US 2019/0275170 A1 Sep. 12, 2019

Related U.S. Application Data

(60) Provisional application No. 62/338,170, filed on May 18, 2016.

(51) Int. Cl.

| | |
|---|---|
| ***A61K 48/00*** | (2006.01) |
| ***A61K 9/00*** | (2006.01) |
| ***A61K 9/51*** | (2006.01) |
| ***A61K 47/00*** | (2006.01) |
| ***A61K 47/14*** | (2017.01) |
| ***A61K 47/16*** | (2006.01) |
| ***A61K 47/22*** | (2006.01) |
| ***A61K 47/24*** | (2006.01) |
| ***C12N 15/88*** | (2006.01) |
| *A61K 9/127* | (2006.01) |
| *A61K 47/10* | (2017.01) |
| *A61K 47/28* | (2006.01) |
| *C07K 14/705* | (2006.01) |

(52) U.S. Cl.

CPC ............ *A61K 48/0066* (2013.01); *A61K 9/51* (2013.01); *A61K 47/14* (2013.01); *A61K 47/16* (2013.01); *A61K 47/22* (2013.01); *A61K 47/24* (2013.01); *A61K 48/0041* (2013.01); *C12N 15/88* (2013.01); *A61K 9/1271* (2013.01); *A61K 9/5123* (2013.01); *A61K 47/10* (2013.01); *A61K 47/28* (2013.01); *C07K 14/705* (2013.01)

(58) Field of Classification Search

None

See application file for complete search history.

(56) References Cited

U.S. PATENT DOCUMENTS

| | | | |
|---|---|---|---|
| 6,500,419 | B1 | 12/2002 | Hone et al. |
| 7,001,890 | B1 | 2/2006 | Wagner et al. |
| 8,444,992 | B2 | 5/2013 | Borkowski |
| 8,710,200 | B2 | 4/2014 | Schrum et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,980,864 | B2 | 3/2015 | Hoge et al. |
| 8,999,380 | B2 | 4/2015 | Bancel et al. |
| 9,221,891 | B2 | 12/2015 | Bancel et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |

(Continued)

FOREIGN PATENT DOCUMENTS

| | | | |
|---|---|---|---|
| EP | 1083232 | B1 | 2/2005 |
| EP | 1026253 | B2 | 12/2012 |

(Continued)

OTHER PUBLICATIONS

Woodle et al., BBA, 1992, 14: 171-199; Abstract.*

(Continued)

*Primary Examiner* — Ileana Popa

(74) *Attorney, Agent, or Firm* — Fish & Richardson P.C.

(57) ABSTRACT

The invention relates to mRNA therapy for the treatment of Alagille syndrome (ALGS), mRNAs for use in the invention, when administered in vivo, encode JAGGED 1 (JAG1), isoforms thereof functional fragments thereof, and fusion proteins comprising JAG1, mRNAs of the invention are preferably encapsulated in lipid nanoparticles (LNPs) to effect efficient delivery to cells and/or tissues in subjects, when administered thereto. mRNA therapies of the invention increase and/or restore deficient levels of JAG1 expression and/or activity in subjects. mRNA therapies of the invention further decrease levels of toxic metabolites associated with deficient JAG1 activity in subjects.

32 Claims, 50 Drawing Sheets

Specification includes a Sequence Listing.

(56) References Cited

U.S. PATENT DOCUMENTS 9,533,047 B2 1/2017 de Fougerolles et al.
9,572,896 B2 2/2017 Bancel et al.
9,597,380 B2 3/2017 Chakraborty et al.
9,675,668 B2 6/2017 Bancel et al.
9,868,691 B2 1/2018 Benenato et al.
9,872,900 B2 1/2018 Ciaramella et al.
10,023,626 B2 7/2018 Bolen et al.
10,064,934 B2 9/2018 Ciaramella et al.
10,064,935 B2 9/2018 Ciaramella et al.
10,124,022 B2 11/2018 Keeling et al.
10,124,055 B2 11/2018 Ciaramella et al.
10,207,010 B2 2/2019 Besin et al.
10,232,055 B2 3/2019 Kariko et al.
10,238,731 B2 3/2019 Ciaramella et al.
10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,406,112 B2 9/2019 Martini et al.
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,543,269 B2 1/2020 Ciaramella et al.
10,556,018 B2 2/2020 Besin et al.
10,653,712 B2 5/2020 Hoge
10,653,767 B2 5/2020 Ciaramella et al.
10,675,342 B2 6/2020 Ciaramella et al.
10,695,419 B2 6/2020 Ciaramella et al.
10,857,105 B2 12/2020 Benenato et al.
10,925,958 B2 2/2021 Ciaramella
10,993,918 B2 5/2021 Martini et al.
11,001,861 B2 5/2021 Martini et al.
11,027,025 B2 6/2021 Hoge et al.
11,045,540 B2 6/2021 Ciaramella
11,103,578 B2 8/2021 Ciaramella et al.
11,235,052 B2 2/2022 Ciaramella et al.
11,278,611 B2 3/2022 Ciaramella et al.
11,351,242 B1 6/2022 Lori et al.
11,384,352 B2 7/2022 Miracco
11,406,703 B2 8/2022 Kramarczyk et al.
11,464,848 B2 10/2022 Ciaramella et al.
11,485,960 B2 11/2022 Dousis et al.
11,497,807 B2 11/2022 Ciaramella et al.
11,504,337 B2 11/2022 Martini et al.
11,564,893 B2 1/2023 Smith
11,576,961 B2 2/2023 Ciaramella et al.
11,649,461 B2 4/2023 Martini et al.
2003/0092653 A1 5/2003 Kisich et al.
2005/0032730 A1 2/2005 Von Der Mulbe et al.
2005/0059624 A1 3/2005 Hoerr et al.
2005/0250723 A1 11/2005 Hoerr et al.
2007/0280929 A1 12/2007 Hoerr et al.
2010/0130588 A1 5/2010 Yaworski et al.
2010/0203076 A1 8/2010 Fotin-Mleczek et al.
2010/0239608 A1 9/2010 Von Der Mulbe et al.
2010/0303851 A1 12/2010 Hoerr et al.
2011/0053829 A1 3/2011 Baumhof et al.
2011/0250225 A1 10/2011 Fotin-Mleczek et al.
2011/0269950 A1 11/2011 Von Der Mulbe et al.
2011/0311472 A1 12/2011 Hoerr et al.
2012/0189700 A1 7/2012 Aguilar et al.
2012/0219573 A1 8/2012 Baumhof et al.
2012/0258046 A1 10/2012 Mutske
2013/0102034 A1 4/2013 Schrum et al.
2013/0121988 A1 5/2013 Hoerr et al.
2013/0123481 A1* 5/2013 De Fougerolles ... A61K 38/193
536/23.1
2013/0142818 A1 6/2013 Baumhof et al.
2013/0189351 A1 7/2013 Geall
2013/0195968 A1 8/2013 Geall et al.
2013/0195969 A1 8/2013 Geall et al.
2013/0202684 A1 8/2013 Geall et al.
2013/0236974 A1 9/2013 De Fougerolles
2013/0243848 A1 9/2013 Lobovkina et al.
2013/0245103 A1 9/2013 de Fougerolles et al.
2013/0259923 A1 10/2013 Bancel et al.
2013/0295043 A1 11/2013 Kallen et al.
2013/0336998 A1 12/2013 Kallen et al.
2014/0037660 A1 2/2014 Folin-Mleczek et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0271829 A1 9/2014 Lilja et al.
2014/0378538 A1 12/2014 Bancel
2015/0051268 A1 2/2015 Bancel et al.
2015/0056253 A1 2/2015 Bancel et al.
2015/0141499 A1 5/2015 Bancel et al.
2015/0307542 A1 10/2015 Roy et al.
2015/0315541 A1 11/2015 Bancel et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0151474 A1 6/2016 Kallen et al.
2016/0243221 A1 8/2016 Hoge et al.
2017/0043037 A1 2/2017 Kariko et al.
2017/0202979 A1 7/2017 Chakraborty et al.
2017/0204152 A1 7/2017 Nelson et al.
2017/0224758 A1* 8/2017 Lindblad-Toh ........ A61K 38/00
2017/0130255 A1 10/2017 Wang et al.
2018/0000953 A1 1/2018 Almarsson et al.
2018/0002393 A1 1/2018 Bancel et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0303925 A1 10/2018 Weissman et al.
2018/0303929 A1 10/2018 Ciaramella et al.
2018/0311336 A1 11/2018 Ciaramella et al.
2018/0311343 A1 11/2018 Huang et al.
2018/0318409 A1 11/2018 Valiante et al.
2018/0369374 A1 12/2018 Frederick et al.
2018/0371047 A1 12/2018 Ticho et al.
2019/0002890 A1 1/2019 Martini et al.
2019/0008938 A1 1/2019 Ciaramella et al.
2019/0085368 A1 3/2019 Bancel et al.
2019/0125839 A1 5/2019 Frederick et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0241633 A1 8/2019 Fotin-Mleczek et al.
2019/0275170 A1 9/2019 Benenato et al.
2019/0298657 A1 10/2019 Martini et al.
2019/0298658 A1 10/2019 Benenato
2019/0300906 A1 10/2019 Martini et al.
2019/0314292 A1 10/2019 Benenato et al.
2019/0336452 A1 11/2019 Brader
2019/0336595 A1 11/2019 Ciaramella
2019/0351040 A1 11/2019 Valiante et al.
2019/0382774 A1 12/2019 Hoge et al.
2019/0390181 A1 12/2019 Benenato et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0069599 A1 3/2020 Smith et al.
2020/0069793 A1 3/2020 Ciaramella
2020/0069794 A1 3/2020 Ciaramella et al.
2020/0071689 A1 3/2020 Miracco
2020/0078314 A1 3/2020 Martini et al.
2020/0085916 A1 3/2020 Martini et al.
2020/0109420 A1 4/2020 Brito et al.
2020/0129445 A1 4/2020 Patel et al.
2020/0129608 A1 4/2020 Ciaramella et al.
2020/0129615 A1 4/2020 Ciaramella et al.
2020/0239869 A1 7/2020 Issa et al.
2020/0254086 A1 8/2020 Hoge et al.

(56) References Cited

U.S. PATENT DOCUMENTS

| | | | |
|---|---|---|---|
| 2020/0268666 | A1 | 8/2020 | Rajendran et al. |
| 2020/0282047 | A1 | 9/2020 | Ciaramella et al. |
| 2020/0306191 | A1 | 10/2020 | Schariter et al. |
| 2020/0338004 | A1 | 10/2020 | Hansson et al. |
| 2020/0368162 | A1 | 11/2020 | Martini |
| 2021/0040456 | A1 | 2/2021 | Rajendran et al. |
| 2021/0046173 | A1 | 2/2021 | Ciaramella et al. |
| 2021/0087135 | A1 | 3/2021 | Benenato et al. |
| 2021/0163919 | A1 | 6/2021 | Issa et al. |
| 2021/0206818 | A1 | 7/2021 | Huang et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0269830 | A1 | 9/2021 | Martini et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0071915 | A1 | 3/2022 | Martini et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0265856 | A1 | 8/2022 | Jiang et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |

FOREIGN PATENT DOCUMENTS

| | | | |
|---|---|---|---|
| EP | 3310384 | A1 | 4/2018 |
| WO | WO 1990/11092 | A1 | 10/1990 |
| WO | WO 1995/33835 | | 12/1995 |
| WO | WO 07/000668 | * | 1/2007 |
| WO | WO 2007/024708 | A2 | 3/2007 |
| WO | WO 2008/052770 | A2 | 5/2008 |
| WO | WO 2010/037408 | A1 | 4/2010 |
| WO | WO 2010/037539 | A1 | 4/2010 |
| WO | WO 2010/042877 | A1 | 4/2010 |
| WO | WO 2010/054406 | A1 | 5/2010 |
| WO | WO 2010/149743 | A2 | 12/2010 |
| WO | WO 2011/005799 | A2 | 1/2011 |
| WO | WO 2011/068810 | A1 | 6/2011 |
| WO | WO 2012/006369 | A2 | 1/2012 |
| WO | WO 2012/019630 | A1 | 2/2012 |
| WO | WO 2012/019780 | A1 | 2/2012 |
| WO | WO 2012/075040 | A2 | 6/2012 |
| WO | WO 2012/113513 | A1 | 8/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2012/117377 | A1 | 9/2012 |
| WO | WO 2012/158736 | A1 | 11/2012 |
| WO | WO 2013/006842 | A2 | 1/2013 |
| WO | WO 2013086373 | | 6/2013 |
| WO | WO 2013151666 | | 10/2013 |
| WO | WO 2013151672 | | 10/2013 |
| WO | WO 2013151736 | | 10/2013 |
| WO | WO 2016176330 | | 11/2013 |
| WO | WO 2014/081507 | A1 | 5/2014 |
| WO | WO 2014/089121 | A2 | 6/2014 |
| WO | WO 2014/093574 | A1 | 6/2014 |
| WO | WO 2014089486 | | 6/2014 |
| WO | WO 2014152940 | | 9/2014 |
| WO | WO 17/075531 | * | 10/2014 |
| WO | WO 2014/159813 | A1 | 10/2014 |
| WO | WO 2014/160243 | A1 | 10/2014 |
| WO | WO 2014/179562 | A1 | 11/2014 |
| WO | WO 2015/101414 | A2 | 7/2015 |
| WO | WO 2015/101415 | A1 | 7/2015 |
| WO | WO 15/199952 | * | 12/2015 |
| WO | WO 2016/011306 | A2 | 1/2016 |
| WO | WO 2016/061509 | A1 | 4/2016 |
| WO | WO 17/070616 | * | 10/2016 |
| WO | WO 2016/164762 | A1 | 10/2016 |
| WO | WO 2016/201377 | A1 | 12/2016 |
| WO | WO 2017/011773 | A2 | 1/2017 |
| WO | WO 2017/015457 | A1 | 1/2017 |
| WO | WO 2017049245 | | 3/2017 |
| WO | WO 2017/066789 | A1 | 4/2017 |
| WO | WO 2017/070601 | A1 | 4/2017 |
| WO | WO 2017/127750 | A1 | 7/2017 |
| WO | PCT/US2017/033413 | | 8/2017 |
| WO | WO 2017/201333 | A1 | 11/2017 |
| WO | WO 2017201342 | | 11/2017 |
| WO | WO 2018/157009 | A1 | 8/2018 |
| WO | WO 2018/170245 | A1 | 9/2018 |
| WO | WO 2018/232355 | A1 | 12/2018 |
| WO | WO 2018/232357 | A1 | 12/2018 |
| WO | WO 2019/036683 | A1 | 2/2019 |
| WO | WO 2019/036685 | A1 | 2/2019 |
| WO | WO 2019/148101 | A1 | 8/2019 |
| WO | WO 2020/006242 | A1 | 1/2020 |
| WO | WO 2020/056370 | A1 | 3/2020 |
| WO | WO 2020/061284 | A1 | 3/2020 |
| WO | WO 2020/061295 | A1 | 3/2020 |
| WO | WO 2020/061367 | A1 | 3/2020 |
| WO | WO 2020/097291 | A1 | 5/2020 |
| WO | WO 2020/172239 | A1 | 8/2020 |
| WO | WO 2020/185811 | A1 | 9/2020 |
| WO | WO 2020/190750 | A1 | 9/2020 |
| WO | WO 2020/243561 | A1 | 12/2020 |
| WO | WO 2021/050864 | A1 | 3/2021 |
| WO | WO 2021/155243 | A1 | 8/2021 |
| WO | WO 2021/155274 | A1 | 8/2021 |
| WO | WO 2021/159040 | A2 | 8/2021 |
| WO | WO 2021/159130 | A2 | 8/2021 |
| WO | WO 2021/211343 | A1 | 10/2021 |
| WO | WO 2021/222304 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/247817 | A1 | 12/2021 |
| WO | WO 2022/067010 | A1 | 3/2022 |
| WO | WO 2022/155524 | A1 | 7/2022 |
| WO | WO 2022/155530 | A1 | 7/2022 |
| WO | WO 2022/187698 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A2 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/232585 | A1 | 11/2022 |
| WO | WO 2022/241103 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A2 | 1/2023 |
| WO | WO 2023/283645 | A1 | 1/2023 |
| WO | WO 2023/283651 | A1 | 1/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |

OTHER PUBLICATIONS

Yuan et al., Colloids and Surfaces B: Biointerfaces, 2007, 58: 157-164.*

Yuan et al., Colloids and Surfaces B: Biointerfaces, 2007, 58: 157.*

U.S. Appl. No. 15/753,293, filed Feb. 17, 2018, Smith.

U.S. Appl. No. 15/748,782, filed Jan. 30, 2018, Mousavi et al.

U.S. Appl. No. 16/833,409, filed Mar. 27, 2020, Ciaramella.

U.S. Appl. No. 16/853,973, filed Apr. 21, 2020, Ciaramella et al.

U.S. Appl. No. 16/850,519, filed Apr. 16, 2020, Ciaramella et al.

U.S. Appl. No. 15/746,286, filed Jan. 19, 2018, Ciaramella et al.

U.S. Appl. No. 16/898,268, filed Jun. 10, 2020, Ciaramella et al.

(56) References Cited

OTHER PUBLICATIONS

U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/880,829, filed May 21, 2020, Ciaramella et al.
U.S. Appl. No. 16/468,838, filed Jun. 12, 2019, Miracco.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/496,135, filed Sep. 20, 2019, Narayanan et al.
U.S. Appl. No. 16/657,122, filed Oct. 18, 2019, Rabideau et al.
U.S. Appl. No. 16/493,986, filed Sep. 13, 2019, Ciaramella et al.
U.S. Appl. No. 16/494,103, filed Sep. 13, 2019, Ciaramella et al.
U.S. Appl. No. 16/494,162, filed Sep. 13, 2019, Ciaramella.
U.S. Appl. No. 17/155,592, filed Jan. 22, 2021, Ciaramella et al.
U.S. Appl. No. 16/848,318, filed Apr. 14, 2020, Ciaramella et al.
U.S. Appl. No. 16/608,451, filed Oct. 25, 2019, Ciaramella et al.
U.S. Appl. No. 16/788,182, filed Feb. 11, 2020, Panther et al.
U.S. Appl. No. 17/000,201, filed Aug. 21, 2020, Stewart-Jones et al.
U.S. Appl. No. 17/000,215, filed Aug. 21, 2020, Stewart-Jones et al.
International Search Report and Written Opinion for Application No. PCT/US2017/033413, mailed Aug. 24, 2017.
Boyer-Di Ponio et al., Biological function of mutant forms of JAGGED1 proteins in Alagille syndrome: inhibitory effect on Notch signaling. Hum Mol Genet. Nov. 15, 2007;16(22):2683-92. Epub Aug. 24, 2007.
Carralot, J.P. et al., Polarization of immunity induced by direct injection of naked sequence-stabilized mRNA vaccines. Cell Mal Life Sci. Sep. 2004;61(18):2418-24.
Deering et al., Nucleic Acid Vaccines: Prospects for Non-Viral Delivery of mRNA Vaccines, Expert Opinion, 2014, vol. 11, No. 6, pp. 1-15.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Hajj et al., Tools for translation: non-viral materials for therapeutic mRNA delivery. Nat Rev Mat. Sep. 2017;2:17056.
Hoerr, I. et al., In vivo application of RNA leads to induction of specific cytotoxic T lymphocytes and antibodies. EurJ Immunol. Jan. 2000;30(1):1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kariko et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kuhn, A.N., et al., mRNA as a versatile tool for exogenous protein expression. Current Gene Therapy. Oct. 2012; 12 (5): 347-361.
Leitner, W.W. et al., DNA and RNA-based vaccines: principles, progress and prospects. Vaccine. Dec. 10, 1999;18 (9-10):765-77.
Li et al., Alagille syndrome is caused by mutations in human Jagged1, which encodes a ligand for Notch1. Nat Genet. Jul. 1997;16(3):243-51.
Lian, T. et al., Trends and developments in liposome drug delivery systems. J Pharm Sci. Jun. 2001;90(6):667-80.
Maruggi et al., Immunogenicity and protective efficacy induced by self-amplifying mRNA vaccines encoding bacterial antigens. Vaccine. Jan. 5, 2017;35(2):361-368. doi: 10.1016/j.vaccine.2016.11.040. Epub Dec. 7, 2016.
Mckenzie, B.S. et al., Nucleic acid vaccines: tasks and tactics. Immunol Res. 2001 ;24(3):225-44.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Oda et al., Mutations in the human Jagged1 gene are responsible for Alagille syndrome. Nat Genet. Jul. 1997;16(3):235-42.
Pascolo, S. Vaccination with messenger RNA (mRNA). Handb Exp Pharmacol. 2008; 183:221-235.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weide, B. et al., Results of the first phase I/II clinical vaccination trial with direct injection of mRNA. J Immunother. Feb.-Mar. 31, 2008(2):180-8.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Yuan et al., Human Jagged 1 mutants cause liver defect in Alagille syndrome by overexpression of hepatocyte growth factor. J Mol Biol. Feb. 24, 2006;356(3):559-68. Epub Dec. 20, 2005.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Danaei et al., Impact of Particle Size and Polydispersity Index on the Clinical Applications of Lipidic Nanocarrier Systems. Pharmaceutics. May 18, 2018;10(2):57. doi: 10.3390/pharmaceutics10020057.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263.
Li et al., Effects of local structural transformation of lipid-like compounds on delivery of messenger RNA. Sci Rep. Feb. 26, 2016;6:22137. doi: 10.1038/srep22137.
Li et al., Lipid-based nanoparticles for nucleic acid delivery. Pharm Res. Mar. 2007;24(3):438-49. doi: 10.1007/s11095-006-9180-5.
Li et al., Targeted delivery of antisense oligodeoxynucleotide and small interference RNA into lung cancer cells. Mol Pharm. Sep.-Oct. 2006;3(5):579-88. doi: 10.1021/mp060039w.
Machlachlan, Chapter 9 Liposomal Formulations for Nucleic Acid Delivery. Retrieved from the Internet on Aug. 10, 2020 from http://arbutusbio.com/docs/Liposome_Formulations_Proof_for_Distribution.pdf; originally published 2007, pp. 237-270.
Tam et al., Advances in Lipid Nanoparticles for siRNA Delivery. Pharmaceutics. Sep. 18, 2013;5(3):498-507. doi: 10.3390/pharmaceutics5030498.
Wang et al., Delivery of oligonucleotides with lipid nanoparticles. Adv Drug Deliv Rev. Jun. 29, 2015;87:68-80. doi: 10.1016/j.addr.2015.02.007. Epub Feb. 27, 2015.
Weissman, mRNA transcript therapy. Expert Rev Vaccines. Feb. 2015;14(2):265-81. doi: 10.1586/14760584.2015.973859. Epub Oct. 31, 2014.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 18/161,857, filed Jan. 30, 2023, Smith.
U.S. Appl. No. 15/767,587, filed Apr. 11, 2018, Ciaramella.
U.S. Appl. No. 18/176,014, filed Feb. 28, 2023, Ciaramella.
U.S. Appl. No. 17/819,414, filed Aug. 12, 2022, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.

(56) References Cited

OTHER PUBLICATIONS

U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 17/830,742, filed Jun. 2, 2022, Miracco.
U.S. Appl. No. 16/001,765, filed Jun. 6, 2018, Marquardt et al.
U.S. Appl. No. 17/852,974, filed Jun. 29, 2022, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/483,012, filed Aug. 1, 2019, Mauger et al.
U.S. Appl. No. 18/093,119, filed Jan. 4, 2023, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 18/055,193, filed Nov. 14, 2022, Ciaramella et al.
U.S. Appl. No. 16/494,130, filed Sep. 13, 2019, Ciaramella et al.
U.S. Appl. No. 17/823,255, filed Aug. 30, 2022, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/938,823, filed Oct. 7, 2022, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/816,696, filed Aug. 1, 2022, Dousis et al.
U.S. Appl. No. 17/737,581, filed May 5, 2022, Panther et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.
U.S. Appl. No. 17/641,967, filed Mar. 10, 2022, John et al.
U.S. Appl. No. 17/840,478, filed Jun. 14, 2022, Kramarczyk et al.
U.S. Appl. No. 18/008,139, filed Dec. 2, 2022, Smith et al.
U.S. Appl. No. 17/796,401, filed Jul. 29, 2022, Shaw et al.
U.S. Appl. No. 17/926,353, filed Nov. 18, 2022, Brader et al.
U.S. Appl. No. 17/925,114, filed Nov. 14, 2022, White et al.
U.S. Appl. No. 17/797,784, filed Aug. 5, 2022, Stewart-Jones et al.
U.S. Appl. No. 17/572,465, filed Jan. 10, 2022, Nachbagauer et al.
U.S. Appl. No. 17/726,971, filed Apr. 22, 2022, Hennessy.
U.S. Appl. No. 17/925,125, filed Nov. 14, 2022, White et al.
U.S. Appl. No. 18/085,457, filed Dec. 20, 2022, Joyal et al.
Berniczei-Royko et al., "Medical and dental management of Alagille syndrome: a review," Medical Science Monitor: International Medical Journal of Experimental and Clinical Research, 2014, 20:476.
Boyer et al., "Expression of mutant JAGGED1 alleles in patients with Alagille syndrome," Hum Genet., May 2005, 116(6):445-53.
Final Office Action in U.S. Appl. No. 16/487,734, dated Dec. 15, 2022, 25 pages.
GenBank Accession No. NP_000205.1, "protein jagged-1 precursor [*Homo sapiens*]," Dec. 8, 2016, 5 pages.
GenBank Accession No. NM_000214.2, "*Homo sapiens* jagged 1 (JAG1), mRNA," May 1, 2018, 6 pages.
International Preliminary Report on Patentability in International Application No. PCT/US2018/019597, dated Sep. 6, 2019, 12 pages.
International Preliminary Report on Patentability in International Application. No. PCT/US2017/033413, mailed on Nov. 29, 2018, 12 pages.
International Search Report and Written Opinion in International Application No. PCT/US2018/019597, dated May 25, 2018, 21 pages.
Jiang et al., "Notch signaling deficiency underlies age-dependent depletion of satellite cells in muscular dystrophy," Disease Models & Mechanisms, 2014, 7:997-1004.
Kauffman et al., "Optimization of Lipid Nanoparticle Formulations for mRNA Delivery with Fractional Factorial and Definitive Screening Designs," Nanoletters, 2015, 15:7300-7306.
Non-Final Office Action in U.S. Appl. No. 16/487,734, dated Apr. 7, 2022, 14 pages.
Response to Non-Final Office Action in U.S. Appl. No. 16/487,734, dated Sep. 12, 2022, 22 pages.
Response to Restriction Requirement in U.S. Appl. No. 16/487,734, dated Jan. 25, 2022, 6 pages.
Restriction Requirement in U.S. Appl. No. 16/487,734, dated Oct. 25, 2021, 14 pages.
Supplementary European Search Report in EP 17800205, dated Jan. 17, 2020, 12 pages.
Tada et al., "Functional analysis of the Notch ligand Jagged1 missense mutant proteins underlying Alagille syndrome," FEBS J., Jun. 2012, 279(12):2096-2107.
Turnpenny et al., "Alagille syndrome: pathogenesis, diagnosis and management," Eur. J. Hum. Genet., Mar. 2012, 20(3):251-257.
Vieira et al., "Jagged 1 Rescues the Duchenne Muscular Dystrophy Phenotype," Cell, 2015, 163:1204-1213.
U.S. Appl. No. 16/487,734, 20200368162, filed Aug. 21, 2019, Martini.
U.S. Appl. No. 18/322,744, filed May 24, 2023, Martini.

* cited by examiner

A

SEQ ID NO: 1 (JAG1; Jagged-1, wt)

MRSPRTRGRSGRPLSLLLALLCALRAKVCGASGQFELEILSMQNVNGELQNGNCCGGAR
NPGDRKCTRDECDTYFKVCLKEYQSRVTAGGPCSFGSGSTPVIGGNTFNLKASRGNDRN
RIVLPFSFAWPRSYTLLVEAWDSSNDTVQPDSIIEKASHSGMINPSRQWQTLKQNTGVA
HFEYQIRVTCDDYYYGFGCNKFCRPRDDFFGHYACDQNGNKTCMEGWMGPECNRAICRQ
GCSPKHGSCKLPGDCRCQYGWQGLYCDKCIPHPGCVHGICNEPWQCLCETNWGGQLCDK
DLNYCGTHQPCLNGGTCSNTGPDKYQCSCPEGYSGPNCEIAEHACLSDPCHNRGSCKET
SLGFECECSPGWTGPTCSTNIDDCSPNNCSHGGTCQDLVNGFKCVCPPQWTGKTCQLDA
NECEAKPCVNAKSCKNLIASYYCDCLPGWMGQNCDININDCLGQCQNDASCRDLVNGYR
CICPPGYAGDHCERDIDECASNPCLNGGHCQNEINRFQCLCPTGFSGNLCQLDIDYCEP
NPCQNGAQCYNRASDYFCKCPEDYEGKNCSHLKDHCRTTPCEVIDSCTVAMASNDTPEG
VRYISSNVCGPHGKCKSQSGGKFTCDCNKGFTGTYCHENINDCESNPCRNGGTCIDGVN
SYKCICSDGWEGAYCETNINDCSQNPCHNGGTCRDLVNDFYCDCKNGWKGKTCHSRDSQ
CDEATCNNGGTCYDEGDAFKCMCPGGWEGTTCNIARNSSCLPNPCHNGGTCVVNGESFT
CVCKEGWEGPICAQNTNDCSPHPCYNSGTCVDGDNWYRCECAPGFAGPDCRININECQS
SPCAFGATCVDEINGYRCVCPPGHSGAKCQEVSGRPCITMGSVIPDGAKWDDDCNTCQC
LNGRIACSKVWCGPRPCLLHKGHSECPSGQSCIPILDDQCFVHPCTGVGECRSSSLQPV
KTKCTSDSYYQDNCANITFTFNKEMMSPGLTTEHICSELRNLNILKNVSAEYSIYIACE
PSPSANNEIHVAISAEDIRDDGNPIKEITDKIIDLVSKRDGNSSLIAAVAEVRVQRRPL
KNRTDFLVPLLSSVLTVAWICCLVTAFYWCLRKRRKPGSHTHSASEDNTTNNVREQLNQ
IKNPIEKHGANTVPIKDYENKNSKMSKIRTHNSEVEEDDMDKHQQKARFAKQPAYTLVD
REEKPPNGTPTKHPNWTNKQDNRDLESAQSLNRMEYIV

See Jagged-1, Uniprot Acc. No. P78504. This is the 'canonical' sequence. All positional information in related variants and isoforms refer to it.

| Feature | Position | Length | Description |
|---|---|---|---|
| Signal peptide | 1 – 33 | 33 | Signal peptide |
| Topological domain | 34 – 1067 | 1034 | Extracellular |
| Topological domain | 1094 – 1218 | 125 | Cytoplasmic |
| Transmembrane | 1068 – 1093 | 26 | Helical |
| Chain | 34 – 1218 | 1185 | Protein jagged-1 |
| Domain | 185 – 229 | 45 | DSL |
| Domain | 230 – 263 | 34 | EGF-like 1 |
| Domain | 264 – 294 | 31 | EGF-like 2; atypical |
| Domain | 296 – 334 | 39 | EGF-like 3 |
| Domain | 336 – 372 | 37 | EGF-like 4 |
| Domain | 374 – 410 | 37 | EGF-like 5; calcium-binding |
| Domain | 412 – 448 | 37 | EGF-like 6; calcium-binding |
| Domain | 450 – 485 | 36 | EGF-like 7; calcium-binding |
| Domain | 487 – 523 | 37 | EGF-like 8; calcium-binding |
| Domain | 525 – 561 | 37 | EGF-like 9 |
| Domain | 586 – 627 | 42 | EGF-like 10 |
| Domain | 629 – 665 | 37 | EGF-like 11; calcium-binding |
| Domain | 667 – 703 | 37 | EGF-like 12; calcium-binding |
| Domain | 705 – 741 | 37 | EGF-like 13 |
| Domain | 744 – 780 | 37 | EGF-like 14 |
| Domain | 782 – 818 | 37 | EGF-like 15; calcium-binding |
| Domain | 820 – 856 | 37 | EGF-like 16; calcium-binding |

*All positional information refers to the 'canonical' sequence*

C

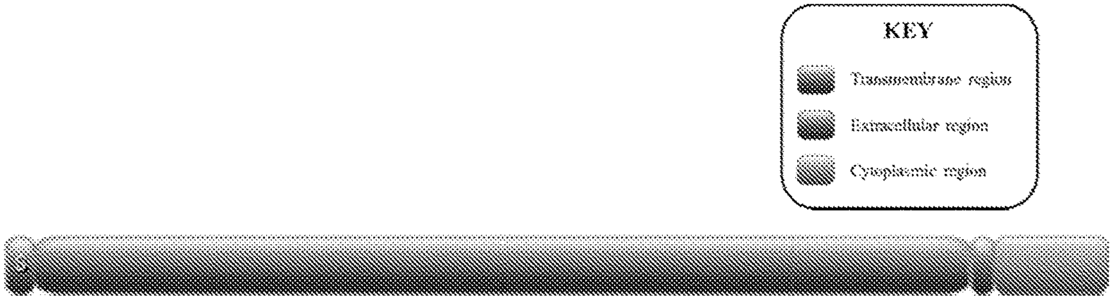

FIG. 1

SEQ ID NO: 2

ATGCGTTCCCCACGGACGCGCGGCCGGTCCGGGCGCCCCCTAAGCCTCCTGCTCGCCCTGCTCTGTGCCCTGCG
AGCCAAGGTGTGTGGGGCCTCGGGTCAGTTCGAGTTGGAGATCCTGTCCATGCAGAACGTGAACGGGGAGCTGC
AGAACGGGAACTGCTGCGGCGGCGCCCGGAACCCGGGAGACCGCAAGTGCACCCGCGACGAGTGTGACACATAC
TTCAAAGTGTGCCTCAAGGAGTATCAGTCCCGCGTCACGGCCGGGGGGCCCTGCAGCTTCGGCTCAGGGTCCAC
GCCTGTCATCGGGGGCAACACCTTCAACCTCAAGGCCAGCCGCGGCAACGACCGCAACCGCATCGTGCTGCCTT
TCAGTTTCGCCTGGCCGAGGTCCTATACGTTGCTTGTGGAGGCGTGGGATTCCAGTAATGACACCGTTCAACCT
GACAGTATTATTGAAAAGGCTTCTCACTCGGGCATGATCAACCCCAGCCGGCAGTGGCAGACGCTGAAGCAGAA
CACGGGCGTTGCCCACTTTGAGTATCAGATCCGCGTGACCTGTGATGACTACTACTATGGCTTTGGCTGCAATA
AGTTCTGCCGCCCCAGAGATGACTTCTTTGGACACTATGCCTGTGACCAGAATGGCAACAAAACTTGCATGGAA
GGCTGGATGGGCCCCGAATGTAACAGAGCTATTTGCCGACAAGGCTGCAGTCCTAAGCATGGGTCTTGCAAACT
CCCAGGTGACTGCAGGTGCCAGTACGGCTGGCAAGGCCTGTACTGTGATAAGTGCATCCCACACCCGGGATGCG
TCCACGGCATCTGTAATGAGCCCTGGCAGTGCCTCTGTGAGACCAACTGGGGCGGCCAGCTCTGTGACAAAGAT
CTCAATTACTGTGGGACTCATCAGCCGTGTCTCAACGGGGGAACTTGTAGCAACACAGGCCCTGACAAATATCA
GTGTTCCTGCCCTGAGGGGTATTCAGGACCCAACTGTGAAATTGCTGAGCACGCCTGCCTCTCTGATCCCTGTC
ACAACAGAGGCAGCTGTAAGGAGACCTCCCTGGGCTTTGAGTGTGAGTGTTCCCCAGGCTGGACCGGCCCCACA
TGCTCTACAAACATTGATGACTGTTCTCCTAATAACTGTTCCCACGGGGGCACCTGCCAGGACCTGGTTAACGG
ATTTAAGTGTGTGTGCCCCCCACAGTGGACTGGGAAAACGTGCCAGTTAGATGCAAATGAATGTGAGGCCAAAC
CTTGTGTAAACGCCAAATCCTGTAAGAATCTCATTGCCAGCTACTACTGCGACTGTCTTCCCGGCTGGATGGGT
CAGAATTGTGACATAAATATTAATGACTGCCTTGGCCAGTGTCAGAATGACGCCTCCTGTCGGGATTTGGTTAA
TGGTTATCGCTGTATCTGTCCACCTGGCTATGCAGGCGATCACTGTGAGAGAGACATCGATGAATGTGCCAGCA
ACCCCTGTTTGAATGGGGGTCACTGTCAGAATGAAATCAACAGATTCCAGTGTCTGTGTCCCACTGGTTTCTCT
GGAAACCTCTGTCAGCTGGACATCGATTATTGTGAGCCTAATCCCTGCCAGAACGGTGCCCAGTGCTACAACCG
TGCCAGTGACTATTTCTGCAAGTGCCCCGAGGACTATGAGGGCAAGAACTGCTCACACCTGAAAGACCACTGCC
GCACGACCCCCTGTGAAGTGATTGACAGCTGCACAGTGGCCATGGCTTCCAACGACACACCTGAAGGGGTGCGG
TATATTTCCTCCAACGTCTGTGGTCCTCACGGGAAGTGCAAGAGTCAGTCGGGAGGCAAATTCACCTGTGACTG
TAACAAAGGCTTCACGGGAACATACTGCCATGAAAATATTAATGACTGTGAGAGCAACCCTTGTAGAAACGGTG
GCACTTGCATCGATGGTGTCAACTCCTACAAGTGCATCTGTAGTGACGGCTGGGAGGGGGCCTACTGTGAAACC
AATATTAATGACTGCAGCCAGAACCCCTGCCACAATGGGGGCACGTGTCGCGACCTGGTCAATGACTTCTACTG
TGACTGTAAAAATGGGTGGAAAGGAAAGACCTGCCACTCACGTGACAGTCAGTGTGATGAGGCCACGTGCAACA
ACGGTGGCACCTGCTATGATGAGGGGGATGCTTTTAAGTGCATGTGTCCTGGCGGCTGGGAAGGAACAACCTGT
AACATAGCCCGAAACAGTAGCTGCCTGCCCAACCCCTGCCATAATGGGGGCACATGTGTGGTCAACGGCGAGTC
CTTTACGTGCGTCTGCAAGGAAGGCTGGGAGGGGCCCATCTGTGCTCAGAATACCAATGACTGCAGCCCTCATC
CCTGTTACAACAGCGGCACCTGTGTGGATGGAGACAACTGGTACCGGTGCGAATGTGCCCCGGGTTTTGCTGGG
CCCGACTGCAGAATAAACATCAATGAATGCCAGTCTTCACCTTGTGCCTTTGGAGCGACCTGTGTGGATGAGAT
CAATGGCTACCGGTGTGTCTGCCCTCCAGGGCACAGTGGTGCCAAGTGCCAGGAAGTTTCAGGGAGACCTTGCA
TCACCATGGGGAGTGTGATACCAGATGGGGCCAAATGGGATGATGACTGTAATACCTGCCAGTGCCTGAATGGA
CGGATCGCCTGCTCAAAGGTCTGGTGTGGCCCTCGACCTTGCCTGCTCCACAAAGGGCACAGCGAGTGCCCCAG
CGGGCAGAGCTGCATCCCCATCCTGGACGACCAGTGCTTCGTCCACCCCTGCACTGGTGTGGGCGAGTGTCGGT
CTTCCAGTCTCCAGCCGGTGAAGACAAAGTGCACCTCTGACTCCTATTACCAGGATAACTGTGCGAACATCACA
TTTACCTTTAACAAGGAGATGATGTCACCAGGTCTTACTACGGAGCACATTTGCAGTGAATTGAGGAATTTGAA
TATTTTGAAGAATGTTTCCGCTGAATATTCAATCTACATCGCTTGCGAGCCTTCCCCTTCAGCGAACAATGAAA
TACATGTGGCCATTTCTGCTGAAGATATACGGATGATGGGAACCCGATCAAGGAAATCACTGACAAAATAATC
GATCTTGTTAGTAAACGTGATGGAAACAGCTCGCTGATTGCTGCCGTTGCAGAAGTAAGAGTTCAGAGGCGGCC
TCTGAAGAACAGAACAGATTTCCTTGTTCCCTTGCTGAGCTCTGTCTTAACTGTGGCTTGGATCTGTTGCTTGG
TGACGGCCTTCTACTGGTGCCTGCGGAAGCGGCGGAAGCCGGGCAGCCACACACACTCAGCCTCTGAGGACAAC
ACCACCAACAACGTGCGGGAGCAGCTGAACCAGATCAAAAACCCCATTGAGAAACATGGGGCCAACACGGTCCC
CATCAAGGATTATGAGAACAAGAACTCCAAAATGTCTAAAATAAGGACACACAATTCTGAAGTAGAAGAGGACG
ACATGGACAAACACCAGCAGAAAGCCCGGTTTGCCAAGCAGCCGGCGTACACGCTGGTAGACAGAGAAGAGAAG
CCCCCCAACGGCACGCCGACAAAACACCCAAACTGGACAAACAAACAGGACAACAGAGACTTGGAAAGTGCCCA
GAGCTTAAACCGAATGGAGTACATCGTA

Underlined nucleobases indicate region encoding the signal peptide (1-99)

FIG. 2

A SEQ ID NO: 3 (JAG1; Jagged-1, 1-1054)

MRSPRTRGRSGRPLSLLLALLCALRAKVCGASGQFELEILSMQNVNGELQNGNCCGGAR
NPGDRKCTRDECDTYFKVCLKEYQSRVTAGGPCSFGSGSTPVIGGNTFNLKASRGNDRN
RIVLPFSFAWPRSYTLLVEAWDSSNDTVQPDSIIEKASHSGMINPSRQWQTLKQNTGVA
HFEYQIRVTCDDYYYGFGCNKFCRPRDDFFGHYACDQNGNKTCMEGWMGPECNRAICRQ
GCSPKHGSCKLPGDCRCQYGWQGLYCDKCIPHPGCVHGICNEPWQCLCETNWGGQLCDK
DLNYCGTHQPCLNGGTCSNTGPDKYQCSCPEGYSGPNCEIAEHACLSDPCHNRGSCKET
SLGFECECSPGWTGPTCSTNIDDCSPNNCSHGGTCQDLVNGFKCVCPPQWTGKTCQLDA
NECEAKPCVNAKSCKNLIASYYCDCLPGWMGQNCDININDCLGQCQNDASCRDLVNGYR
CICPPGYAGDHCERDIDECASNPCLNGGHCQNEINRFQCLCPTGFSGNLCQLDIDYCEP
NPCQNGAQCYNRASDYFCKCPEDYEGKNCSHLKDHCRTTPCEVIDSCTVAMASNDTPEG
VRYISSNVCGPHGKCKSQSGGKFTCDCNKGFTGTYCHENINDCESNPCRNGGTCIDGVN
SYKCICSDGWEGAYCETNINDCSQNPCHNGGTCRDLVNDFYCDCKNGWKGKTCHSRDSQ
CDEATCNNGGTCYDEGDAFKCMCPGGWEGTTCNIARNSSCLPNPCHNGGTCVVNGESFT
CVCKEGWEGPICAQNTNDCSPHPCYNSGTCVDGDNWYRCECAPGFAGPDCRININECQS
SPCAFGATCVDEINGYRCVCPPGHSGAKCQEVSGRPCITMGSVIPDGAKWDDDCNTCQC
LNGRIACSKVWCGPRPCLLHKGHSECPSGQSCIPILDDQCFVHPCTGVGECRSSSLQPV
KTKCTSDSYYQDNCANITFTFNKEMMSPGLTTEHICSELRNLNILKNVSAEYSIYIACE
PSPSANNEIHVAISAEDIRDDGNPIKEITDKIIDLVSKRDGNSSLIAAVAE

See Jagged-1, Uniprot Acc. No. P78504. This is only amino acids 1-1054 of protein Jagged-1

| Feature | Position | Length | Description |
|---|---|---|---|
| Signal peptide | 1 – 33 | 33 | Signal peptide |
| Topological domain | 34 – 1067 | 1034 | Extracellular |
| Chain | 34 – 1218 | 1185 | Protein jagged-1 |
| Domain | 185 – 229 | 45 | DSL |
| Domain | 230 – 263 | 34 | EGF-like 1 |
| Domain | 264 – 294 | 31 | EGF-like 2; atypical |
| Domain | 296 – 334 | 39 | EGF-like 3 |
| Domain | 336 – 372 | 37 | EGF-like 4 |
| Domain | 374 – 410 | 37 | EGF-like 5; calcium-binding |
| Domain | 412 – 448 | 37 | EGF-like 6; calcium-binding |
| Domain | 450 – 485 | 36 | EGF-like 7; calcium-binding |
| Domain | 487 – 523 | 37 | EGF-like 8; calcium-binding |
| Domain | 525 – 561 | 37 | EGF-like 9 |
| Domain | 586 – 627 | 42 | EGF-like 10 |
| Domain | 629 – 665 | 37 | EGF-like 11; calcium-binding |
| Domain | 667 – 703 | 37 | EGF-like 12; calcium-binding |
| Domain | 705 – 741 | 37 | EGF-like 13 |
| Domain | 744 – 780 | 37 | EGF-like 14 |
| Domain | 782 – 818 | 37 | EGF-like 15; calcium-binding |
| Domain | 820 – 856 | 37 | EGF-like 16; calcium-binding |
| Topological domain | 1094 – 1218 | 125 | Cytoplasmic (not present) |
| Transmembrane | 1068 – 1093 | 26 | Helical (not present) |

*All positional information refers to the 'canonical' sequence*

C

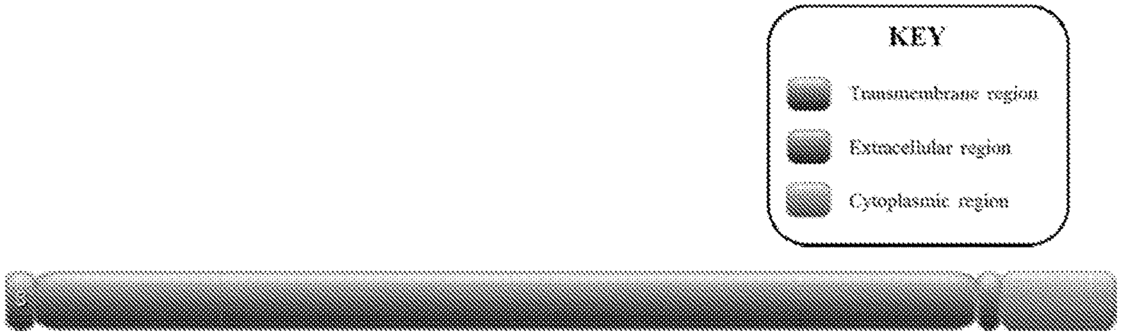

FIG. 3

SEQ ID NO: 4

ATGAGAAGTCCACGGACGCGCGGCCGCTCAGGGCGTCCATTGTCCCTCCTGCTCGCCCTGCTCTGCGCCCTCCG
AGCCAAGGTCTGTGGTGCCAGTGGTCAGTTCGAGTTGGAGATCCTGTCCATGCAGAATGTGAACGGGGAACTGC
AGAATGGGAACTGCTGCGGCGGCGCCCGGAATCCGGGAGACCGAAAATGCACACGCGACGAATGCGACACGTAC
TTCAAAGTCTGTCTCAAGGAATACCAATCACGCGTTACGGCCGGGGGGCCCTGTAGCTTCGGATCAGGGTCCAC
CCCTGTTATCGGGGGTAACACCTTCAACCTTAAGGCCAGCAGGGGCAACGACCGCAACCGCATCGTGCTGCCTT
TCTCGTTTGCCTGGCCGAGGTCCTATACGTTGCTTGTGGAGGCGTGGGATTCTTCTAATGATACCGTTCAGCCT
GACAGCATTATTGAAAAGGCTTCTCACAGCGGCATGATCAATCCCAGCCGGCAATGGCAAACGCTGAAGCAAAA
CACGGGGGTGGCCCACTTTGAGTATCAAATCCGCGTGACATGCGATGACTACTACTACGGCTTCGGATGTAATA
AGTTCTGCCGCCCTAGAGACGATTTCTTTGGCCACTATGCCTGTGATCAGAATGGCAACAAAACTTGTATGGAG
GGCTGGATGGGGCCCGAATGTAACAGAGCAATTTGTCGACAGGGCTGTAGTCCTAAGCACGGGTCTTGCAAACT
CCCAGGTGATTGTAGGTGTCAGTACGGTTGGCAAGGCCTGTATTGTGATAAGTGTATTCCACATCCCGGATGCG
TCCACGGTATCTGCAACGAGCCCTGGCAATGTCTCTGTGAGACAAATTGGGGGGGCCAGCTTTGCGACAAAGAT
CTCAATTATTGCGGTACGCATCAACCGTGCCTTAATGGGGGAACTTGCAGCAATACAGGACCTGATAAGTACCA
GTGCTCCTGCCCTGAGGGGTATTCAGGACCCAACTGTGAGATTGCCGAGCACGCTTGCTTGTCAGATCCCTGCC
ACAATCGAGGCTCATGTAAGGAGACAAGCCTGGGCTTTGAATGTGAGTGTTCTCCAGGCTGGACCGGACCCACA
TGCTCAACAAACATTGATGATTGTTCTCCTAACAACTGTTCTCATGGCGGGACCTGCCAAGACCTGGTTAACGG
TTTTAAGTGTGTATGCCCACCCCAGTGGACTGGGAAGACGTGCCAACTAGATGCGAACGAATGCGAAGCCAAAC
CCTGTGTGAACGCCAAATCCTGTAAGAATTTAATTGCTAGCTACTACTGCGATTGCCTTCCTGGCTGGATGGGT
CAGAATTGTGACATAAATATTAATGACTGCTTGGGCCAGTGTCAGAATGACGCCTCTTGCCGGGATTTGGTGAA
TGGTTATCGCTGTATCTGTCCACCGGGCTATGCAGGCGATCACTGCGAGAGAGATATTGATGAGTGTGCCAGCA
ATCCCTGTTTGAATGGGGGTCACTGCCAGAACGAAATTAACAGATTCCAGTGCCTGTGTCCCACGGGTTTTTCT
GGAAACCTCTGTCAGCTGGATATCGACTATTGTGAGCCTAACCCCTGCCAGAATGGTGCGCAATGCTACAATAG
GGCGAGTGACTACTTCTGTAAGTGTCCCGAAGATTATGAGGGAAAGAACTGCTCACACCTGAAGGACCACTGCA
GAACAACCCCCTGTGAAGTGATAGATAGCTGCACAGTTGCGATGGCTTCCAATGATACACCAGAGGGGGTGCGG
TATATTTCTTCCAACGTCTGCGGTCCACACGGCAAGTGCAAGAGTCAATCGGGAGGAAAATTCACCTGCGACTG
TAACAAGGGCTTCACCGGAACCTACTGCCATGAGAATATCAATGATTGCGAGAGCAACCCATGCAGGAACGGTG
GGACCTGCATCGACGGGGTCAACTCCTACAAATGCATCTGCAGTGACGGCTGGGAAGGGGCCTACTGTGAAACC
AACATTAATGACTGCAGCCAGAACCCTTGTCATAATGGGGGCACGTGTCGCGACCTAGTCAACGACTTCTATTG
TGACTGTAAAAATGGGTGGAAAGGAAAGACATGCCACAGCCGTGATAGCCAGTGTGATGAGGCAACGTGCAACA
ACGGTGGCACTTGCTATGATGAGGGGGATGCTTTTAAGTGCATGTGTCCTGGCGGCTGGGAAGGAACTACATGC
AATATCGCCCGAAACAGTAGCTGCCTGCCTAATCCCTGCCATAACGGGGGAACATGTGTGGTTAACGGCGAGTC
CTTCACGTGCGTTTGTAAAGAAGGCTGGGAGGGCCCTATATGTGCTCAGAATACCAATGACTGCAGCCCGCATC
CCTGTTACAATAGCGGCACCTGTGTTGACGGTGACAATTGGTATCGGTGCGAATGTGCGCCGGGTTTCGCAGGT
CCAGACTGCAGAATAAATATCAATGAATGCCAAAGCTCACCGTGCGCCTTTGGAGCGACCTGTGTGGATGAAAT
CAACGGCTATCGGTGTGTCTGCCCTCCCGGGCATAGTGGTGCCAAATGCCAGGAAGTGTCCGGCAGACCTTGCA
TCACCATGGGGAGTGTGATACCGGATGGCGCTAAATGGGATGATGATTGTAATACCTGTCAGTGCCTGAACGGA
CGGATCGCTTGTTCAAAGGTCTGGTGTGGCCCTCGACCATGCTTGTTACATAAGGGACACTCCGAGTGCCCCAG
CGGTCAGTCGTGTATCCCTATTCTGGACGACCAGTGCTTCGTCCATCCCTGTACTGGTGTGGGCGAGTGTAGGT
CTAGCAGTCTCCAGCCGGTTAAGACAAAATGCACCAGTGACTCCTATTACCAAGATAACTGTGCGAACATCACA
TTTACCTTTAATAAAGAGATGATGTCACCAGGTCTTACCACGGAGCACATTTGCAGTGAATTGAGGAATTTGAA
TATTTTGAAGAATGTTTCCGCTGAATATTCAATCTACATCGCTTGCGAGCCTTCCCCTTCAGCGAACAATGAAA
TACATGTGGCCATTTCTGCTGAAGATATACGGGATGATGGGAACCCGATCAAGGAAATCACTGACAAAATAATC
GATCTTGTTAGTAAACGTGATGGGAACAGCTCGCTGATTGCTGCAGTTGCAGAA

Underlined nucleobases indicate region encoding the signal peptide (1-99)

SEQ ID NO: 5 (JAG1; Jagged-1; 1-1046)

MRSPRTRGRSGRPLSLLLALLCALRAKVCGASGQFELEILSMQNVNGELQNGNCCGGAR
NPGDRKCTRDECDTYFKVCLKEYQSRVTAGGPCSFGSGSTPVIGGNTFNLKASRGNDRN
RIVLPFSFAWPRSYTLLVEAWDSSNDTVQPDSIIEKASHSGMINPSRQWQTLKQNTGVA
HFEYQIRVTCDDYYYGFGCNKFCRPRDDFFGHYACDQNGNKTCMEGWMGPECNRAICRQ
GCSPKHGSCKLPGDCRCQYGWQGLYCDKCIPHPGCVHGICNEPWQCLCETNWGGQLCDK
DLNYCGTHQPCLNGGTCSNTGPDKYQCSCPEGYSGPNCEIAEHACLSDPCHNRGSCKET
SLGFECECSPGWTGPTCSTNIDDCSPNNCSHGGTCQDLVNGFKCVCPPQWTGKTCQLDA
NECEAKPCVNAKSCKNLIASYYCDCLPGWMGQNCDININDCLGQCQNDASCRDLVNGYR
CICPPGYAGDHCERDIDECASNPCLNGGHCQNEINRFQCLCPTGFSGNLCQLDIDYCEP
NPCQNGAQCYNRASDYFCKCPEDYEGKNCSHLKDHCRTTPCEVIDSCTVAMASNDTPEG
VRYISSNVCGPHGKCKSQSGGKFTCDCNKGFTGTYCHENINDCESNPCRNGGTCIDGVN
SYKCICSDGWEGAYCETNINDCSQNPCHNGGTCRDLVNDFYCDCKNGWKGKTCHSRDSQ
CDEATCNNGGTCYDEGDAFKCMCPGGWEGTTCNIARNSSCLPNPCHNGGTCVVNGESFT
CVCKEGWEGPICAQNTNDCSPHPCYNSGTCVDGDNWYRCECAPGFAGPDCRININECQS
SPCAFGATCVDEINGYRCVCPPGHSGAKCQEVSGRPCITMGSVIPDGAKWDDDCNTCQC
LNGRIACSKVWCGPRPCLLHKGHSECPSGQSCIPILDDQCFVHPCTGVGECRSSSLQPV
KTKCTSDSYYQDNCANITFTFNKEMMSPGLTTEHICSELRNLNILKNVSAEYSIYIACE
PSPSANNEIHVAISAEDIRDDGNPIKEITDKIIDLVSKRDGNS

See Jagged-1, Uniprot Acc. No. P78504. This is only amino acids 1-1046 of protein Jagged-1

| Feature | Position | Length | Description |
|---|---|---|---|
| Signal peptide | 1 – 33 | 33 | Signal peptide |
| Topological domain | 34 – 1067 | 1034 | Extracellular |
| Chain | 34 – 1218 | 1185 | Protein jagged-1 |
| Domain | 185 – 229 | 45 | DSL |
| Domain | 230 – 263 | 34 | EGF-like 1 |
| Domain | 264 – 294 | 31 | EGF-like 2; atypical |
| Domain | 296 – 334 | 39 | EGF-like 3 |
| Domain | 336 – 372 | 37 | EGF-like 4 |
| Domain | 374 – 410 | 37 | EGF-like 5; calcium-binding |
| Domain | 412 – 448 | 37 | EGF-like 6; calcium-binding |
| Domain | 450 – 485 | 36 | EGF-like 7; calcium-binding |
| Domain | 487 – 523 | 37 | EGF-like 8; calcium-binding |
| Domain | 525 – 561 | 37 | EGF-like 9 |
| Domain | 586 – 627 | 42 | EGF-like 10 |
| Domain | 629 – 665 | 37 | EGF-like 11; calcium-binding |
| Domain | 667 – 703 | 37 | EGF-like 12; calcium-binding |
| Domain | 705 – 741 | 37 | EGF-like 13 |
| Domain | 744 – 780 | 37 | EGF-like 14 |
| Domain | 782 – 818 | 37 | EGF-like 15; calcium-binding |
| Domain | 820 – 856 | 37 | EGF-like 16; calcium-binding |
| Topological domain | 1094 – 1218 | 125 | Cytoplasmic (not present) |
| Transmembrane | 1068 – 1093 | 26 | Helical (not present) |

*All positional information refers to the 'canonical' sequence*

C

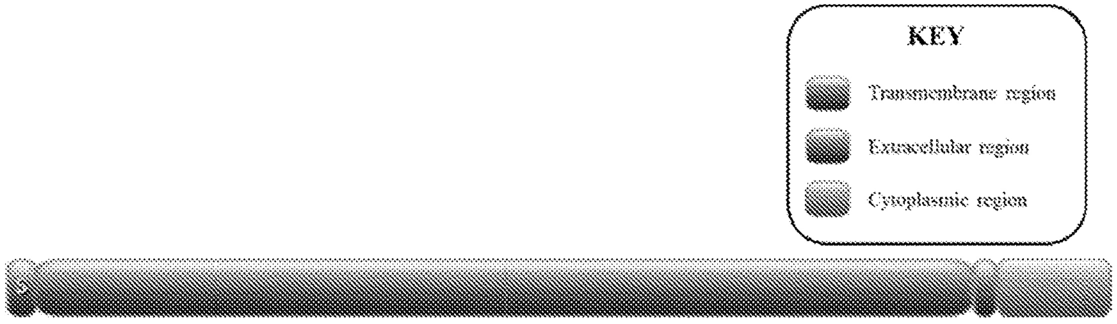

FIG. 5

SEQ ID NO: 6

ATGAGGTCACCTCGGACGAGAGGTCGGAGCGGGCGACCTTTATCTCTCCTCCTAGCTCTGCTGTGCGCGCTAAGG
GCGAAAGTGTGCGGTGCGAGCGGTCAATTCGAACTTGAAATTCTTAGTATGCAAAACGTAAATGGCGAACTGCAA
AATGGGAATTGCTGTGGCGGGGCGCGGAATCCCGGCGACAGAAAATGCACGCGGGATGAGTGCGACACGTACTTT
AAAGTCTGCCTTAAGGAGTACCAAAGTAGGGTGACAGCAGGCGGGCCTTGTAGTTTCGGCTCGGGTAGCACCCCT
GTAATTGGCGGTAATACCTTCAACTTGAAGGCCTCACGCGGCAATGACAGAAATCGTATAGTTCTGCCCTTTAGT
TTTGCATGGCCGAGGTCGTATACCTTGTTGGTAGAGGCGTGGGACTCATCGAACGACACTGTCCAGCCCGACTCG
ATCATTGAAAAGGCCTCGCACAGTGGGATGATAAATCCTAGCCGGCAGTGGCAAACACTCAAGCAGAACACGGGC
GTCGCGCACTTTGAGTACCAGATAAGAGTAACATGTGATGATTACTATTACGGTTTCGGTTGTAACAAATTCTGT
CGTCCTCGAGACGACTTCTTTGGACATTACGCATGTGACCAAAACGGTAATAAGACATGTATGGAAGGCTGGATG
GGCCCCGAGTGCAACAGGGCGATCTGTAGACAGGGTTGTTCCCCGAAACATGGTTCTTGCAAACTACCGGGTGAC
TGCAGGTGTCAATATGGTTGGCAGGGCCTGTACTGTGATAAATGCATACCGCATCCTGGGTGCGTCCATGGTATC
TGTAATGAGCCATGGCAGTGCCTCTGTGAGACAAATTGGGGTGGCCAACTTTGTGACAAGGACCTAAACTATTGT
GGGACTCATCAACCGTGTCTGAATGGGGGAACATGTTCAAATACTGGTCCTGACAAGTATCAGTGTAGTTGTCCA
GAAGGTTACTCGGGGCCAAATTGTGAGATAGCGGAACATGCCTGCCTCTCAGACCCGTGTCATAATCGGGGCTCT
TGCAAGGAAACATCCCTAGGGTTTGAGTGCGAGTGTTCTCCTGGTTGGACGGGTCCGACGTGCTCCACAAACATC
GACGATTGTAGCCCGAATAACTGTTCCCACGGGGGAACATGCCAGGATCTAGTTAACGGTTTTAAGTGTGTTTGT
CCGCCCCAATGGACCGGAAAAACCTGTCAGTTGGATGCCAATGAATGTGAGGCCAAACCGTGCGTGAACGCGAAA
TCGTGTAAGAATTTGATCGCTTCGTACTACTGTGATTGTTTGCCGGGATGGATGGGACAAAACTGCGATATAAAT
ATTAATGACTGTTTGGGCCAATGCCAAAATGATGCATCCTGTAGGGATCTTGTAAACGGATACAGGTGCATATGT
CCTCCAGGCTACGCTGGTGATCACTGCGAGAGAGATATAGACGAATGTGCCTCGAACCCTTGCCTAAATGGTGGT
CATTGTCAAAATGAGATAAATCGATTCCAGTGTCTATGCCCGACCGGCTTCTCGGGGAATCTTTGTCAGTTAGAC
ATAGATTATTGTGAGCCCAATCCATGTCAAAACGGCGCCCAGTGCTACAATCGGGCTAGCGATTACTTCTGTAAG
TGCCCGGAGGATTACGAAGGGAAGAATTGCTCACATTTAAAAGACCACTGCCGTACGACGCCTTGCGAAGTTATT
GACTCCTGCACCGTGGCCATGGCCTCCAACGATACGCCTGAGGGGGTCAGGTACATATCTAGTAACGTTTGTGGC
CCCCATGGAAAGTGCAAATCCCAGTCCGGCGGGAAATTCACATGCGATTGCAACAAGGGTTTTACGGGTACTTAT
TGCCACGAGAACATTAATGATTGTGAAAGCAACCCATGTAGAAATGGGGGTACCTGTATTGATGGTGTCAACAGT
TACAAATGTATTTGTAGCGATGGCTGGGAAGGCGCCTACTGCGAGACAAATATAAACGACTGCTCCCAGAACCCC
TGCCACAATGGGGGCACCTGCCGCGACTTGGTAAATGATTTTTATTGCGATTGCAAGAACGGTTGGAAGGGCAAA
ACATGCCACTCGCGAGACTCGCAGTGTGACGAAGCCACGTGCAATAATGGTGGCACGTGCTATGACGAGGGAGAC
GCCTTCAAGTGTATGTGCCCTGGCGGGTGGGAGGGTACAACATGTAACATCGCCAGGAACTCGAGTTGTCTCCCT
AATCCCTGTCATAACGGTGGGACCTGTGTAGTCAACGGGGAATCCTTTACATGTGTTTGCAAGGAAGGCTGGGAA
GGCCCAATCTGTGCCCAGAATACGAACGATTGCTCACCGCATCCGTGTTATAACTCGGGCACGTGTGTAGATGGC
GATAATTGGTATCGCTGTGAATGCGCTCCAGGATTCGCCGGTCCGGATTGTCGAATAAATATTAACGAGTGTCAG
TCATCGCCTTGTGCCTTTGGCGCGACATGTGTTGACGAAATTAACGGATATCGTTGCGTTTGTCCGCCCGGCCAT
TCCGGCGCAAAATGCCAAGAAGTTAGTGGAAGACCTTGCATCACTATGGGCTCCGTTATCCCTGACGGCGCGAAG
TGGGACGACGATTGCAACACCTGCCAGTGTTTAAATGGCAGGATCGCGTGTTCGAAAGTTTGGTGCGGGCCACGT
CCCTGCCTCCTGCACAAAGGACATTCTGAGTGCCCTAGTGGTCAAAGTTGTATACCGATATTGGATGATCAATGT
TTTGTACACCCGTGCACAGGAGTTGGAGAATGTCGCTCAAGCTCACTCCAACCAGTTAAAACGAAGTGTACGAGT
GACAGTTATTACCAGGATAACTGTGCGAATATAACATTCACATTTAACAAAGAGATGATGTCTCCTGGGCTGACG
ACTGAACATATCTGTAGTGAGCTAAGGAACCTTAACATCTTGAAAAACGTATCTGCTGAATACTCAATATACATA
GCCTGTGAGCCATCCCCTTCCGCGAACAATGAAATACATGTAGCCATTTCAGCAGAAGACATCCGTGATGACGGA
AACCCGATCAAGGAAATAACAGACAAAATAATCGACCTGGTCTCAAAACGGGATGGAAATTCC

Underlined nucleobases indicate region encoding the signal peptide (1-99)

FIG. 6

A 7 Alagille; JAG1; Jagged-1; (peptide + Fc) fusion;
MGVKVLFALICIAVAEACDDYYYGFGCNKFCRPRDKTHTCPPCPAPEAAGGPSVFLFPPKPKDTLYITREPE
VTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALKFHYTQKSLSLSPGK

B 8 Alagille; JAG1; Jagged-1; (peptide + Fc) fusion;
ATGGGAGTCAAAGTTCTGTTTGCCCTGATCTGCATCGCTGTGGCCGAGGCCTGTGATGACTACTACTA
TGGCTTTGGCTGCAATAAGTTCTGCCGCCCCAGAGACAAGACCCACACCTGCCCCCCCTGCCCCGCCC
CCGAGGCCGCCGGCGGGCCCAGCGTGTTCCTGTTCCCCCCCAAGCCCAAGGACACCCTGTACATCACC
AGGGAGCCCGAGGTGACCTGCGTGGTGGTGGACGTGAGCCACGAGGACCCCGAGGTGAAGTTCAAC
TGGTACGTGGACGGCGTGGAGGTGCACAACGCCAAGACCAAGCCCAGGGAGGAGCAGTACAACAGC
ACCTACAGGGTGGTGAGCGTGCTGACCGTGCTGCACCAGGACTGGCTGAACGGCAAGGAGTACAAG
TGCAAGGTGAGCAACAAGGCCCTGCCCGCCCCCATCGAGAAGACCATCAGCAAGGCCAAGGGCCAG
CCCAGGGAGCCCCAGGTGTACACCCTGCCCCCCAGCAGGGACGAGCTGACCAAGAACCAGGTGAGCC
TGACCTGCCTGGTGAAGGGCTTCTACCCCAGCGACATCGCCGTGGAGTGGGAGAGCAACGGCCAGCC
CGAGAACAACTACAAGACCACCCCCCCCGTGCTGGACAGCGACGGCAGCTTCTTCCTGTACAGCAAGC
TGACCGTGGACAAGAGCAGGTGGCAGCAGGGCAACGTGTTCAGCTGCAGCGTGATGCACGAGGCCC
TGAAGTTCCACTACACCCAGAAGAGCCTGAGCCTGAGCCCCGGCAAG

C 9 Alagille; JAG1; Jagged-1; (Fc + peptide) fusion;
MGVKVLFALICIAVAEADKTHTCPPCPAPEAAGGPSVFLFPPKPKDTLYITREPEVTCVVVDVSHEDPEVKF
NWYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDKSRW
QQGNVFSCSVMHEALKFHYTQKSLSLSPGKGGGGSGGGGSGGGGSCDDYYYGFGCNKFCRPR

D 10 Alagille; JAG1; Jagged-1; (Fc + peptide) fusion;
ATGGGAGTCAAAGTTCTGTTTGCCCTGATCTGCATCGCTGTGGCCGAGGCCGACAAGACCCACACCTG
CCCCCCCTGCCCCGCCCCCGAGGCCGCCGGCGGTCCCAGCGTGTTCCTGTTCCCCCCCAAGCCCAAGG
ACACCCTGTACATCACCAGGGAGCCCGAGGTGACCTGCGTGGTGGTGGACGTGAGCCACGAGGACCC
CGAGGTGAAGTTCAACTGGTACGTGGACGGCGTGGAGGTGCACAACGCCAAGACCAAGCCCAGGGA
GGAGCAGTACAACAGCACCTACAGGGTGGTGAGCGTGCTGACCGTGCTGCACCAGGACTGGCTGAA
CGGCAAGGAGTACAAGTGCAAGGTGAGCAACAAGGCCCTGCCCGCCCCCATCGAGAAGACCATCAG
CAAGGCCAAGGGCCAGCCCAGGGAGCCCCAGGTGTACACCCTGCCCCCCAGCAGGGACGAGCTGAC
CAAGAACCAGGTGAGCCTGACCTGCCTGGTGAAGGGCTTCTACCCCAGCGACATCGCCGTGGAGTGG
GAGAGCAACGGCCAGCCCGAGAACAACTACAAGACCACCCCCCCCGTGCTGGACAGCGACGGCAGCT
TCTTCCTGTACAGCAAGCTGACCGTGGACAAGAGCAGGTGGCAGCAGGGCAACGTGTTCAGCTGCAG
CGTGATGCACGAGGCCCTGAAGTTCCACTACACCCAGAAGAGCCTGAGCCTGAGCCCCGGCAAGGGT
GGCGGTGGCTCGGGCGGTGGTGGGTCGGGTGGCGGCGGATCTTGTGATGACTACTACTATGGCTTTG
GCTGCAATAAGTTCTGCCGCCCCAGA

FIG. 7

| Protein | Length | Theoretical Minimum U (%) | Theoretical Minimum U (abs) | | | | | | | |
|---|---|---|---|---|---|---|---|---|---|---|
| JAG1 Protein | 1218 | 7.96% | 291 | | | | | | | |
| **Nucleic Acid** | **Length** | **U Content(abs)** | **U Content(%)** | **U Content v WT (%)** | **U Content v Theoretical Minimum (%)** | **UU pairs** | **UU pairs v WT (%)** | **UUU** | **UUUU** | **UUUUU** |
| JAG1-WT | 3654 | 778 | 21.29% | 100.00% | 267.35% | 81 | 100.00% | 24 | 3 | 0 |
| JAG1-CO01 | 3654 | 544 | 14.89% | 69.92% | 186.94% | 42 | 51.85% | 5 | 0 | 0 |
| JAG1-CO02 | 3654 | 540 | 14.78% | 69.41% | 185.57% | 33 | 40.74% | 7 | 1 | 0 |
| JAG1-CO03 | 3654 | 547 | 14.97% | 70.31% | 187.97% | 44 | 54.32% | 5 | 3 | 0 |
| JAG1-CO04 | 3654 | 560 | 15.33% | 71.98% | 192.44% | 31 | 38.27% | 8 | 2 | 0 |
| JAG1-CO05 | 3654 | 551 | 15.08% | 70.82% | 189.35% | 41 | 50.62% | 8 | 3 | 0 |
| JAG1-CO06 | 3654 | 574 | 15.71% | 73.78% | 197.25% | 43 | 53.09% | 3 | 1 | 0 |
| JAG1-CO07 | 3654 | 551 | 15.08% | 70.82% | 189.35% | 39 | 48.15% | 8 | 0 | 1 |
| JAG1-CO08 | 3654 | 548 | 15.00% | 70.44% | 188.32% | 37 | 45.68% | 5 | 2 | 0 |
| JAG1-CO09 | 3654 | 547 | 14.97% | 70.31% | 187.97% | 42 | 51.85% | 7 | 1 | 0 |
| JAG1-CO10 | 3654 | 564 | 15.44% | 72.49% | 193.81% | 38 | 46.91% | 7 | 2 | 0 |
| JAG1-CO11 | 3654 | 566 | 15.49% | 72.75% | 194.50% | 45 | 55.56% | 11 | 0 | 0 |
| JAG1-CO12 | 3654 | 546 | 14.94% | 70.18% | 187.63% | 39 | 48.15% | 9 | 2 | 0 |
| JAG1-CO13 | 3654 | 553 | 15.13% | 71.08% | 190.03% | 32 | 39.51% | 10 | 2 | 1 |
| JAG1-CO14 | 3654 | 561 | 15.35% | 72.11% | 192.78% | 44 | 54.32% | 7 | 1 | 0 |
| JAG1-CO15 | 3654 | 568 | 15.54% | 73.01% | 195.19% | 38 | 46.91% | 6 | 0 | 1 |
| JAG1-CO16 | 3654 | 554 | 15.16% | 71.21% | 190.38% | 41 | 50.62% | 6 | 2 | 0 |
| JAG1-CO17 | 3654 | 536 | 14.67% | 68.89% | 184.19% | 31 | 38.27% | 6 | 2 | 0 |
| JAG1-CO18 | 3654 | 550 | 15.05% | 70.69% | 189.00% | 40 | 49.38% | 7 | 0 | 0 |
| JAG1-CO19 | 3654 | 547 | 14.97% | 70.31% | 187.97% | 32 | 39.51% | 9 | 0 | 0 |
| JAG1-CO20 | 3654 | 575 | 15.74% | 73.91% | 197.59% | 37 | 45.68% | 9 | 2 | 0 |
| JAG1-CO21 | 3654 | 558 | 15.27% | 71.72% | 191.75% | 38 | 46.91% | 10 | 2 | 1 |
| JAG1-CO22 | 3654 | 553 | 15.13% | 71.08% | 190.03% | 37 | 45.68% | 9 | 0 | 0 |
| JAG1-CO23 | 3654 | 566 | 15.49% | 72.75% | 194.50% | 46 | 56.79% | 7 | 1 | 0 |
| JAG1-CO24 | 3654 | 544 | 14.89% | 69.92% | 186.94% | 44 | 54.32% | 2 | 1 | 1 |
| JAG1-CO25 | 3654 | 565 | 15.46% | 72.62% | 194.16% | 37 | 45.68% | 11 | 2 | 0 |
| | MAX | 575 | 15.74% | 73.91% | 197.59% | 46 | 56.79% | 11 | 3 | 1 |
| | MIN | 536 | 14.67% | 68.89% | 184.19% | 31 | 38.27% | 2 | 0 | 0 |
| | AVERAGE | 554.72 | 15.18% | 71.30% | 190.63% | 38.84 | 47.95% | 7.28 | 1.28 | 0.2 |
| | MEDIAN | 553 | 15.13% | 71.08% | 190.03% | 39 | 48.15% | 7 | 1 | 0 |
| | STD DEV | 10.48 | 0.29% | 1.35% | 3.60% | 4.49 | 5.54% | | | |

FIG. 8

| Protein | Length | Theoretical Maximum G (%) | Theoretical Maximum G (abs) | | |
|---|---|---|---|---|---|
| JAG1 Protein | 1218 | 39.05% | 1427 | | |
| **Nucleic Acid** | **Length** | **G Content(abs)** | **G Content(%)** | **G Content v WT (%)** | **G Content v Theoretical Maximum (%)** |
| JAG1-WT | 3654 | 999 | 27.34% | 100.00% | 70.01% |
| JAG1-CO01 | 3654 | 1090 | 29.83% | 109.11% | 76.38% |
| JAG1-CO02 | 3654 | 1068 | 29.23% | 106.91% | 74.84% |
| JAG1-CO03 | 3654 | 1078 | 29.50% | 107.91% | 75.54% |
| JAG1-CO04 | 3654 | 1080 | 29.56% | 108.11% | 75.68% |
| JAG1-CO05 | 3654 | 1074 | 29.39% | 107.51% | 75.26% |
| JAG1-CO06 | 3654 | 1076 | 29.45% | 107.71% | 75.40% |
| JAG1-CO07 | 3654 | 1089 | 29.80% | 109.01% | 76.31% |
| JAG1-CO08 | 3654 | 1061 | 29.04% | 106.21% | 74.35% |
| JAG1-CO09 | 3654 | 1078 | 29.50% | 107.91% | 75.54% |
| JAG1-CO10 | 3654 | 1069 | 29.26% | 107.01% | 74.91% |
| JAG1-CO11 | 3654 | 1065 | 29.15% | 106.61% | 74.63% |
| JAG1-CO12 | 3654 | 1074 | 29.39% | 107.51% | 75.26% |
| JAG1-CO13 | 3654 | 1075 | 29.42% | 107.61% | 75.33% |
| JAG1-CO14 | 3654 | 1075 | 29.42% | 107.61% | 75.33% |
| JAG1-CO15 | 3654 | 1070 | 29.28% | 107.11% | 74.98% |
| JAG1-CO16 | 3654 | 1069 | 29.26% | 107.01% | 74.91% |
| JAG1-CO17 | 3654 | 1070 | 29.28% | 107.11% | 74.98% |
| JAG1-CO18 | 3654 | 1077 | 29.47% | 107.81% | 75.47% |
| JAG1-CO19 | 3654 | 1070 | 29.28% | 107.11% | 74.98% |
| JAG1-CO20 | 3654 | 1076 | 29.45% | 107.71% | 75.40% |
| JAG1-CO21 | 3654 | 1082 | 29.61% | 108.31% | 75.82% |
| JAG1-CO22 | 3654 | 1075 | 29.42% | 107.61% | 75.33% |
| JAG1-CO23 | 3654 | 1071 | 29.31% | 107.21% | 75.05% |
| JAG1-CO24 | 3654 | 1073 | 29.37% | 107.41% | 75.19% |
| JAG1-CO25 | 3654 | 1091 | 29.86% | 109.21% | 76.45% |
| | MAX | 1091 | 29.86% | 109.21% | 76.45% |
| | MIN | 1061 | 29.04% | 106.21% | 74.35% |
| | MEAN | 1075.04 | 29.42% | 107.61% | 75.34% |
| | MEDIAN | 1075 | 29.42% | 107.61% | 75.33% |
| | STD DEV | 7.33 | 0.20% | 0.73% | 0.51% |

FIG. 9

| Protein | Length | Theoretical Maximum C | Theoretical Maximum C (abs) | | |
|---|---|---|---|---|---|
| JAG1 Protein | 1218 | 42.78% | 1563 | | |
| **Nucleic Acid** | **Length** | **C Content(abs)** | **C Content(%)** | **C Content v WT (%)** | **C Content v Theoretical Maximum (%)** |
| JAG1-WT | 3654 | 973 | 26.63% | 100.00% | 62.25% |
| JAG1-CO01 | 3654 | 1169 | 31.99% | 120.14% | 74.79% |
| JAG1-CO02 | 3654 | 1189 | 32.54% | 122.20% | 76.07% |
| JAG1-CO03 | 3654 | 1178 | 32.24% | 121.07% | 75.37% |
| JAG1-CO04 | 3654 | 1157 | 31.66% | 118.91% | 74.02% |
| JAG1-CO05 | 3654 | 1177 | 32.21% | 120.97% | 75.30% |
| JAG1-CO06 | 3654 | 1154 | 31.58% | 118.60% | 73.83% |
| JAG1-CO07 | 3654 | 1157 | 31.66% | 118.91% | 74.02% |
| JAG1-CO08 | 3654 | 1191 | 32.59% | 122.40% | 76.20% |
| JAG1-CO09 | 3654 | 1180 | 32.29% | 121.27% | 75.50% |
| JAG1-CO10 | 3654 | 1155 | 31.61% | 118.71% | 73.90% |
| JAG1-CO11 | 3654 | 1148 | 31.42% | 117.99% | 73.45% |
| JAG1-CO12 | 3654 | 1162 | 31.80% | 119.42% | 74.34% |
| JAG1-CO13 | 3654 | 1179 | 32.27% | 121.17% | 75.43% |
| JAG1-CO14 | 3654 | 1161 | 31.77% | 119.32% | 74.28% |
| JAG1-CO15 | 3654 | 1169 | 31.99% | 120.14% | 74.79% |
| JAG1-CO16 | 3654 | 1178 | 32.24% | 121.07% | 75.37% |
| JAG1-CO17 | 3654 | 1183 | 32.38% | 121.58% | 75.69% |
| JAG1-CO18 | 3654 | 1171 | 32.05% | 120.35% | 74.92% |
| JAG1-CO19 | 3654 | 1190 | 32.57% | 122.30% | 76.14% |
| JAG1-CO20 | 3654 | 1146 | 31.36% | 117.78% | 73.32% |
| JAG1-CO21 | 3654 | 1168 | 31.96% | 120.04% | 74.73% |
| JAG1-CO22 | 3654 | 1169 | 31.99% | 120.14% | 74.79% |
| JAG1-CO23 | 3654 | 1173 | 32.10% | 120.55% | 75.05% |
| JAG1-CO24 | 3654 | 1191 | 32.59% | 122.40% | 76.20% |
| JAG1-CO25 | 3654 | 1140 | 31.20% | 117.16% | 72.94% |
| | MAX | 1191 | 32.59% | 122.40% | 76.20% |
| | MIN | 1140 | 31.20% | 117.16% | 72.94% |
| | AVERAGE | 1169.4 | 32.00% | 120.18% | 74.82% |
| | MEDIAN | 1169 | 31.99% | 120.14% | 74.79% |
| | STD DEV | 14.58 | 0.40% | 1.50% | 0.93% |

FIG. 10

| Protein | Length | Theoretical Maximum GC | Theoretical Maximum GC (abs) | | |
|---|---|---|---|---|---|
| JAG1 Protein | 1218 | 66.67% | 2436 | | |
| **Nucleic Acid** | **Length** | **GC Content(abs)** | **GC Content(%)** | **GC Content v WT (%)** | **GC Content v Theoretical Maximum (%)** |
| JAG1-WT | 3654 | 1972 | 53.97% | 100.00% | 80.95% |
| JAG1-CO01 | 3654 | 2259 | 61.82% | 114.55% | 92.73% |
| JAG1-CO02 | 3654 | 2257 | 61.77% | 114.45% | 92.65% |
| JAG1-CO03 | 3654 | 2256 | 61.74% | 114.40% | 92.61% |
| JAG1-CO04 | 3654 | 2237 | 61.22% | 113.44% | 91.83% |
| JAG1-CO05 | 3654 | 2251 | 61.60% | 114.15% | 92.41% |
| JAG1-CO06 | 3654 | 2230 | 61.03% | 113.08% | 91.54% |
| JAG1-CO07 | 3654 | 2246 | 61.47% | 113.89% | 92.20% |
| JAG1-CO08 | 3654 | 2252 | 61.63% | 114.20% | 92.45% |
| JAG1-CO09 | 3654 | 2258 | 61.80% | 114.50% | 92.69% |
| JAG1-CO10 | 3654 | 2224 | 60.86% | 112.78% | 91.30% |
| JAG1-CO11 | 3654 | 2213 | 60.56% | 112.22% | 90.85% |
| JAG1-CO12 | 3654 | 2236 | 61.19% | 113.39% | 91.79% |
| JAG1-CO13 | 3654 | 2254 | 61.69% | 114.30% | 92.53% |
| JAG1-CO14 | 3654 | 2236 | 61.19% | 113.39% | 91.79% |
| JAG1-CO15 | 3654 | 2239 | 61.28% | 113.54% | 91.91% |
| JAG1-CO16 | 3654 | 2247 | 61.49% | 113.95% | 92.24% |
| JAG1-CO17 | 3654 | 2253 | 61.66% | 114.25% | 92.49% |
| JAG1-CO18 | 3654 | 2248 | 61.52% | 114.00% | 92.28% |
| JAG1-CO19 | 3654 | 2260 | 61.85% | 114.60% | 92.78% |
| JAG1-CO20 | 3654 | 2222 | 60.81% | 112.68% | 91.22% |
| JAG1-CO21 | 3654 | 2250 | 61.58% | 114.10% | 92.36% |
| JAG1-CO22 | 3654 | 2244 | 61.41% | 113.79% | 92.12% |
| JAG1-CO23 | 3654 | 2244 | 61.41% | 113.79% | 92.12% |
| JAG1-CO24 | 3654 | 2264 | 61.96% | 114.81% | 92.94% |
| JAG1-CO25 | 3654 | 2231 | 61.06% | 113.13% | 91.58% |
| | MAX | 2264 | 61.96% | 114.81% | 92.94% |
| | MIN | 2213 | 60.56% | 112.22% | 90.85% |
| | AVERAGE | 2244.44 | 61.42% | 113.82% | 92.14% |
| | MEDIAN | 2247 | 61.49% | 113.95% | 92.24% |
| | STD DEV | 13.16 | 0.36% | 0.67% | 0.54% |

FIG. 11

| Sequence | GC | GC 1st | GC 2nd | GC 3rd |
|---|---|---|---|---|
| JAG1-WT | 53.97 | 48.44 | 49.1 | 64.37 |
| JAG1-CO11 | 60.56 | 48.11 | 49.1 | 84.48 |
| JAG1-CO20 | 60.81 | 47.95 | 49.1 | 85.39 |
| JAG1-CO10 | 60.86 | 48.69 | 49.1 | 84.81 |
| JAG1-CO06 | 61.03 | 48.36 | 49.1 | 85.63 |
| JAG1-CO25 | 61.06 | 48.19 | 49.1 | 85.88 |
| JAG1-CO14 | 61.19 | 48.52 | 49.1 | 85.96 |
| JAG1-CO12 | 61.19 | 48.28 | 49.1 | 86.21 |
| JAG1-CO04 | 61.22 | 47.7 | 49.1 | 86.86 |
| JAG1-CO15 | 61.28 | 48.85 | 49.1 | 85.88 |
| JAG1-CO23 | 61.41 | 48.36 | 49.1 | 86.78 |
| JAG1-CO22 | 61.41 | 48.19 | 49.1 | 86.95 |
| JAG1-CO07 | 61.47 | 48.19 | 49.1 | 87.11 |
| JAG1-CO16 | 61.49 | 48.11 | 49.1 | 87.27 |
| JAG1-CO18 | 61.52 | 48.28 | 49.1 | 87.19 |
| JAG1-CO21 | 61.58 | 48.77 | 49.1 | 86.86 |
| JAG1-CO05 | 61.6 | 48.28 | 49.1 | 87.44 |
| JAG1-CO08 | 61.63 | 48.44 | 49.1 | 87.36 |
| JAG1-CO17 | 61.66 | 48.28 | 49.1 | 87.6 |
| JAG1-CO13 | 61.69 | 49.43 | 49.1 | 86.54 |
| JAG1-CO03 | 61.74 | 48.52 | 49.1 | 87.6 |
| JAG1-CO02 | 61.77 | 48.6 | 49.1 | 87.6 |
| JAG1-CO09 | 61.8 | 48.28 | 49.1 | 88.01 |
| JAG1-CO01 | 61.82 | 48.19 | 49.1 | 88.18 |
| JAG1-CO19 | 61.85 | 48.69 | 49.1 | 87.77 |
| JAG1-CO24 | 61.96 | 48.36 | 49.1 | 88.42 |
| Overall | 61.14 | 48.39 | 49.1 | 85.93 |

FIG. 12

```
JAG1-WT      ATGCGTTCCCCACGGACGCGCGGCCGGTCCGGGCGCCCCCTAAGCCTCCTGCTCGCCCTG
JAG1-CO01    ATGCGAAGCCCCAGGACCCGCGGCCGTAGCGGTAGGCCCCTGTCCCTGCTGCTGGCCCTG
JAG1-CO17    ATGAGAAGCCCCAGGACCCGAGGCAGGAGCGGCAGGCCACTGAGCCTGCTCCTTGCCCTG
JAG1-CO11    ATGAGGAGCCCCCGGACCAGGGGGCGGAGCGGCAGGCCCCTGAGCCTCCTGCTGGCCCTG
JAG1-CO12    ATGAGGAGCCCGAGAACGAGGGGGCGGTCCGGCAGGCCGCTGAGCCTCCTGCTGGCCCTG
JAG1-CO25    ATGCGCAGCCCCCGGACCAGGGGAAGGTCCGGCAGGCCCCTGTCCCTGCTGCTGGCGCTG
JAG1-CO04    ATGAGGAGCCCCAGGACCAGGGGGAGGAGCGGGAGGCCGCTGAGCCTGCTCCTGGCCCTG
JAG1-CO18    ATGAGAAGTCCCAGGACCCGCGGGCGGAGCGGGCGCCCCCTGAGCCTGTTACTGGCCCTC
JAG1-CO05    ATGAGGTCACCCCGGACCCGGGGACGCTCCGGCAGGCCCCTGAGCCTGCTGCTGGCCCTG
JAG1-CO23    ATGCGGTCCCCCCGGACCAGGGGTAGGAGCGGCCGCCCACTGTCCCTGCTGCTGGCCCTG
JAG1-CO24    ATGAGGTCCCCCAGAACTCGGGGGAGGTCCGGCAGGCCGCTCAGCCTCCTGCTCGCCCTG
JAG1-CO21    ATGAGGAGCCCCCGCACCAGGGGGCGTAGCGGCCGCCCCCTGAGCCTGCTGCTGGCTCTG
JAG1-CO22    ATGAGGTCCCCCAGGACCAGGGGCAGGAGCGGGAGGCCCCTGTCCCTTCTGCTGGCGCTG
JAG1-CO15    ATGCGAAGCCCCCGAACCCGGGGCAGGAGCGGGAGGCCCCTGAGCCTGCTGCTGGCCCTT
JAG1-CO16    ATGCGAAGCCCGAGGACCCGGGGCAGGAGCGGCAGGCCGCTAAGCCTGCTGCTGGCCCTC
JAG1-CO07    ATGAGGAGCCCCAGGACAAGGGGCCGGAGCGGCAGGCCCCTGAGCCTGCTGCTCGCCCTC
JAG1-CO02    ATGAGGAGCCCCAGGACCCGGGGCCGTAGCGGGAGGCCGCTCTCGCTGCTGCTGGCCCTG
JAG1-CO20    ATGAGGAGCCCAAGGACCAGGGGGAGGAGCGGCAGGCCGCTCAGCCTGCTGCTCGCCCTG
JAG1-CO13    ATGAGAAGCCCAAGGACGCGCGGTAGGAGCGGCAGGCCCCTCAGCCTGCTGCTGGCTCTA
JAG1-CO19    ATGCGTAGCCCCAGGACCAGGGGTAGGTCCGGGAGGCCCCTGTCACTCCTCCTGGCCCTG
JAG1-CO08    ATGCGGAGCCCCAGAACCCGTGGCCGGAGCGGCAGGCCCCTGTCACTACTGCTGGCCCTG
JAG1-CO03    ATGAGGTCCCCGCGTACCCGAGGCAGGTCCGGGAGGCCCCTGTCCCTGCTGCTCGCCTTA
JAG1-CO14    ATGCGGTCGCCGAGAACCAGGGGCCGGAGCGGCCGGCCCCTGTCGCTGCTGCTGGCCCTG
JAG1-CO09    ATGAGGTCCCCCCGAACCAGGGGCAGGTCCGGTCGGCCCCTGAGCCTGCTCCTGGCCCTC
JAG1-CO10    ATGAGGAGCCCCAGGACACGGGGCCGGAGCGGGCGACCTCTGTCCCTGCTCCTGGCCCTG
JAG1-CO06    ATGCGGTCCCCCAGGACCAGGGGGCGCAGCGGGAGGCCCCTGAGCCTGCTGCTGGCCTTA
             *** *     **  * **  * **  *    ***  * ** **     ** .* ** ** .*

JAG1-WT      CTCTGTGCCCTGCGAGCCAAGGTGTGTGGGGCCTCGGGTCAGTTCGAGTTGGAGATCCTG
JAG1-CO01    CTGTGCGCCCTCAGGGCCAAGGTGTGCGGCGCCAGCGGCCAGTTCGAGCTCGAGATCCTG
JAG1-CO17    CTGTGCGCCCTGAGGGCAAAGGTGTGCGGCGCCAGCGGCCAGTTCGAGCTGGAAATCCTG
JAG1-CO11    CTTTGCGCACTGAGGGCCAAGGTGTGTGGGGCCAGCGGGCAGTTCGAGCTCGAAATCCTG
JAG1-CO12    CTGTGCGCCCTGCGGGCAAAGGTGTGTGGCGCCTCCGGGCAGTTCGAGCTGGAGATCCTG
JAG1-CO25    CTCTGCGCCCTGCGAGCCAAAGTGTGTGGTGCCTCCGGGCAGTTTGAGCTGGAGATCCTC
JAG1-CO04    CTGTGTGCCCTGCGCGCCAAGGTGTGCGGCGCGTCCGGACAGTTTGAGCTGGAGATCCTG
JAG1-CO18    CTGTGTGCCCTGCGCGCGAAGGTGTGCGGGGCCAGCGGCCAGTTCGAGCTGGAGATCCTG
JAG1-CO05    CTGTGCGCCCTCAGGGCCAAGGTCTGCGGCGCCTCCGGTCAGTTCGAACTCGAGATCCTG
JAG1-CO23    CTGTGTGCCCTGAGGGCCAAGGTGTGCGGCGCCTCCGGACAATTCGAGCTGGAGATTCTC
JAG1-CO24    CTGTGCGCCCTGAGGGCCAAGGTGTGCGGCGCCTCCGGCCAGTTCGAGCTGGAGATTCTG
JAG1-CO21    CTGTGTGCCCTGCGAGCCAAAGTGTGCGGGGCCTCCGGCCAGTTCGAGCTGGAGATCCTG
JAG1-CO22    CTGTGCGCCCTGCGCGCCAAGGTGTGCGGGGCAAGCGGCCAGTTCGAGCTCGAAATACTC
JAG1-CO15    CTGTGCGCCCTTAGGGCCAAGGTGTGTGGGGCCTCCGGCCAGTTCGAGCTGGAGATCCTG
JAG1-CO16    CTCTGCGCCCTCAGGGCCAAGGTGTGCGGCGCCTCCGGCCAATTCGAGCTCGAGATCCTG
JAG1-CO07    CTCTGTGCCCTGCGCGCCAAAGTGTGCGGGGCCTCAGGCCAGTTCGAGCTCGAGATCCTG
JAG1-CO02    CTCTGCGCCCTGAGGGCCAAGGTGTGTGGCGCCTCCGGGCAGTTCGAGCTGGAAATCCTG
JAG1-CO20    CTGTGCGCCCTGCGGGCAAAGGTGTGCGGGGCCAGCGGCCAGTTCGAGCTGGAAATCCTG
JAG1-CO13    CTGTGCGCCCTGCGGGCCAAGGTTTGTGGGGCCAGTGGGCAATTCGAGCTGGAGATCCTG
JAG1-CO19    CTCTGTGCCCTCCGGGCCAAGGTGTGCGGCGCCAGCGGACAGTTTGAGCTGGAGATCCTG
JAG1-CO08    CTGTGCGCGCTTAGGGCCAAGGTCTGCGGCGCCAGCGGCCAGTTCGAGCTGGAGATCCTG
JAG1-CO03    CTTTGCGCCCTGAGGGCCAAAGTCTGCGGCGCCTCCGGCCAATTCGAGCTGGAGATCCTC
JAG1-CO14    CTCTGCGCGCTGAGAGCCAAGGTGTGTGGCGCCAGCGGCCAGTTCGAGCTTGAGATCCTG
JAG1-CO09    CTGTGCGCCCTGAGAGCCAAGGTGTGTGGAGCCAGCGGGCAGTTCGAGCTCGAGATCCTC
JAG1-CO10    CTGTGCGCCCTGAGAGCCAAAGTGTGCGGCGCCAGCGGGCAGTTCGAGCTGGAGATACTG
JAG1-CO06    CTGTGTGCCCTGAGGGCCAAGGTGTGCGGCGCCAGCGGGCAGTTCGAGCTGGAGATACTG
             ** **.** **   * ** **.** **.** **     ** **.**.**..* **.** **
```

FIG. 13

```
JAG1-WT        TCCATGCAGAACGTGAACGGGGAGCTGCAGAACGGGAACTGCTGCGGCGGCGCCCGGAAC
JAG1-CO01      AGCATGCAGAACGTGAACGGCGAGCTCCAGAATGGGAATTGTTGCGGCGGCGCCAGGAAC
JAG1-CO17      TCCATGCAGAACGTGAACGGGGAGCTGCAGAATGGCAATTGCTGTGGCGGCGCGCGGAAC
JAG1-CO11      AGCATGCAGAACGTGAACGGCGAGCTGCAGAATGGCAATTGTTGCGGCGGCGCCAGGAAC
JAG1-CO12      AGCATGCAAAACGTGAACGGCGAACTCCAGAACGGCAATTGCTGCGGCGGCGCCAGAAAC
JAG1-CO25      AGCATGCAGAACGTGAACGGGGAGCTGCAGAATGGGAACTGCTGCGGCGGCGCCAGGAAT
JAG1-CO04      TCCATGCAGAACGTGAACGGCGAGCTCCAGAACGGGAACTGCTGCGGGGGCGCAAGGAAC
JAG1-CO18      AGCATGCAGAACGTGAACGGGGAACTACAGAACGGCAACTGCTGCGGCGGCGCCCGCAAT
JAG1-CO05      AGCATGCAGAACGTGAACGGTGAACTGCAGAACGGCAACTGCTGCGGCGGCGCCAGGAAT
JAG1-CO23      TCGATGCAGAACGTGAACGGCGAACTGCAGAACGGAAATTGCTGTGGCGGCGCCAGGAAT
JAG1-CO24      AGCATGCAGAACGTGAACGGCGAACTGCAGAACGGAAACTGCTGCGGTGGGGCCAGGAAC
JAG1-CO21      AGCATGCAGAACGTGAACGGCGAGCTCCAGAACGGCAACTGCTGCGGCGGCGCCCGCAAC
JAG1-CO22      AGCATGCAAAACGTCAACGGCGAGCTGCAGAACGGCAACTGTTGCGGTGGCGCCAGGAAC
JAG1-CO15      AGCATGCAGAACGTGAACGGTGAGCTGCAGAATGGTAACTGTTGCGGCGGAGCCAGGAAC
JAG1-CO16      TCAATGCAGAACGTGAACGGCGAGCTGCAGAACGGCAACTGCTGCGGCGGCGCCAGGAAC
JAG1-CO07      TCCATGCAAAACGTGAACGGCGAACTGCAGAACGGAAATTGCTGCGGTGGCGCCCGTAAC
JAG1-CO02      AGCATGCAGAACGTCAACGGCGAGCTGCAGAACGGCAACTGCTGCGGCGGAGCGCGGAAC
JAG1-CO20      AGCATGCAGAACGTGAACGGCGAGCTGCAAAATGGTAATTGCTGCGGGGGCGCCAGGAAC
JAG1-CO13      AGCATGCAAAACGTGAACGGGGAGCTTCAGAATGGTAACTGCTGCGGCGGGGCCCGGAAT
JAG1-CO19      TCCATGCAGAACGTGAACGGTGAGCTCCAGAACGGGAACTGCTGCGGCGGCGCCAGGAAC
JAG1-CO08      AGCATGCAGAACGTGAACGGCGAGCTGCAGAACGGCAACTGCTGCGGCGGGGCCAGGAAC
JAG1-CO03      AGCATGCAGAACGTGAACGGCGAGCTGCAAAACGGGAACTGCTGCGGGGGAGCCCGCAAC
JAG1-CO14      TCCATGCAAAACGTCAACGGCGAGCTCCAGAACGGAAACTGTTGCGGCGGCGCCCGCAAC
JAG1-CO09      TCCATGCAGAACGTGAACGGCGAGCTGCAGAACGGCAACTGCTGCGGAGGCGCCAGGAAT
JAG1-CO10      AGCATGCAGAACGTGAACGGCGAGCTGCAGAACGGCAACTGTTGTGGGGGCGCGCGGAAC
JAG1-CO06      TCCATGCAAAACGTGAACGGCGAACTGCAGAATGGGAATTGCTGCGGTGGCGCCAGGAAC
                 *****.***** ***** **.** **.**.** **.**.**.** ** **  * **.

JAG1-WT        CCGGGAGACCGCAAGTGCACCCGCGACGAGTGTGACACATACTTCAAAGTGTGCCTCAAG
JAG1-CO01      CCCGGTGACAGGAAATGCACCCGCGACGAGTGCGACACCTACTTCAAAGTGTGCCTCAAG
JAG1-CO17      CCCGGCGACAGGAAGTGCACACGGGACGAATGCGACACGTACTTCAAGGTGTGCCTCAAG
JAG1-CO11      CCCGGCGACCGGAAGTGCACCCGGGACGAATGCGACACCTACTTCAAGGTGTGCCTCAAG
JAG1-CO12      CCCGGGGATCGAAAGTGCACCCGGGACGAGTGCGACACCTACTTCAAAGTGTGTCTCAAA
JAG1-CO25      CCCGGGGACAGGAAGTGCACCCGAGATGAGTGCGACACCTATTTCAAGGTGTGCCTGAAG
JAG1-CO04      CCCGGTGACAGGAAGTGCACCCGCGACGAGTGCGACACGTACTTTAAGGTGTGCCTGAAA
JAG1-CO18      CCGGGAGACAGGAAGTGTACCAGGGATGAGTGCGACACCTACTTTAAAGTGTGCCTGAAG
JAG1-CO05      CCCGGCGACCGAAAGTGCACCAGGGACGAGTGCGACACCTACTTTAAGGTGTGCCTAAAG
JAG1-CO23      CCCGGCGATAGAAAGTGCACCAGGGACGAGTGTGACACGTACTTCAAGGTGTGCCTGAAG
JAG1-CO24      CCCGGCGACCGGAAGTGCACCAGGGATGAATGCGACACCTACTTCAAGGTCTGCCTCAAG
JAG1-CO21      CCCGGCGACAGGAAGTGCACTCGGGACGAGTGCGACACCTATTTCAAGGTCTGCCTGAAG
JAG1-CO22      CCCGGGGATCGCAAGTGCACCAGGGACGAGTGTGATACCTACTTCAAAGTGTGTCTGAAG
JAG1-CO15      CCGGGCGATAGGAAATGTACCAGGGACGAGTGCGACACCTACTTTAAGGTGTGCCTCAAA
JAG1-CO16      CCCGGCGACAGGAAGTGCACCAGGGACGAATGTGACACCTACTTCAAGGTGTGCCTGAAG
JAG1-CO07      CCCGGCGACCGCAAGTGCACCAGGGACGAGTGCGACACCTACTTCAAGGTGTGTCTGAAG
JAG1-CO02      CCCGGGGACAGGAAGTGCACCAGGGACGAGTGTGACACGTACTTCAAAGTCTGCCTCAAG
JAG1-CO20      CCGGGCGACAGGAAGTGCACCAGGGACGAGTGCGACACCTATTTCAAGGTGTGCCTGAAG
JAG1-CO13      CCCGGCGACCGGAAGTGTACGAGGGATGAGTGTGACACCTACTTTAAGGTGTGCCTGAAG
JAG1-CO19      CCCGGCGATCGCAAGTGTACCAGGGACGAATGTGACACCTACTTTAAGGTGTGCCTGAAA
JAG1-CO08      CCCGGAGACCGCAAATGCACCCGGGACGAGTGCGACACCTATTTTAAAGTGTGCCTGAAG
JAG1-CO03      CCCGGCGACCGGAAGTGCACCAGGGACGAGTGCGACACCTACTTCAAGGTGTGCCTCAAG
JAG1-CO14      CCCGGCGACAGGAAGTGCACCCGCGACGAGTGCGACACCTACTTCAAGGTGTGCCTGAAG
JAG1-CO09      CCCGGCGATCGGAAGTGCACCAGGGACGAGTGCGACACCTATTTCAAGGTGTGCCTCAAG
JAG1-CO10      CCCGGGGACAGGAAGTGCACCCGGGACGAGTGCGACACCTACTTCAAGGTGTGCCTCAAG
JAG1-CO06      CCTGGGGACCGCAAGTGTACCCGGGACGAGTGCGACACCTACTTCAAGGTGTGTCTCAAG
               ** ** **. * **.**.**  * **.**.**.**.** **.**.**.** **.** **.
```

FIG. 13 (cont)

```
JAG1-WT          GAGTATCAGTCCCGCGTCACGGCCGGGGGCCCTGCAGCTTCGGCTCAGGGTCCACGCCT
JAG1-CO01        GAGTACCAGAGCAGGGTGACCGCCGGCGGGCCCTGCAGCTTCGGAGCGGCTCCACGCCC
JAG1-CO17        GAGTACCAGTCCAGGGTCACCGCCGGCGGGCCCTGCAGCTTCGGAAGCGGCTCCACCCCC
JAG1-CO11        GAGTACCAGAGCCGCGTGACCGCCGGCGGACCCTGCAGCTTCGGCAGCGGCAGCACCCCC
JAG1-CO12        GAATACCAGAGCAGGGTGACCGCCGGCGGGCCCTGCAGCTTCGGCAGCGGCAGCACCCCC
JAG1-CO25        GAGTACCAGAGCCGTGTGACGGCCGGCGGCCCCTGCAGCTTTGGCAGCGGCAGCACCCCC
JAG1-CO04        GAGTACCAGAGCAGGGTGACTGCCGGCGGACCCTGCTCGTTTGGAAGCGGCAGCACTCCT
JAG1-CO18        GAGTACCAGAGCAGGGTGACCGCCGGCGGCCCCTGTAGCTTCGGCAGCGGGAGCACCCCG
JAG1-CO05        GAGTACCAGAGCCGGGTGACGGCCGGCGGCCCCTGTTCCTTCGGCAGCGGCAGCACGCCC
JAG1-CO23        GAGTACCAGAGCCGCGTGACCGCCGGCGGGCCCTGCTCCTTCGGGTCAGGCAGCACCCCC
JAG1-CO24        GAGTACCAGAGCAGGGTGACCGCCGGGGGCCCGTGTAGCTTCGGCTCCGGCAGCACCCCC
JAG1-CO21        GAGTACCAAAGCCGTGTGACCGCCGGCGGGCCGTGCAGCTTCGGAAGCGGCTCCACCCCG
JAG1-CO22        GAGTACCAGAGCCGGGTGACCGCCGGGGGCCCCTGTTCCTTCGGCAGCGGGAGCACCCCC
JAG1-CO15        GAGTACCAGAGCCGGGTCACCGCCGGCGGCCCCTGCTCGTTCGGCAGCGGTAGCACCCCC
JAG1-CO16        GAGTACCAGAGCCGGGTGACCGCTGGCGGCCCATGTAGCTTCGGGAGCGGCAGCACCCCG
JAG1-CO07        GAGTACCAGAGCAGGGTCACCGCCGGCGGCCCCTGCAGCTTTGGCTCCGGCAGCACCCCC
JAG1-CO02        GAGTACCAGAGCCGGGTGACCGCCGGGGGCCCATGCTCCTTCGGCAGCGGCAGCACCCCC
JAG1-CO20        GAATACCAGAGCCGCGTCACGGCCGGGGGCCCGTGCTCCTTCGGCAGTGGCTCCACCCCC
JAG1-CO13        GAGTACCAGAGCAGGGTTACGGCAGGCGGCCCCTGCAGCTTTGGCAGCGGCTCCACCCCG
JAG1-CO19        GAGTACCAGAGCCGCGTCACCGCCGGCGGGCCCTGTTCCTTTGGCTCCGGCAGCACTCCC
JAG1-CO08        GAGTACCAGAGCAGGGTGACCGCCGGCGGCCCCTGCAGCTTCGGCAGCGGCAGCACCCCC
JAG1-CO03        GAGTATCAGTCAAGGGTGACCGCCGGAGGCCCCTGTAGCTTCGGCTCCGGGTCGACCCCC
JAG1-CO14        GAGTACCAGTCCCGCGTGACCGCTGGCGGACCGTGCAGCTTCGGCTCAGGCAGCACCCCC
JAG1-CO09        GAGTACCAAAGCAGGGTGACCGCCGGCGGCCCCTGCTCCTTCGGCAGCGGCAGCACCCCC
JAG1-CO10        GAATACCAAAGCCGTGTGACAGCTGGGGGCCCCTGCAGCTTCGGGTCCGGATCCACCCCC
JAG1-CO06        GAATATCAGTCCCGCGTGACCGCCGGGGGCCCCTGCAGCTTCGGCTCAGGCAGCACCCCA
                 **.**.**.    * ** ** ** ** ** ** **.   **.**    **    ** **

JAG1-WT          GTCATCGGGGGCAACACCTTCAACCTCAAGGCCAGCCGCGGCAACGACCGCAACCGCATC
JAG1-CO01        GTGATCGGCGGGAACACCTTCAACCTGAAGGCCAGCAGGGGCAACGATCGGAACCGGATC
JAG1-CO17        GTGATCGGCGGCAACACATTCAACCTGAAAGCGTCGAGGGGGAATGACCGCAACAGGATC
JAG1-CO11        GTGATCGGGGGCAACACCTTCAACCTGAAGGCATCCCGCGGGAACGACAGGAACAGGATC
JAG1-CO12        GTGATCGGCGGGAACACCTTCAACCTGAAGGCCAGCCGCGGCAACGACAGGAATCGGATC
JAG1-CO25        GTGATCGGCGGAAACACATTCAACCTGAAGGCCAGCAGGGGCAACGACAGGAACAGGATC
JAG1-CO04        GTGATCGGTGGCAACACCTTCAATCTGAAGGCCTCCAGGGGGAACGATAGGAACAGGATC
JAG1-CO18        GTGATCGGCGGCAACACCTTCAACCTCAAGGCCTCCAGGGGCAACGACAGGAACCGGATC
JAG1-CO05        GTGATCGGCGGCAACACCTTCAACCTCAAGGCCTCGCGCGGCAACGATCGGAACAGGATC
JAG1-CO23        GTGATCGGCGGGAACACCTTCAACCTCAAGGCCTCCAGGGGCAACGACAGGAATAGGATC
JAG1-CO24        GTGATAGGCGGCAACACGTTCAACCTTAAAGCCTCCAGGGGCAACGACCGCAACAGGATC
JAG1-CO21        GTCATCGGGGGGAACACCTTTAACCTGAAGGCCAGCCGGGGTAACGACAGGAACCGAATC
JAG1-CO22        GTCATCGGCGGGAATACGTTTAACCTGAAGGCCTCCAGGGGCAACGATAGGAACCGGATC
JAG1-CO15        GTGATCGGCGGCAACACATTCAACCTGAAAGCCAGCAGGGGGAACGACAGGAACCGGATC
JAG1-CO16        GTGATCGGGGGTAACACCTTTAACCTCAAGGCTTCCCGCGGCAACGACAGGAACCGGATC
JAG1-CO07        GTGATCGGCGGCAACACCTTCAACCTGAAGGCTAGCCGCGGCAACGACAGGAACAGGATC
JAG1-CO02        GTCATCGGAGGCAACACCTTTAATCTGAAGGCCAGCAGGGGGAACGACAGGAATAGGATC
JAG1-CO20        GTGATCGGCGGCAACACCTTTAACCTGAAGGCCTCCCGGGGTAACGACAGGAACAGGATC
JAG1-CO13        GTGATCGGCGGCAACACATTCAACCTGAAGGCCAGCCGCGGGAACGATCGTAACAGGATC
JAG1-CO19        GTGATCGGCGGCAACACCTTCAACCTCAAGGCGAGCAGGGGGAACGACAGGAACAGGATC
JAG1-CO08        GTGATCGGCGGGAATACCTTCAACCTGAAGGCCAGCCGCGGCAACGACAGGAACCGAATC
JAG1-CO03        GTGATAGGCGGAAACACCTTCAACCTGAAGGCCAGCAGGGGGAACGACAGGAATAGGATC
JAG1-CO14        GTGATCGGGGGCAATACCTTCAATCTCAAGGCCAGCCGAGGAAACGACAGGAACAGGATC
JAG1-CO09        GTGATAGGGGGCAACACGTTCAACCTCAAGGCCAGCAGGGGCAACGACAGGAACCGCATC
JAG1-CO10        GTCATCGGCGGCAACACCTTCAACCTCAAGGCCAGCAGGGGCAACGACAGGAACCGAATC
JAG1-CO06        GTCATCGGGGGCAACACCTTCAACCTGAAGGCCAGCCGTGGCAACGACAGGAACAGGATA
                 ** ** ** ** **.** **.**.** **.**     * ** **.**. * **. * **
```

FIG. 13 (cont)

```
JAG1-WT      GTGCTGCCTTTCAGTTTCGCCTGGCCGAGGTCCTATACGTTGCTTGTGGAGGCGTGGGAT
JAG1-CO01    GTGCTGCCGTTCTCCTTCGCCTGGCCGCGAAGCTACACCCTGCTGGTGGAAGCGTGGGAC
JAG1-CO17    GTGCTGCCGTTTTCCTTCGCCTGGCCCCGCAGCTACACGCTGCTGGTGGAGGCATGGGAC
JAG1-CO11    GTGCTGCCGTTCAGCTTCGCCTGGCCGCGATCCTACACGCTGCTGGTTGAGGCCTGGGAC
JAG1-CO12    GTGTTGCCGTTCAGCTTCGCCTGGCCCCGTTCCTACACCCTGCTGGTGGAGGCCTGGGAC
JAG1-CO25    GTGCTGCCCTTCAGCTTCGCCTGGCCCAGGTCCTACACCCTGCTGGTGGAGGCCTGGGAT
JAG1-CO04    GTGCTGCCATTCAGCTTTGCCTGGCCCCGGTCATACACCCTGCTGGTGGAGGCCTGGGAC
JAG1-CO18    GTGCTGCCCTTCAGCTTCGCCTGGCCCCGCAGCTACACGCTGCTGGTGGAGGCCTGGGAC
JAG1-CO05    GTGCTGCCGTTTTCCTTTGCCTGGCCCAGGTCGTACACCCTGCTGGTGGAGGCCTGGGAC
JAG1-CO23    GTGCTCCCCTTCAGCTTCGCCTGGCCCAGGTCCTACACCCTGCTGGTAGAGGCCTGGGAC
JAG1-CO24    GTGCTGCCCTTCTCCTTCGCGTGGCCCCGCAGCTACACCCTGCTGGTGGAGGCGTGGGAT
JAG1-CO21    GTACTGCCCTTCAGCTTCGCCTGGCCCCGGAGCTACACCCTGCTGGTCGAGGCATGGGAC
JAG1-CO22    GTGCTCCCTTTCAGCTTCGCCTGGCCCAGGTCCTACACCCTGCTGGTGGAGGCCTGGGAC
JAG1-CO15    GTGCTCCCCTTCTCCTTCGCCTGGCCCAGGTCGTACACCCTGCTCGTCGAGGCCTGGGAC
JAG1-CO16    GTGCTGCCCTTCTCCTTCGCCTGGCCCAGGAGCTATACCCTGCTGGTCGAGGCCTGGGAC
JAG1-CO07    GTGCTTCCATTTAGCTTCGCCTGGCCCAGGAGCTACACCCTGCTTGTGGAGGCCTGGGAC
JAG1-CO02    GTCCTGCCCTTTAGCTTCGCCTGGCCCAGGTCCTACACCCTGCTGGTCGAGGCCTGGGAC
JAG1-CO20    GTGCTGCCCTTCTCCTTCGCCTGGCCGAGGTCCTACACCCTCCTGGTAGAGGCCTGGGAC
JAG1-CO13    GTGCTCCCCTTTAGCTTCGCCTGGCCCCGCAGCTACACGCTGCTGGTGGAGGCCTGGGAC
JAG1-CO19    GTGCTGCCCTTCAGCTTCGCGTGGCCCCGGTCCTACACCCTGCTCGTGGAGGCTTGGGAC
JAG1-CO08    GTGCTGCCCTTTAGCTTCGCCTGGCCTCGGAGCTACACCCTGCTGGTGGAAGCCTGGGAC
JAG1-CO03    GTGCTCCCCTTCTCGTTCGCCTGGCCCAGGAGCTACACCCTCCTCGTGGAGGCCTGGGAC
JAG1-CO14    GTGCTCCCCTTTAGCTTTGCCTGGCCTCGTAGCTACACCCTGCTGGTGGAGGCCTGGGAC
JAG1-CO09    GTGCTGCCCTTCAGCTTTGCGTGGCCCCGTTCCTACACCCTGCTGGTCGAGGCCTGGGAC
JAG1-CO10    GTGCTGCCCTTTTCGTTTGCCTGGCCCCGCAGCTACACCCTCCTAGTGGAGGCCTGGGAC
JAG1-CO06    GTGCTGCCCTTCTCCTTCGCGTGGCCCAGGTCCTACACCCTGCTGGTGGAGGCGTGGGAT
             ** .* ** **.   **.** *****  *    **.** .* ** ** **.** *****.

JAG1-WT      TCCAGTAATGACACCGTTCAACCTGACAGTATTATTGAAAAGGCTTCTCACTCGGGCATG
JAG1-CO01    AGCAGCAACGACACCGTGCAGCCCGACAGCATCATCGAGAAGGCCTCACACTCCGGTATG
JAG1-CO17    AGCTCCAACGATACCGTGCAGCCCGACAGCATCATCGAGAAGGCCTCCCACAGCGGCATG
JAG1-CO11    AGCAGCAATGACACGGTGCAACCCGACAGCATTATCGAGAAGGCCAGCCACTCCGGCATG
JAG1-CO12    AGCAGCAACGATACCGTGCAGCCAGACAGCATAATCGAGAAGGCCAGCCACTCCGGTATG
JAG1-CO25    AGCAGCAATGACACCGTGCAGCCCGACTCCATCATCGAGAAGGCCAGTCACTCTGGAATG
JAG1-CO04    TCCAGCAACGACACCGTGCAGCCCGACTCCATCATAGAGAAGGCGAGCCACAGCGGCATG
JAG1-CO18    AGCTCTAATGACACGGTGCAGCCTGACTCAATTATAGAGAAGGCCAGCCACAGCGGCATG
JAG1-CO05    AGCTCCAATGACACCGTGCAGCCAGACTCCATAATCGAGAAGGCCAGCCACAGCGGGATG
JAG1-CO23    TCCAGCAACGACACCGTGCAGCCCGATAGCATCATCGAGAAGGCTAGCCACAGCGGAATG
JAG1-CO24    AGCAGCAACGACACCGTCCAGCCCGATTCAATCATCGAAAAGGCCAGCCACAGCGGCATG
JAG1-CO21    TCCAGCAACGATACCGTGCAGCCCGACAGCATCATCGAGAAAGCCAGCCACAGCGGGATG
JAG1-CO22    TCCAGCAATGACACTGTCCAGCCTGACAGTATCATAGAGAAAGCCTCCCACTCCGGCATG
JAG1-CO15    AGCAGCAACGACACCGTGCAGCCCGACAGCATCATCGAAAAGGCCAGCCACAGCGGAATG
JAG1-CO16    AGCTCCAACGACACCGTGCAACCCGACAGCATCATCGAGAAGGCCTCCCACTCCGGCATG
JAG1-CO07    AGCTCCAACGACACCGTGCAGCCCGACAGCATCATCGAGAAGGCCAGCCACTCCGGCATG
JAG1-CO02    AGCTCCAACGACACCGTCCAGCCCGACAGTATCATCGAGAAGGCGTCCCACTCCGGCATG
JAG1-CO20    AGCAGCAATGATACGGTGCAGCCCGACTCCATCATAGAAAAGGCCAGCCACTCCGGGATG
JAG1-CO13    AGCAGCAACGACACCGTCCAGCCCGATAGCATTATCGAGAAGGCCTCCCACAGCGGTATG
JAG1-CO19    TCCTCAAACGACACGGTCCAGCCGGATAGCATCATTGAGAAGGCGAGCCACTCCGGCATG
JAG1-CO08    TCCTCCAACGACACCGTGCAACCCGACTCCATTATCGAGAAGGCCTCCCACAGCGGCATG
JAG1-CO03    AGCAGCAACGATACGGTGCAGCCCGACTCCATCATCGAGAAGGCCAGCCACTCCGGCATG
JAG1-CO14    TCAAGCAATGACACGGTTCAGCCCGACAGCATCATCGAAAAGGCCTCTCACAGCGGAATG
JAG1-CO09    AGCTCCAACGATACCGTGCAGCCCGACTCCATCATTGAGAAGGCCAGCCACAGCGGCATG
JAG1-CO10    AGCAGCAACGACACCGTGCAGCCCGACTCCATCATCGAGAAGGCATCCCACAGCGGGATG
JAG1-CO06    AGCTCGAATGATACCGTCCAGCCCGACTCCATCATCGAGAAAGCCTCCCACTCCGGTATG
                   **.**.** ** **.** **.   ** ** **.**.**    ***   ** ***
```

FIG. 13 (cont)

```
JAG1-WT      ATCAACCCCAGCCGGCAGTGGCAGACGCTGAAGCAGAACACGGGCGTTGCCCACTTTGAG
JAG1-CO01    ATCAACCCCAGCAGGCAGTGGCAGACCCTGAAGCAGAACACCGGAGTGGCCCACTTCGAA
JAG1-CO17    ATCAACCCGAGCAGGCAGTGGCAGACCCTCAAGCAGAACACCGGCGTGGCCCACTTCGAG
JAG1-CO11    ATCAACCCCTCCCGGCAGTGGCAGACCCTGAAGCAGAACACTGGAGTTGCACACTTCGAG
JAG1-CO12    ATCAACCCCAGCAGGCAGTGGCAGACCCTGAAGCAAAACACCGGCGTGGCCCATTTCGAG
JAG1-CO25    ATCAACCCGAGCAGGCAGTGGCAGACCCTGAAGCAGAACACCGGCGTGGCCCACTTCGAG
JAG1-CO04    ATCAACCCCTCCAGGCAGTGGCAGACCCTCAAGCAGAACACCGGCGTCGCCCACTTCGAA
JAG1-CO18    ATCAACCCCTCAAGACAGTGGCAGACCCTGAAGCAGAACACCGGTGTGGCACACTTCGAG
JAG1-CO05    ATTAATCCAAGCAGGCAGTGGCAAACCCTGAAGCAGAACACCGGAGTGGCCCATTTCGAG
JAG1-CO23    ATCAACCCCAGCCGCCAGTGGCAGACCCTGAAACAGAACACCGGCGTAGCCCACTTTGAG
JAG1-CO24    ATCAACCCCTCCAGGCAGTGGCAGACCCTGAAGCAAAACACCGGCGTGGCCCACTTCGAG
JAG1-CO21    ATTAATCCCAGCAGACAGTGGCAGACCCTGAAGCAGAACACCGGCGTGGCCCACTTCGAG
JAG1-CO22    ATCAACCCCAGTCGCCAGTGGCAGACCCTGAAGCAGAACACCGGCGTGGCCCACTTCGAG
JAG1-CO15    ATCAACCCCAGCCGACAGTGGCAGACCCTGAAGCAGAACACCGGCGTGGCCCACTTCGAG
JAG1-CO16    ATCAACCCCAGCAGGCAGTGGCAGACCCTCAAGCAAAACACCGGGGTCGCGCACTTCGAG
JAG1-CO07    ATCAACCCCAGCCGGCAGTGGCAGACCCTGAAGCAGAACACCGGCGTCGCGCACTTCGAG
JAG1-CO02    ATCAATCCCAGCAGGCAGTGGCAGACGCTGAAGCAGAACACCGGCGTGGCCCACTTCGAG
JAG1-CO20    ATCAATCCGAGCAGGCAGTGGCAAACCCTCAAGCAGAACACCGGTGTGGCCCACTTTGAG
JAG1-CO13    ATCAACCCGAGCCGGCAGTGGCAGACCCTGAAGCAGAACACCGGCGTGGCCCACTTCGAG
JAG1-CO19    ATCAACCCCAGCCGGCAGTGGCAGACCCTCAAGCAGAACACCGGCGTGGCCCACTTCGAG
JAG1-CO08    ATAAACCCCAGCCGGCAGTGGCAGACACTGAAGCAAAACACCGGGGTCGCACATTTCGAG
JAG1-CO03    ATCAACCCCAGCCGCCAGTGGCAGACCCTGAAGCAAAACACGGGCGTGGCACACTTCGAG
JAG1-CO14    ATCAACCCCAGCAGGCAGTGGCAGACCCTCAAGCAGAACACGGGCGTGGCCCACTTCGAG
JAG1-CO09    ATCAACCCCAGCAGGCAGTGGCAAACCCTGAAGCAGAACACCGGAGTGGCCCATTTCGAA
JAG1-CO10    ATCAATCCCTCCCGCCAGTGGCAGACGCTGAAGCAGAACACCGGCGTGGCCCACTTCGAA
JAG1-CO06    ATCAATCCAAGCAGGCAGTGGCAGACCCTGAAGCAGAACACGGGCGTGGCCCACTTTGAG
             ** **.**      * ********.** ** **.**.***** ** ** ** **.**.**.

JAG1-WT      TATCAGATCCGCGTGACCTGTGATGACTACTACTATGGCTTTGGCTGCAATAAGTTCTGC
JAG1-CO01    TACCAGATCAGGGTGACATGCGACGACTACTACTACGGCTTCGGGTGCAACAAGTTCTGC
JAG1-CO17    TATCAGATCCGGGTGACCTGCGACGACTATTACTACGGTTTCGGCTGCAACAAGTTTTGT
JAG1-CO11    TACCAAATCAGGGTCACGTGCGACGACTACTATTACGGGTTCGGCTGTAACAAGTTCTGC
JAG1-CO12    TACCAGATCAGGGTCACGTGCGACGACTATTACTACGGGTTCGGGTGCAACAAGTTCTGC
JAG1-CO25    TACCAGATCAGGGTGACCTGTGACGATTACTACTACGGTTTTGGCTGCAACAAGTTCTGT
JAG1-CO04    TACCAGATCAGGGTCACGTGCGACGACTACTACTACGGCTTTGGCTGCAATAAGTTCTGC
JAG1-CO18    TATCAGATCAGGGTGACATGCGATGACTACTACTACGGGTTTGGCTGTAATAAGTTCTGC
JAG1-CO05    TACCAGATCAGGGTGACCTGCGACGACTACTACTACGGCTTCGGATGCAACAAGTTCTGC
JAG1-CO23    TACCAGATCAGGGTGACCTGCGACGACTATTACTATGGCTTCGGTTGCAACAAGTTCTGC
JAG1-CO24    TACCAAATCAGGGTTACCTGCGACGACTACTACTATGGGTTCGGCTGCAATAAGTTCTGT
JAG1-CO21    TACCAAATCCGGGTGACCTGCGACGATTATTACTACGGGTTTGGCTGTAATAAATTCTGC
JAG1-CO22    TACCAGATCCGGGTGACCTGCGACGACTATTACTACGGCTTCGGATGCAATAAGTTCTGT
JAG1-CO15    TACCAGATCCGGGTGACCTGCGATGACTATTACTATGGCTTCGGCTGTAACAAGTTCTGT
JAG1-CO16    TACCAGATCAGGGTCACCTGCGACGACTACTACTACGGCTTCGGCTGCAATAAGTTTTGC
JAG1-CO07    TACCAGATCAGGGTGACATGTGACGACTATTACTATGGCTTTGGATGTAACAAGTTCTGC
JAG1-CO02    TATCAGATCCGGGTGACGTGCGACGACTACTACTACGGGTTCGGCTGCAACAAGTTCTGT
JAG1-CO20    TACCAGATCAGGGTCACCTGCGACGACTACTACTACGGCTTCGGCTGCAACAAGTTTTGC
JAG1-CO13    TACCAGATCCGGGTGACCTGCGACGACTACTATTACGGTTTCGGCTGCAACAAGTTTTGC
JAG1-CO19    TATCAGATCCGCGTGACCTGCGATGATTACTACTACGGCTTTGGATGCAACAAGTTCTGC
JAG1-CO08    TACCAGATCAGGGTGACGTGTGACGACTACTACTACGGGTTCGGATGCAACAAGTTCTGC
JAG1-CO03    TACCAGATAAGGGTCACTTGCGACGACTACTACTACGGGTTCGGGTGCAACAAGTTTTGC
JAG1-CO14    TACCAGATCCGTGTGACCTGCGATGACTACTATTACGGTTTCGGGTGTAATAAGTTCTGC
JAG1-CO09    TACCAGATCAGGGTGACCTGCGATGACTACTATTATGGTTTTGGGTGCAACAAATTCTGC
JAG1-CO10    TACCAAATCAGGGTGACGTGCGATGACTACTATTACGGCTTCGGGTGCAACAAGTTCTGC
JAG1-CO06    TACCAGATCAGGGTCACCTGCGACGACTACTACTACGGCTTCGGCTGTAATAAATTTTGC
             **.**.**  * ** ** **.**.**.**.**.**.** **.** **.**.**.**.**.
```

FIG. 13 (cont)

```
JAG1-WT       CGCCCCAGAGATGACTTCTTTGGACACTATGCCTGTGACCAGAATGGCAACAAAACTTGC
JAG1-CO01     AGGCCCCGCGACGACTTCTTCGGACACTACGCCTGTGACCAGAACGGGAACAAGACGTGT
JAG1-CO17     AGGCCCCGAGACGACTTCTTCGGCCACTACGCCTGCGATCAGAACGGGAATAAAACCTGT
JAG1-CO11     AGGCCCCGTGATGACTTCTTTGGACACTACGCCTGCGACCAGAACGGAAACAAGACCTGC
JAG1-CO12     AGGCCCCGGGATGACTTCTTTGGACACTACGCCTGTGACCAGAACGGAAACAAAACTTGC
JAG1-CO25     AGGCCCCGCGACGACTTCTTTGGTCATTACGCCTGCGATCAGAACGGCAATAAGACCTGC
JAG1-CO04     AGGCCCCGGGACGACTTCTTCGGGCACTACGCCTGCGACCAGAACGGGAACAAAACCTGT
JAG1-CO18     AGGCCCCGAGACGATTTCTTCGGGCACTATGCCTGCGACCAAAATGGCAACAAGACCTGC
JAG1-CO05     AGGCCCCGGGACGACTTCTTCGGCCATTACGCCTGCGACCAGAACGGCAACAAGACCTGC
JAG1-CO23     CGGCCTCGCGACGACTTCTTCGGACACTACGCCTGTGATCAGAACGGGAACAAGACCTGT
JAG1-CO24     CGGCCGCGGGACGACTTTTTCGGGCATTATGCCTGCGACCAGAATGGCAATAAGACCTGC
JAG1-CO21     CGGCCCCGGGATGACTTTTTCGGCCATTACGCCTGCGATCAGAACGGTAACAAGACCTGC
JAG1-CO22     AGGCCCCGCGACGATTTCTTCGGCCATTATGCCTGCGACCAGAACGGCAACAAGACCTGC
JAG1-CO15     CGACCCAGGGACGACTTCTTCGGCCACTATGCCTGCGACCAGAACGGTAATAAGACTTGC
JAG1-CO16     CGGCCCAGGGACGATTTCTTCGGACACTACGCCTGTGACCAGAATGGCAATAAGACCTGT
JAG1-CO07     AGGCCCAGAGACGACTTCTTCGGCCACTACGCCTGCGACCAGAACGGAAATAAGACCTGT
JAG1-CO02     AGGCCCCGGGACGATTTCTTCGGCCACTACGCATGCGACCAGAACGGCAACAAGACCTGC
JAG1-CO20     AGGCCGAGGGACGACTTCTTCGGCCACTACGCCTGCGACCAGAATGGCAACAAGACCTGC
JAG1-CO13     CGACCCCGGGACGACTTTTTCGGGCATTACGCCTGCGACCAAAACGGCAACAAAACCTGC
JAG1-CO19     CGGCCCCGCGACGACTTCTTCGGACACTATGCCTGTGACCAGAACGGGAACAAGACCTGC
JAG1-CO08     AGGCCCAGGGACGACTTCTTCGGCCACTACGCCTGTGACCAGAACGGCAATAAGACCTGC
JAG1-CO03     AGGCCCCGGGACGACTTCTTCGGACACTATGCCTGCGACCAGAACGGCAACAAGACCTGT
JAG1-CO14     AGGCCCAGGGATGACTTTTTTGGCCACTACGCCTGCGACCAGAATGGCAACAAGACCTGC
JAG1-CO09     CGGCCCCGAGACGACTTCTTCGGTCACTATGCCTGCGACCAGAACGGCAACAAGACCTGT
JAG1-CO10     AGGCCGAGGGATGACTTCTTCGGCCACTATGCCTGCGACCAGAACGGAAACAAAACCTGC
JAG1-CO06     CGGCCTCGGGACGACTTCTTCGGCCACTACGCCTGCGACCAGAACGGCAATAAGACGTGT
               * **  * **.**.**.**.** **.**.** **.**.**.**.** **.**.** **.

JAG1-WT       ATGGAAGGCTGGATGGGCCCCGAATGTAACAGAGCTATTTGCCGACAAGGCTGCAGTCCT
JAG1-CO01     ATGGAGGGGTGGATGGGGCCCGAATGCAACAGGGCCATCTGTCGGCAGGGTTGCTCCCCC
JAG1-CO17     ATGGAGGGGTGGATGGGCCCCGAGTGCAACAGGGCCATCTGCAGGCAGGGATGCTCCCCC
JAG1-CO11     ATGGAAGGGTGGATGGGCCCCGAGTGCAACAGGGCCATCTGTAGACAAGGCTGCAGCCCC
JAG1-CO12     ATGGAGGGCTGGATGGGCCCGGAGTGCAATAGGGCCATTTGCAGGCAAGGCTGCAGCCCC
JAG1-CO25     ATGGAAGGCTGGATGGGCCCCGAATGCAACAGGGCCATTTGCAGGCAGGGGTGCAGCCCG
JAG1-CO04     ATGGAGGGGTGGATGGGCCCCGAATGCAACCGAGCCATCTGCCGCCAGGGGTGCTCCCCC
JAG1-CO18     ATGGAGGGGTGGATGGGCCCGGAGTGTAACCGAGCCATATGTAGGCAAGGCTGCAGCCCG
JAG1-CO05     ATGGAGGGTTGGATGGGCCCCGAATGCAATAGGGCCATCTGCAGGCAAGGCTGTTCCCCC
JAG1-CO23     ATGGAGGGTTGGATGGGCCCCGAATGCAACAGGGCCATCTGCAGGCAGGGCTGCTCCCCC
JAG1-CO24     ATGGAGGGCTGGATGGGACCCGAGTGCAACCGCGCCATCTGCAGGCAGGGCTGCTCCCCC
JAG1-CO21     ATGGAGGGCTGGATGGGACCGGAGTGTAACAGGGCTATCTGCCGACAGGGTTGTAGCCCC
JAG1-CO22     ATGGAGGGCTGGATGGGGCCCGAGTGCAACAGGGCCATCTGCAGGCAGGGGTGCTCCCCC
JAG1-CO15     ATGGAGGGCTGGATGGGCCCCGAGTGTAACAGGGCCATCTGCAGGCAGGGCTGCTCCCCC
JAG1-CO16     ATGGAAGGGTGGATGGGGCCAGAGTGCAATCGGGCCATCTGCAGGCAAGGCTGCAGCCCC
JAG1-CO07     ATGGAAGGCTGGATGGGGCCCGAGTGCAACCGAGCCATCTGCAGGCAAGGCTGCAGCCCC
JAG1-CO02     ATGGAGGGCTGGATGGGCCCCGAGTGCAACAGGGCTATCTGCCGCCAGGGCTGCTCCCCC
JAG1-CO20     ATGGAAGGCTGGATGGGCCCGGAATGCAATCGCGCCATCTGTAGGCAGGGGTGCAGCCCA
JAG1-CO13     ATGGAGGGCTGGATGGGCCCGGAGTGCAACCGGGCCATCTGCCGGCAGGGGTGTAGCCCC
JAG1-CO19     ATGGAGGGATGGATGGGTCCCGAGTGCAACCGGGCCATCTGCAGGCAGGGCTGTAGCCCC
JAG1-CO08     ATGGAGGGGTGGATGGGCCCGGAGTGCAACAGGGCCATATGCCGGCAGGGCTGCTCCCCA
JAG1-CO03     ATGGAGGGTTGGATGGGCCCCGAATGCAATCGCGCCATTTGCCGGCAGGGGTGCAGCCCT
JAG1-CO14     ATGGAGGGATGGATGGGCCCCGAGTGCAACCGTGCCATCTGTCGGCAGGGCTGCTCGCCC
JAG1-CO09     ATGGAGGGGTGGATGGGCCCTGAGTGCAACCGGGCCATCTGTCGCCAGGGGTGCTCCCCC
JAG1-CO10     ATGGAGGGTTGGATGGGACCCGAGTGCAACAGGGCCATCTGCCGCCAGGGCTGCTCACCA
JAG1-CO06     ATGGAGGGCTGGATGGGCCCGGAGTGTAATAGGGCCATCTGCCGACAGGGGTGCAGCCCC
              *****.** ******** ** **.**.**. * **.** **. * **.** **.   **
```

FIG. 13 (cont)

```
JAG1-WT      AAGCATGGGTCTTGCAAACTCCCAGGTGACTGCAGGTGCCAGTACGGCTGGCAAGGCCTG
JAG1-CO01    AAGCACGGCTCCTGCAAACTGCCCGGCGATTGCCGGTGCCAGTACGGGTGGCAAGGTCTG
JAG1-CO17    AAGCACGGCAGCTGCAAGCTGCCAGGAGACTGCAGGTGTCAGTATGGCTGGCAGGGGCTG
JAG1-CO11    AAACACGGCTCCTGTAAGCTGCCCGGCGACTGCCGGTGCCAGTACGGCTGGCAGGGGCTC
JAG1-CO12    AAGCACGGCTCCTGCAAGCTCCCCGGCGACTGCCGATGCCAATATGGCTGGCAGGGCCTC
JAG1-CO25    AAGCACGGCAGCTGCAAGCTGCCCGGCGACTGCAGGTGTCAGTACGGCTGGCAGGGCCTG
JAG1-CO04    AAGCACGGCTCCTGTAAACTCCCCGGCGATTGCAGGTGTCAGTACGGCTGGCAGGGTCTC
JAG1-CO18    AAGCACGGCTCCTGCAAGCTGCCCGGTGATTGCAGGTGCCAGTACGGCTGGCAAGGCCTC
JAG1-CO05    AAACACGGGAGCTGTAAACTCCCCGGCGACTGCCGATGCCAGTACGGGTGGCAAGGCCTC
JAG1-CO23    AAGCACGGGAGCTGCAAGCTGCCCGGCGACTGCCGGTGCCAGTACGGCTGGCAGGGTCTG
JAG1-CO24    AAGCACGGCAGCTGCAAGCTGCCCGGCGACTGCAGGTGCCAGTACGGGTGGCAGGGCCTC
JAG1-CO21    AAGCACGGAAGCTGCAAGCTGCCCGGCGACTGCCGGTGTCAGTACGGCTGGCAGGGCCTG
JAG1-CO22    AAACACGGGAGCTGCAAACTGCCGGGGGACTGCAGGTGCCAATACGGCTGGCAGGGCCTG
JAG1-CO15    AAACACGGCTCCTGCAAACTGCCCGGCGACTGCCGCTGCCAGTACGGCTGGCAGGGGCTC
JAG1-CO16    AAACACGGCTCGTGTAAGCTGCCCGGCGACTGCAGGTGCCAGTATGGTTGGCAGGGCCTC
JAG1-CO07    AAGCACGGCAGCTGCAAGCTGCCCGGGGACTGCCGGTGCCAGTACGGCTGGCAGGGCTTG
JAG1-CO02    AAGCACGGCAGCTGTAAGCTGCCCGGCGATTGCCGGTGTCAGTACGGGTGGCAGGGACTG
JAG1-CO20    AAGCATGGGAGCTGCAAGCTGCCCGGGGACTGCAGGTGTCAGTACGGATGGCAGGGGCTG
JAG1-CO13    AAGCACGGCAGCTGCAAGCTGCCCGGCGATTGCCGGTGCCAGTACGGGTGGCAGGGCCTG
JAG1-CO19    AAGCACGGGAGCTGCAAGCTGCCCGGCGACTGCAGGTGCCAGTACGGCTGGCAGGGGCTG
JAG1-CO08    AAACACGGGTCCTGCAAGCTGCCTGGCGACTGCAGGTGTCAGTACGGCTGGCAGGGGCTG
JAG1-CO03    AAGCACGGAAGCTGTAAGCTCCCCGGCGACTGCCGCTGCCAGTACGGCTGGCAGGGACTG
JAG1-CO14    AAGCACGGCAGCTGCAAGCTTCCCGGCGACTGTCGGTGCCAGTACGGATGGCAAGGGCTG
JAG1-CO09    AAGCACGGCAGCTGCAAGCTGCCTGGCGATTGCCGGTGTCAGTACGGGTGGCAGGGTCTC
JAG1-CO10    AAGCACGGCAGCTGTAAGCTACCCGGCGACTGTCGGTGCCAGTACGGTTGGCAGGGCCTG
JAG1-CO06    AAGCACGGCAGCTGCAAGCTGCCCGGCGACTGCAGGTGTCAGTACGGCTGGCAAGGACTG
             **.**.**     **.**.** ** ** **.**. * **.**.**.** *****.** .*

JAG1-WT      TACTGTGATAAGTGCATCCCACACCCGGGATGCGTCCACGGCATCTGTAATGAGCCCTGG
JAG1-CO01    TACTGCGACAAGTGCATCCCGCATCCCGGCTGCGTGCACGGCATCTGCAACGAGCCCTGG
JAG1-CO17    TACTGCGATAAGTGCATTCCGCACCCAGGATGTGTGCACGGAATCTGTAACGAGCCCTGG
JAG1-CO11    TACTGCGACAAGTGCATTCCCCATCCCGGCTGCGTGCACGGCATATGTAACGAACCCTGG
JAG1-CO12    TACTGTGACAAGTGCATCCCCCACCCGGGCTGCGTCCACGGAATCTGCAATGAGCCCTGG
JAG1-CO25    TACTGCGACAAATGCATCCCCCACCCTGGGTGCGTGCACGGCATCTGTAACGAGCCCTGG
JAG1-CO04    TACTGCGACAAGTGCATCCCGCACCCCGGCTGCGTCCACGGCATCTGTAATGAGCCCTGG
JAG1-CO18    TACTGCGACAAGTGCATCCCGCACCCCGGTTGCGTCCACGGCATCTGCAACGAGCCCTGG
JAG1-CO05    TACTGCGACAAGTGCATCCCCCATCCCGGCTGCGTGCATGGCATTTGCAACGAACCCTGG
JAG1-CO23    TACTGCGACAAGTGCATCCCCCATCCTGGCTGCGTGCACGGCATATGCAACGAGCCCTGG
JAG1-CO24    TACTGCGACAAGTGCATCCCCCACCCCGGCTGCGTGCATGGGATATGCAACGAGCCGTGG
JAG1-CO21    TACTGCGATAAGTGCATCCCCCACCCCGGCTGCGTTCACGGCATCTGCAACGAGCCCTGG
JAG1-CO22    TACTGCGACAAGTGCATCCCGCACCCCGGGTGCGTGCACGGCATTTGCAACGAACCCTGG
JAG1-CO15    TACTGCGATAAGTGCATCCCCCATCCCGGCTGCGTGCATGGCATCTGCAACGAACCCTGG
JAG1-CO16    TATTGCGACAAGTGCATCCCCCACCCAGGCTGTGTGCATGGCATCTGTAACGAACCCTGG
JAG1-CO07    TATTGCGACAAGTGCATCCCGCACCCCGGCTGCGTGCACGGGATCTGCAACGAGCCCTGG
JAG1-CO02    TATTGCGACAAGTGCATACCCCACCCAGGCTGCGTGCACGGCATCTGTAACGAGCCCTGG
JAG1-CO20    TACTGTGACAAGTGTATCCCACATCCGGGCTGCGTGCACGGAATATGCAACGAGCCCTGG
JAG1-CO13    TACTGCGACAAGTGCATCCCGCACCCCGGATGTGTGCACGGCATCTGCAACGAGCCCTGG
JAG1-CO19    TACTGCGACAAGTGCATCCCCCACCCGGGATGCGTGCACGGCATCTGCAACGAGCCCTGG
JAG1-CO08    TACTGCGATAAGTGCATCCCCCACCCCGGCTGCGTCCACGGCATCTGCAACGAGCCATGG
JAG1-CO03    TACTGTGACAAGTGTATCCCCCACCCCGGCTGCGTGCACGGCATCTGCAATGAGCCTTGG
JAG1-CO14    TACTGCGACAAGTGCATCCCCCATCCCGGCTGTGTCCACGGTATCTGCAACGAGCCCTGG
JAG1-CO09    TACTGCGACAAGTGCATCCCCCACCCGGGCTGTGTGCACGGCATCTGCAACGAGCCCTGG
JAG1-CO10    TACTGTGACAAGTGCATCCCCCACCCCGGCTGCGTGCACGGCATCTGCAATGAGCCGTGG
JAG1-CO06    TATTGTGACAAGTGCATTCCCCATCCGGGCTGTGTGCACGGAATCTGCAATGAGCCCTGG
             **.**.**.**.**.** ** **.** ** **.** **.** ** **.**.**.** ***
```

FIG. 13 (cont)

```
JAG1-WT       CAGTGCCTCTGTGAGACCAACTGGGGCGGCCAGCTCTGTGACAAAGATCTCAATTACTGT
JAG1-CO01     CAGTGCCTGTGCGAAACCAACTGGGGCGGCCAGCTCTGTGACAAGGACCTTAACTACTGC
JAG1-CO17     CAGTGCCTGTGCGAAACCAACTGGGGGGGCCAACTCTGCGACAAGGACCTGAACTACTGC
JAG1-CO11     CAATGCCTCTGCGAGACCAACTGGGGCGGGCAGCTGTGCGACAAAGACCTGAACTACTGT
JAG1-CO12     CAGTGTCTGTGCGAGACGAACTGGGGTGGCCAGCTGTGCGACAAGGACCTGAACTACTGC
JAG1-CO25     CAGTGCCTGTGTGAGACCAACTGGGGTGGCAACTGTGCGATAAGGACCTGAACTACTGC
JAG1-CO04     CAATGCCTGTGCGAGACCAACTGGGGCGGCCAGCTGTGCGACAAGGACCTCAATTATTGT
JAG1-CO18     CAGTGCCTGTGCGAGACCAACTGGGGGGGCCAGCTGTGCGACAAGGACCTCAATTACTGT
JAG1-CO05     CAATGCCTCTGCGAGACCAACTGGGGGGGCCAGCTCTGCGACAAGGATCTGAACTACTGC
JAG1-CO23     CAGTGCCTGTGCGAGACCAATTGGGGCGGCCAGCTGTGCGACAAGGACCTGAATTACTGT
JAG1-CO24     CAGTGCCTGTGCGAAACCAACTGGGGGGGCCAGCTGTGCGATAAGGACCTCAACTACTGC
JAG1-CO21     CAGTGCCTGTGTGAAACCAACTGGGGTGGACAGCTGTGCGACAAGGATCTGAACTATTGC
JAG1-CO22     CAGTGCCTCTGCGAAACCAATTGGGGAGGCCAGCTGTGCGACAAGGATCTGAACTACTGC
JAG1-CO15     CAGTGCCTGTGCGAGACCAACTGGGGGGGCCAGCTATGCGATAAGGATCTGAACTACTGT
JAG1-CO16     CAGTGCCTGTGCGAGACGAACTGGGGGGGCCAACTGTGCGACAAGGACCTGAACTATTGC
JAG1-CO07     CAGTGCCTGTGCGAGACGAACTGGGGCGGCCAGCTGTGCGACAAGGACCTGAACTACTGC
JAG1-CO02     CAATGCCTCTGCGAGACCAACTGGGGGGGACAACTGTGCGACAAGGACCTGAACTACTGC
JAG1-CO20     CAGTGCCTGTGTGAAACGAACTGGGGCGGTCAGCTGTGCGACAAGGACCTGAACTACTGC
JAG1-CO13     CAGTGCCTGTGCGAAACCAACTGGGGGGGTCAGCTGTGTGACAAGGATCTGAACTACTGC
JAG1-CO19     CAGTGCCTCTGCGAGACCAACTGGGGCGGCCAGCTGTGCGACAAGGACCTGAACTACTGT
JAG1-CO08     CAGTGTCTGTGCGAGACCAACTGGGGTGGGCAGCTGTGCGACAAGGATCTGAACTACTGC
JAG1-CO03     CAGTGCCTGTGCGAGACCAATTGGGGCGGCCAGCTGTGCGACAAGGACCTGAACTACTGC
JAG1-CO14     CAGTGTCTGTGCGAGACCAACTGGGGCGGCCAGCTGTGCGACAAGGACCTGAACTACTGC
JAG1-CO09     CAGTGCCTGTGCGAAACCAATTGGGGCGGCCAACTGTGCGACAAGGACCTGAACTACTGT
JAG1-CO10     CAGTGCCTGTGTGAAACCAACTGGGGTGGGCAGCTGTGCGACAAGGACCTGAATTACTGC
JAG1-CO06     CAGTGCCTGTGCGAGACCAACTGGGGCGGCCAGCTGTGTGACAAGGATCTGAACTACTGT
              **.**.** **.**.** **.***** ** **.** **.**.**.**.** **.**.**.

JAG1-WT       GGGACTCATCAGCCGTGTCTCAACGGGGGAACTTGTAGCAACACAGGCCCTGACAAATAT
JAG1-CO01     GGCACCCACCAGCCCTGCCTGAACGGCGGACCTGCAGCAACACCGGGCCCGACAAGTAC
JAG1-CO17     GGCACCCACCAACCCTGTCTGAACGGCGGCACCTGCAGCAACACCGGCCCCGACAAATAC
JAG1-CO11     GGCACCCATCAGCCCTGCCTGAACGGGGGGACTTGCTCCAATACCGGTCCCGACAAGTAT
JAG1-CO12     GGGACCCACCAGCCCTGCCTGAACGGCGGGACCTGTTCCAACACCGGCCCGGACAAGTAT
JAG1-CO25     GGAACCCACCAGCCCTGCCTGAACGGCGGCACATGCAGCAACACCGGGCCCGACAAGTAC
JAG1-CO04     GGCACCCACCAGCCATGCCTGAATGGTGGCACCTGCAGCAACACAGGCCCAGACAAGTAC
JAG1-CO18     GGCACCCACCAGCCCTGCCTCAACGGTGGCACCTGCTCCAACACCGGCCCCGACAAGTAC
JAG1-CO05     GGCACACACCAGCCTTGCCTGAACGGAGGGACCTGCAGTAATACCGGCCCCGACAAGTAC
JAG1-CO23     GGCACCCACCAGCCCTGCCTCAACGGCGGCACCTGCTCCAACACCGGCCCCGACAAGTAC
JAG1-CO24     GGCACCCACCAGCCCTGCCTCAACGGCGGCACCTGCTCCAATACCGGGCCCGATAAATAC
JAG1-CO21     GGCACCCACCAGCCCTGCCTGAACGGCGGAACCTGCAGCAACACCGGCCCCGATAAGTAC
JAG1-CO22     GGCACGCACCAGCCCTGCCTCAACGGGGGGACCTGTAGCAACACGGGCCCCGACAAGTAC
JAG1-CO15     GGCACCCACCAGCCCTGCCTGAACGGGGGCACGTGCTCAAACACCGGCCCCGACAAATAC
JAG1-CO16     GGCACCCACCAGCCGTGCCTGAATGGCGGAACCTGTTCCAACACCGGCCCCGACAAGTAC
JAG1-CO07     GGGACGCATCAACCCTGTCTCAACGGCGGTACCTGCAGCAATACCGGCCCCGACAAGTAC
JAG1-CO02     GGTACCCACCAGCCCTGCCTGAACGGCGGCACCTGCAGTAACACCGGCCCCGACAAGTAT
JAG1-CO20     GGCACCCACCAGCCCTGCCTGAACGGCGGGACGTGTTCCAACACCGGCCCCGACAAGTAT
JAG1-CO13     GGAACCCACCAACCCTGCCTGAACGGCGGAACTTGCTCGAACACGGGCCCCGACAAGTAC
JAG1-CO19     GGCACGCATCAGCCATGCCTCAATGGTGGCACCTGCAGCAACACGGGCCCCGATAAGTAC
JAG1-CO08     GGCACCCACCAGCCCTGCCTCAACGGGGGAACGTGCTCGAACACCGGGCCCGATAAGTAC
JAG1-CO03     GGCACCCACCAGCCCTGCCTGAACGGTGGGACCTGCAGCAACACCGGGCCAGACAAGTAC
JAG1-CO14     GGCACCCACCAGCCCTGCCTGAATGGGGGCACCTGTTCTAACACCGGGCCGGACAAGTAC
JAG1-CO09     GGCACCCACCAGCCCTGCCTGAACGGGGGCACTTGCTCCAACACGGGCCCCGACAAGTAT
JAG1-CO10     GGCACCCACCAGCCCTGTCTGAACGGCGGCACCTGCTCCAACACCGGCCCGGACAAGTAT
JAG1-CO06     GGCACCCACCAGCCCTGCCTGAACGGCGGGACCTGCTCCAATACCGGGCCCGACAAGTAC
              ** ** **.**.** **.** **.** ** ** **.   **.** ** ** **.**.**.
```

FIG. 13 (cont)

```
JAG1-WT         CAGTGTTCCTGCCCTGAGGGGTATTCAGGACCCAACTGTGAAATTGCTGAGCACGCCTGC
JAG1-CO01       CAGTGTAGCTGCCCCGAAGGGTACTCGGGTCCCAACTGCGAGATCGCCGAGCACGCCTGC
JAG1-CO17       CAGTGCAGCTGCCCCGAGGGCTACTCCGGGCCCAACTGCGAGATCGCCGAACACGCATGT
JAG1-CO11       CAGTGCAGCTGCCCCGAGGGCTACTCCGGGCCCAACTGCGAGATCGCCGAACACGCCTGT
JAG1-CO12       CAGTGCAGCTGCCCGGAAGGGTACTCCGGCCCGAACTGCGAAATCGCCGAACACGCTTGC
JAG1-CO25       CAGTGCAGCTGCCCCGAAGGGTATAGCGGGCCCAATTGCGAAATCGCCGAGCACGCCTGC
JAG1-CO04       CAGTGCAGCTGTCCCGAGGGCTACTCGGGCCCCAACTGCGAAATCGCCGAGCACGCTTGC
JAG1-CO18       CAGTGTAGCTGCCCCGAGGGGTACAGCGGCCCGAACTGCGAGATCGCCGAGCACGCCTGC
JAG1-CO05       CAGTGCAGCTGCCCCGAGGGCTATAGCGGCCCCAACTGCGAAATTGCCGAGCACGCCTGC
JAG1-CO23       CAGTGCAGCTGCCCCGAAGGCTACAGCGGCCCGAATTGCGAGATCGCCGAACACGCCTGC
JAG1-CO24       CAGTGCTCCTGCCCTGAGGGCTACAGCGGGCCCAACTGTGAGATCGCCGAGCATGCCTGC
JAG1-CO21       CAGTGCAGCTGCCCCGAAGGCTACTCCGGCCCCAACTGCGAGATCGCCGAGCACGCCTGC
JAG1-CO22       CAGTGCTCCTGCCCGGAGGGATACTCTGGCCCCAACTGCGAGATCGCCGAGCACGCCTGC
JAG1-CO15       CAATGCAGCTGCCCCGAGGGCTACAGCGGCCCCAACTGCGAGATCGCCGAGCATGCCTGC
JAG1-CO16       CAGTGCTCCTGTCCCGAGGGGTACAGCGGCCCCAACTGCGAGATCGCCGAGCATGCCTGC
JAG1-CO07       CAGTGCTCTTGCCCCGAGGGCTATAGCGGGCCCAACTGTGAGATCGCCGAGCACGCTTGC
JAG1-CO02       CAGTGCAGCTGCCCCGAGGGGTATTCCGGCCCGAACTGCGAGATCGCCGAGCACGCCTGC
JAG1-CO20       CAGTGTAGCTGCCCCGAGGGCTATAGCGGCCCGAACTGCGAGATCGCCGAACATGCCTGT
JAG1-CO13       CAGTGCAGCTGTCCCGAGGGCTACAGCGGGCCCAACTGTGAGATCGCCGAACACGCTTGC
JAG1-CO19       CAATGCTCGTGCCCCGAAGGGTACTCCGGCCCAAATTGCGAGATCGCCGAGCACGCCTGC
JAG1-CO08       CAGTGCTCCTGCCCCGAAGGCTACTCGGGACCTAACTGTGAGATCGCTGAGCACGCATGC
JAG1-CO03       CAGTGCAGCTGCCCCGAGGGCTATAGCGGGCCCAATTGCGAGATCGCCGAGCACGCCTGC
JAG1-CO14       CAGTGTTCCTGCCCCGAGGGCTACAGCGGCCCCAACTGCGAGATCGCCGAGCACGCCTGC
JAG1-CO09       CAGTGCAGCTGTCCTGAGGGCTACAGCGGCCCCAACTGTGAGATCGCCGAGCATGCCTGC
JAG1-CO10       CAGTGCAGTTGCCCCGAGGGCTATAGCGGCCCCAACTGCGAGATCGCCGAGCACGCCTGC
JAG1-CO06       CAGTGTTCCTGCCCCGAGGGCTACAGCGGTCCAAACTGCGAGATCGCCGAGCACGCCTGC
                **.**.   **.** **.** **.    ** ** **.**.**.**.**.**.**.** **.

JAG1-WT         CTCTCTGATCCCTGTCACAACAGAGGCAGCTGTAAGGAGACCTCCCTGGGCTTTGAGTGT
JAG1-CO01       CTGTCCGACCCCTGCCATAACAGGGGCAGCTGTAAGGAGACCTCCCTGGGCTTCGAGTGT
JAG1-CO17       CTGAGCGACCCTTGCCACAACAGGGGCAGCTGCAAGGAGACCTCCCTCGGCTTTGAGTGC
JAG1-CO11       CTGTCCGACCCCTGCCACAACAGAGGCAGCTGCAAGGAGACCAGCCTGGGCTTTGAGTGC
JAG1-CO12       CTCAGCGACCCCTGCCACAACCGCGGGAGCTGCAAGGAGACCAGCCTGGGCTTTGAGTGC
JAG1-CO25       CTGAGCGATCCCTGTCATAATCGCGGATCCTGCAAGGAGACCAGCCTCGGCTTTGAGTGC
JAG1-CO04       CTGAGCGACCCCTGTCACAACAGGGGCAGCTGCAAGGAAACCAGCCTGGGGTTCGAGTGC
JAG1-CO18       CTGTCCGACCCCTGCCACAATCGCGGCAGCTGCAAGGAGACCAGCCTGGGGTTCGAATGC
JAG1-CO05       CTGAGCGACCCCTGTCACAACAGGGGCAGCTGCAAGGAGACCAGTCTGGGCTTCGAGTGC
JAG1-CO23       CTCAGCGACCCCTGCCACAACCGGGGCAGCTGTAAGGAGACCTCCCTGGGCTTTGAATGC
JAG1-CO24       CTCTCGGACCCCTGCCATAACAGGGGCAGCTGTAAGGAAACCAGCCTGGGCTTCGAGTGC
JAG1-CO21       CTGAGCGACCCGTGCCACAACAGGGGGAGCTGCAAAGAGACCAGCCTGGGTTTCGAGTGC
JAG1-CO22       CTCTCCGATCCGTGCCACAATAGGGGCAGCTGCAAGGAAACGTCCCTGGGCTTCGAATGC
JAG1-CO15       CTGAGCGACCCGTGCCACAATAGGGGCTCCTGTAAGGAGACCAGCCTGGGCTTCGAGTGT
JAG1-CO16       CTCAGCGATCCCTGCCACAACAGGGGCAGCTGCAAGGAGACGAGCCTGGGCTTCGAGTGC
JAG1-CO07       CTGTCCGACCCCTGCCACAACCGGGGCTCCTGCAAGGAGACCTCCCTGGGCTTCGAGTGC
JAG1-CO02       CTCAGCGACCCATGCCACAATAGAGGCAGCTGCAAGGAAACCTCCCTGGGGTTCGAGTGT
JAG1-CO20       CTCAGCGACCCCTGTCACAACAGGGGTAGCTGTAAGGAAACCAGCCTCGGGTTTGAGTGT
JAG1-CO13       CTGAGCGACCCGTGTCACAACCGGGGCAGCTGCAAGGAGACCTCCCTCGGCTTCGAGTGC
JAG1-CO19       CTGTCCGACCCCTGCCACAACAGGGGCTCCTGTAAGGAGACCTCCCTGGGCTTCGAGTGT
JAG1-CO08       CTGAGCGACCCATGCCATAACAGGGGTAGTTGCAAGGAGACCTCCCTCGGTTTTGAATGC
JAG1-CO03       CTGTCCGACCCCTGTCACAACCGGGGCTCCTGCAAGGAGACCTCCCTGGGGTTTGAGTGC
JAG1-CO14       CTGTCCGACCCCTGCCATAATAGGGGCTCCTGCAAGGAGACCTCCCTGGGCTTTGAGTGC
JAG1-CO09       CTGAGCGACCCGTGCCACAATCGTGGCAGCTGTAAGGAGACCAGCCTGGGCTTCGAGTGC
JAG1-CO10       CTGTCCGACCCGTGCCACAACAGGGGGAGCTGCAAAGAGACCAGCCTGGGGTTCGAGTGC
JAG1-CO06       CTGAGCGACCCCTGCCATAACAGGGGCTCCTGCAAGGAGACCAGCCTGGGCTTCGAATGC
                **    **.** **.**.**. * **   .**.**.**.**   .** ** **.**.**.
```

FIG. 13 (cont)

```
JAG1-WT      GAGTGTTCCCCAGGCTGGACCGGCCCCACATGCTCTACAAACATTGATGACTGTTCTCCT
JAG1-CO01    GAGTGCTCCCCCGGATGGACCGGCCCCACCTGCAGCACCAATATTGACGACTGCAGCCCA
JAG1-CO17    GAATGCAGCCCCGGCTGGACCGGGCCCACCTGCAGCACGAACATCGACGACTGCAGCCCC
JAG1-CO11    GAGTGCTCCCCCGGCTGGACCGGGCCCACCTGCAGCACCAACATCGACGATTGCAGCCCC
JAG1-CO12    GAATGTTCCCCCGGCTGGACCGGGCCCACATGCTCCACCAACATAGACGATTGTAGCCCC
JAG1-CO25    GAATGCTCCCCCGGCTGGACCGGTCCCACGTGCAGCACGAACATCGACGACTGTTCCCCG
JAG1-CO04    GAGTGCAGCCCCGGGTGGACCGGCCCCACCTGCAGCACCAACATCGACGACTGCAGCCCC
JAG1-CO18    GAGTGTTCCCCGGGCTGGACCGGCCCCACCTGCAGCACCAATATCGATGACTGCTCCCCC
JAG1-CO05    GAGTGCAGCCCAGGCTGGACGGGCCCCACCTGCTCCACCAACATCGACGACTGCTCCCCC
JAG1-CO23    GAATGTAGCCCCGGTTGGACCGGACCCACCTGTTCCACCAACATCGACGACTGCAGCCCC
JAG1-CO24    GAGTGCAGCCCCGGGTGGACCGGGCCAACCTGCTCCACCAACATCGACGACTGTAGCCCG
JAG1-CO21    GAGTGCAGCCCCGGCTGGACCGGGCCCACTTGCTCCACCAACATTGACGACTGTAGCCCG
JAG1-CO22    GAATGCAGTCCCGGATGGACCGGCCCCACCTGCAGCACCAACATCGACGACTGCAGCCCC
JAG1-CO15    GAGTGCAGCCCCGGCTGGACCGGCCCCACCTGCTCAACTAACATCGACGACTGTTCCCCC
JAG1-CO16    GAATGCAGCCCCGGTTGGACCGGCCCCACGTGCTCCACCAACATCGACGACTGCTCCCCC
JAG1-CO07    GAATGCAGCCCCGGGTGGACCGGTCCCACGTGCAGCACCAACATCGATGACTGTAGCCCC
JAG1-CO02    GAGTGCTCCCCCGGGTGGACCGGGCCCACCTGCTCCACCAACATCGACGACTGCAGCCCC
JAG1-CO20    GAATGCTCCCCGGGCTGGACCGGGCCCACCTGTTCCACCAACATCGACGACTGCTCCCCC
JAG1-CO13    GAGTGCTCCCCAGGGTGGACCGGCCCCACCTGCAGCACCAACATCGACGATTGCAGCCCC
JAG1-CO19    GAGTGCAGCCCCGGGTGGACCGGCCCCACCTGTTCCACCAACATCGACGACTGCAGCCCC
JAG1-CO08    GAGTGCAGCCCCGGCTGGACCGGCCCCACCTGCTCGACCAACATCGACGACTGCAGCCCA
JAG1-CO03    GAGTGCTCCCCCGGTTGGACCGGCCCCACCTGCTCCACCAACATCGACGACTGCTCCCCC
JAG1-CO14    GAGTGTTCGCCCGGCTGGACCGGCCCCACCTGCAGTACCAACATCGACGACTGCAGCCCC
JAG1-CO09    GAGTGCAGCCCGGGTTGGACCGGACCCACCTGCAGCACCAACATCGACGATTGCAGCCCC
JAG1-CO10    GAGTGCAGCCCCGGGTGGACCGGACCCACCTGCAGCACCAACATCGATGATTGCAGCCCT
JAG1-CO06    GAGTGCTCCCCCGGGTGGACCGGCCCCACCTGCAGTACCAACATCGATGACTGCAGCCCC
             **.**.    ** ** ***** ** ** ** **.    ** **.** **.**.**.   .**

JAG1-WT      AATAACTGTTCCCACGGGGGCACCTGCCAGGACCTGGTTAACGGATTTAAGTGTGTGTGC
JAG1-CO01    AATAACTGCTCCCACGGCGGCACCTGCCAGGACCTCGTGAACGGCTTTAAGTGCGTCTGT
JAG1-CO17    AACAACTGCTCCCACGGCGGGACGTGCCAGGATCTCGTCAACGGCTTCAAGTGCGTGTGC
JAG1-CO11    AACAATTGCTCCCACGGCGGCACTTGCCAAGACCTGGTGAACGGCTTCAAGTGCGTGTGC
JAG1-CO12    AACAACTGCTCCCACGGGGGGACCTGCCAAGACCTGGTCAACGGATTCAAGTGCGTGTGT
JAG1-CO25    AACAACTGCTCCCACGGCGGCACCTGCCAGGATCTGGTGAATGGATTCAAATGCGTGTGC
JAG1-CO04    AACAACTGTAGCCATGGCGGCACCTGCCAGGATCTGGTCAACGGCTTCAAGTGCGTGTGT
JAG1-CO18    AACAACTGCAGCCACGGCGGCACCTGTCAGGACCTGGTGAATGGCTTCAAGTGTGTGTGC
JAG1-CO05    AACAATTGCAGCCACGGCGGCACCTGCCAAGATCTCGTGAACGGCTTCAAGTGCGTGTGT
JAG1-CO23    AATAACTGCAGCCACGGTGGCACGTGCCAGGACCTCGTCAACGGCTTTAAGTGCGTGTGC
JAG1-CO24    AACAACTGCTCCCACGGCGGGACCTGCCAGGACCTGGTGAATGGCTTCAAGTGCGTATGT
JAG1-CO21    AACAATTGCAGCCACGGCGGCACCTGCCAGGACCTGGTGAATGGCTTCAAGTGCGTGTGT
JAG1-CO22    AACAACTGCAGCCACGGCGGCACCTGCCAAGATCTCGTGAACGGCTTCAAGTGCGTGTGC
JAG1-CO15    AACAATTGCAGCCACGGCGGCACCTGCCAGGACCTGGTGAACGGCTTTAAGTGTGTGTGC
JAG1-CO16    AACAATTGCAGCCACGGGGGCACATGTCAGGACCTGGTGAACGGCTTCAAGTGCGTGTGC
JAG1-CO07    AACAACTGCAGCCACGGCGGCACGTGCCAGGACCTCGTGAACGGCTTCAAGTGCGTGTGC
JAG1-CO02    AATAACTGCAGCCACGGGGGCACCTGTCAGGACCTGGTGAACGGCTTTAAGTGCGTCTGC
JAG1-CO20    AATAACTGCAGCCATGGCGGCACGTGTCAGGACCTCGTCAATGGCTTTAAGTGTGTGTGC
JAG1-CO13    AACAACTGTAGCCACGGCGGGACGTGCCAGGACCTGGTCAACGGCTTCAAATGTGTCTGT
JAG1-CO19    AACAACTGCAGCCATGGAGGCACCTGTCAGGACCTGGTGAATGGTTTCAAGTGTGTGTGC
JAG1-CO08    AACAACTGCTCCCACGGCGGCACGTGTCAGGACCTGGTGAATGGCTTCAAGTGTGTGTGC
JAG1-CO03    AACAATTGCAGCCACGGCGGCACATGCCAGGATCTGGTGAACGGCTTCAAGTGTGTGTGT
JAG1-CO14    AACAACTGTAGCCACGGCGGCACATGCCAAGACCTGGTGAACGGCTTCAAGTGCGTCTGC
JAG1-CO09    AACAACTGTTCACACGGGGGCACGTGCCAAGACCTGGTGAACGGGTTCAAGTGTGTCTGC
JAG1-CO10    AACAACTGCTCCCACGGCGGCACCTGCCAGGACCTGGTGAACGGCTTTAAGTGCGTATGC
JAG1-CO06    AATAACTGTTCCCACGGCGGCACCTGCCAGGACCTGGTGAACGGCTTCAAATGCGTCTGT
             **.**.**.    **.** ** ** **.**.**.** ** **.** **.**.**.** **.
```

FIG. 13 (cont)

```
JAG1-WT      CCCCCACAGTGGACTGGGAAAACGTGCCAGTTAGATGCAAATGAATGTGAGGCCAAACCT
JAG1-CO01    CCCCCCCAGTGGACCGGCAAGACCTGCCAGCTGGACGCCAATGAGTGCGAGGCCAAGCCC
JAG1-CO17    CCCCCCCAGTGGACCGGCAAAACCTGCCAGCTGGACGCAAACGAGTGCGAAGCCAAGCCG
JAG1-CO11    CCCCCCCAGTGGACCGGTAAAACATGCCAGCTGGACGCCAACGAGTGCGAGGCCAAGCCC
JAG1-CO12    CCCCCCCAGTGGACGGGTAAGACCTGCCAACTGGACGCCAACGAATGCGAGGCCAAGCCC
JAG1-CO25    CCCCCCCAATGGACCGGGAAGACCTGCCAACTGGACGCCAACGAGTGCGAAGCCAAGCCC
JAG1-CO04    CCCCCCCAGTGGACCGGCAAGACCTGCCAGCTCGACGCCAACGAGTGTGAAGCAAAGCCC
JAG1-CO18    CCACCGCAGTGGACCGGCAAAACCTGCCAGCTCGACGCCAACGAGTGCGAGGCCAAGCCC
JAG1-CO05    CCGCCGCAGTGGACCGGGAAAACCTGCCAACTGGACGCCAACGAGTGTGAGGCAAAGCCC
JAG1-CO23    CCCCCCCAGTGGACCGGGAAGACCTGCCAGCTGGACGCCAACGAGTGCGAGGCCAAGCCC
JAG1-CO24    CCCCCACAGTGGACCGGCAAGACCTGTCAACTCGACGCCAACGAGTGCGAGGCCAAACCC
JAG1-CO21    CCCCCCCAGTGGACCGGGAAGACCTGCCAGCTGGACGCCAACGAGTGCGAGGCCAAGCCC
JAG1-CO22    CCCCCCCAGTGGACCGGGAAAACCTGCCAACTCGACGCCAATGAGTGTGAGGCCAAGCCC
JAG1-CO15    CCCCCCCAGTGGACCGGGAAGACCTGTCAGCTGGACGCTAACGAGTGTGAGGCCAAGCCC
JAG1-CO16    CCGCCCCAATGGACCGGCAAGACGTGCCAGCTGGACGCCAACGAGTGCGAAGCCAAGCCA
JAG1-CO07    CCCCCCCAGTGGACCGGCAAGACCTGCCAGCTCGACGCCAATGAGTGCGAAGCCAAGCCC
JAG1-CO02    CCCCCCCAGTGGACCGGTAAGACGTGCCAGCTGGACGCCAATGAGTGCGAAGCCAAGCCC
JAG1-CO20    CCCCCGCAGTGGACCGGCAAGACGTGCCAGCTGGACGCCAACGAGTGTGAGGCCAAGCCC
JAG1-CO13    CCCCCCCAGTGGACCGGCAAAACCTGCCAGCTCGACGCCAACGAGTGCGAAGCCAAGCCG
JAG1-CO19    CCGCCCCAGTGGACCGGGAAGACCTGCCAGCTGGACGCCAACGAGTGCGAGGCTAAGCCC
JAG1-CO08    CCCCCCCAGTGGACCGGAAAAACCTGCCAGCTGGATGCCAACGAGTGTGAGGCCAAGCCC
JAG1-CO03    CCCCCCCAGTGGACCGGCAAGACCTGCCAGCTGGACGCGAACGAGTGCGAAGCAAAGCCC
JAG1-CO14    CCGCCGCAGTGGACCGGGAAGACCTGTCAGCTGGATGCCAACGAGTGCGAGGCTAAACCC
JAG1-CO09    CCCCCCCAGTGGACCGGCAAAACCTGTCAGCTCGACGCCAACGAATGTGAGGCCAAGCCC
JAG1-CO10    CCCCCCCAATGGACGGGGAAGACCTGTCAGCTCGACGCCAATGAATGCGAGGCAAAACCG
JAG1-CO06    CCGCCCCAGTGGACCGGAAAGACCTGTCAGCTCGACGCAAACGAGTGCGAGGCCAAGCCC
             ** ** **.***** ** **.** **.**..* **.** **.**.**.**.** **.**

JAG1-WT      TGTGTAAACGCCAAATCCTGTAAGAATCTCATTGCCAGCTACTACTGCGACTGTCTTCCC
JAG1-CO01    TGTGTAAACGCCAAGAGCTGCAAGAACCTGATCGCCAGCTACTACTGTGACTGCCTGCCC
JAG1-CO17    TGCGTCAACGCGAAGAGCTGCAAGAACCTCATCGCCAGCTACTATTGCGACTGCCTGCCC
JAG1-CO11    TGCGTGAACGCCAAGAGCTGCAAAAACCTGATCGCCAGTTACTACTGCGACTGCCTGCCT
JAG1-CO12    TGTGTGAATGCCAAGAGCTGCAAGAACCTGATCGCCAGCTACTACTGTGACTGCCTGCCC
JAG1-CO25    TGTGTGAACGCCAAGAGCTGCAAAAACCTCATCGCTAGCTACTACTGCGACTGCCTGCCC
JAG1-CO04    TGCGTGAATGCCAAGTCCTGCAAGAACCTGATAGCCTCCTACTACTGCGACTGCCTGCCC
JAG1-CO18    TGTGTGAATGCCAAGTCCTGCAAGAACCTGATCGCCAGCTACTACTGCGACTGCCTGCCC
JAG1-CO05    TGCGTGAACGCGAAGTCCTGTAAGAACCTGATCGCCAGCTACTATTGCGACTGCCTGCCG
JAG1-CO23    TGCGTGAACGCCAAGAGCTGCAAGAACCTCATCGCCAGCTACTATTGTGACTGCCTGCCC
JAG1-CO24    TGCGTGAACGCCAAGTCCTGCAAGAACCTGATCGCCTCCTACTACTGCGACTGTCTGCCC
JAG1-CO21    TGTGTGAACGCCAAGTCCTGCAAGAACCTGATCGCCTCCTACTACTGTGACTGTCTCCCC
JAG1-CO22    TGCGTGAACGCCAAGTCGTGCAAAAACCTGATCGCCAGCTACTACTGCGACTGCCTGCCC
JAG1-CO15    TGTGTCAACGCCAAAAGCTGCAAGAACCTGATAGCCTCCTACTACTGCGACTGCCTGCCC
JAG1-CO16    TGCGTGAACGCCAAGAGCTGCAAGAACCTGATCGCCAGCTACTACTGCGACTGCCTCCCA
JAG1-CO07    TGCGTCAACGCCAAGTCCTGCAAGAACCTGATCGCCAGTTACTACTGCGACTGTCTGCCC
JAG1-CO02    TGCGTCAATGCCAAGAGCTGTAAGAACCTCATCGCGTCCTACTATTGCGACTGCCTGCCC
JAG1-CO20    TGCGTCAACGCAAAGAGCTGCAAGAACCTGATCGCCTCCTACTATTGTGACTGCCTGCCC
JAG1-CO13    TGCGTGAACGCGAAGAGCTGCAAGAACCTGATCGCCTCCTACTACTGCGACTGCCTGCCC
JAG1-CO19    TGCGTCAACGCCAAGAGCTGCAAGAACCTCATCGCCTCCTACTACTGCGACTGCCTGCCG
JAG1-CO08    TGCGTGAACGCGAAGTCCTGCAAGAACCTGATCGCCTCCTACTACTGTGACTGCCTGCCC
JAG1-CO03    TGCGTGAACGCCAAGTCCTGCAAAAACCTGATCGCCAGCTATTACTGCGACTGCCTGCCC
JAG1-CO14    TGCGTGAACGCGAAGAGCTGTAAGAACCTGATTGCCAGCTACTACTGCGACTGCCTGCCG
JAG1-CO09    TGCGTGAATGCGAAGAGCTGCAAGAACCTGATCGCGTCGTACTATTGCGATTGCCTGCCC
JAG1-CO10    TGTGTGAACGCCAAGAGCTGCAAAAACCTCATCGCGTCCTACTACTGCGACTGCCTGCCC
JAG1-CO06    TGCGTGAACGCCAAGAGCTGCAAGAATCTGATCGCCTCCTACTACTGCGATTGTCTGCCC
             **.** **.** **.   **.**.**.** ** **    **.**.**.**.**.** **
```

FIG. 13 (cont)

```
JAG1-WT         GGCTGGATGGGTCAGAATTGTGACATAAATATTAATGACTGCCTTGGCCAGTGTCAGAAT
JAG1-CO01       GGCTGGATGGGCCAGAACTGCGACATCAACATCAACGACTGCCTCGGGCAGTGCCAGAAC
JAG1-CO17       GGCTGGATGGGCCAGAACTGCGACATAAACATCAACGACTGCCTGGGCCAGTGTCAGAAC
JAG1-CO11       GGATGGATGGGCCAGAACTGCGACATCAACATCAACGACTGCCTGGGCCAGTGCCAGAAC
JAG1-CO12       GGCTGGATGGGCCAGAATTGCGACATCAATATCAACGACTGCCTGGGCCAGTGCCAGAAT
JAG1-CO25       GGCTGGATGGGTCAGAACTGTGACATCAACATCAACGATTGTCTGGGCCAGTGCCAGAAC
JAG1-CO04       GGCTGGATGGGCCAGAACTGTGACATCAACATCAACGACTGCCTGGGGCAGTGTCAGAAT
JAG1-CO18       GGGTGGATGGGGCAAAATTGCGACATAAACATAAACGACTGCCTGGGCCAGTGCCAGAAC
JAG1-CO05       GGCTGGATGGGGCAGAACTGTGACATCAACATCAACGATTGCCTGGGCCAGTGTCAGAAC
JAG1-CO23       GGGTGGATGGGCCAGAACTGTGACATAAACATCAACGATTGTCTGGGCCAGTGCCAGAAC
JAG1-CO24       GGCTGGATGGGCCAGAACTGCGATATCAACATCAACGATTGCCTCGGCCAGTGTCAGAAC
JAG1-CO21       GGGTGGATGGGCCAGAACTGCGACATCAACATCAACGATTGCCTCGGCCAGTGCCAGAAC
JAG1-CO22       GGCTGGATGGGGCAGAACTGCGACATCAACATCAACGACTGCCTGGGGCAGTGCCAGAAT
JAG1-CO15       GGATGGATGGGCCAGAACTGCGACATCAACATCAATGACTGCCTGGGGCAGTGCCAGAAC
JAG1-CO16       GGCTGGATGGGCCAGAACTGTGATATCAACATCAACGACTGCCTCGGCCAGTGCCAGAAC
JAG1-CO07       GGATGGATGGGCCAGAATTGCGACATCAACATCAATGACTGCCTGGGCCAGTGCCAGAAT
JAG1-CO02       GGGTGGATGGGACAGAACTGCGACATCAACATCAACGACTGCCTCGGGCAGTGCCAGAAC
JAG1-CO20       GGGTGGATGGGACAGAACTGCGACATCAATATCAACGATTGCCTGGGGCAGTGCCAGAAC
JAG1-CO13       GGCTGGATGGGCCAGAACTGCGACATAAACATCAACGACTGCCTGGGCCAGTGCCAGAAC
JAG1-CO19       GGATGGATGGGCCAGAACTGTGACATCAACATCAACGACTGTCTGGGCCAGTGCCAGAAT
JAG1-CO08       GGTTGGATGGGCCAAAACTGCGACATCAACATCAACGACTGCCTGGGCCAGTGCCAGAAC
JAG1-CO03       GGCTGGATGGGGCAGAACTGTGACATAAACATAAACGACTGCCTCGGCCAGTGCCAGAAT
JAG1-CO14       GGCTGGATGGGGCAGAATTGCGACATCAACATCAACGACTGTCTGGGCCAATGCCAGAAC
JAG1-CO09       GGCTGGATGGGCCAGAACTGCGACATCAACATCAACGACTGCCTGGGCCAGTGCCAAAAC
JAG1-CO10       GGCTGGATGGGGCAGAACTGTGACATCAACATCAACGATTGCCTGGGCCAATGCCAGAAT
JAG1-CO06       GGATGGATGGGCCAAAACTGCGACATCAACATCAACGATTGTCTGGGGCAGTGCCAGAAC
                ** ******** **.**.**.**.** **.** **.**.**.** ** **.**.**.**.

JAG1-WT         GACGCCTCCTGTCGGGATTTGGTTAATGGTTATCGCTGTATCTGTCCACCTGGCTATGCA
JAG1-CO01       GACGCCAGCTGCAGGGATCTGGTGAACGGCTACAGGTGCATCTGCCCCCCCGGATACGCC
JAG1-CO17       GATGCCTCCTGCAGGGACCTGGTGAACGGGTACCGGTGTATCTGCCCCCCCGGGTACGCG
JAG1-CO11       GACGCAAGCTGCCGTGACCTGGTGAACGGCTACAGGTGCATCTGCCCCCCCGGGTACGCC
JAG1-CO12       GACGCCTCCTGCAGGGACCTGGTGAACGGCTACAGGTGCATATGCCCCCCCGGCTACGCC
JAG1-CO25       GACGCCAGCTGCAGGGACCTGGTGAATGGGTACCGCTGCATCTGCCCCCCCGGCTACGCC
JAG1-CO04       GACGCCAGCTGCCGCGACCTGGTGAATGGCTATAGGTGCATCTGCCCCCCCGGATACGCC
JAG1-CO18       GACGCCTCCTGTCGGGACCTGGTCAACGGCTACAGGTGCATCTGCCCACCCGGCTACGCC
JAG1-CO05       GACGCCAGCTGCAGGGACCTGGTCAACGGCTACAGGTGCATCTGTCCCCCGGGGTATGCC
JAG1-CO23       GATGCCAGCTGTCGGGACCTGGTGAACGGCTACCGGTGCATCTGTCCCCCCGGCTACGCC
JAG1-CO24       GACGCCTCCTGCCGGGACCTGGTGAACGGCTACCGGTGCATTTGCCCCCCGGGCTACGCC
JAG1-CO21       GACGCCAGCTGTAGGGACCTCGTGAACGGCTACCGGTGCATCTGCCCGCCCGGGTACGCC
JAG1-CO22       GACGCTAGCTGCCGAGACCTGGTCAATGGATACCGGTGCATATGCCCCCCGGGCTACGCC
JAG1-CO15       GACGCCAGCTGCCGGGACCTGGTGAATGGGTACCGCTGCATCTGCCCCCCCGGCTACGCG
JAG1-CO16       GACGCCAGCTGCCGGGACCTGGTGAACGGGTACCGCTGCATCTGTCCGCCCGGCTACGCC
JAG1-CO07       GACGCGTCCTGTAGGGATCTGGTGAACGGGTACAGGTGCATATGTCCCCCCGGCTATGCC
JAG1-CO02       GACGCCAGCTGCCGGGACCTGGTGAACGGCTATAGATGCATCTGCCCCCCCGGCTACGCC
JAG1-CO20       GACGCGAGCTGCAGGGACCTGGTCAACGGCTACCGATGCATCTGCCCCCCGGGCTACGCC
JAG1-CO13       GATGCCAGCTGTCGAGACCTGGTGAACGGGTACCGGTGCATCTGCCCCCCCGGATACGCC
JAG1-CO19       GACGCCAGCTGCCGAGACCTGGTCAACGGCTACAGGTGCATATGCCCCCCCGGATATGCC
JAG1-CO08       GACGCCAGCTGCAGGGACCTAGTGAACGGGTATCGGTGCATCTGCCCCCCCGGCTACGCC
JAG1-CO03       GACGCGAGCTGCCGGGACCTCGTGAACGGCTACCGATGCATCTGCCCCCCGGGCTACGCC
JAG1-CO14       GACGCCAGCTGTCGGGACCTGGTCAACGGATACAGGTGTATCTGTCCCCCCGGCTACGCC
JAG1-CO09       GACGCCTCTTGCCGCGATCTGGTCAACGGGTACCGCTGCATCTGCCCTCCGGGGTACGCC
JAG1-CO10       GATGCCTCCTGCAGGGACCTTGTGAACGGCTACAGGTGCATATGCCCCCCCGGCTACGCC
JAG1-CO06       GACGCCAGCTGCAGGGACCTGGTCAACGGCTACAGGTGCATCTGCCCCCCCGGCTATGCC
                **.**    .**. * **..* ** **.** **. * **.** **.** ** ** **.**
```

FIG. 13 (cont)

```
JAG1-WT        GGCGATCACTGTGAGAGAGACATCGATGAATGTGCCAGCAACCCCTGTTTGAATGGGGGT
JAG1-CO01      GGCGACCATTGCGAAAGGGACATCGATGAGTGCGCCTCCAATCCCTGTCTGAACGGCGGC
JAG1-CO17      GGGGACCACTGCGAGAGAGACATCGATGAGTGCGCCTCCAATCCCTGCCTGAACGGCGGC
JAG1-CO11      GGTGACCACTGCGAACGGGACATAGATGAGTGCGCCAGCAACCCCTGCCTGAACGGCGGA
JAG1-CO12      GGCGACCACTGCGAACGTGACATCGACGAGTGCGCCTCAAACCCCTGCCTGAACGGCGGA
JAG1-CO25      GGAGATCATTGCGAGCGGGACATCGACGAGTGCGCCAGCAACCCCTGCCTGAACGGCGGT
JAG1-CO04      GGCGACCACTGCGAGAGGGATATCGATGAGTGCGCCAGCAACCCTTGCCTGAACGGCGGG
JAG1-CO18      GGCGACCACTGCGAGCGAGATATCGACGAATGCGCCAGCAACCCCTGCCTGAACGGGGGG
JAG1-CO05      GGGGACCACTGCGAACGAGATATCGACGAGTGCGCCTCGAACCCTTGCCTCAATGGCGGC
JAG1-CO23      GGAGATCACTGTGAGCGAGACATCGACGAGTGCGCCTCCAACCCCTGCCTCAACGGCGGG
JAG1-CO24      GGCGATCACTGCGAGCGCGACATCGACGAGTGCGCATCCAACCCCTGTCTGAACGGGGGG
JAG1-CO21      GGAGACCACTGCGAGAGGGACATTGACGAGTGCGCCTCGAACCCCTGCCTGAACGGCGGC
JAG1-CO22      GGCGACCATTGCGAGCGGGACATCGACGAGTGCGCCAGCAACCCATGCCTGAACGGCGGG
JAG1-CO15      GGCGACCACTGCGAGAGGGACATCGACGAGTGCGCCTCGAACCCCTGCCTCAACGGGGGC
JAG1-CO16      GGAGACCACTGCGAGCGCGACATCGACGAGTGTGCCAGCAACCCCTGCTTAAACGGCGGC
JAG1-CO07      GGGGATCACTGCGAGAGGGATATCGATGAGTGCGCCAGCAACCCCTGTCTGAACGGTGGC
JAG1-CO02      GGGGACCACTGCGAGAGGGACATCGACGAGTGCGCCTCCAACCCCTGCCTGAATGGAGGC
JAG1-CO20      GGCGACCACTGTGAAAGGGACATCGACGAGTGCGCCAGCAACCCCTGCCTGAACGGGGGC
JAG1-CO13      GGGGACCACTGCGAGCGCGACATCGACGAATGTGCCTCGAACCCCTGCCTGAACGGGGGC
JAG1-CO19      GGGGATCACTGCGAGCGGGACATCGACGAGTGCGCCAGCAACCCATGTCTGAACGGCGGG
JAG1-CO08      GGCGATCACTGCGAAAGGGACATCGACGAGTGCGCCAGCAACCCGTGCCTGAACGGGGGG
JAG1-CO03      GGCGACCATTGCGAACGGGATATCGACGAGTGTGCCAGCAACCCCTGCCTGAACGGGGGG
JAG1-CO14      GGCGACCACTGCGAGCGGGACATCGACGAATGCGCCAGCAACCCTTGTCTGAACGGAGGC
JAG1-CO09      GGGGATCACTGTGAGAGGGACATAGATGAGTGCGCGTCCAACCCCTGCCTGAACGGGGGG
JAG1-CO10      GGCGATCACTGCGAGCGGGATATAGACGAGTGTGCCAGCAACCCCTGCCTCAACGGGGGG
JAG1-CO06      GGAGACCATTGCGAGCGAGACATCGACGAGTGTGCCTCGAACCCCTGCCTGAACGGGGGG
               ** **.**.**.**. * **.** **.**.**.**     **.** **..* **.** **

JAG1-WT        CACTGTCAGAATGAAATCAACAGATTCCAGTGTCTGTGTCCCACTGGTTTCTCTGGAAAC
JAG1-CO01      CACTGCCAGAACGAGATCAACAGGTTCCAGTGCCTGTGCCCCACCGGCTTCAGCGGGAAC
JAG1-CO17      CATTGCCAGAACGAGATCAACCGGTTCCAGTGCCTGTGCCCCACCGGCTTCTCCGGCAAC
JAG1-CO11      CACTGCCAGAATGAGATCAATAGGTTCCAATGCCTCTGCCCCACCGGCTTTAGCGGCAAT
JAG1-CO12      CACTGCCAGAACGAGATCAACCGATTCCAGTGTCTGTGCCCCACCGGGTTTAGCGGGAAC
JAG1-CO25      CACTGTCAGAATGAGATCAACCGCTTCCAGTGCCTGTGCCCCACCGGCTTCAGCGGAAAT
JAG1-CO04      CACTGCCAGAACGAGATTAACAGGTTCCAGTGCCTGTGCCCCACCGGCTTCAGCGGCAAT
JAG1-CO18      CACTGCCAGAATGAGATCAACAGGTTTCAGTGCCTGTGCCCCACCGGCTTCAGCGGCAAC
JAG1-CO05      CACTGCCAGAACGAGATCAACAGGTTCCAGTGCCTGTGCCCCACCGGCTTCAGCGGCAAT
JAG1-CO23      CACTGTCAGAATGAGATCAACAGGTTCCAGTGCCTGTGCCCGACGGGATTCTCCGGTAAC
JAG1-CO24      CACTGTCAGAACGAGATCAATAGGTTCCAGTGCCTGTGCCCCACCGGCTTCTCCGGGAAT
JAG1-CO21      CACTGTCAGAACGAGATCAATAGGTTCCAGTGTCTGTGTCCCACCGGCTTCTCCGGCAAC
JAG1-CO22      CACTGCCAGAACGAAATAAACAGGTTCCAGTGTCTGTGCCCGACGGGCTTTAGCGGCAAC
JAG1-CO15      CACTGCCAGAACGAGATCAACCGGTTCCAGTGTCTGTGCCCTACTGGCTTCTCTGGCAAC
JAG1-CO16      CACTGCCAAAATGAAATCAATAGGTTTCAGTGCCTGTGCCCCACCGGGTTCAGCGGCAAC
JAG1-CO07      CACTGCCAGAACGAGATTAACAGGTTCCAGTGCCTGTGCCCCACCGGCTTCAGCGGCAAC
JAG1-CO02      CACTGCCAGAACGAAATCAACAGGTTCCAGTGTCTGTGCCCCACCGGATTCAGCGGAAAC
JAG1-CO20      CACTGCCAGAACGAGATCAATAGGTTCCAGTGCCTGTGCCCGACCGGTTTTAGCGGCAAC
JAG1-CO13      CACTGCCAAAACGAGATCAATCGTTTCCAGTGCCTGTGCCCCACCGGCTTCTCTGGGAAC
JAG1-CO19      CACTGCCAGAACGAGATCAACAGGTTTCAATGCCTGTGCCCCACCGGATTTAGTGGGAAC
JAG1-CO08      CACTGCCAGAACGAGATCAACAGGTTCCAGTGCCTCTGCCCCACCGGGTTCAGCGGGAAC
JAG1-CO03      CACTGCCAGAACGAGATAAACAGGTTCCAGTGCCTGTGCCCCACCGGCTTCAGCGGCAAC
JAG1-CO14      CACTGCCAGAACGAGATCAACAGGTTTCAGTGCCTCTGCCCCACCGGGTTCAGCGGGAAC
JAG1-CO09      CACTGCCAGAACGAGATCAACAGGTTTCAGTGCCTGTGCCCCACCGGCTTCTCCGGCAAC
JAG1-CO10      CACTGCCAGAATGAGATCAACAGATTTCAATGCCTGTGCCCCACAGGATTTAGCGGAAAT
JAG1-CO06      CACTGCCAGAACGAAATCAACAGGTTCCAATGCCTCTGCCCCACCGGGTTCAGCGGCAAC
               **.**.**.**.**.** **. * **.**.**.** **.** ** ** **.  .** **.
```

FIG. 13 (cont)

```
JAG1-WT       CTCTGTCAGCTGGACATCGATTATTGTGAGCCTAATCCCTGCCAGAACGGTGCCCAGTGC
JAG1-CO01     CTGTGCCAGCTGGACATCGACTATTGCGAGCCCAATCCCTGCCAGAACGGGGCGCAGTGC
JAG1-CO17     CTGTGCCAACTAGACATCGACTACTGCGAGCCCAATCCCTGCCAGAACGGCGCCCAATGC
JAG1-CO11     CTGTGCCAGCTGGACATCGATTACTGTGAGCCCAACCCCTGCCAGAATGGAGCCCAGTGC
JAG1-CO12     CTCTGCCAGCTCGATATCGACTACTGCGAACCCAACCCCTGCCAGAACGGCGCCCAGTGC
JAG1-CO25     CTGTGCCAGCTAGACATTGATTACTGCGAACCGAACCCTTGCCAGAACGGCGCCCAGTGC
JAG1-CO04     CTGTGCCAGCTGGATATCGACTACTGCGAGCCCAACCCGTGCCAGAACGGCGCCCAGTGC
JAG1-CO18     CTGTGTCAACTGGACATCGACTATTGTGAGCCCAACCCTTGCCAAAACGGGGCCCAGTGC
JAG1-CO05     CTGTGCCAGCTGGACATCGACTATTGTGAACCCAACCCGTGCCAGAACGGCGCCCAGTGC
JAG1-CO23     CTGTGCCAGCTCGACATCGACTACTGTGAGCCCAACCCCTGTCAAAATGGCGCCCAATGC
JAG1-CO24     CTGTGCCAGCTGGACATCGATTACTGCGAGCCCAACCCCTGCCAGAACGGCGCCCAGTGT
JAG1-CO21     CTGTGTCAGCTGGACATCGACTACTGTGAGCCCAATCCCTGCCAGAATGGCGCCCAGTGC
JAG1-CO22     CTCTGCCAGTTGGATATCGACTATTGCGAGCCTAACCCTTGCCAGAACGGCGCCCAGTGC
JAG1-CO15     CTGTGTCAGCTGGATATCGATTACTGCGAGCCAAACCCATGCCAGAACGGGGCCCAGTGC
JAG1-CO16     CTGTGCCAGCTGGACATCGACTATTGCGAGCCGAACCCCTGCCAGAACGGGGCCCAGTGC
JAG1-CO07     CTGTGCCAGCTGGATATCGACTACTGTGAGCCCAACCCGTGCCAGAACGGCGCCCAGTGC
JAG1-CO02     CTGTGCCAGCTGGACATCGACTATTGCGAACCCAACCCCTGTCAGAACGGCGCCCAGTGC
JAG1-CO20     CTGTGCCAGCTGGACATTGACTATTGCGAGCCCAACCCCTGCCAGAACGGGGCCCAGTGC
JAG1-CO13     CTGTGCCAGCTGGACATCGACTACTGCGAGCCCAACCCCTGCCAGAACGGGGCGCAGTGC
JAG1-CO19     CTCTGTCAGCTGGACATAGACTACTGCGAGCCGAACCCCTGCCAAAACGGCGCGCAGTGC
JAG1-CO08     CTCTGCCAGCTCGACATCGACTACTGCGAGCCCAATCCCTGCCAGAACGGCGCGCAATGC
JAG1-CO03     CTGTGCCAACTCGACATCGACTACTGCGAGCCCAACCCCTGCCAAAACGGTGCCCAATGC
JAG1-CO14     CTGTGCCAGCTTGACATCGATTACTGCGAGCCCAACCCCTGTCAGAATGGGGCGCAGTGC
JAG1-CO09     CTGTGCCAGCTTGACATCGACTACTGCGAGCCCAATCCCTGCCAGAATGGCGCCCAGTGC
JAG1-CO10     CTGTGCCAACTGGACATCGACTACTGCGAGCCCAATCCCTGCCAGAACGGGGCCCAGTGC
JAG1-CO06     CTGTGCCAGCTGGACATCGACTATTGCGAGCCCAACCCCTGCCAGAACGGGGCGCAGTGT
              ** **.**..* **.** **.**.**.**.** **.** **.**.**.** ** **.**.

JAG1-WT       TACAACCGTGCCAGTGACTATTTCTGCAAGTGCCCCGAGGACTATGAGGGCAAGAACTGC
JAG1-CO01     TACAACAGGGCCAGCGACTACTTCTGCAAGTGCCCCGAGGACTACGAGGGCAAGAATTGC
JAG1-CO17     TACAACAGGGCCAGCGACTACTTCTGTAAGTGCCCCGAGGACTACGAGGGCAAGAACTGC
JAG1-CO11     TACAACCGGGCCTCCGACTATTTCTGTAAGTGTCCCGAAGACTACGAGGGTAAGAACTGC
JAG1-CO12     TACAACCGGGCCAGCGACTATTTCTGTAAATGCCCCGAGGACTACGAGGGGAAAAACTGT
JAG1-CO25     TACAACAGGGCCAGCGACTACTTTGCAAGTGCCCCGAGGACTACGAGGGGAAGAATTGC
JAG1-CO04     TACAACAGGGCCTCCGACTACTTCTGTAAGTGTCCCGAGGACTATGAGGGCAAGAACTGT
JAG1-CO18     TACAACCGGGCCAGCGATTACTTCTGCAAGTGCCCCGAGGACTACGAAGGCAAGAACTGC
JAG1-CO05     TACAACCGCGCCTCCGACTACTTCTGCAAGTGCCCGGAGGACTACGAGGGCAAGAACTGC
JAG1-CO23     TACAACCGGGCCTCCGACTACTTCTGTAAGTGCCCCGAGGATTACGAGGGTAAGAACTGT
JAG1-CO24     TACAACAGGGCCAGCGATTACTTCTGCAAGTGTCCCGAAGACTATGAGGGCAAGAATTGC
JAG1-CO21     TATAACCGGGCCTCCGACTACTTTTGCAAGTGCCCCGAAGATTACGAGGGCAAGAACTGC
JAG1-CO22     TATAACCGCGCAAGCGATTATTTCTGCAAATGCCCCGAGGACTACGAGGGCAAGAATTGC
JAG1-CO15     TACAATAGGGCCTCCGACTATTTTTGCAAGTGCCCCGAGGACTACGAGGGTAAGAACTGT
JAG1-CO16     TACAATAGGGCCAGCGATTATTTCTGCAAGTGTCCCGAGGACTACGAGGGAAAAAACTGC
JAG1-CO07     TACAACCGAGCCAGCGATTATTTTTGCAAATGTCCCGAGGATTACGAAGGGAAGAATTGC
JAG1-CO02     TACAACCGGGCAAGCGACTACTTCTGCAAGTGCCCTGAGGACTACGAGGGCAAGAACTGC
JAG1-CO20     TACAACAGGGCCTCGGACTACTTCTGTAAGTGCCCCGAGGACTATGAGGGCAAGAACTGC
JAG1-CO13     TATAACCGGGCCTCCGATTACTTCTGCAAGTGCCCCGAGGACTATGAGGGAAAAAACTGC
JAG1-CO19     TACAACAGGGCCAGCGATTACTTCTGCAAGTGCCCGGAGGACTACGAGGGGAAGAACTGC
JAG1-CO08     TACAATAGGGCCTCGGACTACTTCTGCAAGTGCCCCGAGGACTACGAGGGCAAAAACTGC
JAG1-CO03     TACAACCGGGCCTCGGACTACTTTTGCAAGTGCCCGGAGGACTATGAGGGCAAGAATTGT
JAG1-CO14     TACAACCGAGCTTCCGATTACTTCTGCAAGTGCCCCGAGGATTACGAGGGTAAAAATTGC
JAG1-CO09     TACAACAGGGCCAGCGACTATTTCTGCAAGTGTCCCGAGGACTACGAGGGGAAGAATTGC
JAG1-CO10     TACAACCGGGCCAGCGACTACTTTTGCAAGTGCCCCGAGGACTACGAGGGAAAAAACTGC
JAG1-CO06     TATAACCGGGCCTCGGACTACTTCTGTAAGTGTCCCGAGGACTACGAGGGCAAAAACTGC
              **.**. * **    **.**.**.**.**.**.** **.**.**.**.** **.**.**.
```

FIG. 13 (cont)

```
JAG1-WT       TCACACCTGAAAGACCACTGCCGCACGACCCCCTGTGAAGTGATTGACAGCTGCACAGTG
JAG1-CO01     AGCCACCTGAAAGACCACTGCCGCACCACCCCCTGTGAGGTTATCGACAGCTGTACGGTC
JAG1-CO17     TCCCATCTGAAGGACCACTGCCGGACCACCCCCTGCGAAGTGATCGACAGCTGCACCGTG
JAG1-CO11     TCCCACCTGAAGGACCACTGCCGGACCACTCCGTGCGAGGTCATCGACAGCTGCACCGTC
JAG1-CO12     AGCCACCTGAAGGACCACTGCAGGACCACACCCTGCGAAGTGATCGACAGCTGCACCGTG
JAG1-CO25     TCCCACCTAAAGGACCACTGCCGGACCACCCCCTGCGAGGTGATCGACAGCTGCACCGTC
JAG1-CO04     TCCCACCTGAAAGACCACTGCAGGACCACCCCCTGCGAGGTGATCGACTCGTGCACCGTG
JAG1-CO18     AGCCACCTGAAGGACCACTGTCGGACCACCCCCTGCGAAGTGATCGACAGCTGCACCGTG
JAG1-CO05     AGCCATCTGAAGGACCACTGTAGAACCACGCCCTGCGAGGTGATCGACTCCTGCACCGTC
JAG1-CO23     AGCCATCTGAAGGACCACTGCAGGACTACCCCGTGCGAGGTGATCGACTCCTGCACCGTC
JAG1-CO24     AGCCATCTGAAAGACCACTGCCGCACCACCCCCTGTGAGGTGATCGACTCGTGCACCGTG
JAG1-CO21     AGCCATCTGAAGGACCACTGCAGGACGACTCCCTGCGAGGTGATCGACAGCTGTACTGTC
JAG1-CO22     AGCCATCTGAAAGACCACTGTCGGACGACCCCCTGCGAGGTGATCGACAGCTGCACCGTG
JAG1-CO15     TCCCATCTCAAGGACCACTGTCGAACCACCCCCTGCGAGGTGATCGACAGCTGCACCGTG
JAG1-CO16     AGCCACCTCAAGGACCACTGTAGGACCACGCCCTGCGAAGTGATCGACTCCTGCACCGTG
JAG1-CO07     AGCCACCTGAAGGACCATTGCAGGACCACCCCCTGCGAAGTGATCGACAGCTGCACCGTG
JAG1-CO02     AGCCACCTCAAGGACCACTGCAGGACGACCCCCTGTGAGGTGATCGACAGCTGTACCGTG
JAG1-CO20     AGCCATCTGAAGGACCACTGCAGGACCACCCCGTGCGAGGTCATCGACAGCTGCACCGTG
JAG1-CO13     TCCCACCTGAAGGATCACTGTAGGACCACCCCCTGTGAGGTGATCGACAGCTGCACCGTG
JAG1-CO19     TCCCACCTGAAGGACCACTGCAGGACCACCCCCTGCGAGGTGATCGACTCGTGCACCGTC
JAG1-CO08     AGCCACCTGAAGGACCACTGTAGGACAACCCCCTGCGAAGTCATCGACTCCTGCACCGTG
JAG1-CO03     TCCCACCTCAAGGACCACTGCCGGACCACCCCCTGCGAGGTGATCGACTCCTGCACCGTG
JAG1-CO14     AGCCACCTGAAGGATCACTGCAGGACCACCCCGTGCGAGGTGATAGACAGCTGCACCGTG
JAG1-CO09     TCCCACCTGAAAGACCACTGCAGGACGACCCCCTGTGAGGTGATCGACAGCTGCACCGTG
JAG1-CO10     AGCCACCTGAAGGACCATTGCAGGACCACCCCCTGTGAGGTGATTGACAGCTGCACCGTG
JAG1-CO06     TCCCACCTGAAGGACCACTGCCGTACCACACCCTGCGAAGTCATCGACTCCTGCACCGTG
                 **.** **.**.**.**. * ** ** ** **.**.** ** ***   **.** **

JAG1-WT       GCCATGGCTTCCAACGACACACCTGAAGGGGTGCGGTATATTTCCTCCAACGTCTGTGGT
JAG1-CO01     GCCATGGCCTCGAACGACACCCCCGAAGGCGTGAGGTATATCTCCAGCAACGTGTGCGGG
JAG1-CO17     GCCATGGCCAGCAATGACACCCCCGAGGGCGTGAGGTATATCAGCAGCAACGTGTGCGGG
JAG1-CO11     GCCATGGCCAGCAATGACACACCCGAGGGCGTGAGGTACATCTCCTCCAACGTGTGTGGC
JAG1-CO12     GCCATGGCCAGCAATGACACCCCCGAAGGCGTGAGGTATATAAGCAGCAACGTATGCGGC
JAG1-CO25     GCGATGGCCAGCAACGACACCCCCGAGGGCGTCAGGTACATCTCCAGCAACGTGTGCGGT
JAG1-CO04     GCCATGGCGAGCAATGACACCCCGGAAGGCGTGCGCTATATCAGCAGCAATGTGTGCGGG
JAG1-CO18     GCCATGGCCAGCAACGACACCCCCGAGGGCGTGAGGTACATCAGCAGCAATGTGTGTGGC
JAG1-CO05     GCCATGGCCTCAAACGACACCCCCGAGGGAGTGCGCTACATCAGCTCGAACGTGTGCGGC
JAG1-CO23     GCCATGGCCTCCAACGACACCCCCGAGGGCGTGCGGTACATCAGCAGCAACGTGTGTGGG
JAG1-CO24     GCGATGGCCAGCAATGACACCCCGGAGGGCGTGCGGTACATCAGCAGCAACGTGTGTGGG
JAG1-CO21     GCCATGGCCAGCAACGACACCCCCGAGGGGGTCCGCTATATCAGCAGCAACGTGTGCGGG
JAG1-CO22     GCCATGGCCTCCAACGACACCCCCGAAGGGGTGCGCTATATCTCCAGCAACGTGTGCGGC
JAG1-CO15     GCCATGGCCAGCAATGACACCCCCGAGGGCGTGCGGTACATCTCCAGCAACGTGTGCGGC
JAG1-CO16     GCCATGGCCAGCAACGACACCCCCGAGGGCGTGCGCTACATCAGCAGCAACGTGTGTGGC
JAG1-CO07     GCCATGGCCTCGAATGACACGCCCGAGGGAGTGAGGTACATCAGTAGCAATGTGTGCGGC
JAG1-CO02     GCCATGGCCTCGAACGACACCCCTGAGGGCGTGAGGTATATCTCCAGCAACGTCTGCGGC
JAG1-CO20     GCCATGGCCTCCAATGATACCCCCGAGGGCGTGAGGTACATCTCCTCCAACGTGTGTGGC
JAG1-CO13     GCCATGGCCAGCAACGACACCCCCGAGGGCGTGCGCTACATCAGCTCCAACGTGTGCGGC
JAG1-CO19     GCCATGGCCTCAAACGACACCCCCGAGGGGGTCCGCTACATCTCGAGCAACGTCTGTGGC
JAG1-CO08     GCCATGGCCTCCAACGACACCCCAGAAGGCGTACGTTACATCAGCTCCAACGTCTGCGGG
JAG1-CO03     GCCATGGCTAGTAACGATACCCCCGAGGGCGTTAGGTACATCTCCTCCAACGTGTGCGGC
JAG1-CO14     GCCATGGCCAGCAACGACACCCCCGAGGGCGTGCGATACATCAGCAGCAACGTGTGCGGC
JAG1-CO09     GCCATGGCCTCCAACGACACCCCCGAGGGCGTGAGGTACATCAGCAGCAACGTCTGCGGC
JAG1-CO10     GCCATGGCCTCAAACGACACCCCCGAGGGTGTGAGGTATATCAGCTCGAACGTGTGCGGC
JAG1-CO06     GCCATGGCCAGCAACGACACCCCCGAGGGAGTGCGGTACATCAGCAGCAACGTGTGCGGG
              ** *****    **.**.** ** **.** **  * **.**       **.** **.**
```

FIG. 13 (cont)

```
JAG1-WT         CCTCACGGGAAGTGCAAGAGTCAGTCGGGAGGCAAATTCACCTGTGACTGTAACAAAGGC
JAG1-CO01       CCACACGGCAAATGTAAGTCCCAGAGCGGCGGGAAGTTCACCTGCGACTGCAACAAGGGC
JAG1-CO17       CCCCACGGGAAATGCAAGAGCCAGAGCGGCGGCAAGTTCACATGCGACTGTAACAAGGGC
JAG1-CO11       CCCCACGGCAAGTGCAAGAGCCAGAGCGGAGGCAAGTTCACCTGCGACTGCAACAAGGGG
JAG1-CO12       CCCCACGGCAAGTGTAAGAGCCAGAGCGGCGGCAAGTTTACGTGCGACTGCAACAAAGGC
JAG1-CO25       CCCCATGGCAAATGCAAGAGCCAGAGCGGGGGGAAGTTTACCTGCGACTGCAACAAGGGC
JAG1-CO04       CCCCACGGCAAGTGCAAGAGCCAGAGCGGCGGGAAGTTCACCTGCGACTGCAACAAGGGC
JAG1-CO18       CCGCACGGCAAGTGCAAGAGCCAGAGCGGCGGCAAGTTCACGTGCGACTGCAACAAGGGC
JAG1-CO05       CCCCATGGAAAATGCAAGAGCCAGTCCGGGGGCAAGTTCACCTGCGACTGCAACAAGGGC
JAG1-CO23       CCGCACGGCAAGTGCAAGAGCCAGAGCGGGGGCAAGTTCACCTGTGATTGCAACAAGGGC
JAG1-CO24       CCCCACGGCAAGTGCAAGTCCCAGAGCGGGGGCAAGTTCACCTGCGACTGCAACAAAGGC
JAG1-CO21       CCCCATGGGAAATGCAAATCCCAGTCAGGGGGCAAGTTTACCTGCGACTGTAACAAAGGC
JAG1-CO22       CCCCACGGCAAGTGCAAGAGCCAGTCAGGGGGCAAATTCACCTGCGACTGCAACAAGGGC
JAG1-CO15       CCCCACGGCAAGTGCAAGAGCCAGTCCGGCGGCAAATTTACCTGCGATTGCAACAAGGGG
JAG1-CO16       CCTCACGGCAAATGCAAGAGCCAAAGCGGCGGCAAGTTCACCTGTGACTGCAATAAGGGC
JAG1-CO07       CCCCATGGGAAGTGCAAGAGCCAGTCGGGCGGAAAGTTTACCTGCGACTGTAACAAGGGC
JAG1-CO02       CCCCACGGCAAATGTAAGAGCCAATCCGGGGGCAAGTTCACCTGCGACTGCAACAAGGGA
JAG1-CO20       CCCCACGGCAAGTGCAAAAGCCAGAGCGGCGGCAAGTTCACCTGTGACTGTAACAAGGGC
JAG1-CO13       CCCCATGGTAAGTGTAAGTCGCAGAGCGGCGGGAAGTTCACCTGCGACTGCAACAAGGGC
JAG1-CO19       CCCCACGGCAAGTGCAAGAGCCAGAGCGGGGGGAAGTTCACCTGCGACTGCAACAAAGGC
JAG1-CO08       CCCCACGGGAAGTGCAAGAGCCAGAGCGGCGGCAAGTTCACGTGTGACTGCAACAAAGGG
JAG1-CO03       CCCCACGGGAAGTGCAAGTCGCAGAGCGGCGGCAAGTTCACCTGCGACTGCAATAAGGGC
JAG1-CO14       CCCCACGGCAAGTGCAAAAGCCAGAGCGGCGGAAAATTCACATGCGACTGCAACAAGGGG
JAG1-CO09       CCCCACGGCAAGTGCAAGAGCCAGAGCGGCGGAAAGTTCACCTGCGACTGCAACAAGGGG
JAG1-CO10       CCCCACGGCAAGTGCAAGTCACAAAGCGGGGGAAAGTTCACCTGCGACTGCAACAAGGGC
JAG1-CO06       CCGCATGGCAAGTGTAAGTCCCAGAGCGGGGGCAAGTTTACATGTGACTGTAACAAGGGC
                ** **.** **.**.**.   **.   ** ** **.**.** **.**.**.**.**.**

JAG1-WT         TTCACGGGAACATACTGCCATGAAAATATTAATGACTGTGAGAGCAACCCTTGTAGAAAC
JAG1-CO01       TTCACAGGCACGTACTGCCATGAGAACATCAACGATTGTGAGAGCAACCCCTGCAGGAAC
JAG1-CO17       TTCACGGGAACCTACTGTCACGAGAACATCAACGACTGCGAGAGCAACCCCTGCCGCAAC
JAG1-CO11       TTCACCGGCACTTACTGCCACGAGAACATCAACGACTGCGAATCCAACCCCTGTCGAAAC
JAG1-CO12       TTCACCGGCACCTACTGTCACGAGAACATCAACGACTGCGAGAGCAACCCCTGCCGCAAC
JAG1-CO25       TTCACCGGGACCTACTGCCATGAGAACATCAATGACTGCGAGAGCAACCCCTGCAGGAAC
JAG1-CO04       TTCACCGGCACGTACTGCCACGAGAACATCAACGATTGCGAGTCCAACCCCTGCCGGAAC
JAG1-CO18       TTTACCGGCACCTACTGCCACGAAAACATCAATGACTGCGAGAGCAACCCGTGTCGGAAC
JAG1-CO05       TTCACCGGCACGTATTGCCATGAGAACATCAATGACTGCGAGAGCAACCCGTGCCGTAAC
JAG1-CO23       TTCACCGGGACGTATTGCCACGAGAACATCAACGACTGCGAGAGCAACCCCTGCAGGAAC
JAG1-CO24       TTTACAGGGACATATTGCCACGAAAACATCAATGACTGCGAGAGCAACCCCTGCCGCAAT
JAG1-CO21       TTCACCGGCACCTACTGCCACGAAAACATCAACGACTGCGAATCGAACCCCTGCCGGAAC
JAG1-CO22       TTCACCGGGACCTACTGCCACGAGAACATCAACGACTGCGAGAGCAACCCCTGCCGGAAC
JAG1-CO15       TTCACCGGCACCTACTGTCACGAGAACATCAATGACTGCGAATCCAATCCCTGCAGGAAC
JAG1-CO16       TTCACCGGCACCTACTGTCACGAGAACATCAACGACTGCGAGAGCAACCCCTGCAGAAAC
JAG1-CO07       TTCACCGGGACCTACTGTCACGAAAACATCAACGACTGCGAGTCCAACCCGTGTAGGAAC
JAG1-CO02       TTTACCGGCACCTACTGCCACGAGAACATCAACGACTGCGAGTCCAATCCCTGCCGTAAC
JAG1-CO20       TTCACCGGCACCTACTGCCATGAAAACATCAACGATTGCGAGTCTAATCCCTGCCGGAAC
JAG1-CO13       TTTACGGGGACCTACTGTCATGAAAACATCAACGACTGCGAGAGCAACCCCTGTCGCAAC
JAG1-CO19       TTCACCGGCACGTACTGTCACGAGAACATCAATGATTGCGAGAGCAACCCCTGCCGGAAC
JAG1-CO08       TTCACCGGCACCTACTGCCATGAGAACATAAATGACTGCGAGTCCAACCCCTGTCGGAAC
JAG1-CO03       TTCACCGGTACCTACTGCCACGAGAACATCAACGACTGCGAGAGCAATCCCTGCCGGAAC
JAG1-CO14       TTCACGGGCACCTATTGCCACGAGAACATCAACGACTGCGAGTCCAACCCGTGCCGGAAT
JAG1-CO09       TTCACGGGCACCTACTGCCACGAGAACATCAACGACTGCGAGTCCAACCCCTGCAGGAAC
JAG1-CO10       TTCACCGGTACCTACTGCCACGAGAACATCAACGACTGTGAGAGCAACCCCTGTAGAAAC
JAG1-CO06       TTCACCGGCACATACTGCCACGAGAACATCAACGATTGCGAGAGCAACCCCTGCCGGAAT
                **.** ** ** **.**.**.**.**.** **.**.**.**.   **.** **. * **.
```

FIG. 13 (cont)

```
JAG1-WT      GGTGGCACTTGCATCGATGGTGTCAACTCCTACAAGTGCATCTGTAGTGACGGCTGGGAG
JAG1-CO01    GGCGGGACCTGCATAGACGGCGTGAACAGCTATAAGTGCATCTGCAGCGATGGCTGGGAG
JAG1-CO17    GGCGGCACCTGCATCGACGGCGTGAACTCCTATAAGTGCATCTGTAGCGATGGCTGGGAA
JAG1-CO11    GGGGGCACCTGCATTGACGGCGTGAACAGCTATAAGTGCATCTGCTCCGACGGGTGGGAG
JAG1-CO12    GGGGGCACCTGCATCGACGGTGTGAACAGCTACAAGTGCATCTGCAGCGACGGCTGGGAG
JAG1-CO25    GGCGGGACATGCATCGACGGGGTGAACTCCTATAAGTGCATCTGCTCCGACGGGTGGGAA
JAG1-CO04    GGCGGCACCTGCATAGATGGAGTGAACTCCTATAAGTGCATCTGCTCCGATGGGTGGGAG
JAG1-CO18    GGCGGCACCTGCATCGACGGGGTGAACAGCTACAAGTGCATATGCAGCGACGGCTGGGAG
JAG1-CO05    GGGGGCACCTGTATCGATGGCGTGAACAGCTACAAGTGCATCTGTAGCGACGGCTGGGAG
JAG1-CO23    GGGGGGACCTGCATAGACGGCGTGAACAGCTACAAATGCATCTGCAGCGATGGGTGGGAG
JAG1-CO24    GGCGGCACTTGCATCGACGGCGTGAACAGCTACAAATGTATCTGCTCAGACGGGTGGGAA
JAG1-CO21    GGCGGGACCTGCATCGATGGAGTGAACAGCTACAAGTGCATCTGCAGCGACGGGTGGGAG
JAG1-CO22    GGCGGCACCTGCATCGATGGGGTGAACTCCTATAAGTGCATCTGTAGCGATGGATGGGAG
JAG1-CO15    GGTGGCACGTGCATCGACGGGGTGAATAGCTATAAGTGCATCTGCAGCGACGGGTGGGAA
JAG1-CO16    GGTGGCACCTGTATAGATGGCGTGAACAGCTACAAGTGCATCTGCAGCGACGGATGGGAA
JAG1-CO07    GGCGGGACCTGCATAGACGGGGTGAATAGCTATAAGTGCATCTGTTCAGACGGATGGGAG
JAG1-CO02    GGCGGCACCTGCATCGACGGTGTCAACAGCTACAAGTGCATCTGCAGCGACGGCTGGGAG
JAG1-CO20    GGCGGCACCTGCATCGATGGCGTGAACAGCTATAAATGTATCTGCTCCGATGGGTGGGAG
JAG1-CO13    GGCGGCACCTGCATCGATGGCGTCAACAGCTACAAGTGCATCTGCTCCGACGGATGGGAG
JAG1-CO19    GGCGGCACCTGCATCGACGGCGTGAACAGCTACAAGTGCATCTGTAGCGACGGCTGGGAG
JAG1-CO08    GGCGGCACCTGCATCGACGGCGTAAACTCTTACAAATGTATCTGCAGCGACGGCTGGGAG
JAG1-CO03    GGGGGTACCTGCATCGACGGCGTGAACTCCTACAAGTGTATCTGCTCAGATGGCTGGGAA
JAG1-CO14    GGCGGCACCTGCATCGACGGCGTGAACTCCTATAAGTGTATCTGCTCGGACGGCTGGGAG
JAG1-CO09    GGCGGCACGTGCATAGACGGGGTTAACAGCTATAAGTGTATCTGCTCGGACGGGTGGGAA
JAG1-CO10    GGGGGGACCTGCATCGACGGAGTGAATTCCTATAAGTGCATCTGTAGCGACGGGTGGGAG
JAG1-CO06    GGGGGCACCTGCATCGACGGGGTGAACAGCTATAAGTGTATCTGCTCCGATGGCTGGGAG
             ** ** ** **.** **.** ** **.  .**.**.**.** **.   **.** *****.

JAG1-WT      GGGGCCTACTGTGAAACCAATATTAATGACTGCAGCCAGAACCCCTGCCACAATGGGGGC
JAG1-CO01    GGAGCCTACTGCGAAACCAACATCAATGACTGCAGCCAGAACCCCTGTCACAACGGGGGC
JAG1-CO17    GGGGCCTACTGCGAGACCAACATAAACGACTGCAGCCAGAATCCCTGCCATAACGGGGGC
JAG1-CO11    GGGGCCTACTGCGAAACCAATATAAACGATTGCAGCCAGAACCCCTGTCACAACGGGGGC
JAG1-CO12    GGCGCCTACTGTGAGACGAACATCAACGACTGCAGCCAGAACCCGTGCCATAACGGGGGC
JAG1-CO25    GGTGCCTATTGCGAGACAAACATCAACGACTGCAGCCAAAACCCCTGCCACAACGGGGGC
JAG1-CO04    GGCGCCTACTGTGAAACCAACATCAACGACTGCAGCCAGAACCCCTGCCATAATGGTGGC
JAG1-CO18    GGCGCCTACTGTGAAACCAACATCAACGACTGCAGCCAGAACCCCTGCCACAATGGCGGG
JAG1-CO05    GGCGCCTATTGCGAAACCAACATCAACGACTGTTCCCAGAACCCATGCCACAACGGGGGC
JAG1-CO23    GGCGCCTACTGTGAGACCAACATTAACGACTGCAGCCAGAACCCCTGCCACAACGGGGGT
JAG1-CO24    GGCGCGTATTGCGAGACCAACATCAACGATTGTAGCCAGAATCCCTGCCATAACGGTGGT
JAG1-CO21    GGCGCGTACTGCGAAACCAATATCAATGACTGCAGCCAGAACCCCTGCCATAACGGAGGC
JAG1-CO22    GGGGCCTACTGCGAAACCAACATCAACGACTGCAGCCAGAACCCCTGCCACAACGGGGGC
JAG1-CO15    GGGGCCTACTGCGAGACCAACATCAACGACTGTAGCCAGAACCCGTGCCACAATGGCGGC
JAG1-CO16    GGCGCCTACTGTGAGACCAACATTAACGACTGCAGCCAGAACCCCTGCCACAATGGCGGC
JAG1-CO07    GGGGCCTACTGCGAGACCAACATCAACGATTGCTCGCAGAACCCCTGCCACAACGGCGGC
JAG1-CO02    GGAGCGTACTGCGAAACCAACATAAACGATTGTTCCCAGAACCCCTGCCACAACGGCGGC
JAG1-CO20    GGCGCATACTGCGAAACCAACATCAACGACTGCTCCCAGAACCCCTGCCATAACGGCGGC
JAG1-CO13    GGCGCCTACTGCGAGACCAACATCAACGACTGCAGCCAGAACCCGTGCCACAATGGCGGC
JAG1-CO19    GGGGCCTACTGCGAGACCAACATCAACGACTGCAGCCAGAACCCCTGTCACAACGGCGGC
JAG1-CO08    GGCGCCTACTGCGAGACCAACATCAACGACTGCAGCCAAAACCCCTGTCACAACGGCGGG
JAG1-CO03    GGCGCGTACTGTGAGACCAACATAAACGACTGTAGCCAGAACCCCTGTCATAACGGGGGC
JAG1-CO14    GGGGCCTATTGCGAGACCAACATCAACGACTGCAGCCAGAACCCCTGCCACAACGGCGGC
JAG1-CO09    GGCGCCTACTGCGAGACCAACATCAACGACTGCTCACAGAATCCGTGCCACAACGGGGGC
JAG1-CO10    GGCGCCTACTGCGAGACCAATATCAACGATTGCAGCCAGAACCCCTGCCACAACGGGGGC
JAG1-CO06    GGCGCCTACTGCGAGACTAACATCAATGACTGCTCGCAGAACCCGTGCCACAACGGGGGA
             ** ** **.**.**.** **.** **.**.**.   **.**.** **.**.**.** **
```

FIG. 13 (cont)

```
JAG1-WT      ACGTGTCGCGACCTGGTCAATGACTTCTACTGTGACTGTAAAAATGGGTGGAAAGGAAAG
JAG1-CO01    ACATGCCGGGACCTGGTGAATGATTTCTACTGCGACTGCAAGAATGGCTGGAAGGGCAAG
JAG1-CO17    ACCTGTCGTGACCTGGTCAACGACTTCTACTGCGACTGTAAGAACGGATGGAAGGGTAAG
JAG1-CO11    ACATGCAGGGACCTGGTCAACGACTTCTACTGTGACTGCAAGAACGGCTGGAAGGGCAAG
JAG1-CO12    ACCTGCAGGGATCTGGTGAACGACTTTTATTGCGACTGCAAGAACGGCTGGAAGGGCAAG
JAG1-CO25    ACCTGCAGGGATCTGGTGAACGACTTCTACTGTGACTGCAAGAACGGGTGGAAGGGAAAG
JAG1-CO04    ACGTGCCGGGACCTGGTTAATGACTTCTACTGCGACTGCAAGAACGGCTGGAAGGGCAAG
JAG1-CO18    ACCTGCAGGGACCTGGTGAATGACTTCTACTGCGACTGCAAGAACGGCTGGAAGGGCAAA
JAG1-CO05    ACCTGTAGGGACCTGGTCAACGACTTTTACTGTGACTGCAAGAACGGTTGGAAAGGCAAG
JAG1-CO23    ACCTGTCGCGACCTGGTGAACGACTTCTACTGTGACTGCAAGAACGGCTGGAAGGGCAAG
JAG1-CO24    ACCTGCCGGGATCTGGTGAACGACTTCTATTGCGACTGCAAGAACGGCTGGAAGGGCAAG
JAG1-CO21    ACCTGCAGGGACCTGGTGAACGACTTCTACTGCGATTGCAAGAACGGCTGGAAGGGGAAG
JAG1-CO22    ACCTGCAGGGACCTCGTGAACGACTTCTACTGCGACTGCAAGAACGGCTGGAAGGGCAAG
JAG1-CO15    ACTTGTAGGGATCTCGTGAATGACTTCTATTGCGACTGCAAAAATGGATGGAAGGGGAAG
JAG1-CO16    ACCTGCCGCGACCTGGTCAATGACTTTTACTGCGACTGTAAGAACGGGTGGAAGGGCAAG
JAG1-CO07    ACCTGCCGGGACCTGGTGAACGACTTCTACTGCGACTGTAAAAACGGCTGGAAGGGGAAG
JAG1-CO02    ACCTGCCGGGACCTTGTGAACGACTTTTACTGTGACTGCAAGAATGGGTGGAAGGGCAAA
JAG1-CO20    ACCTGCCGCGACCTCGTCAACGATTTCTACTGCGACTGCAAGAACGGCTGGAAGGGCAAG
JAG1-CO13    ACCTGCCGTGACCTGGTGAACGACTTTTACTGCGACTGCAAGAACGGGTGGAAAGGCAAA
JAG1-CO19    ACCTGCAGGGACCTCGTGAATGACTTCTACTGCGACTGCAAAAACGGGTGGAAAGGTAAA
JAG1-CO08    ACCTGCCGCGACCTCGTCAACGACTTCTACTGCGACTGCAAGAACGGCTGGAAGGGCAAG
JAG1-CO03    ACCTGCAGGGACCTGGTGAACGACTTCTACTGCGACTGCAAGAACGGGTGGAAAGGCAAA
JAG1-CO14    ACCTGCAGGGACCTGGTGAACGACTTCTATTGCGACTGCAAGAACGGCTGGAAGGGCAAG
JAG1-CO09    ACCTGCAGGGACCTGGTGAACGACTTCTATTGCGACTGCAAGAACGGCTGGAAAGGTAAG
JAG1-CO10    ACCTGCCGAGATCTCGTGAACGACTTCTACTGCGACTGTAAAAACGGTTGGAAAGGCAAA
JAG1-CO06    ACCTGCAGGGATCTCGTGAACGACTTCTACTGCGACTGCAAGAACGGGTGGAAGGGGAAG
             ** **. * **.** ** **.**.**.**.**.**.**.**.**.** *****.** **.

JAG1-WT      ACCTGCCACTCACGTGACAGTCAGTGTGATGAGGCCACGTGCAACAACGGTGGCACCTGC
JAG1-CO01    ACCTGCCACAGCAGGGACTCCCAGTGTGACGAGGCCACCTGCAATAACGGGGGCACCTGC
JAG1-CO17    ACCTGCCACTCCAGGGACTCCCAGTGTGACGAAGCCACCTGCAACAACGGAGGCACCTGC
JAG1-CO11    ACATGTCACAGCAGGGACAGCCAGTGCGACGAGGCCACCTGTAACAATGGCGGCACCTGC
JAG1-CO12    ACCTGCCACAGCCGGGACAGCCAGTGTGACGAGGCCACCTGCAACAACGGCGGCACCTGC
JAG1-CO25    ACCTGTCACAGCCGGGACTCCCAGTGCGACGAGGCCACATGCAACAACGGCGGCACGTGC
JAG1-CO04    ACCTGCCACAGCAGAGATAGCCAGTGCGACGAGGCCACGTGCAACAATGGCGGGACCTGC
JAG1-CO18    ACCTGCCACAGCAGGGACAGCCAGTGCGACGAGGCCACCTGCAACAACGGCGGCACCTGC
JAG1-CO05    ACCTGCCACTCGAGGGACAGCCAGTGTGACGAGGCCACGTGCAACAATGGCGGCACCTGT
JAG1-CO23    ACCTGTCATTCCCGCGACAGCCAGTGCGACGAAGCCACCTGCAACAACGGCGGCACCTGC
JAG1-CO24    ACCTGCCATTCGAGGGATAGCCAGTGCGACGAGGCCACCTGCAACAACGGCGGCACCTGC
JAG1-CO21    ACCTGCCATAGCAGGGACAGCCAGTGTGACGAGGCCACCTGCAACAACGGCGGCACATGT
JAG1-CO22    ACATGCCACTCCCGGGACTCACAATGCGACGAAGCGACCTGCAACAATGGCGGCACCTGT
JAG1-CO15    ACCTGCCACTCCCGGGACTCCCAGTGCGACGAGGCCACCTGCAATAACGGCGGTACCTGC
JAG1-CO16    ACCTGCCATAGCCGCGACTCCCAGTGCGACGAGGCAACCTGCAACAACGGCGGCACCTGT
JAG1-CO07    ACCTGCCACTCCAGGGACAGCCAGTGCGACGAGGCGACCTGCAACAACGGCGGCACCTGC
JAG1-CO02    ACGTGCCACAGCAGAGACAGCCAGTGCGACGAAGCCACCTGTAACAACGGCGGCACCTGC
JAG1-CO20    ACCTGCCACAGCCGAGACAGCCAGTGCGACGAGGCCACGTGCAACAACGGAGGGACCTGT
JAG1-CO13    ACCTGCCACTCCAGGGACAGCCAGTGCGACGAGGCGACCTGCAACAATGGCGGGACGTGC
JAG1-CO19    ACCTGCCATAGCCGGGACAGCCAGTGCGACGAGGCCACCTGTAATAACGGCGGCACCTGC
JAG1-CO08    ACCTGCCACAGCCGGGACTCGCAGTGTGATGAGGCCACCTGCAACAATGGCGGCACCTGC
JAG1-CO03    ACTTGCCACTCCAGGGACTCCCAGTGCGATGAGGCCACCTGCAATAACGGCGGCACGTGC
JAG1-CO14    ACCTGTCACTCCAGGGACAGCCAGTGCGACGAGGCCACCTGTAACAACGGCGGGACCTGT
JAG1-CO09    ACATGCCACTCCCGGGACTCCCAGTGCGACGAGGCCACCTGCAACAACGGAGGAACCTGC
JAG1-CO10    ACCTGCCACTCCCGCGATTCCCAGTGCGATGAGGCGACCTGCAATAATGGAGGCACCTGC
JAG1-CO06    ACCTGCCACAGCCGCGACTCCCAGTGCGACGAGGCCACCTGCAACAATGGGGGCACCTGC
             ** **.**.    * **.   **.**.**.**.** ** **.**.**.** ** ** **.
```

FIG. 13 (cont)

```
JAG1-WT      TATGATGAGGGGGATGCTTTTAAGTGCATGTGTCCTGGCGGCTGGGAAGGAACAACCTGT
JAG1-CO01    TACGACGAGGGCGACGCCTTTAAGTGCATGTGCCCCGGCGGTTGGGAGGGTACCACCTGC
JAG1-CO17    TACGACGAGGGTGACGCCTTTAAGTGCATGTGCCCCGGTGGCTGGGAGGGGACCACGTGC
JAG1-CO11    TATGACGAAGGCGACGCCTTCAAATGTATGTGCCCCGGCGGTTGGGAGGGGACGACGTGC
JAG1-CO12    TACGACGAAGGGGACGCCTTTAAGTGCATGTGCCCGGGCGGGTGGGAGGGCACCACCTGC
JAG1-CO25    TACGACGAAGGAGACGCCTTTAAGTGCATGTGCCCCGGCGGCTGGGAGGGCACCACCTGC
JAG1-CO04    TACGACGAGGGGGACGCCTTCAAATGCATGTGCCCCGGCGGATGGGAGGGGACCACCTGC
JAG1-CO18    TATGACGAGGGCGACGCCTTCAAGTGCATGTGCCCCGGCGGATGGGAGGGCACGACCTGC
JAG1-CO05    TACGACGAGGGCGACGCCTTTAAGTGCATGTGTCCCGGGGGTTGGGAGGGTACCACCTGT
JAG1-CO23    TACGACGAGGGCGATGCCTTCAAGTGCATGTGCCCGGGCGGCTGGGAGGGGACCACCTGT
JAG1-CO24    TACGACGAGGGCGATGCCTTCAAGTGCATGTGCCCTGGCGGCTGGGAGGGCACCACCTGC
JAG1-CO21    TACGATGAGGGCGACGCCTTCAAATGCATGTGCCCCGGCGGCTGGGAGGGCACCACATGC
JAG1-CO22    TACGATGAGGGGGATGCCTTTAAGTGCATGTGCCCCGGTGGCTGGGAGGGCACCACCTGC
JAG1-CO15    TACGACGAGGGCGATGCCTTTAAATGCATGTGCCCCGGCGGCTGGGAGGGAACCACGTGC
JAG1-CO16    TATGATGAGGGGGACGCATTCAAGTGCATGTGTCCGGGGGGCTGGGAGGGCACAACCTGC
JAG1-CO07    TACGACGAGGGCGATGCCTTCAAGTGTATGTGCCCCGGAGGCTGGGAGGGCACCACCTGC
JAG1-CO02    TACGACGAGGGCGACGCCTTTAAGTGTATGTGCCCGGGCGGCTGGGAAGGCACGACCTGC
JAG1-CO20    TATGACGAGGGCGACGCCTTCAAGTGCATGTGCCCCGGGGGCTGGGAGGGCACGACCTGC
JAG1-CO13    TACGACGAGGGCGACGCCTTCAAGTGCATGTGCCCCGGCGGATGGGAAGGCACTACCTGT
JAG1-CO19    TACGACGAGGGTGACGCCTTTAAGTGTATGTGCCCCGGCGGCTGGGAGGGCACCACCTGC
JAG1-CO08    TATGATGAGGGGGACGCCTTCAAATGTATGTGCCCCGGCGGGTGGGAGGGCACCACTTGC
JAG1-CO03    TACGACGAGGGGGACGCCTTCAAGTGCATGTGCCCCGGGGGCTGGGAGGGGACCACCTGC
JAG1-CO14    TACGACGAGGGGGACGCGTTCAAGTGCATGTGCCCCGGCGGCTGGGAGGGCACCACGTGC
JAG1-CO09    TACGATGAGGGCGACGCCTTCAAGTGCATGTGCCCCGGGGGATGGAAGGCACCACCTGC
JAG1-CO10    TACGACGAGGGCGACGCCTTTAAGTGCATGTGCCCCGGCGGCTGGGAAGGCACCACCTGC
JAG1-CO06    TACGACGAGGGCGACGCCTTCAAGTGCATGTGCCCCGGCGGGTGGGAGGGCACCACCTGC
             **.**.**.** **.** **.**.**.*****.** ** ** *****.** ** ** **.

JAG1-WT      AACATAGCCCGAAACAGTAGCTGCCTGCCCAACCCCTGCCATAATGGGGGCACATGTGTG
JAG1-CO01    AACATCGCGCGGAACAGCAGCTGTCTGCCCAACCCCTGCCACAACGGGGGCACGTGCGTG
JAG1-CO17    AACATCGCCCGCAACAGCAGCTGCCTTCCGAACCCATGCCATAACGGCGGCACCTGTGTC
JAG1-CO11    AATATTGCGAGGAACTCCAGCTGTCTGCCCAACCCCTGCCACAACGGAGGCACCTGTGTG
JAG1-CO12    AACATCGCCAGGAATTCCTCCTGTCTGCCCAACCCATGTCACAACGGTGGCACGTGCGTG
JAG1-CO25    AATATCGCCCGCAACTCCTCCTGCCTGCCCAACCCGTGCCACAACGGGGGCACCTGCGTG
JAG1-CO04    AACATCGCCAGGAACTCCAGCTGCCTGCCCAACCCGTGCCATAACGGTGGCACCTGCGTG
JAG1-CO18    AATATCGCAAGGAACAGCTCCTGTCTGCCCAATCCCTGCCACAACGGCGGTACCTGCGTG
JAG1-CO05    AACATCGCCAGGAACTCAAGCTGCCTGCCCAATCCCTGCCATAACGGTGGGACCTGCGTG
JAG1-CO23    AATATCGCCAGGAATTCCAGCTGCCTCCCCAATCCGTGCCATAATGGCGGCACCTGCGTG
JAG1-CO24    AACATCGCCAGGAACAGCTCCTGCCTGCCCAACCCCTGCCACAACGGCGGGACCTGTGTC
JAG1-CO21    AACATCGCCCGGAACAGCAGCTGCCTCCCCAACCCCTGCCATAATGGCGGTACCTGCGTG
JAG1-CO22    AATATCGCCAGGAATTCCTCCTGCCTGCCCAACCCCTGCCATAATGGCGGGACCTGCGTC
JAG1-CO15    AACATCGCGAGGAACAGCAGCTGCCTCCCCAATCCCTGTCACAATGGCGGTACCTGCGTC
JAG1-CO16    AACATCGCCCGGAACAGCAGCTGCCTCCCAAACCCCTGCCACAACGGGGGCACCTGCGTG
JAG1-CO07    AACATCGCCCGCAACAGCAGCTGCCTGCCCAATCCCTGCCACAATGGTGGAACATGCGTG
JAG1-CO02    AACATCGCCCGGAACAGCAGCTGCCTCCCGAACCCTTGCCACAACGGCGGGACCTGCGTG
JAG1-CO20    AACATTGCCCGCAATAGCAGCTGCTTGCCCAACCCCTGTCACAACGGCGGAACCTGCGTC
JAG1-CO13    AACATCGCCCGGAATAGCTCCTGCCTGCCGAACCCCTGCCACAACGGGGGCACGTGCGTC
JAG1-CO19    AATATCGCCCGCAACAGCAGCTGTCTCCCCAACCCCTGCCACAACGGGGGTACCTGCGTG
JAG1-CO08    AACATCGCCAGGAACTCCTCCTGCCTCCCCAACCCCTGCCACAACGGAGGGACGTGCGTG
JAG1-CO03    AACATCGCCAGGAACAGCTCCTGCCTGCCCAACCCATGCCACAATGGAGGCACCTGCGTA
JAG1-CO14    AACATCGCGCGTAACAGCAGCTGTCTGCCGAATCCCTGTCACAATGGCGGCACCTGCGTC
JAG1-CO09    AACATCGCCAGGAACTCCAGCTGTCTCCCCAACCCGTGCCACAACGGCGGGACGTGCGTG
JAG1-CO10    AATATCGCGAGAAATAGCAGCTGCCTGCCCAACCCCTGCCATAACGGCGGGACCTGCGTG
JAG1-CO06    AACATCGCCCGGAACTCCAGCTGCCTGCCCAATCCGTGTCACAATGGGGGCACCTGCGTG
             **.** **  * **.      ***..* ** **.** **.**.**.** ** ** **.**
```

FIG. 13 (cont)

```
JAG1-WT         GTCAACGGCGAGTCCTTTACGTGCGTCTGCAAGGAAGGCTGGGAGGGGCCCATCTGTGCT
JAG1-CO01       GTGAACGGCGAGAGCTTCACCTGCGTGTGTAAGGAGGGGTGGGAGGGCCCCATCTGCGCC
JAG1-CO17       GTGAACGGCGAGTCGTTCACCTGTGTGTGCAAGGAAGGCTGGGAAGGCCCCATATGCGCC
JAG1-CO11       GTGAACGGCGAGAGCTTTACGTGCGTCTGTAAAGAGGGCTGGGAAGGCCCCATCTGCGCC
JAG1-CO12       GTGAACGGGGAGTCCTTTACCTGTGTGTGCAAGGAGGGGTGGGAGGGACCCATATGTGCG
JAG1-CO25       GTGAACGGCGAGTCCTTCACCTGCGTCTGCAAGGAGGGCTGGGAGGGTCCCATCTGTGCC
JAG1-CO04       GTGAACGGCGAAAGCTTCACCTGCGTGTGCAAGGAGGGCTGGGAGGGCCCCATCTGCGCC
JAG1-CO18       GTGAACGGGGAAAGCTTCACCTGCGTGTGCAAGGAGGGGTGGGAGGGGCCCATCTGCGCC
JAG1-CO05       GTGAACGGCGAAAGCTTCACCTGCGTGTGCAAGGAGGGCTGGGAGGGCCCCATCTGTGCC
JAG1-CO23       GTCAACGGCGAAAGCTTTACCTGCGTCTGTAAGGAAGGCTGGGAAGGTCCGATCTGTGCC
JAG1-CO24       GTGAACGGGGAGAGCTTCACGTGCGTGTGCAAGGAGGGCTGGGAAGGGCCCATCTGCGCC
JAG1-CO21       GTGAACGGCGAGAGTTTCACCTGCGTGTGCAAGGAGGGCTGGGAGGGCCCCATCTGCGCG
JAG1-CO22       GTGAACGGCGAGAGCTTCACCTGCGTGTGCAAAGAGGGGTGGGAAGGACCCATCTGCGCC
JAG1-CO15       GTGAACGGGGAGAGCTTCACCTGCGTGTGCAAGGAGGGCTGGGAGGGCCCGATCTGCGCC
JAG1-CO16       GTGAACGGCGAGAGCTTCACCTGCGTGTGTAAGGAGGGCTGGGAGGGCCCCATCTGTGCC
JAG1-CO07       GTGAACGGGGAGAGCTTTACGTGCGTGTGCAAGGAGGGATGGGAGGGCCCCATCTGTGCC
JAG1-CO02       GTGAATGGCGAATCCTTCACCTGCGTGTGCAAGGAGGGCTGGGAGGGCCCCATCTGCGCC
JAG1-CO20       GTGAACGGCGAGTCCTTCACCTGCGTTTGCAAAGAGGGCTGGGAGGGCCCAATCTGTGCC
JAG1-CO13       GTGAACGGCGAAAGCTTCACCTGCGTGTGCAAGGAGGGCTGGGAGGGCCCCATCTGTGCC
JAG1-CO19       GTCAACGGCGAGTCCTTTACCTGCGTGTGCAAGGAGGGCTGGGAAGGGCCCATCTGCGCC
JAG1-CO08       GTGAACGGGGAGAGCTTCACCTGCGTGTGCAAGGAGGGCTGGGAAGGCCCCATTTGCGCG
JAG1-CO03       GTGAATGGCGAGTCCTTCACCTGTGTGTGCAAGGAGGGCTGGGAGGGGCCCATCTGCGCC
JAG1-CO14       GTGAACGGCGAAAGCTTCACCTGCGTGTGTAAGGAAGGCTGGGAGGGCCCCATCTGCGCC
JAG1-CO09       GTGAATGGCGAGTCCTTCACGTGCGTGTGCAAGGAGGGCTGGGAGGGCCCCATCTGCGCG
JAG1-CO10       GTGAATGGCGAGAGCTTCACCTGCGTCTGTAAGGAGGGCTGGGAAGGTCCCATCTGTGCC
JAG1-CO06       GTGAACGGCGAGTCGTTCACGTGCGTGTGCAAGGAAGGCTGGGAGGGACCGATCTGCGCC
                ** **.** **.   **.** **.** **.**.**.** *****.** ** ** **.**

JAG1-WT         CAGAATACCAATGACTGCAGCCCTCATCCCTGTTACAACAGCGGCACCTGTGTGGATGGA
JAG1-CO01       CAGAACACCAACGATTGCTCGCCCCACCCCTGTTACAACAGCGGGACCTGCGTGGACGGT
JAG1-CO17       CAGAACACCAACGACTGCAGCCCCCATCCCTGCTACAACTCCGGCACCTGCGTGGACGGG
JAG1-CO11       CAAAACACGAACGACTGCAGCCCCCACCCCTGTTACAATAGCGGCACCTGCGTCGACGGT
JAG1-CO12       CAGAATACCAACGACTGCTCCCCCCACCCATGTTATAACAGCGGTACATGTGTGGATGGG
JAG1-CO25       CAGAATACCAATGACTGCAGCCCCCATCCTTGTTACAATTCCGGCACCTGCGTGGATGGC
JAG1-CO04       CAGAACACCAATGACTGCTCCCCCCACCCATGCTACAACTCCGGGACCTGTGTGGACGGC
JAG1-CO18       CAGAACACCAACGACTGCAGCCCACACCCCTGCTACAATTCCGGCACCTGTGTGGACGGC
JAG1-CO05       CAGAACACCAATGACTGCAGCCCCCACCCCTGTTACAACAGCGGGACCTGCGTGGATGGT
JAG1-CO23       CAGAACACCAACGACTGTAGCCCCCACCCCTGCTACAATAGCGGAACGTGCGTGGACGGC
JAG1-CO24       CAAAACACCAACGACTGCAGCCCCCATCCCTGTTACAACTCCGGCACCTGCGTGGACGGC
JAG1-CO21       CAGAACACCAATGACTGCTCGCCCCACCCCTGCTACAACAGCGGCACCTGCGTGGACGGT
JAG1-CO22       CAAAATACGAACGACTGCAGCCCCCACCCCTGTTACAACAGCGGCACGTGCGTGGATGGG
JAG1-CO15       CAGAACACCAACGACTGCAGCCCACACCCCTGCTACAATAGCGGGACCTGCGTGGACGGA
JAG1-CO16       CAGAATACCAACGATTGCTCCCCCCACCCCTGCTACAACAGCGGCACTTGCGTGGACGGC
JAG1-CO07       CAGAACACCAACGACTGCTCCCCCCATCCCTGTTACAACAGCGGCACCTGTGTGGACGGG
JAG1-CO02       CAAAACACCAATGACTGTAGCCCCCACCCCTGCTACAACTCCGGCACATGTGTGGATGGC
JAG1-CO20       CAGAACACCAATGACTGCAGCCCCCACCCCTGCTACAATTCCGGTACCTGCGTGGACGGC
JAG1-CO13       CAGAACACCAACGACTGCAGCCCCCACCCCTGCTACAATAGCGGCACCTGCGTGGACGGA
JAG1-CO19       CAGAACACCAACGACTGTAGCCCCCATCCCTGCTACAACTCCGGTACCTGCGTGGACGGC
JAG1-CO08       CAGAACACTAACGATTGCAGCCCCCACCCCTGCTACAACTCCGGCACCTGCGTGGACGGG
JAG1-CO03       CAGAACACCAACGACTGCAGCCCACACCCGTGCTACAACTCCGGCACCTGCGTCGACGGC
JAG1-CO14       CAAAACACCAACGACTGTAGCCCCCACCCGTGCTACAACAGCGGCACCTGCGTGGATGGC
JAG1-CO09       CAGAACACCAACGATTGCAGCCCCCACCCGTGCTACAACTCAGGCACCTGCGTCGACGGT
JAG1-CO10       CAGAACACCAACGACTGCAGCCCCCATCCCTGCTACAACAGCGGCACCTGCGTGGACGGC
JAG1-CO06       CAAAATACCAACGACTGTAGCCCCCACCCCTGTTATAACAGCGGCACCTGCGTCGACGGG
                **.**.** **.**.**.   ** **.** **.**.**.   ** ** **.** **.**
```

FIG. 13 (cont)

```
JAG1-WT        GACAACTGGTACCGGTGCGAATGTGCCCCGGGTTTTGCTGGGCCCGACTGCAGAATAAAC
JAG1-CO01      GATAACTGGTACAGGTGCGAGTGCGCACCAGGCTTCGCCGGGCCGGACTGCAGGATCAAC
JAG1-CO17      GACAACTGGTACAGGTGTGAGTGCGCCCCCGGATTCGCCGGTCCCGACTGCCGGATCAAC
JAG1-CO11      GACAACTGGTATAGGTGCGAGTGTGCCCCGGGCTTTGCCGGGCCCGACTGCCGGATCAAT
JAG1-CO12      GACAACTGGTACCGGTGTGAGTGCGCCCCCGGCTTCGCCGGCCCCGATTGCAGGATCAAC
JAG1-CO25      GACAACTGGTATCGGTGTGAGTGCGCCCCCGGCTTCGCGGGCCCCGACTGTAGGATCAAC
JAG1-CO04      GACAACTGGTATAGGTGCGAGTGTGCCCCCGGCTTCGCCGGCCCCGACTGCAGGATCAAC
JAG1-CO18      GACAACTGGTATAGGTGCGAGTGCGCCCCCGGTTTCGCCGGCCCGGACTGCAGGATCAAC
JAG1-CO05      GACAACTGGTACAGGTGTGAGTGCGCCCCCGGGTTTGCCGGCCCCGACTGCAGGATCAAC
JAG1-CO23      GACAACTGGTATCGGTGCGAGTGCGCCCCCGGCTTTGCGGGGCCGGACTGCCGGATCAAT
JAG1-CO24      GACAACTGGTACCGATGCGAGTGCGCCCCCGGCTTCGCCGGCCCCGACTGCCGGATCAAC
JAG1-CO21      GACAACTGGTACCGTTGCGAGTGCGCCCCAGGCTTCGCCGGCCCGGACTGCAGGATCAAC
JAG1-CO22      GACAACTGGTACCGCTGCGAGTGCGCCCCCGGCTTTGCAGGCCCGGACTGTCGGATCAAC
JAG1-CO15      GACAACTGGTACCGGTGCGAGTGCGCCCCCGGCTTCGCCGGCCCCGACTGCAGGATCAAC
JAG1-CO16      GATAACTGGTATAGGTGTGAGTGCGCCCCCGGCTTCGCAGGCCCCGACTGCCGCATCAAC
JAG1-CO07      GACAACTGGTACCGCTGCGAGTGCGCCCCCGGCTTCGCCGGCCCGGACTGCCGTATCAAC
JAG1-CO02      GACAACTGGTACAGGTGTGAGTGCGCCCCCGGATTCGCCGGCCCCGACTGCCGGATCAAC
JAG1-CO20      GACAACTGGTATAGGTGCGAGTGCGCCCCGGGATTCGCCGGCCCGGACTGCAGGATCAAC
JAG1-CO13      GACAACTGGTACCGATGCGAGTGCGCCCCTGGCTTCGCCGGACCCGATTGCCGCATTAAC
JAG1-CO19      GACAATTGGTACAGGTGTGAATGCGCACCAGGCTTCGCGGGGCCCGACTGCAGGATCAAC
JAG1-CO08      GACAACTGGTACCGGTGCGAGTGCGCCCCCGGCTTCGCCGGCCCGGACTGCAGGATCAAC
JAG1-CO03      GACAACTGGTACAGGTGCGAGTGCGCCCCCGGCTTCGCGGGCCCGGACTGCCGGATTAAT
JAG1-CO14      GACAACTGGTATCGGTGCGAGTGTGCCCCTGGCTTTGCGGGCCCCGACTGCCGGATAAAC
JAG1-CO09      GACAACTGGTACCGGTGCGAGTGCGCCCCAGGGTTCGCGGGCCCCGACTGCAGGATCAAC
JAG1-CO10      GACAATTGGTACAGGTGCGAGTGCGCCCCCGGGTTTGCCGGCCCCGACTGCAGGATCAAC
JAG1-CO06      GACAATTGGTACCGGTGCGAGTGCGCCCCCGGCTTCGCCGGCCCCGACTGCCGAATCAAC
               **.**.*****. * **.**.**.** ** ** **.** ** ** **.**. * ** **.

JAG1-WT        ATCAATGAATGCCAGTCTTCACCTTGTGCCTTTGGAGCGACCTGTGTGGATGAGATCAAT
JAG1-CO01      ATCAACGAATGTCAGAGCTCCCCGTGCGCCTTCGGCGCCACGTGCGTAGACGAGATCAAT
JAG1-CO17      ATCAATGAGTGTCAATCCAGCCCCTGCGCCTTCGGCGCCACCTGCGTGGATGAGATCAAC
JAG1-CO11      ATCAACGAGTGCCAGTCCAGCCCATGTGCGTTCGGCGCCACCTGCGTGGACGAAATCAAC
JAG1-CO12      ATCAATGAGTGCCAGAGCTCCCCCTGCGCCTTCGGCGCCACATGCGTCGACGAAATCAAC
JAG1-CO25      ATCAACGAGTGCCAGAGCTCCCCATGCGCGTTTGGGGCGACCTGTGTCGACGAGATCAAT
JAG1-CO04      ATCAACGAATGTCAGAGCTCCCCCTGCGCCTTTGGCGCCACATGTGTCGATGAGATTAAC
JAG1-CO18      ATCAACGAGTGTCAGTCCAGCCCCTGCGCCTTCGGGGCCACCTGCGTGGACGAGATCAAC
JAG1-CO05      ATCAACGAGTGCCAGAGCAGCCCCTGTGCCTTCGGCGCCACCTGCGTGGACGAGATCAAC
JAG1-CO23      ATCAACGAGTGCCAGAGCAGCCCCTGCGCCTTCGGCGCCACCTGCGTGGACGAGATCAAC
JAG1-CO24      ATCAACGAGTGCCAGAGCAGCCCCTGCGCGTTCGGCGCCACCTGCGTGGATGAAATCAAC
JAG1-CO21      ATCAACGAGTGCCAAAGCTCCCCTTGCGCCTTTGGCGCAACCTGTGTGGACGAGATCAAT
JAG1-CO22      ATCAACGAGTGCCAGAGCAGCCCCTGCGCCTTCGGAGCCACGTGCGTGGACGAGATCAAT
JAG1-CO15      ATCAACGAGTGCCAGAGCAGCCCCTGTGCCTTCGGCGCGACCTGCGTGGATGAAATCAAT
JAG1-CO16      ATCAACGAGTGCCAGAGCAGCCCCTGTGCCTTCGGGGCCACCTGCGTGGACGAGATCAAC
JAG1-CO07      ATCAACGAGTGTCAGAGCAGCCCCTGCGCATTCGGCGCCACCTGCGTGGATGAAATAAAC
JAG1-CO02      ATTAACGAGTGTCAGAGCAGCCCCTGCGCCTTCGGCGCCACCTGCGTCGATGAGATAAAC
JAG1-CO20      ATCAACGAGTGCCAGAGCAGCCCCTGCGCCTTCGGGGCCACCTGTGTGGACGAGATCAAT
JAG1-CO13      ATCAATGAATGCCAGAGCAGCCCCTGCGCCTTTGGAGCCACCTGCGTCGATGAGATCAAC
JAG1-CO19      ATCAACGAATGCCAGAGCAGCCCCTGCGCGTTCGGCGCCACCTGCGTGGACGAGATCAAC
JAG1-CO08      ATCAACGAATGTCAGAGCAGCCCCTGCGCCTTCGGAGCCACCTGCGTGGACGAGATAAAC
JAG1-CO03      ATCAACGAGTGCCAGAGCAGCCCCTGCGCCTTCGGGGCCACCTGCGTCGACGAAATCAAC
JAG1-CO14      ATAAACGAGTGTCAATCGAGCCCCTGCGCCTTCGGGGCCACCTGCGTGGACGAGATCAAC
JAG1-CO09      ATCAACGAGTGCCAGTCCAGCCCCTGCGCCTTTGGCGCCACCTGCGTGGACGAGATCAAC
JAG1-CO10      ATCAACGAGTGCCAGAGTAGCCCCTGTGCCTTCGGCGCCACCTGCGTGGACGAGATCAAC
JAG1-CO06      ATCAACGAATGTCAAAGCTCACCCTGTGCCTTCGGGGCAACCTGTGTGGACGAGATCAAC
               ** **.**.**.**.      ** **.** **.** ** ** **.** **.**.** **.
```

FIG. 13 (cont)

```
JAG1-WT        GGCTACCGGTGTGTCTGCCCTCCAGGGCACAGTGGTGCCAAGTGCCAGGAAGTTTCAGGG
JAG1-CO01      GGCTACAGGTGCGTGTGCCCCCCAGGCCACAGCGGGGCCAAATGCCAGGAAGTCAGCGGC
JAG1-CO17      GGCTACAGGTGCGTCTGTCCCCCCGGCCACTCCGGCGCCAAATGCCAGGAGGTCAGCGGC
JAG1-CO11      GGCTACAGGTGCGTCTGCCCCCCGGGGCACAGCGGAGCCAAATGTCAGGAAGTCTCTGGG
JAG1-CO12      GGCTACAGGTGTGTGTGCCCCCCGGGACACAGCGGTGCCAAGTGCCAGGAAGTGTCAGGC
JAG1-CO25      GGGTACAGGTGCGTGTGTCCCCCGGGGCACTCCGGGGCCAAATGCCAGGAGGTAAGCGGC
JAG1-CO04      GGCTACCGGTGCGTCTGCCCCCCCGGCCACAGCGGCGCGAAGTGCCAGGAAGTCTCCGGC
JAG1-CO18      GGCTATCGTTGCGTGTGCCCCCCCGGCCACTCCGGCGCCAAGTGCCAGGAAGTGTCCGGG
JAG1-CO05      GGGTACCGGTGCGTGTGCCCCCCCGGCCACTCCGGCGCCAAGTGCCAGGAGGTGTCCGGC
JAG1-CO23      GGCTACAGGTGCGTGTGTCCCCCCGGCCACTCCGGCGCCAAGTGCCAGGAGGTGAGCGGT
JAG1-CO24      GGATATAGGTGCGTGTGCCCCCCCGGCCACAGCGGGGCCAAGTGCCAGGAGGTCAGCGGG
JAG1-CO21      GGGTACAGGTGCGTGTGCCCCCCCGGCCATTCCGGGGCCAAGTGCCAAGAGGTGTCCGGC
JAG1-CO22      GGCTACAGATGCGTGTGCCCCCCGGGACACAGCGGCGCCAAGTGCCAGGAAGTGTCCGGC
JAG1-CO15      GGCTACCGGTGCGTGTGCCCCCCCGGCCACAGCGGCGCGAAGTGCCAGGAGGTTAGCGGC
JAG1-CO16      GGCTACCGGTGTGTGTGCCCCCCCGGGCACTCCGGCGCGAAATGCCAGGAGGTGTCCGGC
JAG1-CO07      GGCTACAGGTGTGTGTGCCCCCCCGGCCACAGCGGAGCCAAATGCCAGGAGGTGAGCGGG
JAG1-CO02      GGATATAGGTGCGTGTGCCCCCCCGGACACAGCGGCGCGAAGTGCCAGGAGGTGAGCGGC
JAG1-CO20      GGCTACAGGTGTGTCTGCCCCCCCGGACACTCGGGCGCGAAATGCCAAGAGGTGTCCGGC
JAG1-CO13      GGCTACCGCTGTGTCTGCCCCCCCGGCCACAGCGGGGCCAAGTGCCAGGAGGTCTCAGGT
JAG1-CO19      GGGTACAGGTGCGTGTGCCCCCCCGGGCACAGCGGGGCCAAGTGCCAGGAGGTCTCCGGG
JAG1-CO08      GGCTACCGGTGCGTCTGCCCCCCCGGTCACTCTGGTGCCAAGTGCCAAGAGGTCAGCGGC
JAG1-CO03      GGGTACCGGTGCGTGTGCCCCCCCGGCCACAGCGGGGCAAAGTGCCAGGAAGTCAGCGGC
JAG1-CO14      GGCTACAGGTGCGTGTGCCCGCCCGGCCACAGCGGCGCGAAATGCCAAGAGGTGAGCGGC
JAG1-CO09      GGCTACAGGTGCGTGTGCCCCCCCGGCCATAGCGGCGCCAAGTGCCAGGAGGTGAGCGGC
JAG1-CO10      GGCTACCGGTGCGTGTGCCCCCCCGGCCACTCCGGCGCCAAGTGTCAAGAGGTGAGCGGA
JAG1-CO06      GGCTACCGGTGTGTGTGCCCCCCGGGACACTCCGGGGCCAAGTGCCAGGAGGTGAGCGGG
               ** **. * **.** **.** ** ** **.    ** ** **.**.**.**.**    **

JAG1-WT        AGACCTTGCATCACCATGGGGAGTGTGATACCAGATGGGGCCAAATGGGATGATGACTGT
JAG1-CO01      CGACCCTGCATCACCATGGGTTCCGTTATCCCAGACGGAGCCAAGTGGGATGACGATTGT
JAG1-CO17      AGGCCCTGCATCACCATGGGCTCCGTTATCCCCGACGGCGCCAAGTGGGACGACGACTGC
JAG1-CO11      AGGCCCTGCATCACCATGGGCAGCGTAATCCCCGACGGGGCTAAGTGGGACGACGACTGC
JAG1-CO12      AGGCCCTGTATTACCATGGGCAGCGTGATCCCCGACGGAGCCAAGTGGGATGACGACTGC
JAG1-CO25      CGGCCATGCATTACCATGGGCTCGGTGATCCCAGACGGTGCCAAGTGGGACGACGACTGC
JAG1-CO04      AGGCCCTGTATCACCATGGGCAGCGTGATCCCCGACGGCGCCAAGTGGGACGACGACTGC
JAG1-CO18      CGCCCCTGCATCACCATGGGCTCCGTGATCCCCGATGGCGCCAAGTGGGATGACGACTGC
JAG1-CO05      AGGCCCTGCATCACCATGGGCAGCGTCATCCCCGACGGCGCCAAATGGGACGACGACTGC
JAG1-CO23      AGGCCCTGCATCACCATGGGCAGCGTGATCCCCGACGGGGCCAAGTGGGACGATGACTGT
JAG1-CO24      CGCCCCTGCATCACCATGGGCAGCGTGATACCCGACGGCGCCAAGTGGGACGACGACTGC
JAG1-CO21      CGGCCCTGCATTACCATGGGCAGCGTTATCCCCGACGGCGCCAAGTGGGACGACGACTGC
JAG1-CO22      CGTCCCTGCATCACCATGGGTAGCGTCATCCCCGACGGCGCCAAGTGGGACGATGACTGC
JAG1-CO15      AGGCCCTGCATCACCATGGGATCGGTGATCCCCGATGGCGCCAAGTGGGATGACGACTGT
JAG1-CO16      AGGCCCTGCATCACCATGGGCAGCGTGATCCCTGACGGCGCCAAATGGGACGACGACTGT
JAG1-CO07      CGCCCATGCATCACCATGGGGAGCGTGATCCCAGACGGGGCGAAGTGGGATGACGACTGT
JAG1-CO02      AGGCCCTGCATCACAATGGGCAGCGTGATCCCGGACGGCGCCAAGTGGGACGACGATTGC
JAG1-CO20      AGGCCCTGCATCACCATGGGTTCCGTGATACCCGACGGGGCAAAGTGGGACGACGATTGC
JAG1-CO13      CGGCCCTGCATCACCATGGGCAGCGTCATCCCCGACGGGGCCAAATGGGATGACGACTGC
JAG1-CO19      CGGCCCTGCATCACCATGGGCTCCGTGATCCCGGATGGGGCGAAGTGGGACGACGATTGC
JAG1-CO08      AGGCCGTGCATCACCATGGGCTCCGTGATCCCGGATGGCGCCAAATGGGACGATGACTGC
JAG1-CO03      AGGCCCTGCATCACCATGGGCAGCGTCATTCCCGATGGCGCAAAGTGGGACGACGACTGC
JAG1-CO14      AGGCCCTGCATCACCATGGGTTCCGTGATCCCCGACGGGGCAAAATGGGACGACGACTGC
JAG1-CO09      AGGCCCTGCATCACCATGGGCAGCGTGATCCCCGACGGCGCCAAGTGGGACGACGACTGC
JAG1-CO10      CGACCCTGTATCACCATGGGCTCGGTGATCCCCGACGGCGCCAAGTGGGACGACGACTGC
JAG1-CO06      CGACCATGCATCACCATGGGCTCCGTGATCCCCGACGGCGCCAAGTGGGACGACGACTGC
                * ** **.**.** *****    ** ** ** **.** ** **.*****.**.**.**.
```

FIG. 13 (cont)

```
JAG1-WT         AATACCTGCCAGTGCCTGAATGGACGGATCGCCTGCTCAAAGGTCTGGTGTGGCCCTCGA
JAG1-CO01       AACACCTGTCAGTGTCTGAATGGCCGGATCGCGTGCAGCAAGGTGTGGTGCGGCCCCAGG
JAG1-CO17       AATACCTGCCAGTGTCTGAACGGGAGGATCGCCTGCTCCAAGGTGTGGTGCGGCCCCAGG
JAG1-CO11       AATACCTGTCAGTGTCTGAACGGCAGGATTGCCTGCAGCAAAGTGTGGTGTGGCCCGCGG
JAG1-CO12       AACACCTGCCAGTGCCTGAACGGCCGTATCGCCTGCAGCAAGGTGTGGTGCGGCCCCCGG
JAG1-CO25       AACACCTGCCAGTGCCTGAATGGCAGGATCGCCTGCAGCAAGGTATGGTGCGGACCCAGG
JAG1-CO04       AACACCTGTCAATGCCTGAATGGCAGGATCGCCTGCAGCAAAGTCTGGTGCGGGCCCCGG
JAG1-CO18       AACACCTGTCAGTGCCTGAACGGCAGGATCGCCTGCAGCAAGGTGTGGTGCGGCCCCCGA
JAG1-CO05       AACACCTGTCAGTGCCTGAACGGCAGGATCGCCTGCTCCAAGGTTTGGTGCGGGCCCAGG
JAG1-CO23       AACACCTGCCAGTGCCTGAACGGGAGGATCGCCTGTTCCAAAGTGTGGTGCGGCCCGCGT
JAG1-CO24       AACACCTGCCAGTGCCTGAACGGCAGGATCGCCTGCTCCAAGGTGTGGTGCGGGCCGCGG
JAG1-CO21       AATACCTGCCAGTGCCTCAACGGCAGGATCGCCTGCAGCAAGGTGTGGTGCGGACCCAGG
JAG1-CO22       AACACGTGTCAGTGTCTGAACGGCCGAATCGCCTGCTCCAAGGTGTGGTGCGGCCCCCGG
JAG1-CO15       AACACATGCCAATGTCTGAATGGACGGATCGCATGTTCCAAGGTGTGGTGCGGCCCCAGG
JAG1-CO16       AATACCTGCCAGTGCCTGAATGGCCGAATCGCCTGCTCCAAGGTGTGGTGCGGCCCCAGG
JAG1-CO07       AACACCTGCCAGTGCCTGAACGGCCGAATCGCCTGCAGCAAGGTGTGGTGCGGGCCCCGG
JAG1-CO02       AACACCTGCCAGTGCCTGAACGGCCGGATAGCCTGCTCCAAAGTGTGGTGCGGCCCCCGC
JAG1-CO20       AATACCTGCCAATGCCTGAACGGCAGGATCGCCTGTAGCAAGGTGTGGTGTGGCCCGAGG
JAG1-CO13       AATACCTGCCAGTGTCTGAACGGCCGAATCGCCTGCTCCAAGGTGTGGTGCGGGCCCAGG
JAG1-CO19       AACACCTGCCAATGCCTGAACGGGAGGATCGCCTGTAGCAAGGTCTGGTGCGGACCCCGG
JAG1-CO08       AACACCTGCCAGTGCCTTAACGGTCGGATCGCGTGCAGCAAGGTGTGGTGTGGCCCCAGG
JAG1-CO03       AACACTTGCCAGTGCCTGAATGGCAGGATCGCCTGCAGCAAGGTGTGGTGCGGCCCAAGG
JAG1-CO14       AATACCTGCCAGTGCCTCAACGGGAGGATCGCCTGCAGCAAGGTGTGGTGCGGCCCCAGG
JAG1-CO09       AATACGTGCCAGTGCCTGAACGGACGCATTGCCTGCTCCAAGGTGTGGTGCGGCCCCCGG
JAG1-CO10       AACACGTGCCAGTGCCTCAACGGGAGGATCGCCTGCAGCAAGGTGTGGTGCGGTCCCAGG
JAG1-CO06       AACACCTGCCAGTGCCTGAACGGCAGGATCGCCTGCTCCAAGGTGTGGTGTGGCCCCCGG
                **.** **.**.**.** **.**   * ** ** **.    **.** *****.** **   *

JAG1-WT         CCTTGCCTGCTCCACAAAGGGCACAGCGAGTGCCCCAGCGGGCAGAGCTGCATCCCCATC
JAG1-CO01       CCGTGCCTGCTGCACAAGGGCCACTCCGAATGTCCCTCCGGTCAGAGCTGCATCCCCATC
JAG1-CO17       CCCTGCCTGCTGCACAAGGGCCACAGCGAGTGCCCCAGCGGCCAGTCCTGCATCCCGATC
JAG1-CO11       CCCTGTCTCCTGCACAAGGGCCACTCCGAGTGTCCCAGCGGCCAATCCTGCATCCCCATC
JAG1-CO12       CCGTGCCTGCTGCACAAGGGGCACTCCGAGTGCCCCAGCGGGCAGAGCTGCATCCCCATC
JAG1-CO25       CCGTGCCTGCTGCACAAAGGACACTCCGAGTGTCCGAGCGGCCAGAGCTGCATCCCCATC
JAG1-CO04       CCCTGCCTGCTGCACAAGGGCCACAGCGAGTGCCCTTCCGGCCAGAGCTGCATCCCGATC
JAG1-CO18       CCCTGCCTGCTGCACAAGGGGCACAGCGAGTGCCCCTCCGGCCAGTCCTGCATCCCCATA
JAG1-CO05       CCCTGCCTGCTGCACAAGGGACATAGCGAATGCCCCAGCGGCCAGAGCTGCATCCCCATC
JAG1-CO23       CCCTGCCTACTCCACAAGGGGCATTCCGAGTGTCCCAGCGGACAGAGCTGTATCCCCATC
JAG1-CO24       CCGTGCCTGCTGCACAAGGGCCACAGCGAGTGCCCCAGCGGCCAGTCCTGTATCCCAATC
JAG1-CO21       CCGTGCCTGCTGCATAAGGGCCACAGCGAGTGCCCGAGCGGTCAGTCCTGCATCCCCATC
JAG1-CO22       CCCTGCCTGCTGCACAAGGGCCACAGCGAGTGCCCCAGCGGCCAGTCGTGTATCCCCATC
JAG1-CO15       CCCTGTCTCCTGCACAAAGGCCACAGCGAGTGTCCCAGCGGCCAAAGCTGCATCCCCATC
JAG1-CO16       CCTTGCCTGTTGCACAAGGGCCACAGCGAGTGCCCCAGCGGCCAGAGCTGTATCCCCATC
JAG1-CO07       CCCTGCCTGCTGCACAAAGGCCACAGCGAGTGCCCCAGCGGCCAGAGCTGCATACCGATC
JAG1-CO02       CCCTGCCTGCTGCACAAGGGCCACAGCGAGTGCCCCTCCGGCCAGAGCTGCATCCCCATA
JAG1-CO20       CCTTGCCTCCTGCATAAAGGCCACAGCGAGTGTCCCTCCGGCCAGAGCTGTATCCCCATC
JAG1-CO13       CCCTGCCTCCTTCACAAAGGCCATAGCGAGTGCCCCTCCGGGCAATCCTGCATCCCCATC
JAG1-CO19       CCCTGCCTCCTGCACAAAGGCCACTCCGAATGCCCCAGCGGACAAAGCTGCATACCGATC
JAG1-CO08       CCCTGCCTCCTGCACAAGGGGCACAGCGAGTGCCCCTCCGGACAGTCCTGTATCCCCATC
JAG1-CO03       CCCTGCCTGCTGCACAAAGGCCACAGCGAATGCCCAAGCGGTCAGAGCTGCATCCCCATC
JAG1-CO14       CCCTGCCTGCTGCATAAAGGGCACAGCGAGTGCCCCAGCGGGCAGAGCTGCATCCCCATC
JAG1-CO09       CCGTGCCTGCTCCACAAGGGGCACAGCGAGTGCCCCTCCGGCCAGAGCTGCATCCCCATC
JAG1-CO10       CCCTGCCTGCTGCACAAAGGCCACTCCGAGTGCCCCAGCGGCCAGAGCTGTATCCCCATC
JAG1-CO06       CCCTGTCTCCTGCACAAAGGTCACAGCGAGTGCCCCAGCGGCCAGAGCTGCATCCCGATC
                ** **.** .* **.**.** **.  ***.**.**   *** **.    **.** ** **
```

FIG. 13 (cont)

```
JAG1-WT       CTGGACGACCAGTGCTTCGTCCACCCCTGCACTGGTGTGGGCGAGTGTCGGTCTTCCAGT
JAG1-CO01     CTCGACGACCAGTGCTTTGTACACCCCTGCACCGGAGTCGGCGAGTGCAGGTCCTCGTCT
JAG1-CO17     CTGGACGACCAGTGCTTTGTGCACCCCTGCACCGGGGTAGGCGAGTGCCGGTCCAGCAGC
JAG1-CO11     CTCGACGACCAGTGCTTTGTGCACCCCTGCACAGGCGTGGGAGAGTGTAGGTCGAGCTCC
JAG1-CO12     TTGGACGACCAGTGCTTCGTGCACCCCTGCACCGGCGTGGGCGAATGCCGTAGCAGCTCC
JAG1-CO25     CTGGACGACCAGTGCTTCGTGCATCCCTGCACTGGCGTCGGCGAGTGCCGCAGCTCCAGC
JAG1-CO04     CTGGACGATCAGTGTTTTGTCCATCCATGCACCGGCGTGGGCGAGTGTAGGTCGAGCAGC
JAG1-CO18     CTGGACGATCAGTGCTTCGTGCACCCCTGCACCGGCGTGGGCGAGTGTAGGAGCTCCAGC
JAG1-CO05     CTGGACGACCAGTGCTTCGTGCATCCCTGCACCGGGGTGGGCGAGTGCCGGAGCTCCTCG
JAG1-CO23     CTGGACGACCAATGCTTCGTGCACCCCTGCACCGGCGTGGGTGAGTGCAGGTCCAGCAGC
JAG1-CO24     CTGGACGACCAGTGCTTCGTGCATCCCTGCACCGGCGTGGGCGAGTGCAGGTCCTCCTCC
JAG1-CO21     CTCGACGACCAGTGTTTCGTGCACCCCTGCACGGGCGTGGGTGAGTGCCGATCCTCCAGC
JAG1-CO22     CTCGACGACCAATGCTTCGTGCACCCCTGCACCGGCGTGGGCGAGTGCCGCAGCTCGAGC
JAG1-CO15     CTGGACGACCAGTGCTTCGTGCATCCCTGCACCGGCGTGGGGGAGTGCCGTAGCAGCAGC
JAG1-CO16     CTGGACGACCAATGTTTCGTGCATCCCTGCACCGGCGTGGGGGAGTGCCGGTCGTCCAGC
JAG1-CO07     CTGGACGACCAGTGCTTCGTACACCCCTGCACCGGGGTGGGCGAGTGCCGGTCCTCCTCG
JAG1-CO02     CTGGACGACCAATGTTTCGTGCATCCCTGCACCGGCGTGGGCGAGTGTCGGAGCAGCAGC
JAG1-CO20     CTCGACGATCAATGCTTTGTGCACCCTTGCACCGGGGTGGGCGAGTGTCGCAGCAGCAGC
JAG1-CO13     CTGGACGACCAATGCTTCGTGCACCCCTGCACCGGCGTGGGGGAGTGCAGGAGCAGCAGC
JAG1-CO19     CTGGACGACCAATGCTTCGTGCATCCCTGCACAGGCGTGGGTGAATGCAGGAGCTCCAGC
JAG1-CO08     CTGGACGACCAGTGCTTCGTCCACCCCTGCACCGGAGTGGGCGAATGCAGGAGCAGCTCC
JAG1-CO03     CTGGATGACCAGTGCTTCGTGCACCCCTGCACCGGGGTCGGTGAGTGTAGGAGCAGCAGC
JAG1-CO14     CTGGACGACCAGTGCTTCGTGCACCCGTGCACCGGCGTGGGCGAGTGCAGAAGCTCTAGC
JAG1-CO09     CTCGACGACCAGTGCTTCGTCCACCCCTGCACCGGCGTGGGCGAGTGCAGGTCCTCCAGC
JAG1-CO10     CTGGATGATCAGTGCTTCGTCCATCCCTGTACTGGCGTGGGCGAGTGCAGGAGCAGCAGC
JAG1-CO06     CTTGACGACCAGTGCTTCGTGCACCCGTGTACAGGCGTAGGGGAGTGCAGGAGCTCCTCG
              .* **.**.**.**.**.** **.** **.** ** ** ** **.**. *

JAG1-WT       CTCCAGCCGGTGAAGACAAAGTGCACCTCTGACTCCTATTACCAGGATAACTGTGCGAAC
JAG1-CO01     CTGCAGCCCGTGAAAACCAAGTGCACCAGCGACTCCTACTACCAGGACAACTGCGCCAAC
JAG1-CO17     CTGCAGCCCGTGAAAACCAAGTGCACCAGCGACAGCTATTACCAGGACAACTGCGCCAAT
JAG1-CO11     CTGCAGCCCGTGAAGACCAAGTGCACCAGCGATTCCTACTACCAGGACAACTGCGCGAAT
JAG1-CO12     CTGCAGCCCGTGAAGACCAAGTGCACCAGCGATTCCTACTATCAGGATAACTGCGCCAAC
JAG1-CO25     CTGCAGCCCGTGAAGACCAAGTGTACCAGCGACAGCTACTACCAGGACAATTGTGCCAAC
JAG1-CO04     CTGCAGCCCGTGAAAACAAAGTGCACCAGCGACAGCTACTACCAGGATAACTGTGCCAAC
JAG1-CO18     CTGCAGCCCGTGAAAACCAAGTGCACCTCGGACAGCTACTATCAGGATAACTGCGCCAAC
JAG1-CO05     CTGCAACCCGTCAAGACCAAGTGCACCTCGGACAGCTATTACCAGGACAACTGCGCCAAC
JAG1-CO23     CTGCAGCCCGTGAAGACAAAGTGCACCAGTGATTCCTACTACCAGGATAACTGCGCCAAC
JAG1-CO24     CTGCAGCCCGTGAAGACCAAATGCACCAGCGACTCGTACTACCAGGATAACTGCGCCAAC
JAG1-CO21     CTGCAGCCCGTCAAAACCAAGTGCACCTCCGACAGCTACTACCAGGACAACTGCGCCAAC
JAG1-CO22     CTGCAGCCCGTGAAGACCAAGTGCACCAGCGATAGCTACTACCAGGACAATTGCGCCAAC
JAG1-CO15     CTGCAGCCCGTGAAGACGAAGTGCACCTCAGACAGCTATTACCAGGATAACTGCGCGAAC
JAG1-CO16     CTGCAGCCCGTGAAGACCAAGTGTACCAGCGACTCCTACTATCAGGACAATTGCGCCAAC
JAG1-CO07     CTCCAGCCCGTCAAGACCAAGTGCACCAGCGATAGCTACTACCAGGACAACTGCGCCAAC
JAG1-CO02     CTGCAGCCCGTGAAGACTAAGTGCACCTCCGACTCCTACTATCAGGACAACTGTGCCAAC
JAG1-CO20     CTGCAGCCCGTGAAGACCAAATGCACCAGCGATAGCTACTACCAGGACAACTGCGCGAAT
JAG1-CO13     CTGCAGCCCGTGAAGACCAAGTGCACCTCCGATAGCTATTACCAGGACAACTGCGCCAAC
JAG1-CO19     CTGCAGCCAGTGAAGACGAAGTGCACCAGCGATAGCTACTACCAGGATAATTGTGCCAAC
JAG1-CO08     CTGCAGCCGGTGAAGACCAAGTGCACCAGCGACTCCTACTACCAGGACAATTGCGCCAAC
JAG1-CO03     CTGCAGCCCGTGAAGACCAAGTGCACCTCCGATTCCTACTACCAGGACAATTGCGCCAAC
JAG1-CO14     CTGCAACCCGTGAAGACCAAGTGCACGAGCGACAGCTACTACCAGGACAACTGCGCGAAC
JAG1-CO09     CTGCAGCCAGTGAAAACCAAGTGTACCAGCGACTCCTACTACCAGGACAACTGCGCCAAC
JAG1-CO10     CTCCAGCCCGTGAAAACCAAGTGCACGAGCGACTCCTATTACCAAGATAACTGTGCCAAC
JAG1-CO06     CTCCAGCCCGTGAAAACCAAGTGTACCAGCGACTCATACTATCAGGACAACTGTGCCAAT
              ** **.** ** **.** **.**.**    **.   **.**.**.**.**.**.** **.
```

FIG. 13 (cont)

```
JAG1-WT      ATCACATTTACCTTTAACAAGGAGATGATGTCACCAGGTCTTACTACGGAGCACATTTGC
JAG1-CO01    ATCACGTTCACCTTTAACAAGGAGATGATGAGCCCCGGGCTGACCACGGAGCACATCTGC
JAG1-CO17    ATCACCTTTACGTTCAATAAAGAGATGATGAGCCCCGGCCTGACCACCGAACACATCTGC
JAG1-CO11    ATCACCTTTACCTTTAACAAGGAGATGATGAGCCCCGGGCTGACCACCGAGCACATCTGC
JAG1-CO12    ATCACCTTCACCTTCAACAAGGAGATGATGAGCCCCGGCCTGACCACGGAACACATCTGC
JAG1-CO25    ATCACCTTCACCTTCAACAAGGAGATGATGAGCCCTGGCCTGACCACCGAGCATATCTGT
JAG1-CO04    ATCACCTTTACCTTCAACAAGGAGATGATGAGCCCCGGACTGACCACCGAGCATATCTGT
JAG1-CO18    ATTACGTTCACCTTCAACAAGGAGATGATGTCCCCCGGCCTGACCACGGAGCACATCTGT
JAG1-CO05    ATCACCTTCACCTTCAACAAGGAAATGATGAGCCCCGGCCTGACCACCGAGCATATCTGC
JAG1-CO23    ATCACCTTCACCTTCAATAAGGAGATGATGAGCCCGGGCCTGACCACGGAGCACATCTGC
JAG1-CO24    ATCACCTTCACCTTCAACAAGGAAATGATGAGCCCCGGCCTGACCACCGAGCACATCTGC
JAG1-CO21    ATAACCTTCACGTTTAACAAGGAGATGATGAGCCCCGGCCTGACCACCGAGCACATCTGC
JAG1-CO22    ATCACCTTCACCTTTAACAAGGAGATGATGAGCCCCGGCCTGACGACCGAACACATCTGC
JAG1-CO15    ATCACCTTCACCTTTAACAAGGAGATGATGTCCCCCGGCCTGACCACCGAGCACATCTGC
JAG1-CO16    ATCACCTTCACCTTTAACAAGGAGATGATGAGCCCCGGCCTGACCACCGAGCACATCTGT
JAG1-CO07    ATCACCTTTACCTTTAACAAGGAGATGATGAGCCCCGGCCTGACCACGGAGCACATCTGC
JAG1-CO02    ATCACCTTCACCTTCAACAAGGAGATGATGAGCCCCGGCCTGACAACGGAGCACATCTGC
JAG1-CO20    ATCACCTTTACGTTCAACAAGGAGATGATGAGCCCGGGCCTGACCACAGAGCACATCTGC
JAG1-CO13    ATCACCTTCACCTTTAACAAAGAAATGATGTCACCCGGCCTGACGACCGAGCATATCTGC
JAG1-CO19    ATAACCTTCACCTTCAACAAGGAGATGATGTCCCCCGGCCTGACCACCGAGCACATCTGT
JAG1-CO08    ATCACCTTCACCTTCAACAAGGAGATGATGAGCCCCGGCCTGACCACCGAGCACATCTGC
JAG1-CO03    ATAACTTTTACCTTCAACAAGGAGATGATGAGCCCCGGCCTCACCACGGAGCACATCTGC
JAG1-CO14    ATCACCTTCACCTTCAATAAGGAGATGATGAGCCCGGGACTCACCACCGAACATATCTGC
JAG1-CO09    ATCACATTCACATTCAACAAGGAGATGATGAGCCCGGGCCTGACCACCGAGCACATCTGC
JAG1-CO10    ATCACCTTCACCTTTAACAAGGAGATGATGTCGCCCGGACTGACCACCGAGCATATCTGC
JAG1-CO06    ATCACCTTTACCTTCAACAAGGAAATGATGAGCCCCGGGCTGACCACCGAGCACATCTGC
             ** ** **.** **.**.**.**.******    ** ** ** ** ** **.**.**.**.

JAG1-WT      AGTGAATTGAGGAATTTGAATATTTTGAAGAATGTTTCCGCTGAATATTCAATCTACATC
JAG1-CO01    TCGGAGCTGAGGAACCTGAACATACTGAAGAACGTGAGCGCCGAGTACAGCATCTACATT
JAG1-CO17    AGCGAGCTGCGCAACCTGAACATTCTGAAGAACGTGAGCGCCGAGTACAGCATCTATATA
JAG1-CO11    AGCGAGCTGCGGAACCTGAACATCCTCAAAAACGTCAGCGCCGAGTATAGCATCTACATT
JAG1-CO12    AGCGAGCTGAGGAACCTGAACATCCTGAAGAACGTGTCCGCCGAATACAGCATCTACATC
JAG1-CO25    AGCGAGCTGAGGAACTTGAACATCCTGAAGAATGTGAGCGCCGAGTATTCCATTTACATA
JAG1-CO04    TCAGAGCTGAGGAACCTGAACATCCTCAAGAACGTCAGCGCCGAGTACAGCATCTACATC
JAG1-CO18    TCCGAGCTGAGGAACCTCAACATCCTGAAAAATGTGAGCGCCGAGTATAGCATCTATATA
JAG1-CO05    AGCGAGCTGCGGAACCTGAACATACTGAAGAACGTTAGCGCCGAGTACTCCATCTACATC
JAG1-CO23    AGCGAGCTGCGCAACCTGAACATCCTGAAGAACGTCTCCGCCGAGTACAGCATATACATC
JAG1-CO24    AGCGAGCTCCGGAACCTGAACATCCTGAAGAACGTGTCCGCCGAGTATAGCATCTACATC
JAG1-CO21    AGCGAGCTGAGGAACCTGAACATCCTGAAGAACGTGTCCGCCGAGTACAGCATCTACATC
JAG1-CO22    TCCGAGCTGAGGAACCTGAACATCCTGAAGAATGTCAGCGCTGAGTACTCCATCTACATC
JAG1-CO15    TCGGAGCTGCGCAATCTTAACATCCTGAAAAACGTGTCCGCCGAGTACAGCATTTACATC
JAG1-CO16    TCCGAGCTGAGGAACCTGAACATCCTGAAGAACGTCAGTGCCGAGTACTCCATCTACATC
JAG1-CO07    AGCGAGCTGCGCAACCTCAACATCCTGAAAAACGTGTCGGCCGAGTACTCCATCTACATC
JAG1-CO02    AGCGAGCTGCGCAATCTGAACATCCTGAAAAATGTGAGCGCCGAGTACAGCATCTACATC
JAG1-CO20    AGCGAGCTGCGCAACCTGAACATCCTGAAGAACGTGTCTGCCGAGTATAGCATCTACATC
JAG1-CO13    AGCGAGCTGCGGAACCTGAACATCCTGAAAAACGTGTCGGCCGAGTACAGTATATACATC
JAG1-CO19    AGCGAGCTCCGCAACCTGAACATCCTCAAGAACGTGAGCGCCGAGTACTCCATCTACATC
JAG1-CO08    AGCGAGCTGCGCAACCTGAACATCTTGAAGAACGTGAGCGCCGAGTATTCCATCTACATC
JAG1-CO03    AGCGAGCTGCGCAACCTCAACATCCTGAAGAACGTGAGCGCCGAGTACAGCATTTACATC
JAG1-CO14    TCCGAGCTGCGCAACCTCAACATACTGAAGAATGTGAGCGCCGAGTACTCCATTTACATT
JAG1-CO09    AGCGAACTCAGAAACCTGAACATCCTGAAGAACGTGTCGGCCGAGTACAGCATCTATATC
JAG1-CO10    AGCGAGCTGAGGAACCTGAACATACTGAAGAATGTGTCCGCCGAATATTCCATCTACATC
JAG1-CO06    AGCGAGCTGCGGAACCTTAACATTCTGAAAAATGTGTCCGCCGAGTACAGCATATACATC
                **..*  * **..* **.** .* **.**.**    **.**.**.   ** **.**
```

FIG. 13 (cont)

```
JAG1-WT         GCTTGCGAGCCTTCCCCTTCAGCGAACAATGAAATACATGTGGCCATTTCTGCTGAAGAT
JAG1-CO01       GCCTGCGAGCCCAGCCCCAGCGCCAACAACGAGATCCACGTGGCGATCTCCGCCGAAGAC
JAG1-CO17       GCCTGCGAGCCCAGCCCCTCGGCTAATAACGAGATCCACGTGGCCATAAGCGCGGAGGAC
JAG1-CO11       GCCTGCGAGCCCAGCCCCAGCGCCAACAACGAAATACACGTGGCCATCAGCGCCGAGGAC
JAG1-CO12       GCCTGCGAGCCCAGCCCCAGCGCCAACAACGAAATCCACGTCGCCATCTCTGCCGAGGAC
JAG1-CO25       GCCTGTGAGCCCAGCCCAAGCGCTAACAATGAGATCCACGTGGCCATCAGCGCCGAGGAC
JAG1-CO04       GCCTGCGAGCCCAGCCCCTCCGCCAACAACGAAATCCACGTGGCCATAAGCGCCGAGGAC
JAG1-CO18       GCCTGTGAGCCGTCCCCCTCCGCCAACAACGAGATCCACGTCGCCATCTCCGCAGAGGAC
JAG1-CO05       GCCTGCGAGCCCAGCCCGAGCGCGAATAATGAGATCCACGTCGCCATCAGCGCCGAGGAC
JAG1-CO23       GCCTGCGAGCCCAGCCCCTCCGCCAATAACGAGATCCACGTGGCCATCTCCGCGGAGGAC
JAG1-CO24       GCGTGCGAACCAAGTCCGTCCGCCAACAACGAGATCCACGTGGCAATCTCCGCCGAGGAC
JAG1-CO21       GCCTGTGAGCCCAGCCCCTCCGCCAACAACGAGATCCATGTTGCCATCTCGGCCGAAGAT
JAG1-CO22       GCCTGTGAGCCCAGCCCAAGCGCCAACAATGAGATCCACGTCGCGATCTCCGCCGAGGAC
JAG1-CO15       GCCTGTGAGCCGAGCCCCTCCGCCAACAATGAGATCCATGTCGCCATCAGCGCCGAGGAC
JAG1-CO16       GCCTGTGAACCGTCCCCGTCCGCCAACAATGAGATTCACGTGGCCATCAGCGCCGAAGAC
JAG1-CO07       GCCTGCGAGCCCTCCCCCTCCGCCAACAATGAAATCCACGTGGCCATCAGCGCCGAGGAC
JAG1-CO02       GCCTGTGAGCCGAGCCCCAGCGCTAATAACGAGATCCACGTGGCCATCTCCGCCGAGGAC
JAG1-CO20       GCCTGCGAACCCAGCCCCTCCGCAAATAATGAGATCCACGTGGCGATCTCGGCCGAGGAC
JAG1-CO13       GCCTGCGAGCCCAGCCCCAGCGCCAACAACGAGATACATGTGGCCATAAGCGCCGAAGAC
JAG1-CO19       GCCTGCGAGCCCTCGCCCAGCGCCAATAACGAGATCCACGTGGCCATCTCCGCCGAGGAC
JAG1-CO08       GCCTGCGAGCCCAGCCCGAGCGCCAATAACGAGATCCACGTGGCCATCAGCGCCGAGGAC
JAG1-CO03       GCCTGCGAGCCCAGCCCCTCCGCCAACAACGAGATCCACGTGGCCATCAGCGCCGAGGAC
JAG1-CO14       GCCTGCGAGCCCAGCCCCTCCGCCAATAATGAAATACACGTCGCCATCAGCGCCGAGGAC
JAG1-CO09       GCGTGCGAGCCCAGCCCCAGCGCGAATAACGAGATCCACGTGGCCATAAGCGCGGAGGAC
JAG1-CO10       GCCTGTGAGCCTAGCCCGAGCGCCAACAACGAGATCCACGTGGCCATCTCCGCCGAGGAT
JAG1-CO06       GCCTGCGAGCCGAGCCCTAGCGCCAACAATGAGATACACGTGGCCATCAGCGCTGAGGAC
                ** **.**.**     **     ** **.**.**.** **.** ** **     ** **.**.

JAG1-WT         ATACGGGATGATGGGAACCCGATCAAGGAAATCACTGACAAAATAATCGATCTTGTTAGT
JAG1-CO01       ATCCGGGACGACGGCAACCCCATCAAGGAGATAACCGACAAGATCATCGACCTGGTGAGC
JAG1-CO17       ATCCGGGACGACGGCAACCCCATCAAGGAGATCACCGACAAGATCATCGACCTGGTGAGC
JAG1-CO11       ATCAGGGACGACGGCAACCCGATCAAGGAGATCACCGATAAGATAATCGACCTGGTGTCC
JAG1-CO12       ATCCGCGACGACGGCAACCCCATTAAGGAGATAACCGACAAGATCATCGACCTGGTGTCC
JAG1-CO25       ATCCGGGACGACGGCAACCCCATCAAAGAAATCACCGACAAGATCATCGATCTGGTAAGC
JAG1-CO04       ATCAGGGACGACGGCAATCCGATCAAGGAGATAACCGACAAGATCATCGACCTCGTGAGT
JAG1-CO18       ATTCGCGACGACGGGAACCCCATAAAGGAAATTACGGACAAAATCATCGACCTGGTGAGC
JAG1-CO05       ATCCGGGACGACGGCAACCCCATCAAGGAGATCACCGACAAGATCATCGACCTGGTCAGC
JAG1-CO23       ATCAGGGACGATGGCAACCCCATCAAGGAGATCACCGACAAGATTATCGACCTGGTCAGC
JAG1-CO24       ATCCGGGACGACGGCAACCCCATCAAGGAGATAACCGACAAAATCATCGACCTGGTGAGC
JAG1-CO21       ATTAGGGACGACGGCAACCCCATCAAGGAGATCACCGACAAGATCATAGACCTGGTGAGC
JAG1-CO22       ATCCGCGACGATGGCAACCCCATCAAGGAGATCACCGACAAGATCATCGACCTGGTGAGC
JAG1-CO15       ATCCGGGACGACGGTAATCCGATCAAGGAGATCACAGATAAGATCATCGACCTGGTGTCC
JAG1-CO16       ATCAGGGACGACGGCAACCCCATCAAGGAGATCACCGACAAGATCATAGACCTTGTGTCC
JAG1-CO07       ATCCGAGACGATGGGAACCCCATCAAGGAAATCACCGACAAGATAATCGACCTGGTGAGT
JAG1-CO02       ATCAGGGATGACGGCAACCCCATCAAAGAGATCACCGACAAGATCATCGACCTGGTGTCC
JAG1-CO20       ATCAGGGACGACGGGAACCCCATCAAAGAGATCACCGACAAGATCATCGATCTGGTGAGC
JAG1-CO13       ATCAGGGACGATGGCAACCCCATCAAGGAGATCACCGACAAAATAATCGACCTGGTGAGC
JAG1-CO19       ATCCGCGACGACGGCAATCCCATCAAGGAGATTACCGACAAGATCATCGACCTGGTGAGC
JAG1-CO08       ATCCGGGATGACGGCAATCCCATCAAGGAGATCACCGATAAGATCATCGACCTGGTCAGC
JAG1-CO03       ATAAGGGATGACGGGAATCCCATCAAGGAGATCACCGACAAGATCATCGACCTGGTGTCC
JAG1-CO14       ATCAGGGACGACGGCAACCCCATCAAGGAGATCACCGACAAGATCATCGACCTGGTGAGC
JAG1-CO09       ATCCGGGACGACGGCAACCCCATCAAGGAGATCACCGACAAGATTATTGACCTGGTCTCC
JAG1-CO10       ATCAGGGACGACGGGAACCCCATCAAAGAGATCACCGATAAGATCATCGACCTGGTGTCT
JAG1-CO06       ATCAGGGATGACGGCAACCCGATCAAGGAGATCACCGACAAGATAATAGACCTCGTCAGC
                **  * **.**.** **.** ** **.**.** ** **.**.** ** **.** **    .
```

FIG. 13 (cont)

```
JAG1-WT        AAACGTGATGGAAACAGCTCGCTGATTGCTGCCGTTGCAGAAGTAAGAGTTCAGAGGCGG
JAG1-CO01      AAGCGGGACGGCAACAGCTCCCTGATCGCCGCCGTGGCCGAGGTGCGGGTACAGAGGCGG
JAG1-CO17      AAGCGCGACGGGAACTCATCACTGATCGCCGCCGTGGCCGAGGTGAGGGTGCAGAGGCGG
JAG1-CO11      AAGAGGGACGGCAATAGCTCCCTGATCGCCGCCGTGGCCGAAGTGAGGGTGCAGAGGAGG
JAG1-CO12      AAGCGAGACGGAAATTCTAGCCTGATCGCCGCCGTAGCCGAGGTACGTGTGCAGAGGAGG
JAG1-CO25      AAGAGGGACGGGAACAGCAGCCTCATCGCCGCCGTGGCCGAGGTGCGCGTCCAGCGGAGG
JAG1-CO04      AAGAGGGACGGGAACAGTAGCCTCATCGCCGCCGTCGCCGAGGTGAGGGTGCAGCGGAGG
JAG1-CO18      AAGAGGGACGGCAACTCCAGCCTGATCGCCGCCGTGGCCGAGGTGCGCGTGCAACGCAGG
JAG1-CO05      AAGCGTGACGGCAACTCCAGCCTGATCGCCGCGGTGGCTGAGGTGCGAGTCCAGAGGAGG
JAG1-CO23      AAAAGGGACGGCAACTCCAGCCTCATCGCCGCCGTGGCCGAGGTCAGGGTACAGCGCAGG
JAG1-CO24      AAAAGGGACGGCAATTCTAGCCTGATCGCCGCAGTGGCCGAAGTGAGGGTGCAGCGCAGG
JAG1-CO21      AAGCGGGACGGCAATTCCAGCCTGATCGCCGCCGTGGCCGAGGTGAGAGTGCAGAGGAGG
JAG1-CO22      AAGAGGGACGGCAACAGCTCCCTGATCGCCGCGGTGGCCGAGGTGAGGGTCCAAAGGAGG
JAG1-CO15      AAGCGGGACGGCAACAGCAGCCTGATCGCCGCCGTCGCCGAGGTGCGTGTGCAGAGACGG
JAG1-CO16      AAGAGGGACGGCAACTCGTCCCTGATCGCCGCCGTGGCGGAGGTGAGGGTGCAGAGGAGG
JAG1-CO07      AAAAGGGACGGGAACAGCAGCCTGATCGCTGCCGTGGCGGAGGTGAGGGTCCAGAGGAGG
JAG1-CO02      AAGCGGGACGGCAACTCCAGCCTGATCGCAGCCGTGGCCGAAGTGAGGGTCCAGCGGCGG
JAG1-CO20      AAGCGGGACGGCAACAGCTCCCTCATCGCCGCCGTGGCTGAGGTCCGAGTGCAGCGGCGT
JAG1-CO13      AAGCGGGATGGCAATAGCAGCCTGATCGCCGCCGTGGCCGAGGTGAGGGTGCAGCGGAGG
JAG1-CO19      AAGCGCGATGGCAACAGCAGCCTGATCGCCGCGGTGGCCGAGGTGAGGGTGCAGAGGCGG
JAG1-CO08      AAGCGCGACGGCAATAGCTCGCTGATCGCGGCCGTGGCCGAGGTGAGGGTGCAGCGGCGG
JAG1-CO03      AAGCGGGACGGCAATAGCAGCCTGATCGCCGCCGTCGCGGAGGTGCGGGTGCAGAGGCGC
JAG1-CO14      AAAAGGGACGGCAATAGCAGCCTCATCGCCGCCGTGGCCGAGGTGAGGGTGCAGAGGAGG
JAG1-CO09      AAGAGGGACGGCAATAGCTCCCTGATTGCCGCCGTCGCCGAAGTGCGGGTGCAAAGAAGG
JAG1-CO10      AAGCGCGACGGTAACAGCTCCCTAATCGCCGCCGTGGCCGAGGTGCGCGTGCAGCGCAGG
JAG1-CO06      AAAAGGGACGGCAACAGCAGCCTGATCGCCGCCGTCGCCGAGGTGAGGGTGCAGCGCCGG
               **. * **.** **.      ** **.** ** ** ** **.**  * ** **. *  *

JAG1-WT        CCTCTGAAGAACAGAACAGATTTCCTTGTTCCCTTGCTGAGCTCTGTCTTAACTGTGGCT
JAG1-CO01      CCCCTCAAGAACAGGACGGACTTCCTCGTGCCGCTCCTGTCGTCCGTGCTGACCGTGGCC
JAG1-CO17      CCCCTCAAGAACAGGACCGACTTCCTCGTCCCCCTGCTGTCGAGCGTGCTCACCGTGGCC
JAG1-CO11      CCCCTGAAAAACAGGACCGATTTCCTGGTTCCCCTGCTGAGCAGCGTGCTGACAGTGGCT
JAG1-CO12      CCCCTCAAGAATAGGACCGACTTCCTGGTGCCCCTGCTGAGCAGCGTGCTCACCGTGGCG
JAG1-CO25      CCCCTCAAAAACCGGACCGACTTTCTGGTGCCGCTGCTCAGCTCCGTGCTGACCGTGGCC
JAG1-CO04      CCCCTGAAGAACAGGACCGATTTTCTGGTCCCCCTGCTGAGCTCCGTGCTGACCGTGGCC
JAG1-CO18      CCGCTGAAAAACAGGACGGACTTTCTGGTGCCGCTGCTGTCCTCGGTGCTGACCGTCGCT
JAG1-CO05      CCCCTGAAGAACAGGACGGACTTCCTCGTCCCTCTGCTGAGCAGCGTGCTGACCGTGGCC
JAG1-CO23      CCGCTGAAAAACCGGACCGACTTCCTGGTGCCCCTGCTTTCCTCCGTGCTCACGGTGGCC
JAG1-CO24      CCCCTCAAGAATAGGACCGACTTCCTGGTGCCGCTCCTCAGCAGCGTGCTGACCGTGGCC
JAG1-CO21      CCCCTGAAGAACCGGACCGATTTCCTGGTGCCCCTGCTGAGCAGCGTGCTGACCGTGGCC
JAG1-CO22      CCCCTGAAGAACAGGACCGACTTCCTGGTGCCCCTGCTGTCGAGCGTGCTGACCGTGGCC
JAG1-CO15      CCCCTCAAGAACCGCACCGACTTCCTCGTGCCCCTCCTGAGCTCGGTGCTGACCGTCGCC
JAG1-CO16      CCCCTGAAGAACCGCACCGACTTCCTGGTGCCGCTCCTGTCCTCCGTGCTGACCGTGGCC
JAG1-CO07      CCGCTGAAAAATCGGACCGACTTTCTGGTGCCCCTGCTGAGCTCCGTGCTGACCGTCGCC
JAG1-CO02      CCCCTGAAGAACCGAACCGACTTCCTGGTCCCCCTGCTGAGCAGCGTGCTGACCGTCGCA
JAG1-CO20      CCCCTTAAGAACAGGACCGACTTCCTGGTGCCCCTCCTGTCGTCCGTGCTCACCGTGGCC
JAG1-CO13      CCCCTGAAGAATCGCACCGACTTCCTGGTCCCGCTGCTTAGCTCCGTCCTGACGGTCGCC
JAG1-CO19      CCCCTCAAGAACCGCACGGACTTCCTGGTGCCACTGCTGAGCTCCGTGCTGACCGTGGCC
JAG1-CO08      CCCCTGAAGAACAGGACCGACTTTCTGGTACCCCTCCTGAGCTCGGTGCTGACCGTTGCC
JAG1-CO03      CCGCTGAAGAACCGGACCGACTTCCTCGTGCCCCTGCTGAGCAGCGTGCTGACGGTGGCC
JAG1-CO14      CCGCTGAAAAACAGAACCGATTTTCTCGTCCCCCTGCTGTCCTCCGTGCTGACCGTCGCC
JAG1-CO09      CCCCTGAAAAACCGGACGGATTTCCTGGTCCCCCTCCTGAGCAGCGTGCTGACCGTCGCC
JAG1-CO10      CCGCTGAAGAACCGCACCGACTTCCTGGTGCCCCTGCTGAGCAGCGTGCTCACCGTGGCC
JAG1-CO06      CCCCTGAAGAACAGGACCGACTTCCTGGTGCCCCTCCTGAGCTCCGTGCTGACCGTGGCC
               ** ** **.**. * ** **.**.** ** ** .* **       ** .* ** ** **
```

FIG. 13 (cont)

```
JAG1-WT      TGGATCTGTTGCTTGGTGACGGCCTTCTACTGGTGCCTGCGGAAGCGGCGGAAGCCGGGC
JAG1-CO01    TGGATCTGCTGTCTGGTGACCGCCTTCTACTGGTGCCTGCGGAAGCGGCGCAAGCCGGGG
JAG1-CO17    TGGATCTGCTGTCTCGTGACCGCATTCTACTGGTGCCTGAGGAAACGGCGCAAGCCCGGC
JAG1-CO11    TGGATCTGCTGCCTCGTAACTGCATTCTACTGGTGCCTGAGGAAGAGGAGGAAGCCCGGC
JAG1-CO12    TGGATCTGCTGCCTGGTGACCGCCTTTTACTGGTGCCTGCGAAAGAGGAGGAAGCCCGGT
JAG1-CO25    TGGATATGCTGCCTGGTGACCGCCTTCTACTGGTGCCTGCGGAAGAGGAGGAAGCCCGGC
JAG1-CO04    TGGATCTGCTGCCTGGTGACGGCGTTCTACTGGTGCCTCCGGAAACGACGGAAGCCCGGG
JAG1-CO18    TGGATCTGCTGCCTGGTGACCGCCTTCTACTGGTGCCTGCGCAAAAGGCGCAAGCCCGGT
JAG1-CO05    TGGATCTGTTGCCTGGTGACCGCCTTTTACTGGTGCCTGCGAAAGAGGAGGAAGCCGGGC
JAG1-CO23    TGGATTTGCTGCCTGGTAACCGCGTTTTACTGGTGCCTGAGGAAGAGGAGGAAGCCCGGC
JAG1-CO24    TGGATCTGCTGCCTGGTGACCGCCTTTTACTGGTGCCTGAGGAAGCGTAGGAAGCCCGGA
JAG1-CO21    TGGATCTGCTGCCTGGTGACCGCATTTTACTGGTGTCTGAGGAAGCGGAGGAAACCCGGC
JAG1-CO22    TGGATCTGCTGCCTGGTGACCGCGTTCTACTGGTGCCTGCGTAAGAGGAGGAAGCCCGGC
JAG1-CO15    TGGATCTGCTGCCTGGTGACCGCCTTCTACTGGTGCCTGCGAAAACGCCGGAAGCCGGGG
JAG1-CO16    TGGATCTGCTGCCTGGTGACCGCCTTCTACTGGTGCCTGAGGAAGCGCCGCAAGCCCGGG
JAG1-CO07    TGGATCTGCTGCCTGGTCACCGCCTTCTACTGGTGCCTGAGGAAGCGTAGGAAGCCCGGC
JAG1-CO02    TGGATCTGTTGCCTGGTGACGGCCTTCTACTGGTGCCTCAGGAAAAGACGGAAGCCCGGG
JAG1-CO20    TGGATCTGTTGCCTGGTGACCGCCTTCTACTGGTGCCTGCGTAAGCGAAGGAAGCCCGGA
JAG1-CO13    TGGATCTGCTGCCTGGTGACCGCCTTCTACTGGTGCTTGAGGAAGCGGAGGAAGCCCGGG
JAG1-CO19    TGGATCTGCTGTCTGGTCACCGCCTTCTACTGGTGCCTGCGGAAACGGAGGAAGCCCGGA
JAG1-CO08    TGGATCTGTTGTCTGGTGACCGCCTTCTACTGGTGCCTGCGGAAAAGGCGGAAGCCCGGC
JAG1-CO03    TGGATCTGCTGCCTGGTGACAGCCTTCTACTGGTGCCTGCGGAAGAGGAGGAAGCCCGGG
JAG1-CO14    TGGATCTGTTGCCTGGTGACCGCCTTCTACTGGTGTCTCCGCAAGAGGCGCAAGCCCGGC
JAG1-CO09    TGGATCTGCTGTCTGGTGACGGCCTTCTACTGGTGCCTCAGAAAGAGGCGCAAACCCGGC
JAG1-CO10    TGGATATGCTGCCTGGTGACCGCCTTCTACTGGTGCCTGCGGAAGCGGCGTAAACCGGGA
JAG1-CO06    TGGATCTGCTGCCTGGTGACCGCCTTCTACTGGTGTCTGAGGAAAAGGAGGAAGCCTGGC
             ***** **.**..* ** ** ** **.********..*  * **. *  * **.** **

JAG1-WT      AGCCACACACACTCAGCCTCTGAGGACAACACCACCAACAACGTGCGGGAGCAGCTGAAC
JAG1-CO01    AGCCACACCCACTCGGCCAGCGAAGACAACACGACCAACAACGTGAGGGAGCAGCTGAAT
JAG1-CO17    TCGCACACCCACAGCGCCAGCGAAGATAACACCACCAACAACGTGAGGGAGCAGCTCAAC
JAG1-CO11    AGTCACACCCACAGCGCCTCCGAGGATAACACCACTAACAATGTGCGGGAGCAGCTGAAC
JAG1-CO12    TCACACACGCACAGCGCCAGCGAAGACAACACCACCAACAATGTGCGCGAGCAGCTCAAC
JAG1-CO25    AGCCACACGCACAGCGCGAGCGAGGACAACACCACCAACAACGTGCGGGAGCAACTGAAC
JAG1-CO04    AGCCATACCCACTCCGCCAGCGAGGACAACACCACCAATAACGTGAGGGAGCAGCTGAAT
JAG1-CO18    AGCCATACCCACTCCGCCTCCGAAGACAACACCACCAACAACGTGAGGGAGCAGCTGAAT
JAG1-CO05    AGCCACACCCACAGCGCCTCAGAAGACAACACCACAAACAACGTCCGCGAGCAGCTCAAC
JAG1-CO23    AGCCATACCCACAGCGCCAGCGAGGACAACACAACCAACAACGTGAGGGAGCAGCTCAAC
JAG1-CO24    AGCCACACACACTCCGCCAGCGAGGACAACACCACCAACAACGTGCGGGAGCAACTGAAC
JAG1-CO21    AGCCACACCCACAGCGCAAGCGAGGATAACACCACGAATAACGTGCGCGAGCAGCTGAAC
JAG1-CO22    AGCCACACCCATAGCGCGTCCGAGGATAACACCACCAATAACGTGAGGGAGCAGCTCAAC
JAG1-CO15    AGCCACACCCACAGCGCCAGCGAGGATAACACCACCAATAACGTGAGGGAACAGCTGAAC
JAG1-CO16    TCCCACACGCACAGCGCCAGCGAGGATAACACCACCAACAACGTGCGGGAGCAACTGAAC
JAG1-CO07    AGCCACACGCACAGCGCCAGCGAGGACAACACCACCAACAACGTGCGGGAGCAGCTGAAC
JAG1-CO02    AGCCACACCCACAGCGCCAGCGAGGACAACACCACCAACAACGTGCGGGAGCAGCTGAAC
JAG1-CO20    TCCCACACCCACAGCGCCAGCGAAGACAACACCACCAATAACGTCCGAGAGCAGCTGAAC
JAG1-CO13    TCACATACCCACTCCGCCAGCGAGGACAACACCACCAATAACGTGCGGGAACAGCTGAAC
JAG1-CO19    TCCCACACCCACTCCGCCTCCGAAGACAACACCACGAACAACGTCAGGGAGCAGCTGAAC
JAG1-CO08    TCCCATACCCATAGCGCATCCGAAGACAACACCACCAACAACGTCCGTGAGCAGCTGAAC
JAG1-CO03    AGCCACACCCATAGCGCGTCCGAGGACAACACGACAAACAACGTCAGAGAGCAGCTGAAC
JAG1-CO14    AGCCACACGCATAGCGCCAGCGAGGACAACACTACTAACAACGTGCGGGAGCAGCTGAAT
JAG1-CO09    TCGCACACCCATAGCGCCTCAGAGGACAACACCACGAATAACGTGCGGGAACAGCTGAAC
JAG1-CO10    AGCCATACCCACAGCGCCAGCGAGGATAATACCACCAATAACGTGCGGGAGCAGCTGAAC
JAG1-CO06    AGCCACACCCATAGCGCCTCCGAGGACAATACCACCAACAACGTCAGGGAACAGCTCAAC
                 **.** **.   **    **.**.**.** ** **.**.**  * **.**.** **.
```

FIG. 13 (cont)

```
JAG1-WT      CAGATCAAAAACCCCATTGAGAAACATGGGGCCAACACGGTCCCCATCAAGGATTATGAG
JAG1-CO01    CAGATCAAGAATCCCATAGAGAAACACGGCGCCAACACCGTGCCCATCAAGGATTACGAG
JAG1-CO17    CAGATCAAGAACCCCATAGAGAAGCACGGCGCCAACACGGTGCCAATCAAGGACTATGAG
JAG1-CO11    CAGATCAAGAATCCCATAGAAAAACATGGCGCCAACACCGTGCCCATTAAAGATTACGAG
JAG1-CO12    CAGATCAAGAATCCCATCGAGAAGCACGGCGCCAACACGGTCCCCATCAAGGACTACGAG
JAG1-CO25    CAGATCAAGAACCCCATCGAGAAGCACGGCGCCAACACCGTGCCCATCAAGGACTACGAG
JAG1-CO04    CAGATCAAGAATCCGATCGAGAAGCACGGCGCCAACACCGTGCCGATCAAAGACTACGAG
JAG1-CO18    CAGATCAAGAACCCTATCGAGAAGCACGGCGCCAACACGGTGCCCATCAAGGACTATGAA
JAG1-CO05    CAGATCAAAAACCCCATCGAAAAGCACGGCGCCAACACCGTGCCCATCAAGGACTACGAG
JAG1-CO23    CAGATAAAGAACCCCATCGAGAAACACGGCGCCAACACGGTGCCCATCAAGGACTATGAG
JAG1-CO24    CAGATCAAGAACCCCATCGAGAAGCACGGAGCCAACACCGTCCCTATCAAAGACTACGAG
JAG1-CO21    CAAATCAAGAACCCCATCGAGAAGCACGGGGCCAACACCGTGCCCATCAAGGACTACGAG
JAG1-CO22    CAGATCAAGAACCCAATCGAGAAGCACGGTGCCAACACTGTGCCCATCAAGGACTATGAG
JAG1-CO15    CAGATCAAGAACCCCATCGAAAAACACGGCGCCAACACCGTGCCGATCAAGGACTACGAG
JAG1-CO16    CAGATAAAGAACCCCATCGAAAAACACGGAGCGAACACCGTCCCCATCAAGGACTACGAA
JAG1-CO07    CAGATCAAGAACCCCATCGAGAAGCACGGCGCGAACACAGTGCCGATCAAGGATTACGAG
JAG1-CO02    CAAATCAAGAACCCCATCGAGAAGCATGGCGCCAATACCGTGCCCATCAAAGACTACGAG
JAG1-CO20    CAGATCAAGAACCCCATAGAGAAACACGGGGCCAACACCGTGCCTATCAAGGACTACGAG
JAG1-CO13    CAGATCAAGAACCCCATCGAGAAGCATGGTGCCAACACCGTGCCCATCAAGGACTATGAA
JAG1-CO19    CAGATCAAGAACCCCATCGAGAAGCATGGCGCCAACACCGTGCCAATCAAAGACTACGAG
JAG1-CO08    CAGATCAAGAACCCCATAGAGAAACACGGCGCCAACACCGTGCCCATCAAGGACTACGAA
JAG1-CO03    CAAATCAAGAATCCCATCGAAAAACACGGCGCCAACACCGTGCCCATCAAAGATTACGAG
JAG1-CO14    CAGATCAAGAACCCCATCGAGAAACACGGCGCCAACACTGTGCCCATCAAAGACTACGAG
JAG1-CO09    CAAATAAAAAACCCCATCGAGAAGCACGGGGCTAACACCGTGCCGATCAAGGACTACGAG
JAG1-CO10    CAGATCAAGAACCCCATCGAAAAGCACGGGGCGAACACCGTGCCCATCAAGGACTACGAG
JAG1-CO06    CAAATCAAGAACCCCATCGAGAAGCACGGCGCCAATACCGTGCCCATCAAGGATTACGAG
             **.** **.**.** ** **.**.**.** ** **.** ** ** **.**.**.**.**.

JAG1-WT      AACAAGAACTCCAAAATGTCTAAAATAAGGACACACAATTCTGAAGTAGAAGAGGACGAC
JAG1-CO01    AACAAGAACAGCAAGATGTCCAAAATCAGAACCCACAATAGCGAAGTGGAGGAAGACGAC
JAG1-CO17    AACAAGAACAGCAAGATGTCCAAGATCCGCACCCACAACAGCGAAGTCGAGGAAGACGAC
JAG1-CO11    AACAAAAATAGCAAGATGTCCAAGATCCGCACCCACAACAGCGAGGTGGAGGAGGACGAC
JAG1-CO12    AACAAAAACAGCAAGATGTCCAAGATCCGCACCCATAACAGCGAGGTCGAAGAAGACGAC
JAG1-CO25    AACAAGAATAGCAAGATGAGTAAGATTAGGACCCACAACAGCGAGGTGGAGGAGGACGAC
JAG1-CO04    AACAAGAATTCCAAGATGAGCAAGATCAGGACCCACAACTCCGAGGTGGAGGAAGATGAC
JAG1-CO18    AACAAGAACAGCAAGATGTCCAAGATCAGGACCCACAACAGCGAGGTGGAGGAAGACGAC
JAG1-CO05    AACAAGAATAGCAAGATGAGCAAGATCCGCACTCACAACAGCGAGGTGGAGGAGGACGAC
JAG1-CO23    AACAAGAACAGCAAGATGAGCAAGATCCGCACCCACAACAGCGAGGTTGAGGAAGACGAC
JAG1-CO24    AACAAGAACAGCAAGATGAGCAAGATCAGGACCCACAACAGCGAGGTTGAGGAAGACGAC
JAG1-CO21    AATAAGAACTCGAAGATGAGCAAGATCAGGACGCACAACTCCGAGGTGGAGGAGGACGAC
JAG1-CO22    AACAAGAACAGCAAGATGAGTAAGATCAGGACACACAACTCCGAGGTGGAAGAAGACGAC
JAG1-CO15    AACAAAAATAGCAAGATGAGCAAGATCAGGACACACAACTCTGAGGTGGAGGAGGACGAC
JAG1-CO16    AACAAGAACAGCAAGATGAGCAAGATCAGGACCCATAACTCCGAGGTGGAGGAGGACGAC
JAG1-CO07    AACAAGAATTCCAAGATGAGCAAGATCAGGACCCACAACAGCGAGGTGGAGGAGGACGAC
JAG1-CO02    AACAAGAACAGCAAGATGAGCAAGATCCGCACCCATAACTCGGAGGTGGAAGAAGACGAT
JAG1-CO20    AACAAAAATAGCAAAATGAGCAAGATTAGGACCCACAACTCCGAGGTGGAGGAGGACGAC
JAG1-CO13    AACAAGAACTCCAAGATGAGCAAGATCAGGACCCACAACTCCGAGGTGGAAGAGGACGAC
JAG1-CO19    AACAAGAACAGCAAGATGAGCAAGATCCGGACCCACAACAGCGAAGTAGAAGAGGACGAC
JAG1-CO08    AACAAGAACTCCAAGATGTCCAAAATCAGGACCCACAACAGCGAGGTGGAAGAGGACGAC
JAG1-CO03    AACAAGAACAGCAAGATGAGCAAAATCCGGACCCACAACTCGGAGGTGGAGGAGGACGAC
JAG1-CO14    AACAAAAACTCGAAAATGAGCAAGATCCGCACCCACAACAGCGAGGTGGAGGAGGACGAC
JAG1-CO09    AACAAGAACAGCAAGATGTCCAAGATCCGAACCCACAACAGCGAGGTCGAGGAGGACGAC
JAG1-CO10    AATAAGAACTCCAAGATGAGCAAGATCCGCACACACAACAGCGAGGTGGAGGAGGACGAT
JAG1-CO06    AACAAGAATAGCAAGATGTCCAAGATCCGCACACATAATTCCGAGGTCGAGGAAGACGAC
             **.**.**.   **.***  .**.**  * ** **.**.   **.** **.**.**.**.
```

FIG. 13 (cont)

```
JAG1-WT         ATGGACAAACACCAGCAGAAAGCCCGGTTTGCCAAGCAGCCGGCGTACACGCTGGTAGAC
JAG1-CO01       ATGGATAAGCACCAGCAGAAGGCCAGGTTCGCCAAGCAGCCCGCCTACACCCTGGTAGAC
JAG1-CO17       ATGGACAAGCACCAGCAGAAAGCGCGTTTCGCCAAGCAGCCCGCCTACACCCTGGTGGAC
JAG1-CO11       ATGGACAAGCACCAGCAGAAGGCCAGGTTCGCCAAGCAGCCCGCGTACACCCTGGTGGAC
JAG1-CO12       ATGGACAAACACCAGCAAAAGGCCAGGTTCGCCAAGCAGCCGGCCTACACCCTGGTGGAC
JAG1-CO25       ATGGACAAGCACCAGCAGAAGGCCCGCTTCGCCAAGCAGCCCGCCTATACCCTGGTCGAC
JAG1-CO04       ATGGACAAGCACCAGCAGAAAGCCAGGTTTGCCAAGCAGCCCGCCTATACCCTGGTGGAC
JAG1-CO18       ATGGACAAGCACCAGCAGAAGGCCCGATTCGCCAAGCAGCCCGCTTACACCCTGGTGGAC
JAG1-CO05       ATGGACAAGCACCAGCAGAAGGCCAGGTTTGCCAAGCAGCCCGCCTACACCCTGGTGGAC
JAG1-CO23       ATGGACAAGCACCAGCAGAAGGCCAGGTTCGCCAAGCAGCCCGCCTACACCCTGGTGGAT
JAG1-CO24       ATGGACAAGCACCAGCAGAAAGCCAGGTTCGCGAAGCAGCCCGCCTACACCCTGGTGGAC
JAG1-CO21       ATGGATAAGCACCAGCAGAAAGCCCGGTTCGCCAAGCAGCCCGCCTACACCCTGGTTGAC
JAG1-CO22       ATGGACAAGCACCAGCAGAAGGCCCGGTTCGCCAAGCAGCCCGCCTACACCCTGGTGGAC
JAG1-CO15       ATGGACAAGCACCAGCAGAAGGCCCGCTTCGCCAAGCAGCCCGCCTACACCCTGGTCGAC
JAG1-CO16       ATGGACAAGCACCAGCAAAAGGCCCGGTTCGCCAAGCAGCCCGCCTACACCCTGGTGGAT
JAG1-CO07       ATGGATAAACACCAGCAGAAGGCCAGGTTCGCCAAGCAGCCCGCCTATACCCTGGTCGAC
JAG1-CO02       ATGGATAAGCACCAGCAAAAGGCCCGGTTCGCGAAGCAGCCCGCCTATACCCTCGTGGAC
JAG1-CO20       ATGGACAAGCATCAGCAGAAGGCCCGCTTCGCCAAGCAACCCGCCTACACCCTGGTGGAC
JAG1-CO13       ATGGACAAGCACCAGCAGAAAGCCCGTTTCGCCAAGCAGCCCGCCTACACCCTGGTGGAC
JAG1-CO19       ATGGATAAGCACCAGCAGAAGGCCAGGTTCGCCAAGCAACCCGCCTACACCCTCGTGGAC
JAG1-CO08       ATGGATAAACACCAGCAGAAGGCCCGTTTCGCCAAGCAGCCCGCCTACACCTTAGTGGAC
JAG1-CO03       ATGGACAAGCACCAACAGAAGGCCCGCTTTGCCAAGCAGCCCGCCTACACCCTGGTGGAC
JAG1-CO14       ATGGACAAGCACCAGCAGAAAGCGAGATTCGCCAAACAGCCCGCCTACACCCTGGTGGAC
JAG1-CO09       ATGGACAAGCACCAGCAGAAGGCGAGGTTCGCCAAGCAGCCCGCCTACACCCTGGTAGAC
JAG1-CO10       ATGGACAAGCACCAGCAGAAGGCCAGGTTCGCCAAGCAGCCCGCCTACACCCTTGTGGAC
JAG1-CO06       ATGGATAAGCACCAGCAGAAGGCCAGATTCGCCAAGCAGCCCGCCTACACCCTGGTGGAC
                *****.**.**.**.**.**.**  * **.** **.**.** ** **.** .* ** **.

JAG1-WT         AGAGAAGAGAAGCCCCCCAACGGCACGCCGACAAAACACCCAAACTGGACAAACAAACAG
JAG1-CO01       AGGGAGGAGAAGCCCCCCAACGGCACCCCCACGAAACACCCGAACTGGACCAACAAGCAG
JAG1-CO17       AGGGAGGAGAAGCCCCCCAACGGAACCCCCACAAAGCACCCAAACTGGACGAATAAGCAG
JAG1-CO11       CGTGAGGAGAAGCCCCCCAACGGCACCCCCACCAAGCACCCCAACTGGACCAACAAGCAA
JAG1-CO12       AGGGAGGAGAAGCCCCCGAACGGCACCCCCACCAAGCACCCCAACTGGACCAACAAACAG
JAG1-CO25       AGGGAAGAGAAGCCGCCCAATGGGACCCCCACCAAGCATCCCAACTGGACCAACAAGCAG
JAG1-CO04       AGGGAGGAGAAACCCCCGAATGGCACCCCCACCAAACACCCAAACTGGACCAACAAGCAG
JAG1-CO18       AGGGAGGAAAAGCCCCCGAACGGCACCCCCACCAAACACCCCAACTGGACTAATAAACAG
JAG1-CO05       CGGGAGGAGAAGCCGCCCAATGGCACCCCCACGAAGCACCCGAACTGGACCAACAAACAG
JAG1-CO23       CGTGAGGAGAAACCGCCCAACGGGACCCCCACCAAGCATCCCAATTGGACCAACAAACAG
JAG1-CO24       CGGGAGGAAAAGCCCCCCAACGGCACCCCCACCAAGCACCCGAACTGGACCAACAAGCAG
JAG1-CO21       CGCGAGGAGAAACCCCCCAACGGCACCCCCACCAAGCACCCCAACTGGACCAACAAGCAG
JAG1-CO22       AGGGAAGAGAAACCCCCCAACGGTACACCCACGAAACACCCCAACTGGACCAATAAGCAG
JAG1-CO15       CGGGAAGAGAAGCCCCCGAACGGCACCCCCACCAAGCATCCTAACTGGACCAACAAGCAA
JAG1-CO16       CGGGAGGAGAAGCCCCCCAACGGTACCCCGACCAAACACCCCAACTGGACCAATAAACAG
JAG1-CO07       AGGGAGGAGAAACCCCCTAATGGCACCCCCACCAAGCACCCCAACTGGACAAACAAGCAG
JAG1-CO02       CGGGAAGAAAAGCCGCCCAACGGCACCCCCACCAAGCACCCCAACTGGACCAACAAACAG
JAG1-CO20       CGAGAGGAAAAGCCCCCCAACGGGACCCCCACGAAGCACCCCAACTGGACCAATAAGCAG
JAG1-CO13       CGAGAGGAAAAGCCGCCCAACGGCACCCCCACCAAGCATCCCAACTGGACCAACAAGCAG
JAG1-CO19       CGCGAGGAGAAACCCCCCAACGGCACCCCCACCAAGCACCCCAATTGGACCAACAAGCAA
JAG1-CO08       AGGGAGGAGAAACCCCCCAACGGGACCCCCACCAAGCACCCAAACTGGACGAACAAGCAG
JAG1-CO03       CGGGAGGAAAAGCCGCCGAATGGTACACCGACCAAGCATCCCAATTGGACAAACAAGCAG
JAG1-CO14       AGGGAGGAGAAGCCCCCAAACGGCACACCCACCAAGCACCCGAACTGGACCAACAAGCAG
JAG1-CO09       CGGGAGGAGAAGCCGCCCAACGGCACCCCCACGAAACACCCCAACTGGACCAACAAACAA
JAG1-CO10       CGCGAAGAGAAGCCCCCGAACGGCACCCCCACCAAGCACCCCAACTGGACCAACAAACAG
JAG1-CO06       AGGGAGGAGAAGCCCCCCAACGGCACACCCACCAAGCATCCCAACTGGACCAACAAGCAG
                 * **.**.**.** ** **.** ** ** ** **.**.** **.***** **.**.**.
```

FIG. 13 (cont)

```
JAG1-WT      GACAACAGAGACTTGGAAAGTGCCCAGAGCTTAAACCGAATGGAGTACATCGTA   ← SEQ ID NO:2
JAG1-CO01    GATAATAGGGACCTGGAGTCCGCGCAGAGCCTGAACCGCATGGAGTACATCGTG   ← SEQ ID NO:11
JAG1-CO17    GACAACAGGGACCTGGAGAGCGCCCAGAGTCTGAACCGGATGGAGTACATCGTG   ← SEQ ID NO:27
JAG1-CO11    GATAATCGGGACCTGGAATCCGCCCAGAGCCTGAACAGGATGGAGTACATCGTG   ← SEQ ID NO:21
JAG1-CO12    GACAACCGGGATCTGGAGAGTGCGCAGAGCCTGAACAGGATGGAGTACATCGTG   ← SEQ ID NO:22
JAG1-CO25    GACAACCGGGATCTGGAGAGCGCCCAAAGCCTGAATAGGATGGAGTACATCGTG   ← SEQ ID NO:35
JAG1-CO04    GACAACAGGGATCTGGAGAGCGCCCAGAGCCTCAACCGTATGGAGTACATCGTG   ← SEQ ID NO:14
JAG1-CO18    GACAACCGAGACCTGGAGAGCGCCCAGAGCCTGAACAGGATGGAATATATCGTC   ← SEQ ID NO:28
JAG1-CO05    GACAACAGGGACCTGGAGAGCGCCCAGAGCCTGAACCGCATGGAGTACATCGTG   ← SEQ ID NO:15
JAG1-CO23    GACAACAGGGACCTGGAGTCCGCCCAAAGCCTGAACCGGATGGAGTACATCGTC   ← SEQ ID NO:33
JAG1-CO24    GACAACAGGGACCTGGAGAGCGCCCAGAGCCTGAACCGGATGGAGTACATCGTC   ← SEQ ID NO:34
JAG1-CO21    GACAACCGAGACCTGGAGAGCGCCCAGAGCCTGAACAGGATGGAGTATATCGTG   ← SEQ ID NO:31
JAG1-CO22    GACAACAGGGACCTGGAGTCCGCCCAGAGTCTGAACAGGATGGAGTACATCGTG   ← SEQ ID NO:32
JAG1-CO15    GACAACAGGGACCTGGAAAGTGCCCAGAGCCTGAACCGGATGGAGTACATCGTG   ← SEQ ID NO:25
JAG1-CO16    GACAATAGGGACCTGGAGTCCGCCCAGAGCCTGAACAGGATGGAGTACATAGTG   ← SEQ ID NO:26
JAG1-CO07    GACAACAGGGACCTGGAGAGCGCCCAGAGCCTGAACCGTATGGAGTATATCGTG   ← SEQ ID NO:18
JAG1-CO02    GACAACAGGGACCTCGAGAGCGCCCAGTCCCTCAACCGTATGGAGTACATCGTC   ← SEQ ID NO:12
JAG1-CO20    GATAACAGGGACCTCGAGAGCGCCCAGTCCCTGAATCGCATGGAGTACATCGTG   ← SEQ ID NO:30
JAG1-CO13    GACAACCGTGACCTGGAGAGCGCCCAGTCGCTCAACCGCATGGAGTACATCGTG   ← SEQ ID NO:23
JAG1-CO19    GATAACCGCGACCTGGAGAGCGCCCAGAGCCTCAACCGGATGGAATACATCGTG   ← SEQ ID NO:29
JAG1-CO08    GATAACCGGGACCTGGAATCAGCGCAGTCCCTGAACAGAATGGAATACATCGTC   ← SEQ ID NO:18
JAG1-CO03    GATAACAGGGACCTGGAAAGCGCCCAGAGCCTGAACCGGATGGAGTACATCGTA   ← SEQ ID NO:13
JAG1-CO14    GACAACCGTGACCTGGAAAGCGCCCAGTCCCTGAATCGCATGGAATATATCGTG   ← SEQ ID NO:24
JAG1-CO09    GACAACAGGGACCTGGAGAGCGCCCAGTCCCTGAACAGGATGGAATATATTGTC   ← SEQ ID NO:19
JAG1-CO10    GATAACCGTGACCTGGAAAGCGCGCAGTCCCTGAACCGCATGGAGTACATAGTG   ← SEQ ID NO:20
JAG1-CO06    GACAACAGGGACCTGGAGAGCGCCCAGTCCCTGAACCGTATGGAGTACATCGTC   ← SEQ ID NO:16
             **.**. * **..* **.   ** **.   .* **. * *****.**.** **
```

FIG. 13 (cont)

Dose Response

PK

Dose Response

PK

SEQUENCE LISTING

```
<160> NUMBER OF SEQ ID NOS: 133

<210> SEQ ID NO 1
<211> LENGTH: 1218
<212> TYPE: PRT
<213> ORGANISM: Homo sapiens

<400> SEQUENCE: 1

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
```

-continued

```
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735
```

```
Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Pro Ser Ala
        995                 1000                 1005

Asn Asn  Glu Ile His Val Ala  Ile Ser Ala Glu Asp  Ile Arg Asp
    1010                 1015                 1020

Asp Gly  Asn Pro Ile Lys Glu  Ile Thr Asp Lys Ile  Ile Asp Leu
    1025                 1030                 1035

Val Ser  Lys Arg Asp Gly Asn  Ser Ser Leu Ile Ala  Ala Val Ala
    1040                 1045                 1050

Glu Val  Arg Val Gln Arg Arg  Pro Leu Lys Asn Arg  Thr Asp Phe
    1055                 1060                 1065

Leu Val  Pro Leu Leu Ser Ser  Val Leu Thr Val Ala  Trp Ile Cys
    1070                 1075                 1080

Cys Leu  Val Thr Ala Phe Tyr  Trp Cys Leu Arg Lys  Arg Arg Lys
    1085                 1090                 1095

Pro Gly  Ser His Thr His Ser  Ala Ser Glu Asp Asn  Thr Thr Asn
    1100                 1105                 1110

Asn Val  Arg Glu Gln Leu Asn  Gln Ile Lys Asn Pro  Ile Glu Lys
    1115                 1120                 1125

His Gly  Ala Asn Thr Val Pro  Ile Lys Asp Tyr Glu  Asn Lys Asn
    1130                 1135                 1140
```

```
Ser Lys  Met Ser Lys Ile Arg  Thr His Asn Ser Glu  Val Glu Glu
    1145                 1150                 1155

Asp Asp  Met Asp Lys His Gln  Gln Lys Ala Arg Phe  Ala Lys Gln
    1160                 1165                 1170

Pro Ala  Tyr Thr Leu Val Asp  Arg Glu Glu Lys Pro  Pro Asn Gly
    1175                 1180                 1185

Thr Pro  Thr Lys His Pro Asn  Trp Thr Asn Lys Gln  Asp Asn Arg
    1190                 1195                 1200

Asp Leu  Glu Ser Ala Gln Ser  Leu Asn Arg Met Glu  Tyr Ile Val
    1205                 1210                 1215
```

<210> SEQ ID NO 2
<211> LENGTH: 3654
<212> TYPE: DNA
<213> ORGANISM: Homo sapiens

<400> SEQUENCE: 2

```
atgcgttccc cacggacgcg cggccggtcc gggcgccccc taagcctcct gctcgccctg     60

ctctgtgccc tgcgagccaa ggtgtgtggg gcctcgggtc agttcgagtt ggagatcctg    120

tccatgcaga acgtgaacgg ggagctgcag aacgggaact gctgcggcgg cgcccggaac    180

ccgggagacc gcaagtgcac ccgcgacgag tgtgacacat acttcaaagt gtgcctcaag    240

gagtatcagt cccgcgtcac ggccgggggg ccctgcagct tcggctcagg gtccacgcct    300

gtcatcgggg gcaacacctt caacctcaag gccagccgcg gcaacgaccg caaccgcatc    360

gtgctgcctt tcagtttcgc ctggccgagg tcctatacgt tgcttgtgga ggcgtgggat    420

tccagtaatg acaccgttca acctgacagt attattgaaa aggcttctca ctcgggcatg    480

atcaacccca gccggcagtg gcagacgctg aagcagaaca cgggcgttgc ccactttgag    540

tatcagatcc gcgtgacctg tgatgactac tactatggct ttggctgcaa taagttctgc    600

cgccccagag atgacttctt tggacactat gcctgtgacc agaatggcaa caaaacttgc    660

atggaaggct ggatgggccc cgaatgtaac agagctattt gccgacaagg ctgcagtcct    720

aagcatgggt cttgcaaact cccaggtgac tgcaggtgcc agtacggctg gcaaggcctg    780

tactgtgata agtgcatccc acacccggga tgcgtccacg gcatctgtaa tgagccctgg    840

cagtgcctct gtgagaccaa ctggggcggc cagctctgtg acaaagatct caattactgt    900

gggactcatc agccgtgtct caacggggga acttgtagca acacaggccc tgacaaatat    960

cagtgttcct gccctgaggg gtattcagga cccaactgtg aaattgctga gcacgcctgc   1020

ctctctgatc cctgtcacaa cagaggcagc tgtaaggaga cctccctggg ctttgagtgt   1080

gagtgttccc caggctggac cggccccaca tgctctacaa acattgatga ctgttctcct   1140

aataactgtt cccacggggg cacctgccag gacctggtta acggatttaa gtgtgtgtgc   1200

cccccacagt ggactgggaa aacgtgccag ttagatgcaa atgaatgtga ggccaaacct   1260

tgtgtaaacg ccaaatcctg taagaatctc attgccagct actactgcga ctgtcttccc   1320

ggctggatgg gtcagaattg tgacataaat attaatgact gccttggcca gtgtcagaat   1380

gacgcctcct gtcgggattt ggttaatggt tatcgctgta tctgtccacc tggctatgca   1440

ggcgatcact gtgagagaga catcgatgaa tgtgccagca acccctgttt gaatgggggt   1500

cactgtcaga atgaaatcaa cagattccag tgtctgtgtc ccactggttt ctctggaaac   1560

ctctgtcagc tggacatcga ttattgtgag cctaatccct gccagaacgg tgcccagtgc   1620

tacaaccgtg ccagtgacta tttctgcaag tgccccgagg actatgaggg caagaactgc   1680
```

-continued

```
tcacacctga aagaccactg ccgcacgacc ccctgtgaag tgattgacag ctgcacagtg   1740
gccatggctt ccaacgacac acctgaaggg gtgcggtata tttcctccaa cgtctgtggt   1800
cctcacggga agtgcaagag tcagtcggga ggcaaattca cctgtgactg taacaaaggc   1860
ttcacgggaa catactgcca tgaaaatatt aatgactgtg agagcaaccc ttgtagaaac   1920
ggtggcactt gcatcgatgg tgtcaactcc tacaagtgca tctgtagtga cggctgggag   1980
ggggcctact gtgaaaccaa tattaatgac tgcagccaga acccctgcca caatgggggc   2040
acgtgtcgcg acctggtcaa tgacttctac tgtgactgta aaaatgggtg gaaaggaaag   2100
acctgccact cacgtgacag tcagtgtgat gaggccacgt gcaacaacgg tggcacctgc   2160
tatgatgagg gggatgcttt taagtgcatg tgtcctggcg gctgggaagg aacaacctgt   2220
aacatagccc gaaacagtag ctgcctgccc aacccctgcc ataatggggg cacatgtgtg   2280
gtcaacggcg agtcctttac gtgcgtctgc aaggaaggct gggaggggcc catctgtgct   2340
cagaatacca atgactgcag ccctcatccc tgttacaaca gcggcacctg tgtggatgga   2400
gacaactggt accggtgcga atgtgccccg ggttttgctg ggcccgactg cagaataaac   2460
atcaatgaat gccagtcttc accttgtgcc tttggagcga cctgtgtgga tgagatcaat   2520
ggctaccggt gtgtctgccc tccagggcac agtggtgcca agtgccagga agtttcaggg   2580
agaccttgca tcaccatggg gagtgtgata ccagatgggg ccaaatggga tgatgactgt   2640
aatacctgcc agtgcctgaa tggacggatc gcctgctcaa aggtctggtg tggccctcga   2700
ccttgcctgc tccacaaagg gcacagcgag tgccccagcg ggcagagctg catccccatc   2760
ctggacgacc agtgcttcgt ccacccctgc actggtgtgg gcgagtgtcg gtcttccagt   2820
ctccagccgg tgaagacaaa gtgcacctct gactcctatt accaggataa ctgtgcgaac   2880
atcacattta cctttaacaa ggagatgatg tcaccaggtc ttactacgga gcacatttgc   2940
agtgaattga ggaatttgaa tattttgaag aatgtttccg ctgaatattc aatctacatc   3000
gcttgcgagc cttccccttc agcgaacaat gaaatacatg tggccatttc tgctgaagat   3060
atacgggatg atgggaaccc gatcaaggaa atcactgaca aaataatcga tcttgttagt   3120
aaacgtgatg gaaacagctc gctgattgct gccgttgcag aagtaagagt tcagaggcgg   3180
cctctgaaga acagaacaga tttccttgtt cccttgctga gctctgtctt aactgtggct   3240
tggatctgtt gcttggtgac ggccttctac tggtgcctgc ggaagcggcg gaagccgggc   3300
agccacacac actcagcctc tgaggacaac accaccaaca acgtgcggga gcagctgaac   3360
cagatcaaaa accccattga gaaacatggg gccaacacgg tccccatcaa ggattatgag   3420
aacaagaact ccaaaatgtc taaaataagg acacacaatt ctgaagtaga agaggacgac   3480
atggacaaac accagcagaa agcccggttt gccaagcagc cggcgtacac gctggtagac   3540
agagaagaga agccccccaa cggcacgccg acaaaacacc caaactggac aaacaaacag   3600
gacaacagag acttggaaag tgcccagagc ttaaaccgaa tggagtacat cgta         3654
```

<210> SEQ ID NO 3
<211> LENGTH: 1054
<212> TYPE: PRT
<213> ORGANISM: Artificial Sequence
<220> FEATURE:
<223> OTHER INFORMATION: Synthetic polypeptide

<400> SEQUENCE: 3

```
Met Arg Ser Pro Arg Thr Arg Gly Arg Ser Gly Arg Pro Leu Ser Leu
1               5                   10                  15
```

-continued

```
Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
```

-continued

```
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860
```

```
Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Pro Ser Ala
        995                 1000                1005

Asn Asn  Glu Ile His Val Ala  Ile Ser Ala Glu Asp  Ile Arg Asp
    1010                1015                1020

Asp Gly  Asn Pro Ile Lys Glu  Ile Thr Asp Lys Ile  Ile Asp Leu
    1025                1030                1035

Val Ser  Lys Arg Asp Gly Asn  Ser Ser Leu Ile Ala  Ala Val Ala
    1040                1045                1050

Glu


<210> SEQ ID NO 4
<211> LENGTH: 3162
<212> TYPE: DNA
<213> ORGANISM: Artificial Sequence
<220> FEATURE:
<223> OTHER INFORMATION: Synthetic polynucleotide

<400> SEQUENCE: 4

atgagaagtc cacggacgcg cggccgctca gggcgtccat tgtccctcct gctcgccctg     60

ctctgcgccc tccgagccaa ggtctgtggt gccagtggtc agttcgagtt ggagatcctg    120

tccatgcaga atgtgaacgg ggaactgcag aatgggaact gctgcggcgg cgcccggaat    180

ccgggagacc gaaaatgcac acgcgacgaa tgcgacacgt acttcaaagt ctgtctcaag    240

gaataccaat cacgcgttac ggccgggggg ccctgtagct tcggatcagg gtccacccct    300

gttatcgggg gtaacacctt caaccttaag gccagcaggg gcaacgaccg caaccgcatc    360

gtgctgcctt tctcgtttgc ctggccgagg tcctatacgt tgcttgtgga ggcgtgggat    420

tcttctaatg ataccgttca gcctgacagc attattgaaa aggcttctca cagcggcatg    480

atcaatccca gccggcaatg gcaaacgctg aagcaaaaca cgggggtggc ccactttgag    540

tatcaaatcc gcgtgacatg cgatgactac tactacggct tcggatgtaa taagttctgc    600

cgccctagag acgatttctt tggccactat gcctgtgatc agaatggcaa caaaacttgt    660

atggagggct ggatggggcc cgaatgtaac agagcaattt gtcgacaggg ctgtagtcct    720

aagcacgggt cttgcaaact cccaggtgat tgtaggtgtc agtacggttg gcaaggcctg    780

tattgtgata agtgtattcc acatcccgga tgcgtccacg gtatctgcaa cgagccctgg    840

caatgtctct gtgagacaaa ttgggggggc cagctttgcg acaaagatct caattattgc    900
```

```
ggtacgcatc aaccgtgcct taatggggga acttgcagca atacaggacc tgataagtac    960
cagtgctcct gccctgaggg gtattcagga cccaactgtg agattgccga gcacgcttgc   1020
ttgtcagatc cctgccacaa tcgaggctca tgtaaggaga caagcctggg ctttgaatgt   1080
gagtgttctc caggctggac cggacccaca tgctcaacaa acattgatga ttgttctcct   1140
aacaactgtt ctcatggcgg gacctgccaa gacctggtta acggttttaa gtgtgtatgc   1200
ccaccccagt ggactgggaa gacgtgccaa ctagatgcga acgaatgcga agccaaaccc   1260
tgtgtgaacg ccaaatcctg taagaattta attgctagct actactgcga ttgccttcct   1320
ggctggatgg gtcagaattg tgacataaat attaatgact gcttgggcca gtgtcagaat   1380
gacgcctctt gccgggattt ggtgaatggt tatcgctgta tctgtccacc gggctatgca   1440
ggcgatcact gcgagagaga tattgatgag tgtgccagca atccctgttt gaatgggggt   1500
cactgccaga acgaaattaa cagattccag tgcctgtgtc ccacgggttt ttctggaaac   1560
ctctgtcagc tggatatcga ctattgtgag cctaacccct gccagaatgg tgcgcaatgc   1620
tacaataggg cgagtgacta cttctgtaag tgtcccgaag attatgaggg aaagaactgc   1680
tcacacctga aggaccactg cagaacaacc ccctgtgaag tgatagatag ctgcacagtt   1740
gcgatggctt ccaatgatac accagagggg gtgcggtata tttcttccaa cgtctgcggt   1800
ccacacggca agtgcaagag tcaatcggga ggaaaattca cctgcgactg taacaagggc   1860
ttcaccggaa cctactgcca tgagaatatc aatgattgcg agagcaaccc atgcaggaac   1920
ggtgggacct gcatcgacgg ggtcaactcc tacaaatgca tctgcagtga cggctgggaa   1980
ggggcctact gtgaaaccaa cattaatgac tgcagccaga acccttgtca taatgggggc   2040
acgtgtcgcg acctagtcaa cgacttctat tgtgactgta aaaatgggtg gaaaggaaag   2100
acatgccaca gccgtgatag ccagtgtgat gaggcaacgt gcaacaacgg tggcacttgc   2160
tatgatgagg gggatgcttt taagtgcatg tgtcctggcg gctgggaagg aactacatgc   2220
aatatcgccc gaaacagtag ctgcctgcct aatccctgcc ataacggggg aacatgtgtg   2280
gttaacggcg agtccttcac gtgcgtttgt aaagaaggct gggagggccc tatatgtgct   2340
cagaatacca atgactgcag cccgcatccc tgttacaata gcggcacctg tgttgacggt   2400
gacaattggt atcggtgcga atgtgcgccg ggtttcgcag gtccagactg cagaataaat   2460
atcaatgaat gccaaagctc accgtgcgcc tttggagcga cctgtgtgga tgaaatcaac   2520
ggctatcggt gtgtctgccc tcccgggcat agtggtgcca aatgccagga agtgtccggc   2580
agaccttgca tcaccatggg gagtgtgata ccggatggcg ctaaatggga tgatgattgt   2640
aatacctgtc agtgcctgaa cggacggatc gcttgttcaa aggtctggtg tggccctcga   2700
ccatgcttgt tacataaggg acactccgag tgccccagcg gtcagtcgtg tatccctatt   2760
ctggacgacc agtgcttcgt ccatccctgt actggtgtgg gcgagtgtag gtctagcagt   2820
ctccagccgg ttaagacaaa atgcaccagt gactcctatt accaagataa ctgtgcgaac   2880
atcacattta cctttaataa agagatgatg tcaccaggtc ttaccacgga gcacatttgc   2940
agtgaattga ggaatttgaa tattttgaag aatgtttccg ctgaatattc aatctacatc   3000
gcttgcgagc cttccccttc agcgaacaat gaaatacatg tggccatttc tgctgaagat   3060
atacgggatg atgggaaccc gatcaaggaa atcactgaca aaataatcga tcttgttagt   3120
aaacgtgatg ggaacagctc gctgattgct gcagttgcag aa                      3162
```

<210> SEQ ID NO 5
<211> LENGTH: 1046

<212> TYPE: PRT
<213> ORGANISM: Artificial Sequence
<220> FEATURE:
<223> OTHER INFORMATION: Synthetic polypeptide

<400> SEQUENCE: 5

```
Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380
```

-continued

```
His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
```

```
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
            885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
            965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Pro Ser Ala
        995                 1000                1005

Asn Asn  Glu Ile His Val Ala  Ile Ser Ala Glu Asp  Ile Arg Asp
    1010                1015                1020

Asp Gly  Asn Pro Ile Lys Glu  Ile Thr Asp Lys Ile  Ile Asp Leu
    1025                1030                1035

Val Ser  Lys Arg Asp Gly Asn  Ser
    1040                1045


<210> SEQ ID NO 6
<211> LENGTH: 3138
<212> TYPE: DNA
<213> ORGANISM: Artificial Sequence
<220> FEATURE:
<223> OTHER INFORMATION: Synthetic polynucleotide

<400> SEQUENCE: 6

atgaggtcac ctcggacgag aggtcggagc gggcgacctt tatctctcct cctagctctg     60

ctgtgcgcgc taagggcgaa agtgtgcggt gcgagcggtc aattcgaact tgaaattctt    120

agtatgcaaa acgtaaatgg cgaactgcaa aatgggaatt gctgtggcgg ggcgcggaat    180

cccggcgaca gaaaatgcac gcgggatgag tgcgacacgt actttaaagt ctgccttaag    240

gagtaccaaa gtagggtgac agcaggcggg ccttgtagtt tcggctcggg tagcacccct    300

gtaattggcg gtaatacctt caacttgaag gcctcacgcg gcaatgacag aaatcgtata    360

gttctgccct ttagttttgc atggccgagg tcgtatacct tgttggtaga ggcgtgggac    420

tcatcgaacg acactgtcca gcccgactcg atcattgaaa aggcctcgca cagtgggatg    480

ataaatccta gccggcagtg gcaaacactc aagcagaaca cgggcgtcgc gcactttgag    540

taccagataa gagtaacatg tgatgattac tattacggtt tcggttgtaa caaattctgt    600

cgtcctcgag acgacttctt tggacattac gcatgtgacc aaaacggtaa taagacatgt    660
```

-continued

```
atggaaggct ggatgggccc cgagtgcaac agggcgatct gtagacaggg ttgttccccg    720
aaacatggtt cttgcaaact accgggtgac tgcaggtgtc aatatggttg gcagggcctg    780
tactgtgata aatgcatacc gcatcctggg tgcgtccatg gtatctgtaa tgagccatgg    840
cagtgcctct gtgagacaaa ttggggtggc caactttgtg acaaggacct aaactattgt    900
gggactcatc aaccgtgtct gaatggggga acatgttcaa atactggtcc tgacaagtat    960
cagtgtagtt gtccagaagg ttactcgggg ccaaattgtg agatagcgga acatgcctgc   1020
ctctcagacc cgtgtcataa tcggggctct tgcaaggaaa catccctagg gtttgagtgc   1080
gagtgttctc ctggttggac gggtccgacg tgctccacaa acatcgacga ttgtagcccg   1140
aataactgtt cccacggggg aacatgccag gatctagtta acggttttaa gtgtgtttgt   1200
ccgccccaat ggaccggaaa aacctgtcag ttggatgcca atgaatgtga ggccaaaccg   1260
tgcgtgaacg cgaaatcgtg taagaatttg atcgcttcgt actactgtga ttgtttgccg   1320
ggatggatgg gacaaaactg cgatataaat attaatgact gtttgggcca atgccaaaat   1380
gatgcatcct gtagggatct tgtaaacgga tacaggtgca tatgtcctcc aggctacgct   1440
ggtgatcact gcgagagaga tatagacgaa tgtgcctcga acccttgcct aaatggtggt   1500
cattgtcaaa atgagataaa tcgattccag tgtctatgcc cgaccggctt ctcggggaat   1560
ctttgtcagt tagacataga ttattgtgag cccaatccat gtcaaaacgg cgcccagtgc   1620
tacaatcggg ctagcgatta cttctgtaag tgcccggagg attacgaagg gaagaattgc   1680
tcacatttaa aagaccactg ccgtacgacg ccttgcgaag ttattgactc ctgcaccgtg   1740
gccatggcct ccaacgatac gcctgagggg gtcaggtaca tatctagtaa cgtttgtggc   1800
ccccatggaa agtgcaaatc ccagtccggc gggaaattca catgcgattg caacaagggt   1860
tttacgggta cttattgcca cgagaacatt aatgattgtg aaagcaaccc atgtagaaat   1920
gggggtacct gtattgatgg tgtcaacagt tacaaatgta tttgtagcga tggctgggaa   1980
ggcgcctact gcgagacaaa tataaacgac tgctcccaga acccctgcca caatgggggc   2040
acctgccgcg acttggtaaa tgattttat tgcgattgca agaacggttg gaagggcaaa   2100
acatgccact cgcgagactc gcagtgtgac gaagccacgt gcaataatgg tggcacgtgc   2160
tatgacgagg gagacgcctt caagtgtatg tgccctggcg ggtgggaggg tacaacatgt   2220
aacatcgcca ggaactcgag ttgtctccct aatccctgtc ataacggtgg gacctgtgta   2280
gtcaacgggg aatcctttac atgtgtttgc aaggaaggct gggaaggccc aatctgtgcc   2340
cagaatacga acgattgctc accgcatccg tgttataact cggcacgtg tgtagatggc    2400
gataattggt atcgctgtga atgcgctcca ggattcgccg gtccggattg tcgaataaat   2460
attaacgagt gtcagtcatc gccttgtgcc tttggcgcga catgtgttga cgaaattaac   2520
ggatatcgtt gcgtttgtcc gcccggccat tccggcgcaa aatgccaaga agttagtgga   2580
agaccttgca tcactatggg ctccgttatc cctgacggcg cgaagtggga cgacgattgc   2640
aacacctgcc agtgtttaaa tggcaggatc gcgtgttcga aagtttggtg cgggccacgt   2700
ccctgcctcc tgcacaaagg acattctgag tgccctagtg gtcaaagttg tataccgata   2760
ttggatgatc aatgttttgt acacccgtgc acaggagttg gagaatgtcg ctcaagctca   2820
ctccaaccag ttaaaacgaa gtgtacgagt gacagttatt accaggataa ctgtgcgaat   2880
ataacattca catttaacaa agagatgatg tctcctgggc tgacgactga acatatctgt   2940
agtgagctaa ggaaccttaa catcttgaaa aacgtatctg ctgaatactc aatatacata   3000
gcctgtgagc catcccottc cgcgaacaat gaaatacatg tagccatttc agcagaagac   3060
```

atccgtgatg acggaaaccc gatcaaggaa ataacagaca aaataatcga cctggtctca 3120
aaacgggatg gaaattcc 3138

<210> SEQ ID NO 7
<211> LENGTH: 261
<212> TYPE: PRT
<213> ORGANISM: Artificial Sequence
<220> FEATURE:
<223> OTHER INFORMATION: Synthetic polypeptide

<400> SEQUENCE: 7

Met Gly Val Lys Val Leu Phe Ala Leu Ile Cys Ile Ala Val Ala Glu
1 5 10 15

Ala Cys Asp Asp Tyr Tyr Tyr Gly Phe Gly Cys Asn Lys Phe Cys Arg
20 25 30

Pro Arg Asp Lys Thr His Thr Cys Pro Pro Cys Pro Ala Pro Glu Ala
35 40 45

Ala Gly Gly Pro Ser Val Phe Leu Phe Pro Pro Lys Pro Lys Asp Thr
50 55 60

Leu Tyr Ile Thr Arg Glu Pro Glu Val Thr Cys Val Val Val Asp Val
65 70 75 80

Ser His Glu Asp Pro Glu Val Lys Phe Asn Trp Tyr Val Asp Gly Val
85 90 95

Glu Val His Asn Ala Lys Thr Lys Pro Arg Glu Glu Gln Tyr Asn Ser
100 105 110

Thr Tyr Arg Val Val Ser Val Leu Thr Val Leu His Gln Asp Trp Leu
115 120 125

Asn Gly Lys Glu Tyr Lys Cys Lys Val Ser Asn Lys Ala Leu Pro Ala
130 135 140

Pro Ile Glu Lys Thr Ile Ser Lys Ala Lys Gly Gln Pro Arg Glu Pro
145 150 155 160

Gln Val Tyr Thr Leu Pro Pro Ser Arg Asp Glu Leu Thr Lys Asn Gln
165 170 175

Val Ser Leu Thr Cys Leu Val Lys Gly Phe Tyr Pro Ser Asp Ile Ala
180 185 190

Val Glu Trp Glu Ser Asn Gly Gln Pro Glu Asn Asn Tyr Lys Thr Thr
195 200 205

Pro Pro Val Leu Asp Ser Asp Gly Ser Phe Phe Leu Tyr Ser Lys Leu
210 215 220

Thr Val Asp Lys Ser Arg Trp Gln Gln Gly Asn Val Phe Ser Cys Ser
225 230 235 240

Val Met His Glu Ala Leu Lys Phe His Tyr Thr Gln Lys Ser Leu Ser
245 250 255

Leu Ser Pro Gly Lys
260

<210> SEQ ID NO 8
<211> LENGTH: 783
<212> TYPE: DNA
<213> ORGANISM: Artificial Sequence
<220> FEATURE:
<223> OTHER INFORMATION: Synthetic polynucleotide

<400> SEQUENCE: 8
atgggagtca aagttctgtt tgccctgatc tgcatcgctg tggccgaggc ctgtgatgac 60
tactactatg gctttggctg caataagttc tgccgcccca gagacaagac ccacacctgc 120

```
ccccccctgcc ccgcccccga ggccgccggc gggcccagcg tgttcctgtt cccccccaag    180

cccaaggaca ccctgtacat caccagggag cccgaggtga cctgcgtggt ggtggacgtg    240

agccacgagg accccgaggt gaagttcaac tggtacgtgg acggcgtgga ggtgcacaac    300

gccaagacca agcccaggga ggagcagtac aacagcacct acagggtggt gagcgtgctg    360

accgtgctgc accaggactg gctgaacggc aaggagtaca agtgcaaggt gagcaacaag    420

gccctgcccg cccccatcga gaagaccatc agcaaggcca agggccagcc cagggagccc    480

caggtgtaca ccctgccccc cagcagggac gagctgacca agaaccaggt gagcctgacc    540

tgcctggtga agggcttcta ccccagcgac atcgccgtgg agtgggagag caacggccag    600

cccgagaaca actacaagac caccccccc gtgctggaca gcgacggcag cttcttcctg    660

tacagcaagc tgaccgtgga caagagcagg tggcagcagg gcaacgtgtt cagctgcagc    720

gtgatgcacg aggccctgaa gttccactac acccagaaga gcctgagcct gagccccggc    780

aag                                                                 783
```

<210> SEQ ID NO 9
<211> LENGTH: 276
<212> TYPE: PRT
<213> ORGANISM: Artificial Sequence
<220> FEATURE:
<223> OTHER INFORMATION: Synthetic polypeptide

<400> SEQUENCE: 9

```
Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Ala Ala
            20                  25                  30

Gly Gly Pro Ser Val Phe Leu Phe Pro Pro Lys Pro Lys Asp Thr Leu
        35                  40                  45

Tyr Ile Thr Arg Glu Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Ser Arg Asp Glu Leu Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu Lys Phe His Tyr Thr Gln Lys Ser Leu Ser Leu
225                 230                 235                 240
```

-continued

```
Ser Pro Gly Lys Gly Gly Gly Gly Ser Gly Gly Gly Gly Ser Gly Gly
                245                 250                 255

Gly Gly Ser Cys Asp Asp Tyr Tyr Tyr Gly Phe Gly Cys Asn Lys Phe
            260                 265                 270

Cys Arg Pro Arg
        275
```

<210> SEQ ID NO 10
<211> LENGTH: 828
<212> TYPE: DNA
<213> ORGANISM: Artificial Sequence
<220> FEATURE:
<223> OTHER INFORMATION: Synthetic polynucleotide

<400> SEQUENCE: 10

```
atgggagtca aagttctgtt tgccctgatc tgcatcgctg tggccgaggc cgacaagacc     60

cacacctgcc ccccctgccc cgccccccgag gccgccggcg gtcccagcgt gttcctgttc    120

ccccccaagc ccaaggacac cctgtacatc accagggagc ccgaggtgac ctgcgtggtg    180

gtggacgtga gccacgagga ccccgaggtg aagttcaact ggtacgtgga cggcgtggag    240

gtgcacaacg ccaagaccaa gcccagggag gagcagtaca acagcaccta cagggtggtg    300

agcgtgctga ccgtgctgca ccaggactgg ctgaacggca aggagtacaa gtgcaaggtg    360

agcaacaagg ccctgcccgc ccccatcgag aagaccatca gcaaggccaa gggccagccc    420

agggagcccc aggtgtacac cctgcccccc agcagggacg agctgaccaa gaaccaggtg    480

agcctgacct gcctggtgaa gggcttctac cccagcgaca tcgccgtgga gtgggagagc    540

aacggccagc ccgagaacaa ctacaagacc accccccccg tgctggacag cgacggcagc    600

ttcttcctgt acagcaagct gaccgtggac aagagcaggt ggcagcaggg caacgtgttc    660

agctgcagcg tgatgcacga ggccctgaag ttccactaca cccagaagag cctgagcctg    720

agccccggca agggtggcgg tggctcgggc ggtggtgggt cgggtggcgg cggatcttgt    780

gatgactact actatggctt tggctgcaat aagttctgcc gccccaga                 828
```

<210> SEQ ID NO 11
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 11

```
atgcgaagcc ccaggacccg cggccgtagc ggtaggcccc tgtccctgct gctggccctg     60

ctgtgcgccc tcagggccaa ggtgtgcggc gccagcggcc agttcgagct cgagatcctg    120

agcatgcaga acgtgaacgg cgagctccag aatgggaatt gttgcggcgg cgccaggaac    180

cccggtgaca ggaaatgcac ccgcgacgag tgcgacacct acttcaaagt gtgcctcaag    240

gagtaccaga gcagggtgac cgccggcggg ccctgcagct tcgggagcgg ctccacgccc    300

gtgatcggcg ggaacacctt caacctgaag gccagcaggg gcaacgatcg gaaccggatc    360

gtgctgccgt tctccttcgc ctggccgcga agctacaccc tgctggtgga agcgtgggac    420

agcagcaacg acaccgtgca gcccgacagc atcatcgaga aggcctcaca ctccggtatg    480

atcaacccca gcaggcagtg gcagaccctg aagcagaaca ccggagtggc ccacttcgaa    540

taccagatca gggtgacatg cgacgactac tactacggct tcgggtgcaa caagttctgc    600

aggccccgcg acgacttctt cggacactac gcctgtgacc agaacgggaa caagacgtgt    660
```

-continued

```
atggaggggt ggatggggcc cgaatgcaac agggccatct gtcggcaggg ttgctccccc    720
aagcacggct cctgcaaact gcccggcgat tgccggtgcc agtacgggtg gcaaggtctg    780
tactgcgaca agtgcatccc gcatcccggc tgcgtgcacg gcatctgcaa cgagccctgg    840
cagtgcctgt gcgaaaccaa ctggggcggc cagctctgtg acaaggacct taactactgc    900
ggcacccacc agccctgcct gaacggcggg acctgcagca acaccgggcc cgacaagtac    960
cagtgtagct gccccgaagg gtactcgggt cccaactgcg agatcgccga gcacgcctgc   1020
ctgtccgacc cctgccataa caggggcagc tgtaaggaga cctccctggg cttcgagtgt   1080
gagtgctccc ccggatggac cggcccccacc tgcagcacca atattgacga ctgcagccca   1140
aataactgct cccacggcgg cacctgccag gacctcgtga acggctttaa gtgcgtctgt   1200
ccccccccagt ggaccggcaa gacctgccag ctggacgcca atgagtgcga ggccaagccc   1260
tgtgtaaacg ccaagagctg caagaacctg atcgccagct actactgtga ctgcctgccc   1320
ggctggatgg gccagaactg cgacatcaac atcaacgact gcctcgggca gtgccagaac   1380
gacgccagct gcagggatct ggtgaacggc tacaggtgca tctgcccccc cggatacgcc   1440
ggcgaccatt gcgaaaggga catcgatgag tgcgcctcca atccctgtct gaacggcggc   1500
cactgccaga acgagatcaa caggttccag tgcctgtgcc ccaccggctt cagcgggaac   1560
ctgtgccagc tggacatcga ctattgcgag cccaatccct gccagaacgg ggcgcagtgc   1620
tacaacaggg ccagcgacta cttctgcaag tgccccgagg actacgaggg caagaattgc   1680
agccacctga aagaccactg ccgcaccacc ccctgtgagg ttatcgacag ctgtacggtc   1740
gccatggcct cgaacgacac ccccgaaggc gtgaggtata tctccagcaa cgtgtgcggg   1800
ccacacggca aatgtaagtc ccagagcggc gggaagttca cctgcgactg caacaagggc   1860
ttcacaggca cgtactgcca tgagaacatc aacgattgtg agagcaaccc ctgcaggaac   1920
ggcgggacct gcatagacgg cgtgaacagc tataagtgca tctgcagcga tggctgggag   1980
ggagcctact gcgaaaccaa catcaatgac tgcagccaga acccctgtca caacgggggc   2040
acatgccggg acctggtgaa tgatttctac tgcgactgca agaatggctg gaagggcaag   2100
acctgccaca gcagggactc ccagtgtgac gaggccacct gcaataacgg gggcacctgc   2160
tacgacgagg gcgacgcctt taagtgcatg tgccccggcg gttgggaggg taccacctgc   2220
aacatcgcgc ggaacagcag ctgtctgccc aacccctgcc acaacggggg cacgtgcgtg   2280
gtgaacggcg agagcttcac ctgcgtgtgt aaggaggggt gggagggccc catctgcgcc   2340
cagaacacca acgattgctc gccccacccc tgttacaaca gcgggacctg cgtggacggt   2400
gataactggt acaggtgcga gtgcgcacca ggcttcgccg ggccggactg caggatcaac   2460
atcaacgaat gtcagagctc cccgtgcgcc ttcggcgcca cgtgcgtaga cgagatcaat   2520
ggctacaggt gcgtgtgccc cccaggccac agcggggcca aatgccagga agtcagcggc   2580
cgaccctgca tcaccatggg ttccgttatc ccagacggag ccaagtggga tgacgattgt   2640
aacacctgtc agtgtctgaa tggccggatc gcgtgcagca aggtgtggtg cggcccccagg   2700
ccgtgcctgc tgcacaaggg ccactccgaa tgtccctccg gtcagagctg catccccatc   2760
ctcgacgacc agtgctttgt acacccctgc accggagtcg gcgagtgcag gtcctcgtct   2820
ctgcagcccg tgaaaaccaa gtgcaccagc gactcctact accaggacaa ctgcgccaac   2880
atcacgttca cctttaacaa ggagatgatg agccccgggc tgaccacgga gcacatctgc   2940
tcggagctga ggaacctgaa catactgaag aacgtgagcg ccgagtacag catctacatt   3000
```

gcctgcgagc ccagccccag cgccaacaac gagatccacg tggcgatctc cgccgaagac 3060
atccgggacg acggcaaccc catcaaggag ataaccgaca agatcatcga cctggtgagc 3120
aagcgggacg gcaacagctc cctgatcgcc gccgtggccg aggtgcgggt acagaggcgg 3180
cccctcaaga acaggacgga cttcctcgtg ccgctcctgt cgtccgtgct gaccgtggcc 3240
tggatctgct gtctggtgac cgccttctac tggtgcctgc ggaagcggcg caagccgggg 3300
agccacaccc actcggccag cgaagacaac acgaccaaca acgtgaggga gcagctgaat 3360
cagatcaaga atcccataga gaaacacggc gccaacaccg tgcccatcaa ggattacgag 3420
aacaagaaca gcaagatgtc caaaatcaga acccacaata gcgaagtgga ggaagacgac 3480
atggataagc accagcagaa ggccaggttc gccaagcagc ccgcctacac cctggtagac 3540
agggaggaga agccccccaa cggcaccccc acgaaacacc cgaactggac caacaagcag 3600
gataataggg acctggagtc cgcgcagagc ctgaaccgca tggagtacat cgtg 3654

<210> SEQ ID NO 12
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 12
atgaggagcc ccaggacccg gggccgtagc gggaggccgc tctcgctgct gctggccctg 60
ctctgcgccc tgagggccaa ggtgtgtggc gcctccgggc agttcgagct ggaaatcctg 120
agcatgcaga acgtcaacgg cgagctgcag aacggcaact gctgcggcgg agcgcggaac 180
cccggggaca ggaagtgcac cagggacgag tgtgacacgt acttcaaagt ctgcctcaag 240
gagtaccaga gccgggtgac cgccgggggc ccatgctcct tcggcagcgg cagcaccccc 300
gtcatcggag gcaacacctt taatctgaag gccagcaggg ggaacgacag gaataggatc 360
gtcctgccct ttagcttcgc ctggcccagg tcctacaccc tgctggtcga ggcctgggac 420
agctccaacg acaccgtcca gcccgacagt atcatcgaga aggcgtccca ctccggcatg 480
atcaatccca gcaggcagtg gcagacgctg aagcagaaca ccggcgtggc ccacttcgag 540
tatcagatcc gggtgacgtg cgacgactac tactacgggt tcggctgcaa caagttctgt 600
aggccccggg acgatttctt cggccactac gcatgcgacc agaacggcaa caagacctgc 660
atggagggct ggatgggccc cgagtgcaac agggctatct gccgccaggg ctgctccccc 720
aagcacggca gctgtaagct gcccggcgat tgccggtgtc agtacgggtg gcagggactg 780
tattgcgaca agtgcatacc ccacccaggc tgcgtgcacg gcatctgtaa cgagccctgg 840
caatgcctct gcgagaccaa ctggggggga caactgtgcg acaaggacct gaactactgc 900
ggtacccacc agccctgcct gaacggcggc acctgcagta acaccggccc cgacaagtat 960
cagtgcagct gccccgaggg gtattccggc ccgaactgcg agatcgccga gcacgcctgc 1020
ctcagcgacc catgccacaa tagaggcagc tgcaaggaaa cctccctggg gttcgagtgt 1080
gagtgctccc ccgggtggac cgggcccacc tgctccacca acatcgacga ctgcagcccc 1140
aataactgca gccacggggg cacctgtcag gacctggtga acggctttaa gtgcgtctgc 1200 ccccccagt ggaccggtaa gacgtgccag ctggacgcca atgagtgcga agccaagccc 1260
tgcgtcaatg ccaagagctg taagaacctc atcgcgtcct actattgcga ctgcctgccc 1320
gggtggatgg gacagaactg cgacatcaac atcaacgact gcctcgggca gtgccagaac 1380
gacgccagct gccgggacct ggtgaacggc tatagatgca tctgcccccc cggctacgcc 1440

```
ggggaccact gcgagaggga catcgacgag tgcgcctcca acccctgcct gaatggaggc   1500
cactgccaga acgaaatcaa caggttccag tgtctgtgcc ccaccggatt cagcggaaac   1560
ctgtgccagc tggacatcga ctattgcgaa cccaacccct gtcagaacgg cgcccagtgc   1620
tacaaccggg caagcgacta cttctgcaag tgccctgagg actacgaggg caagaactgc   1680
agccacctca aggaccactg caggacgacc ccctgtgagg tgatcgacag ctgtaccgtg   1740
gccatggcct cgaacgacac ccctgagggc gtgaggtata tctccagcaa cgtctgcggc   1800
ccccacggca aatgtaagag ccaatccggg ggcaagttca cctgcgactg caacaaggga   1860
tttaccggca cctactgcca cgagaacatc aacgactgcg agtccaatcc ctgccgtaac   1920
ggcggcacct gcatcgacgg tgtcaacagc tacaagtgca tctgcagcga cggctgggag   1980
ggagcgtact gcgaaaccaa cataaacgat tgttcccaga acccctgcca caacggcggc   2040
acctgccggg accttgtgaa cgacttttac tgtgactgca agaatgggtg gaagggcaaa   2100
acgtgccaca gcagagacag ccagtgcgac gaagccacct gtaacaacgg cggcacctgc   2160
tacgacgagg gcgacgcctt taagtgtatg tgcccgggcg gctgggaagg cacgacctgc   2220
aacatcgccc ggaacagcag ctgcctcccg aacccttgcc acaacggcgg gacctgcgtg   2280
gtgaatggcg aatccttcac ctgcgtgtgc aaggagggct gggagggccc catctgcgcc   2340
caaaacacca atgactgtag cccccacccc tgctacaact ccggcacatg tgtggatggc   2400
gacaactggt acaggtgtga gtgcgccccc ggattcgccg gccccgactg ccggatcaac   2460
attaacgagt gtcagagcag cccctgcgcc ttcggcgcca cctgcgtcga tgagataaac   2520
ggatataggt gcgtgtgccc ccccggacac agcggcgcga agtgccagga ggtgagcggc   2580
aggccctgca tcacaatggg cagcgtgatc ccggacggcg ccaagtggga cgacgattgc   2640
aacacctgcc agtgcctgaa cggccggata gcctgctcca aagtgtggtg cggcccccgc   2700
ccctgcctgc tgcacaaggg ccacagcgag tgcccctccg gccagagctg catccccata   2760
ctggacgacc aatgtttcgt gcatccctgc accggcgtgg gcgagtgtcg gagcagcagc   2820
ctgcagcccg tgaagactaa gtgcacctcc gactcctact atcaggacaa ctgtgccaac   2880
atcaccttca ccttcaacaa ggagatgatg agccccggcc tgacaacgga gcacatctgc   2940
agcgagctgc gcaatctgaa catcctgaaa aatgtgagcg ccgagtacag catctacatc   3000
gcctgtgagc cgagccccag cgctaataac gagatccacg tggccatctc cgccgaggac   3060
atcagggatg acggcaaccc catcaaagag atcaccgaca agatcatcga cctggtgtcc   3120
aagcgggacg gcaactccag cctgatcgca gccgtggccg aagtgagggt ccagcggcgg   3180
cccctgaaga accgaaccga cttcctggtc cccctgctga gcagcgtgct gaccgtcgca   3240
tggatctgtt gcctggtgac ggccttctac tggtgcctca ggaaaagacg gaagcccggg   3300
agccacaccc acagcgccag cgaggacaac accaccaaca acgtgcggga gcagctgaac   3360
caaatcaaga accccatcga gaagcatggc gccaataccg tgcccatcaa agactacgag   3420
aacaagaaca gcaagatgag caagatccgc acccataact cggaggtgga agaagacgat   3480
atggataagc accagcaaaa ggcccggttc gcgaagcagc ccgcctatac cctcgtggac   3540
cgggaagaaa agccgcccaa cggcaccccc accaagcacc ccaactggac caacaaacag   3600
gacaacaggg acctcgagag cgcccagtcc ctcaaccgta tggagtacat cgtc         3654
```

<210> SEQ ID NO 13
<211> LENGTH: 3654
<212> TYPE: DNA

<213> ORGANISM: Artificial Sequence
<220> FEATURE:
<223> OTHER INFORMATION: Synthetic polynucleotide

<400> SEQUENCE: 13
atgaggtccc cgcgtacccg aggcaggtcc gggaggcccc tgtccctgct gctcgcctta 60
ctttgcgccc tgagggccaa agtctgcggc gcctccggcc aattcgagct ggagatcctc 120
agcatgcaga acgtgaacgg cgagctgcaa aacgggaact gctgcggggg agcccgcaac 180
cccggcgacc ggaagtgcac cagggacgag tgcgacacct acttcaaggt gtgcctcaag 240
gagtatcagt caagggtgac cgccggaggc ccctgtagct tcggctccgg gtcgaccccc 300
gtgataggcg gaaacacctt caacctgaag gccagcaggg ggaacgacag gaataggatc 360
gtgctcccct tctcgttcgc ctggcccagg agctacaccc tcctcgtgga ggcctgggac 420
agcagcaacg atacggtgca gcccgactcc atcatcgaga aggccagcca ctccggcatg 480
atcaacccca gccgccagtg gcagaccctg aagcaaaaca cgggcgtggc acacttcgag 540
taccagataa gggtcacttg cgacgactac tactacgggt tcgggtgcaa caagttttgc 600
aggccccggg acgacttctt cggacactat gcctgcgacc agaacggcaa caagacctgt 660
atggagggtt ggatgggccc cgaatgcaat cgcgccattt gccggcaggg gtgcagccct 720
aagcacggaa gctgtaagct ccccggcgac tgccgctgcc agtacggctg gcagggactg 780
tactgtgaca agtgtatccc ccaccccggc tgcgtgcacg gcatctgcaa tgagccttgg 840
cagtgcctgt gcgagaccaa ttggggcggc cagctgtgcg acaaggacct gaactactgc 900
ggcacccacc agccctgcct gaacggtggg acctgcagca acaccgggcc agacaagtac 960
cagtgcagct gccccgaggg ctatagcggg cccaattgcg agatcgccga gcacgcctgc 1020
ctgtccgacc cctgtcacaa ccggggctcc tgcaaggaga cctccctggg gtttgagtgc 1080
gagtgctccc ccggttggac cggcccccacc tgctccacca acatcgacga ctgctccccc 1140
aacaattgca gccacggcgg cacatgccag gatctggtga acggcttcaa gtgtgtgtgt 1200
ccccccccagt ggaccggcaa gacctgccag ctggacgcga acgagtgcga agcaaagccc 1260
tgcgtgaacg ccaagtcctg caaaaacctg atcgccagct attactgcga ctgcctgccc 1320
ggctggatgg ggcagaactg tgacataaac ataaacgact gcctcggcca gtgccagaat 1380
gacgcgagct gccgggacct cgtgaacggc taccgatgca tctgcccccc gggctacgcc 1440
ggcgaccatt gcgaacggga tatcgacgag tgtgccagca acccctgcct gaacgggggg 1500
cactgccaga acgagataaa caggttccag tgcctgtgcc ccaccggctt cagcggcaac 1560
ctgtgccaac tcgacatcga ctactgcgag cccaacccct gccaaaacgg tgcccaatgc 1620
tacaaccggg cctcggacta cttttgcaag tgcccggagg actatgaggg caagaattgt 1680
tcccacctca aggaccactg ccggaccacc ccctgcgagg tgatcgactc ctgcaccgtg 1740
gccatggcta gtaacgatac ccccgagggc gttaggtaca tctcctccaa cgtgtgcggc 1800
ccccacggga agtgcaagtc gcagagcggc ggcaagttca cctgcgactg caataagggc 1860
ttcaccggta cctactgcca cgagaacatc aacgactgcg agagcaatcc ctgccggaac 1920
gggggtacct gcatcgacgg cgtgaactcc tacaagtgta tctgctcaga tggctgggaa 1980
ggcgcgtact gtgagaccaa cataaacgac tgtagccaga acccctgtca taacgggggc 2040
acctgcaggg acctggtgaa cgacttctac tgcgactgca agaacgggtg gaaaggcaaa 2100
acttgccact ccagggactc ccagtgcgat gaggccacct gcaataacgg cggcacgtgc 2160
tacgacgagg gggacgcctt caagtgcatg tgccccgggg gctgggaggg gaccacctgc 2220
aacatcgcca ggaacagctc ctgcctgccc aacccatgcc acaatggagg cacctgcgta 2280
gtgaatggcg agtccttcac ctgtgtgtgc aaggagggct gggaggggcc catctgcgcc 2340
cagaacacca acgactgcag cccacacccg tgctacaact ccggcacctg cgtcgacggc 2400
gacaactggt acaggtgcga gtgcgccccc ggcttcgcgg gcccggactg ccggattaat 2460
atcaacgagt gccagagcag cccctgcgcc ttcggggcca cctgcgtcga cgaaatcaac 2520
gggtaccggt gcgtgtgccc ccccggccac agcggggcaa agtgccagga agtcagcggc 2580
aggccctgca tcaccatggg cagcgtcatt cccgatggcg caaagtggga cgacgactgc 2640
aacacttgcc agtgcctgaa tggcaggatc gcctgcagca aggtgtggtg cggcccaagg 2700
ccctgcctgc tgcacaaagg ccacagcgaa tgcccaagcg gtcagagctg catccccatc 2760
ctggatgacc agtgcttcgt gcacccctgc accggggtcg gtgagtgtag gagcagcagc 2820
ctgcagcccg tgaagaccaa gtgcacctcc gattcctact accaggacaa ttgcgccaac 2880
ataactttta ccttcaacaa ggagatgatg agccccggcc tcaccacgga gcacatctgc 2940
agcgagctgc gcaacctcaa catcctgaag aacgtgagcg ccgagtacag catttacatc 3000
gcctgcgagc ccagcccctc cgccaacaac gagatccacg tggccatcag cgccgaggac 3060
ataagggatg acgggaatcc catcaaggag atcaccgaca agatcatcga cctggtgtcc 3120
aagcgggacg gcaatagcag cctgatcgcc gccgtcgcgg aggtgcgggt gcagaggcgc 3180
ccgctgaaga accggaccga cttcctcgtg cccctgctga gcagcgtgct gacggtggcc 3240
tggatctgct gcctggtgac agccttctac tggtgcctgc ggaagaggag gaagcccggg 3300
agccacaccc atagcgcgtc cgaggacaac acgacaaaca acgtcagaga gcagctgaac 3360
caaatcaaga atcccatcga aaaacacggc gccaacaccg tgcccatcaa agattacgag 3420
aacaagaaca gcaagatgag caaaatccgg acccacaact cggaggtgga ggaggacgac 3480
atggacaagc accaacagaa ggcccgcttt gccaagcagc ccgcctacac cctggtggac 3540
cgggaggaaa agccgccgaa tggtacaccg accaagcatc ccaattggac aaacaagcag 3600
gataacaggg acctggaaag cgcccagagc ctgaaccgga tggagtacat cgta 3654

<210> SEQ ID NO 14
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 14
atgaggagcc ccaggaccag ggggaggagc gggaggccgc tgagcctgct cctggccctg 60
ctgtgtgccc tgcgcgccaa ggtgtgcggc gcgtccggac agtttgagct ggagatcctg 120
tccatgcaga acgtgaacgg cgagctccag aacgggaact gctgcggggg cgcaaggaac 180
cccggtgaca ggaagtgcac ccgcgacgag tgcgacacgt actttaaggt gtgcctgaaa 240
gagtaccaga gcagggtgac tgccggcgga ccctgctcgt ttggaagcgg cagcactcct 300
gtgatcggtg gcaacacctt caatctgaag gcctccaggg ggaacgatag gaacaggatc 360
gtgctgccat tcagctttgc ctggccccgg tcatacaccc tgctggtgga ggcctgggac 420
tccagcaacg acaccgtgca gcccgactcc atcatagaga aggcgagcca cagcggcatg 480
atcaacccct ccaggcagtg gcagaccctc aagcagaaca ccggcgtcgc ccacttcgaa 540
taccagatca gggtcacgtg cgacgactac tactacggct ttggctgcaa taagttctgc 600

-continued

```
aggccccggg acgacttctt cgggcactac gcctgcgacc agaacgggaa caaaacctgt    660

atggaggggt ggatgggccc cgaatgcaac cgagccatct gccgccaggg gtgctccccc    720

aagcacggct cctgtaaact ccccggcgat tgcaggtgtc agtacggctg gcagggtctc    780

tactgcgaca agtgcatccc gcaccccggc tgcgtccacg gcatctgtaa tgagccctgg    840

caatgcctgt gcgagaccaa ctggggcggc cagctgtgcg acaaggacct caattattgt    900

ggcacccacc agccatgcct gaatggtggc acctgcagca acacaggccc agacaagtac    960

cagtgcagct gtcccgaggg ctactcgggc cccaactgcg aaatcgccga gcacgcttgc   1020

ctgagcgacc cctgtcacaa caggggcagc tgcaaggaaa ccagcctggg gttcgagtgc   1080

gagtgcagcc ccgggtggac cggccccacc tgcagcacca acatcgacga ctgcagcccc   1140

aacaactgta gccatggcgg cacctgccag gatctggtca acggcttcaa gtgcgtgtgt   1200

ccccccagt ggaccggcaa gacctgccag ctcgacgcca acgagtgtga agcaaagccc   1260

tgcgtgaatg ccaagtcctg caagaacctg atagcctcct actactgcga ctgcctgccc   1320

ggctggatgg gccagaactg tgacatcaac atcaacgact gcctggggca gtgtcagaat   1380

gacgccagct gccgcgacct ggtgaatggc tataggtgca tctgccccc cggatacgcc   1440

ggcgaccact gcgagaggga tatcgatgag tgcgccagca acccttgcct gaacggcggg   1500

cactgccaga acgagattaa caggttccag tgcctgtgcc ccaccggctt cagcggcaat   1560

ctgtgccagc tggatatcga ctactgcgag cccaacccgt gccagaacgg cgcccagtgc   1620

tacaacaggg cctccgacta cttctgtaag tgtcccgagg actatgaggg caagaactgt   1680

tcccacctga aagaccactg caggaccacc ccctgcgagg tgatcgactc gtgcaccgtg   1740

gccatggcga gcaatgacac ccggaaggc gtgcgctata tcagcagcaa tgtgtgcggg   1800

ccccacggca agtgcaagag ccagagcggc gggaagttca cctgcgactg caacaagggc   1860

ttcaccggca cgtactgcca cgagaacatc aacgattgcg agtccaaccc ctgccggaac   1920

ggcggcacct gcatagatgg agtgaactcc tataagtgca tctgctccga tgggtgggag   1980

ggcgcctact gtgaaaccaa catcaacgac tgcagccaga accccctgcca taatggtggc   2040

acgtgccggg acctggttaa tgacttctac tgcgactgca agaacggctg gaagggcaag   2100

acctgccaca gcagagatag ccagtgcgac gaggccacgt gcaacaatgg cgggacctgc   2160

tacgacgagg gggacgcctt caaatgcatg tgccccggcg gatgggaggg gaccacctgc   2220

aacatcgcca ggaactccag ctgcctgccc aacccgtgcc ataacggtgg cacctgcgtg   2280

gtgaacggcg aaagcttcac ctgcgtgtgc aaggagggct gggagggccc catctgcgcc   2340

cagaacacca atgactgctc cccccaccca tgctacaact ccgggacctg tgtggacggc   2400

gacaactggt ataggtgcga gtgtgccccc ggcttcgccg gccccgactg caggatcaac   2460

atcaacgaat gtcagagctc cccctgcgcc tttggcgcca catgtgtcga tgagattaac   2520

ggctaccggt gcgtctgccc ccccggccac agcggcgcga agtgccagga agtctccggc   2580

aggccctgta tcaccatggg cagcgtgatc cccgacggcg ccaagtggga cgacgactgc   2640

aacacctgtc aatgcctgaa tggcaggatc gcctgcagca aagtctggtg cgggccccgg   2700

ccctgcctgc tgcacaaggg ccacagcgag tgcccttccg gccagagctg catcccgatc   2760

ctggacgatc agtgttttgt ccatccatgc accggcgtgg gcgagtgtag gtcgagcagc   2820

ctgcagcccg tgaaaacaaa gtgcaccagc gacagctact accaggataa ctgtgccaac   2880

atcaccttta ccttcaacaa ggagatgatg agccccggac tgaccaccga gcatatctgt   2940

tcagagctga ggaacctgaa catcctcaag aacgtcagcg ccgagtacag catctacatc   3000
```

gcctgcgagc ccagcccctc cgccaacaac gaaatccacg tggccataag cgccgaggac 3060
atcagggacg acggcaatcc gatcaaggag ataaccgaca agatcatcga cctcgtgagt 3120
aagagggacg ggaacagtag cctcatcgcc gccgtcgccg aggtgagggt gcagcggagg 3180
cccctgaaga acaggaccga ttttctggtc cccctgctga gctccgtgct gaccgtggcc 3240
tggatctgct gcctggtgac ggcgttctac tggtgcctcc ggaaacgacg gaagcccggg 3300
agccataccc actccgccag cgaggacaac accaccaata acgtgaggga gcagctgaat 3360
cagatcaaga atccgatcga gaagcacggc gccaacaccg tgccgatcaa agactacgag 3420
aacaagaatt ccaagatgag caagatcagg acccacaact ccgaggtgga ggaagatgac 3480
atggacaagc accagcagaa agccaggttt gccaagcagc ccgcctatac cctggtggac 3540
agggaggaga aacccccgaa tggcaccccc accaaacacc caaactggac caacaagcag 3600
gacaacaggg atctggagag cgcccagagc ctcaaccgta tggagtacat cgtg 3654

<210> SEQ ID NO 15
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 15
atgaggtcac cccggacccg gggacgctcc ggcaggcccc tgagcctgct gctggccctg 60
ctgtgcgccc tcagggccaa ggtctgcggc gcctccggtc agttcgaact cgagatcctg 120
agcatgcaga acgtgaacgg tgaactgcag aacggcaact gctgcggcgg cgccaggaat 180
cccggcgacc gaaagtgcac cagggacgag tgcgacacct actttaaggt gtgcctaaag 240
gagtaccaga gccgggtgac ggccggcggc ccctgttcct tcggcagcgg cagcacgccc 300
gtgatcggcg gcaacacctt caacctcaag gcctcgcgcg gcaacgatcg gaacaggatc 360
gtgctgccgt tttcctttgc ctggcccagg tcgtacaccc tgctggtgga ggcctgggac 420
agctccaatg acaccgtgca gccagactcc ataatcgaga aggccagcca cagcgggatg 480
attaatccaa gcaggcagtg gcaaaccctg aagcagaaca ccggagtggc ccatttcgag 540
taccagatca gggtgacctg cgacgactac tactacggct tcggatgcaa caagttctgc 600
aggccccggg acgacttctt cggccattac gcctgcgacc agaacggcaa caagacctgc 660
atggagggtt ggatgggccc cgaatgcaat agggccatct gcaggcaagg ctgttccccc 720
aaacacggga gctgtaaact ccccggcgac tgccgatgcc agtacgggtg gcaaggcctc 780
tactgcgaca agtgcatccc ccatcccggc tgcgtgcatg gcatttgcaa cgaaccctgg 840
caatgcctct gcgagaccaa ctgggggggc cagctctgcg acaaggatct gaactactgc 900
ggcacacacc agccttgcct gaacggaggg acctgcagta ataccggccc cgacaagtac 960
cagtgcagct gccccgaggg ctatagcggc cccaactgcg aaattgccga gcacgcctgc 1020
ctgagcgacc cctgtcacaa caggggcagc tgcaaggaga ccagtctggg cttcgagtgc 1080
gagtgcagcc caggctggac gggccccacc tgctccacca acatcgacga ctgctccccc 1140
aacaattgca gccacggcgg cacctgccaa gatctcgtga acggcttcaa gtgcgtgtgt 1200
ccgccgcagt ggaccgggaa aacctgccaa ctggacgcca acgagtgtga ggcaaagccc 1260
tgcgtgaacg cgaagtcctg taagaacctg atcgccagct actattgcga ctgcctgccg 1320
ggctggatgg ggcagaactg tgacatcaac atcaacgatt gcctgggcca gtgtcagaac 1380

-continued

```
gacgccagct gcagggacct ggtcaacggc tacaggtgca tctgtccccc ggggtatgcc   1440
ggggaccact gcgaacgaga tatcgacgag tgcgcctcga acccttgcct caatggcggc   1500
cactgccaga acgagatcaa caggttccag tgcctgtgcc ccaccggctt cagcggcaat   1560
ctgtgccagc tggacatcga ctattgtgaa cccaacccgt gccagaacgg cgcccagtgc   1620
tacaaccgcg cctccgacta cttctgcaag tgcccggagg actacgaggg caagaactgc   1680
agccatctga aggaccactg tagaaccacg ccctgcgagg tgatcgactc ctgcaccgtc   1740
gccatggcct caaacgacac ccccgaggga gtgcgctaca tcagctcgaa cgtgtgcggc   1800
ccccatggaa aatgcaagag ccagtccggg ggcaagttca cctgcgactg caacaagggc   1860
ttcaccggca cgtattgcca tgagaacatc aatgactgcg agagcaaccc gtgccgtaac   1920
gggggcacct gtatcgatgg cgtgaacagc tacaagtgca tctgtagcga cggctgggag   1980
ggcgcctatt gcgaaaccaa catcaacgac tgttcccaga acccatgcca caacgggggc   2040
acctgtaggg acctggtcaa cgacttttac tgtgactgca agaacggttg gaaaggcaag   2100
acctgccact cgagggacag ccagtgtgac gaggccacgt gcaacaatgg cggcacctgt   2160
tacgacgagg gcgacgcctt taagtgcatg tgtcccgggg gttgggaggg taccacctgt   2220
aacatcgcca ggaactcaag ctgcctgccc aatccctgcc ataacggtgg gacctgcgtg   2280
gtgaacggcg aaagcttcac ctgcgtgtgc aaggagggct gggagggccc catctgtgcc   2340
cagaacacca atgactgcag cccccacccc tgttacaaca gcgggacctg cgtggatggt   2400
gacaactggt acaggtgtga gtgcgccccc gggtttgccg gccccgactg caggatcaac   2460
atcaacgagt gccagagcag cccctgtgcc ttcggcgcca cctgcgtgga cgagatcaac   2520
gggtaccggt gcgtgtgccc ccccggccac tccggcgcca agtgccagga ggtgtccggc   2580
aggccctgca tcaccatggg cagcgtcatc cccgacggcg ccaaatggga cgacgactgc   2640
aacacctgtc agtgcctgaa cggcaggatc gcctgctcca aggtttggtg cgggcccagg   2700
ccctgcctgc tgcacaaggg acatagcgaa tgccccagcg gccagagctg catccccatc   2760
ctggacgacc agtgcttcgt gcatccctgc accggggtgg gcgagtgccg gagctcctcg   2820
ctgcaacccg tcaagaccaa gtgcacctcg gacagctatt accaggacaa ctgcgccaac   2880
atcaccttca ccttcaacaa ggaaatgatg agccccggcc tgaccaccga gcatatctgc   2940
agcgagctgc ggaacctgaa catactgaag aacgttagcg ccgagtactc catctacatc   3000
gcctgcgagc ccagcccgag cgcgaataat gagatccacg tcgccatcag cgccgaggac   3060
atccgggacg acggcaaccc catcaaggag atcaccgaca agatcatcga cctggtcagc   3120
aagcgtgacg gcaactccag cctgatcgcc gcggtggctg aggtgcgagt ccagaggagg   3180
cccctgaaga acaggacgga cttcctcgtc cctctgctga gcagcgtgct gaccgtggcc   3240
tggatctgtt gcctggtgac cgccttttac tggtgcctgc gaaagaggag gaagccgggc   3300
agccacaccc acagcgcctc agaagacaac accacaaaca acgtccgcga gcagctcaac   3360
cagatcaaaa accccatcga aaagcacggc gccaacaccg tgcccatcaa ggactacgag   3420
aacaagaata gcaagatgag caagatccgc actcacaaca gcgaggtgga ggaggacgac   3480
atggacaagc accagcagaa ggccaggttt gccaagcagc ccgcctacac cctggtggac   3540
cgggaggaga agccgcccaa tggcaccccc acgaagcacc cgaactggac caacaaacag   3600
gacaacaggg acctggagag cgcccagagc ctgaaccgca tggagtacat cgtg         3654
```

<210> SEQ ID NO 16
<211> LENGTH: 3654

<212> TYPE: DNA
<213> ORGANISM: Artificial Sequence
<220> FEATURE:
<223> OTHER INFORMATION: Synthetic polynucleotide

<400> SEQUENCE: 16
atgcggtccc ccaggaccag ggggcgcagc gggaggcccc tgagcctgct gctggcctta 60
ctgtgtgccc tgagggccaa ggtgtgcggc gccagcgggc agttcgagct ggagatactg 120
tccatgcaaa acgtgaacgg cgaactgcag aatgggaatt gctgcggtgg cgccaggaac 180
cctggggacc gcaagtgtac ccgggacgag tgcgacacct acttcaaggt gtgtctcaag 240
gaatatcagt cccgcgtgac cgccgggggc ccctgcagct tcggctcagg cagcacccca 300
gtcatcgggg gcaacacctt caacctgaag gccagccgtg gcaacgacag gaacaggata 360
gtgctgccct tctccttcgc gtggcccagg tcctacaccc tgctggtgga ggcgtgggat 420
agctcgaatg ataccgtcca gcccgactcc atcatcgaga aagcctccca ctccggtatg 480
atcaatccaa gcaggcagtg gcagaccctg aagcagaaca cgggcgtggc ccactttgag 540
taccagatca gggtcacctg cgacgactac tactacggct tcggctgtaa taaattttgc 600
cggcctcggg acgacttctt cggccactac gcctgcgacc agaacggcaa taagacgtgt 660
atggagggct ggatgggccc ggagtgtaat agggccatct gccgacaggg gtgcagcccc 720
aagcacggca gctgcaagct gcccggcgac tgcaggtgtc agtacggctg gcaaggactg 780
tattgtgaca agtgcattcc ccatccgggc tgtgtgcacg gaatctgcaa tgagccctgg 840
cagtgcctgt gcgagaccaa ctggggcggc cagctgtgtg acaaggatct gaactactgt 900
ggcacccacc agccctgcct gaacggcggg acctgctcca ataccgggcc cgacaagtac 960
cagtgttcct gccccgaggg ctacagcggt ccaaactgcg agatcgccga gcacgcctgc 1020
ctgagcgacc cctgccataa caggggctcc tgcaaggaga ccagcctggg cttcgaatgc 1080
gagtgctccc ccgggtggac cggcccccacc tgcagtacca acatcgatga ctgcagcccc 1140
aataactgtt cccacggcgg cacctgccag gacctggtga acggcttcaa atgcgtctgt 1200
ccgccccagt ggaccggaaa gacctgtcag ctcgacgcaa acgagtgcga ggccaagccc 1260
tgcgtgaacg ccaagagctg caagaatctg atcgcctcct actactgcga ttgtctgccc 1320
ggatggatgg gccaaaactg cgacatcaac atcaacgatt gtctggggca gtgccagaac 1380
gacgccagct gcagggacct ggtcaacggc tacaggtgca tctgcccccc cggctatgcc 1440
ggagaccatt gcgagcgaga catcgacgag tgtgcctcga acccctgcct gaacgggggg 1500
cactgccaga acgaaatcaa caggttccaa tgcctctgcc ccaccgggtt cagcggcaac 1560
ctgtgccagc tggacatcga ctattgcgag cccaacccct gccagaacgg ggcgcagtgt 1620
tataaccggg cctcggacta cttctgtaag tgtcccgagg actacgaggg caaaaactgc 1680
tcccacctga aggaccactg ccgtaccaca ccctgcgaag tcatcgactc ctgcaccgtg 1740
gccatggcca gcaacgacac ccccgaggga gtgcggtaca tcagcagcaa cgtgtgcggg 1800
ccgcatggca agtgtaagtc ccagagcggg ggcaagttta catgtgactg taacaagggc 1860
ttcaccggca catactgcca cgagaacatc aacgattgcg agagcaaccc ctgccggaat 1920
gggggcacct gcatcgacgg ggtgaacagc tataagtgta tctgctccga tggctgggag 1980
ggcgcctact gcgagactaa catcaatgac tgctcgcaga acccgtgcca caacggggga 2040
acctgcaggg atctcgtgaa cgacttctac tgcgactgca agaacgggtg gaaggggaag 2100
acctgccaca gccgcgactc ccagtgcgac gaggccacct gcaacaatgg gggcacctgc 2160
tacgacgagg gcgacgcctt caagtgcatg tgccccggcg ggtgggaggg caccacctgc 2220
aacatcgccc ggaactccag ctgcctgccc aatccgtgtc acaatggggg cacctgcgtg 2280
gtgaacggcg agtcgttcac gtgcgtgtgc aaggaaggct gggagggacc gatctgcgcc 2340
caaaatacca acgactgtag cccccacccc tgttataaca gcggcacctg cgtcgacggg 2400
gacaattggt accggtgcga gtgcgccccc ggcttcgccg gccccgactg ccgaatcaac 2460
atcaacgaat gtcaaagctc accctgtgcc ttcggggcaa cctgtgtgga cgagatcaac 2520
ggctaccggt gtgtgtgccc cccgggacac tccggggcca agtgccagga ggtgagcggg 2580
cgaccatgca tcaccatggg ctccgtgatc cccgacggcg ccaagtggga cgacgactgc 2640
aacacctgcc agtgcctgaa cggcaggatc gcctgctcca aggtgtggtg tggcccccgg 2700
ccctgtctcc tgcacaaagg tcacagcgag tgccccagcg gccagagctg catcccgatc 2760
cttgacgacc agtgcttcgt gcacccgtgt acaggcgtag gggagtgcag gagctcctcg 2820
ctccagcccg tgaaaaccaa gtgtaccagc gactcatact atcaggacaa ctgtgccaat 2880
atcaccttta ccttcaacaa ggaaatgatg agccccgggc tgaccaccga gcacatctgc 2940
agcgagctgc ggaaccttaa cattctgaaa aatgtgtccg ccgagtacag catatacatc 3000
gcctgcgagc cgagccctag cgccaacaat gagatacacg tggccatcag cgctgaggac 3060
atcagggatg acggcaaccc gatcaaggag atcaccgaca agataataga cctcgtcagc 3120
aaaagggacg gcaacagcag cctgatcgcc gccgtcgccg aggtgagggt gcagcgccgg 3180
cccctgaaga acaggaccga cttcctggtg cccctcctga gctccgtgct gaccgtggcc 3240
tggatctgct gcctggtgac cgccttctac tggtgtctga ggaaaaggag gaagcctggc 3300
agccacaccc atagcgcctc cgaggacaat accaccaaca acgtcaggga acagctcaac 3360
caaatcaaga accccatcga gaagcacggc gccaataccg tgcccatcaa ggattacgag 3420
aacaagaata gcaagatgtc caagatccgc acacataatt ccgaggtcga ggaagacgac 3480
atggataagc accagcagaa ggccagattc gccaagcagc ccgcctacac cctggtggac 3540
agggaggaga agcccccaa cggcacaccc accaagcatc ccaactggac caacaagcag 3600
gacaacaggg acctggagag cgcccagtcc ctgaaccgta tggagtacat cgtc 3654

<210> SEQ ID NO 17
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 17
atgaggagcc ccaggacaag gggccggagc ggcaggcccc tgagcctgct gctcgccctc 60
ctctgtgccc tgcgcgccaa agtgtgcggg gcctcaggcc agttcgagct cgagatcctg 120
tccatgcaaa acgtgaacgg cgaactgcag aacggaaatt gctgcggtgg cgcccgtaac 180
cccggcgacc gcaagtgcac cagggacgag tgcgacacct acttcaaggt gtgtctgaag 240
gagtaccaga gcagggtcac cgccggcggc ccctgcagct ttggctccgg cagcaccccc 300
gtgatcggcg gcaacacctt caacctgaag gctagccgcg gcaacgacag gaacaggatc 360
gtgcttccat ttagcttcgc ctggcccagg agctacaccc tgcttgtgga ggcctgggac 420
agctccaacg acaccgtgca gcccgacagc atcatcgaga aggccagcca ctccggcatg 480
atcaacccca gccggcagtg gcagaccctg aagcagaaca ccggcgtcgc gcacttcgag 540
taccagatca gggtgacatg tgacgactat tactatggct ttggatgtaa caagttctgc 600

-continued

```
aggcccagag acgacttctt cggccactac gcctgcgacc agaacggaaa taagacctgt    660
atggaaggct ggatggggcc cgagtgcaac cgagccatct gcaggcaagg ctgcagcccc    720
aagcacggca gctgcaagct gcccggggac tgccggtgcc agtacggctg gcagggcttg    780
tattgcgaca agtgcatccc gcaccccggc tgcgtgcacg ggatctgcaa cgagccctgg    840
cagtgcctgt gcgagacgaa ctggggcggc cagctgtgcg acaaggacct gaactactgc    900
gggacgcatc aaccctgtct caacggcggt acctgcagca ataccggccc cgacaagtac    960
cagtgctctt gccccgaggg ctatagcggg cccaactgtg agatcgccga gcacgcttgc   1020
ctgtccgacc cctgccacaa ccggggctcc tgcaaggaga cctccctggg cttcgagtgc   1080
gaatgcagcc ccgggtggac cggtcccacg tgcagcacca acatcgatga ctgtagcccc   1140
aacaactgca gccacggcgg cacgtgccag gacctcgtga acggcttcaa gtgcgtgtgc   1200
ccccccagt ggaccggcaa gacctgccag ctcgacgcca atgagtgcga agccaagccc   1260
tgcgtcaacg ccaagtcctg caagaacctg atcgccagtt actactgcga ctgtctgccc   1320
ggatggatgg gccagaattg cgacatcaac atcaatgact gcctgggcca gtgccagaat   1380
gacgcgtcct gtagggatct ggtgaacggg tacaggtgca tatgtccccc cggctatgcc   1440
ggggatcact gcgagaggga tatcgatgag tgcgccagca acccctgtct gaacggtggc   1500
cactgccaga acgagattaa caggttccag tgcctgtgcc ccaccggctt cagcggcaac   1560
ctgtgccagc tggatatcga ctactgtgag cccaacccgt gccagaacgg cgcccagtgc   1620
tacaaccgag ccagcgatta tttttgcaaa tgtcccgagg attacgaagg gaagaattgc   1680
agccacctga aggaccattg caggaccacc ccctgcgaag tgatcgacag ctgcaccgtg   1740
gccatggcct cgaatgacac gcccgaggga gtgaggtaca tcagtagcaa tgtgtgcggc   1800
ccccatggga agtgcaagag ccagtcgggc ggaaagttta cctgcgactg taacaagggc   1860
ttcaccggga cctactgtca cgaaaacatc aacgactgcg agtccaaccc gtgtaggaac   1920
ggcgggacct gcatagacgg ggtgaatagc tataagtgca tctgttcaga cggatgggag   1980
ggggcctact gcgagaccaa catcaacgat tgctcgcaga acccctgcca caacggcggc   2040
acctgccggg acctggtgaa cgacttctac tgcgactgta aaaacggctg gaaggggaag   2100
acctgccact ccagggacag ccagtgcgac gaggcgacct gcaacaacgg cggcacctgc   2160
tacgacgagg gcgatgcctt caagtgtatg tgccccggag gctgggaggg caccacctgc   2220
aacatcgccc gcaacagcag ctgcctgccc aatccctgcc acaatggtgg aacatgcgtg   2280
gtgaacgggg agagctttac gtgcgtgtgc aaggagggat gggagggccc catctgtgcc   2340
cagaacacca acgactgctc cccccatccc tgttacaaca gcggcacctg tgtggacggg   2400
gacaactggt accgctgcga gtgcgccccc ggcttcgccg gcccggactg ccgtatcaac   2460
atcaacgagt gtcagagcag cccctgcgca ttcggcgcca cctgcgtgga tgaaataaac   2520
ggctacaggt gtgtgtgccc ccccggccac agcggagcca aatgccagga ggtgagcggg   2580
cgcccatgca tcaccatggg gagcgtgatc ccagacgggg cgaagtggga tgacgactgt   2640
aacacctgcc agtgcctgaa cggccgaatc gcctgcagca aggtgtggtg cgggccccgg   2700
ccctgcctgc tgcacaaagg ccacagcgag tgccccagcg gccagagctg cataccgatc   2760
ctggacgacc agtgcttcgt acacccctgc accggggtgg gcgagtgccg gtcctcctcg   2820
ctccagcccg tcaagaccaa gtgcaccagc gatagctact accaggacaa ctgcgccaac   2880
atcaccttta cctttaacaa ggagatgatg agccccggcc tgaccacgga gcacatctgc   2940
```

agcgagctgc gcaacctcaa catcctgaaa aacgtgtcgg ccgagtactc catctacatc 3000
gcctgcgagc cctccccctc cgccaacaat gaaatccacg tggccatcag cgccgaggac 3060
atccgagacg atgggaaccc catcaaggaa atcaccgaca agataatcga cctggtgagt 3120
aaaagggacg ggaacagcag cctgatcgct gccgtggcgg aggtgagggt ccagaggagg 3180
ccgctgaaaa atcggaccga ctttctggtg cccctgctga gctccgtgct gaccgtcgcc 3240
tggatctgct gcctggtcac cgccttctac tggtgcctga ggaagcgtag gaagcccggc 3300
agccacacgc acagcgccag cgaggacaac accaccaaca acgtgcggga gcagctgaac 3360
cagatcaaga accccatcga gaagcacggc gcgaacacag tgccgatcaa ggattacgag 3420
aacaagaatt ccaagatgag caagatcagg acccacaaca gcgaggtgga ggaggacgac 3480
atggataaac accagcagaa ggccaggttc gccaagcagc ccgcctatac cctggtcgac 3540
agggaggaga aacccctaa tggcaccccc accaagcacc ccaactggac aaacaagcag 3600
gacaacaggg acctggagag cgcccagagc ctgaaccgta tggagtatat cgtg 3654

<210> SEQ ID NO 18
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 18
atgcggagcc ccagaacccg tggccggagc ggcaggcccc tgtcactact gctggccctg 60
ctgtgcgcgc ttagggccaa ggtctgcggc gccagcggcc agttcgagct ggagatcctg 120
agcatgcaga acgtgaacgg cgagctgcag aacggcaact gctgcggcgg ggccaggaac 180
cccggagacc gcaaatgcac ccgggacgag tgcgacacct attttaaagt gtgcctgaag 240
gagtaccaga gcagggtgac cgccggcggc ccctgcagct tcggcagcgg cagcaccccc 300
gtgatcggcg ggaatacctt caacctgaag gccagccgcg gcaacgacag gaaccgaatc 360
gtgctgccct ttagcttcgc ctggcctcgg agctacaccc tgctggtgga agcctgggac 420
tcctccaacg acaccgtgca acccgactcc attatcgaga aggcctccca cagcggcatg 480
ataaacccca gccggcagtg gcagacactg aagcaaaaca ccggggtcgc acatttcgag 540
taccagatca gggtgacgtg tgacgactac tactacgggt tcggatgcaa caagttctgc 600
aggcccaggg acgacttctt cggccactac gcctgtgacc agaacggcaa taagacctgc 660
atggaggggt ggatgggccc ggagtgcaac agggccatat gccggcaggg ctgctcccca 720
aaacacgggt cctgcaagct gcctggcgac tgcaggtgtc agtacggctg gcaggggctg 780
tactgcgata agtgcatccc ccaccccggc tgcgtccacg gcatctgcaa cgagccatgg 840
cagtgtctgt gcgagaccaa ctggggtggg cagctgtgcg acaaggatct gaactactgc 900
ggcacccacc agccctgcct caacgggggga acgtgctcga acaccgggcc cgataagtac 960
cagtgctcct gccccgaagg ctactcggga cctaactgtg agatcgctga gcacgcatgc 1020
ctgagcgacc catgccataa caggggtagt tgcaaggaga cctccctcgg ttttgaatgc 1080
gagtgcagcc ccggctggac cggcccccacc tgctcgacca acatcgacga ctgcagccca 1140
aacaactgct cccacggcgg cacgtgtcag gacctggtga atggcttcaa gtgtgtgtgc 1200 ccccccccagt ggaccggaaa aacctgccag ctggatgcca acgagtgtga ggccaagccc 1260
tgcgtgaacg cgaagtcctg caagaacctg atcgcctcct actactgtga ctgcctgccc 1320
ggttggatgg gccaaaactg cgacatcaac atcaacgact gcctgggcca gtgccagaac 1380

-continued

```
gacgccagct gcagggacct agtgaacggg tatcggtgca tctgcccccc cggctacgcc   1440
ggcgatcact gcgaaaggga catcgacgag tgcgccagca acccgtgcct gaacgggggg   1500
cactgccaga acgagatcaa caggttccag tgcctctgcc ccaccgggtt cagcgggaac   1560
ctctgccagc tcgacatcga ctactgcgag cccaatccct gccagaacgg cgcgcaatgc   1620
tacaataggg cctcggacta cttctgcaag tgccccgagg actacgaggg caaaaactgc   1680
agccacctga aggaccactg taggacaacc ccctgcgaag tcatcgactc ctgcaccgtg   1740
gccatggcct ccaacgacac cccagaaggc gtacgttaca tcagctccaa cgtctgcggg   1800
ccccacggga agtgcaagag ccagagcggc ggcaagttca cgtgtgactg caacaaaggg   1860
ttcaccggca cctactgcca tgagaacata aatgactgcg agtccaaccc ctgtcggaac   1920
ggcggcacct gcatcgacgg cgtaaactct tacaaatgta tctgcagcga cggctgggag   1980
ggcgcctact gcgagaccaa catcaacgac tgcagccaaa acccctgtca caacggcggg   2040
acctgccgcg acctcgtcaa cgacttctac tgcgactgca agaacggctg gaagggcaag   2100
acctgccaca gccgggactc gcagtgtgat gaggccacct gcaacaatgg cggcacctgc   2160
tatgatgagg gggacgcctt caaatgtatg tgccccggcg ggtgggaggg caccacttgc   2220
aacatcgcca ggaactcctc ctgcctcccc aacccctgcc acaacggagg gacgtgcgtg   2280
gtgaacgggg agagcttcac ctgcgtgtgc aaggagggct gggaaggccc catttgcgcg   2340
cagaacacta acgattgcag cccccacccc tgctacaact ccggcacctg cgtggacggg   2400
gacaactggt accggtgcga gtgcgccccc ggcttcgccg gcccggactg caggatcaac   2460
atcaacgaat gtcagagcag cccctgcgcc ttcggagcca cctgcgtgga cgagataaac   2520
ggctaccggt gcgtctgccc ccccggtcac tctggtgcca agtgccaaga ggtcagcggc   2580
aggccgtgca tcaccatggg ctccgtgatc ccggatggcg ccaaatggga cgatgactgc   2640
aacacctgcc agtgccttaa cggtcggatc gcgtgcagca aggtgtggtg tggccccagg   2700
ccctgcctcc tgcacaaggg gcacagcgag tgcccctccg gacagtcctg tatccccatc   2760
ctggacgacc agtgcttcgt ccacccctgc accggagtgg gcgaatgcag gagcagctcc   2820
ctgcagccgg tgaagaccaa gtgcaccagc gactcctact accaggacaa ttgcgccaac   2880
atcaccttca ccttcaacaa ggagatgatg agccccggcc tgaccaccga gcacatctgc   2940
agcgagctgc gcaacctgaa catcttgaag aacgtgagcg ccgagtattc catctacatc   3000
gcctgcgagc ccagcccgag cgccaataac gagatccacg tggccatcag cgccgaggac   3060
atccgggatg acggcaatcc catcaaggag atcaccgata agatcatcga cctggtcagc   3120
aagcgcgacg gcaatagctc gctgatcgcg gccgtggccg aggtgagggt gcagcggcgg   3180
cccctgaaga acaggaccga ctttctggta cccctcctga gctcggtgct gaccgttgcc   3240
tggatctgtt gtctggtgac cgccttctac tggtgcctgc ggaaaaggcg gaagcccggc   3300
tcccataccc atagcgcatc cgaagacaac accaccaaca acgtccgtga gcagctgaac   3360
cagatcaaga accccataga gaaacacggc gccaacaccg tgcccatcaa ggactacgaa   3420
aacaagaact ccaagatgtc caaaatcagg acccacaaca gcgaggtgga agaggacgac   3480
atggataaac accagcagaa ggcccgtttc gccaagcagc ccgcctacac cttagtggac   3540
agggaggaga aacccccaa cgggaccccc accaagcacc caaactggac gaacaagcag   3600
gataaccggg acctggaatc agcgcagtcc ctgaacagaa tggaatacat cgtc         3654
```

<210> SEQ ID NO 19

<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 19
atgaggtccc cccgaaccag gggcaggtcc ggtcggcccc tgagcctgct cctggccctc 60
ctgtgcgccc tgagagccaa ggtgtgtgga gccagcgggc agttcgagct cgagatcctc 120
tccatgcaga acgtgaacgg cgagctgcag aacggcaact gctgcggagg cgccaggaat 180
cccggcgatc ggaagtgcac cagggacgag tgcgacacct atttcaaggt gtgcctcaag 240
gagtaccaaa gcagggtgac cgccggcggc ccctgctcct tcggcagcgg cagcaccccc 300
gtgatagggg gcaacacgtt caacctcaag gccagcaggg gcaacgacag gaaccgcatc 360
gtgctgccct tcagctttgc gtggccccgt tcctacaccc tgctggtcga ggcctgggac 420
agctccaacg ataccgtgca gcccgactcc atcattgaga aggccagcca cagcggcatg 480
atcaacccca gcaggcagtg gcaaaccctg aagcagaaca ccggagtggc ccatttcgaa 540
taccagatca gggtgacctg cgatgactac tattatggtt ttgggtgcaa caaattctgc 600
cggccccgag acgacttctt cggtcactat gcctgcgacc agaacggcaa caagacctgt 660
atggaggggt ggatgggccc tgagtgcaac cgggccatct gtcgccaggg gtgctccccc 720
aagcacggca gctgcaagct gcctggcgat tgccggtgtc agtacgggtg gcagggtctc 780
tactgcgaca agtgcatccc ccacccgggc tgtgtgcacg gcatctgcaa cgagccctgg 840
cagtgcctgt gcgaaaccaa ttggggcggc caactgtgcg acaaggacct gaactactgt 900
ggcacccacc agccctgcct gaacgggggc acttgctcca acacgggccc cgacaagtat 960
cagtgcagct gtcctgaggg ctacagcggc cccaactgtg agatcgccga gcatgcctgc 1020
ctgagcgacc cgtgccacaa tcgtggcagc tgtaaggaga ccagcctggg cttcgagtgc 1080
gagtgcagcc cgggttggac cggacccacc tgcagcacca acatcgacga ttgcagcccc 1140
aacaactgtt cacacggggg cacgtgccaa gacctggtga acgggttcaa gtgtgtctgc 1200 ccccccagt ggaccggcaa aacctgtcag ctcgacgcca acgaatgtga ggccaagccc 1260
tgcgtgaatg cgaagagctg caagaacctg atcgcgtcgt actattgcga ttgcctgccc 1320
ggctggatgg gccagaactg cgacatcaac atcaacgact gcctgggcca gtgccaaaac 1380
gacgcctctt gccgcgatct ggtcaacggg taccgctgca tctgccctcc ggggtacgcc 1440
ggggatcact gtgagaggga catagatgag tgcgcgtcca acccctgcct gaacgggggg 1500
cactgccaga acgagatcaa caggtttcag tgcctgtgcc ccaccggctt ctccggcaac 1560
ctgtgccagc ttgacatcga ctactgcgag cccaatccct gccagaatgg cgcccagtgc 1620
tacaacaggg ccagcgacta tttctgcaag tgtcccgagg actacgaggg gaagaattgc 1680
tcccacctga aagaccactg caggacgacc ccctgtgagg tgatcgacag ctgcaccgtg 1740
gccatggcct ccaacgacac ccccgagggc gtgaggtaca tcagcagcaa cgtctgcggc 1800
ccccacggca agtgcaagag ccagagcggc ggaaagttca cctgcgactg caacaagggg 1860
ttcacgggca cctactgcca cgagaacatc aacgactgcg agtccaaccc ctgcaggaac 1920
ggcggcacgt gcatagacgg ggttaacagc tataagtgta tctgctcgga cgggtgggaa 1980
ggcgcctact gcgagaccaa catcaacgac tgctcacaga atccgtgcca caacgggggc 2040
acctgcaggg acctggtgaa cgacttctat tgcgactgca agaacggctg gaaaggtaag 2100
acatgccact cccgggactc ccagtgcgac gaggccacct gcaacaacgg aggaacctgc 2160

```
tacgatgagg gcgacgcctt caagtgcatg tgccccgggg gatgggaagg caccacctgc   2220
aacatcgcca ggaactccag ctgtctcccc aacccgtgcc acaacggcgg gacgtgcgtg   2280
gtgaatggcg agtccttcac gtgcgtgtgc aaggagggct gggagggccc catctgcgcg   2340
cagaacacca acgattgcag cccccacccg tgctacaact caggcacctg cgtcgacggt   2400
gacaactggt accggtgcga gtgcgcccca gggttcgcgg gccccgactg caggatcaac   2460
atcaacgagt gccagtccag cccctgcgcc tttggcgcca cctgcgtgga cgagatcaac   2520
ggctacaggt gcgtgtgccc ccccggccat agcggcgcca agtgccagga ggtgagcggc   2580
aggccctgca tcaccatggg cagcgtgatc cccgacggcg ccaagtggga cgacgactgc   2640
aatacgtgcc agtgcctgaa cggacgcatt gcctgctcca aggtgtggtg cggcccccgg   2700
ccgtgcctgc tccacaaggg gcacagcgag tgcccctccg gccagagctg catccccatc   2760
ctcgacgacc agtgcttcgt ccacccctgc accggcgtgg gcgagtgcag gtcctccagc   2820
ctgcagccag tgaaaaccaa gtgtaccagc gactcctact accaggacaa ctgcgccaac   2880
atcacattca cattcaacaa ggagatgatg agcccgggcc tgaccaccga gcacatctgc   2940
agcgaactca gaaacctgaa catcctgaag aacgtgtcgg ccgagtacag catctatatc   3000
gcgtgcgagc ccagccccag cgcgaataac gagatccacg tggccataag cgcggaggac   3060
atccgggacg acggcaaccc catcaaggag atcaccgaca agattattga cctggtctcc   3120
aagagggacg gcaatagctc cctgattgcc gccgtcgccg aagtgcgggt gcaaagaagg   3180
cccctgaaaa accggacgga tttcctggtc cccctcctga gcagcgtgct gaccgtcgcc   3240
tggatctgct gtctggtgac ggccttctac tggtgcctca gaaagaggcg caaacccggc   3300
tcgcacaccc atagcgcctc agaggacaac accacgaata acgtgcggga acagctgaac   3360
caaataaaaa accccatcga gaagcacggg gctaacaccg tgccgatcaa ggactacgag   3420
aacaagaaca gcaagatgtc caagatccga acccacaaca gcgaggtcga ggaggacgac   3480
atggacaagc accagcagaa ggcgaggttc gccaagcagc ccgcctacac cctggtagac   3540
cgggaggaga agccgcccaa cggcaccccc acgaaacacc ccaactggac caacaaacaa   3600
gacaacaggg acctggagag cgcccagtcc ctgaacagga tggaatatat tgtc         3654
```

<210> SEQ ID NO 20
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 20

```
atgaggagcc ccaggacacg gggccggagc gggcgacctc tgtccctgct cctggccctg     60
ctgtgcgccc tgagagccaa agtgtgcggc gccagcgggc agttcgagct ggagatactg    120
agcatgcaga acgtgaacgg cgagctgcag aacggcaact gttgtggggg cgcgcggaac    180
cccggggaca ggaagtgcac ccgggacgag tgcgacacct acttcaaggt gtgcctcaag    240
gaataccaaa gccgtgtgac agctgggggc ccctgcagct tcgggtccgg atccaccccc    300
gtcatcggcg gcaacacctt caacctcaag gccagcaggg gcaacgacag gaaccgaatc    360
gtgctgccct tttcgtttgc ctggccccgc agctacaccc tcctagtgga ggcctgggac    420
agcagcaacg acaccgtgca gcccgactcc atcatcgaga aggcatccca cagcgggatg    480
atcaatccct cccgccagtg gcagacgctg aagcagaaca ccggcgtggc ccacttcgaa    540
```

-continued

```
taccaaatca gggtgacgtg cgatgactac tattacggct tcgggtgcaa caagttctgc    600
aggccgaggg atgacttctt cggccactat gcctgcgacc agaacggaaa caaaacctgc    660
atggagggtt ggatgggacc cgagtgcaac agggccatct gccgccaggg ctgctcacca    720
aagcacggca gctgtaagct acccggcgac tgtcggtgcc agtacggttg gcagggcctg    780
tactgtgaca agtgcatccc ccaccccggc tgcgtgcacg gcatctgcaa tgagccgtgg    840
cagtgcctgt gtgaaaccaa ctggggtggg cagctgtgcg acaaggacct gaattactgc    900
ggcacccacc agccctgtct gaacggcggc acctgctcca acaccggccc ggacaagtat    960
cagtgcagtt gccccgaggg ctatagcggc cccaactgcg agatcgccga gcacgcctgc   1020
ctgtccgacc cgtgccacaa cagggggagc tgcaaagaga ccagcctggg gttcgagtgc   1080
gagtgcagcc ccgggtggac cggacccacc tgcagcacca acatcgatga ttgcagccct   1140
aacaactgct cccacggcgg cacctgccag gacctggtga acggctttaa gtgcgtatgc   1200
ccccccaat ggacggggaa gacctgtcag ctcgacgcca atgaatgcga ggcaaaaccg   1260
tgtgtgaacg ccaagagctg caaaaacctc atcgcgtcct actactgcga ctgcctgccc   1320
ggctggatgg gcagaactg tgacatcaac atcaacgatt gcctgggcca atgccagaat   1380
gatgcctcct gcagggacct tgtgaacggc tacaggtgca tatgcccccc cggctacgcc   1440
ggcgatcact gcgagcggga tatagacgag tgtgccagca acccctgcct caacgggggg   1500
cactgccaga atgagatcaa cagatttcaa tgcctgtgcc ccacaggatt tagcggaaat   1560
ctgtgccaac tggacatcga ctactgcgag cccaatccct gccagaacgg ggcccagtgc   1620
tacaaccggg ccagcgacta cttttgcaag tgccccgagg actacgaggg aaaaaactgc   1680
agccacctga aggaccattg caggaccacc ccctgtgagg tgattgacag ctgcaccgtg   1740
gccatggcct caaacgacac ccccgagggt gtgaggtata tcagctcgaa cgtgtgcggc   1800
ccccacggca agtgcaagtc acaaagcggg ggaaagttca cctgcgactg caacaagggc   1860
ttcaccggta cctactgcca cgagaacatc aacgactgtg agagcaaccc ctgtagaaac   1920
ggggggacct gcatcgacgg agtgaattcc tataagtgca tctgtagcga cgggtgggag   1980
ggcgcctact gcgagaccaa tatcaacgat tgcagccaga acccctgcca caacgggggc   2040
acctgccgag atctcgtgaa cgacttctac tgcgactgta aaaacggttg gaaaggcaaa   2100
acctgccact cccgcgattc ccagtgcgat gaggcgacct gcaataatgg aggcacctgc   2160
tacgacgagg gcgacgcctt taagtgcatg tgccccggcg gctgggaagg caccacctgc   2220
aatatcgcga gaaatagcag ctgcctgccc aacccctgcc ataacggcgg gacctgcgtg   2280
gtgaatggcg agagcttcac ctgcgtctgt aaggagggct gggaaggtcc catctgtgcc   2340
cagaacacca acgactgcag cccccatccc tgctacaaca gcggcacctg cgtggacggc   2400
gacaattggt acaggtgcga gtgcgccccc gggtttgccg gccccgactg caggatcaac   2460
atcaacgagt gccagagtag cccctgtgcc ttcggcgcca cctgcgtgga cgagatcaac   2520
ggctaccggt gcgtgtgccc ccccggccac tccggcgcca agtgtcaaga ggtgagcgga   2580
cgaccctgta tcaccatggg ctcggtgatc cccgacggcg ccaagtggga cgacgactgc   2640
aacacgtgcc agtgcctcaa cgggaggatc gcctgcagca aggtgtggtg cggtcccagg   2700
ccctgcctgc tgcacaaagg ccactccgag tgccccagcg gccagagctg tatccccatc   2760
ctggatgatc agtgcttcgt ccatccctgt actggcgtgg gcgagtgcag gagcagcagc   2820
ctccagcccg tgaaaaccaa gtgcacgagc gactcctatt accaagataa ctgtgccaac   2880
atcaccttca cctttaacaa ggagatgatg tcgcccggac tgaccaccga gcatatctgc   2940
```

```
agcgagctga ggaacctgaa catactgaag aatgtgtccg ccgaatattc catctacatc   3000

gcctgtgagc ctagcccgag cgccaacaac gagatccacg tggccatctc cgccgaggat   3060

atcagggacg acgggaaccc catcaaagag atcaccgata agatcatcga cctggtgtct   3120

aagcgcgacg gtaacagctc cctaatcgcc gccgtggccg aggtgcgcgt gcagcgcagg   3180

ccgctgaaga accgcaccga cttcctggtg cccctgctga gcagcgtgct caccgtggcc   3240

tggatatgct gcctggtgac cgccttctac tggtgcctgc ggaagcggcg taaaccggga   3300

agccataccc acagcgccag cgaggataat accaccaata acgtgcggga gcagctgaac   3360

cagatcaaga accccatcga aaagcacggg gcgaacaccg tgcccatcaa ggactacgag   3420

aataagaact ccaagatgag caagatccgc acacacaaca gcgaggtgga ggaggacgat   3480

atggacaagc accagcagaa ggccaggttc gccaagcagc ccgcctacac ccttgtggac   3540

cgcgaagaga agcccccgaa cggcaccccc accaagcacc ccaactggac caacaaacag   3600

gataaccgtg acctggaaag cgcgcagtcc ctgaaccgca tggagtacat agtg         3654
```

<210> SEQ ID NO 21
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 21

```
atgaggagcc cccggaccag gggcggagc ggcaggcccc tgagcctcct gctggccctg      60

ctttgcgcac tgagggccaa ggtgtgtggg gccagcgggc agttcgagct cgaaatcctg    120

agcatgcaga acgtgaacgg cgagctgcag aatggcaatt gttgcggcgg cgccaggaac    180

cccggcgacc ggaagtgcac ccgggacgaa tgcgacacct acttcaaggt gtgcctcaag    240

gagtaccaga gccgcgtgac cgccggcgga ccctgcagct tcggcagcgg cagcaccccc    300

gtgatcgggg gcaacacctt caacctgaag gcatcccgcg ggaacgacag gaacaggatc    360

gtgctgccgt tcagcttcgc ctggccgcga tcctacacgc tgctggttga ggcctgggac    420

agcagcaatg acacggtgca acccgacagc attatcgaga aggccagcca ctccggcatg    480

atcaacccct cccggcagtg gcagaccctg aagcagaaca ctggagttgc acacttcgag    540

taccaaatca gggtcacgtg cgacgactac tattacgggt tcggctgtaa caagttctgc    600

aggccccgtg atgacttctt tggacactac gcctgcgacc agaacggaaa caagacctgc    660

atggaagggt ggatgggccc cgagtgcaac agggccatct gtagacaagg ctgcagcccc    720

aaacacggct cctgtaagct gcccggcgac tgccggtgcc agtacggctg gcaggggctc    780

tactgcgaca agtgcattcc ccatcccggc tgcgtgcacg gcatatgtaa cgaaccctgg    840

caatgcctct gcgagaccaa ctggggcggg cagctgtgcg acaaagacct gaactactgt    900

ggcacccatc agccctgcct gaacgggggg acttgctcca ataccggtcc cgacaagtat    960

cagtgcagct gccccgaggg ctactccggg cccaactgcg agatcgccga acacgcctgt   1020

ctgtccgacc cctgccacaa cagaggcagc tgcaaggaga ccagcctggg ctttgagtgc   1080

gagtgctccc ccggctggac cggcccacc tgcagcacca acatcgacga ttgcagcccc    1140

aacaattgct cccacggcgg cacttgccaa gacctggtga acggcttcaa gtgcgtgtgc   1200

ccccccagt ggaccggtaa aacatgccag ctggacgcca acgagtgcga ggccaagccc     1260

tgcgtgaacg ccaagagctg caaaaacctg atcgccagtt actactgcga ctgcctgcct   1320
```

-continued

```
ggatggatgg gccagaactg cgacatcaac atcaacgact gcctgggcca gtgccagaac   1380
gacgcaagct gccgtgacct ggtgaacggc tacaggtgca tctgccccc cgggtacgcc   1440
ggtgaccact gcgaacggga catagatgag tgcgccagca acccctgcct gaacggcgga   1500
cactgccaga atgagatcaa taggttccaa tgcctctgcc ccaccggctt tagcggcaat   1560
ctgtgccagc tggacatcga ttactgtgag cccaacccct gccagaatgg agcccagtgc   1620
tacaaccggg cctccgacta tttctgtaag tgtcccgaag actacgaggg taagaactgc   1680
tcccacctga aggaccactg ccggaccact ccgtgcgagg tcatcgacag ctgcaccgtc   1740
gccatggcca gcaatgacac acccgagggc gtgaggtaca tctcctccaa cgtgtgtggc   1800
ccccacggca agtgcaagag ccagagcgga ggcaagttca cctgcgactg caacaagggg   1860
ttcaccggca cttactgcca cgagaacatc aacgactgcg aatccaaccc ctgtcgaaac   1920
gggggcacct gcattgacgg cgtgaacagc tataagtgca tctgctccga cgggtgggag   1980
ggggcctact gcgaaaccaa tataaacgat tgcagccaga acccctgtca caacgggggc   2040
acatgcaggg acctggtcaa cgacttctac tgtgactgca agaacggctg gaagggcaag   2100
acatgtcaca gcagggacag ccagtgcgac gaggccacct gtaacaatgg cggcacctgc   2160
tatgacgaag gcgacgcctt caaatgtatg tgccccggcg gttgggaggg gacgacgtgc   2220
aatattgcga ggaactccag ctgtctgccc aacccctgcc acaacggagg cacctgtgtg   2280
gtgaacggcg agagctttac gtgcgtctgt aaagagggct gggaaggccc catctgcgcc   2340
caaaacacga acgactgcag cccccacccc tgttacaata gcggcacctg cgtcgacggt   2400
gacaactggt ataggtgcga gtgtgccccg ggctttgccg ggcccgactg ccggatcaat   2460
atcaacgagt gccagtccag cccatgtgcg ttcggcgcca cctgcgtgga cgaaatcaac   2520
ggctacaggt gcgtctgccc cccggggcac agcggagcca aatgtcagga agtctctggg   2580
aggccctgca tcaccatggg cagcgtaatc cccgacgggg ctaagtggga cgacgactgc   2640
aatacctgtc agtgtctgaa cggcaggatt gcctgcagca aagtgtggtg tggcccgcgg   2700
ccctgtctcc tgcacaaggg ccactccgag tgtcccagcg gccaatcctg catccccatc   2760
ctcgacgacc agtgctttgt gcacccctgc acaggcgtgg gagagtgtag gtcgagctcc   2820
ctgcagcccg tgaagaccaa gtgcaccagc gattcctact accaggacaa ctgcgcgaat   2880
atcaccttta cctttaacaa ggagatgatg agccccgggc tgaccaccga gcacatctgc   2940
agcgagctgc ggaacctgaa catcctcaaa aacgtcagcg ccgagtatag catctacatt   3000
gcctgcgagc ccagccccag cgccaacaac gaaatacacg tggccatcag cgccgaggac   3060
atcagggacg acggcaaccc gatcaaggag atcaccgata agataatcga cctggtgtcc   3120
aagagggacg gcaatagctc cctgatcgcc gccgtggccg aagtgagggt gcagaggagg   3180
cccctgaaaa acaggaccga tttcctggtt cccctgctga gcagcgtgct gacagtggct   3240
tggatctgct gcctcgtaac tgcattctac tggtgcctga ggaagaggag gaagcccggc   3300
agtcacaccc acagcgcctc cgaggataac accactaaca atgtgcggga gcagctgaac   3360
cagatcaaga atcccataga aaaacatggc gccaacaccg tgcccattaa agattacgag   3420
aacaaaaata gcaagatgtc caagatccgc acccacaaca gcgaggtgga ggaggacgac   3480
atggacaagc accagcagaa ggccaggttc gccaagcagc ccgcgtacac cctggtggac   3540
cgtgaggaga agccccccaa cggcaccccc accaagcacc ccaactggac caacaagcaa   3600
gataatcggg acctggaatc cgcccagagc ctgaacagga tggagtacat cgtg         3654
```

<210> SEQ ID NO 22
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 22
atgaggagcc cgagaacgag ggggcggtcc ggcaggccgc tgagcctcct gctggccctg 60
ctgtgcgccc tgcgggcaaa ggtgtgtggc gcctccgggc agttcgagct ggagatcctg 120
agcatgcaaa acgtgaacgg cgaactccag aacggcaatt gctgcggcgg cgccagaaac 180
cccggggatc gaaagtgcac ccgggacgag tgcgacacct acttcaaagt gtgtctcaaa 240
gaataccaga gcagggtgac cgccggcggg ccctgcagct tcggcagcgg cagcaccccc 300
gtgatcggcg ggaacacctt caacctgaag gccagccgcg gcaacgacag gaatcggatc 360
gtgttgccgt tcagcttcgc ctggccccgt tcctacaccc tgctggtgga ggcctgggac 420
agcagcaacg ataccgtgca gccagacagc ataatcgaga aggccagcca ctccggtatg 480
atcaacccca gcaggcagtg gcagaccctg aagcaaaaca ccggcgtggc ccatttcgag 540
taccagatca gggtcacgtg cgacgactat tactacgggt tcgggtgcaa caagttctgc 600
aggccccggg atgacttctt tggacactac gcctgtgacc agaacggaaa caaaacttgc 660
atggagggct ggatgggccc ggagtgcaat agggccattt gcaggcaagg ctgcagcccc 720
aagcacggct cctgcaagct ccccggcgac tgccgatgcc aatatggctg gcagggcctc 780
tactgtgaca agtgcatccc ccacccgggc tgcgtccacg gaatctgcaa tgagccctgg 840
cagtgtctgt gcgagacgaa ctggggtggc cagctgtgcg acaaggacct gaactactgc 900
gggacccacc agccctgcct gaacggcggg acctgttcca acaccggccc ggacaagtat 960
cagtgcagct gcccggaagg gtactccggc ccgaactgcg aaatcgccga acacgcttgc 1020
ctcagcgacc cctgccacaa ccgcgggagc tgcaaggaga ccagcctggg ctttgagtgc 1080
gaatgttccc ccggctggac cgggcccaca tgctccacca acatagacga ttgtagcccc 1140
aacaactgct cccacggggg gacctgccaa gacctggtca acggattcaa gtgcgtgtgt 1200 ccccccagt ggacgggtaa gacctgccaa ctggacgcca acgaatgcga ggccaagccc 1260
tgtgtgaatg ccaagagctg caagaacctg atcgccagct actactgtga ctgcctgccc 1320
ggctggatgg gccagaattg cgacatcaat atcaacgact gcctgggcca gtgccagaat 1380
gacgcctcct gcagggacct ggtgaacggc tacaggtgca tatgccccc cggctacgcc 1440 ggcgaccact gcgaacgtga catcgacgag tgcgcctcaa acccctgcct gaacggcgga 1500
cactgccaga acgagatcaa ccgattccag tgtctgtgcc ccaccgggtt tagcgggaac 1560
ctctgccagc tcgatatcga ctactgcgaa cccaacccct gccagaacgg cgcccagtgc 1620
tacaaccggg ccagcgacta tttctgtaaa tgccccgagg actacgaggg gaaaaactgt 1680
agccacctga aggaccactg caggaccaca ccctgcgaag tgatcgacag ctgcaccgtg 1740
gccatggcca gcaatgacac ccccgaaggc gtgaggtata taagcagcaa cgtatgcggc 1800
ccccacggca agtgtaagag ccagagcggc ggcaagttta cgtgcgactg caacaaaggc 1860
ttcaccggca cctactgtca cgagaacatc aacgactgcg agagcaaccc ctgccgcaac 1920
gggggcacct gcatcgacgg tgtgaacagc tacaagtgca tctgcagcga cggctgggag 1980
ggcgcctact gtgagacgaa catcaacgac tgcagccaga acccgtgcca taacgggggc 2040
acctgcaggg atctggtgaa cgacttttat tgcgactgca agaacggctg gaagggcaag 2100

-continued

```
acctgccaca gccgggacag ccagtgtgac gaggccacct gcaacaacgg cggcacctgc   2160

tacgacgaag ggacgccttt taagtgcatg tgcccgggcg ggtgggaggg caccacctgc   2220

aacatcgcca ggaattcctc ctgtctgccc aacccatgtc acaacggtgg cacgtgcgtg   2280

gtgaacgggg agtcctttac ctgtgtgtgc aaggaggggt gggagggacc catatgtgcg   2340

cagaatacca acgactgctc cccccaccca tgttataaca gcggtacatg tgtggatggg   2400

gacaactggt accggtgtga gtgcgccccc ggcttcgccg gccccgattg caggatcaac   2460

atcaatgagt gccagagctc cccctgcgcc ttcggcgcca catgcgtcga cgaaatcaac   2520

ggctacaggt gtgtgtgccc cccgggacac agcggtgcca agtgccagga agtgtcaggc   2580

aggccctgta ttaccatggg cagcgtgatc cccgacggag ccaagtggga tgacgactgc   2640

aacacctgcc agtgcctgaa cggccgtatc gcctgcagca aggtgtggtg cggcccccgg   2700

ccgtgcctgc tgcacaaggg gcactccgag tgccccagcg ggcagagctg catccccatc   2760

ttggacgacc agtgcttcgt gcacccctgc accggcgtgg gcgaatgccg tagcagctcc   2820

ctgcagcccg tgaagaccaa gtgcaccagc gattcctact atcaggataa ctgcgccaac   2880

atcaccttca ccttcaacaa ggagatgatg agccccggcc tgaccacgga acacatctgc   2940

agcgagctga ggaacctgaa catcctgaag aacgtgtccg ccgaatacag catctacatc   3000

gcctgcgagc ccagccccag cgccaacaac gaaatccacg tcgccatctc tgccgaggac   3060

atccgcgacg acggcaaccc cattaaggag ataaccgaca agatcatcga cctggtgtcc   3120

aagcgagacg gaaattctag cctgatcgcc gccgtagccg aggtacgtgt gcagaggagg   3180

cccctcaaga ataggaccga cttcctggtg cccctgctga gcagcgtgct caccgtggcg   3240

tggatctgct gcctggtgac cgccttttac tggtgcctgc gaaagaggag gaagcccggt   3300

tcacacacgc acagcgccag cgaagacaac accaccaaca atgtgcgcga gcagctcaac   3360

cagatcaaga atcccatcga gaagcacggc gccaacacgg tccccatcaa ggactacgag   3420

aacaaaaaca gcaagatgtc caagatccgc acccataaca gcgaggtcga agaagacgac   3480

atggacaaac accagcaaaa ggccaggttc gccaagcagc cggcctacac cctggtggac   3540

agggaggaga agcccccgaa cggcaccccc accaagcacc ccaactggac caacaaacag   3600

gacaaccggg atctggagag tgcgcagagc ctgaacagga tggagtacat cgtg         3654
```

```
<210> SEQ ID NO 23
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 23

atgagaagcc caaggacgcg cggtaggagc ggcaggcccc tcagcctgct gctggctcta     60

ctgtgcgccc tgcgggccaa ggtttgtggg gccagtgggc aattcgagct ggagatcctg    120

agcatgcaaa acgtgaacgg ggagcttcag aatggtaact gctgcggcgg ggcccggaat    180

cccggcgacc ggaagtgtac gagggatgag tgtgacacct actttaaggt gtgcctgaag    240

gagtaccaga gcagggttac ggcaggcggc ccctgcagct ttggcagcgg ctccaccccg    300

gtgatcggcg gcaacacatt caacctgaag gccagccgcg ggaacgatcg taacaggatc    360

gtgctcccct ttagcttcgc ctggccccgc agctacacgc tgctggtgga ggcctgggac    420

agcagcaacg acaccgtcca gcccgatagc attatcgaga aggcctccca cagcggtatg    480

atcaacccga gccggcagtg gcagaccctg aagcagaaca ccggcgtggc ccacttcgag    540
```

-continued

```
taccagatcc gggtgacctg cgacgactac tattacggtt tcggctgcaa caagttttgc    600
cgaccccggg acgacttttt cgggcattac gcctgcgacc aaaacggcaa caaaacctgc    660
atggagggct ggatgggccc ggagtgcaac cgggccatct gccggcaggg gtgtagcccc    720
aagcacggca gctgcaagct gcccggcgat tgccggtgcc agtacgggtg gcagggcctg    780
tactgcgaca agtgcatccc gcaccccgga tgtgtgcacg gcatctgcaa cgagccctgg    840
cagtgcctgt gcgaaaccaa ctgggggggt cagctgtgtg acaaggatct gaactactgc    900
ggaacccacc aaccctgcct gaacggcgga acttgctcga acacgggccc cgacaagtac    960
cagtgcagct gtcccgaggg ctacagcggg cccaactgtg agatcgccga acacgcttgc   1020
ctgagcgacc cgtgtcacaa ccggggcagc tgcaaggaga cctccctcgg cttcgagtgc   1080
gagtgctccc cagggtggac cggccccacc tgcagcacca acatcgacga ttgcagcccc   1140
aacaactgta gccacggcgg gacgtgccag gacctggtca acggcttcaa atgtgtctgt   1200
ccccccagt ggaccggcaa aacctgccag ctcgacgcca acgagtgcga agccaagccg   1260
tgcgtgaacg cgaagagctg caagaacctg atcgcctcct actactgcga ctgcctgccc   1320
ggctggatgg gccagaactg cgacataaac atcaacgact gcctgggcca gtgccagaac   1380
gatgccagct gtcgagacct ggtgaacggg taccggtgca tctgccccc cggatacgcc   1440
ggggaccact gcgagcgcga catcgacgaa tgtgcctcga acccctgcct gaacgggggc   1500
cactgccaaa acgagatcaa tcgtttccag tgcctgtgcc ccaccggctt ctctgggaac   1560
ctgtgccagc tggacatcga ctactgcgag cccaacccct gccagaacgg ggcgcagtgc   1620
tataaccggg cctccgatta cttctgcaag tgccccgagg actatgaggg aaaaaactgc   1680
tcccacctga aggatcactg taggaccacc ccctgtgagg tgatcgacag ctgcaccgtg   1740
gccatggcca gcaacgacac ccccgagggc gtgcgctaca tcagctccaa cgtgtgcggc   1800
ccccatggta agtgtaagtc gcagagcggc gggaagttca cctgcgactg caacaagggc   1860
tttacgggga cctactgtca tgaaaacatc aacgactgcg agagcaaccc ctgtcgcaac   1920
ggcggcacct gcatcgatgg cgtcaacagc tacaagtgca tctgctccga cggatgggag   1980
ggcgcctact gcgagaccaa catcaacgac tgcagccaga acccgtgcca caatggcggc   2040
acctgccgtg acctggtgaa cgacttttac tgcgactgca agaacgggtg gaaaggcaaa   2100
acctgccact ccagggacag ccagtgcgac gaggcgacct gcaacaatgg cgggacgtgc   2160
tacgacgagg gcgacgcctt caagtgcatg tgccccggcg gatgggaagg cactacctgt   2220
aacatcgccc ggaatagctc ctgcctgccg aacccctgcc acaacggggg cacgtgcgtc   2280
gtgaacggcg aaagcttcac ctgcgtgtgc aaggagggct gggagggccc catctgtgcc   2340
cagaacacca acgactgcag cccccacccc tgctacaata gcggcacctg cgtggacgga   2400
gacaactggt accgatgcga gtgcgcccct ggcttcgccg gacccgattg ccgcattaac   2460
atcaatgaat gccagagcag cccctgcgcc tttggagcca cctgcgtcga tgagatcaac   2520
ggctaccgct gtgtctgccc ccccggccac agcggggcca agtgccagga ggtctcaggt   2580
cggccctgca tcaccatggg cagcgtcatc cccgacgggg ccaaatggga tgacgactgc   2640
aatacctgcc agtgtctgaa cggccgaatc gcctgctcca aggtgtggtg cgggcccagg   2700
ccctgcctcc ttcacaaagg ccatagcgag tgcccctccg ggcaatcctg catccccatc   2760
ctggacgacc aatgcttcgt gcacccctgc accggcgtgg gggagtgcag gagcagcagc   2820
ctgcagcccg tgaagaccaa gtgcacctcc gatagctatt accaggacaa ctgcgccaac   2880
```

-continued atcaccttca cctttaacaa agaaatgatg tcacccggcc tgacgaccga gcatatctgc 2940
agcgagctgc ggaacctgaa catcctgaaa aacgtgtcgg ccgagtacag tatatacatc 3000
gcctgcgagc ccagccccag cgccaacaac gagatacatg tggccataag cgccgaagac 3060
atcagggacg atggcaaccc catcaaggag atcaccgaca aaataatcga cctggtgagc 3120
aagcgggatg gcaatagcag cctgatcgcc gccgtggccg aggtgagggt gcagcggagg 3180
cccctgaaga atcgcaccga cttcctggtc ccgctgctta gctccgtcct gacggtcgcc 3240
tggatctgct gcctggtgac cgccttctac tggtgcttga ggaagcggag gaagcccggg 3300
tcacataccc actccgccag cgaggacaac accaccaata acgtgcggga acagctgaac 3360
cagatcaaga accccatcga gaagcatggt gccaacaccg tgcccatcaa ggactatgaa 3420
aacaagaact ccaagatgag caagatcagg acccacaact ccgaggtgga agaggacgac 3480
atggacaagc accagcagaa agcccgtttc gccaagcagc ccgcctacac cctggtggac 3540
cgagaggaaa agccgcccaa cggcaccccc accaagcatc ccaactggac caacaagcag 3600
gacaaccgtg acctggagag cgcccagtcg ctcaaccgca tggagtacat cgtg 3654

<210> SEQ ID NO 24
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 24
atgcggtcgc cgagaaccag gggccggagc ggccggcccc tgtcgctgct gctggccctg 60
ctctgcgcgc tgagagccaa ggtgtgtggc gccagcggcc agttcgagct tgagatcctg 120
tccatgcaaa acgtcaacgg cgagctccag aacggaaact gttgcggcgg cgcccgcaac 180
cccggcgaca ggaagtgcac ccgcgacgag tgcgacacct acttcaaggt gtgcctgaag 240
gagtaccagt cccgcgtgac cgctggcgga ccgtgcagct tcggctcagg cagcaccccc 300
gtgatcgggg gcaatacctt caatctcaag gccagccgag gaaacgacag gaacaggatc 360
gtgctcccct ttagctttgc ctggcctcgt agctacaccc tgctggtgga ggcctgggac 420
tcaagcaatg acacggttca gcccgacagc atcatcgaaa aggcctctca cagcggaatg 480
atcaacccca gcaggcagtg gcagaccctc aagcagaaca cgggcgtggc ccacttcgag 540
taccagatcc gtgtgacctg cgatgactac tattacggtt tcgggtgtaa taagttctgc 600
aggcccaggg atgacttttt tggccactac gcctgcgacc agaatggcaa caagacctgc 660
atggagggat ggatgggccc cgagtgcaac cgtgccatct gtcggcaggg ctgctcgccc 720
aagcacggca gctgcaagct tcccggcgac tgtcggtgcc agtacggatg gcaagggctg 780
tactgcgaca agtgcatccc ccatcccggc tgtgtccacg gtatctgcaa cgagccctgg 840
cagtgtctgt gcgagaccaa ctggggcggc cagctgtgcg acaaggacct gaactactgc 900
ggcacccacc agccctgcct gaatgggggc acctgttcta acaccgggcc ggacaagtac 960
cagtgttcct gccccgaggg ctacagcggc cccaactgcg agatcgccga gcacgcctgc 1020
ctgtccgacc cctgccataa taggggctcc tgcaaggaga cctccctggg ctttgagtgc 1080
gagtgttcgc ccggctggac cggcccccacc tgcagtacca acatcgacga ctgcagcccc 1140
aacaactgta gccacggcgg cacatgccaa gacctggtga acggcttcaa gtgcgtctgc 1200
ccgccgcagt ggaccgggaa gacctgtcag ctggatgcca acgagtgcga ggctaaaccc 1260
tgcgtgaacg cgaagagctg taagaacctg attgccagct actactgcga ctgcctgccg 1320

-continued

```
ggctggatgg ggcagaattg cgacatcaac atcaacgact gtctgggcca atgccagaac   1380
gacgccagct gtcgggacct ggtcaacgga tacaggtgta tctgtccccc cggctacgcc   1440
ggcgaccact gcgagcggga catcgacgaa tgcgccagca acccttgtct gaacggaggc   1500
cactgccaga acgagatcaa caggtttcag tgcctctgcc ccaccgggtt cagcgggaac   1560
ctgtgccagc ttgacatcga ttactgcgag cccaacccct gtcagaatgg ggcgcagtgc   1620
tacaaccgag cttccgatta cttctgcaag tgccccgagg attacgaggg taaaaattgc   1680
agccacctga aggatcactg caggaccacc ccgtgcgagg tgatagacag ctgcaccgtg   1740
gccatggcca gcaacgacac ccccgagggc gtgcgataca tcagcagcaa cgtgtgcggc   1800
ccccacggca agtgcaaaag ccagagcggc ggaaaattca catgcgactg caacaagggg   1860
ttcacgggca cctattgcca cgagaacatc aacgactgcg agtccaaccc gtgccggaat   1920
ggcggcacct gcatcgacgg cgtgaactcc tataagtgta tctgctcgga cggctgggag   1980
ggggcctatt gcgagaccaa catcaacgac tgcagccaga acccctgcca caacggcggc   2040
acctgcaggg acctggtgaa cgacttctat tgcgactgca agaacggctg gaagggcaag   2100
acctgtcact ccagggacag ccagtgcgac gaggccacct gtaacaacgg cgggacctgt   2160
tacgacgagg gggacgcgtt caagtgcatg tgccccggcg gctgggaggg caccacgtgc   2220
aacatcgcgc gtaacagcag ctgtctgccg aatccctgtc acaatggcgg cacctgcgtc   2280
gtgaacggcg aaagcttcac ctgcgtgtgt aaggaaggct gggagggccc catctgcgcc   2340
caaaacacca acgactgtag cccccacccg tgctacaaca gcggcacctg cgtggatggc   2400
gacaactggt atcggtgcga gtgtgcccct ggctttgcgg gccccgactg ccggataaac   2460
ataaacgagt gtcaatcgag cccctgcgcc ttcggggcca cctgcgtgga cgagatcaac   2520
ggctacaggt gcgtgtgccc gcccggccac agcggcgcga aatgccaaga ggtgagcggc   2580
aggccctgca tcaccatggg ttccgtgatc cccgacgggg caaaatggga cgacgactgc   2640
aatacctgcc agtgcctcaa cgggaggatc gcctgcagca aggtgtggtg cggcccccagg   2700
ccctgcctgc tgcataaagg gcacagcgag tgccccagcg ggcagagctg catccccatc   2760
ctggacgacc agtgcttcgt gcacccgtgc accggcgtgg gcgagtgcag aagctctagc   2820
ctgcaacccg tgaagaccaa gtgcacgagc gacagctact accaggacaa ctgcgcgaac   2880
atcaccttca ccttcaataa ggagatgatg agcccgggac tcaccaccga acatatctgc   2940
tccgagctgc gcaacctcaa catactgaag aatgtgagcg ccgagtactc catttacatt   3000
gcctgcgagc ccagcccctc cgccaataat gaaatacacg tcgccatcag cgccgaggac   3060
atcagggacg acggcaaccc catcaaggag atcaccgaca agatcatcga cctggtgagc   3120
aaaagggacg gcaatagcag cctcatcgcc gccgtggccg aggtgagggt gcagaggagg   3180
ccgctgaaaa acagaaccga ttttctcgtc cccctgctgt cctccgtgct gaccgtcgcc   3240
tggatctgtt gcctggtgac cgccttctac tggtgtctcc gcaagaggcg caagcccggc   3300
agccacacgc atagcgccag cgaggacaac actactaaca acgtgcggga gcagctgaat   3360
cagatcaaga accccatcga gaaacacggc gccaacactg tgcccatcaa agactacgag   3420
aacaaaaact cgaaaatgag caagatccgc acccacaaca gcgaggtgga ggaggacgac   3480
atggacaagc accagcagaa agcgagattc gccaaacagc ccgcctacac cctggtggac   3540
agggaggaga agcccccaaa cggcacaccc accaagcacc cgaactggac caacaagcag   3600
gacaaccgtg acctggaaag cgcccagtcc ctgaatcgca tggaatatat cgtg         3654
```

<210> SEQ ID NO 25
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 25
atgcgaagcc cccgaacccg gggcaggagc gggaggcccc tgagcctgct gctggccctt 60
ctgtgcgccc ttagggccaa ggtgtgtggg gcctccggcc agttcgagct ggagatcctg 120
agcatgcaga acgtgaacgg tgagctgcag aatggtaact gttgcggcgg agccaggaac 180
ccgggcgata ggaaatgtac cagggacgag tgcgacacct actttaaggt gtgcctcaaa 240
gagtaccaga gccgggtcac cgccggcggc ccctgctcgt tcggcagcgg tagcaccccc 300
gtgatcggcg gcaacacatt caacctgaaa gccagcaggg ggaacgacag gaaccggatc 360
gtgctcccct tctccttcgc ctggcccagg tcgtacaccc tgctcgtcga ggcctgggac 420
agcagcaacg acaccgtgca gcccgacagc atcatcgaaa aggccagcca cagcggaatg 480
atcaacccca gccgacagtg gcagaccctg aagcagaaca ccggcgtggc ccacttcgag 540
taccagatcc gggtgacctg cgatgactat tactatggct tcggctgtaa caagttctgt 600
cgacccaggg acgacttctt cggccactat gcctgcgacc agaacggtaa taagacttgc 660
atggagggct ggatgggccc cgagtgtaac agggccatct gcaggcaggg ctgctccccc 720
aaacacggct cctgcaaact gcccggcgac tgccgctgcc agtacggctg gcaggggctc 780
tactgcgata agtgcatccc ccatcccggc tgcgtgcatg gcatctgcaa cgaaccctgg 840
cagtgcctgt gcgagaccaa ctggggggc cagctatgcg ataaggatct gaactactgt 900
ggcacccacc agccctgcct gaacgggggc acgtgctcaa acaccggccc cgacaaatac 960
caatgcagct gccccgaggg ctacagcggc cccaactgcg agatcgccga gcatgcctgc 1020
ctgagcgacc cgtgccacaa taggggctcc tgtaaggaga ccagcctggg cttcgagtgt 1080
gagtgcagcc ccggctggac cggcccccacc tgctcaacta acatcgacga ctgttccccc 1140
aacaattgca gccacggcgg cacctgccag gacctggtga acggctttaa gtgtgtgtgc 1200 ccccccagt ggaccgggaa gacctgtcag ctggacgcta acgagtgtga ggccaagccc 1260
tgtgtcaacg ccaaaagctg caagaacctg atagcctcct actactgcga ctgcctgccc 1320
ggatggatgg gccagaactg cgacatcaac atcaatgact gcctggggca gtgccagaac 1380
gacgccagct gccgggacct ggtgaatggg taccgctgca tctgcccccc cggctacgcg 1440
ggcgaccact gcgagaggga catcgacgag tgcgcctcga acccctgcct caacgggggc 1500
cactgccaga acgagatcaa ccggttccag tgtctgtgcc ctactggctt ctctggcaac 1560
ctgtgtcagc tggatatcga ttactgcgag ccaaacccat gccagaacgg ggcccagtgc 1620
tacaataggg cctccgacta tttttgcaag tgccccgagg actacgaggg taagaactgt 1680
tcccatctca aggaccactg tcgaaccacc ccctgcgagg tgatcgacag ctgcaccgtg 1740
gccatggcca gcaatgacac ccccgagggc gtgcggtaca tctccagcaa cgtgtgcggc 1800
ccccacggca agtgcaagag ccagtccggc ggcaaattta cctgcgattg caacaagggg 1860
ttcaccggca cctactgtca cgagaacatc aatgactgcg aatccaatcc ctgcaggaac 1920
ggtggcacgt gcatcgacgg ggtgaatagc tataagtgca tctgcagcga cgggtgggaa 1980
ggggcctact gcgagaccaa catcaacgac tgtagccaga acccgtgcca caatggcggc 2040
acttgtaggg atctcgtgaa tgacttctat tgcgactgca aaaatggatg gaaggggaag 2100
acctgccact cccgggactc ccagtgcgac gaggccacct gcaataacgg cggtacctgc 2160
tacgacgagg gcgatgcctt taaatgcatg tgccccggcg gctgggaggg aaccacgtgc 2220
aacatcgcga ggaacagcag ctgcctcccc aatccctgtc acaatggcgg tacctgcgtc 2280
gtgaacgggg agagcttcac ctgcgtgtgc aaggagggct gggagggccc gatctgcgcc 2340
cagaacacca acgactgcag cccacacccc tgctacaata gcgggacctg cgtggacgga 2400
gacaactggt accggtgcga gtgcgccccc ggcttcgccg gccccgactg caggatcaac 2460
atcaacgagt gccagagcag cccctgtgcc ttcggcgcga cctgcgtgga tgaaatcaat 2520
ggctaccggt gcgtgtgccc ccccggccac agcggcgcga agtgccagga ggttagcggc 2580
aggccctgca tcaccatggg atcggtgatc cccgatggcg ccaagtggga tgacgactgt 2640
aacacatgcc aatgtctgaa tggacggatc gcatgttcca aggtgtggtg cggccccagg 2700
ccctgtctcc tgcacaaagg ccacagcgag tgtcccagcg gccaaagctg catccccatc 2760
ctggacgacc agtgcttcgt gcatccctgc accggcgtgg gggagtgccg tagcagcagc 2820
ctgcagcccg tgaagacgaa gtgcacctca gacagctatt accaggataa ctgcgcgaac 2880
atcaccttca cctttaacaa ggagatgatg tcccccggcc tgaccaccga gcacatctgc 2940
tcggagctgc gcaatcttaa catcctgaaa aacgtgtccg ccgagtacag catttacatc 3000
gcctgtgagc cgagcccctc cgccaacaat gagatccatg tcgccatcag cgccgaggac 3060
atccgggacg acggtaatcc gatcaaggag atcacagata agatcatcga cctggtgtcc 3120
aagcgggacg gcaacagcag cctgatcgcc gccgtcgccg aggtgcgtgt gcagagacgg 3180
cccctcaaga accgcaccga cttcctcgtg cccctcctga gctcggtgct gaccgtcgcc 3240
tggatctgct gcctggtgac cgccttctac tggtgcctgc gaaaacgccg gaagccgggg 3300
agccacaccc acagcgccag cgaggataac accaccaata acgtgaggga acagctgaac 3360
cagatcaaga accccatcga aaaacacggc gccaacaccg tgccgatcaa ggactacgag 3420
aacaaaaata gcaagatgag caagatcagg acacacaact ctgaggtgga ggaggacgac 3480
atggacaagc accagcagaa ggcccgcttc gccaagcagc ccgcctacac cctggtcgac 3540
cgggaagaga agcccccgaa cggcaccccc accaagcatc ctaactggac caacaagcaa 3600
gacaacaggg acctggaaag tgcccagagc ctgaaccgga tggagtacat cgtg 3654

<210> SEQ ID NO 26
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 26
atgcgaagcc cgaggacccg gggcaggagc ggcaggccgc taagcctgct gctggccctc 60
ctctgcgccc tcagggccaa ggtgtgcggc gcctccggcc aattcgagct cgagatcctg 120
tcaatgcaga acgtgaacgg cgagctgcag aacggcaact gctgcggcgg cgccaggaac 180
cccggcgaca ggaagtgcac cagggacgaa tgtgacacct acttcaaggt gtgcctgaag 240
gagtaccaga gccgggtgac cgctggcggc ccatgtagct tcgggagcgg cagcaccccg 300
gtgatcgggg gtaacacctt taacctcaag gcttcccgcg gcaacgacag gaaccggatc 360
gtgctgccct tctccttcgc ctggcccagg agctataccc tgctggtcga ggcctgggac 420
agctccaacg acaccgtgca acccgacagc atcatcgaga aggcctccca ctccggcatg 480

-continued

```
atcaacccca gcaggcagtg gcagaccctc aagcaaaaca ccggggtcgc gcacttcgag    540
taccagatca gggtcacctg cgacgactac tactacggct tcggctgcaa taagttttgc    600
cggcccaggg acgatttctt cggacactac gcctgtgacc agaatggcaa taagacctgt    660
atggaagggt ggatggggcc agagtgcaat cgggccatct gcaggcaagg ctgcagcccc    720
aaacacggct cgtgtaagct gcccggcgac tgcaggtgcc agtatggttg gcagggcctc    780
tattgcgaca agtgcatccc ccacccaggc tgtgtgcatg gcatctgtaa cgaaccctgg    840
cagtgcctgt gcgagacgaa ctgggggggc caactgtgcg acaaggacct gaactattgc    900
ggcacccacc agccgtgcct gaatggcgga acctgttcca acaccggccc cgacaagtac    960
cagtgctcct gtcccgaggg gtacagcggc cccaactgcg agatcgccga gcatgcctgc   1020
ctcagcgatc cctgccacaa caggggcagc tgcaaggaga cgagcctggg cttcgagtgc   1080
gaatgcagcc ccggttggac cggccccacg tgctccacca acatcgacga ctgctccccc   1140
aacaattgca gccacggggg cacatgtcag gacctggtga acggcttcaa gtgcgtgtgc   1200
ccgccccaat ggaccggcaa gacgtgccag ctggacgcca acgagtgcga agccaagcca   1260
tgcgtgaacg ccaagagctg caagaacctg atcgccagct actactgcga ctgcctccca   1320
ggctggatgg gccagaactg tgatatcaac atcaacgact gcctcggcca gtgccagaac   1380
gacgccagct gccgggacct ggtgaacggg taccgctgca tctgtccgcc cggctacgcc   1440
ggagaccact gcgagcgcga catcgacgag tgtgccagca acccctgctt aaacggcggc   1500
cactgccaaa atgaaatcaa taggtttcag tgcctgtgcc ccaccgggtt cagcggcaac   1560
ctgtgccagc tggacatcga ctattgcgag ccgaacccct gccagaacgg ggcccagtgc   1620
tacaataggg ccagcgatta tttctgcaag tgtcccgagg actacgaggg aaaaaactgc   1680
agccacctca aggaccactg taggaccacg ccctgcgaag tgatcgactc ctgcaccgtg   1740
gccatggcca gcaacgacac ccccgagggc gtgcgctaca tcagcagcaa cgtgtgtggc   1800
cctcacggca aatgcaagag ccaaagcggc ggcaagttca cctgtgactg caataagggc   1860
ttcaccggca cctactgtca cgagaacatc aacgactgcg agagcaaccc ctgcagaaac   1920
ggtggcacct gtatagatgg cgtgaacagc tacaagtgca tctgcagcga cggatgggaa   1980
ggcgcctact gtgagaccaa cattaacgac tgcagccaga accoctgcca caatggcggc   2040
acctgccgcg acctggtcaa tgacttttac tgcgactgta agaacgggtg gaagggcaag   2100
acctgccata gccgcgactc ccagtgcgac gaggcaacct gcaacaacgg cggcacctgt   2160
tatgatgagg gggacgcatt caagtgcatg tgtccggggg gctgggaggg cacaacctgc   2220
aacatcgccc ggaacagcag ctgcctccca aacccctgcc acaacggggg cacctgcgtg   2280
gtgaacggcg agagcttcac ctgcgtgtgt aaggagggct gggagggccc catctgtgcc   2340
cagaatacca acgattgctc cccccacccc tgctacaaca gcggcacttg cgtggacggc   2400
gataactggt ataggtgtga gtgcgccccc ggcttcgcag gccccgactg ccgcatcaac   2460
atcaacgagt gccagagcag cccctgtgcc ttcggggcca cctgcgtgga cgagatcaac   2520
ggctaccggt gtgtgtgccc ccccgggcac tccggcgcga aatgccagga ggtgtccggc   2580
aggccctgca tcaccatggg cagcgtgatc cctgacggcg ccaaatggga cgacgactgt   2640
aatacctgcc agtgcctgaa tggccgaatc gcctgctcca aggtgtggtg cggccccagg   2700
ccttgcctgt tgcacaaggg ccacagcgag tgccccagcg gccagagctg tatccccatc   2760
ctggacgacc aatgtttcgt gcatccctgc accggcgtgg gggagtgccg gtcgtccagc   2820
ctgcagcccg tgaagaccaa gtgtaccagc gactcctact atcaggacaa ttgcgccaac   2880
```

atcaccttca cctttaacaa ggagatgatg agccccggcc tgaccaccga gcacatctgt 2940
tccgagctga ggaacctgaa catcctgaag aacgtcagtg ccgagtactc catctacatc 3000
gcctgtgaac cgtccccgtc cgccaacaat gagattcacg tggccatcag cgccgaagac 3060
atcagggacg acggcaaccc catcaaggag atcaccgaca agatcataga ccttgtgtcc 3120
aagagggacg gcaactcgtc cctgatcgcc gccgtggcgg aggtgagggt gcagaggagg 3180
cccctgaaga accgcaccga cttcctggtg ccgctcctgt cctccgtgct gaccgtggcc 3240
tggatctgct gcctggtgac cgccttctac tggtgcctga ggaagcgccg caagcccggg 3300
tcccacacgc acagcgccag cgaggataac accaccaaca acgtgcggga gcaactgaac 3360
cagataaaga accccatcga aaaacacgga gcgaacaccg tccccatcaa ggactacgaa 3420
aacaagaaca gcaagatgag caagatcagg acccataact ccgaggtgga ggaggacgac 3480
atggacaagc accagcaaaa ggcccggttc gccaagcagc ccgcctacac cctggtggat 3540
cgggaggaga agccccccaa cggtaccccg accaaacacc ccaactggac caataaacag 3600
gacaataggg acctggagtc cgcccagagc ctgaacagga tggagtacat agtg 3654

<210> SEQ ID NO 27
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 27
atgagaagcc ccaggacccg aggcaggagc ggcaggccac tgagcctgct ccttgccctg 60
ctgtgcgccc tgagggcaaa ggtgtgcggc gccagcggcc agttcgagct ggaaatcctg 120
tccatgcaga acgtgaacgg ggagctgcag aatggcaatt gctgtggcgg cgcgcggaac 180
cccggcgaca ggaagtgcac acgggacgaa tgcgacacgt acttcaaggt gtgcctcaag 240
gagtaccagt ccagggtcac cgccggcggg ccctgcagct tcggaagcgg ctccaccccc 300
gtgatcggcg gcaacacatt caacctgaaa gcgtcgaggg ggaatgaccg caacaggatc 360
gtgctgccgt tttccttcgc ctggccccgc agctacacgc tgctggtgga ggcatgggac 420
agctccaacg ataccgtgca gcccgacagc atcatcgaga aggcctccca cagcggcatg 480
atcaacccga gcaggcagtg gcagaccctc aagcagaaca ccggcgtggc ccacttcgag 540
tatcagatcc gggtgacctg cgacgactat tactacggtt tcggctgcaa caagttttgt 600
aggccccgag acgacttctt cggccactac gcctgcgatc agaacgggaa taaaacctgt 660
atggaggggt ggatgggccc cgagtgcaac agggccatct gcaggcaggg atgctccccc 720
aagcacggca gctgcaagct gccaggagac tgcaggtgtc agtatggctg gcaggggctg 780
tactgcgata agtgcattcc gcacccagga tgtgtgcacg gaatctgtaa cgagccctgg 840
cagtgcctgt gcgaaaccaa ctggggggcc caactctgcg acaaggacct gaactactgc 900
ggcacccacc aaccctgtct gaacggcggc acctgcagca acaccggccc cgacaaatac 960
cagtgcagct gccccgaggg ctactccggg cccaactgcg agatcgccga acacgcatgt 1020
ctgagcgacc cttgccacaa caggggcagc tgcaaggaga cctccctcgg ctttgagtgc 1080
gaatgcagcc ccggctggac cggcccacc tgcagcacga acatcgacga ctgcagcccc 1140
aacaactgct cccacggcgg gacgtgccag gatctcgtca acggcttcaa gtgcgtgtgc 1200 ccccccagt ggaccggcaa aacctgccag ctggacgcaa acgagtgcga agccaagccg 1260

-continued

```
tgcgtcaacg cgaagagctg caagaacctc atcgccagct actattgcga ctgcctgccc   1320
ggctggatgg gccagaactg cgacataaac atcaacgact gcctgggcca gtgtcagaac   1380
gatgcctcct gcagggacct ggtgaacggg taccggtgta tctgcccccc cgggtacgcg   1440
ggggaccact gcgagagaga catcgatgag tgcgcctcca atccctgcct gaacggcggc   1500
cattgccaga acgagatcaa ccggttccag tgcctgtgcc ccaccggctt ctccggcaac   1560
ctgtgccaac tagacatcga ctactgcgag cccaatccct gccagaacgg cgcccaatgc   1620
tacaacaggg ccagcgacta cttctgtaag tgccccgagg actacgaggg caagaactgc   1680
tcccatctga aggaccactg ccggaccacc ccctgcgaag tgatcgacag ctgcaccgtg   1740
gccatggcca gcaatgacac ccccgagggc gtgaggtata tcagcagcaa cgtgtgcggg   1800
ccccacggga aatgcaagag ccagagcggc ggcaagttca catgcgactg taacaagggc   1860
ttcacgggaa cctactgtca cgagaacatc aacgactgcg agagcaaccc ctgccgcaac   1920
ggcggcacct gcatcgacgg cgtgaactcc tataagtgca tctgtagcga tggctgggaa   1980
ggggcctact gcgagaccaa cataaacgac tgcagccaga atccctgcca taacgggggc   2040
acctgtcgtg acctggtcaa cgacttctac tgcgactgta agaacggatg gaagggtaag   2100
acctgccact ccagggactc ccagtgtgac gaagccacct gcaacaacgg aggcacctgc   2160
tacgacgagg gtgacgcctt taagtgcatg tgccccggtg gctgggaggg gaccacgtgc   2220
aacatcgccc gcaacagcag ctgccttccg aacccatgcc ataacggcgg cacctgtgtc   2280
gtgaacggcg agtcgttcac ctgtgtgtgc aaggaaggct gggaaggccc catatgcgcc   2340
cagaacacca acgactgcag cccccatccc tgctacaact ccggcacctg cgtggacggg   2400
gacaactggt acaggtgtga gtgcgccccc ggattcgccg gtcccgactg ccggatcaac   2460
atcaatgagt gtcaatccag cccctgcgcc ttcggcgcca cctgcgtgga tgagatcaac   2520
ggctacaggt gcgtctgtcc ccccggccac tccggcgcca aatgccagga ggtcagcggc   2580
aggccctgca tcaccatggg ctccgttatc cccgacggcg ccaagtggga cgacgactgc   2640
aatacctgcc agtgtctgaa cgggaggatc gcctgctcca aggtgtggtg cggccccagg   2700
ccctgcctgc tgcacaaggg ccacagcgag tgccccagcg gccagtcctg catcccgatc   2760
ctggacgacc agtgctttgt gcacccctgc accggggtag gcgagtgccg gtccagcagc   2820
ctgcagcccg tgaaaaccaa gtgcaccagc gacagctatt accaggacaa ctgcgccaat   2880
atcaccttta cgttcaataa agagatgatg agccccggcc tgaccaccga acacatctgc   2940
agcgagctgc gcaacctgaa cattctgaag aacgtgagcg ccgagtacag catctatata   3000
gcctgcgagc ccagcccctc ggctaataac gagatccacg tggccataag cgcggaggac   3060
atccgggacg acggcaaccc catcaaggag atcaccgaca agatcatcga cctggtgagc   3120
aagcgcgacg ggaactcatc actgatcgcc gccgtggccg aggtgagggt gcagaggcgg   3180
cccctcaaga acaggaccga cttcctcgtc cccctgctgt cgagcgtgct caccgtggcc   3240
tggatctgct gtctcgtgac cgcattctac tggtgcctga ggaaacggcg caagcccggc   3300
tcgcacaccc acagcgccag cgaagataac accaccaaca acgtgaggga gcagctcaac   3360
cagatcaaga accccataga gaagcacggc gccaacacgg tgccaatcaa ggactatgag   3420
aacaagaaca gcaagatgtc caagatccgc acccacaaca gcgaagtcga ggaagacgac   3480
atggacaagc accagcagaa agcgcgtttc gccaagcagc ccgcctacac cctggtggac   3540
agggaggaga agcccccaa cggaaccccc acaaagcacc caaactggac gaataagcag    3600
gacaacaggg acctggagag cgcccagagt ctgaaccgga tggagtacat cgtg         3654
```

<210> SEQ ID NO 28
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 28
atgagaagtc ccaggacccg cgggcggagc gggcgccccc tgagcctgtt actggccctc 60
ctgtgtgccc tgcgcgcgaa ggtgtgcggg gccagcggcc agttcgagct ggagatcctg 120
agcatgcaga acgtgaacgg ggaactacag aacggcaact gctgcggcgg cgcccgcaat 180
ccgggagaca ggaagtgtac cagggatgag tgcgacacct actttaaagt gtgcctgaag 240
gagtaccaga gcagggtgac cgccggcggc ccctgtagct tcggcagcgg gagcaccccg 300
gtgatcggcg gcaacacctt caacctcaag gcctccaggg gcaacgacag gaaccggatc 360
gtgctgccct tcagcttcgc ctggccccgc agctacacgc tgctggtgga ggcctgggac 420
agctctaatg acacggtgca gcctgactca attatagaga aggccagcca cagcggcatg 480
atcaacccct caagacagtg gcagaccctg aagcagaaca ccggtgtggc acacttcgag 540
tatcagatca gggtgacatg cgatgactac tactacgggt ttggctgtaa taagttctgc 600
aggccccgag acgatttctt cgggcactat gcctgcgacc aaaatggcaa caagacctgc 660
atggaggggt ggatgggccc ggagtgtaac cgagccatat gtaggcaagg ctgcagcccg 720
aagcacggct cctgcaagct gcccggtgat tgcaggtgcc agtacggctg gcaaggcctc 780
tactgcgaca agtgcatccc gcaccccggt tgcgtccacg gcatctgcaa cgagccctgg 840
cagtgcctgt gcgagaccaa ctgggggggc cagctgtgcg acaaggacct caattactgt 900
ggcacccacc agccctgcct caacggtggc acctgctcca acaccggccc cgacaagtac 960
cagtgtagct gccccgaggg gtacagcggc ccgaactgcg agatcgccga gcacgcctgc 1020
ctgtccgacc cctgccacaa tcgcggcagc tgcaaggaga ccagcctggg gttcgaatgc 1080
gagtgttccc cgggctggac cggccccacc tgcagcacca atatcgatga ctgctccccc 1140
aacaactgca gccacggcgg cacctgtcag gacctggtga atggcttcaa gtgtgtgtgc 1200
ccaccgcagt ggaccggcaa aacctgccag ctcgacgcca acgagtgcga ggccaagccc 1260
tgtgtgaatg ccaagtcctg caagaacctg atcgccagct actactgcga ctgcctgccc 1320
gggtggatgg ggcaaaattg cgacataaac ataaacgact gcctgggcca gtgccagaac 1380
gacgcctcct gtcgggacct ggtcaacggc tacaggtgca tctgcccacc cggctacgcc 1440
ggcgaccact gcgagcgaga tatcgacgaa tgcgccagca acccctgcct gaacgggggg 1500
cactgccaga atgagatcaa caggtttcag tgcctgtgcc ccaccggctt cagcggcaac 1560
ctgtgtcaac tggacatcga ctattgtgag cccaaccctt gccaaaacgg ggcccagtgc 1620
tacaaccggg ccagcgatta cttctgcaag tgccccgagg actacgaagg caagaactgc 1680
agccacctga aggaccactg tcggaccacc ccctgcgaag tgatcgacag ctgcaccgtg 1740
gccatggcca gcaacgacac ccccgagggc gtgaggtaca tcagcagcaa tgtgtgtggc 1800
ccgcacggca agtgcaagag ccagagcggc ggcaagttca cgtgcgactg caacaagggc 1860
tttaccggca cctactgcca cgaaaacatc aatgactgcg agagcaaccc gtgtcggaac 1920
ggcggcacct gcatcgacgg ggtgaacagc tacaagtgca tatgcagcga cggctgggag 1980
ggcgcctact gtgaaaccaa catcaacgac tgcagccaga acccctgcca caatggcggg 2040
acctgcaggg acctggtgaa tgacttctac tgcgactgca agaacggctg gaagggcaaa 2100
acctgccaca gcagggacag ccagtgcgac gaggccacct gcaacaacgg cggcacctgc 2160
tatgacgagg gcgacgcctt caagtgcatg tgccccggcg gatgggaggg cacgacctgc 2220
aatatcgcaa ggaacagctc ctgtctgccc aatccctgcc acaacggcgg tacctgcgtg 2280
gtgaacgggg aaagcttcac ctgcgtgtgc aaggaggggt gggaggggcc catctgcgcc 2340
cagaacacca acgactgcag cccacacccc tgctacaatt ccggcacctg tgtggacggc 2400
gacaactggt ataggtgcga gtgcgccccc ggtttcgccg gcccggactg caggatcaac 2460
atcaacgagt gtcagtccag cccctgcgcc ttcggggcca cctgcgtgga cgagatcaac 2520
ggctatcgtt gcgtgtgccc ccccggccac tccggcgcca agtgccagga agtgtccggg 2580
cgcccctgca tcaccatggg ctccgtgatc cccgatggcg ccaagtggga tgacgactgc 2640
aacacctgtc agtgcctgaa cggcaggatc gcctgcagca aggtgtggtg cggcccccga 2700
ccctgcctgc tgcacaaggg gcacagcgag tgcccctccg gccagtcctg catccccata 2760
ctggacgatc agtgcttcgt gcacccctgc accggcgtgg gcgagtgtag gagctccagc 2820
ctgcagcccg tgaaaaccaa gtgcacctcg gacagctact atcaggataa ctgcgccaac 2880
attacgttca ccttcaacaa ggagatgatg tcccccggcc tgaccacgga gcacatctgt 2940
tccgagctga ggaacctcaa catcctgaaa aatgtgagcg ccgagtatag catctatata 3000
gcctgtgagc cgtccccctc cgccaacaac gagatccacg tcgccatctc cgcagaggac 3060
attcgcgacg acgggaaccc cataaaggaa attacggaca aaatcatcga cctggtgagc 3120
aagagggacg gcaactccag cctgatcgcc gccgtggccg aggtgcgcgt gcaacgcagg 3180
ccgctgaaaa acaggacgga ctttctggtg ccgctgctgt cctcggtgct gaccgtcgct 3240
tggatctgct gcctggtgac cgccttctac tggtgcctgc gcaaaaggcg caagcccggt 3300
agccataccc actccgcctc cgaagacaac accaccaaca acgtgaggga gcagctgaat 3360
cagatcaaga accctatcga gaagcacggc gccaacacgg tgcccatcaa ggactatgaa 3420
aacaagaaca gcaagatgtc caagatcagg acccacaaca gcgaggtgga ggaagacgac 3480
atggacaagc accagcagaa ggcccgattc gccaagcagc ccgcttacac cctggtggac 3540
agggaggaaa agcccccgaa cggcaccccc accaaacacc ccaactggac taataaacag 3600
gacaaccgag acctggagag cgcccagagc ctgaacagga tggaatatat cgtc 3654

<210> SEQ ID NO 29
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 29
atgcgtagcc ccaggaccag gggtaggtcc gggaggcccc tgtcactcct cctggccctg 60
ctctgtgccc tccgggccaa ggtgtgcggc gccagcggac agtttgagct ggagatcctg 120
tccatgcaga acgtgaacgg tgagctccag aacgggaact gctgcggcgg cgccaggaac 180
cccggcgatc gcaagtgtac cagggacgaa tgtgacacct actttaaggt gtgcctgaaa 240
gagtaccaga gccgcgtcac cgccggcggg ccctgttcct ttggctccgg cagcactccc 300
gtgatcggcg gcaacacctt caacctcaag gcgagcaggg ggaacgacag gaacaggatc 360
gtgctgccct tcagcttcgc gtggccccgg tcctacaccc tgctcgtgga ggcttgggac 420
tcctcaaacg acacggtcca gccggatagc atcattgaga aggcgagcca ctccggcatg 480

```
atcaacccca gccggcagtg gcagaccctc aagcagaaca ccggcgtggc ccacttcgag    540
tatcagatcc gcgtgacctg cgatgattac tactacggct ttggatgcaa caagttctgc    600
cggccccgcg acgacttctt cggacactat gcctgtgacc agaacgggaa caagacctgc    660
atggagggat ggatgggtcc cgagtgcaac cgggccatct gcaggcaggg ctgtagcccc    720
aagcacggga gctgcaagct gcccggcgac tgcaggtgcc agtacggctg gcaggggctg    780
tactgcgaca agtgcatccc ccacccggga tgcgtgcacg gcatctgcaa cgagccctgg    840
cagtgcctct gcgagaccaa ctggggcggc cagctgtgcg acaaggacct gaactactgt    900
ggcacgcatc agccatgcct caatggtggc acctgcagca acacgggccc cgataagtac    960
caatgctcgt gccccgaagg gtactccggc ccaaattgcg agatcgccga gcacgcctgc   1020
ctgtccgacc cctgccacaa caggggctcc tgtaaggaga cctccctggg cttcgagtgt   1080
gagtgcagcc ccgggtggac cggccccacc tgttccacca acatcgacga ctgcagcccc   1140
aacaactgca gccatggagg cacctgtcag gacctggtga atggtttcaa gtgtgtgtgc   1200
ccgccccagt ggaccgggaa gacctgccag ctggacgcca acgagtgcga ggctaagccc   1260
tgcgtcaacg ccaagagctg caagaacctc atcgcctcct actactgcga ctgcctgccg   1320
ggatggatgg gccagaactg tgacatcaac atcaacgact gtctgggcca gtgccagaat   1380
gacgccagct gccgagacct ggtcaacggc tacaggtgca tatgccccc cggatatgcc   1440
ggggatcact gcgagcggga catcgacgag tgcgccagca acccatgtct gaacggcggg   1500
cactgccaga acgagatcaa caggtttcaa tgcctgtgcc ccaccggatt tagtgggaac   1560
ctctgtcagc tggacataga ctactgcgag ccgaacccct gccaaaacgg cgcgcagtgc   1620
tacaacaggg ccagcgatta cttctgcaag tgcccggagg actacgaggg gaagaactgc   1680
tcccacctga aggaccactg caggaccacc ccctgcgagg tgatcgactc gtgcaccgtc   1740
gccatggcct caaacgacac ccccgagggg gtccgctaca tctcgagcaa cgtctgtggc   1800
ccccacggca agtgcaagag ccagagcggg gggaagttca cctgcgactg caacaaaggc   1860
ttcaccggca cgtactgtca cgagaacatc aatgattgcg agagcaaccc ctgccggaac   1920
ggcggcacct gcatcgacgg cgtgaacagc tacaagtgca tctgtagcga cggctgggag   1980
ggggcctact gcgagaccaa catcaacgac tgcagccaga acccctgtca caacggcggc   2040
acctgcaggg acctcgtgaa tgacttctac tgcgactgca aaaacgggtg gaaaggtaaa   2100
acctgccata gccgggacag ccagtgcgac gaggccacct gtaataacgg cggcacctgc   2160
tacgacgagg gtgacgcctt taagtgtatg tgccccggcg gctgggaggg caccacctgc   2220
aatatcgccc gcaacagcag ctgtctcccc aacccctgcc acaacggggg tacctgcgtg   2280
gtcaacggcg agtcctttac ctgcgtgtgc aaggagggct gggaagggcc catctgcgcc   2340
cagaacacca acgactgtag cccccatccc tgctacaact ccggtacctg cgtggacggc   2400
gacaattggt acaggtgtga atgcgcacca ggcttcgcgg ggcccgactg caggatcaac   2460
atcaacgaat gccagagcag cccctgcgcg ttcggcgcca cctgcgtgga cgagatcaac   2520
gggtacaggt gcgtgtgccc ccccgggcac agcggggcca agtgccagga ggtctccggg   2580
cggccctgca tcaccatggg ctccgtgatc ccggatgggg cgaagtggga cgacgattgc   2640
aacacctgcc aatgcctgaa cgggaggatc gcctgtagca aggtctggtg cggacccccgg   2700
ccctgcctcc tgcacaaagg ccactccgaa tgccccagcg gacaaagctg cataccgatc   2760
ctggacgacc aatgcttcgt gcatccctgc acaggcgtgg gtgaatgcag gagctccagc   2820
```

ctgcagccag tgaagacgaa gtgcaccagc gatagctact accaggataa ttgtgccaac 2880
ataaccttca ccttcaacaa ggagatgatg tcccccggcc tgaccaccga gcacatctgt 2940
agcgagctcc gcaacctgaa catcctcaag aacgtgagcg ccgagtactc catctacatc 3000
gcctgcgagc cctcgcccag cgccaataac gagatccacg tggccatctc cgccgaggac 3060
atccgcgacg acggcaatcc catcaaggag attaccgaca agatcatcga cctggtgagc 3120
aagcgcgatg gcaacagcag cctgatcgcc gcggtggccg aggtgagggt gcagaggcgg 3180
cccctcaaga accgcacgga cttcctggtg ccactgctga gctccgtgct gaccgtggcc 3240
tggatctgct gtctggtcac cgccttctac tggtgcctgc ggaaacggag gaagcccgga 3300
tcccacaccc actccgcctc cgaagacaac accacgaaca acgtcaggga gcagctgaac 3360
cagatcaaga accccatcga gaagcatggc gccaacaccg tgccaatcaa agactacgag 3420
aacaagaaca gcaagatgag caagatccgg acccacaaca gcgaagtaga agaggacgac 3480
atggataagc accagcagaa ggccaggttc gccaagcaac ccgcctacac cctcgtggac 3540
cgcgaggaga aacccccaa cggcaccccc accaagcacc ccaattggac caacaagcaa 3600
gataaccgcg acctggagag cgcccagagc ctcaaccgga tggaatacat cgtg 3654

<210> SEQ ID NO 30
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 30
atgaggagcc caaggaccag ggggaggagc ggcaggccgc tcagcctgct gctcgccctg 60
ctgtgcgccc tgcgggcaaa ggtgtgcggg gccagcggcc agttcgagct ggaaatcctg 120
agcatgcaga acgtgaacgg cgagctgcaa aatggtaatt gctgcggggg cgccaggaac 180
ccgggcgaca ggaagtgcac cagggacgag tgcgacacct atttcaaggt gtgcctgaag 240
gaataccaga gccgcgtcac ggccgggggc ccgtgctcct tcggcagtgg ctccaccccc 300
gtgatcggcg gcaacacctt taacctgaag gcctcccggg gtaacgacag gaacaggatc 360
gtgctgccct tctccttcgc ctggccgagg tcctacaccc tcctggtaga ggcctgggac 420
agcagcaatg atacggtgca gcccgactcc atcatagaaa aggccagcca ctccgggatg 480
atcaatccga gcaggcagtg gcaaaccctc aagcagaaca ccggtgtggc ccactttgag 540
taccagatca gggtcacctg cgacgactac tactacggct tcggctgcaa caagttttgc 600
aggccgaggg acgacttctt cggccactac gcctgcgacc agaatggcaa caagacctgc 660
atggaaggct ggatgggccc ggaatgcaat cgcgccatct gtaggcaggg gtgcagccca 720
aagcatggga gctgcaagct gcccggggac tgcaggtgtc agtacggatg gcaggggctg 780
tactgtgaca agtgtatccc acatccgggc tgcgtgcacg gaatatgcaa cgagccctgg 840
cagtgcctgt gtgaaacgaa ctggggcggt cagctgtgcg acaaggacct gaactactgc 900
ggcacccacc agccctgcct gaacggcggg acgtgttcca acaccggccc cgacaagtat 960
cagtgtagct gccccgaggg ctatagcggc ccgaactgcg agatcgccga acatgcctgt 1020
ctcagcgacc cctgtcacaa caggggtagc tgtaaggaaa ccagcctcgg gtttgagtgt 1080
gaatgctccc cgggctggac cgggcccacc tgttccacca acatcgacga ctgctccccc 1140
aataactgca gccatggcgg cacgtgtcag gacctcgtca atggctttaa gtgtgtgtgc 1200
cccccgcagt ggaccggcaa gacgtgccag ctggacgcca acgagtgtga ggccaagccc 1260

-continued

```
tgcgtcaacg caaagagctg caagaacctg atcgcctcct actattgtga ctgcctgccc   1320
gggtggatgg gacagaactg cgacatcaat atcaacgatt gcctggggca gtgccagaac   1380
gacgcgagct gcagggacct ggtcaacggc taccgatgca tctgcccccc gggctacgcc   1440
ggcgaccact gtgaaaggga catcgacgag tgcgccagca acccctgcct gaacgggggc   1500
cactgccaga acgagatcaa taggttccag tgcctgtgcc cgaccggttt tagcggcaac   1560
ctgtgccagc tggacattga ctattgcgag cccaacccct gccagaacgg ggcccagtgc   1620
tacaacaggg cctcggacta cttctgtaag tgccccgagg actatgaggg caagaactgc   1680
agccatctga aggaccactg caggaccacc ccgtgcgagg tcatcgacag ctgcaccgtg   1740
gccatggcct ccaatgatac cccccgagggc gtgaggtaca tctcctccaa cgtgtgtggc   1800
ccccacggca agtgcaaaag ccagagcggc ggcaagttca cctgtgactg taacaagggc   1860
ttcaccggca cctactgcca tgaaaacatc aacgattgcg agtctaatcc ctgccggaac   1920
ggcggcacct gcatcgatgg cgtgaacagc tataaatgta tctgctccga tgggtgggag   1980
ggcgcatact gcgaaaccaa catcaacgac tgctcccaga acccctgcca taacggcggc   2040
acctgccgcg acctcgtcaa cgatttctac tgcgactgca agaacggctg gaagggcaag   2100
acctgccaca gccgagacag ccagtgcgac gaggccacgt gcaacaacgg agggacctgt   2160
tatgacgagg gcgacgcctt caagtgcatg tgccccgggg gctgggaggg cacgacctgc   2220
aacattgccc gcaatagcag ctgcttgccc aacccctgtc acaacggcgg aacctgcgtc   2280
gtgaacggcg agtccttcac ctgcgtttgc aaagagggct gggagggccc aatctgtgcc   2340
cagaacacca atgactgcag cccccacccc tgctacaatt ccggtacctg cgtggacggc   2400
gacaactggt ataggtgcga gtgcgccccg ggattcgccg gcccggactg caggatcaac   2460
atcaacgagt gccagagcag cccctgcgcc ttcggggcca cctgtgtgga cgagatcaat   2520
ggctacaggt gtgtctgccc ccccggacac tcgggcgcga aatgccaaga ggtgtccggc   2580
aggccctgca tcaccatggg ttccgtgata cccgacgggg caaagtggga cgacgattgc   2640
aatacctgcc aatgcctgaa cggcaggatc gcctgtagca aggtgtggtg tggcccgagg   2700
ccttgcctcc tgcataaagg ccacagcgag tgtccctccg gccagagctg tatccccatc   2760
ctcgacgatc aatgctttgt gcacccttgc accggggtgg gcgagtgtcg cagcagcagc   2820
ctgcagcccg tgaagaccaa atgcaccagc gatagctact accaggacaa ctgcgcgaat   2880
atcaccttta cgttcaacaa ggagatgatg agcccgggcc tgaccacaga gcacatctgc   2940
agcgagctgc gcaacctgaa catcctgaag aacgtgtctg ccgagtatag catctacatc   3000
gcctgcgaac ccagcccctc cgcaaataat gagatccacg tggcgatctc ggccgaggac   3060
atcagggacg acgggaaccc catcaaagag atcaccgaca agatcatcga tctggtgagc   3120
aagcgggacg gcaacagctc cctcatcgcc gccgtggctg aggtccgagt gcagcggcgt   3180
ccccttaaga acaggaccga cttcctggtg cccctcctgt cgtccgtgct caccgtggcc   3240
tggatctgtt gcctggtgac cgccttctac tggtgcctgc gtaagcgaag gaagcccgga   3300
tcccacaccc acagcgccag cgaagacaac accaccaata acgtccgaga gcagctgaac   3360
cagatcaaga accccataga gaaacacggg gccaacaccg tgcctatcaa ggactacgag   3420
aacaaaaata gcaaaatgag caagattagg acccacaact ccgaggtgga ggaggacgac   3480
atggacaagc atcagcagaa ggcccgcttc gccaagcaac ccgcctacac cctggtggac   3540
cgagaggaaa agcccccaa cgggaccccc acgaagcacc ccaactggac caataagcag   3600
```

gataacaggg acctcgagag cgcccagtcc ctgaatcgca tggagtacat cgtg 3654

<210> SEQ ID NO 31
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 31
atgaggagcc cccgcaccag ggggcgtagc ggccgccccc tgagcctgct gctggctctg 60
ctgtgtgccc tgcgagccaa agtgtgcggg gcctccggcc agttcgagct ggagatcctg 120
agcatgcaga acgtgaacgg cgagctccag aacggcaact gctgcggcgg cgcccgcaac 180
cccggcgaca ggaagtgcac tcgggacgag tgcgacacct atttcaaggt ctgcctgaag 240
gagtaccaaa gccgtgtgac cgccggcggg ccgtgcagct tcggaagcgg ctccaccccg 300
gtcatcgggg ggaacacctt taacctgaag gccagccggg gtaacgacag gaaccgaatc 360
gtactgccct tcagcttcgc ctggccccgg agctacaccc tgctggtcga ggcatgggac 420
tccagcaacg ataccgtgca gcccgacagc atcatcgaga aagccagcca cagcgggatg 480
attaatccca gcagacagtg gcagaccctg aagcagaaca ccggcgtggc ccacttcgag 540
taccaaatcc gggtgacctg cgacgattat tactacgggt ttggctgtaa taaattctgc 600
cggccccggg atgacttttt cggccattac gcctgcgatc agaacggtaa caagacctgc 660
atggagggct ggatgggacc ggagtgtaac agggctatct gccgacaggg ttgtagcccc 720
aagcacggaa gctgcaagct gcccggcgac tgccggtgtc agtacggctg gcagggcctg 780
tactgcgata agtgcatccc ccacccggc tgcgttcacg gcatctgcaa cgagccctgg 840
cagtgcctgt gtgaaaccaa ctggggtgga cagctgtgcg acaaggatct gaactattgc 900
ggcacccacc agccctgcct gaacggcgga acctgcagca acaccggccc cgataagtac 960
cagtgcagct gccccgaagg ctactccggc cccaactgcg agatcgccga gcacgcctgc 1020
ctgagcgacc cgtgccacaa cagggggagc tgcaaagaga ccagcctggg tttcgagtgc 1080
gagtgcagcc ccggctggac cggcccact tgctccacca acattgacga ctgtagcccg 1140
aacaattgca gccacggcgg cacctgccag gacctggtga atggcttcaa gtgcgtgtgt 1200
cccccccagt ggaccgggaa gacctgccag ctggacgcca acgagtgcga ggccaagccc 1260
tgtgtgaacg ccaagtcctg caagaacctg atcgcctcct actactgtga ctgtctcccc 1320
gggtggatgg gccagaactg cgacatcaac atcaacgatt gcctcggcca gtgccagaac 1380
gacgccagct gtagggacct cgtgaacggc taccggtgca tctgcccgcc cgggtacgcc 1440
ggagaccact gcgagaggga cattgacgag tgcgcctcga acccctgcct gaacggcggc 1500
cactgtcaga acgagatcaa taggttccag tgtctgtgtc ccaccggctt ctccggcaac 1560
ctgtgtcagc tggacatcga ctactgtgag cccaatccct gccagaatgg cgcccagtgc 1620
tataaccggg cctccgacta cttttgcaag tgccccgaag attacgaggg caagaactgc 1680
agccatctga aggaccactg caggacgact ccctgcgagg tgatcgacag ctgtactgtc 1740
gccatggcca gcaacgacac ccccgagggg gtccgctata tcagcagcaa cgtgtgcggg 1800
ccccatggga aatgcaaatc ccagtcaggg ggcaagttta cctgcgactg taacaaaggc 1860
ttcaccggca cctactgcca cgaaaacatc aacgactgcg aatcgaaccc ctgccggaac 1920
ggcgggacct gcatcgatgg agtgaacagc tacaagtgca tctgcagcga cgggtgggag 1980
ggcgcgtact gcgaaaccaa tatcaatgac tgcagccaga acccctgcca taacggaggc 2040
acctgcaggg acctggtgaa cgacttctac tgcgattgca agaacggctg gaaggggaag 2100
acctgccata gcagggacag ccagtgtgac gaggccacct gcaacaacgg cggcacatgt 2160
tacgatgagg gcgacgcctt caaatgcatg tgccccggcg gctgggaggg caccacatgc 2220
aacatcgccc ggaacagcag ctgcctcccc aacccctgcc ataatggcgg tacctgcgtg 2280
gtgaacggcg agagtttcac ctgcgtgtgc aaggagggct gggagggccc catctgcgcg 2340
cagaacacca atgactgctc gccccacccc tgctacaaca gcggcacctg cgtggacggt 2400
gacaactggt accgttgcga gtgcgcccca ggcttcgccg gcccggactg caggatcaac 2460
atcaacgagt gccaaagctc cccttgcgcc tttggcgcaa cctgtgtgga cgagatcaat 2520
gggtacaggt gcgtgtgccc ccccggccat tccggggcca agtgccaaga ggtgtccggc 2580
cggccctgca ttaccatggg cagcgttatc cccgacggcg ccaagtggga cgacgactgc 2640
aatacctgcc agtgcctcaa cggcaggatc gcctgcagca aggtgtggtg cggacccagg 2700
ccgtgcctgc tgcataaggg ccacagcgag tgcccgagcg gtcagtcctg catccccatc 2760
ctcgacgacc agtgtttcgt gcacccctgc acgggcgtgg gtgagtgccg atcctccagc 2820
ctgcagcccg tcaaaaccaa gtgcacctcc gacagctact accaggacaa ctgcgccaac 2880
ataaccttca cgtttaacaa ggagatgatg agccccggcc tgaccaccga gcacatctgc 2940
agcgagctga ggaacctgaa catcctgaag aacgtgtccg ccgagtacag catctacatc 3000
gcctgtgagc ccagcccctc cgccaacaac gagatccatg ttgccatctc ggccgaagat 3060
attagggacg acggcaaccc catcaaggag atcaccgaca agatcataga cctggtgagc 3120
aagcgggacg gcaattccag cctgatcgcc gccgtggccg aggtgagagt gcagaggagg 3180
cccctgaaga accggaccga tttcctggtg cccctgctga gcagcgtgct gaccgtggcc 3240
tggatctgct gcctggtgac cgcattttac tggtgtctga ggaagcggag gaaacccggc 3300
agccacaccc acagcgcaag cgaggataac accacgaata acgtgcgcga gcagctgaac 3360
caaatcaaga accccatcga gaagcacggg gccaacaccg tgcccatcaa ggactacgag 3420
aataagaact cgaagatgag caagatcagg acgcacaact ccgaggtgga ggaggacgac 3480
atggataagc accagcagaa agcccggttc gccaagcagc ccgcctacac cctggttgac 3540
cgcgaggaga aaccccccaa cggcaccccc accaagcacc ccaactggac caacaagcag 3600
gacaaccgag acctggagag cgcccagagc ctgaacagga tggagtatat cgtg 3654

<210> SEQ ID NO 32
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 32
atgaggtccc ccaggaccag gggcaggagc gggaggcccc tgtcccttct gctggcgctg 60
ctgtgcgccc tgcgcgccaa ggtgtgcggg gcaagcggcc agttcgagct cgaaatactc 120
agcatgcaaa acgtcaacgg cgagctgcag aacggcaact gttgcggtgg cgccaggaac 180
cccggggatc gcaagtgcac cagggacgag tgtgatacct acttcaaagt gtgtctgaag 240
gagtaccaga gccgggtgac cgccgggggc ccctgttcct tcggcagcgg gagcaccccc 300
gtcatcggcg ggaatacgtt taacctgaag gcctccaggg gcaacgatag gaaccggatc 360
gtgctccctt tcagcttcgc ctggcccagg tcctacaccc tgctggtgga ggcctgggac 420

-continued

```
tccagcaatg acactgtcca gcctgacagt atcatagaga aagcctccca ctccggcatg    480
atcaacccca gtcgccagtg gcagaccctg aagcagaaca ccggcgtggc ccacttcgag    540
taccagatcc gggtgacctg cgacgactat tactacggct tcggatgcaa taagttctgt    600
aggccccgcg acgatttctt cggccattat gcctgcgacc agaacggcaa caagacctgc    660
atggagggct ggatggggcc cgagtgcaac agggccatct gcaggcaggg gtgctccccc    720
aaacacggga gctgcaaact gccgggggac tgcaggtgcc aatacggctg gcagggcctg    780
tactgcgaca agtgcatccc gcaccccggg tgcgtgcacg gcatttgcaa cgaaccctgg    840
cagtgcctct gcgaaaccaa ttggggaggc cagctgtgcg acaaggatct gaactactgc    900
ggcacgcacc agccctgcct caacgggggg acctgtagca acacgggccc cgacaagtac    960
cagtgctcct gcccggaggg atactctggc cccaactgcg agatcgccga gcacgcctgc   1020
ctctccgatc cgtgccacaa taggggcagc tgcaaggaaa cgtccctggg cttcgaatgc   1080
gaatgcagtc ccggatggac cggccccacc tgcagcacca acatcgacga ctgcagcccc   1140
aacaactgca gccacggcgg cacctgccaa gatctcgtga acggcttcaa gtgcgtgtgc   1200
cccccccagt ggaccgggaa aacctgccaa ctcgacgcca atgagtgtga ggccaagccc   1260
tgcgtgaacg ccaagtcgtg caaaaacctg atcgccagct actactgcga ctgcctgccc   1320
ggctggatgg ggcagaactg cgacatcaac atcaacgact gcctggggca gtgccagaat   1380
gacgctagct gccgagacct ggtcaatgga taccggtgca tatgcccccc gggctacgcc   1440
ggcgaccatt gcgagcggga catcgacgag tgcgccagca acccatgcct gaacggcggg   1500
cactgccaga acgaaataaa caggttccag tgtctgtgcc cgacgggctt tagcggcaac   1560
ctctgccagt tggatatcga ctattgcgag cctaaccctt gccagaacgg cgcccagtgc   1620
tataaccgcg caagcgatta tttctgcaaa tgccccgagg actacgaggg caagaattgc   1680
agccatctga aagaccactg tcggacgacc ccctgcgagg tgatcgacag ctgcaccgtg   1740
gccatggcct ccaacgacac ccccgaaggg gtgcgctata tctccagcaa cgtgtgcggc   1800
ccccacggca agtgcaagag ccagtcaggg ggcaaattca cctgcgactg caacaagggc   1860
ttcaccggga cctactgcca cgagaacatc aacgactgcg agagcaaccc ctgccggaac   1920
ggcggcacct gcatcgatgg ggtgaactcc tataagtgca tctgtagcga tggatgggag   1980
ggggcctact gcgaaaccaa catcaacgac tgcagccaga acccctgcca caacgggggc   2040
acctgcaggg acctcgtgaa cgacttctac tgcgactgca agaacggctg gaagggcaag   2100
acatgccact cccgggactc acaatgcgac gaagcgacct gcaacaatgg cggcacctgt   2160
tacgatgagg gggatgcctt taagtgcatg tgccccggtg gctgggaggg caccacctgc   2220
aatatcgcca ggaattcctc ctgcctgccc aacccctgcc ataatggcgg gacctgcgtc   2280
gtgaacggcg agagcttcac ctgcgtgtgc aaagaggggt gggaaggacc catctgcgcc   2340
caaaatacga acgactgcag cccccacccc tgttacaaca gcggcacgtg cgtggatggg   2400
gacaactggt accgctgcga gtgcgccccc ggctttgcag gcccggactg tcggatcaac   2460
atcaacgagt gccagagcag cccctgcgcc ttcggagcca cgtgcgtgga cgagatcaat   2520
ggctacagat gcgtgtgccc cccgggacac agcggcgcca agtgccagga agtgtccggc   2580
cgtccctgca tcaccatggg tagcgtcatc cccgacggcg ccaagtggga cgatgactgc   2640
aacacgtgtc agtgtctgaa cggccgaatc gcctgctcca aggtgtggtg cggccccccgg   2700
ccctgcctgc tgcacaaggg ccacagcgag tgccccagcg gccagtcgtg tatccccatc   2760
ctcgacgacc aatgcttcgt gcacccctgc accggcgtgg gcgagtgccg cagctcgagc   2820
```

```
ctgcagcccg tgaagaccaa gtgcaccagc gatagctact accaggacaa ttgcgccaac   2880

atcaccttca cctttaacaa ggagatgatg agccccggcc tgacgaccga acacatctgc   2940

tccgagctga ggaacctgaa catcctgaag aatgtcagcg ctgagtactc catctacatc   3000

gcctgtgagc ccagcccaag cgccaacaat gagatccacg tcgcgatctc cgccgaggac   3060

atccgcgacg atggcaaccc catcaaggag atcaccgaca agatcatcga cctggtgagc   3120

aagagggacg gcaacagctc cctgatcgcc gcggtggccg aggtgagggt ccaaaggagg   3180

cccctgaaga acaggaccga cttcctggtg cccctgctgt cgagcgtgct gaccgtggcc   3240

tggatctgct gcctggtgac cgcgttctac tggtgcctgc gtaagaggag gaagcccggc   3300

agccacaccc atagcgcgtc cgaggataac accaccaata acgtgaggga gcagctcaac   3360

cagatcaaga acccaatcga gaagcacggt gccaacactg tgcccatcaa ggactatgag   3420

aacaagaaca gcaagatgag taagatcagg acacacaact ccgaggtgga agaagacgac   3480

atggacaagc accagcagaa ggcccggttc gccaagcagc ccgcctacac cctggtggac   3540

agggaagaga aaccccccaa cggtacaccc acgaaacacc ccaactggac caataagcag   3600

gacaacaggg acctggagtc cgcccagagt ctgaacagga tggagtacat cgtg         3654
```

<210> SEQ ID NO 33
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 33

```
atgcggtccc cccggaccag gggtaggagc ggccgcccac tgtccctgct gctggccctg     60

ctgtgtgccc tgagggccaa ggtgtgcggc gcctccggac aattcgagct ggagattctc    120

tcgatgcaga acgtgaacgg cgaactgcag aacggaaatt gctgtggcgg cgccaggaat    180

cccggcgata gaaagtgcac cagggacgag tgtgacacgt acttcaaggt gtgcctgaag    240

gagtaccaga gccgcgtgac cgccggcggg ccctgctcct tcgggtcagg cagcaccccc    300

gtgatcggcg ggaacacctt caacctcaag gcctccaggg gcaacgacag gaataggatc    360

gtgctcccct tcagcttcgc ctggcccagg tcctacaccc tgctggtaga ggcctgggac    420

tccagcaacg acaccgtgca gcccgatagc atcatcgaga aggctagcca cagcggaatg    480

atcaacccca gccgccagtg gcagaccctg aaacagaaca ccggcgtagc ccactttgag    540

taccagatca gggtgacctg cgacgactat tactatggct tcggttgcaa caagttctgc    600

cggcctcgcg acgacttctt cggacactac gcctgtgatc agaacgggaa caagacctgt    660

atggagggtt ggatgggccc cgaatgcaac agggccatct gcaggcaggg ctgctccccc    720

aagcacggga gctgcaagct gcccggcgac tgccggtgcc agtacggctg gcagggtctg    780

tactgcgaca agtgcatccc ccatcctggc tgcgtgcacg gcatatgcaa cgagccctgg    840

cagtgcctgt gcgagaccaa ttggggcggc cagctgtgcg acaaggacct gaattactgt    900

ggcacccacc agccctgcct caacggcggc acctgctcca acaccggccc cgacaagtac    960

cagtgcagct gccccgaagg ctacagcggc ccgaattgcg agatcgccga acacgcctgc   1020

ctcagcgacc cctgccacaa ccggggcagc tgtaaggaga cctccctggg ctttgaatgc   1080

gaatgtagcc ccggttggac cggacccacc tgttccacca acatcgacga ctgcagcccc   1140

aataactgca gccacggtgg cacgtgccag gacctcgtca acggctttaa gtgcgtgtgc   1200
```

-continued

```
ccccccccagt ggaccgggaa gacctgccag ctggacgcca acgagtgcga ggccaagccc   1260
tgcgtgaacg ccaagagctg caagaacctc atcgccagct actattgtga ctgcctgccc   1320
gggtggatgg gccagaactg tgacataaac atcaacgatt gtctgggcca gtgccagaac   1380
gatgccagct gtcgggacct ggtgaacggc taccggtgca tctgtccccc cggctacgcc   1440
ggagatcact gtgagcgaga catcgacgag tgcgcctcca acccctgcct caacggcggg   1500
cactgtcaga atgagatcaa caggttccag tgcctgtgcc cgacgggatt ctccggtaac   1560
ctgtgccagc tcgacatcga ctactgtgag cccaacccct gtcaaaatgg cgcccaatgc   1620
tacaaccggg cctccgacta cttctgtaag tgccccgagg attacgaggg taagaactgt   1680
agccatctga aggaccactg caggactacc ccgtgcgagg tgatcgactc ctgcaccgtc   1740
gccatggcct ccaacgacac ccccgagggc gtgcggtaca tcagcagcaa cgtgtgtggg   1800
ccgcacggca agtgcaagag ccagagcggg ggcaagttca cctgtgattg caacaagggc   1860
ttcaccggga cgtattgcca cgagaacatc aacgactgcg agagcaaccc ctgcaggaac   1920
ggggggacct gcatagacgg cgtgaacagc tacaaatgca tctgcagcga tgggtgggag   1980
ggcgcctact gtgagaccaa cattaacgac tgcagccaga acccctgcca caacgggggt   2040
acctgtcgcg acctggtgaa cgacttctac tgtgactgca agaacggctg gaagggcaag   2100
acctgtcatt cccgcgacag ccagtgcgac gaagccacct gcaacaacgg cggcacctgc   2160
tacgacgagg gcgatgcctt caagtgcatg tgcccgggcg gctgggaggg gaccacctgt   2220
aatatcgcca ggaattccag ctgcctcccc aatccgtgcc ataatggcgg cacctgcgtg   2280
gtcaacggcg aaagctttac ctgcgtctgt aaggaaggct gggaaggtcc gatctgtgcc   2340
cagaacacca acgactgtag cccccacccc tgctacaata gcggaacgtg cgtggacggc   2400
gacaactggt atcggtgcga gtgcgccccc ggctttgcgg ggccggactg ccggatcaat   2460
atcaacgagt gccagagcag cccctgcgcc ttcggcgcca cctgcgtgga cgagatcaac   2520
ggctacaggt gcgtgtgtcc ccccggccac tccggcgcca agtgccagga ggtgagcggt   2580
aggccctgca tcaccatggg cagcgtgatc cccgacgggg ccaagtggga cgatgactgt   2640
aacacctgcc agtgcctgaa cgggaggatc gcctgttcca aagtgtggtg cggcccgcgt   2700
ccctgcctac tccacaaggg gcattccgag tgtcccagcg gacagagctg tatccccatc   2760
ctggacgacc aatgcttcgt gcacccctgc accggcgtgg gtgagtgcag gtccagcagc   2820
ctgcagcccg tgaagacaaa gtgcaccagt gattcctact accaggataa ctgcgccaac   2880
atcaccttca ccttcaataa ggagatgatg agcccgggcc tgaccacgga gcacatctgc   2940
agcgagctgc gcaacctgaa catcctgaag aacgtctccg ccgagtacag catatacatc   3000
gcctgcgagc ccagcccctc cgccaataac gagatccacg tggccatctc cgcggaggac   3060
atcagggacg atggcaaccc catcaaggag atcaccgaca agattatcga cctggtcagc   3120
aaaagggacg gcaactccag cctcatcgcc gccgtggccg aggtcagggt acagcgcagg   3180
ccgctgaaaa accggaccga cttcctggtg cccctgcttt cctccgtgct cacggtggcc   3240
tggatttgct gcctggtaac cgcgttttac tggtgcctga ggaagaggag gaagcccggc   3300
agccataccc acagcgccag cgaggacaac acaaccaaca acgtgaggga gcagctcaac   3360
cagataaaga accccatcga gaaacacggc gccaacacgg tgcccatcaa ggactatgag   3420
aacaagaaca gcaagatgag caagatccgc acccacaaca gcgaggttga ggaagacgac   3480
atggacaagc accagcagaa ggccaggttc gccaagcagc ccgcctacac cctggtggat   3540
cgtgaggaga aaccgcccaa cgggaccccc accaagcatc ccaattggac caacaaacag   3600
```

gacaacaggg acctggagtc cgcccaaagc ctgaaccgga tggagtacat cgtc 3654

<210> SEQ ID NO 34
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 34
atgaggtccc ccagaactcg ggggaggtcc ggcaggccgc tcagcctcct gctcgccctg 60
ctgtgcgccc tgagggccaa ggtgtgcggc gcctccggcc agttcgagct ggagattctg 120
agcatgcaga acgtgaacgg cgaactgcag aacggaaact gctgcggtgg ggccaggaac 180
cccggcgacc ggaagtgcac cagggatgaa tgcgacacct acttcaaggt ctgcctcaag 240
gagtaccaga gcagggtgac cgccgggggc ccgtgtagct tcggctccgg cagcaccccc 300
gtgataggcg gcaacacgtt caaccttaaa gcctccaggg gcaacgaccg caacaggatc 360
gtgctgccct tctccttcgc gtggccccgc agctacaccc tgctggtgga ggcgtgggat 420
agcagcaacg acaccgtcca gcccgattca atcatcgaaa aggccagcca cagcggcatg 480
atcaacccct ccaggcagtg gcagaccctg aagcaaaaca ccggcgtggc ccacttcgag 540
taccaaatca gggttacctg cgacgactac tactatgggt tcggctgcaa taagttctgt 600
cggccgcggg acgacttttt cgggcattat gcctgcgacc agaatggcaa taagacctgc 660
atggagggct ggatgggacc cgagtgcaac cgcgccatct gcaggcaggg ctgctccccc 720
aagcacggca gctgcaagct gcccggcgac tgcaggtgcc agtacgggtg gcagggcctc 780
tactgcgaca agtgcatccc ccaccccggc tgcgtgcatg ggatatgcaa cgagccgtgg 840
cagtgcctgt gcgaaaccaa ctgggggggc cagctgtgcg ataaggacct caactactgc 900
ggcacccacc agccctgcct caacggcggc acctgctcca ataccgggcc cgataaatac 960
cagtgctcct gccctgaggg ctacagcggg cccaactgtg agatcgccga gcatgcctgc 1020
ctctcggacc cctgccataa caggggcagc tgtaaggaaa ccagcctggg cttcgagtgc 1080
gagtgcagcc ccgggtggac cgggccaacc tgctccacca acatcgacga ctgtagcccg 1140
aacaactgct cccacggcgg gacctgccag gacctggtga atggcttcaa gtgcgtatgt 1200
cccccacagt ggaccggcaa gacctgtcaa ctcgacgcca acgagtgcga ggccaaaccc 1260
tgcgtgaacg ccaagtcctg caagaacctg atcgcctcct actactgcga ctgtctgccc 1320
ggctggatgg gccagaactg cgatatcaac atcaacgatt gcctcggcca gtgtcagaac 1380
gacgcctcct gccgggacct ggtgaacggc taccggtgca tttgcccccc gggctacgcc 1440
ggcgatcact gcgagcgcga catcgacgag tgcgcatcca acccctgtct gaacgggggg 1500
cactgtcaga acgagatcaa taggttccag tgcctgtgcc ccaccggctt ctccgggaat 1560
ctgtgccagc tggacatcga ttactgcgag cccaacccct gccagaacgg cgcccagtgt 1620
tacaacaggg ccagcgatta cttctgcaag tgtcccgaag actatgaggg caagaattgc 1680
agccatctga aagaccactg ccgcaccacc ccctgtgagg tgatcgactc gtgcaccgtg 1740
gcgatggcca gcaatgacac cccggagggc gtgcggtaca tcagcagcaa cgtgtgtggg 1800
ccccacggca agtgcaagtc ccagagcggg ggcaagttca cctgcgactg caacaaaggc 1860
tttacaggga catattgcca cgaaaacatc aatgactgcg agagcaaccc ctgccgcaat 1920
ggcggcactt gcatcgacgg cgtgaacagc tacaaatgta tctgctcaga cgggtgggaa 1980

```
ggcgcgtatt gcgagaccaa catcaacgat tgtagccaga atccctgcca taacggtggt   2040
acctgccggg atctggtgaa cgacttctat tgcgactgca agaacggctg gaagggcaag   2100
acctgccatt cgagggatag ccagtgcgac gaggccacct gcaacaacgg cggcacctgc   2160
tacgacgagg gcgatgcctt caagtgcatg tgccctggcg gctgggaggg caccacctgc   2220
aacatcgcca ggaacagctc ctgcctgccc aacccctgcc acaacggcgg gacctgtgtc   2280
gtgaacgggg agagcttcac gtgcgtgtgc aaggagggct gggaagggcc catctgcgcc   2340
caaaacacca acgactgcag cccccatccc tgttacaact ccggcacctg cgtggacggc   2400
gacaactggt accgatgcga gtgcgccccc ggcttcgccg gccccgactg ccggatcaac   2460
atcaacgagt gccagagcag cccctgcgcg ttcggcgcca cctgcgtgga tgaaatcaac   2520
ggatataggt gcgtgtgccc ccccggccac agcggggcca agtgccagga ggtcagcggg   2580
cgcccctgca tcaccatggg cagcgtgata cccgacggcg ccaagtggga cgacgactgc   2640
aacacctgcc agtgcctgaa cggcaggatc gcctgctcca aggtgtggtg cgggccgcgg   2700
ccgtgcctgc tgcacaaggg ccacagcgag tgccccagcg gccagtcctg tatcccaatc   2760
ctggacgacc agtgcttcgt gcatccctgc accggcgtgg gcgagtgcag gtcctcctcc   2820
ctgcagcccg tgaagaccaa atgcaccagc gactcgtact accaggataa ctgcgccaac   2880
atcaccttca ccttcaacaa ggaaatgatg agccccggcc tgaccaccga gcacatctgc   2940
agcgagctcc ggaacctgaa catcctgaag aacgtgtccg ccgagtatag catctacatc   3000
gcgtgcgaac caagtccgtc cgccaacaac gagatccacg tggcaatctc cgccgaggac   3060
atccgggacg acggcaaccc catcaaggag ataaccgaca aaatcatcga cctggtgagc   3120
aaaagggacg gcaattctag cctgatcgcc gcagtggccg aagtgagggt gcagcgcagg   3180
cccctcaaga ataggaccga cttcctggtg ccgctcctca gcagcgtgct gaccgtggcc   3240
tggatctgct gcctggtgac cgccttttac tggtgcctga ggaagcgtag gaagcccgga   3300
agccacacac actccgccag cgaggacaac accaccaaca acgtgcggga gcaactgaac   3360
cagatcaaga accccatcga gaagcacgga gccaacaccg tccctatcaa agactacgag   3420
aacaagaaca gcaagatgag caagatcagg acccacaaca gcgaggttga ggaagacgac   3480
atggacaagc accagcagaa agccaggttc gcgaagcagc ccgcctacac cctggtggac   3540
cgggaggaaa agcccccaa cggcaccccc accaagcacc cgaactggac caacaagcag     3600
gacaacaggg acctggagag cgcccagagc ctgaaccgga tggagtacat cgtc          3654
```

```
<210> SEQ ID NO 35
<211> LENGTH: 3654
<212> TYPE: DNA
<213> ORGANISM: Artificial Sequence
<220> FEATURE:
<223> OTHER INFORMATION: Synthetic polynucleotide

<400> SEQUENCE: 35
```

```
atgcgcagcc cccggaccag gggaaggtcc ggcaggcccc tgtccctgct gctggcgctg     60
ctctgcgccc tgcgagccaa agtgtgtggt gcctccgggc agtttgagct ggagatcctc    120
agcatgcaga acgtgaacgg ggagctgcag aatgggaact gctgcggcgg cgccaggaat    180
cccggggaca ggaagtgcac ccgagatgag tgcgacacct atttcaaggt gtgcctgaag    240
gagtaccaga gccgtgtgac ggccggcggc ccctgcagct ttggcagcgg cagcaccccc    300
gtgatcggcg gaaacacatt caacctgaag gccagcaggg gcaacgacag gaacaggatc    360
gtgctgccct tcagcttcgc ctggcccagg tcctacaccc tgctggtgga ggcctgggat    420
```

```
agcagcaatg acaccgtgca gcccgactcc atcatcgaga aggccagtca ctctggaatg    480
atcaacccga gcaggcagtg gcagaccctg aagcagaaca ccggcgtggc ccacttcgag    540
taccagatca gggtgacctg tgacgattac tactacggtt ttggctgcaa caagttctgt    600
aggccccgcg acgacttctt tggtcattac gcctgcgatc agaacggcaa taagacctgc    660
atggaaggct ggatgggccc cgaatgcaac agggccattt gcaggcaggg gtgcagcccg    720
aagcacggca gctgcaagct gcccggcgac tgcaggtgtc agtacggctg gcagggcctg    780
tactgcgaca aatgcatccc ccaccctggg tgcgtgcacg gcatctgtaa cgagccctgg    840
cagtgcctgt gtgagaccaa ctggggtggg caactgtgcg ataaggacct gaactactgc    900
ggaacccacc agccctgcct gaacggcggc acatgcagca acaccgggcc cgacaagtac    960
cagtgcagct gccccgaagg gtatagcggg cccaattgcg aaatcgccga gcacgcctgc   1020
ctgagcgatc cctgtcataa tcgcggatcc tgcaaggaga ccagcctcgg ctttgagtgc   1080
gaatgctccc ccggctggac cggtcccacg tgcagcacga acatcgacga ctgttccccg   1140
aacaactgct cccacggcgg cacctgccag gatctggtga atggattcaa atgcgtgtgc   1200
ccccccaat ggaccgggaa gacctgccaa ctggacgcca acgagtgcga agccaagccc   1260
tgtgtgaacg ccaagagctg caaaaacctc atcgctagct actactgcga ctgcctgccc   1320
ggctggatgg gtcagaactg tgacatcaac atcaacgatt gtctgggcca gtgccagaac   1380
gacgccagct gcagggacct ggtgaatggg taccgctgca tctgcccccc cggctacgcc   1440
ggagatcatt gcgagcggga catcgacgag tgcgccagca acccctgcct gaacggcggt   1500
cactgtcaga atgagatcaa ccgcttccag tgcctgtgcc ccaccggctt cagcggaaat   1560
ctgtgccagc tagacattga ttactgcgaa ccgaaccctt gccagaacgg cgcccagtgc   1620
tacaacaggg ccagcgacta cttttgcaag tgccccgagg actacgaggg gaagaattgc   1680
tcccacctaa aggaccactg ccggaccacc ccctgcgagg tgatcgacag ctgcaccgtc   1740
gcgatggcca gcaacgacac ccccgagggc gtcaggtaca tctccagcaa cgtgtgcggt   1800
ccccatggca aatgcaagag ccagagcggg gggaagttta cctgcgactg caacaagggc   1860
ttcaccggga cctactgcca tgagaacatc aatgactgcg agagcaaccc ctgcaggaac   1920
ggcgggacat gcatcgacgg ggtgaactcc tataagtgca tctgctccga cgggtgggaa   1980
ggtgcctatt gcgagacaaa catcaacgac tgcagccaaa acccctgcca caacgggggc   2040
acctgcaggg atctggtgaa cgacttctac tgtgactgca agaacgggtg gaagggaaag   2100
acctgtcaca gccgggactc ccagtgcgac gaggccacat gcaacaacgg cggcacgtgc   2160
tacgacgaag gagacgcctt taagtgcatg tgccccggcg gctgggaggg caccacctgc   2220
aatatcgccc gcaactcctc ctgcctgccc aacccgtgcc acaacggggg cacctgcgtg   2280
gtgaacggcg agtccttcac ctgcgtctgc aaggagggct gggagggtcc catctgtgcc   2340
cagaatacca atgactgcag cccccatcct tgttacaatt ccggcacctg cgtggatggc   2400
gacaactggt atcggtgtga gtgcgccccc ggcttcgcgg gccccgactg taggatcaac   2460
atcaacgagt gccagagctc cccatgcgcg tttggggcga cctgtgtcga cgagatcaat   2520
gggtacaggt gcgtgtgtcc cccggggcac tccggggcca aatgccagga ggtaagcggc   2580
cggccatgca ttaccatggg ctcggtgatc ccagacggtg ccaagtggga cgacgactgc   2640
aacacctgcc agtgcctgaa tggcaggatc gcctgcagca aggtatggtg cggacccagg   2700
ccgtgcctgc tgcacaaagg acactccgag tgtccgagcg gccagagctg catccccatc   2760
```

ctggacgacc agtgcttcgt gcatccctgc actggcgtcg gcgagtgccg cagctccagc 2820
ctgcagcccg tgaagaccaa gtgtaccagc gacagctact accaggacaa ttgtgccaac 2880
atcaccttca ccttcaacaa ggagatgatg agccctggcc tgaccaccga gcatatctgt 2940
agcgagctga ggaacttgaa catcctgaag aatgtgagcg ccgagtattc catttacata 3000
gcctgtgagc ccagcccaag cgctaacaat gagatccacg tggccatcag cgccgaggac 3060
atccgggacg acggcaaccc catcaaagaa atcaccgaca agatcatcga tctggtaagc 3120
aagagggacg ggaacagcag cctcatcgcc gccgtggccg aggtgcgcgt ccagcggagg 3180
cccctcaaaa accggaccga ctttctggtg ccgctgctca gctccgtgct gaccgtggcc 3240
tggatatgct gcctggtgac cgccttctac tggtgcctgc ggaagaggag gaagcccggc 3300
agccacacgc acagcgcgag cgaggacaac accaccaaca acgtgcggga gcaactgaac 3360
cagatcaaga accccatcga gaagcacggc gccaacaccg tgcccatcaa ggactacgag 3420
aacaagaata gcaagatgag taagattagg acccacaaca gcgaggtgga ggaggacgac 3480
atggacaagc accagcagaa ggcccgcttc gccaagcagc ccgcctatac cctggtcgac 3540
agggaagaga agccgcccaa tgggaccccc accaagcatc ccaactggac caacaagcag 3600
gacaaccggg atctggagag cgcccaaagc ctgaatagga tggagtacat cgtg 3654

<210> SEQ ID NO 36
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 36
gggaaauaag agagaaaaga agaguaagaa gaaauauaag agccacc 47

<210> SEQ ID NO 37
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 37
gggagaucag agagaaaaga agaguaagaa gaaauauaag agccacc 47

<210> SEQ ID NO 38
<211> LENGTH: 145
<212> TYPE: RNA
<213> ORGANISM: Artificial Sequence
<220> FEATURE:
<223> OTHER INFORMATION: Synthetic polynucleotide

<400> SEQUENCE: 38
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 39
<211> LENGTH: 42
<212> TYPE: RNA
<213> ORGANISM: Artificial Sequence
<220> FEATURE:
<223> OTHER INFORMATION: Synthetic polynucleotide

<400> SEQUENCE: 39
gggagacaag cuuggcauuc cgguacuguu gguaaagcca cc 42

<210> SEQ ID NO 40
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 40
gggagaucag agagaaaaga agaguaagaa gaaauauaag agccacc 47

<210> SEQ ID NO 41
<211> LENGTH: 145
<212> TYPE: RNA
<213> ORGANISM: Artificial Sequence
<220> FEATURE:
<223> OTHER INFORMATION: Synthetic polynucleotide

<400> SEQUENCE: 41
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 42
<211> LENGTH: 42
<212> TYPE: RNA
<213> ORGANISM: Artificial Sequence
<220> FEATURE:
<223> OTHER INFORMATION: Synthetic polynucleotide

<400> SEQUENCE: 42
gggagacaag cuuggcauuc cgguacuguu gguaaagcca cc 42

<210> SEQ ID NO 43
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 43
gggaauuaac agagaaaaga agaguaagaa gaaauauaag agccacc 47

<210> SEQ ID NO 44
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 44
gggaaauuag acagaaaaga agaguaagaa gaaauauaag agccacc 47

<210> SEQ ID NO 45
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 45
gggaaauaag agaguaaaga acaguaagaa gaaauauaag agccacc 47

<210> SEQ ID NO 46
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 46
gggaaaaaag agagaaaaga agacuaagaa gaaauauaag agccacc 47

<210> SEQ ID NO 47
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 47
gggaaauaag agagaaaaga agaguaagaa gauauauaag agccacc 47

<210> SEQ ID NO 48
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 48
gggaaauaag agacaaaaca agaguaagaa gaaauauaag agccacc 47

<210> SEQ ID NO 49
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 49
gggaaauuag agaguaaaga acaguaagua gaauuaaaag agccacc 47

<210> SEQ ID NO 50
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 50
gggaaauaag agagaauaga agaguaagaa gaaauauaag agccacc 47

<210> SEQ ID NO 51
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 51
gggaaauaag agagaaaaga agaguaagaa gaaaauuaag agccacc 47

<210> SEQ ID NO 52
<211> LENGTH: 47
<212> TYPE: RNA
<213> ORGANISM: Artificial Sequence
<220> FEATURE:
<223> OTHER INFORMATION: Synthetic polynucleotide

<400> SEQUENCE: 52
gggaaauaag agagaaaaga agaguaagaa gaaauuuaag agccacc 47

<210> SEQ ID NO 53
<211> LENGTH: 92
<212> TYPE: RNA
<213> ORGANISM: Artificial Sequence
<220> FEATURE:
<223> OTHER INFORMATION: Synthetic polynucleotide

<400> SEQUENCE: 53
ucaagcuuuu ggacccucgu acagaagcua auacgacuca cuauagggaa auaagagaga 60
aaagaagagu aagaagaaau auaagagcca cc 92

<210> SEQ ID NO 54
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 54
ugauaauagu ccauaaagua ggaaacacua cagcuggagc cucgguggcc augcuucuug 60
ccccuugggc cucccccag ccccuccucc ccuuccugca cccguacccc cguggucuuu 120
gaauaaaguc ugagugggcg gc 142

<210> SEQ ID NO 55
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 55
ugauaauagg cuggagccuc gguggcucca uaaaguagga aacacuacac augcuucuug 60
ccccuugggc cucccccag ccccuccucc ccuuccugca cccguacccc cguggucuuu 120
gaauaaaguc ugagugggcg gc 142

<210> SEQ ID NO 56
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 56
ugauaauagg cuggagccuc gguggccaug cuucuugccc cuuccauaaa guaggaaaca 60
cuacaugggc cucccccag ccccuccucc ccuuccugca cccguacccc cguggucuuu 120
gaauaaaguc ugagugggcg gc 142

<210> SEQ ID NO 57
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 57
ugauaauagg cuggagccuc gguggccaug cuucuugccc cuugggccuc cccccagucc 60
auaaaguagg aaacacuaca ccccuccucc ccuuccugca cccguacccc cguggucuuu 120
gaauaaaguc ugagugggcg gc 142

<210> SEQ ID NO 58
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 58
ugauaauagg cuggagccuc gguggccaug cuucuugccc cuugggccuc cccccagccc 60
cuccuccccu ucuccauaaa guaggaaaca cuacacugca cccguacccc cguggucuuu 120
gaauaaaguc ugagugggcg gc 142

<210> SEQ ID NO 59
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 59
ugauaauagg cuggagccuc gguggccaug cuucuugccc cuugggccuc cccccagccc 60
cuccuccccu uccugcaccc guaccccuc cauaaaguag gaaacacuac aguggucuuu 120
gaauaaaguc ugagugggcg gc 142

<210> SEQ ID NO 60
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 60
ugauaauagg cuggagccuc gguggccaug cuucuugccc cuugggccuc cccccagccc 60
cuccuccccu uccugcaccc guacccccgu ggucuuugaa uaaaguucca uaaaguagga 120
aacacuacac ugagugggcg gc 142

<210> SEQ ID NO 61
<211> LENGTH: 371
<212> TYPE: RNA
<213> ORGANISM: Artificial Sequence
<220> FEATURE:
<223> OTHER INFORMATION: Synthetic polynucleotide

<400> SEQUENCE: 61
gcgccugccc accugccacc gacugcugga acccagccag ugggagggcc uggcccacca 60
gaguccugcu cccucacucc ucgccccgcc cccuguccca gagucccacc ugggggcucu 120
cuccacccuu cucagaguuc caguuucaac cagaguucca accaaugggc uccauccucu 180
ggauucuggc caaugaaaua ucucccuggc aggguccucu ucuuuuccca gagcuccacc 240
ccaaccagga gcucuaguua auggagagcu cccagcacac ucggagcuug ugcuuugucu 300
ccacgcaaag cgauaaauaa aagcauuggu ggccuuuggu cuuugaauaa agccugagua 360
ggaagucuag a 371

<210> SEQ ID NO 62
<211> LENGTH: 568

-continued

<212> TYPE: RNA
<213> ORGANISM: Artificial Sequence
<220> FEATURE:
<223> OTHER INFORMATION: Synthetic polynucleotide

<400> SEQUENCE: 62
gccccugccg cucccacccc cacccaucug ggccccgggu ucaagagaga gcggggucug 60
aucucgugua gccauauaga guuugcuucu gagugucugc uuuguuuagu agaggugggc 120
aggaggagcu gaggggcugg ggcuggggug uugaaguugg cuuugcaugc ccagcgaugc 180
gccucccugu gggaugucau cacccuggga accgggagug gcccuuggcu cacuguguuc 240
ugcaugguuu ggaucugaau uaauuguccu uucuucuaaa ucccaaccga acuucuucca 300
accuccaaac uggcuguaac cccaaaucca agccauuaac uacaccugac aguagcaauu 360
gucugauuaa ucacuggccc cuugaagaca gcagaauguc ccuuugcaau gaggaggaga 420
ucugggcugg gcgggccagc uggggaagca uuugacuauc uggaacuugu gugugccucc 480
ucagguaugg cagugacuca ccugguuuua auaaaacaac cugcaacauc ucauggucuu 540
ugaauaaagc cugaguagga agucuaga 568

<210> SEQ ID NO 63
<211> LENGTH: 289
<212> TYPE: RNA
<213> ORGANISM: Artificial Sequence
<220> FEATURE:
<223> OTHER INFORMATION: Synthetic polynucleotide

<400> SEQUENCE: 63
acacacucca ccuccagcac gcgacuucuc aggacgacga aucuucucaa ugggggggcg 60
gcugagcucc agccaccccg cagucacuuu cuuuguaaca acuuccguug cugccaucgu 120
aaacugacac aguguuuaua acguguacau acauuaacuu auuaccucau uuuguuauuu 180
uucgaaacaa agcccugugg aagaaaaugg aaaacuugaa gaagcauuaa agucauucug 240
uuaagcugcg uaaauggucu uugaauaaag ccugaguagg aagucuaga 289

<210> SEQ ID NO 64
<211> LENGTH: 379
<212> TYPE: RNA
<213> ORGANISM: Artificial Sequence
<220> FEATURE:
<223> OTHER INFORMATION: Synthetic polynucleotide

<400> SEQUENCE: 64
caucacauuu aaaagcaucu cagccuacca ugagaauaag agaaagaaaa ugaagaucaa 60
aagcuuauuc aucuguuuuu cuuuuucguu gguguaaagc caacacccug ucuaaaaaac 120
auaaauuucu uuaaucauuu ugccucuuuu cucugugcuu caauuaauaa aaaauggaaa 180
gaaucuaaua gagugguaca gcacuguuau uuuucaaaga uguguugcua uccugaaaau 240
ucuguagguu cuguggaagu uccaguguuc ucucuuauuc cacuucggua gaggauuucu 300
aguuucuugu gggcuaauua aauaaaucau uaauacucuu cuaauggucu uugaauaaag 360
ccugaguagg aagucuaga 379

<210> SEQ ID NO 65
<211> LENGTH: 118
<212> TYPE: RNA
<213> ORGANISM: Artificial Sequence
<220> FEATURE:
<223> OTHER INFORMATION: Synthetic polynucleotide

<400> SEQUENCE: 65
gcugccuucu gcggggcuug ccuucuggcc augcccuucu ucucucccuu gcaccuguac 60
cucuuggucu uugaauaaag ccugaguagg aaggcggccg cucgagcaug caucuaga 118

<210> SEQ ID NO 66
<211> LENGTH: 908
<212> TYPE: RNA
<213> ORGANISM: Artificial Sequence
<220> FEATURE:
<223> OTHER INFORMATION: Synthetic polynucleotide

<400> SEQUENCE: 66
gccaagcccu ccccauccca uguauuuauc ucuauuuaau auuuaugucu auuuaagccu 60
cauauuuaaa gacagggaag agcagaacgg agccccaggc cucugugucc uucccugcau 120
uucugaguuu cauucuccug ccuguagcag ugagaaaaag cuccuguccu cccaucccu 180 ggacugggag guagauaggu aaauaccaag uauuuauuac uaugacugcu ccccagcccu 240
ggcucugcaa ugggcacugg gaugagccgc ugugagcccc ugguccugag gguccccacc 300
ugggacccuu gagaguauca ggucucccac gugggagaca agaaaucccu guuuaauauu 360
uaaacagcag uguuccccau cugggucuu gcaccccuca cucuggccuc agccgacugc 420
acagcggccc cugcaucccc uuggcuguga ggccccugga caagcagagg uggccagagc 480
ugggaggcau ggcccugggg ucccacgaau uugcuggga aucucguuuu ucuucuuaag 540
acuuuuggga caugguuuga cucccgaaca ucaccgacgc gucuccuguu uuucugggug 600
gccucgggac accugcccug cccccacgag ggucaggacu gugacucuuu uuagggccag 660
gcaggugccu ggacauuugc cuugcuggac ggggacuggg gaugugggag ggagcagaca 720
ggaggaauca ugucaggccu gugugugaaa ggaagcucca cugucacccu ccaccucuuc 780
accccccacu caccaguguc cccuccacug ucacauugua acugaacuuc aggauaauaa 840
aguguuugcc uccauggucu uugaauaaag ccugaguagg aaggcggccg cucgagcaug 900
caucuaga 908

<210> SEQ ID NO 67
<211> LENGTH: 835
<212> TYPE: RNA
<213> ORGANISM: Artificial Sequence
<220> FEATURE:
<223> OTHER INFORMATION: Synthetic polynucleotide

<400> SEQUENCE: 67
acucaaucua aauuaaaaaa gaaagaaauu ugaaaaaacu uucucuuugc cauuucuucu 60
ucuucuuuuu uaacugaaag cugaauccuu ccauuucuuc ugcacaucua cuugcuuaaa 120
uugugggcaa aagagaaaaa gaaggauuga ucagagcauu gugcaauaca guuucauuaa 180
cuccuucccc cgcuccccca aaaauuugaa uuuuuuuuuc aacacucuua caccuguuau 240
ggaaaauguc aaccuuugua agaaaaccaa aauaaaaauu gaaaaauaaa aaccauaaac 300
auuugcacca cuuguggcuu uugaauaucu uccacagagg gaaguuuaaa acccaaacuu 360
ccaaagguuu aaacuaccuc aaaacacuuu cccaugagug ugauccacau uguuaggugc 420
ugaccuagac agagaugaac ugagguccuu guuuuguuuu guucauaaua caaaggugcu 480
aauuaauagu auuucagaua cuugaagaau guugauggug cuagaagaau uugagaagaa 540
auacuccugu auugaguugu aucguguggu guauuuuuua aaaaauuuga uuuagcauuc 600
auauuuucca ucuuauuccc aauuaaaagu augcagauua uuugcccaaa ucuucuucag 660
auucagcauu uguucuuugc cagucucauu uucaucuucu uccaugguuc cacagaagcu 720
uuguuucuug ggcaagcaga aaaauuaaau uguaccuauu uuguauaugu gagauguuua 780
aauaaauugu gaaaaaaaug aaauaaagca uguuugguuu uccaaaagaa cauau 835

<210> SEQ ID NO 68
<211> LENGTH: 297
<212> TYPE: RNA
<213> ORGANISM: Artificial Sequence
<220> FEATURE:
<223> OTHER INFORMATION: Synthetic polynucleotide

<400> SEQUENCE: 68
cgccgccgcc cgggccccgc agucgagggu cgugagccca ccccguccau ggugcuaagc 60
gggcccgggu cccacacggc cagcaccgcu gcucacucgg acgacgcccu gggccugcac 120
cucuccagcu ccucccacgg gguccccgua gccccggccc ccgcccagcc ccaggucucc 180
ccaggcccuc cgcaggcugc ccggccuccc ucccccugca gccaucccaa ggcuccugac 240
cuaccuggcc ccugagcucu ggagcaagcc cugacccaau aaaggcuuug aacccau 297

<210> SEQ ID NO 69
<211> LENGTH: 602
<212> TYPE: RNA
<213> ORGANISM: Artificial Sequence
<220> FEATURE:
<223> OTHER INFORMATION: Synthetic polynucleotide

<400> SEQUENCE: 69
ggggcuagag cccucucccgc acagcgugga gacggggcaa ggaggggggu uauuaggauu 60
ggugguuuug uuuugcuuug uuuaaagccg ugggaaaaug gcacaacuuu accucugugg 120
gagaugcaac acugagagcc aaggggguggg aguugggaua auuuuuauau aaaagaaguu 180
uuuccacuuu gaauugcuaa aaguggcauu uuuccuaugu gcagucacuc cucucauuuc 240
uaaaauaggg acguggccag gcacggugggc ucaugccugu aaucccagca cuuugggagg 300
ccgaggcagg cggcucacga ggucaggaga ucgagacuau ccuggcuaac acgguaaaac 360
ccugucucua cuaaaaguac aaaaaauuag cugggcgugg uggugggcac cuguaguccc 420
agcuacucgg gaggcugagg caggagaaag gcaugaaucc aagaggcaga gcuugcagug 480
agcugagauc acgccauugc acuccagccu gggcaacagu guuaagacuc ugucucaaau 540
auaaauaaau aaauaaauaa auaaauaaau aaauaaaaau aaagcgagau guugcccuca 600
aa 602

<210> SEQ ID NO 70
<211> LENGTH: 785
<212> TYPE: RNA
<213> ORGANISM: Artificial Sequence
<220> FEATURE:
<223> OTHER INFORMATION: Synthetic polynucleotide

<400> SEQUENCE: 70
ggcccugccc cgucggacug cccccagaaa gccuccugcc cccugccagu gaaguccuuc 60
agugagcccc uccccagcca gcccuucccu ggccccgccg gauguauaaa uguaaaaaug 120
aaggaauuac auuuuauaug ugagcgagca agccggcaag cgagcacagu auuauuucuc 180
cauccccucc cugccugcuc cuuggcaccc ccaugcugcc uucagggaga caggcaggga 240
gggcuugggg cugcaccucc uacccuccca ccagaacgca ccccacuggg agagcuggug 300

-continued

```
gugcagccuu ccccucccug uauaagacac uuugccaagg cucuccccuc ucgccccauc    360

ccugcuugcc cgcucccaca gcuuccugag ggcuaauucu gggaagggag aguucuuugc    420

ugccccuguc uggaagacgu ggcucugggu gagguaggcg ggaaaggaug gaguguuuua    480

guucuugggg gaggccaccc caaaccccag ccccaacucc aggggcaccu augagauggc    540

caugcucaac cccccuccca gacaggcccu cccugucucc agggccccca ccgagguucc    600

cagggcugga gacuuccucu gguaaacauu ccuccagccu ccccuccccu ggggacgcca    660

aggagguggg ccacacccag gaagggaaag cgggcagccc cguuuugggg acgugaacgu    720

uuuaauaauu uuugcugaau uccuuuacaa cuaaauaaca cagauauugu uauaaauaaa    780

auugu                                                                785
```

<210> SEQ ID NO 71
<211> LENGTH: 3001
<212> TYPE: RNA
<213> ORGANISM: Artificial Sequence
<220> FEATURE:
<223> OTHER INFORMATION: Synthetic polynucleotide

<400> SEQUENCE: 71

```
auauuaagga ucaagcuguu agcuaauaau gccaccucug caguuuuggg aacaggcaaa     60

uaaaguauca guauacaugg ugauguacau cuguagcaaa gcucuuggag aaaaugaaga    120

cugaagaaag caaagcaaaa acuguauaga gagauuuuuc aaaagcagua aucccucaau    180

uuuaaaaaag gauugaaaau ucuaaauguc uuucugugca uauuuuuugu guuaggaauc    240

aaaaguauuu uauaaaagga gaaagaacag ccucauuuua gauguagucc uguuggauuu    300

uuuaugccuc cucaguaacc agaaauguuu uaaaaaacua aguguuuagg auuucaagac    360

aacauuauac auggcucuga aauaucugac acaauguaaa cauugcaggc accugcauuu    420

uauguuuuuu uuuucaacaa augugacuaa uuugaaacuu uuaugaacuu cugagcuguc    480

cccuugcaau ucaaccgcag uuugaauuaa ucauaucaaa ucaguuuuaa uuuuuuaaau    540

uguacuucag agucuauauu ucaagggcac auuuucucac uacuauuuua auacauuaaa    600

ggacuaaaua aucuuucaga gaugcuggaa acaaaucauu ugcuuuauau guuucauuag    660

aauaccaaug aaacauacaa cuugaaaauu aguaauagua uuuuugaaga ucccauuucu    720

aauuggagau cucuuuaauu ucgaucaacu uauaaugugu aguacuauau uaagugcacu    780

ugaguggaau ucaacauuug acuaauaaaa ugaguucauc auguuggcaa gugauguggc    840

aauuaucucu ggugacaaaa gaguaaaauc aaauauuucu gccuguuaca aauaucaagg    900

aagaccugcu acuaugaaau agaugacauu aaucugucuu cacuguuuau aauacggaug    960

gauuuuuuuu caaaucagug uguguuuuga ggucuuaugu aauugaugac auuugagaga   1020

aaugguggcu uuuuuuagcu accucuuugu ucauuuaagc accaguaaag aucaugucuu   1080

uuuauagaag uguagauuuu cuuugugacu uugcuaucgu gccuaaagcu cuaaauauag   1140

gugaaugugu gaugaauacu cagauuauuu gucucucuau auaauuaguu ugguacuaag   1200

uuucucaaaa aauuauuaac acaugaaaga caaucucuaa accagaaaaa gaaguaguac   1260

aaauuuuguu acuguaaugc ucgcguuuag ugaguuuaaa acacacagua ucuuuugguu   1320

uuauaaucag uuucuauuuu gcugugccug agauuaagau cuguguaugu gugugugugu   1380

gugugugcgu uuguguguua aagcagaaaa gacuuuuuua aaaguuuuaa gugauaaaug   1440

caauuuguua auugaucuua gaucacuagu aaacucaggg cugaauuaua ccauguauau   1500

ucuauuagaa gaaaguaaac accaucuuua uuccugcccu uuuucuucuc ucaaaguagu   1560
```

-continued uguaguuaua ucuagaaaga agcaauuuug auuucuugaa aagguaguuc cugcacucag 1620
uuuaaacuaa aaauaaucau acuuggauuu uauuuauuuu ugucauagua aaaauuuuaa 1680
uuuauauaua uuuuuauuua guauuaucuu auucuuugcu auuugccaau ccuuugucau 1740
caauuguguu aaaugaauug aaaauucaug cccuguucau uuuauuuuac uuuauugguu 1800
aggauauuua aaggauuuuu guauauauaa uuucuuaaau uaauauucca aaagguuagu 1860
ggacuuagau uauaaauuau ggcaaaaauc uaaaaacaac aaaaaugauu uuuauacauu 1920
cuauuucauu auucccucuuu uuccaauaag ucauacaauu gguagauaug acuuauuuua 1980
uuuuuguauu auucacuaua ucuuuaugau auuuaaguau aaauaauuaa aaaaauuuau 2040
uguaccuuau agucugucac caaaaaaaaa aaauuaucug uagguaguga aaugcuaaug 2100
uugauuuguc uuuaagggcu uguuaacuau ccuuuauuuu cucauuuguc uuaaauuagg 2160
aguuuguguu uaaauuacuc aucuaagcaa aaaauguaua uaaaucccau uacuggguau 2220
auacccaaag gauuauaaau caugcugcua uaaagacaca ugcacacgua uguuuauugc 2280
agcacuauuc acaauagcaa agacuuggaa ccaacccaaa uguccaucaa ugauagacuu 2340
gauuaagaaa augugcacau auacaccaug gaauacuaug cagccauaaa aaaggaugag 2400
uucauguccu uuguagggac auggauaaag cuggaaacca ucauucugag caaacuauug 2460
caaggacaga aaaccaaaca cugcauguuc ucacucauag gugggaauug aacaaugaga 2520
acacuuggac acaaggugggg gaacaccaca caccagggcc ugucaugggg ugggggggagu 2580 ggggagggau agcauuagga gauauaccua auguaaauga ugaguuaaug ggugcagcac 2640
accaacaugg cacauguaua cauauguagc aaaccugcac guugugcaca uguacccuag 2700
aacuuaaagu auaauuaaaa aaaaaaagaa aacagaagcu auuuauaaag aaguuauuug 2760
cugaaauaaa ugugaucuuu cccauuaaaa aaauaaagaa auuuuggggu aaaaaaacac 2820
aauauauugu auucuugaaa aauucuaaga gaguggaugu gaaguguucu caccacaaaa 2880
gugauaacua auugagguaa ugcacauauu aauuagaaag auuuugucau uccacaaugu 2940
auauauacuu aaaaaauaugu uauacacaau aaauacauac auuaaaaaau aaguaaaugu 3000
a 3001

<210> SEQ ID NO 72
<211> LENGTH: 1037
<212> TYPE: RNA
<213> ORGANISM: Artificial Sequence
<220> FEATURE:
<223> OTHER INFORMATION: Synthetic polynucleotide

<400> SEQUENCE: 72
cccacccugc acgccggcac caaacccugu ccucccaccc cuccccacuc aucacuaaac 60
agaguaaaau gugaugcgaa uuuucccgac caaccugauu cgcuagauuu uuuuuaagga 120
aaagcuugga aagccaggac acaacgcugc ugccugcuuu gugcaggguc cuccggggcu 180
cagcccugag uuggcaucac cugcgcaggg cccucugggg cucagcccug agcuaguguc 240
accugcacag ggcccucuga ggcucagccc ugagcuggcg ucaccugugc agggcccucu 300
ggggcucagc ccugagcugg ccucaccugg guuccccacc ccgggcucuc cugcccugcc 360
cuccugcccg cccucccucc ugccugcgca gcuccuuccc uaggcaccuc ugugcugcau 420
cccaccagcc ugagcaagac gcccucucgg ggccugugcc gcacuagccu cccucuccuc 480
uguccccaua gcugguuuuu cccaccaauc cucaccuaac aguuacuuua caauuaaacu 540

-continued

```
caaagcaagc ucuucuccuc agcuuggggc agccauuggc cucugucucg uuuugggaaa    600

ccaaggucag gaggccguug cagacauaaa ucucggcgac ucggccccgu cuccugaggg    660

uccugcuggu gaccggccug gaccuuggcc cuacagcccu ggaggccgcu gcugaccagc    720

acugaccccg accucagaga guacucgcag gggcgcuggc ugcacucaag acccucgaga    780

uuaacggugc uaaccccguc ugcuccuccc ucccgcagag acuggggccu ggacuggaca    840

ugagagcccc uuggugccac agagggcugu gucuuacuag aaacaacgca aaccucuccu    900

uccucagaau agugaugugu ucgacguuuu aucaaaggcc cccuuucuau guucauguua    960

guuuugcucc uucuguguuu uuuucugaac cauauccaug uugcugacuu uuccaaauaa   1020

agguuuucac uccucuc                                                  1037
```

<210> SEQ ID NO 73
<211> LENGTH: 577
<212> TYPE: RNA
<213> ORGANISM: Artificial Sequence
<220> FEATURE:
<223> OTHER INFORMATION: Synthetic polynucleotide

<400> SEQUENCE: 73

```
agaggccugc cuccagggcu ggacugaggc cugagcgcuc cugccgcaga gcuggccgcg     60

ccaaauaaug ucucugugag acucgagaac uuucauuuuu uuccaggcug guucggauuu    120

ggggguggau uugguuuugu uccccuccuc cacucucccc cacccccucc ccgcccuuuu    180

uuuuuuuuuu uuuuaaacug guauuuuauc uuugauucuc cuucagcccu caccccuggu    240

ucucaucuuu cuugaucaac aucuuuucuu gccucugucc ccuucucuca ucucuuagcu    300

ccccuccaac cugggggggca guggugugga gaagccacag gccugagauu ucaucugcuc    360

uccuuccugg agcccagagg agggcagcag aagggggugg ugucuccaac cccccagcac    420

ugaggaagaa cggggcucuu cucauuucac cccucccuuu cuccccugcc cccaggacug    480

ggccacuucu ggguggggca gugggguccca gauuggcuca cacugagaau guaagaacua    540

caaacaaaau uucuauuaaa uuaaauuuug ugucucc                             577
```

<210> SEQ ID NO 74
<211> LENGTH: 2212
<212> TYPE: RNA
<213> ORGANISM: Artificial Sequence
<220> FEATURE:
<223> OTHER INFORMATION: Synthetic polynucleotide

<400> SEQUENCE: 74

```
cucccuccau cccaaccugg cucccuccca cccaaccaac uuucccccca acccggaaac     60

agacaagcaa cccaaacuga acccccucaa aagccaaaaa augggagaca auuucacaug    120

gacuuuggaa aauauuuuuu uccuuugcau ucaucucuca aacuuaguuu uuaucuuuga    180

ccaaccgaac augaccaaaa accaaaagug cauucaaccu uaccaaaaaa aaaaaaaaaa    240

aaagaauaaa uaaauaacuu uuuaaaaaag gaagcuuggu ccacuugcuu gaagacccau    300

gcgggggguaa gucccuuucu gcccguuggg cuuaugaaac cccaaugcug cccuuucugc    360

uccuuucucc acaccccccu uggggccucc ccuccacucc uucccaaauc ugucucccca    420

gaagacacag gaaacaaugu auugucugcc cagcaaucaa aggcaaugcu caaacaccca    480

aguggccccc acccucagcc cgcuccugcc cgcccagcac ccccaggccc ugggggaccu    540

gggguucuca gacugccaaa gaagccuugc caucuggcgc ucccauggcu cuugcaacau    600

cucccccuucg uuuuugaggg ggucaugccg ggggagccac cagccccuca cuggguucgg    660
```

```
aggagaguca ggaagggcca cgacaaagca gaaacaucgg auuuggggaa cgcgugucaa    720
ucccuugugc cgcagggcug ggcgggagag acuguucugu uccuugugua acuguguugc    780
ugaaagacua ccucguucuu gucuugaugu gucaccgggg caacugccug ggggcgggga    840
ugggggcagg guggaagcgg cuccccauuu uauaccaaag gugcuacauc uaugugaugg    900
gugggguggg gagggaauca cuggugcuau agaaauugag augccccccc aggccagcaa    960
auguuccuuu uuguucaaag ucuauuuuua uuccuugaua uuuuucuuuu uuuuuuuuuu   1020
uuuuugugga uggggacuug ugaauuuuuc uaaaggugcu auuuaacaug ggaggagagc   1080
gugugcggcu ccagcccagc ccgcugcuca cuuuccaccc ucucuccacc ugccucuggc   1140
uucucaggcc ucugcucucc gaccucucuc cucugaaacc cuccuccaca gcugcagccc   1200
auccucccgg cucccuccua gucuguccug cguccucugu ccccggguuu cagagacaac   1260
uucccaaagc acaaagcagu uuuucccccu aggggugggga ggaagcaaaa gacucuguac   1320
cuauuuugua uguguauaau aauuugagau guuuuuaauu auuuugauug cuggaauaaa   1380
gcauguggaa augacccaaa cauaauccgc aguggccucc uaauuuccuu cuuuggaguu   1440
gggggagggg uagacauggg gaaggggcuu uggggugaug ggcuugccuu ccauuccugc   1500
ccuuucccuc cccacuauuc ucuucuagau cccuccauaa ccccacuccc cuuucucuca   1560
cccuucuuau accgcaaacc uuucuacuuc cucuuucauu uucuauucuu gcaauuuccu   1620
ugcaccuuuu ccaaauccuc uucuccccug caauaccaua caggcaaucc acgugcacaa   1680
cacacacaca cacucuucac aucuggggguu guccaaaccu cauacccacu ccccuucaag   1740
cccauccacu cuccaccccc uggaugcccu gcacuuggug gcggugggau gcucauggau   1800
acugggaggg ugaggggagu ggaacccgug aggaggaccu gggggccucu ccuugaacug   1860
acaugaaggg ucaucuggcc ucugcucccu ucucacccac gcugaccucc ugccgaagga   1920
gcaacgcaac aggagagggg ucugcugagc cuggcgaggg ucugggaggg accaggagga   1980
aggcgugcuc ccugcucgcu guccuggccc ugggggagug agggagacag acaccuggga   2040
gagcuguggg gaaggcacuc gcaccgugcu cuugggaagg aaggagaccu ggcccugcuc   2100
accacggacu gggugccucg accuccugaa uccccagaac acaacccccc ugggcugggg   2160
uggucugggg aaccaucgug cccccgccuc ccgccuacuc cuuuuuaagc uu           2212

<210> SEQ ID NO 75
<211> LENGTH: 729
<212> TYPE: RNA
<213> ORGANISM: Artificial Sequence
<220> FEATURE:
<223> OTHER INFORMATION: Synthetic polynucleotide

<400> SEQUENCE: 75

uuggccaggc cugacccucu uggaccuuuc uucuuugccg acaaccacug cccagcagcc     60
ucugggaccu cggggucccca gggaacccag uccagccucc uggcuguuga cuucccauug    120
cucuuggagc caccaaucaa agagauucaa agagauuccu gcaggccaga ggcggaacac    180
accuuuaugg cuggggcucu ccgugguguu cuggacccag ccccuggaga caccauucac    240
uuuuacugcu uuguagugac ucgugcucuc caaccugucu uccugaaaaa ccaaggcccc    300
cuucccccac cucuuccaug gggugagacu ugagcagaac aggggcuucc ccaaguugcc    360
cagaaagacu gucuggguga gaagccaugg ccagagcuuc ucccaggcac agguguugca    420
ccagggacuu cugcuucaag uuuuggggua aagacaccug gaucagacuc caagggcugc    480
```

-continued

```
ccugagucug ggacuucugc cuccauggcu ggucaugaga gcaaaccgua guccccugga    540

gacagcgacu ccagagaacc ucuugggaga cagaagaggc aucugugcac agcucgaucu    600

ucuacuugcc uguggggagg ggagugacag guccacacac cacacugggu cacccugucc    660

uggaugccuc ugaagagagg gacagaccgu cagaaacugg agaguuucua uuaaagguca    720

uuuaaacca                                                            729
```

<210> SEQ ID NO 76
<211> LENGTH: 847
<212> TYPE: RNA
<213> ORGANISM: Artificial Sequence
<220> FEATURE:
<223> OTHER INFORMATION: Synthetic polynucleotide

<400> SEQUENCE: 76

```
uccuccggga ccccagcccu caggauuccu gaugcuccaa ggcgacugau gggcgcugga     60

ugaaguggca cagucagcuu cccugggggc uggugucaug uugggcuccu ggggcggggg    120

cacggccugg cauuucacgc auugcugcca ccccaggucc accugucucc acuuucacag    180

ccuccaaguc uguggcucuu cccuucuguc cuccgagggg cuugccuucu cucgugucca    240

gugaggugcu cagugaucgg cuuaacuuag agaagcccgc cccucccccu ucuccgucug    300

ucccaagagg gucugcucug agccugcguu ccuagguggc ucggccucag cugccugggu    360

uguggccgcc cuagcauccu guaugcccac agcuacugga auccccgcug cugcuccggg    420

ccaagcuucu gguugauuaa ugagggcaug ggguggcccc ucaagaccuu ccccuaccuu    480

uuguggaacc agugaugccu caaagacagu guccccucca cagcugggug ccaggggcag    540

gggauccuca guauagccgg ugaacccuga uaccaggagc cugggccucc cugaaccccu    600

ggcuuccagc caucucaucg ccagccuccu ccuggaccuc uuggccccca gccccuuccc    660

cacacagccc cagaaggguc ccagagcuga ccccacucca ggaccuaggc ccagccccuc    720

agccucaucu ggagccccug aagaccaguc ccacccaccu uucuggccuc aucugacacu    780

gcuccgcauc cugcugugug uccuguucca uguuccgguu ccauccaaau acacuuucug    840

gaacaaa                                                              847
```

<210> SEQ ID NO 77
<211> LENGTH: 110
<212> TYPE: RNA
<213> ORGANISM: Artificial Sequence
<220> FEATURE:
<223> OTHER INFORMATION: Synthetic polynucleotide

<400> SEQUENCE: 77

```
gcuggagccu cgguggccau gcuucuugcc ccuugggccu ccccccagcc ccuccucccc     60

uuccugcacc cguaccccg uggucuuuga auaaagucug agugggcggc               110
```

<210> SEQ ID NO 78
<211> LENGTH: 119
<212> TYPE: RNA
<213> ORGANISM: Artificial Sequence
<220> FEATURE:
<223> OTHER INFORMATION: Synthetic polynucleotide

<400> SEQUENCE: 78

```
ugauaauagg cuggagccuc gguggccuag cuucuugccc cuugggccuc cccccagccc     60

cuccuccccu uccugcaccc guaccccgu ggucuuugaa uaaagucuga gugggcggc     119
```

<210> SEQ ID NO 79
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 79
gacagugcag ucacccauaa aguagaaagc acuacuaaca gcacuggagg guguaguguu 60
uccuacuuua uggaugagug uacugug 87

<210> SEQ ID NO 80
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 80
uguaguguuu ccuacuuuau gga 23

<210> SEQ ID NO 81
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 81
uccauaaagu aggaaacacu aca 23

<210> SEQ ID NO 82
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 82
cauaaaguag aaagcacuac u 21

<210> SEQ ID NO 83
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 83
aguagugcuu ucuacuuuau g 21

<210> SEQ ID NO 84
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 84
tcaagctttt ggaccctcgt acagaagcta atacgactca ctatagggaa ataagagaga 60
aaagaagagt aagaagaaat ataagagcca cc 92

<210> SEQ ID NO 85
<211> LENGTH: 119
<212> TYPE: DNA

<213> ORGANISM: Artificial Sequence
<220> FEATURE:
<223> OTHER INFORMATION: Synthetic polynucleotide

<400> SEQUENCE: 85
tgataatagg ctggagcctc ggtggccatg cttcttgccc cttgggcctc cccccagccc 60
ctcctcccct tcctgcaccc gtacccccgt ggtctttgaa taaagtctga gtgggcggc 119

<210> SEQ ID NO 86
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 86
attgggcacc cgtaaggg 18

<210> SEQ ID NO 87
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 87
augcgaagcc ccaggacccg cggccguagc gguaggcccc ugucccugcu gcuggcccug 60
cugugcgccc ucagggccaa ggugugcggc gccagcggcc aguucgagcu cgagauccug 120
agcaugcaga acgugaacgg cgagcuccag aaugggaauu guugcggcgg cgccaggaac 180
cccggugaca ggaaaugcac ccgcgacgag ugcgacaccu acuucaaagu gugccucaag 240
gaguaccaga gcagggugac cgccggcggg cccugcagcu ucgggagcgg cuccacgccc 300
gugaucggcg ggaacaccuu caaccugaag gccagcaggg gcaacgaucg gaaccggauc 360
gugcugccgu ucuccuucgc cuggccgcga agcuacaccc ugcuggugga agcgugggac 420
agcagcaacg acaccgugca gcccgacagc aucaucgaga aggccucaca cuccgguaug 480
aucaacccca gcaggcagug gcagacccug aagcagaaca ccggaguggc ccacuucgaa 540
uaccagauca gggugacaug cgacgacuac uacuacggcu ucgggugcaa caaguucugc 600
aggccccgcg acgacuucuu cggacacuac gccugugacc agaacgggaa caagacgugu 660
auggaggggu ggauggggcc cgaaugcaac agggccaucu gucggcaggg uugcuccccc 720
aagcacggcu ccugcaaacu gcccggcgau ugccggugcc aguacgggug gcaaggucug 780
uacugcgaca agugcauccc gcaucccggc ugcgugcacg gcaucugcaa cgagcccugg 840
cagugccugu gcgaaaccaa cuggggcggc cagcucugug acaaggaccu uaacuacugc 900
ggcacccacc agcccugccu gaacggcggg accugcagca acaccgggcc cgacaaguac 960
caguguagcu gccccgaagg guacucgggu cccaacugcg agaucgccga gcacgccugc 1020
cuguccgacc ccugccauaa caggggcagc uguaaggaga ccucccuggg cuucgagugu 1080
gagugcuccc ccggauggac cggccccacc ugcagcacca auauugacga cugcagccca 1140
aauaacugcu cccacggcgg caccugccag gaccucguga acggcuuuaa gugcgucugu 1200 ccccccccagu ggaccggcaa gaccugccag cuggacgcca augagugcga ggccaagccc 1260
uguguaaacg ccaagagcug caagaaccug aucgccagcu acuacuguga cugccugccc 1320
ggcuggaugg gccagaacug cgacaucaac aucaacgacu gccucgggca gugccagaac 1380
gacgccagcu gcagggaucu ggugaacggc uacaggugca ucugcccccc cggauacgcc 1440

-continued ggcgaccauu gcgaaaggga caucgaugag ugcgccucca aucccugucu gaacggcggc 1500
cacugccaga acgagaucaa cagguuccag ugccugugcc ccaccggcuu cagcgggaac 1560
cugugccagc uggacaucga cuauugcgag cccaaucccu gccagaacgg ggcgcagugc 1620
uacaacaggg ccagcgacua cuucugcaag ugccccgagg acuacgaggg caagaauugc 1680
agccaccuga aagaccacug ccgcaccacc cccugugagg uuaucgacag cuguacgguc 1740
gccauggccu cgaacgacac ccccgaaggc gugagguaua ucuccagcaa cgugugcggg 1800
ccacacggca aauguaaguc ccagagcggc gggaaguuca ccugcgacug caacaagggc 1860
uucacaggca cguacugcca ugagaacauc aacgauugug agagcaaccc cugcaggaac 1920
ggcgggaccu gcauagacgg cgugaacagc uauaagugca ucugcagcga uggcugggag 1980
ggagccuacu gcgaaaccaa caucaaugac ugcagccaga accccuguca caacgggggc 2040
acaugccggg accuggugaa ugauuucuac ugcgacugca agaauggcug gaagggcaag 2100
accugccaca gcagggacuc ccagugugac gaggccaccu gcaauaacgg gggcaccugc 2160
uacgacgagg gcgacgccuu uaagugcaug ugccccggcg guugggaggg uaccaccugc 2220
aacaucgcgc ggaacagcag cugucugccc aaccccugcc acaacggggg cacgugcgug 2280
gugaacggcg agagcuucac cugcgugugu aaggaggggu gggagggccc caucugcgcc 2340
cagaacacca acgauugcuc gccccacccc uguuacaaca gcgggaccug cguggacggu 2400
gauaacuggu acaggugcga gugcgcacca ggcuucgccg ggccggacug caggaucaac 2460
aucaacgaau gucagagcuc cccgugcgcc uucggcgcca cgugcguaga cgagaucaau 2520
ggcuacaggu gcgugugccc cccaggccac agcggggcca aaugccagga agucagcggc 2580
cgacccugca ucaccauggg uuccguuauc ccagacggag ccaaguggga ugacgauugu 2640
aacaccuguc agugucugaa uggccggauc gcgugcagca aggugugggug cggccccagg 2700
ccgugccugc ugcacaaggg ccacuccgaa ugucccuccg gucagagcug cauccccauc 2760
cucgacgacc agugcuuugu acaccccugc accggagucg gcgagugcag guccucgucu 2820
cugcagcccg ugaaaaccaa gugcaccagc gacuccuacu accaggacaa cugcgccaac 2880
aucacguuca ccuuuaacaa ggagaugaug agccccgggc ugaccacgga gcacaucugc 2940
ucggagcuga ggaaccugaa cauacugaag aacgugagcg ccgaguacag caucuacauu 3000
gccugcgagc ccagccccag cgccaacaac gagauccacg uggcgaucuc cgccgaagac 3060
auccgggacg acggcaaccc caucaaggag auaaccgaca agaucaucga ccuggugagc 3120
aagcgggacg gcaacagcuc ccugaucgcc gccguggccg aggugcgggu acagaggcgg 3180
ccccucaaga acaggacgga cuuccucgug ccgcuccugu cguccgugcu gaccguggcc 3240
uggaucugcu gucuggugac cgccuucuac uggugccugc ggaagcggcg caagccgggg 3300
agccacaccc acucggccag cgaagacaac acgaccaaca acgugaggga gcagcugaau 3360
cagaucaaga aucccauaga gaaacacggc gccaacaccg ugcccaucaa ggauuacgag 3420
aacaagaaca gcaagaugac caaaaucaga acccacaaua gcgaagugga ggaagacgac 3480
auggauaagc accagcagaa ggccagguuc gccaagcagc ccgccuacac ccugguagac 3540
agggaggaga agccccccaa cggcaccccc acgaaacacc cgaacuggac caacaagcag 3600
gauaauaggg accuggaguc cgcgcagagc cugaaccgca uggaguacau cgug 3654

<210> SEQ ID NO 88
<211> LENGTH: 3654
<212> TYPE: RNA

<213> ORGANISM: Artificial Sequence
<220> FEATURE:
<223> OTHER INFORMATION: Synthetic polynucleotide

<400> SEQUENCE: 88
augaggagcc ccaggacccg gggccguagc gggaggccgc ucucgcugcu gcuggcccug 60
cucugcgccc ugagggccaa ggugugugge gccucccggc aguucgagcu ggaaauccug 120
agcaugcaga acgucaacgg cgagcugcag aacggcaacu gcugcggcgg agcgcggaac 180
cccggggaca ggaagugcac cagggacgag ugugacacgu acuucaaagu cugccucaag 240
gaguaccaga gccgggugac cgccgggggc ccaugcuccu ucggcagcgg cagcaccccc 300
gucaucggag gcaacaccuu uaaucugaag gccagcaggg ggaacgacag gaauaggauc 360
guccugcccu uuagcuucgc cuggcccagg uccuacaccc ugcuggucga ggccugggac 420
agcuccaacg acaccgucca gcccgacagu aucaucgaga aggcguccca cuccggcaug 480
aucaauccca gcaggcagug gcagacgcug aagcagaaca ccggcguggc ccacuucgag 540
uaucagaucc gggugacgug cgacgacuac uacuacgggu ucggcugcaa caaguucugu 600
aggccccggg acgauuucuu cggccacuac gcaugcgacc agaacggcaa caagaccugc 660
auggagggcu ggaugggccc cgagugcaac agggcuaucu gccgccaggg cugcuccccc 720
aagcacggca gcuguaagcu gcccggcgau ugccggugu c aguacgggug gcagggacug 780
uauugcgaca agugcauacc ccacccaggc ugcgugcacg gcaucuguaa cgagcccugg 840
caaugccucu gcgagaccaa cuggggggga caacugugcg acaaggaccu gaacuacugc 900
gguacccacc agcccugccu gaacggcggc accugcagua acaccggccc cgacaaguau 960
cagugcagcu gccccgaggg guauuccggc ccgaacugcg agaucgccga gcacgccugc 1020
cucagcgacc caugccacaa uagaggcagc ugcaaggaaa ccucccuggg guucgagugu 1080
gagugcuccc ccgggugac cggcccacc ugcuccacca acaucgacga cugcagcccc 1140
aauaacugca gccacggggg caccugucag gaccugguga acggcuuuaa gugcgucugc 1200
cccccccagu ggaccgguaa gacgugccag cuggacgcca augagugcga agccaagccc 1260
ugcgucaaug ccaagagcug uaagaaccuc aucgcguccu acuauugcga cugccugccc 1320
ggguggaugg gacagaacug cgacaucaac aucaacgacu gccucgggca gugccagaac 1380
gacgccagcu gccgggaccu ggugaacggc uauagaugca ucugcccccc cggcuacgcc 1440
ggggaccacu gcgagaggga caucgacgag ugcgccucca accccugccu gaauggaggc 1500
cacugccaga acgaaaucaa cagguuccag ugucugugcc ccaccggauu cagcggaaac 1560
cugugccagc uggacaucga cuauugcgaa cccaaccccu gucagaacgg cgcccagugc 1620
uacaaccggg caagcgacua cuucugcaag ugcccugagg acuacgaggg caagaacugc 1680
agccaccuca aggaccacug caggacgacc cccugugagg ugaucgacag cuguaccgug 1740
gccauggccu cgaacgacac cccugagggc gugagguaua ucuccagcaa cgucugcggc 1800
ccccacggca aauguaagag ccaauccggg ggcaaguuca ccugcgacug caacaaggga 1860
uuuaccggca ccuacugcca cgagaacauc aacgacugcg aguccaaucc cugccguaac 1920
ggcggcaccu gcaucgacgg ugucaacagc uacaagugca ucugcagcga cggcugggag 1980
ggagcguacu gcgaaaccaa cauaaacgau uguucccaga accccugcca caacggcggc 2040
accugccggg accuugugaa cgacuuuuac ugugacugca agaaugggug gaagggcaaa 2100
acgugccaca gcagagacag ccagugcgac gaagccaccu guaacaacgg cggcaccugc 2160
uacgacgagg gcgacgccuu uaaguguaug ugcccgggcg gcugggaagg cacgaccugc 2220
aacaucgccc ggaacagcag cugccucccg aacccuugcc acaacggcgg gaccugcgug 2280
gugaauggcg aauccuucac cugcgugugc aaggagggcu gggagggccc caucugcgcc 2340
caaaacacca augacuguag cccccacccc ugcuacaacu ccggcacaug uguggauggc 2400
gacaacuggu acagguguga gugcgccccc ggauucgccg gccccgacug ccggaucaac 2460
auuaacgagu gucagagcag ccccugcgcc uucggcgcca ccugcgucga ugagauaaac 2520
ggauauaggu gcgugugccc ccccggacac agcggcgcga agugccagga ggugagcggc 2580
aggcccugca ucacaauggg cagcgugauc ccggacggcg ccaaguggga cgacgauugc 2640
aacaccugcc agugccugaa cggccggaua gccugcucca aagugugguag cggcccccgc 2700 cccugccugc ugcacaaggg ccacagcgag ugccccuccg gccagagcug cauccccaua 2760
cuggacgacc aauguuucgu gcaucccugc accggcgugg gcgagugucg gagcagcagc 2820
cugcagcccg ugaagacuaa gugcaccucc gacuccuacu aucaggacaa cugugccaac 2880
aucaccuuca ccuucaacaa ggagaugaug agccccggcc ugacaacgga gcacaucugc 2940
agcgagcugc gcaaucugaa cauccugaaa aaugugagcg ccgaguacag caucuacauc 3000
gccugugagc cgagccccag cgcuaauaac gagauccacg uggccaucuc cgccgaggac 3060
aucagggaug acggcaaccc caucaaagag aucaccgaca agaucaucga ccuggugucc 3120
aagcgggacg gcaacuccag ccugaucgca gccguggccg aagugagggu ccagcggcgg 3180
ccccugaaga accgaaccga cuuccugguc ccccugcuga gcagcgugcu gaccgucgca 3240
uggaucuguu gccuggugac ggccuucuac uggugccuca ggaaaagacg gaagcccggg 3300
agccacaccc acagcgccag cgaggacaac accaccaaca acgugcggga gcagcugaac 3360
caaaucaaga accccaucga gaagcauggc gccaauaccg ugcccaucaa agacuacgag 3420
aacaagaaca gcaagaugag caagauccgc acccauaacu cggaggugga agaagacgau 3480
auggauaagc accagcaaaa ggcccgguuc gcgaagcagc ccgccuauac ccucguggac 3540
cgggaagaaa agccgcccaa cggcaccccc accaagcacc ccaacuggac caacaaacag 3600
gacaacaggg accucgagag cgcccagucc cucaaccgua uggaguacau cguc 3654

<210> SEQ ID NO 89
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 89
augagguccc cgcguacccg aggcaggucc gggaggcccc ugucccugcu gcucgccuua 60
cuuugcgccc ugagggccaa agucugcggc gccuccggcc aauucgagcu ggagauccuc 120
agcaugcaga acgugaacgg cgagcugcaa aacgggaacu gcugcggggg agcccgcaac 180
cccggcgacc ggaagugcac cagggacgag ugcgacaccu acuucaaggu gugccucaag 240
gaguaucagu caagggugac cgccggaggc cccuguagcu ucggcuccgg gucgaccccc 300
gugauaggcg gaaacaccuu caaccugaag gccagcaggg ggaacgacag gaauaggauc 360
gugcuccccu ucucguucgc cuggcccagg agcuacaccc uccucgugga ggccugggac 420
agcagcaacg auacggugca gcccgacucc aucaucgaga aggccagcca cuccggcaug 480
aucaacccca gccgccagug gcagacccug aagcaaaaca cgggcguggc acacuucgag 540
uaccagauaa gggucacuug cgacgacuac uacuacgggu ucgggugcaa caaguuugc 600

-continued

```
aggccccggg acgacuucuu cggacacuau gccugcgacc agaacggcaa caagaccugu    660
auggagggguu ggaugggccc cgaaugcaau cgcgccauuu gccggcaggg gugcagcccu    720
aagcacggaa gcuguaagcu ccccggcgac ugccgcugcc aguacggcug gcagggacug    780
uacugugaca aguguauccc ccaccccggc ugcgugcacg gcaucugcaa ugagccuugg    840
cagugccugu gcgagaccaa uuggggcggc cagcugugcg acaaggaccu gaacuacugc    900
ggcacccacc agcccugccu gaacggugggg accugcagca acaccgggcc agacaaguac    960
cagugcagcu gccccgaggg cuauagcggg cccaauugcg agaucgccga gcacgccugc   1020
cuguccgacc ccugucacaa ccggggcucc ugcaaggaga ccucccuggg guuugagugc   1080
gagugcuccc ccgguuggac cggccccacc ugcuccacca acaucgacga cugcuccccc   1140
aacaauugca gccacggcgg cacaugccag gaucugguga acggcuucaa gugugugugu   1200
ccccccagu ggaccggcaa gaccugccag cuggacgcga acgagugcga agcaaagccc   1260
ugcgugaacg ccaaguccug caaaaaccug aucgccagcu auuacugcga cugccugccc   1320
ggcuggaugg ggcagaacug ugacauaaac auaaacgacu gccucggcca gugccagaau   1380
gacgcgagcu gccgggaccu cgugaacggc uaccgaugca ucugcccccc gggcuacgcc   1440
ggcgaccauu gcgaacggga uaucgacgag ugugccagca accccugccu gaacgggggg   1500
cacugccaga acgagauaaa cagguuccag ugccugugcc ccaccggcuu cagcggcaac   1560
cugugccaac ucgacaucga cuacugcgag cccaaccccu gccaaaacgg ugcccaaugc   1620
uacaaccggg ccucggacua cuuuugcaag ugcccggagg acuaugaggg caagaauugu   1680
ucccaccuca aggaccacug ccggaccacc cccugcgagg ugaucgacuc cugcaccgug   1740
gccauggcua guaacgauac ccccgagggc guuagguaca ucuccuccaa cgugugcggc   1800
ccccacggga agugcaaguc gcagagcggc ggcaaguuca ccugcgacug caauaagggc   1860
uucaccggua ccuacugcca cgagaacauc aacgacugcg agagcaaucc cugccggaac   1920
gggggguaccu gcaucgacgg cgugaacucc uacaagugua ucugcucaga uggcugggaa   1980
ggcgcguacu gugagaccaa cauaaacgac uguagccaga accccuguca uaacgggggc   2040
accugcaggg accuggugaa cgacuucuac ugcgacugca agaacgggug gaaaggcaaa   2100
acuugccacu ccagggacuc ccagugcgau gaggccaccu gcaauaacgg cggcacgugc   2160
uacgacgagg gggacgccuu caagugcaug ugcccccgggg gcugggaggg gaccaccugc   2220
aacaucgcca ggaacagcuc cugccugccc aacccaugcc acaauggagg caccugcgua   2280
gugaauggcg aguccuucac cugugugugc aaggagggcu gggaggggcc caucugcgcc   2340
cagaacacca acgacugcag cccacacccg ugcuacaacu ccggcaccug cgucgacggc   2400
gacaacuggu acaggugcga gugcgccccc ggcuucgcgg gcccggacug ccggauuaau   2460
aucaacgagu gccagagcag ccccugcgcc uucggggcca ccugcgucga cgaaaucaac   2520
ggguaccggu gcgugugccc ccccggccac agcggggcaa agugccagga agucagcggc   2580
aggcccugca ucaccauggg cagcgucauu cccgauggcg caaaguggga cgacgacugc   2640
aacacuugcc agugccugaa uggcaggauc gccugcagca aggugguggug cggcccaagg   2700
cccugccugc ugcacaaagg ccacagcgaa ugcccaagcg gucagagcug cauccccauc   2760
cuggaugacc agugcuucgu gcaccccugc accggggucg gugaguguag gagcagcagc   2820
cugcagcccg ugaagaccaa gugcaccucc gauuccuacu accaggacaa uugcgccaac   2880
auaacuuuua ccuucaacaa ggagaugaug agccccggcc ucaccacgga gcacaucugc   2940
agcgagcugc gcaaccucaa cauccugaag aacgugagcg ccgaguacag cauuuacauc   3000
```

gccugcgagc ccagccccuc cgccaacaac gagauccacg uggccaucag cgccgaggac 3060
auaagggaug acgggaaucc caucaaggag aucaccgaca agaucaucga ccuggugucc 3120
aagcgggacg gcaauagcag ccugaucgcc gccgucgcgg aggugcgggu gcagaggcgc 3180
ccgcugaaga accggaccga cuuccucgug ccccugcuga gcagcgugcu gacgguggcc 3240
uggaucugcu gccuggugac agccuucuac uggugccugc ggaagaggag gaagcccggg 3300
agccacaccc auagcgcguc cgaggacaac acgacaaaca acgucagaga gcagcugaac 3360
caaaucaaga aucccaucga aaaacacggc gccaacaccg ugcccaucaa agauuacgag 3420
aacaagaaca gcaagaugag caaaauccgg acccacaacu cggaggugga ggaggacgac 3480
auggacaagc accaacagaa ggcccgcuuu gccaagcagc ccgccuacac ccugguggac 3540
cgggaggaaa agccgccgaa ugguacaccg accaagcauc ccaauuggac aaacaagcag 3600
gauaacaggg accuggaaag cgcccagagc cugaaccgga uggaguacau cgua 3654

<210> SEQ ID NO 90
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 90
augaggagcc ccaggaccag ggggaggagc gggaggccgc ugagccugcu ccuggcccug 60
cugugugccc ugcgcgccaa ggugugcggc gcguccggac aguuugagcu ggagauccug 120
uccaugcaga acgugaacgg cgagcuccag aacgggaacu gcugcggggg cgcaaggaac 180
cccggugaca ggaagugcac ccgcgacgag ugcgacacgu acuuuaaggu gugccugaaa 240
gaguaccaga gcagggugac ugccggcgga cccugcucgu uuggaagcgg cagcacuccu 300
gugaucggug gcaacaccuu caaucugaag gccuccaggg ggaacgauag gaacaggauc 360
gugcugccau ucagcuuugc cuggccccgg ucauacaccc ugcuggugga ggccugggac 420
uccagcaacg acaccgugca gcccgacucc aucauagaga aggcgagcca cagcggcaug 480
aucaaccccu ccaggcagug gcagacccuc aagcagaaca ccggcgucgc ccacuucgaa 540
uaccagauca gggucacgug cgacgacuac uacuacggcu uggcugcaa uaaguucugc 600 aggccccggg acgacuucuu cgggcacuac gccugcgacc agaacgggaa caaaaccugu 660
auggaggggu ggaugggccc cgaaugcaac cgagccaucu gccgccaggg gugcuccccc 720
aagcacggcu ccuguaaacu ccccggcgau ugcaggugu c aguacggcug gcagggucuc 780
uacugcgaca agugcauccc gcaccccggc ugcguccacg gcaucuguaa ugagcccugg 840
caaugccugu gcgagaccaa cuggggcggc cagcugugcg acaaggaccu caauuauugu 900
ggcacccacc agccaugccu gaaugguggc accugcagca acacaggccc agacaaguac 960
cagugcagcu gucccgaggg cuacucgggc cccaacugcg aaaucgccga gcacgcuugc 1020
cugagcgacc ccugucacaa caggggcagc ugcaaggaaa ccagccuggg guucgagugc 1080
gagugcagcc ccggguggac cggccccacc ugcagcacca acaucgacga cugcagcccc 1140
aacaacugua gccauggcgg caccugccag gaucugguca acggcuucaa gugcgugugu 1200
cccccccagu ggaccggcaa gaccugccag cucgacgcca acgaguguga agcaaagccc 1260
ugcgugaaug ccaaguccug caagaaccug auagccuccu acuacugcga cugccugccc 1320
ggcuggaugg gccagaacug ugacaucaac aucaacgacu gccuggggca gugucagaau 1380

```
gacgccagcu gccgcgaccu ggugaauggc uauaggugca ucugcccccc cggauacgcc   1440
ggcgaccacu gcgagaggga uaucgaugag ugcgccagca acccuugccu gaacggcggg   1500
cacugccaga acgagauuaa cagguuccag ugccugugcc ccaccggcuu cagcggcaau   1560
cugugccagc uggauaucga cuacugcgag cccaacccgu gccagaacgg cgcccagugc   1620
uacaacaggg ccuccgacua cuucuguaag ugucccgagg acuaugaggg caagaacugu   1680
ucccaccuga aagaccacug caggaccacc cccugcgagg ugaucgacuc gugcaccgug   1740
gccauggcga gcaaugacac cccggaaggc gugcgcuaua ucagcagcaa ugugugcggg   1800
ccccacggca agugcaagag ccagagcggc gggaaguuca ccugcgacug caacaagggc   1860
uucaccggca cguacugcca cgagaacauc aacgauugcg aguccaaccc cugccggaac   1920
ggcggcaccu gcauagaugg agugaacucc uauaagugca ucugcuccga ugggugggag   1980
ggcgccuacu gugaaaccaa caucaacgac ugcagccaga accccugcca uaauggugc   2040
acgugccggg accugguuaa ugacuucuac ugcgacugca agaacggcug gaagggcaag   2100
accugccaca gcagagauag ccagugcgac gaggccacgu gcaacaaugg cgggaccugc   2160
uacgacgagg gggacgccuu caaaugcaug ugccccggcg gaugggaggg gaccaccugc   2220
aacaucgcca ggaacuccag cugccugccc aacccgugcc auaacggugg caccugcgug   2280
gugaacggcg aaagcuucac cugcgugugc aaggagggcu gggagggccc caucugcgcc   2340
cagaacacca augacugcuc cccccaccca ugcuacaacu ccgggaccug uguggacggc   2400
gacaacuggu auaggugcga gugugccccc ggcuucgccg gccccgacug caggaucaac   2460
aucaacgaau gucagagcuc ccccugcgcc uuuggcgcca caugugucga ugagauuaac   2520
ggcuaccggu gcgucugccc ccccggccac agcggcgcga agugccagga agucuccggc   2580
aggcccugua ucaccauggg cagcgugauc cccgacggcg ccaaguggga cgacgacugc   2640
aacaccuguc aaugccugaa uggcaggauc gccugcagca aagucuggug cgggccccgg   2700
cccugccugc ugcacaaggg ccacagcgag ugcccuuccg gccagagcug caucccgauc   2760
cuggacgauc aguguuuugu ccauccaugc accggcgugg gcgagugaug gucgagcagc   2820
cugcagcccg ugaaaacaaa gugcaccagc gacagcuacu accaggauaa cugugccaac   2880
aucaccuuua ccuucaacaa ggagaugaug agccccggac ugaccaccga gcauaucugu   2940
ucagagcuga ggaaccugaa cauccucaag aacgucagcg ccgaguacag caucuacauc   3000
gccugcgagc ccagccccuc cgccaacaac gaaauccacg uggccauaag cgccgaggac   3060
aucagggacg acggcaaucc gaucaaggag auaaccgaca agaucaucga ccucgugagu   3120
aagagggacg ggaacaguag ccucaucgcc gccgucgccg aggugagggu gcagcggagg   3180
ccccugaaga acaggaccga uuuucugguc cccugcuga gcuccgugcu gaccguggcc   3240
uggaucugcu gccuggugac ggcguucuac uggugccucc ggaaacgacg gaagcccggg   3300
agccauaccc acuccgccag cgaggacaac accaccaaua acgugaggga gcagcugaau   3360
cagaucaaga auccgaucga gaagcacggc gccaacaccg ugccgaucaa agacuacgag   3420
aacaagaauu ccaagaugag caagaucagg acccacaacu ccgaggugga ggaagaugac   3480
auggacaagc accagcagaa agccagguuu gccaagcagc ccgccuauac ccugguggac   3540
agggaggaga aacccccgaa uggcaccccc accaaacacc caaacuggac caacaagcag   3600
gacaacaggg aucuggagag cgcccagagc cucaaccgua uggaguacau cgug         3654
```

<210> SEQ ID NO 91
<211> LENGTH: 3654

-continued

<212> TYPE: RNA
<213> ORGANISM: Artificial Sequence
<220> FEATURE:
<223> OTHER INFORMATION: Synthetic polynucleotide

<400> SEQUENCE: 91
augaggucac cccggacccg gggacgcucc ggcaggcccc ugagccugcu gcuggcccug 60
cugugcgccc ucagggccaa ggucugcggc gccuccgguc aguucgaacu cgagauccug 120
agcaugcaga acgugaacgg ugaacugcag aacggcaacu gcugcggcgg cgccaggaau 180
cccggcgacc gaaagugcac cagggacgag ugcgacaccu acuuuaaggu gugccuaaag 240
gaguaccaga gccgggugac ggccggcggc cccuguuccu ucggcagcgg cagcacgccc 300
gugaucggcg gcaacaccuu caaccucaag gccucgcgcg gcaacgaucg gaacaggauc 360
gugcugccgu uuuccuuugc cuggcccagg ucguacaccc ugcuggugga ggccugggac 420
agcuccaaug acaccgugca gccagacucc auaaucgaga aggccagcca cagcgggaug 480
auuaauccaa gcaggcagug gcaaacccug aagcagaaca ccggaguggc ccauuucgag 540
uaccagauca gggugaccug cgacgacuac uacuacggcu ucggaugcaa caaguucugc 600
aggccccggg acgacuucuu cggccauuac gccugcgacc agaacggcaa caagaccugc 660
auggaggguu ggaugggccc cgaaugcaau agggccaucu gcaggcaagg cuguuccccc 720
aaacacggga gcuguaaacu ccccggcgac ugccgaugcc aguacgggug gcaaggccuc 780
uacugcgaca agugcauccc ccaucccggc ugcgugcaug gcauuugcaa cgaacccugg 840
caaugccucu gcgagaccaa cuggggggc cagcucugcg acaaggaucu gaacuacugc 900
ggcacacacc agccuugccu gaacggaggg accugcagua auaccggccc cgacaaguac 960
cagugcagcu gccccgaggg cuauagcggc cccaacugcg aaauugccga gcacgccugc 1020
cugagcgacc ccugucacaa caggggcagc ugcaaggaga ccagucuggg cuucgagugc 1080
gagugcagcc caggcuggac gggccccacc ugcuccacca acaucgacga cugcuccccc 1140
aacaauugca gccacggcgg caccugccaa gaucucguga acggcuucaa gugcgugugu 1200
ccgccgcagu ggaccgggaa aaccugccaa cuggacgcca acgagaguga ggcaaagccc 1260
ugcgugaacg cgaaguccug uaagaaccug aucgccagcu acuauugcga cugccugccg 1320
ggcuggaugg ggcagaacug ugacaucaac aucaacgauu gccugggcca gugucagaac 1380
gacgccagcu gcagggaccu ggucaacggc uacaggugca ucuguccccc ggggaugcc 1440 ggggaccacu gcgaacgaga uaucgacgag ugcgccucga acccuugccu caauggcggc 1500
cacugccaga acgagaucaa cagguuccag ugccugugcc ccaccggcuu cagcggcaau 1560
cugugccagc uggacaucga cuauugugaa cccaacccgu gccagaacgg cgcccagugc 1620
uacaaccgcg ccuccgacua cuucugcaag ugcccggagg acuacgaggg caagaacugc 1680
agccaucuga aggaccacug uagaaccacg cccugcgagg ugaucgacuc cugcaccguc 1740
gccauggccu caaacgacac ccccgaggga gugcgcuaca ucagcucgaa cgugugcggc 1800
ccccauggaa aaugcaagag ccaguccggg ggcaaguuca ccugcgacug caacaagggc 1860
uucaccggca cguauugcca ugagaacauc aaugacugcg agagcaaccc gugccguaac 1920
gggggcaccu guaucgaugg cgugaacagc uacaagugca ucuguagcga cggcugggag 1980
ggcgccuauu gcgaaaccaa caucaacgac uguucccaga acccaugcca caacgggggc 2040
accuguaggg accuggucaa cgacuuuuac ugugacugca agaacgguug gaaaggcaag 2100
accugccacu cgagggacag ccagugugac gaggccacgu gcaacaaugg cggcaccugu 2160
uacgacgagg gcgacgccuu uaagugcaug ugucccgggg guugggaggg uaccaccugu 2220
aacaucgcca ggaacucaag cugccugccc aaucccugcc auaacggugg gaccugcgug 2280
gugaacggcg aaagcuucac cugcgugugc aaggagggcu gggagggccc caucugugcc 2340
cagaacacca augacugcag cccccacccc uguuacaaca gcgggaccug cguggauggu 2400
gacaacuggu acagguguga gugcgccccc ggguuugccg gccccgacug caggaucaac 2460
aucaacgagu gccagagcag ccccugugcc uucggcgcca ccugcgugga cgagaucaac 2520
ggguaccggu gcgugugccc ccccggccac uccggcgcca agugccagga ggguguccggc 2580 aggcccugca ucaccauggg cagcgucauc cccgacggcg ccaaauggga cgacgacugc 2640
aacaccuguc agugccugaa cggcaggauc gccugcucca agguuuggug cgggcccagg 2700
cccugccugc ugcacaaggg acauagcgaa ugccccagcg gccagagcug cauccccauc 2760
cuggacgacc agugcuucgu gcaucccugc accggggugg gcgagugccg gagcuccucg 2820
cugcaacccg ucaagaccaa gugcaccucg gacagcuauu accaggacaa cugcgccaac 2880
aucaccuuca ccuucaacaa ggaaaugaug agccccggcc ugaccaccga gcauaucugc 2940
agcgagcugc ggaaccugaa cauacugaag aacguuagcg ccgaguacuc caucuacauc 3000
gccugcgagc ccagcccgag cgcgaauaau gagauccacg ucgccaucag cgccgaggac 3060
auccgggacg acggcaaccc caucaaggag aucaccgaca agaucaucga ccuggucagc 3120
aagcgugacg gcaacuccag ccugaucgcc gcgguggcug aggugcgagu ccagaggagg 3180
ccccugaaga acaggacgga cuuccucguc ccucugcuga gcagcgugcu gaccguggcc 3240
uggaucuguu gccuggugac cgccuuuuac uggugccugc gaaagaggag gaagccgggc 3300
agccacaccc acagcgccuc agaagacaac accacaaaca acguccgcga gcagcucaac 3360
cagaucaaaa accccaucga aaagcacggc gccaacaccg ugcccaucaa ggacuacgag 3420
aacaagaaua gcaagaugag caagauccgc acucacaaca gcgaggugga ggaggacgac 3480
auggacaagc accagcagaa ggccagguuu gccaagcagc ccgccuacac ccugguggac 3540
cgggaggaga agccgcccaa uggcaccccc acgaagcacc cgaacuggac caacaaacag 3600
gacaacaggg accuggagag cgcccagagc cugaaccgca uggaguacau cgug 3654

<210> SEQ ID NO 92
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 92
augcgguccc ccaggaccag ggggcgcagc gggaggcccc ugagccugcu gcuggccuua 60
cugugugccc ugagggccaa ggugugcggc gccagcgggc aguucgagcu ggagauacug 120
uccaugcaaa acgugaacgg cgaacugcag aaugggaauu gcugcggugg cgccaggaac 180
ccuggggacc gcaaguguac ccgggacgag ugcgacaccu acuucaaggu gugucucaag 240
gaauaucagu cccgcgugac cgccgggggc cccugcagcu ucggcucagg cagcacccca 300
gucaucgggg gcaacaccuu caaccugaag gccagccgug gcaacgacag gaacaggaua 360
gugcugcccu ucuccuucgc guggcccagg uccuacaccc ugcuggugga ggcgugggau 420
agcucgaaug auaccgucca gcccgacucc aucaucgaga aagccuccca cuccgguaug 480
aucaauccaa gcaggcagug gcagacccug aagcagaaca cgggcguggc ccacuuugag 540
uaccagauca gggucaccug cgacgacuac uacuacggcu ucggcuguaa uaaauuuugc 600

-continued

```
cggccucggg acgacuucuu cggccacuac gccugcgacc agaacggcaa uaagacgugu    660
auggagggcu ggaugggccc ggaguguaau agggccaucu gccgacaggg gugcagcccc    720
aagcacggca gcugcaagcu gcccggcgac ugcaggugue aguacggcug gcaaggacug    780
uauugugaca agugcauucc ccauccgggc ugugugcacg gaaucugcaa ugagcccugg    840
cagugccugu gcgagaccaa cuggggcggc cagcugugug acaaggaucu gaacuacugu    900
ggcacccacc agcccugccu gaacggcggg accugcucca auaccgggcc cgacaaguac    960
caguguuccu gccccgaggg cuacagcggu ccaaacugcg agaucgccga gcacgccugc   1020
cugagcgacc ccugccauaa caggggcucc ugcaaggaga ccagccuggg cuucgaaugc   1080
gagugcuccc ccggguggac cggcccccacc ugcaguacca acaucgauga cugcagcccc   1140
aauaacuguu cccacggcgg caccugccag gaccugguga acggcuucaa augcgucugu   1200
ccgccccagu ggaccggaaa gaccugucag cucgacgcaa acgagugcga ggccaagccc   1260
ugcgugaacg ccaagagcug caagaaucug aucgccuccu acuacugcga uugucugccc   1320
ggauggaugg gccaaaacug cgacaucaac aucaacgauu gucuggggca gugccagaac   1380
gacgccagcu gcagggaccu ggucaacggc uacaggugca ucugcccccc cggcuaugcc   1440
ggagaccauu gcgagcgaga caucgacgag ugugccucga accccugccu gaacgggggg   1500
cacugccaga acgaaaucaa cagguuccaa ugccucugcc ccaccggguu cagcggcaac   1560
cugugccagc uggacaucga cuauugcgag cccaaccccu gccagaacgg ggcgcagugu   1620
uauaaccggg ccucggacua cuucuguaag ugucccgagg acuacgaggg caaaaacugc   1680
ucccaccuga aggaccacug ccguaccaca cccugcgaag ucaucgacuc cugcaccgug   1740
gccauggcca gcaacgacac ccccgaggga gugcgguaca ucagcagcaa cgugugcggg   1800
ccgcauggca aguguaaguc ccagagcggg ggcaaguuua caugugacug uaacaagggc   1860
uucaccggca cauacugcca cgagaacauc aacgauugcg agagcaaccc cugccggaau   1920
gggggcaccu gcaucgacgg ggugaacagc uauaagugua ucugcuccga uggcugggag   1980
ggcgccuacu gcgagacuaa caucaaugac ugcucgcaga acccgugcca caacgggggga   2040
accugcaggg aucucgugaa cgacuucuac ugcgacugca agaacgggug gaaggggaag   2100
accugccaca gccgcgacuc ccagugcgac gaggccaccu gcaacaaugg gggcaccugc   2160
uacgacgagg gcgacgccuu caagugcaug ugccccggcg ggugggaggg caccaccugc   2220
aacaucgccc ggaacuccag cugccugccc aauccguguc acaauggggg caccugcgug   2280
gugaacggcg agucguucac gugcgugugc aaggaaggcu gggagggacc gaucugcgcc   2340
caaaauacca acgacuguag ccccccacccc uguuauaaca gcggcaccug cgucgacggg   2400
gacaauuggu accggugcga gugcgccccc ggcuucgccg gccccgacug ccgaaucaac   2460
aucaacgaau gucaaagcuc acccugugcc uucggggcaa ccugugugga cgagaucaac   2520
ggcuaccggu gugugugccc cccgggacac uccggggcca agugccagga ggugagcggg   2580
cgaccaugca ucaccauggg cuccgugauc cccgacggcg ccaagugga cgacgacugc   2640
aacaccugcc agugccugaa cggcaggauc gccugcucca aggugugug uggccccccgg   2700
cccugucucc ugcacaaagg ucacagcgag ugccccagcg gccagagcug caucccgauc   2760
cuugacgacc agugcuucgu gcacccgugu acaggcguag gggagugcag gagcuccucg   2820
cuccagcccg ugaaaaccaa guguaccagc gacucauacu aucaggacaa cugugccaau   2880
aucaccuuua ccuucaacaa ggaaaugaug agccccgggc ugaccaccga gcacaucugc   2940
```

agcgagcugc ggaaccuuaa cauucugaaa aaugugucg ccgaguacag cauauacauc 3000
gccugcgagc cgagcccuag cgccaacaau gagauacacg uggccaucag cgcugaggac 3060
aucagggaug acggcaaccc gaucaaggag aucaccgaca agauaauaga ccucgucagc 3120
aaaagggacg gcaacagcag ccugaucgcc gccgucgccg aggugagggu gcagcgccgg 3180
ccccugaaga acaggaccga cuuccuggug ccccuccuga gcuccgugcu gaccguggcc 3240
uggaucugcu gccuggugac cgccuucuac uggugucuga ggaaaaggag gaagccuggc 3300
agccacaccc auagcgccuc cgaggacaau accaccaaca acgucaggga acagcucaac 3360
caaaucaaga accccaucga gaagcacggc gccaauaccg ugcccaucaa ggauuacgag 3420
aacaagaaua gcaagauguc caagauccgc acacauaauu ccgaggucga ggaagacgac 3480
auggauaagc accagcagaa ggccagauuc gccaagcagc ccgccuacac ccugguggac 3540
agggaggaga agccccccaa cggcacaccc accaagcauc ccaacuggac caacaagcag 3600
gacaacaggg accuggagag cgcccagucc cugaaccgua uggaguacau cguc 3654

<210> SEQ ID NO 93
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 93
augaggagcc ccaggacaag gggccggagc ggcaggcccc ugagccugcu gcucgcccuc 60
cucugugccc ugcgcgccaa agugugcggg gccucaggcc aguucgagcu cgagauccug 120
uccaugcaaa acgugaacgg cgaacugcag aacggaaauu gcugcggugg cgcccguaac 180
cccggcgacc gcaagugcac cagggacgag ugcgacaccu acuucaaggu gugucugaag 240
gaguaccaga gcagggucac cgccggcggc cccugcagcu uuggcuccgg cagcaccccc 300
gugaucggcg gcaacaccuu caaccugaag gcuagccgcg gcaacgacag gaacaggauc 360
gugcuuccau uuagcuucgc cuggcccagg agcuacaccc ugcuugugga ggccugggac 420
agcuccaacg acaccgugca gcccgacagc aucaucgaga aggccagcca cuccggcaug 480
aucaacccca gccggcagug gcagacccug aagcagaaca ccggcgucgc gcacuucgag 540
uaccagauca gggugacaug ugacgacuau uacuauggcu uuggauguaa caaguucugc 600
aggcccagag acgacuucuu cggccacuac gccugcgacc agaacggaaa uaagaccugu 660
auggaaggcu ggaugggggcc cgagugcaac cgagccaucu gcaggcaagg cugcagcccc 720
aagcacggca gcugcaagcu gcccggggac ugccggugcc aguacggcug gcagggcuug 780
uauugcgaca agugcauccc gcacccggc ugcgugcacg ggaucugcaa cgagcccugg 840
cagugccugu gcgagacgaa cuggggcggc cagcugugcg acaaggaccu gaacuacugc 900
gggacgcauc aacccugucu caacggcggu accugcagca auaccggccc cgacaaguac 960
cagugcucuu gccccgaggg cuauagcggg cccaacugug agaucgccga gcacgcuugc 1020
cuguccgacc ccugccacaa ccggggcucc ugcaaggaga ccucccuggg cuucgagugc 1080
gaaugcagcc ccgggguggac cggucccacg ugcagcacca acaucgauga cuguagcccc 1140
aacaacugca gccacggcgg cacgugccag gaccucguga acggcuucaa gugcgugugc 1200 ccccccccagu ggaccggcaa gaccugccag cucgacgcca augagugcga agccaagccc 1260
ugcgucaacg ccaaguccug caagaaccug aucgccaguu acuacugcga cugucugccc 1320
ggauggaugg gccagaauug cgacaucaac aucaaugacu gccugggcca gugccagaau 1380

```
gacgcguccu guagggaucu ggugaacggg uacaggugca uauguccccc cggcuaugcc   1440
ggggaucacu gcgagaggga uaucgaugag ugcgccagca accccugucu gaacgguggc   1500
cacugccaga acgagauuaa cagguuccag ugccugugcc ccaccggcuu cagcggcaac   1560
cugugccagc uggauaucga cuacugugag cccaacccgu gccagaacgg cgcccagugc   1620
uacaaccgag ccagcgauua uuuuugcaaa ugucccgagg auuacgaagg gaagaauugc   1680
agccaccuga aggaccauug caggaccacc cccugcgaag ugaucgacag cugcaccgug   1740
gccauggccu cgaaugacac gcccgaggga gugagguaca ucaguagcaa ugugugcggc   1800
ccccauggga agugcaagag ccagucgggc ggaaaguuua ccugcgacug uaacaagggc   1860
uucaccggga ccuacuguca cgaaaacauc aacgacugcg aguccaaccc guguaggaac   1920
ggcgggaccu gcauagacgg ggugaauagc uauaagugca ucuguucaga cggaugggag   1980
ggggccuacu gcgagaccaa caucaacgau ugcucgcaga accccugcca caacggcggc   2040
accugccggg accuggugaa cgacuucuac ugcgacugua aaaacggcug gaaggggaag   2100
accugccacu ccagggacag ccagugcgac gaggcgaccu gcaacaacgg cggcaccugc   2160
uacgacgagg gcgaugccuu caaguguaug ugccccggag gcugggaggg caccaccugc   2220
aacaucgccc gcaacagcag cugccugccc aaucccugcc acaauggugg aacaugcgug   2280
gugaacgggg agagcuuuac gugcgugugc aaggagggau gggagggccc caucugugcc   2340
cagaacacca acgacugcuc cccccauccc uguuacaaca gcggcaccug uguggacggg   2400
gacaacuggu accgcugcga gugcgccccc ggcuucgccg gcccggacug ccguaucaac   2460
aucaacgagu gucagagcag ccccugcgca uucggcgcca ccugcgugga ugaaauaaac   2520
ggcuacaggu gugugugccc ccccggccac agcggagcca aaugccagga ggugagcggg   2580
cgcccaugca ucaccauggg gagcgugauc ccagacgggg cgaaguggga ugacgacugu   2640
aacaccugcc agugccugaa cggccgaauc gccugcagca aggugugggug cgggccccgg   2700
cccugccugc ugcacaaagg ccacagcgag ugccccagcg gccagagcug cauaccgauc   2760
cuggacgacc agugcuucgu acaccccugc accggggugg gcgagugccg guccuccucg   2820
cuccagcccg ucaagaccaa gugcaccagc gauagcuacu accaggacaa cugcgccaac   2880
aucaccuuua ccuuuaacaa ggagaugaug agccccggcc ugaccacgga gcacaucugc   2940
agcgagcugc gcaaccucaa cauccugaaa aacgugucgg ccgaguacuc caucuacauc   3000
gccugcgagc ccuccccccuc cgccaacaau gaaauccacg uggccaucag cgccgaggac   3060
auccgagacg augggaaccc caucaaggaa aucaccgaca agauaaucga ccugguggagu   3120
aaaagggacg ggaacagcag ccugaucgcu gccguggcgg aggugagggu ccagaggagg   3180
ccgcugaaaa aucggaccga cuuucuggug ccccugcuga gcuccgugcu gaccgucgcc   3240
uggaucugcu gccuggucac cgccuucuac uggugccuga ggaagcguag gaagcccggc   3300
agccacacgc acagcgccag cgaggacaac accaccaaca acgugcggga gcagcugaac   3360
cagaucaaga accccaucga gaagcacggc gcgaacacag ugccgaucaa ggauuacgag   3420
aacaagaauu ccaagaugag caagaucagg acccacaaca gcgaggugga ggaggacgac   3480
auggauaaac accagcagaa ggccagguuc gccaagcagc ccgccuauac ccuggucgac   3540
agggaggaga aacccccuaa uggcaccccc accaagcacc ccaacuggac aaacaagcag   3600
gacaacaggg accuggagag cgcccagagc cugaaccgua uggaguauau cgug         3654
```

<210> SEQ ID NO 94

<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 94
augcggagcc ccagaacccg uggccggagc ggcaggcccc ugucacuacu gcuggcccug 60
cugugcgcgc uuagggccaa ggucugcggc gccagcggcc aguucgagcu ggagauccug 120
agcaugcaga acgugaacgg cgagcugcag aacggcaacu gcugcggcgg ggccaggaac 180
cccggagacc gcaaaugcac ccgggacgag ugcgacaccu auuuuaaagu gugccugaag 240
gaguaccaga gcagggugac cgccggcggc cccugcagcu ucggcagcgg cagcaccccc 300
gugaucggcg ggaauaccuu caaccugaag gccagccgcg gcaacgacag gaaccgaauc 360
gugcugcccu uuagcuucgc cuggccucgg agcuacaccc ugcugguggga agccugggac 420 uccuccaacg acaccgugca acccgacucc auuaucgaga aggccuccca cagcggcaug 480
auaaacccca gccggcagug gcagacacug aagcaaaaca ccggggucgc acauuucgag 540
uaccagauca gggugacgug ugacgacuac uacuacgggu ucggaugcaa caaguucugc 600
aggcccaggg acgacuucuu cggccacuac gccugugacc agaacggcaa uaagaccugc 660
auggaggggu ggaugggccc ggagugcaac agggccauau gccggcaggg cugcuccccca 720 aaacacgggu ccugcaagcu gccuggcgac ugcaggugguc aguacggcug gcaggggcug 780
uacugcgaua agugcauccc ccaccccggc ugcguccacg gcaucugcaa cgagccaugg 840
cagugucugu gcgagaccaa cuggggguggg cagcugugcg acaaggaucu gaacuacugc 900
ggcacccacc agcccugccu caacgggggga acgugcucga acaccgggcc cgauaaguac 960
cagugcuccu gccccgaagg cuacucggga ccuaacugug agaucgcuga gcacgcaugc 1020
cugagcgacc caugccauaa caggggguagu ugcaaggaga ccucccucgg uuuugaaugc 1080
gagugcagcc ccggcuggac cggcccccacc ugcucgacca acaucgacga cugcagccca 1140
aacaacugcu cccacggcgg cacgugucag gaccugguga auggcuucaa gugugugugc 1200
cccccccagu ggaccggaaa aaccugccag cuggaugcca acgagugugga ggccaagccc 1260 ugcgugaacg cgaaguccug caagaaccug aucgccuccu acuacugugga cugccugccc 1320 gguuggaugg gccaaaacug cgacaucaac aucaacgacu gccugggcca gugccagaac 1380
gacgccagcu gcagggaccu agugaacggg uaucggugca ucugccccccc cggcuacgcc 1440 ggcgaucacu gcgaaaggga caucgacgag ugcgccagca acccgugccu gaacggggggg 1500 cacugccaga acgagaucaa cagguuccag ugccucugcc ccaccgggguu cagcgggaac 1560 cucugccagc ucgacaucga cuacugcgag cccaaucccu gccagaacgg cgcgcaaugc 1620
uacaauaggg ccucggacua cuucugcaag ugccccgagg acuacgaggg caaaaacugc 1680
agccaccuga aggaccacug uaggacaacc cccugcgaag ucaucgacuc cugcaccgug 1740
gccauggccu ccaacgacac cccagaaggc guacguuaca ucagcuccaa cgucugcggg 1800
ccccacggga agugcaagag ccagagcggc ggcaaguuca cgugugacug caacaaaggg 1860
uucaccggca ccuacugcca ugagaacaua aaugacugcg aguccaaccc cugucggaac 1920
ggcggcaccu gcaucgacgg cguaaacucu uacaaaugua ucugcagcga cggcugggag 1980
ggcgccuacu gcgagaccaa caucaacgac ugcagccaaa accccuguca caacggcggg 2040
accugccgcg accucgucaa cgacuucuac ugcgacugca agaacggcug gaagggcaag 2100
accugccaca gccgggacuc gcagugugau gaggccaccu gcaacaaugg cggcaccugc 2160
uaugaugagg gggacgccuu caaauguaug ugccccggcg ggugggaggg caccacuugc 2220
aacaucgcca ggaacuccuc cugccucccc aaccccugcc acaacggagg gacgugcgug 2280
gugaacgggg agagcuucac cugcgugugc aaggagggcu gggaaggccc cauuugcgcg 2340
cagaacacua acgauugcag cccccacccc ugcuacaacu ccggcaccug cguggacggg 2400
gacaacuggu accggugcga gugcgccccc ggcuucgccg gcccggacug caggaucaac 2460
aucaacgaau gucagagcag ccccugcgcc uucggagcca ccugcgugga cgagauaaac 2520
ggcuaccggu gcgucugccc ccccggucac ucuggugcca agugccaaga ggucagcggc 2580
aggccgugca ucaccauggg cuccgugauc ccggauggcg ccaaauggga cgaugacugc 2640
aacaccugcc agugccuuaa cggucggauc gcgugcagca aggugguggug uggccccagg 2700 cccugccucc ugcacaaggg gcacagcgag ugccccuccg gacaguccug uauccccauc 2760
cuggacgacc agugcuucgu ccaccccugc accggagugg gcgaaugcag gagcagcucc 2820
cugcagccgg ugaagaccaa gugcaccagc gacuccuacu accaggacaa uugcgccaac 2880
aucaccuuca ccuucaacaa ggagaugaug agccccggcc ugaccaccga gcacaucugc 2940
agcgagcugc gcaaccugaa caucuugaag aacgugagcg ccgaguauuc caucuacauc 3000
gccugcgagc ccagcccgag cgccaauaac gagauccacg uggccaucag cgccgaggac 3060
auccgggaug acggcaaucc caucaaggag aucaccgaua agaucaucga ccuggucagc 3120
aagcgcgacg gcaauagcuc gcugaucgcg gccguggccg aggugagggu gcagcggcgg 3180
ccccugaaga acaggaccga cuuucuggua ccccuccuga gcucggugcu gaccguugcc 3240
uggaucuguu gucuggugac cgccuucuac uggugccugc ggaaaaggcg gaagcccggc 3300
ucccauaccc auagcgcauc cgaagacaac accaccaaca acguccguga gcagcugaac 3360
cagaucaaga accccauaga gaaacacggc gccaacaccg ugcccaucaa ggacuacgaa 3420
aacaagaacu ccaagauguc caaaaucagg acccacaaca gcgaggugga agaggacgac 3480
auggauaaac accagcagaa ggcccguuuc gccaagcagc ccgccuacac cuuaguggac 3540
agggaggaga aaccccccaa cgggaccccc accaagcacc caaacuggac gaacaagcag 3600
gauaaccggg accuggaauc agcgcagucc cugaacagaa uggaauacau cguc 3654

<210> SEQ ID NO 95
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 95 augaggucce cccgaaccag gggcaggucc ggucggcccc ugagccugcu ccuggcccuc 60
cugugcgccc ugagagccaa ggugugugga gccagcgggc aguucgagcu cgagauccuc 120
uccaugcaga acgugaacgg cgagcugcag aacggcaacu gcugcggagg cgccaggaau 180
cccggcgauc ggaagugcac cagggacgag ugcgacaccu auuucaaggu gugccucaag 240
gaguaccaaa gcagggugac cgccggcggc cccugcuccu ucggcagcgg cagcaccccc 300
gugauagggg gcaacacguu caaccucaag gccagcaggg gcaacgacag gaaccgcauc 360
gugcugcccu ucagcuuugc guggccccgu uccuacaccc ugcuggucga ggccugggac 420
agcuccaacg auaccgugca gcccgacucc aucauugaga aggccagcca cagcggcaug 480
aucaacccca gcaggcagug gcaaacccug aagcagaaca ccggaguggc ccauuucgaa 540

-continued

```
uaccagauca gggugaccug cgaugacuac uauuaugguu uugggugcaa caaauucugc    600
cggccccgag acgacuucuu cggucacuau gccugcgacc agaacggcaa caagaccugu    660
auggaggggu ggaugggccc ugagugcaac cgggccaucu gucgccaggg gugcuccccc    720
aagcacggca gcugcaagcu gccuggcgau ugccggugucc aguacgggug gcagggucuc   780
uacugcgaca agugcauccc ccacccgggc ugugugcacg gcaucugcaa cgagcccugg    840
cagugccugu gcgaaaccaa uuggggcggc caacugugcg acaaggaccu gaacuacugu    900
ggcacccacc agcccugccu gaacgggggc acuugcucca acacgggccc cgacaaguau    960
cagugcagcu guccugaggg cuacagcggc cccaacugug agaucgccga gcaugccugc   1020
cugagcgacc cgugccacaa ucguggcagc uguaaggaga ccagccuggg cuucgagugc   1080
gagugcagcc cggguuggac cggacccacc ugcagcacca acaucgacga uugcagcccc   1140
aacaacuguu cacacggggg cacgugccaa gaccugguga acggguucaa gugugucugc   1200
cccccccagu ggaccggcaa aaccugucag cucgacgcca acgaauguga ggccaagccc   1260
ugcgugaaug cgaagagcug caagaaccug aucgcgucgu acuauugcga uugccugccc   1320
ggcuggaugg gccagaacug cgacaucaac aucaacgacu gccugggcca gugccaaaac   1380
gacgccucuu gccgcgaucu ggucaacggg uaccgcugca ucugcccucc gggguacgcc   1440
ggggaucacu gugagaggga cauagaugag ugcgcgucca accccugccu gaacgggggg   1500
cacugccaga acgagaucaa cagguuucag ugccugugcc ccaccggcuu cuccggcaac   1560
cugugccagc uugacaucga cuacugcgag cccaaucccu gccagaaugg cgcccagugc   1620
uacaacaggg ccagcgacua uuucugcaag ugucccgagg acuacgaggg gaagaauugc   1680
ucccaccuga aagaccacug caggacgacc cccugugagg ugaucgacag cugcaccgug   1740
gccauggccu ccaacgacac ccccgagggc gugagguaca ucagcagcaa cgucugcggc   1800
ccccacggca agugcaagag ccagagcggc ggaaaguuca ccugcgacug caacaagggg   1860
uucacgggca ccuacugcca cgagaacauc aacgacugcg aguccaaccc cugcaggaac   1920
ggcggcacgu gcauagacgg gguuaacagc uauaagugua ucugcucgga cgggugggaa   1980
ggcgccuacu gcgagaccaa caucaacgac ugcucacaga auccgugcca caacgggggc   2040
accugcaggg accuggugaa cgacuucuau ugcgacugca agaacggcug gaaagguaag   2100
acaugccacu cccgggacuc ccagugcgac gaggccaccu gcaacaacgg aggaaccugc   2160
uacgaugagg gcgacgccuu caagugcaug ugccccgggg gaugggaagg caccaccugc   2220
aacaucgcca ggaacuccag cugucucccc aacccgugcc acaacggcgg gacgugcgug   2280
gugaauggcg aguccuucac gugcgugugc aaggagggcu gggagggccc caucugcgcg   2340
cagaacacca acgauugcag cccccacccg ugcuacaacu caggcaccug cgucgacggu   2400
gacaacuggu accggugcga gugcgcccca ggguucgcgg gccccgacug caggaucaac   2460
aucaacgagu gccaguccag ccccugcgcc uuuggcgcca ccugcgugga cgagaucaac   2520
ggcuacaggu gcgugugccc ccccggccau agcggcgcca agugccagga ggugagcggc   2580
aggcccugca ucaccauggg cagcgugauc cccgacggcg ccaaguggga cgacgacugc   2640
aauacgugcc agugccugaa cggacgcauu gccugcucca aggugguggug cggcccccgg   2700
ccgugccugc uccacaaggg gcacagcgag ugccccuccg gccagagcug caucccccauc  2760
cucgacgacc agugcuucgu ccaccccugc accggcgugg gcgagugcag guccuccagc   2820
cugcagccag ugaaaaccaa guguaccagc gacuccuacu accaggacaa cugcgccaac   2880
aucacauuca cauucaacaa ggagaugaug agcccgggcc ugaccaccga gcacaucugc   2940
```

agcgaacuca gaaaccugaa cauccugaag aacgugucgg ccgaguacag caucuauauc 3000
gcgugcgagc ccagccccag cgcgaauaac gagauccacg uggccauaag cgcggaggac 3060
auccgggacg acggcaaccc caucaaggag aucaccgaca agauuauuga ccuggucucc 3120
aagagggacg gcaauagcuc ccugauugcc gccgucgccg aagugcgggu gcaaagaagg 3180
ccccugaaaa accggacgga uuuccugguc ccccuccuga gcagcgugcu gaccgucgcc 3240
uggaucugcu gucuggugac ggccuucuac uggugccuca gaaagaggcg caaacccggc 3300
ucgcacaccc auagcgccuc agaggacaac accacgaaua acgugcggga acagcugaac 3360
caaauaaaaa accccaucga gaagcacggg gcuaacaccg ugccgaucaa ggacuacgag 3420
aacaagaaca gcaagauguc caagauccga acccacaaca gcgaggucga ggaggacgac 3480
auggacaagc accagcagaa ggcgagguuc gccaagcagc ccgccuacac ccugguagac 3540
cgggaggaga agccgcccaa cggcaccccc acgaaacacc ccaacuggac caacaaacaa 3600
gacaacaggg accuggagag cgcccagucc cugaacagga uggaauauau uguc 3654

<210> SEQ ID NO 96
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 96
augaggagcc ccaggacacg gggccggagc gggcgaccuc ugucccugcu ccuggcccug 60
cugugcgccc ugagagccaa agugugcggc gccagcgggc aguucgagcu ggagauacug 120
agcaugcaga acgugaacgg cgagcugcag aacggcaacu guuguggggg cgcgcggaac 180
cccggggaca ggaagugcac ccgggacgag ugcgacaccu acuucaaggu gugccucaag 240
gaauaccaaa gccgugugac agcugggggc cccugcagcu ucggguccgg auccaccccc 300
gucaucggcg gcaacaccuu caaccucaag gccagcaggg gcaacgacag gaaccgaauc 360
gugcugcccu uuucguuugc cuggccccgc agcuacaccc uccuagugga ggccugggac 420
agcagcaacg acaccgugca gcccgacucc aucaucgaga aggcauccca cagcgggaug 480
aucaaucccu cccgccagug gcagacgcug aagcagaaca ccggcguggc ccacuucgaa 540
uaccaaauca gggugacgug cgaugacuac uauuacggcu ucgggugcaa caaguucugc 600
aggccgaggg augacuucuu cggccacuau gccugcgacc agaacggaaa caaaaaccugc 660 auggaggguu ggaugggacc cgagugcaac agggccaucu gccgccaggg cugcucacca 720
aagcacggca gcuguaagcu acccggcgac ugucggugcc aguacgguug gcagggccug 780
uacugugaca agugcauccc ccacccccggc ugcgugcacg gcaucugcaa ugagccgugg 840
cagugccugu gugaaaccaa cuggggguggg cagcugugcg acaaggaccu gaauuacugc 900
ggcacccacc agcccugucu gaacggcggc accugcucca acaccggccc ggacaaguau 960
cagugcaguu gccccgaggg cuauagcggc cccaacugcg agaucgccga gcacgccugc 1020
cuguccgacc cgugccacaa caggggggagc ugcaaagaga ccagccuggg guucgagugc 1080
gagugcagcc ccggguggac cggacccacc ugcagcacca acaucgauga uugcagcccu 1140
aacaacugcu cccacggcgg caccugccag gaccugguga acggcuuuaa gugcguaugc 1200
cccccccaau ggacggggaa gaccugucag cucgacgcca augaaugcga ggcaaaaccg 1260
ugugugaacg ccaagagcug caaaaaccuc aucgcguccu acuacugcga cugccugccc 1320

-continued

```
ggcuggaugg ggcagaacug ugacaucaac aucaacgauu gccugggcca augccagaau   1380
gaugccuccu gcagggaccu ugugaacggc uacaggugca uaugcccccc cggcuacgcc   1440
ggcgaucacu gcgagcggga uauagacgag ugugccagca accccugccu caacgggggg   1500
cacugccaga augagaucaa cagauuucaa ugccugugcc ccacaggauu uagcggaaau   1560
cugugccaac uggacaucga cuacugcgag cccaaucccu gccagaacgg ggcccagugc   1620
uacaaccggg ccagcgacua cuuuugcaag ugccccgagg acuacgaggg aaaaaacugc   1680
agccaccuga aggaccauug caggaccacc cccugugagg ugauugacag cugcaccgug   1740
gccauggccu caaacgacac ccccgagggu gugagguaua ucagcucgaa cgugugcggc   1800
ccccacggca agugcaaguc acaaagcggg ggaaaguuca ccugcgacug caacaagggc   1860
uucaccggua ccuacugcca cgagaacauc aacgacugug agagcaaccc cuguagaaac   1920
ggggggaccu gcaucgacgg agugaauucc uauaagugca ucuguagcga cgggugggag   1980
ggcgccuacu gcgagaccaa uaucaacgau ugcagccaga accccugcca caacgggggc   2040
accugccgag aucucgugaa cgacuucuac ugcgacugua aaaacgguug gaaaggcaaa   2100
accugccacu cccgcgauuc ccagugcgau gaggcgaccu gcaauaaugg aggcaccugc   2160
uacgacgagg gcgacgccuu uaagugcaug ugccccggcg gcugggaagg caccaccugc   2220
aauaucgcga gaaauagcag cugccugccc aaccccugcc auaacggcgg gaccugcgug   2280
gugaauggcg agagcuucac cugcgucugu aaggagggcu gggaaggucc caucugugcc   2340
cagaacacca acgacugcag cccccauccc ugcuacaaca gcggcaccug cguggacggc   2400
gacaauuggu acaggugcga gugcgccccc ggguuugccg gccccgacug caggaucaac   2460
aucaacgagu gccagaguag ccccugugcc uucggcgcca ccugcgugga cgagaucaac   2520
ggcuaccggu gcgugugccc ccccggccac uccggcgcca agugucaaga ggugagcgga   2580
cgacccugua ucaccauggg cucggugauc cccgacggcg ccaaguggga cgacgacugc   2640
aacacgugcc agugccucaa cgggaggauc gccugcagca aggugugguag cgguccccagg   2700
cccugccugc ugcacaaagg ccacuccgag ugccccagcg gccagagcug uaucccccauc   2760
cuggaugauc agugcuucgu ccaucccugu acuggcgugg gcgagugcag gagcagcagc   2820
cuccagcccg ugaaaaccaa gugcacgagc gacuccuauu accaagauaa cugugccaac   2880
aucaccuuca ccuuuaacaa ggagaugaug ucgcccggac ugaccaccga gcauaucugc   2940
agcgagcuga ggaaccugaa cauacugaag aaugugucccg ccgaauauuc caucuacauc   3000
gccugugagc cuagcccgag cgccaacaac gagauccacg uggccaucuc cgccgaggau   3060
aucagggacg acgggaaccc caucaaagag aucaccgaua agaucaucga ccuggugucu   3120
aagcgcgacg guaacagcuc ccuaaucgcc gccguggccg aggugcgcgu gcagcgcagg   3180
ccgcugaaga accgcaccga cuuccuggug ccccugcuga gcagcgugcu caccguggcc   3240
uggauaugcu gccuggugac cgccuucuac uggugccugc ggaagcggcg uaaaccggga   3300
agccauaccc acagcgccag cgaggauaau accaccaaua acgugcggga gcagcugaac   3360
cagaucaaga accccaucga aaagcacggg gcgaacaccg ugcccaucaa ggacuacgag   3420
aauaagaacu ccaagaugag caagauccgc acacacaaca gcgaggugga ggaggacgau   3480
auggacaagc accagcagaa ggccagguuc gccaagcagc ccgccuacac ccuuguggac   3540
cgcgaagaga agcccccgaa cggcaccccc accaagcacc ccaacuggac caacaaacag   3600
gauaaccgug accuggaaag cgcgcagucc cugaaccgca uggaguacau agug         3654
```

<210> SEQ ID NO 97
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 97
augaggagcc cccggaccag ggggcggagc ggcaggcccc ugagccuccu gcuggcccug 60
cuuugcgcac ugagggccaa ggugugugg gccagcgggc aguucgagcu cgaaauccug 120
agcaugcaga acgugaacgg cgagcugcag aauggcaauu guugcggcgg cgccaggaac 180
cccggcgacc ggaagugcac ccgggacgaa ugcgacaccu acuucaaggu gugccucaag 240
gaguaccaga gccgcgugac cgccggcgga cccugcagcu ucggcagcgg cagcaccccc 300
gugaucgggg gcaacaccuu caaccugaag gcaucccgcg ggaacgacag gaacaggauc 360
gugcugccgu ucagcuucgc cuggccgcga uccuacacgc ugcugguuga ggccugggac 420
agcagcaaug acacggugca acccgacagc auuaucgaga aggccagcca cuccggcaug 480
aucaaccccu cccggcagug gcagacccug aagcagaaca cuggaguugc acacuucgag 540
uaccaaauca gggucacgug cgacgacuac uauuacgggu ucggcuguaa caaguucugc 600
aggccccgug augacuucuu uggacacuac gccugcgacc agaacggaaa caagaccugc 660
auggaagggu ggaugggccc cgagugcaac agggccaucu guagacaagg cugcagcccc 720
aaacacggcu ccuguaagcu gcccggcgac ugccggugcc aguacggcug gcaggggcuc 780
uacugcgaca agugcauucc ccaucccggc ugcgugcacg gcauauguaa cgaacccugg 840
caaugccucu gcgagaccaa cuggggcggg cagcugugcg acaaagaccu gaacuacugu 900
ggcacccauc agcccugccu gaacgggggg acuugcucca auaccggucc cgacaaguau 960
cagugcagcu gccccgaggg cuacuccggg cccaacugcg agaucgccga acacgccugu 1020
cuguccgacc ccugccacaa cagaggcagc ugcaaggaga ccagccuggg cuuugagugc 1080
gagugcuccc ccggcuggac cgggcccacc ugcagcacca acaucgacga uugcagcccc 1140
aacaauugcu cccacggcgg cacuugccaa gaccugguga acggcuucaa gugcgugugc 1200 ccccccagu ggaccgguaa aacaugccag cuggacgcca acgagugcga ggccaagccc 1260
ugcgugaacg ccaagagcug caaaaaccug aucgccaguu acuacugcga cugccugccu 1320
ggauggaugg gccagaacug cgacaucaac aucaacgacu gccugggcca gugccagaac 1380
gacgcaagcu gccgugaccu ggugaacggc uacaggugca ucugcccccc cggguacgcc 1440
ggugaccacu gcgaacggga cauagaugag ugcgccagca accccugccu gaacggcgga 1500
cacugccaga augagaucaa uagguuccaa ugccucugcc ccaccggcuu uagcggcaau 1560
cugugccagc uggacaucga uuacugugag cccaaccccu gccagaaugg agcccagugc 1620
uacaaccggg ccuccgacua uuucuguaag uguccccgaag acuacgaggg uaagaacugc 1680
ucccaccuga aggaccacug ccggaccacu ccgugcgagg ucaucgacag cugcaccguc 1740
gccauggcca gcaaugacac acccgagggc gugagguaca ucuccuccaa cgugugugc 1800 ccccacggca agugcaagag ccagagcgga ggcaaguuca ccugcgacug caacaagggg 1860
uucaccggca cuuacugcca cgagaacauc aacgacugcg aauccaaccc cugucgaaac 1920
gggggcaccu gcauugacgg cgugaacagc uauaagugca ucugcuccga cggguggggag 1980 ggggccuacu gcgaaaccaa uauaaacgau ugcagccaga accccuguca caacgggggc 2040
acaugcaggg accuggucaa cgacuucuac ugugacugca agaacggcug gaagggcaag 2100

-continued acaugucaca gcagggacag ccagugcgac gaggccaccu guaacaaugg cggcaccugc 2160
uaugacgaag gcgacgccuu caaauguaug ugccccggcg guugggaggg gacgacgugc 2220
aauauugcga ggaacuccag cugucugccc aaccccugcc acaacggagg caccugugug 2280
gugaacggcg agagcuuuac gugcgucugu aaagagggcu gggaaggccc caucugcgcc 2340
caaaacacga acgacugcag cccccacccc uguuacaaua gcggcaccug cgucgacggu 2400
gacaacuggu auaggugcga gugugccccg ggcuuugccg ggcccgacug ccggaucaau 2460
aucaacgagu gccaguccag cccaugugcg uucggcgcca ccugcgugga cgaaaucaac 2520
ggcuacaggu gcgucugccc cccggggcac agcggagcca aaugucagga agucucuggg 2580
aggcccugca ucaccauggg cagcguaauc cccgacgggg cuaaguggga cgacgacugc 2640
aauaccuguc agugucugaa cggcaggauu gccugcagca aaguguggug uggcccgcgg 2700
cccugucucc ugcacaaggg ccacuccgag ugucccagcg gccaauccug cauccccauc 2760
cucgacgacc agugcuuugu gcaccccugc acaggcgugg gagaguguag gucgagcucc 2820
cugcagcccg ugaagaccaa gugcaccagc gauuccuacu accaggacaa cugcgcgaau 2880
aucaccuuua ccuuuaacaa ggagaugaug agccccgggc ugaccaccga gcacaucugc 2940
agcgagcugc ggaaccugaa cauccucaaa aacgucagcg ccgaguauag caucuacauu 3000
gccugcgagc ccagccccag cgccaacaac gaaauacacg uggccaucag cgccgaggac 3060
aucagggacg acggcaaccc gaucaaggag aucaccgaua agauaaucga ccuggugucc 3120
aagagggacg gcaauagcuc ccugaucgcc gccguggccg aagugagggu gcagaggagg 3180
ccccugaaaa acaggaccga uuuccugguu ccccugcuga gcagcgugcu gacaguggcu 3240
uggaucugcu gccucguaac ugcauucuac uggugccuga ggaagaggag gaagcccggc 3300
agucacaccc acagcgccuc cgaggauaac accacuaaca augugcggga gcagcugaac 3360
cagaucaaga aucccauaga aaaacauggc gccaacaccg ugcccauuaa agauuacgag 3420
aacaaaaaua gcaagauguc caagauccgc acccacaaca gcgaggugga ggaggacgac 3480
auggacaagc accagcagaa ggccagguuc gccaagcagc ccgcguacac ccugguggac 3540
cgugaggaga agcccccaa cggcaccccc accaagcacc ccaacuggac caacaagcaa 3600
gauaaucggg accuggaauc cgcccagagc cugaacagga uggaguacau cgug 3654

<210> SEQ ID NO 98
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 98
augaggagcc cgagaacgag ggggcggucc ggcaggccgc ugagccuccu gcuggcccug 60
cugugcgccc ugcgggcaaa ggugugugge gccuccgggc aguucgagcu ggagauccug 120
agcaugcaaa acgugaacgg cgaacuccag aacggcaauu gcugcggcgg cgccagaaac 180
cccggggauc gaaagugcac ccgggacgag ugcgacaccu acuucaaagu gugucucaaa 240
gaauaccaga gcagggugac cgccggcggg cccugcagcu ucggcagcgg cagcaccccc 300
gugaucggcg ggaacaccuu caaccugaag gccagccgcg gcaacgacag gaaucggauc 360
guguugccgu ucagcuucgc cuggccccgu uccuacaccc ugcuggugga ggccugggac 420
agcagcaacg auaccgugca gccagacagc auaaucgaga aggccagcca cuccgguaug 480
aucaacccca gcaggcagug gcagacccug aagcaaaaca ccggcguggc ccauuucgag 540

```
uaccagauca gggucacgug cgacgacuau uacuacgggu ucgggugcaa caaguucugc    600
aggccccggg augacuucuu uggacacuac gccugugacc agaacggaaa caaaacuugc    660
auggagggcu ggaugggccc ggagugcaau agggccauuu gcaggcaagg cugcagcccc    720
aagcacggcu ccugcaagcu ccccggcgac ugccgaugcc aauauggcug gcagggccuc    780
uacugugaca agugcauccc ccacccgggc ugcguccacg gaaucugcaa ugagcccugg    840
cagugucugu gcgagacgaa cuggggguggc cagcugugcg acaaggaccu gaacuacugc    900
gggacccacc agcccugccu gaacggcggg accuguucca acaccggccc ggacaaguau    960
cagugcagcu gcccggaagg guacuccggc ccgaacugcg aaaucgccga acacgcuugc   1020
cucagcgacc ccugccacaa ccgcgggagc ugcaaggaga ccagccuggg cuuugagugc   1080
gaauguuccc ccggcuggac cgggcccaca ugcuccacca acauagacga uuguagcccc   1140
aacaacugcu cccacggggg gaccugccaa gaccugguca acggauucaa gugcgugugu   1200
ccccccagu ggacggguaa gaccugccaa cuggacgcca acgaaugcga ggccaagccc   1260
ugugugaaug ccaagagcug caagaaccug aucgccagcu acuacuguga cugccugccc   1320
ggcuggaugg gccagaauug cgacaucaau aucaacgacu gccugggcca gugccagaau   1380
gacgccuccu gcagggaccu ggugaacggc uacaggugca uaugcccccc cggcuacgcc   1440
ggcgaccacu gcgaacguga caucgacgag ugcgccucaa accccugccu gaacggcgga   1500
cacugccaga acgagaucaa ccgauuccag ugucugugcc ccaccggguu uagcgggaac   1560
cucugccagc ucgauaucga cuacugcgaa cccaaccccu gccagaacgg cgcccagugc   1620
uacaaccggg ccagcgacua uuucuguaaa ugccccgagg acuacgaggg gaaaaacugu   1680
agccaccuga aggaccacug caggaccaca cccugcgaag ugaucgacag cugcaccgug   1740
gccauggcca gcaaugacac ccccgaaggc gugagguaua uaagcagcaa cguaugcggc   1800
ccccacggca aguguaagag ccagagcggc ggcaaguuua cgugcgacug caacaaaggc   1860
uucaccggca ccuacuguca cgagaacauc aacgacugcg agagcaaccc cugccgcaac   1920
gggggcaccu gcaucgacgg ugugaacagc uacaagugca ucugcagcga cggcugggag   1980
ggcgccuacu gugagacgaa caucaacgac ugcagccaga acccgugcca uaacgggggc   2040
accugcaggg aucuggugaa cgacuuuuau ugcgacugca agaacggcug gaagggcaag   2100
accugccaca gccgggacag ccagugugac gaggccaccu gcaacaacgg cggcaccugc   2160
uacgacgaag gggacgccuu uaagugcaug ugcccgggcg gguggggaggg caccaccugc   2220
aacaucgcca ggaauuccuc cugucugccc aacccauguc acaacggugg cacgugcgug   2280
gugaacgggg aguccuuuac cugugugugc aaggaggggu gggagggacc cauaugugcg   2340
cagaauacca acgacugcuc cccccaccca uguuauaaca gcgguacaug uguggauggg   2400
gacaacuggu accgguguga gugcgccccc ggcuucgccg gccccgauug caggaucaac   2460
aucaaugagu gccagagcuc ccccugcgcc uucggcgcca caugcgucga cgaaaucaac   2520
ggcuacaggu gugugugccc cccgggacac agcggugcca agugccagga agugucaggc   2580
aggcccugua uuaccauggg cagcgugauc cccgacggag ccaaguggga ugacgacugc   2640
aacaccugcc agugccugaa cggccguauc gccugcagca aggugguggug cggcccccgg   2700
ccgugccugc ugcacaaggg gcacuccgag ugccccagcg ggcagagcug cauccccauc   2760
uuggacgacc agugcuucgu gcaccccugc accggcgugg gcgaaugccg uagcagcucc   2820
cugcagcccg ugaagaccaa gugcaccagc gauuccuacu aucaggauaa cugcgccaac   2880
```

aucaccuuca ccuucaacaa ggagaugaug agccccggcc ugaccacgga acacaucugc 2940
agcgagcuga ggaaccugaa cauccugaag aacguguccg ccgaauacag caucuacauc 3000
gccugcgagc ccagccccag cgccaacaac gaaauccacg ucgccaucuc ugccgaggac 3060
auccgcgacg acggcaaccc cauuaaggag auaaccgaca agaucaucga ccuggugucc 3120
aagcgagacg gaaauucuag ccugaucgcc gccguagccg agguacgugu gcagaggagg 3180
ccccucaaga auaggaccga cuuccuggug ccccugcuga gcagcgugcu caccguggcg 3240
uggaucugcu gccuggugac cgccuuuuac uggugccugc gaaagaggag gaagcccggu 3300
ucacacacgc acagcgccag cgaagacaac accaccaaca augugcgcga gcagcucaac 3360
cagaucaaga aucccaucga gaagcacggc gccaacacgg uccccaucaa ggacuacgag 3420
aacaaaaaca gcaagauguc caagauccgc acccauaaca gcgaggucga agaagacgac 3480
auggacaaac accagcaaaa ggccagguuc gccaagcagc cggccuacac ccugguggac 3540
agggaggaga agcccccgaa cggcaccccc accaagcacc ccaacuggac caacaaacag 3600
gacaaccggg aucuggagag ugcgcagagc cugaacagga uggaguacau cgug 3654

<210> SEQ ID NO 99
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 99
augagaagcc caaggacgcg cgguaggagc ggcaggcccc ucagccugcu gcuggcucua 60
cugugcgccc ugcgggccaa gguuuguggg gccagugggc aauucgagcu ggagauccug 120
agcaugcaaa acgugaacgg ggagcuucag aaugguaacu gcugcggcgg ggcccggaau 180
cccggcgacc ggaaguguac gagggaugag ugugacaccu acuuuaaggu gugccugaag 240
gaguaccaga gcaggguuac ggcaggcggc cccugcagcu uuggcagcgg cuccaccccg 300
gugaucggcg gcaacacauu caaccugaag gccagccgcg ggaacgaucg uaacaggauc 360
gugcuccccu uuagcuucgc cuggccccgc agcuacacgc ugcuggugga ggccugggac 420
agcagcaacg acaccgucca gcccgauagc auuaucgaga aggccuccca cagcgguaug 480
aucaacccga gccggcagug gcagacccug aagcagaaca ccggcguggc ccacuucgag 540
uaccagaucc gggugaccug cgacgacuac uauuacgguu ucggcugcaa caaguuuugc 600
cgaccccggg acgacuuuuu cggcauuac gccugcgacc aaaacggcaa caaaaccugc 660
auggagggcu ggaugggccc ggagugcaac cgggccaucu gccggcaggg guguagcccc 720
aagcacggca gcugcaagcu gcccggcgau ugccggugcc aguacgggug gcagggccug 780
uacugcgaca agugcauccc gcaccccgga ugugugcacg gcaucugcaa cgagcccugg 840
cagugccugu gcgaaaccaa cugggggggu cagcugugug acaaggaucu gaacuacugc 900
ggaacccacc aacccugccu gaacggcgga acuugcucga acacgggccc cgacaaguac 960
cagugcagcu gucccgaggg cuacagcggg cccaacugug agaucgccga acacgcuugc 1020
cugagcgacc cgugucacaa ccggggcagc ugcaaggaga ccucccucgg cuucgagugc 1080
gagugcuccc cagggguggac cggccccacc ugcagcacca acaucgacga uugcagcccc 1140
aacaacugua gccacggcgg gacgugccag gaccugguca acggcuucaa augugucugu 1200 ccccccagu ggaccggcaa aaccugccag cucgacgcca acgagugcga agccaagccg 1260
ugcgugaacg cgaagagcug caagaaccug aucgccuccu acuacugcga cugccugccc 1320

-continued

```
ggcuggaugg gccagaacug cgacauaaac aucaacgacu gccugggcca gugccagaac   1380
gaugccagcu gucgagaccu ggugaacggg uaccggugca ucugcccccc cggauacgcc   1440
ggggaccacu gcgagcgcga caucgacgaa ugugccucga accccugccu gaacgggggc   1500
cacugccaaa acgagaucaa ucguuuccag ugccugugcc ccaccggcuu cucugggaac   1560
cugugccagc uggacaucga cuacugcgag cccaaccccu gccagaacgg ggcgcagugc   1620
uauaaccggg ccuccgauua cuucugcaag ugccccgagg acuaugaggg aaaaaacugc   1680
ucccaccuga aggaucacug uaggaccacc cccugugagg ugaucgacag cugcaccgug   1740
gccauggcca gcaacgacac ccccgagggc gugcgcuaca ucagcuccaa cgugugcggc   1800
ccccauggua aguguaaguc gcagagcggc gggaaguuca ccugcgacug caacaagggc   1860
uuuacgggga ccuacuguca ugaaaacauc aacgacugcg agagcaaccc cugucgcaac   1920
ggcggcaccu gcaucgaugg cgucaacagc uacaagugca ucugcuccga cggaugggag   1980
ggcgccuacu gcgagaccaa caucaacgac ugcagccaga acccgugcca caauggcggc   2040
accugccgug accuggugaa cgacuuuuac ugcgacugca agaacgggug gaaaggcaaa   2100
accugccacu ccagggacag ccagugcgac gaggcgaccu gcaacaaugg cgggacgugc   2160
uacgacgagg gcgacgccuu caagugcaug ugccccggcg gaugggaagg cacuaccugu   2220
aacaucgccc ggaauagcuc cugccugccg aaccccugcc acaacggggg cacgugcguc   2280
gugaacggcg aaagcuucac cugcgugugc aaggagggcu gggagggccc caucugugcc   2340
cagaacacca acgacugcag cccccacccc ugcuacaaua gcggcaccug cguggacgga   2400
gacaacuggu accgaugcga gugcgccccu ggcuucgccg gacccgauug ccgcauuaac   2460
aucaaugaau gccagagcag ccccugcgcc uuuggagcca ccugcgucga ugagaucaac   2520
ggcuaccgcu gugucugccc ccccggccac agcggggcca agugccagga ggucucaggu   2580
cggcccugca ucaccauggg cagcgucauc cccgacgggg ccaaauggga ugacgacugc   2640
aauaccugcc agugucugaa cggccgaauc gccugcucca agguguggug cgggcccagg   2700
cccugccucc uucacaaagg ccauagcgag ugccccuccg ggcaauccug caucccccauc   2760
cuggacgacc aaugcuucgu gcaccccugc accggcgugg gggagugcag gagcagcagc   2820
cugcagcccg ugaagaccaa gugcaccucc gauagcuauu accaggacaa cugcgccaac   2880
aucaccuuca ccuuuaacaa agaaaugaug ucacccggcc ugacgaccga gcauaucugc   2940
agcgagcugc ggaaccugaa cauccugaaa aacgugucgg ccgaguacag uauauacauc   3000
gccugcgagc ccagccccag cgccaacaac gagauacaug uggccauaag cgccgaagac   3060
aucagggacg auggcaaccc caucaaggag aucaccgaca aaauaaucga ccuggugagc   3120
aagcgggaug gcaauagcag ccugaucgcc gccguggccg aggugagggu gcagcggagg   3180
ccccugaaga aucgcaccga cuuccugguc ccgcugcuua gcuccguccu gacggucgcc   3240
uggaucugcu gccugguagac cgccuucuac uggugcuuga ggaagcggag gaagcccggg   3300
ucacauaccc acuccgccag cgaggacaac accaccaaua acgugcggga acagcugaac   3360
cagaucaaga accccaucga gaagcauggu gccaacaccg ugcccaucaa ggacuaugaa   3420
aacaagaacu ccaagaugag caagaucagg acccacaacu ccgaggugga agaggacgac   3480
auggacaagc accagcagaa agcccguuuc gccaagcagc ccgccuacac ccugguggac   3540
cgagaggaaa agccgcccaa cggcaccccc accaagcauc ccaacuggac caacaagcag   3600
gacaaccgug accuggagag cgcccagucg cucaaccgca uggaguacau cgug         3654
```

<210> SEQ ID NO 100
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 100
augcggucgc cgagaaccag gggccggagc ggccggcccc ugucgcugcu gcuggcccug 60
cucugcgcgc ugagagccaa ggugugugge gccagcggcc aguucgagcu ugagauccug 120
uccaugcaaa acgucaacgg cgagcuccag aacggaaacu guugcggcgg cgcccgcaac 180
cccggcgaca ggaagugcac ccgcgacgag ugcgacaccu acuucaaggu gugccugaag 240
gaguaccagu cccgcgugac cgcuggcgga ccgugcagcu ucggcucagg cagcaccccc 300
gugaucgggg gcaauaccuu caaucucaag gccagccgag gaaacgacag gaacaggauc 360
gugcuccccu uuagcuuugc cuggccucgu agcuacaccc ugcuggugga ggccugggac 420
ucaagcaaug acacgguuca gcccgacagc aucaucgaaa aggccucuca cagcggaaug 480
aucaacccca gcaggcagug gcagacccuc aagcagaaca cgggcguggc ccacuucgag 540
uaccagaucc gugugaccug cgaugacuac uauuacgguu ucgggugua uaaguucugc 600 aggcccaggg augacuuuuu uggccacuac gccugcgacc agaauggcaa caagaccugc 660
auggagggau ggaugggccc cgagugcaac cgugccaucu gucggcaggg cugcucgccc 720
aagcacggca gcugcaagcu ucccggcgac ugucggugcc aguacggaug gcaagggcug 780
uacugcgaca agugcauccc ccaucccggc uguguccacg guaucugcaa cgagcccugg 840
cagugucugu gcgagaccaa cuggggcggc cagcugugcg acaaggaccu gaacuacugc 900
ggcacccacc agcccugccu gaaugggggc accuguucua acaccgggcc ggacaaguac 960
caguguuccu gccccgaggg cuacagcggc cccaacugcg agaucgccga gcacgccugc 1020
cuguccgacc ccugccauaa uaggggcucc ugcaaggaga ccucccuggg cuuugagugc 1080
gaguguucgc ccggcuggac cggccccacc ugcaguacca acaucgacga cugcagcccc 1140
aacaacugua gccacggcgg cacaugccaa gaccugguga acggcuucaa gugcgucugc 1200
ccgccgcagu ggaccgggaa gaccugucag cuggaugcca acgagugcga ggcuaaaccc 1260
ugcgugaacg cgaagagcug uaagaaccug auugccagcu acuacugcga cugccugccg 1320
ggcuggaugg ggcagaauug cgacaucaac aucaacgacu gucugggcca augccagaac 1380
gacgccagcu gucgggaccu ggucaacgga uacaggugua ucuguccccc cggcuacgcc 1440
ggcgaccacu gcgagcggga caucgacgaa ugcgccagca acccuugucu gaacggaggc 1500
cacugccaga acgagaucaa cagguuucag ugccucugcc ccaccggguu cagcgggaac 1560
cugugccagc uugacaucga uuacugcgag cccaaccccu gucagaaugg ggcgcagugc 1620
uacaaccgag cuuccgauua cuucugcaag ugccccgagg auuacgaggg uaaaaauugc 1680
agccaccuga aggaucacug caggaccacc ccgugcgagg ugauagacag cugcaccgug 1740
gccauggcca gcaacgacac ccccgagggc gugcgauaca ucagcagcaa cgugugcggc 1800
ccccacggca agugcaaaag ccagagcggc ggaaaauuca caugcgacug caacaagggg 1860
uucacgggca ccuauugcca cgagaacauc aacgacugcg aguccaaccc gugccggaau 1920
ggcggcaccu gcaucgacgg cgugaacucc uauaagugua ucugcucgga cggcugggag 1980
ggggccuauu gcgagaccaa caucaacgac ugcagccaga accccugcca caacggcggc 2040
accugcaggg accuggugaa cgacuucuau ugcgacugca agaacggcug gaagggcaag 2100

-continued

```
accugucacu ccagggacag ccagugcgac gaggccaccu guaacaacgg cgggaccugu   2160

uacgacgagg gggacgcguu caagugcaug ugccccggcg gcugggaggg caccacgugc   2220

aacaucgcgc guaacagcag cugucugccg aaucccuguc acaauggcgg caccugcguc   2280

gugaacggcg aaagcuucac cugcgugugu aaggaaggcu gggagggccc caucugcgcc   2340

caaaacacca acgacuguag cccccacccg ugcuacaaca gcggcaccug cguggauggc   2400

gacaacuggu aucggugcga gugugccccu ggcuuugcgg gccccgacug ccggauaaac   2460

auaaacgagu gucaaucgag ccccugcgcc uucggggcca ccugcgugga cgagaucaac   2520

ggcuacaggu gcgugugccc gcccggccac agcggcgcga aaugccaaga ggugagcggc   2580

aggcccugca ucaccauggg uuccgugauc cccgacgggg caaaauggga cgacgacugc   2640

aauaccugcc agugccucaa cgggaggauc gccugcagca aggugugguug cggccccagg   2700

cccugccugc ugcauaaagg gcacagcgag ugccccagcg ggcagagcug cauccccauc   2760

cuggacgacc agugcuucgu gcacccgugc accggcgugg gcgagugcag aagcucuagc   2820

cugcaacccg ugaagaccaa gugcacgagc gacagcuacu accaggacaa cugcgcgaac   2880

aucaccuuca ccuucaauaa ggagaugaug agcccgggac ucaccaccga acauaucugc   2940

uccgagcugc gcaaccucaa cauacugaag aaugugagcg ccgaguacuc cauuuacauu   3000

gccugcgagc ccagccccuc cgccaauaau gaaauacacg ucgccaucag cgccgaggac   3060

aucagggacg acggcaaccc caucaaggag aucaccgaca agaucaucga ccuggugagc   3120

aaaagggacg gcaauagcag ccucaucgcc gccguggccg aggugagggu gcagaggagg   3180

ccgcugaaaa acagaaccga uuuucucguc ccccugcugu ccuccgugcu gaccgucgcc   3240

uggaucuguu gccuggugac cgccuucuac uggugucucc gcaagaggcg caagcccggc   3300

agccacacgc auagcgccag cgaggacaac acuacuaaca acgugcggga gcagcugaau   3360

cagaucaaga accccaucga gaaacacggc gccaacacug ugcccaucaa agacuacgag   3420

aacaaaaacu cgaaaaugag caagauccgc acccacaaca gcgaggugga ggaggacgac   3480

auggacaagc accagcagaa agcgagauuc gccaaacagc ccgccuacac ccugguggac   3540

agggaggaga agcccccaaa cggcacaccc accaagcacc cgaacuggac caacaagcag   3600

gacaaccgug accuggaaag cgcccagucc cugaaucgca uggaauauau cgug         3654
```

<210> SEQ ID NO 101
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 101

```
augcgaagcc cccgaacccg gggcaggagc gggaggcccc ugagccugcu gcuggcccuu     60

cugugcgccc uuagggccaa ggugugguggg gccuccggcc aguucgagcu ggagauccug    120

agcaugcaga acgugaacgg ugagcugcag aaugguaacu guugcggcgg agccaggaac    180

ccgggcgaua ggaaauguac cagggacgag ugcgacaccu acuuuaaggu gugccucaaa    240

gaguaccaga gccgggucac cgccggcggc cccugcucgu ucggcagcgg uagcaccccc    300

gugaucggcg gcaacacauu caaccugaaa gccagcaggg ggaacgacag gaaccggauc    360

gugcuccccu ucuccuucgc cuggcccagg ucguacaccc ugcucgucga ggccugggac    420

agcagcaacg acaccgugca gcccgacagc aucaucgaaa aggccagcca cagcggaaug    480
```

-continued

```
aucaacccca gccgacagug gcagacccug aagcagaaca ccggcguggc ccacuucgag    540
uaccagaucc gggugaccug cgaugacuau uacuauggcu ucggcuguaa caaguucugu    600
cgacccaggg acgacuucuu cggccacuau gccugcgacc agaacgguaa uaagacuugc    660
auggagggcu ggaugggccc cgaguguaac agggccaucu gcaggcaggg cugcuccccc    720
aaacacggcu ccugcaaacu gcccggcgac ugccgcugcc aguacggcug gcaggggcuc    780
uacugcgaua agugcauccc ccaucccggc ugcgugcaug gcaucugcaa cgaacccugg    840
cagugccugu gcgagaccaa cuggggggc cagcuaugcg auaaggaucu gaacuacugu    900
ggcacccacc agcccugccu gaacgggggc acgugcucaa acaccggccc cgacaaauac    960
caaugcagcu gccccgaggg cuacagcggc cccaacugcg agaucgccga gcaugccugc   1020
cugagcgacc cgugccacaa uaggggcucc uguaaggaga ccagccuggg cuucgagugu   1080
gagugcagcc ccggcuggac cggccccacc ugcucaacua acaucgacga cuguuccccc   1140
aacaauugca gccacggcgg caccugccag gaccugguga acggcuuuaa gugugugugc   1200
ccccccagu ggaccgggaa gaccugucag cuggacgcua acgagaguga ggccaagccc   1260
ugugucaacg ccaaaagcug caagaaccug auagccuccu acuacugcga cugccugccc   1320
ggauggaugg gccagaacug cgacaucaac aucaaugacu gccuggggca gugccagaac   1380
gacgccagcu gccgggaccu ggugaauggg uaccgcugca ucugcccccc cggcuacgcg   1440
ggcgaccacu gcgagaggga caucgacgag ugcgccucga accccugccu caacgggggc   1500
cacugccaga acgagaucaa ccgguuccag ugucugugcc cuacuggcuu cucuggcaac   1560
cugugucagc uggauaucga uuacugcgag ccaaacccau gccagaacgg ggcccagugc   1620
uacaauaggg ccuccgacua uuuuugcaag ugccccgagg acuacgaggg uaagaacugu   1680
ucccaucuca aggaccacug ucgaaccacc cccugcgagg ugaucgacag cugcaccgug   1740
gccauggcca gcaaugacac ccccgagggc gugcgguaca ucuccagcaa cgugugcggc   1800
ccccacggca agugcaagag ccaguccggc ggcaaauuua ccugcgauug caacaagggg   1860
uucaccggca ccuacuguca cgagaacauc aaugacugcg aauccaaucc cugcaggaac   1920
gguggcacgu gcaucgacgg ggugaauagc uauaagugca ucugcagcga cggguggga   1980
ggggccuacu gcgagaccaa caucaacgac uguagccaga acccgugcca caauggcggc   2040
acuuguaggg aucucgugaa ugacuucuau ugcgacugca aaaauggaug gaaggggaag   2100
accugccacu cccgggacuc ccagugcgac gaggccaccu gcaauaacgg cgguaccugc   2160
uacgacgagg gcgaugccuu uaaaugcaug ugccccggcg gcugggaggg aaccacgugc   2220
aacaucgcga ggaacagcag cugccucccc aaucccuguc acaauggcgg uaccugcguc   2280
gugaacgggg agagcuucac cugcgugugc aaggagggcu gggagggccc gaucugcgcc   2340
cagaacacca acgacugcag cccacacccc ugcuacaaua gcgggaccug cguggacgga   2400
gacaacuggu accggugcga gugcgccccc ggcuucgccg gccccgacug caggaucaac   2460
aucaacgagu gccagagcag ccccugugcc uucggcgcga ccugcgugga ugaaaucaau   2520
ggcuaccggu gcgugugccc ccccggccac agcggcgcga agugccagga gguuagcggc   2580
aggcccugca ucaccauggg aucggugauc cccgauggcg ccaaguggga ugacgacugu   2640
aacacaugcc aaugucugaa uggacggauc gcauguucca aggugugug cggccccagg   2700
cccugucucc ugcacaaagg ccacagcgag ugucccagcg gccaaagcug cauccccauc   2760
cuggacgacc agugcuucgu gcaucccugc accggcgugg gggagugccg uagcagcagc   2820
cugcagcccg ugaagacgaa gugcaccuca gacagcuauu accaggauaa cugcgcgaac   2880
```

```
aucaccuuca ccuuuaacaa ggagaugaug ucccccggcc ugaccaccga gcacaucugc   2940
ucggagcugc gcaaucuuaa cauccugaaa aacguguccg ccgaguacag cauuuacauc   3000
gccugugagc cgagccccuc cgccaacaau gagauccaug ucgccaucag cgccgaggac   3060
auccgggacg acgguaaucc gaucaaggag aucacagaua agaucaucga ccuggugucc   3120
aagcgggacg gcaacagcag ccugaucgcc gccgucgccg aggugcgugu gcagagacgg   3180
ccccucaaga accgcaccga cuuccucgug ccccuccuga gcucggugcu gaccgucgcc   3240
uggaucugcu gccuggugac cgccuucuac uggugccugc gaaaacgccg gaagccgggg   3300
agccacaccc acagcgccag cgaggauaac accaccaaua acgugaggga acagcugaac   3360
cagaucaaga accccaucga aaaacacggc gccaacaccg ugccgaucaa ggacuacgag   3420
aacaaaaaua gcaagaugag caagaucagg acacacaacu cugaggugga ggaggacgac   3480
auggacaagc accagcagaa ggcccgcuuc gccaagcagc ccgccuacac ccuggucgac   3540
cgggaagaga agcccccgaa cggcaccccc accaagcauc cuaacuggac caacaagcaa   3600
gacaacaggg accuggaaag ugcccagagc cugaaccgga uggaguacau cgug         3654
```

<210> SEQ ID NO 102
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 102

```
augcgaagcc cgaggacccg gggcaggagc ggcaggccgc uaagccugcu gcuggcccuc     60
cucugcgccc ucagggccaa ggugugcggc gccuccggcc aauucgagcu cgagauccug    120
ucaaugcaga acgugaacgg cgagcugcag aacggcaacu gcugcggcgg cgccaggaac    180
cccggcgaca ggaagugcac cagggacgaa ugugacaccu acuucaaggu gugccugaag    240
gaguaccaga gccgggugac cgcuggcggc ccauguagcu ucgggagcgg cagcaccccg    300
gugaucgggg guaacaccuu uaaccucaag gcuucccgcg gcaacgacag gaaccggauc    360
gugcugcccu ucuccuucgc cuggcccagg agcuauaccc ugcuggucga ggccugggac    420
agcuccaacg acaccgugca acccgacagc aucaucgaga aggccuccca cuccggcaug    480
aucaacccca gcaggcagug gcagacccuc aagcaaaaca ccggggucgc gcacuucgag    540
uaccagauca gggucaccug cgacgacuac uacuacggcu ucggcugcaa uaaguuuugc    600
cggcccaggg acgauuucuu cggacacuac gccugugacc agaauggcaa uaagaccugu    660
auggaagggu ggauggggcc agagugcaau cgggccaucu gcaggcaagg cugcagcccc    720
aaacacggcu cguguaagcu gcccggcgac ugcaggugcc aguaugguug gcagggccuc    780
uauugcgaca agugcauccc ccacccaggc ugugugcaug gcaucuguaa cgaacccugg    840
cagugccugu gcgagacgaa cuggggggc caacugugcg acaaggaccu gaacuauugc    900
ggcacccacc agccgugccu gaauggcgga accuguucca acaccggccc cgacaaguac    960
cagugcuccu gucccgaggg guacagcggc cccaacugcg agaucgccga gcaugccugc   1020
cucagcgauc ccugccacaa caggggcagc ugcaaggaga cgagccuggg cuucgagugc   1080
gaaugcagcc ccgguuggac cggccccacg ugcuccacca acaucgacga cugcuccccc   1140
aacaauugca gccacggggg cacaugucag gaccugguga acggcuucaa gugcgugugc   1200
ccgccccaau ggaccggcaa gacgugccag cuggacgcca acgagugcga agccaagcca   1260
```

-continued

```
ugcgugaacg ccaagagcug caagaaccug aucgccagcu acuacugcga cugccuccca   1320
ggcuggaugg gccagaacug ugauaucaac aucaacgacu gccucggcca gugccagaac   1380
gacgccagcu gccgggaccu ggugaacggg uaccgcugca ucuguccgcc cggcuacgcc   1440
ggagaccacu gcgagcgcga caucgacgag ugugccagca accccugcuu aaacggcggc   1500
cacugccaaa augaaaucaa uagguuucag ugccugugcc ccaccggguu cagcggcaac   1560
cugugccagc uggacaucga cuauugcgag ccgaaccccu gccagaacgg ggcccagugc   1620
uacaauaggg ccagcgauua uuucugcaag ugucccgagg acuacgaggg aaaaaacugc   1680
agccaccuca aggaccacug uaggaccacg cccugcgaag ugaucgacuc cugcaccgug   1740
gccauggcca gcaacgacac ccccgagggc gugcgcuaca ucagcagcaa cgugugnggc   1800
ccucacggca aaugcaagag ccaaagcggc ggcaaguuca ccugugacug caauaagggc   1860
uucaccggca ccuacuguca cgagaacauc aacgacugcg agagcaaccc cugcagaaac   1920
gguggcaccu guauagaugg cgugaacagc uacaagugca ucugcagcga cggaugggaa   1980
ggcgccuacu gugagaccaa cauuaacgac ugcagccaga accccugcca caauggcggc   2040
accugccgcg accuggucaa ugacuuuuac ugcgacugua agaacgggug gaagggcaag   2100
accugccaua gccgcgacuc ccagugcgac gaggcaaccu gcaacaacgg cggcaccugu   2160
uaugaugagg gggacgcauu caagugcaug uguccggggg gcugggaggg cacaaccugc   2220
aacaucgccc ggaacagcag cugccuccca aaccccugcc acaacggggg caccugcgug   2280
gugaacggcg agagcuucac cugcgugugu aaggagggcu gggagggccc caucugugcc   2340
cagaauacca acgauugcuc cccccacccc ugcuacaaca gcggcacuug cguggacggc   2400
gauaacuggu auagguguga gugcgccccc ggcuucgcag gccccgacug ccgcaucaac   2460
aucaacgagu gccagagcag ccccugugcc uucggggcca ccugcgugga cgagaucaac   2520
ggcuaccggu gugugugccc ccccgggcac uccggcgcga aaugccagga ggguguccggc   2580
aggcccugca ucaccauggg cagcgugauc ccugacggcg ccaaauggga cgacgacugu   2640
aauaccugcc agugccugaa uggccgaauc gccugcucca aggugugugug cggccccagg   2700
ccuugccugu ugcacaaggg ccacagcgag ugccccagcg gccagagcug uaucccccauc   2760
cuggacgacc aauguuucgu gcaucccugc accggcgugg gggagugccg gucguccagc   2820
cugcagcccg ugaagaccaa guguaccagc gacuccuacu aucaggacaa uugcgccaac   2880
aucaccuuca ccuuuaacaa ggagaugaug agccccggcc ugaccaccga gcacaucugu   2940
uccgagcuga ggaaccugaa cauccugaag aacgucagug ccgaguacuc caucuacauc   3000
gccugugaac cguccccguc cgccaacaau gagauucacg uggccaucag cgccgaagac   3060
aucagggacg acggcaaccc caucaaggag aucaccgaca agaucauaga ccuugugucc   3120
aagagggacg gcaacucguc ccugaucgcc gccguggcgg aggugagggu gcagaggagg   3180
ccccugaaga accgcaccga cuuccuggug ccgcuccugu ccuccgugcu gaccguggcc   3240
uggaucugcu gccuggugac cgccuucuac uggugccuga ggaagcgccg caagcccggg   3300
ucccacacgc acagcgccag cgaggauaac accaccaaca acgugcggga gcaacugaac   3360
cagauaaaga accccaucga aaaacacgga gcgaacaccg uccccaucaa ggacuacgaa   3420
aacaagaaca gcaagaugag caagaucagg acccauaacu ccgaggugga ggaggacgac   3480
auggacaagc accagcaaaa ggcccgguuc gccaagcagc ccgccuacac ccugguggau   3540
cgggaggaga agccccccaa cgguaccccg accaaacacc ccaacuggac caauaaacag   3600
gacaauaggg accuggaguc cgcccagagc cugaacagga uggaguacau agug         3654
```

<210> SEQ ID NO 103
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 103
augagaagcc ccaggacccg aggcaggagc ggcaggccac ugagccugcu ccuugcccug 60
cugugcgccc ugagggcaaa ggugugcggc gccagcggcc aguucgagcu ggaaauccug 120
uccaugcaga acgugaacgg ggagcugcag aauggcaauu gcuguggcgg cgcgcggaac 180
cccggcgaca ggaagugcac acgggacgaa ugcgacacgu acuucaaggu gugccucaag 240
gaguaccagu ccagggucac cgccggcggg cccugcagcu ucggaagcgg cuccaccccc 300
gugaucggcg gcaacacauu caaccugaaa gcgucgaggg ggaaugaccg caacaggauc 360
gugcugccgu uuuccuucgc cuggccccgc agcuacacgc ugcugguga ggcaugggac 420 agcuccaacg auaccgugca gcccgacagc aucaucgaga aggccuccca cagcggcaug 480
aucaacccga gcaggcagug gcagacccuc aagcagaaca ccggcguggc ccacuucgag 540
uaucagaucc gggugaccug cgacgacuau uacuacgguu ucggcugcaa caaguuuugu 600
aggccccgag acgacuucuu cggccacuac gccugcgauc agaacgggaa uaaaaccugu 660
auggaggggu ggaugggccc cgagugcaac agggccaucu gcaggcaggg augcuccccc 720
aagcacggca gcugcaagcu gccaggagac ugcaggguguc aguauggcug gcaggggcug 780
uacugcgaua agugcauucc gcacccagga ugugugcacg gaaucuguaa cgagcccugg 840
cagugccugu gcgaaaccaa cuggggggggc caacucugcg acaaggaccu gaacuacugc 900
ggcacccacc aacccugucu gaacggcggc accugcagca acaccggccc cgacaaauac 960
cagugcagcu gccccgaggg cuacuccggg cccaacugcg agaucgccga acacgcaugu 1020
cugagcgacc cuugccacaa caggggcagc ugcaaggaga ccucccucgg cuuugagugc 1080
gaaugcagcc ccggcuggac cgggcccacc ugcagcacga acaucgacga cugcagcccc 1140
aacaacugcu cccacggcgg gacgugccag gaucucguca acggcuucaa gugcgugugc 1200
cccccccagu ggaccggcaa aaccugccag cuggacgcaa acgagugcga agccaagccg 1260
ugcgucaacg cgaagagcug caagaaccuc aucgccagcu acuauugcga cugccugccc 1320
ggcuggaugg gccagaacug cgacauaaac aucaacgacu gccugggcca gugucagaac 1380
gaugccuccu gcagggaccu ggugaacggg uaccggugua ucugcccccc cggguacgcg 1440
ggggaccacu gcgagagaga caucgaugag ugcgccucca aucccugccu gaacggcggc 1500
cauugccaga acgagaucaa ccgguuccag ugccugugcc ccaccggcuu cuccggcaac 1560
cugugccaac uagacaucga cuacugcgag cccaaucccu gccagaacgg cgcccaaugc 1620
uacaacaggg ccagcgacua cuucuguaag ugccccgagg acuacgaggg caagaacugc 1680
ucccaucuga aggaccacug ccggaccacc cccugcgaag ugaucgacag cugcaccgug 1740
gccauggcca gcaaugacac ccccgagggc gugagguaua ucagcagcaa cgugugcggg 1800
ccccacggga aaugcaagag ccagagcggc ggcaaguuca caugcgacug uaacaagggc 1860
uucacgggaa ccuacuguca cgagaacauc aacgacugcg agagcaaccc cugccgcaac 1920
ggcggcaccu gcaucgacgg cgugaacucc uauaagugca ucuguagcga uggcugggaa 1980
ggggccuacu gcgagaccaa cauaaacgac ugcagccaga aucccugcca uaacgggggc 2040
accugucgug accuggucaa cgacuucuac ugcgacugua agaacggaug gaaggguaag 2100
accugccacu ccagggacuc ccagugugac gaagccaccu gcaacaacgg aggcaccugc 2160
uacgacgagg gugacgccuu uaagugcaug ugccccggug gcugggaggg gaccacgugc 2220
aacaucgccc gcaacagcag cugccuuccg aacccaugcc auaacggcgg caccugugyc 2280
gugaacggcg agucguucac cugugugugc aaggaaggcu gggaaggccc cauaugcgcc 2340
cagaacacca acgacugcag cccccauccc ugcuacaacu ccggcaccug cguggacggg 2400
gacaacuggu acagguguga gugcgccccc ggauucgccg gucccgacug ccggaucaac 2460
aucaaugagu gucaauccag ccccugcgcc uucggcgcca ccugcgugga ugagaucaac 2520
ggcuacaggu gcgucugucc ccccggccac uccggcgcca aaugccagga ggucagcggc 2580
aggcccugca ucaccauggg cuccguuauc cccgacggcg ccaaguggga cgacgacugc 2640
aauaccugcc agugucugaa cgggaggauc gccugcucca aggugugggug cggccccagg 2700 cccugccugc ugcacaaggg ccacagcgag ugccccagcg gccaguccug caucccgauc 2760
cuggacgacc agugcuuugu gcaccccugc accgggguag gcgagugccg guccagcagc 2820
cugcagcccg ugaaaaccaa gugcaccagc gacagcuauu accaggacaa cugcgccaau 2880
aucaccuuua cguucaauaa agagaugaug agccccggcc ugaccaccga acacaucugc 2940
agcgagcugc gcaaccugaa cauucugaag aacgugagcg ccgaguacag caucuauaua 3000
gccugcgagc ccagccccuc ggcuaauaac gagauccacg uggccauaag cgcggaggac 3060
auccgggacg acggcaaccc caucaaggag aucaccgaca agaucaucga ccuggugagc 3120
aagcgcgacg ggaacucauc acugaucgcc gccguggccg aggugagggu gcagaggcgg 3180
ccccucaaga acaggaccga cuuccucguc ccccugcugu cgagcgugcu caccguggcc 3240
uggaucugcu gucucgugac cgcauucuac uggugccuga ggaaacggcg caagcccggc 3300
ucgcacaccc acagcgccag cgaagauaac accaccaaca acgugaggga gcagcucaac 3360
cagaucaaga accccauaga gaagcacggc gccaacacgg ugccaaucaa ggacuaugag 3420
aacaagaaca gcaagauguc caagauccgc acccacaaca gcgaagucga ggaagacgac 3480
auggacaagc accagcagaa agcgcguuuc gccaagcagc ccgccuacac ccugguggac 3540
agggaggaga agccccccaa cggaaccccc acaaagcacc caaacuggac gaauaagcag 3600
gacaacaggg accuggagag cgcccagagu cugaaccgga uggaguacau cgug 3654

<210> SEQ ID NO 104
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 104
augagaaguc ccaggacccg cgggcggagc gggcgccccc ugagccuguu acuggcccuc 60
cugugugccc ugcgcgcgaa ggugugcggg gccagcggcc aguucgagcu ggagauccug 120
agcaugcaga acgugaacgg ggaacuacag aacggcaacu gcugcggcgg cgcccgcaau 180
ccgggagaca ggaaguguac cagggaugag ugcgacaccu acuuuaaagu gugccugaag 240
gaguaccaga gcagggugac cgccggcggc cccuguagcu ucggcagcgg gagcaccccg 300
gugaucggcg gcaacaccuu caaccucaag gccuccaggg gcaacgacag gaaccggauc 360
gugcugcccu ucagcuucgc cuggccccgc agcuacacgc ugcuggugga ggccugggac 420
agcucuaaug acacggugca gccugacuca auuauagaga aggccagcca cagcggcaug 480
aucaaccccu caagacagug gcagacccug aagcagaaca ccggugugge acacuucgag 540
uaucagauca gggugacaug cgaugacuac uacuacgggu uuggcuguaa uaaguucugc 600
aggccccgag acgauuucuu cgggcacuau gccugcgacc aaaauggcaa caagaccugc 660
auggaggggu ggaugggccc ggaguguaac cgagccauau guaggcaagg cugcagcccg 720
aagcacggcu ccugcaagcu gcccggugau ugcaggugcc aguacggcug gcaaggccuc 780
uacugcgaca agugcauccc gcaccccggu ugcguccacg gcaucugcaa cgagcccugg 840
cagugccugu gcgagaccaa cugggggggc cagcugugcg acaaggaccu caauuacugu 900
ggcacccacc agcccugccu caacggugge accugcucca acaccggccc cgacaaguac 960
caguguagcu gccccgaggg guacagcggc ccgaacugcg agaucgccga gcacgccugc 1020
cuguccgacc ccugccacaa ucgcggcagc ugcaaggaga ccagccuggg guucgaaugc 1080
gaguguuccc cgggcuggac cggccccacc ugcagcacca auaucgauga cugcuccccc 1140
aacaacugca gccacggcgg caccugucag gaccugguga auggcuucaa gugugugugc 1200
ccaccgcagu ggaccggcaa aaccugccag cucgacgcca acgagugcga ggccaagccc 1260
ugugugaaug ccaaguccug caagaaccug aucgccagcu acuacugcga cugccugccc 1320
ggguggaugg ggcaaaauug cgacauaaac auaaacgacu gccugggcca gugccagaac 1380
gacgccuccu gucgggaccu ggucaacggc uacaggugca ucugcccacc cggcuacgcc 1440
ggcgaccacu gcgagcgaga uaucgacgaa ugcgccagca accccugccu gaacgggggg 1500
cacugccaga augagaucaa cagguuucag ugccugugcc ccaccggcuu cagcggcaac 1560
cugugucaac uggacaucga cuauugugag cccaaccccu gccaaaacgg ggcccagugc 1620
uacaaccggg ccagcgauua cuucugcaag ugccccgagg acuacgaagg caagaacugc 1680
agccaccuga aggaccacug ucggaccacc cccugcgaag ugaucgacag cugcaccgug 1740
gccauggcca gcaacgacac ccccgagggc gugagguaca ucagcagcaa ugugugugge 1800
ccgcacggca agugcaagag ccagagcggc ggcaaguuca cgugcgacug caacaagggc 1860
uuuaccggca ccuacugcca cgaaaacauc aaugacugcg agagcaaccc gugucggaac 1920
ggcggcaccu gcaucgacgg ggugaacagc uacaagugca uaugcagcga cggcugggag 1980
ggcgccuacu gugaaaccaa caucaacgac ugcagccaga accccugcca caauggcggg 2040
accugcaggg accuggugaa ugacuucuac ugcgacugca agaacggcug gaagggcaaa 2100
accugccaca gcagggacag ccagugcgac gaggccaccu gcaacaacgg cggcaccugc 2160
uaugacgagg gcgacgccuu caagugcaug ugccccggcg gaugggaggg cacgaccugc 2220
aauaucgcaa ggaacagcuc cugucugccc aaucccugcc acaacggcgg uaccugcgug 2280
gugaacgggg aaagcuucac cugcgugugc aaggaggggu gggaggggcc caucugcgcc 2340
cagaacacca acgacugcag cccacacccc ugcuacaauu ccggcaccug uguggacggc 2400
gacaacuggu auaggugcga gugcgccccc gguuucgccg gcccggacug caggaucaac 2460
aucaacgagu gucaguccag ccccugcgcc uucggggcca ccugcgugga cgagaucaac 2520
ggcuaucguu gcgugugccc ccccggccac uccggcgcca agugccagga aguguccggg 2580
cgccccugca ucaccauggg cuccgugauc cccgauggcg ccaaguggga ugacgacugc 2640
aacaccuguc agugccugaa cggcaggauc gccugcagca aggugugggug cggcccccga 2700
cccugccugc ugcacaaggg gcacagcgag ugccccuccg gccaguccug cauccccaua 2760
cuggacgauc agugcuucgu gcaccccugc accggcgugg gcgaguguag gagcuccagc 2820
cugcagcccg ugaaaaccaa gugcaccucg gacagcuacu aucaggauaa cugcgccaac 2880
auuacguuca ccuucaacaa ggagaugaug ucccccggcc ugaccacgga gcacaucugu 2940
uccgagcuga ggaaccucaa cauccugaaa aaugugagcg ccgaguauag caucuauaua 3000
gccugugagc cguccccuc cgccaacaac gagauccacg ucgccaucuc cgcagaggac 3060
auucgcgacg acgggaaccc cauaaaggaa auuacggaca aaaucaucga ccuggugagc 3120
aagagggacg gcaacuccag ccugaucgcc gccguggccg aggugcgcgu gcaacgcagg 3180
ccgcugaaaa acaggacgga cuuucuggug ccgcugcugu ccucggugcu gaccgucgcu 3240
uggaucugcu gccuggugac cgccuucuac uggugccugc gcaaaaggcg caagcccggu 3300
agccauaccc acuccgccuc cgaagacaac accaccaaca acgugaggga gcagcugaau 3360
cagaucaaga acccuaucga gaagcacggc gccaacacgg ugcccaucaa ggacuaugaa 3420
aacaagaaca gcaagauguc caagaucagg acccacaaca gcgaggugga ggaagacgac 3480
auggacaagc accagcagaa ggcccgauuc gccaagcagc ccgcuuacac ccugguggac 3540
agggaggaaa agcccccgaa cggcaccccc accaaacacc ccaacuggac uaauaaacag 3600
gacaaccgag accuggagag cgcccagagc cugaacagga uggaauauau cguc 3654

<210> SEQ ID NO 105
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 105
augcguagcc ccaggaccag ggguaggucc gggaggcccc ugucacuccu ccuggcccug 60
cucugugccc uccgggccaa ggugugcggc gccagcggac aguuugagcu ggagauccug 120
uccaugcaga acgugaacgg ugagcuccag aacgggaacu gcugcggcgg cgccaggaac 180
cccggcgauc gcaaguguac cagggacgaa ugugacaccu acuuuaaggu gugccugaaa 240
gaguaccaga gccgcgucac cgccggcggg cccuguuccu uuggcuccgg cagcacuccc 300
gugaucggcg gcaacaccuu caaccucaag gcgagcaggg ggaacgacag gaacaggauc 360
gugcugcccu ucagcuucgc guggccccgg uccuacaccc ugcucgugga ggcuugggac 420
uccucaaacg acacggucca gccggauagc aucauugaga aggcgagcca cuccggcaug 480
aucaacccca gccggcagug gcagacccuc aagcagaaca ccggcguggc ccacuucgag 540
uaucagaucc gcgugaccug cgaugauuac uacuacggcu uuggaugcaa caaguucugc 600
cggccccgcg acgacuucuu cggacacuau gccugugacc agaacgggaa caagaccugc 660
auggagggau ggaugggucc cgagugcaac cgggccaucu gcaggcaggg cuguagcccc 720
aagcacggga gcugcaagcu gcccggcgac ugcaggugcc aguacggcug gcaggggcug 780
uacugcgaca agugcauccc ccacccggga ugcgugcacg gcaucugcaa cgagcccugg 840
cagugccucu gcgagaccaa cuggggcggc cagcugugcg acaaggaccu gaacuacugu 900
ggcacgcauc agccaugccu caaugguggc accugcagca acacgggccc cgauaaguac 960
caaugcucgu gccccgaagg guacuccggc ccaaauugcg agaucgccga gcacgccugc 1020
cuguccgacc ccugccacaa caggggcucc uguaaggaga ccucccuggg cuucgagugu 1080
gagugcagcc ccggguggac cggccccacc uguuccacca acaucgacga cugcagcccc 1140
aacaacugca gccauggagg caccugucag gaccugguga augguuucaa gugugugugc 1200
ccgccccagu ggaccgggaa gaccugccag cuggacgcca acgagugcga ggcuaagccc 1260

```
ugcgucaacg ccaagagcug caagaaccuc aucgccuccu acuacugcga cugccugccg   1320
ggauggaugg gccagaacug ugacaucaac aucaacgacu gucugggcca gugccagaau   1380
gacgccagcu gccgagaccu ggucaacggc uacaggugca uaugcccccc cggauaugcc   1440
ggggaucacu gcgagcggga caucgacgag ugcgccagca acccaugucu gaacggcggg   1500
cacugccaga acgagaucaa cagguuucaa ugccugugcc ccaccggauu uagugggaac   1560
cucugucagc uggacauaga cuacugcgag ccgaaccccu gccaaaacgg cgcgcagugc   1620
uacaacaggg ccagcgauua cuucugcaag ugcccggagg acuacgaggg gaagaacugc   1680
ucccaccuga aggaccacug caggaccacc cccugcgagg ugaucgacuc gugcaccguc   1740
gccauggccu caaacgacac ccccgagggg guccgcuaca ucucgagcaa cgucuguggc   1800
ccccacggca agugcaagag ccagagcggg gggaaguuca ccugcgacug caacaaaggc   1860
uucaccggca cguacuguca cgagaacauc aaugauugcg agagcaaccc cugccggaac   1920
ggcggcaccu gcaucgacgg cgugaacagc uacaagugca ucuguagcga cggcugggag   1980
ggggccuacu gcgagaccaa caucaacgac ugcagccaga accccuguca caacggcggc   2040
accugcaggg accucgugaa ugacuucuac ugcgacugca aaaacgggug gaaagguaaa   2100
accugccaua gccgggacag ccagugcgac gaggccaccu guaauaacgg cggcaccugc   2160
uacgacgagg gugacgccuu uaaguguaug ugccccggcg gcugggaggg caccaccugc   2220
aauaucgccc gcaacagcag cugucucccc aaccccugcc acaacggggg uaccugcgug   2280
gucaacggcg aguccuuuac cugcgugugc aaggagggcu gggaagggcc caucugcgcc   2340
cagaacacca acgacuguag cccccauccc ugcuacaacu ccgguaccug cguggacggc   2400
gacaauuggu acagguguga augcgcacca ggcuucgcgg ggcccgacug caggaucaac   2460
aucaacgaau gccagagcag ccccugcgcg uucggcgcca ccugcgugga cgagaucaac   2520
ggguacaggu gcgugugccc ccccgggcac agcggggcca agugccagga ggucuccggg   2580
cggcccugca ucaccauggg cuccgugauc ccggaugggg cgaaguggga cgacgauugc   2640
aacaccugcc aaugccugaa cgggaggauc gccuguagca aggucuggug cggaccccgg   2700
cccugccucc ugcacaaagg ccacuccgaa ugccccagcg gacaaagcug cauaccgauc   2760
cuggacgacc aaugcuucgu gcaucccugc acaggcgugg gugaaugcag gagcuccagc   2820
cugcagccag ugaagacgaa gugcaccagc gauagcuacu accaggauaa uugugccaac   2880
auaaccuuca ccuucaacaa ggagaugaug ucccccggcc ugaccaccga gcacaucugu   2940
agcgagcucc gcaaccugaa cauccucaag aacgugagcg ccgaguacuc caucuacauc   3000
gccugcgagc ccucgcccag cgccaauaac gagauccacg uggccaucuc cgccgaggac   3060
auccgcgacg acggcaaucc caucaaggag auuaccgaca agaucaucga ccuggugagc   3120
aagcgcgaug gcaacagcag ccugaucgcc gcgguggccg aggugagggu gcagaggcgg   3180
ccccucaaga accgcacgga cuuccuggug ccacugcuga gcuccgugcu gaccguggcc   3240
uggaucugcu gucuggucac cgccuucuac uggugccugc ggaaacggag gaagcccgga   3300
ucccacaccc acuccgccuc cgaagacaac accacgaaca acgucaggga gcagcugaac   3360
cagaucaaga accccaucga gaagcauggc gccaacaccg ugccaaucaa agacuacgag   3420
aacaagaaca gcaagaugag caagauccgg acccacaaca gcgaaguaga agaggacgac   3480
auggauaagc accagcagaa ggccagguuc gccaagcaac ccgccuacac ccucguggac   3540
cgcgaggaga aaccccccaa cggcaccccc accaagcacc ccaauuggac caacaagcaa   3600
```

-continued gauaaccgcg accuggagag cgcccagagc cucaaccgga uggaauacau cgug 3654

<210> SEQ ID NO 106
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 106
augaggagcc caaggaccag ggggaggagc ggcaggccgc ucagccugcu gcucgcccug 60
cugugcgccc ugcgggcaaa ggugugcggg gccagcggcc aguucgagcu ggaaauccug 120
agcaugcaga acgugaacgg cgagcugcaa aaugguaauu gcugcggggg cgccaggaac 180
ccgggcgaca ggaagugcac cagggacgag ugcgacaccu auuucaaggu gugccugaag 240
gaauaccaga gccgcgucac ggccgggggc ccgugcuccu ucggcagugg cuccaccccc 300
gugaucggcg gcaacaccuu uaaccugaag gccucccggg guaacgacag gaacaggauc 360
gugcugcccu ucuccuucgc cuggccgagg uccuacaccc uccugguaga ggccugggac 420
agcagcaaug auacggugca gcccgacucc aucauagaaa aggccagcca cuccgggaug 480
aucaauccga gcaggcagug gcaaacccuc aagcagaaca ccggugugggc ccacuuugag 540 uaccagauca gggucaccug cgacgacuac uacuacggcu ucggcugcaa caaguuuugc 600
aggccgaggg acgacuucuu cggccacuac gccugcgacc agaauggcaa caagaccugc 660
auggaaggcu ggaugggccc ggaaugcaau cgcgccaucu guaggcaggg gugcagccca 720
aagcauggga gcugcaagcu gcccggggac ugcaggugucc aguacggaug gcaggggcug 780
uacugugaca aguguauccc acauccgggc ugcgugcacg gaauaugcaa cgagcccugg 840
cagugccugu gugaaacgaa cuggggcggu cagcugugcg acaaggaccu gaacuacugc 900
ggcacccacc agcccugccu gaacggcggg acguguucca acaccggccc cgacaaguau 960
caguguagcu gccccgaggg cuauagcggc ccgaacugcg agaucgccga acaugccugu 1020
cucagcgacc ccugucacaa cagggguagc uguaaggaaa ccagccucgg guuugagugu 1080
gaaugcuccc cgggcuggac cgggcccacc uguuccacca acaucgacga cugcuccccc 1140
aauaacugca gccauggcgg cacgugucag gaccucguca auggcuuuaa gugugugugc 1200
cccccgcagu ggaccggcaa gacgugccag cuggacgcca acgaguguga ggccaagccc 1260
ugcgucaacg caaagagcug caagaaccug aucgccuccu acuauuguga cugccugccc 1320
ggguggaugg gacagaacug cgacaucaau aucaacgauu gccuggggca gugccagaac 1380
gacgcgagcu gcagggaccu ggucaacggc uaccgaugca ucugcccccc gggcuacgcc 1440
ggcgaccacu gugaaaggga caucgacgag ugcgccagca accccugccu gaacgggggc 1500
cacugccaga acgagaucaa uagguuccag ugccugugcc cgaccgguuu uagcggcaac 1560
cugugccagc uggacauuga cuauugcgag cccaaccccu gccagaacgg ggcccagugc 1620
uacaacaggg ccucggacua cuucuguaag ugccccgagg acuaugaggg caagaacugc 1680
agccaucuga aggaccacug caggaccacc ccgugcgagg ucaucgacag cugcaccgug 1740
gccauggccu ccaaugauac ccccgagggc gugagguaca ucuccuccaa cgugugugggc 1800 ccccacggca agugcaaaag ccagagcggc ggcaaguuca ccugugacug uaacaagggc 1860
uucaccggca ccuacugcca ugaaaacauc aacgauugcg agucuaaucc cugccggaac 1920
ggcggcaccu gcaucgaugg cgugaacagc uauaaaugua ucugcuccga ugggugggag 1980
ggcgcauacu gcgaaaccaa caucaacgac ugcucccaga accccugcca uaacggcggc 2040

-continued accugccgcg accucgucaa cgauuucuac ugcgacugca agaacggcug gaagggcaag 2100
accugccaca gccgagacag ccagugcgac gaggccacgu gcaacaacgg agggaccugu 2160
uaugacgagg gcgacgccuu caagugcaug ugccccgggg gcugggaggg cacgaccugc 2220
aacauugccc gcaauagcag cugcuugccc aaccccuguc acaacggcgg aaccugcguc 2280
gugaacggcg aguccuucac cugcguuugc aaagagggcu gggagggccc aaucugugcc 2340
cagaacacca augacugcag cccccacccc ugcuacaauu ccgguaccug cguggacggc 2400
gacaacuggu auaggugcga gugcgccccg ggauucgccg gcccggacug caggaucaac 2460
aucaacgagu gccagagcag ccccugcgcc uucggggcca ccugugugga cgagaucaau 2520
ggcuacaggu gugucugccc ccccggacac ucgggcgcga aaugccaaga gguguccggc 2580
aggcccugca ucaccauggg uuccgugaua cccgacgggg caaaguggga cgacgauugc 2640
aauaccugcc aaugccugaa cggcaggauc gccuguagca agguguggug uggcccgagg 2700
ccuugccucc ugcauaaagg ccacagcgag uguccouccg gccagagcug uauccccauc 2760
cucgacgauc aaugcuuugu gcacccuugc accggggugg gcgagugucg cagcagcagc 2820
cugcagcccg ugaagaccaa augcaccagc gauagcuacu accaggacaa cugcgcgaau 2880
aucaccuuua cguucaacaa ggagaugaug agcccgggcc ugaccacaga gcacaucugc 2940
agcgagcugc gcaaccugaa cauccugaag aacgugucug ccgaguauag caucuacauc 3000
gccugcgaac ccagccccuc cgcaaauaau gagauccacg uggcgaucuc ggccgaggac 3060
aucagggacg acgggaaccc caucaaagag aucaccgaca agaucaucga ucuggugagc 3120
aagcgggacg gcaacagcuc ccucaucgcc gccguggcug agguccgagu gcagcggcgu 3180
ccccuuaaga acaggaccga cuuccuggug ccccuccugu cguccgugcu caccguggcc 3240
uggaucuguu gccuggugac cgccuucuac uggugccugc guaagcgaag gaagcccgga 3300
ucccacaccc acagcgccag cgaagacaac accaccaaua acguccgaga gcagcugaac 3360
cagaucaaga accccauaga gaaacacggg gccaacaccg ugccuaucaa ggacuacgag 3420
aacaaaaaua gcaaaaugag caagauuagg acccacaacu ccgaggugga ggaggacgac 3480
auggacaagc aucagcagaa ggcccgcuuc gccaagcaac ccgccuacac ccugguggac 3540
cgagaggaaa agccccccaa cgggaccccc acgaagcacc ccaacuggac caauaagcag 3600
gauaacaggg accucgagag cgcccagucc cugaaucgca uggaguacau cgug 3654

<210> SEQ ID NO 107
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 107
augaggagcc cccgcaccag ggggcguagc ggccgccccc ugagccugcu gcuggcucug 60
cugugugccc ugcgagccaa agugugcggg gccuccggcc aguucgagcu ggagauccug 120
agcaugcaga acgugaacgg cgagcuccag aacggcaacu gcugcggcgg cgcccgcaac 180
cccggcgaca ggaagugcac ucgggacgag ugcgacaccu auuucaaggu cugccugaag 240
gaguaccaaa gccgugugac cgccggcggg ccgugcagcu ucggaagcgg cuccaccccg 300
gucaucgggg ggaacaccuu uaaccugaag gccagccggg guaacgacag gaaccgaauc 360
guacugcccu ucagcuucgc cuggccccgg agcuacaccc ugcugglcga ggcaugggac 420

-continued

```
uccagcaacg auaccgugca gcccgacagc aucaucgaga aagccagcca cagcgggaug    480
auuaauccca gcagacagug gcagacccug aagcagaaca ccggcguggc ccacuucgag    540
uaccaaaucc gggugaccug cgacgauuau uacuacgggu uuggcuguaa uaaauucugc    600
cggccccggg augacuuuuu cggccauuac gccugcgauc agaacgguaa caagaccugc    660
auggagggcu ggaugggacc ggaguguaac agggcuaucu gccgacaggg uuguagcccc    720
aagcacggaa gcugcaagcu gcccggcgac ugccggguguc aguacggcug gcagggccug    780
uacugcgaua agugcauccc ccaccccggc ugcguucacg gcaucugcaa cgagcccugg    840
cagugccugu gugaaaccaa cuggggugga cagcugugcg acaaggaucu gaacuauugc    900
ggcacccacc agcccugccu gaacggcgga accugcagca acaccggccc cgauaaguac    960
cagugcagcu gccccgaagg cuacuccggc cccaacugcg agaucgccga gcacgccugc   1020
cugagcgacc cgugccacaa cagggggagc ugcaaagaga ccagccuggg uuucgagugc   1080
gagugcagcc ccggcuggac cgggcccacu ugcuccacca acauugacga cuguagcccg   1140
aacaauugca gccacggcgg caccugccag gaccugguga auggcuucaa gugcgugugu   1200
cccccccagu ggaccgggaa gaccugccag cuggacgcca acgagugcga ggccaagccc   1260
ugugugaacg ccaaguccug caagaaccug aucgccuccu acuacuguga cugucucccc   1320
ggguggaugg gccagaacug cgacaucaac aucaacgauu gccucggcca gugccagaac   1380
gacgccagcu guagggaccu cgugaacggc uaccggugca ucugcccgcc cggguacgcc   1440
ggagaccacu gcgagaggga cauugacgag ugcgccucga accccugccu gaacggcggc   1500
cacugucaga acgagaucaa uagguuccag ugucugugucc ccaccggcuu cuccggcaac   1560
cugugucagc uggacaucga cuacugugag cccaaucccu gccagaaugg cgcccagugc   1620
uauaaccggg ccuccgacua cuuuugcaag ugccccgaag auuacgaggg caagaacugc   1680
agccaucuga aggaccacug caggacgacu cccugcgagg ugaucgacag cuguacuguc   1740
gccauggcca gcaacgacac ccccgagggg guccgcuaua ucagcagcaa cgugugcggg   1800
ccccauggga aaugcaaauc ccagucaggg ggcaaguuua ccugcgacug uaacaaaggc   1860
uucaccggca ccuacugcca cgaaaacauc aacgacugcg aaucgaaccc cugccggaac   1920
ggcgggaccu gcaucgaugg agugaacagc uacaagugca ucugcagcga cggguggggag   1980
ggcgcguacu gcgaaaccaa uaucaaugac ugcagccaga accccugcca uaacggaggc   2040
accugcaggg accuggugaa cgacuucuac ugcgauugca agaacggcug gaaggggaag   2100
accugccaua gcagggacag ccagugugac gaggccaccu gcaacaacgg cggcacaugu   2160
uacgaugagg gcgacgccuu caaaugcaug ugccccggcg gcugggaggg caccacaugc   2220
aacaucgccc ggaacagcag cugccucccc aaccccugcc auaauggcgg uaccugcgug   2280
gugaacggcg agaguuucac cugcgugugc aaggagggcu gggagggccc caucugcgcg   2340
cagaacacca augacugcuc gccccacccc ugcuacaaca gcggcaccug cguggacggu   2400
gacaacuggu accguugcga gugcgcccca ggcuucgccg gcccggacug caggaucaac   2460
aucaacgagu gccaaagcuc cccuugcgcc uuuggcgcaa ccugugugga cgagaucaau   2520
ggguacaggu gcgugugccc ccccggccau uccggggcca agugccaaga gguguccggc   2580
cggcccugca uuaccauggg cagcguuauc cccgacggcg ccaagugggga cgacgacugc   2640
aauaccugcc agugccucaa cggcaggauc gccugcagca agguguggug cggacccagg   2700
ccgugccugc ugcauaaggg ccacagcgag ugcccgagcg gucaguccug cauccccauc   2760
cucgacgacc aguguuucgu gcaccccugc acgggcgugg gugagugccg auccuccagc   2820
```

cugcagcccg ucaaaaccaa gugcaccucc gacagcuacu accaggacaa cugcgccaac 2880
auaaccuuca cguuuaacaa ggagaugaug agccccggcc ugaccaccga gcacaucugc 2940
agcgagcuga ggaaccugaa cauccugaag aacguguccg ccgaguacag caucuacauc 3000
gccugugagc ccagccccuc cgccaacaac gagauccaug uugccaucuc ggccgaagau 3060
auuagggacg acggcaaccc caucaaggag aucaccgaca agaucauaga ccuggugagc 3120
aagcgggacg gcaauuccag ccugaucgcc gccguggccg aggugagagu gcagaggagg 3180
ccccugaaga accggaccga uuuccuggug ccccugcuga gcagcgugcu gaccguggcc 3240
uggaucugcu gccuggugac cgcauuuuac uggugucuga ggaagcggag gaaacccggc 3300
agccacaccc acagcgcaag cgaggauaac accacgaaua acgugcgcga gcagcugaac 3360
caaaucaaga accccaucga gaagcacggg gccaacaccg ugcccaucaa ggacuacgag 3420
aauaagaacu cgaagaugag caagaucagg acgcacaacu ccgaggugga ggaggacgac 3480
auggauaagc accagcagaa agcccgguuc gccaagcagc ccgccuacac ccugguugac 3540
cgcgaggaga aacccccaa cggcaccccc accaagcacc ccaacuggac caacaagcag 3600
gacaaccgag accuggagag cgcccagagc cugaacagga uggaguauau cgug 3654

<210> SEQ ID NO 108
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 108
augaggaccc ccaggaccag gggcaggagc gggaggcccc ugucccuucu gcuggcgcug 60
cugugcgccc ugcgcgccaa ggugugcggg gcaagcggcc aguucgagcu cgaaauacuc 120
agcaugcaaa acgucaacgg cgagcugcag aacggcaacu guugcggugg cgccaggaac 180
cccggggauc gcaagugcac cagggacgag ugugauaccu acuucaaagu gugucugaag 240
gaguaccaga gccgggugac cgccgggggc cccuguuccu ucggcagcgg gagcaccccc 300
gucaucggcg ggaauacguu uaaccugaag gccuccaggg gcaacgauag gaaccggauc 360
gugcucccuu ucagcuucgc cuggcccagg uccuacaccc ugcuggugga ggccugggac 420
uccagcaaug acacugucca gccugacagu aucauagaga aagccuccca cuccggcaug 480
aucaacccca gucgccagug gcagacccug aagcagaaca ccggcguggc ccacuucgag 540
uaccagaucc gggugaccug cgacgacuau uacuacggcu ucggaugcaa uaaguucugu 600
aggccccgcg acgauuucuu cggccauuau gccugcgacc agaacggcaa caagaccugc 660
auggagggcu ggauggggcc cgagugcaac agggccaucu gcaggcaggg gugcucccc 720 aaacacggga gcugcaaacu gccgggggac ugcaggugcc aauacggcug gcagggccug 780
uacugcgaca agugcauccc gcaccccggg ugcgugcacg gcauuugcaa cgaacccugg 840
cagugccucu gcgaaaccaa uuggggaggc cagcugugcg acaaggaucu gaacuacugc 900
ggcacgcacc agcccugccu caacgggggg accuguagca acacgggccc cgacaaguac 960
cagugcuccu gcccggaggg auacucuggc cccaacugcg agaucgccga gcacgccugc 1020
cucuccgauc cgugccacaa uaggggcagc ugcaaggaaa cgucccuggg cuucgaaugc 1080
gaaugcaguc ccggauggac cggccccacc ugcagcacca acaucgacga cugcagcccc 1140
aacaacugca gccacggcgg caccugccaa gaucucguga acggcuucaa gugcgugugc 1200

-continued

```
ccccccccagu ggaccgggaa aaccugccaa cucgacgcca augaguguga ggccaagccc   1260
ugcgugaacg ccaagucgug caaaaaccug aucgccagcu acuacugcga cugccugccc   1320
ggcuggaugg ggcagaacug cgacaucaac aucaacgacu gccuggggca gugccagaau   1380
gacgcuagcu gccgagaccu ggucaaugga uaccggugca uaugcccccc gggcuacgcc   1440
ggcgaccauu gcgagcggga caucgacgag ugcgccagca acccaugccu gaacggcggg   1500
cacugccaga acgaaauaaa cagguuccag ugucugugcc cgacgggcuu uagcggcaac   1560
cucugccagu uggauaucga cuauugcgag ccuaacccuu gccagaacgg cgcccagugc   1620
uauaaccgcg caagcgauua uuucugcaaa ugccccgagg acuacgaggg caagaauugc   1680
agccaucuga aagaccacug ucggacgacc cccugcgagg ugaucgacag cugcaccgug   1740
gccauggccu ccaacgacac ccccgaaggg gugcgcuaua ucuccagcaa cgugugcggc   1800
ccccacggca agugcaagag ccagucaggg ggcaaauuca ccugcgacug caacaagggc   1860
uucaccggga ccuacugcca cgagaacauc aacgacugcg agagcaaccc cugccggaac   1920
ggcggcaccu gcaucgaugg ggugaacucc uauaagugca ucuguagcga uggaugggag   1980
ggggccuacu gcgaaaccaa caucaacgac ugcagccaga accccugcca caacgggggc   2040
accugcaggg accucgugaa cgacuucuac ugcgacugca agaacggcug gaagggcaag   2100
acaugccacu cccgggacuc acaaugcgac gaagcgaccu gcaacaaugg cggcaccugu   2160
uacgaugagg gggaugccuu uaagugcaug ugccccggug gcugggaggg caccaccugc   2220
aauaucgcca ggaauuccuc cugccugccc aaccccugcc auaauggcgg gaccugcguc   2280
gugaacggcg agagcuucac cugcgugugc aaagaggggu gggaaggacc caucugcgcc   2340
caaaauacga acgacugcag cccccacccc uguuacaaca gcggcacgug cguggauggg   2400
gacaacuggu accgcugcga gugcgccccc ggcuuugcag gcccggacug ucggaucaac   2460
aucaacgagu gccagagcag ccccugcgcc uucggagcca cgugcgugga cgagaucaau   2520
ggcuacagau gcgugugccc cccgggacac agcggcgcca agugccagga aguguccggc   2580
cgucccugca ucaccauggg uagcgucauc cccgacggcg ccaaguggga cgaugacugc   2640
aacacguguc agugucugaa cggccgaauc gccugcucca agguguggug cggcccccgg   2700
cccugccugc ugcacaaggg ccacagcgag ugccccagcg gccagucgug uauccccauc   2760
cucgacgacc aaugcuucgu gcaccccugc accggcgugg gcgagugccg cagcucgagc   2820
cugcagcccg ugaagaccaa gugcaccagc gauagcuacu accaggacaa uugcgccaac   2880
aucaccuuca ccuuuaacaa ggagaugaug agccccggcc ugacgaccga acacaucugc   2940
uccgagcuga ggaaccugaa cauccugaag aaugucagcg cugaguacuc caucuacauc   3000
gccugugagc ccagcccaag cgccaacaau gagauccacg ucgcgaucuc cgccgaggac   3060
auccgcgacg auggcaaccc caucaaggag aucaccgaca agaucaucga ccuggugagc   3120
aagagggacg gcaacagcuc ccugaucgcc gcgguggccg aggugagggu ccaaaggagg   3180
ccccugaaga acaggaccga cuuccuggug ccccugcugu cgagcgugcu gaccguggcc   3240
uggaucugcu gccuggugac cgcguucuac uggugccugc guaagaggag gaagcccggc   3300
agccacaccc auagcgcguc cgaggauaac accaccaaua acgugaggga gcagcucaac   3360
cagaucaaga acccaaucga gaagcacggu gccaacacug ugcccaucaa ggacuaugag   3420
aacaagaaca gcaagaugag uaagaucagg acacacaacu ccgaggugga agaagacgac   3480
auggacaagc accagcagaa ggcccgguuc gccaagcagc ccgccuacac ccugguggac   3540
agggaagaga aaccccccaa cgguacaccc acgaaacacc ccaacuggac caauaagcag   3600
```

gacaacaggg accuggaguc cgcccagagu cugaacagga uggaguacau cgug 3654

<210> SEQ ID NO 109
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 109
augcggaccc cccggaccag ggguaggagc ggccgcccac ugucccugcu gcuggcccug 60
cugugugccc ugagggccaa ggugugcggc gccuccggac aauucgagcu ggagauucuc 120
ucgaugcaga acgugaacgg cgaacugcag aacggaaauu gcuguggcgg cgccaggaau 180
cccggcgaua gaaagugcac cagggacgag ugugacacgu acuucaaggu gugccugaag 240
gaguaccaga gccgcgugac cgccggcggg cccugcuccu ucgggucagg cagcaccccc 300
gugaucggcg ggaacaccuu caaccucaag gccuccaggg gcaacgacag gaauaggauc 360
gugcuccccu ucagcuucgc cuggcccagg uccuacaccc ugcugguaga ggccugggac 420
uccagcaacg acaccgugca gcccgauagc aucaucgaga aggcuagcca cagcggaaug 480
aucaacccca gccgccagug gcagacccug aaacagaaca ccggcguagc ccacuuugag 540
uaccagauca gggugaccug cgacgacuau uacuauggcu ucgguugcaa caaguucugc 600
cggccucgcg acgacuucuu cggacacuac gccugugauc agaacgggaa caagaccugu 660
auggaggguu ggaugggccc cgaaugcaac agggccaucu gcaggcaggg cugcuccccc 720
aagcacggga gcugcaagcu gcccggcgac ugccggugcc aguacggcug gcagggucug 780
uacugcgaca agugcauccc ccauccuggc ugcgugcacg gcauaugcaa cgagcccugg 840
cagugccugu gcgagaccaa uuggggcggc cagcugugcg acaaggaccu gaauuacugu 900
ggcacccacc agcccugccu caacggcggc accugcucca acaccggccc cgacaaguac 960
cagugcagcu gccccgaagg cuacagcggc ccgaauugcg agaucgccga acacgccugc 1020
cucagcgacc ccugccacaa ccggggcagc uguaaggaga ccucccuggg cuuugaaugc 1080
gaauguagcc ccgguuggac cggacccacc uguuccacca acaucgacga cugcagcccc 1140
aauaacugca gccacggugg cacgugccag gaccucguca acggcuuuaa gugcgugugc 1200
cccccccagu ggaccgggaa gaccugccag cuggacgcca acgagugcga ggccaagccc 1260
ugcgugaacg ccaagagcug caagaaccuc aucgccagcu acuauuguga cugccugccc 1320
ggguggaugg gccagaacug ugacauaaac aucaacgauu gucugggcca gugccagaac 1380
gaugccagcu gucgggaccu ggugaacggc uaccggugca ucuguccccc cggcuacgcc 1440
ggagaucacu gugagcgaga caucgacgag ugcgccucca accccugccu caacggcggg 1500
cacugucaga augagaucaa cagguuccag ugccugugcc cgacgggauu cuccgguaac 1560
cugugccagc ucgacaucga cuacugugag cccaaccccu gucaaaaugg cgcccaaugc 1620
uacaaccggg ccuccgacua cuucuguaag ugccccgagg auuacgaggg uaagaacugu 1680
agccaucuga aggaccacug caggacuacc ccgugcgagg ugaucgacuc cugcaccguc 1740
gccauggccu ccaacgacac ccccgagggc gugcgguaca ucagcagcaa cgugugcggg 1800
ccgcacggca agugcaagag ccagagcggg ggcaaguuca ccugugauug caacaagggc 1860
uucaccggga cguauugcca cgagaacauc aacgacugcg agagcaaccc cugcaggaac 1920
ggggggaccu gcauagacgg cgugaacagc uacaaaugca ucugcagcga uggguggggag 1980 ggcgccuacu gugagaccaa cauuaacgac ugcagccaga accccugcca caacgggggu 2040
accugucgcg accuggugaa cgacuucuac ugugacugca agaacggcug gaagggcaag 2100
accugucauu cccgcgacag ccagugcgac gaagccaccu gcaacaacgg cggcaccugc 2160
uacgacgagg gcgaugccuu caagugcaug ugcccgggcg gcugggaggg gaccaccugu 2220
aauaucgcca ggaauuccag cugccucccc aauccgugcc auaauggcgg caccugcgug 2280
gucaacggcg aaagcuuuac cugcgucugu aaggaaggcu gggaaggucc gaucugugcc 2340
cagaacacca acgacuguag cccccacccc ugcuacaaua gcggaacgug cguggacggc 2400
gacaacuggu aucggugcga gugcgccccc ggcuuugcgg ggccggacug ccggaucaau 2460
aucaacgagu gccagagcag ccccugcgcc uucggcgcca ccugcgugga cgagaucaac 2520
ggcuacaggu gcgugugucc ccccggccac uccggcgcca agugccagga ggugagcggu 2580
aggcccugca ucaccauggg cagcgugauc cccgacgggg ccaaguggga cgaugacugu 2640
aacaccugcc agugccugaa cgggaggauc gccuguucca aaguguggug cggcccgcgu 2700
cccugccuac uccacaaggg gcauuccgag ugucccagcg gacagagcug uauccccauc 2760
cuggacgacc aaugcuucgu gcaccccugc accggcgugg gugagugcag guccagcagc 2820
cugcagcccg ugaagacaaa gugcaccagu gauuccuacu accaggauaa cugcgccaac 2880
aucaccuuca ccuucaauaa ggagaugaug agcccgggcc ugaccacgga gcacaucugc 2940
agcgagcugc gcaaccugaa cauccugaag aacgucuccg ccgaguacag cauauacauc 3000
gccugcgagc ccagccccuc cgccaauaac gagauccacg uggccaucuc cgcggaggac 3060
aucagggacg auggcaaccc caucaaggag aucaccgaca agauuaucga ccuggucagc 3120
aaaagggacg gcaacuccag ccucaucgcc gccguggccg aggucagggu acagcgcagg 3180
ccgcugaaaa accggaccga cuuccuggug ccccugcuuu ccuccgugcu cacgguggcc 3240
uggauuugcu gccugguaac cgcguuuuac uggugccuga ggaagaggag gaagcccggc 3300
agccauaccc acagcgccag cgaggacaac acaaccaaca acgugaggga gcagcucaac 3360
cagauaaaga accccaucga gaaacacggc gccaacacgg ugcccaucaa ggacuaugag 3420
aacaagaaca gcaagaugag caagauccgc acccacaaca gcgagguuga ggaagacgac 3480
auggacaagc accagcagaa ggccagguuc gccaagcagc ccgccuacac ccugguggau 3540
cgugaggaga aaccgcccaa cgggaccccc accaagcauc ccaauuggac caacaaacag 3600
gacaacaggg accuggaguc cgcccaaagc cugaaccgga uggaguacau cguc 3654

<210> SEQ ID NO 110
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 110 augaggucccc ccagaacucg ggggaggucc ggcaggccgc ucagccuccu gcucgcccug 60
cugugcgccc ugagggccaa ggugugcggc gccuccggcc aguucgagcu ggagauucug 120
agcaugcaga acgugaacgg cgaacugcag aacggaaacu gcugcggugg ggccaggaac 180
cccggcgacc ggaagugcac cagggaugaa ugcgacaccu acuucaaggu cugccucaag 240
gaguaccaga gcagggugac cgccgggggc ccguguagcu ucggcuccgg cagcaccccc 300
gugauaggcg gcaacacguu caaccuuaaa gccuccaggg gcaacgaccg caacaggauc 360
gugcugcccu ucuccuucgc guggccccgc agcuacaccc ugcugguuga ggcgugggau 420

-continued

```
agcagcaacg acaccgucca gcccgauuca aucaucgaaa aggccagcca cagcggcaug    480
aucaaccccu ccaggcagug gcagacccug aagcaaaaca ccggcguggc ccacuucgag    540
uaccaaauca ggguuaccug cgacgacuac uacuaugggu ucggcugcaa uaaguucugu    600
cggccgcggg acgacuuuuu cgggcauuau gccugcgacc agaauggcaa uaagaccugc    660
auggagggcu ggaugggacc cgagugcaac cgcgccaucu gcaggcaggg cugcucccccc   720
aagcacggca gcugcaagcu gcccggcgac ugcaggugcc aguacgggug gcagggccuc    780
uacugcgaca agugcauccc ccacccccggc ugcgugcaug ggauaugcaa cgagccgugg   840
cagugccugu gcgaaaccaa cuggggggggc cagcugugcg auaaggaccu caacuacugc   900
ggcacccacc agcccugccu caacggcggc accugcucca auaccgggcc cgauaaauac    960
cagugcuccu gcccugaggg cuacagcggg cccaacugug agaucgccga gcaugccugc   1020
cucucggacc ccugccauaa caggggcagc uguaaggaaa ccagccuggg cuucgagugc   1080
gagugcagcc ccgggugggac cgggccaacc ugcuccacca acaucgacga cuguagcccg  1140
aacaacugcu cccacggcgg gaccugccag gaccugguga auggcuucaa gugcguaugu   1200
cccccacagu ggaccggcaa gaccugucaa cucgacgcca acgagugcga ggccaaaccc   1260
ugcgugaacg ccaaguccug caagaaccug aucgccuccu acuacugcga cugucugccc   1320
ggcuggaugg gccagaacug cgauaucaac aucaacgauu gccucggcca gugucagaac   1380
gacgccuccu gccgggaccu ggugaacggc uaccggugca uuugcccccc gggcuacgcc   1440
ggcgaucacu gcgagcgcga caucgacgag ugcgcaucca accccugucu gaacgggggg   1500
cacugucaga acgagaucaa uagguuccag ugccugugcc ccaccggcuu cuccgggaau   1560
cugugccagc uggacaucga uuacugcgag cccaaccccu gccagaacgg cgcccagugu   1620
uacaacaggg ccagcgauua cuucugcaag ugucccgaag acuaugaggg caagaauugc   1680
agccaucuga aagaccacug ccgcaccacc cccugugagg ugaucgacuc gugcaccgug   1740
gcgauggcca gcaaugacac cccggagggc gugcgguaca ucagcagcaa cgugugu ggg  1800
ccccacggca agugcaaguc ccagagcggg ggcaaguuca ccugcgacug caacaaaggc   1860
uuuacaggga cauauugcca cgaaaacauc aaugacugcg agagcaaccc cugccgcaau   1920
ggcggcacuu gcaucgacgg cgugaacagc uacaaaugua ucugcucaga cggguggg aa  1980
ggcgcguauu gcgagaccaa caucaacgau uguagccaga aucccugcca uaacggu ggu  2040
accugccggg aucuggugaa cgacuucuau ugcgacugca agaacggcug gaagggcaag   2100
accugccauu cgagggauag ccagugcgac gaggccaccu gcaacaacgg cggcaccugc   2160
uacgacgagg gcgaugccuu caagugcaug ugcccuggcg gcugggaggg caccaccugc   2220
aacaucgcca ggaacagcuc cugccugccc aaccccugcc acaacggcgg gaccugugu c  2280
gugaacgggg agagcuucac gugcgugugc aaggagggcu gggaagggcc caucugcgcc   2340
caaaacacca acgacugcag cccccauccc uguuacaacu ccggcaccug cguggacggc   2400
gacaacuggu accgaugcga gugcgccccc ggcuucgccg gccccgacug ccggaucaac   2460
aucaacgagu gccagagcag ccccugcgcg uucggcgcca ccugcgugga ugaaaucaac   2520
ggauauaggu gcgugugccc ccccggccac agcggggcca agugccagga ggucagcggg   2580
cgccccugca ucaccauggg cagcgugaua cccgacggcg ccaaguggga cgacgacugc   2640
aacaccugcc agugccugaa cggcaggauc gccugcucca aggugugg ug cgggccgcgg  2700
ccgugccugc ugcacaaggg ccacagcgag ugccccagcg gccaguccug uaucccaauc   2760
```

```
cuggacgacc agugcuucgu gcaucccugc accggcgugg gcgagugcag guccuccucc   2820

cugcagcccg ugaagaccaa augcaccagc gacucguacu accaggauaa cugcgccaac   2880

aucaccuuca ccuucaacaa ggaaaugaug agccccggcc ugaccaccga gcacaucugc   2940

agcgagcucc ggaaccugaa cauccugaag aacguguccg ccgaguauag caucuacauc   3000

gcgugcgaac caaguccguc cgccaacaac gagauccacg uggcaaucuc cgccgaggac   3060

auccgggacg acggcaaccc caucaaggag auaaccgaca aaaucaucga ccuggugagc   3120

aaaagggacg gcaauucuag ccugaucgcc gcaguggccg aagugagggu gcagcgcagg   3180

ccccucaaga auaggaccga cuuccuggug ccgcuccuca gcagcgugcu gaccguggcc   3240

uggaucugcu gccuggugac cgccuuuuac uggugccuga ggaagcguag gaagcccgga   3300

agccacacac acuccgccag cgaggacaac accaccaaca acgugcggga gcaacugaac   3360

cagaucaaga accccaucga gaagcacgga gccaacaccg ucccuaucaa agacuacgag   3420

aacaagaaca gcaagaugag caagaucagg acccacaaca gcgagguuga ggaagacgac   3480

auggacaagc accagcagaa agccagguuc gcgaagcagc ccgccuacac ccugguggac   3540

cgggaggaaa agcccccaa cggcacccc accaagcacc cgaacuggac caacaagcag   3600

gacaacaggg accuggagag cgcccagagc cugaaccgga uggaguacau cguc        3654
```

```
<210> SEQ ID NO 111
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 111
```

```
augcgcagcc cccggaccag gggaagguce ggcaggcccc ugucccugcu gcuggcgcug     60

cucugcgccc ugcgagccaa agugugugu gccuccgggc aguuugagcu ggagauccuc    120

agcaugcaga acgugaacgg ggagcugcag aaugggaacu gcugcggcgg cgccaggaau    180

cccggggaca ggaagugcac ccgagaugag ugcgacaccu auuucaaggu gugccugaag    240

gaguaccaga gccgugugac ggccggcggc cccugcagcu uuggcagcgg cagcaccccc    300

gugaucggcg gaaacacauu caaccugaag gccagcaggg gcaacgacag gaacaggauc    360

gugcugcccu ucagcuucgc cuggcccagg uccuacaccc ugcuggugga ggccugggau    420

agcagcaaug acaccgugca gcccgacucc aucaucgaga aggccaguca cucuggaaug    480

aucaacccga gcaggcagug gcagacccug aagcagaaca ccggcguggc ccacuucgag    540

uaccagauca gggugaccug ugacgauuac uacuacgguu uuggcugcaa caaguucugu    600

aggccccgcg acgacuucuu uggucauuac gccugcgauc agaacggcaa uaagaccugc    660

auggaaggcu ggaugggccc cgaaugcaac agggccauuu gcaggcaggg gugcagcccg    720

aagcacggca gcugcaagcu gcccggcgac ugcaggugue aguacggcug gcagggccug    780

uacugcgaca aaugcauccc ccacccuggg ugcgugcacg gcaucuguaa cgagcccugg    840

cagugccugu gugagaccaa cuggggugg caacugugcg auaaggaccu gaacuacugc    900

ggaacccacc agcccugccu gaacggcggc acaugcagca acaccgggcc cgacaaguac    960

cagugcagcu gccccgaagg guauagcggg cccaauugcg aaaucgccga gcacgccugc   1020

cugagcgauc ccugucauaa ucgcggaucc ugcaaggaga ccagccucgg cuuugagugc   1080

gaaugcuccc ccggcuggac cggucccacg ugcagcacga acaucgacga cuguuccccg   1140

aacaacugcu cccacggcgg caccugccag gaucugguga auggauucaa augcgugugc   1200
```

```
ccccccccaau ggaccgggaa gaccugccaa cuggacgcca acgagugcga agccaagccc   1260
ugugugaacg ccaagagcug caaaaaccuc aucgcuagcu acuacugcga cugccugccc   1320
ggcuggaugg gucagaacug ugacaucaac aucaacgauu gucugggcca gugccagaac   1380
gacgccagcu gcagggaccu ggugaauggg uaccgcugca ucugcccccc cggcuacgcc   1440
ggagaucauu gcgagcggga caucgacgag ugcgccagca accccugccu gaacggcggu   1500
cacugucaga augagaucaa ccgcuuccag ugccugugcc ccaccggcuu cagcggaaau   1560
cugugccagc uagacauuga uuacugcgaa ccgaacccuu gccagaacgg cgcccagugc   1620
uacaacaggg ccagcgacua cuuuugcaag ugccccgagg acuacgaggg gaagaauugc   1680
ucccaccuaa aggaccacug ccggaccacc cccugcgagg ugaucgacag cugcaccguc   1740
gcgauggcca gcaacgacac ccccgagggc gucagguaca ucuccagcaa cgugugcggu   1800
ccccauggca aaugcaagag ccagagcggg gggaaguuua ccugcgacug caacaagggc   1860
uucaccggga ccuacugcca ugagaacauc aaugacugcg agagcaaccc cugcaggaac   1920
ggcgggacau gcaucgacgg ggugaacucc uauaagugca ucugcuccga cgggugggaa   1980
ggugccuauu gcgagacaaa caucaacgac ugcagccaaa accccugcca caacgggggc   2040
accugcaggg aucuggugaa cgacuucuac ugugacugca agaacgggug gaagggaaag   2100
accugucaca gccgggacuc ccagugcgac gaggccacau gcaacaacgg cggcacgugc   2160
uacgacgaag gagacgccuu uaagugcaug ugccccggcg gcugggaggg caccaccugc   2220
aauaucgccc gcaacuccuc cugccugccc aacccgugcc acaacggggg caccugcgug   2280
gugaacggcg aguccuucac cugcgucugc aaggagggcu gggagggucc caucugugcc   2340
cagaauacca augacugcag cccccauccu uguuacaauu ccggcaccug cguggauggc   2400
gacaacuggu aucgguguga gugcgccccc ggcuucgcgg gccccgacug uaggaucaac   2460
aucaacgagu gccagagcuc cccaugcgcg uuuggggcga ccugugucga cgagaucaau   2520
ggguacaggu gcgugugucc cccggggcac uccggggcca aaugccagga gguaagcggc   2580
cggccaugca uuaccauggg cucggugauc ccagacggug ccaaguggga cgacgacugc   2640
aacaccugcc agugccugaa uggcaggauc gccugcagca agguauggug cggacccagg   2700
ccgugccugc ugcacaaagg acacuccgag uguccgagcg gccagagcug caucccccauc   2760
cuggacgacc agugcuucgu gcaucccugc acuggcgucg gcgagugccg cagcuccagc   2820
cugcagcccg ugaagaccaa guguaccagc gacagcuacu accaggacaa uugugccaac   2880
aucaccuuca ccuucaacaa ggagaugaug agcccuggcc ugaccaccga gcauaucugu   2940
agcgagcuga ggaacuugaa cauccugaag aaugugagcg ccgaguauuc cauuuacaua   3000
gccugugagc ccagcccaag cgcuaacaau gagauccacg uggccaucag cgccgaggac   3060
auccgggacg acggcaaccc caucaaagaa aucaccgaca agaucaucga ucugguaagc   3120
aagagggacg ggaacagcag ccucaucgcc gccguggccg aggugcgcgu ccagcggagg   3180
ccccucaaaa accggaccga cuuucuggug ccgcugcuca gcuccgugcu gaccguggcc   3240
uggauaugcu gccuggugac cgccuucuac uggugccugc ggaagaggag gaagcccggc   3300
agccacacgc acagcgcgag cgaggacaac accaccaaca acgugcggga gcaacugaac   3360
cagaucaaga accccaucga gaagcacggc gccaacaccg ugcccaucaa ggacuacgag   3420
aacaagaaua gcaagaugag uaagauuagg acccacaaca gcgaggugga ggaggacgac   3480
auggacaagc accagcagaa ggcccgcuuc gccaagcagc ccgccuauac ccuggucgac   3540
```

agggaagaga agccgcccaa ugggaccccc accaagcauc ccaacuggac caacaagcag 3600
gacaaccggg aucuggagag cgcccaaagc cugaauagga uggaguacau cgug 3654

<210> SEQ ID NO 112
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 112
ugauaauagg cuggagccuc gguggccuag cuucuugccc cuugggccuc cccccagccc 60
cuccuccccu uccugcaccc guacccccuc cauaaaguag gaaacacuac aguggucuuu 120
gaauaaaguc ugagugggcg gc 142

<210> SEQ ID NO 113
<211> LENGTH: 141
<212> TYPE: RNA
<213> ORGANISM: Artificial Sequence
<220> FEATURE:
<223> OTHER INFORMATION: Synthetic polynucleotide

<400> SEQUENCE: 113
ugauaauagg cuggagccuc gguggccuag cuucuugccc cuugggccuc cccccagccc 60
cuccuccccu uccugcaccc guacccccg cauuauuacu cacgguacga guggucuuug 120
aauaaagucu gagugggcgg c 141

<210> SEQ ID NO 114
<211> LENGTH: 164
<212> TYPE: RNA
<213> ORGANISM: Artificial Sequence
<220> FEATURE:
<223> OTHER INFORMATION: Synthetic polynucleotide

<400> SEQUENCE: 114
ugauaauagu ccauaaagua ggaaacacua cagcuggagc cucgguggcc uagcuucuug 60
ccccuugggc cucccccag ccccuccucc ccuuccugca cccguacccc ccgcauuauu 120
acucacggua cgaguggucu uugaauaaag ucugaguggg cggc 164

<210> SEQ ID NO 115
<211> LENGTH: 188
<212> TYPE: RNA
<213> ORGANISM: Artificial Sequence
<220> FEATURE:
<223> OTHER INFORMATION: Synthetic polynucleotide

<400> SEQUENCE: 115
ugauaauagu ccauaaagua ggaaacacua cagcuggagc cucgguggcc uagcuucuug 60
ccccuugggc cuccauaaag uaggaaacac uacaucccccc cagccccucc uccccuuccu 120
gcacccguac cccccuccauaa aaguaggaaa cacuacagug gucuuugaau aaagucugag 180
ugggcggc 188

<210> SEQ ID NO 116
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 116
ugauaauagg cuggagccuc gguggccaug cuucuugccc cuugggccuc cccccagccc 60
cuccuccccu uccugcaccc guacccccag uagugcuuuc uacuuuaugg uggucuuuga 120
auaaagucug agugggcggc 140

<210> SEQ ID NO 117
<211> LENGTH: 181
<212> TYPE: RNA
<213> ORGANISM: Artificial Sequence
<220> FEATURE:
<223> OTHER INFORMATION: Synthetic polynucleotide

<400> SEQUENCE: 117
ugauaauaga guagugcuuu cuacuuuaug gcuggagccu cgguggccau gcuucuugcc 60
ccuugggcca guagugcuuu cuacuuuaug uccccccagc cccucucccc uuccugcacc 120
cguaccccca guagugcuuu cuacuuuaug guggucuuug aauaaagucu gagugggcgg 180
c 181

<210> SEQ ID NO 118
<211> LENGTH: 184
<212> TYPE: RNA
<213> ORGANISM: Artificial Sequence
<220> FEATURE:
<223> OTHER INFORMATION: Synthetic polynucleotide

<400> SEQUENCE: 118
ugauaauaga guagugcuuu cuacuuuaug gcuggagccu cgguggccau gcuucuugcc 60
ccuugggccu ccauaaagua ggaaacacua cauccccca gccccuccuc cccuuccugc 120
acccguaccc ccaguagugc uuucuacuuu augguggucu uugaauaaag ucugaguggg 180
cggc 184

<210> SEQ ID NO 119
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 119
ugauaauagu ccauaaagua ggaaacacua cagcuggagc cucgguggcc uagcuucuug 60
ccccuugggc cuccccccag ccccuccucc ccuuccugca cccguacccc cguggucuuu 120
gaauaaaguc ugagugggcg gc 142

<210> SEQ ID NO 120
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 120
ugauaauagg cuggagccuc gguggcucca uaaaguagga aacacuacac uagcuucuug 60
ccccuugggc cuccccccag ccccuccucc ccuuccugca cccguacccc cguggucuuu 120
gaauaaaguc ugagugggcg gc 142

<210> SEQ ID NO 121
<211> LENGTH: 142
<212> TYPE: RNA

<213> ORGANISM: Artificial Sequence
<220> FEATURE:
<223> OTHER INFORMATION: Synthetic polynucleotide

<400> SEQUENCE: 121
ugauaauagg cuggagccuc gguggccuag cuucuugccc cuugggccuc cauaaaguag 60
gaaacacuac aucccccag ccccuccucc ccuuccugca cccguacccc cguggucuuu 120
gaauaaaguc ugagugggcg gc 142

<210> SEQ ID NO 122
<211> LENGTH: 142
<212> TYPE: RNA
<213> ORGANISM: Artificial Sequence
<220> FEATURE:
<223> OTHER INFORMATION: Synthetic polynucleotide

<400> SEQUENCE: 122
ugauaauagg cuggagccuc gguggccuag cuucuugccc cuugggccuc cccccagccc 60
cuccuccccu uccugcaccc guacccccac cccuaucaca auuagcauua aguggucuuu 120
gaauaaaguc ugagugggcg gc 142

<210> SEQ ID NO 123
<211> LENGTH: 188
<212> TYPE: RNA
<213> ORGANISM: Artificial Sequence
<220> FEATURE:
<223> OTHER INFORMATION: Synthetic polynucleotide

<400> SEQUENCE: 123
ugauaauaga ccccuaucac aauuagcauu aagcuggagc cucgguggcc uagcuucuug 60
ccccuugggc caccccuauc acaauuagca uuaauccccc cagccccucc uccccuuccu 120
gcacccguac ccccaccccu aucacaauua gcauuaagug gucuuugaau aaagucugag 180
ugggcggc 188

<210> SEQ ID NO 124
<211> LENGTH: 188
<212> TYPE: RNA
<213> ORGANISM: Artificial Sequence
<220> FEATURE:
<223> OTHER INFORMATION: Synthetic polynucleotide

<400> SEQUENCE: 124
ugauaauaga ccccuaucac aauuagcauu aagcuggagc cucgguggcc uagcuucuug 60
ccccuugggc cuccauaaag uaggaaacac uacauccccc cagccccucc uccccuuccu 120
gcacccguac ccccaccccu aucacaauua gcauuaagug gucuuugaau aaagucugag 180
ugggcggc 188

<210> SEQ ID NO 125
<211> LENGTH: 3678
<212> TYPE: RNA
<213> ORGANISM: Artificial Sequence
<220> FEATURE:
<223> OTHER INFORMATION: Synthetic polynucleotide

<400> SEQUENCE: 125
augcguuccc cacggacgcg cggccggucc gggcgccccc uaagccuccu gcucgcccug 60
cucugugccc ugcgagccaa ggugugug gg gccucggguc aguucgaguu ggagauccug 120
uccaugcaga acgugaacgg ggagcugcag aacgggaacu gcugcggcgg cgcccggaac 180

```
ccgggagacc gcaagugcac ccgcgacgag ugugacacau acuucaaagu gugccucaag    240
gaguaucagu cccgcgucac ggccgggggg cccugcagcu ucggcucagg guccacgccu    300
gucaucgggg gcaacaccuu caaccucaag gccagccgcg gcaacgaccg caaccgcauc    360
gugcugccuu ucaguuucgc cuggccgagg uccuauacgu ugcuugugga ggcgugggau    420
uccaguaaug acaccguuca accugacagu auuauugaaa aggcuucuca cucgggcaug    480
aucaacccca gccggcagug gcagacgcug aagcagaaca cgggcguugc ccacuuugag    540
uaucagaucc gcgugaccug ugaugacuac uacuauggcu uuggcugcaa uaaguucugc    600
cgccccagag augacuucuu uggacacuau gccugugacc agaauggcaa caaaacuugc    660
auggaaggcu ggaugggccc cgaauguaac agagcuauuu gccgacaagg cugcaguccu    720
aagcaugggu cuugcaaacu cccaggugac ugcaggugcc aguacggcug gcaaggccug    780
uacugugaua agugcauccc acacccggga ugcguccacg gcaucuguaa ugagcccugg    840
cagugccucu gugagaccaa cuggggcggc cagcucugug acaaagaucu caauuacugu    900
gggacucauc agccgugucu caacggggga acuuguagca acacaggccc ugacaaauau    960
caguguuccu gcccugaggg guauucagga cccaacugug aaauugcuga gcacgccugc   1020
cucucugauc ccugucacaa cagaggcagc uguaaggaga ccucccuggg cuuugagugu   1080
gaguguuccc caggcuggac cggccccaca ugcucuacaa acauugauga cuguucuccu   1140
aauaacuguu cccacggggg caccugccag gaccugguua acggauuuaa gugugugugc   1200
cccccacagu ggacugggaa aacgugccag uuagaugcaa augaauguga ggccaaaccu   1260
uguguaaacg ccaaauccug uaagaaucuc auugccagcu acuacugcga cugucuuccc   1320
ggcuggaugg gucagaauug ugacauaaau auuaaugacu gccuuggcca gugucagaau   1380
gacgccuccu gucgggauuu gguuaauggu uaucgcugua ucuguccacc uggcuaugca   1440
ggcgaucacu gugagagaga caucgaugaa ugugccagca accccuguuu gaaugggggu   1500
cacugucaga augaaaucaa cagauuccag ugucuguguc ccacugguuu cucuggaaac   1560
cucugucagc uggacaucga uuauugugag ccuaaucccu gccagaacgg ugcccagugc   1620
uacaaccgug ccagugacua uuucugcaag ugccccgagg acuaugaggg caagaacugc   1680
ucacaccuga aagaccacug ccgcacgacc cccugugaag ugauugacag cugcacagug   1740
gccauggcuu ccaacgacac accugaaggg gugcgguaua uuuccuccaa cgucuguggu   1800
ccucacggga agugcaagag ucagucggga ggcaaauuca ccugugacug uaacaaaggc   1860
uucacgggaa cauacugcca ugaaaauauu aaugacugug agagcaaccc uuguagaaac   1920
gguggcacuu gcaucgaugg ugucaacucc uacaagugca ucuguaguga cggcugggag   1980
ggggccuacu gugaaaccaa uauuaaugac ugcagccaga accccugcca caaugggggc   2040
acgugucgcg accuggucaa ugacuucuac ugugacugua aaaaugggug gaaaggaaag   2100
accugccacu cacgugacag ucagugugau gaggccacgu gcaacaacgg uggcaccugc   2160
uaugaugagg gggaugcuuu uaagugcaug uguccuggcg gcugggaagg aacaaccugu   2220
aacauagccc gaaacaguag cugccugccc aaccccugcc auaauggggg cacaugugug   2280
gucaacggcg aguccuuuac gugcgucugc aaggaaggcu gggaggggcc caucugugcu   2340
cagaauacca augacugcag cccucauccc uguuacaaca gcggcaccug uguggaugga   2400
gacaacuggu accggugcga augugccccg gguuuugcug ggcccgacug cagaauaaac   2460
aucaaugaau gccagucuuc accuugugcc uuuggagcga ccugugugga ugagaucaau   2520
```

ggcuaccggu gugucugccc uccagggcac aguggugcca agugccagga aguuucaggg 2580
agaccuugca ucaccauggg gagugugaua ccagaugggg ccaaauggga ugaugacugu 2640
aauaccugcc agugccugaa uggacggauc gccugcucaa aggucuggug uggcccucga 2700
ccuugccugc uccacaaagg gcacagcgag ugccccagcg ggcagagcug cauccccauc 2760
cuggacgacc agugcuucgu ccaccccugc acuggugugg gcgagugucg gucuuccagu 2820
cuccagccgg ugaagacaaa gugcaccucu gacuccuauu accaggauaa cugugcgaac 2880
aucacauuua ccuuuaacaa ggagaugaug ucaccagguc uuacuacgga gcacauuugc 2940
agugaauuga ggaauuugaa uauuuugaag aauguuuccg cugaauauuc aaucuacauc 3000
gcuugcgagc cuuccccuuc agcgaacaau gaaauacaug uggccauuuc ugcugaagau 3060
auacgggaug augggaaccc gaucaaggaa aucacugaca aaauaaucga ucuuguuagu 3120
aaacgugaug gaaacagcuc gcugauugcu gccguugcag aaguaagagu ucagaggcgg 3180
ccucugaaga acagaacaga uuuccuuguu cccuugcuga gcucugucuu aacuguggcu 3240
uggaucuguu gcuuggugac ggccuucuac uggugccugc ggaagcggcg gaagccgggc 3300
agccacacac acucagccuc ugaggacaac accaccaaca acgugcggga gcagcugaac 3360
cagaucaaaa accccauuga gaaacauggg gccaacacgg uccccaucaa ggauuaugag 3420
aacaagaacu ccaaaauguc uaaaauaagg acacacaauu cugaaguaga agaggacgac 3480
auggacaaac accagcagaa agcccgguuu gccaagcagc cggcguacac gcugguagac 3540
agagaagaga agccccccaa cggcacgccg acaaaacacc caaacuggac aaacaaacag 3600
gacaacagag acuuggaaag ugcccagagc uuaaaccgaa uggaguacau cguagacuac 3660
aaagacgaug acgacaag 3678

<210> SEQ ID NO 126
<211> LENGTH: 3654
<212> TYPE: RNA
<213> ORGANISM: Artificial Sequence
<220> FEATURE:
<223> OTHER INFORMATION: Synthetic polynucleotide

<400> SEQUENCE: 126
augcgguccc cacggacgcg cggccggccc gggcgccccc ugagucuucu gcucgcccug 60
cucugugccc ugcgagccaa ggugugcggg gccucggguc aguuugagcu ggagauccug 120
uccaugcaga acgugaaugg agagcuacag aaugggaacu guuguggugg aguccggaac 180
ccuggcgacc gcaagugcac ccgcgacgag ugugauacgu acuucaaagu gugccucaag 240
gaguaucagu cccgcgucac ugccggggga cccugcagcu ucggcucagg gucuacgccu 300
gucaucgggg guaacaccuu caaucucaag gccagccgug gcaacgaccg uaaucgcauc 360
guacugccuu ucaguuucgc cuggccgagg uccuacacuu ugcuggugga ggccugggau 420
uccaguaaug acacuauuca accugauagc auaauugaaa aggcuucuca cucaggcaug 480
auaaacccua gccggcaaug gcagacacug aaacaaaaca cagggauugc ccacuucgag 540
uaucagaucc gagugaccug ugaugaccac uacuauggcu uuggcugcaa uaaguucugu 600
cgucccagag augacuucuu uggacauuau gccugugacc agaacggcaa caaaacuugc 660
auggaaggcu ggaugggucc ugauugcaac aaagcuaucu gccgacaggg cugcaguccc 720
aagcaugggu cuuguaaacu uccaggugac ugcaggugcc aguacgguug gcagggccug 780
uacugcgaca agugcauccc gcacccagga uguguccacg gcaccugcaa ugaacccugg 840
cagugccucu gugagaccaa cuggggugga cagcucugug acaaagaucu gaauuacugu 900
gggacucauc agcccugucu caaccgggga acauguagca acacugggcc ugacaaauac 960
cagugcuccu gcccagaggg cuacucgggc cccaacugug aaauugcuga gcaugcuugu 1020
cucucugacc ccugccauaa ccgaggcagc ugcaaggaga ccuccucagg cuuugagugu 1080
gaguguucuc caggcuggac uggccccacg uguuccacaa acaucgauga cuguucucca 1140
aauaacuguu cccauggggg caccugccag gaucugguga auggauucaa gugugugugc 1200
ccgccccagu ggacuggcaa gacuugucag uuagaugcaa augagugcga ggccaaaccu 1260
uguguaaaug ccagauccug uaagaaucug auugccagcu acuacuguga uugccuuccu 1320
ggcuggaugg gucagaacug ugacauaaau aucaaugacu gccuuggcca gugucagaau 1380
gacgccuccu gucgggauuu gguuaauggu uaucgcugua ucuguccacc uggcuaugca 1440
ggcgaucacu gugagagaga caucgaugag ugugcuagca accccugcuu gaaugggggu 1500
cacugucaga augaaaucaa cagauuccag ugucucuguc ccacugguuu cucuggaaac 1560
cucugucagc uggacaucga uuacugcgag cccaacccuu gccagaaugg cgcccagugc 1620
uacaaucgug ccagugacua uuucugcaag ugccccgagg acuaugaggg caagaacugc 1680
ucacaccuga aagaccacug ccguaccacc accugcgaag ugauugacag cugcacugug 1740
gccauggccu ccaacgacac gccugaaggg gugcgguaua ucucuucuaa cgucuguggu 1800
ccccauggga agugcaagag ccagucggga ggcaaauuca ccugugacug uaacaaaggc 1860
uucaccggca ccuacugcca ugaaaauauc aacgacugcg agagcaaccc cuguaaaaac 1920
gguggcaccu gcaucgaugg cguuaacucc uacaagugua ucuguaguga cggcugggag 1980
ggagcgcacu gugagaacaa cauaaaugac uguagccaga acccuuguca cuacgggggu 2040
acaugucgag accuggucaa ugacuuuuac ugugacugca aaaauggcug gaaaggaaag 2100
acuugccauu cccgugacag ccagugugac gaagccacgu guaauaaugg ugguaccugc 2160
uaugaugaag uggacacguu uaagugcaug ugucccggug gcugggaagg aacaaccugu 2220
aauauagcua gaaacaguag cugccugccg aaccccuguc auaauggagg uaccugcgug 2280
gucaauggag acuccuucac cugugucugc aaagaaggcu gggaggggcc uauuuguacu 2340
caaaauacca acgacugcag uccccauccu uguuacaaua gcgggaccug uguggacgga 2400
gacaacuggu aucggugcga augugccccg gguuuugcug ggccagacug caggauaaac 2460
aucaaugagu gccagucuuc cccuugugcc uuuggggcca ccugugugga ugagaucaau 2520
ggcuaccagu guaucugccc uccaggacau aguggugcca agugccauga aguuucaggg 2580
cgaucuugca ucaccauggg gagagugaua cuugaugggg ccaaguggga ugaugacugu 2640
aacaccugcc agugccugaa uggacgggug gccugcucca aggucuggug uggcccgaga 2700
ccuugcaggc uccacaaaag ccacaaugag ugccccagug ggcagagcug caucccgguc 2760
cuggaugacc aguguuucgu gcgccccugc acuggugaug gcgagugucg guccuccagc 2820
cuccagccag ugaagaccaa gugcacaucu gacuccuauu accaggauaa cugugcaaac 2880
aucacuuuca ccuuuaacaa agagaugaug ucuccagguc uuaccaccga acacauuugc 2940
agcgaauuga ggaauuugaa uauccugaag aauguuucug cugaauauuc gaucuacaua 3000
gccugugagc cuucccuguc agcaaacaau gaaauacacg uggccaucuc ugcagaagac 3060
auccgggaug augggaaccc ugucaaggaa auuaccgaua aaauaauaga ucucguuagu 3120
aaacgggaug gaaacagcuc acuuauugcu gcgguugcag aagucagagu ucagaggcgu 3180
ccucugaaaa acagaacaga uuuccugguu ccucugcuga gcucugucuu aacaguggcu 3240

-continued

```
ugggucuguu gcuuggugac agccuucuac uggugugaaa ggaagcggcg gaagcccagc   3300

agccacacuc acuccgcccc cgaggacaac accaccaaca augugcggga gcagcugaac   3360

caaaucaaaa accccaucga gaaacacgga gccaacacgg uccccauuaa ggauuacgag   3420

aacaaaaacu cgaaaauguc aaaaaucagg acacacaacu cggaagugga ggaggaugac   3480

auggauaaac accagcagaa aguccgcuuu gccaaacagc caguguauac gcugguagac   3540

agagaggaga aggcccccag cggcacgccg acaaaacacc cgaacuggac aaauaaacag   3600

gacaacagag acuuggaaag ugcccagagc uugaaccgga uggaauacau cgua         3654
```

<210> SEQ ID NO 127
<211> LENGTH: 3162
<212> TYPE: RNA
<213> ORGANISM: Artificial Sequence
<220> FEATURE:
<223> OTHER INFORMATION: Synthetic polynucleotide

<400> SEQUENCE: 127

```
augcgguccc cacggacgcg cggccggccc gggcgccccc ugagucuucu gcucgcccug     60

cucugugccc ugcgagccaa ggugugcggg gccucggguc aguuugagcu ggagauccug    120

uccaugcaga acgugaaugg agagcuacag aaugggaacu guugugguggg aguccggaac    180

ccuggcgacc gcaagugcac ccgcgacgag ugugauacgu acuucaaagu gugccucaag    240

gaguaucagu cccgcgucac ugccgggga cccugcagcu ucggcucagg gucuacgccu    300

gucaucgggg guaacaccuu caaucucaag gccagccgug gcaacgaccg uaaucgcauc    360

guacugccuu ucaguuucgc cuggccgagg uccuacacuu ugcuggugga ggccugggau    420

uccaguaaug acacuauuca accugauagc auaaauugaaa aggcuucuca cucaggcaug    480

auaaacccua gccggcaaug gcagacacug aaacaaaaca cagggauugc ccacuucgag    540

uaucagaucc gagugaccug ugaugaccac uacuauggcu uuggcugcaa uaaguucugu    600

cgucccagag augacuucuu uggacauuau gccugugacc agaacggcaa caaaacuugc    660

auggaaggcu ggaugggucc ugauugcaac aaagcuaucu gccgacaggg cugcaguccc    720

aagcaugggu cuuguaaacu uccaggugac ugcaggugcc aguacgguug gcagggccug    780

uacugcgaca agugcauccc gcacccagga ugugucccacg gcaccugcaa ugaacccugg    840

cagugccucu gugagaccaa cuggggggugga cagcucugug acaaagaucu gaauuacugu    900

gggacucauc agcccugucu caaccgggga acauguagca acacugggcc ugacaaauac    960

cagugcuccu gcccagaggg cuacucgggc cccaacugug aaauugcuga gcaugcuugu   1020

cucucugacc ccugccauaa ccgaggcagc ugcaaggaga ccuccucagg cuuugagugu   1080

gaguguucuc caggcuggac uggccccacg uguuccacaa acaucgauga cuguucucca   1140

aauaacuguu cccauggggg caccugccag gaucugguga auggauucaa gugugugugc   1200

ccgccccagu ggacuggcaa gacuugucag uuagaugcaa augagugcga ggccaaaccu   1260

uguguaaaug ccagauccug uaagaaucug auugccagcu acuacuguga uugccuuccu   1320

ggcuggaugg gucagaacug ugacauaaau aucaaugacu gccuuggcca gugucagaau   1380

gacgccuccu gucgggauuu gguuaauggu uaucgcugua ucuguccacc uggcuaugca   1440

ggcgaucacu gugagagaga caucgaugag ugugcuagca accccugcuu gaaugggggu   1500

cacugucaga augaaaucaa cagauuccag ugucucuguc ccacugguuu cucuggaaac   1560

cucugucagc uggacaucga uuacugcgag cccaacccuu gccagaaugg cgcccagugc   1620

uacaaucgug ccagugacua uuucugcaag ugccccgagg acuaugaggg caagaacugc   1680
```

ucacaccuga aagaccacug ccguaccacc accugcgaag ugauugacag cugcacugug 1740
gccauggccu ccaacgacac gccugaaggg gugcgguaua ucucuucuaa cgucuguggu 1800
ccccauggga agugcaagag ccagucggga ggcaaauuca ccugugacug uaacaaaggc 1860
uucaccggca ccuacugcca ugaaaauauc aacgacugcg agagcaaccc cuguaaaaac 1920
gguggcaccu gcaucgaugg cguuaacucc uacaagugua ucuguaguga cggcugggag 1980
ggagcgcacu gugagaacaa cauaaaugac uguagccaga acccuuguca cuacgggggu 2040
acaugucgag accuggucaa ugacuuuuac ugugacugca aaaauggcug gaaaggaaag 2100
acuugccauu cccgugacag ccagugugac gaagccacgu guaauaaugg ugguaccugc 2160
uaugaugaag uggacacguu uaagugcaug ugucccggug gcugggaagg aacaaccugu 2220
aauauagcua gaaacaguag cugccugccg aaccccuguc auaauggagg uaccugcgug 2280
gucaauggag acuccuucac cugugucugc aaagaaggcu gggaggggcc uauuuguacu 2340
caaaauacca acgacugcag uccccauccu uguuacaaua gcgggaccug uguggacgga 2400
gacaacuggu aucggugcga augugccccg gguuuugcug ggccagacug caggauaaac 2460
aucaaugagu gccagucuuc cccuugugcc uuuggggcca ccugugugga ugagaucaau 2520
ggcuaccagu guaucugccc uccaggacau aguggugcca agugccauga aguuucaggg 2580
cgaucuugca ucaccauggg gagagugaua cuugaugggg ccaaguggga ugaugacugu 2640
aacaccugcc agugccugaa uggacgggug gccugcucca aggucuggug uggcccgaga 2700
ccuugcaggc uccacaaaag ccacaaugag ugccccagug ggcagagcug caucccgguc 2760
cuggaugacc aguguuucgu gcgccccugc acuggguuug gcgagugucg guccuccagc 2820
cuccagccag ugaagaccaa gugcacaucu gacuccuauu accaggauaa cugugcaaac 2880
aucacuuuca ccuuuaacaa agagaugaug ucuccagguc uuaccaccga acacauuugc 2940
agcgaauuga ggaauuugaa uauccugaag aauguuucug cugaauauuc gaucuacaua 3000
gccugugagc cuucccuguc agcaaacaau gaaauacacg uggccaucuc ugcagaagac 3060
auccgggaug augggaaccc ugucaaggaa auuaccgaua aaauaauaga ucucguuagu 3120
aaacgggaug gaaacagcuc acuuauugcu gcgguugcag aa 3162

<210> SEQ ID NO 128
<211> LENGTH: 3138
<212> TYPE: RNA
<213> ORGANISM: Artificial Sequence
<220> FEATURE:
<223> OTHER INFORMATION: Synthetic polynucleotide

<400> SEQUENCE: 128
augcgguccc cacggacgcg cggccggccc gggcgccccc ugagucuucu gcucgcccug 60
cucugugccc ugcgagccaa ggugugcggg gccucggguc aguuugagcu ggagauccug 120
uccaugcaga acgugaaugg agagcuacag aaugggaacu guugugguugg aguccggaac 180
ccuggcgacc gcaagugcac ccgcgacgag ugugauacgu acuucaaagu gugccucaag 240
gaguaucagu cccgcgucac ugccgggga cccugcagcu ucggcucagg gucuacgccu 300
gucaucgggg guaacaccuu caaucucaag gccagccgug gcaacgaccg uaaucgcauc 360
guacugccuu ucaguuucgc cuggccgagg uccuacacuu ugcuggugga ggccugggau 420
uccaguaaug acacuauuca accugauagc auaauugaaa aggcuucuca cucaggcaug 480
auaaacccua gccggcaaug gcagacacug aaacaaaaca cagggauugc ccacuucgag 540

-continued

```
uaucagaucc gagugaccug ugaugaccac uacuauggcu uuggcugcaa uaaguucugu    600
cgucccagag augacuucuu uggacauuau gccugugacc agaacggcaa caaaacuugc    660
auggaaggcu ggaugggucc ugauugcaac aaagcuaucu gccgacaggg cugcaguccc    720
aagcaugggu cuuguaaacu uccaggugac ugcaggugcc aguacgguug gcagggccug    780
uacugcgaca agugcauccc gcacccagga uguguccacg gcaccugcaa ugaacccugg    840
cagugccucu gugagaccaa cuggggugga cagcucugug acaaagaucu gaauuacugu    900
gggacucauc agcccugucu caaccgggga acauguagca acacugggcc ugacaaauac    960
cagugcuccu gcccagaggg cuacucgggc cccaacugug aaauugcuga gcaugcuugu   1020
cucucugacc ccugccauaa ccgaggcagc ugcaaggaga ccuccucagg cuuugagugu   1080
gaguguucuc caggcuggac uggccccacg uguuccacaa acaucgauga cuguucucca   1140
aauaacuguu cccauggggg caccugccag gaucugguga auggauucaa gugugugugc   1200
ccgccccagu ggacuggcaa gacuugucag uuagaugcaa augagugcga ggccaaaccu   1260
uguguaaaug ccagauccug uaagaaucug auugccagcu acuacuguga uugccuuccu   1320
ggcuggaugg gucagaacug ugacauaaau aucaaugacu gccuuggcca gugucagaau   1380
gacgccuccu gucgggauuu gguuaauggu uaucgcugua ucuguccacc uggcuaugca   1440
ggcgaucacu gugagagaga caucgaugag ugugcuagca accccugcuu gaauggggu   1500
cacugucaga augaaaucaa cagauuccag ugucucuguc ccacugguuu cucuggaaac   1560
cucugucagc uggacaucga uuacugcgag cccaacccuu gccagaaugg cgcccagugc   1620
uacaaucgug ccagugacua uuucugcaag ugccccgagg acuaugaggg caagaacugc   1680
ucacaccuga aagaccacug ccguaccacc accugcgaag ugauugacag cugcacugug   1740
gccauggccu ccaacgacac gccugaaggg gugcgguaua ucucuucuaa cgucuguggu   1800
ccccauggga agugcaagag ccagucggga ggcaaauuca ccugugacug uaacaaaggc   1860
uucaccggca ccuacugcca ugaaaauauc aacgacugcg agagcaaccc cuguaaaaac   1920
gguggcaccu gcaucgaugg cguuaacucc uacaagugua ucuguaguga cggcugggag   1980
ggagcgcacu gugagaacaa cauaaaugac uguagccaga acccuuguca cuacgggggu   2040
acaugucgag accuggucaa ugacuuuuac ugugacugca aaaauggcug gaaaggaaag   2100
acuugccauu cccgugacag ccagugugac gaagccacgu guaauaaugg ugguaccugc   2160
uaugaugaag uggacacguu uaagugcaug ugucccggug gcugggaagg aacaaccugu   2220
aauauagcua gaaacaguag cugccugccg aaccccuguc auaauggagg uaccugcgug   2280
gucaauggag acuccuucac cugugucugc aaagaaggcu gggaggggcc uauuuguacu   2340
caaaauacca acgacugcag uccccauccu uguuacaaua gcgggaccug uguggacgga   2400
gacaacuggu aucggugcga augugccccg gguuuugcug ggccagacug caggauaaac   2460
aucaaugagu gccagucuuc cccuugugcc uuuggggcca ccugugugga ugagaucaau   2520
ggcuaccagu guaucugccc uccaggacau aguggugcca agugccauga aguuucaggg   2580
cgaucuugca ucaccauggg gagagugaua cuugaugggg ccaaguggga ugaugacugu   2640
aacaccugcc agugccugaa uggacgggug gccugcucca aggucuggug uggcccgaga   2700
ccuugcaggc uccacaaaag ccacaaugag ugccccagug ggcagagcug caucccgguc   2760
cuggaugacc aguguuucgu gcgccccugc acuggugug gcgagugucg guccuccagc   2820
cuccagccag ugaagaccaa gugcacaucu gacuccuauu accaggauaa cugugcaaac   2880
aucacuuuca ccuuuaacaa agagagaugaug ucuccagguc uuaccaccga acacauuugc   2940
```

agcgaauuga ggaauuugaa uauccugaag aauguuucug cugaauauuc gaucuacaua 3000
gccugugagc cuucccuguc agcaaacaau gaaauacacg uggccaucuc ugcagaagac 3060
auccgggaug augggaaccc ugucaaggaa auuaccgaua aaauaauaga ucucguuagu 3120
aaacgggaug gaaacagc 3138

<210> SEQ ID NO 129
<211> LENGTH: 783
<212> TYPE: RNA
<213> ORGANISM: Artificial Sequence
<220> FEATURE:
<223> OTHER INFORMATION: Synthetic polynucleotide

<400> SEQUENCE: 129
augggaguca aaguucuguu ugcccugauc ugcaucgcug uggccgaggc cugugaugac 60
uacuacuaug gcuuuggcug caauaaguuc ugccgcccca gagacaagac ccacaccugc 120
ccccccugcc ccgcccccga ggccgccggc ggccccagcg uguuccuguu cccccccaag 180
cccaaggaca cccuguacau caccagggag cccgagguga ccugcguggu gguggacgug 240
agccacgagg accccgaggu gaaguucaac ugguacgugg acggcgugga ggugcacaac 300
gccaagacca agcccaggga ggagcaguac aacagcaccu acaggguggu gagcgugcug 360
accgugcugc accaggacug gcugaacggc aaggaguaca agugcaaggu gagcaacaag 420
gcccugcccg cccccaucga gaagaccauc agcaaggcca agggccagcc cagggagccc 480
cagguguaca cccugccccc cagcagggac gagcugacca agaaccaggu gagccugacc 540
ugccugguga agggcuucua ccccagcgac aucgccgugg agugggagag caacggccag 600
cccgagaaca acuacaagac cacccccccc gugcuggaca gcgacggcag cuucuuccug 660
uacagcaagc ugaccgugga caagagcagg uggcagcagg gcaacguguu cagcugcagc 720
gugaugcacg aggcccugaa guuccacuac acccagaaga gccugagccu gagccccggc 780
aag 783

<210> SEQ ID NO 130
<211> LENGTH: 828
<212> TYPE: RNA
<213> ORGANISM: Artificial Sequence
<220> FEATURE:
<223> OTHER INFORMATION: Synthetic polynucleotide

<400> SEQUENCE: 130
augggaguca aaguucuguu ugcccugauc ugcaucgcug uggccgaggc cgacaagacc 60
cacaccugcc cccccugccc cgcccccgag gccgccggcg gccccagcgu guuccuguuc 120
ccccccaagc ccaaggacac ccuguacauc accagggagc ccgaggugac cugcguggug 180
guggacguga gccacgagga ccccgaggug aaguucaacu gguacgugga cggcguggag 240
gugcacaacg ccaagaccaa gcccagggag gagcaguaca acagcaccua caggguggug 300
agcgugcuga ccgugcugca ccaggacugg cugaacggca aggaguacaa gugcaaggug 360
agcaacaagg cccugcccgc ccccaucgag aagaccauca gcaaggccaa gggccagccc 420
agggagcccc agguguacac ccugcccccc agcagggacg agcugaccaa gaaccaggug 480
agccugaccu gccuggugaa gggcuucuac cccagcgaca ucgccgugga gugggagagc 540
aacggccagc ccgagaacaa cuacaagacc acccccccccg ugcuggacag cgacggcagc 600
uucuuccugu acagcaagcu gaccguggac aagagcaggu ggcagcaggg caacguguuc 660
agcugcagcg ugaugcacga ggcccugaag uuccacuaca cccagaagag ccugagccug 720
agccccggca aggguggcgg uggcucgggc gguggugggu cggguggcgg cggaucuugu 780
gaugacuacu acuauggcuu uggcugcaau aaguucugcc gccccaga 828

<210> SEQ ID NO 131
<211> LENGTH: 1218
<212> TYPE: PRT
<213> ORGANISM: Artificial Sequence
<220> FEATURE:
<223> OTHER INFORMATION: Synthetic polypeptide

<400> SEQUENCE: 131

Met Arg Ser Pro Arg Thr Arg Gly Arg Pro Gly Arg Pro Leu Ser Leu
1 5 10 15

Leu Leu Ala Leu Leu Cys Ala Leu Arg Ala Lys Val Cys Gly Ala Ser
20 25 30

Gly Gln Phe Glu Leu Glu Ile Leu Ser Met Gln Asn Val Asn Gly Glu
35 40 45

Leu Gln Asn Gly Asn Cys Cys Gly Gly Val Arg Asn Pro Gly Asp Arg
50 55 60

Lys Cys Thr Arg Asp Glu Cys Asp Thr Tyr Phe Lys Val Cys Leu Lys
65 70 75 80

Glu Tyr Gln Ser Arg Val Thr Ala Gly Gly Pro Cys Ser Phe Gly Ser
85 90 95

Gly Ser Thr Pro Val Ile Gly Gly Asn Thr Phe Asn Leu Lys Ala Ser
100 105 110

Arg Gly Asn Asp Arg Asn Arg Ile Val Leu Pro Phe Ser Phe Ala Trp
115 120 125

Pro Arg Ser Tyr Thr Leu Leu Val Glu Ala Trp Asp Ser Ser Asn Asp
130 135 140

Thr Ile Gln Pro Asp Ser Ile Ile Glu Lys Ala Ser His Ser Gly Met
145 150 155 160

Ile Asn Pro Ser Arg Gln Trp Gln Thr Leu Lys Gln Asn Thr Gly Ile
165 170 175

Ala His Phe Glu Tyr Gln Ile Arg Val Thr Cys Asp Asp His Tyr Tyr
180 185 190

Gly Phe Gly Cys Asn Lys Phe Cys Arg Pro Arg Asp Asp Phe Phe Gly
195 200 205

His Tyr Ala Cys Asp Gln Asn Gly Asn Lys Thr Cys Met Glu Gly Trp
210 215 220

Met Gly Pro Asp Cys Asn Lys Ala Ile Cys Arg Gln Gly Cys Ser Pro
225 230 235 240

Lys His Gly Ser Cys Lys Leu Pro Gly Asp Cys Arg Cys Gln Tyr Gly
245 250 255

Trp Gln Gly Leu Tyr Cys Asp Lys Cys Ile Pro His Pro Gly Cys Val
260 265 270

His Gly Thr Cys Asn Glu Pro Trp Gln Cys Leu Cys Glu Thr Asn Trp
275 280 285

Gly Gly Gln Leu Cys Asp Lys Asp Leu Asn Tyr Cys Gly Thr His Gln
290 295 300

Pro Cys Leu Asn Arg Gly Thr Cys Ser Asn Thr Gly Pro Asp Lys Tyr
305 310 315 320

Gln Cys Ser Cys Pro Glu Gly Tyr Ser Gly Pro Asn Cys Glu Ile Ala
325 330 335

```
Glu His Ala Cys Leu Ser Asp Pro Cys His Asn Arg Gly Ser Cys Lys
            340                 345                 350

Glu Thr Ser Ser Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Arg Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Thr Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
```

-continued

```
        755                 760                 765

Val Cys Lys Glu Gly Trp Glu Gly Pro Ile Cys Thr Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
        835                 840                 845

Gly His Ser Gly Ala Lys Cys His Glu Val Ser Gly Arg Ser Cys Ile
    850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
                885                 890                 895

Cys Gly Pro Arg Pro Cys Arg Leu His Lys Ser His Asn Glu Cys Pro
            900                 905                 910

Ser Gly Gln Ser Cys Ile Pro Val Leu Asp Asp Gln Cys Phe Val Arg
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Leu Ser Ala
        995                 1000                1005

Asn Asn  Glu Ile His Val Ala  Ile Ser Ala Glu Asp  Ile Arg Asp
    1010                1015                1020

Asp Gly  Asn Pro Val Lys Glu  Ile Thr Asp Lys Ile  Ile Asp Leu
    1025                1030                1035

Val Ser  Lys Arg Asp Gly Asn  Ser Ser Leu Ile Ala  Ala Val Ala
    1040                1045                1050

Glu Val  Arg Val Gln Arg Arg  Pro Leu Lys Asn Arg  Thr Asp Phe
    1055                1060                1065

Leu Val  Pro Leu Leu Ser Ser  Val Leu Thr Val Ala  Trp Val Cys
    1070                1075                1080

Cys Leu  Val Thr Ala Phe Tyr  Trp Cys Val Arg Lys  Arg Arg Lys
    1085                1090                1095

Pro Ser  Ser His Thr His Ser  Ala Pro Glu Asp Asn  Thr Thr Asn
    1100                1105                1110

Asn Val  Arg Glu Gln Leu Asn  Gln Ile Lys Asn Pro  Ile Glu Lys
    1115                1120                1125

His Gly  Ala Asn Thr Val Pro  Ile Lys Asp Tyr Glu  Asn Lys Asn
    1130                1135                1140

Ser Lys  Met Ser Lys Ile Arg  Thr His Asn Ser Glu  Val Glu Glu
    1145                1150                1155

Asp Asp  Met Asp Lys His Gln  Gln Lys Val Arg Phe  Ala Lys Gln
    1160                1165                1170
```

```
Pro Val  Tyr Thr Leu Val Asp  Arg Glu Glu Lys Ala  Pro Ser Gly
    1175                 1180                 1185

Thr Pro  Thr Lys His Pro Asn  Trp Thr Asn Lys Gln  Asp Asn Arg
    1190                 1195                 1200

Asp Leu  Glu Ser Ala Gln Ser  Leu Asn Arg Met Glu  Tyr Ile Val
    1205                 1210                 1215


<210> SEQ ID NO 132
<211> LENGTH: 1054
<212> TYPE: PRT
<213> ORGANISM: Artificial Sequence
<220> FEATURE:
<223> OTHER INFORMATION: Synthetic polypeptide

<400> SEQUENCE: 132

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Val Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Asp Cys Asn Lys Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Thr Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Arg Gly Thr Cys Ser Asn Thr Gly Pro Asp Lys Tyr
305                 310                 315                 320
```

```
Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Ser Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Arg Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Thr Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735
```

-continued

```
Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
        755                 760                 765

Val Cys Lys Glu Gly Trp Glu Gly Pro Ile Cys Thr Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
        835                 840                 845

Gly His Ser Gly Ala Lys Cys His Glu Val Ser Gly Arg Ser Cys Ile
    850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
                885                 890                 895

Cys Gly Pro Arg Pro Cys Arg Leu His Lys Ser His Asn Glu Cys Pro
            900                 905                 910

Ser Gly Gln Ser Cys Ile Pro Val Leu Asp Asp Gln Cys Phe Val Arg
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Leu Ser Ala
        995                 1000                1005

Asn Asn  Glu Ile His Val Ala  Ile Ser Ala Glu Asp  Ile Arg Asp
    1010                1015                1020

Asp Gly  Asn Pro Val Lys Glu  Ile Thr Asp Lys Ile  Ile Asp Leu
    1025                1030                1035

Val Ser  Lys Arg Asp Gly Asn  Ser Ser Leu Ile Ala  Ala Val Ala
    1040                1045                1050

Glu


<210> SEQ ID NO 133
<211> LENGTH: 1046
<212> TYPE: PRT
<213> ORGANISM: Artificial Sequence
<220> FEATURE:
<223> OTHER INFORMATION: Synthetic polypeptide

<400> SEQUENCE: 133

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
```

-continued

```
        35                  40                  45

Leu Gln Asn Gly Asn Cys Cys Gly Gly Val Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Asp Cys Asn Lys Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Thr Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Arg Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Ser Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Arg Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460
```

-continued

```
Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Thr Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala His Cys Glu Asn Asn Ile Asn Asp Cys Ser
            660                 665                 670

Gln Asn Pro Cys His Tyr Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
        755                 760                 765

Val Cys Lys Glu Gly Trp Glu Gly Pro Ile Cys Thr Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
        835                 840                 845

Gly His Ser Gly Ala Lys Cys His Glu Val Ser Gly Arg Ser Cys Ile
    850                 855                 860

Thr Met Gly Arg Val Ile Leu Asp Gly Ala Lys Trp Asp Asp Asp Cys
865                 870                 875                 880
```

-continued

```
Asn Thr Cys Gln Cys Leu Asn Gly Arg Val Ala Cys Ser Lys Val Trp
                885                 890                 895

Cys Gly Pro Arg Pro Cys Arg Leu His Lys Ser His Asn Glu Cys Pro
            900                 905                 910

Ser Gly Gln Ser Cys Ile Pro Val Leu Asp Asp Gln Cys Phe Val Arg
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Leu Ser Ala
        995                 1000                1005

Asn Asn  Glu Ile His Val Ala  Ile Ser Ala Glu Asp  Ile Arg Asp
    1010                 1015                 1020

Asp Gly  Asn Pro Val Lys Glu  Ile Thr Asp Lys Ile  Ile Asp Leu
    1025                 1030                 1035

Val Ser  Lys Arg Asp Gly Asn  Ser
    1040                 1045
```

POLYNUCLEOTIDES ENCODING JAGGED1 FOR THE TREATMENT OF Alagille SYNDROME

RELATED APPLICATIONS

This application is a national stage filing under 35 U.S.C. § 371 of international application number PCT/US2017/033413, filed May 18, 2017, which claims the benefit under 35 U.S.C. § 119(e) of U.S. provisional application No. 62/338,170, filed May 18, 2016, each of which are incorporated by reference herein in their entirety.

BACKGROUND

Alagille syndrome (ALGS), also known as arteriohepatic dysplasia, is an autosomal dominant multisystem disorder characterized by abnormal development of liver, heart, skeleton, eye, face and, less frequently, kidney. See, e.g., Berniczei-Royko et al., *Med Sci Monit.* 20:476-80 (2014); Turnpenny et al., *Eur J Hum Genet.* 20(3):251-7 (2012). ALGS patients have malformed or poorly functioning bile ducts or a reduced number of bile ducts in the liver. The prevalence of the disease is reported to be 1:70,000 births. ALGS results from defects in the Notch signaling pathway, which is due in the overwhelming majority of the cases to mutation in JAGGED1 (ALGS type 1). A small proportion of cases are due to mutation in NOTCH2 (ALGS type 2).

The association between ALGS and mutations in JAGGED1 (JAG1) was simultaneously reported by Li et al., *Nat Genet.* 16(3):243-51 (1997) and Oda et al., *Nat Genet.* 16(3):235-42 (1997). JAG1 encodes a cell surface protein (GenBank Accession No. NP_000205.1 and NM_000214.2) that functions as a ligand for the NOTCH receptors, NOTCH 1, 2, 3, and 4. These receptors are transmembrane proteins, and interaction with their ligands triggers a cascade of intracellular downstream effects that result in transcription of genes that help determine cell fate and differentiation, for example segmentation boundaries in the presomitic mesoderm. Approximately 70% of JAG1 mutations are truncations, some of which have been shown to have a dominant negative effect. Boyer et al., *Hum Genet.* 116(6):445-53 (2005). Other studies have identified missense mutations in JAG1 associated with ALGS which do not have dominant negative effects. Tada et al., *FEBS J.* 279(12):2096-107 (2012). Tada et al. also suggested that the mutations affect cell-surface localization of JAG1, but the pathology of JAG1 mutations is still being determined.

The classic, i.e., pre-molecular genetic testing, diagnostic criteria was based on the five main systems involved: cholestasis due to bile duct paucity, congenital heart disease (most commonly peripheral pulmonary artery stenosis), the face (mild, but recognizable dysmorphic features), the skeleton (abnormal vertebral segmentation, most commonly in the form of butterfly vertebrae), and the eye (anterior chamber defects, most commonly posterior embryotoxon). Due to the malformed or poorly functioning bile ducts or a reduced number of bile ducts in ALGS patients, bile accumulates in the liver and leads to scarring and complications such as jaundice and puritis. No disease-specific treatment option for Alagille syndrome is currently available. Rather, current clinical management focuses on alleviating the organ specific symptoms. Pruritus can be treated with choloretic agents such as ursodeoxycholic acid and cholestyramine, rifampin, or naltrexone. Biliary diversion or partial external biliary diversion is used to alleviate liver symptoms. However, deteriorating liver function in ALGS patients often necessitates liver transplantation. The treatment of cardiac and renal symptoms follows the practice appropriate for the particular problems present. A key aspect of disease management is careful attention to nutrition to maximize growth potential, which is compromised in a significant proportion of cases.

BRIEF SUMMARY

In certain aspects, the present disclosure relates to compositions and delivery formulations comprising a polynucleotide, e.g., a ribonucleic acid (RNA), e.g., a messenger RNA (mRNA), encoding jagged1 and methods for treating Alagille syndrome (ALGS) in a subject in need thereof by administering the same.

The present disclosure provides a polynucleotide comprising an open reading frame (ORF) encoding a Jagged-1 (JAG1) polypeptide, wherein the uracil or thymine content of the ORF relative to the theoretical minimum uracil or thymine content of a nucleotide sequence encoding the JAG1 polypeptide (% $U_{TM}$ or % $T_{TM}$) is between about 175% and about 225%.

In some embodiments, the % $U_{TM}$ or % $T_{TM}$ is between about 180% and about 2200%, about 184% and about 220%, about 184% and about 215%, about 180% and about 215%, about 180% and about 210%, about 184% and about 210%, about 180% and about 200%, about 184% and about 200%, or about 184% and about 198%.

In some embodiments, the % $U_{TM}$ or % $T_{TM}$ is between (i) 174%, 175%, 176%, 177%, 178%, 179%, 180%, 181%, 182%, 183%, or 184%, and (ii) 198%, 199%, 200%, 201%, 202%, 203%, 204%, 205%, 206%, 207%, or 208%.

In some embodiments, the uracil or thymine content of the ORF relative to the uracil or thymine content of the corresponding wild-type ORF (% $U_{WT}$ or % $T_{WT}$) is less than 100%.

In some embodiments, the % $U_{WT}$ or % $T_{WT}$ is less than about 95%, less than about 90%, less than about 85%, less than about 80%, less than about 75%, or less than 74%.

In some embodiments, the % $U_{WT}$ or % $T_{WT}$ is between 68%/0 and 74%.

In some embodiments, the uracil or thymine content in the ORF relative to the total nucleotide content in the ORF (% $U_{TL}$ or % $T_{TL}$) is less than about 50%, less than about 40%, less than about 30%, or less than about 21%.

In some embodiments, the % $U_{TL}$ or % $T_{TL}$ is less than about 21%.

In some embodiments, the % $U_{TL}$ or % $T_{TL}$ is between about 14% and about 16%.

In some embodiments, the guanine content of the ORF with respect to the theoretical maximum guanine content of a nucleotide sequence encoding the JAG1 polypeptide (% $G_{TMX}$) is at least 71%, at least 72%, at least about 75%, at least about 80%, at least about 85%, at least about 90%, at least about 95%, or about 100%.

In some embodiments, the % $G_{TMX}$ is between about 72% and about 80%, between about 72% and about 79%, between about 73% and about 78%, or between about 74% and about 77%.

In some embodiments, the cytosine content of the ORF relative to the theoretical maximum cytosine content of a nucleotide sequence encoding the JAG1 polypeptide (% $C_{TMX}$) is at least 63%, at least 64%, at least about 65%, at least about 700%, at least about 75%, at least about 80%, at least about 85%, at least about 90%, or about 100%.

In some embodiments, the % $C_{TMX}$ is between about 65% and about 80%, between about 65% and about 79%, between about 65% and about 78%, or between about 72% and about 77%.

In some embodiments, the guanine and cytosine content (G/C) of the ORF relative to the theoretical maximum G/C content in a nucleotide sequence encoding the JAG1 polypeptide (% $G/C_{TMX}$) is at least about 81%, at least about 82%, at least about 85%, at least about 90%, at least about 95%, or about 100%.

In some embodiments, the ° % $G/C_{TMX}$ is between about 80% and about 100%, between about 85% and about 99%, between about 90% and about 97%, or between about 90% and about 93%.

In some embodiments, the G/C content in the ORF relative to the G/C content in the corresponding wild-type ORF (% $G/C_{WT}$) is at least 102%, at least 103%, at least 104%, at least 105%, at least 106%, at least 107%, or at least about 110%.

In some embodiments, the average G/C content in the $3^{rd}$ codon position in the ORF is at least 20%, at least 21%, at least 22%, at least 23%, or at least 24% higher than the average G/C content in the $3^{rd}$ codon position in the corresponding wild-type ORF.

In some embodiments, the ORF further comprises at least one low-frequency codon.

In some embodiments, the ORF is at least 91%, at least 92%, at least 93%, at least 94%, at least 95%, at least 96%, at least 97%, at least 98%, at least 99%, or 100% identical to JAG1-CO21, JAG1-CO17, JAG1-CO7, JAG1-CO2, JAG1-CO18, JAG1-CO1, JAG1-CO16, JAG1-CO12, JAG1-CO4, JAG1-CO24, JAG1-CO15, JAG1-CO5, JAG1-CO25, or JAG1-CO23;

In some embodiments, the ORF is at least 90%, at least 91%, at least 92%, at least 93%, at least 94%, at least 95%, at least 96%, at least 97%/i, at least 98%, at least 99%, or 100% identical to JAG1-CO14, JAG1-CO11, JAG1-CO13, JAG1-CO10, JAG1-CO22, JAG1-CO8, JAG1-CO9, JAG1-CO19, JAG1-CO3, or JAG1-CO20; or In some embodiments, the ORF is at least 89%, at least 90%, at least 91%, at least 92%, at least 93%, at least 94%, at least 95%, at least 96%, at least 97%, at least 98%, at least 99%, or 100% identical to JAG1-CO6.

In some embodiments, the ORF is at least 91%, at least 92%, at least 93%, at least 94%, at least 95%, at least 96%, at least 97%, at least 98%, at least 99%, or 100% identical to JAG CO21, JAG1-CO17, JAG1-CO7, JAG1-CO2, JAG1-CO18, JAG1-CO1, JAG1-CO16, JAG1-CO12, JAG1-CO4, JAG1-CO24, JAG1-CO15, JAG1-CO5, JAG1-CO25, or JAG1-CO23;

In some embodiments, the ORF is at least 900, at least 91%, at least 92%, at least 93%, at least 94%, at least 95%, at least 96%, at least 97%, at least 98%, at least 99%, or 100% identical to JAG1-CO14, JAG1-CO11, JAG1-CO13, JAG1-CO10, JAG1-CO22, JAG1-CO8, JAG1-CO9, JAG1-CO19, JAG1-CO3, or JAG1-CO20; or In some embodiments, the ORF is at least 89%, at least 90%, at least 91%, at least 92%, at least 93%, at least 94%, at least 95%, at least 96%, at least 97%, at least 98%, at least 99%, or 100% identical to JAG1-CO6.

In some embodiments, the ORF has at least 89%, at least 90%, at least 91%, at least 92%, at least 93%, at least 94%, at least 95%, at least 969%, at least 97%, at least 98%, at least 99%, or 100% sequence identity to a sequence selected from the group consisting of SEQ ID NOs: 11 to 35.

In some embodiments, the JAG1 polypeptide comprises an amino acid sequence at least about 95%, at least about 96%, at least about 97%, at least about 98%, at least about 99%, or about 100% identical to the polypeptide sequence of wild type JAG1 (SEQ ID NO: 1), and wherein the JAG1 polypeptide has NOTCH receptor ligand activity.

In some embodiments, the JAG1 polypeptide is a variant, derivative, or mutant having an NOTCH receptor ligand activity.

In some embodiments, the polynucleotide sequence further comprises a nucleotide sequence encoding a transit peptide.

In some embodiments, the polynucleotide is single stranded.

In some embodiments, the polynucleotide is double stranded.

In some embodiments, the polynucleotide is DNA.

In some embodiments, the polynucleotide is RNA.

In some embodiments, the polynucleotide is mRNA.

In some embodiments, the polynucleotide comprises at least one chemically modified nucleobase, sugar, backbone, or any combination thereof.

In some embodiments, the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combination thereof.

In some embodiments, the at least one chemically modified nucleobase is 5-methoxyuracil.

In some embodiments, at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils.

In some embodiments, the polynucleotide further comprises a miRNA binding site.

In some embodiments, the miRNA binding site comprises one or more nucleotide sequences selected from Table 3.

In some embodiments, the miRNA binding site binds to miR-142.

In some embodiments, the miRNA binding site binds to miR-142-3p or miR-142-5p.

In some embodiments, the miR-142 comprises SEQ ID NO: 79.

In some embodiments, the polynucleotide further comprises a 5' UTR.

In some embodiments, the 5' UTR comprises a nucleic acid sequence at least 90%, at least about 95%, at least about 96%, at least about 97%, at least about 98%, at least about 99%, or about 100% identical to a sequence selected from the group consisting of SEQ ID NOs:36-78.

In some embodiments, the polynucleotide further comprises a 3' UTR.

In some embodiments, the 3' UTR comprises a nucleic acid sequence at least about 90%, at least about 95%, at least about 96%, at least about 97%, at least about 98%, at least about 99%, or about 100% identical to a sequence selected from the group consisting of SEQ ID NOs:36-78.

In some embodiments, the miRNA binding site is located within the 3' UTR.

In some embodiments, the polynucleotide further comprises a 5' terminal cap.

In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the polynucleotide further comprises a poly-A region.

In some embodiments, the poly-A region is at least about 10, at least about 20, at least about 30, at least about 40, at least about 50, at least about 60, at least about 70, at least about 80, or at least about 90 nucleotides in length.

In some embodiments, the poly-A region has about 10 to about 200, about 20 to about 180, about 50 to about 160, about 70 to about 140, or about 80 to about 120 nucleotides in length.

In some embodiments, the polynucleotide encodes a JAG1 polypeptide that is fused to one or more heterologous polypeptides.

In some embodiments, the one or more heterologous polypeptides increase a pharmacokinetic property of the JAG1 polypeptide.

In some embodiments, the polynucleotide has:
(i) a longer plasma half-life;
(ii) increased expression of a JAG1 polypeptide encoded by the ORF;
(iii) a lower frequency of arrested translation resulting in an expression fragment;
(iv) greater structural stability; or
(v) any combination thereof, relative to a corresponding polynucleotide comprising SEQ ID NO: 2.

In some embodiments, the polynucleotide comprises:
(i) a 5'-terminal cap;
(ii) a 5'-UTR;
(iii) an ORF encoding a JAG1 polypeptide;
(iv) a 3'-UTR; and
(v) a poly-A region.

In some embodiments, the 3'-UTR comprises a miRNA binding site.

The present disclosure provides, in certain aspects, a method of producing a polynucleotide as described herein, the method comprising modifying an ORF encoding a JAG1 polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions.

In some embodiments, the method further comprises replacing at least about 90%, at least about 95%, at least about 99%, or about 100% of uracils with 5-methoxyuracils.

The present disclosure provides, in certain aspects, a composition comprising a polynucleotide as described herein; and a delivery agent.

In some embodiments, the delivery agent comprises a lipidoid, a liposome, a lipoplex, a lipid nanoparticle, a polymeric compound, a peptide, a protein, a cell, a nanoparticle mimic, a nanotube, or a conjugate.

In some embodiments, the delivery agent comprises a lipid nanoparticle.

In some embodiments, the lipid nanoparticle comprises a lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,165Z)—N,N-dimethyl-3-nonydocosa-13-16-di en-1-amine (L608), 2-({8-[(3β)-cholest-5-en-3-yloxy]octyl}oxy)-N,N-dimethyl-3-[(9Z,12Z)-octadeca-9,12-dien-1-yl oxy]propan-1-amine (Octyl-CLinDMA), (2R)-2-({8-[(3β)-cholest-5-en-3-yloxy]octyl})oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), and any combination thereof.

In some embodiments, the delivery agent comprises a compound having the Formula (I)

(I)

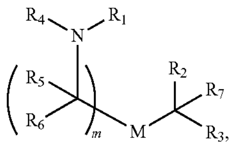

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —C(O)$N(R)_2$, —N(R)C(O)R, —N(R)S$(O)_2$R, —N(R)C(O)$N(R)_2$, —N(R)C(S)$N(R)_2$, and —C(R)$N(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_n$Q, —$(CH_2)$, —CHQR, —CHQR, or —CQ$(R)_2$, then (i) Q is not —$N(R)_2$ when n is 1, 2, 3, 4 or 5, or (ii) Q is not 5, 6, or 7-membered heterocycloalkyl when n is 1 or 2.

The present disclosure provides, in certain aspects, a composition comprising a nucleotide sequence encoding a JAG1 polypeptide and a delivery agent, wherein the delivery agent comprises a compound having the Formula (I)

(I)

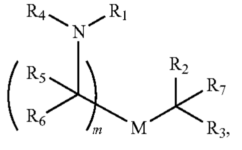

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In some embodiments, the compound is of Formula (IA):

(IA)

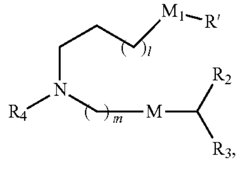

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or $—(CH_2)_nQ$, in which n is 1, 2, 3, 4, or 5 and Q is OH, $—NHC(S)N(R)_2$, or $—NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (II):

(II)

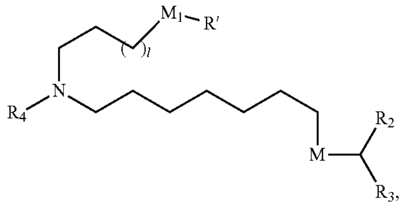

or a salt or stereoisomer thereof, wherein l is selected from 1, 2, 3, 4, and 5;

$M_1$ is a bond or M';

$R_4$ is unsubstituted $C_{1-3}$ alkyl, or $—(CH_2)_nQ$, in which n is 2, 3, or 4 and Q is OH, $—NHC(S)N(R)_2$, or $—NHC(O)N(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In some embodiments, $M_1$ is M'.

In some embodiments, M and M' are independently —C(O)O— or —OC(O)—.

In some embodiments, l is 1, 3, or 5.

In some embodiments, the compound is selected from the group consisting of Compound 1 to Compound 147, salts and stereoisomers thereof, and any combination thereof.

In some embodiments, the compound is of the Formula (IIa), (IIa)

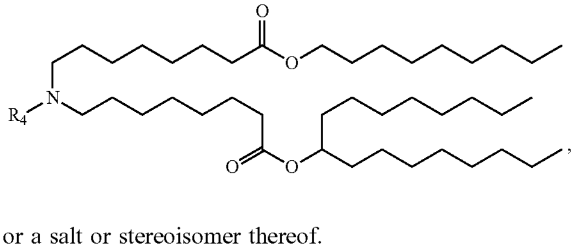

or a salt or stereoisomer thereof.

In some embodiments, the compound is of the Formula (IIb).

(IIb)

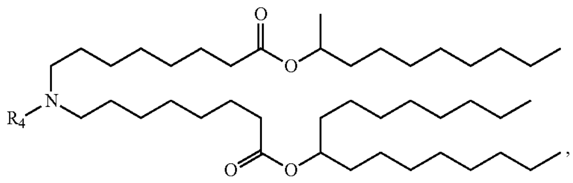

or a salt or stereoisomer thereof.

In some embodiments, the compound is of the Formula (IIc) or (He), (IIc)

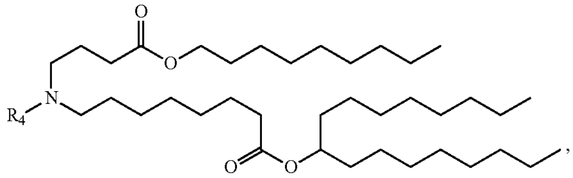

(IIe)

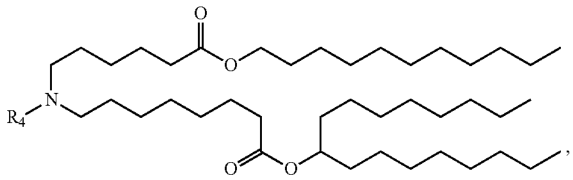

or a salt or stereoisomer thereof.

In some embodiments, $R_4$ is selected from $—(CH_2)_nQ$ and $—(CH_2)_nCHQR$.

In some embodiments, the compound is of the Formula (IId), (IId)

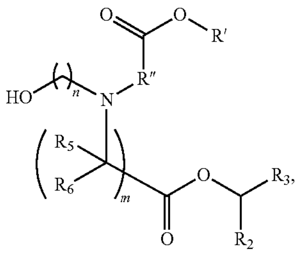

or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R'', $R_5$, $R_6$ and m are as defined above.

In some embodiments, $R_2$ is $C_8$ alkyl.

In some embodiments, $R_3$ is $C_5$ alkyl, $C_6$ alkyl, $C_7$ alkyl, $C_8$ alkyl, or $C_9$ alkyl.

In some embodiments, m is 5, 7, or 9.

In some embodiments, each $R_5$ is H.

In some embodiments, each $R_6$ is H.

In some embodiments, the composition is a nanoparticle composition.

In some embodiments, the delivery agent further comprises a phospholipid.

In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-di stearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

In some embodiments, the delivery agent further comprises a structural lipid.

In some embodiments, the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

In some embodiments, the delivery agent further comprises a PEG lipid.

In some embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof.

In some embodiments, the delivery agent further comprises an ionizable lipid selected from the group consisting of 3-(didodecylamino)-N1,N1,4-tridodecyl-1-piperazineethanamine (KL10), N1-[2-(di dodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yl oxy]propan-1-amine (Octyl-CLinDMA), . (2R)-2-({8-[(3β)-cholest-5-en-3-yloxy]octyl}oxy)-N,N-dimethyl-3-[(9Z,12Z)-octadeca-9,12-di en-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

In some embodiments, the delivery agent further comprises a phospholipid, a structural lipid, a PEG lipid, or any combination thereof.

In some embodiments, the composition is formulated for in vivo delivery.

In some embodiments, the composition is formulated for intramuscular, subcutaneous, or intradermal delivery.

The present disclosure provides, in certain aspects, a host cell comprising a polynucleotide as described herein.

In some embodiments, the host cell is a eukaryotic cell.

The present disclosure provides, in certain aspects, a vector comprising a polynucleotide as described herein.

The present disclosure provides, in certain aspects, a method of making a polynucleotide comprising enzymatically or chemically synthesizing a polynucleotide as described herein.

The present disclosure provides, in certain aspects, a polypeptide encoded by a polynucleotide as described herein, a composition as described herein, a host cell as described herein, or a vector as described herein or produced by a method as described herein.

The present disclosure provides, in certain aspects, a method of expressing in vivo an active JAG1 polypeptide in a subject in need thereof comprising administering to the subject an effective amount of a polynucleotide as described herein, a composition as described herein, a host cell as described herein, or a vector as described herein.

The present disclosure provides, in certain aspects, a method of treating Alagille syndrome in a subject in need thereof comprising administering to the subject a therapeutically effective amount of a polynucleotide as described herein, a composition as described herein, a host cell as described herein, or a vector as described herein, wherein the administration alleviates the signs or symptoms of Alagille syndrome in the subject.

The present disclosure provides, in certain aspects, a method to prevent or delay the onset of Alagille syndrome signs or symptoms in a subject in need thereof comprising administering to the subject a prophylactically effective amount of a polynucleotide as described herein, a composition as described herein, a host cell as described herein, or a vector as described herein before Alagille syndrome signs or symptoms manifest, wherein the administration prevents or delays the onset of Alagille syndrome signs or symptoms in the subject.

The present disclosure provides, in certain aspects, a method to ameliorate the signs or symptoms of Alagille syndrome in a subject in need thereof comprising administering to the subject a therapeutically effective amount of a polynucleotide as described herein, a composition as described herein, a host cell as described herein, or a vector as described herein before Alagille syndrome or symptoms manifest, wherein the administration ameliorates Alagille syndrome signs or symptoms in the subject.

Also provided herein are pharmaceutical compositions comprising a lipid nanoparticle encapsulated mRNA that comprises an open reading frame (ORF) encoding a Jagged 1 (JAG1) polypeptide, wherein the composition is suitable for administration to a human subject in need of treatment for Alagille syndrome (ALGS).

Further provided herein are pharmaceutical compositions comprising: (a) a mRNA that comprises (i) an open reading frame (ORF) encoding a Jagged1 (JAG1) polypeptide, wherein the ORF comprises at least one chemically modified nucleobase, sugar, backbone, or any combination thereof, (ii) a patterned untranslated region (UTR), and (iii) a microRNA (miRNA) binding site; and (b) a delivery agent, wherein the pharmaceutical composition is suitable for administration to a human subject in need of treatment for Alagille syndrome (ALGS).

The present disclosure also provides pharmaceutical compositions comprising an mRNA comprising an open reading frame (ORF) encoding a Jagged1 (JAG1) polypeptide, wherein the composition when administered to a subject in need of treatment for Alagille syndrome (ALGS) is sufficient to improve heart, liver, kidney and/or spleen function by at least 10%, at least 20%, at least 300%, at least 40%, or at least 50%, as compared to heart, liver, kidney and/or spleen function in a reference subject untreated for ALGS.

In some embodiments, (a) an improvement of heart function includes a reduction (e.g., a reduction of at least 10%, 20%, 30%, 40% or 50%) in the occurrence of and/or severity of heart murmurs, pulmonary stenosis, overriding aorta, ventricular septal defect, and/or right ventricular hypertrophy in the subject in need of treatment for ALGS; and/or (b) an improvement of liver function includes a reduction in the occurrence of and/or severity of jaundice (e.g., caused by excess bilirubin in the blood), pruritus, acholia, hepatomegaly, and/or xanthomas in the subject in need of treatment for ALGS; (c) an improvement of kidney function includes a reduction in the occurrence of and/or severity of splenomegaly in the subject in need of treatment for ALGS.

Further, the present disclosure provides pharmaceutical compositions comprising an mRNA comprising an open reading frame (ORF) encoding a Jagged 1 (JAG1) polypeptide, wherein the composition when administered to a subject in need of treatment for Alagille syndrome (ALGS) as a single intravenous dose is sufficient to improve the bile flow rate by at least 10%, at least 20%, at least 30%, at least 40%, or at least 50%, as compared to the bile flow rate in a subject untreated for ALGS, for at least 24 hours, at least 48 hours, at least 72 hours, at least 96 hours, or at least 120 hours post-administration.

Also provided herein are pharmaceutical compositions comprising an mRNA comprising an open reading frame (ORF) encoding a Jagged 1 (JAG1) polypeptide, wherein the composition when administered to a subject in need of treatment for Alagille syndrome (ALGS) as a single intravenous dose is sufficient to increase the rate of waste elimination from the bloodstream by at least 10%, at least 20%, at least 30%, at least 40%, or at least 50%, as compared to the rate of waste elimination from the bloodstream in a subject untreated for ALGS, for at least 24 hours, at least 48 hours, at least 72 hours, at least 96 hours, or at least 120 hours post-administration Pharmaceutical compositions, in some aspects, comprising an mRNA comprising an open reading frame (ORF) encoding a Jagged 1 (JAG1) polypeptide, wherein the composition when administered to a subject in need thereof as a single intravenous dose is sufficient to (i) maintain JAG1 activity levels at a normal physiological level or a supraphysiological level for at least 24 hours, at least 48 hours, at least 72 hours, at least 96 hours, or at least 120 hours post-administration, and/or (ii) maintain JAG1 activity levels at 50% or more of the normal JAG1 activity level for at least 24 hours, at least 48 hours, at least 72 hours, or at least 96 hours post-administration.

BRIEF DESCRIPTION OF THE DRAWINGS/FIGURES

FIG. 1 shows the protein sequence (panel A), table with domain features (panel B), and graphic representation of domain structure (panel C) of wild type JAG1.

FIG. 2 shows the nucleic acid sequence of wild type JAG1.

FIG. 3 shows the protein sequence (panel A), table with domain features (panel B), and graphic representation of domain structure (panel C) of a truncated JAG1 having amino acids 1-1054.

FIG. 4 shows the nucleic acid sequence of a truncated JAG1 having amino acids 1-1054.

FIG. 5 shows the protein sequence (panel A), table with domain features (panel B), and graphic representation of domain structure (panel C) of a truncated JAG1 having amino acids 1-1046.

FIG. 6 shows the nucleic acid sequence of a truncated JAG1 having amino acids 1-1046.

FIG. 7A-D shows the amino acid and nucleic acid sequences of peptides with an Fc antibody domain and JAG1.

FIG. 8 shows uracil (U) metrics corresponding to wild type JAG1 and 25 sequence optimized JAG1 polynucleotides. The column labeled "U content (%)" corresponds to the % $U_{TL}$ parameter. The column labeled "U Content v. WT (%)" corresponds to % $U_{WT}$. The column labeled "U Content v. Theoretical Minimum (%)" corresponds to % Um. The column labeled "UU pairs v. WT (%)" corresponds to % $UU_{WT}$.

FIG. 9 shows guanine (G) metrics corresponding to wild type JAG1 and 25 sequence optimized JAG1 polynucleotides. The column labeled "G Content (%)" corresponds to % $G_{TL}$. The column labeled "G Content v. WT (%)" corresponds to % $G_{WT}$. The column labeled "G Content v. Theoretical Maximum (%)" corresponds to % $G_{TMX}$.

FIG. 10 shows cytosine (C) metrics corresponding to wild type JAG1 and 25 sequence optimized JAG1 polynucleotides. The column labeled "C Content (%)" corresponds to % $C_{TL}$. The column labeled "C Content v. WT (%)" corresponds to % $C_{WT}$. The column labeled "C Content v. Theoretical Maximum (%)" corresponds to % $C_{TMX}$.

FIG. 11 shows guanine plus cytosine (G/C) metrics corresponding to wild type JAG1 and 25 sequence optimized JAG1 polynucleotides. The column labeled "G/C Content (%)" corresponds to % G/Cm. The column labeled "G/C Content v. WT (%)" corresponds to % $G/C_{WT}$. The column labeled "G/C Content v. Theoretical Maximum (%)" corresponds to % $G/C_{TMX}$.

FIG. 12 shows a comparison between the G/C compositional bias for codon positions 1, 2, 3 corresponding to wild type JAG1 and 25 sequence optimized JAG1 polynucleotides.

FIG. 13 shows a multiple sequence alignment wild type JAG1 and 25 sequence optimized JAG1 polynucleotides. Asterisks below the alignment indicate the location of conserved nucleobases that are identical between the wild type polynucleotide sequence and the sequence optimized JAG1 polynucleotides. Non-conserved nucleobases are indicated by spaces and periods below the alignment.

Figure 14A:
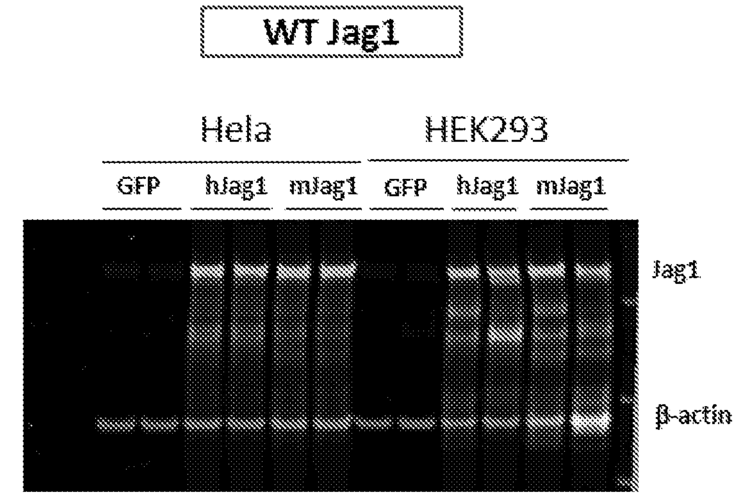
Figure 14B:
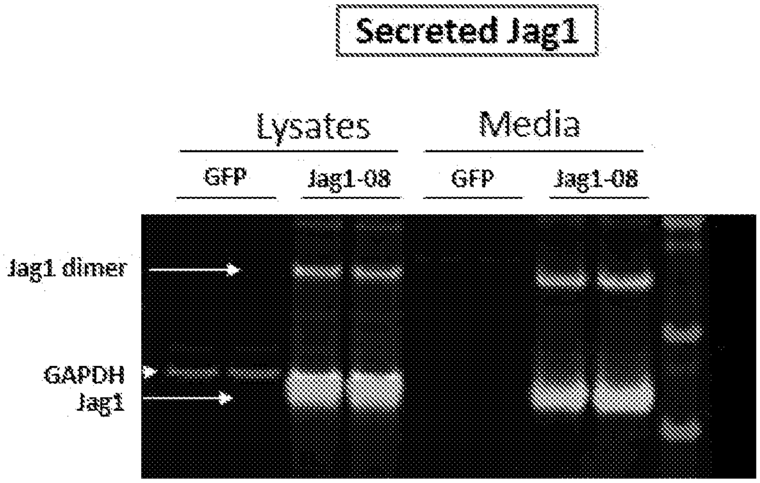

FIGS. 14A-14B are Western blot images showing the in vitro expression of mRNA constructs encoding the wild-type mouse JAG1 (mJAG1) or human JAG1 (hJAG1) (FIG. 14A), and a secreted form of JAG1 (a JAG1 peptide fused to a Fc domain) (FIG. 14B). Both mJAG1 and hJAG1 were expressed in Hela and HEK293 cells (FIG. 14A). The secreted form of JAG1 was detected in both the cell lysates and the culture media, indicating that that the protein was secreted by the cells following expression (FIG. 14B).

Figure 15A:
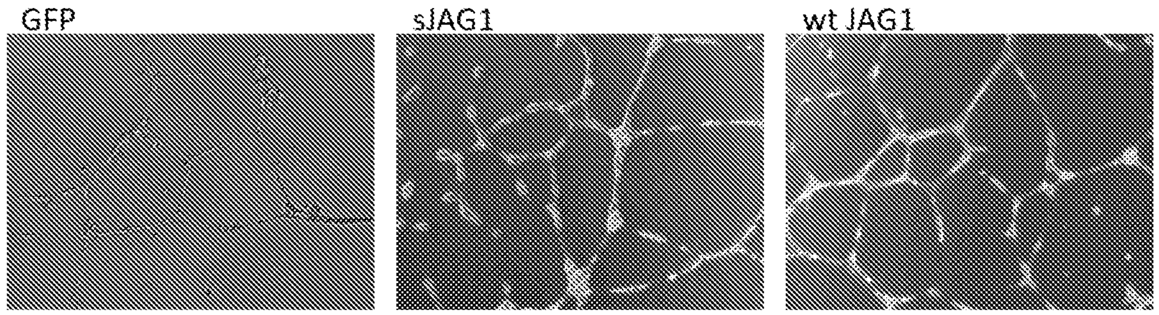
Figure 15B:
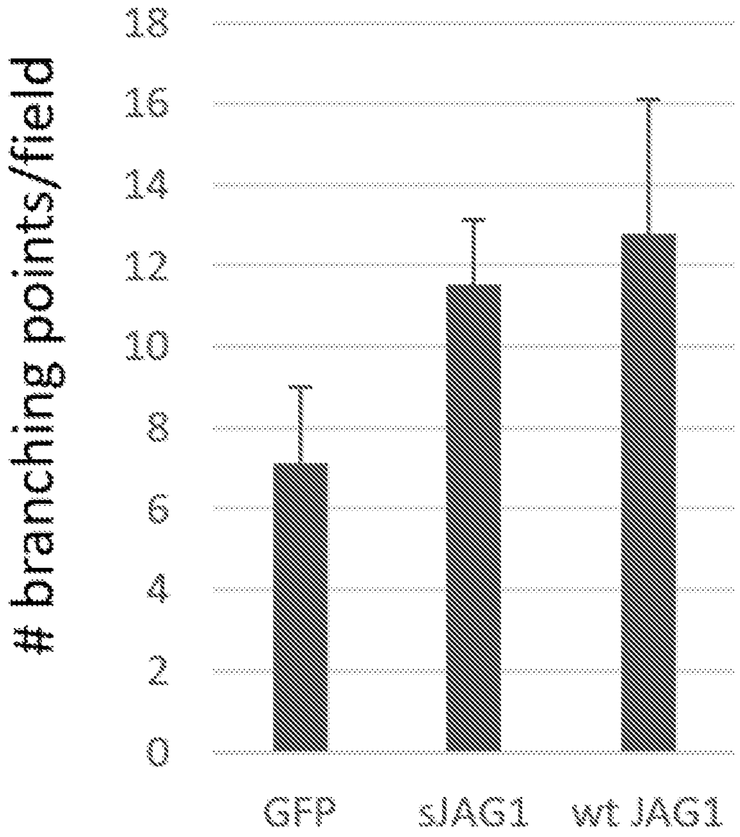

FIGS. 15A-15B show that the activity of secreted JAG1 or wild-type JAG1 on embryonic cells. FIG. 15A shows that both secreted JAG1 and wild-type JAG1 induced branching in embryonic cells. FIG. 15B is a graph showing the quantification of the branching points per imaging field.

Figure 16A:
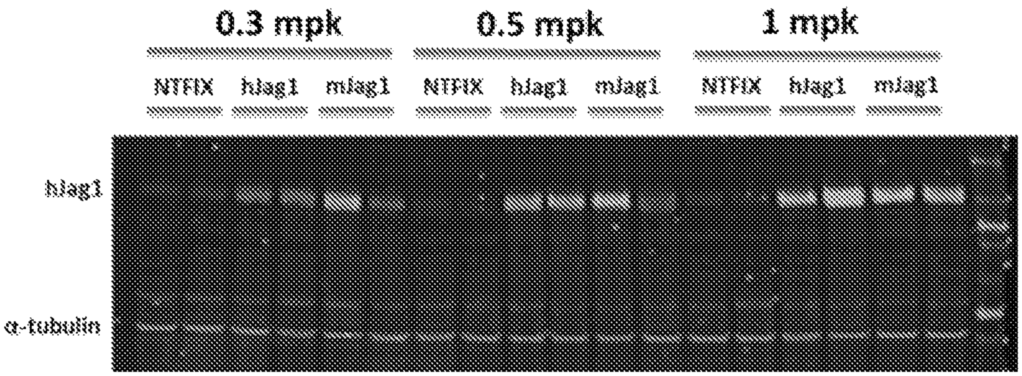
Figure 16B:
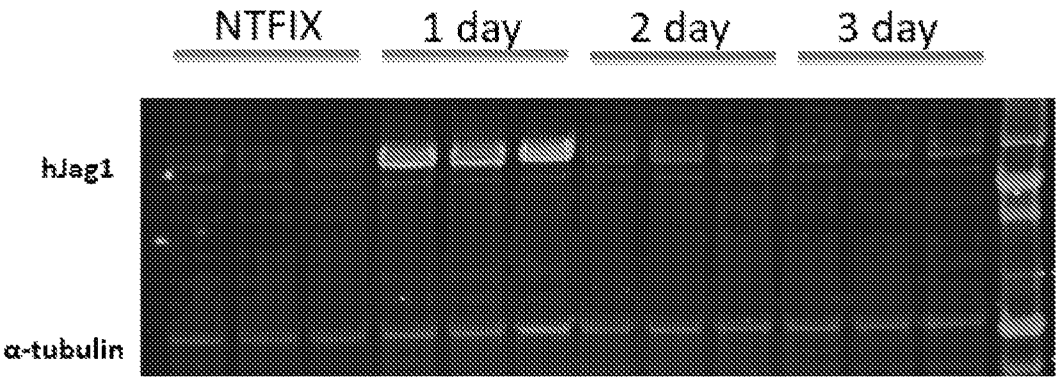

FIGS. 16A-16B are Western blot images showing the expression of mRNA constructs encoding wild-type human JAG1 or mouse JAG1 in the liver of C678BL6 mice. FIG. 16A shows that the expression level of wild-type human JAG1 or mouse JAG1 increases with an increasing dose of mRNA administered to the mice (0.3 mpk, 0.5 mg/kg, or 1 mg/kg doses). FIG. 16B shows the half-life of wild-type human JAG1 in the liver of C678BL6 mice. The results indicates that wild-type human JAG1 has a relatively short half-life in the liver of C678BL6 mice.

Figure 17A:
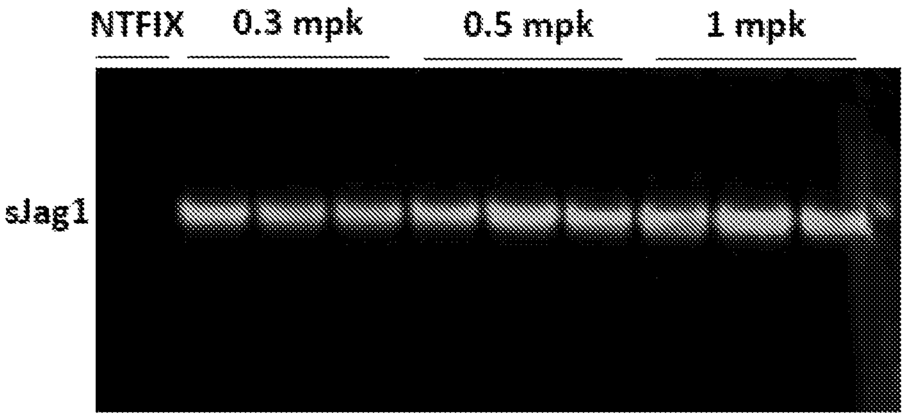
Figure 17B:
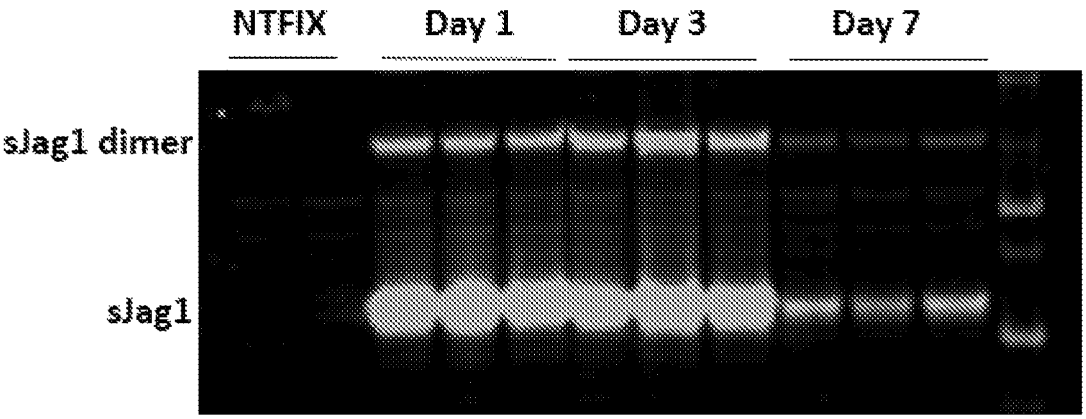

FIGS. 17A-17B are Western blot images showing the expression of mRNA constructs encoding secreted JAG1 in the liver of C678BL6 mice. FIG. 17A shows that the expression level of secreted JAG1 increases with an increasing dose of mRNA administered to the mice (0.3 mg/kg, 0.5 mg/kg, or 1 mg/kg doses). FIG. 17B shows that the secreted JAG1 can be detected 7 days after administration of the mRNA to the mice (by injection).

DETAILED DESCRIPTION

The present disclosure provides mRNA therapeutics for the treatment of Alagille syndrome (ALGS). Alagille syndrome is an autosomal dominant genetic disorder defined by a paucity of intrahepatic bile ducts, in association with five main clinical abnormalities: cholestasis, cardiac disease, skeletal abnormalities, ocular abnormalities, and a characteristic facial phenotype. In more than 90 percent of cases, mutations in the JAG1 gene cause Alagille syndrome. Another 7 percent of individuals with Alagille syndrome have small deletions of genetic material on chromosome 20 that include the JAG1 gene. mRNA therapeutics are particularly well-suited for the treatment of ALGS as the technology provides for the intracellular delivery of mRNA encoding JAG1 followed by de novo synthesis of functional JAG1 protein within target cells. After delivery of mRNA to the target cells, the desired JAG1 protein is expressed by the cells' own translational machinery, and hence, fully functional JAG1 protein replaces the defective or missing protein.

One challenge associated with delivering nucleic acid-based therapeutics (e.g., mRNA therapeutics) in vivo stems from the innate immune response that can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution and a strong type I interferon (type I IFN) response. The present disclosure features the incorporation of different modified nucleotides within therapeutic mRNAs to minimize the immune activation and optimize the translation efficiency of mRNA to protein. Particular embodiments provided herein feature a combination of nucleotide modification to reduce the innate immune response and sequence optimization, in particular, within the open reading frame (ORF) of therapeutic mRNAs encoding JAG1 to enhance protein expression.

The mRNA therapeutic technology of the present disclosure also features delivery of mRNA encoding JAG1 via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. Some embodiments provided herein feature novel ionizable lipid-based LNPs that have improved properties when administered in vivo. Without being bound in theory, it is believed that the novel ionizable lipid-based LNPs of the present disclosure have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient proteins (e.g., JAG1) in a therapeutic context. This is because repeat administration of mRNA therapeutics is in most instances essential to maintain necessary levels of enzyme in target tissues in subjects (e.g., subjects suffering from ALGS.) Repeat dosing challenges can be addressed on multiple levels. mRNA engineering and/or efficient delivery by LNPs can result in increased levels and or enhanced duration of protein (e.g., JAG1) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the present disclosure in one aspect, combats the ABC phenomenon. Moreover, LNPs can be engineered to avoid immune sensing and/or recognition and can thus further avoid ABC upon subsequent or repeat dosing. Exemplary aspect of the present disclosure feature novel LNPs which have been engineered to have reduced ABC.

Jagged 1 (JAG1)

Jagged 1 (JAG1), also known as CD339 (cluster of differentiation 339), a cell surface protein (ligand) that interacts with 4 receptors in the mammalian Notch signaling pathway. The Notch Signaling Pathway is a highly conserved pathway that functions to establish and regulate cell fate in many organ systems. Once the JAG1-NOTCH (receptor-ligand) interactions take place, a cascade of proteolytic cleavages is triggered resulting in activation of the transcription for downstream target genes. The JAG1 gene is expressed in multiple organ systems in the body.

The structure of the JAG1 protein includes a small intracellular component, a transmembrane motif, proceeded by an extracellular region containing a cystine-rich region, 16 EGF-like repeats, a DSL domain, and finally a signal peptide totaling 1218 amino acids in length over 26 coding exons. Guarnaccia C, et al. *FEBS Lett.* 574(1-3):156-60 (2004). The extracellular region of the JAG1 protein physically interacts with its respective Notch receptor. This interaction kicks off a cascade of proteolytic cleavages leading to the original NOTCH intracellular domain being trafficked into the nucleus of the cell leading to the activation of different target genes. Shimizu K, et al. *Biochem. Biophys. Res. Commun.* 276(1):385-9 (2000).

Mutations in JAG1 are known to cause Alagille syndrome (ALGS). Patients who are clinically consistent with the disorder usually have a mutation in JAG1, while a smaller (less than 2%) of patients have a mutation in NOTCH2. Over half of individuals with mutations in the gene did not inherit it from either parent, thus the mutation appeared de novo. JAG1 mutation types include protein truncating (splice site, frameshift, and nonsense), missense, and whole gene deletions accounting for 80%, 7%, and 12% respectively. Since all mutation types lead to a patient phenotype, it is thought that haploinsufficiency for JAG1 is the likely disease mechanism of action. Although individuals can have a range of mutation types in JAG1, all of the known mutations lead to loss of the function of one copy, and, there is no known correlation between mutation type or location and disease severity. Krantz I D, et al. *Am. J. Hum. Genet.* 62(6): 1361-9(1998).

The coding sequence (CDS) for wild type JAG1 canonical mRNA sequence is described at the NCBI Reference Sequence database (RefSeq) under accession number NM_000214.2 ("*Homo sapiens* jagged 1 (JAG1), mRNA"). The wild type JAG1 canonical protein sequence is described at the RefSeq database under accession number NP_000205.1 ("protein jagged-1 precursor [*Homo sapiens*]"). The JAG1 protein is 1218 amino acids long. It is noted that the specific nucleic acid sequences encoding the reference protein sequence in the Ref Seq sequences are the coding sequence (CDS) as indicated in the respective RefSeq database entry.

In certain aspects, the present disclosure provides a polynucleotide (e.g., a ribonucleic acid (RNA), e.g., a messenger RNA (mRNA)) comprising a nucleotide sequence (e.g., an open reading frame (ORF)) encoding a JAG1 polypeptide. In some embodiments, the JAG1 polypeptide of the present disclosure is a wild type JAG1 protein. In some embodiments, the JAG1 polypeptide of the present disclosure is a variant, a peptide or a polypeptide containing a substitution, and insertion and/or an addition, a deletion and/or a covalent modification with respect to a wild-type JAG1 sequence. In some embodiments, sequence tags or amino acids, can be added to the sequences encoded by the polynucleotides of the present disclosure (e.g., at the N-terminal or C-terminal ends), e.g., for localization. In some embodiments, amino acid residues located at the carboxy, amino terminal, or internal regions of a polypeptide of the present disclosure can optionally be deleted providing for fragments.

In some embodiments, the polynucleotide (e.g., a RNA, e.g., an mRNA) comprising a nucleotide sequence (e.g., an ORF) of the present disclosure encodes a substitutional variant of a JAG1 sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

As recognized by those skilled in the art, JAG1 protein fragments, functional protein domains, variants, and homologous proteins (orthologs) are also considered to be within the scope of the JAG1 polypeptides of the present disclosure. Nonlimiting examples of polypeptides encoded by the polynucleotides of the present disclosure are shown in FIGS. 1-6. For example, FIG. 1 shows the amino acid sequence of human wild type JAG1.

Certain compositions and methods presented in this disclosure refer to the protein or polynucleotide sequences of JAG1. A person skilled in the art will understand that such disclosures are equally applicable to any other isoforms of JAG1 known in the art.

The skilled artisan will appreciate that the therapeutic effectiveness of a drug or a treatment of the instant invention can be characterized or determined by measuring the level of expression of an encoded protein in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

JAG1 Protein Expression Levels

Certain aspects of the invention feature measurement, determination and/or monitoring of the expression level or levels of JAG1 protein in a subject, for example, in an animal (e.g., rodents, primates, and the like) or in a human subject. Animals include normal, healthy or wildtype animals, as well as animal models for use in understanding ALGS and treatments thereof. Exemplary animal models include rodent models, for example, JAG1 deficient mice or JAG1 deficient zebrafish. JAG1 protein expression levels can be measured or determined by any art-recognized method for determining protein levels in biological samples, e.g., needle liver biopsy. The term "level" or "level of a protein" as used herein, preferably means the weight, mass or concentration of the protein within a sample or a subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased JAG1 protein expression levels in the liver tissue of the subject (e.g., 2-fold, 3-fold, 4-fold, 5-fold, 6-fold, 7-fold, 8-fold, 9-fold, or 10-fold increase and/or increased to at least 50%, at least 60%, at least 70%, at least 75%, 80%, at least 85%, at least 90%, at least 95%, or at least 100% normal levels) for at least 6 hours, at least 12 hours, at least 24 hours, at least 36 hours, at least 48 hours, at least 60 hours, at least 72 hours, at least 84 hours, at least 96 hours, at least 108 hours, at least 122 hours after administration of a single dose of the mRNA therapy.

JAG1 Protein Activity

In ALGS patients, JAG1 activity is reduced, e.g., to about 50% of normal. Further aspects of the invention feature measurement, determination and/or monitoring of the activity level(s) (i.e., activity level(s)) of JAG1 protein in a subject, for example, in an animal (e.g., rodent, primate, and the like) or in a human subject. Activity levels can be measured or determined by any art-recognized method for determining activity levels in biological samples. The term "activity level" as used herein, preferably means the activity of the protein per volume, mass or weight of sample or total protein within a sample. In exemplary embodiments, the "activity level" is described in terms of units per milliliter of fluid (e.g., bodily fluid, e.g., serum, plasma, urine and the like) or is described in terms of units per weight of tissue or per weight of protein (e.g., total protein) within a sample. JAG1 is the ligand for the receptor notch 1 and can be characterized in terms of receptor binding activity.

In exemplary embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of JAG1 activity in tissue between 6 and 12 hours, or between 12 and 24, between 24 and 48, or between 48 and 72 hours post administration (e.g., at 48 or at 72 hours post administration). In exemplary embodiments, an mRNA therapy of the invention features a pharmaceutical composition comprising a dose of mRNA effective to result in at least 50 U/mg, at least 100 U/mg, at least 200 U/mg, at least 300 U/mg, at least 400 U/mg, at least 500 U/mg, at least 600 U/mg, at least 700 U/mg, at least 800 U/mg, at least 900 U/mg, at least 1,000 U/mg, or at least 1,500 U/mg of JAG1 activity between 6 and 12 hours, or between 12 and 24, between 24 and 48, or between 48 and 72 hours post administration (e.g., at 48 or at 72 hours post administration).

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

Polynucleotides and Open Reading Frames (ORFs)

In certain aspects, the present disclosure provides polynucleotides (e.g., a RNA, e.g., an mRNA) that comprise a nucleotide sequence (e.g., an ORF) encoding one or more JAG1 polypeptides. In some embodiments, the encoded JAG1 polypeptide of the present disclosure can be selected from:

- a full length JAG1 polypeptide (e.g., having the same or essentially the same length as wild-type JAG1);
- a functional fragment of any of the JAG1 sequences described herein (e.g., a truncated (e.g., deletion of carboxy, amino terminal, or internal regions) sequence shorter than one of wild-type;

but still retaining NOTCH receptor ligand activity);

- a variant thereof (e.g., full length or truncated proteins in which one or more amino acids have been replaced, e.g., variants that retain all or most of the JAG1 activity of the polypeptide with respect to a reference sequence (or any other natural or artificial variants known in the art); or
- a fusion protein comprising (i) a full length JAG1 protein, a functional fragment or a variant thereof, and (ii) a heterologous protein.

In certain embodiments, the encoded JAG1 polypeptide is a mammalian JAG1 polypeptide, such as a human JAG1 polypeptide, a functional fragment or a variant thereof.

In some embodiments, the polynucleotide (e.g., a RNA, e.g., an mRNA) of the present disclosure increases JAG1 protein expression levels and/or detectable JAG1 enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to JAG1 protein expression levels and/or detectable NOTCH receptor ligand activity levels in the cells prior to the administration of the polynucleotide of the present disclosure. JAG1 protein expression levels and/or NOTCH receptor ligand activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the present disclosure comprise a nucleotide sequence (e.g., an ORF) that encodes a wild-type human JAG1, e.g., wild-type human JAG1 (SEQ ID NO: 1, see FIG. 1).

In some embodiments, the polynucleotide (e.g., a RNA, e.g., an mRNA) of the present disclosure comprises a codon optimized nucleic acid sequence, wherein the open reading frame (ORF) of the codon optimized nucleic sequence is derived from a wild-type JAG1 sequence. For example, for polynucleotides of present disclosure comprising a sequence optimized ORF encoding JAG1, the corresponding wild type sequence is the native JAG1.

In some embodiments, the polynucleotides (e.g., a RNA, e.g., an mRNA) of the present disclosure comprise a nucleotide sequence encoding JAG1 having the full length sequence of human JAG1 (i.e., including the initiator methionine). In mature human JAG1, the initiator methionine can be removed to yield a "mature JAG1" comprising amino acid residues of 2-1218 of the translated product. The teachings of the present disclosure directed to the full sequence of human JAG1 (amino acids 1-1218) are also applicable to the mature form of human JAG1 lacking the initiator methionine (amino acids 2-1218). Thus, in some embodiments, the polynucleotides (e.g., a RNA, e.g., an mRNA) of the present disclosure comprise a nucleotide sequence encoding JAG1 having the mature sequence of human JAG1 (i.e., lacking the initiator methionine). In some embodiments, the polynucleotide (e.g., a RNA, e.g., an mRNA) of the present disclosure comprising a nucleotide sequence encoding JAG1 having the full length or mature sequence of human JAG1 is sequence optimized.

In some embodiments, the polynucleotides (e.g., a RNA, e.g., an mRNA) of the present disclosure comprise a nucleotide sequence (e.g., an ORF) encoding a mutant JAG1 polypeptide. In some embodiments, the polynucleotides of the present disclosure comprise an ORF encoding a JAG1 polypeptide that comprises at least one point mutation in the JAG1 sequence and retains NOTCH receptor ligand activity. In some embodiments, the mutant JAG1 polypeptide has a JAG1 activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the JAG1 activity of the corresponding wild-type JAG1 (i.e., the same JAG1 sequence but without the mutation(s)). In some embodiments, the polynucleotide (e.g., a RNA, e.g., an mRNA) of the present disclosure comprising an ORF encoding a mutant JAG1 polypeptide is sequence optimized.

In some embodiments, the polynucleotide (e.g., a RNA, e.g., an mRNA) of the present disclosure comprises a nucleotide sequence (e.g., an ORF) that encodes a JAG1 polypeptide with mutations that do not alter NOTCH receptor ligand activity. Such mutant JAG1 polypeptides can be referred to as function-neutral. In some embodiments, the polynucleotide comprises an ORF that encodes a mutant JAG1 polypeptide comprising one or more function-neutral point mutations.

In some embodiments, the mutant JAG1 polypeptide has higher NOTCH receptor ligand activity than the corresponding wild-type JAG1. In some embodiments, the mutant JAG1 polypeptide has a JAG1 activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type JAG1 (i.e., the same JAG1 sequence but without the mutation(s)).

In some embodiments, the polynucleotides (e.g., a RNA, e.g., an mRNA) of the present disclosure comprise a nucleotide sequence (e.g., an ORF) encoding a functional JAG1 fragment, e.g., where one or more fragments correspond to a polypeptide subsequence of a wild type JAG1 polypeptide and retain NOTCH receptor ligand activity. In some embodiments, the JAG1 fragment has a JAG1 activity which is at least 10%, at least 15%, at least 20%, at least 25%, at least 30%, at least 35%, at least 40%, at least 45%, at least 50%, at least 55%, at least 60%, at least 65%, at least 700%, at least 75%, at least 80%, at least 85%, at least 90%, at least 95%, or at least 100% of the JAG1 activity of the corresponding full length JAG1. In some embodiments, the polynucleotides (e.g., a RNA, e.g., an mRNA) of the present disclosure comprising an ORF encoding a functional JAG1 fragment is sequence optimized.

In some embodiments, the polynucleotide (e.g., a RNA, e.g., an mRNA) of the present disclosure comprises a nucleotide sequence (e.g., an ORF) encoding a JAG1 fragment that has higher NOTCH receptor ligand activity than the corresponding full length JAG1. Thus, in some embodiments the JAG1 fragment has a JAG1 activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the JAG1 activity of the corresponding full length JAG1.

In some embodiments, the polynucleotide (e.g., a RNA, e.g., an mRNA) of the present disclosure comprises a nucleotide sequence (e.g., an ORF) encoding a JAG1 fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type JAG1.

In some embodiments, the polynucleotide (e.g., a RNA, e.g., an mRNA) of the present disclosure comprises a nucleotide sequence (e.g., an ORF) encoding a JAG1 polypeptide (e.g., the wild-type sequence, functional fragment, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:2, 4, or 6 (see, e.g., FIG. 2, 4 or 6).

In some embodiments, the polynucleotide (e.g., a RNA, e.g., an mRNA) of the present disclosure comprises a nucleotide sequence (e.g., an ORF) encoding a JAG1 polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 11 to 35. See TABLE 2; FIG. 13.

In some embodiments, the polynucleotide (e.g., a RNA, e.g., an mRNA) of the present disclosure comprises a nucleotide sequence (e.g., an ORF) encoding a JAG1 polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 11 to 35. See TABLE 2; FIG. 13.

In some embodiments, the polynucleotide (e.g., a RNA, e.g., an mRNA) of the present disclosure comprises a nucleotide sequence (e.g., an ORF) encoding a JAG polypeptide (e.g., the wild-type sequence, functional fragment, or variant thereof), wherein the nucleotide sequence is at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence of SEQ ID NO:2, 4 or 6 (see, FIG. 2, 4 or 6).

In some embodiments the polynucleotide (e.g., a RNA, e.g., an mRNA) of the present disclosure comprises a nucleotide sequence (e.g., an ORF) encoding a JAG1 polypeptide (e.g., the wild-type sequence, functional fragment, or variant thereof), wherein the nucleotide sequence is between 75% and 85% identical; between 76% and 84% identical; between 77% and 83% identical, between 77% and 82% identical, between 78% and 81% or between 79% and 81% identical to the sequence of SEQ ID NO:2, 4 or 6 (see, FIG. 2, 4 or 6).

In some embodiments, the polynucleotide (e.g., a RNA, e.g., an mRNA) of the present disclosure comprises from about 3.105 to about 100,000 nucleotides (e.g., from 3,105 to 3,700, from 3,105 to 3,800, from 3,105 to 3,900, from 3,105 to 4,000, from 3,105 to 4,100 from 3,105 to 4,200, from 3,105 to 4,300, from 3,105 to 4,400, 3,654 to 3,700, from 3,654 to 3,800, from 3,654 to 3,900, from 3,654 to 4,000, from 3,654 to 4,100 from 3,654 to 4,200, from 3,654 to 4,300, from 3,654 to 4,400, from 3,654 to 5,000, from 3,654 to 7,000, from 3,654 to 10,000, from 3,654 to 25,000, from 3,654 to 50,000, from 3,654 to 70,000, or from 3,654 to 100,000).

In some embodiments, the polynucleotide of the present disclosure (e.g., a RNA, e.g., an mRNA) comprises a nucleotide sequence (e.g., an ORF) encoding a JAG1 polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,654, 3,700, 3,800, 3,900, 4,000, 4,100, 4,200, 4,300, 4,400, 4,500, 4,600, 4,700, 4,800, 4,900, 5,000, 5.100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the present disclosure (e.g., a RNA, e.g., an mRNA) comprises a nucleotide sequence (e.g., an ORF) encoding a JAG1 polypeptide (e.g., the wild-type sequence, functional fragment, or variant thereof) further comprises at least one nucleic acid sequence that is noncoding, e.g., a miRNA binding site.

In some embodiments, the polynucleotide of the present disclosure (e.g., a RNA, e.g., an mRNA) comprises a nucleotide sequence (e.g., an ORF) encoding a JAG1 polypeptide is single stranded or double stranded.

In some embodiments, the polynucleotide of the present disclosure comprising a nucleotide sequence (e.g., an ORF) encoding a JAG1 polypeptide (e.g., the wild-type sequence, functional fragment, or variant thereof) is DNA or RNA. In some embodiments, the polynucleotide of the present disclosure is RNA. In some embodiments, the polynucleotide of the present disclosure is, or functions as, a messenger RNA (mRNA). In some embodiments, the mRNA comprises a nucleotide sequence (e.g., an ORF) that encodes at least one JAG1 polypeptide, and is capable of being translated to produce the encoded JAG1 polypeptide in vitro, in vivo, in situ or ex vivo.

In some embodiments, the polynucleotide of the present disclosure (e.g., a RNA, e.g., an mRNA) comprises a sequence-optimized nucleotide sequence (e.g., an ORF) encoding a JAG1 polypeptide (e.g., the wild-type sequence, functional fragment, or variant thereof), wherein the polynucleotide comprises at least one chemically modified nucleobase, e.g., 5-methoxyuracil. In some embodiments, the polynucleotide further comprises a miRNA binding site, e.g., a miRNA binding site that binds to miR-142. In some embodiments, the polynucleotide disclosed herein is formulated with a delivery agent, e.g., a compound having Formula (I), (IA), (II), (IIa), (IIb), (IIc), (IId) or (IIe), e.g., any of Compounds 1-232.

Signal Sequences

The polynucleotides (e.g., a RNA, e.g., an mRNA) of the present disclosure can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked a nucleotide sequence that encodes a JAG1 polypeptide described herein.

In some embodiments, the "signal sequence" or "signal peptide" is a polynucleotide or polypeptide, respectively, which is from about 9 to 200 nucleotides (3-70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the present disclosure comprises a nucleotide sequence encoding a JAG1 polypeptide, wherein the nucleotide sequence further comprises a 5' nucleic acid sequence encoding a native signal peptide. In another embodiment, the polynucleotide of the present disclosure comprises a nucleotide sequence encoding a JAG1 polypeptide, wherein the nucleotide sequence lacks the nucleic acid sequence encoding a native signal peptide. The native signal peptide of JAG1 is from amino acids 1-33 of SEQ ID NO. 1, 3 or 5, see FIG. 1, 3 or 5.

In some embodiments, the polynucleotide of the present disclosure comprises a nucleotide sequence encoding a JAG1 polypeptide, wherein the nucleotide sequence further comprises a 5' nucleic acid sequence encoding a heterologous signal peptide.

Fusion Proteins

In some embodiments, the polynucleotide of the present disclosure (e.g., a RNA, e.g., an mRNA) can comprise more than one nucleic acid sequence (e.g., an ORF) encoding a polypeptide of interest. In some embodiments, polynucleotides of the present disclosure comprise a single ORF encoding a JAG1 polypeptide, a functional fragment, or a variant thereof. However, in some embodiments, the polynucleotide of the present disclosure can comprise more than one ORF, for example, a first ORF encoding a JAG1 polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a $G_4S$ peptide linker or another linker known in the art) between two or more polypeptides of interest.

In some embodiments, a polynucleotide of the present disclosure (e.g., a RNA, e.g., an mRNA) can comprise two, three, four, or more ORFs, each expressing a polypeptide of interest.

In some embodiments, the polynucleotide of the present disclosure (e.g., a RNA, e.g., an mRNA) can comprise a first nucleic acid sequence (e.g., a first ORF) encoding a JAG1 polypeptide and a second nucleic acid sequence (e.g., a second ORF) encoding a second polypeptide of interest. Examples of JAG1 fusion proteins are SEQ ID NO: 7-10, which are fusions of JAG1 with an antibody Fc domain.

Sequence Optimization of Nucleotide Sequence Encoding a JAG1 Polypeptide

In some embodiments, the polynucleotide (e.g., a RNA, e.g., an mRNA) of the present disclosure is sequence optimized. In some embodiments, the polynucleotide (e.g., a RNA, e.g., an mRNA) of the present disclosure comprises a nucleotide sequence (e.g., an ORF) encoding a JAG1 polypeptide, a nucleotide sequence (e.g., an ORF) encoding another polypeptide of interest, a 5'-UTR, a 3'-UTR, a miRNA binding site, a nucleotide sequence encoding a linker, or any combination thereof) that is sequence optimized.

A sequence-optimized nucleotide sequence, e.g., an codon-optimized mRNA sequence encoding a JAG1 polypeptide, is a sequence comprising at least one synonymous nucleobase substitution with respect to a reference sequence (e.g., a wild type nucleotide sequence encoding a JAG1 polypeptide).

A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon. T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%/o. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

Codon options for each amino acid are given in TABLE 1.

TABLE 1

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAG |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocysteine insertion element (SECIS) |
| Stop codons | Stop | TAA, TAG, TGA |

In some embodiments, a polynucleotide (e.g., a RNA, e.g., an mRNA) of the present disclosure comprises a sequence-optimized nucleotide sequence (e.g., an ORF) encoding a JAG1 polypeptide, a functional fragment, or a variant thereof, wherein the JAG1 polypeptide, functional fragment, or a variant thereof encoded by the sequence-optimized nucleotide sequence has improved properties (e.g., compared to a JAG1 polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the present disclosure comprise a nucleotide sequence (e.g., a nucleotide sequence (e.g, an ORF) encoding a JAG1 polypeptide, a nucleotide sequence (e.g, an ORF) encoding another polypeptide of interest, a 5'-UTR, a 3'-UTR, a microRNA, a nucleic acid sequence encoding a linker, or any combination thereof) that is sequence-optimized according to a method comprising:

(i) substituting at least one codon in a reference nucleotide sequence (e.g., an ORF encoding a JAG1 polypeptide) with an alternative codon to increase or decrease uridine content to generate a uridine-modified sequence;

(ii) substituting at least one codon in a reference nucleotide sequence (e.g., an ORF encoding a JAG1 polypeptide) with an alternative codon having a higher codon frequency in the synonymous codon set;

(iii) substituting at least one codon in a reference nucleotide sequence (e.g., an ORF encoding a JAG1 polypeptide) with an alternative codon to increase G/C content; or (iv) a combination thereof.

In some embodiments, the sequence-optimized nucleotide sequence (e.g., an ORF encoding a JAG1 polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the present disclosure, can be encoded by or within regions of the polynucleotide and such regions can be upstream (5') to, downstream (3') to, or within the region that encodes the JAG1 polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the present disclosure comprises a 5' UTR. a 3' UTR and/or a miRNA binding site. In some embodiments, the polynucleotide comprises two or more 5' UTRs and/or 3' UTRs, which can be the same or different sequences. In some embodiments, the polynucleotide comprises two or more miRNA binding site, which can be the same or different sequences. Any portion of the 5' UTR, 3' UTR, and/or miRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, neurospora, maize, drosophila, etc. where high copy plasmid-like or chromosome structures occur by methods described herein.

Sequence-Optimized Nucleotide Sequences Encoding JAG1 Polypeptides

In some embodiments, the polynucleotide of the present disclosure comprises a sequence-optimized nucleotide sequence encoding a JAG1 polypeptide disclosed herein. In some embodiments, the polynucleotide of the present disclosure comprises an open reading frame (ORF) encoding a JAG1 polypeptide, wherein the ORF has been sequence optimized.

Exemplary sequence-optimized nucleotide sequences encoding human JAG1 are shown in TABLE 2. In some embodiments, the sequence optimized JAG1 sequences in Table 2, fragments, and variants thereof are used to practice the methods disclosed herein. In some embodiments, the sequence optimized JAG1 sequences in Table 2, fragments and variants thereof are combined with or alternatives to the wild-type sequences disclosed in FIGS. 1-6.

TABLE 2

Sequence optimized sequences for human JAG1

| SEQ ID NO | NAME | SEQUENCE |
|---|---|---|
| 11 | JAG1-CO01 | ATGCGAAGCCCCAGGACCCGCGGCCGTAGCGGTAGGCCCCTGTC<br>CCTGCTGCTGGCCCTGCTGTGCGCCCTCAGGGCCAAGGTGTGCG<br>GCGCCAGCGGCCAGTTCGAGCTCGAGATCCTGAGCATGCAGAA<br>CGTGAACGGCGAGCTCCAGAATGGGAATTGTTGCGGCGGCGCC<br>AGGAACCCCGGTGACAGGAAATGCACCCGCGACGAGTGCGACA<br>CCTACTTCAAAGTGTGCCTCAAGGAGTACCAGAGCAGGGTGACC<br>GCCGGCGGGCCCTGCAGCTTCGGGAGCGGCTCCACGCCCGTGAT<br>CGGCGGGAACACCTTCAACCTGAAGGCCAGCAGGGGCAACGAT<br>CGGAACCGGATCGTGCTGCCGTTCTCCTTCGCCTGGCCGCGAAG<br>CTACACCCTGCTGGTGGAAGCGTGGGACAGCAGCAACGACACC<br>GTGCAGCCCGACAGCATCATCGAGAAGGCCTCACACTCCGGTAT<br>GATCAACCCCAGCAGGCAGTGGCAGACCCTGAAGCAGAACACC<br>GGAGTGGCCCACTTCGAATACCAGATCAGGGTGACATGCGACG<br>ACTACTACTACGGCTTCGGGTGCAACAAGTTCTGCAGGCCCCGC<br>GACGACTTCTTCGGACACTACGCCTGTGACCAGAACGGGAACAA<br>GACGTGTATGGAGGGGTGGATGGGGCCCGAATGCAACAGGGCC<br>ATCTGTCGGCAGGGTTGCTCCCCCAAGCACGGCTCCTGCAAACT<br>GCCCGGCGATTGCCGGTGCCAGTACGGGTGGCAAGGTCTGTACT<br>GCGACAAGTGCATCCCGCATCCCGGCTGCGTGCACGGCATCTGC<br>AACGAGCCCTGGCAGTGCCTGTGCGAAACCAACTGGGGCGGCC |

TABLE 2-continued

Sequence optimized sequences for human JAG1

| SEQ ID NO | NAME | SEQUENCE |
|---|---|---|
| | | AGCTCTGTGACAAGGACCTTAACTACTGCGGCACCCACCAGCCC<br>TGCCTGAACGGCGGGACCTGCAGCAACACCGGGCCCGACAAGT<br>ACCAGTGTAGCTGCCCCGAAGGGTACTCGGGTCCCAACTGCGAG<br>ATCGCCGAGCACGCCTGCCTGTCCGACCCCTGCCATAACAGGGG<br>CAGCTGTAAGGAGACCTCCCTGGGCTTCGAGTGTGAGTGCTCCC<br>CCGGATGGACCGGCCCCACCTGCAGCACCAATATTGACGACTGC<br>AGCCCAAATAACTGCTCCCACGGCGGCACCTGCCAGGACCTCGT<br>GAACGGCTTTAAGTGCGTCTGTCCCCCCAGTGGACCGGCAAGA<br>CCTGCCAGCTGGACGCCAATGAGTGCGAGGCCAAGCCCTGTGTA<br>AACGCCAAGAGCTGCAAGAACCTGATCGCCAGCTACTACTGTGA<br>CTGCCTGCCCGGCTGGATGGGCCAGAACTGCGACATCAACATCA<br>ACGACTGCCTCGGGCAGTGCCAGAACGACGCCAGCTGCAGGGA<br>TCTGGTGAACGGCTACAGGTGCATCTGCCCCCCCGGATACGCCG<br>GCGACCATTGCGAAAGGGACATCGATGAGTGCGCCTCCAATCCC<br>TGTCTGAACGGCGGCCACTGCCAGAACGAGATCAACAGGTTCCA<br>GTGCCTGTGCCCCACCGGCTTCAGCGGGAACCTGTGCCAGCTGG<br>ACATCGACTATTGCGAGCCCAATCCCTGCCAGAACGGGGCGCAG<br>TGCTACAACAGGGCCAGCGACTACTTCTGCAAGTGCCCCGAGGA<br>CTACGAGGGCAAGAATTGCAGCCACCTGAAAGACCACTGCCGC<br>ACCACCCCCTGTGAGGTTATCGACAGCTGTACGGTCGCCATGGC<br>CTCGAACGACACCCCCGAAGGCGTGAGGTATATCTCCAGCAACG<br>TGTGCGGGCCACACGGCAAATGTAAGTCCCAGAGCGGCGGGAA<br>GTTCACCTGCGACTGCAACAAGGGCTTCACAGGCACGTACTGCC<br>ATGAGAACATCAACGATTGTGAGAGCAACCCCTGCAGGAACGG<br>CGGGACCTGCATAGACGGCGTGAACAGCTATAAGTGCATCTGCA<br>GCGATGGCTGGGAGGGAGCCTACTGCGAAACCAACATCAATGA<br>CTGCAGCCAGAACCCCTGTCACAACGGGGGCACATGCCGGGAC<br>CTGGTGAATGATTTCTACTGCGACTGCAAGAATGGCTGGAAGGG<br>CAAGACCTGCCACAGCAGGGACTCCCAGTGTGACGAGGCCACC<br>TGCAATAACGGGGGCACCTGCTACGACGAGGGCGACGCCTTTA<br>AGTGCATGTGCCCCGGCGGTTGGGAGGGTACCACCTGCAACATC<br>GCGCGGAACAGCAGCTGTCTGCCCAACCCCTGCCACAACGGGG<br>GCACGTGCGTGGTGAACGGCGAGAGCTTCACCTGCGTGTGTAAG<br>GAGGGGTGGGAGGGCCCCATCTGCGCCCAGAACACCAACGATT<br>GCTCGCCCCACCCCTGTTACAACAGCGGGACCTGCGTGGACGGT<br>GATAACTGGTACAGGTGCGAGTGCGCACCAGGCTTCGCCGGGCC<br>GGACTGCAGGATCAACATCAACGAATGTCAGAGCTCCCCGTGCG<br>CCTTCGGCGCCACGTGCGTAGACGAGATCAATGGCTACAGGTGC<br>GTGTGCCCCCCAGGCCACAGCGGGGCCAAATGCCAGGAAGTCA<br>GCGGCCGACCCTGCATCACCATGGGTTCCGTTATCCCAGACGGA<br>GCCAAGTGGGATGACGATTGTAACACCTGTCAGTGTCTGAATGG<br>CCGGATCGCGTGCAGCAAGGTGTGGTGCGGCCCCAGGCCGTGCC<br>TGCTGCACAAGGGCCACTCCGAATGTCCCTCCGGTCAGAGCTGC<br>ATCCCCATCCTCGACGACCAGTGCTTTGTACACCCCTGCACCGG<br>AGTCGGCGAGTGCAGGTCCTCGTCTCTGCAGCCCGTGAAAACCA<br>AGTGCACCAGCGACTCCTACTACCAGGACAACTGCGCCAACATC<br>ACGTTCACCTTTAACAAGGAGATGATGAGCCCCGGGCTGACCAC<br>GGAGCACATCTGCTCGGAGCTGAGGAACCTGAACATACTGAAG<br>AACGTGAGCGCCGAGTACAGCATCTACATTGCCTGCGAGCCCAG<br>CCCCAGCGCCAACAACGAGATCCACGTGGCGATCTCCGCCGAA<br>GACATCCGGGACGACGGCAACCCCATCAAGGAGATAACCGACA<br>AGATCATCGACCTGGTGAGCAAGCGGGACGGCAACAGCTCCCT<br>GATCGCCGCCGTGGCCGAGGTGCGGGTACAGAGGCGGCCCCTC<br>AAGAACAGGACGGACTTCCTCGTGCCGCTCCTGTCGTCCGTGCT<br>GACCGTGGCCTGGATCTGCTGTCTGGTGACCGCCTTCTACTGGT<br>GCCTGCGGAAGCGGCGCAAGCCGGGGAGCCACACCCACTCGGC<br>CAGCGAAGACAACACGACCAACAACGTGAGGGAGCAGCTGAAT<br>CAGATCAAGAATCCCATAGAGAAACACGGCGCCAACACCGTGC<br>CCATCAAGGATTACGAGAACAAGAACAGCAAGATGTCCAAAAT<br>CAGAACCCACAATAGCGAAGTGGAGGAAGACGACATGGATAAG<br>CACCAGCAGAAGGCCAGGTTCGCCAAGCAGCCCGCCTACACCCT<br>GGTAGACAGGGAGGAGAAGCCCCCCAACGGCACCCCCACGAAA<br>CACCCGAACTGGACCAACAAGCAGGATAATAGGGACCTGGAGT<br>CCGCGCAGAGCCTGAACCGCATGGAGTACATCGTG |
| 12 | JAG1-CO02 | ATGAGGAGCCCCAGGACCCGGGGCCGTAGCGGGAGGCCGCTCT<br>CGCTGCTGCTGGCCCTGCTCTGCGCCCTGAGGGCCAAGGTGTGT<br>GGCGCCTCCGGGCAGTTCGAGCTGGAAATCCTGAGCATGCAGA<br>ACGTCAACGGCGAGCTGCAGAACGGCAACTGCTGCGGCGGAGC<br>GCGGAACCCCGGGGACAGGAAGTGCACCAGGGACGAGTGTGAC<br>ACGTACTTCAAAGTCTGCCTCAAGGAGTACCAGAGCCGGGTGAC<br>CGCCGGGGGCCCATGCTCCTTCGGCAGCGGCAGCACCCCCGTCA<br>TCGGAGGCAACACCTTTAATCTGAAGGCCAGCAGGGGGAACGA<br>CAGGAATAGGATCGTCCTGCCCTTTAGCTTCGCCTGGCCCAGGT<br>CCTACACCCTGCTGGTCGAGGCCTGGGACAGCTCCAACGACACC |

TABLE 2-continued

| SEQ ID NO | NAME | SEQUENCE |
|---|---|---|
| | | GTCCAGCCCGACAGTATCATCGAGAAGGCGTCCCACTCCGGCAT<br>GATCAATCCCAGCAGGCAGTGGCAGACGCTGAAGCAGAACACC<br>GGCGTGGCCCACTTCGAGTATCAGATCCGGGTGACGTGCGACGA<br>CTACTACTACGGGTTCGGCTGCAACAAGTTCTGTAGGCCCCGGG<br>ACGATTTCTTCGGCCACTACGCATGCGACCAGAACGGCAACAAG<br>ACCTGCATGGAGGGCTGGATGGGCCCCGAGTGCAACAGGGCTA<br>TCTGCCGCCAGGGCTGCTCCCCCAAGCACGGCAGCTGTAAGCTG<br>CCCGGCGATTGCCGGTGTCAGTACGGGTGGCAGGGACTGTATTG<br>CGACAAGTGCATACCCCACCCAGGCTGCGTGCACGGCATCTGTA<br>ACGAGCCCTGGCAATGCCTCTGCGAGACCAACTGGGGGGGACA<br>ACTGTGCGACAAGGACCTGAACTACTGCGGTACCCACCAGCCCT<br>GCCTGAACGGCGGCACCTGCAGTAACACCGGCCCCGACAAGTA<br>TCAGTGCAGCTGCCCCGAGGGGTATTCCGGCCCGAACTGCGAGA<br>TCGCCGAGCACGCCTGCCTCAGCGACCCATGCCACAATAGAGGC<br>AGCTGCAAGGAAACCTCCCTGGGGTTCGAGTGTGAGTGCTCCCC<br>CGGGTGGACCGGGCCCACCTGCTCCACCAACATCGACGACTGCA<br>GCCCCAATAACTGCAGCCACGGGGGCACCTGTCAGGACCTGGTG<br>AACGGCTTTAAGTGCGTCTGCCCCCCCCAGTGGACCGGTAAGAC<br>GTGCCAGCTGGACGCCAATGAGTGCGAAGCCAAGCCCTGCGTC<br>AATGCCAAGAGCTGTAAGAACCTCATCGCGTCCTACTATTGCGA<br>CTGCCTGCCCGGGTGGATGGGACAGAACTGCGACATCAACATCA<br>ACGACTGCCTCGGGCAGTGCCAGAACGACGCCAGCTGCCGGGA<br>CCTGGTGAACGGCTATAGATGCATCTGCCCCCCCGGCTACGCCG<br>GGGACCACTGCGAGAGGGACATCGACGAGTGCGCCTCCAACCC<br>CTGCCTGAATGGAGGCCACTGCCAGAACGAAATCAACAGGTTCC<br>AGTGTCTGTGCCCCACCGGATTCAGCGGAAACCTGTGCCAGCTG<br>GACATCGACTATTGCGAACCCAACCCCTGTCAGAACGGCGCCCA<br>GTGCTACAACCGGGCAAGCGACTACTTCTGCAAGTGCCCTGAGG<br>ACTACGAGGGCAAGAACTGCAGCCACCTCAAGGACCACTGCAG<br>GACGACCCCCTGTGAGGTGATCGACAGCTGTACCGTGGCCATGG<br>CCTCGAACGACACCCCTGAGGGCGTGAGGTATATCTCCAGCAAC<br>GTCTGCGGCCCCCACGGCAAATGTAAGAGCCAATCCGGGGGCA<br>AGTTCACCTGCGACTGCAACAAGGGATTTACCGGCACCTACTGC<br>CACGAGAACATCAACGACTGCGAGTCCAATCCCTGCCGTAACGG<br>CGGCACCTGCATCGACGGTGTCAACAGCTACAAGTGCATCTGCA<br>GCGACGGCTGGGAGGGAGCGTACTGCGAAACCAACATAAACGA<br>TTGTTCCCAGAACCCCTGCCACAACGGCGGCACCTGCCGGGACC<br>TTGTGAACGACTTTTACTGTGACTGCAAGAATGGGTGGAAGGGC<br>AAAACGTGCCACAGCAGAGACAGCCAGTGCGACGAAGCCACCT<br>GTAACAACGGCGGCACCTGCTACGACGAGGGCGACGCCTTTAA<br>GTGTATGTGCCCGGGCGGCTGGGAAGGCACGACCTGCAACATC<br>GCCCGGAACAGCAGCTGCCTCCCGAACCCTTGCCACAACGGCGG<br>GACCTGCGTGGTGAATGGCGAATCCTTCACCTGCGTGTGCAAGG<br>AGGGCTGGGAGGGCCCCATCTGCGCCCAAAACACCAATGACTG<br>TAGCCCCCACCCCTGCTACAACTCCGGCACATGTGTGGATGGCG<br>ACAACTGGTACAGGTGTGAGTGCGCCCCCGGATTCGCCGGCCCC<br>GACTGCCGGATCAACATTAACGAGTGTCAGAGCAGCCCCTGCGC<br>CTTCGGCGCCACCTGCGTCGATGAGATAAACGGATATAGGTGCG<br>TGTGCCCCCCCGGACACAGCGGCGCGAAGTGCCAGGAGGTGAG<br>CGGCAGGCCCTGCATCACAATGGGCAGCGTGATCCCGGACGGC<br>GCCAAGTGGGACGACGATTGCAACACCTGCCAGTGCCTGAACG<br>GCCGGATAGCCTGCTCCAAAGTGTGGTGCGGCCCCCGCCCCTGC<br>CTGCTGCACAAGGGCCACAGCGAGTGCCCCTCCGGCCAGAGCTG<br>CATCCCCATACTGGACGACCAATGTTTCGTGCATCCCTGCACCG<br>GCGTGGGCGAGTGTCGGAGCAGCAGCCTGCAGCCCGTGAAGAC<br>TAAGTGCACCTCCGACTCCTACTATCAGGACAACTGTGCCAACA<br>TCACCTTCACCTTCAACAAGGAGATGATGAGCCCCGGCCTGACA<br>ACGGAGCACATCTGCAGCGAGCTGCGCAATCTGAACATCCTGAA<br>AAATGTGAGCGCCGAGTACAGCATCTACATCGCCTGTGAGCCGA<br>GCCCCAGCGCTAATAACGAGATCCACGTGGCCATCTCCGCCGAG<br>GACATCAGGGATGACGGCAACCCCATCAAAGAGATCACCGACA<br>AGATCATCGACCTGGTGTCCAAGCGGGACGGCAACTCCAGCCTG<br>ATCGCAGCCGTGGCCGAAGTGAGGGTCCAGCGGCGGCCCCTGA<br>AGAACCGAACCGACTTCCTGGTCCCCCTGCTGAGCAGCGTGCTG<br>ACCGTCGCATGGATCTGTTGCCTGGTGACGGCCTTCTACTGGTG<br>CCTCAGGAAAAGACGGAAGCCCGGGAGCCACACCCACAGCGCC<br>AGCGAGGACAACACCACCAACAACGTGCGGGAGCAGCTGAACC<br>AAATCAAGAACCCCATCGAGAAGCATGGCGCCAATACCGTGCC<br>CATCAAAGACTACGAGAACAAGAACAGCAAGATGAGCAAGATC<br>CGCACCCATAACTCGGAGGTGGAAGAAGACGATATGGATAAGC<br>ACCAGCAAAAGGCCCGGTTCGCGAAGCAGCCCGCCTATACCCTC<br>GTGGACCGGGAAGAAAAGCCGCCCAACGGCACCCCCACCAAGC<br>ACCCCAACTGGACCAACAAACAGGACAACAGGGACCTCGAGAG<br>CGCCCAGTCCCTCAACCGTATGGAGTACATCGTC |

Sequence optimized sequences for human JAG1

TABLE 2-continued

Sequence optimized sequences for human JAG1

| SEQ ID NO | NAME | SEQUENCE |
|---|---|---|
| 13 | JAG1-CO03 | ATGAGGTCCCCGCGTACCCGAGGCAGGTCCGGGAGGCCCCTGTC<br>CCTGCTGCTCGCCTTACTTTGCGCCCTGAGGGCCAAAGTCTGCG<br>GCGCCTCCGGCCAATTCGAGCTGGAGATCCTCAGCATGCAGAAC<br>GTGAACGGCGAGCTGCAAAACGGGAACTGCTGCGGGGGAGCCC<br>GCAACCCCGGCGACCGGAAGTGCACCAGGGACGAGTGCGACAC<br>CTACTTCAAGGTGTGCCTCAAGGAGTATCAGTCAAGGGTGACCG<br>CCGGAGGCCCCTGTAGCTTCGGCTCCGGGTCGACCCCCGTGATA<br>GGCGGAAACACCTTCAACCTGAAGGCCAGCAGGGGGAACGACA<br>GGAATAGGATCGTGCTCCCCTTCTCGTTCGCCTGGCCCAGGAGC<br>TACACCCTCCTCGTGGAGGCCTGGGACAGCAGCAACGATACGGT<br>GCAGCCCGACTCCATCATCGAGAAGGCCAGCCACTCCGGCATGA<br>TCAACCCCAGCCGCCAGTGGCAGACCCTGAAGCAAAACACGGG<br>CGTGGCACACTTCGAGTACCAGATAAGGGTCACTTGCGACGACT<br>ACTACTACGGGTTCGGGTGCAACAAGTTTTGCAGGCCCCGGGAC<br>GACTTCTTCGGACACTATGCCTGCGACCAGAACGGCAACAAGAC<br>CTGTATGGAGGGTTGGATGGGCCCCGAATGCAATCGCGCCATTT<br>GCCGGCAGGGGTGCAGCCCTAAGCACGGAAGCTGTAAGCTCCC<br>CGGCGACTGCCGCTGCCAGTACGGCTGGCAGGGACTGTACTGTG<br>ACAAGTGTATCCCCCACCCCGGCTGCGTGCACGGCATCTGCAAT<br>GAGCCTTGGCAGTGCCTGTGCGAGACCAATTGGGGCGGCCAGCT<br>GTGCGACAAGGACCTGAACTACTGCGGCACCCACCAGCCCTGCC<br>TGAACGGTGGGACCTGCAGCAACACCGGGCCAGACAAGTACCA<br>GTGCAGCTGCCCCGAGGGCTATAGCGGGCCCAATTGCGAGATCG<br>CCGAGCACGCCTGCCTGTCCGACCCCTGTCACAACCGGGGCTCC<br>TGCAAGGAGACCTCCCTGGGGTTTGAGTGCGAGTGCTCCCCCGG<br>TTGGACCGGCCCCACCTGCTCCACCAACATCGACGACTGCTCCC<br>CCAACAATTGCAGCCACGGCGGCACATGCCAGGATCTGGTGAA<br>CGGCTTCAAGTGTGTGTGTCCCCCCCAGTGGACCGGCAAGACCT<br>GCCAGCTGGACGCGAACGAGTGCGAAGCAAAGCCCTGCGTGAA<br>CGCCAAGTCCTGCAAAAACCTGATCGCCAGCTATTACTGCGACT<br>GCCTGCCCGGCTGGATGGGGCAGAACTGTGACATAAACATAAA<br>CGACTGCCTCGGCCAGTGCCAGAATGACGCGAGCTGCCGGGAC<br>CTCGTGAACGGCTACCGATGCATCTGCCCCCCGGGCTACGCCGG<br>CGACCATTGCGAACGGGATATCGACGAGTGTGCCAGCAACCCCT<br>GCCTGAACGGGGGGCACTGCCAGAACGAGATAAACAGGTTCCA<br>GTGCCTGTGCCCCACCGGCTTCAGCGGCAACCTGTGCCAACTCG<br>ACATCGACTACTGCGAGCCCAACCCCTGCCAAAACGGTGCCCAA<br>TGCTACAACCGGGCCTCGGACTACTTTTGCAAGTGCCCGGAGGA<br>CTATGAGGGCAAGAATTGTTCCCACCTCAAGGACCACTGCCGGA<br>CCACCCCCTGCGAGGTGATCGACTCCTGCACCGTGGCCATGGCT<br>AGTAACGATACCCCCGAGGGCGTTAGGTACATCTCCTCCAACGT<br>GTGCGGCCCCCACGGGAAGTGCAAGTCGCAGAGCGGCGGCAAG<br>TTCACCTGCGACTGCAATAAGGGCTTCACCGGTACCTACTGCCA<br>CGAGAACATCAACGACTGCGAGAGCAATCCCTGCCGGAACGGG<br>GGTACCTGCATCGACGGCGTGAACTCCTACAAGTGTATCTGCTC<br>AGATGGCTGGGAAGGCGCGTACTGTGAGACCAACATAAACGAC<br>TGTAGCCAGAACCCCTGTCATAACGGGGGCACCTGCAGGGACCT<br>GGTGAACGACTTCTACTGCGACTGCAAGAACGGGTGGAAAGGC<br>AAAACTTGCCACTCCAGGGACTCCCAGTGCGATGAGGCCACCTG<br>CAATAACGGCGGCACGTGCTACGACGAGGGGGACGCCTTCAAG<br>TGCATGTGCCCCGGGGGCTGGGAGGGGACCACCTGCAACATCG<br>CCAGGAACAGCTCCTGCCTGCCCAACCCATGCCACAATGGAGGC<br>ACCTGCGTAGTGAATGGCGAGTCCTTCACCTGTGTGTGCAAGGA<br>GGGCTGGGAGGGGCCCATCTGCGCCCAGAACACCAACGACTGC<br>AGCCCACACCCGTGCTACAACTCCGGCACCTGCGTCGACGGCGA<br>CAACTGGTACAGGTGCGAGTGCGCCCCCGGCTTCGCGGGCCCGG<br>ACTGCCGGATTAATATCAACGAGTGCCAGAGCAGCCCCTGCGCC<br>TTCGGGGCCACCTGCGTCGACGAAATCAACGGGTACCGGTGCGT<br>GTGCCCCCCCGGCCACAGCGGGGCAAAGTGCCAGGAAGTCAGC<br>GGCAGGCCCTGCATCACCATGGGCAGCGTCATTCCCGATGGCGC<br>AAAGTGGGACGACGACTGCAACACTTGCCAGTGCCTGAATGGC<br>AGGATCGCCTGCAGCAAGGTGTGGTGCGGCCCAAGGCCCTGCCT<br>GCTGCACAAAGGCCACAGCGAATGCCCAAGCGGTCAGAGCTGC<br>ATCCCCATCCTGGATGACCAGTGCTTCGTGCACCCCTGCACCGG<br>GGTCGGTGAGTGTAGGAGCAGCAGCCTGCAGCCCGTGAAGACC<br>AAGTGCACCTCCGATTCCTACTACCAGGACAATTGCGCCAACAT<br>AACTTTTACCTTCAACAAGGAGATGATGAGCCCCGGCCTCACCA<br>CGGAGCACATCTGCAGCGAGCTGCGCAACCTCAACATCCTGAAG<br>AACGTGAGCGCCGAGTACAGCATTTACATCGCCTGCGAGCCCAG<br>CCCCTCCGCCAACAACGAGATCCACGTGGCCATCAGCGCCGAGG<br>ACATAAGGGATGACGGGAATCCCATCAAGGAGATCACCGACAA<br>GATCATCGACCTGGTGTCCAAGCGGGACGGCAATAGCAGCCTG<br>ATCGCCGCCGTCGCGGAGGTGCGGGTGCAGAGGCGCCCGCTGA<br>AGAACCGGACCGACTTCCTCGTGCCCCTGCTGAGCAGCGTGCTG<br>ACGGTGGCCTGGATCTGCTGCCTGGTGACAGCCTTCTACTGGTG |

TABLE 2-continued

| Sequence optimized sequences for human JAG1 | | |
|---|---|---|
| SEQ ID NO | NAME | SEQUENCE |
| | | CCTGCGGAAGAGGAGGAAGCCCGGGAGCCACACCCATAGCGCG<br>TCCGAGGACAACACGACAAACAACGTCAGAGAGCAGCTGAACC<br>AAATCAAGAATCCCATCGAAAAACACGGCGCCAACACCGTGCC<br>CATCAAAGATTACGAGAACAAGAACAGCAAGATGAGCAAAATC<br>CGGACCCACAACTCGGAGGTGGAGGAGGACGACATGGACAAGC<br>ACCAACAGAAGGCCCGCTTTGCCAAGCAGCCCGCCTACACCCTG<br>GTGGACCGGGAGGAAAAGCCGCCGAATGGTACACCGACCAAGC<br>ATCCCAATTGGACAAACAAGCAGGATAACAGGGACCTGGAAAG<br>CGCCCAGAGCCTGAACCGGATGGAGTACATCGTA |
| 14 | JAG1-CO04 | ATGAGGAGCCCCAGGACCAGGGGGAGGAGCGGGAGGCCGCTGA<br>GCCTGCTCCTGGCCCTGCTGTGTGCCCTGCGCGCCAAGGTGTGC<br>GGCGCGTCCGGACAGTTTGAGCTGGAGATCCTGTCCATGCAGAA<br>CGTGAACGGCGAGCTCCAGAACGGGAACTGCTGCGGGGGCGCA<br>AGGAACCCCGGTGACAGGAAGTGCACCCGCGACGAGTGCGACA<br>CGTACTTTAAGGTGTGCCTGAAAGAGTACCAGAGCAGGGTGACT<br>GCCGGCGGACCCTGCTCGTTTGGAAGCGGCAGCACTCCTGTGAT<br>CGGTGGCAACACCTTCAATCTGAAGGCCTCCAGGGGGAACGAT<br>AGGAACAGGATCGTGCTGCCATTCAGCTTTGCCTGGCCCCGGTC<br>ATACACCCTGCTGGTGGAGGCCTGGGACTCCAGCAACGACACCG<br>TGCAGCCCGACTCCATCATAGAGAAGGCGAGCCACAGCGGCAT<br>GATCAACCCCTCCAGGCAGTGGCAGACCCTCAAGCAGAACACC<br>GGCGTCGCCCACTTCGAATACCAGATCAGGGTCACGTGCGACGA<br>CTACTACTACGGCTTTGGCTGCAATAAGTTCTGCAGGCCCCGGG<br>ACGACTTCTTCGGGCACTACGCCTGCGACCAGAACGGGAACAA<br>AACCTGTATGGAGGGGTGGATGGGCCCCGAATGCAACCGAGCC<br>ATCTGCCGCCAGGGGTGCTCCCCCAAGCACGGCTCCTGTAAACT<br>CCCCGGCGATTGCAGGTGTCAGTACGGCTGGCAGGGTCTCTACT<br>GCGACAAGTGCATCCCGCACCCCGGCTGCGTCCACGGCATCTGT<br>AATGAGCCCTGGCAATGCCTGTGCGAGACCAACTGGGGCGGCC<br>AGCTGTGCGACAAGGACCTCAATTATTGTGGCACCCACCAGCCA<br>TGCCTGAATGGTGGCACCTGCAGCAACACAGGCCCAGACAAGT<br>ACCAGTGCAGCTGTCCCGAGGGCTACTCGGGCCCCAACTGCGAA<br>ATCGCCGAGCACGCTTGCCTGAGCGACCCCTGTCACAACAGGGG<br>CAGCTGCAAGGAAACCAGCCTGGGGTTCGAGTGCGAGTGCAGC<br>CCCGGGTGGACCGGCCCCACCTGCAGCACCAACATCGACGACTG<br>CAGCCCCAACAACTGTAGCCATGGCGGCACCTGCCAGGATCTGG<br>TCAACGGCTTCAAGTGCGTGTGTCCCCCCCAGTGGACCGGCAAG<br>ACCTGCCAGCTCGACGCCAACGAGTGTGAAGCAAAGCCCTGCGT<br>GAATGCCAAGTCCTGCAAGAACCTGATAGCCTCCTACTACTGCG<br>ACTGCCTGCCCGGCTGGATGGGCCAGAACTGTGACATCAACATC<br>AACGACTGCCTGGGGCAGTGTCAGAATGACGCCAGCTGCCGCG<br>ACCTGGTGAATGGCTATAGGTGCATCTGCCCCCCCGGATACGCC<br>GGCGACCACTGCGAGAGGGATATCGATGAGTGCGCCAGCAACC<br>CTTGCCTGAACGGCGGGCACTGCCAGAACGAGATTAACAGGTTC<br>CAGTGCCTGTGCCCCACCGGCTTCAGCGGCAATCTGTGCCAGCT<br>GGATATCGACTACTGCGAGCCCAACCCGTGCCAGAACGGCGCCC<br>AGTGCTACAACAGGGCCTCCGACTACTTCTGTAAGTGTCCCGAG<br>GACTATGAGGGCAAGAACTGTTCCCACCTGAAAGACCACTGCA<br>GGACCACCCCCTGCGAGGTGATCGACTCGTGCACCGTGGCCATG<br>GCGAGCAATGACACCCCGGAAGGCGTGCGCTATATCAGCAGCA<br>ATGTGTGCGGGCCCCACGGCAAGTGCAAGAGCCAGAGCGGCGG<br>GAAGTTCACCTGCGACTGCAACAAGGGCTTCACCGGCACGTACT<br>GCCACGAGAACATCAACGATTGCGAGTCCAACCCCTGCCGGAA<br>CGGCGGCACCTGCATAGATGGAGTGAACTCCTATAAGTGCATCT<br>GCTCCGATGGGTGGGAGGGCGCCTACTGTGAAACCAACATCAA<br>CGACTGCAGCCAGAACCCCTGCCATAATGGTGGCACGTGCCGGG<br>ACCTGGTTAATGACTTCTACTGCGACTGCAAGAACGGCTGGAAG<br>GGCAAGACCTGCCACAGCAGAGATAGCCAGTGCGACGAGGCCA<br>CGTGCAACAATGGCGGGACCTGCTACGACGAGGGGGACGCCTT<br>CAAATGCATGTGCCCCGGCGGATGGGAGGGGACCACCTGCAAC<br>ATCGCCAGGAACTCCAGCTGCCTGCCCAACCCGTGCCATAACGG<br>TGGCACCTGCGTGGTGAACGGCGAAAGCTTCACCTGCGTGTGCA<br>AGGAGGGCTGGGAGGGCCCCATCTGCGCCCAGAACACCAATGA<br>CTGCTCCCCCCACCCATGCTACAACTCCGGGACCTGTGTGGACG<br>GCGACAACTGGTATAGGTGCGAGTGTGCCCCCGGCTTCGCCGGC<br>CCCGACTGCAGGATCAACATCAACGAATGTCAGAGCTCCCCCTG<br>CGCCTTTGGCGCCACATGTGTCGATGAGATTAACGGCTACCGGT<br>GCGTCTGCCCCCCCGGCCACAGCGGCGCGAAGTGCCAGGAAGT<br>CTCCGGCAGGCCCTGTATCACCATGGGCAGCGTGATCCCCGACG<br>GCGCCAAGTGGGACGACGACTGCAACACCTGTCAATGCCTGAAT<br>GGCAGGATCGCCTGCAGCAAAGTCTGGTGCGGGCCCCGGCCCTG<br>CCTGCTGCACAAGGGCCACAGCGAGTGCCCTTCCGGCCAGAGCT<br>GCATCCCGATCCTGGACGATCAGTGTTTTGTCCATCCATGCACC<br>GGCGTGGGCGAGTGTAGGTCGAGCAGCCTGCAGCCCGTGAAAA |

TABLE 2-continued

Sequence optimized sequences for human JAG1

| SEQ ID NO | NAME | SEQUENCE |
|---|---|---|
| | | CAAAGTGCACCAGCGACAGCTACTACCAGGATAACTGTGCCAA<br>CATCACCTTTACCTTCAACAAGGAGATGATGAGCCCCGGACTGA<br>CCACCGAGCATATCTGTTCAGAGCTGAGGAACCTGAACATCCTC<br>AAGAACGTCAGCGCCGAGTACAGCATCTACATCGCCTGCGAGCC<br>CAGCCCCTCCGCCAACAACGAAATCCACGTGGCCATAAGCGCCG<br>AGGACATCAGGGACGACGGCAATCCGATCAAGGAGATAACCGA<br>CAAGATCATCGACCTCGTGAGTAAGAGGGACGGGAACAGTAGC<br>CTCATCGCCGCCGTCGCCGAGGTGAGGGTGCAGCGGAGGCCCCT<br>GAAGAACAGGACCGATTTTCTGGTCCCCCTGCTGAGCTCCGTGC<br>TGACCGTGGCCTGGATCTGCTGCCTGGTGACGGCGTTCTACTGG<br>TGCCTCCGGAAACGACGGAAGCCCGGGAGCCATACCCACTCCG<br>CCAGCGAGGACAACACCACCAATAACGTGAGGGAGCAGCTGAA<br>TCAGATCAAGAATCCGATCGAGAAGCACGGCGCCAACACCGTG<br>CCGATCAAAGACTACGAGAACAAGAATTCCAAGATGAGCAAGA<br>TCAGGACCCACAACTCCGAGGTGGAGGAAGATGACATGGACAA<br>GCACCAGCAGAAAGCCAGGTTTGCCAAGCAGCCCGCCTATACCC<br>TGGTGGACAGGGAGGAGAAACCCCCGAATGGCACCCCCACCAA<br>ACACCCAAACTGGACCAACAAGCAGGACAACAGGGATCTGGAG<br>AGCGCCCAGAGCCTCAACCGTATGGAGTACATCGTG |
| 15 | JAG1-CO05 | ATGAGGTCACCCCGGACCCGGGGACGCTCCGGCAGGCCCCTGA<br>GCCTGCTGCTGGCCCTGCTGTGCGCCCTCAGGGCCAAGGTCTGC<br>GGCGCCTCCGGTCAGTTCGAACTCGAGATCCTGAGCATGCAGAA<br>CGTGAACGGTGAACTGCAGAACGGCAACTGCTGCGGCGGCGCC<br>AGGAATCCCGGCGACCGAAAGTGCACCAGGGACGAGTGCGACA<br>CCTACTTTAAGGTGTGCCTAAAGGAGTACCAGAGCCGGGTGACG<br>GCCGGCGGCCCCTGTTCCTTCGGCAGCGGCAGCACGCCCGTGAT<br>CGGCGGCAACACCTTCAACCTCAAGGCCTCGCGCGGCAACGATC<br>GGAACAGGATCGTGCTGCCGTTTTCCTTTGCCTGGCCCAGGTCG<br>TACACCCTGCTGGTGGAGGCCTGGGACAGCTCCAATGACACCGT<br>GCAGCCAGACTCCATAATCGAGAAGGCCAGCCACAGCGGGATG<br>ATTAATCCAAGCAGGCAGTGGCAAACCCTGAAGCAGAACACCG<br>GAGTGGCCCATTTCGAGTACCAGATCAGGGTGACCTGCGACGAC<br>TACTACTACGGCTTCGGATGCAACAAGTTCTGCAGGCCCCGGGA<br>CGACTTCTTCGGCCATTACGCCTGCGACCAGAACGGCAACAAGA<br>CCTGCATGGAGGGTTGGATGGGCCCCGAATGCAATAGGGCCATC<br>TGCAGGCAAGGCTGTTCCCCCAAACACGGGAGCTGTAAACTCCC<br>CGGCGACTGCCGATGCCAGTACGGGTGGCAAGGCCTCTACTGCG<br>ACAAGTGCATCCCCCATCCCGGCTGCGTGCATGGCATTTGCAAC<br>GAACCCTGGCAATGCCTCTGCGAGACCAACTGGGGGGGCCAGC<br>TCTGCGACAAGGATCTGAACTACTGCGGCACACACCAGCCTTGC<br>CTGAACGGAGGGACCTGCAGTAATACCGGCCCCGACAAGTACC<br>AGTGCAGCTGCCCCGAGGGCTATAGCGGCCCCAACTGCGAAATT<br>GCCGAGCACGCCTGCCTGAGCGACCCCTGTCACAACAGGGGCA<br>GCTGCAAGGAGACCAGTCTGGGCTTCGAGTGCGAGTGCAGCCC<br>AGGCTGGACGGGCCCCACCTGCTCCACCAACATCGACGACTGCT<br>CCCCCAACAATTGCAGCCACGGCGGCACCTGCCAAGATCTCGTG<br>AACGGCTTCAAGTGCGTGTGTCCGCCGCAGTGGACCGGGAAAA<br>CCTGCCAACTGGACGCCAACGAGTGTGAGGCAAAGCCCTGCGT<br>GAACGCGAAGTCCTGTAAGAACCTGATCGCCAGCTACTATTGCG<br>ACTGCCTGCCGGGCTGGATGGGGCAGAACTGTGACATCAACATC<br>AACGATTGCCTGGGCCAGTGTCAGAACGACGCCAGCTGCAGGG<br>ACCTGGTCAACGGCTACAGGTGCATCTGTCCCCCGGGGTATGCC<br>GGGGACCACTGCGAACGAGATATCGACGAGTGCGCCTCGAACC<br>CTTGCCTCAATGGCGGCCACTGCCAGAACGAGATCAACAGGTTC<br>CAGTGCCTGTGCCCCACCGGCTTCAGCGGCAATCTGTGCCAGCT<br>GGACATCGACTATTGTGAACCCAACCCGTGCCAGAACGGCGCCC<br>AGTGCTACAACCGCGCCTCCGACTACTTCTGCAAGTGCCCGGAG<br>GACTACGAGGGCAAGAACTGCAGCCATCTGAAGGACCACTGTA<br>GAACCACGCCCTGCGAGGTGATCGACTCCTGCACCGTCGCCATG<br>GCCTCAAACGACACCCCCGAGGGAGTGCGCTACATCAGCTCGA<br>ACGTGTGCGGCCCCCATGGAAAATGCAAGAGCCAGTCCGGGGG<br>CAAGTTCACCTGCGACTGCAACAAGGGCTTCACCGGCACGTATT<br>GCCATGAGAACATCAATGACTGCGAGAGCAACCCGTGCCGTAA<br>CGGGGGCACCTGTATCGATGGCGTGAACAGCTACAAGTGCATCT<br>GTAGCGACGGCTGGGAGGGCGCCTATTGCGAAACCAACATCAA<br>CGACTGTTCCCAGAACCCATGCCACAACGGGGGCACCTGTAGGG<br>ACCTGGTCAACGACTTTTACTGTGACTGCAAGAACGGTTGGAAA<br>GGCAAGACCTGCCACTCGAGGGACAGCCAGTGTGACGAGGCCA<br>CGTGCAACAATGGCGGCACCTGTTACGACGAGGGCGACGCCTTT<br>AAGTGCATGTGTCCCGGGGGTTGGGAGGGTACCACCTGTAACAT<br>CGCCAGGAACTCAAGCTGCCTGCCCAATCCCTGCCATAACGGTG<br>GGACCTGCGTGGTGAACGGCGAAAGCTTCACCTGCGTGTGCAAG<br>GAGGGCTGGGAGGGCCCCATCTGTGCCCAGAACACCAATGACT<br>GCAGCCCCCACCCCTGTTACAACAGCGGGACCTGCGTGGATGGT |

TABLE 2-continued

Sequence optimized sequences for human JAG1

| SEQ ID NO | NAME | SEQUENCE |
|---|---|---|
| | | GACAACTGGTACAGGTGTGAGTGCGCCCCCGGGTTTGCCGGCCC<br>CGACTGCAGGATCAACATCAACGAGTGCCAGAGCAGCCCCTGT<br>GCCTTCGGCGCCACCTGCGTGGACGAGATCAACGGGTACCGGTG<br>CGTGTGCCCCCCCGGCCACTCCGGCGCCAAGTGCCAGGAGGTGT<br>CCGGCAGGCCCTGCATCACCATGGGCAGCGTCATCCCCGACGGC<br>GCCAAATGGGACGACGACTGCAACACCTGTCAGTGCCTGAACG<br>GCAGGATCGCCTGCTCCAAGGTTTGGTGCGGGCCCAGGCCCTGC<br>CTGCTGCACAAGGGACATAGCGAATGCCCCAGCGGCCAGAGCT<br>GCATCCCCATCCTGGACGACCAGTGCTTCGTGCATCCCTGCACC<br>GGGGTGGGCGAGTGCCGGAGCTCCTCGCTGCAACCCGTCAAGA<br>CCAAGTGCACCTCGGACAGCTATTACCAGGACAACTGCGCCAAC<br>ATCACCTTCACCTTCAACAAGGAAATGATGAGCCCCGGCCTGAC<br>CACCGAGCATATCTGCAGCGAGCTGCGGAACCTGAACATACTGA<br>AGAACGTTAGCGCCGAGTACTCCATCTACATCGCCTGCGAGCCC<br>AGCCCGAGCGCGAATAATGAGATCCACGTCGCCATCAGCGCCG<br>AGGACATCCGGGACGACGGCAACCCCATCAAGGAGATCACCGA<br>CAAGATCATCGACCTGGTCAGCAAGCGTGACGGCAACTCCAGCC<br>TGATCGCCGCGGTGGCTGAGGTGCGAGTCCAGAGGAGGCCCCT<br>GAAGAACAGGACGGACTTCCTCGTCCCTCTGCTGAGCAGCGTGC<br>TGACCGTGGCCTGGATCTGTTGCCTGGTGACCGCCTTTTACTGGT<br>GCCTGCGAAAGAGGAGGAAGCCGGGCAGCCACACCCACAGCGC<br>CTCAGAAGACAACACCACAAACAACGTCCGCGAGCAGCTCAAC<br>CAGATCAAAAACCCCATCGAAAAGCACGGCGCCAACACCGTGC<br>CCATCAAGGACTACGAGAACAAGAATAGCAAGATGAGCAAGAT<br>CCGCACTCACAACAGCGAGGTGGAGGAGGACGACATGGACAAG<br>CACCAGCAGAAGGCCAGGTTTGCCAAGCAGCCCGCCTACACCCT<br>GGTGGACCGGGAGGAGAAGCCGCCCAATGGCACCCCCACGAAG<br>CACCCGAACTGGACCAACAAACAGGACAACAGGGACCTGGAGA<br>GCGCCCAGAGCCTGAACCGCATGGAGTACATCGTG |
| 16 | JAG1-CO06 | ATGCGGTCCCCCAGGACCAGGGGGCGCAGCGGGAGGCCCCTGA<br>GCCTGCTGCTGGCCTTACTGTGTGCCCTGAGGGCCAAGGTGTGC<br>GGCGCCAGCGGGCAGTTCGAGCTGGAGATACTGTCCATGCAAA<br>ACGTGAACGGCGAACTGCAGAATGGGAATTGCTGCGGTGGCGC<br>CAGGAACCCTGGGGACCGCAAGTGTACCCGGGACGAGTGCGAC<br>ACCTACTTCAAGGTGTGTCTCAAGGAATATCAGTCCCGCGTGAC<br>CGCCGGGGGCCCCTGCAGCTTCGGCTCAGGCAGCACCCCAGTCA<br>TCGGGGGCAACACCTTCAACCTGAAGGCCAGCCGTGGCAACGA<br>CAGGAACAGGATAGTGCTGCCCTTCTCCTTCGCGTGGCCCAGGT<br>CCTACACCCTGCTGGTGGAGGCGTGGGATAGCTCGAATGATACC<br>GTCCAGCCCGACTCCATCATCGAGAAAGCCTCCCACTCCGGTAT<br>GATCAATCCAAGCAGGCAGTGGCAGACCCTGAAGCAGAACACG<br>GGCGTGGCCCACTTTGAGTACCAGATCAGGGTCACCTGCGACGA<br>CTACTACTACGGCTTCGGCTGTAATAAATTTTGCCGGCCTCGGG<br>ACGACTTCTTCGGCCACTACGCCTGCGACCAGAACGGCAATAAG<br>ACGTGTATGGAGGGCTGGATGGGCCCGGAGTGTAATAGGGCCA<br>TCTGCCGACAGGGGTGCAGCCCCAAGCACGGCAGCTGCAAGCT<br>GCCCGGCGACTGCAGGTGTCAGTACGGCTGGCAAGGACTGTATT<br>GTGACAAGTGCATTCCCCATCCGGGCTGTGTGCACGGAATCTGC<br>AATGAGCCCTGGCAGTGCCTGTGCGAGACCAACTGGGGCGGCC<br>AGCTGTGTGACAAGGATCTGAACTACTGTGGCACCCACCAGCCC<br>TGCCTGAACGGCGGACCTGCTCCAATACCGGGCCCGACAAGTA<br>CCAGTGTTCCTGCCCCGAGGGCTACAGCGGTCCAAACTGCGAGA<br>TCGCCGAGCACGCCTGCCTGAGCGACCCCTGCCATAACAGGGGC<br>TCCTGCAAGGAGACCAGCCTGGGCTTCGAATGCGAGTGCTCCCC<br>CGGGTGGACCGGCCCCACCTGCAGTACCAACATCGATGACTGCA<br>GCCCCAATAACTGTTCCCACGGCGGCACCTGCCAGGACCTGGTG<br>AACGGCTTCAAATGCGTCTGTCCGCCCCAGTGGACCGGAAAGAC<br>CTGTCAGCTCGACGCAAACGAGTGCGAGGCCAAGCCCTGCGTG<br>AACGCCAAGAGCTGCAAGAATCTGATCGCCTCCTACTACTGCGA<br>TTGTCTGCCCGGATGGATGGGCCAAAACTGCGACATCAACATCA<br>ACGATTGTCTGGGGCAGTGCCAGAACGACGCCAGCTGCAGGGA<br>CCTGGTCAACGGCTACAGGTGCATCTGCCCCCCCGGCTATGCCG<br>GAGACCATTGCGAGCGAGACATCGACGAGTGTGCCTCGAACCC<br>CTGCCTGAACGGGGGGCACTGCCAGAACGAAATCAACAGGTTC<br>CAATGCCTCTGCCCCACCGGGTTCAGCGGCAACCTGTGCCAGCT<br>GGACATCGACTATTGCGAGCCCAACCCCTGCCAGAACGGGGCG<br>CAGTGTTATAACCGGGCCTCGGACTACTTCTGTAAGTGTCCCGA<br>GGACTACGAGGGCAAAAACTGCTCCCACCTGAAGGACCACTGC<br>CGTACCACACCCTGCGAAGTCATCGACTCCTGCACCGTGGCCAT<br>GGCCAGCAACGACACCCCCGAGGGAGTGCGGTACATCAGCAGC<br>AACGTGTGCGGGCCGCATGGCAAGTGTAAGTCCCAGAGCGGGG<br>GCAAGTTTACATGTGACTGTAACAAGGGCTTCACCGGCACATAC<br>TGCCACGAGAACATCAACGATTGCGAGAGCAACCCCTGCCGGA<br>ATGGGGGCACCTGCATCGACGGGGTGAACAGCTATAAGTGTATC |

TABLE 2-continued

Sequence optimized sequences for human JAG1

| SEQ ID NO | NAME | SEQUENCE |
|---|---|---|
| | | TGCTCCGATGGCTGGGAGGGCGCCTACTGCGAGACTAACATCAA<br>TGACTGCTCGCAGAACCCGTGCCACAACGGGGGAACCTGCAGG<br>GATCTCGTGAACGACTTCTACTGCGACTGCAAGAACGGGTGGAA<br>GGGGAAGACCTGCCACAGCCGCGACTCCCAGTGCGACGAGGCC<br>ACCTGCAACAATGGGGGCACCTGCTACGACGAGGGCGACGCCT<br>TCAAGTGCATGTGCCCCGGCGGGTGGGAGGGCACCACCTGCAA<br>CATCGCCCGGAACTCCAGCTGCCTGCCCAATCCGTGTCACAATG<br>GGGGCACCTGCGTGGTGAACGGCGAGTCGTTCACGTGCGTGTGC<br>AAGGAAGGCTGGGAGGGACCGATCTGCGCCCAAAATACCAACG<br>ACTGTAGCCCCCACCCCTGTTATAACAGCGGCACCTGCGTCGAC<br>GGGGACAATTGGTACCGGTGCGAGTGCGCCCCCGGCTTCGCCGG<br>CCCCGACTGCCGAATCAACATCAACGAATGTCAAAGCTCACCCT<br>GTGCCTTCGGGGCAACCTGTGTGGACGAGATCAACGGCTACCGG<br>TGTGTGTGCCCCCCGGGACACTCCGGGGCCAAGTGCCAGGAGGT<br>GAGCGGGCGACCATGCATCACCATGGGCTCCGTGATCCCCGACG<br>GCGCCAAGTGGGACGACGACTGCAACACCTGCCAGTGCCTGAA<br>CGGCAGGATCGCCTGCTCCAAGGTGTGGTGTGGCCCCCGGCCCT<br>GTCTCCTGCACAAAGGTCACAGCGAGTGCCCCAGCGGCCAGAG<br>CTGCATCCCGATCCTTGACGACCAGTGCTTCGTGCACCCGTGTA<br>CAGGCGTAGGGGAGTGCAGGAGCTCCTCGCTCCAGCCCGTGAA<br>AACCAAGTGTACCAGCGACTCATACTATCAGGACAACTGTGCCA<br>ATATCACCTTTACCTTCAACAAGGAAATGATGAGCCCCGGGCTG<br>ACCACCGAGCACATCTGCAGCGAGCTGCGGAACCTTAACATTCT<br>GAAAAATGTGTCCGCCGAGTACAGCATATACATCGCCTGCGAGC<br>CGAGCCCTAGCGCCAACAATGAGATACACGTGGCCATCAGCGCT<br>GAGGACATCAGGGATGACGGCAACCCGATCAAGGAGATCACCG<br>ACAAGATAATAGACCTCGTCAGCAAAAGGGACGGCAACAGCAG<br>CCTGATCGCCGCCGTCGCCGAGGTGAGGGTGCAGCGCCGGCCCC<br>TGAAGAACAGGACCGACTTCCTGGTGCCCCTCCTGAGCTCCGTG<br>CTGACCGTGGCCTGGATCTGCTGCCTGGTGACCGCCTTCTACTG<br>GTGTCTGAGGAAAAGGAGGAAGCCTGGCAGCCACACCCATAGC<br>GCCTCCGAGGACAATACCACCAACAACGTCAGGGAACAGCTCA<br>ACCAAATCAAGAACCCCATCGAGAAGCACGGCGCCAATACCGT<br>GCCCATCAAGGATTACGAGAACAAGAATAGCAAGATGTCCAAG<br>ATCCGCACACATAATTCCGAGGTCGAGGAAGACGACATGGATA<br>AGCACCAGCAGAAGGCCAGATTCGCCAAGCAGCCCGCCTACAC<br>CCTGGTGGACAGGGAGGAGAAGCCCCCCAACGGCACACCCACC<br>AAGCATCCCAACTGGACCAACAAGCAGGACAACAGGGACCTGG<br>AGAGCGCCCAGTCCCTGAACCGTATGGAGTACATCGTC |
| 17 | JAG1-CO07 | ATGAGGAGCCCCAGGACAAGGGGCCGGAGCGGCAGGCCCCTGA<br>GCCTGCTGCTCGCCCTCCTCTGTGCCCTGCGCGCCAAAGTGTGC<br>GGGGCCTCAGGCCAGTTCGAGCTCGAGATCCTGTCCATGCAAAA<br>CGTGAACGGCGAACTGCAGAACGGAAATTGCTGCGGTGGCGCC<br>CGTAACCCCGGCGACCGCAAGTGCACCAGGGACGAGTGCGACA<br>CCTACTTCAAGGTGTGTCTGAAGGAGTACCAGAGCAGGGTCACC<br>GCCGGCGGCCCCTGCAGCTTTGGCTCCGGCAGCACCCCCGTGAT<br>CGGCGGCAACACCTTCAACCTGAAGGCTAGCCGCGGCAACGAC<br>AGGAACAGGATCGTGCTTCCATTTAGCTTCGCCTGGCCCAGGAG<br>CTACACCCTGCTTGTGGAGGCCTGGGACAGCTCCAACGACACCG<br>TGCAGCCCGACAGCATCATCGAGAAGGCCAGCCACTCCGGCAT<br>GATCAACCCCAGCCGGCAGTGGCAGACCCTGAAGCAGAACACC<br>GGCGTCGCGCACTTCGAGTACCAGATCAGGGTGACATGTGACGA<br>CTATTACTATGGCTTTGGATGTAACAAGTTCTGCAGGCCCAGAG<br>ACGACTTCTTCGGCCACTACGCCTGCGACCAGAACGGAAATAAG<br>ACCTGTATGGAAGGCTGGATGGGGCCCGAGTGCAACCGAGCCA<br>TCTGCAGGCAAGGCTGCAGCCCCAAGCACGGCAGCTGCAAGCT<br>GCCCGGGGACTGCCGGTGCCAGTACGGCTGGCAGGGCTTGTATT<br>GCGACAAGTGCATCCCGCACCCCGGCTGCGTGCACGGGATCTGC<br>AACGAGCCCTGGCAGTGCCTGTGCGAGACGAACTGGGGCGGCC<br>AGCTGTGCGACAAGGACCTGAACTACTGCGGGACGCATCAACC<br>CTGTCTCAACGGCGGTACCTGCAGCAATACCGGCCCCGACAAGT<br>ACCAGTGCTCTTGCCCCGAGGGCTATAGCGGGCCCAACTGTGAG<br>ATCGCCGAGCACGCTTGCCTGTCCGACCCCTGCCACAACCGGGG<br>CTCCTGCAAGGAGACCTCCCTGGGCTTCGAGTGCGAATGCAGCC<br>CCGGGTGGACCGGTCCCACGTGCAGCACCAACATCGATGACTGT<br>AGCCCCAACAACTGCAGCCACGGCGGCACGTGCCAGGACCTCG<br>TGAACGGCTTCAAGTGCGTGTGCCCCCCCCAGTGGACCGGCAAG<br>ACCTGCCAGCTCGACGCCAATGAGTGCGAAGCCAAGCCCTGCGT<br>CAACGCCAAGTCCTGCAAGAACCTGATCGCCAGTTACTACTGCG<br>ACTGTCTGCCCGGATGGATGGGCCAGAATTGCGACATCAACATC<br>AATGACTGCCTGGGCCAGTGCCAGAATGACGCGTCCTGTAGGGA<br>TCTGGTGAACGGGTACAGGTGCATATGTCCCCCCGGCTATGCCG<br>GGGATCACTGCGAGAGGGATATCGATGAGTGCGCCAGCAACCC<br>CTGTCTGAACGGTGGCCACTGCCAGAACGAGATTAACAGGTTCC |

TABLE 2-continued

Sequence optimized sequences for human JAG1

| SEQ ID NO | NAME | SEQUENCE |
| --- | --- | --- |
| | | AGTGCCTGTGCCCCACCGGCTTCAGCGGCAACCTGTGCCAGCTG<br>GATATCGACTACTGTGAGCCCAACCCGTGCCAGAACGGCGCCCA<br>GTGCTACAACCGAGCCAGCGATTATTTTTGCAAATGTCCCGAGG<br>ATTACGAAGGGAAGAATTGCAGCCACCTGAAGGACCATTGCAG<br>GACCACCCCCTGCGAAGTGATCGACAGCTGCACCGTGGCCATGG<br>CCTCGAATGACACGCCCGAGGGAGTGAGGTACATCAGTAGCAA<br>TGTGTGCGGCCCCCATGGGAAGTGCAAGAGCCAGTCGGGCGGA<br>AAGTTTACCTGCGACTGTAACAAGGGCTTCACCGGGACCTACTG<br>TCACGAAAACATCAACGACTGCGAGTCCAACCCGTGTAGGAAC<br>GGCGGGACCTGCATAGACGGGGTGAATAGCTATAAGTGCATCT<br>GTTCAGACGGATGGGAGGGGGCCTACTGCGAGACCAACATCAA<br>CGATTGCTCGCAGAACCCCTGCCACAACGGCGGCACCTGCCGGG<br>ACCTGGTGAACGACTTCTACTGCGACTGTAAAAACGGCTGGAAG<br>GGGAAGACCTGCCACTCCAGGGACAGCCAGTGCGACGAGGCGA<br>CCTGCAACAACGGCGGCACCTGCTACGACGAGGGCGATGCCTTC<br>AAGTGTATGTGCCCCGGAGGCTGGGAGGGCACCACCTGCAACA<br>TCGCCCGCAACAGCAGCTGCCTGCCCAATCCCTGCCACAATGGT<br>GGAACATGCGTGGTGAACGGGGAGAGCTTTACGTGCGTGTGCA<br>AGGAGGGATGGGAGGGCCCCATCTGTGCCCAGAACACCAACGA<br>CTGCTCCCCCCATCCCTGTTACAACAGCGGCACCTGTGTGGACG<br>GGGACAACTGGTACCGCTGCGAGTGCGCCCCCGGCTTCGCCGGC<br>CCGGACTGCCGTATCAACATCAACGAGTGTCAGAGCAGCCCCTG<br>CGCATTCGGCGCCACCTGCGTGGATGAAATAAACGGCTACAGGT<br>GTGTGTGCCCCCCCGGCCACAGCGGAGCCAAATGCCAGGAGGT<br>GAGCGGGCGCCCATGCATCACCATGGGGAGCGTGATCCCAGAC<br>GGGGCGAAGTGGGATGACGACTGTAACACCTGCCAGTGCCTGA<br>ACGGCCGAATCGCCTGCAGCAAGGTGTGGTGCGGGCCCCGGCC<br>CTGCCTGCTGCACAAAGGCCACAGCGAGTGCCCCAGCGGCCAG<br>AGCTGCATACCGATCCTGGACGACCAGTGCTTCGTACACCCCTG<br>CACCGGGGTGGGCGAGTGCCGGTCCTCCTCGCTCCAGCCCGTCA<br>AGACCAAGTGCACCAGCGATAGCTACTACCAGGACAACTGCGC<br>CAACATCACCTTTACCTTTAACAAGGAGATGATGAGCCCCGGCC<br>TGACCACGGAGCACATCTGCAGCGAGCTGCGCAACCTCAACATC<br>CTGAAAAACGTGTCGGCCGAGTACTCCATCTACATCGCCTGCGA<br>GCCCTCCCCCTCCGCCAACAATGAAATCCACGTGGCCATCAGCG<br>CCGAGGACATCCGAGACGATGGGAACCCCATCAAGGAAATCAC<br>CGACAAGATAATCGACCTGGTGAGTAAAAGGGACGGGAACAGC<br>AGCCTGATCGCTGCCGTGGCGGAGGTGAGGGTCCAGAGGAGGC<br>CGCTGAAAAATCGGACCGACTTTCTGGTGCCCCTGCTGAGCTCC<br>GTGCTGACCGTCGCCTGGATCTGCTGCCTGGTCACCGCCTTCTAC<br>TGGTGCCTGAGGAAGCGTAGGAAGCCCGGCAGCCACACGCACA<br>GCGCCAGCGAGGACAACACCACCAACAACGTGCGGGAGCAGCT<br>GAACCAGATCAAGAACCCCATCGAGAAGCACGGCGCGAACACA<br>GTGCCGATCAAGGATTACGAGAACAAGAATTCCAAGATGAGCA<br>AGATCAGGACCCACAACAGCGAGGTGGAGGAGGACGACATGGA<br>TAAACACCAGCAGAAGGCCAGGTTCGCCAAGCAGCCCGCCTAT<br>ACCCTGGTCGACAGGGAGGAGAAACCCCCTAATGGCACCCCCA<br>CCAAGCACCCCAACTGGACAAACAAGCAGGACAACAGGGACCT<br>GGAGAGCGCCCAGAGCCTGAACCGTATGGAGTATATCGTG |
| 18 | JAG1-CO08 | ATGCGGAGCCCCAGAACCCGTGGCCGGAGCGGCAGGCCCCTGT<br>CACTACTGCTGGCCCTGCTGTGCGCGCTTAGGGCCAAGGTCTGC<br>GGCGCCAGCGGCCAGTTCGAGCTGGAGATCCTGAGCATGCAGA<br>ACGTGAACGGCGAGCTGCAGAACGGCAACTGCTGCGGCGGGGC<br>CAGGAACCCCGGAGACCGCAAATGCACCCGGGACGAGTGCGAC<br>ACCTATTTTAAAGTGTGCCTGAAGGAGTACCAGAGCAGGGTGAC<br>CGCCGGCGGCCCCTGCAGCTTCGGCAGCGGCAGCACCCCCGTGA<br>TCGGCGGGAATACCTTCAACCTGAAGGCCAGCCGCGGCAACGA<br>CAGGAACCGAATCGTGCTGCCCTTTAGCTTCGCCTGGCCTCGGA<br>GCTACACCCTGCTGGTGGAAGCCTGGGACTCCTCCAACGACACC<br>GTGCAACCCGACTCCATTATCGAGAAGGCCTCCCACAGCGGCAT<br>GATAAACCCCAGCCGGCAGTGGCAGACACTGAAGCAAAACACC<br>GGGGTCGCACATTTCGAGTACCAGATCAGGGTGACGTGTGACGA<br>CTACTACTACGGGTTCGGATGCAACAAGTTCTGCAGGCCCAGGG<br>ACGACTTCTTCGGCCACTACGCCTGTGACCAGAACGGCAATAAG<br>ACCTGCATGGAGGGGTGGATGGGCCCGGAGTGCAACAGGGCCA<br>TATGCCGGCAGGGCTGCTCCCCAAAACACGGGTCCTGCAAGCTG<br>CCTGGCGACTGCAGGTGTCAGTACGGCTGGCAGGGGCTGTACTG<br>CGATAAGTGCATCCCCCACCCCGGCTGCGTCCACGGCATCTGCA<br>ACGAGCCATGGCAGTGTCTGTGCGAGACCAACTGGGGTGGGCA<br>GCTGTGCGACAAGGATCTGAACTACTGCGGCACCCACCAGCCCT<br>GCCTCAACGGGGGAACGTGCTCGAACACCGGGCCCGATAAGTA<br>CCAGTGCTCCTGCCCCGAAGGCTACTCGGGACCTAACTGTGAGA<br>TCGCTGAGCACGCATGCCTGAGCGACCCATGCCATAACAGGGGT<br>AGTTGCAAGGAGACCTCCCTCGGTTTTGAATGCGAGTGCAGCCC |

TABLE 2-continued

Sequence optimized sequences for human JAG1

| SEQ ID NO | NAME | SEQUENCE |
|---|---|---|
| | | CGGCTGGACCGGCCCCACCTGCTCGACCAACATCGACGACTGCA<br>GCCCAAACAACTGCTCCCACGGCGGCACGTGTCAGGACCTGGTG<br>AATGGCTTCAAGTGTGTGTGCCCCCCCCAGTGGACCGGAAAAAC<br>CTGCCAGCTGGATGCCAACGAGTGTGAGGCCAAGCCCTGCGTGA<br>ACGCGAAGTCCTGCAAGAACCTGATCGCCTCCTACTACTGTGAC<br>TGCCTGCCCGGTTGGATGGGCCAAAACTGCGACATCAACATCAA<br>CGACTGCCTGGGCCAGTGCCAGAACGACGCCAGCTGCAGGGAC<br>CTAGTGAACGGGTATCGGTGCATCTGCCCCCCCGGCTACGCCGG<br>CGATCACTGCGAAAGGGACATCGACGAGTGCGCCAGCAACCCG<br>TGCCTGAACGGGGGGCACTGCCAGAACGAGATCAACAGGTTCC<br>AGTGCCTCTGCCCCACCGGGTTCAGCGGGAACCTCTGCCAGCTC<br>GACATCGACTACTGCGAGCCCAATCCCTGCCAGAACGGCGCGCA<br>ATGCTACAATAGGGCCTCGGACTACTTCTGCAAGTGCCCCGAGG<br>ACTACGAGGGCAAAAACTGCAGCCACCTGAAGGACCACTGTAG<br>GACAACCCCCTGCGAAGTCATCGACTCCTGCACCGTGGCCATGG<br>CCTCCAACGACACCCCAGAAGGCGTACGTTACATCAGCTCCAAC<br>GTCTGCGGGCCCCACGGGAAGTGCAAGAGCCAGAGCGGCGGCA<br>AGTTCACGTGTGACTGCAACAAAGGGTTCACCGGCACCTACTGC<br>CATGAGAACATAAATGACTGCGAGTCCAACCCCTGTCGGAACG<br>GCGGCACCTGCATCGACGGCGTAAACTCTTACAAATGTATCTGC<br>AGCGACGGCTGGGAGGGCGCCTACTGCGAGACCAACATCAACG<br>ACTGCAGCCAAAACCCCTGTCACAACGGCGGGACCTGCCGCGA<br>CCTCGTCAACGACTTCTACTGCGACTGCAAGAACGGCTGGAAGG<br>GCAAGACCTGCCACAGCCGGGACTCGCAGTGTGATGAGGCCAC<br>CTGCAACAATGGCGGCACCTGCTATGATGAGGGGGACGCCTTCA<br>AATGTATGTGCCCCGGCGGGTGGGAGGGCACCACTTGCAACATC<br>GCCAGGAACTCCTCCTGCCTCCCCAACCCCTGCCACAACGGAGG<br>GACGTGCGTGGTGAACGGGGAGAGCTTCACCTGCGTGTGCAAG<br>GAGGGCTGGGAAGGCCCCATTTGCGCGCAGAACACTAACGATT<br>GCAGCCCCCACCCCTGCTACAACTCCGGCACCTGCGTGGACGGG<br>GACAACTGGTACCGGTGCGAGTGCGCCCCCGGCTTCGCCGGCCC<br>GGACTGCAGGATCAACATCAACGAATGTCAGAGCAGCCCCTGC<br>GCCTTCGGAGCCACCTGCGTGGACGAGATAAACGGCTACCGGTG<br>CGTCTGCCCCCCCGGTCACTCTGGTGCCAAGTGCCAAGAGGTCA<br>GCGGCAGGCCGTGCATCACCATGGGCTCCGTGATCCCGGATGGC<br>GCCAAATGGGACGATGACTGCAACACCTGCCAGTGCCTTAACGG<br>TCGGATCGCGTGCAGCAAGGTGTGGTGTGGCCCCAGGCCCTGCC<br>TCCTGCACAAGGGGCACAGCGAGTGCCCCTCCGGACAGTCCTGT<br>ATCCCCATCCTGGACGACCAGTGCTTCGTCCACCCCTGCACCGG<br>AGTGGGCGAATGCAGGAGCAGCTCCCTGCAGCCGGTGAAGACC<br>AAGTGCACCAGCGACTCCTACTACCAGGACAATTGCGCCAACAT<br>CACCTTCACCTTCAACAAGGAGATGATGAGCCCCGGCCTGACCA<br>CCGAGCACATCTGCAGCGAGCTGCGCAACCTGAACATCTTGAAG<br>AACGTGAGCGCCGAGTATTCCATCTACATCGCCTGCGAGCCCAG<br>CCCGAGCGCCAATAACGAGATCCACGTGGCCATCAGCGCCGAG<br>GACATCCGGGATGACGGCAATCCCATCAAGGAGATCACCGATA<br>AGATCATCGACCTGGTCAGCAAGCGCGACGGCAATAGCTCGCTG<br>ATCGCGGCCGTGGCCGAGGTGAGGGTGCAGCGGCGGCCCCTGA<br>AGAACAGGACCGACTTTCTGGTACCCCTCCTGAGCTCGGTGCTG<br>ACCGTTGCCTGGATCTGTTGTCTGGTGACCGCCTTCTACTGGTGC<br>CTGCGGAAAAGGCGGAAGCCCGGCTCCCATACCCATAGCGCAT<br>CCGAAGACAACACCACCAACAACGTCCGTGAGCAGCTGAACCA<br>GATCAAGAACCCCATAGAGAAACACGGCGCCAACACCGTGCCC<br>ATCAAGGACTACGAAAACAAGAACTCCAAGATGTCCAAAATCA<br>GGACCCACAACAGCGAGGTGGAAGAGGACGACATGGATAAACA<br>CCAGCAGAAGGCCCGTTTCGCCAAGCAGCCCGCCTACACCTTAG<br>TGGACAGGGAGGAGAAACCCCCCAACGGGACCCCCACCAAGCA<br>CCCAAACTGGACGAACAAGCAGGATAACCGGGACCTGGAATCA<br>GCGCAGTCCCTGAACAGAATGGAATACATCGTC |
| 19 | JAG1-CO09 | ATGAGGTCCCCCCGAACCAGGGGCAGGTCCGGTCGGCCCCTGA<br>GCCTGCTCCTGGCCCTCCTGTGCGCCCTGAGAGCCAAGGTGTGT<br>GGAGCCAGCGGGCAGTTCGAGCTCGAGATCCTCTCCATGCAGAA<br>CGTGAACGGCGAGCTGCAGAACGGCAACTGCTGCGGAGGCGCC<br>AGGAATCCCGGCGATCGGAAGTGCACCAGGGACGAGTGCGACA<br>CCTATTTCAAGGTGTGCCTCAAGGAGTACCAAAGCAGGGTGACC<br>GCCGGCGGCCCCTGCTCCTTCGGCAGCGGCAGCACCCCCGTGAT<br>AGGGGGCAACACGTTCAACCTCAAGGCCAGCAGGGGCAACGAC<br>AGGAACCGCATCGTGCTGCCCTTCAGCTTTGCGTGGCCCCGTTC<br>CTACACCCTGCTGGTCGAGGCCTGGGACAGCTCCAACGATACCG<br>TGCAGCCCGACTCCATCATTGAGAAGGCCAGCCACAGCGGCATG<br>ATCAACCCCAGCAGGCAGTGGCAAACCCTGAAGCAGAACACCG<br>GAGTGGCCCATTTCGAATACCAGATCAGGGTGACCTGCGATGAC<br>TACTATTATGGTTTTGGGTGCAACAAATTCTGCCGGCCCCGAGA<br>CGACTTCTTCGGTCACTATGCCTGCGACCAGAACGGCAACAAGA |

TABLE 2-continued

| Sequence optimized sequences for human JAG1 | | |
|---|---|---|
| SEQ ID NO | NAME | SEQUENCE |
| | | CCTGTATGGAGGGGTGGATGGGCCCTGAGTGCAACCGGGCCATC |
| | | TGTCGCCAGGGGTGCTCCCCCAAGCACGGCAGCTGCAAGCTGCC |
| | | TGGCGATTGCCGGTGTCAGTACGGGTGGCAGGGTCTCTACTGCG |
| | | ACAAGTGCATCCCCCACCCGGGCTGTGTGCACGGCATCTGCAAC |
| | | GAGCCCTGGCAGTGCCTGTGCGAAACCAATTGGGGCGGCCAACT |
| | | GTGCGACAAGGACCTGAACTACTGTGGCACCCACCAGCCCTGCC |
| | | TGAACGGGGGCACTTGCTCCAACACGGGCCCCGACAAGTATCA |
| | | GTGCAGCTGTCCTGAGGGCTACAGCGGCCCCAACTGTGAGATCG |
| | | CCGAGCATGCCTGCCTGAGCGACCCGTGCCACAATCGTGGCAGC |
| | | TGTAAGGAGACCAGCCTGGGCTTCGAGTGCGAGTGCAGCCCGG |
| | | GTTGGACCGGACCCACCTGCAGCACCAACATCGACGATTGCAGC |
| | | CCCAACAACTGTTCACACGGGGGCACGTGCCAAGACCTGGTGA |
| | | ACGGGTTCAAGTGTGTCTGCCCCCCCCAGTGGACCGGCAAAACC |
| | | TGTCAGCTCGACGCCAACGAATGTGAGGCCAAGCCCTGCGTGAA |
| | | TGCGAAGAGCTGCAAGAACCTGATCGCGTCGTACTATTGCGATT |
| | | GCCTGCCCGGCTGGATGGGCCAGAACTGCGACATCAACATCAAC |
| | | GACTGCCTGGGCCAGTGCCAAAACGACGCCTCTTGCCGCGATCT |
| | | GGTCAACGGGTACCGCTGCATCTGCCCTCCGGGGTACGCCGGGG |
| | | ATCACTGTGAGAGGGACATAGATGAGTGCGCGTCCAACCCCTGC |
| | | CTGAACGGGGGGCACTGCCAGAACGAGATCAACAGGTTTCAGT |
| | | GCCTGTGCCCCACCGGCTTCTCCGGCAACCTGTGCCAGCTTGAC |
| | | ATCGACTACTGCGAGCCCAATCCCTGCCAGAATGGCGCCCAGTG |
| | | CTACAACAGGGCCAGCGACTATTTCTGCAAGTGTCCCGAGGACT |
| | | ACGAGGGGAAGAATTGCTCCCACCTGAAAGACCACTGCAGGAC |
| | | GACCCCCTGTGAGGTGATCGACAGCTGCACCGTGGCCATGGCCT |
| | | CCAACGACACCCCCGAGGGCGTGAGGTACATCAGCAGCAACGT |
| | | CTGCGGCCCCCACGGCAAGTGCAAGAGCCAGAGCGGCGGAAAG |
| | | TTCACCTGCGACTGCAACAAGGGGTTCACGGGCACCTACTGCCA |
| | | CGAGAACATCAACGACTGCGAGTCCAACCCCTGCAGGAACGGC |
| | | GGCACGTGCATAGACGGGGTTAACAGCTATAAGTGTATCTGCTC |
| | | GGACGGGTGGGAAGGCGCCTACTGCGAGACCAACATCAACGAC |
| | | TGCTCACAGAATCCGTGCCACAACGGGGGCACCTGCAGGGACCT |
| | | GGTGAACGACTTCTATTGCGACTGCAAGAACGGCTGGAAAGGT |
| | | AAGACATGCCACTCCCGGGACTCCCAGTGCGACGAGGCCACCTG |
| | | CAACAACGGAGGAACCTGCTACGATGAGGGCGACGCCTTCAAG |
| | | TGCATGTGCCCCGGGGGATGGGAAGGCACCACCTGCAACATCG |
| | | CCAGGAACTCCAGCTGTCTCCCCAACCCGTGCCACAACGGCGGG |
| | | ACGTGCGTGGTGAATGGCGAGTCCTTCACGTGCGTGTGCAAGGA |
| | | GGGCTGGGAGGGCCCCATCTGCGCGCAGAACACCAACGATTGC |
| | | AGCCCCCACCCGTGCTACAACTCAGGCACCTGCGTCGACGGTGA |
| | | CAACTGGTACCGGTGCGAGTGCGCCCCAGGGTTCGCGGGCCCCG |
| | | ACTGCAGGATCAACATCAACGAGTGCCAGTCCAGCCCCTGCGCC |
| | | TTTGGCGCCACCTGCGTGGACGAGATCAACGGCTACAGGTGCGT |
| | | GTGCCCCCCCGGCCATAGCGGCGCCAAGTGCCAGGAGGTGAGC |
| | | GGCAGGCCCTGCATCACCATGGGCAGCGTGATCCCCGACGGCGC |
| | | CAAGTGGGACGACGACTGCAATACGTGCCAGTGCCTGAACGGA |
| | | CGCATTGCCTGCTCCAAGGTGTGGTGCGGCCCCCGGCCGTGCCT |
| | | GCTCCACAAGGGGCACAGCGAGTGCCCCTCCGGCCAGAGCTGC |
| | | ATCCCCATCCTCGACGACCAGTGCTTCGTCCACCCCTGCACCGG |
| | | CGTGGGCGAGTGCAGGTCCTCCAGCCTGCAGCCAGTGAAAACC |
| | | AAGTGTACCAGCGACTCCTACTACCAGGACAACTGCGCCAACAT |
| | | CACATTCACATTCAACAAGGAGATGATGAGCCCGGGCCTGACCA |
| | | CCGAGCACATCTGCAGCGAACTCAGAAACCTGAACATCCTGAA |
| | | GAACGTGTCGGCCGAGTACAGCATCTATATCGCGTGCGAGCCCA |
| | | GCCCCAGCGCGAATAACGAGATCCACGTGGCCATAAGCGCGGA |
| | | GGACATCCGGGACGACGGCAACCCCATCAAGGAGATCACCGAC |
| | | AAGATTATTGACCTGGTCTCCAAGAGGGACGGCAATAGCTCCCT |
| | | GATTGCCGCCGTCGCCGAAGTGCGGGTGCAAAGAAGGCCCCTG |
| | | AAAAACCGGACGGATTTCCTGGTCCCCCTCCTGAGCAGCGTGCT |
| | | GACCGTCGCCTGGATCTGCTGTCTGGTGACGGCCTTCTACTGGT |
| | | GCCTCAGAAAGAGGCGCAAACCCGGCTCGCACACCCATAGCGC |
| | | CTCAGAGGACAACACCACGAATAACGTGCGGGAACAGCTGAAC |
| | | CAAATAAAAAACCCCATCGAGAAGCACGGGGCTAACACCGTGC |
| | | CGATCAAGGACTACGAGAACAAGAACAGCAAGATGTCCAAGAT |
| | | CCGAACCCACAACAGCGAGGTCGAGGAGGACGACATGGACAAG |
| | | CACCAGCAGAAGGCGAGGTTCGCCAAGCAGCCCGCCTACACCC |
| | | TGGTAGACCGGGAGGAGAAGCCGCCCAACGGCACCCCCACGAA |
| | | ACACCCCAACTGGACCAACAAACAAGACAACAGGGACCTGGAG |
| | | AGCGCCCAGTCCCTGAACAGGATGGAATATATTGTC |
| 20 | JAG1- | ATGAGGAGCCCCAGGACACGGGGCCGGAGCGGGCGACCTCTGT |
| | CO10 | CCCTGCTCCTGGCCCTGCTGTGCGCCCTGAGAGCCAAAGTGTGC |
| | | GGCGCCAGCGGGCAGTTCGAGCTGGAGATACTGAGCATGCAGA |
| | | ACGTGAACGGCGAGCTGCAGAACGGCAACTGTTGTGGGGGCGC |
| | | GCGGAACCCCGGGGACAGGAAGTGCACCCGGGACGAGTGCGAC |

TABLE 2-continued

Sequence optimized sequences for human JAG1

| SEQ ID NO | NAME | SEQUENCE |
|---|---|---|
| | | ACCTACTTCAAGGTGTGCCTCAAGGAATACCAAAGCCGTGTGAC<br>AGCTGGGGGCCCCTGCAGCTTCGGGTCCGGATCCACCCCCGTCA<br>TCGGCGGCAACACCTTCAACCTCAAGGCCAGCAGGGGCAACGA<br>CAGGAACCGAATCGTGCTGCCCTTTTCGTTTGCCTGGCCCCGCA<br>GCTACACCCTCCTAGTGGAGGCCTGGGACAGCAGCAACGACAC<br>CGTGCAGCCCGACTCCATCATCGAGAAGGCATCCCACAGCGGG<br>ATGATCAATCCCTCCCGCCAGTGGCAGACGCTGAAGCAGAACAC<br>CGGCGTGGCCCACTTCGAATACCAAATCAGGGTGACGTGCGATG<br>ACTACTATTACGGCTTCGGGTGCAACAAGTTCTGCAGGCCGAGG<br>GATGACTTCTTCGGCCACTATGCCTGCGACCAGAACGGAAACAA<br>AACCTGCATGGAGGGTTGGATGGGACCCGAGTGCAACAGGGCC<br>ATCTGCCGCCAGGGCTGCTCACCAAAGCACGGCAGCTGTAAGCT<br>ACCCGGCGACTGTCGGTGCCAGTACGGTTGGCAGGGCCTGTACT<br>GTGACAAGTGCATCCCCCACCCCGGCTGCGTGCACGGCATCTGC<br>AATGAGCCGTGGCAGTGCCTGTGTGAAACCAACTGGGGTGGGC<br>AGCTGTGCGACAAGGACCTGAATTACTGCGGCACCCACCAGCCC<br>TGTCTGAACGGCGGCACCTGCTCCAACACCGGCCCGGACAAGTA<br>TCAGTGCAGTTGCCCCGAGGGCTATAGCGGCCCCAACTGCGAGA<br>TCGCCGAGCACGCCTGCCTGTCCGACCCGTGCCACAACAGGGGG<br>AGCTGCAAAGAGACCAGCCTGGGGTTCGAGTGCGAGTGCAGCC<br>CCGGGTGGACCGGACCCACCTGCAGCACCAACATCGATGATTGC<br>AGCCCTAACAACTGCTCCCACGGCGGCACCTGCCAGGACCTGGT<br>GAACGGCTTTAAGTGCGTATGCCCCCCCCAATGGACGGGGAAG<br>ACCTGTCAGCTCGACGCCAATGAATGCGAGGCAAAACCGTGTGT<br>GAACGCCAAGAGCTGCAAAAACCTCATCGCGTCCTACTACTGCG<br>ACTGCCTGCCCGGCTGGATGGGGCAGAACTGTGACATCAACATC<br>AACGATTGCCTGGGCCAATGCCAGAATGATGCCTCCTGCAGGGA<br>CCTTGTGAACGGCTACAGGTGCATATGCCCCCCCGGCTACGCCG<br>GCGATCACTGCGAGCGGGATATAGACGAGTGTGCCAGCAACCC<br>CTGCCTCAACGGGGGGCACTGCCAGAATGAGATCAACAGATTTC<br>AATGCCTGTGCCCCACAGGATTTAGCGGAAATCTGTGCCAACTG<br>GACATCGACTACTGCGAGCCCAATCCCTGCCAGAACGGGGCCCA<br>GTGCTACAACCGGGCCAGCGACTACTTTTGCAAGTGCCCCGAGG<br>ACTACGAGGGAAAAAACTGCAGCCACCTGAAGGACCATTGCAG<br>GACCACCCCCTGTGAGGTGATTGACAGCTGCACCGTGGCCATGG<br>CCTCAAACGACACCCCCGAGGGTGTGAGGTATATCAGCTCGAAC<br>GTGTGCGGCCCCCACGGCAAGTGCAAGTCACAAAGCGGGGGAA<br>AGTTCACCTGCGACTGCAACAAGGGCTTCACCGGTACCTACTGC<br>CACGAGAACATCAACGACTGTGAGAGCAACCCCTGTAGAAACG<br>GGGGGACCTGCATCGACGGAGTGAATTCCTATAAGTGCATCTGT<br>AGCGACGGGTGGGAGGGCGCCTACTGCGAGACCAATATCAACG<br>ATTGCAGCCAGAACCCCTGCCACAACGGGGGCACCTGCCGAGA<br>TCTCGTGAACGACTTCTACTGCGACTGTAAAAACGGTTGGAAAG<br>GCAAAACCTGCCACTCCCGCGATTCCCAGTGCGATGAGGCGACC<br>TGCAATAATGGAGGCACCTGCTACGACGAGGGCGACGCCTTTAA<br>GTGCATGTGCCCCGGCGGCTGGGAAGGCACCACCTGCAATATCG<br>CGAGAAATAGCAGCTGCCTGCCCAACCCCTGCCATAACGGCGG<br>GACCTGCGTGGTGAATGGCGAGAGCTTCACCTGCGTCTGTAAGG<br>AGGGCTGGGAAGGTCCCATCTGTGCCCAGAACACCAACGACTG<br>CAGCCCCCATCCCTGCTACAACAGCGGCACCTGCGTGGACGGCG<br>ACAATTGGTACAGGTGCGAGTGCGCCCCCGGGTTTGCCGGCCCC<br>GACTGCAGGATCAACATCAACGAGTGCCAGAGTAGCCCCTGTGC<br>CTTCGGCGCCACCTGCGTGGACGAGATCAACGGCTACCGGTGCG<br>TGTGCCCCCCCGGCCACTCCGGCGCCAAGTGTCAAGAGGTGAGC<br>GGACGACCCTGTATCACCATGGGCTCGGTGATCCCCGACGGCGC<br>CAAGTGGGACGACGACTGCAACACGTGCCAGTGCCTCAACGGG<br>AGGATCGCCTGCAGCAAGGTGTGGTGCGGTCCCAGGCCCTGCCT<br>GCTGCACAAAGGCCACTCCGAGTGCCCCAGCGGCCAGAGCTGT<br>ATCCCCATCCTGGATGATCAGTGCTTCGTCCATCCCTGTACTGGC<br>GTGGGCGAGTGCAGGAGCAGCAGCCTCCAGCCCGTGAAAACCA<br>AGTGCACGAGCGACTCCTATTACCAAGATAACTGTGCCAACATC<br>ACCTTCACCTTTAACAAGGAGATGATGTCGCCCGGACTGACCAC<br>CGAGCATATCTGCAGCGAGCTGAGGAACCTGAACATACTGAAG<br>AATGTGTCCGCCGAATATTCCATCTACATCGCCTGTGAGCCTAG<br>CCCGAGCGCCAACAACGAGATCCACGTGGCCATCTCCGCCGAG<br>GATATCAGGGACGACGGGAACCCCATCAAAGAGATCACCGATA<br>AGATCATCGACCTGGTGTCTAAGCGCGACGGTAACAGCTCCCTA<br>ATCGCCGCCGTGGCCGAGGTGCGCGTGCAGCGCAGGCCGCTGA<br>AGAACCGCACCGACTTCCTGGTGCCCCTGCTGAGCAGCGTGCTC<br>ACCGTGGCCTGGATATGCTGCCTGGTGACCGCCTTCTACTGGTG<br>CCTGCGGAAGCGGCGTAAACCGGGAAGCCATACCCACAGCGCC<br>AGCGAGGATAATACCACCAATAACGTGCGGGAGCAGCTGAACC<br>AGATCAAGAACCCCATCGAAAAGCACGGGGCGAACACCGTGCC<br>CATCAAGGACTACGAGAATAAGAACTCCAAGATGAGCAAGATC<br>CGCACACACAACAGCGAGGTGGAGGAGGACGATATGGACAAGC |

TABLE 2-continued

Sequence optimized sequences for human JAG1

| SEQ ID NO | NAME | SEQUENCE |
|---|---|---|
| | | ACCAGCAGAAGGCCAGGTTCGCCAAGCAGCCCGCCTACACCCTT<br>GTGGACCGCGAAGAGAAGCCCCCGAACGGCACCCCCACCAAGC<br>ACCCCAACTGGACCAACAAACAGGATAACCGTGACCTGGAAAG<br>CGCGCAGTCCCTGAACCGCATGGAGTACATAGTG |
| 21 | JAG1-CO11 | ATGAGGAGCCCCCGGACCAGGGGGCGGAGCGGCAGGCCCCTGA<br>GCCTCCTGCTGGCCCTGCTTTGCGCACTGAGGGCCAAGGTGTGT<br>GGGGCCAGCGGGCAGTTCGAGCTCGAAATCCTGAGCATGCAGA<br>ACGTGAACGGCGAGCTGCAGAATGGCAATTGTTGCGGCGGCGC<br>CAGGAACCCCGGCGACCGGAAGTGCACCCGGGACGAATGCGAC<br>ACCTACTTCAAGGTGTGCCTCAAGGAGTACCAGAGCCGCGTGAC<br>CGCCGGCGGACCCTGCAGCTTCGGCAGCGGCAGCACCCCCGTGA<br>TCGGGGGCAACACCTTCAACCTGAAGGCATCCCGCGGGAACGA<br>CAGGAACAGGATCGTGCTGCCGTTCAGCTTCGCCTGGCCGCGAT<br>CCTACACGCTGCTGGTTGAGGCCTGGGACAGCAGCAATGACACG<br>GTGCAACCCGACAGCATTATCGAGAAGGCCAGCCACTCCGGCAT<br>GATCAACCCCTCCCGGCAGTGGCAGACCCTGAAGCAGAACACT<br>GGAGTTGCACACTTCGAGTACCAAATCAGGGTCACGTGCGACGA<br>CTACTATTACGGGTTCGGCTGTAACAAGTTCTGCAGGCCCCGTG<br>ATGACTTCTTTGGACACTACGCCTGCGACCAGAACGGAAACAAG<br>ACCTGCATGGAAGGGTGGATGGGCCCCGAGTGCAACAGGGCCA<br>TCTGTAGACAAGGCTGCAGCCCCAAACACGGCTCCTGTAAGCTG<br>CCCGGCGACTGCCGGTGCCAGTACGGCTGGCAGGGGCTCTACTG<br>CGACAAGTGCATTCCCCATCCCGGCTGCGTGCACGGCATATGTA<br>ACGAACCCTGGCAATGCCTCTGCGAGACCAACTGGGGCGGGCA<br>GCTGTGCGACAAAGACCTGAACTACTGTGGCACCCATCAGCCCT<br>GCCTGAACGGGGGACTTGCTCCAATACCGGTCCCGACAAGTAT<br>CAGTGCAGCTGCCCCGAGGGCTACTCCGGGCCCAACTGCGAGAT<br>CGCCGAACACGCCTGTCTGTCCGACCCCTGCCACAACAGAGGCA<br>GCTGCAAGGAGACCAGCCTGGGCTTTGAGTGCGAGTGCTCCCCC<br>GGCTGGACCGGGCCCACCTGCAGCACCAACATCGACGATTGCA<br>GCCCCAACAATTGCTCCCACGGCGGCACTTGCCAAGACCTGGTG<br>AACGGCTTCAAGTGCGTGTGCCCCCCCCAGTGGACCGGTAAAAC<br>ATGCCAGCTGGACGCCAACGAGTGCGAGGCCAAGCCCTGCGTG<br>AACGCCAAGAGCTGCAAAAACCTGATCGCCAGTTACTACTGCGA<br>CTGCCTGCCTGGATGGATGGGCCAGAACTGCGACATCAACATCA<br>ACGACTGCCTGGGCCAGTGCCAGAACGACGCAAGCTGCCGTGA<br>CCTGGTGAACGGCTACAGGTGCATCTGCCCCCCCGGGTACGCCG<br>GTGACCACTGCGAACGGGACATAGATGAGTGCGCCAGCAACCC<br>CTGCCTGAACGGCGGACACTGCCAGAATGAGATCAATAGGTTCC<br>AATGCCTCTGCCCCACCGGCTTTAGCGGCAATCTGTGCCAGCTG<br>GACATCGATTACTGTGAGCCCAACCCCTGCCAGAATGGAGCCCA<br>GTGCTACAACCGGGCCTCCGACTATTTCTGTAAGTGTCCCGAAG<br>ACTACGAGGGTAAGAACTGCTCCCACCTGAAGGACCACTGCCG<br>GACCACTCCGTGCGAGGTCATCGACAGCTGCACCGTCGCCATGG<br>CCAGCAATGACACACCCGAGGGCGTGAGGTACATCTCCTCCAAC<br>GTGTGTGGCCCCCACGGCAAGTGCAAGAGCCAGAGCGGAGGCA<br>AGTTCACCTGCGACTGCAACAAGGGGTTCACCGGCACTTACTGC<br>CACGAGAACATCAACGACTGCGAATCCAACCCCTGTCGAAACG<br>GGGGCACCTGCATTGACGGCGTGAACAGCTATAAGTGCATCTGC<br>TCCGACGGGTGGGAGGGGGCCTACTGCGAAACCAATATAAACG<br>ATTGCAGCCAGAACCCCTGTCACAACGGGGGCACATGCAGGGA<br>CCTGGTCAACGACTTCTACTGTGACTGCAAGAACGGCTGGAAGG<br>GCAAGACATGTCACAGCAGGGACAGCCAGTGCGACGAGGCCAC<br>CTGTAACAATGGCGGCACCTGCTATGACGAAGGCGACGCCTTCA<br>AATGTATGTGCCCCGGCGGTTGGGAGGGGACGACGTGCAATATT<br>GCGAGGAACTCCAGCTGTCTGCCCAACCCCTGCCACAACGGAGG<br>CACCTGTGTGGTGAACGGCGAGAGCTTTACGTGCGTCTGTAAAG<br>AGGGCTGGGAAGGCCCCATCTGCGCCCAAAACACGAACGACTG<br>CAGCCCCCACCCCTGTTACAATAGCGGCACCTGCGTCGACGGTG<br>ACAACTGGTATAGGTGCGAGTGTGCCCCGGGCTTTGCCGGGCCC<br>GACTGCCGGATCAATATCAACGAGTGCCAGTCCAGCCCATGTGC<br>GTTCGGCGCCACCTGCGTGGACGAAATCAACGGCTACAGGTGCG<br>TCTGCCCCCCGGGGCACAGCGGAGCCAAATGTCAGGAAGTCTCT<br>GGGAGGCCCTGCATCACCATGGGCAGCGTAATCCCCGACGGGG<br>CTAAGTGGGACGACGACTGCAATACCTGTCAGTGTCTGAACGGC<br>AGGATTGCCTGCAGCAAAGTGTGGTGTGGCCCGCGGCCCTGTCT<br>CCTGCACAAGGGCCACTCCGAGTGTCCCAGCGGCCAATCCTGCA<br>TCCCCATCCTCGACGACCAGTGCTTTGTGCACCCCTGCACAGGC<br>GTGGGAGAGTGTAGGTCGAGCTCCCTGCAGCCCGTGAAGACCA<br>AGTGCACCAGCGATTCCTACTACCAGGACAACTGCGCGAATATC<br>ACCTTTACCTTTAACAAGGAGATGATGAGCCCCGGGCTGACCAC<br>CGAGCACATCTGCAGCGAGCTGCGGAACCTGAACATCCTCAAA<br>AACGTCAGCGCCGAGTATAGCATCTACATTGCCTGCGAGCCCAG<br>CCCCAGCGCCAACAACGAAATACACGTGGCCATCAGCGCCGAG |

TABLE 2-continued

Sequence optimized sequences for human JAG1

| SEQ ID NO | NAME | SEQUENCE |
|---|---|---|
| | | GACATCAGGGACGACGGCAACCCGATCAAGGAGATCACCGATA |
| | | AGATAATCGACCTGGTGTCCAAGAGGGACGGCAATAGCTCCCTG |
| | | ATCGCCGCCGTGGCCGAAGTGAGGGTGCAGAGGAGGCCCCTGA |
| | | AAAACAGGACCGATTTCCTGGTTCCCCTGCTGAGCAGCGTGCTG |
| | | ACAGTGGCTTGGATCTGCTGCCTCGTAACTGCATTCTACTGGTGC |
| | | CTGAGGAAGAGGAGGAAGCCCGGCAGTCACACCCACAGCGCCT |
| | | CCGAGGATAACACCACTAACAATGTGCGGGAGCAGCTGAACCA |
| | | GATCAAGAATCCCATAGAAAAACATGGCGCCAACACCGTGCCC |
| | | ATTAAAGATTACGAGAACAAAAATAGCAAGATGTCCAAGATCC |
| | | GCACCCACAACAGCGAGGTGGAGGAGGACGACATGGACAAGCA |
| | | CCAGCAGAAGGCCAGGTTCGCCAAGCAGCCCGCGTACACCCTG |
| | | GTGGACCGTGAGGAGAAGCCCCCCAACGGCACCCCCACCAAGC |
| | | ACCCCAACTGGACCAACAAGCAAGATAATCGGGACCTGGAATC |
| | | CGCCCAGAGCCTGAACAGGATGGAGTACATCGTG |
| 22 | JAG1-CO12 | ATGAGGAGCCCGAGAACGAGGGGGCGGTCCGGCAGGCCGCTGA |
| | | GCCTCCTGCTGGCCCTGCTGTGCGCCCTGCGGGCAAAGGTGTGT |
| | | GGCGCCTCCGGGCAGTTCGAGCTGGAGATCCTGAGCATGCAAA |
| | | ACGTGAACGGCGAACTCCAGAACGGCAATTGCTGCGGCGGCGC |
| | | CAGAAACCCCGGGGATCGAAAGTGCACCCGGGACGAGTGCGAC |
| | | ACCTACTTCAAAGTGTGTCTCAAAGAATACCAGAGCAGGGTGAC |
| | | CGCCGGCGGGCCCTGCAGCTTCGGCAGCGGCAGCACCCCCGTGA |
| | | TCGGCGGGAACACCTTCAACCTGAAGGCCAGCCGCGGCAACGA |
| | | CAGGAATCGGATCGTGTTGCCGTTCAGCTTCGCCTGGCCCCGTT |
| | | CCTACACCCTGCTGGTGGAGGCCTGGGACAGCAGCAACGATACC |
| | | GTGCAGCCAGACAGCATAATCGAGAAGGCCAGCCACTCCGGTA |
| | | TGATCAACCCCAGCAGGCAGTGGCAGACCCTGAAGCAAAACAC |
| | | CGGCGTGGCCCATTTCGAGTACCAGATCAGGGTCACGTGCGACG |
| | | ACTATTACTACGGGTTCGGGTGCAACAAGTTCTGCAGGCCCCGG |
| | | GATGACTTCTTTGGACACTACGCCTGTGACCAGAACGGAAACAA |
| | | AACTTGCATGGAGGGCTGGATGGGCCCGGAGTGCAATAGGGCC |
| | | ATTTGCAGGCAAGGCTGCAGCCCCAAGCACGGCTCCTGCAAGCT |
| | | CCCCGGCGACTGCCGATGCCAATATGGCTGGCAGGGCCTCTACT |
| | | GTGACAAGTGCATCCCCCACCCGGGCTGCGTCCACGGAATCTGC |
| | | AATGAGCCCTGGCAGTGTCTGTGCGAGACGAACTGGGGTGGCC |
| | | AGCTGTGCGACAAGGACCTGAACTACTGCGGGACCCACCAGCC |
| | | CTGCCTGAACGGCGGGACCTGTTCCAACACCGGCCCGGACAAGT |
| | | ATCAGTGCAGCTGCCCGGAAGGGTACTCCGGCCCGAACTGCGA |
| | | AATCGCCGAACACGCTTGCCTCAGCGACCCCTGCCACAACCGCG |
| | | GGAGCTGCAAGGAGACCAGCCTGGGCTTTGAGTGCGAATGTTCC |
| | | CCCGGCTGGACCGGGCCCACATGCTCCACCAACATAGACGATTG |
| | | TAGCCCCAACAACTGCTCCCACGGGGGGACCTGCCAAGACCTGG |
| | | TCAACGGATTCAAGTGCGTGTGTCCCCCCCAGTGGACGGGTAAG |
| | | ACCTGCCAACTGGACGCCAACGAATGCGAGGCCAAGCCCTGTGT |
| | | GAATGCCAAGAGCTGCAAGAACCTGATCGCCAGCTACTACTGTG |
| | | ACTGCCTGCCCGGCTGGATGGGCCAGAATTGCGACATCAATATC |
| | | AACGACTGCCTGGGCCAGTGCCAGAATGACGCCTCCTGCAGGG |
| | | ACCTGGTGAACGGCTACAGGTGCATATGCCCCCCCGGCTACGCC |
| | | GGCGACCACTGCGAACGTGACATCGACGAGTGCGCCTCAAACC |
| | | CCTGCCTGAACGGCGGACACTGCCAGAACGAGATCAACCGATTC |
| | | CAGTGTCTGTGCCCCACCGGGTTTAGCGGGAACCTCTGCCAGCT |
| | | CGATATCGACTACTGCGAACCCAACCCCTGCCAGAACGGCGCCC |
| | | AGTGCTACAACCGGGCCAGCGACTATTTCTGTAAATGCCCCGAG |
| | | GACTACGAGGGGAAAAACTGTAGCCACCTGAAGGACCACTGCA |
| | | GGACCACACCCTGCGAAGTGATCGACAGCTGCACCGTGGCCATG |
| | | GCCAGCAATGACACCCCCGAAGGCGTGAGGTATATAAGCAGCA |
| | | ACGTATGCGGCCCCCACGGCAAGTGTAAGAGCCAGAGCGGCGG |
| | | CAAGTTTACGTGCGACTGCAACAAAGGCTTCACCGGCACCTACT |
| | | GTCACGAGAACATCAACGACTGCGAGAGCAACCCCTGCCGCAA |
| | | CGGGGGCACCTGCATCGACGGTGTGAACAGCTACAAGTGCATCT |
| | | GCAGCGACGGCTGGGAGGGCGCCTACTGTGAGACGAACATCAA |
| | | CGACTGCAGCCAGAACCCGTGCCATAACGGGGGCACCTGCAGG |
| | | GATCTGGTGAACGACTTTTATTGCGACTGCAAGAACGGCTGGAA |
| | | GGGCAAGACCTGCCACAGCCGGGACAGCCAGTGTGACGAGGCC |
| | | ACCTGCAACAACGGCGGCACCTGCTACGACGAAGGGGACGCCT |
| | | TTAAGTGCATGTGCCCGGGCGGGTGGGAGGGCACCACCTGCAA |
| | | CATCGCCAGGAATTCCTCCTGTCTGCCCAACCCATGTCACAACG |
| | | GTGGCACGTGCGTGGTGAACGGGGAGTCCTTTACCTGTGTGTGC |
| | | AAGGAGGGGTGGGAGGGACCCATATGTGCGCAGAATACCAACG |
| | | ACTGCTCCCCCCACCCATGTTATAACAGCGGTACATGTGTGGAT |
| | | GGGGACAACTGGTACCGGTGTGAGTGCGCCCCCGGCTTCGCCGG |
| | | CCCCGATTGCAGGATCAACATCAATGAGTGCCAGAGCTCCCCCT |
| | | GCGCCTTCGGCGCCACATGCGTCGACGAAATCAACGGCTACAGG |
| | | TGTGTGTGCCCCCCGGGACACAGCGGTGCCAAGTGCCAGGAAGT |
| | | GTCAGGCAGGCCCTGTATTACCATGGGCAGCGTGATCCCCGACG |

TABLE 2-continued

Sequence optimized sequences for human JAG1

| SEQ ID NO | NAME | SEQUENCE |
|---|---|---|
| | | GAGCCAAGTGGGATGACGACTGCAACACCTGCCAGTGCCTGAA |
| | | CGGCCGTATCGCCTGCAGCAAGGTGTGGTGCGGCCCCCGGCCGT |
| | | GCCTGCTGCACAAGGGGCACTCCGAGTGCCCCAGCGGGCAGAG |
| | | CTGCATCCCCATCTTGGACGACCAGTGCTTCGTGCACCCCTGCA |
| | | CCGGCGTGGGCGAATGCCGTAGCAGCTCCCTGCAGCCCGTGAAG |
| | | ACCAAGTGCACCAGCGATTCCTACTATCAGGATAACTGCGCCAA |
| | | CATCACCTTCACCTTCAACAAGGAGATGATGAGCCCCGGCCTGA |
| | | CCACGGAACACATCTGCAGCGAGCTGAGGAACCTGAACATCCT |
| | | GAAGAACGTGTCCGCCGAATACAGCATCTACATCGCCTGCGAGC |
| | | CCAGCCCCAGCGCCAACAACGAAATCCACGTCGCCATCTCTGCC |
| | | GAGGACATCCGCGACGACGGCAACCCCATTAAGGAGATAACCG |
| | | ACAAGATCATCGACCTGGTGTCCAAGCGAGACGGAAATTCTAGC |
| | | CTGATCGCCGCCGTAGCCGAGGTACGTGTGCAGAGGAGGCCCCT |
| | | CAAGAATAGGACCGACTTCCTGGTGCCCCTGCTGAGCAGCGTGC |
| | | TCACCGTGGCGTGGATCTGCTGCCTGGTGACCGCCTTTTACTGGT |
| | | GCCTGCGAAAGAGGAGGAAGCCCGGTTCACACACGCACAGCGC |
| | | CAGCGAAGACAACACCACCAACAATGTGCGCGAGCAGCTCAAC |
| | | CAGATCAAGAATCCCATCGAGAAGCACGGCGCCAACACGGTCC |
| | | CCATCAAGGACTACGAGAACAAAAACAGCAAGATGTCCAAGAT |
| | | CCGCACCCATAACAGCGAGGTCGAAGAAGACGACATGGACAAA |
| | | CACCAGCAAAAGGCCAGGTTCGCCAAGCAGCCGGCCTACACCC |
| | | TGGTGGACAGGGAGGAGAAGCCCCCGAACGGCACCCCCACCAA |
| | | GCACCCCAACTGGACCAACAAACAGGACAACCGGGATCTGGAG |
| | | AGTGCGCAGAGCCTGAACAGGATGGAGTACATCGTG |
| 23 | JAG1-CO13 | ATGAGAAGCCCAAGGACGCGCGGTAGGAGCGGCAGGCCCCTCA |
| | | GCCTGCTGCTGGCTCTACTGTGCGCCCTGCGGGCCAAGGTTTGT |
| | | GGGGCCAGTGGGCAATTCGAGCTGGAGATCCTGAGCATGCAAA |
| | | ACGTGAACGGGGAGCTTCAGAATGGTAACTGCTGCGGCGGGGC |
| | | CCGGAATCCCGGCGACCGGAAGTGTACGAGGGATGAGTGTGAC |
| | | ACCTACTTTAAGGTGTGCCTGAAGGAGTACCAGAGCAGGGTTAC |
| | | GGCAGGCGGCCCCTGCAGCTTTGGCAGCGGCTCCACCCCGGTGA |
| | | TCGGCGGCAACACATTCAACCTGAAGGCCAGCCGCGGGAACGA |
| | | TCGTAACAGGATCGTGCTCCCCTTTAGCTTCGCCTGGCCCCGCA |
| | | GCTACACGCTGCTGGTGGAGGCCTGGGACAGCAGCAACGACAC |
| | | CGTCCAGCCCGATAGCATTATCGAGAAGGCCTCCCACAGCGGTA |
| | | TGATCAACCCGAGCCGGCAGTGGCAGACCCTGAAGCAGAACAC |
| | | CGGCGTGGCCCACTTCGAGTACCAGATCCGGGTGACCTGCGACG |
| | | ACTACTATTACGGTTTCGGCTGCAACAAGTTTTGCCGACCCCGG |
| | | GACGACTTTTTCGGGCATTACGCCTGCGACCAAAACGGCAACAA |
| | | AACCTGCATGGAGGGCTGGATGGGCCCGGAGTGCAACCGGGCC |
| | | ATCTGCCGGCAGGGGTGTAGCCCCAAGCACGGCAGCTGCAAGC |
| | | TGCCCGGCGATTGCCGGTGCCAGTACGGGTGGCAGGGCCTGTAC |
| | | TGCGACAAGTGCATCCCGCACCCCGGATGTGTGCACGGCATCTG |
| | | CAACGAGCCCTGGCAGTGCCTGTGCGAAACCAACTGGGGGGGT |
| | | CAGCTGTGTGACAAGGATCTGAACTACTGCGGAACCCACCAACC |
| | | CTGCCTGAACGGCGGAACTTGCTCGAACACGGGCCCCGACAAGT |
| | | ACCAGTGCAGCTGTCCCGAGGGCTACAGCGGGCCCAACTGTGA |
| | | GATCGCCGAACACGCTTGCCTGAGCGACCCGTGTCACAACCGGG |
| | | GCAGCTGCAAGGAGACCTCCCTCGGCTTCGAGTGCGAGTGCTCC |
| | | CCAGGGTGGACCGGCCCCACCTGCAGCACCAACATCGACGATTG |
| | | CAGCCCCAACAACTGTAGCCACGGCGGGACGTGCCAGGACCTG |
| | | GTCAACGGCTTCAAATGTGTCTGTCCCCCCCAGTGGACCGGCAA |
| | | AACCTGCCAGCTCGACGCCAACGAGTGCGAAGCCAAGCCGTGC |
| | | GTGAACGCGAAGAGCTGCAAGAACCTGATCGCCTCCTACTACTG |
| | | CGACTGCCTGCCCGGCTGGATGGGCCAGAACTGCGACATAAAC |
| | | ATCAACGACTGCCTGGGCCAGTGCCAGAACGATGCCAGCTGTCG |
| | | AGACCTGGTGAACGGGTACCGGTGCATCTGCCCCCCCGGATACG |
| | | CCGGGGACCACTGCGAGCGCGACATCGACGAATGTGCCTCGAA |
| | | CCCCTGCCTGAACGGGGGCCACTGCCAAAACGAGATCAATCGTT |
| | | TCCAGTGCCTGTGCCCCACCGGCTTCTCTGGGAACCTGTGCCAG |
| | | CTGGACATCGACTACTGCGAGCCCAACCCCTGCCAGAACGGGGC |
| | | GCAGTGCTATAACCGGGCCTCCGATTACTTCTGCAAGTGCCCCG |
| | | AGGACTATGAGGGAAAAAACTGCTCCCACCTGAAGGATCACTG |
| | | TAGGACCACCCCCTGTGAGGTGATCGACAGCTGCACCGTGGCCA |
| | | TGGCCAGCAACGACACCCCCGAGGGCGTGCGCTACATCAGCTCC |
| | | AACGTGTGCGGCCCCCATGGTAAGTGTAAGTCGCAGAGCGGCG |
| | | GGAAGTTCACCTGCGACTGCAACAAGGGCTTTACGGGGACCTAC |
| | | TGTCATGAAAACATCAACGACTGCGAGAGCAACCCCTGTCGCAA |
| | | CGGCGGCACCTGCATCGATGGCGTCAACAGCTACAAGTGCATCT |
| | | GCTCCGACGGATGGGAGGGCGCCTACTGCGAGACCAACATCAA |
| | | CGACTGCAGCCAGAACCCGTGCCACAATGGCGGCACCTGCCGTG |
| | | ACCTGGTGAACGACTTTTACTGCGACTGCAAGAACGGGTGGAAA |
| | | GGCAAAACCTGCCACTCCAGGGACAGCCAGTGCGACGAGGCGA |
| | | CCTGCAACAATGGCGGGACGTGCTACGACGAGGGCGACGCCTT |

TABLE 2-continued

Sequence optimized sequences for human JAG1

| SEQ ID NO | NAME | SEQUENCE |
|---|---|---|
| | | CAAGTGCATGTGCCCCGGCGGATGGGAAGGCACTACCTGTAAC<br>ATCGCCCGGAATAGCTCCTGCCTGCCGAACCCCTGCCACAACGG<br>GGGCACGTGCGTCGTGAACGGCGAAAGCTTCACCTGCGTGTGCA<br>AGGAGGGCTGGGAGGGCCCCATCTGTGCCCAGAACACCAACGA<br>CTGCAGCCCCCACCCCTGCTACAATAGCGGCACCTGCGTGGACG<br>GAGACAACTGGTACCGATGCGAGTGCGCCCCTGGCTTCGCCGGA<br>CCCGATTGCCGCATTAACATCAATGAATGCCAGAGCAGCCCCTG<br>CGCCTTTGGAGCCACCTGCGTCGATGAGATCAACGGCTACCGCT<br>GTGTCTGCCCCCCCGGCCACAGCGGGGCCAAGTGCCAGGAGGTC<br>TCAGGTCGGCCCTGCATCACCATGGGCAGCGTCATCCCCGACGG<br>GGCCAAATGGGATGACGACTGCAATACCTGCCAGTGTCTGAACG<br>GCCGAATCGCCTGCTCCAAGGTGTGGTGCGGGCCCAGGCCCTGC<br>CTCCTTCACAAAGGCCATAGCGAGTGCCCCTCCGGGCAATCCTG<br>CATCCCCATCCTGGACGACCAATGCTTCGTGCACCCCTGCACCG<br>GCGTGGGGGAGTGCAGGAGCAGCAGCCTGCAGCCCGTGAAGAC<br>CAAGTGCACCTCCGATAGCTATTACCAGGACAACTGCGCCAACA<br>TCACCTTCACCTTTAACAAAGAAATGATGTCACCCGGCCTGACG<br>ACCGAGCATATCTGCAGCGAGCTGCGGAACCTGAACATCCTGAA<br>AAACGTGTCGGCCGAGTACAGTATATACATCGCCTGCGAGCCCA<br>GCCCCAGCGCCAACAACGAGATACATGTGGCCATAAGCGCCGA<br>AGACATCAGGGACGATGGCAACCCCATCAAGGAGATCACCGAC<br>AAAATAATCGACCTGGTGAGCAAGCGGGATGGCAATAGCAGCC<br>TGATCGCCGCCGTGGCCGAGGTGAGGGTGCAGCGGAGGCCCCT<br>GAAGAATCGCACCGACTTCCTGGTCCCGCTGCTTAGCTCCGTCC<br>TGACGGTCGCCTGGATCTGCTGCCTGGTGACCGCCTTCTACTGGT<br>GCTTGAGGAAGCGGAGGAAGCCCGGGTCACATACCCACTCCGC<br>CAGCGAGGACAACACCACCAATAACGTGCGGGAACAGCTGAAC<br>CAGATCAAGAACCCCATCGAGAAGCATGGTGCCAACACCGTGC<br>CCATCAAGGACTATGAAAACAAGAACTCCAAGATGAGCAAGAT<br>CAGGACCCACAACTCCGAGGTGGAAGAGGACGACATGGACAAG<br>CACCAGCAGAAAGCCCGTTTCGCCAAGCAGCCCGCCTACACCCT<br>GGTGGACCGAGAGGAAAAGCCGCCCAACGGCACCCCCACCAAG<br>CATCCCAACTGGACCAACAAGCAGGACAACCGTGACCTGGAGA<br>GCGCCCAGTCGCTCAACCGCATGGAGTACATCGTG |
| 24 | JAG1-CO14 | ATGCGGTCGCCGAGAACCAGGGGCCGGAGCGGCCGGCCCCTGT<br>CGCTGCTGCTGGCCCTGCTCTGCGCGCTGAGAGCCAAGGTGTGT<br>GGCGCCAGCGGCCAGTTCGAGCTTGAGATCCTGTCCATGCAAAA<br>CGTCAACGGCGAGCTCCAGAACGGAAACTGTTGCGGCGGCGCC<br>CGCAACCCCGGCGACAGGAAGTGCACCCGCGACGAGTGCGACA<br>CCTACTTCAAGGTGTGCCTGAAGGAGTACCAGTCCCGCGTGACC<br>GCTGGCGGACCGTGCAGCTTCGGCTCAGGCAGCACCCCCGTGAT<br>CGGGGGCAATACCTTCAATCTCAAGGCCAGCCGAGGAAACGAC<br>AGGAACAGGATCGTGCTCCCCTTTAGCTTTGCCTGGCCTCGTAG<br>CTACACCCTGCTGGTGGAGGCCTGGGACTCAAGCAATGACACGG<br>TTCAGCCCGACAGCATCATCGAAAAGGCCTCTCACAGCGGAATG<br>ATCAACCCCAGCAGGCAGTGGCAGACCCTCAAGCAGAACACGG<br>GCGTGGCCCACTTCGAGTACCAGATCCGTGTGACCTGCGATGAC<br>TACTATTACGGTTTCGGGTGTAATAAGTTCTGCAGGCCCAGGGA<br>TGACTTTTTTGGCCACTACGCCTGCGACCAGAATGGCAACAAGA<br>CCTGCATGGAGGGATGGATGGGCCCCGAGTGCAACCGTGCCATC<br>TGTCGGCAGGGCTGCTCGCCCAAGCACGGCAGCTGCAAGCTTCC<br>CGGCGACTGTCGGTGCCAGTACGGATGGCAAGGGCTGTACTGCG<br>ACAAGTGCATCCCCCATCCCGGCTGTGTCCACGGTATCTGCAAC<br>GAGCCCTGGCAGTGTCTGTGCGAGACCAACTGGGGCGGCCAGCT<br>GTGCGACAAGGACCTGAACTACTGCGGCACCCACCAGCCCTGCC<br>TGAATGGGGGCACCTGTTCTAACACCGGGCCGGACAAGTACCA<br>GTGTTCCTGCCCCGAGGGCTACAGCGGCCCCAACTGCGAGATCG<br>CCGAGCACGCCTGCCTGTCCGACCCCTGCCATAATAGGGGCTCC<br>TGCAAGGAGACCTCCCTGGGCTTTGAGTGCGAGTGTTCGCCCGG<br>CTGGACCGGCCCCACCTGCAGTACCAACATCGACGACTGCAGCC<br>CCAACAACTGTAGCCACGGCGGCACATGCCAAGACCTGGTGAA<br>CGGCTTCAAGTGCGTCTGCCCGCCGCAGTGGACCGGGAAGACCT<br>GTCAGCTGGATGCCAACGAGTGCGAGGCTAAACCCTGCGTGAA<br>CGCGAAGAGCTGTAAGAACCTGATTGCCAGCTACTACTGCGACT<br>GCCTGCCGGGCTGGATGGGGCAGAATTGCGACATCAACATCAA<br>CGACTGTCTGGGCCAATGCCAGAACGACGCCAGCTGTCGGGACC<br>TGGTCAACGGATACAGGTGTATCTGTCCCCCCGGCTACGCCGGC<br>GACCACTGCGAGCGGGACATCGACGAATGCGCCAGCAACCCTT<br>GTCTGAACGGAGGCCACTGCCAGAACGAGATCAACAGGTTTCA<br>GTGCCTCTGCCCCACCGGGTTCAGCGGGAACCTGTGCCAGCTTG<br>ACATCGATTACTGCGAGCCCAACCCCTGTCAGAATGGGGCGCAG<br>TGCTACAACCGAGCTTCCGATTACTTCTGCAAGTGCCCCGAGGA<br>TTACGAGGGTAAAAATTGCAGCCACCTGAAGGATCACTGCAGG<br>ACCACCCCGTGCGAGGTGATAGACAGCTGCACCGTGGCCATGGC |

TABLE 2-continued

Sequence optimized sequences for human JAG1

| SEQ ID NO | NAME | SEQUENCE |
|---|---|---|
| | | CAGCAACGACACCCCCGAGGGCGTGCGATACATCAGCAGCAAC GTGTGCGGCCCCCACGGCAAGTGCAAAAGCCAGAGCGGCGGAA AATTCACATGCGACTGCAACAAGGGGTTCACGGGCACCTATTGC CACGAGAACATCAACGACTGCGAGTCCAACCCGTGCCGGAATG GCGGCACCTGCATCGACGGCGTGAACTCCTATAAGTGTATCTGC TCGGACGGCTGGGAGGGGGCCTATTGCGAGACCAACATCAACG ACTGCAGCCAGAACCCCTGCCACAACGGCGGCACCTGCAGGGA CCTGGTGAACGACTTCTATTGCGACTGCAAGAACGGCTGGAAGG GCAAGACCTGTCACTCCAGGGACAGCCAGTGCGACGAGGCCAC CTGTAACAACGGCGGGACCTGTTACGACGAGGGGGACGCGTTC AAGTGCATGTGCCCCGGCGGCTGGGAGGGCACCACGTGCAACA TCGCGCGTAACAGCAGCTGTCTGCCGAATCCCTGTCACAATGGC GGCACCTGCGTCGTGAACGGCGAAAGCTTCACCTGCGTGTGTAA GGAAGGCTGGGAGGGCCCCATCTGCGCCCAAAACACCAACGAC TGTAGCCCCCACCCGTGCTACAACAGCGGCACCTGCGTGGATGG CGACAACTGGTATCGGTGCGAGTGTGCCCCTGGCTTTGCGGGCC CCGACTGCCGGATAAACATAAACGAGTGTCAATCGAGCCCCTGC GCCTTCGGGGCCACCTGCGTGGACGAGATCAACGGCTACAGGTG CGTGTGCCCGCCCGGCCACAGCGGCGCGAAATGCCAAGAGGTG AGCGGCAGGCCCTGCATCACCATGGGTTCCGTGATCCCCGACGG GGCAAAATGGGACGACGACTGCAATACCTGCCAGTGCCTCAAC GGGAGGATCGCCTGCAGCAAGGTGTGGTGCGGCCCCAGGCCCT GCCTGCTGCATAAAGGGCACAGCGAGTGCCCCAGCGGGCAGAG CTGCATCCCCATCCTGGACGACCAGTGCTTCGTGCACCCGTGCA CCGGCGTGGGCGAGTGCAGAAGCTCTAGCCTGCAACCCGTGAA GACCAAGTGCACGAGCGACAGCTACTACCAGGACAACTGCGCG AACATCACCTTCACCTTCAATAAGGAGATGATGAGCCCGGGACT CACCACCGAACATATCTGCTCCGAGCTGCGCAACCTCAACATAC TGAAGAATGTGAGCGCCGAGTACTCCATTTACATTGCCTGCGAG CCCAGCCCCTCCGCCAATAATGAAATACACGTCGCCATCAGCGC CGAGGACATCAGGGACGACGGCAACCCCATCAAGGAGATCACC GACAAGATCATCGACCTGGTGAGCAAAAGGGACGGCAATAGCA GCCTCATCGCCGCCGTGGCCGAGGTGAGGGTGCAGAGGAGGCC GCTGAAAAACAGAACCGATTTTCTCGTCCCCCTGCTGTCCTCCGT GCTGACCGTCGCCTGGATCTGTTGCCTGGTGACCGCCTTCTACTG GTGTCTCCGCAAGAGGCGCAAGCCCGGCAGCCACACGCATAGC GCCAGCGAGGACAACACTACTAACAACGTGCGGGAGCAGCTGA ATCAGATCAAGAACCCCATCGAGAAACACGGCGCCAACACTGT GCCCATCAAAGACTACGAGAACAAAAACTCGAAAATGAGCAAG ATCCGCACCCACAACAGCGAGGTGGAGGAGGACGACATGGACA AGCACCAGCAGAAAGCGAGATTCGCCAAACAGCCCGCCTACAC CCTGGTGGACAGGGAGGAGAAGCCCCCAAACGGCACACCCACC AAGCACCCGAACTGGACCAACAAGCAGGACAACCGTGACCTGG AAAGCGCCCAGTCCCTGAATCGCATGGAATATATCGTG |
| 25 | JAG1-CO15 | ATGCGAAGCCCCCGAACCCGGGGCAGGAGCGGGAGGCCCCTGA GCCTGCTGCTGGCCCTTCTGTGCGCCCTTAGGGCCAAGGTGTGT GGGGCCTCCGGCCAGTTCGAGCTGGAGATCCTGAGCATGCAGA ACGTGAACGGTGAGCTGCAGAATGGTAACTGTTGCGGCGGAGC CAGGAACCCGGGCGATAGGAAATGTACCAGGGACGAGTGCGAC ACCTACTTTAAGGTGTGCCTCAAAGAGTACCAGAGCCGGGTCAC CGCCGGCGGCCCCTGCTCGTTCGGCAGCGGTAGCACCCCCGTGA TCGGCGGCAACACATTCAACCTGAAAGCCAGCAGGGGGAACGA CAGGAACCGGATCGTGCTCCCCTTCTCCTTCGCCTGGCCCAGGT CGTACACCCTGCTCGTCGAGGCCTGGGACAGCAGCAACGACACC GTGCAGCCCGACAGCATCATCGAAAAGGCCAGCCACAGCGGAA TGATCAACCCCAGCCGACAGTGGCAGACCCTGAAGCAGAACAC CGGCGTGGCCCACTTCGAGTACCAGATCCGGGTGACCTGCGATG ACTATTACTATGGCTTCGGCTGTAACAAGTTCTGTCGACCCAGG GACGACTTCTTCGGCCACTATGCCTGCGACCAGAACGGTAATAA GACTTGCATGGAGGGCTGGATGGGCCCCGAGTGTAACAGGGCC ATCTGCAGGCAGGGCTGCTCCCCCAAACACGGCTCCTGCAAACT GCCCGGCGACTGCCGCTGCCAGTACGGCTGGCAGGGGCTCTACT GCGATAAGTGCATCCCCCATCCCGGCTGCGTGCATGGCATCTGC AACGAACCCTGGCAGTGCCTGTGCGAGACCAACTGGGGGGGCC AGCTATGCGATAAGGATCTGAACTACTGTGGCACCCACCAGCCC TGCCTGAACGGGGGCACGTGCTCAAACACCGGCCCCGACAAAT ACCAATGCAGCTGCCCCGAGGGCTACAGCGGCCCCAACTGCGA GATCGCCGAGCATGCCTGCCTGAGCGACCCGTGCCACAATAGGG GCTCCTGTAAGGAGACCAGCCTGGGCTTCGAGTGTGAGTGCAGC CCCGGCTGGACCGGCCCCACCTGCTCAACTAACATCGACGACTG TTCCCCCAACAATTGCAGCCACGGCGGCACCTGCCAGGACCTGG TGAACGGCTTTAAGTGTGTGTGCCCCCCCCAGTGGACCGGGAAG ACCTGTCAGCTGGACGCTAACGAGTGTGAGGCCAAGCCCTGTGT CAACGCCAAAAGCTGCAAGAACCTGATAGCCTCCTACTACTGCG |

TABLE 2-continued

Sequence optimized sequences for human JAG1

| SEQ ID NO | NAME | SEQUENCE |
|---|---|---|
| | | ACTGCCTGCCCGGATGGATGGGCCAGAACTGCGACATCAACATC<br>AATGACTGCCTGGGGCAGTGCCAGAACGACGCCAGCTGCCGGG<br>ACCTGGTGAATGGGTACCGCTGCATCTGCCCCCCCGGCTACGCG<br>GGCGACCACTGCGAGAGGGACATCGACGAGTGCGCCTCGAACC<br>CCTGCCTCAACGGGGGCCACTGCCAGAACGAGATCAACCGGTTC<br>CAGTGTCTGTGCCCTACTGGCTTCTCTGGCAACCTGTGTCAGCTG<br>GATATCGATTACTGCGAGCCAAACCCATGCCAGAACGGGGCCC<br>AGTGCTACAATAGGGCCTCCGACTATTTTTGCAAGTGCCCCGAG<br>GACTACGAGGGTAAGAACTGTTCCCATCTCAAGGACCACTGTCG<br>AACCACCCCCTGCGAGGTGATCGACAGCTGCACCGTGGCCATGG<br>CCAGCAATGACACCCCCGAGGGCGTGCGGTACATCTCCAGCAAC<br>GTGTGCGGCCCCCACGGCAAGTGCAAGAGCCAGTCCGGCGGCA<br>AATTTACCTGCGATTGCAACAAGGGGTTCACCGGCACCTACTGT<br>CACGAGAACATCAATGACTGCGAATCCAATCCCTGCAGGAACG<br>GTGGCACGTGCATCGACGGGGTGAATAGCTATAAGTGCATCTGC<br>AGCGACGGGTGGGAAGGGGCCTACTGCGAGACCAACATCAACG<br>ACTGTAGCCAGAACCCGTGCCACAATGGCGGCACTTGTAGGGAT<br>CTCGTGAATGACTTCTATTGCGACTGCAAAAATGGATGGAAGGG<br>GAAGACCTGCCACTCCCGGGACTCCCAGTGCGACGAGGCCACCT<br>GCAATAACGGCGGTACCTGCTACGACGAGGGCGATGCCTTTAAA<br>TGCATGTGCCCCGGCGGCTGGGAGGGAACCACGTGCAACATCG<br>CGAGGAACAGCAGCTGCCTCCCCAATCCCTGTCACAATGGCGGT<br>ACCTGCGTCGTGAACGGGGAGAGCTTCACCTGCGTGTGCAAGGA<br>GGGCTGGGAGGGCCCGATCTGCGCCCAGAACACCAACGACTGC<br>AGCCCACACCCCTGCTACAATAGCGGGACCTGCGTGGACGGAG<br>ACAACTGGTACCGGTGCGAGTGCGCCCCCGGCTTCGCCGGCCCC<br>GACTGCAGGATCAACATCAACGAGTGCCAGAGCAGCCCCTGTG<br>CCTTCGGCGCGACCTGCGTGGATGAAATCAATGGCTACCGGTGC<br>GTGTGCCCCCCCGGCCACAGCGGCGCGAAGTGCCAGGAGGTTA<br>GCGGCAGGCCCTGCATCACCATGGGATCGGTGATCCCCGATGGC<br>GCCAAGTGGGATGACGACTGTAACACATGCCAATGTCTGAATGG<br>ACGGATCGCATGTTCCAAGGTGTGGTGCGGCCCCAGGCCCTGTC<br>TCCTGCACAAAGGCCACAGCGAGTGTCCCAGCGGCCAAAGCTG<br>CATCCCCATCCTGGACGACCAGTGCTTCGTGCATCCCTGCACCG<br>GCGTGGGGGAGTGCCGTAGCAGCAGCCTGCAGCCCGTGAAGAC<br>GAAGTGCACCTCAGACAGCTATTACCAGGATAACTGCGCGAAC<br>ATCACCTTCACCTTTAACAAGGAGATGATGTCCCCCGGCCTGAC<br>CACCGAGCACATCTGCTCGGAGCTGCGCAATCTTAACATCCTGA<br>AAAACGTGTCCGCCGAGTACAGCATTTACATCGCCTGTGAGCCG<br>AGCCCCTCCGCCAACAATGAGATCCATGTCGCCATCAGCGCCGA<br>GGACATCCGGGACGACGGTAATCCGATCAAGGAGATCACAGAT<br>AAGATCATCGACCTGGTGTCCAAGCGGGACGGCAACAGCAGCC<br>TGATCGCCGCCGTCGCCGAGGTGCGTGTGCAGAGACGGCCCCTC<br>AAGAACCGCACCGACTTCCTCGTGCCCCTCCTGAGCTCGGTGCT<br>GACCGTCGCCTGGATCTGCTGCCTGGTGACCGCCTTCTACTGGT<br>GCCTGCGAAAACGCCGGAAGCCGGGGAGCCACACCCACAGCGC<br>CAGCGAGGATAACACCACCAATAACGTGAGGGAACAGCTGAAC<br>CAGATCAAGAACCCCATCGAAAAACACGGCGCCAACACCGTGC<br>CGATCAAGGACTACGAGAACAAAAATAGCAAGATGAGCAAGAT<br>CAGGACACACAACTCTGAGGTGGAGGAGGACGACATGGACAAG<br>CACCAGCAGAAGGCCCGCTTCGCCAAGCAGCCCGCCTACACCCT<br>GGTCGACCGGGAAGAGAAGCCCCCGAACGGCACCCCCACCAAG<br>CATCCTAACTGGACCAACAAGCAAGACAACAGGGACCTGGAAA<br>GTGCCCAGAGCCTGAACCGGATGGAGTACATCGTG |
| 26 | JAG1-CO16 | ATGCGAAGCCCGAGGACCCGGGGCAGGAGCGGCAGGCCGCTAA<br>GCCTGCTGCTGGCCCTCCTCTGCGCCCTCAGGGCCAAGGTGTGC<br>GGCGCCTCCGGCCAATTCGAGCTCGAGATCCTGTCAATGCAGAA<br>CGTGAACGGCGAGCTGCAGAACGGCAACTGCTGCGGCGGCGCC<br>AGGAACCCCGGCGACAGGAAGTGCACCAGGGACGAATGTGACA<br>CCTACTTCAAGGTGTGCCTGAAGGAGTACCAGAGCCGGGTGACC<br>GCTGGCGGCCCATGTAGCTTCGGGAGCGGCAGCACCCCGGTGAT<br>CGGGGGTAACACCTTTAACCTCAAGGCTTCCCGCGGCAACGACA<br>GGAACCGGATCGTGCTGCCCTTCTCCTTCGCCTGGCCCAGGAGC<br>TATACCCTGCTGGTCGAGGCCTGGGACAGCTCCAACGACACCGT<br>GCAACCCGACAGCATCATCGAGAAGGCCTCCCACTCCGGCATGA<br>TCAACCCCAGCAGGCAGTGGCAGACCCTCAAGCAAAACACCGG<br>GGTCGCGCACTTCGAGTACCAGATCAGGGTCACCTGCGACGACT<br>ACTACTACGGCTTCGGCTGCAATAAGTTTTGCCGGCCCAGGGAC<br>GATTTCTTCGGACACTACGCCTGTGACCAGAATGGCAATAAGAC<br>CTGTATGGAAGGGTGGATGGGGCCAGAGTGCAATCGGGCCATC<br>TGCAGGCAAGGCTGCAGCCCCAAACACGGCTCGTGTAAGCTGCC<br>CGGCGACTGCAGGTGCCAGTATGGTTGGCAGGGCCTCTATTGCG<br>ACAAGTGCATCCCCCACCCAGGCTGTGTGCATGGCATCTGTAAC<br>GAACCCTGGCAGTGCCTGTGCGAGACGAACTGGGGGGGCCAAC |

TABLE 2-continued

Sequence optimized sequences for human JAG1

| SEQ ID NO | NAME | SEQUENCE |
|---|---|---|
| | | TGTGCGACAAGGACCTGAACTATTGCGGCACCCACCAGCCGTGC<br>CTGAATGGCGGAACCTGTTCCAACACCGGCCCCGACAAGTACCA<br>GTGCTCCTGTCCCGAGGGGTACAGCGGCCCCAACTGCGAGATCG<br>CCGAGCATGCCTGCCTCAGCGATCCCTGCCACAACAGGGGCAGC<br>TGCAAGGAGACGAGCCTGGGCTTCGAGTGCGAATGCAGCCCCG<br>GTTGGACCGGCCCCACGTGCTCCACCAACATCGACGACTGCTCC<br>CCCAACAATTGCAGCCACGGGGGCACATGTCAGGACCTGGTGA<br>ACGGCTTCAAGTGCGTGTGCCCGCCCCAATGGACCGGCAAGACG<br>TGCCAGCTGGACGCCAACGAGTGCGAAGCCAAGCCATGCGTGA<br>ACGCCAAGAGCTGCAAGAACCTGATCGCCAGCTACTACTGCGAC<br>TGCCTCCCAGGCTGGATGGGCCAGAACTGTGATATCAACATCAA<br>CGACTGCCTCGGCCAGTGCCAGAACGACGCCAGCTGCCGGGAC<br>CTGGTGAACGGGTACCGCTGCATCTGTCCGCCCGGCTACGCCGG<br>AGACCACTGCGAGCGCGACATCGACGAGTGTGCCAGCAACCCC<br>TGCTTAAACGGCGGCCACTGCCAAAATGAAATCAATAGGTTTCA<br>GTGCCTGTGCCCCACCGGGTTCAGCGGCAACCTGTGCCAGCTGG<br>ACATCGACTATTGCGAGCCGAACCCCTGCCAGAACGGGGCCCA<br>GTGCTACAATAGGGCCAGCGATTATTTCTGCAAGTGTCCCGAGG<br>ACTACGAGGGAAAAAACTGCAGCCACCTCAAGGACCACTGTAG<br>GACCACGCCCTGCGAAGTGATCGACTCCTGCACCGTGGCCATGG<br>CCAGCAACGACACCCCCGAGGGCGTGCGCTACATCAGCAGCAA<br>CGTGTGTGGCCCTCACGGCAAATGCAAGAGCCAAAGCGGCGGC<br>AAGTTCACCTGTGACTGCAATAAGGGCTTCACCGGCACCTACTG<br>TCACGAGAACATCAACGACTGCGAGAGCAACCCCTGCAGAAAC<br>GGTGGCACCTGTATAGATGGCGTGAACAGCTACAAGTGCATCTG<br>CAGCGACGGATGGGAAGGCGCCTACTGTGAGACCAACATTAAC<br>GACTGCAGCCAGAACCCCTGCCACAATGGCGGCACCTGCCGCG<br>ACCTGGTCAATGACTTTTACTGCGACTGTAAGAACGGGTGGAAG<br>GGCAAGACCTGCCATAGCCGCGACTCCCAGTGCGACGAGGCAA<br>CCTGCAACAACGGCGGCACCTGTTATGATGAGGGGGACGCATTC<br>AAGTGCATGTGTCCGGGGGGCTGGGAGGGCACAACCTGCAACA<br>TCGCCCGGAACAGCAGCTGCCTCCCAAACCCCTGCCACAACGGG<br>GGCACCTGCGTGGTGAACGGCGAGAGCTTCACCTGCGTGTGTAA<br>GGAGGGCTGGGAGGGCCCCATCTGTGCCCAGAATACCAACGAT<br>TGCTCCCCCCACCCCTGCTACAACAGCGGCACTTGCGTGGACGG<br>CGATAACTGGTATAGGTGTGAGTGCGCCCCCGGCTTCGCAGGCC<br>CCGACTGCCGCATCAACATCAACGAGTGCCAGAGCAGCCCCTGT<br>GCCTTCGGGGCCACCTGCGTGGACGAGATCAACGGCTACCGGTG<br>TGTGTGCCCCCCCGGGCACTCCGGCGCGAAATGCCAGGAGGTGT<br>CCGGCAGGCCCTGCATCACCATGGGCAGCGTGATCCCTGACGGC<br>GCCAAATGGGACGACGACTGTAATACCTGCCAGTGCCTGAATGG<br>CCGAATCGCCTGCTCCAAGGTGTGGTGCGGCCCCAGGCCTTGCC<br>TGTTGCACAAGGGCCACAGCGAGTGCCCCAGCGGCCAGAGCTG<br>TATCCCCATCCTGGACGACCAATGTTTCGTGCATCCCTGCACCG<br>GCGTGGGGGAGTGCCGGTCGTCCAGCCTGCAGCCCGTGAAGAC<br>CAAGTGTACCAGCGACTCCTACTATCAGGACAATTGCGCCAACA<br>TCACCTTCACCTTTAACAAGGAGATGATGAGCCCCGGCCTGACC<br>ACCGAGCACATCTGTTCCGAGCTGAGGAACCTGAACATCCTGAA<br>GAACGTCAGTGCCGAGTACTCCATCTACATCGCCTGTGAACCGT<br>CCCCGTCCGCCAACAATGAGATTCACGTGGCCATCAGCGCCGAA<br>GACATCAGGGACGACGGCAACCCCATCAAGGAGATCACCGACA<br>AGATCATAGACCTTGTGTCCAAGAGGGACGGCAACTCGTCCCTG<br>ATCGCCGCCGTGGCGGAGGTGAGGGTGCAGAGGAGGCCCCTGA<br>AGAACCGCACCGACTTCCTGGTGCCGCTCCTGTCCTCCGTGCTG<br>ACCGTGGCCTGGATCTGCTGCCTGGTGACCGCCTTCTACTGGTG<br>CCTGAGGAAGCGCCGCAAGCCCGGGTCCCACACGCACAGCGCC<br>AGCGAGGATAACACCACCAACAACGTGCGGGAGCAACTGAACC<br>AGATAAAGAACCCCATCGAAAAACACGGAGCGAACACCGTCCC<br>CATCAAGGACTACGAAAACAAGAACAGCAAGATGAGCAAGATC<br>AGGACCCATAACTCCGAGGTGGAGGAGGACGACATGGACAAGC<br>ACCAGCAAAAGGCCCGGTTCGCCAAGCAGCCCGCCTACACCCTG<br>GTGGATCGGGAGGAGAAGCCCCCCAACGGTACCCCGACCAAAC<br>ACCCCAACTGGACCAATAAACAGGACAATAGGGACCTGGAGTC<br>CGCCCAGAGCCTGAACAGGATGGAGTACATAGTG |
| 27 | JAG1-CO17 | ATGAGAAGCCCCAGGACCCGAGGCAGGAGCGGCAGGCCACTGA<br>GCCTGCTCCTTGCCCTGCTGTGCGCCCTGAGGGCAAAGGTGTGC<br>GGCGCCAGCGGCCAGTTCGAGCTGGAAATCCTGTCCATGCAGAA<br>CGTGAACGGGGAGCTGCAGAATGGCAATTGCTGTGGCGGCGCG<br>CGGAACCCCGGCGACAGGAAGTGCACACGGGACGAATGCGACA<br>CGTACTTCAAGGTGTGCCTCAAGGAGTACCAGTCCAGGGTCACC<br>GCCGGCGGGCCCTGCAGCTTCGGAAGCGGCTCCACCCCCGTGAT<br>CGGCGGCAACACATTCAACCTGAAAGCGTCGAGGGGGAATGAC<br>CGCAACAGGATCGTGCTGCCGTTTTCCTTCGCCTGGCCCCGCAG<br>CTACACGCTGCTGGTGGAGGCATGGGACAGCTCCAACGATACCG |

TABLE 2-continued

Sequence optimized sequences for human JAG1

| SEQ ID NO | NAME | SEQUENCE |
|---|---|---|
| | | TGCAGCCCGACAGCATCATCGAGAAGGCCTCCCACAGCGGCAT |
| | | GATCAACCCGAGCAGGCAGTGGCAGACCCTCAAGCAGAACACC |
| | | GGCGTGGCCCACTTCGAGTATCAGATCCGGGTGACCTGCGACGA |
| | | CTATTACTACGGTTTCGGCTGCAACAAGTTTTGTAGGCCCCGAG |
| | | ACGACTTCTTCGGCCACTACGCCTGCGATCAGAACGGGAATAAA |
| | | ACCTGTATGGAGGGGTGGATGGGCCCCGAGTGCAACAGGGCCA |
| | | TCTGCAGGCAGGGATGCTCCCCCAAGCACGGCAGCTGCAAGCTG |
| | | CCAGGAGACTGCAGGTGTCAGTATGGCTGGCAGGGGCTGTACTG |
| | | CGATAAGTGCATTCCGCACCCAGGATGTGTGCACGGAATCTGTA |
| | | ACGAGCCCTGGCAGTGCCTGTGCGAAACCAACTGGGGGGGCCA |
| | | ACTCTGCGACAAGGACCTGAACTACTGCGGCACCCACCAACCCT |
| | | GTCTGAACGGCGGCACCTGCAGCAACACCGGCCCCGACAAATA |
| | | CCAGTGCAGCTGCCCCGAGGGCTACTCCGGGCCCAACTGCGAGA |
| | | TCGCCGAACACGCATGTCTGAGCGACCCTTGCCACAACAGGGGC |
| | | AGCTGCAAGGAGACCTCCCTCGGCTTTGAGTGCGAATGCAGCCC |
| | | CGGCTGGACCGGGCCCACCTGCAGCACGAACATCGACGACTGC |
| | | AGCCCCAACAACTGCTCCCACGGCGGGACGTGCCAGGATCTCGT |
| | | CAACGGCTTCAAGTGCGTGTGCCCCCCCCAGTGGACCGGCAAAA |
| | | CCTGCCAGCTGGACGCAAACGAGTGCGAAGCCAAGCCGTGCGT |
| | | CAACGCGAAGAGCTGCAAGAACCTCATCGCCAGCTACTATTGCG |
| | | ACTGCCTGCCCGGCTGGATGGGCCAGAACTGCGACATAAACATC |
| | | AACGACTGCCTGGGCCAGTGTCAGAACGATGCCTCCTGCAGGGA |
| | | CCTGGTGAACGGGTACCGGTGTATCTGCCCCCCCGGGTACGCGG |
| | | GGGACCACTGCGAGAGAGACATCGATGAGTGCGCCTCCAATCC |
| | | CTGCCTGAACGGCGGCCATTGCCAGAACGAGATCAACCGGTTCC |
| | | AGTGCCTGTGCCCCACCGGCTTCTCCGGCAACCTGTGCCAACTA |
| | | GACATCGACTACTGCGAGCCCAATCCCTGCCAGAACGGCGCCCA |
| | | ATGCTACAACAGGGCCAGCGACTACTTCTGTAAGTGCCCCGAGG |
| | | ACTACGAGGGCAAGAACTGCTCCCATCTGAAGGACCACTGCCG |
| | | GACCACCCCCTGCGAAGTGATCGACAGCTGCACCGTGGCCATGG |
| | | CCAGCAATGACACCCCCGAGGGCGTGAGGTATATCAGCAGCAA |
| | | CGTGTGCGGGCCCCACGGGAAATGCAAGAGCCAGAGCGGCGGC |
| | | AAGTTCACATGCGACTGTAACAAGGGCTTCACGGGAACCTACTG |
| | | TCACGAGAACATCAACGACTGCGAGAGCAACCCCTGCCGCAAC |
| | | GGCGGCACCTGCATCGACGGCGTGAACTCCTATAAGTGCATCTG |
| | | TAGCGATGGCTGGGAAGGGGCCTACTGCGAGACCAACATAAAC |
| | | GACTGCAGCCAGAATCCCTGCCATAACGGGGGCACCTGTCGTGA |
| | | CCTGGTCAACGACTTCTACTGCGACTGTAAGAACGGATGGAAGG |
| | | GTAAGACCTGCCACTCCAGGGACTCCCAGTGTGACGAAGCCACC |
| | | TGCAACAACGGAGGCACCTGCTACGACGAGGGTGACGCCTTTA |
| | | AGTGCATGTGCCCCGGTGGCTGGGAGGGGACCACGTGCAACAT |
| | | CGCCCGCAACAGCAGCTGCCTTCCGAACCCATGCCATAACGGCG |
| | | GCACCTGTGTCGTGAACGGCGAGTCGTTCACCTGTGTGTGCAAG |
| | | GAAGGCTGGGAAGGCCCCATATGCGCCCAGAACACCAACGACT |
| | | GCAGCCCCCATCCCTGCTACAACTCCGGCACCTGCGTGGACGGG |
| | | GACAACTGGTACAGGTGTGAGTGCGCCCCCGGATTCGCCGGTCC |
| | | CGACTGCCGGATCAACATCAATGAGTGTCAATCCAGCCCCTGCG |
| | | CCTTCGGCGCCACCTGCGTGGATGAGATCAACGGCTACAGGTGC |
| | | GTCTGTCCCCCCGGCCACTCCGGCGCCAAATGCCAGGAGGTCAG |
| | | CGGCAGGCCCTGCATCACCATGGGCTCCGTTATCCCCGACGGCG |
| | | CCAAGTGGGACGACGACTGCAATACCTGCCAGTGTCTGAACGG |
| | | GAGGATCGCCTGCTCCAAGGTGTGGTGCGGCCCCAGGCCCTGCC |
| | | TGCTGCACAAGGGCCACAGCGAGTGCCCCAGCGGCCAGTCCTGC |
| | | ATCCCGATCCTGGACGACCAGTGCTTTGTGCACCCCTGCACCGG |
| | | GGTAGGCGAGTGCCGGTCCAGCAGCCTGCAGCCCGTGAAAACC |
| | | AAGTGCACCAGCGACAGCTATTACCAGGACAACTGCGCCAATAT |
| | | CACCTTTACGTTCAATAAAGAGATGATGAGCCCCGGCCTGACCA |
| | | CCGAACACATCTGCAGCGAGCTGCGCAACCTGAACATTCTGAAG |
| | | AACGTGAGCGCCGAGTACAGCATCTATATAGCCTGCGAGCCCAG |
| | | CCCCTCGGCTAATAACGAGATCCACGTGGCCATAAGCGCGGAG |
| | | GACATCCGGGACGACGGCAACCCCATCAAGGAGATCACCGACA |
| | | AGATCATCGACCTGGTGAGCAAGCGCGACGGGAACTCATCACT |
| | | GATCGCCGCCGTGGCCGAGGTGAGGGTGCAGAGGCGGCCCCTC |
| | | AAGAACAGGACCGACTTCCTCGTCCCCCTGCTGTCGAGCGTGCT |
| | | CACCGTGGCCTGGATCTGCTGTCTCGTGACCGCATTCTACTGGTG |
| | | CCTGAGGAAACGGCGCAAGCCCGGCTCGCACACCCACAGCGCC |
| | | AGCGAAGATAACACCACCAACAACGTGAGGGAGCAGCTCAACC |
| | | AGATCAAGAACCCCATAGAGAAGCACGGCGCCAACACGGTGCC |
| | | AATCAAGGACTATGAGAACAAGAACAGCAAGATGTCCAAGATC |
| | | CGCACCCACAACAGCGAAGTCGAGGAAGACGACATGGACAAGC |
| | | ACCAGCAGAAAGCGCGTTTCGCCAAGCAGCCCGCCTACACCCTG |
| | | GTGGACAGGGAGGAGAAGCCCCCCAACGGAACCCCCACAAAGC |
| | | ACCCAAACTGGACGAATAAGCAGGACAACAGGGACCTGGAGAG |
| | | CGCCCAGAGTCTGAACCGGATGGAGTACATCGTG |

TABLE 2-continued

| Sequence optimized sequences for human JAG1 | | |
|---|---|---|
| SEQ ID NO | NAME | SEQUENCE |
| 28 | JAG1-CO18 | ATGAGAAGTCCCAGGACCCGCGGGCGGAGCGGGCGCCCCCTGA<br>GCCTGTTACTGGCCCTCCTGTGTGCCCTGCGCGCGAAGGTGTGC<br>GGGGCCAGCGGCCAGTTCGAGCTGGAGATCCTGAGCATGCAGA<br>ACGTGAACGGGGAACTACAGAACGGCAACTGCTGCGGCGGCGC<br>CCGCAATCCGGGAGACAGGAAGTGTACCAGGGATGAGTGCGAC<br>ACCTACTTTAAAGTGTGCCTGAAGGAGTACCAGAGCAGGGTGAC<br>CGCCGGCGGCCCCTGTAGCTTCGGCAGCGGGAGCACCCCGGTGA<br>TCGGCGGCAACACCTTCAACCTCAAGGCCTCCAGGGGCAACGAC<br>AGGAACCGGATCGTGCTGCCCTTCAGCTTCGCCTGGCCCCGCAG<br>CTACACGCTGCTGGTGGAGGCCTGGGACAGCTCTAATGACACGG<br>TGCAGCCTGACTCAATTATAGAGAAGGCCAGCCACAGCGGCAT<br>GATCAACCCCTCAAGACAGTGGCAGACCCTGAAGCAGAACACC<br>GGTGTGGCACACTTCGAGTATCAGATCAGGGTGACATGCGATGA<br>CTACTACTACGGGTTTGGCTGTAATAAGTTCTGCAGGCCCCAG<br>ACGATTTCTTCGGGCACTATGCCTGCGACCAAAATGGCAACAAG<br>ACCTGCATGGAGGGGTGGATGGGCCCGGAGTGTAACCGAGCCA<br>TATGTAGGCAAGGCTGCAGCCCGAAGCACGGCTCCTGCAAGCTG<br>CCCGGTGATTGCAGGTGCCAGTACGGCTGGCAAGGCCTCTACTG<br>CGACAAGTGCATCCCGCACCCCGGTTGCGTCCACGGCATCTGCA<br>ACGAGCCCTGGCAGTGCCTGTGCGAGACCAACTGGGGGGGCCA<br>GCTGTGCGACAAGGACCTCAATTACTGTGGCACCCACCAGCCCT<br>GCCTCAACGGTGGCACCTGCTCCAACACCGGCCCCGACAAGTAC<br>CAGTGTAGCTGCCCCGAGGGGTACAGCGGCCCGAACTGCGAGA<br>TCGCCGAGCACGCCTGCCTGTCCGACCCCTGCCACAATCGCGGC<br>AGCTGCAAGGAGACCAGCCTGGGGTTCGAATGCGAGTGTTCCCC<br>GGGCTGGACCGGCCCCACCTGCAGCACCAATATCGATGACTGCT<br>CCCCCAACAACTGCAGCCACGGCGGCACCTGTCAGGACCTGGTG<br>AATGGCTTCAAGTGTGTGTGCCCACCGCAGTGGACCGGCAAAAC<br>CTGCCAGCTCGACGCCAACGAGTGCGAGGCCAAGCCCTGTGTGA<br>ATGCCAAGTCCTGCAAGAACCTGATCGCCAGCTACTACTGCGAC<br>TGCCTGCCCGGGTGGATGGGGCAAAATTGCGACATAAACATAA<br>ACGACTGCCTGGGCCAGTGCCAGAACGACGCCTCCTGTCGGGAC<br>CTGGTCAACGGCTACAGGTGCATCTGCCCACCCGGCTACGCCGG<br>CGACCACTGCGAGCGAGATATCGACGAATGCGCCAGCAACCCC<br>TGCCTGAACGGGGGGCACTGCCAGAATGAGATCAACAGGTTTC<br>AGTGCCTGTGCCCCACCGGCTTCAGCGGCAACCTGTGTCAACTG<br>GACATCGACTATTGTGAGCCCAACCCTTGCCAAAACGGGGCCCA<br>GTGCTACAACCGGGCCAGCGATTACTTCTGCAAGTGCCCCGAGG<br>ACTACGAAGGCAAGAACTGCAGCCACCTGAAGGACCACTGTCG<br>GACCACCCCCTGCGAAGTGATCGACAGCTGCACCGTGGCCATGG<br>CCAGCAACGACACCCCCGAGGGCGTGAGGTACATCAGCAGCAA<br>TGTGTGTGGCCCGCACGGCAAGTGCAAGAGCCAGAGCGGCGGC<br>AAGTTCACGTGCGACTGCAACAAGGGCTTTACCGGCACCTACTG<br>CCACGAAAACATCAATGACTGCGAGAGCAACCCGTGTCGGAAC<br>GGCGGCACCTGCATCGACGGGGTGAACAGCTACAAGTGCATAT<br>GCAGCGACGGCTGGGAGGGCGCCTACTGTGAAACCAACATCAA<br>CGACTGCAGCCAGAACCCCTGCCACAATGGCGGGACCTGCAGG<br>GACCTGGTGAATGACTTCTACTGCGACTGCAAGAACGGCTGGAA<br>GGGCAAAACCTGCCACAGCAGGGACAGCCAGTGCGACGAGGCC<br>ACCTGCAACAACGGCGGCACCTGCTATGACGAGGGCGACGCCTT<br>CAAGTGCATGTGCCCCGGCGGATGGGAGGGCACGACCTGCAAT<br>ATCGCAAGGAACAGCTCCTGTCTGCCCAATCCCTGCCACAACGG<br>CGGTACCTGCGTGGTGAACGGGGAAAGCTTCACCTGCGTGTGCA<br>AGGAGGGGTGGGAGGGGCCCATCTGCGCCCAGAACACCAACGA<br>CTGCAGCCCACACCCCTGCTACAATTCCGGCACCTGTGTGGACG<br>GCGACAACTGGTATAGGTGCGAGTGCGCCCCCGGTTTCGCCGGC<br>CCGGACTGCAGGATCAACATCAACGAGTGTCAGTCCAGCCCCTG<br>CGCCTTCGGGGCCACCTGCGTGGACGAGATCAACGGCTATCGTT<br>GCGTGTGCCCCCCCGGCCACTCCGGCGCCAAGTGCCAGGAAGTG<br>TCCGGGCGCCCCTGCATCACCATGGGCTCCGTGATCCCCGATGG<br>CGCCAAGTGGGATGACGACTGCAACACCTGTCAGTGCCTGAACG<br>GCAGGATCGCCTGCAGCAAGGTGTGGTGCGGCCCCCGACCCTGC<br>CTGCTGCACAAGGGGCACAGCGAGTGCCCCTCCGGCCAGTCCTG<br>CATCCCCATACTGGACGATCAGTGCTTCGTGCACCCCTGCACCG<br>GCGTGGGCGAGTGTAGGAGCTCCAGCCTGCAGCCCGTGAAAAC<br>CAAGTGCACCTCGGACAGCTACTATCAGGATAACTGCGCCAACA<br>TTACGTTCACCTTCAACAAGGAGATGATGTCCCCCGGCCTGACC<br>ACGGAGCACATCTGTTCCGAGCTGAGGAACCTCAACATCCTGAA<br>AAATGTGAGCGCCGAGTATAGCATCTATATAGCCTGTGAGCCGT<br>CCCCCTCCGCCAACAACGAGATCCACGTCGCCATCTCCGCAGAG<br>GACATTCGCGACGACGGGAACCCCATAAAGGAAATTACGGACA<br>AAATCATCGACCTGGTGAGCAAGAGGGACGGCAACTCCAGCCT<br>GATCGCCGCCGTGGCCGAGGTGCGCGTGCAACGCAGGCCGCTG<br>AAAAACAGGACGGACTTTCTGGTGCCGCTGCTGTCCTCGGTGCT<br>GACCGTCGCTTGGATCTGCTGCCTGGTGACCGCCTTCTACTGGTG |

TABLE 2-continued

| Sequence optimized sequences for human JAG1 | | |
|---|---|---|
| SEQ ID NO | NAME | SEQUENCE |
| | | CCTGCGCAAAAGGCGCAAGCCCGGTAGCCATACCCACTCCGCCT<br>CCGAAGACAACACCACCAACAACGTGAGGGAGCAGCTGAATCA<br>GATCAAGAACCCTATCGAGAAGCACGGCGCCAACACGGTGCCC<br>ATCAAGGACTATGAAAACAAGAACAGCAAGATGTCCAAGATCA<br>GGACCCACAACAGCGAGGTGGAGGAAGACGACATGGACAAGCA<br>CCAGCAGAAGGCCCGATTCGCCAAGCAGCCCGCTTACACCCTGG<br>TGGACAGGGAGGAAAAGCCCCCGAACGGCACCCCCACCAAACA<br>CCCCAACTGGACTAATAAACAGGACAACCGAGACCTGGAGAGC<br>GCCCAGAGCCTGAACAGGATGGAATATATCGTC |
| 29 | JAG1-CO19 | ATGCGTAGCCCCAGGACCAGGGGTAGGTCCGGGAGGCCCCTGT<br>CACTCCTCCTGGCCCTGCTCTGTGCCCTCCGGGCCAAGGTGTGC<br>GGCGCCAGCGGACAGTTTGAGCTGGAGATCCTGTCCATGCAGAA<br>CGTGAACGGTGAGCTCCAGAACGGGAACTGCTGCGGCGGCGCC<br>AGGAACCCCGGCGATCGCAAGTGTACCAGGGACGAATGTGACA<br>CCTACTTTAAGGTGTGCCTGAAAGAGTACCAGAGCCGCGTCACC<br>GCCGGCGGGCCCTGTTCCTTTGGCTCCGGCAGCACTCCCGTGAT<br>CGGCGGCAACACCTTCAACCTCAAGGCGAGCAGGGGGAACGAC<br>AGGAACAGGATCGTGCTGCCCTTCAGCTTCGCGTGGCCCCGGTC<br>CTACACCCTGCTCGTGGAGGCTTGGGACTCCTCAAACGACACGG<br>TCCAGCCGGATAGCATCATTGAGAAGGCGAGCCACTCCGGCATG<br>ATCAACCCCAGCCGGCAGTGGCAGACCCTCAAGCAGAACACCG<br>GCGTGGCCCACTTCGAGTATCAGATCCGCGTGACCTGCGATGAT<br>TACTACTACGGCTTTGGATGCAACAAGTTCTGCCGGCCCCGCGA<br>CGACTTCTTCGGACACTATGCCTGTGACCAGAACGGGAACAAGA<br>CCTGCATGGAGGGATGGATGGGTCCCGAGTGCAACCGGGCCAT<br>CTGCAGGCAGGGCTGTAGCCCCAAGCACGGGAGCTGCAAGCTG<br>CCCGGCGACTGCAGGTGCCAGTACGGCTGGCAGGGGCTGTACTG<br>CGACAAGTGCATCCCCCACCCGGGATGCGTGCACGGCATCTGCA<br>ACGAGCCCTGGCAGTGCCTCTGCGAGACCAACTGGGGCGGCCA<br>GCTGTGCGACAAGGACCTGAACTACTGTGGCACGCATCAGCCAT<br>GCCTCAATGGTGGCACCTGCAGCAACACGGGCCCCGATAAGTAC<br>CAATGCTCGTGCCCCGAAGGGTACTCCGGCCCAAATTGCGAGAT<br>CGCCGAGCACGCCTGCCTGTCCGACCCCTGCCACAACAGGGGCT<br>CCTGTAAGGAGACCTCCCTGGGCTTCGAGTGTGAGTGCAGCCCC<br>GGGTGGACCGGCCCCACCTGTTCCACCAACATCGACGACTGCAG<br>CCCCAACAACTGCAGCCATGGAGGCACCTGTCAGGACCTGGTGA<br>ATGGTTTCAAGTGTGTGTGCCCGCCCCAGTGGACCGGGAAGACC<br>TGCCAGCTGGACGCCAACGAGTGCGAGGCTAAGCCCTGCGTCA<br>ACGCCAAGAGCTGCAAGAACCTCATCGCCTCCTACTACTGCGAC<br>TGCCTGCCGGGATGGATGGGCCAGAACTGTGACATCAACATCAA<br>CGACTGTCTGGGCCAGTGCCAGAATGACGCCAGCTGCCGAGACC<br>TGGTCAACGGCTACAGGTGCATATGCCCCCCCGGATATGCCGGG<br>GATCACTGCGAGCGGGACATCGACGAGTGCGCCAGCAACCCAT<br>GTCTGAACGGCGGGCACTGCCAGAACGAGATCAACAGGTTTCA<br>ATGCCTGTGCCCCACCGGATTTAGTGGGAACCTCTGTCAGCTGG<br>ACATAGACTACTGCGAGCCGAACCCCTGCCAAAACGGCGCGCA<br>GTGCTACAACAGGGCCAGCGATTACTTCTGCAAGTGCCCGGAGG<br>ACTACGAGGGGAAGAACTGCTCCCACCTGAAGGACCACTGCAG<br>GACCACCCCCTGCGAGGTGATCGACTCGTGCACCGTCGCCATGG<br>CCTCAAACGACACCCCCGAGGGGGTCCGCTACATCTCGAGCAAC<br>GTCTGTGGCCCCCACGGCAAGTGCAAGAGCCAGAGCGGGGGA<br>AGTTCACCTGCGACTGCAACAAAGGCTTCACCGGCACGTACTGT<br>CACGAGAACATCAATGATTGCGAGAGCAACCCCTGCCGGAACG<br>GCGGCACCTGCATCGACGGCGTGAACAGCTACAAGTGCATCTGT<br>AGCGACGGCTGGGAGGGGGCCTACTGCGAGACCAACATCAACG<br>ACTGCAGCCAGAACCCCTGTCACAACGGCGGCACCTGCAGGGA<br>CCTCGTGAATGACTTCTACTGCGACTGCAAAAACGGGTGGAAAG<br>GTAAAACCTGCCATAGCCGGGACAGCCAGTGCGACGAGGCCAC<br>CTGTAATAACGGCGGCACCTGCTACGACGAGGGTGACGCCTTTA<br>AGTGTATGTGCCCCGGCGGCTGGGAGGGCACCACCTGCAATATC<br>GCCCGCAACAGCAGCTGTCTCCCCAACCCCTGCCACAACGGGGG<br>TACCTGCGTGGTCAACGGCGAGTCCTTTACCTGCGTGTGCAAGG<br>AGGGCTGGGAAGGGCCCATCTGCGCCCAGAACACCAACGACTG<br>TAGCCCCCATCCCTGCTACAACTCCGGTACCTGCGTGGACGGCG<br>ACAATTGGTACAGGTGTGAATGCGCACCAGGCTTCGCGGGGCCC<br>GACTGCAGGATCAACATCAACGAATGCCAGAGCAGCCCCTGCG<br>CGTTCGGCGCCACCTGCGTGGACGAGATCAACGGGTACAGGTGC<br>GTGTGCCCCCCCGGGCACAGCGGGGCCAAGTGCCAGGAGGTCT<br>CCGGGCGGCCCTGCATCACCATGGGCTCCGTGATCCCGGATGGG<br>GCGAAGTGGGACGACGATTGCAACACCTGCCAATGCCTGAACG<br>GGAGGATCGCCTGTAGCAAGGTCTGGTGCGGACCCCGGCCCTGC<br>CTCCTGCACAAAGGCCACTCCGAATGCCCCAGCGGACAAAGCTG<br>CATACCGATCCTGGACGACCAATGCTTCGTGCATCCCTGCACAG<br>GCGTGGGTGAATGCAGGAGCTCCAGCCTGCAGCCAGTGAAGAC |

TABLE 2-continued

Sequence optimized sequences for human JAG1

| SEQ ID NO | NAME | SEQUENCE |
|---|---|---|
| | | GAAGTGCACCAGCGATAGCTACTACCAGGATAATTGTGCCAACA<br>TAACCTTCACCTTCAACAAGGAGATGATGTCCCCCGGCCTGACC<br>ACCGAGCACATCTGTAGCGAGCTCCGCAACCTGAACATCCTCAA<br>GAACGTGAGCGCCGAGTACTCCATCTACATCGCCTGCGAGCCCT<br>CGCCCAGCGCCAATAACGAGATCCACGTGGCCATCTCCGCCGAG<br>GACATCCGCGACGACGGCAATCCCATCAAGGAGATTACCGACA<br>AGATCATCGACCTGGTGAGCAAGCGCGATGGCAACAGCAGCCT<br>GATCGCCGCGGTGGCCGAGGTGAGGGTGCAGAGGCGGCCCCTC<br>AAGAACCGCACGGACTTCCTGGTGCCACTGCTGAGCTCCGTGCT<br>GACCGTGGCCTGGATCTGCTGTCTGGTCACCGCCTTCTACTGGTG<br>CCTGCGGAAACGGAGGAAGCCCGGATCCCACACCCACTCCGCCT<br>CCGAAGACAACACCACGAACAACGTCAGGGAGCAGCTGAACCA<br>GATCAAGAACCCCATCGAGAAGCATGGCGCCAACACCGTGCCA<br>ATCAAAGACTACGAGAACAAGAACAGCAAGATGAGCAAGATCC<br>GGACCCACAACAGCGAAGTAGAAGAGGACGACATGGATAAGCA<br>CCAGCAGAAGGCCAGGTTCGCCAAGCAACCCGCCTACACCCTCG<br>TGGACCGCGAGGAGAAACCCCCCAACGGCACCCCCACCAAGCA<br>CCCCAATTGGACCAACAAGCAAGATAACCGCGACCTGGAGAGC<br>GCCCAGAGCCTCAACCGGATGGAATACATCGTG |
| 30 | JAG1-CO20 | ATGAGGAGCCCAAGGACCAGGGGGAGGAGCGGCAGGCCGCTCA<br>GCCTGCTGCTCGCCCTGCTGTGCGCCCTGCGGGCAAAGGTGTGC<br>GGGGCCAGCGGCCAGTTCGAGCTGGAAATCCTGAGCATGCAGA<br>ACGTGAACGGCGAGCTGCAAAATGGTAATTGCTGCGGGGGCGC<br>CAGGAACCCGGGCGACAGGAAGTGCACCAGGGACGAGTGCGAC<br>ACCTATTTCAAGGTGTGCCTGAAGGAATACCAGAGCCGCGTCAC<br>GGCCGGGGGCCCGTGCTCCTTCGGCAGTGGCTCCACCCCCGTGA<br>TCGGCGGCAACACCTTTAACCTGAAGGCCTCCCGGGGTAACGAC<br>AGGAACAGGATCGTGCTGCCCTTCTCCTTCGCCTGGCCGAGGTC<br>CTACACCCTCCTGGTAGAGGCCTGGGACAGCAGCAATGATACGG<br>TGCAGCCCGACTCCATCATAGAAAAGGCCAGCCACTCCGGGATG<br>ATCAATCCGAGCAGGCAGTGGCAAACCCTCAAGCAGAACACCG<br>GTGTGGCCCACTTTGAGTACCAGATCAGGGTCACCTGCGACGAC<br>TACTACTACGGCTTCGGCTGCAACAAGTTTTGCAGGCCGAGGGA<br>CGACTTCTTCGGCCACTACGCCTGCGACCAGAATGGCAACAAGA<br>CCTGCATGGAAGGCTGGATGGGCCCGGAATGCAATCGCGCCATC<br>TGTAGGCAGGGGTGCAGCCCAAAGCATGGGAGCTGCAAGCTGC<br>CCGGGGACTGCAGGTGTCAGTACGGATGGCAGGGGCTGTACTGT<br>GACAAGTGTATCCCACATCCGGGCTGCGTGCACGGAATATGCAA<br>CGAGCCCTGGCAGTGCCTGTGTGAAACGAACTGGGGCGGTCAG<br>CTGTGCGACAAGGACCTGAACTACTGCGGCACCCACCAGCCCTG<br>CCTGAACGGCGGGACGTGTTCCAACACCGGCCCCGACAAGTATC<br>AGTGTAGCTGCCCCGAGGGCTATAGCGGCCCGAACTGCGAGATC<br>GCCGAACATGCCTGTCTCAGCGACCCCTGTCACAACAGGGGTAG<br>CTGTAAGGAAACCAGCCTCGGGTTTGAGTGTGAATGCTCCCCGG<br>GCTGGACCGGGCCCACCTGTTCCACCAACATCGACGACTGCTCC<br>CCCAATAACTGCAGCCATGGCGGCACGTGTCAGGACCTCGTCAA<br>TGGCTTTAAGTGTGTGTGCCCCCCGCAGTGGACCGGCAAGACGT<br>GCCAGCTGGACGCCAACGAGTGTGAGGCCAAGCCCTGCGTCAA<br>CGCAAAGAGCTGCAAGAACCTGATCGCCTCCTACTATTGTGACT<br>GCCTGCCCGGGTGGATGGGACAGAACTGCGACATCAATATCAA<br>CGATTGCCTGGGGCAGTGCCAGAACGACGCGAGCTGCAGGGAC<br>CTGGTCAACGGCTACCGATGCATCTGCCCCCCGGGCTACGCCGG<br>CGACCACTGTGAAAGGGACATCGACGAGTGCGCCAGCAACCCC<br>TGCCTGAACGGGGGCCACTGCCAGAACGAGATCAATAGGTTCC<br>AGTGCCTGTGCCCGACCGGTTTTAGCGGCAACCTGTGCCAGCTG<br>GACATTGACTATTGCGAGCCCAACCCCTGCCAGAACGGGGCCCA<br>GTGCTACAACAGGGCCTCGGACTACTTCTGTAAGTGCCCCGAGG<br>ACTATGAGGGCAAGAACTGCAGCCATCTGAAGGACCACTGCAG<br>GACCACCCCGTGCGAGGTCATCGACAGCTGCACCGTGGCCATGG<br>CCTCCAATGATACCCCCGAGGGCGTGAGGTACATCTCCTCCAAC<br>GTGTGTGGCCCCCACGGCAAGTGCAAAAGCCAGAGCGGCGGCA<br>AGTTCACCTGTGACTGTAACAAGGGCTTCACCGGCACCTACTGC<br>CATGAAAACATCAACGATTGCGAGTCTAATCCCTGCCGGAACGG<br>CGGCACCTGCATCGATGGCGTGAACAGCTATAAATGTATCTGCT<br>CCGATGGGTGGGAGGGCGCATACTGCGAAACCAACATCAACGA<br>CTGCTCCCAGAACCCCTGCCATAACGGCGGCACCTGCCGCGACC<br>TCGTCAACGATTTCTACTGCGACTGCAAGAACGGCTGGAAGGGC<br>AAGACCTGCCACAGCCGAGACAGCCAGTGCGACGAGGCCACGT<br>GCAACAACGGAGGGACCTGTTATGACGAGGGCGACGCCTTCAA<br>GTGCATGTGCCCCGGGGGCTGGGAGGGCACGACCTGCAACATT<br>GCCCGCAATAGCAGCTGCTTGCCCAACCCCTGTCACAACGGCGG<br>AACCTGCGTCGTGAACGGCGAGTCCTTCACCTGCGTTTGCAAAG<br>AGGGCTGGGAGGGCCCAATCTGTGCCCAGAACACCAATGACTG<br>CAGCCCCCACCCCTGCTACAATTCCGGTACCTGCGTGGACGGCG |

TABLE 2-continued

Sequence optimized sequences for human JAG1

| SEQ ID NO | NAME | SEQUENCE |
|---|---|---|
| | | ACAACTGGTATAGGTGCGAGTGCGCCCCGGGATTCGCCGGCCCG |
| | | GACTGCAGGATCAACATCAACGAGTGCCAGAGCAGCCCCTGCG |
| | | CCTTCGGGGCCACCTGTGTGGACGAGATCAATGGCTACAGGTGT |
| | | GTCTGCCCCCCCGGACACTCGGGCGCGAAATGCCAAGAGGTGTC |
| | | CGGCAGGCCCTGCATCACCATGGGTTCCGTGATACCCGACGGGG |
| | | CAAAGTGGGACGACGATTGCAATACCTGCCAATGCCTGAACGG |
| | | CAGGATCGCCTGTAGCAAGGTGTGGTGTGGCCCGAGGCCTTGCC |
| | | TCCTGCATAAAGGCCACAGCGAGTGTCCCTCCGGCCAGAGCTGT |
| | | ATCCCCATCCTCGACGATCAATGCTTTGTGCACCCTTGCACCGG |
| | | GGTGGGCGAGTGTCGCAGCAGCAGCCTGCAGCCCGTGAAGACC |
| | | AAATGCACCAGCGATAGCTACTACCAGGACAACTGCGCGAATA |
| | | TCACCTTTACGTTCAACAAGGAGATGATGAGCCCGGGCCTGACC |
| | | ACAGAGCACATCTGCAGCGAGCTGCGCAACCTGAACATCCTGA |
| | | AGAACGTGTCTGCCGAGTATAGCATCTACATCGCCTGCGAACCC |
| | | AGCCCCTCCGCAAATAATGAGATCCACGTGGCGATCTCGGCCGA |
| | | GGACATCAGGGACGACGGGAACCCCATCAAAGAGATCACCGAC |
| | | AAGATCATCGATCTGGTGAGCAAGCGGGACGGCAACAGCTCCC |
| | | TCATCGCCGCCGTGGCTGAGGTCCGAGTGCAGCGGCGTCCCCTT |
| | | AAGAACAGGACCGACTTCCTGGTGCCCCTCCTGTCGTCCGTGCT |
| | | CACCGTGGCCTGGATCTGTTGCCTGGTGACCGCCTTCTACTGGTG |
| | | CCTGCGTAAGCGAAGGAAGCCCGGATCCCACACCCACAGCGCC |
| | | AGCGAAGACAACACCACCAATAACGTCCGAGAGCAGCTGAACC |
| | | AGATCAAGAACCCCATAGAGAAACACGGGGCCAACACCGTGCC |
| | | TATCAAGGACTACGAGAACAAAAATAGCAAAATGAGCAAGATT |
| | | AGGACCCCACAACTCCGAGGTGGAGGAGGACGACATGGACAAGC |
| | | ATCAGCAGAAGGCCCGCTTCGCCAAGCAACCCGCCTACACCCTG |
| | | GTGGACCGAGAGGAAAAGCCCCCCAACGGGACCCCCACGAAGC |
| | | ACCCCAACTGGACCAATAAGCAGGATAACAGGGACCTCGAGAG |
| | | CGCCCAGTCCCTGAATCGCATGGAGTACATCGTG |
| 31 | JAG1-CO21 | ATGAGGAGCCCCCGCACCAGGGGGCGTAGCGGCCGCCCCCTGA |
| | | GCCTGCTGCTGGCTCTGCTGTGTGCCCTGCGAGCCAAAGTGTGC |
| | | GGGGCCTCCGGCCAGTTCGAGCTGGAGATCCTGAGCATGCAGA |
| | | ACGTGAACGGCGAGCTCCAGAACGGCAACTGCTGCGGCGGCGC |
| | | CCGCAACCCCGGCGACAGGAAGTGCACTCGGGACGAGTGCGAC |
| | | ACCTATTTCAAGGTCTGCCTGAAGGAGTACCAAAGCCGTGTGAC |
| | | CGCCGGCGGGCCGTGCAGCTTCGGAAGCGGCTCCACCCCGGTCA |
| | | TCGGGGGGAACACCTTTAACCTGAAGGCCAGCCGGGGTAACGA |
| | | CAGGAACCGAATCGTACTGCCCTTCAGCTTCGCCTGGCCCCGGA |
| | | GCTACACCCTGCTGGTCGAGGCATGGGACTCCAGCAACGATACC |
| | | GTGCAGCCCGACAGCATCATCGAGAAAGCCAGCCACAGCGGGA |
| | | TGATTAATCCCAGCAGACAGTGGCAGACCCTGAAGCAGAACAC |
| | | CGGCGTGGCCCACTTCGAGTACCAAATCCGGGTGACCTGCGACG |
| | | ATTATTACTACGGGTTTGGCTGTAATAAATTCTGCCGGCCCCGG |
| | | GATGACTTTTTCGGCCATTACGCCTGCGATCAGAACGGTAACAA |
| | | GACCTGCATGGAGGGCTGGATGGGACCGGAGTGTAACAGGGCT |
| | | ATCTGCCGACAGGGTTGTAGCCCCAAGCACGGAAGCTGCAAGCT |
| | | GCCCGGCGACTGCCGGTGTCAGTACGGCTGGCAGGGCCTGTACT |
| | | GCGATAAGTGCATCCCCCACCCCGGCTGCGTTCACGGCATCTGC |
| | | AACGAGCCCTGGCAGTGCCTGTGTGAAACCAACTGGGGTGGAC |
| | | AGCTGTGCGACAAGGATCTGAACTATTGCGGCACCCACCAGCCC |
| | | TGCCTGAACGGCGGAACCTGCAGCAACACCGGCCCCGATAAGT |
| | | ACCAGTGCAGCTGCCCCGAAGGCTACTCCGGCCCCAACTGCGAG |
| | | ATCGCCGAGCACGCCTGCCTGAGCGACCCGTGCCACAACAGGG |
| | | GGAGCTGCAAAGAGACCAGCCTGGGTTTCGAGTGCGAGTGCAG |
| | | CCCCGGCTGGACCGGGCCCACTTGCTCCACCAACATTGACGACT |
| | | GTAGCCCGAACAATTGCAGCCACGGCGGCACCTGCCAGGACCT |
| | | GGTGAATGGCTTCAAGTGCGTGTGTCCCCCCCAGTGGACCGGGA |
| | | AGACCTGCCAGCTGGACGCCAACGAGTGCGAGGCCAAGCCCTG |
| | | TGTGAACGCCAAGTCCTGCAAGAACCTGATCGCCTCCTACTACT |
| | | GTGACTGTCTCCCCGGGTGGATGGGCCAGAACTGCGACATCAAC |
| | | ATCAACGATTGCCTCGGCCAGTGCCAGAACGACGCCAGCTGTAG |
| | | GGACCTCGTGAACGGCTACCGGTGCATCTGCCCGCCCGGGTACG |
| | | CCGGAGACCACTGCGAGAGGGACATTGACGAGTGCGCCTCGAA |
| | | CCCCTGCCTGAACGGCGGCCACTGTCAGAACGAGATCAATAGGT |
| | | TCCAGTGTCTGTGTCCCACCGGCTTCTCCGGCAACCTGTGTCAGC |
| | | TGGACATCGACTACTGTGAGCCCAATCCCTGCCAGAATGGCGCC |
| | | CAGTGCTATAACCGGGCCTCCGACTACTTTTGCAAGTGCCCCGA |
| | | AGATTACGAGGGCAAGAACTGCAGCCATCTGAAGGACCACTGC |
| | | AGGACGACTCCCTGCGAGGTGATCGACAGCTGTACTGTCGCCAT |
| | | GGCCAGCAACGACACCCCCGAGGGGGTCCGCTATATCAGCAGC |
| | | AACGTGTGCGGGCCCCATGGGAAATGCAAATCCCAGTCAGGGG |
| | | GCAAGTTTACCTGCGACTGTAACAAAGGCTTCACCGGCACCTAC |
| | | TGCCACGAAAACATCAACGACTGCGAATCGAACCCCTGCCGGA |
| | | ACGGCGGGACCTGCATCGATGGAGTGAACAGCTACAAGTGCAT |

TABLE 2-continued

Sequence optimized sequences for human JAG1

| SEQ ID NO | NAME | SEQUENCE |
|---|---|---|
| | | CTGCAGCGACGGGTGGGAGGGCGCGTACTGCGAAACCAATATC<br>AATGACTGCAGCCAGAACCCCTGCCATAACGGAGGCACCTGCA<br>GGGACCTGGTGAACGACTTCTACTGCGATTGCAAGAACGGCTGG<br>AAGGGGAAGACCTGCCATAGCAGGGACAGCCAGTGTGACGAGG<br>CCACCTGCAACAACGGCGGCACATGTTACGATGAGGGCGACGC<br>CTTCAAATGCATGTGCCCCGGCGGCTGGGAGGGCACCACATGCA<br>ACATCGCCCGGAACAGCAGCTGCCTCCCCAACCCCTGCCATAAT<br>GGCGGTACCTGCGTGGTGAACGGCGAGAGTTTCACCTGCGTGTG<br>CAAGGAGGGCTGGGAGGGCCCCATCTGCGCGCAGAACACCAAT<br>GACTGCTCGCCCCACCCCTGCTACAACAGCGGCACCTGCGTGGA<br>CGGTGACAACTGGTACCGTTGCGAGTGCGCCCCAGGCTTCGCCG<br>GCCCGGACTGCAGGATCAACATCAACGAGTGCCAAAGCTCCCCT<br>TGCGCCTTTGGCGCAACCTGTGTGGACGAGATCAATGGGTACAG<br>GTGCGTGTGCCCCCCCGGCCATTCCGGGGCCAAGTGCCAAGAGG<br>TGTCCGGCCGGCCCTGCATTACCATGGGCAGCGTTATCCCCGAC<br>GGCGCCAAGTGGGACGACGACTGCAATACCTGCCAGTGCCTCA<br>ACGGCAGGATCGCCTGCAGCAAGGTGTGGTGCGGACCCAGGCC<br>GTGCCTGCTGCATAAGGGCCACAGCGAGTGCCCGAGCGGTCAGT<br>CCTGCATCCCCATCCTCGACGACCAGTGTTTCGTGCACCCCTGCA<br>CGGGCGTGGGTGAGTGCCGATCCTCCAGCCTGCAGCCCGTCAAA<br>ACCAAGTGCACCTCCGACAGCTACTACCAGGACAACTGCGCCAA<br>CATAACCTTCACGTTTAACAAGGAGATGATGAGCCCCGGCCTGA<br>CCACCGAGCACATCTGCAGCGAGCTGAGGAACCTGAACATCCTG<br>AAGAACGTGTCCGCCGAGTACAGCATCTACATCGCCTGTGAGCC<br>CAGCCCCTCCGCCAACAACGAGATCCATGTTGCCATCTCGGCCG<br>AAGATATTAGGGACGACGGCAACCCCATCAAGGAGATCACCGA<br>CAAGATCATAGACCTGGTGAGCAAGCGGGACGGCAATTCCAGC<br>CTGATCGCCGCCGTGGCCGAGGTGAGAGTGCAGAGGAGGCCCC<br>TGAAGAACCGGACCGATTTCCTGGTGCCCCTGCTGAGCAGCGTG<br>CTGACCGTGGCCTGGATCTGCTGCCTGGTGACCGCATTTTACTG<br>GTGTCTGAGGAAGCGGAGGAAACCCGGCAGCCACACCCACAGC<br>GCAAGCGAGGATAACACCACGAATAACGTGCGCGAGCAGCTGA<br>ACCAAATCAAGAACCCCATCGAGAAGCACGGGGCCAACACCGT<br>GCCCATCAAGGACTACGAGAATAAGAACTCGAAGATGAGCAAG<br>ATCAGGACGCACAACTCCGAGGTGGAGGAGGACGACATGGATA<br>AGCACCAGCAGAAAGCCCGGTTCGCCAAGCAGCCCGCCTACAC<br>CCTGGTTGACCGCGAGGAGAAACCCCCCAACGGCACCCCCACC<br>AAGCACCCCAACTGGACCAACAAGCAGGACAACCGAGACCTGG<br>AGAGCGCCCAGAGCCTGAACAGGATGGAGTATATCGTG |
| 32 | JAG1-CO22 | ATGAGGTCCCCCAGGACCAGGGGCAGGAGCGGGAGGCCCCTGT<br>CCCTTCTGCTGGCGCTGCTGTGCGCCCTGCGCGCCAAGGTGTGC<br>GGGGCAAGCGGCCAGTTCGAGCTCGAAATACTCAGCATGCAAA<br>ACGTCAACGGCGAGCTGCAGAACGGCAACTGTTGCGGTGGCGC<br>CAGGAACCCCGGGGATCGCAAGTGCACCAGGGACGAGTGTGAT<br>ACCTACTTCAAAGTGTGTCTGAAGGAGTACCAGAGCCGGGTGAC<br>CGCCGGGGGCCCCTGTTCCTTCGGCAGCGGGAGCACCCCCGTCA<br>TCGGCGGGAATACGTTTAACCTGAAGGCCTCCAGGGGCAACGAT<br>AGGAACCGGATCGTGCTCCCTTTCAGCTTCGCCTGGCCCAGGTC<br>CTACACCCTGCTGGTGGAGGCCTGGGACTCCAGCAATGACACTG<br>TCCAGCCTGACAGTATCATAGAGAAAGCCTCCCACTCCGGCATG<br>ATCAACCCCAGTCGCCAGTGGCAGACCCTGAAGCAGAACACCG<br>GCGTGGCCCACTTCGAGTACCAGATCCGGGTGACCTGCGACGAC<br>TATTACTACGGCTTCGGATGCAATAAGTTCTGTAGGCCCCGCGA<br>CGATTTCTTCGGCCATTATGCCTGCGACCAGAACGGCAACAAGA<br>CCTGCATGGAGGGCTGGATGGGGCCCGAGTGCAACAGGGCCAT<br>CTGCAGGCAGGGGTGCTCCCCCAAACACGGGAGCTGCAAACTG<br>CCGGGGGACTGCAGGTGCCAATACGGCTGGCAGGGCCTGTACT<br>GCGACAAGTGCATCCCGCACCCCGGGTGCGTGCACGGCATTTGC<br>AACGAACCCTGGCAGTGCCTCTGCGAAACCAATTGGGGAGGCC<br>AGCTGTGCGACAAGGATCTGAACTACTGCGGCACGCACCAGCCC<br>TGCCTCAACGGGGGGACCTGTAGCAACACGGGCCCCGACAAGT<br>ACCAGTGCTCCTGCCCGGAGGGATACTCTGGCCCCAACTGCGAG<br>ATCGCCGAGCACGCCTGCCTCTCCGATCCGTGCCACAATAGGGG<br>CAGCTGCAAGGAAACGTCCCTGGGCTTCGAATGCGAATGCAGTC<br>CCGGATGGACCGGCCCCACCTGCAGCACCAACATCGACGACTGC<br>AGCCCCAACAACTGCAGCCACGGCGGCACCTGCCAAGATCTCGT<br>GAACGGCTTCAAGTGCGTGTGCCCCCCCCAGTGGACCGGGAAA<br>ACCTGCCAACTCGACGCCAATGAGTGTGAGGCCAAGCCCTGCGT<br>GAACGCCAAGTCGTGCAAAAACCTGATCGCCAGCTACTACTGCG<br>ACTGCCTGCCCGGCTGGATGGGGCAGAACTGCGACATCAACATC<br>AACGACTGCCTGGGGCAGTGCCAGAATGACGCTAGCTGCCGAG<br>ACCTGGTCAATGGATACCGGTGCATATGCCCCCCGGGCTACGCC<br>GGCGACCATTGCGAGCGGGACATCGACGAGTGCGCCAGCAACC<br>CATGCCTGAACGGCGGGCACTGCCAGAACGAAATAAACAGGTT |

TABLE 2-continued

Sequence optimized sequences for human JAG1

| SEQ ID NO | NAME | SEQUENCE |
|---|---|---|
| | | CCAGTGTCTGTGCCCGACGGGCTTTAGCGGCAACCTCTGCCAGT<br>TGGATATCGACTATTGCGAGCCTAACCCTTGCCAGAACGGCGCC<br>CAGTGCTATAACCGCGCAAGCGATTATTTCTGCAAATGCCCCGA<br>GGACTACGAGGGCAAGAATTGCAGCCATCTGAAAGACCACTGT<br>CGGACGACCCCCTGCGAGGTGATCGACAGCTGCACCGTGGCCAT<br>GGCCTCCAACGACACCCCCGAAGGGGTGCGCTATATCTCCAGCA<br>ACGTGTGCGGCCCCCACGGCAAGTGCAAGAGCCAGTCAGGGGG<br>CAAATTCACCTGCGACTGCAACAAGGGCTTCACCGGGACCTACT<br>GCCACGAGAACATCAACGACTGCGAGAGCAACCCCTGCCGGAA<br>CGGCGGCACCTGCATCGATGGGGTGAACTCCTATAAGTGCATCT<br>GTAGCGATGGATGGGAGGGGGCCTACTGCGAAACCAACATCAA<br>CGACTGCAGCCAGAACCCCTGCCACAACGGGGGCACCTGCAGG<br>GACCTCGTGAACGACTTCTACTGCGACTGCAAGAACGGCTGGAA<br>GGGCAAGACATGCCACTCCCGGGACTCACAATGCGACGAAGCG<br>ACCTGCAACAATGGCGGCACCTGTTACGATGAGGGGGATGCCTT<br>TAAGTGCATGTGCCCCGGTGGCTGGGAGGGCACCACCTGCAATA<br>TCGCCAGGAATTCCTCCTGCCTGCCCAACCCCTGCCATAATGGC<br>GGGACCTGCGTCGTGAACGGCGAGAGCTTCACCTGCGTGTGCAA<br>AGAGGGGTGGGAAGGACCCATCTGCGCCCAAAATACGAACGAC<br>TGCAGCCCCCACCCCTGTTACAACAGCGGCACGTGCGTGGATGG<br>GGACAACTGGTACCGCTGCGAGTGCGCCCCCGGCTTTGCAGGCC<br>CGGACTGTCGGATCAACATCAACGAGTGCCAGAGCAGCCCCTGC<br>GCCTTCGGAGCCACGTGCGTGGACGAGATCAATGGCTACAGATG<br>CGTGTGCCCCCCGGGACACAGCGGCGCCAAGTGCCAGGAAGTG<br>TCCGGCCGTCCCTGCATCACCATGGGTAGCGTCATCCCCGACGG<br>CGCCAAGTGGGACGATGACTGCAACACGTGTCAGTGTCTGAACG<br>GCCGAATCGCCTGCTCCAAGGTGTGGTGCGGCCCCCGGCCCTGC<br>CTGCTGCACAAGGGCCACAGCGAGTGCCCCAGCGGCCAGTCGT<br>GTATCCCCATCCTCGACGACCAATGCTTCGTGCACCCCTGCACC<br>GGCGTGGGCGAGTGCCGCAGCTCGAGCCTGCAGCCCGTGAAGA<br>CCAAGTGCACCAGCGATAGCTACTACCAGGACAATTGCGCCAAC<br>ATCACCTTCACCTTTAACAAGGAGATGATGAGCCCCGGCCTGAC<br>GACCGAACACATCTGCTCCGAGCTGAGGAACCTGAACATCCTGA<br>AGAATGTCAGCGCTGAGTACTCCATCTACATCGCCTGTGAGCCC<br>AGCCCAAGCGCCAACAATGAGATCCACGTCGCGATCTCCGCCGA<br>GGACATCCGCGACGATGGCAACCCCATCAAGGAGATCACCGAC<br>AAGATCATCGACCTGGTGAGCAAGAGGGACGGCAACAGCTCCC<br>TGATCGCCGCGGTGGCCGAGGTGAGGGTCCAAAGGAGGCCCCT<br>GAAGAACAGGACCGACTTCCTGGTGCCCCTGCTGTCGAGCGTGC<br>TGACCGTGGCCTGGATCTGCTGCCTGGTGACCGCGTTCTACTGG<br>TGCCTGCGTAAGAGGAGGAAGCCCGGCAGCCACACCCATAGCG<br>CGTCCGAGGATAACACCACCAATAACGTGAGGGAGCAGCTCAA<br>CCAGATCAAGAACCCAATCGAGAAGCACGGTGCCAACACTGTG<br>CCCATCAAGGACTATGAGAACAAGAACAGCAAGATGAGTAAGA<br>TCAGGACACACAACTCCGAGGTGGAAGAAGACGACATGGACAA<br>GCACCAGCAGAAGGCCCGGTTCGCCAAGCAGCCCGCCTACACC<br>CTGGTGGACAGGGAAGAGAAACCCCCCAACGGTACACCCACGA<br>AACACCCCAACTGGACCAATAAGCAGGACAACAGGGACCTGGA<br>GTCCGCCCAGAGTCTGAACAGGATGGAGTACATCGTG |
| 33 | JAG1-CO23 | ATGCGGTCCCCCCGGACCAGGGGTAGGAGCGGCCGCCCACTGTC<br>CCTGCTGCTGGCCCTGCTGTGTGCCCTGAGGGCCAAGGTGTGCG<br>GCGCCTCCGGACAATTCGAGCTGGAGATTCTCTCGATGCAGAAC<br>GTGAACGGCGAACTGCAGAACGGAAATTGCTGTGGCGGCGCCA<br>GGAATCCCGGCGATAGAAAGTGCACCAGGGACGAGTGTGACAC<br>GTACTTCAAGGTGTGCCTGAAGGAGTACCAGAGCCGCGTGACCG<br>CCGGCGGGCCCTGCTCCTTCGGGTCAGGCAGCACCCCCGTGATC<br>GGCGGGAACACCTTCAACCTCAAGGCCTCCAGGGGCAACGACA<br>GGAATAGGATCGTGCTCCCCTTCAGCTTCGCCTGGCCCAGGTCC<br>TACACCCTGCTGGTAGAGGCCTGGGACTCCAGCAACGACACCGT<br>GCAGCCCGATAGCATCATCGAGAAGGCTAGCCACAGCGGAATG<br>ATCAACCCCAGCCGCCAGTGGCAGACCCTGAAACAGAACACCG<br>GCGTAGCCCACTTTGAGTACCAGATCAGGGTGACCTGCGACGAC<br>TATTACTATGGCTTCGGTTGCAACAAGTTCTGCCGGCCTCGCGA<br>CGACTTCTTCGGACACTACGCCTGTGATCAGAACGGGAACAAGA<br>CCTGTATGGAGGGTTGGATGGGCCCCGAATGCAACAGGGCCATC<br>TGCAGGCAGGGCTGCTCCCCCAAGCACGGGAGCTGCAAGCTGC<br>CCGGCGACTGCCGGTGCCAGTACGGCTGGCAGGGTCTGTACTGC<br>GACAAGTGCATCCCCCATCCTGGCTGCGTGCACGGCATATGCAA<br>CGAGCCCTGGCAGTGCCTGTGCGAGACCAATTGGGGCGGCCAG<br>CTGTGCGACAAGGACCTGAATTACTGTGGCACCCACCAGCCCTG<br>CCTCAACGGCGGCACCTGCTCCAACACCGGCCCCGACAAGTACC<br>AGTGCAGCTGCCCCGAAGGCTACAGCGGCCCGAATTGCGAGAT<br>CGCCGAACACGCCTGCCTCAGCGACCCCTGCCACAACCGGGGCA<br>GCTGTAAGGAGACCTCCCTGGGCTTTGAATGCGAATGTAGCCCC |

TABLE 2-continued

Sequence optimized sequences for human JAG1

| SEQ ID NO | NAME | SEQUENCE |
|---|---|---|
| | | GGTTGGACCGGACCCACCTGTTCCACCAACATCGACGACTGCAG<br>CCCCAATAACTGCAGCCACGGTGGCACGTGCCAGGACCTCGTCA<br>ACGGCTTTAAGTGCGTGTGCCCCCCCCAGTGGACCGGGAAGACC<br>TGCCAGCTGGACGCCAACGAGTGCGAGGCCAAGCCCTGCGTGA<br>ACGCCAAGAGCTGCAAGAACCTCATCGCCAGCTACTATTGTGAC<br>TGCCTGCCCGGGTGGATGGGCCAGAACTGTGACATAAACATCAA<br>CGATTGTCTGGGCCAGTGCCAGAACGATGCCAGCTGTCGGGACC<br>TGGTGAACGGCTACCGGTGCATCTGTCCCCCCGGCTACGCCGGA<br>GATCACTGTGAGCGAGACATCGACGAGTGCGCCTCCAACCCCTG<br>CCTCAACGGCGGGCACTGTCAGAATGAGATCAACAGGTTCCAGT<br>GCCTGTGCCCGACGGGATTCTCCGGTAACCTGTGCCAGCTCGAC<br>ATCGACTACTGTGAGCCCAACCCCTGTCAAAATGGCGCCCAATG<br>CTACAACCGGGCCTCCGACTACTTCTGTAAGTGCCCCGAGGATT<br>ACGAGGGTAAGAACTGTAGCCATCTGAAGGACCACTGCAGGAC<br>TACCCCGTGCGAGGTGATCGACTCCTGCACCGTCGCCATGGCCT<br>CCAACGACACCCCCGAGGGCGTGCGGTACATCAGCAGCAACGT<br>GTGTGGGCCGCACGGCAAGTGCAAGAGCCAGAGCGGGGGCAAG<br>TTCACCTGTGATTGCAACAAGGGCTTCACCGGGACGTATTGCCA<br>CGAGAACATCAACGACTGCGAGAGCAACCCCTGCAGGAACGGG<br>GGGACCTGCATAGACGGCGTGAACAGCTACAAATGCATCTGCA<br>GCGATGGGTGGGAGGGCGCCTACTGTGAGACCAACATTAACGA<br>CTGCAGCCAGAACCCCTGCCACAACGGGGGTACCTGTCGCGACC<br>TGGTGAACGACTTCTACTGTGACTGCAAGAACGGCTGGAAGGGC<br>AAGACCTGTCATTCCCGCGACAGCCAGTGCGACGAAGCCACCTG<br>CAACAACGGCGGCACCTGCTACGACGAGGGCGATGCCTTCAAG<br>TGCATGTGCCCGGGCGGCTGGGAGGGGACCACCTGTAATATCGC<br>CAGGAATTCCAGCTGCCTCCCCAATCCGTGCCATAATGGCGGCA<br>CCTGCGTGGTCAACGGCGAAAGCTTTACCTGCGTCTGTAAGGAA<br>GGCTGGGAAGGTCCGATCTGTGCCCAGAACACCAACGACTGTA<br>GCCCCCACCCCTGCTACAATAGCGGAACGTGCGTGGACGGCGAC<br>AACTGGTATCGGTGCGAGTGCGCCCCCGGCTTTGCGGGGCCGGA<br>CTGCCGGATCAATATCAACGAGTGCCAGAGCAGCCCCTGCGCCT<br>TCGGCGCCACCTGCGTGGACGAGATCAACGGCTACAGGTGCGTG<br>TGTCCCCCCGGCCACTCCGGCGCCAAGTGCCAGGAGGTGAGCGG<br>TAGGCCCTGCATCACCATGGGCAGCGTGATCCCCGACGGGGCCA<br>AGTGGGACGATGACTGTAACACCTGCCAGTGCCTGAACGGGAG<br>GATCGCCTGTTCCAAAGTGTGGTGCGGCCCGCGTCCCTGCCTAC<br>TCCACAAGGGGCATTCCGAGTGTCCCAGCGGACAGAGCTGTATC<br>CCCATCCTGGACGACCAATGCTTCGTGCACCCCTGCACCGGCGT<br>GGGTGAGTGCAGGTCCAGCAGCCTGCAGCCCGTGAAGACAAAG<br>TGCACCAGTGATTCCTACTACCAGGATAACTGCGCCAACATCAC<br>CTTCACCTTCAATAAGGAGATGATGAGCCCGGGCCTGACCACGG<br>AGCACATCTGCAGCGAGCTGCGCAACCTGAACATCCTGAAGAA<br>CGTCTCCGCCGAGTACAGCATATACATCGCCTGCGAGCCCAGCC<br>CCTCCGCCAATAACGAGATCCACGTGGCCATCTCCGCGGAGGAC<br>ATCAGGGACGATGGCAACCCCATCAAGGAGATCACCGACAAGA<br>TTATCGACCTGGTCAGCAAAAGGGACGGCAACTCCAGCCTCATC<br>GCCGCCGTGGCCGAGGTCAGGGTACAGCGCAGGCCGCTGAAAA<br>ACCGGACCGACTTCCTGGTGCCCCTGCTTTCCTCCGTGCTCACGG<br>TGGCCTGGATTTGCTGCCTGGTAACCGCGTTTTACTGGTGCCTGA<br>GGAAGAGGAGGAAGCCCGGCAGCCATACCCACAGCGCCAGCGA<br>GGACAACACAACCAACAACGTGAGGGAGCAGCTCAACCAGATA<br>AAGAACCCCATCGAGAAACACGGCGCCAACACGGTGCCCATCA<br>AGGACTATGAGAACAAGAACAGCAAGATGAGCAAGATCCGCAC<br>CCACAACAGCGAGGTTGAGGAAGACGACATGGACAAGCACCAG<br>CAGAAGGCCAGGTTCGCCAAGCAGCCCGCCTACACCCTGGTGG<br>ATCGTGAGGAGAAACCGCCCAACGGGACCCCCACCAAGCATCC<br>CAATTGGACCAACAAACAGGACAACAGGGACCTGGAGTCCGCC<br>CAAAGCCTGAACCGGATGGAGTACATCGTC |
| 34 | JAG1-CO24 | ATGAGGTCCCCCAGAACTCGGGGGAGGTCCGGCAGGCCGCTCA<br>GCCTCCTGCTCGCCCTGCTGTGCGCCCTGAGGGCCAAGGTGTGC<br>GGCGCCTCCGGCCAGTTCGAGCTGGAGATTCTGAGCATGCAGAA<br>CGTGAACGGCGAACTGCAGAACGGAAACTGCTGCGGTGGGGCC<br>AGGAACCCCGGCGACCGGAAGTGCACCAGGGATGAATGCGACA<br>CCTACTTCAAGGTCTGCCTCAAGGAGTACCAGAGCAGGGTGACC<br>GCCGGGGGCCCGTGTAGCTTCGGCTCCGGCAGCACCCCCGTGAT<br>AGGCGGCAACACGTTCAACCTTAAAGCCTCCAGGGGCAACGAC<br>CGCAACAGGATCGTGCTGCCCTTCTCCTTCGCGTGGCCCCGCAG<br>CTACACCCTGCTGGTGGAGGCGTGGGATAGCAGCAACGACACC<br>GTCCAGCCCGATTCAATCATCGAAAAGGCCAGCCACAGCGGCAT<br>GATCAACCCCTCCAGGCAGTGGCAGACCCTGAAGCAAAACACC<br>GGCGTGGCCCACTTCGAGTACCAAATCAGGGTTACCTGCGACGA<br>CTACTACTATGGGTTCGGCTGCAATAAGTTCTGTCGGCCGCGGG<br>ACGACTTTTTCGGGCATTATGCCTGCGACCAGAATGGCAATAAG |

TABLE 2-continued

| SEQ ID NO | NAME | SEQUENCE |
|---|---|---|
| | | Sequence optimized sequences for human JAG1 |
| | | ACCTGCATGGAGGGCTGGATGGGACCCGAGTGCAACCGCGCCA<br>TCTGCAGGCAGGGCTGCTCCCCCAAGCACGGCAGCTGCAAGCTG<br>CCCGGCGACTGCAGGTGCCAGTACGGGTGGCAGGGCCTCTACTG<br>CGACAAGTGCATCCCCCACCCCGGCTGCGTGCATGGGATATGCA<br>ACGAGCCGTGGCAGTGCCTGTGCGAAACCAACTGGGGGGGCCA<br>GCTGTGCGATAAGGACCTCAACTACTGCGGCACCCACCAGCCCT<br>GCCTCAACGGCGGCACCTGCTCCAATACCGGGCCCGATAAATAC<br>CAGTGCTCCTGCCCTGAGGGCTACAGCGGGCCCAACTGTGAGAT<br>CGCCGAGCATGCCTGCCTCTCGGACCCCTGCCATAACAGGGGCA<br>GCTGTAAGGAAACCAGCCTGGGCTTCGAGTGCGAGTGCAGCCCC<br>GGGTGGACCGGGCCAACCTGCTCCACCAACATCGACGACTGTAG<br>CCCGAACAACTGCTCCCACGGCGGGACCTGCCAGGACCTGGTGA<br>ATGGCTTCAAGTGCGTATGTCCCCCACAGTGGACCGGCAAGACC<br>TGTCAACTCGACGCCAACGAGTGCGAGGCCAAACCCTGCGTGA<br>ACGCCAAGTCCTGCAAGAACCTGATCGCCTCCTACTACTGCGAC<br>TGTCTGCCCGGCTGGATGGGCCAGAACTGCGATATCAACATCAA<br>CGATTGCCTCGGCCAGTGTCAGAACGACGCCTCCTGCCGGGACC<br>TGGTGAACGGCTACCGGTGCATTTGCCCCCCGGGCTACGCCGGC<br>GATCACTGCGAGCGCGACATCGACGAGTGCGCATCCAACCCCTG<br>TCTGAACGGGGGGCACTGTCAGAACGAGATCAATAGGTTCCAGT<br>GCCTGTGCCCCACCGGCTTCTCCGGGAATCTGTGCCAGCTGGAC<br>ATCGATTACTGCGAGCCCAACCCCTGCCAGAACGGCGCCCAGTG<br>TTACAACAGGGCCAGCGATTACTTCTGCAAGTGTCCCGAAGACT<br>ATGAGGGCAAGAATTGCAGCCATCTGAAAGACCACTGCCGCAC<br>CACCCCCTGTGAGGTGATCGACTCGTGCACCGTGGCGATGGCCA<br>GCAATGACACCCCGGAGGGCGTGCGGTACATCAGCAGCAACGT<br>GTGTGGGCCCCACGGCAAGTGCAAGTCCCAGAGCGGGGGCAAG<br>TTCACCTGCGACTGCAACAAAGGCTTTACAGGGACATATTGCCA<br>CGAAAACATCAATGACTGCGAGAGCAACCCCTGCCGCAATGGC<br>GGCACTTGCATCGACGGCGTGAACAGCTACAAATGTATCTGCTC<br>AGACGGGTGGGAAGGCGCGTATTGCGAGACCAACATCAACGAT<br>TGTAGCCAGAATCCCTGCCATAACGGTGGTACCTGCCGGGATCT<br>GGTGAACGACTTCTATTGCGACTGCAAGAACGGCTGGAAGGGC<br>AAGACCTGCCATTCGAGGGATAGCCAGTGCGACGAGGCCACCT<br>GCAACAACGGCGGCACCTGCTACGACGAGGGCGATGCCTTCAA<br>GTGCATGTGCCCTGGCGGCTGGGAGGGCACCACCTGCAACATCG<br>CCAGGAACAGCTCCTGCCTGCCCAACCCCTGCCACAACGGCGGG<br>ACCTGTGTCGTGAACGGGGAGAGCTTCACGTGCGTGTGCAAGGA<br>GGGCTGGGAAGGGCCCATCTGCGCCCAAAACACCAACGACTGC<br>AGCCCCCATCCCTGTTACAACTCCGGCACCTGCGTGGACGGCGA<br>CAACTGGTACCGATGCGAGTGCGCCCCCGGCTTCGCCGGCCCCG<br>ACTGCCGGATCAACATCAACGAGTGCCAGAGCAGCCCCTGCGC<br>GTTCGGCGCCACCTGCGTGGATGAAATCAACGGATATAGGTGCG<br>TGTGCCCCCCCGGCCACAGCGGGGCCAAGTGCCAGGAGGTCAG<br>CGGGCGCCCCTGCATCACCATGGGCAGCGTGATACCCGACGGCG<br>CCAAGTGGGACGACGACTGCAACACCTGCCAGTGCCTGAACGG<br>CAGGATCGCCTGCTCCAAGGTGTGGTGCGGGCCGCGGCCGTGCC<br>TGCTGCACAAGGGCCACAGCGAGTGCCCCAGCGGCCAGTCCTGT<br>ATCCCAATCCTGGACGACCAGTGCTTCGTGCATCCCTGCACCGG<br>CGTGGGCGAGTGCAGGTCCTCCTCCCTGCAGCCCGTGAAGACCA<br>AATGCACCAGCGACTCGTACTACCAGGATAACTGCGCCAACATC<br>ACCTTCACCTTCAACAAGGAAATGATGAGCCCCGGCCTGACCAC<br>CGAGCACATCTGCAGCGAGCTCCGGAACCTGAACATCCTGAAG<br>AACGTGTCCGCCGAGTATAGCATCTACATCGCGTGCGAACCAAG<br>TCCGTCCGCCAACAACGAGATCCACGTGGCAATCTCCGCCGAGG<br>ACATCCGGGACGACGGCAACCCCATCAAGGAGATAACCGACAA<br>AATCATCGACCTGGTGAGCAAAAGGGACGGCAATTCTAGCCTG<br>ATCGCCGCAGTGGCCGAAGTGAGGGTGCAGCGCAGGCCCCTCA<br>AGAATAGGACCGACTTCCTGGTGCCGCTCCTCAGCAGCGTGCTG<br>ACCGTGGCCTGGATCTGCTGCCTGGTGACCGCCTTTTACTGGTGC<br>CTGAGGAAGCGTAGGAAGCCCGGAAGCCACACACACTCCGCCA<br>GCGAGGACAACACCACCAACAACGTGCGGGAGCAACTGAACCA<br>GATCAAGAACCCCATCGAGAAGCACGGAGCCAACACCGTCCCT<br>ATCAAAGACTACGAGAACAAGAACAGCAAGATGAGCAAGATCA<br>GGACCCACAACAGCGAGGTTGAGGAAGACGACATGGACAAGCA<br>CCAGCAGAAAGCCAGGTTCGCGAAGCAGCCCGCCTACACCCTG<br>GTGGACCGGGAGGAAAAGCCCCCCAACGGCACCCCCACCAAGC<br>ACCCGAACTGGACCAACAAGCAGGACAACAGGGACCTGGAGAG<br>CGCCCAGAGCCTGAACCGGATGGAGTACATCGTC |
| 35 | JAG1-CO25 | ATGCGCAGCCCCCGGACCAGGGGAAGGTCCGGCAGGCCCCTGT<br>CCCTGCTGCTGGCGCTGCTCTGCGCCCTGCGAGCCAAAGTGTGT<br>GGTGCCTCCGGGCAGTTTGAGCTGGAGATCCTCAGCATGCAGAA<br>CGTGAACGGGGAGCTGCAGAATGGGAACTGCTGCGGCGGCGCC<br>AGGAATCCCGGGGACAGGAAGTGCACCCGAGATGAGTGCGACA |

TABLE 2-continued

Sequence optimized sequences for human JAG1

| SEQ ID NO | NAME | SEQUENCE |
|---|---|---|
| | | CCTATTTCAAGGTGTGCCTGAAGGAGTACCAGAGCCGTGTGACG |
| | | GCCGGCGGCCCCTGCAGCTTTGGCAGCGGCAGCACCCCCGTGAT |
| | | CGGCGGAAACACATTCAACCTGAAGGCCAGCAGGGGCAACGAC |
| | | AGGAACAGGATCGTGCTGCCCTTCAGCTTCGCCTGGCCCAGGTC |
| | | CTACACCCTGCTGGTGGAGGCCTGGGATAGCAGCAATGACACCG |
| | | TGCAGCCCGACTCCATCATCGAGAAGGCCAGTCACTCTGGAATG |
| | | ATCAACCCGAGCAGGCAGTGGCAGACCCTGAAGCAGAACACCG |
| | | GCGTGGCCCACTTCGAGTACCAGATCAGGGTGACCTGTGACGAT |
| | | TACTACTACGGTTTTGGCTGCAACAAGTTCTGTAGGCCCCGCGA |
| | | CGACTTCTTTGGTCATTACGCCTGCGATCAGAACGGCAATAAGA |
| | | CCTGCATGGAAGGCTGGATGGGCCCCGAATGCAACAGGGCCAT |
| | | TTGCAGGCAGGGGTGCAGCCCGAAGCACGGCAGCTGCAAGCTG |
| | | CCCGGCGACTGCAGGTGTCAGTACGGCTGGCAGGGCCTGTACTG |
| | | CGACAAATGCATCCCCCACCCTGGGTGCGTGCACGGCATCTGTA |
| | | ACGAGCCCTGGCAGTGCCTGTGTGAGACCAACTGGGGTGGGCA |
| | | ACTGTGCGATAAGGACCTGAACTACTGCGGAACCCACCAGCCCT |
| | | GCCTGAACGGCGGCACATGCAGCAACACCGGGCCCGACAAGTA |
| | | CCAGTGCAGCTGCCCCGAAGGGTATAGCGGGCCCAATTGCGAA |
| | | ATCGCCGAGCACGCCTGCCTGAGCGATCCCTGTCATAATCGCGG |
| | | ATCCTGCAAGGAGACCAGCCTCGGCTTTGAGTGCGAATGCTCCC |
| | | CCGGCTGGACCGGTCCCACGTGCAGCACGAACATCGACGACTGT |
| | | TCCCCGAACAACTGCTCCCACGGCGGCACCTGCCAGGATCTGGT |
| | | GAATGGATTCAAATGCGTGTGCCCCCCCCAATGGACCGGGAAG |
| | | ACCTGCCAACTGGACGCCAACGAGTGCGAAGCCAAGCCCTGTGT |
| | | GAACGCCAAGAGCTGCAAAAACCTCATCGCTAGCTACTACTGCG |
| | | ACTGCCTGCCCGGCTGGATGGGTCAGAACTGTGACATCAACATC |
| | | AACGATTGTCTGGGCCAGTGCCAGAACGACGCCAGCTGCAGGG |
| | | ACCTGGTGAATGGGTACCGCTGCATCTGCCCCCCCGGCTACGCC |
| | | GGAGATCATTGCGAGCGGGACATCGACGAGTGCGCCAGCAACC |
| | | CCTGCCTGAACGGCGGTCACTGTCAGAATGAGATCAACCGCTTC |
| | | CAGTGCCTGTGCCCCACCGGCTTCAGCGGAAATCTGTGCCAGCT |
| | | AGACATTGATTACTGCGAACCGAACCCTTGCCAGAACGGCGCCC |
| | | AGTGCTACAACAGGGCCAGCGACTACTTTTGCAAGTGCCCCGAG |
| | | GACTACGAGGGGAAGAATTGCTCCCACCTAAAGGACCACTGCC |
| | | GGACCACCCCCTGCGAGGTGATCGACAGCTGCACCGTCGCGATG |
| | | GCCAGCAACGACACCCCCGAGGGCGTCAGGTACATCTCCAGCA |
| | | ACGTGTGCGGTCCCCATGGCAAATGCAAGAGCCAGAGCGGGGG |
| | | GAAGTTTACCTGCGACTGCAACAAGGGCTTCACCGGGACCTACT |
| | | GCCATGAGAACATCAATGACTGCGAGAGCAACCCCTGCAGGAA |
| | | CGGCGGGACATGCATCGACGGGGTGAACTCCTATAAGTGCATCT |
| | | GCTCCGACGGGTGGGAAGGTGCCTATTGCGAGACAAACATCAA |
| | | CGACTGCAGCCAAAACCCCTGCCACAACGGGGGCACCTGCAGG |
| | | GATCTGGTGAACGACTTCTACTGTGACTGCAAGAACGGGTGGAA |
| | | GGGAAAGACCTGTCACAGCCGGGACTCCCAGTGCGACGAGGCC |
| | | ACATGCAACAACGGCGGCACGTGCTACGACGAAGGAGACGCCT |
| | | TTAAGTGCATGTGCCCCGGCGGCTGGGAGGGCACCACCTGCAAT |
| | | ATCGCCCGCAACTCCTCCTGCCTGCCCAACCCGTGCCACAACGG |
| | | GGGCACCTGCGTGGTGAACGGCGAGTCCTTCACCTGCGTCTGCA |
| | | AGGAGGGCTGGGAGGGTCCCATCTGTGCCCAGAATACCAATGA |
| | | CTGCAGCCCCCATCCTTGTTACAATTCCGGCACCTGCGTGGATG |
| | | GCGACAACTGGTATCGGTGTGAGTGCGCCCCCGGCTTCGCGGGC |
| | | CCCGACTGTAGGATCAACATCAACGAGTGCCAGAGCTCCCCATG |
| | | CGCGTTTGGGGCGACCTGTGTCGACGAGATCAATGGGTACAGGT |
| | | GCGTGTGTCCCCCGGGGCACTCCGGGGCCAAATGCCAGGAGGT |
| | | AAGCGGCCGGCCATGCATTACCATGGGCTCGGTGATCCCAGACG |
| | | GTGCCAAGTGGGACGACGACTGCAACACCTGCCAGTGCCTGAAT |
| | | GGCAGGATCGCCTGCAGCAAGGTATGGTGCGGACCCAGGCCGT |
| | | GCCTGCTGCACAAAGGACACTCCGAGTGTCCGAGCGGCCAGAG |
| | | CTGCATCCCCATCCTGGACGACCAGTGCTTCGTGCATCCCTGCA |
| | | CTGGCGTCGGCGAGTGCCGCAGCTCCAGCCTGCAGCCCGTGAAG |
| | | ACCAAGTGTACCAGCGACAGCTACTACCAGGACAATTGTGCCAA |
| | | CATCACCTTCACCTTCAACAAGGAGATGATGAGCCCTGGCCTGA |
| | | CCACCGAGCATATCTGTAGCGAGCTGAGGAACTTGAACATCCTG |
| | | AAGAATGTGAGCGCCGAGTATTCCATTTACATAGCCTGTGAGCC |
| | | CAGCCCAAGCGCTAACAATGAGATCCACGTGGCCATCAGCGCC |
| | | GAGGACATCCGGGACGACGGCAACCCCATCAAAGAAATCACCG |
| | | ACAAGATCATCGATCTGGTAAGCAAGAGGGACGGGAACAGCAG |
| | | CCTCATCGCCGCCGTGGCCGAGGTGCGCGTCCAGCGGAGGCCCC |
| | | TCAAAAACCGGACCGACTTTCTGGTGCCGCTGCTCAGCTCCGTG |
| | | CTGACCGTGGCCTGGATATGCTGCCTGGTGACCGCCTTCTACTG |
| | | GTGCCTGCGGAAGAGGAGGAAGCCCGGCAGCCACACGCACAGC |
| | | GCGAGCGAGGACAACACCACCAACAACGTGCGGGAGCAACTGA |
| | | ACCAGATCAAGAACCCCATCGAGAAGCACGGCGCCAACACCGT |
| | | GCCCATCAAGGACTACGAGAACAAGAATAGCAAGATGAGTAAG |
| | | ATTAGGACCCACAACAGCGAGGTGGAGGAGGACGACATGGACA |

TABLE 2-continued

Sequence optimized sequences for human JAG1

| SEQ ID NO | NAME | SEQUENCE |
|---|---|---|
| | | AGCACCAGCAGAAGGCCCGCTTCGCCAAGCAGCCCGCCTATACC |
| | | CTGGTCGACAGGGAAGAGAAGCCGCCCAATGGGACCCCCACCA |
| | | AGCATCCCAACTGGACCAACAAGCAGGACAACCGGGATCTGGA |
| | | GAGCGCCCAAAGCCTGAATAGGATGGAGTACATCGTG |
| SEQID NO | NAME | mRNA SEQUENCE |
| 87 | JAG1- | AUGCGAAGCCCCAGGACCCGCGGCCGUAGCGGUAGGCCCCUGU |
| | CO01 | CCCUGCUGCUGGCCCUGCUGUGCGCCCUCAGGGCCAAGGUGUG |
| | | CGGCGCCAGCGGCCAGUUCGAGCUCGAGAUCCUGAGCAUGCAG |
| | | AACGUGAACGGCGAGCUCCAGAAUGGGAAUUGUUGCGGCGGC |
| | | GCCAGGAACCCCGGUGACAGGAAAUGCACCCGCGACGAGUGCG |
| | | ACACCUACUUCAAAGUGUGCCUCAAGGAGUACCAGAGCAGGG |
| | | UGACCGCCGGCGGGCCCUGCAGCUUCGGGAGCGGCUCCACGCC |
| | | CGUGAUCGGCGGGAACACCUUCAACCUGAAGGCCAGCAGGGG |
| | | CAACGAUCGGAACCGGAUCGUGCUGCCGUUCUCCUUCGCCUGG |
| | | CCGCGAAGCUACACCCUGCUGGUGGAAGCGUGGGACAGCAGC |
| | | AACGACACCGUGCAGCCCGACAGCAUCAUCGAGAAGGCCUCAC |
| | | ACUCCGGUAUGAUCAACCCCAGCAGGCAGUGGCAGACCCUGAA |
| | | GCAGAACACCGGAGUGGCCCACUUCGAAUACCAGAUCAGGGU |
| | | GACAUGCGACGACUACUACUACGGCUUCGGGUGCAACAAGUU |
| | | CUGCAGGCCCCGCGACGACUUCUUCGGACACUACGCCUGUGAC |
| | | CAGAACGGGAACAAGACGUGUAUGGAGGGGUGGAUGGGGCCC |
| | | GAAUGCAACAGGGCCAUCUGUCGGCAGGGUUGCUCCCCCAAGC |
| | | ACGGCUCCUGCAAACUGCCCGGCGAUUGCCGGUGCCAGUACGG |
| | | GUGGCAAGGUCUGUACUGCGACAAGUGCAUCCCGCAUCCCGGC |
| | | UGCGUGCACGGCAUCUGCAACGAGCCCUGGCAGUGCCUGUGCG |
| | | AAACCAACUGGGGCGGCCAGCUCUGUGACAAGGACCUUAACU |
| | | ACUGCGGCACCCACCAGCCCUGCCUGAACGGCGGGACCUGCAG |
| | | CAACACCGGGCCCGACAAGUACCAGUGUAGCUGCCCCGAAGGG |
| | | UACUCGGGUCCCAACUGCGAGAUCGCCGAGCACGCCUGCCUGU |
| | | CCGACCCCUGCCAUAACAGGGGCAGCUGUAAGGAGACCUCCCU |
| | | GGGCUUCGAGUGUGAGUGCUCCCCCGGAUGGACCGGCCCCACC |
| | | UGCAGCACCAAUAUUGACGACUGCAGCCCAAAUAACUGCUCCC |
| | | ACGGCGGCACCUGCCAGGACCUCGUGAACGGCUUUAAGUGCG |
| | | UCUGUCCCCCCCAGUGGACCGGCAAGACCUGCCAGCUGGACGC |
| | | CAAUGAGUGCGAGGCCAAGCCCUGUGUAAACGCCAAGAGCUG |
| | | CAAGAACCUGAUCGCCAGCUACUACUGUGACUGCCUGCCCGGC |
| | | UGGAUGGGCCAGAACUGCGACAUCAACAUCAACGACUGCCUC |
| | | GGGCAGUGCCAGAACGACGCCAGCUGCAGGGAUCUGGUGAAC |
| | | GGCUACAGGUGCAUCUGCCCCCCCGGAUACGCCGGCGACCAUU |
| | | GCGAAAGGGACAUCGAUGAGUGCGCCUCCAAUCCCUGUCUGA |
| | | ACGGCGGCCACUGCCAGAACGAGAUCAACAGGUUCCAGUGCCU |
| | | GUGCCCCACCGGCUUCAGCGGGAACCUGUGCCAGCUGGACAUC |
| | | GACUAUUGCGAGCCCAAUCCCUGCCAGAACGGGGCGCAGUGCU |
| | | ACAACAGGGCCAGCGACUACUUCUGCAAGUGCCCCGAGGACUA |
| | | CGAGGGCAAGAAUUGCAGCCACCUGAAAGACCACUGCCGCACC |
| | | ACCCCCUGUGAGGUUAUCGACAGCUGUACGGUCGCCAUGGCCU |
| | | CGAACGACACCCCCGAAGGCGUGAGGUAUAUCUCCAGCAACGU |
| | | GUGCGGGCCACACGGCAAAUGUAAGUCCCAGAGCGGCGGGAA |
| | | GUUCACCUGCGACUGCAACAAGGGCUUCACAGGCACGUACUGC |
| | | CAUGAGAACAUCAACGAUUGUGAGAGCAACCCCUGCAGGAAC |
| | | GGCGGGACCUGCAUAGACGGCGUGAACAGCUAUAAGUGCAUC |
| | | UGCAGCGAUGGCUGGGAGGGAGCCUACUGCGAAACCAACAUC |
| | | AAUGACUGCAGCCAGAACCCCUGUCACAACGGGGGCACAUGCC |
| | | GGGACCUGGUGAAUGAUUUCUACUGCGACUGCAAGAAUGGCU |
| | | GGAAGGGCAAGACCUGCCACAGCAGGGACUCCCAGUGUGACG |
| | | AGGCCACCUGCAAUAACGGGGGCACCUGCUACGACGAGGGCG |
| | | ACGCCUUUAAGUGCAUGUGCCCCGGCGGUUGGGAGGGUACCA |
| | | CCUGCAACAUCGCGCGGAACAGCAGCUGUCUGCCCAACCCCUG |
| | | CCACAACGGGGGCACGUGCGUGGUGAACGGCGAGAGCUUCAC |
| | | CUGCGUGUGUAAGGAGGGGUGGGAGGGCCCCAUCUGCGCCCA |
| | | GAACACCAACGAUUGCUCGCCCCACCCCUGUUACAACAGCGGG |
| | | ACCUGCGUGGACGGUGAUAACUGGUACAGGUGCGAGUGCGCA |
| | | CCAGGCUUCGCCGGGCCGGACUGCAGGAUCAACAUCAACGAAU |
| | | GUCAGAGCUCCCCGUGCGCCUUCGGCGCCACGUGCGUAGACGA |
| | | GAUCAAUGGCUACAGGUGCGUGUGCCCCCCAGGCCACAGCGGG |
| | | GCCAAAUGCCAGGAAGUCAGCGGCCGACCCUGCAUCACCAUGG |
| | | GUUCCGUUAUCCCAGACGGAGCCAAGUGGGAUGACGAUUGUA |
| | | ACACCUGUCAGUGUCUGAAUGGCCGGAUCGCGUGCAGCAAGG |
| | | UGUGGUGCGGCCCCAGGCCGUGCCUGCUGCACAAGGGCCACUC |
| | | CGAAUGUCCCUCCGGUCAGAGCUGCAUCCCCAUCCUCGACGAC |
| | | CAGUGCUUUGUACACCCCUGCACCGGAGUCGGCGAGUGCAGG |
| | | UCCUCGUCUCUGCAGCCCGUGAAAACCAAGUGCACCAGCGACU |
| | | CCUACUACCAGGACAACUGCGCCAACAUCACGUUCACCUUUAA |

TABLE 2-continued

Sequence optimized sequences for human JAG1

| SEQ ID NO | NAME | SEQUENCE |
|---|---|---|
| | | CAAGGAGAUGAUGAGCCCCGGGCUGACCACGGAGCACAUCUG<br>CUCGGAGCUGAGGAACCUGAACAUACUGAAGAACGUGAGCGC<br>CGAGUACAGCAUCUACAUUGCCUGCGAGCCCAGCCCCAGCGCC<br>AACAACGAGAUCCACGUGGCGAUCUCCGCCGAAGACAUCCGGG<br>ACGACGGCAACCCCAUCAAGGAGAUAACCGACAAGAUCAUCG<br>ACCUGGUGAGCAAGCGGGACGGCAACAGCUCCCUGAUCGCCGC<br>CGUGGCCGAGGUGCGGGUACAGAGGCGGCCCCUCAAGAACAG<br>GACGGACUUCCUCGUGCCGCUCCUGUCGUCCGUGCUGACCGUG<br>GCCUGGAUCUGCUGUCUGGUGACCGCCUUCUACUGGUGCCUGC<br>GGAAGCGGCGCAAGCCGGGGAGCCACACCCACUCGGCCAGCGA<br>AGACAACACGACCAACAACGUGAGGGAGCAGCUGAAUCAGAU<br>CAAGAAUCCCAUAGAGAAACACGGCGCCAACACCGUGCCCAUC<br>AAGGAUUACGAGAACAAGAACAGCAAGAUGUCCAAAAUCAGA<br>ACCCACAAUAGCGAAGUGGAGGAAGACGACAUGGAUAAGCAC<br>CAGCAGAAGGCCAGGUUCGCCAAGCAGCCCGCCUACACCCUGG<br>UAGACAGGGAGGAGAAGCCCCCCAACGGCACCCCCACGAAACA<br>CCCGAACUGGACCAACAAGCAGGAUAAUAGGGACCUGGAGUC<br>CGCGCAGAGCCUGAACCGCAUGGAGUACAUCGUG |
| 88 | JAG1-CO02 | AUGAGGAGCCCCAGGACCCGGGGCCGUAGCGGGAGGCCGCUCU<br>CGCUGCUGCUGGCCCUGCUCUGCGCCCUGAGGGCCAAGGUGUG<br>UGGCGCCUCCGGGCAGUUCGAGCUGGAAAUCCUGAGCAUGCA<br>GAACGUCAACGGCGAGCUGCAGAACGGCAACUGCUGCGGCGG<br>AGCGCGGAACCCCGGGGACAGGAAGUGCACCAGGGACGAGUG<br>UGACACGUACUUCAAAGUCUGCCUCAAGGAGUACCAGAGCCG<br>GGUGACCGCCGGGGGCCCAUGCUCCUUCGGCAGCGGCAGCACC<br>CCCGUCAUCGGAGGCAACACCUUUAAUCUGAAGGCCAGCAGG<br>GGGAACGACAGGAAUAGGAUCGUCCUGCCCUUUAGCUUCGCC<br>UGGCCCAGGUCCUACACCCUGCUGGUCGAGGCCUGGGACAGCU<br>CCAACGACACCGUCCAGCCCGACAGUAUCAUCGAGAAGGCGUC<br>CCACUCCGGCAUGAUCAAUCCCAGCAGGCAGUGGCAGACGCUG<br>AAGCAGAACACCGGCGUGGCCCACUUCGAGUAUCAGAUCCGG<br>GUGACGUGCGACGACUACUACUACGGGUUCGGCUGCAACAAG<br>UUCUGUAGGCCCCGGGACGAUUUCUUCGGCCACUACGCAUGCG<br>ACCAGAACGGCAACAAGACCUGCAUGGAGGGCUGGAUGGGCC<br>CCGAGUGCAACAGGGCUAUCUGCCGCCAGGGCUGCUCCCCCAA<br>GCACGGCAGCUGUAAGCUGCCCGGCGAUUGCCGGUGUCAGUA<br>CGGGUGGCAGGGACUGUAUUGCGACAAGUGCAUACCCCACCC<br>AGGCUGCGUGCACGGCAUCUGUAACGAGCCCUGGCAAUGCCUC<br>UGCGAGACCAACUGGGGGGGACAACUGUGCGACAAGGACCUG<br>AACUACUGCGGUACCCACCAGCCCUGCCUGAACGGCGGCACCU<br>GCAGUAACACCGGCCCCGACAAGUAUCAGUGCAGCUGCCCCGA<br>GGGGUAUUCCGGCCCGAACUGCGAGAUCGCCGAGCACGCCUGC<br>CUCAGCGACCCAUGCCACAAUAGAGGCAGCUGCAAGGAAACCU<br>CCCUGGGGUUCGAGUGUGAGUGCUCCCCCGGGUGGACCGGGCC<br>CACCUGCUCCACCAACAUCGACGACUGCAGCCCCAAUAACUGC<br>AGCCACGGGGGCACCUGUCAGGACCUGGUGAACGGCUUUAAG<br>UGCGUCUGCCCCCCCCAGUGGACCGGUAAGACGUGCCAGCUGG<br>ACGCCAAUGAGUGCGAAGCCAAGCCCUGCGUCAAUGCCAAGA<br>GCUGUAAGAACCUCAUCGCGUCCUACUAUUGCGACUGCCUGCC<br>CGGGUGGAUGGGACAGAACUGCGACAUCAACAUCAACGACUG<br>CCUCGGGCAGUGCCAGAACGACGCCAGCUGCCGGGACCUGGUG<br>AACGGCUAUAGAUGCAUCUGCCCCCCCGGCUACGCCGGGGACC<br>ACUGCGAGAGGGACAUCGACGAGUGCGCCUCCAACCCCUGCCU<br>GAAUGGAGGCCACUGCCAGAACGAAAUCAACAGGUUCCAGUG<br>UCUGUGCCCCACCGGAUUCAGCGGAAACCUGUGCCAGCUGGAC<br>AUCGACUAUUGCGAACCCAACCCCUGUCAGAACGGCGCCCAGU<br>GCUACAACCGGGCAAGCGACUACUUCUGCAAGUGCCCUGAGG<br>ACUACGAGGGCAAGAACUGCAGCCACCUCAAGGACCACUGCAG<br>GACGACCCCCUGUGAGGUGAUCGACAGCUGUACCGUGGCCAU<br>GGCCUCGAACGACACCCCUGAGGGCGUGAGGUAUAUCUCCAGC<br>AACGUCUGCGGCCCCCACGGCAAAUGUAAGAGCCAAUCCGGGG<br>GCAAGUUCACCUGCGACUGCAACAAGGGAUUUACCGGCACCU<br>ACUGCCACGAGAACAUCAACGACUGCGAGUCCAAUCCCUGCCG<br>UAACGGCGGCACCUGCAUCGACGGUGUCAACAGCUACAAGUG<br>CAUCUGCAGCGACGGCUGGGAGGGAGCGUACUGCGAAACCAA<br>CAUAAACGAUUGUUCCCAGAACCCCUGCCACAACGGCGGCACC<br>UGCCGGGACCUUGUGAACGACUUUUACUGUGACUGCAAGAAU<br>GGGUGGAAGGGCAAAACGUGCCACAGCAGAGACAGCCAGUGC<br>GACGAAGCCACCUGUAACAACGGCGGCACCUGCUACGACGAGG<br>GCGACGCCUUUAAGUGUAUGUGCCCGGGCGGCUGGGAAGGCA<br>CGACCUGCAACAUCGCCCGGAACAGCAGCUGCCUCCCGAACCC<br>UUGCCACAACGGCGGGACCUGCGUGGUGAAUGGCGAAUCCUU<br>CACCUGCGUGUGCAAGGAGGGCUGGGAGGGCCCCAUCUGCGCC<br>CAAAACACCAAUGACUGUAGCCCCCACCCCUGCUACAACUCCG |

TABLE 2-continued

Sequence optimized sequences for human JAG1

| SEQ ID NO | NAME | SEQUENCE |
|---|---|---|
| | | GCACAUGUGUGGAUGGCGACAACUGGUACAGGUGUGAGUGCG<br>CCCCCGGAUUCGCCGGCCCCGACUGCCGGAUCAACAUUAACGA<br>GUGUCAGAGCAGCCCCUGCGCCUUCGGCGCCACCUGCGUCGAU<br>GAGAUAAACGGAUAUAGGUGCGUGUGCCCCCCGGACACAGC<br>GGCGCGAAGUGCCAGGAGGUGAGCGGCAGGCCCUGCAUCACA<br>AUGGGCAGCGUGAUCCCGGACGGCGCCAAGUGGGACGACGAU<br>UGCAACACCUGCCAGUGCCUGAACGGCCGGAUAGCCUGCUCCA<br>AAGUGUGGUGCGGCCCCCGCCCCUGCCUGCUGCACAAGGGCCA<br>CAGCGAGUGCCCCUCCGGCCAGAGCUGCAUCCCCAUACUGGAC<br>GACCAAUGUUUCGUGCAUCCCUGCACCGGCGUGGGCGAGUGU<br>CGGAGCAGCAGCCUGCAGCCCGUGAAGACUAAGUGCACCUCCG<br>ACUCCUACUAUCAGGACAACUGUGCCAACAUCACCUUCACCUU<br>CAACAAGGAGAUGAUGAGCCCCGGCCUGACAACGGAGCACAU<br>CUGCAGCGAGCUGCGCAAUCUGAACAUCCUGAAAAAUGUGAG<br>CGCCGAGUACAGCAUCUACAUCGCCUGUGAGCCGAGCCCCAGC<br>GCUAAUAACGAGAUCCACGUGGCCAUCUCCGCCGAGGACAUCA<br>GGGAUGACGGCAACCCCAUCAAAGAGAUCACCGACAAGAUCA<br>UCGACCUGGUGUCCAAGCGGGACGGCAACUCCAGCCUGAUCGC<br>AGCCGUGGCCGAAGUGAGGGUCCAGCGGCGGCCCCUGAAGAA<br>CCGAACCGACUUCCUGGUCCCCCUGCUGAGCAGCGUGCUGACC<br>GUCGCAUGGAUCUGUUGCCUGGUGACGGCCUUCUACUGGUGC<br>CUCAGGAAAAGACGGAAGCCCGGGAGCCACACCCACAGCGCCA<br>GCGAGGACAACACCACCAACAACGUGCGGGAGCAGCUGAACCA<br>AAUCAAGAACCCCAUCGAGAAGCAUGGCGCCAAUACCGUGCCC<br>AUCAAAGACUACGAGAACAAGAACAGCAAGAUGAGCAAGAUC<br>CGCACCCAUAACUCGGAGGUGGAAGAAGACGAUAUGGAUAAG<br>CACCAGCAAAAGGCCCGGUUCGCGAAGCAGCCCGCCUAUACCC<br>UCGUGGACCGGGAAGAAAAGCCGCCCAACGGCACCCCCACCAA<br>GCACCCCAACUGGACCAACAAACAGGACAACAGGGACCUCGAG<br>AGCGCCCAGUCCCUCAACCGUAUGGAGUACAUCGUC |
| 89 | JAG1-CO03 | AUGAGGUCCCCGCGUACCCGAGGCAGGUCCGGGAGGCCCCUGU<br>CCCUGCUGCUCGCCUUACUUUGCGCCCUGAGGGCCAAAGUCUG<br>CGGCGCCUCCGGCCAAUUCGAGCUGGAGAUCCUCAGCAUGCAG<br>AACGUGAACGGCGAGCUGCAAAACGGGAACUGCUGCGGGGGA<br>GCCCGCAACCCCGGCGACCGGAAGUGCACCAGGGACGAGUGCG<br>ACACCUACUUCAAGGUGUGCCUCAAGGAGUAUCAGUCAAGGG<br>UGACCGCCGGAGGCCCCUGUAGCUUCGGCUCCGGGUCGACCCC<br>CGUGAUAGGCGGAAACACCUUCAACCUGAAGGCCAGCAGGGG<br>GAACGACAGGAAUAGGAUCGUGCUCCCCUUCUCGUUCGCCUG<br>GCCCAGGAGCUACACCCUCCUCGUGGAGGCCUGGGACAGCAGC<br>AACGAUACGGUGCAGCCCGACUCCAUCAUCGAGAAGGCCAGCC<br>ACUCCGGCAUGAUCAACCCCAGCCGCCAGUGGCAGACCCUGAA<br>GCAAAACACGGGCGUGGCACACUUCGAGUACCAGAUAAGGGU<br>CACUUGCGACGACUACUACUACGGGUUCGGGUGCAACAAGUU<br>UUGCAGGCCCCGGGACGACUUCUUCGGACACUAUGCCUGCGAC<br>CAGAACGGCAACAAGACCUGUAUGGAGGGUUGGAUGGGCCCC<br>GAAUGCAAUCGCGCCAUUUGCCGGCAGGGGUGCAGCCCUAAG<br>CACGGAAGCUGUAAGCUCCCCGGCGACUGCCGCUGCCAGUACG<br>GCUGGCAGGGACUGUACUGUGACAAGUGUAUCCCCCACCCCGG<br>CUGCGUGCACGGCAUCUGCAAUGAGCCUUGGCAGUGCCUGUG<br>CGAGACCAAUUGGGGCGGCCAGCUGUGCGACAAGGACCUGAA<br>CUACUGCGGCACCCACCAGCCCUGCCUGAACGGUGGGACCUGC<br>AGCAACACCGGGCCAGACAAGUACCAGUGCAGCUGCCCCGAGG<br>GCUAUAGCGGGCCCAAUUGCGAGAUCGCCGAGCACGCCUGCCU<br>GUCCGACCCCUGUCACAACCGGGGCUCCUGCAAGGAGACCUCC<br>CUGGGGUUUGAGUGCGAGUGCUCCCCCGGUUGGACCGGCCCCA<br>CCUGCUCCACCAACAUCGACGACUGCUCCCCCAACAAUUGCAG<br>CCACGGCGGCACAUGCCAGGAUCUGGUGAACGGCUUCAAGUG<br>UGUGUGUCCCCCCCAGUGGACCGGCAAGACCUGCCAGCUGGAC<br>GCGAACGAGUGCGAAGCAAAGCCCUGCGUGAACGCCAAGUCC<br>UGCAAAAACCUGAUCGCCAGCUAUUACUGCGACUGCCUGCCCG<br>GCUGGAUGGGGCAGAACUGUGACAUAAACAUAAACGACUGCC<br>UCGGCCAGUGCCAGAAUGACGCGAGCUGCCGGGACCUCGUGA<br>ACGGCUACCGAUGCAUCUGCCCCCCGGGCUACGCCGGCGACCA<br>UUGCGAACGGGAUAUCGACGAGUGUGCCAGCAACCCCUGCCU<br>GAACGGGGGGCACUGCCAGAACGAGAUAAACAGGUUCCAGUG<br>CCUGUGCCCCACCGGCUUCAGCGGCAACCUGUGCCAACUCGAC<br>AUCGACUACUGCGAGCCCAACCCCUGCCAAAACGGUGCCCAAU<br>GCUACAACCGGGCCUCGGACUACUUUUGCAAGUGCCCGGAGG<br>ACUAUGAGGGCAAGAAUUGUUCCCACCUCAAGGACCACUGCC<br>GGACCACCCCCUGCGAGGUGAUCGACUCCUGCACCGUGGCCAU<br>GGCUAGUAACGAUACCCCCGAGGGCGUUAGGUACAUCUCCUCC<br>AACGUGUGCGGCCCCCACGGGAAGUGCAAGUCGCAGAGCGGC<br>GGCAAGUUCACCUGCGACUGCAAUAAGGGCUUCACCGGUACC |

TABLE 2-continued

Sequence optimized sequences for human JAG1

| SEQ ID NO | NAME | SEQUENCE |
|---|---|---|
| | | UACUGCCACGAGAACAUCAACGACUGCGAGAGCAAUCCCUGCC GGAACGGGGGUACCUGCAUCGACGGCGUGAACUCCUACAAGU GUAUCUGCUCAGAUGGCUGGGAAGGCGCGUACUGUGAGACCA ACAUAAACGACUGUAGCCAGAACCCCUGUCAUAACGGGGGCA CCUGCAGGGACCUGGUGAACGACUUCUACUGCGACUGCAAGA ACGGGUGGAAAGGCAAAACUUGCCACUCCAGGGACUCCCAGU GCGAUGAGGCCACCUGCAAUAACGGCGGCACGUGCUACGACG AGGGGGACGCCUUCAAGUGCAUGUGCCCCGGGGGCUGGGAGG GGACCACCUGCAACAUCGCCAGGAACAGCUCCUGCCUGCCCAA CCCAUGCCACAAUGGAGGCACCUGCGUAGUGAAUGGCGAGUC CUUCACCUGUGUGUGCAAGGAGGGCUGGGAGGGGCCCAUCUG CGCCCAGAACACCAACGACUGCAGCCCACACCCGUGCUACAAC UCCGGCACCUGCGUCGACGGCGACAACUGGUACAGGUGCGAG UGCGCCCCCGGCUUCGCGGGCCCGGACUGCCGGAUUAAUAUCA ACGAGUGCCAGAGCAGCCCCUGCGCCUUCGGGGCCACCUGCGU CGACGAAAUCAACGGGUACCGGUGCGUGUGCCCCCCCGGCCAC AGCGGGGCAAAGUGCCAGGAAGUCAGCGGCAGGCCCUGCAUC ACCAUGGGCAGCGUCAUUCCCGAUGGCGCAAAGUGGGACGAC GACUGCAACACUUGCCAGUGCCUGAAUGGCAGGAUCGCCUGC AGCAAGGUGUGGUGCGGCCCAAGGCCCUGCCUGCUGCACAAA GGCCACAGCGAAUGCCCAAGCGGUCAGAGCUGCAUCCCCAUCC UGGAUGACCAGUGCUUCGUGCACCCCUGCACCGGGGUCGGUG AGUGUAGGAGCAGCAGCCUGCAGCCCGUGAAGACCAAGUGCA CCUCCGAUUCCUACUACCAGGACAAUUGCGCCAACAUAACUUU UACCUUCAACAAGGAGAUGAUGAGCCCCGGCCUCACCACGGAG CACAUCUGCAGCGAGCUGCGCAACCUCAACAUCCUGAAGAACG UGAGCGCCGAGUACAGCAUUUACAUCGCCUGCGAGCCCAGCCC CUCCGCCAACAACGAGAUCCACGUGGCCAUCAGCGCCGAGGAC AUAAGGGAUGACGGGAAUCCCAUCAAGGAGAUCACCGACAAG AUCAUCGACCUGGUGUCCAAGCGGGACGGCAAUAGCAGCCUG AUCGCCGCCGUCGCGGAGGUGCGGGUGCAGAGGCGCCCGCUGA AGAACCGGACCGACUUCCUCGUGCCCCUGCUGAGCAGCGUGCU GACGGUGGCCUGGAUCUGCUGCCUGGUGACAGCCUUCUACUG GUGCCUGCGGAAGAGGAGGAAGCCCGGGAGCCACACCCAUAG CGCGUCCGAGGACAACACGACAAACAACGUCAGAGAGCAGCU GAACCAAAUCAAGAAUCCCAUCGAAAAACACGGCGCCAACACC GUGCCCAUCAAAGAUUACGAGAACAAGAACAGCAAGAUGAGC AAAAUCCGGACCCACAACUCGGAGGUGGAGGAGGACGACAUG GACAAGCACCAACAGAAGGCCCGCUUUGCCAAGCAGCCCGCCU ACACCCUGGUGGACCGGGAGGAAAAGCCGCCGAAUGGUACAC CGACCAAGCAUCCCAAUUGGACAAACAAGCAGGAUAACAGGG ACCUGGAAAGCGCCCAGAGCCUGAACCGGAUGGAGUACAUCG UA |
| 90 | JAG1-CO04 | AUGAGGAGCCCCAGGACCAGGGGGAGGAGCGGGAGGCCGCUG AGCCUGCUCCUGGCCCUGCUGUGUGCCCUGCGCGCCAAGGUGU GCGGCGCGUCCGGACAGUUUGAGCUGGAGAUCCUGUCCAUGC AGAACGUGAACGGCGAGCUCCAGAACGGGAACUGCUGCGGGG GCGCAAGGAACCCCGGUGACAGGAAGUGCACCCGCGACGAGU GCGACACGUACUUUAAGGUGUGCCUGAAAGAGUACCAGAGCA GGGUGACUGCCGGCGGACCCUGCUCGUUUGGAAGCGGCAGCA CUCCUGUGAUCGGUGGCAACACCUUCAAUCUGAAGGCCUCCAG GGGGAACGAUAGGAACAGGAUCGUGCUGCCAUUCAGCUUUGC CUGGCCCCGGUCAUACACCCUGCUGGUGGAGGCCUGGGACUCC AGCAACGACACCGUGCAGCCCGACUCCAUCAUAGAGAAGGCGA GCCACAGCGGCAUGAUCAACCCCUCCAGGCAGUGGCAGACCCU CAAGCAGAACACCGGCGUCGCCCACUUCGAAUACCAGAUCAGG GUCACGUGCGACGACUACUACUACGGCUUUGGCUGCAAUAAG UUCUGCAGGCCCCGGGACGACUUCUUCGGGCACUACGCCUGCG ACCAGAACGGGAACAAAACCUGUAUGGAGGGGUGGAUGGGCC CCGAAUGCAACCGAGCCAUCUGCCGCCAGGGGUGCUCCCCCAA GCACGGCUCCUGUAAACUCCCCGGCGAUUGCAGGUGUCAGUAC GGCUGGCAGGGUCUCUACUGCGACAAGUGCAUCCCGCACCCCG GCUGCGUCCACGGCAUCUGUAAUGAGCCCUGGCAAUGCCUGU GCGAGACCAACUGGGGCGGCCAGCUGUGCGACAAGGACCUCA AUUAUUGUGGCACCCACCAGCCAUGCCUGAAUGGUGGCACCU GCAGCAACACAGGCCCAGACAAGUACCAGUGCAGCUGUCCCGA GGGCUACUCGGGCCCCAACUGCGAAAUCGCCGAGCACGCUUGC CUGAGCGACCCCUGUCACAACAGGGGCAGCUGCAAGGAAACCA GCCUGGGGUUCGAGUGCGAGUGCAGCCCCGGGUGGACCGGCCC CACCUGCAGCACCAACAUCGACGACUGCAGCCCCAACAACUGU AGCCAUGGCGGCACCUGCCAGGAUCUGGUCAACGGCUUCAAG UGCGUGUGUCCCCCCCAGUGGACCGGCAAGACCUGCCAGCUCG ACGCCAACGAGUGUGAAGCAAAGCCCUGCGUGAAUGCCAAGU CCUGCAAGAACCUGAUAGCCUCCUACUACUGCGACUGCCUGCC |

TABLE 2-continued

Sequence optimized sequences for human JAG1

| SEQ ID NO | NAME | SEQUENCE |
|---|---|---|
| | | CGGCUGGAUGGGCCAGAACUGUGACAUCAACAUCAACGACUG<br>CCUGGGGCAGUGUCAGAAUGACGCCAGCUGCCGCGACCUGGU<br>GAAUGGCUAUAGGUGCAUCUGCCCCCCGGAUACGCCGGCGAC<br>CACUGCGAGAGGGAUAUCGAUGAGUGCGCCAGCAACCCUUGC<br>CUGAACGGCGGGCACUGCCAGAACGAGAUUAACAGGUUCCAG<br>UGCCUGUGCCCCACCGGCUUCAGCGGCAAUCUGUGCCAGCUGG<br>AUAUCGACUACUGCGAGCCCAACCCGUGCCAGAACGGCGCCCA<br>GUGCUACAACAGGGCCUCCGACUACUUCUGUAAGUGUCCCGA<br>GGACUAUGAGGGCAAGAACUGUUCCCACCUGAAAGACCACUG<br>CAGGACCACCCCCUGCGAGGUGAUCGACUCGUGCACCGUGGCC<br>AUGGCGAGCAAUGACACCCCGGAAGGCGUGCGCUAUAUCAGC<br>AGCAAUGUGUGCGGGCCCCACGGCAAGUGCAAGAGCCAGAGC<br>GGCGGGAAGUUCACCUGCGACUGCAACAAGGGCUUCACCGGC<br>ACGUACUGCCACGAGAACAUCAACGAUUGCGAGUCCAACCCCU<br>GCCGGAACGGCGGCACCUGCAUAGAUGGAGUGAACUCCUAUA<br>AGUGCAUCUGCUCCGAUGGGUGGGAGGGCGCCUACUGUGAAA<br>CCAACAUCAACGACUGCAGCCAGAACCCCUGCCAUAAUGGUGG<br>CACGUGCCGGGACCUGGUUAAUGACUUCUACUGCGACUGCAA<br>GAACGGCUGGAAGGGCAAGACCUGCCACAGCAGAGAUAGCCA<br>GUGCGACGAGGCCACGUGCAACAAUGGCGGGACCUGCUACGA<br>CGAGGGGGACGCCUUCAAAUGCAUGUGCCCCGGCGGAUGGGA<br>GGGGACCACCUGCAACAUCGCCAGGAACUCCAGCUGCCUGCCC<br>AACCCGUGCCAUAACGGUGGCACCUGCGUGGUGAACGGCGAA<br>AGCUUCACCUGCGUGUGCAAGGAGGGCUGGGAGGGCCCCAUC<br>UGCGCCCAGAACACCAAUGACUGCUCCCCCCACCCAUGCUACA<br>ACUCCGGGACCUGUGUGGACGGCGACAACUGGUAUAGGUGCG<br>AGUGUGCCCCCGGCUUCGCCGGCCCCGACUGCAGGAUCAACAU<br>CAACGAAUGUCAGAGCUCCCCCUGCGCCUUUGGCGCCACAUGU<br>GUCGAUGAGAUUAACGGCUACCGGUGCGUCUGCCCCCCCGGCC<br>ACAGCGGCGCGAAGUGCCAGGAAGUCUCCGGCAGGCCCUGUA<br>UCACCAUGGGCAGCGUGAUCCCCGACGGCGCCAAGUGGGACGA<br>CGACUGCAACACCUGUCAAUGCCUGAAUGGCAGGAUCGCCUGC<br>AGCAAAGUCUGGUGCGGGCCCCGGCCCUGCCUGCUGCACAAGG<br>GCCACAGCGAGUGCCCUUCCGGCCAGAGCUGCAUCCCGAUCCU<br>GGACGAUCAGUGUUUUGUCCAUCCAUGCACCGGCGUGGGCGA<br>GUGUAGGUCGAGCAGCCUGCAGCCCGUGAAAACAAAGUGCAC<br>CAGCGACAGCUACUACCAGGAUAACUGUGCCAACAUCACCUUU<br>ACCUUCAACAAGGAGAUGAUGAGCCCCGGACUGACCACCGAGC<br>AUAUCUGUUCAGAGCUGAGGAACCUGAACAUCCUCAAGAACG<br>UCAGCGCCGAGUACAGCAUCUACAUCGCCUGCGAGCCCAGCCC<br>CUCCGCCAACAACGAAAUCCACGUGGCCAUAAGCGCCGAGGAC<br>AUCAGGGACGACGGCAAUCCGAUCAAGGAGAUAACCGACAAG<br>AUCAUCGACCUCGUGAGUAAGAGGGACGGGAACAGUAGCCUC<br>AUCGCCGCCGUCGCCGAGGUGAGGGUGCAGCGGAGGCCCCUGA<br>AGAACAGGACCGAUUUUCUGGUCCCCCUGCUGAGCUCCGUGCU<br>GACCGUGGCCUGGAUCUGCUGCCUGGUGACGGCGUUCUACUG<br>GUGCCUCCGGAAACGACGGAAGCCCGGGAGCCAUACCCACUCC<br>GCCAGCGAGGACAACACCACCAAUAACGUGAGGGAGCAGCUG<br>AAUCAGAUCAAGAAUCCGAUCGAGAAGCACGGCGCCAACACC<br>GUGCCGAUCAAAGACUACGAGAACAAGAAUUCCAAGAUGAGC<br>AAGAUCAGGACCCACAACUCCGAGGUGGAGGAAGAUGACAUG<br>GACAAGCACCAGCAGAAAGCCAGGUUUGCCAAGCAGCCCGCCU<br>AUACCCUGGUGGACAGGGAGGAGAAACCCCCGAAUGGCACCCC<br>CACCAAACACCCAAACUGGACCAACAAGCAGGACAACAGGGAU<br>CUGGAGAGCGCCCAGAGCCUCAACCGUAUGGAGUACAUCGUG |
| 91 | JAG1-CO05 | AUGAGGUCACCCCGGACCCGGGGACGCUCCGGCAGGCCCCUGA<br>GCCUGCUGCUGGCCCUGCUGUGCGCCCUCAGGGCCAAGGUCUG<br>CGGCGCCUCCGGUCAGUUCGAACUCGAGAUCCUGAGCAUGCAG<br>AACGUGAACGGUGAACUGCAGAACGGCAACUGCUGCGGCGGC<br>GCCAGGAAUCCCGGCGACCGAAAGUGCACCAGGGACGAGUGC<br>GACACCUACUUUAAGGUGUGCCUAAAGGAGUACCAGAGCCGG<br>GUGACGGCCGGCGGCCCCUGUUCCUUCGGCAGCGGCAGCACGC<br>CCGUGAUCGGCGGCAACACCUUCAACCUCAAGGCCUCGCGCGG<br>CAACGAUCGGAACAGGAUCGUGCUGCCGUUUUCCUUUGCCUG<br>GCCCAGGUCGUACACCCUGCUGGUGGAGGCCUGGGACAGCUCC<br>AAUGACACCGUGCAGCCAGACUCCAUAAUCGAGAAGGCCAGCC<br>ACAGCGGGAUGAUUAAUCCAAGCAGGCAGUGGCAAACCCUGA<br>AGCAGAACACCGGAGUGGCCCAUUUCGAGUACCAGAUCAGGG<br>UGACCUGCGACGACUACUACUACGGCUUCGGAUGCAACAAGU<br>UCUGCAGGCCCCGGGACGACUUCUUCGGCCAUUACGCCUGCGA<br>CCAGAACGGCAACAAGACCUGCAUGGAGGGUUGGAUGGGCCC<br>CGAAUGCAAUAGGGCCAUCUGCAGGCAAGGCUGUUCCCCCAA<br>ACACGGGAGCUGUAAACUCCCCGGCGACUGCCGAUGCCAGUAC<br>GGGUGGCAAGGCCUCUACUGCGACAAGUGCAUCCCCCAUCCCG |

TABLE 2-continued

Sequence optimized sequences for human JAG1

| SEQ ID NO | NAME | SEQUENCE |
|---|---|---|
| | | GCUGCGUGCAUGGCAUUUGCAACGAACCCUGGCAAUGCCUCU<br>GCGAGACCAACUGGGGGGCCAGCUCUGCGACAAGGAUCUGA<br>ACUACUGCGGCACACACCAGCCUUGCCUGAACGGAGGGACCUG<br>CAGUAAUACCGGCCCCGACAAGUACCAGUGCAGCUGCCCCGAG<br>GGCUAUAGCGGCCCCAACUGCGAAAUUGCCGAGCACGCCUGCC<br>UGAGCGACCCCUGUCACAACAGGGGCAGCUGCAAGGAGACCA<br>GUCUGGGCUUCGAGUGCGAGUGCAGCCCAGGCUGGACGGGCC<br>CCACCUGCUCCACCAACAUCGACGACUGCUCCCCCAACAAUUG<br>CAGCCACGGCGGCACCUGCCAAGAUCUCGUGAACGGCUUCAAG<br>UGCGUGUGUCCGCCGCAGUGGACCGGGAAAACCUGCCAACUG<br>GACGCCAACGAGUGUGAGGCAAAGCCCUGCGUGAACGCGAAG<br>UCCUGUAAGAACCUGAUCGCCAGCUACUAUUGCGACUGCCUGC<br>CGGGCUGGAUGGGGCAGAACUGUGACAUCAACAUCAACGAUU<br>GCCUGGGCCAGUGUCAGAACGACGCCAGCUGCAGGGACCUGG<br>UCAACGGCUACAGGUGCAUCUGUCCCCCGGGGUAUGCCGGGG<br>ACCACCGCGAACGAGAUAUCGACGAGUGCGCCUCGAACCCUUG<br>CCUCAAUGGCGGCCACUGCCAGAACGAGAUCAACAGGUUCCAG<br>UGCCUGUGCCCCACCGGCUUCAGCGGCAAUCUGUGCCAGCUGG<br>ACAUCGACUAUUGUGAACCCAACCCGUGCCAGAACGGCGCCCA<br>GUGCUACAACCGCGCCUCCGACUACUUCUGCAAGUGCCCGGAG<br>GACUACGAGGGCAAGAACUGCAGCCAUCUGAAGGACCACUGU<br>AGAACCACGCCCUGCGAGGUGAUCGACUCCUGCACCGUCGCCA<br>UGGCCUCAAACGACACCCCCGAGGGAGUGCGCUACAUCAGCUC<br>GAACGUGUGCGGCCCCCAUGGAAAAUGCAAGAGCCAGUCCGG<br>GGGCAAGUUCACCUGCGACUGCAACAAGGGCUUCACCGGCACG<br>UAUUGCCAUGAGAACAUCAAUGACUGCGAGAGCAACCCGUGC<br>CGUAACGGGGGCACCUGUAUCGAUGGCGUGAACAGCUACAAG<br>UGCAUCUGUAGCGACGGCUGGGAGGGCGCCUAUUGCGAAACC<br>AACAUCAACGACUGUUCCCAGAACCCAUGCCACAACGGGGGCA<br>CCUGUAGGGACCUGGUCAACGACUUUUACUGUGACUGCAAGA<br>ACGGUUGGAAAGGCAAGACCUGCCACUCGAGGGACAGCCAGU<br>GUGACGAGGCCACGUGCAACAAUGGCGGCACCUGUUACGACG<br>AGGGCGACGCCUUUAAGUGCAUGUGUCCCGGGGGUUGGGAGG<br>GUACCACCUGUAACAUCGCCAGGAACUCAAGCUGCCUGCCCAA<br>UCCCUGCCAUAACCGGUGGGACCUGCGUGGUGAACGGCGAAAG<br>CUUCACCUGCGUGUGCAAGGAGGGCUGGGAGGGCCCCAUCUG<br>UGCCCAGAACACCAAUGACUGCAGCCCCCACCCCUGUUACAAC<br>AGCGGGACCUGCGUGGAUGGUGACAACUGGUACAGGUGUGAG<br>UGCGCCCCCGGGUUUGCCGGCCCCGACUGCAGGAUCAACAUCA<br>ACGAGUGCCAGAGCAGCCCCUGUGCCUUCGGCGCCACCUGCGU<br>GGACGAGAUCAACGGGUACCGGUGCGUGUGCCCCCCGGCCAC<br>UCCGGCGCCAAGUGCCAGGAGGUGUCCGGCAGGCCCUGCAUCA<br>CCAUGGGCAGCGUCAUCCCCGACGGCGCCAAAUGGGACGACGA<br>CUGCAACACCUGUCAGUGCCUGAACGGCAGGAUCGCCUGCUCC<br>AAGGUUUGGUGCGGGCCCAGGCCCUGCCUGCUGCACAAGGGA<br>CAUAGCGAAUGCCCCAGCGGCCAGAGCUGCAUCCCCAUCCUGG<br>ACGACCAGUGCUUCGUGCAUCCCUGCACCGGGGUGGGCGAGU<br>GCCGGAGCUCCUCGCUGCAACCCGUCAAGACCAAGUGCACCUC<br>GGACAGCUAUUACCAGGACAACUGCGCCAACAUCACCUUCACC<br>UUCAACAAGGAAAUGAUGAGCCCCGGCCUGACCACCGAGCAU<br>AUCUGCAGCGAGCUGCGGAACCUGAACAUACUGAAGAACGUU<br>AGCGCCGAGUACUCCAUCUACAUCGCCUGCGAGCCCAGCCCGA<br>GCGCGAAUAAUGAGAUCCACGUCGCCAUCAGCGCCGAGGACA<br>UCCGGGACGACGGCAACCCCAUCAAGGAGAUCACCGACAAGAU<br>CAUCGACCUGGUCAGCAAGCGUGACGGCAACUCCAGCCUGAUC<br>GCCGCGGUGGCUGAGGUGCGAGUCCAGAGGAGGCCCCUGAAG<br>AACAGGACGGACUUCCUCGUCCCUCUGCUGAGCAGCGUGCUGA<br>CCGUGGCCUGGAUCUGUUGCCUGGUGACCGCCUUUUACUGGU<br>GCCUGCGAAAGAGGAGGAAGCCGGGCAGCCACACCCACAGCGC<br>CUCAGAAGACAACACCACAAACAACGUCCGCGAGCAGCUCAAC<br>CAGAUCAAAAACCCCAUCGAAAAGCACGGCGCCAACACCGUGC<br>CCAUCAAGGACUACGAGAACAAGAAUAGCAAGAUGAGCAAGA<br>UCCGCACUCACAACAGCGAGGUGGAGGAGGACGACAUGGACA<br>AGCACCAGCAGAAGGCCAGGUUUGCCAAGCAGCCCGCCUACAC<br>CCUGGUGGACCGGGAGGAGAAGCCGCCCAAUGGCACCCCCACG<br>AAGCACCCGAACUGGACCAACAAACAGGACAACAGGGACCUG<br>GAGAGCGCCCAGAGCCUGAACCGCAUGGAGUACAUCGUG |
| 92 | JAG1-<br>CO06 | AUGCGGUCCCCCAGGACCAGGGGGCGCAGCGGGAGGCCCCUGA<br>GCCUGCUGCUGGCCUUACUGUGUGCCCUGAGGGCCAAGGUGU<br>GCGGCGCCAGCGGGCAGUUCGAGCUGGAGAUACUGUCCAUGC<br>AAAACGUGAACGGCGAACUGCAGAAUGGGAAUUGCUGCGGUG<br>GCGCCAGGAACCCUGGGGACCGCAAGUGUACCCGGGACGAGU<br>GCGACACCUACUUCAAGGUGUGUCUCAAGGAAUAUCAGUCCC<br>GCGUGACCGCCGGGGGCCCCUGCAGCUUCGGCUCAGGCAGCAC |

TABLE 2-continued

Sequence optimized sequences for human JAG1

| SEQ ID NO | NAME | SEQUENCE |
|---|---|---|
| | | CCCAGUCAUCGGGGGCAACACCUUCAACCUGAAGGCCAGCCGU<br>GGCAACGACAGGAACAGGAUAGUGCUGCCCUUCUCCUUCGCG<br>UGGCCCAGGUCCUACACCCUGCUGGUGGAGGCGUGGGAUAGC<br>UCGAAUGAUACCGUCCAGCCCGACUCCAUCAUCGAGAAAGCCU<br>CCCACUCCGGUAUGAUCAAUCCAAGCAGGCAGUGGCAGACCCU<br>GAAGCAGAACACGGGCGUGGCCCACUUUGAGUACCAGAUCAG<br>GGUCACCUGCGACGACUACUACUACGGCUUCGGCUGUAAUAA<br>AUUUUGCCGGCCUCGGGACGACUUCUUCGGCCACUACGCCUGC<br>GACCAGAACGGCAAUAAGACGUGUAUGGAGGGCUGGAUGGGC<br>CCGGAGUGUAAUAGGGCCAUCUGCCGACAGGGGUGCAGCCCC<br>AAGCACGGCAGCUGCAAGCUGCCCGGCGACUGCAGGUGUCAG<br>UACGGCUGGCAAGGACUGUAUUGUGACAAGUGCAUUCCCCAU<br>CCGGGCUGUGUGCACGGAAUCUGCAAUGAGCCCUGGCAGUGC<br>CUGUGCGAGACCAACUGGGGCGGCCAGCUGUGUGACAAGGAU<br>CUGAACUACUGUGGCACCCACCAGCCCUGCCUGAACGGCGGGA<br>CCUGCUCCAAUACCGGGCCCGACAAGUACCAGUGUUCCUGCCC<br>CGAGGGCUACAGCGGUCCAAACUGCGAGAUCGCCGAGCACGCC<br>UGCCUGAGCGACCCCUGCCAUAACAGGGGCUCCUGCAAGGAGA<br>CCAGCCUGGGCUUCGAAUGCGAGUGCUCCCCCGGGUGGACCGG<br>CCCCACCUGCAGUACCAACAUCGAUGACUGCAGCCCCAAUAAC<br>UGUUCCCACGGCGGCACCUGCCAGGACCUGGUGAACGGCUUCA<br>AAUGCGUCUGUCCGCCCCAGUGGACCGGAAAGACCUGUCAGCU<br>CGACGCAAACGAGUGCGAGGCCAAGCCCUGCGUGAACGCCAAG<br>AGCUGCAAGAAUCUGAUCGCCUCCUACUACUGCGAUUGUCUG<br>CCCGGAUGGAUGGGCCAAAACUGCGACAUCAACAUCAACGAU<br>UGUCUGGGGCAGUGCCAGAACGACGCCAGCUGCAGGGACCUG<br>GUCAACGGCUACAGGUGCAUCUGCCCCCCCGGCUAUGCCGGAG<br>ACCAUUGCGAGCGAGACAUCGACGAGUGUGCCUCGAACCCCUG<br>CCUGAACGGGGGGCACUGCCAGAACGAAAUCAACAGGUUCCA<br>AUGCCUCUGCCCCACCGGGUUCAGCGGCAACCUGUGCCAGCUG<br>GACAUCGACUAUUGCGAGCCCAACCCCUGCCAGAACGGGGCGC<br>AGUGUUAUAACCGGGCCUCGGACUACUUCUGUAAGUGUCCCG<br>AGGACUACGAGGGCAAAAACUGCUCCCACCUGAAGGACCACU<br>GCCGUACCACACCCUGCGAAGUCAUCGACUCCUGCACCGUGGC<br>CAUGGCCAGCAACGACACCCCCGAGGGAGUGCGGUACAUCAGC<br>AGCAACGUGUGCGGGCCGCAUGGCAAGUGUAAGUCCCAGAGC<br>GGGGGCAAGUUUACAUGUGACUGUAACAAGGGCUUCACCGGC<br>ACAUACUGCCACGAGAACAUCAACGAUUGCGAGAGCAACCCCU<br>GCCGGAAUGGGGGCACCUGCAUCGACGGGGUGAACAGCUAUA<br>AGUGUAUCUGCUCCGAUGGCUGGGAGGGCGCCUACUGCGAGA<br>CUAACAUCAAUGACUGCUCGCAGAACCCGUGCCACAACGGGGG<br>AACCUGCAGGGAUCUCGUGAACGACUUCUACUGCGACUGCAA<br>GAACGGGUGGAAGGGGAAGACCUGCCACAGCCGCGACUCCCA<br>GUGCGACGAGGCCACCUGCAACAAUGGGGGCACCUGCUACGAC<br>GAGGGCGACGCCUUCAAGUGCAUGUGCCCCGGCGGGUGGGAG<br>GGCACCACCUGCAACAUCGCCCGGAACUCCAGCUGCCUGCCCA<br>AUCCGUGUCACAAUGGGGGCACCUGCGUGGUGAACGGCGAGU<br>CGUUCACGUGCGUGUGCAAGGAAGGCUGGGAGGGACCGAUCU<br>GCGCCCAAAAUACCAACGACUGUAGCCCCCACCCCUGUUAUAA<br>CAGCGGCACCUGCGUCGACGGGGACAAUUGGUACCGGUGCGA<br>GUGCGCCCCCGGCUUCGCCGGCCCCGACUGCCGAAUCAACAUC<br>AACGAAUGUCAAAGCUCACCCUGUGCCUUCGGGGCAACCUGU<br>GUGGACGAGAUCAACGGCUACCGGUGUGUGUGCCCCCCGGGA<br>CACUCCGGGGCCAAGUGCCAGGAGGUGAGCGGGCGACCAUGC<br>AUCACCAUGGGCUCCGUGAUCCCCGACGGCGCCAAGUGGGACG<br>ACGACUGCAACACCUGCCAGUGCCUGAACGGCAGGAUCGCCUG<br>CUCCAAGGUGUGGUGUGGCCCCCGGCCCUGUCUCCUGCACAAA<br>GGUCACAGCGAGUGCCCCAGCGGCCAGAGCUGCAUCCCGAUCC<br>UUGACGACCAGUGCUUCGUGCACCCGUGUACAGGCGUAGGGG<br>AGUGCAGGAGCUCCUCGCUCCAGCCCGUGAAAACCAAGUGUAC<br>CAGCGACUCAUACUAUCAGGACAACUGUGCCAAUAUCACCUU<br>UACCUUCAACAAGGAAAUGAUGAGCCCCGGGCUGACCACCGA<br>GCACAUCUGCAGCGAGCUGCGGAACCUUAACAUUCUGAAAAA<br>UGUGUCCGCCGAGUACAGCAUAUACAUCGCCUGCGAGCCGAGC<br>CCUAGCGCCAACAAUGAGAUACACGUGGCCAUCAGCGCUGAG<br>GACAUCAGGGAUGACGGCAACCCGAUCAAGGAGAUCACCGAC<br>AAGAUAAUAGACCUCGUCAGCAAAAGGGACGGCAACAGCAGC<br>CUGAUCGCCGCCGUCGCCGAGGUGAGGGUGCAGCGCCGGCCCC<br>UGAAGAACAGGACCGACUUCCUGGUGCCCCUCCUGAGCUCCGU<br>GCUGACCGUGGCCUGGAUCUGCUGCCUGGUGACCGCCUUCUAC<br>UGGUGUCUGAGGAAAAGGAGGAAGCCUGGCAGCCACACCCAU<br>AGCGCCUCCGAGGACAAUACCACCAACAACGUCAGGGAACAGC<br>UCAACCAAAUCAAGAACCCCAUCGAGAAGCACGGCGCCAAUAC<br>CGUGCCCAUCAAGGAUUACGAGAACAAGAAUAGCAAGAUGUC<br>CAAGAUCCGCACACAUAAUUCCGAGGUCGAGGAAGACGACAU |

TABLE 2-continued

Sequence optimized sequences for human JAG1

| SEQ ID NO | NAME | SEQUENCE |
|---|---|---|
| | | GGAUAAGCACCAGCAGAAGGCCAGAUUCGCCAAGCAGCCCGCC UACACCCUGGUGGACAGGGAGGAGAAGCCCCCCAACGGCACAC CCACCAAGCAUCCCAACUGGACCAACAAGCAGGACAACAGGGA CCUGGAGAGCGCCCAGUCCCUGAACCGUAUGGAGUACAUCGUC |
| 93 | JAG1-CO07 | AUGAGGAGCCCCAGGACAAGGGGCCGGAGCGGCAGGCCCCUG AGCCUGCUGCUCGCCCUCCUCUGUGCCCUGCGCGCCAAAGUGU GCGGGGCCUCAGGCCAGUUCGAGCUCGAGAUCCUGUCCAUGCA AAACGUGAACGGCGAACUGCAGAACGGAAAUUGCUGCGGUGG CGCCCGUAACCCCGGCGACCGCAAGUGCACCAGGGACGAGUGC GACACCUACUUCAAGGUGUGUCUGAAGGAGUACCAGAGCAGG GUCACCGCCGGCGGCCCCUGCAGCUUUGGCUCCGGCAGCACCC CCGUGAUCGGCGGCAACACCUUCAACCUGAAGGCUAGCCGCGG CAACGACAGGAACAGGAUCGUGCUUCCAUUUAGCUUCGCCUG GCCCAGGAGCUACACCCUGCUUGUGGAGGCCUGGGACAGCUCC AACGACACCGUGCAGCCCGACAGCAUCAUCGAGAAGGCCAGCC ACUCCGGCAUGAUCAACCCCAGCCGGCAGUGGCAGACCCUGAA GCAGAACACCGGCGUCGCGCACUUCGAGUACCAGAUCAGGGU GACAUGUGACGACUAUUACUAUGGCUUUGGAUGUAACAAGUU CUGCAGGCCCAGAGACGACUUCUUCGGCCACUACGCCUGCGAC CAGAACGGAAAUAAGACCUGUAUGGAAGGCUGGAUGGGGCCC GAGUGCAACCGAGCCAUCUGCAGGCAAGGCUGCAGCCCCAAGC ACGGCAGCUGCAAGCUGCCCGGGGACUGCCGGUGCCAGUACGG CUGGCAGGGCUUGUAUUGCGACAAGUGCAUCCCGCACCCCGGC UGCGUGCACGGGAUCUGCAACGAGCCCUGGCAGUGCCUGUGC GAGACGAACUGGGGCGGCCAGCUGUGCGACAAGGACCUGAAC UACUGCGGGACGCAUCAACCCUGUCUCAACGGCGGUACCUGCA GCAAUACCGGCCCCGACAAGUACCAGUGCUCUUGCCCCGAGGG CUAUAGCGGGCCCAACUGUGAGAUCGCCGAGCACGCUUGCCUG UCCGACCCCUGCCACAACCGGGGCUCCUGCAAGGAGACCUCCC UGGGCUUCGAGUGCGAAUGCAGCCCCGGGUGGACCGGUCCCAC GUGCAGCACCAACAUCGAUGACUGUAGCCCCAACAACUGCAGC CACGGCGGCACGUGCCAGGACCUCGUGAACGGCUUCAAGUGCG UGUGCCCCCCCCAGUGGACCGGCAAGACCUGCCAGCUCGACGC CAAUGAGUGCGAAGCCAAGCCCUGCGUCAACGCCAAGUCCUGC AAGAACCUGAUCGCCAGUUACUACUGCGACUGUCUGCCCGGA UGGAUGGGCCAGAAUUGCGACAUCAACAUCAAUGACUGCCUG GGCCAGUGCCAGAAUGACGCGUCCUGUAGGGAUCUGGUGAAC GGGUACAGGUGCAUAUGUCCCCCCGGCUAUGCCGGGGAUCAC UGCGAGAGGGAUAUCGAUGAGUGCGCCAGCAACCCCUGUCUG AACGGUGGCCACUGCCAGAACGAGAUUAACAGGUUCCAGUGC CUGUGCCCCACCGGCUUCAGCGGCAACCUGUGCCAGCUGGAUA UCGACUACUGUGAGCCCAACCCGUGCCAGAACGGCGCCCAGUG CUACAACCGAGCCAGCGAUUAUUUUUGCAAAUGUCCCGAGGA UUACGAAGGGAAGAAUUGCAGCCACCUGAAGGACCAUUGCAG GACCACCCCCUGCGAAGUGAUCGACAGCUGCACCGUGGCCAUG GCCUCGAAUGACACGCCCGAGGGAGUGAGGUACAUCAGUAGC AAUGUGUGCGGCCCCCAUGGGAAGUGCAAGAGCCAGUCGGGC GGAAAGUUUACCUGCGACUGUAACAAGGGCUUCACCGGGACC UACUGUCACGAAAACAUCAACGACUGCGAGUCCAACCCGUGU AGGAACGGCGGGACCUGCAUAGACGGGGUGAAUAGCUAUAAG UGCAUCUGUUCAGACGGAUGGGAGGGGGCCUACUGCGAGACC AACAUCAACGAUUGCUCGCAGAACCCCUGCCACAACGGCGGCA CCUGCCGGGACCUGGUGAACGACUUCUACUGCGACUGUAAAA ACGGCUGGAAGGGGAAGACCUGCCACUCCAGGGACAGCCAGU GCGACGAGGCGACCUGCAACAACGGCGGCACCUGCUACGACGA GGGCGAUGCCUUCAAGUGUAUGUGCCCCGGAGGCUGGGAGGG CACCACCUGCAACAUCGCCCGCAACAGCAGCUGCCUGCCCAAU CCCUGCCACAAUGGUGGAACAUGCGUGGUGAACGGGGAGAGC UUUACGUGCGUGUGCAAGGAGGGAUGGGAGGGCCCCAUCUGU GCCCAGAACACCAACGACUGCUCCCCCCAUCCCUGUUACAACA GCGGCACCUGUGUGGACGGGGACAACUGGUACCGCUGCGAGU GCGCCCCCGGCUUCGCCGGCCCGGACUGCCGUAUCAACAUCAA CGAGUGUCAGAGCAGCCCCUGCGCAUUCGGCGCCACCUGCGUG GAUGAAAUAAACGGCUACAGGUGUGUGUGCCCCCCGGCCAC AGCGGAGCCAAAUGCCAGGAGGUGAGCGGGCGCCCAUGCAUC ACCAUGGGGAGCGUGAUCCCAGACGGGGCGAAGUGGGAUGAC GACUGUAACACCUGCCAGUGCCUGAACGGCCGAAUCGCCUGCA GCAAGGUGUGGUGCGGGCCCCGGCCCUGCCUGCUGCACAAAGG CCACAGCGAGUGCCCCAGCGGCCAGAGCUGCAUACCGAUCCUG GACGACCAGUGCUUCGUACACCCCUGCACCGGGGUGGGCGAGU GCCGGUCCUCCUCGCUCCAGCCCGUCAAGACCAAGUGCACCAG CGAUAGCUACUACCAGGACAACUGCGCCAACAUCACCUUUACC UUUAACAAGGAGAUGAUGAGCCCCGGCCUGACCACGGAGCAC AUCUGCAGCGAGCUGCGCAACCUCAACAUCCUGAAAAACGUG |

TABLE 2-continued

Sequence optimized sequences for human JAG1

| SEQ ID NO | NAME | SEQUENCE |
|---|---|---|
| | | UCGGCCGAGUACUCCAUCUACAUCGCCUGCGAGCCCUCCCCCU<br>CCGCCAACAAUGAAAUCCACGUGGCCAUCAGCGCCGAGGACAU<br>CCGAGACGAUGGGAACCCCAUCAAGGAAAUCACCGACAAGAU<br>AAUCGACCUGGUGAGUAAAAGGGACGGGAACAGCAGCCUGAU<br>CGCUGCCGUGGCGGAGGUGAGGGUCCAGAGGAGGCCGCUGAA<br>AAAUCGGACCGACUUUCUGGUGCCCCUGCUGAGCUCCGUGCUG<br>ACCGUCGCCUGGAUCUGCUGCCUGGUCACCGCCUUCUACUGGU<br>GCCUGAGGAAGCGUAGGAAGCCCGGCAGCCACACGCACAGCGC<br>CAGCGAGGACAACACCACCAACAACGUGCGGGAGCAGCUGAAC<br>CAGAUCAAGAACCCCAUCGAGAAGCACGGCGCGAACACAGUGC<br>CGAUCAAGGAUUACGAGAACAAGAAUUCCAAGAUGAGCAAGA<br>UCAGGACCCACAACAGCGAGGUGGAGGAGGACGACAUGGAUA<br>AACACCAGCAGAAGGCCAGGUUCGCCAAGCAGCCCGCCUAUAC<br>CCUGGUCGACAGGGAGGAGAAACCCCCUAAUGGCACCCCCACC<br>AAGCACCCCAACUGGACAAACAAGCAGGACAACAGGGACCUG<br>GAGAGCGCCCAGAGCCUGAACCGUAUGGAGUAUAUCGUG |
| 94 | JAG1-CO08 | AUGCGGAGCCCCAGAACCCGUGGCCGGAGCGGCAGGCCCCUGU<br>CACUACUGCUGGCCCUGCUGUGCGCGCUUAGGGCCAAGGUCUG<br>CGGCGCCAGCGGCCAGUUCGAGCUGGAGAUCCUGAGCAUGCA<br>GAACGUGAACGGCGAGCUGCAGAACGGCAACUGCUGCGGCGG<br>GGCCAGGAACCCCGGAGACCGCAAAUGCACCCGGGACGAGUGC<br>GACACCUAUUUUAAAGUGUGCCUGAAGGAGUACCAGAGCAGG<br>GUGACCGCCGGCGGCCCCUGCAGCUUCGGCAGCGGCAGCACCC<br>CCGUGAUCGGCGGGAAUACCUUCAACCUGAAGGCCAGCCGCGG<br>CAACGACAGGAACCGAAUCGUGCUGCCCUUUAGCUUCGCCUGG<br>CCUCGGAGCUACACCCUGCUGGUGGAAGCCUGGGACUCCUCCA<br>ACGACACCGUGCAACCCGACUCCAUUAUCGAGAAGGCCUCCCA<br>CAGCGGCAUGAUAAACCCCAGCCGGCAGUGGCAGACACUGAA<br>GCAAAACACCGGGGUCGCACAUUUCGAGUACCAGAUCAGGGU<br>GACGUGUGACGACUACUACUACGGGUUCGGAUGCAACAAGUU<br>CUGCAGGCCCAGGGACGACUUCUUCGGCCACUACGCCUGUGAC<br>CAGAACGGCAAUAAGACCUGCAUGGAGGGGUGGAUGGGCCCG<br>GAGUGCAACAGGGCCAUAUGCCGGCAGGGCUGCUCCCCAAAAC<br>ACGGGUCCUGCAAGCUGCCUGGCGACUGCAGGUGUCAGUACG<br>GCUGGCAGGGGCUGUACUGCGAUAAGUGCAUCCCCCACCCCGG<br>CUGCGUCCACGGCAUCUGCAACGAGCCAUGGCAGUGUCUGUGC<br>GAGACCAACUGGGGUGGGCAGCUGUGCGACAAGGAUCUGAAC<br>UACUGCGGCACCCACCAGCCCUGCCUCAACGGGGGAACGUGCU<br>CGAACACCGGGCCCGAUAAGUACCAGUGCUCCUGCCCCGAAGG<br>CUACUCGGGACCUAACUGUGAGAUCGCUGAGCACGCAUGCCU<br>GAGCGACCCAUGCCAUAACAGGGGUAGUUGCAAGGAGACCUC<br>CCUCGGUUUUGAAUGCGAGUGCAGCCCCGGCUGGACCGGCCCC<br>ACCUGCUCGACCAACAUCGACGACUGCAGCCCAAACAACUGCU<br>CCCACGGCGGCACGUGUCAGGACCUGGUGAAUGGCUUCAAGU<br>GUGUGUGCCCCCCCAGUGGACCGGAAAAACCUGCCAGCUGGA<br>UGCCAACGAGUGUGAGGCCAAGCCCUGCGUGAACGCGAAGUC<br>CUGCAAGAACCUGAUCGCCUCCUACUACUGUGACUGCCUGCCC<br>GGUUGGAUGGGCCAAAACUGCGACAUCAACAUCAACGACUGC<br>CUGGGCCAGUGCCAGAACGACGCCAGCUGCAGGGACCUAGUG<br>AACGGGUAUCGGUGCAUCUGCCCCCCCGGCUACGCCGGCGAUC<br>ACUGCGAAAGGGACAUCGACGAGUGCGCCAGCAACCCGUGCCU<br>GAACGGGGGGCACUGCCAGAACGAGAUCAACAGGUUCCAGUG<br>CCUCUGCCCCACCGGGUUCAGCGGGAACCUCUGCCAGCUCGAC<br>AUCGACUACUGCGAGCCCAAUCCCUGCCAGAACGGCGCGCAAU<br>GCUACAAUAGGGCCUCGGACUACUUCUGCAAGUGCCCCGAGG<br>ACUACGAGGGCAAAAACUGCAGCCACCUGAAGGACCACUGUA<br>GGACAACCCCCUGCGAAGUCAUCGACUCCUGCACCGUGGCCAU<br>GGCCUCCAACGACACCCCAGAAGGCGUACGUUACAUCAGCUCC<br>AACGUCUGCGGGCCCCACGGGAAGUGCAAGAGCCAGAGCGGC<br>GGCAAGUUCACGUGUGACUGCAACAAAGGGUUCACCGGCACC<br>UACUGCCAUGAGAACAUAAAUGACUGCGAGUCCAACCCCUGU<br>CGGAACGGCGGCACCUGCAUCGACGGCGUAAACUCUUACAAA<br>UGUAUCUGCAGCGACGGCUGGGAGGGCGCCUACUGCGAGACC<br>AACAUCAACGACUGCAGCCAAAACCCCUGUCACAACGGCGGGA<br>CCUGCCGCGACCUCGUCAACGACUUCUACUGCGACUGCAAGAA<br>CGGCUGGAAGGGCAAGACCUGCCACAGCCGGGACUCGCAGUG<br>UGAUGAGGCCACCUGCAACAAUGGCGGCACCUGCUAUGAUGA<br>GGGGGACGCCUUCAAAUGUAUGUGCCCCGGCGGGUGGGAGGG<br>CACCACUUGCAACAUCGCCAGGAACUCCUCCUGCCUCCCCAAC<br>CCCUGCCACAACGGAGGGACGUGCGUGGUGAACGGGGAGAGC<br>UUCACCUGCGUGUGCAAGGAGGGCUGGGAAGGCCCCAUUUGC<br>GCGCAGAACACUAACGAUUGCAGCCCCCACCCCUGCUACAACU<br>CCGGCACCUGCGUGGACGGGGACAACUGGUACCGGUGCGAGU<br>GCGCCCCCGGCUUCGCCGGCCCGGACUGCAGGAUCAACAUCAA |

TABLE 2-continued

Sequence optimized sequences for human JAG1

| SEQ ID NO | NAME | SEQUENCE |
|---|---|---|
| | | CGAAUGUCAGAGCAGCCCCUGCGCCUUCGGAGCCACCUGCGUG |
| | | GACGAGAUAAACGGCUACCGGUGCGUCUGCCCCCCCGGUCACU |
| | | CUGGUGCCAAGUGCCAAGAGGUCAGCGGCAGGCCGUGCAUCA |
| | | CCAUGGGCUCCGUGAUCCCGGAUGGCGCCAAAUGGGACGAUG |
| | | ACUGCAACACCUGCCAGUGCCUUAACGGUCGGAUCGCGUGCAG |
| | | CAAGGUGUGGUGUGGCCCCAGGCCCUGCCUCCUGCACAAGGGG |
| | | CACAGCGAGUGCCCCUCCGGACAGUCCUGUAUCCCCAUCCUGG |
| | | ACGACCAGUGCUUCGUCCACCCCUGCACCGGAGUGGGCGAAUG |
| | | CAGGAGCAGCUCCCUGCAGCCGGUGAAGACCAAGUGCACCAGC |
| | | GACUCCUACUACCAGGACAAUUGCGCCAACAUCACCUUCACCU |
| | | UCAACAAGGAGAUGAUGAGCCCCGGCCUGACCACCGAGCACAU |
| | | CUGCAGCGAGCUGCGCAACCUGAACAUCUUGAAGAACGUGAG |
| | | CGCCGAGUAUUCCAUCUACAUCGCCUGCGAGCCCAGCCCGAGC |
| | | GCCAAUAACGAGAUCCACGUGGCCAUCAGCGCCGAGGACAUCC |
| | | GGGAUGACGGCAAUCCCAUCAAGGAGAUCACCGAUAAGAUCA |
| | | UCGACCUGGUCAGCAAGCGCGACGGCAAUAGCUCGCUGAUCGC |
| | | GGCCGUGGCCGAGGUGAGGGUGCAGCGGCGGCCCCUGAAGAA |
| | | CAGGACCGACUUUCUGGUACCCCUCCUGAGCUCGGUGCUGACC |
| | | GUUGCCUGGAUCUGUUGUCUGGUGACCGCCUUCUACUGGUGC |
| | | CUGCGGAAAAGGCGGAAGCCCGGCUCCCAUACCCAUAGCGCAU |
| | | CCGAAGACAACACCACCAACAACGUCCGUGAGCAGCUGAACCA |
| | | GAUCAAGAACCCCAUAGAGAAACACGGCGCCAACACCGUGCCC |
| | | AUCAAGGACUACGAAAACAAGAACUCCAAGAUGUCCAAAAUC |
| | | AGGACCCACAACAGCGAGGUGGAAGAGGACGACAUGGAUAAA |
| | | CACCAGCAGAAGGCCCGUUUCGCCAAGCAGCCCGCCUACACCU |
| | | UAGUGGACAGGGAGGAGAAACCCCCCAACGGACCCCCACCAA |
| | | GCACCCAAACUGGACGAACAAGCAGGAUAACCGGGACCUGGA |
| | | AUCAGCGCAGUCCCUGAACAGAAUGGAAUACAUCGUC |
| 95 | JAG1-CO09 | AUGAGGUCCCCCCGAACCAGGGGCAGGUCCGGUCGGCCCCUGA |
| | | GCCUGCUCCUGGCCCUCCUGUGCGCCCUGAGAGCCAAGGUGUG |
| | | UGGAGCCAGCGGGCAGUUCGAGCUCGAGAUCCUCUCCAUGCA |
| | | GAACGUGAACGGCGAGCUGCAGAACGGCAACUGCUGCGGAGG |
| | | CGCCAGGAAUCCCGGCGAUCGGAAGUGCACCAGGGACGAGUG |
| | | CGACACCUAUUUCAAGGUGUGCCUCAAGGAGUACCAAAGCAG |
| | | GGUGACCGCCGGCGGCCCCUGCUCCUUCGGCAGCGGCAGCACC |
| | | CCCGUGAUAGGGGGCAACACGUUCAACCUCAAGGCCAGCAGG |
| | | GGCAACGACAGGAACCGCAUCGUGCUGCCCUUCAGCUUUGCGU |
| | | GGCCCCGUUCCUACACCCUGCUGGUCGAGGCCUGGGACAGCUC |
| | | CAACGAUACCGUGCAGCCCGACUCCAUCAUUGAGAAGGCCAGC |
| | | CACAGCGGCAUGAUCAACCCCAGCAGGCAGUGGCAAACCCUGA |
| | | AGCAGAACACCGGAGUGGCCCAUUUCGAAUACCAGAUCAGGG |
| | | UGACCUGCGAUGACUACUAUUAUGGUUUUGGGUGCAACAAAU |
| | | UCUGCCGGCCCCGAGACGACUUCUUCGGUCACUAUGCCUGCGA |
| | | CCAGAACGGCAACAAGACCUGUAUGGAGGGGUGGAUGGGCCC |
| | | UGAGUGCAACCGGGCCAUCUGUCGCCAGGGGUGCUCCCCCAAG |
| | | CACGGCAGCUGCAAGCUGCCUGGCGAUUGCCGGUGUCAGUAC |
| | | GGGUGGCAGGGUCUCUACUGCGACAAGUGCAUCCCCCACCCGG |
| | | GCUGUGUGCACGGCAUCUGCAACGAGCCCUGGCAGUGCCUGU |
| | | GCGAAACCAAUUGGGGCGGCCAACUGUGCGACAAGGACCUGA |
| | | ACUACUGUGGCACCCACCAGCCCUGCCUGAACGGGGGCACUUG |
| | | CUCCAACACGGGCCCCGACAAGUAUCAGUGCAGCUGUCCUGAG |
| | | GGCUACAGCGGCCCCAACUGUGAGAUCGCCGAGCAUGCCUGCC |
| | | UGAGCGACCCGUGCCACAAUCGUGGCAGCUGUAAGGAGACCA |
| | | GCCUGGGCUUCGAGUGCGAGUGCAGCCCGGGUUGGACCGGAC |
| | | CCACCUGCAGCACCAACAUCGACGAUUGCAGCCCCAACAACUG |
| | | UUCACACGGGGGCACGUGCCAAGACCUGGUGAACGGGUUCAA |
| | | GUGUGUCUGCCCCCCCCAGUGGACCGGCAAAACCUGUCAGCUC |
| | | GACGCCAACGAAUGUGAGGCCAAGCCCUGCGUGAAUGCGAAG |
| | | AGCUGCAAGAACCUGAUCGCGUCGUACUAUUGCGAUUGCCUG |
| | | CCCGGCUGGAUGGGCCAGAACUGCGACAUCAACAUCAACGACU |
| | | GCCUGGGCCAGUGCCAAAACGACGCCUCUUGCCGCGAUCUGGU |
| | | CAACGGGUACCGCUGCAUCUGCCCUCCGGGGUACGCCGGGGAU |
| | | CACUGUGAGAGGGACAUAGAUGAGUGCGCGUCCAACCCCUGC |
| | | CUGAACGGGGGGCACUGCCAGAACGAGAUCAACAGGUUUCAG |
| | | UGCCUGUGCCCCACCGGCUUCUCCGGCAACCUGUGCCAGCUUG |
| | | ACAUCGACUACUGCGAGCCCAAUCCCUGCCAGAAUGGCGCCCA |
| | | GUGCUACAACAGGGCCAGCGACUAUUUCUGCAAGUGUCCCGA |
| | | GGACUACGAGGGGAAGAAUUGCUCCCACCUGAAAGACCACUG |
| | | CAGGACGACCCCCUGUGAGGUGAUCGACAGCUGCACCGUGGCC |
| | | AUGGCCUCCAACGACACCCCCGAGGGCGUGAGGUACAUCAGCA |
| | | GCAACGUCUGCGGCCCCCACGGCAAGUGCAAGAGCCAGAGCGG |
| | | CGGAAAGUUCACCUGCGACUGCAACAAGGGGUUCACGGGCAC |
| | | CUACUGCCACGAGAACAUCAACGACUGCGAGUCCAACCCCUGC |
| | | AGGAACGGCGGCACGUGCAUAGACGGGGUUAACAGCUAUAAG |

TABLE 2-continued

Sequence optimized sequences for human JAG1

| SEQ ID NO | NAME | SEQUENCE |
|---|---|---|
| | | UGUAUCUGCUCGGACGGGUGGGAAGGCGCCUACUGCGAGACC<br>AACAUCAACGACUGCUCACAGAAUCCGUGCCACAACGGGGGCA<br>CCUGCAGGGACCUGGUGAACGACUUCUAUUGCGACUGCAAGA<br>ACGGCUGGAAAGGUAAGACAUGCCACUCCCGGGACUCCCAGU<br>GCGACGAGGCCACCUGCAACAACGGAGGAACCUGCUACGAUG<br>AGGGCGACGCCUUCAAGUGCAUGUGCCCCGGGGGAUGGGAAG<br>GCACCACCUGCAACAUCGCCAGGAACUCCAGCUGUCUCCCCAA<br>CCCGUGCCACAACGGCGGGACGUGCGUGGUGAAUGGCGAGUC<br>CUUCACGUGCGUGUGCAAGGAGGGCUGGGAGGGCCCCAUCUG<br>CGCGCAGAACACCAACGAUUGCAGCCCCCACCCGUGCUACAAC<br>UCAGGCACCUGCGUCGACGGUGACAACUGGUACCGGUGCGAG<br>UGCGCCCCAGGGUUCGCGGGCCCCGACUGCAGGAUCAACAUCA<br>ACGAGUGCCAGUCCAGCCCCUGCGCCUUUGGCGCCACCUGCGU<br>GGACGAGAUCAACGGCUACAGGUGCGUGUGCCCCCCCGGCCAU<br>AGCGGCGCCAAGUGCCAGGAGGUGAGCGGCAGGCCCUGCAUC<br>ACCAUGGGCAGCGUGAUCCCCGACGGCGCCAAGUGGGACGACG<br>ACUGCAAUACGUGCCAGUGCCUGAACGGACGCAUUGCCUGCUC<br>CAAGGUGUGGUGCGGCCCCCGGCCGUGCCUGCUCCACAAGGGG<br>CACAGCGAGUGCCCCUCCGGCCAGAGCUGCAUCCCCAUCCUCG<br>ACGACCAGUGCUUCGUCCACCCCUGCACCGGCGUGGGCGAGUG<br>CAGGUCCUCCAGCCUGCAGCCAGUGAAAACCAAGUGUACCAGC<br>GACUCCUACUACCAGGACAACUGCGCCAACAUCACAUUCACAU<br>UCAACAAGGAGAUGAUGAGCCCGGGCCUGACCACCGAGCACA<br>UCUGCAGCGAACUCAGAAACCUGAACAUCCUGAAGAACGUGU<br>CGGCCGAGUACAGCAUCUAUAUCGCGUGCGAGCCCAGCCCCAG<br>CGCGAAUAACGAGAUCCACGUGGCCAUAAGCGCGGAGGACAU<br>CCGGGACGACGGCAACCCCAUCAAGGAGAUCACCGACAAGAUU<br>AUUGACCUGGUCUCCAAGAGGGACGGCAAUAGCUCCCUGAUU<br>GCCGCCGUCGCCGAAGUGCGGGUGCAAAGAAGGCCCCUGAAA<br>AACCGGACGGAUUUCCUGGUCCCCCUCCUGAGCAGCGUGCUGA<br>CCGUCGCCUGGAUCUGCUGUCUGGUGACGGCCUUCUACUGGU<br>GCCUCAGAAAGAGGCGCAAACCCGGCUCGCACACCCAUAGCGC<br>CUCAGAGGACAACACCACGAAUAACGUGCGGGAACAGCUGAA<br>CCAAAUAAAAAACCCCAUCGAGAAGCACGGGGCUAACACCGU<br>GCCGAUCAAGGACUACGAGAACAAGAACAGCAAGAUGUCCAA<br>GAUCCGAACCCACAACAGCGAGGUCGAGGAGGACGACAUGGA<br>CAAGCACCAGCAGAAGGCGAGGUUCGCCAAGCAGCCCGCCUAC<br>ACCCUGGUAGACCGGGAGGAGAAGCCGCCCAACGGCACCCCCA<br>CGAAACACCCCAACUGGACCAACAAACAAGACAACAGGGACCU<br>GGAGAGCGCCCAGUCCCUGAACAGGAUGGAAUAUAUUGUC |
| 96 | JAG1-CO10 | AUGAGGAGCCCCAGGACACGGGGCCGGAGCGGGCGACCUCUG<br>UCCCUGCUCCUGGCCCUGCUGUGCGCCCUGAGAGCCAAAGUGU<br>GCGGCGCCAGCGGGCAGUUCGAGCUGGAGAUACUGAGCAUGC<br>AGAACGUGAACGGCGAGCUGCAGAACGGCAACUGUUGUGGGG<br>GCGCGCGGAACCCCGGGGACAGGAAGUGCACCCGGGACGAGU<br>GCGACACCUACUUCAAGGUGUGCCUCAAGGAAUACCAAAGCC<br>GUGUGACAGCUGGGGGCCCCUGCAGCUUCGGGUCCGGAUCCAC<br>CCCCGUCAUCGGCGGCAACACCUUCAACCUCAAGGCCAGCAGG<br>GGCAACGACAGGAACCGAAUCGUGCUGCCCUUUUCGUUUGCC<br>UGGCCCCGCAGCUACACCCUCCUAGUGGAGGCCUGGGACAGCA<br>GCAACGACACCGUGCAGCCCGACUCCAUCAUCGAGAAGGCAUC<br>CCACAGCGGGAUGAUCAAUCCCUCCCGCCAGUGGCAGACGCUG<br>AAGCAGAACACCGGCGUGGCCCACUUCGAAUACCAAAUCAGG<br>GUGACGUGCGAUGACUACUAUUACGGCUUCGGGUGCAACAAG<br>UUCUGCAGGCCGAGGGAUGACUUCUUCGGCCACUAUGCCUGC<br>GACCAGAACGGAAACAAAACCUGCAUGGAGGGUUGGAUGGGA<br>CCCGAGUGCAACAGGGCCAUCUGCCGCCAGGGCUGCUCACCAA<br>AGCACGGCAGCUGUAAGCUACCCGGCGACUGUCGGUGCCAGU<br>ACGGUUGGCAGGGCCUGUACUGUGACAAGUGCAUCCCCCACCC<br>CGGCUGCGUGCACGGCAUCUGCAAUGAGCCGUGGCAGUGCCU<br>GUGUGAAACCAACUGGGGUGGGCAGCUGUGCGACAAGGACCU<br>GAAUUACUGCGGCACCCACCAGCCCUGUCUGAACGGCGGCACC<br>UGCUCCAACACCGGCCCGGACAAGUAUCAGUGCAGUUGCCCCG<br>AGGGCUAUAGCGGCCCCAACUGCGAGAUCGCCGAGCACGCCUG<br>CCUGUCCGACCCGUGCCACAACAGGGGGAGCUGCAAAGAGACC<br>AGCCUGGGGUUCGAGUGCGAGUGCAGCCCCGGGUGGACCGGA<br>CCCACCUGCAGCACCAACAUCGAUGAUUGCAGCCCUAACAACU<br>GCUCCCACGGCGGCACCUGCCAGGACCUGGUGAACGGCUUUAA<br>GUGCGUAUGCCCCCCCAAUGGACGGGGAAGACCUGUCAGCUC<br>GACGCCAAUGAAUGCGAGGCAAAACCGUGUGUGAACGCCAAG<br>AGCUGCAAAAACCUCAUCGCGUCCUACUACUGCGACUGCCUGC<br>CCGGCUGGAUGGGGCAGAACUGUGACAUCAACAUCAACGAUU<br>GCCUGGGCCAAUGCCAGAAUGAUGCCUCCUGCAGGGACCUUG<br>UGAACGGCUACAGGUGCAUAUGCCCCCCGGCUACGCCGGCGA |

TABLE 2-continued

Sequence optimized sequences for human JAG1

| SEQ ID NO | NAME | SEQUENCE |
|---|---|---|
| | | UCACUGCGAGCGGGAUAUAGACGAGUGUGCCAGCAACCCCUG CCUCAACGGGGGCACUGCCAGAAUGAGAUCAACAGAUUUCA AUGCCUGUGCCCCACAGGAUUUAGCGGAAAUCUGUGCCAACU GGACAUCGACUACUGCGAGCCCAAUCCCUGCCAGAACGGGGCC CAGUGCUACAACCGGGCCAGCGACUACUUUUGCAAGUGCCCCG AGGACUACGAGGGAAAAAACUGCAGCCACCUGAAGGACCAUU GCAGGACCACCCCCUGUGAGGUGAUUGACAGCUGCACCGUGGC CAUGGCCUCAAACGACACCCCCGAGGGUGUGAGGUAUAUCAG CUCGAACGUGUGCGGCCCCCACGGCAAGUGCAAGUCACAAAGC GGGGGAAAGUUCACCUGCGACUGCAACAAGGGCUUCACCGGU ACCUACUGCCACGAGAACAUCAACGACUGUGAGAGCAACCCCU GUAGAAACGGGGGGACCUGCAUCGACGGAGUGAAUUCCUAUA AGUGCAUCUGUAGCGACGGGUGGGAGGGCGCCUACUGCGAGA CCAAUAUCAACGAUUGCAGCCAGAACCCCUGCCACAACGGGGG CACCUGCCGAGAUCUCGUGAACGACUUCUACUGCGACUGUAA AAACGGUUGGAAAGGCAAAACCUGCCACUCCCGCGAUUCCCAG UGCGAUGAGGCGACCUGCAAUAAUGGAGGCACCUGCUACGAC GAGGGCGACGCCUUUAAGUGCAUGUGCCCCGGCGGCUGGGAA GGCACCACCUGCAAUAUCGCGAGAAAUAGCAGCUGCCUGCCCA ACCCCUGCCAUAACGGCGGGACCUGCGUGGUGAAUGGCGAGA GCUUCACCUGCGUCUGUAAGGAGGGCUGGGAAGGUCCCAUCU GUGCCCAGAACACCAACGACUGCAGCCCCCAUCCCUGCUACAA CAGCGGCACCUGCGUGGACGGCGACAAUUGGUACAGGUGCGA GUGCGCCCCCGGGUUUGCCGGCCCCGACUGCAGGAUCAACAUC AACGAGUGCCAGAGUAGCCCCUGUGCCUUCGGCGCCACCUGCG UGGACGAGAUCAACGGCUACCGGUGCGUGUGCCCCCCGGCCA CUCCGGCGCCAAGUGUCAAGAGGUGAGCGGACGACCCUGUAU CACCAUGGGCUCGGUGAUCCCCGACGGCGCCAAGUGGGACGAC GACUGCAACACGUGCCAGUGCCUCAACGGGAGGAUCGCCUGCA GCAAGGUGUGGUGCGGUCCCAGGCCCUGCCUGCUGCACAAAG GCCACUCCGAGUGCCCCAGCGGCCAGAGCUGUAUCCCCAUCCU GGAUGAUCAGUGCUUCGUCCAUCCCUGUACUGGCGUGGGCGA GUGCAGGAGCAGCAGCCUCCAGCCCGUGAAAACCAAGUGCACG AGCGACUCCUAUUACCAAGAUAACUGUGCCAACAUCACCUUCA CCUUUAACAAGGAGAUGAUGUCGCCCGGACUGACCACCGAGC AUAUCUGCAGCGAGCUGAGGAACCUGAACAUACUGAAGAAUG UGUCCGCCGAAUAUUCCAUCUACAUCGCCUGUGAGCCUAGCCC GAGCGCCAACAACGAGAUCCACGUGGCCAUCUCCGCCGAGGAU AUCAGGGACGACGGGAACCCCAUCAAAGAGAUCACCGAUAAG AUCAUCGACCUGGUGUCUAAGCGCGACGGUAACAGCUCCCUA AUCGCCGCCGUGGCCGAGGUGCGCGUGCAGCGCAGGCCGCUGA AGAACCGCACCGACUUCCUGGUGCCCCUGCUGAGCAGCGUGCU CACCGUGGCCUGGAUAUGCUGCCUGGUGACCGCCUUCUACUGG UGCCUGCGGAAGCGGCGUAAACCGGGAAGCCAUACCCACAGCG CCAGCGAGGAUAAUACCACCAAUAACGUGCGGGAGCAGCUGA ACCAGAUCAAGAACCCCAUCGAAAAGCACGGGGCGAACACCGU GCCCAUCAAGGACUACGAGAAUAAGAACUCCAAGAUGAGCAA GAUCCGCACACACAACAGCGAGGUGGAGGAGGACGAUAUGGA CAAGCACCAGCAGAAGGCCAGGUUCGCCAAGCAGCCCGCCUAC ACCCUUGUGGACCGCGAAGAGAAGCCCCCGAACGGCACCCCCA CCAAGCACCCCAACUGGACCAACAAACAGGAUAACCGUGACCU GGAAAGCGCGCAGUCCCUGAACCGCAUGGAGUACAUAGUG |
| 97 | JAG1-CO11 | AUGAGGAGCCCCCGGACCAGGGGGCGGAGCGGCAGGCCCCUGA GCCUCCUGCUGGCCCUGCUUUGCGCACUGAGGGCCAAGGUGUG UGGGGCCAGCGGGCAGUUCGAGCUCGAAAUCCUGAGCAUGCA GAACGUGAACGGCGAGCUGCAGAAUGGCAAUUGUUGCGGCGG CGCCAGGAACCCCGGCGACCGGAAGUGCACCCGGGACGAAUGC GACACCUACUUCAAGGUGUGCCUCAAGGAGUACCAGAGCCGC GUGACCGCCGGCGGACCCUGCAGCUUCGGCAGCGGCAGCACCC CCGUGAUCGGGGGCAACACCUUCAACCUGAAGGCAUCCCGCGG GAACGACAGGAACAGGAUCGUGCUGCCGUUCAGCUUCGCCUG GCCGCGAUCCUACACGCUGCUGGUUGAGGCCUGGGACAGCAGC AAUGACACGGUGCAACCCGACAGCAUUAUCGAGAAGGCCAGC CACUCCGGCAUGAUCAACCCCUCCCGGCAGUGGCAGACCCUGA AGCAGAACACUGGAGUUGCACACUUCGAGUACCAAAUCAGGG UCACGUGCGACGACUACUAUUACGGGUUCGGCUGUAACAAGU UCUGCAGGCCCCGUGAUGACUUCUUUGGACACUACGCCUGCGA CCAGAACGGAAACAAGACCUGCAUGGAAGGGUGGAUGGGCCC CGAGUGCAACAGGGCCAUCUGUAGACAAGGCUGCAGCCCCAA ACACGGCUCCUGUAAGCUGCCCGGCGACUGCCGGUGCCAGUAC GGCUGGCAGGGGCUCUACUGCGACAAGUGCAUUCCCCAUCCCG GCUGCGUGCACGGCAUAUGUAACGAACCCUGGCAAUGCCUCU GCGAGACCAACUGGGGCGGGCAGCUGUGCGACAAAGACCUGA ACUACUGUGGCACCCAUCAGCCCUGCCUGAACGGGGGACUUG |

TABLE 2-continued

Sequence optimized sequences for human JAG1

| SEQ ID NO | NAME | SEQUENCE |
|---|---|---|
| | | CUCCAAUACCGGUCCCGACAAGUAUCAGUGCAGCUGCCCCGAG<br>GGCUACUCCGGGCCCAACUGCGAGAUCGCCGAACACGCCUGUC<br>UGUCCGACCCCUGCCACAACAGAGGCAGCUGCAAGGAGACCAG<br>CCUGGGCUUUGAGUGCGAGUGCUCCCCCGGCUGGACCGGGCCC<br>ACCUGCAGCACCAACAUCGACGAUUGCAGCCCCAACAAUUGCU<br>CCCACGGCGGCACUUGCCAAGACCUGGUGAACGGCUUCAAGUG<br>CGUGUGCCCCCCCCAGUGGACCGGUAAAACAUGCCAGCUGGAC<br>GCCAACGAGUGCGAGGCCAAGCCCUGCGUGAACGCCAAGAGCU<br>GCAAAAACCUGAUCGCCAGUUACUACUGCGACUGCCUGCCUGG<br>AUGGAUGGGCCAGAACUGCGACAUCAACAUCAACGACUGCCU<br>GGGCCAGUGCCAGAACGACGCAAGCUGCCGUGACCUGGUGAA<br>CGGCUACAGGUGCAUCUGCCCCCCCGGGUACGCCGGUGACCAC<br>UGCGAACGGGACAUAGAUGAGUGCGCCAGCAACCCCUGCCUG<br>AACGGCGGACACUGCCAGAAUGAGAUCAAUAGGUUCCAAUGC<br>CUCUGCCCCACCGGCUUUAGCGGCAAUCUGUGCCAGCUGGACA<br>UCGAUUACUGUGAGCCCAACCCCUGCCAGAAUGGAGCCCAGUG<br>CUACAACCGGGCCUCCGACUAUUUCUGUAAGUGUCCCGAAGAC<br>UACGAGGGUAAGAACUGCUCCCACCUGAAGGACCACUGCCGG<br>ACCACUCCGUGCGAGGUCAUCGACAGCUGCACCGUCGCCAUGG<br>CCAGCAAUGACACACCCGAGGGCGUGAGGUACAUCUCCUCCAA<br>CGUGUGUGGCCCCCACGGCAAGUGCAAGAGCCAGAGCGGAGG<br>CAAGUUCACCUGCGACUGCAACAAGGGGUUCACCGGCACUUAC<br>UGCCACGAGAACAUCAACGACUGCGAAUCCAACCCCUGUCGAA<br>ACGGGGGCACCUGCAUUGACGGCGUGAACAGCUAUAAGUGCA<br>UCUGCUCCGACGGGUGGGAGGGGGCCUACUGCGAAACCAAUA<br>UAAACGAUUGCAGCCAGAACCCCUGUCACAACGGGGGCACAU<br>GCAGGGACCUGGUCAACGACUUCUACUGUGACUGCAAGAACG<br>GCUGGAAGGGCAAGACAUGUCACAGCAGGGACAGCCAGUGCG<br>ACGAGGCCACCUGUAACAAUGGCGGCACCUGCUAUGACGAAG<br>GCGACGCCUUCAAAUGUAUGUGCCCCGGCGGUUGGGAGGGGA<br>CGACGUGCAAUAUUGCGAGGAACUCCAGCUGUCUGCCCAACCC<br>CUGCCACAACGGAGGCACCUGUGUGGUGAACGGCGAGAGCUU<br>UACGUGCGUCUGUAAAGAGGGCUGGGAAGGCCCCAUCUGCGC<br>CCAAAACACGAACGACUGCAGCCCCCACCCCUGUUACAAUAGC<br>GGCACCUGCGUCGACGGUGACAACUGGUAUAGGUGCGAGUGU<br>GCCCCGGGCUUUGCCGGGCCCGACUGCCGGAUCAAUAUCAACG<br>AGUGCCAGUCCAGCCCAUGUGCGUUCGGCGCCACCUGCGUGGA<br>CGAAAUCAACGGCUACAGGUGCGUCUGCCCCCCGGGGCACAGC<br>GGAGCCAAAUGUCAGGAAGUCUCUGGGAGGCCCUGCAUCACC<br>AUGGGCAGCGUAAUCCCCGACGGGGCUAAGUGGGACGACGAC<br>UGCAAUACCUGUCAGUGUCUGAACGGCAGGAUUGCCUGCAGC<br>AAAGUGUGGUGUGGCCCGCGGCCCUGUCUCCUGCACAAGGGCC<br>ACUCCGAGUGUCCCAGCGGCCAAUCCUGCAUCCCCAUCCUCGA<br>CGACCAGUGCUUUGUGCACCCCUGCACAGGCGUGGGAGAGUG<br>UAGGUCGAGCUCCCUGCAGCCCGUGAAGACCAAGUGCACCAGC<br>GAUUCCUACUACCAGGACAACUGCGCGAAUAUCACCUUUACCU<br>UUAACAAGGAGAUGAUGAGCCCCGGGCUGACCACCGAGCACA<br>UCUGCAGCGAGCUGCGGAACCUGAACAUCCUCAAAAACGUCA<br>GCGCCGAGUAUAGCAUCUACAUUGCCUGCGAGCCCAGCCCCAG<br>CGCCAACAACGAAAUACACGUGGCCAUCAGCGCCGAGGACAUC<br>AGGGACGACGGCAACCCGAUCAAGGAGAUCACCGAUAAGAUA<br>AUCGACCUGGUGUCCAAGAGGGACGGCAAUAGCUCCCUGAUC<br>GCCGCCGUGGCCGAAGUGAGGGUGCAGAGGAGGCCCCUGAAA<br>AACAGGACCGAUUUCCUGGUUCCCCUGCUGAGCAGCGUGCUG<br>ACAGUGGCUUGGAUCUGCUGCCUCGUAACUGCAUUCUACUGG<br>UGCCUGAGGAAGAGGAGGAAGCCCGGCAGUCACACCCACAGC<br>GCCUCCGAGGAUAACACCACUAACAAUGUGCGGGAGCAGCUG<br>AACCAGAUCAAGAAUCCCAUAGAAAAACAUGGCGCCAACACC<br>GUGCCCAUUAAAGAUUACGAGAACAAAAAUAGCAAGAUGUCC<br>AAGAUCCGCACCCACAACAGCGAGGUGGAGGAGGACGACAUG<br>GACAAGCACCAGCAGAAGGCCAGGUUCGCCAAGCAGCCCGCGU<br>ACACCCUGGUGGACCGUGAGGAGAAGCCCCCCAACGGCACCCC<br>CACCAAGCACCCCAACUGGACCAACAAGCAAGAUAAUCGGGAC<br>CUGGAAUCCGCCCAGAGCCUGAACAGGAUGGAGUACAUCGUG |
| 98 | JAG1-<br>CO12 | AUGAGGAGCCCGAGAACGAGGGGGCGGUCCGGCAGGCCGCUG<br>AGCCUCCUGCUGGCCCUGCUGUGCGCCCUGCGGGCAAAGGUGU<br>GUGGCGCCUCCGGGCAGUUCGAGCUGGAGAUCCUGAGCAUGC<br>AAAACGUGAACGGCGAACUCCAGAACGGCAAUUGCUGCGGCG<br>GCGCCAGAAACCCCGGGGAUCGAAAGUGCACCCGGGACGAGU<br>GCGACACCUACUUCAAAGUGUGUCUCAAAGAAUACCAGAGCA<br>GGGUGACCGCCGGCGGGCCCUGCAGCUUCGGCAGCGGCAGCAC<br>CCCCGUGAUCGGCGGGAACACCUUCAACCUGAAGGCCAGCCGC<br>GGCAACGACAGGAAUCGGAUCGUGUUGCCGUUCAGCUUCGCC<br>UGGCCCCGUUCCUACACCCUGCUGGUGGAGGCCUGGGACAGCA |

TABLE 2-continued

Sequence optimized sequences for human JAG1

| SEQ ID NO | NAME | SEQUENCE |
|---|---|---|
| | | GCAACGAUACCGUGCAGCCAGACAGCAUAAUCGAGAAGGCCA<br>GCCACUCCGGUAUGAUCAACCCCAGCAGGCAGUGGCAGACCCU<br>GAAGCAAAACACCGGCGUGGCCCAUUUCGAGUACCAGAUCAG<br>GGUCACGUGCGACGACUAUUACUACGGGUUCGGGUGCAACAA<br>GUUCUGCAGGCCCCGGGAUGACUUCUUUGGACACUACGCCUG<br>UGACCAGAACGGAAACAAAACUUGCAUGGAGGGCUGGAUGGG<br>CCCGGAGUGCAAUAGGGCCAUUUGCAGGCAAGGCUGCAGCCCC<br>AAGCACGGCUCCUGCAAGCUCCCCGGCGACUGCCGAUGCCAAU<br>AUGGCUGGCAGGGCCUCUACUGUGACAAGUGCAUCCCCCACCC<br>GGGCUGCGUCCACGGAAUCUGCAAUGAGCCCUGGCAGUGUCU<br>GUGCGAGACGAACUGGGGUGGCCAGCUGUGCGACAAGGACCU<br>GAACUACUGCGGGACCCACCAGCCCUGCCUGAACGGCGGGACC<br>UGUUCCAACACCGGCCCGGACAAGUAUCAGUGCAGCUGCCCGG<br>AAGGGUACUCCGGCCCGAACUGCGAAAUCGCCGAACACGCUUG<br>CCUCAGCGACCCCUGCCACAACCGCGGGAGCUGCAAGGAGACC<br>AGCCUGGGCUUUGAGUGCGAAUGUUCCCCCGGCUGGACCGGG<br>CCCACAUGCUCCACCAACAUAGACGAUUGUAGCCCCAACAACU<br>GCUCCCACGGGGGACCUGCCAAGACCUGGUCAACGGAUUCAA<br>GUGCGUGUGUCCCCCCAGUGGACGGGUAAGACCUGCCAACUG<br>GACGCCAACGAAUGCGAGGCCAAGCCCUGUGUGAAUGCCAAG<br>AGCUGCAAGAACCUGAUCGCCAGCUACUACUGUGACUGCCUGC<br>CCGGCUGGAUGGGCCAGAAUUGCGACAUCAAUAUCAACGACU<br>GCCUGGGCCAGUGCCAGAAUGACGCCUCCUGCAGGGACCUGGU<br>GAACGGCUACAGGUGCAUAUGCCCCCCGGCUACGCCGGCGAC<br>CACUGCGAACGUGACAUCGACGAGUGCGCCUCAAACCCCUGCC<br>UGAACGGCGGACACUGCCAGAACGAGAUCAACCGAUUCCAGU<br>GUCUGUGCCCCACCGGGUUUAGCGGGAACCUCUGCCAGCUCGA<br>UAUCGACUACUGCGAACCCAACCCCUGCCAGAACGGCGCCCAG<br>UGCUACAACCGGGCCAGCGACUAUUUCUGUAAAUGCCCCGAG<br>GACUACGAGGGGAAAAACUGUAGCCACCUGAAGGACCACUGC<br>AGGACCACACCCUGCGAAGUGAUCGACAGCUGCACCGUGGCCA<br>UGGCCAGCAAUGACACCCCCGAAGGCGUGAGGUAUAUAAGCA<br>GCAACGUAUGCGGCCCCCACGGCAAGUGUAAGAGCCAGAGCG<br>GCGGCAAGUUUACGUGCGACUGCAACAAAGGCUUCACCGGCA<br>CCUACUGUCACGAGAACAUCAACGACUGCGAGAGCAACCCCUG<br>CCGCAACGGGGGCACCUGCAUCGACGGUGUGAACAGCUACAA<br>GUGCAUCUGCAGCGACGGCUGGGAGGGCGCCUACUGUGAGAC<br>GAACAUCAACGACUGCAGCCAGAACCCGUGCCAUAACGGGGGC<br>ACCUGCAGGGAUCUGGUGAACGACUUUUAUUGCGACUGCAAG<br>AACGGCUGGAAGGGCAAGACCUGCCACAGCCGGGACAGCCAG<br>UGUGACGAGGCCACCUGCAACAACGGCGGCACCUGCUACGACG<br>AAGGGGACGCCUUUAAGUGCAUGUGCCCGGGCGGGUGGGAGG<br>GCACCACCUGCAACAUCGCCAGGAAUUCCUCCUGUCUGCCCAA<br>CCCAUGUCACAACGGUGGCACGUGCGUGGUGAACGGGGAGUC<br>CUUUACCUGUGUGUGCAAGGAGGGGUGGGAGGGACCCAUAUG<br>UGCGCAGAAUACCAACGACUGCUCCCCCCACCCAUGUUAUAAC<br>AGCGGUACAUGUGUGGAUGGGGACAACUGGUACCGGUGUGAG<br>UGCGCCCCCGGCUUCGCCGGCCCCGAUUGCAGGAUCAACAUCA<br>AUGAGUGCCAGAGCUCCCCCUGCGCCUUCGGCGCCACAUGCGU<br>CGACGAAAUCAACGGCUACAGGUGUGUGUGCCCCCCGGGACAC<br>AGCGGUGCCAAGUGCCAGGAAGUGUCAGGCAGGCCCUGUAUU<br>ACCAUGGGCAGCGUGAUCCCCGACGGAGCCAAGUGGGAUGAC<br>GACUGCAACACCUGCCAGUGCCUGAACGGCCGUAUCGCCUGCA<br>GCAAGGUGUGGUGCGGCCCCCGGCCGUGCCUGCUGCACAAGGG<br>GCACUCCGAGUGCCCCAGCGGGCAGAGCUGCAUCCCCAUCUUG<br>GACGACCAGUGCUUCGUGCACCCCUGCACCGGCGUGGGCGAAU<br>GCCGUAGCAGCUCCCUGCAGCCCGUGAAGACCAAGUGCACCAG<br>CGALNJCCUACUAUCAGGAUAACUGCGCCAACAUCACCUUCACC<br>UUCAACAAGGAGAUGAUGAGCCCCGGCCUGACCACGGAACAC<br>AUCUGCAGCGAGCUGAGGAACCUGAACAUCCUGAAGAACGUG<br>UCCGCCGAAUACAGCAUCUACAUCGCCUGCGAGCCCAGCCCCA<br>GCGCCAACAACGAAAUCCACGUCGCCAUCUCUGCCGAGGACAU<br>CCGCGACGACGGCAACCCCAUUAAGGAGAUAACCGACAAGAUC<br>AUCGACCUGGUGUCCAAGCGAGACGGAAAUUCUAGCCUGAUC<br>GCCGCCGUAGCCGAGGUACGUGUGCAGAGGAGGCCCCUCAAG<br>AAUAGGACCGACUUCCUGGUGCCCCUGCUGAGCAGCGUGCUCA<br>CCGUGGCGUGGAUCUGCUGCCUGGUGACCGCCUUUUACUGGU<br>GCCUGCGAAAGAGGAGGAAGCCCGGUUCACACACGCACAGCGC<br>CAGCGAAGACAACACCACCAACAAUGUGCGCGAGCAGCUCAAC<br>CAGAUCAAGAAUCCCAUCGAGAAGCACGGCGCCAACACGGUCC<br>CCAUCAAGGACUACGAGAACAAAAACAGCAAGAUGUCCAAGA<br>UCCGCACCCAUAACAGCGAGGUCGAAGAAGACGACAUGGACA<br>AACACCAGCAAAAGGCCAGGUUCGCCAAGCAGCCGGCCUACAC |

TABLE 2-continued

Sequence optimized sequences for human JAG1

| SEQ ID NO | NAME | SEQUENCE |
|---|---|---|
| | | CCUGGUGGACAGGGAGGAGAAGCCCCCGAACGGCACCCCCACC<br>AAGCACCCCAACUGGACCAACAAACAGGACAACCGGGAUCUGG<br>AGAGUGCGCAGAGCCUGAACAGGAUGGAGUACAUCGUG |
| 99 | JAG1-CO13 | AUGAGAAGCCCAAGGACGCGCGGUAGGAGCGGCAGGCCCCUC<br>AGCCUGCUGCUGGCUCUACUGUGCGCCCUGCGGGCCAAGGUUU<br>GUGGGGCCAGUGGGCAAUUCGAGCUGGAGAUCCUGAGCAUGC<br>AAAACGUGAACGGGGAGCUUCAGAAUGGUAACUGCUGCGGCG<br>GGGCCCGGAAUCCCGGCGACCGGAAGUGUACGAGGGAUGAGU<br>GUGACACCUACUUUAAGGUGUGCCUGAAGGAGUACCAGAGCA<br>GGGUUACGGCAGGCGGCCCCUGCAGCUUUGGCAGCGGCUCCAC<br>CCCGGUGAUCGGCGGCAACACAUUCAACCUGAAGGCCAGCCGC<br>GGGAACGAUCGUAACAGGAUCGUGCUCCCCUUUAGCUUCGCC<br>UGGCCCCGCAGCUACACGCUGCUGGUGGAGGCCUGGGACAGCA<br>GCAACGACACCGUCCAGCCCGAUAGCAUUAUCGAGAAGGCCUC<br>CCACAGCGGUAUGAUCAACCCGAGCCGGCAGUGGCAGACCCUG<br>AAGCAGAACACCGGCGUGGCCCACUUCGAGUACCAGAUCCGGG<br>UGACCUGCGACGACUACUAUUACGGUUUCGGCUGCAACAAGU<br>UUUGCCGACCCCGGGACGACUUUUUCGGGCAUUACGCCUGCGA<br>CCAAAACGGCAACAAAACCUGCAUGGAGGGCUGGAUGGGCCC<br>GGAGUGCAACCGGGCCAUCUGCCGGCAGGGGUGUAGCCCCAA<br>GCACGGCAGCUGCAAGCUGCCCGGCGAUUGCCGGUGCCAGUAC<br>GGGUGGCAGGGCCUGUACUGCGACAAGUGCAUCCCGCACCCCG<br>GAUGUGUGCACGGCAUCUGCAACGAGCCCUGGCAGUGCCUGU<br>GCGAAACCAACUGGGGGGGUCAGCUGUGUGACAAGGAUCUGA<br>ACUACUGCGGAACCCACCAACCCUGCCUGAACGGCGGAACUUG<br>CUCGAACACGGGCCCCGACAAGUACCAGUGCAGCUGUCCCGAG<br>GGCUACAGCGGGCCCAACUGUGAGAUCGCCGAACACGCUUGCC<br>UGAGCGACCCGUGUCACAACCGGGGCAGCUGCAAGGAGACCUC<br>CCUCGGCUUCGAGUGCGAGUGCUCCCCAGGGUGGACCGGCCCC<br>ACCUGCAGCACCAACAUCGACGAUUGCAGCCCCAACAACUGUA<br>GCCACGGCGGGACGUGCCAGGACCUGGUCAACGGCUUCAAAU<br>GUGUCUGUCCCCCCCAGUGGACCGGCAAAACCUGCCAGCUCGA<br>CGCCAACGAGUGCGAAGCCAAGCCGUGCGUGAACGCGAAGAG<br>CUGCAAGAACCUGAUCGCCUCCUACUACUGCGACUGCCUGCCC<br>GGCUGGAUGGGCCAGAACUGCGACAUAAACAUCAACGACUGC<br>CUGGGCCAGUGCCAGAACGAUGCCAGCUGUCGAGACCUGGUG<br>AACGGGUACCGGUGCAUCUGCCCCCCCGGAUACGCCGGGGACC<br>ACUGCGAGCGCGACAUCGACGAAUGUGCCUCGAACCCCUGCCU<br>GAACGGGGGCCACUGCCAAAACGAGAUCAAUCGUUUCCAGUG<br>CCUGUGCCCCACCGGCUUCUCUGGGAACCUGUGCCAGCUGGAC<br>AUCGACUACUGCGAGCCCAACCCCUGCCAGAACGGGGCGCAGU<br>GCUAUAACCGGGCCUCCGAUUACUUCUGCAAGUGCCCCGAGGA<br>CUAUGAGGGAAAAAACUGCUCCCACCUGAAGGAUCACUGUAG<br>GACCACCCCCUGUGAGGUGAUCGACAGCUGCACCGUGGCCAUG<br>GCCAGCAACGACACCCCCGAGGGCGUGCGCUACAUCAGCUCCA<br>ACGUGUGCGGCCCCCAUGGUAAGUGUAAGUCGCAGAGCGGCG<br>GGAAGUUCACCUGCGACUGCAACAAGGGCUUUACGGGGACCU<br>ACUGUCAUGAAAACAUCAACGACUGCGAGAGCAACCCCUGUC<br>GCAACGGCGGCACCUGCAUCGAUGGCGUCAACAGCUACAAGU<br>GCAUCUGCUCCGACGGAUGGGAGGGCGCCUACUGCGAGACCA<br>ACAUCAACGACUGCAGCCAGAACCCGUGCCACAAUGGCGGCAC<br>CUGCCGUGACCUGGUGAACGACUUUUACUGCGACUGCAAGAA<br>CGGGUGGAAAGGCAAAACCUGCCACUCCAGGGACAGCCAGUG<br>CGACGAGGCGACCUGCAACAAUGGCGGGACGUGCUACGACGA<br>GGGCGACGCCUUCAAGUGCAUGUGCCCCGGCGGAUGGGAAGG<br>CACUACCUGUAACAUCGCCCGGAAUAGCUCCUGCCUGCCGAAC<br>CCCUGCCACAACGGGGGCACGUGCGUCGUGAACGGCGAAAGCU<br>UCACCUGCGUGUGCAAGGAGGGCUGGGAGGGCCCCAUCUGUG<br>CCCAGAACACCAACGACUGCAGCCCCCACCCCUGCUACAAUAG<br>CGGCACCUGCGUGGACGGAGACAACUGGUACCGAUGCGAGUG<br>CGCCCCUGGCUUCGCCGGACCCGAUUGCCGCAUUAACAUCAAU<br>GAAUGCCAGAGCAGCCCCUGCGCCUUUGGAGCCACCUGCGUCG<br>AUGAGAUCAACGGCUACCGCUGUGUCUGCCCCCCCGGCCACAG<br>CGGGGCCAAGUGCCAGGAGGUCUCAGGUCGGCCCUGCAUCACC<br>AUGGGCAGCGUCAUCCCCGACGGGGCCAAAUGGGAUGACGAC<br>UGCAAUACCUGCCAGUGUCUGAACGGCCGAAUCGCCUGCUCCA<br>AGGUGUGGUGCGGGCCCAGGCCCUGCCUCCUUCACAAAGGCCA<br>UAGCGAGUGCCCCUCCGGGCAAUCCUGCAUCCCCAUCCUGGAC<br>GACCAAUGCUUCGUGCACCCCUGCACCGGCGUGGGGGAGUGCA<br>GGAGCAGCAGCCUGCAGCCCGUGAAGACCAAGUGCACCUCCGA<br>UAGCUAUUACCAGGACAACUGCGCCAACAUCACCUUCACCUUU<br>AACAAAGAAAUGAUGUCACCCGGCCUGACGACCGAGCAUAUC<br>UGCAGCGAGCUGCGGAACCUGAACAUCCUGAAAAACGUGUCG<br>GCCGAGUACAGUAUAUACAUCGCCUGCGAGCCCAGCCCCAGCG |

TABLE 2-continued

Sequence optimized sequences for human JAG1

| SEQ ID NO | NAME | SEQUENCE |
|---|---|---|
| | | CCAACAACGAGAUACAUGUGGCCAUAAGCGCCGAAGACAUCA<br>GGGACGAUGGCAACCCCAUCAAGGAGAUCACCGACAAAAUAA<br>UCGACCUGGUGAGCAAGCGGGAUGGCAAUAGCAGCCUGAUCG<br>CCGCCGUGGCCGAGGUGAGGGUGCAGCGGAGGCCCCUGAAGA<br>AUCGCACCGACUUCCUGGUCCCGCUGCUUAGCUCCGUCCUGAC<br>GGUCGCCUGGAUCUGCUGCCUGGUGACCGCCUUCUACUGGUGC<br>UUGAGGAAGCGGAGGAAGCCCGGGUCACAUACCCACUCCGCCA<br>GCGAGGACAACACCACCAAUAACGUGCGGGAACAGCUGAACC<br>AGAUCAAGAACCCCAUCGAGAAGCAUGGUGCCAACACCGUGCC<br>CAUCAAGGACUAUGAAAACAAGAACUCCAAGAUGAGCAAGAU<br>CAGGACCCACAACUCCGAGGUGGAAGAGGACGACAUGGACAA<br>GCACCAGCAGAAAGCCCGUUUCGCCAAGCAGCCCGCCUACACC<br>CUGGUGGACCGAGAGGAAAAGCCGCCCAACGGCACCCCCACCA<br>AGCAUCCCAACUGGACCAACAAGCAGGACAACCGUGACCUGGA<br>GAGCGCCCAGUCGCUCAACCGCAUGGAGUACAUCGUG |
| 100 | JAG1-CO14 | AUGCGGUCGCCGAGAACCAGGGGCCGGAGCGGCCGGCCCCUGU<br>CGCUGCUGCUGGCCCUGCUCUGCGCGCUGAGAGCCAAGGUGUG<br>UGGCGCCAGCGGCCAGUUCGAGCUUGAGAUCCUGUCCAUGCA<br>AAACGUCAACGGCGAGCUCCAGAACGGAAACUGUUGCGGCGG<br>CGCCCGCAACCCCGGCGACAGGAAGUGCACCCGCGACGAGUGC<br>GACACCUACUUCAAGGUGUGCCUGAAGGAGUACCAGUCCCGC<br>GUGACCGCUGGCGGACCGUGCAGCUUCGGCUCAGGCAGCACCC<br>CCGUGAUCGGGGGCAAUACCUUCAAUCUCAAGGCCAGCCGAG<br>GAAACGACAGGAACAGGAUCGUGCUCCCCUUUAGCUUUGCCU<br>GGCCUCGUAGCUACACCCUGCUGGUGGAGGCCUGGGACUCAA<br>GCAAUGACACGGUUCAGCCCGACAGCAUCAUCGAAAAGGCCUC<br>UCACAGCGGAAUGAUCAACCCCAGCAGGCAGUGGCAGACCCUC<br>AAGCAGAACACGGGCGUGGCCCACUUCGAGUACCAGAUCCGU<br>GUGACCUGCGAUGACUACUAUUACGGUUUCGGGUGUAAUAAG<br>UUCUGCAGGCCCAGGGAUGACUUUUUGGCCACUACGCCUGC<br>GACCAGAAUGGCAACAAGACCUGCAUGGAGGGAUGGAUGGGC<br>CCCGAGUGCAACCGUGCCAUCUGUCGGCAGGGCUGCUCGCCCA<br>AGCACGGCAGCUGCAAGCUUCCCGGCGACUGUCGGUGCCAGUA<br>CGGAUGGCAAGGGCUGUACUGCGACAAGUGCAUCCCCCAUCCC<br>GGCUGUGUCCACGGUAUCUGCAACGAGCCCUGGCAGUGUCUG<br>UGCGAGACCAACUGGGGCGGCCAGCUGUGCGACAAGGACCUG<br>AACUACUGCGGCACCCACCAGCCCUGCCUGAAUGGGGGCACCU<br>GUUCUAACACCGGGCCGGACAAGUACCAGUGUUCCUGCCCCGA<br>GGGCUACAGCGGCCCCAACUGCGAGAUCGCCGAGCACGCCUGC<br>CUGUCCGACCCCUGCCAUAAUAGGGGCUCCUGCAAGGAGACCU<br>CCCUGGGCUUUGAGUGCGAGUGUUCGCCCGGCUGGACCGGCCC<br>CACCUGCAGUACCAACAUCGACGACUGCAGCCCCAACAACUGU<br>AGCCACGGCGGCACAUGCCAAGACCUGGUGAACGGCUUCAAG<br>UGCGUCUGCCCGCCGCAGUGGACCGGGAAGACCUGUCAGCUGG<br>AUGCCAACGAGUGCGAGGCUAAACCCUGCGUGAACGCGAAGA<br>GCUGUAAGAACCUGAUUGCCAGCUACUACUGCGACUGCCUGCC<br>GGGCUGGAUGGGGCAGAAUUGCGACAUCAACAUCAACGACUG<br>UCUGGGCCAAUGCCAGAACGACGCCAGCUGUCGGGACCUGGUC<br>AACGGAUACAGGUGUAUCUGUCCCCCGGCUACGCCGGCGACC<br>ACUGCGAGCGGGACAUCGACGAAUGCGCCAGCAACCCUUGUCU<br>GAACGGAGGCCACUGCCAGAACGAGAUCAACAGGUUUCAGUG<br>CCUCUGCCCCACCGGGUUCAGCGGGAACCUGUGCCAGCUUGAC<br>AUCGAUUACUGCGAGCCCAACCCCUGUCAGAAUGGGGCGCAG<br>UGCUACAACCGAGCUUCCGAUUACUUCUGCAAGUGCCCCGAGG<br>AUUACGAGGGUAAAAAUUGCAGCCACCUGAAGGAUCACUGCA<br>GGACCACCCCGUGCGAGGUGAUAGACAGCUGCACCGUGGCCAU<br>GGCCAGCAACGACACCCCCGAGGGCGUGCGAUACAUCAGCAGC<br>AACGUGUGCGGCCCCCACGGCAAGUGCAAAAGCCAGAGCGGCG<br>GAAAAUUCACAUGCGACUGCAACAAGGGGUUCACGGGCACCU<br>AUUGCCACGAGAACAUCAACGACUGCGAGUCCAACCCGUGCCG<br>GAAUGGCGGCACCUGCAUCGACGGCGUGAACUCCUAUAAGUG<br>UAUCUGCUCGGACGGCUGGGAGGGGGCCUAUUGCGAGACCAA<br>CAUCAACGACUGCAGCCAGAACCCCUGCCACAACGGCGGCACC<br>UGCAGGGACCUGGUGAACGACUUCUAUUGCGACUGCAAGAAC<br>GGCUGGAAGGGCAAGACCUGUCACUCCAGGGACAGCCAGUGC<br>GACGAGGCCACCUGUAACAACGGCGGGACCUGUUACGACGAG<br>GGGGACGCGUUCAAGUGCAUGUGCCCCGGCGGCUGGGAGGGC<br>ACCACGUGCAACAUCGCGCGUAACAGCAGCUGUCUGCCGAAUC<br>CCUGUCACAAUGGCGGCACCUGCGUCGUGAACGGCGAAAGCU<br>UCACCUGCGUGUGUAAGGAAGGCUGGGAGGGCCCCAUCUGCG<br>CCCAAAACACCAACGACUGUAGCCCCCACCCGUGCUACAACAG<br>CGGCACCUGCGUGGAUGGCGACAACUGGUAUCGGUGCGAGUG<br>UGCCCCUGGCUUUGCGGGCCCCGACUGCCGGAUAAACAUAAAC<br>GAGUGUCAAUCGAGCCCCUGCGCCUUCGGGGCCACCUGCGUGG |

TABLE 2-continued

Sequence optimized sequences for human JAG1

| SEQ ID NO | NAME | SEQUENCE |
|---|---|---|
| | | ACGAGAUCAACGGCUACAGGUGCGUGUGCCCGCCCGGCCACAG<br>CGGCGCGAAAUGCCAAGAGGUGAGCGGCAGGCCCUGCAUCACC<br>AUGGGUUCCGUGAUCCCCGACGGGGCAAAAUGGGACGACGAC<br>UGCAAUACCUGCCAGUGCCUCAACGGGAGGAUCGCCUGCAGCA<br>AGGUGUGGUGCGGCCCCAGGCCCUGCCUGCUGCAUAAAGGGC<br>ACAGCGAGUGCCCCAGCGGGCAGAGCUGCAUCCCCAUCCUGGA<br>CGACCAGUGCUUCGUGCACCCGUGCACCGGCGUGGGCGAGUGC<br>AGAAGAAGCUCUAGCCUGCAACCCGUGAAGACCAAGUGCACGAGC<br>GACAGCUACUACCAGGACAACUGCGCGAACAUCACCUUCACCU<br>UCAAUAAGGAGAUGAUGAGCCCGGGACUCACCACCGAACAUA<br>UCUGCUCCGAGCUGCGCAACCUCAACAUACUGAAGAAUGUGA<br>GCGCCGAGUACUCCAUUUACAUUGCCUGCGAGCCCAGCCCCUC<br>CGCCAAUAAUGAAAUACACGUCGCCAUCAGCGCCGAGGACAUC<br>AGGGACGACGGCAACCCCAUCAAGGAGAUCACCGACAAGAUC<br>AUCGACCUGGUGAGCAAAAGGGACGGCAAUAGCAGCCUCAUC<br>GCCGCCGUGGCCGAGGUGAGGGUGCAGAGGAGGCCGCUGAAA<br>AACAGAACCGAUUUUCUCGUCCCCCUGCUGUCCUCCGUGCUGA<br>CCGUCGCCUGGAUCUGUUGCCUGGUGACCGCCUUCUACUGGUG<br>UCUCCGCAAGAGGCGCAAGCCCGGCAGCCACACGCAUAGCGCC<br>AGCGAGGACAACACUACUAACAACGUGCGGGAGCAGCUGAAU<br>CAGAUCAAGAACCCCAUCGAGAAACACGGCGCCAACACUGUGC<br>CCAUCAAAGACUACGAGAACAAAAACUCGAAAAUGAGCAAGA<br>UCCGCACCCACAACAGCGAGGUGGAGGAGGACGACAUGGACA<br>AGCACCAGCAGAAAGCGAGAUUCGCCAAACAGCCCGCCUACAC<br>CCUGGUGGACAGGGAGGAGAAGCCCCCAAACGGCACACCCACC<br>AAGCACCCGAACUGGACCAACAAGCAGGACAACCGUGACCUGG<br>AAAGCGCCCAGUCCCUGAAUCGCAUGGAAUAUAUCGUG |
| 101 | JAG1-CO15 | AUGCGAAGCCCCCGAACCCGGGGCAGGAGCGGGAGGCCCCUGA<br>GCCUGCUGCUGGCCCUUCUGUGCGCCCUUAGGGCCAAGGUGUG<br>UGGGGCCUCCGGCCAGUUCGAGCUGGAGAUCCUGAGCAUGCA<br>GAACGUGAACGGUGAGCUGCAGAAUGGUAACUGUUGCGGCGG<br>AGCCAGGAACCCGGGCGAUAGGAAAUGUACCAGGGACGAGUG<br>CGACACCUACUUUAAGGUGUGCCUCAAAGAGUACCAGAGCCG<br>GGUCACCGCCGGCGGCCCCUGCUCGUUCGGCAGCGGUAGCACC<br>CCCGUGAUCGGCGGCAACACAUUCAACCUGAAAGCCAGCAGGG<br>GGAACGACAGGAACCGGAUCGUGCUCCCCUUCUCCUUCGCCUG<br>GCCCAGGUCGUACACCCUGCUCGUCGAGGCCUGGGACAGCAGC<br>AACGACACCGUGCAGCCCGACAGCAUCAUCGAAAAGGCCAGCC<br>ACAGCGGAAUGAUCAACCCCAGCCGACAGUGGCAGACCCUGAA<br>GCAGAACACCGGCGUGGCCCACUUCGAGUACCAGAUCCGGGUG<br>ACCUGCGAUGACUAUUACUAUGGCUUCGGCUGUAACAAGUUC<br>UGUCGACCCAGGGACGACUUCUUCGGCCACUAUGCCUGCGACC<br>AGAACGGUAAUAAGACUUGCAUGGAGGGCUGGAUGGGCCCCG<br>AGUGUAACAGGGCCAUCUGCAGGCAGGGCUGCUCCCCCAAACA<br>CGGCUCCUGCAAACUGCCCGGCGACUGCCGCUGCCAGUACGGC<br>UGGCAGGGGCUCUACUGCGAUAAGUGCAUCCCCCAUCCCGGCU<br>GCGUGCAUGGCAUCUGCAACGAACCCUGGCAGUGCCUGUGCG<br>AGACCAACUGGGGGGGCCAGCUAUGCGAUAAGGAUCUGAACU<br>ACUGUGGCACCCACCAGCCCUGCCUGAACGGGGGCACGUGCUC<br>AAACACCGGCCCCGACAAAUACCAAUGCAGCUGCCCCGAGGGC<br>UACAGCGGCCCCAACUGCGAGAUCGCCGAGCAUGCCUGCCUGA<br>GCGACCCGUGCCACAAUAGGGGCUCCUGUAAGGAGACCAGCCU<br>GGGCUUCGAGUGUGAGUGCAGCCCCGGCUGGACCGGCCCCACC<br>UGCUCAACUAACAUCGACGACUGUUCCCCCAACAAUUGCAGCC<br>ACGGCGGCACCUGCCAGGACCUGGUGAACGGCUUUAAGUGUG<br>UGUGCCCCCCCCAGUGGACCGGGAAGACCUGUCAGCUGGACGC<br>UAACGAGUGUGAGGCCAAGCCCUGUGUCAACGCCAAAAGCUG<br>CAAGAACCUGAUAGCCUCCUACUACUGCGACUGCCUGCCCGGA<br>UGGAUGGGCCAGAACUGCGACAUCAACAUCAAUGACUGCCUG<br>GGGCAGUGCCAGAACGACGCCAGCUGCCGGGACCUGGUGAAU<br>GGGUACCGCUGCAUCUGCCCCCCGGCUACGCGGGCGACCACU<br>GCGAGAGGGACAUCGACGAGUGCGCCUCGAACCCCUGCCUCAA<br>CGGGGGCCACUGCCAGAACGAGAUCAACCGGUUCCAGUGUCU<br>GUGCCCUACUGGCUUCUCUGGCAACCUGUGUCAGCUGGAUAU<br>CGAUUACUGCGAGCCAAACCCAUGCCAGAACGGGGCCCAGUGC<br>UACAAUAGGGCCUCCGACUAUUUUUGCAAGUGCCCCGAGGAC<br>UACGAGGGUAAGAACUGUUCCCAUCUCAAGGACCACUGUCGA<br>ACCACCCCCUGCGAGGUGAUCGACAGCUGCACCGUGGCCAUGG<br>CCAGCAAUGACACCCCCGAGGGCGUGCGGUACAUCUCCAGCAA<br>CGUGUGCGGCCCCCACGGCAAGUGCAAGAGCCAGUCCGGCGGC<br>AAAUUUACCUGCGAUUGCAACAAGGGGUUCACCGGCACCUAC<br>UGUCACGAGAACAUCAAUGACUGCGAAUCCAAUCCCUGCAGG<br>AACGGUGGCACGUGCAUCGACGGGGUGAAUAGCUAUAAGUGC<br>AUCUGCAGCGACGGGUGGGAAGGGGCCUACUGCGAGACCAAC |

TABLE 2-continued

| SEQ ID NO | NAME | SEQUENCE |
| --- | --- | --- |
| | | AUCAACGACUGUAGCCAGAACCCGUGCCACAAUGGCGGCACUU GUAGGGAUCUCGUGAAUGACUUCUAUUGCGACUGCAAAAAUG GAUGGAAGGGGAAGACCUGCCACUCCCGGGACUCCCAGUGCG ACGAGGCCACCUGCAAUAACGGCGGUACCUGCUACGACGAGG GCGAUGCCUUUAAAUGCAUGUGCCCCGGCGGCUGGGAGGGAA CCACGUGCAACAUCGCGAGGAACAGCAGCUGCCUCCCCAAUCC CUGUCACAAUGGCGGUACCUGCGUCGUGAACGGGGAGAGCUU CACCUGCGUGUGCAAGGAGGGCUGGGAGGGCCCGAUCUGCGC CCAGAACACCAACGACUGCAGCCCACACCCCUGCUACAAUAGC GGGACCUGCGUGGACGGAGACAACUGGUACCGGUGCGAGUGC GCCCCCGGCUUCGCCGGCCCCGACUGCAGGAUCAACAUCAACG AGUGCCAGAGCAGCCCCUGUGCCUUCGGCGCGACCUGCGUGGA UGAAAUCAAUGGCUACCGGUGCGUGUGCCCCCCGGCCACAGC GGCGCGAAGUGCCAGGAGGUUAGCGGCAGGCCCUGCAUCACC AUGGGAUCGGUGAUCCCCGAUGGCGCCAAGUGGGAUGACGAC UGUAACACAUGCCAAUGUCUGAAUGGACGGAUCGCAUGUUCC AAGGUGUGGUGCGGCCCCAGGCCCUGUCUCCUGCACAAAGGCC ACAGCGAGUGUCCCAGCGGCCAAAGCUGCAUCCCCAUCCUGGA CGACCAGUGCUUCGUGCAUCCCUGCACCGGCGUGGGGGAGUGC CGUAGCAGCAGCCUGCAGCCCGUGAAGACGAAGUGCACCUCAG ACAGCUAUUACCAGGAUAACUGCGCGAACAUCACCUUCACCUU UAACAAGGAGAUGAUGUCCCCGGCCUGACCACCGAGCACAUC UGCUCGGAGCUGCGCAAUCUUAACAUCCUGAAAAACGUGUCC GCCGAGUACAGCAUUUACAUCGCCUGUGAGCCGAGCCCCUCCG CCAACAAUGAGAUCCAUGUCGCCAUCAGCGCCGAGGACAUCCG GGACGACGGUAAUCCGAUCAAGGAGAUCACAGAUAAGAUCAU CGACCUGGUGUCCAAGCGGGACGGCAACAGCAGCCUGAUCGCC GCCGUCGCCGAGGUGCGUGUGCAGAGACGGCCCCUCAAGAACC GCACCGACUUCCUCGUGCCCCUCCUGAGCUCGGUGCUGACCGU CGCCUGGAUCUGCUGCCUGGUGACCGCCUUCUACUGGUGCCUG CGAAAACGCCGGAAGCCGGGGAGCCACACCCACAGCGCCAGCG AGGAUAACACCACCAAUAACGUGAGGGAACAGCUGAACCAGA UCAAGAACCCCAUCGAAAAACACGGCGCCAACACCGUGCCGAU CAAGGACUACGAGAACAAAAAUAGCAAGAUGAGCAAGAUCAG GACACACAACUCUGAGGUGGAGGAGGACGACAUGGACAAGCA CCAGCAGAAGGCCCGCUUCGCCAAGCAGCCCGCCUACACCCUG GUCGACCGGGAAGAGAAGCCCCCGAACGGCACCCCCACCAAGC AUCCUAACUGGACCAACAAGCAAGACAACAGGGACCUGGAAA GUGCCCAGAGCCUGAACCGGAUGGAGUACAUCGUG |
| 102 | JAG1-CO16 | AUGCGAAGCCCGAGGACCCGGGGCAGGAGCGGCAGGCCGCUA AGCCUGCUGCUGGCCCUCCUCUGCGCCCUCAGGGCCAAGGUGU GCGGCGCCUCCGGCCAAUUCGAGCUCGAGAUCCUGUCAAUGCA GAACGUGAACGGCGAGCUGCAGAACGGCAACUGCUGCGGCGG CGCCAGGAACCCCGGCGACAGGAAGUGCACCAGGGACGAAUG UGACACCUACUUCAAGGUGUGCCUGAAGGAGUACCAGAGCCG GGUGACCGCUGGCGGCCCAUGUAGCUUCGGGAGCGGCAGCACC CCGGUGAUCGGGGGUAACACCUUUAACCUCAAGGCUUCCCGCG GCAACGACAGGAACCGGAUCGUGCUGCCCUUCUCCUUCGCCUG GCCCAGGAGCUAUACCCUGCUGGUCGAGGCCUGGGACAGCUCC AACGACACCGUGCAACCCGACAGCAUCAUCGAGAAGGCCUCCC ACUCCGGCAUGAUCAACCCCAGCAGGCAGUGGCAGACCCUCAA GCAAAACACCGGGGUCGCGCACUUCGAGUACCAGAUCAGGGU CACCUGCGACGACUACUACUACGGCUUCGGCUGCAAUAAGUU UUGCCGGCCCAGGGACGAUUUCUUCGGACACUACGCCUGUGAC CAGAAUGGCAAUAAGACCUGUAUGGAAGGGUGGAUGGGGCCA GAGUGCAAUCGGGCCAUCUGCAGGCAAGGCUGCAGCCCCAAAC ACGGCUCGUGUAAGCUGCCCGGCGACUGCAGGUGCCAGUAUG GUUGGCAGGGCCUCUAUUGCGACAAGUGCAUCCCCCACCCAGG CUGUGUGCAUGGCAUCUGUAACGAACCCUGGCAGUGCCUGUG CGAGACGAACUGGGGGGGCCAACUGUGCGACAAGGACCUGAA CUAUUGCGGCACCCACCAGCCGUGCCUGAAUGGCGGAACCUGU UCCAACACCGGCCCCGACAAGUACCAGUGCUCCUGUCCCGAGG GGUACAGCGGCCCCAACUGCGAGAUCGCCGAGCAUGCCUGCCU CAGCGAUCCCUGCCACAACAGGGGCAGCUGCAAGGAGACGAGC CUGGGCUUCGAGUGCGAAUGCAGCCCCGGUUGGACCGGCCCCA CGUGCUCCACCAACAUCGACGACUGCUCCCCCAACAAUUGCAG CCACGGGGGCACAUGUCAGGACCUGGUGAACGGCUUCAAGUG CGUGUGCCCGCCCCAAUGGACCGGCAAGACGUGCCAGCUGGAC GCCAACGAGUGCGAAGCCAAGCCAUGCGUGAACGCCAAGAGC UGCAAGAACCUGAUCGCCAGCUACUACUGCGACUGCCUCCCAG GCUGGAUGGGCCAGAACUGUGAUAUCAACAUCAACGACUGCC UCGGCCAGUGCCAGAACGACGCCAGCUGCCGGGACCUGGUGAA CGGGUACCGCUGCAUCUGUCCGCCCGGCUACGCCGGAGACCAC UGCGAGCGCGACAUCGACGAGUGUGCCAGCAACCCCUGCUUAA |

TABLE 2-continued

Sequence optimized sequences for human JAG1

| SEQ ID NO | NAME | SEQUENCE |
|---|---|---|
| | | ACGGCGGCCACUGCCAAAAUGAAAUCAAUAGGUUUCAGUGCC UGUGCCCCACCGGGUUCAGCGGCAACCUGUGCCAGCUGGACAU CGACUAUUGCGAGCCGAACCCCUGCCAGAACGGGGCCCAGUGC UACAAUAGGGCCAGCGAUUAUUUCUGCAAGUGUCCCGAGGAC UACGAGGGAAAAAACUGCAGCCACCUCAAGGACCACUGUAGG ACCACGCCCUGCGAAGUGAUCGACUCCUGCACCGUGGCCAUGG CCAGCAACGACACCCCCGAGGGCGUGCGCUACAUCAGCAGCAA CGUGUGUGGCCCUCACGGCAAAUGCAAGAGCCAAAGCGGCGG CAAGUUCACCUGUGACUGCAAUAAGGGCUUCACCGGCACCUAC UGUCACGAGAACAUCAACGACUGCGAGAGCAACCCCUGCAGA AACGGUGGCACCUGUAUAGAUGGCGUGAACAGCUACAAGUGC AUCUGCAGCGACGGAUGGGAAGGCGCCUACUGUGAGACCAAC AUUAACGACUGCAGCCAGAACCCCUGCCACAAUGGCGGCACCU GCCGCGACCUGGUCAAUGACUUUUACUGCGACUGUAAGAACG GGUGGAAGGGCAAGACCUGCCAUAGCCGCGACUCCCAGUGCG ACGAGGCAACCUGCAACAACGGCGGCACCUGUUAUGAUGAGG GGGACGCAUUCAAGUGCAUGUGUCCGGGGGGCUGGGAGGGCA CAACCUGCAACAUCGCCCGGAACAGCAGCUGCCUCCCAAACCC CUGCCACAACGGGGGCACCUGCGUGGUGAACGGCGAGAGCUU CACCUGCGUGUGUAAGGAGGGCUGGGAGGGCCCCAUCUGUGC CCAGAAUACCAACGAUUGCUCCCCCCACCCCUGCUACAACAGC GGCACUUGCGUGGACGGCGAUAACUGGUAUAGGUGUGAGUGC GCCCCCGGCUUCGCAGGCCCCGACUGCCGCAUCAACAUCAACG AGUGCCAGAGCAGCCCCUGUGCCUUCGGGGCCACCUGCGUGGA CGAGAUCAACGGCUACCGGUGUGUGUGCCCCCCGGGCACUCC GGCGCGAAAUGCCAGGAGGUGUCCGGCAGGCCCUGCAUCACCA UGGGCAGCGUGAUCCCUGACGGCGCCAAAUGGGACGACGACU GUAAUACCUGCCAGUGCCUGAAUGGCCGAAUCGCCUGCUCCAA GGUGUGGUGCGGCCCCAGGCCUUGCCUGUUGCACAAGGGCCAC AGCGAGUGCCCCAGCGGCCAGAGCUGUAUCCCCAUCCUGGACG ACCAAUGUUUCGUGCAUCCCUGCACCGGCGUGGGGGAGUGCC GGUCGUCCAGCCUGCAGCCCGUGAAGACCAAGUGUACCAGCGA CUCCUACUAUCAGGACAAUUGCGCCAACAUCACCUUCACCUUU AACAAGGAGAUGAUGAGCCCCGGCCUGACCACCGAGCACAUCU GUUCCGAGCUGAGGAACCUGAACAUCCUGAAGAACGUCAGUG CCGAGUACUCCAUCUACAUCGCCUGUGAACCGUCCCCGUCCGC CAACAAUGAGAUUCACGUGGCCAUCAGCGCCGAAGACAUCAG GGACGACGGCAACCCCAUCAAGGAGAUCACCGACAAGAUCAU AGACCUUGUGUCCAAGAGGGACGGCAACUCGUCCCUGAUCGCC GCCGUGGCGGAGGUGAGGGUGCAGAGGAGGCCCCUGAAGAAC CGCACCGACUUCCUGGUGCCGCUCCUGUCCUCCGUGCUGACCG UGGCCUGGAUCUGCUGCCUGGUGACCGCCUUCUACUGGUGCCU GAGGAAGCGCCGCAAGCCCGGGUCCCACACGCACAGCGCCAGC GAGGAUAACACCACCAACAACGUGCGGGAGCAACUGAACCAG AUAAAGAACCCCAUCGAAAAACACGGAGCGAACACCGUCCCCA UCAAGGACUACGAAAACAAGAACAGCAAGAUGAGCAAGAUCA GGACCCAUAACUCCGAGGUGGAGGAGGACGACAUGGACAAGC ACCAGCAAAAGGCCCGGUUCGCCAAGCAGCCCGCCUACACCCU GGUGGAUCGGGAGGAGAAGCCCCCCAACGGUACCCCGACCAAA CACCCCAACUGGACCAAUAAACAGGACAAUAGGGACCUGGAG UCCGCCCAGAGCCUGAACAGGAUGGAGUACAUAGUG |
| 103 | JAG1-CO17 | AUGAGAAGCCCCAGGACCCGAGGCAGGAGCGGCAGGCCACUG AGCCUGCUCCUUGCCCUGCUGUGCGCCCUGAGGGCAAAGGUGU GCGGCGCCAGCGGCCAGUUCGAGCUGGAAAUCCUGUCCAUGCA GAACGUGAACGGGGAGCUGCAGAAUGGCAAUUGCUGUGGCGG CGCGCGGAACCCCGGCGACAGGAAGUGCACACGGGACGAAUGC GACACGUACUUCAAGGUGUGCCUCAAGGAGUACCAGUCCAGG GUCACCGCCGGCGGGCCCUGCAGCUUCGGAAGCGGCUCCACCC CCGUGAUCGGCGGCAACACAUUCAACCUGAAAGCGUCGAGGG GGAAUGACCGCAACAGGAUCGUGCUGCCGUUUUCCUUCGCCU GGCCCCGCAGCUACACGCUGCUGGUGGAGGCAUGGGACAGCUC CAACGAUACCGUGCAGCCCGACAGCAUCAUCGAGAAGGCCUCC CACAGCGGCAUGAUCAACCCGAGCAGGCAGUGGCAGACCCUCA AGCAGAACACCGGCGUGGCCCACUUCGAGUAUCAGAUCCGGG UGACCUGCGACGACUAUUACUACGGUUUCGGCUGCAACAAGU UUUGUAGGCCCCGAGACGACUUCUUCGGCCACUACGCCUGCGA UCAGAACGGGAAUAAAACCUGUAUGGAGGGGUGGAUGGGCCC CGAGUGCAACAGGGCCAUCUGCAGGCAGGGAUGCUCCCCCAAG CACGGCAGCUGCAAGCUGCCAGGAGACUGCAGGUGUCAGUAU GGCUGGCAGGGGCUGUACUGCGAUAAGUGCAUUCCGCACCCA GGAUGUGUGCACGGAAUCUGUAACGAGCCCUGGCAGUGCCUG UGCGAAACCAACUGGGGGGGCCAACUCUGCGACAAGGACCUG AACUACUGCGGCACCCACCAACCCUGUCUGAACGGCGGCACCU GCAGCAACACCGGCCCCGACAAAUACCAGUGCAGCUGCCCCGA |

TABLE 2-continued

Sequence optimized sequences for human JAG1

| SEQ ID NO | NAME | SEQUENCE |
|---|---|---|
| | | GGGCUACUCCGGGCCCAACUGCGAGAUCGCCGAACACGCAUGU<br>CUGAGCGACCCUUGCCACAACAGGGGCAGCUGCAAGGAGACCU<br>CCCUCGGCUUUGAGUGCGAAUGCAGCCCCGGCUGGACCGGGCC<br>CACCUGCAGCACGAACAUCGACGACUGCAGCCCCAACAACUGC<br>UCCCACGGCGGGACGUGCCAGGAUCUCGUCAACGGCUUCAAGU<br>GCGUGUGCCCCCCCCAGUGGACCGGCAAAACCUGCCAGCUGGA<br>CGCAAACGAGUGCGAAGCCAAGCCGUGCGUCAACGCGAAGAG<br>CUGCAAGAACCUCAUCGCCAGCUACUAUUGCGACUGCCUGCCC<br>GGCUGGAUGGGCCAGAACUGCGACAUAAACAUCAACGACUGC<br>CUGGGCCAGUGUCAGAACGAUGCCUCCUGCAGGGACCUGGUG<br>AACGGGUACCGGUGUAUCUGCCCCCCCGGGUACGCGGGGGACC<br>ACUGCGAGAGAGACAUCGAUGAGUGCGCCUCCAAUCCCUGCCU<br>GAACGGCGGCCAUUGCCAGAACGAGAUCAACCGGUUCCAGUG<br>CCUGUGCCCCACCGGCUUCUCCGGCAACCUGUGCCAACUAGAC<br>AUCGACUACUGCGAGCCCAAUCCCUGCCAGAACGGCGCCCAAU<br>GCUACAACAGGGCCAGCGACUACUUCUGUAAGUGCCCCGAGG<br>ACUACGAGGGCAAGAACUGCUCCCAUCUGAAGGACCACUGCCG<br>GACCACCCCCUGCGAAGUGAUCGACAGCUGCACCGUGGCCAUG<br>GCCAGCAAUGACACCCCCGAGGGCGUGAGGUAUAUCAGCAGC<br>AACGUGUGCGGGCCCCACGGGAAAUGCAAGAGCCAGAGCGGC<br>GGCAAGUUCACAUGCGACUGUAACAAGGGCUUCACGGGAACC<br>UACUGUCACGAGAACAUCAACGACUGCGAGAGCAACCCCUGCC<br>GCAACGGCGGCACCUGCAUCGACGGCGUGAACUCCUAUAAGU<br>GCAUCUGUAGCGAUGGCUGGGAAGGGGCCUACUGCGAGACCA<br>ACAUAAACGACUGCAGCCAGAAUCCCUGCCAUAACGGGGGCAC<br>CUGUCGUGACCUGGUCAACGACUUCUACUGCGACUGUAAGAA<br>CGGAUGGAAGGGUAAGACCUGCCACUCCAGGGACUCCCAGUG<br>UGACGAAGCCACCUGCAACAACGGAGGCACCUGCUACGACGAG<br>GGUGACGCCUUUAAGUGCAUGUGCCCCGGUGGCUGGGAGGGG<br>ACCACGUGCAACAUCGCCCGCAACAGCAGCUGCCUUCCGAACC<br>CAUGCCAUAACGGCGGCACCUGUGUCGUGAACGGCGAGUCGU<br>UCACCUGUGUGUGCAAGGAAGGCUGGGAAGGCCCCAUAUGCG<br>CCCAGAACACCAACGACUGCAGCCCCCAUCCCUGCUACAACUC<br>CGGCACCUGCGUGGACGGGGACAACUGGUACAGGUGUGAGUG<br>CGCCCCCGGAUUCGCCGGUCCCGACUGCCGGAUCAACAUCAAU<br>GAGUGUCAAUCCAGCCCCUGCGCCUUCGGCGCCACCUGCGUGG<br>AUGAGAUCAACGGCUACAGGUGCGUCUGUCCCCCCGGCCACUC<br>CGGCGCCAAAUGCCAGGAGGUCAGCGGCAGGCCCUGCAUCACC<br>AUGGGCUCCGUUAUCCCCGACGGCGCCAAGUGGGACGACGACU<br>GCAAUACCUGCCAGUGUCUGAACGGGAGGAUCGCCUGCUCCA<br>AGGUGUGGUGCGGCCCCAGGCCCUGCCUGCUGCACAAGGGCCA<br>CAGCGAGUGCCCCAGCGGCCAGUCCUGCAUCCCGAUCCUGGAC<br>GACCAGUGCUUUGUGCACCCCUGCACCGGGGUAGGCGAGUGCC<br>GGUCCAGCAGCCUGCAGCCCGUGAAAACCAAGUGCACCAGCGA<br>CAGCUAUUACCAGGACAACUGCGCCAAUAUCACCUUUACGUUC<br>AAUAAAGAGAUGAUGAGCCCCGGCCUGACCACCGAACACAUC<br>UGCAGCGAGCUGCGCAACCUGAACAUUCUGAAGAACGUGAGC<br>GCCGAGUACAGCAUCUAUAUAGCCUGCGAGCCCAGCCCCUCGG<br>CUAAUAACGAGAUCCACGUGGCCAUAAGCGCGGAGGACAUCC<br>GGGACGACGGCAACCCCAUCAAGGAGAUCACCGACAAGAUCA<br>UCGACCUGGUGAGCAAGCGCGACGGGAACUCAUCACUGAUCG<br>CCGCCGUGGCCGAGGUGAGGGUGCAGAGGCGGCCCCUCAAGA<br>ACAGGACCGACUUCCUCGUCCCCCUGCUGUCGAGCGUGCUCAC<br>CGUGGCCUGGAUCUGCUGUCUCGUGACCGCAUUCUACUGGUG<br>CCUGAGGAAACGGCGCAAGCCCGGCUCGCACACCCACAGCGCC<br>AGCGAAGAUAACACCACCAACAACGUGAGGGAGCAGCUCAAC<br>CAGAUCAAGAACCCCAUAGAGAAGCACGGCGCCAACACGGUGC<br>CAAUCAAGGACUAUGAGAACAAGAACAGCAAGAUGUCCAAGA<br>UCCGCACCCACAACAGCGAAGUCGAGGAAGACGACAUGGACA<br>AGCACCAGCAGAAAGCGCGUUUCGCCAAGCAGCCCGCCUACAC<br>CCUGGUGGACAGGGAGGAGAAGCCCCCCAACGGAACCCCCACA<br>AAGCACCCAAACUGGACGAAUAAGCAGGACAACAGGGACCUG<br>GAGAGCGCCCAGAGUCUGAACCGGAUGGAGUACAUCGUG |
| 104 | JAG1-CO18 | AUGAGAAGUCCCAGGACCCGCGGGCGGAGCGGGCGCCCCCUGA<br>GCCUGUUACUGGCCCUCCUGUGUGCCCUGCGCGCGAAGGUGUG<br>CGGGGCCAGCGGCCAGUUCGAGCUGGAGAUCCUGAGCAUGCA<br>GAACGUGAACGGGGAACUACAGAACGGCAACUGCUGCGGCGG<br>CGCCCGCAAUCCGGGAGACAGGAAGUGUACCAGGGAUGAGUG<br>CGACACCUACUUUAAAGUGUGCCUGAAGGAGUACCAGAGCAG<br>GGUGACCGCCGGCGGCCCCUGUAGCUUCGGCAGCGGGAGCACC<br>CCGGUGAUCGGCGGCAACACCUUCAACCUCAAGGCCUCCAGGG<br>GCAACGACAGGAACCGGAUCGUGCUGCCCUUCAGCUUCGCCUG<br>GCCCCGCAGCUACACGCUGCUGGUGGAGGCCUGGGACAGCUCU<br>AAUGACACGGUGCAGCCUGACUCAAUUAUAGAGAAGGCCAGC |

TABLE 2-continued

Sequence optimized sequences for human JAG1

| SEQ ID NO | NAME | SEQUENCE |
|---|---|---|
| | | CACAGCGGCAUGAUCAACCCCUCAAGACAGUGGCAGACCCUGA<br>AGCAGAACACCGGUGUGGCACACUUCGAGUAUCAGAUCAGGG<br>UGACAUGCGAUGACUACUACUACGGGUUUGGCUGUAAUAAGU<br>UCUGCAGGCCCCGAGACGAUUUCUUCGGGCACUAUGCCUGCGA<br>CCAAAAUGGCAACAAGACCUGCAUGGAGGGGUGGAUGGGCCC<br>GGAGUGUAACCGAGCCAUAUGUAGGCAAGGCUGCAGCCCGAA<br>GCACGGCUCCUGCAAGCUGCCCGGUGAUUGCAGGUGCCAGUAC<br>GGCUGGCAAGGCCUCUACUGCGACAAGUGCAUCCCGCACCCCG<br>GUUGCGUCCACGGCAUCUGCAACGAGCCCUGGCAGUGCCUGUG<br>CGAGACCAACUGGGGGGGCCAGCUGUGCGACAAGGACCUCAA<br>UUACUGUGGCACCCACCAGCCCUGCCUCAACGGUGGCACCUGC<br>UCCAACACCGGCCCCGACAAGUACCAGUGUAGCUGCCCCGAGG<br>GGUACAGCGGCCCGAACUGCGAGAUCGCCGAGCACGCCUGCCU<br>GUCCGACCCCUGCCACAAUCGCGGCAGCUGCAAGGAGACCAGC<br>CUGGGGUUCGAAUGCGAGUGUUCCCCGGGCUGGACCGGCCCCA<br>CCUGCAGCACCAAUAUCGAUGACUGCUCCCCCAACAACUGCAG<br>CCACGGCGGCACCUGUCAGGACCUGGUGAAUGGCUUCAAGUG<br>UGUGUGCCCACCGCAGUGGACCGGCAAAACCUGCCAGCUCGAC<br>GCCAACGAGUGCGAGGCCAAGCCCUGUGUGAAUGCCAAGUCC<br>UGCAAGAACCUGAUCGCCAGCUACUACUGCGACUGCCUGCCCG<br>GGUGGAUGGGGCAAAAUUGCGACAUAAACAUAAACGACUGCC<br>UGGGCCAGUGCCAGAACGACGCCUCCUGUCGGGACCUGGUCAA<br>CGGCUACAGGUGCAUCUGCCCACCCGGCUACGCCGGCGACCAC<br>UGCGAGCGAGAUAUCGACGAAUGCGCCAGCAACCCCUGCCUGA<br>ACGGGGGGCACUGCCAGAAUGAGAUCAACAGGUUUCAGUGCC<br>UGUGCCCCACCGGCUUCAGCGGCAACCUGUGUCAACUGGACAU<br>CGACUAUUGUGAGCCCAACCCUUGCCAAAACGGGGCCCAGUGC<br>UACAACCGGGCCAGCGAUUACUUCUGCAAGUGCCCCGAGGACU<br>ACGAAGGCAAGAACUGCAGCCACCUGAAGGACCACUGUCGGA<br>CCACCCCCUGCGAAGUGAUCGACAGCUGCACCGUGGCCAUGGC<br>CAGCAACGACACCCCCGAGGGCGUGAGGUACAUCAGCAGCAAU<br>GUGUGUGGCCCGCACGGCAAGUGCAAGAGCCAGAGCGGCGGC<br>AAGUUCACGUGCGACUGCAACAAGGGCUUUACCGGCACCUAC<br>UGCCACGAAAACAUCAAUGACUGCGAGAGCAACCCGUGUCGG<br>AACGGCGGCACCUGCAUCGACGGGGUGAACAGCUACAAGUGC<br>AUAUGCAGCGACGGCUGGGAGGGCGCCUACUGUGAAACCAAC<br>AUCAACGACUGCAGCCAGAACCCCUGCCACAAUGGCGGGACCU<br>GCAGGGACCUGGUGAAUGACUUCUACUGCGACUGCAAGAACG<br>GCUGGAAGGGCAAAACCUGCCACAGCAGGGACAGCCAGUGCG<br>ACGAGGCCACCUGCAACAACGGCGGCACCUGCUAUGACGAGGG<br>CGACGCCUUCAAGUGCAUGUGCCCCGGCGGAUGGGAGGGCAC<br>GACCUGCAAUAUCGCAAGGAACAGCUCCUGUCUGCCCAAUCCC<br>UGCCACAACGGCGGUACCUGCGUGGUGAACGGGGAAAGCUUC<br>ACCUGCGUGUGCAAGGAGGGGUGGGAGGGGCCCAUCUGCGCC<br>CAGAACACCAACGACUGCAGCCCACACCCCUGCUACAAUUCCG<br>GCACCUGUGUGGACGGCGACAACUGGUAUAGGUGCGAGUGCG<br>CCCCCGGUUUCGCCGGCCCGGACUGCAGGAUCAACAUCAACGA<br>GUGUCAGUCCAGCCCCUGCGCCUUCGGGGCCACCUGCGUGGAC<br>GAGAUCAACGGCUAUCGUUGCGUGUGCCCCCCCGGCCACUCCG<br>GCGCCAAGUGCCAGGAAGUGUCCGGGCGCCCCUGCAUCACCAU<br>GGGCUCCGUGAUCCCCGAUGGCGCCAAGUGGGAUGACGACUG<br>CAACACCUGUCAGUGCCUGAACGGCAGGAUCGCCUGCAGCAAG<br>GUGUGGUGCGGCCCCCGACCCUGCCUGCUGCACAAGGGGCACA<br>GCGAGUGCCCCUCCGGCCAGUCCUGCAUCCCCAUACUGGACGA<br>UCAGUGCUUCGUGCACCCCUGCACCGGCGUGGGCGAGUGUAG<br>GAGCUCCAGCCUGCAGCCCGUGAAAACCAAGUGCACCUCGGAC<br>AGCUACUAUCAGGAUAACUGCGCCAACAUUACGUUCACCUUC<br>AACAAGGAGAUGAUGUCCCCCGGCCUGACCACGGAGCACAUCU<br>GUUCCGAGCUGAGGAACCUCAACAUCCUGAAAAAUGUGAGCG<br>CCGAGUAUAGCAUCUAUAUAGCCUGUGAGCCGUCCCCCUCCGC<br>CAACAACGAGAUCCACGUCGCCAUCUCCGCAGAGGACAUUCGC<br>GACGACGGGAACCCCAUAAAGGAAAUUACGGACAAAAUCAUC<br>GACCUGGUGAGCAAGAGGGACGGCAACUCCAGCCUGAUCGCC<br>GCCGUGGCCGAGGUGCGCGUGCAACGCAGGCCGCUGAAAAAC<br>AGGACGGACUUUCUGGUGCCGCUGCUGUCCUCGGUGCUGACC<br>GUCGCUUGGAUCUGCUGCCUGGUGACCGCCUUCUACUGGUGCC<br>UGCGCAAAAGGCGCAAGCCCGGUAGCCAUACCCACUCCGCCUC<br>CGAAGACAACACCACCAACAACGUGAGGGAGCAGCUGAAUCA<br>GAUCAAGAACCCUAUCGAGAAGCACGGCGCCAACACGGUGCCC<br>AUCAAGGACUAUGAAAACAAGAACAGCAAGAUGUCCAAGAUC<br>AGGACCCACAACAGCGAGGUGGAGGAAGACGACAUGGACAAG<br>CACCAGCAGAAGGCCCGAUUCGCCAAGCAGCCCGCUUACACCC<br>UGGUGGACAGGGAGGAAAAGCCCCCGAACGGCACCCCCACCAA<br>ACACCCCAACUGGACUAAUAAACAGGACAACCGAGACCUGGA<br>GAGCGCCCAGAGCCUGAACAGGAUGGAAUAUAUCGUC |

TABLE 2-continued

Sequence optimized sequences for human JAG1

| SEQ ID NO | NAME | SEQUENCE |
|---|---|---|
| 105 | JAG1-CO19 | AUGCGUAGCCCCAGGACCAGGGGUAGGUCCGGGAGGCCCCUG<br>UCACUCCUCCUGGCCCUGCUCUGUGCCCUCCGGGCCAAGGUGU<br>GCGGCGCCAGCGGACAGUUUGAGCUGGAGAUCCUGUCCAUGC<br>AGAACGUGAACGGUGAGCUCCAGAACGGGAACUGCUGCGGCG<br>GCGCCAGGAACCCCGGCGAUCGCAAGUGUACCAGGGACGAAU<br>GUGACACCUACUUUAAGGUGUGCCUGAAAGAGUACCAGAGCC<br>GCGUCACCGCCGGCGGGCCCUGUUCCUUUGGCUCCGGCAGCAC<br>UCCCGUGAUCGGCGGCAACACCUUCAACCUCAAGGCGAGCAGG<br>GGGAACGACAGGAACAGGAUCGUGCUGCCCUUCAGCUUCGCG<br>UGGCCCCGGUCCUACACCCUGCUCGUGGAGGCUUGGGACUCCU<br>CAAACGACACGGUCCAGCCGGAUAGCAUCAUUGAGAAGGCGA<br>GCCACUCCGGCAUGAUCAACCCCAGCCGGCAGUGGCAGACCCU<br>CAAGCAGAACACCGGCGUGGCCCACUUCGAGUAUCAGAUCCGC<br>GUGACCUGCGAUGAUUACUACUACGGCUUUGGAUGCAACAAG<br>UUCUGCCGGCCCCGCGACGACUUCUUCGGACACUAUGCCUGUG<br>ACCAGAACGGGAACAAGACCUGCAUGGAGGGAUGGAUGGGUC<br>CCGAGUGCAACCGGGCCAUCUGCAGGCAGGGCUGUAGCCCCAA<br>GCACGGGAGCUGCAAGCUGCCCGGCGACUGCAGGUGCCAGUAC<br>GGCUGGCAGGGGCUGUACUGCGACAAGUGCAUCCCCCACCCGG<br>GAUGCGUGCACGGCAUCUGCAACGAGCCCUGGCAGUGCCUCUG<br>CGAGACCAACUGGGGCGGCCAGCUGUGCGACAAGGACCUGAA<br>CUACUGUGGCACGCAUCAGCCAUGCCUCAAUGGUGGCACCUGC<br>AGCAACACGGGCCCCGAUAAGUACCAAUGCUCGUGCCCCGAAG<br>GGUACUCCGGCCCAAAUUGCGAGAUCGCCGAGCACGCCUGCCU<br>GUCCGACCCCUGCCACAACAGGGGCUCCUGUAAGGAGACCUCC<br>CUGGGCUUCGAGUGUGAGUGCAGCCCCGGGUGGACCGGCCCCA<br>CCUGUUCCACCAACAUCGACGACUGCAGCCCCAACAACUGCAG<br>CCAUGGAGGCACCUGUCAGGACCUGGUGAAUGGUUUCAAGUG<br>UGUGUGCCCGCCCCAGUGGACCGGGAAGACCUGCCAGCUGGAC<br>GCCAACGAGUGCGAGGCUAAGCCCUGCGUCAACGCCAAGAGCU<br>GCAAGAACCUCAUCGCCUCCUACUACUGCGACUGCCUGCCGGG<br>AUGGAUGGGCCAGAACUGUGACAUCAACAUCAACGACUGUCU<br>GGGCCAGUGCCAGAAUGACGCCAGCUGCCGAGACCUGGUCAAC<br>GGCUACAGGUGCAUAUGCCCCCCCGGAUAUGCCGGGGAUCACU<br>GCGAGCGGGACAUCGACGAGUGCGCCAGCAACCCAUGUCUGA<br>ACGGCGGGCACUGCCAGAACGAGAUCAACAGGUUUCAAUGCC<br>UGUGCCCCACCGGAUUUAGUGGGAACCUCUGUCAGCUGGACA<br>UAGACUACUGCGAGCCGAACCCCUGCCAAAACGGCGCGCAGUG<br>CUACAACAGGGCCAGCGAUUACUUCUGCAAGUGCCCGGAGGA<br>CUACGAGGGGAAGAACUGCUCCCACCUGAAGGACCACUGCAG<br>GACCACCCCCUGCGAGGUGAUCGACUCGUGCACCGUCGCCAUG<br>GCCUCAAACGACACCCCCGAGGGGGUCCGCUACAUCUCGAGCA<br>ACGUCUGUGGCCCCCACGGCAAGUGCAAGAGCCAGAGCGGGG<br>GGAAGUUCACCUGCGACUGCAACAAAGGCUUCACCGGCACGU<br>ACUGUCACGAGAACAUCAAUGAUUGCGAGAGCAACCCCUGCC<br>GGAACGGCGGCACCUGCAUCGACGGCGUGAACAGCUACAAGU<br>GCAUCUGUAGCGACGGCUGGGAGGGGGCCUACUGCGAGACCA<br>ACAUCAACGACUGCAGCCAGAACCCCUGUCACAACGGCGGCAC<br>CUGCAGGGACCUCGUGAAUGACUUCUACUGCGACUGCAAAAA<br>CGGGUGGAAAGGUAAAACCUGCCAUAGCCGGGACAGCCAGUG<br>CGACGAGGCCACCUGUAAUAACGGCGGCACCUGCUACGACGAG<br>GGUGACGCCUUUAAGUGUAUGUGCCCCGGCGGCUGGGAGGGC<br>ACCACCUGCAAUAUCGCCCGCAACAGCAGCUGUCUCCCCAACC<br>CCUGCCACAACGGGGGUACCUGCGUGGUCAACGGCGAGUCCUU<br>UACCUGCGUGUGCAAGGAGGGCUGGGAAGGGCCCAUCUGCGC<br>CCAGAACACCAACGACUGUAGCCCCCAUCCCUGCUACAACUCC<br>GGUACCUGCGUGGACGGCGACAAUUGGUACAGGUGUGAAUGC<br>GCACCAGGCUUCGCGGGGCCCGACUGCAGGAUCAACAUCAACG<br>AAUGCCAGAGCAGCCCCUGCGCGUUCGGCGCCACCUGCGUGGA<br>CGAGAUCAACGGGUACAGGUGCGUGUGCCCCCCGGGCACAGC<br>GGGGCCAAGUGCCAGGAGGUCUCCGGGCGGCCCUGCAUCACCA<br>UGGGCUCCGUGAUCCCGGAUGGGGCGAAGUGGGACGACGAUU<br>GCAACACCUGCCAAUGCCUGAACGGGAGGAUCGCCUGUAGCA<br>AGGUCUGGUGCGGACCCCGGCCCUGCCUCCUGCACAAAGGCCA<br>CUCCGAAUGCCCCAGCGGACAAAGCUGCAUACCGAUCCUGGAC<br>GACCAAUGCUUCGUGCAUCCCUGCACAGGCGUGGGUGAAUGC<br>AGGAGCUCCAGCCUGCAGCCAGUGAAGACGAAGUGCACCAGC<br>GAUAGCUACUACCAGGAUAAUUGUGCCAACAUAACCUUCACC<br>UUCAACAAGGAGAUGAUGUCCCCCGGCCUGACCACCGAGCACA<br>UCUGUAGCGAGCUCCGCAACCUGAACAUCCUCAAGAACGUGA<br>GCGCCGAGUACUCCAUCUACAUCGCCUGCGAGCCCUCGCCCAG<br>CGCCAAUAACGAGAUCCACGUGGCCAUCUCCGCCGAGGACAUC<br>CGCGACGACGGCAAUCCCAUCAAGGAGAUUACCGACAAGAUC<br>AUCGACCUGGUGAGCAAGCGCGAUGGCAACAGCAGCCUGAUC |

TABLE 2-continued

Sequence optimized sequences for human JAG1

| SEQ ID NO | NAME | SEQUENCE |
|---|---|---|
| | | GCCGCGGUGGCCGAGGUGAGGGUGCAGAGGCGGCCCCUCAAG<br>AACCGCACGGACUUCCUGGUGCCACUGCUGAGCUCCGUGCUGA<br>CCGUGGCCUGGAUCUGCUGUCUGGUCACCGCCUUCUACUGGUG<br>CCUGCGGAAACGGAGGAAGCCCGGAUCCCACACCCACUCCGCC<br>UCCGAAGACAACACCACGAACAACGUCAGGGAGCAGCUGAACC<br>AGAUCAAGAACCCCAUCGAGAAGCAUGGCGCCAACACCGUGCC<br>AAUCAAAGACUACGAGAACAAGAACAGCAAGAUGAGCAAGAU<br>CCGGACCCACAACAGCGAAGUAGAAGAGGACGACAUGGAUAA<br>GCACCAGCAGAAGGCCAGGUUCGCCAAGCAACCCGCCUACACC<br>CUCGUGGACCGCGAGGAGAAACCCCCAACGGCACCCCCACCA<br>AGCACCCCAAUUGGACCAACAAGCAAGAUAACCGCGACCUGGA<br>GAGCGCCCAGAGCCUCAACCGGAUGGAAUACAUCGUG |
| 106 | JAG1-CO20 | AUGAGGAGCCCAAGGACCAGGGGGAGGAGCGGCAGGCCGCUC<br>AGCCUGCUGCUCGCCCUGCUGUGCGCCCUGCGGGCAAAGGUGU<br>GCGGGGCCAGCGGCCAGUUCGAGCUGGAAAUCCUGAGCAUGC<br>AGAACGUGAACGGCGAGCUGCAAAAUGGUAAUUGCUGCGGGG<br>GCGCCAGGAACCCGGGCGACAGGAAGUGCACCAGGGACGAGU<br>GCGACACCUAUUUCAAGGUGUGCCUGAAGGAAUACCAGAGCC<br>GCGUCACGGCCGGGGGCCCGUGCUCCUUCGGCAGUGGCUCCAC<br>CCCCGUGAUCGGCGGCAACACCUUUAACCUGAAGGCCUCCCGG<br>GGUAACGACAGGAACAGGAUCGUGCUGCCCUUCUCCUUCGCCU<br>GGCCGAGGUCCUACACCCUCCUGGUAGAGGCCUGGGACAGCAG<br>CAAUGAUACGGUGCAGCCCGACUCCAUCAUAGAAAAGGCCAG<br>CCACUCCGGGAUGAUCAAUCCGAGCAGGCAGUGGCAAACCCUC<br>AAGCAGAACACCGGUGUGGCCCACUUUGAGUACCAGAUCAGG<br>GUCACCUGCGACGACUACUACUACGGCUUCGGCUGCAACAAGU<br>UUUGCAGGCCGAGGGACGACUUCUUCGGCCACUACGCCUGCGA<br>CCAGAAUGGCAACAAGACCUGCAUGGAAGGCUGGAUGGGCCC<br>GGAAUGCAAUCGCGCCAUCUGUAGGCAGGGGUGCAGCCCAAA<br>GCAUGGGAGCUGCAAGCUGCCCGGGGACUGCAGGUGUCAGUA<br>CGGAUGGCAGGGGCUGUACUGUGACAAGUGUAUCCCACAUCC<br>GGGCUGCGUGCACGGAAUAUGCAACGAGCCCUGGCAGUGCCU<br>GUGUGAAACGAACUGGGGCGGUCAGCUGUGCGACAAGGACCU<br>GAACUACUGCGGCACCCACCAGCCCUGCCUGAACGGCGGGACG<br>UGUUCCAACACCGGCCCCGACAAGUAUCAGUGUAGCUGCCCCG<br>AGGGCUAUAGCGGCCCGAACUGCGAGAUCGCCGAACAUGCCU<br>GUCUCAGCGACCCCUGUCACAACAGGGGUAGCUGUAAGGAAA<br>CCAGCCUCGGGUUUGAGUGUGAAUGCUCCCCGGGCUGGACCG<br>GGCCCACCUGUUCCACCAACAUCGACGACUGCUCCCCCAAUAA<br>CUGCAGCCAUGGCGGCACGUGUCAGGACCUCGUCAAUGGCUU<br>UAAGUGUGUGUGCCCCCCGCAGUGGACCGGCAAGACGUGCCA<br>GCUGGACGCCAACGAGUGUGAGGCCAAGCCCUGCGUCAACGCA<br>AAGAGCUGCAAGAACCUGAUCGCCUCCUACUAUUGUGACUGC<br>CUGCCCGGGUGGAUGGGACAGAACUGCGACAUCAAUAUCAAC<br>GAUUGCCUGGGGCAGUGCCAGAACGACGCGAGCUGCAGGGAC<br>CUGGUCAACGGCUACCGAUGCAUCUGCCCCCCGGGCUACGCCG<br>GCGACCACUGUGAAAGGGACAUCGACGAGUGCGCCAGCAACCC<br>CUGCCUGAACGGGGGCCACUGCCAGAACGAGAUCAAUAGGUU<br>CCAGUGCCUGUGCCCGACCGGUUUUAGCGGCAACCUGUGCCAG<br>CUGGACAUUGACUAUUGCGAGCCCAACCCCUGCCAGAACGGGG<br>CCCAGUGCUACAACAGGGCCUCGGACUACUUCUGUAAGUGCCC<br>CGAGGACUAUGAGGGCAAGAACUGCAGCCAUCUGAAGGACCA<br>CUGCAGGACCACCCCGUGCGAGGUCAUCGACAGCUGCACCGUG<br>GCCAUGGCCUCCAAUGAUACCCCCGAGGGCGUGAGGUACAUCU<br>CCUCCAACGUGUGUGGCCCCCACGGCAAGUGCAAAAGCCAGAG<br>CGGCGGCAAGUUCACCUGUGACUGUAACAAGGGCUUCACCGG<br>CACCUACUGCCAUGAAAACAUCAACGAUUGCGAGUCUAAUCCC<br>UGCCGGAACGGCGGCACCUGCAUCGAUGGCGUGAACAGCUAU<br>AAAUGUAUCUGCUCCGAUGGGUGGGAGGGCGCAUACUGCGAA<br>ACCAACAUCAACGACUGCUCCCAGAACCCCUGCCAUAACGGCG<br>GCACCUGCCGCGACCUCGUCAACGAUUUCUACUGCGACUGCAA<br>GAACGGCUGGAAGGGCAAGACCUGCCACAGCCGAGACAGCCA<br>GUGCGACGAGGCCACGUGCAACAACGGAGGGACCUGUUAUGA<br>CGAGGGCGACGCCUUCAAGUGCAUGUGCCCCGGGGGCUGGGA<br>GGGCACGACCUGCAACAUUGCCCGCAAUAGCAGCUGCUUGCCC<br>AACCCCUGUCACAACGGCGGAACCUGCGUCGUGAACGGCGAGU<br>CCUUCACCUGCGUUUGCAAAGAGGGCUGGGAGGGCCCAAUCU<br>GUGCCCAGAACACCAAUGACUGCAGCCCCCACCCCUGCUACAA<br>UUCCGGUACCUGCGUGGACGGCGACAACUGGUAUAGGUGCGA<br>GUGCGCCCCGGGAUUCGCCGGCCCGGACUGCAGGAUCAACAUC<br>AACGAGUGCCAGAGCAGCCCCUGCGCCUUCGGGGCCACCUGUG<br>UGGACGAGAUCAAUGGCUACAGGUGUGUCUGCCCCCCCGGAC<br>ACUCGGGCGCGAAAUGCCAAGAGGUGUCCGGCAGGCCCUGCA<br>UCACCAUGGGUUCCGUGAUACCCGACGGGGCAAAGUGGGACG |

TABLE 2-continued

Sequence optimized sequences for human JAG1

| SEQ ID NO | NAME | SEQUENCE |
|---|---|---|
| | | ACGAUUGCAAUACCUGCCAAUGCCUGAACGGCAGGAUCGCCU GUAGCAAGGUGUGGUGUGGCCCGAGGCCUUGCCUCCUGCAUA AAGGCCACAGCGAGUGUCCCUCCGGCCAGAGCUGUAUCCCCAU CCUCGACGAUCAAUGCUUUGUGCACCCUUGCACCGGGGUGGGC GAGUGUCGCAGCAGCAGCCUGCAGCCCGUGAAGACCAAAUGC ACCAGCGAUAGCUACUACCAGGACAACUGCGCGAAUAUCACCU UUACGUUCAACAAGGAGAUGAUGAGCCCGGGCCUGACCACAG AGCACAUCUGCAGCGAGCUGCGCAACCUGAACAUCCUGAAGA ACGUGUCUGCCGAGUAUAGCAUCUACAUCGCCUGCGAACCCAG CCCCUCCGCAAAUAAUGAGAUCCACGUGGCGAUCUCGGCCGAG GACAUCAGGGACGACGGGAACCCCAUCAAAGAGAUCACCGAC AAGAUCAUCGAUCUGGUGAGCAAGCGGGACGGCAACAGCUCC CUCAUCGCCGCCGUGGCUGAGGUCCGAGUGCAGCGGCGUCCCC UUAAGAACAGGACCGACUUCCUGGUGCCCCUCCUGUCGUCCGU GCUCACCGUGGCCUGGAUCUGUUGCCUGGUGACCGCCUUCUAC UGGUGCCUGCGUAAGCGAAGGAAGCCCGGAUCCCACACCCACA GCGCCAGCGAAGACAACACCACCAAUAACGUCCGAGAGCAGCU GAACCAGAUCAAGAACCCCAUAGAGAAACACGGGGCCAACACC GUGCCUAUCAAGGACUACGAGAACAAAAAUAGCAAAAUGAGC AAGAUUAGGACCCACAACUCCGAGGUGGAGGAGGACGACAUG GACAAGCAUCAGCAGAAGGCCCGCUUCGCCAAGCAACCCGCCU ACACCCUGGUGGACCGAGAGGAAAAGCCCCCCAACGGACCCC CACGAAGCACCCCAACUGGACCAAUAAGCAGGAUAACAGGGA CCUCGAGAGCGCCCAGUCCCUGAAUCGCAUGGAGUACAUCGUG |
| 107 | JAG1-CO21 | AUGAGGAGCCCCCGCACCAGGGGGCGUAGCGGCCGCCCCCUGA GCCUGCUGCUGGCUCUGCUGUGUGCCCUGCGAGCCAAAGUGU GCGGGGCCUCCGGCCAGUUCGAGCUGGAGAUCCUGAGCAUGC AGAACGUGAACGGCGAGCUCCAGAACGGCAACUGCUGCGGCG GCGCCCGCAACCCCGGCGACAGGAAGUGCACUCGGGACGAGUG CGACACCUAUUUCAAGGUCUGCCUGAAGGAGUACCAAAGCCG UGUGACCGCCGGCGGGCCGUGCAGCUUCGGAAGCGGCUCCACC CCGGUCAUCGGGGGGAACACCUUUAACCUGAAGGCCAGCCGG GGUAACGACAGGAACCGAAUCGUACUGCCCUUCAGCUUCGCCU GGCCCCGGAGCUACACCCUGCUGGUCGAGGCAUGGGACUCCAG CAACGAUACCGUGCAGCCCGACAGCAUCAUCGAGAAAGCCAGC CACAGCGGGAUGAUUAAUCCCAGCAGACAGUGGCAGACCCUG AAGCAGAACACCGGCGUGGCCCACUUCGAGUACCAAAUCCGGG UGACCUGCGACGAUUAUUACUACGGGUUUGGCUGUAAUAAAU UCUGCCGGCCCCGGGAUGACUUUUUCGGCCAUUACGCCUGCGA UCAGAACGGUAACAAGACCUGCAUGGAGGGCUGGAUGGGACC GGAGUGUAACAGGGCUAUCUGCCGACAGGGUUGUAGCCCCAA GCACGGAAGCUGCAAGCUGCCCGGCGACUGCCGGUGUCAGUAC GGCUGGCAGGGCCUGUACUGCGAUAAGUGCAUCCCCCACCCCG GCUGCGUUCACGGCAUCUGCAACGAGCCCUGGCAGUGCCUGUG UGAAACCAACUGGGGUGGACAGCUGUGCGACAAGGAUCUGAA CUAUUGCGGCACCCACCAGCCCUGCCUGAACGGCGGAACCUGC AGCAACACCGGCCCCGAUAAGUACCAGUGCAGCUGCCCCGAAG GCUACUCCGGCCCCAACUGCGAGAUCGCCGAGCACGCCUGCCU GAGCGACCCGUGCCACAACAGGGGGAGCUGCAAAGAGACCAG CCUGGGUUUCGAGUGCGAGUGCAGCCCCGGCUGGACCGGGCCC ACUUGCUCCACCAACAUUGACGACUGUAGCCCGAACAAUUGCA GCCACGGCGGCACCUGCCAGGACCUGGUGAAUGGCUUCAAGU GCGUGUGUCCCCCCCAGUGGACCGGGAAGACCUGCCAGCUGGA CGCCAACGAGUGCGAGGCCAAGCCCUGUGUGAACGCCAAGUCC UGCAAGAACCUGAUCGCCUCCUACUACUGUGACUGUCUCCCCG GGUGGAUGGGCCAGAACUGCGACAUCAACAUCAACGAUUGCC UCGGCCAGUGCCAGAACGACGCCAGCUGUAGGGACCUCGUGA ACGGCUACCGGUGCAUCUGCCCGCCCGGGUACGCCGGAGACCA CUGCGAGAGGGACAUUGACGAGUGCGCCUCGAACCCCUGCCUG AACGGCGGCCACUGUCAGAACGAGAUCAAUAGGUUCCAGUGU CUGUGUCCCACCGGCUUCUCCGGCAACCUGUGUCAGCUGGACA UCGACUACUGUGAGCCCAAUCCCUGCCAGAAUGGCGCCCAGUG CUAUAACCGGGCCUCCGACUACUUUUGCAAGUGCCCCGAAGAU UACGAGGGCAAGAACUGCAGCCAUCUGAAGGACCACUGCAGG ACGACUCCCUGCGAGGUGAUCGACAGCUGUACUGUCGCCAUG GCCAGCAACGACACCCCCGAGGGGGUCCGCUAUAUCAGCAGCA ACGUGUGCGGGCCCCAUGGGAAAUGCAAAUCCCAGUCAGGGG GCAAGUUUACCUGCGACUGUAACAAAGGCUUCACCGGCACCU ACUGCCACGAAAACAUCAACGACUGCGAAUCGAACCCCUGCCG GAACGGCGGGACCUGCAUCGAUGGAGUGAACAGCUACAAGUG CAUCUGCAGCGACGGGUGGGAGGGCGCGUACUGCGAAACCAA UAUCAAUGACUGCAGCCAGAACCCCUGCCAUAACGGAGGCACC UGCAGGGACCUGGUGAACGACUUCUACUGCGAUUGCAAGAAC GGCUGGAAGGGGAAGACCUGCCAUAGCAGGGACAGCCAGUGU |

TABLE 2-continued

Sequence optimized sequences for human JAG1

| SEQ ID NO | NAME | SEQUENCE |
|---|---|---|
| | | GACGAGGCCACCUGCAACAACGGCGGCACAUGUUACGAUGAG GGCGACGCCUUCAAAUGCAUGUGCCCCGGCGGCUGGGAGGGC ACCACAUGCAACAUCGCCCGGAACAGCAGCUGCCUCCCCAACC CCUGCCAUAAUGGCGGUACCUGCGUGGUGAACGGCGAGAGUU UCACCUGCGUGUGCAAGGAGGGCUGGGAGGGCCCCAUCUGCG CGCAGAACACCAAUGACUGCUCGCCCCACCCCUGCUACAACAG CGGCACCUGCGUGGACGGUGACAACUGGUACCGUUGCGAGUG CGCCCCAGGCUUCGCCGGCCCGGACUGCAGGAUCAACAUCAAC GAGUGCCAAAGCUCCCCUUGCGCCUUUGGCGCAACCUGUGUGG ACGAGAUCAAUGGGUACAGGUGCGUGUGCCCCCCGGCCAUUC CGGGGCCAAGUGCCAAGAGGUGUCCGGCCGGCCCUGCAUUACC AUGGGCAGCGUUAUCCCCGACGGCGCCAAGUGGGACGACGAC UGCAAUACCUGCCAGUGCCUCAACGGCAGGAUCGCCUGCAGCA AGGUGUGGUGCGGACCCAGGCCGUGCCUGCUGCAUAAGGGCC ACAGCGAGUGCCCGAGCGGUCAGUCCUGCAUCCCCAUCCUCGA CGACCAGUGUUUCGUGCACCCCUGCACGGGCGUGGGUGAGUG CCGAUCCUCCAGCCUGCAGCCCGUCAAAACCAAGUGCACCUCC GACAGCUACUACCAGGACAACUGCGCCAACAUAACCUUCACGU UUAACAAGGAGAUGAUGAGCCCCGGCCUGACCACCGAGCACA UCUGCAGCGAGCUGAGGAACCUGAACAUCCUGAAGAACGUGU CCGCCGAGUACAGCAUCUACAUCGCCUGUGAGCCCAGCCCCUC CGCCAACAACGAGAUCCAUGUUGCCAUCUCGGCCGAAGAUAU UAGGGACGACGGCAACCCCAUCAAGGAGAUCACCGACAAGAU CAUAGACCUGGUGAGCAAGCGGGACGGCAAUUCCAGCCUGAU CGCCGCCGUGGCCGAGGUGAGAGUGCAGAGGAGGCCCCUGAA GAACCGGACCGAUUUCCUGGUGCCCCUGCUGAGCAGCGUGCUG ACCGUGGCCUGGAUCUGCUGCCUGGUGACCGCAUUUUACUGG UGUCUGAGGAAGCGGAGGAAACCCGGCAGCCACACCCACAGCG CAAGCGAGGAUAACACCACGAAUAACGUGCGCGAGCAGCUGA ACCAAAUCAAGAACCCCAUCGAGAAGCACGGGGCCAACACCGU GCCCAUCAAGGACUACGAGAAUAAGAACUCGAAGAUGAGCAA GAUCAGGACGCACAACUCCGAGGUGGAGGAGGACGACAUGGA UAAGCACCAGCAGAAAGCCCGGUUCGCCAAGCAGCCCGCCUAC ACCCUGGUUGACCGCGAGGAGAAACCCCCCAACGGCACCCCCA CCAAGCACCCCAACUGGACCAACAAGCAGGACAACCGAGACCU GGAGAGCGCCCAGAGCCUGAACAGGAUGGAGUAUAUCGUG |
| 108 | JAG1-CO22 | AUGAGGUCCCCCAGGACCAGGGGCAGGAGCGGGAGGCCCCUG UCCCUUCUGCUGGCGCUGCUGUGCGCCCUGCGCGCCAAGGUGU GCGGGGCAAGCGGCCAGUUCGAGCUCGAAAUACUCAGCAUGC AAAACGUCAACGGCGAGCUGCAGAACGGCAACUGUUGCGGUG GCGCCAGGAACCCCGGGGAUCGCAAGUGCACCAGGGACGAGU GUGAUACCUACUUCAAAGUGUGUCUGAAGGAGUACCAGAGCC GGGUGACCGCCGGGGGCCCCUGUUCCUUCGGCAGCGGGAGCAC CCCCGUCAUCGGCGGGAAUACGUUUAACCUGAAGGCCUCCAGG GGCAACGAUAGGAACCGGAUCGUGCUCCCUUUCAGCUUCGCCU GGCCCAGGUCCUACACCCUGCUGGUGGAGGCCUGGGACUCCAG CAAUGACACUGUCCAGCCUGACAGUAUCAUAGAGAAAGCCUC CCACUCCGGCAUGAUCAACCCCAGUCGCCAGUGGCAGACCCUG AAGCAGAACACCGGCGUGGCCCACUUCGAGUACCAGAUCCGGG UGACCUGCGACGACUAUUACUACGGCUUCGGAUGCAAUAAGU UCUGUAGGCCCCGCGACGAUUUCUUCGGCCAUUAUGCCUGCGA CCAGAACGGCAACAAGACCUGCAUGGAGGGCUGGAUGGGGCC CGAGUGCAACAGGGCCAUCUGCAGGCAGGGGUGCUCCCCCAAA CACGGGAGCUGCAAACUGCCGGGGGACUGCAGGUGCCAAUAC GGCUGGCAGGGCCUGUACUGCGACAAGUGCAUCCCGCACCCCG GGUGCGUGCACGGCAUUUGCAACGAACCCUGGCAGUGCCUCU GCGAAACCAAUUGGGGAGGCCAGCUGUGCGACAAGGAUCUGA ACUACUGCGGCACGCACCAGCCCUGCCUCAACGGGGGACCUG UAGCAACACGGGCCCCGACAAGUACCAGUGCUCCUGCCCGGAG GGAUACUCUGGCCCCAACUGCGAGAUCGCCGAGCACGCCUGCC UCUCCGAUCCGUGCCACAAUAGGGGCAGCUGCAAGGAAACGU CCCUGGGCUUCGAAUGCGAAUGCAGUCCCGGAUGGACCGGCCC CACCUGCAGCACCAACAUCGACGACUGCAGCCCCAACAACUGC AGCCACGGCGGCACCUGCCAAGAUCUCGUGAACGGCUUCAAGU GCGUGUGCCCCCCCAGUGGACCGGGAAAACCUGCCAACUCGA CGCCAAUGAGUGUGAGGCCAAGCCCUGCGUGAACGCCAAGUC GUGCAAAAACCUGAUCGCCAGCUACUACUGCGACUGCCUGCCC GGCUGGAUGGGGCAGAACUGCGACAUCAACAUCAACGACUGC CUGGGGCAGUGCCAGAAUGACGCUAGCUGCCGAGACCUGGUC AAUGGAUACCGGUGCAUAUGCCCCCCGGGCUACGCCGGCGACC AUUGCGAGCGGGACAUCGACGAGUGCGCCAGCAACCCAUGCCU GAACGGCGGGCACUGCCAGAACGAAAUAAACAGGUUCCAGUG UCUGUGCCCGACGGGCUUUAGCGGCAACCUCUGCCAGUUGGA UAUCGACUAUUGCGAGCCUAACCCUUGCCAGAACGGCGCCCAG |

TABLE 2-continued

Sequence optimized sequences for human JAG1

| SEQ ID NO | NAME | SEQUENCE |
|---|---|---|
| | | UGCUAUAACCGCGCAAGCGAUUAUUUCUGCAAAUGCCCCGAG |
| | | GACUACGAGGGCAAGAAUUGCAGCCAUCUGAAAGACCACUGU |
| | | CGGACGACCCCCUGCGAGGUGAUCGACAGCUGCACCGUGGCCA |
| | | UGGCCUCCAACGACACCCCCGAAGGGGUGCGCUAUAUCUCCAG |
| | | CAACGUGUGCGGCCCCCACGGCAAGUGCAAGAGCCAGUCAGGG |
| | | GGCAAAUUCACCUGCGACUGCAACAAGGGCUUCACCGGGACCU |
| | | ACUGCCACGAGAACAUCAACGACUGCGAGAGCAACCCCUGCCG |
| | | GAACGGCGGCACCUGCAUCGAUGGGGUGAACUCCUAUAAGUG |
| | | CAUCUGUAGCGAUGGAUGGGAGGGGGCCUACUGCGAAACCAA |
| | | CAUCAACGACUGCAGCCAGAACCCCUGCCACAACGGGGGCACC |
| | | UGCAGGGACCUCGUGAACGACUUCUACUGCGACUGCAAGAAC |
| | | GGCUGGAAGGGCAAGACAUGCCACUCCCGGGACUCACAAUGC |
| | | GACGAAGCGACCUGCAACAAUGGCGGCACCUGUUACGAUGAG |
| | | GGGGAUGCCUUUAAGUGCAUGUGCCCCGGUGGCUGGGAGGGC |
| | | ACCACCUGCAAUAUCGCCAGGAAUUCCUCCUGCCUGCCCAACC |
| | | CCUGCCAUAAUGGCGGGACCUGCGUCGUGAACGGCGAGAGCU |
| | | UCACCUGCGUGUGCAAAGAGGGGUGGGAAGGACCCAUCUGCG |
| | | CCCAAAAUACGAACGACUGCAGCCCCCACCCCUGUUACAACAG |
| | | CGGCACGUGCGUGGAUGGGGACAACUGGUACCGCUGCGAGUG |
| | | CGCCCCCGGCUUUGCAGGCCCGGACUGUCGGAUCAACAUCAAC |
| | | GAGUGCCAGAGCAGCCCCUGCGCCUUCGGAGCCACGUGCGUGG |
| | | ACGAGAUCAAUGGCUACAGAUGCGUGUGCCCCCCGGGACACA |
| | | GCGGCGCCAAGUGCCAGGAAGUGUCCGGCCGUCCCUGCAUCAC |
| | | CAUGGGUAGCGUCAUCCCCGACGGCGCCAAGUGGGACGAUGA |
| | | CUGCAACACGUGUCAGUGUCUGAACGGCCGAAUCGCCUGCUCC |
| | | AAGGUGUGGUGCGGCCCCCGGCCCUGCCUGCUGCACAAGGGCC |
| | | ACAGCGAGUGCCCCAGCGGCCAGUCGUGUAUCCCCAUCCUCGA |
| | | CGACCAAUGCUUCGUGCACCCCUGCACCGGCGUGGGCGAGUGC |
| | | CGCAGCUCGAGCCUGCAGCCCGUGAAGACCAAGUGCACCAGCG |
| | | AUAGCUACUACCAGGACAAUUGCGCCAACAUCACCUUCACCUU |
| | | UAACAAGGAGAUGAUGAGCCCCGGCCUGACGACCGAACACAU |
| | | CUGCUCCGAGCUGAGGAACCUGAACAUCCUGAAGAAUGUCAG |
| | | CGCUGAGUACUCCAUCUACAUCGCCUGUGAGCCCAGCCCAAGC |
| | | GCCAACAAUGAGAUCCACGUCGCGAUCUCCGCCGAGGACAUCC |
| | | GCGACGAUGGCAACCCCAUCAAGGAGAUCACCGACAAGAUCA |
| | | UCGACCUGGUGAGCAAGAGGGACGGCAACAGCUCCCUGAUCG |
| | | CCGCGGUGGCCGAGGUGAGGGUCCAAAGGAGGCCCCUGAAGA |
| | | ACAGGACCGACUUCCUGGUGCCCCUGCUGUCGAGCGUGCUGAC |
| | | CGUGGCCUGGAUCUGCUGCCUGGUGACCGCGUUCUACUGGUG |
| | | CCUGCGUAAGAGGAGGAAGCCCGGCAGCCACACCCAUAGCGCG |
| | | UCCGAGGAUAACACCACCAAUAACGUGAGGGAGCAGCUCAAC |
| | | CAGAUCAAGAACCCAAUCGAGAAGCACGGUGCCAACACUGUG |
| | | CCCAUCAAGGACUAUGAGAACAAGAACAGCAAGAUGAGUAAG |
| | | AUCAGGACACACAACUCCGAGGUGGAAGAAGACGACAUGGAC |
| | | AAGCACCAGCAGAAGGCCCGGUUCGCCAAGCAGCCCGCCUACA |
| | | CCCUGGUGGACAGGGAAGAGAAACCCCCCAACGGUACACCCAC |
| | | GAAACACCCCAACUGGACCAAUAAGCAGGACAACAGGGACCU |
| | | GGAGUCCGCCCAGAGUCUGAACAGGAUGGAGUACAUCGUG |
| 109 | JAG1-CO23 | AUGCGGUCCCCCCGGACCAGGGGUAGGAGCGGCCGCCCACUGU |
| | | CCCUGCUGCUGGCCCUGCUGUGUGCCCUGAGGGCCAAGGUGUG |
| | | CGGCGCCUCCGGACAAUUCGAGCUGGAGAUUCUCUCGAUGCA |
| | | GAACGUGAACGGCGAACUGCAGAACGGAAAUUGCUGUGGCGG |
| | | CGCCAGGAAUCCCGGCGAUAGAAAGUGCACCAGGGACGAGUG |
| | | UGACACGUACUUCAAGGUGUGCCUGAAGGAGUACCAGAGCCG |
| | | CGUGACCGCCGGCGGGCCCUGCUCCUUCGGGUCAGGCAGCACC |
| | | CCCGUGAUCGGCGGGAACACCUUCAACCUCAAGGCCUCCAGGG |
| | | GCAACGACAGGAAUAGGAUCGUGCUCCCCUUCAGCUUCGCCUG |
| | | GCCCAGGUCCUACACCCUGCUGGUAGAGGCCUGGGACUCCAGC |
| | | AACGACACCGUGCAGCCCGAUAGCAUCAUCGAGAAGGCUAGCC |
| | | ACAGCGGAAUGAUCAACCCCAGCCGCCAGUGGCAGACCCUGAA |
| | | ACAGAACACCGGCGUAGCCCACUUUGAGUACCAGAUCAGGGU |
| | | GACCUGCGACGACUAUUACUAUGGCUUCGGUUGCAACAAGUU |
| | | CUGCCGGCCUCGCGACGACUUCUUCGGACACUACGCCUGUGAU |
| | | CAGAACGGGAACAAGACCUGUAUGGAGGGUUGGAUGGGCCCC |
| | | GAAUGCAACAGGGCCAUCUGCAGGCAGGGCUGCUCCCCCAAGC |
| | | ACGGGAGCUGCAAGCUGCCCGGCGACUGCCGGUGCCAGUACGG |
| | | CUGGCAGGGUCUGUACUGCGACAAGUGCAUCCCCCAUCCUGGC |
| | | UGCGUGCACGGCAUAUGCAACGAGCCCUGGCAGUGCCUGUGC |
| | | GAGACCAAUUGGGGCGGCCAGCUGUGCGACAAGGACCUGAAU |
| | | UACUGUGGCACCCACCAGCCCUGCCUCAACGGCGGCACCUGCU |
| | | CCAACACCGGCCCCGACAAGUACCAGUGCAGCUGCCCCGAAGG |
| | | CUACAGCGGCCCGAAUUGCGAGAUCGCCGAACACGCCUGCCUC |
| | | AGCGACCCCUGCCACAACCGGGGCAGCUGUAAGGAGACCUCCC |
| | | UGGGCUUUGAAUGCGAAUGUAGCCCCGGUUGGACCGGACCCA |

TABLE 2-continued

Sequence optimized sequences for human JAG1

| SEQ ID NO | NAME | SEQUENCE |
|---|---|---|
| | | CCUGUUCCACCAACAUCGACGACUGCAGCCCCAAUAACUGCAG CCACGGUGGCACGUGCCAGGACCUCGUCAACGGCUUUAAGUGC GUGUGCCCCCCCAGUGGACCGGGAAGACCUGCCAGCUGGACG CCAACGAGUGCGAGGCCAAGCCCUGCGUGAACGCCAAGAGCUG CAAGAACCUCAUCGCCAGCUACUAUUGUGACUGCCUGCCCGGG UGGAUGGGCCAGAACUGUGACAUAAACAUCAACGAUUGUCUG GGCCAGUGCCAGAACGAUGCCAGCUGUCGGGACCUGGUGAAC GGCUACCGGUGCAUCUGUCCCCCCGGCUACGCCGGAGAUCACU GUGAGCGAGACAUCGACGAGUGCGCCUCCAACCCCUGCCUCAA CGGCGGGCACUGUCAGAAUGAGAUCAACAGGUUCCAGUGCCU GUGCCCGACGGGAUUCUCCGGUAACCUGUGCCAGCUCGACAUC GACUACUGUGAGCCCAACCCCUGUCAAAAUGGCGCCCAAUGCU ACAACCGGGCCUCCGACUACUUCUGUAAGUGCCCCGAGGAUUA CGAGGGUAAGAACUGUAGCCAUCUGAAGGACCACUGCAGGAC UACCCCGUGCGAGGUGAUCGACUCCUGCACCGUCGCCAUGGCC UCCAACGACACCCCCGAGGGCGUGCGGUACAUCAGCAGCAACG UGUGUGGGCCGCACGGCAAGUGCAAGAGCCAGAGCGGGGGCA AGUUCACCUGUGAUUGCAACAAGGGCUUCACCGGGACGUAUU GCCACGAGAACAUCAACGACUGCGAGAGCAACCCCUGCAGGAA CGGGGGGACCUGCAUAGACGGCGUGAACAGCUACAAAUGCAU CUGCAGCGAUGGGUGGGAGGGCGCCUACUGUGAGACCAACAU UAACGACUGCAGCCAGAACCCCUGCCACAACGGGGGUACCUGU CGCGACCUGGUGAACGACUUCUACUGUGACUGCAAGAACGGC UGGAAGGGCAAGACCUGUCAUUCCCGCGACAGCCAGUGCGAC GAAGCCACCUGCAACAACGGCGGCACCUGCUACGACGAGGGCG AUGCCUUCAAGUGCAUGUGCCCGGGCGGCUGGGAGGGGACCA CCUGUAAUAUCGCCAGGAAUUCCAGCUGCCUCCCCAAUCCGUG CCAUAAUGGCGGCACCUGCGUGGUCAACGGCGAAAGCUUUAC CUGCGUCUGUAAGGAAGGCUGGGAAGGUCCGAUCUGUGCCCA GAACACCAACGACUGUAGCCCCCACCCCUGCUACAAUAGCGGA ACGUGCGUGGACGGCGACAACUGGUAUCGGUGCGAGUGCGCC CCCGGCUUUGCGGGGCCGGACUGCCGGAUCAAUAUCAACGAG UGCCAGAGCAGCCCCUGCGCCUUCGGCGCCACCUGCGUGGACG AGAUCAACGGCUACAGGUGCGUGUGUCCCCCCGGCCACUCCGG CGCCAAGUGCCAGGAGGUGAGCGGUAGGCCCUGCAUCACCAU GGGCAGCGUGAUCCCCGACGGGGCCAAGUGGGACGAUGACUG UAACACCUGCCAGUGCCUGAACGGGAGGAUCGCCUGUUCCAA AGUGUGGUGCGGCCCGCGUCCCUGCCUACUCCACAAGGGGCAU UCCGAGUGUCCCAGCGGACAGAGCUGUAUCCCCAUCCUGGACG ACCAAUGCUUCGUGCACCCCUGCACCGGCGUGGGUGAGUGCAG GUCCAGCAGCCUGCAGCCCGUGAAGACAAAGUGCACCAGUGA UUCCUACUACCAGGAUAACUGCGCCAACAUCACCUUCACCUUC AAUAAGGAGAUGAUGAGCCCGGGCCUGACCACGGAGCACAUC UGCAGCGAGCUGCGCAACCUGAACAUCCUGAAGAACGUCUCCG CCGAGUACAGCAUAUACAUCGCCUGCGAGCCCAGCCCCUCCGC CAAUAACGAGAUCCACGUGGCCAUCUCCGCGGAGGACAUCAG GGACGAUGGCAACCCCAUCAAGGAGAUCACCGACAAGAUUAU CGACCUGGUCAGCAAAAGGGACGGCAACUCCAGCCUCAUCGCC GCCGUGGCCGAGGUCAGGGUACAGCGCAGGCCGCUGAAAAAC CGGACCGACUUCCUGGUGCCCCUGCUUUCCUCCGUGCUCACGG UGGCCUGGAUUUGCUGCCUGGUAACCGCGUUUUACUGGUGCC UGAGGAAGAGGAGGAAGCCCGGCAGCCAUACCCACAGCGCCA GCGAGGACAACACAACCAACAACGUGAGGGAGCAGCUCAACC AGAUAAAGAACCCCAUCGAGAAACACGGCGCCAACACGGUGCC CAUCAAGGACUAUGAGAACAAGAACAGCAAGAUGAGCAAGAU CCGCACCCACAACAGCGAGGUUGAGGAAGACGACAUGGACAA GCACCAGCAGAAGGCCAGGUUCGCCAAGCAGCCCGCCUACACC CUGGUGGAUCGUGAGGAGAAACCGCCCAACGGGACCCCCACCA AGCAUCCCAAUUGGACCAACAAACAGGACAACAGGGACCUGG AGUCCGCCCAAAGCCUGAACCGGAUGGAGUACAUCGUC |
| 110 | JAG1-CO24 | AUGAGGUCCCCCAGAACUCGGGGGAGGUCCGGCAGGCCGCUCA GCCUCCUGCUCGCCCUGCUGUGCGCCCUGAGGGCCAAGGUGUG CGGCGCCUCCGGCCAGUUCGAGCUGGAGAUUCUGAGCAUGCA GAACGUGAACGGCGAACUGCAGAACGGAAACUGCUGCGGUGG GGCCAGGAACCCCGGCGACCGGAAGUGCACCAGGGAUGAAUG CGACACCUACUUCAAGGUCUGCCUCAAGGAGUACCAGAGCAG GGUGACCGCCGGGGGCCCGUGUAGCUUCGGCUCCGGCAGCACC CCCGUGAUAGGCGGCAACACGUUCAACCUUAAAGCCUCCAGGG GCAACGACCGCAACAGGAUCGUGCUGCCCUUCUCCUUCGCGUG GCCCCGCAGCUACACCCUGCUGGUGGAGGCGUGGGAUAGCAGC AACGACACCGUCCAGCCCGAUUCAAUCAUCGAAAAGGCCAGCC ACAGCGGCAUGAUCAACCCCUCCAGGCAGUGGCAGACCCUGAA GCAAAACACCGGCGUGGCCCACUUCGAGUACCAAAUCAGGGU UACCUGCGACGACUACUACUAUGGGUUCGGCUGCAAUAAGUU |

TABLE 2-continued

Sequence optimized sequences for human JAG1

| SEQ ID NO | NAME | SEQUENCE |
|---|---|---|
| | | CUGUCGGCCGCGGGACGACUUUUUCGGGCAUUAUGCCUGCGA CCAGAAUGGCAAUAAGACCUGCAUGGAGGGCUGGAUGGGACC CGAGUGCAACCGCGCCAUCUGCAGGCAGGGCUGCUCCCCCAAG CACGGCAGCUGCAAGCUGCCCGGCGACUGCAGGUGCCAGUACG GGUGGCAGGGCCUCUACUGCGACAAGUGCAUCCCCCACCCCGG CUGCGUGCAUGGGAUAUGCAACGAGCCGUGGCAGUGCCUGUG CGAAACCAACUGGGGGGGCCAGCUGUGCGAUAAGGACCUCAA CUACUGCGGCACCCACCAGCCCUGCCUCAACGGCGGCACCUGC UCCAAUACCGGGCCCGAUAAAUACCAGUGCUCCUGCCCUGAGG GCUACAGCGGGCCCAACUGUGAGAUCGCCGAGCAUGCCUGCCU CUCGGACCCCUGCCAUAACAGGGGCAGCUGUAAGGAAACCAGC CUGGGCUUCGAGUGCGAGUGCAGCCCCGGGUGGACCGGGCCA ACCUGCUCCACCAACAUCGACGACUGUAGCCCGAACAACUGCU CCCACGGCGGGACCUGCCAGGACCUGGUGAAUGGCUUCAAGU GCGUAUGUCCCCCACAGUGGACCGGCAAGACCUGUCAACUCGA CGCCAACGAGUGCGAGGCCAAACCCUGCGUGAACGCCAAGUCC UGCAAGAACCUGAUCGCCUCCUACUACUGCGACUGUCUGCCCG GCUGGAUGGGCCAGAACUGCGAUAUCAACAUCAACGAUUGCC UCGGCCAGUGUCAGAACGACGCCUCCUGCCGGGACCUGGUGAA CGGCUACCGGUGCAUUUGCCCCCCGGGCUACGCCGGCGAUCAC UGCGAGCGCGACAUCGACGAGUGCGCAUCCAACCCCUGUCUGA ACGGGGGGCACUGUCAGAACGAGAUCAAUAGGUUCCAGUGCC UGUGCCCCACCGGCUUCUCCGGGAAUCUGUGCCAGCUGGACAU CGAUUACUGCGAGCCCAACCCCUGCCAGAACGGCGCCCAGUGU UACAACAGGGCCAGCGAUUACUUCUGCAAGUGUCCCGAAGAC UAUGAGGGCAAGAAUUGCAGCCAUCUGAAAGACCACUGCCGC ACCACCCCCUGUGAGGUGAUCGACUCGUGCACCGUGGCGAUGG CCAGCAAUGACACCCCGGAGGGCGUGCGGUACAUCAGCAGCAA CGUGUGUGGGCCCCACGGCAAGUGCAAGUCCCAGAGCGGGGG CAAGUUCACCUGCGACUGCAACAAAGGCUUUACAGGGACAUA UUGCCACGAAAACAUCAAUGACUGCGAGAGCAACCCCUGCCGC AAUGGCGGCACUUGCAUCGACGGCGUGAACAGCUACAAAUGU AUCUGCUCAGACGGGUGGGAAGGCGCGUAUUGCGAGACCAAC AUCAACGAUUGUAGCCAGAAUCCCUGCCAUAACGGUGGUACC UGCCGGGAUCUGGUGAACGACUUCUAUUGCGACUGCAAGAAC GGCUGGAAGGGCAAGACCUGCCAUUCGAGGGAUAGCCAGUGC GACGAGGCCACCUGCAACAACGGCGGCACCUGCUACGACGAGG GCGAUGCCUUCAAGUGCAUGUGCCCUGGCGGCUGGGAGGGCA CCACCUGCAACAUCGCCAGGAACAGCUCCUGCCUGCCCAACCC CUGCCACAACGGCGGGACCUGUGUCGUGAACGGGGAGAGCUU CACGUGCGUGUGCAAGGAGGGCUGGGAAGGGCCCAUCUGCGC CCAAAACACCAACGACUGCAGCCCCCAUCCCUGUUACAACUCC GGCACCUGCGUGGACGGCGACAACUGGUACCGAUGCGAGUGC GCCCCCGGCUUCGCCGGCCCCGACUGCCGGAUCAACAUCAACG AGUGCCAGAGCAGCCCCUGCGCGUUCGGCGCCACCUGCGUGGA UGAAAUCAACGGAUAUAGGUGCGUGUGCCCCCCGGCCACAGC GGGGCCAAGUGCCAGGAGGUCAGCGGGCGCCCCUGCAUCACCA UGGGCAGCGUGAUACCCGACGGCGCCAAGUGGGACGACGACU GCAACACCUGCCAGUGCCUGAACGGCAGGAUCGCCUGCUCCAA GGUGUGGUGCGGGCCGCGGCCGUGCCUGCUGCACAAGGGCCAC AGCGAGUGCCCCAGCGGCCAGUCCUGUAUCCCAAUCCUGGACG ACCAGUGCUUCGUGCAUCCCUGCACCGGCGUGGGCGAGUGCAG GUCCUCCUCCCUGCAGCCCGUGAAGACCAAAUGCACCAGCGAC UCGUACUACCAGGAUAACUGCGCCAACAUCACCUUCACCUUCA ACAAGGAAAUGAUGAGCCCCGGCCUGACCACCGAGCACAUCUG CAGCGAGCUCCGGAACCUGAACAUCCUGAAGAACGUGUCCGCC GAGUAUAGCAUCUACAUCGCGUGCGAACCAAGUCCGUCCGCCA ACAACGAGAUCCACGUGGCAAUCUCCGCCGAGGACAUCCGGGA CGACGGCAACCCCAUCAAGGAGAUAACCGACAAAAUCAUCGAC CUGGUGAGCAAAAGGGACGGCAAUUCUAGCCUGAUCGCCGCA GUGGCCGAAGUGAGGGUGCAGCGCAGGCCCCUCAAGAAUAGG ACCGACUUCCUGGUGCCGCUCCUCAGCAGCGUGCUGACCGUGG CCUGGAUCUGCUGCCUGGUGACCGCCUUUUACUGGUGCCUGA GGAAGCGUAGGAAGCCCGGAAGCCACACACACUCCGCCAGCGA GGACAACACCACCAACAACGUGCGGGAGCAACUGAACCAGAUC AAGAACCCCAUCGAGAAGCACGGAGCCAACACCGUCCCUAUCA AAGACUACGAGAACAAGAACAGCAAGAUGAGCAAGAUCAGGA CCCACAACAGCGAGGUUGAGGAAGACGACAUGGACAAGCACC AGCAGAAAGCCAGGUUCGCGAAGCAGCCCGCCUACACCCUGGU GGACCGGGAGGAAAAGCCCCCCAACGGCACCCCCACCAAGCAC CCGAACUGGACCAACAAGCAGGACAACAGGGACCUGGAGAGC GCCCAGAGCCUGAACCGGAUGGAGUACAUCGUC |

TABLE 2-continued

Sequence optimized sequences for human JAG1

| SEQ ID NO | NAME | SEQUENCE |
|---|---|---|
| 111 | JAG1-CO25 | AUGCGCAGCCCCCGGACCAGGGGAAGGUCCGGCAGGCCCCUGU<br>CCCUGCUGCUGGCGCUGCUCUGCGCCCUGCGAGCCAAAGUGUG<br>UGGUGCCUCCGGGCAGUUUGAGCUGGAGAUCCUCAGCAUGCA<br>GAACGUGAACGGGGAGCUGCAGAAUGGGAACUGCUGCGGCGG<br>CGCCAGGAAUCCCGGGGACAGGAAGUGCACCCGAGAUGAGUG<br>CGACACCUAUUUCAAGGUGUGCCUGAAGGAGUACCAGAGCCG<br>UGUGACGGCCGGCGGCCCCUGCAGCUUUGGCAGCGGCAGCACC<br>CCCGUGAUCGGCGGAAACACAUUCAACCUGAAGGCCAGCAGG<br>GGCAACGACAGGAACAGGAUCGUGCUGCCCUUCAGCUUCGCCU<br>GGCCCAGGUCCUACACCCUGCUGGUGGAGGCCUGGGAUAGCA<br>GCAAUGACACCGUGCAGCCCGACUCCAUCAUCGAGAAGGCCAG<br>UCACUCUGGAAUGAUCAACCCGAGCAGGCAGUGGCAGACCCU<br>GAAGCAGAACACCGGCGUGGCCCACUUCGAGUACCAGAUCAG<br>GGUGACCUGUGACGAUUACUACUACGGUUUUGGCUGCAACAA<br>GUUCUGUAGGCCCCGCGACGACUUCUUUGGUCAUUACGCCUGC<br>GAUCAGAACGGCAAUAAGACCUGCAUGGAAGGCUGGAUGGGC<br>CCCGAAUGCAACAGGGCCAUUUGCAGGCAGGGGUGCAGCCCG<br>AAGCACGGCAGCUGCAAGCUGCCCGGCGACUGCAGGUGUCAG<br>UACGGCUGGCAGGGCCUGUACUGCGACAAAUGCAUCCCCCACC<br>CUGGGUGCGUGCACGGCAUCUGUAACGAGCCCUGGCAGUGCC<br>UGUGUGAGACCAACUGGGGUGGGCAACUGUGCGAUAAGGACC<br>UGAACUACUGCGGAACCCACCAGCCCUGCCUGAACGGCGGCAC<br>AUGCAGCAACACCGGGCCCGACAAGUACCAGUGCAGCUGCCCC<br>GAAGGGUAUAGCGGGCCCAAUUGCGAAAUCGCCGAGCACGCC<br>UGCCUGAGCGAUCCCUGUCAUAAUCGCGGAUCCUGCAAGGAG<br>ACCAGCCUCGGCUUUGAGUGCGAAUGCUCCCCCGGCUGGACCG<br>GUCCCACGUGCAGCACGAACAUCGACGACUGUUCCCCGAACAA<br>CUGCUCCCACGGCGGCACCUGCCAGGAUCUGGUGAAUGGAUUC<br>AAAUGCGUGUGCCCCCCCCAAUGGACCGGGAAGACCUGCCAAC<br>UGGACGCCAACGAGUGCGAAGCCAAGCCCUGUGUGAACGCCA<br>AGAGCUGCAAAAACCUCAUCGCUAGCUACUACUGCGACUGCCU<br>GCCCGGCUGGAUGGGUCAGAACUGUGACAUCAACAUCAACGA<br>UUGUCUGGGCCAGUGCCAGAACGACGCCAGCUGCAGGGACCU<br>GGUGAAUGGGUACCGCUGCAUCUGCCCCCCCGGCUACGCCGGA<br>GAUCAUUGCGAGCGGGACAUCGACGAGUGCGCCAGCAACCCCU<br>GCCUGAACGGCGGUCACUGUCAGAAUGAGAUCAACCGCUUCC<br>AGUGCCUGUGCCCCACCGGCUUCAGCGGAAAUCUGUGCCAGCU<br>AGACAUUGAUUACUGCGAACCGAACCCUUGCCAGAACGGCGCC<br>CAGUGCUACAACAGGGCCAGCGACUACUUUUGCAAGUGCCCCG<br>AGGACUACGAGGGGAAGAAUUGCUCCCACCUAAAGGACCACU<br>GCCGGACCACCCCCUGCGAGGUGAUCGACAGCUGCACCGUCGC<br>GAUGGCCAGCAACGACACCCCCGAGGGCGUCAGGUACAUCUCC<br>AGCAACGUGUGCGGUCCCCAUGGCAAAUGCAAGAGCCAGAGC<br>GGGGGGAAGUUUACCUGCGACUGCAACAAGGGCUUCACCGGG<br>ACCUACUGCCAUGAGAACAUCAAUGACUGCGAGAGCAACCCCU<br>GCAGGAACGGCGGGACAUGCAUCGACGGGGUGAACUCCUAUA<br>AGUGCAUCUGCUCCGACGGGUGGGAAGGUGCCUAUUGCGAGA<br>CAAACAUCAACGACUGCAGCCAAAACCCCUGCCACAACGGGGG<br>CACCUGCAGGGAUCUGGUGAACGACUUCUACUGUGACUGCAA<br>GAACGGGUGGAAGGGAAAGACCUGUCACAGCCGGGACUCCCA<br>GUGCGACGAGGCCACAUGCAACAACGGCGGCACGUGCUACGAC<br>GAAGGAGACGCCUUUAAGUGCAUGUGCCCCGGCGGCUGGGAG<br>GGCACCACCUGCAAUAUCGCCCGCAACUCCUCCUGCCUGCCCA<br>ACCCGUGCCACAACGGGGGCACCUGCGUGGUGAACGGCGAGUC<br>CUUCACCUGCGUCUGCAAGGAGGGCUGGGAGGGUCCCAUCUG<br>UGCCCAGAAUACCAAUGACUGCAGCCCCCAUCCUUGUUACAAU<br>UCCGGCACCUGCGUGGAUGGCGACAACUGGUAUCGGUGUGAG<br>UGCGCCCCCGGCUUCGCGGGCCCCGACUGUAGGAUCAACAUCA<br>ACGAGUGCCAGAGCUCCCCAUGCGCCGUUGGGGCGACCUGUG<br>UCGACGAGAUCAAUGGGUACAGGUGCGUGUGUCCCCCGGGGC<br>ACUCCGGGGCCAAAUGCCAGGAGGUAAGCGGCCGGCCAUGCA<br>UUACCAUGGGCUCGGUGAUCCCAGACGGUGCCAAGUGGGACG<br>ACGACUGCAACACCUGCCAGUGCCUGAAUGGCAGGAUCGCCUG<br>CAGCAAGGUAUGGUGCGGACCCAGGCCGUGCCUGCUGCACAA<br>AGGACACUCCGAGUGUCCGAGCGGCCAGAGCUGCAUCCCCAUC<br>CUGGACGACCAGUGCUUCGUGCAUCCCUGCACUGGCGUCGGCG<br>AGUGCCGCAGCUCCAGCCUGCAGCCCGUGAAGACCAAGUGUAC<br>CAGCGACAGCUACUACCAGGACAAUUGUGCCAACAUCACCUUC<br>ACCUUCAACAAGGAGAUGAUGAGCCCUGGCCUGACCACCGAGC<br>AUAUCUGUAGCGAGCUGAGGAACUUGAACAUCCUGAAGAAUG<br>UGAGCGCCGAGUAUUCCAUUUACAUAGCCUGUGAGCCCAGCCC<br>AAGCGCUAACAAUGAGAUCCACGUGGCCAUCAGCGCCGAGGA<br>CAUCCGGGACGACGGCAACCCCAUCAAAGAAAUCACCGACAAG<br>AUCAUCGAUCUGGUAAGCAAGAGGGACGGGAACAGCAGCCUC |

TABLE 2-continued

Sequence optimized sequences for human JAG1

| SEQ ID NO | NAME | SEQUENCE |
|---|---|---|
| | | AUCGCCGCCGUGGCCGAGGUGCGCGUCCAGCGGAGGCCCCUCA<br>AAAACCGGACCGACUUUCUGGUGCCGCUGCUCAGCUCCGUGCU<br>GACCGUGGCCUGGAUAUGCUGCCUGGUGACCGCCUUCUACUG<br>GUGCCUGCGGAAGAGGAGGAAGCCCGGCAGCCACACGCACAGC<br>GCGAGCGAGGACAACACCACCAACAACGUGCGGGAGCAACUG<br>AACCAGAUCAAGAACCCCAUCGAGAAGCACGGCGCCAACACCG<br>UGCCCAUCAAGGACUACGAGAACAAGAAUAGCAAGAUGAGUA<br>AGAUUAGGACCCACAACAGCGAGGUGGAGGAGGACGACAUGG<br>ACAAGCACCAGCAGAAGGCCCGCUUCGCCAAGCAGCCCGCCUA<br>UACCCUGGUCGACAGGGAAGAGAAGCCGCCCAAUGGGACCCCC<br>ACCAAGCAUCCCAACUGGACCAACAAGCAGGACAACCGGGAUC<br>UGGAGAGCGCCCAAAGCCUGAAUAGGAUGGAGUACAUCGUG |

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding a JAG1 polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the present disclosure is greater than the uracil or thymine content in the reference wild-type sequence and still maintain beneficial effects, e.g., increased expression and/or reduced Toll-Like Receptor (TLR) response when compared to the reference wild-type sequence.

The uracil or thymine content of wild-type JAG1 is about 21%. In some embodiments, the uracil or thymine content of a uracil- or thymine-modified sequence encoding a JAG1 polypeptide is less than 16%. In some embodiments, the uracil or thymine content of a uracil- or thymine-modified sequence encoding a JAG1 polypeptide of the present disclosure is less than 19%, less that 18%, less than 17%, less than 16%, less than 15%, less than 14%, less than 13%, less than 12%, less than 11%, or less than 10%. In some embodiments, the uracil or thymine content is not less than 18%, 17%, 16%, 15%, 14%, or 13%. The uracil or thymine content of a sequence disclosed herein, i.e., its total uracil or thymine content is abbreviated herein as % $U_{TL}$ or % $T_{TL}$.

In some embodiments, the uracil or thymine content (% $U_{TL}$ or % $T_{TL}$) of a uracil- or thymine-modified sequence encoding a JAG1 polypeptide of the present disclosure is between 11% and 20%, between 11% and 19%, between 12% and 19%, between 12% and 18%, between 13% and 18%, between 13% and 17%, between 14% and 17%, or between 14% and 16%.

In some embodiments, the uracil or thymine content (% $U_{TL}$ or % $T_{TL}$) of a uracil- or thymine-modified sequence encoding a JAG1 polypeptide of the present disclosure is between 13% and 17%, between 14% and 17%, or between 14% and 16%.

In a particular embodiment, the uracil or thymine content (% $U_{TL}$, or % $T_{TL}$) of a uracil- or thymine modified sequence encoding a JAG1 polypeptide of the present disclosure is between about 14% and about 16%.

A uracil- or thymine-modified sequence encoding a JAG1 polypeptide of the present disclosure can also be described according to its uracil or thymine content relative to the uracil or thymine content in the corresponding wild-type nucleic acid sequence (% $U_{WT}$ or % $T_{WT}$), or according to its uracil or thymine content relative to the theoretical minimum uracil or thymine content of a nucleic acid encoding the wild-type protein sequence (% $U_{TM}$ or (% $T_{TM}$).

The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as 0% $U_{WT}$ or % $T_{WT}$r.

In some embodiments, the % $U_{WT}$ or % $T_{WT}$ of a uracil- or thymine-modified sequence encoding a JAG1 polypeptide of the present disclosure is above 50%, above 55%, above 60%, above 65%, above 70%, above 75%, above 80%, above 85%, above 90%, or above 95%.

In some embodiments, the % $U_{WT}$ or % $T_{WT}$ of a uracil- or thymine modified sequence encoding a JAG1 polypeptide of the present disclosure is between 58% and 84%, between 59% and 83%, between 60% and 82%, between 61% and 81%, between 60% and 80%, between 62% and 79%, between 63% and 78%, between 64% and 77%, between 65% and 76%, between 66% and 74%, between 67% and 74%, or between 68% and 74%.

In some embodiments, the % $U_{WT}$ or % $T_{WT}$ of a uracil- or thymine-modified sequence encoding a JAG1 polypeptide of the present disclosure is between 66% and 76%, between 67% and 75%, or between 68% and 74%.

In a particular embodiment, the % $U_{WT}$ or % $T_{T}$ of a uracil- or thymine-modified sequence encoding a JAG1 polypeptide of the present disclosure is between about 68% and about 74%.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$ For DNA it is recognized that thymine is present instead of uracil, and one would substitute T where U appears. Thus, all the disclosures related to, e.g., % $U_{TM}$, % $U_{WT}$, or % $U_{TL}$, with respect to RNA are equally applicable to % $T_{TM}$, % $T_{WT}$, or % $T_{TL}$ with respect to DNA.

In some embodiments, the % $U_{TM}$ of a uracil-modified sequence encoding a JAG1 polypeptide of the present disclosure is below 300%, below 295%, below 290%, below 285%, below 280%, below 275%, below 270%, below 265%, below 260%, below 255%, below 250%, below 245%, below 240%, below 235%, below 230%, below 225%, below 220%, below 215%, below 200%, below 195%, below 190%, below 185%, below 1800%, below 175%, below 1700%, below 165%, below 160%, below 155%, below 150%, below 145%, below 140%, below 139%, below 138%, below 137%, below 136%, below 135%, below 134%, below 133%, below 132%, below 131%, below 130%, below 129%, below 128%, below 127%, below 126%, below 125%, below 1240%, below 123%, below 122%, below 121%, below 120%, below 119%, below 118%, below 117%, below 116%, or below 115%.

In some embodiments, the % $U_{TM}$ of a uracil-modified sequence encoding a JAG1 polypeptide of the present disclosure is above 100%, above 101%, above 102%, above 103%, above 104%, above 105%, above 106%, above 107%, above 108%, above 109%, above 110%, above 111%, above 112%, above 113%, above 114%, above 115%, above 116%, above 117%, above 118%, above 119%, above 120%, above 121%, above 122%, above 123%, above 124%, above 125%, or above 126%, above 127%, above 128%, above 129, or above 130%, above 135%, above 130%, above 135%, above 140%, above 150%, above 160%, above 170%, above 180%, above 184%, above 190%, above 197%, or above 200%.

In some embodiments, the % $U_{TM}$ of a uracil-modified sequence encoding a JAG1 polypeptide of the present disclosure is between 189% and 191%, between 188% and 192%, between 187% and 193%, between 186% and 194%, between 185% and 195%, between 184% and 196%, between 183% and 197%, between 182% and 198%, between 181/a and 199%, or between 180% and 2000%.

In some embodiments, the % $U_{TM}$ of a uracil-modified sequence encoding a JAG1 polypeptide of the present disclosure is between about 184% and about 197%.

In some embodiments, a uracil-modified sequence encoding a JAG1 polypeptide of the present disclosure has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster.

Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide. For example, if a polypeptide, e.g., wild type JAG1, has 27, 28, 29 or 30 phenylalanines, the absolute minimum number of uracil pairs (UU) that a uracil-modified sequence encoding the polypeptide, e.g., wild type JAG1, can contain is 27, 28, 29 or 30, respectively.

Wild type JAG1 contains 81 uracil pairs (UU), and 24 uracil triplets (UUU). In some embodiments, a uracil-modified sequence encoding a JAG1 polypeptide of the present disclosure has a reduced number of uracil triplets (UUU) with respect to the wild-type nucleic acid sequence. In some embodiments, a uracil-modified sequence encoding a JAG1 polypeptide of the present disclosure contains 4, 3, 2, 1 or no uracil triplets (UUU).

In some embodiments, a uracil-modified sequence encoding a JAG1 polypeptide has a reduced number of uracil pairs (UU) with respect to the number of uracil pairs (UU) in the wild-type nucleic acid sequence. In some embodiments, a uracil-modified sequence encoding a JAG1 polypeptide of the present disclosure has a number of uracil pairs (UU) corresponding to the minimum possible number of uracil pairs (UU) in the wild-type nucleic acid sequence, e.g., 9 uracil pairs in the case of wild type JAG1.

In some embodiments, a uracil-modified sequence encoding a JAG1 polypeptide of the present disclosure has at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or 72 uracil pairs (UU) less than the number of uracil pairs (UU) in the wild-type nucleic acid sequence. In some embodiments, a uracil-modified sequence encoding a JAG1 polypeptide of the present disclosure has between 31 and 46 uracil pairs (UU).

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$.

In some embodiments, a uracil-modified sequence encoding a JAG1 polypeptide of the present disclosure has a % $U_{wt}$ less than 90%, less than 85%, less than 80%, less than 75%, less than 70%, less than 65%, less than 60%, less than 65%, less than 60%, less than 55%, less than 50%, less than 40%, less than 30%, or less than 20%.

In some embodiments, a uracil-modified sequence encoding a JAG1 polypeptide has a % $UU_{wt}$ between 33% and 62%. In a particular embodiment, a uracil-modified sequence encoding a JAG1 polypeptide of the present disclosure has a % $UU_{wt}$ between 38% and 57%.

In some embodiments, the polynucleotide of the present disclosure comprises a uracil-modified sequence encoding a JAG1 polypeptide disclosed herein. In some embodiments, the uracil-modified sequence encoding a JAG1 polypeptide comprises at least one chemically modified nucleobase, e.g., 5-methoxyuracil. In some embodiments, at least 95% of a nucleobase (e.g., uracil) in a uracil-modified sequence encoding a JAG1 polypeptide of the present disclosure are modified nucleobases. In some embodiments, at least 95% of uracil in a uracil-modified sequence encoding a JAG1 polypeptide is 5-methoxyuracil. In some embodiments, the polynucleotide comprising a uracil-modified sequence further comprises a miRNA binding site, e.g., a miRNA binding site that binds to miR-142. In some embodiments, the polynucleotide comprising a uracil-modified sequence is formulated with a delivery agent, e.g., a compound having Formula (I), (IA), (II), (Ha), (IIb), (IIc), (IId) or (IIe), e.g., any of Compounds 1-232.

In some embodiments, the "guanine content of the sequence optimized ORF encoding JAG1 with respect to the theoretical maximum guanine content of a nucleotide sequence encoding the JAG1 polypeptide," abbreviated as % $G_{TMX}$ is at least about 70%, at least about 74%, at least about 75%, at least about 80%, at least about 85%, at least about 90%, at least about 95%, or about 100%. In some embodiments, the % $G_{TMX}$ is between about 70% and about 80%, between about 71% and about 79%, between about 71% and about 78%, or between about 74%0/and about 77%.

In some embodiments, the "cytosine content of the ORF relative to the theoretical maximum cytosine content of a nucleotide sequence encoding the JAG1 polypeptide," abbreviated as % $C_{TMX}$, is at least about 70%, at least about 72%, at least about 75%, at least about 80%, at least about 85%, at least about 90%, at least about 95%, or about 100%. In some embodiments, the % $C_{TMX}$ is between about 600 and about 800, between about 62% and about 80%, between about 69% and about 79%, or between about 72% and about 76%.

In some embodiments, the "guanine and cytosine content (G/C) of the ORF relative to the theoretical maximum G/C content in a nucleotide sequence encoding the JAG1 polypeptide," abbreviated as % $G/C_{TMX}$ is at least about 80%, at least about 85%, at least about 90%, at least about 95%, or about 100%. The % $G/C_{T}$ix is between about 80% and about 100%, between about 85% and about 99%, between about 88% and about 97%, or between about 90% and about 93%.

In some embodiments, the "G/C content in the ORF relative to the G/C content in the corresponding wild-type ORF," abbreviated as % $G/C_{WT}$ is at least 102%, at least 103%, at least 104%, at least 105%, at least 106%, at least 107%, at least 110%, at least 112%, at least 115%, or at least 120%.

In some embodiments, the average G/C content in the 3rd codon position in the ORF is at least 20%, at least 21%, at least 22%, at least 23%, at least 24%, at least 25%, at least 26%, at least 27%, at least 28%, at least 29%, or at least 30% higher than the average G/C content in the 3rd codon position in the corresponding wild-type ORF.

In some embodiments, the polynucleotide of the present disclosure comprises an open reading frame (ORF) encoding a JAG1 polypeptide, wherein the ORF has been sequence optimized, and wherein each of % $U_{TL}$, % $U_{WT}$, % $U_{TM}$, % $G_{TL}$, % $G_{WT}$, % $G_{TMX}$, % $C_{TL}$, % $C_{WT}$, % $C_{TMX}$, % $G/C_{TL}$, % $G/C_{WT}$, or % $G/C_{TMX}$, alone or in a combination thereof is in a range between (i) a maximum corresponding to the parameter's maximum value (MAX) plus about 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV), and (ii) a minimum corresponding to the parameter's minimum value (MIN) less 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV).

Methods for Sequence Optimization

In some embodiments, a polynucleotide of the present disclosure (e.g., a polynucleotide comprising a nucleotide sequence encoding a JAG1 polypeptide (e.g., the wild-type sequence, functional fragment, or variant thereof) is sequence optimized. A sequence optimized nucleotide sequence (nucleotide sequence is also referred to as "nucleic acid" herein) comprises at least one codon modification with respect to a reference sequence (e.g., a wild-type sequence encoding a JAG1 polypeptide). Thus, in a sequence optimized nucleic acid, at least one codon is different from a corresponding codon in a reference sequence (e.g., a wild-type sequence).

In general, sequence optimized nucleic acids are generated by at least a step comprising substituting codons in a reference sequence with synonymous codons (i.e., codons that encode the same amino acid). Such substitutions can be effected, for example, by applying a codon substitution map (i.e., a table providing the codons that will encode each amino acid in the codon optimized sequence), or by applying a set of rules (e.g., if glycine is next to neutral amino acid, glycine would be encoded by a certain codon, but if it is next to a polar amino acid, it would be encoded by another codon). In addition to codon substitutions (i.e., "codon optimization") the sequence optimization methods disclosed herein comprise additional optimization steps which are not strictly directed to codon optimization such as the removal of deleterious motifs (destabilizing motif substitution). Compositions and formulations comprising these sequence optimized nucleic acids (e.g., a RNA, e.g., an mRNA) can be administered to a subject in need thereof to facilitate in vivo expression of functionally active JAG1.

The recombinant expression of large molecules in cell cultures can be a challenging task with numerous limitations (e.g., poor protein expression levels, stalled translation resulting in truncated expression products, protein misfolding, etc.) These limitations can be reduced or avoided by administering the polynucleotides (e.g., a RNA, e.g., an mRNA), which encode a functionally active JAG1 or compositions or formulations comprising the same to a patient suffering from ALGS, so the synthesis and delivery of the JAG1 polypeptide to treat ALGS takes place endogenously.

Changing from an in vitro expression system (e.g., cell culture) to in vivo expression requires the redesign of the nucleic acid sequence encoding the therapeutic agent. Redesigning a naturally occurring gene sequence by choosing different codons without necessarily altering the encoded amino acid sequence can often lead to dramatic increases in protein expression levels (Gustafsson et al., 2004, Journal/Trends Biotechnol 22, 346-53). Variables such as codon adaptation index (CAI), mRNA secondary structures, cis-regulatory sequences, GC content and many other similar variables have been shown to somewhat correlate with protein expression levels (Villalobos et al., 2006, "Journal/BMC Bioinformatics 7, 285). However, due to the degeneracy of the genetic code, there are numerous different nucleic acid sequences that can all encode the same therapeutic agent. Each amino acid is encoded by up to six synonymous codons; and the choice between these codons influences gene expression. In addition, codon usage (i.e., the frequency with which different organisms use codons for expressing a polypeptide sequence) differs among organisms (for example, recombinant production of human or humanized therapeutic antibodies frequently takes place in hamster cell cultures).

In some embodiments, a reference nucleic acid sequence can be sequence optimized by applying a codon map. The skilled artisan will appreciate that the T bases in the codon maps disclosed below are present in DNA, whereas the T bases would be replaced by U bases in corresponding RNAs. For example, a sequence optimized nucleic acid disclosed herein in DNA form, e.g., a vector or an in-vitro translation (IVT) template, would have its T bases transcribed as U based in its corresponding transcribed mRNA. In this respect, both sequence optimized DNA sequences (comprising T) and their corresponding RNA sequences (comprising U) are considered sequence optimized nucleic acid of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn can correspond to a TPC codon (RNA map in which U has been replaced with pseudouridine).

In one embodiment, a reference sequence encoding JAG1 can be optimized by replacing all the codons encoding a certain amino acid with only one of the alternative codons provided in a codon map. For example, all the valines in the optimized sequence would be encoded by GTG or GTC or GTT.

Sequence optimized polynucleotides of the present disclosure can be generated using one or more codon optimization methods, or a combination thereof. Sequence optimization methods which can be used to sequence optimize nucleic acid sequences are described in detail herein. This list of methods is not comprehensive or limiting.

It will be appreciated that the design principles and rules described for each one of the sequence optimization methods discussed below can be combined in many different ways, for example high G/C content sequence optimization for some regions or uridine content sequence optimization for other regions of the reference nucleic acid sequence, as well as targeted nucleotide mutations to minimize secondary structure throughout the sequence or to eliminate deleterious motifs.

The choice of potential combinations of sequence optimization methods can be, for example, dependent on the specific chemistry used to produce a synthetic polynucleotide. Such a choice can also depend on characteristics of the protein encoded by the sequence optimized nucleic acid, e.g., a full sequence, a functional fragment, or a fusion protein comprising JAG1, etc. In some embodiments, such a choice can depend on the specific tissue or cell targeted by the sequence optimized nucleic acid (e.g., a therapeutic synthetic mRNA).

The mechanisms of combining the sequence optimization methods or design rules derived from the application and analysis of the optimization methods can be either simple or complex. For example, the combination can be:

(i) Sequential: Each sequence optimization method or set of design rules applies to a different subsequence of the overall sequence, for example reducing uridine at codon positions 1 to 30 and then selecting high frequency codons for the remainder of the sequence;

(ii) Hierarchical: Several sequence optimization methods or sets of design rules are combined in a hierarchical, deterministic fashion. For example, use the most GC-rich codons, breaking ties (which are common) by choosing the most frequent of those codons.

(iii) Multifactorial/Multiparametric: Machine learning or other modeling techniques are used to design a single sequence that best satisfies multiple overlapping and possibly contradictory requirements. This approach would require the use of a computer applying a number of mathematical techniques, for example, genetic algorithms.

Ultimately, each one of these approaches can result in a specific set of rules which in many cases can be summarized in a single codon table, i.e., a sorted list of codons for each amino acid in the target protein (i.e., JAG1), with a specific rule or set of rules indicating how to select a specific codon for each amino acid position.

a. Uridine Content Optimization

The presence of local high concentrations of uridine in a nucleic acid sequence can have detrimental effects on translation, e.g., slow or prematurely terminated translation, especially when modified uridine analogs are used in the production of synthetic mRNAs. Furthermore, high uridine content can also reduce the in vive half-life of synthetic mRNAs due to TLR activation.

Accordingly, a nucleic acid sequence can be sequence optimized using a method comprising at least one uridine content optimization step. Such a step comprises, e.g., substituting at least one codon in the reference nucleic acid with an alternative codon to generate a uridine-modified sequence, wherein the uridine-modified sequence has at least one of the following properties:

(i) increase or decrease in global uridine content;

(ii) increase or decrease in local uridine content (i.e., changes in uridine content are limited to specific subsequences);

(iii) changes in uridine distribution without altering the global uridine content;

(iv) changes in uridine clustering (e.g., number of clusters, location of clusters, or distance between clusters); or (v) combinations thereof.

In some embodiments, the sequence optimization process comprises optimizing the global uridine content, i.e., optimizing the percentage of uridine nucleobases in the sequence optimized nucleic acid with respect to the percentage of uridine nucleobases in the reference nucleic acid sequence. For example, 30% of nucleobases can be uridines in the reference sequence and 10%, of nucleobases can be uridines in the sequence optimized nucleic acid.

In other embodiments, the sequence optimization process comprises reducing the local uridine content in specific regions of a reference nucleic acid sequence, i.e., reducing the percentage of uridine nucleobases in a subsequence of the sequence optimized nucleic acid with respect to the percentage of uridine nucleobases in the corresponding subsequence of the reference nucleic acid sequence. For example, the reference nucleic acid sequence can have a 5'-end region (e.g., 30 codons) with a local uridine content of 30%, and the uridine content in that same region could be reduced to 10%, in the sequence optimized nucleic acid.

In specific embodiments, codons can be replaced in the reference nucleic acid sequence to reduce or modify, for example, the number, size, location, or distribution of uridine clusters that could have deleterious effects on protein translation. Although as a general rule it is desirable to reduce the uridine content of the reference nucleic acid sequence, in certain embodiments the uridine content, and in particular the local uridine content, of some subsequences of the reference nucleic acid sequence can be increased.

The reduction of uridine content to avoid adverse effects on translation can be done in combination with other optimization methods disclosed here to achieve other design goals. For example, uridine content optimization can be combined with ramp design, since using the rarest codons for most amino acids will, with a few exceptions, reduce the U content.

In some embodiments, the uridine-modified sequence is designed to induce a lower Toll-Like Receptor (TLR) response when compared to the reference nucleic acid sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:1529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745.

As used herein, the term "TLR response" is defined as the recognition of single-stranded RNA by a TLR7 receptor, and in some embodiments encompasses the degradation of the RNA and/or physiological responses caused by the recognition of the single-stranded RNA by the receptor. Methods to determine and quantitate the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7.

Suppression of TLR7-mediated response can be accomplished via nucleoside modification. RNA undergoes over hundred different nucleoside modifications in nature (see the RNA Modification Database, available at mods.ma.albany.edu). Human rRNA, for example, has ten times more pseudouridine (P) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uridines in close proximity. See Diebold et al. (2006) Eur. J. Immunol. 36:3256-3267, which is herein incorporated by reference in its entirety. Accordingly, one or more of the optimization methods disclosed herein comprises reducing the uridine content (locally and/or locally) and/or reducing or modifying uridine clustering to reduce or to suppress a TLR7-mediated response.

In some embodiments, the TLR response (e.g., a response mediated by TLR7) caused by the uridine-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the TLR response caused by the reference nucleic acid sequence.

In some embodiments, the TLR response caused by the reference nucleic acid sequence is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uridine-modified sequence.

In some embodiments, the uridine content (average global uridine content) (absolute or relative) of the uridine-modified sequence is higher than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more uridine that the reference nucleic acid sequence.

In other embodiments, the uridine content (average global uridine content) (absolute or relative) of the uridine-modified sequence is lower than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uridine that the reference nucleic acid sequence.

In some embodiments, the uridine content (average global uridine content) (absolute or relative) of the uridine-modified sequence is less than 50%, 49%, 48%, 47%, 46%, 45%, 44%, 43%, 42%, 41%, 40%, 39%, 38%, 37%, 36%, 350%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the uridine-modified sequence. In some embodiments, the uridine content of the uridine-modified sequence is between about 10% and about 20%. In some particular embodiments, the uridine content of the uridine-modified sequence is between about 12% and about 16%.

In some embodiments, the uridine content of the reference nucleic acid sequence can be measured using a sliding window. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the sliding window is 20 nucleobases in length. Based on the uridine content measured with a sliding window, it is possible to generate a histogram representing the uridine content throughout the length of the reference nucleic acid sequence and sequence optimized nucleic acids.

In some embodiments, a reference nucleic acid sequence can be modified to reduce or eliminate peaks in the histogram that are above or below a certain percentage value. In some embodiments, the reference nucleic acid sequence can be modified to eliminate peaks in the sliding-window representation which are above 65%, 60%, 55%, 50%, 45%, 40%, 35%, or 30% uridine. In another embodiment, the reference nucleic acid sequence can be modified so no peaks are over 30% uridine in the sequence optimized nucleic acid, as measured using a 20 nucleobase sliding window. In some embodiments, the reference nucleic acid sequence can be modified so no more or no less than a predetermined number of peaks in the sequence optimized nucleic sequence, as measured using a 20 nucleobase sliding window, are above or below a certain threshold value. For example, in some embodiments, the reference nucleic acid sequence can be modified so no peaks or no more than 1, 2, 3, 4, 5, 6, 7, 8, 9 or 10 peaks in the sequence optimized nucleic acid are above 10%, 15%, 20%, 25% or 30% uridine. In another embodiment, the sequence optimized nucleic acid contains between 0 peaks and 2 peaks with uridine contents $30\%_0$ of higher.

In some embodiments, a reference nucleic acid sequence can be sequence optimized to reduce the incidence of consecutive uridines. For example, two consecutive leucines could be encoded by the sequence CUUUUG, which would include a four uridine cluster. Such subsequence could be substituted with CUGCUC, which would effectively remove the uridine cluster. Accordingly, a reference nucleic sequence can be sequence optimized by reducing or eliminating uridine pairs (UU), uridine triplets (UUU) or uridine quadruplets (UUUU). Higher order combinations of U are not considered combinations of lower order combinations. Thus, for example, UUUU is strictly considered a quadruplet, not two consecutive U pairs; or UUUUUU is considered a sextuplet, not three consecutive U pairs, or two consecutive U triplets, etc.

In some embodiments, all uridine pairs (UU) and/or uridine triplets (UUU) and/or uridine quadruplets (UUUU) can be removed from the reference nucleic acid sequence. In other embodiments, uridine pairs (UU) and/or uridine triplets (UUU) and/or uridine quadruplets (UUUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 uridine pairs. In another particular embodiment, the sequence optimized nucleic acid contains no uridine pairs and/or triplets.

Phenylalanine codons, i.e., UUC or UUU, comprise a uridine pair or triples and therefore sequence optimization to reduce uridine content can at most reduce the phenylalanine U triplet to a phenylalanine U pair. In some embodiments, the occurrence of uridine pairs (UU) and/or uridine triplets (UUU) refers only to non-phenylalanine U pairs or triplets. Accordingly, in some embodiments, non-phenylalanine uridine pairs (UU) and/or uridine triplets (UUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 non-phenylalanine uridine pairs and/or triplets. In another particular embodiment, the sequence optimized nucleic acid contains no non-phenylalanine uridine pairs and/or triplets.

In some embodiments, the reduction in uridine combinations (e.g., pairs, triplets, quadruplets) in the sequence optimized nucleic acid can be expressed as a percentage reduction with respect to the uridine combinations present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine triplets present in the reference nucleic acid sequence. In some embodiments, a sequence optimized nucleic acid can contain about 1%, 2%, 3%, 4%, 50%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine quadruplets present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine triplets present in the reference nucleic acid sequence.

In some embodiments, the uridine content in the sequence optimized sequence can be expressed with respect to the theoretical minimum uridine content in the sequence. The term "theoretical minimum uridine content" is defined as the uridine content of a nucleic acid sequence as a percentage of the sequence's length after all the codons in the sequence have been replaced with synonymous codon with the lowest uridine content. In some embodiments, the uridine content of the sequence optimized nucleic acid is identical to the theoretical minimum uridine content of the reference sequence (e.g., a wild type sequence). In some aspects, the uridine content of the sequence optimized nucleic acid is about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195% or about 200% of the theoretical minimum uridine content of the reference sequence (e.g., a wild type sequence).

In some embodiments, the uridine content of the sequence optimized nucleic acid is identical to the theoretical minimum uridine content of the reference sequence (e.g., a wild type sequence).

The reference nucleic acid sequence (e.g., a wild type sequence) can comprise uridine clusters which due to their number, size, location, distribution or combinations thereof have negative effects on translation. As used herein, the term "uridine cluster" refers to a subsequence in a reference nucleic acid sequence or sequence optimized nucleic sequence with contains a uridine content (usually described as a percentage) which is above a certain threshold. Thus, in certain embodiments, if a subsequence comprises more than about 10%, 15%, 20%, 25%, 30%, 35%, 40%, 45%, 50%, 55%, 60% or 65% uridine content, such subsequence would be considered a uridine cluster.

The negative effects of uridine clusters can be, for example, eliciting a TLR7 response. Thus, in some implementations of the nucleic acid sequence optimization methods disclosed herein it is desirable to reduce the number of clusters, size of clusters, location of clusters (e.g., close to the 5' and/or 3' end of a nucleic acid sequence), distance between clusters, or distribution of uridine clusters (e.g., a certain pattern of cluster along a nucleic acid sequence, distribution of clusters with respect to secondary structure elements in the expressed product, or distribution of clusters with respect to the secondary structure of an mRNA).

In some embodiments, the reference nucleic acid sequence comprises at least one uridine cluster, wherein said uridine cluster is a subsequence of the reference nucleic acid sequence wherein the percentage of total uridine nucleobases in said subsequence is above a predetermined threshold. In some embodiments, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some embodiments, the subsequence is longer than 100 nucleobases. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

For example, an amino acid sequence comprising A, D, G, S and R could be encoded by the nucleic acid sequence GCU, GAU, GGU, AGU, CGU. Although such sequence does not contain any uridine pairs, triplets, or quadruplets, one third of the nucleobases would be uridines. Such a uridine cluster could be removed by using alternative codons, for example, by using GCC, GAC, GGC, AGC, and CGC, which would contain no uridines.

In other embodiments, the reference nucleic acid sequence comprises at least one uridine cluster, wherein said uridine cluster is a subsequence of the reference nucleic acid sequence wherein the percentage of uridine nucleobases of said subsequence as measured using a sliding window that is above a predetermined threshold. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

In some embodiments, the reference nucleic acid sequence comprises at least two uridine clusters. In some embodiments, the uridine-modified sequence contains fewer uridine-rich clusters than the reference nucleic acid sequence. In some embodiments, the uridine-modified sequence contains more uridine-rich clusters than the reference nucleic acid sequence. In some embodiments, the uridine-modified sequence contains uridine-rich clusters with are shorter in length than corresponding uridine-rich clusters in the reference nucleic acid sequence. In other embodiments, the uridine-modified sequence contains uridine-rich clusters which are longer in length than the corresponding uridine-rich cluster in the reference nucleic acid sequence.

See, Kariko et al. (2005) Immunity 23:165-175; Kormann et al. (2010) Nature Biotechnology 29:154-157; or Sahin et al. (2014) Nature Reviews Drug Discovery|AOP, published online 19 Sep. 2014m doi:10.1038/nrd4278; all of which are herein incorporated by reference their entireties.

b. Guanine/Cytosine (G/L) Content

A reference nucleic acid sequence can be sequence optimized using methods comprising altering the Guanine/Cytosine (G/C) content (absolute or relative) of the reference nucleic acid sequence. Such optimization can comprise altering (e.g., increasing or decreasing) the global G/C content (absolute or relative) of the reference nucleic acid sequence; introducing local changes in G/C content in the reference nucleic acid sequence (e.g., increase or decrease G/C in selected regions or subsequences in the reference nucleic acid sequence); altering the frequency, size, and distribution of G/C clusters in the reference nucleic acid sequence, or combinations thereof.

In some embodiments, the sequence optimized nucleic acid encoding JAG1 comprises an overall increase in G/C content (absolute or relative) relative to the G/C content (absolute or relative) of the reference nucleic acid sequence. In some embodiments, the overall increase in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding JAG1 comprises an overall decrease in G/C content (absolute or relative) relative to the G/C content of the reference nucleic acid sequence. In some embodiments, the overall decrease in G/C content (absolute or relative) is at least about 5%, at least about 10%, at least about 15%, at least about 200, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding JAG1 comprises a local increase in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local increase in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the sequence optimized nucleic acid encoding JAG1 comprises a local decrease in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local decrease in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the G/C content (absolute or relative) is increased or decreased in a subsequence which is at least about 5, 10, 15, 20, 25, 30, 35, 40, 45, 50, 55, 60, 65, 70, 75, 80, 85, 90, 95, or 100 nucleobases in length.

In some embodiments, the G/C content (absolute or relative) is increased or decreased in a subsequence which is at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleobases in length.

In some embodiments, the G/C content (absolute or relative) is increased or decreased in a subsequence which is at least about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nucleobases in length.

The increases or decreases in G and C content (absolute or relative) described herein can be conducted by replacing synonymous codons with low G/C content with synonymous codons having higher G/C content, or vice versa. For example, L has 6 synonymous codons: two of them have 2 G/C (CUC, CUG), 3 have a single G/C (UUG, CUU, CUA), and one has no G/C (UUA). So if the reference nucleic acid had a CUC codon in a certain position, G/C content at that position could be reduced by replacing CUC with any of the codons having a single G/C or the codon with no G/C.

See, U.S. Publ. Nos. US20140228558, US20050032730 A1; Gustafsson et al. (2012) Protein Expression and Purification 83: 37-46; all of which are incorporated herein by reference in their entireties.

c. Codon Frequency—Codon Usage Bias

Numerous codon optimization methods known in the art are based on the substitution of codons in a reference nucleic acid sequence with codons having higher frequencies. Thus, in some embodiments, a nucleic acid sequence encoding JAG1 disclosed herein can be sequence optimized using methods comprising the use of modifications in the frequency of use of one or more codons relative to other synonymous codons in the sequence optimized nucleic acid with respect to the frequency of use in the non-codon optimized sequence.

As used herein, the term "codon frequency" refers to codon usage bias, i.e., the differences in the frequency of occurrence of synonymous codons in coding DNA/RNA. It is generally acknowledged that codon preferences reflect a balance between mutational biases and natural selection for translational optimization. Optimal codons help to achieve faster translation rates and high accuracy. As a result of these factors, translational selection is expected to be stronger in highly expressed genes. In the field of bioinformatics and computational biology, many statistical methods have been proposed and used to analyze codon usage bias. See, e.g., Comeron & Aguadé (1998) J. Mol. Evol. 47: 268-74. Methods such as the 'frequency of optimal codons'(Fop) (Ikemura (1981) J. Mol. Biol. 151 (3): 389-409), the Relative Codon Adaptation (RCA) (Fox & Eril (2010) DNA Res. 17 (3): 185-96) or the 'Codon Adaptation Index' (CAI) (Sharp & Li (1987) Nucleic Acids Res. 15 (3): 1281-95) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes (Suzuki et al. (2008) DNA Res. 15 (6): 357-65; Sandhu et al., In Silico Biol. 2008; 8(2):187-92).

The nucleic acid sequence encoding a JAG1 polypeptide disclosed herein (e.g., a wild type nucleic acid sequence, a mutant nucleic acid sequence, a chimeric nucleic sequence, etc. which can be, for example, an mRNA), can be codon optimized using methods comprising substituting at least one codon in the reference nucleic acid sequence with an alternative codon having a higher or lower codon frequency in the synonymous codon set; wherein the resulting sequence optimized nucleic acid has at least one optimized property with respect to the reference nucleic acid sequence.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the reference nucleic acid sequence encoding JAG1 are substituted with alternative codons, each alternative codon having a codon frequency higher than the codon frequency of the substituted codon in the synonymous codon set.

In some embodiments, at least one codon in the reference nucleic acid sequence encoding JAG1 is substituted with an alternative codon having a codon frequency higher than the codon frequency of the substituted codon in the synonymous codon set, and at least one codon in the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding JAG1 are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding a JAG1 polypeptide. In some embodiments, when applied locally, regions of the reference nucleic acid sequence can modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding a JAG1 polypeptide is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding a JAG1 polypeptide are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding a JAG1 polypeptide and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding a JAG1 polypeptide and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding a JAG1 polypeptide can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid).

In some embodiments, an sequence optimized nucleic acid encoding a JAG1 polypeptide can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc.

See, U.S. Pat. Nos. 5,082,767, 8,126,653, 7,561,973, 8,401,798; U.S. Publ. No. US 20080046192, US 20080076161; Int'l. Publ. No. WO2000018778; Welch et al. (2009) PLoS ONE 4(9): e7002 Gustafsson et al. (2012) Protein Expression and Purification 83: 37-46; Chung et al. (2012) BMC Systems Biology 6:134; all of which are incorporated herein by reference in their entireties.

d. Destabilizing Motif Substitution

There is a variety of motifs that can affect sequence optimization, which fall into various non-exclusive categories, for example:

(i) Primary sequence based motifs: Motifs defined by a simple arrangement of nucleotides.

(ii) Structural motifs: Motifs encoded by an arrangement of nucleotides that tends to form a certain secondary structure.

(iii) Local motifs: Motifs encoded in one contiguous subsequence.

(iv) Distributed motifs: Motifs encoded in two or more disjoint subsequences.

(v) Advantageous motifs: Motifs which improve nucleotide structure or function.

(vi) Disadvantageous motifs: Motifs with detrimental effects on nucleotide structure or function.

There are many motifs that fit into the category of disadvantageous motifs. Some examples include, for example, restriction enzyme motifs, which tend to be relatively short, exact sequences such as the restriction site motifs for XbaI (TCTAGA), EcoRI (GAATTC), EcoRII (CCWGG, wherein W means A or T, per the IUPAC ambiguity codes), or HindIII (AAGCTT); enzyme sites, which tend to be longer and based on consensus not exact sequence, such in the T7 RNA polymerase (GnnnnWnCRnCTCnCnnWnD, wherein n means any nucleotide, R means A or G, W means A or T, D means A or G or T but not C); structural motifs, such as GGGG repeats (Kim et al. (1991) Nature 351(6324):331-2); or other motifs such as CUG-triplet repeats (Querido et al. (2014) J. Cell Sci. 124:1703-1714).

Accordingly, the nucleic acid sequence encoding a JAG1 polypeptide disclosed herein can be sequence optimized using methods comprising substituting at least one destabilizing motif in a reference nucleic acid sequence, and removing such disadvantageous motif or replacing it with an advantageous motif.

In some embodiments, the optimization process comprises identifying advantageous and/or disadvantageous motifs in the reference nucleic sequence, wherein such motifs are, e.g., specific subsequences that can cause a loss of stability in the reference nucleic acid sequence prior or during the optimization process. For example, substitution of specific bases during optimization can generate a subsequence (motif) recognized by a restriction enzyme. Accordingly, during the optimization process the appearance of disadvantageous motifs can be monitored by comparing the sequence optimized sequence with a library of motifs known to be disadvantageous. Then, the identification of disadvantageous motifs could be used as a post-hoc filter, i.e., to determine whether a certain modification which potentially could be introduced in the reference nucleic acid sequence should be actually implemented or not.

In some embodiments, the identification of disadvantageous motifs can be used prior to the application of the sequence optimization methods disclosed herein, i.e., the identification of motifs in the reference nucleic acid sequence encoding a JAG1 polypeptide and their replacement with alternative nucleic acid sequences can be used as a preprocessing step, for example, before uridine reduction.

In other embodiments, the identification of disadvantageous motifs and their removal is used as an additional sequence optimization technique integrated in a multiparametric nucleic acid optimization method comprising two or more of the sequence optimization methods disclosed herein. When used in this fashion, a disadvantageous motif identified during the optimization process would be removed, for example, by substituting the lowest possible number of nucleobases in order to preserve as closely as possible the original design principle(s) (e.g., low U, high frequency, etc.).

See, e.g., U.S. Publ. Nos. US20140228558, US20050032730, or US20140228558, which are herein incorporated by reference in their entireties.

e. Limited Codon Set Optimization

In some particular embodiments, sequence optimization of a reference nucleic acid sequence encoding a JAG1 polypeptide can be conducted using a limited codon set, e.g., a codon set wherein less than the native number of codons is used to encode the 20 natural amino acids, a subset of the 20 natural amino acids, or an expanded set of amino acids including, for example, non-natural amino acids.

The genetic code is highly similar among all organisms and can be expressed in a simple table with 64 entries which would encode the 20 standard amino acids involved in protein translation plus start and stop codons. The genetic code is degenerate, i.e., in general, more than one codon specifies each amino acid. For example, the amino acid leucine is specified by the UUA, UUG, CUU, CUC, CUA, or CUG codons, while the amino acid serine is specified by UCA, UCG, UCC, UCU, AGU, or AGC codons (difference in the first, second, or third position). Native genetic codes comprise 62 codons encoding naturally occurring amino acids. Thus, in some embodiments of the methods disclosed herein optimized codon sets (genetic codes) comprising less than 62 codons to encode 20 amino acids can comprise 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 30, 29, 28, 27, 26, 25, 24, 23, 22, 21, or 20 codons.

In some embodiments, the limited codon set comprises less than 20 codons. For example, if a protein contains less than 20 types of amino acids, such protein could be encoded by a codon set with less than 20 codons. Accordingly, in some embodiments, an optimized codon set comprises as many codons as different types of amino acids are present in the protein encoded by the reference nucleic acid sequence. In some embodiments, the optimized codon set comprises 19, 18, 17, 16, 15, 14, 13, 12, 11, 10, 9, 8, 7, 6, 5, 4, 3, 2 or even 1 codon.

In some embodiments, at least one amino acid selected from the group consisting of Ala, Arg, Asn, Asp, Cys, Gin, Glu, Gly, His, Ile, Leu, Lys, Phe, Pro, Ser, Thr, Tyr, and Val, i.e., amino acids which are naturally encoded by more than one codon, is encoded with less codons than the naturally occurring number of synonymous codons. For example, in some embodiments, Ala can be encoded in the sequence optimized nucleic acid by 3, 2 or 1 codons; Cys can be encoded in the sequence optimized nucleic acid by 1 codon; Asp can be encoded in the sequence optimized nucleic acid by 1 codon; Glu can be encoded in the sequence optimized nucleic acid by 1 codon; Phe can be encoded in the sequence optimized nucleic acid by 1 codon; Gly can be encoded in the sequence optimized nucleic acid by 3 codons, 2 codons or 1 codon; His can be encoded in the sequence optimized nucleic acid by 1 codon; Ile can be encoded in the sequence optimized nucleic acid by 2 codons or 1 codon; Lys can be encoded in the sequence optimized nucleic acid by 1 codon; Leu can be encoded in the sequence optimized nucleic acid by 5 codons, 4 codons, 3 codons, 2 codons or 1 codon; Asn can be encoded in the sequence optimized nucleic acid by 1 codon; Pro can be encoded in the sequence optimized nucleic acid by 3 codons, 2 codons, or 1 codon; Gin can be encoded in the sequence optimized nucleic acid by 1 codon; Arg can be encoded in the sequence optimized nucleic acid by 5 codons, 4 codons, 3 codons, 2 codons, or 1 codon; Ser can be encoded in the sequence optimized nucleic acid by 5 codons, 4 codons, 3 codons, 2 codons, or 1 codon; Thr can be encoded in the sequence optimized nucleic acid by 3 codons, 2 codons, or 1 codon; Val can be encoded in the sequence optimized nucleic acid by 3 codons, 2 codons, or 1 codon; and, Tyr can be encoded in the sequence optimized nucleic acid by 1 codon.

In some embodiments, at least one amino acid selected from the group consisting of Ala, Arg, Asn, Asp, Cys, Gin, Glu, Gly, His, lie, Leu, Lys, Phe, Pro, Ser, Thr, Tyr, and Val, i.e., amino acids which are naturally encoded by more than one codon, is encoded by a single codon in the limited codon set.

In some specific embodiments, the sequence optimized nucleic acid is a DNA and the limited codon set consists of 20 codons, wherein each codon encodes one of 20 amino acids. In some embodiments, the sequence optimized nucleic acid is a DNA and the limited codon set comprises at least one codon selected from the group consisting of GCT, GCC, GCA, and GCG; at least a codon selected from the group consisting of CGT, CGC, CGA, CGG, AGA, and AGG; at least a codon selected from AAT or ACC; at least a codon selected from GAT or GAC; at least a codon selected from TGT or TGC; at least a codon selected from CAA or CAG; at least a codon selected from GAA or GAG; at least a codon selected from the group consisting of GGT, GGC, GGA, and GGG; at least a codon selected from CAT or CAC; at least a codon selected from the group consisting of ATT, ATC, and ATA; at least a codon selected from the group consisting of TTA, TTG, CTT, CTC, CTA, and CTG; at least a codon selected from AAA or AAG; an ATG codon; at least a codon selected from TTT or TTC; at least a codon selected from the group consisting of CCT, CCC, CCA, and CCG; at least a codon selected from the group consisting of TCT, TCC, TCA, TCG, AGT, and AGC; at least a codon selected from the group consisting of ACT, ACC, ACA, and ACG; a TGG codon; at least a codon selected from TAT or TAC; and, at least a codon selected from the group consisting of GTT, GTC, GTA, and GTG.

In other embodiments, the sequence optimized nucleic acid is an RNA (e.g., an mRNA) and the limited codon set consists of 20 codons, wherein each codon encodes one of 20 amino acids. In some embodiments, the sequence optimized nucleic acid is an RNA and the limited codon set comprises at least one codon selected from the group consisting of GCU, GCC, GCA, and GCG; at least a codon selected from the group consisting of CGU, CGC, CGA, CGG, AGA, and AGG; at least a codon selected from AAU or ACC; at least a codon selected from GAU or GAC; at least a codon selected from UGU or UGC; at least a codon selected from CAA or CAG; at least a codon selected from GAA or GAG; at least a codon selected from the group consisting of GGU, GGC, GGA, and GGG; at least a codon selected from CAU or CAC; at least a codon selected from the group consisting of AUU, AUC, and AUA; at least a codon selected from the group consisting of UUA, UUG, CUU, CUC, CUA, and CUG; at least a codon selected from AAA or AAG; an AUG codon; at least a codon selected from UUU or UUC; at least a codon selected from the group consisting of CCU, CCC, CCA, and CCG; at least a codon selected from the group consisting of UCU, UCC, UCA, UCG, AGU, and AGC; at least a codon selected from the group consisting of ACU, ACC, ACA, and ACG; a UGG codon; at least a codon selected from UAU or UAC; and, at least a codon selected from the group consisting of GUU, GUC, GUA, and GUG.

In some specific embodiments, the limited codon set has been optimized for in vivo expression of a sequence optimized nucleic acid (e.g., a synthetic mRNA) following administration to a certain tissue or cell.

In some embodiments, the optimized codon set (e.g., a 20 codon set encoding 20 amino acids) complies at least with one of the following properties:

the optimized codon set has a higher average G/C content than the original or native codon set; or, the optimized codon set has a lower average U content than the original or native codon set; or, the optimized codon set is composed of codons with the highest frequency; or, the optimized codon set is composed of codons with the lowest frequency; or, a combination thereof.

In some specific embodiments, at least one codon in the optimized codon set has the second highest, the third highest, the fourth highest, the fifth highest or the sixth highest frequency in the synonymous codon set. In some specific embodiments, at least one codon in the optimized codon has the second lowest, the third lowest, the fourth lowest, the fifth lowest, or the sixth lowest frequency in the synonymous codon set.

As used herein, the term "native codon set" refers to the codon set used natively by the source organism to encode the reference nucleic acid sequence. As used herein, the term "original codon set" refers to the codon set used to encode the reference nucleic acid sequence before the beginning of sequence optimization, or to a codon set used to encode an optimized variant of the reference nucleic acid sequence at the beginning of a new optimization iteration when sequence optimization is applied iteratively or recursively.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest frequency. In other embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest frequency.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest uridine content. In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest uridine content.

In some embodiments, the average G/C content (absolute or relative) of the codon set is 5%, 10%, 15%, 20%, 25%, 30%, 35%, 40%, 45%, 50%, 55%6, 60%, 65%, 70%, 75%, 80%, 85%, 90%, 95% or 100% higher than the average G/C content (absolute or relative) of the original codon set. In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average G/C content (absolute or relative) of the original codon set.

In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average uracil content (absolute or relative) of the original codon set. In some embodiments, the uracil content (absolute or relative) of the codon set is 5%, 10, 15%, 20%, 25%, 30%, 35%, 40%, 45%, 50%, 55%, 60%, 65%, 70%, 75%, 80%, 85%, 90%, 95% or 100% lower than the average uracil content (absolute or relative) of the original codon set.

See also U.S. Appl. Publ. No. 2011/0082055, and Int'l. Publ. No. WO2000018778, both of which are incorporated herein by reference in their entireties.

Characterization of Sequence Optimized Nucleic Acids

In some embodiments of the present disclosure, the polynucleotide (e.g., a RNA, e.g., an mRNA) comprising a sequence optimized nucleic acid disclosed herein encoding a JAG1 polypeptide can be can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding a JAG1 polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding a JAG1 polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the present disclosure, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the present disclosure, the desired property of the polynucleotide is the level of expression of a JAG1 polypeptide encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the present disclosure, the sequence optimization of a nucleic acid sequence disclosed herein, e.g., a nucleic acid sequence encoding a JAG1 polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding JAG1 polypeptide or a functional fragment thereof can trigger an immune response, which could be caused by (i) the therapeutic agent (e.g., an mRNA encoding a JAG1 polypeptide), or (ii) the expression product of such therapeutic agent (e.g., the JAG1 polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding a JAG1 polypeptide or by the expression product of JAG1 encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

Modified Nucleotide Sequences Encoding JAG1 Polypeptides

In some embodiments, the polynucleotide (e.g., a RNA, e.g., an mRNA) of the present disclosure comprises a chemically modified nucleobase, e.g., 5-methoxyuracil. In some embodiments, the mRNA is a uracil-modified sequence comprising an ORF encoding a JAG1 polypeptide, wherein the mRNA comprises a chemically modified nucleobase, e.g., 5-methoxyuracil.

In certain aspects of the present disclosure, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that an mRNA provides suitable protein expression levels while inducing little to no immune response. In some embodiments, the uracil content of the ORF is between 189%/o and 191%, between 188% and 192%, between 187% and 193%, between 186% and 194%, between 185% and 195%, between 184% and 196%, between 183% and 1970%, between 182% and 198%, between 181% and 199%, or between 180% and 2000 of the theoretical minimum uracil content in the corresponding wild-type ORF (% Utm). In other embodiments, the uracil content of the ORF is between about 180% and about 200% or between 184% and 198% of the % $U_{TM}$. In some embodiments, the uracil content of the ORF encoding a JAG1 polypeptide is about 115%, about 120%, about 125%, about 130%, about 135%, about 140%, about 145%, about 150%, about 160%, about 170%, about 180%, about 184%, about 190%, about 197%, or about 200% of the % Utm. In this context, the term "uracil" can refer to 5-methoxyuracil and/or naturally occurring uracil.

In some embodiments, the uracil content in the ORF of the mRNA encoding a JAG1 polypeptide of the present disclosure is less than about 50%, about 40%, about 30%, or about 20% of the total nucleobase content in the ORF. In some embodiments, the uracil content in the ORF is between about 15% and about 25% of the total nucleobase content in the ORF. In other embodiments, the uracil content in the ORF is between about 20% and about 30% of the total nucleobase content in the ORF. In one embodiment, the uracil content in the ORF of the mRNA encoding a JAG1 polypeptide is less than about 25% or less than about 20% of the total nucleobase content in the open reading frame. In this context, the term "uracil" can refer to 5-methoxyuracil and/or naturally occurring uracil.

In further embodiments, the ORF of the mRNA encoding a JAG1 polypeptide having 5-methoxyuracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the JAG1 polypeptide (% $G_{TMX}$; % $C_{TMX}$, or % $G/C_{TMX}$). In other embodiments, the G, the C, or the G/C content in the ORF is between about 70% and about 80%, between about 71% and about 79%, between about 71% and about 78%, or between about 71% and about 77% of the % $G_{TMX}$, % $C_{TMX}$, or % $G/C_{TMX}$. In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a JAG1 polypeptide of the present disclosure comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the JAG1 polypeptide. In some embodiments, the ORF of the mRNA encoding a JAG polypeptide of the present disclosure contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the JAG1 polypeptide. In a particular embodiment, the ORF of the mRNA encoding the JAG1 polypeptide of the present disclosure contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the JAG1 polypeptide contains no non-phenylalanine uracil pairs and/or triplets.

In further embodiments, the ORF of the mRNA encoding a JAG1 polypeptide of the present disclosure comprises 5-methoxyuracil and has an adjusted uracil content containing less uracil-rich clusters than the corresponding wild-type nucleotide sequence encoding the JAG1 polypeptide. In some embodiments, the ORF of the mRNA encoding the JAG1 polypeptide of the present disclosure contains uracil-rich clusters that are shorter in length than corresponding uracil-rich clusters in the corresponding wild-type nucleotide sequence encoding the JAG1 polypeptide.

In further embodiments, alternative lower frequency codons are employed. At least about 5%°, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% a, at least about 95%, at least about 99%, or 100% of the codons in the JAG1 polypeptide-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the JAG1 polypeptide is substituted with an alternative codon having a codon frequency lower than the codon frequency of the substituted codon in the synonymous codon set.

In some embodiments, the adjusted uracil content, JAG1 polypeptide-encoding ORF of the 5-methoxyuracil-comprising mRNA exhibits expression levels of JAG1 when administered to a mammalian cell that are higher than expression levels of JAG1 from the corresponding wild-type mRNA. In other embodiments, the expression levels of JAG1 when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of JAG1 when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, JAG1 is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the JAG1 polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 2%, about 3%, about 40%, about 50%, 60%, about 70%, about 80%, about 90%, or about 100%.

In some embodiments, adjusted uracil content, JAG1 polypeptide-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present disclosure induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a JAG1 polypeptide but does not comprise 5-methoxyuracil under the same conditions, or relative to the immune response induced by an mRNA that encodes for a JAG1 polypeptide and that comprises 5-methoxyuracil but that does not have adjusted uracil content under the same conditions. The innate immune response can be manifested by increased expression of pro-inflammatory cytokines, activation of intracellular PRRs (RIG-I, MDA5, etc), cell death, and/or termination or reduction in protein translation. In some embodiments, a reduction in the innate immune response can be measured by expression or activity level of Type I interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the present disclosure into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a JAG1 polypeptide but does not comprise 5-methoxyuracil, or to an mRNA that encodes a JAG1 polypeptide and that comprises 5-methoxyuracil but that does not have adjusted uracil content. In some embodiments, the interferon is IFN-β. In some embodiments, cell death frequency cased by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a JAG1 polypeptide but does not comprise 5-methoxyuracil, or an mRNA that encodes for a JAG1 polypeptide and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes a JAG1 polypeptide, wherein uracil in the mRNA is at least about 95% 5-methoxyuracil, wherein the uracil content of the ORF is between about 115% and about 135% of the theoretical minimum uracil content in the corresponding wild-type ORF, and wherein the uracil content in the ORF encoding the JAG1 polypeptide is less than about 25% or less than about 20% of the total nucleobase content in the ORF. In some embodiments, the ORF that encodes the JAG1 polypeptide is further modified to increase G/C content of the ORF (absolute or relative) by at least about 40%, as compared to the corresponding wild-type ORF. In yet other embodiments, the ORF encoding the JAG1 polypeptide contains less than 20 non-phenylalanine uracil pairs and/or triplets. In some embodiments, at least one codon in the ORF of the mRNA encoding the JAG1 polypeptide is further substituted with an alternative codon having a codon frequency lower than the codon frequency of the substituted codon in the synonymous codon set. In some embodiments, the expression of the JAG1 polypeptide encoded by an mRNA comprising an ORF wherein uracil in the mRNA is at least about 95% 5-methoxyuracil, and wherein the uracil content of the ORF is between about 115% and about 135% of the theoretical minimum uracil content in the corresponding wild-type ORF, is increased by at least about 10-fold when compared to expression of the JAG1 polypeptide from the corresponding wild-type mRNA. In some embodiments, the mRNA comprises an open ORF wherein uracil in the mRNA is at least about 95% 5-methoxyuracil, and wherein the uracil content of the ORF is between about 115% and about 135% of the theoretical minimum uracil content in the corresponding wild-type ORF, and wherein the mRNA does not substantially induce an innate immune response of a mammalian cell into which the mRNA is introduced.

Methods for Modifying Polynucleotides

The present disclosure includes modified polynucleotides comprising a polynucleotide described herein (e.g., a polynucleotide comprising a nucleotide sequence encoding a JAG1 polypeptide). The modified polynucleotides can be chemically modified and/or structurally modified. When the polynucleotides of the present disclosure are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a JAG1 polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can by synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

a. Structural Modifications

In some embodiments, a polynucleotide of the present disclosure (e.g., a polynucleotide comprising a nucleotide sequence encoding a JAG1 polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide “ATCG” can be chemically modified to “AT-5meC-G”. The same polynucleotide can be structurally modified from “ATCG” to “ATCCCG”. Here, the dinucleotide “CC” has been inserted, resulting in a structural modification to the polynucleotide.

b. Chemical Modifications

In some embodiments, the polynucleotides of the present disclosure are chemically modified. As used herein in reference to a polynucleotide, the terms “chemical modification” or, as appropriate, “chemically modified” refer to modification with respect to adenosine (A), guanosine (G), uridine (U), thymidine (T) or cytidine (C) ribo- or deoxyribonucleosides in one or more of their position, pattern, percent or population. Generally, herein, these terms are not intended to refer to the ribonucleotide modifications in naturally occurring 5'-terminal mRNA cap moieties.

In some embodiments, the polynucleotides of the present disclosure can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the polynucleotides can have a uniform chemical modification of two, three, or four of the same nucleoside type throughout the entire polynucleotide (such as all uridines and all cytosines, etc. are modified in the same way).

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

The skilled artisan will appreciate that, except where otherwise noted, polynucleotide sequences set forth in the instant application will recite “T”s in a representative DNA sequence but where the sequence represents RNA, the “T”s would be substituted for “U”s.

Modifications of polynucleotides (e.g., RNA polynucleotides, such as mRNA polynucleotides) that are useful in the compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl)

cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP, 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Tnfluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio) uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 14-4-Amino-benzyl) pseudo-UTP; 1-(4-Amino-butyl)pseudo-UTP; 1-(4-Amino-phenyl)pseudo-UTP, 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1 (4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetyipseudouridine TP; 1-Alkyl-6-(1-propynyl)-pseudo-UTP; 1-Alkyl-6-(2-propynyl)-pseudo-UTP; 1-Alkyl-6-alkyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinyipseudouridine TP; 1-Butyl-pseudo-UTP; 1-Cyanomethyipseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallyipseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethyl pseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP, 1-Methyl-6-trifluoromethyl-pseudo-UTP; 1-Morpholinomethyipseudouridine TP; 1-Pentyl-pseudo-UTP; 1-Phenyl-pseudo-UTP; 1-Pivaloylpseudouridine TP; 1-Propargyipseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethyipseudouridine TP; 1-Thiomorpholinomethyipseudouridine TP; 1-Trifluoroacetyipseudouridine TP; 1-Trifluoromethyl-pseudo-UTP; 1-Vinyipseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-α-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)- pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-(2-(2-ethoxy)-ethoxy)]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl; 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl) isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyl-adenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

(i) Base Modifications

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, at least 95% of a type of nucleobases (e.g., uracil) in a polynucleotide of the present disclosure (e.g., an mRNA polynucleotide encoding TLR4, e.g., caTLR4) are modified nucleobases. In some embodiments, at least 95% of uracil in a polynucleotide of the present disclosure (e.g., an mRNA polynucleotide encoding TLR4, e.g., caTLR4) is 5-methoxyuracil.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the nucleobases, sugar, backbone, or any combination thereof in the open reading frame encoding a JAG1 polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the uridine nucleosides in the open reading frame encoding a JAG1 polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the adenosine nucleosides in the open reading frame encoding a JAG1 polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the cytidine nucleosides in the open reading frame encoding a JAG1 polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the guanosine nucleosides in the open reading frame encoding a JAG1 polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, $—CH_2—O—N(CH_3)—CH_2—$, $—CH_2—N(CH_3)—N(CH_3)—CH_2—$, $—CH_2—NH—CH_2—$, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, $—N(CH_3)—CH_2—CH_2—$, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

(ii) Sugar Modifications

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{1-12}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $—O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'-2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013052523 and WO2014093924, the contents of each of which are incorporated herein by reference in their entireties.

(iii) Combinations of Modifications

The polynucleotides of the present disclosure (e.g., a polynucleotide comprising a nucleotide sequence encoding a JAG1 polypeptide or a functional fragment or variant thereof) can include a combination of modifications to the sugar, the nucleobase, and/or the internucleoside linkage. These combinations can include any one or more modifications described herein.

Combinations of modified nucleotides can be used to form the polynucleotides of the present disclosure. Unless otherwise noted, the modified nucleotides can be completely substituted for the natural nucleotides of the polynucleotides of the present disclosure. As a non-limiting example, the natural nucleotide uridine can be substituted with a modified nucleoside described herein. In another non-limiting example, the natural nucleotide uridine can be partially substituted or replaced (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein.

Untranslated Regions (UTRs)

Untranslated regions (UTRs) are nucleic acid sections of a polynucleotide before a start codon (5'UTR) and after a stop codon (3'UTR) that are not translated. In some embodiments, a polynucleotide (e.g., a ribonucleic acid (RNA), e.g., a messenger RNA (mRNA)) of the present disclosure comprising an open reading frame (ORF) encoding a JAG1 polypeptide further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the JAG1 polypeptide. In some embodiments, the UTR is heterologous to the ORF encoding the JAG1 polypeptide. In some embodiments, the polynucleotide comprises two or more 5'UTRs or functional fragments thereof, each of which have the same or different nucleotide sequences. In some embodiments, the polynucleotide comprises two or more 3'UTRs or functional fragments thereof, each of which have the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR. In some embodiments, the 3'UTR can be derived from a different species than the 5'UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present disclosure as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., elF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial HI-ATP synthase); a growth hormone e (e.g., bovine (bGH) or human (hGH)); an elongation factor (e.g., elongation factor 1 α1 (EEF1A)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col 1A2), collagen type I, alpha 1 (CollA1), collagen type VI, alpha 2 (Col6A2), collagen type VI, alpha 1 (Col6A1)); a ribophorin (e.g., ribophorin 1 (RPN1)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod 1); and a nucleobindin (e.g., Nucb1).

In some embodiments, the 5'UTR is selected from the group consisting of a β-globin 5'UTR; a 5'UTR containing a strong Kozak translational initiation signal; a cytochrome b-245 α polypeptide (CYBA) 5'UTR; a hydroxysteroid (17-β) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR α-globin 3'UTR; a DEN 3'UTR; a PAV barley yellow dwarf virus (BYDV-PAV) 3'UTR; an elongation factor 1 α1 (EEF1A1) 3'UTR; a manganese superoxide dismutase (MnSOD) 3'UTR; a β subunit of mitochondrial H(+)-ATP synthase (β-mRNA) 3'UTR; a GLUT1 3'UTR; a MEF2A 3'UTR; a β-F1-ATPase 3'UTR; functional fragments thereof and combinations thereof.

Wild-type UTRs derived from any gene or mRNA can be incorporated into the polynucleotides of the present disclosure. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, and sequences available at www.addgene.org/Derrick_Rossi/, the contents of each are incorporated herein by reference in their entirety.

UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the present disclosure comprise a 5'UTR and/or a 3'UTR selected from any of the UTRs disclosed herein. In some embodiments, the 5'UTR comprises:

| Name | SEQ ID NO |
|---|---|
| 5'UTR-001 (Upstream UTR) | 36 |
| 5'UTR-002 (Upstream UTR) | 37 |
| 5'UTR-003 (Upstream UTR) | 38 |
| 5'UTR-004 (Upstream UTR) | 39 |
| 5'UTR-005 (Upstream UTR) | 40 |
| 5'UTR-006 (Upstream UTR) | 41 |
| 5'UTR-007 (Upstream UTR) | 42 |
| 5'UTR-008 (Upstream UTR) | 43 |
| 5'UTR-009 (Upstream UTR) | 44 |
| 5'UTR-010 (Upstream UTR) | 45 |
| 5'UTR-011 (Upstream UTR) | 46 |
| 5'UTR-012 (Upstream UTR) | 47 |
| 5'UTR-013 (Upstream UTR) | 48 |
| 5'UTR-014 (Upstream UTR) | 49 |
| 5'UTR-015 (Upstream UTR) | 50 |
| 5'UTR-016 (Upstream UTR) | 51 |
| 5'UTR-017 (Upstream UTR) | 52 |
| 5'UTR-018 (Upstream UTR) | 53 |
| 142-3p 5'UTR-001 (Upstream UTR including miR142-3p binding site) | 54 |
| 142-3p 5'UTR-002 (Upstream UTR including miR142-3p binding site) | 55 |
| 142-3p 5'UTR-003 (Upstream UTR including miR142-3p binding site) | 56 |
| 142-3p 5'UTR-004 (Upstream UTR including miR142-3p binding site) | 57 |
| 142-3p 5'UTR-005 (Upstream UTR including miR142-3p binding site) | 58 |
| 142-3p 5'UTR-006 (Upstream UTR including miR142-3p binding site) | 59 |
| 142-3p 5'UTR-007 (Upstream UTR including miR142-3p binding site) | 60 |
| 3'UTR-001 (Creatine Kinase UTR) | 61 |
| 3'UTR-002 (Myoglobin UTR) | 62 |
| 3'UTR-003 (α-actin UTR) | 63 |
| 3'UTR-004 (Albumin UTR) | 64 |
| 3'UTR-005 (α-globin UTR) | 65 |
| 3'UTR-006 (G-CSF UTR) | 66 |
| 3'UTR-007 (Col1a2; collagen, type I, alpha 2 UTR) | 67 |
| 3'UTR-008 (Col6a2; collagen, type VI, alpha 2 UTR) | 68 |
| 3'UTR-009 (RPN1; ribophorin 1 UTR) | 69 |

-continued

| Name | SEQ ID NO |
|---|---|
| 3'UTR-010 (LRP1; low density lipoprotein receptor-related protein 1 UTR) | 70 |
| 3'UTR-011 (Nnt1; cardiotrophin-like cytokine factor 1 UTR) | 71 |
| 3'UTR-012 (Col6a1; collagen, type VI, alpha 1 UTR) | 72 |
| 3'UTR-013 (Calr; calreticulin UTR) | 73 |
| 3'UTR-014 (Col1a1; collagen, type I, alpha 1 UTR) | 74 |
| 3'UTR-015 (Plod1; procollagen-lysine, 2-oxoglutarate 5-dioxygenase 1 UTR) | 75 |
| 3'UTR-016 (Nucb1; nucleobindin 1 UTR) | 76 |
| 3'UTR-017 (α-globin) | 77 |
| 3'UTR-018 | 78 |
| 3' UTR with miR 142-3p binding site | 112 |
| 3' UTR with miR 126-3p binding site | 113 |
| 3' UTR with miR 142-3p and miR 126-3p binding sites | 114 |
| 3' UTR with 3 miR 142-3p binding sites | 115 |
| 3'UTR with miR 142-5p binding site | 116 |
| 3'UTR with 3 miR 142-5p binding sites | 117 |
| 3'UTR with 2 miR 142-5p binding sites and 1 miR 142-3p binding site | 118 |
| 3'UTR with miR 142-3p binding site, P1 insertion | 119 |
| 3'UTR with miR 142-3p binding site, P2 insertion | 120 |
| 3'UTR with miR 142-3p binding site, P3 insertion | 121 |
| 3'UTR with miR 155-5p binding site | 122 |
| 3' UTR with 3 miR 155-5p binding sites | 123 |
| 3'UTR with 2 miR 155-5p binding sites and 1 miR 142-3p binding site | 124 |

In certain embodiments, the 5'UTR and/or 3'UTR sequence of the present disclosure comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of SEQ ID NOs: 36-60 and/or 3'UTR sequences comprises any of SEQ ID NOs: 61-78, and any combination thereof.

The polynucleotides of the present disclosure can comprise combinations of features. For example, the ORF can be flanked by a 5'UTR that comprises a strong Kozak translational initiation signal and/or a 3'UTR comprising an oligo (dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the present disclosure. For example, introns or portions of intron sequences can be incorporated into the polynucleotides of the present disclosure. Incorporation of intronic sequences can increase protein production as well as polynucleotide expression levels. In some embodiments, the polynucleotide of the present disclosure comprises an internal ribosome entry site (IRES) instead of or in addition to a UTR (see, e.g., Yakubov et al., Biochem. Biophys. Res. Commun. 2010 394(1): 189-193, the contents of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation.

In one non-limiting example, the TEE comprises the TEE sequence in the 5'-leader of the Gtx homeodomain protein. See Chappell et al., PNAS 2004 101:9590-9594, incorporated herein by reference in its entirety.

"Translational enhancer polynucleotide" or "translation enhancer polynucleotide sequence" refer to a polynucleotide that includes one or more of the TEE provided herein and/or known in the art (see. e.g., U.S. Pat. Nos. 6,310,197, 6,849,405, 7,456,273, 7,183,395, US2009/0226470, US2007/0048776, US2011/0124100, US2009/0093049, US2013/0177581, WO2009/075886, WO2007/025008, WO2012/009644, WO2001/055371, WO1999/024595, EP2610341A1, and EP2610340A1; the contents of each of which are incorporated herein by reference in their entirety), or their variants, homologs, or functional derivatives. In some embodiments, the polynucleotide of the present disclosure comprises one or multiple copies of a TEE. The TEE in a translational enhancer polynucleotide can be organized in one or more sequence segments. A sequence segment can harbor one or more of the TEEs provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the present disclosure comprises a translational enhancer polynucleotide sequence.

In some embodiments, a 5'UTR and/or 3'UTR comprising at least one TEE described herein can be incorporated in a monocistronic sequence such as, but not limited to, a vector system or a nucleic acid vector.

In some embodiments, a 5'UTR and/or 3'UTR of a polynucleotide of the present disclosure comprises a TEE or portion thereof described herein. In some embodiments, the TEEs in the 3'UTR can be the same and/or different from the TEE located in the 5'UTR.

In some embodiments, a 5'UTR and/or 3'UTR of a polynucleotide of the present disclosure can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In one embodiment, the 5'UTR of a polynucleotide of the present disclosure can include 1-60, 1-55, 1-50, 1-45, 1-40, 1-35, 1-30, 1-25, 1-20, 1-15, 1-10, 9, 8, 7, 6, 5, 4, 3, 2, or 1 TEE sequences. The TEE sequences in the 5'UTR of the polynucleotide of the present disclosure can be the same or different TEE sequences. A combination of different TEE sequences in the 5'UTR of the polynucleotide of the present disclosure can include combinations in which more than one copy of any of the different TEE sequences are incorporated.

In some embodiments, the 5'UTR and/or 3'UTR comprises a spacer to separate two TEE sequences. As a non-limiting example, the spacer can be a 15 nucleotide spacer and/or other spacers known in the art. As another non-limiting example, the 5'UTR and/or 3'UTR comprises a TEE sequence-spacer module repeated at least once, at least twice, at least 3 times, at least 4 times, at least 5 times, at least 6 times, at least 7 times, at least 8 times, at least 9 times, at least 10 times, or more than 10 times in the 5'UTR and/or 3'UTR, respectively. In some embodiments, the 5'UTR and/or 3'UTR comprises a TEE sequence-spacer module repeated 1, 2, 3, 4, 5, 6, 7, 8, 9, or 10 times.

In some embodiments, the spacer separating two TEE sequences can include other sequences known in the art that can regulate the translation of the polynucleotide of the present disclosure, e.g., miR binding site sequences described herein (e.g., miR binding sites and miR seeds). As a non-limiting example, each spacer used to separate two TEE sequences can include a different miR binding site sequence or component of a miR sequence (e.g., miR seed sequence).

In some embodiments, a polynucleotide of the present disclosure comprises a miR and/or TEE sequence. In some embodiments, the incorporation of a miR sequence and/or a TEE sequence into a polynucleotide of the present disclosure can change the shape of the stem loop region, which can increase and/or decrease translation. See e.g., Kedde et al., Nature Cell Biology 2010 12(10): 1014-20, herein incorporated by reference in its entirety).

MicroRNA (miRNA) Binding Sites

Polynucleotides of the present disclosure can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences". Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the present disclosure comprises an open reading frame (ORF) encoding a polypeptide of interest and further comprises one or more miRNA binding site(s). Inclusion or incorporation of miRNA binding site(s) provides for regulation of polynucleotides of the present disclosure, and in turn, of the polypeptides encoded therefrom, based on tissue-specific and/or cell-type specific expression of naturally-occurring miRNAs.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105, miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the present disclosure comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the present disclosure comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the present disclosure, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the present disclosure, the polynucleotide can be targeted for degradation or reduced translation, provided the miRNA in question is available. This can reduce off-target effects upon delivery of the polynucleotide. For example, if a polynucleotide of the present disclosure is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

In one embodiment, a polynucleotide of the present disclosure can include at least one miRNA-binding site in the 5'UTR and/or 3'UTR in order to regulate cytotoxic or cytoprotective mRNA therapeutics to specific cells such as, but not limited to, normal and/or cancerous cells. In another embodiment, a polynucleotide of the present disclosure can include two, three, four, five, six, seven, eight, nine, ten, or more miRNA-binding sites in the 5'-UTR and/or 3'-UTR in order to regulate cytotoxic or cytoprotective mRNA therapeutics to specific cells such as, but not limited to, normal and/or cancerous cells.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells, miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the present disclosure can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the present disclosure to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the present disclosure.

To further drive the selective degradation and suppression in APCs and macrophage, a polynucleotide of the present disclosure can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2--5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the present disclosure to regulate expression of the polynucleotide in the liver. Liver specific miRNA binding sites can be engineered alone or further in combination with immune cell (e.g., APC) miRNA binding sites in a polynucleotide of the present disclosure.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the present disclosure to regulate expression of the polynucleotide in the lung. Lung specific miRNA binding sites can be engineered alone or further in combination with immune cell (e.g., APC) miRNA binding sites in a polynucleotide of the present disclosure.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. mMiRNA binding sites from any heart specific microRNA can be introduced to or removed from a polynucleotide of the present disclosure to regulate expression of the polynucleotide in the heart. Heart specific miRNA binding sites can be engineered alone or further in combination with immune cell (e.g., APC) miRNA binding sites in a polynucleotide of the present disclosure.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p, miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the present disclosure to regulate expression of the polynucleotide in the nervous system. Nervous system specific miRNA binding sites can be engineered alone or further in combination with immune cell (e.g., APC) miRNA binding sites in a polynucleotide of the present disclosure.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the present disclosure to regulate expression of the polynucleotide in the pancreas. Pancreas specific miRNA binding sites can be engineered alone or further in combination with immune cell (e.g. APC) miRNA binding sites in a polynucleotide of the present disclosure.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the present disclosure to regulate expression of the polynucleotide in the kidney. Kidney specific miRNA binding sites can be engineered alone or further in combination with immune cell (e.g., APC) miRNA binding sites in a polynucleotide of the present disclosure.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the present disclosure to regulate expression of the polynucleotide in the muscle. Muscle specific miRNA binding sites can be engineered alone or further in combination with immune cell (e.g., APC) miRNA binding sites in a polynucleotide of the present disclosure.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the present disclosure to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the present disclosure to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let-7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In one embodiment, the binding sites of embryonic stem cell specific miRNAs can be included in or removed from the 3'UTR of a polynucleotide of the present disclosure to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

As a non-limiting example, miRNA binding sites for miRNAs that are over-expressed in certain cancer and/or tumor cells can be removed from the 3'UTR of a polynucleotide of the present disclosure, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

miRNA can also regulate complex biological processes such as angiogenesis (e.g., miR-132) (Anand and Cheresh Curr Opin Hematol 2011 18:171-176). In the polynucleotides of the present disclosure, miRNA binding sites that are involved in such processes can be removed or introduced, in order to tailor the expression of the polynucleotides to biologically relevant cell types or relevant biological processes. In this context, the polynucleotides of the present disclosure are defined as auxotrophic polynucleotides.

In some embodiments, a polynucleotide of the present disclosure comprises a miRNA binding site, wherein the miRNA binding site comprises one or more nucleotide sequences selected from Table 3, including one or more copies of any one or more of the miRNA binding site sequences. In some embodiments, a polynucleotide of the present disclosure further comprises at least one, two, three, four, five, six, seven, eight, nine, ten, or more of the same or different miRNA binding sites selected from Table 3, including any combination thereof. In some embodiments, the miRNA binding site binds to miR-142 or is complementary to miR-142. In some embodiments, the miR-142 comprises SEQ ID NO:79. In some embodiments, the miRNA binding site binds to miR-142-3p or miR-142-5p. In some embodiments, the miR-142-3p binding site comprises SEQ ID NO:81. In some embodiments, the miR-142-5p binding site comprises SEQ ID NO:83. In some embodiments, the miRNA binding site comprises a nucleotide sequence at least 80%, at least 85%, at least 90%, at least 95%, or 100% identical to SEQ ID NO:81 or SEQ ID NO:83.

TABLE 3 miR-142 and miR-142 binding sites

| SEQ ID NO. | Description | Sequence |
|---|---|---|
| 79 | miR-142 | GACAGUGCAGUCACCCAUAAAGUAGA AAGCACUACUAACAGCACUGGAGGGU GUAGUGUUUCCUACUUUAUGGAUGAG UGUACUGUG |
| 80 | miR-142-3p | UGUAGUGUUUCCUACUUUAUGGA |
| 81 | miR-142-3p binding site | UCCAUAAAGUAGGAAACACUACA |
| 82 | miR-142-5p | CAUAAAGUAGAAAGCACUACU |
| 83 | miR-142-5p binding site | AGUAGUGCUUUCUACUUUAUG |

In some embodiments, a miRNA binding site is inserted in the polynucleotide of the present disclosure in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the present disclosure comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the present disclosure. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the present disclosure.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the present disclosure can further include this structured 5'UTR in order to enhance microRNA mediated gene regulation.

At least one miRNA binding site can be engineered into the 3'UTR of a polynucleotide of the present disclosure. In this context, at least two, at least three, at least four, at least five, at least six, at least seven, at least eight, at least nine, at least ten, or more miRNA binding sites can be engineered into a 3'UTR of a polynucleotide of the present disclosure. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the present disclosure. In one embodiment, miRNA binding sites incorporated into a polynucleotide of the present disclosure can be the same or can be different miRNA sites. A combination of different miRNA binding sites incorporated into a polynucleotide of the present disclosure can include combinations in which more than one copy of any of the different miRNA sites are incorporated. In another embodiment, miRNA binding sites incorporated into a polynucleotide of the present disclosure can target the same or different tissues in the body. As a non-limiting example, through the introduction of tissue-, cell-type-, or disease-specific miRNA binding sites in the 3'-UTR of a polynucleotide of the present disclosure, the degree of expression in specific cell types (e.g., hepatocytes, myeloid cells, endothelial cells, cancer cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the present disclosure. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In one embodiment, a polynucleotide of the present disclosure can be engineered to include more than one miRNA site expressed in different tissues or different cell types of a subject. As a non-limiting example, a polynucleotide of the present disclosure can be engineered to include miR-192 and miR-122 to regulate expression of the polynucleotide in the liver and kidneys of a subject. In another embodiment, a polynucleotide of the present disclosure can be engineered to include more than one miRNA site for the same tissue.

In some embodiments, the expression of a polynucleotide of the present disclosure can be controlled by incorporating at least one miR binding site in the polynucleotide and formulating the polynucleotide for administration. As a non-limiting example, a polynucleotide of the present disclosure can be targeted to a tissue or cell by incorporating a miRNA binding site and formulating the polynucleotide in a lipid nanoparticle comprising an ionizable e.g., an ionizable amino lipid, sometimes referred to in the prior art as an "ionizable cationic lipid", including any of the lipids described herein.

A polynucleotide of the present disclosure can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the present disclosure can be designed for optimal protein expression in a tissue or cell, or in the context of a biological condition.

In some embodiments, a polynucleotide of the present disclosure can be designed to incorporate miRNA binding sites that either have 100% identity to known miRNA seed sequences or have less than 100% identity to miRNA seed sequences. In some embodiments, a polynucleotide of the present disclosure can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A Pumilio-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the present disclosure can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the present disclosure described herein.

In another embodiment, a miRNA sequence in the 5'UTR of a polynucleotide of the present disclosure can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the present disclosure can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site. As another non-limiting example, the site of translation initiation can be located within a miR-122 sequence such as the seed sequence or the mir-122 binding site.

In some embodiments, a polynucleotide of the present disclosure can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the present disclosure can be specific to the hematopoietic system. As another non-limiting example, a miRNA incorporated into a polynucleotide of the present disclosure to dampen antigen presentation is miR-142-3p.

In some embodiments, a polynucleotide of the present disclosure can include at least one miRNA in order to dampen expression of the encoded polypeptide in a tissue or cell of interest. As a non-limiting example, a polynucleotide of the present disclosure can include at least one miR-122 binding site in order to dampen expression of an encoded polypeptide of interest in the liver. As another non-limiting example a polynucleotide of the present disclosure can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the present disclosure can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the present disclosure more unstable in antigen presenting cells. Non-limiting examples of these miRNAs include mir-142-5p, mir-142-3p, mir-146a-5p, and mir-146-3p.

In one embodiment, a polynucleotide of the present disclosure comprises at least one miRNA sequence in a region of the polynucleotide that can interact with a RNA binding protein.

In some embodiments, the polynucleotide of the present disclosure (e.g., a RNA, e.g., an mRNA) comprising (i) a sequence-optimized nucleotide sequence (e.g., an ORF) encoding a JAG1 polypeptide (e.g., the wild-type sequence, functional fragment, or variant thereof) and (ii) a miRNA binding site (e.g., a miRNA binding site that binds to miR-142).

In some embodiments, the polynucleotide of the present disclosure comprises a uracil-modified sequence encoding a JAG1 polypeptide disclosed herein and a miRNA binding site disclosed herein, e.g., a miRNA binding site that binds to miR-142. In some embodiments, the uracil-modified sequence encoding a JAG1 polypeptide comprises at least one chemically modified nucleobase, e.g., 5-methoxyuracil. In some embodiments, at least 95% of a type of nucleobase (e.g., uricil) in a uracil-modified sequence encoding a JAG1 polypeptide of the present disclosure are modified nucleobases. In some embodiments, at least 95% of uricil in a uracil-modified sequence encoding a JAG1 polypeptide is 5-methoxyuridine. In some embodiments, the polynucleotide comprising a nucleotide sequence encoding a JAG1 polypeptide disclosed herein and a miRNA binding site is formulated with a delivery agent, e.g., a compound having the Formula (I), (IA), (II), (IIa), (IIb), (IIc), (IId) or (IIe), e.g., any of Compounds 1-232.

3' UTRs

In certain embodiments, a polynucleotide of the present disclosure (e.g., a polynucleotide comprising a nucleotide sequence encoding a JAG1 polypeptide of the present disclosure) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the present disclosure comprises a binding site for regulatory proteins or microRNAs.

Regions Having a 5' Cap

The present disclosure also includes a polynucleotide that comprises both a 5' Cap and a polynucleotide of the present disclosure (e.g., a polynucleotide comprising a nucleotide sequence encoding a JAG1 polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present disclosure (e.g., a polynucleotide comprising a nucleotide sequence encoding a JAG1 polypeptide) incorporate a cap moiety.

In some embodiments, polynucleotides of the present disclosure (e.g., a polynucleotide comprising a nucleotide sequence encoding a JAG1 polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as a-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the present disclosure.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

In some embodiments, the cap is a dinucleotide cap analog. As a non-limiting example, the dinucleotide cap analog can be modified at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-$m^{3'-O}$G(5')ppp(5')G cap analog (See. e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present disclosure is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the present disclosure (e.g., a polynucleotide comprising a nucleotide sequence encoding a JAG1 polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present disclosure are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present disclosure, 5' terminal caps can include endogenous caps or cap analogs. According to the present disclosure, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

Poly-A Tails

In some embodiments, the polynucleotides of the present disclosure (e.g., a polynucleotide comprising a nucleotide sequence encoding a JAG1 polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present disclosure, terminal groups on the poly A tail can be incorporated for stabilization. Polynucleotides of the present disclosure can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present disclosure can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present disclosure. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present disclosure are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

Start Codon Region

The present disclosure also includes a polynucleotide that comprises both a start codon region and the polynucleotide described herein (e.g., a polynucleotide comprising a nucleotide sequence encoding a JAG1 polypeptide). In some embodiments, the polynucleotides of the present disclosure can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miR binding site. The perfect complement of a miR binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

Stop Codon Region

The present disclosure also includes a polynucleotide that comprises both a stop codon region and the polynucleotide described herein (e.g., a polynucleotide comprising a nucleotide sequence encoding a JAG1 polypeptide). In some embodiments, the polynucleotides of the present disclosure can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present disclosure include the stop codon TGA in the case or DNA, or the stop codon UGA in the case of RNA, and one additional stop codon. In a further embodiment the addition stop codon can be TAA or UAA. In another embodiment, the polynucleotides of the present disclosure include three consecutive stop codons, four stop codons, or more.

Insertions and Substitutions

The present disclosure also includes a polynucleotide of the present disclosure that further comprises insertions and/or substitutions.

In some embodiments, the 5'UTR of the polynucleotide can be replaced by the insertion of at least one region and/or string of nucleosides of the same base. The region and/or string of nucleotides can include, but is not limited to, at least 3, at least 4, at least 5, at least 6, at least 7 or at least 8 nucleotides and the nucleotides can be natural and/or unnatural. As a non-limiting example, the group of nucleotides can include 5-8 adenine, cytosine, thymine, a string of any of the other nucleotides disclosed herein and/or combinations thereof.

In some embodiments, the 5'UTR of the polynucleotide can be replaced by the insertion of at least two regions and/or strings of nucleotides of two different bases such as, but not limited to, adenine, cytosine, thymine, any of the other nucleotides disclosed herein and/or combinations thereof. For example, the 5'UTR can be replaced by inserting 5-8 adenine bases followed by the insertion of 5-8 cytosine bases. In another example, the 5'UTR can be replaced by inserting 5-8 cytosine bases followed by the insertion of 5-8 adenine bases.

In some embodiments, the polynucleotide can include at least one substitution and/or insertion downstream of the transcription start site that can be recognized by an RNA polymerase. As a non-limiting example, at least one substitution and/or insertion can occur downstream of the transcription start site by substituting at least one nucleic acid in the region just downstream of the transcription start site (such as, but not limited to, +1 to +6). Changes to region of nucleotides just downstream of the transcription start site can affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleoside can cause a silent mutation of the sequence or can cause a mutation in the amino acid sequence.

In some embodiments, the polynucleotide can include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In some embodiments, the polynucleotide can include the substitution of at least 1, at least 2, at least 3, at least 4, at least 5 or at least 6 guanine bases in the region just downstream of the transcription start site. As a non-limiting example, if the nucleotides in the region are GGGAGA, the guanine bases can be substituted by at least 1, at least 2, at least 3 or at least 4 adenine nucleotides. In another non-limiting example, if the nucleotides in the region are GGGAGA the guanine bases can be substituted by at least 1, at least 2, at least 3 or at least 4 cytosine bases. In another non-limiting example, if the nucleotides in the region are GGGAGA the guanine bases can be substituted by at least 1, at least 2, at least 3 or at least 4 thymine, and/or any of the nucleotides described herein.

In some embodiments, the polynucleotide can include at least one substitution and/or insertion upstream of the start codon. For the purpose of clarity, one of skill in the art would appreciate that the start codon is the first codon of the protein coding region whereas the transcription start site is the site where transcription begins. The polynucleotide can include, but is not limited to, at least 1, at least 2, at least 3, at least 4, at least 5, at least 6, at least 7 or at least 8 substitutions and/or insertions of nucleotide bases. The nucleotide bases can be inserted or substituted at 1, at least 1, at least 2, at least 3, at least 4 or at least 5 locations upstream of the start codon. The nucleotides inserted and/or substituted can be the same base (e.g., all A or all C or all T or all G), two different bases (e.g., A and C, A and T. or C and T), three different bases (e.g., A, C and T or A, C and T) or at least four different bases.

As a non-limiting example, the guanine base upstream of the coding region in the polynucleotide can be substituted with adenine, cytosine, thymine, or any of the nucleotides described herein. In another non-limiting example the substitution of guanine bases in the polynucleotide can be designed so as to leave one guanine base in the region downstream of the transcription start site and before the start codon (see Esvelt et al. Nature (2011) 472(7344):499-503; the contents of which is herein incorporated by reference in its entirety). As a non-limiting example, at least 5 nucleotides can be inserted at 1 location downstream of the transcription start site but upstream of the start codon and the at least 5 nucleotides can be the same base type.

Polynucleotide Comprising an mRNA Encoding a JAG1 Polypeptide

In certain embodiments, a polynucleotide of the present disclosure, for example a polynucleotide comprising an mRNA nucleotide sequence encoding a JAG1 polypeptide, comprises from 5' to 3' end:

(i) a 5' cap provided above;
(ii) a 5' UTR, such as the sequences provided above;
(iii) an open reading frame encoding a JAG1 polypeptide, e.g., a sequence optimized nucleic acid sequence encoding JAG1 disclosed herein;
(iv) at least one stop codon;
(v) a 3' UTR, such as the sequences provided above; and
(vi) a poly-A tail provided above.

In some embodiments, the polynucleotide further comprises a miRNA binding site, e.g, a miRNA binding site that binds to miRNA-142. In some embodiments, the 5'UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type JAG1.

Methods of Making Polynucleotides

The present disclosure also provides methods for making a polynucleotide of the present disclosure (e.g., a polynucleotide comprising a nucleotide sequence encoding a JAG1 polypeptide) or a complement thereof.

In some aspects, a polynucleotide (e.g., a RNA, e.g., an mRNA) disclosed herein, and encoding a JAG1 polypeptide, can be constructed using in vitro transcription. In other aspects, a polynucleotide (e.g., a RNA, e.g., an mRNA) disclosed herein, and encoding a JAG1 polypeptide, can be constructed by chemical synthesis using an oligonucleotide synthesizer.

In other aspects, a polynucleotide (e.g., a RNA, e.g., an mRNA) disclosed herein, and encoding a JAG1 polypeptide is made by using a host cell. In certain aspects, a polynucleotide (e.g., a RNA, e.g., an mRNA) disclosed herein, and encoding a JAG1 polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a JAG1 polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present disclosure disclosed herein (e.g., a polynucleotide comprising a nucleotide sequence encoding a JAG1 polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present disclosure. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, deletional variants and/or covalent derivatives.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, hermus aqualicus (Taq) DNA polymerases, and the T7 RNA and DNA polymerases, is among the best studied of these families. Another large family is DNA polymerase $\alpha$ (pol $\alpha$) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present disclosure is a Syn5 RNA polymerase. (see Zhu et al. Nucleic Acids Research 2013, doi:10.1093/nar/gkt 1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 86 as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the present disclosure.

For example, polymerase chain reaction (PCR), strand displacement amplification (SDA), nucleic acid sequence-based amplification (NASBA), also called transcription mediated amplification (TMA), and rolling-circle amplification (RCA) can be utilized in the manufacture of one or more regions of the polynucleotides of the present disclosure.

Assembling polynucleotides or nucleic acids by a ligase is also widely used. DNA or RNA ligases promote intermolecular ligation of the 5' and 3' ends of polynucleotide chains through the formation of a phosphodiester bond.

b. Chemical Synthesis

Standard methods can be applied to synthesize an isolated polynucleotide sequence encoding an isolated polypeptide of interest, such as a polynucleotide of the present disclosure (e.g., a polynucleotide comprising a nucleotide sequence encoding a JAG1 polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No.

US20130115272; or U.S. Pat. No. 8,999,380 or 8,710,200, all of which are herein incorporated by reference in their entireties.

c. Purification of Polynucleotides Encoding JAG1

Purification of the polynucleotides described herein (e.g., a polynucleotide comprising a nucleotide sequence encoding a JAG1 polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNA™ oligo-T capture probes (EXIQON Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the present disclosure (e.g., a polynucleotide comprising a nucleotide sequence encoding a JAG1 polypeptide) removes impurities that can reduce or remove an unwanted immune response, e.g., reducing cytokine activity.

In some embodiments, the polynucleotide of the present disclosure (e.g., a polynucleotide comprising a nucleotide sequence encoding a JAG1 polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the present disclosure (e.g., a polynucleotide comprising a nucleotide sequence a JAG1 polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded JAG1 protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a JAG1 polypeptide comprising one or more of the point mutations known in the art.

In some embodiments, the use of RP-HPLC purified polynucleotide increases JAG1 protein expression levels in cells when introduced into those cells, e.g., by 10-100%, i.e., at least about 10%, at least about 200%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of JAG1 protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional JAG1 protein expression levels in cells when introduced into those cells, e.g., by 10-100%, i.e., at least about 10%, at least about 20%, at least about 25%, at least about 300%, at least about 35%, at least about 40%, at least about 45%, at least about 50%, at least about 55%, at least about 60%, at least about 65%, at least about 70%, at least about 75%, at least about 800%, at least about 90%, at least about 95%, or at least about 100% with respect to the functional expression levels of JAG1 protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable JAG1 activity in cells when introduced into those cells, e.g., by 10-100%, i.e., at least about 100%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional JAG1 in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding JAG1

In some embodiments, the polynucleotides of the present disclosure (e.g., a polynucleotide comprising a nucleotide sequence encoding a JAG1 polypeptide), their expression products, as well as degradation products and metabolites can be quantified according to methods known in the art.

In some embodiments, the polynucleotides of the present disclosure can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present disclosure differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Pharmaceutical Compositions and Formulations

The present disclosure provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a JAG1 polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a JAG1 polypeptide. In some embodiments, the polynucleotide further comprises a miRNA binding site, e.g., a miRNA binding site that binds miR-142, and/or miR-126.

Pharmaceutical compositions or formulation can optionally comprise one or more additional active substances, e.g., therapeutically and/or prophylactically active substances. Pharmaceutical compositions or formulation of the present disclosure can be sterile and/or pyrogen-free. General considerations in the formulation and/or manufacture of pharmaceutical agents can be found, for example, in *Remington: The Science and Practice of Pharmacy* 21 ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the present disclosure. As a non-limiting example, the composition or formulation can contain 1, 2, 3, 4 or 5 polynucleotides of the present disclosure. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an IVT polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present disclosure provides pharmaceutical formulations that comprise a polynucleotide described herein (e.g., a polynucleotide comprising a nucleotide sequence encoding a JAG1 polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent, (e.g., a compound having the Formula (I), (IA), (II), (IIa), (IIb), (IIc), (IId) or (IIe), e.g., any of Compounds 1-232).

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition. A. R. Gennaro (Lippincott, Williams & Wilkins. Baltimore, MD, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, acorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present disclosure can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

Accelerated Blood Clearance

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B a cells and they do not activate conventional B cells. Compounds and compositions that do not activate B1a cells and conventional B cells may in some embodiments be referred to herein as B a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as “poly-specific” or “poly-reactive”, indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that “does not promote ABC” refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 300%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body’s abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

Delivery Agents a. Lipid Compound

The present disclosure provides pharmaceutical compositions with advantageous properties. For example, the lipids described herein (e.g. those having any of Formula (I), (IA), (II), (IIa), (IIb), (IIc), (IId), (IIe), (III), (IV), (V), or (VI) may be advantageously used in lipid nanoparticle compositions for the delivery of therapeutic and/or prophylactic agents to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent.

In one set of embodiments, lipid nanoparticles (LNPs) are provided. In one embodiment, a lipid nanoparticle comprises lipids including an ionizable lipid, a structural lipid, a phospholipid, and mRNA. Each of the LNPs described herein may be used as a formulation for the mRNA described herein. In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid:about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% structural lipid. In some embodiments, the LNP comprises a molar ratio of about 55% ionizable lipid, about 2.5% PEG lipid, about 32.5% cholesterol and about 10% structural lipid. In some embodiments, the ionizable lipid is an ionizable amino or "ionizable cationic lipid" and the structural lipid is a neutral lipid, and the sterol is a cholesterol. In some embodiments, the LNP has a molar ratio of 50:38.5:10:1.5 of ionizable lipid:cholesterol:PEG2000-DMG:DSPC.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. For instance, an ionizable lipid may be positively charged at lower pH, in which case it could be referred to as a "Cationic lipid". For example, an ionizable molecule may comprise an amine group. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid. In one embodiment, the ionizable amino lipid may have a positively charged hydrophilic head and a hydrophobic tail that are connected via a linker structure.

A lipid nanoparticle composition of the invention may include one or more ionizable (e.g., ionizable amino) lipids (e.g., lipids that may have a positive or partial positive charge at physiological pH). Ionizable lipids may be selected from the non-limiting group consisting of 3-(didodecylamino)-N1,N1,4-tridodecyl-1-piperazineethanamine (KL10), N1-[2-(didodecylamino)ethyl] N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl-4-(dimethylamino)butanoate (DLin-MC3-DMA), 2,2-dilinoleyl-4-(2 dimethylaminoethyl)-[1,3]-dioxolane (DLin-KC2-DMA), 1,2-dioleyloxy-N,N-dimethylaminopropane (DODMA), 2-({8 [(3β)-cholest-5-en-3-yloxy]octyl}oxy) N,N dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S) 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable lipid may also be a lipid including a cyclic amine group.

Ionizable lipids can also be the compounds disclosed in International Publication No. WO 2017/075531 A1, hereby incorporated by reference in its entirety. For example, the ionizable amino lipids include, but not limited to:

Compound A

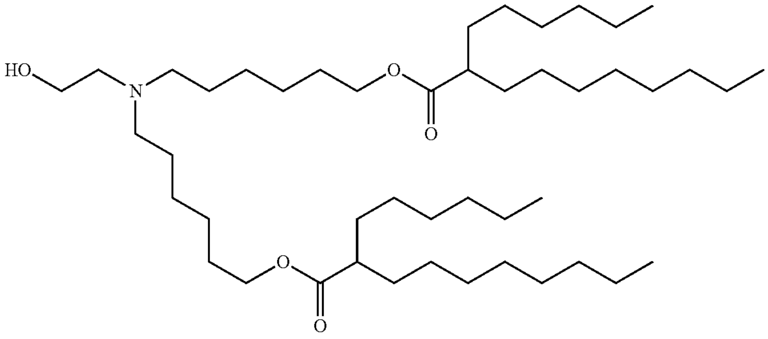

Compound B

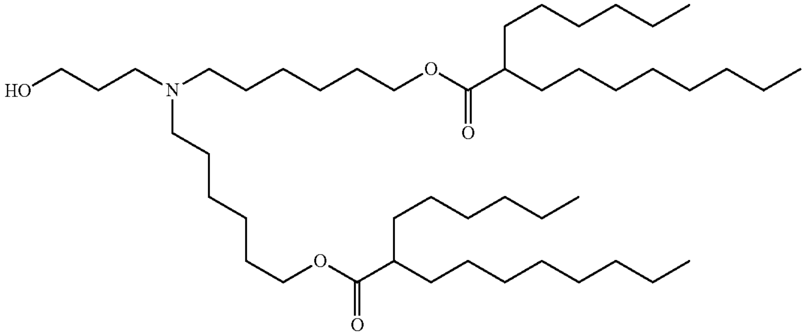

Compound C

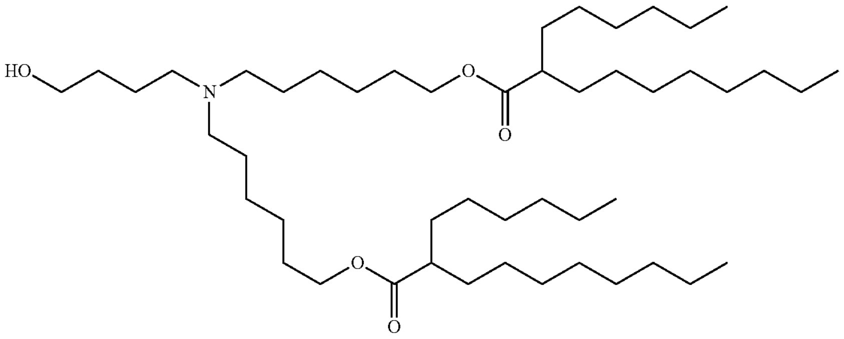

Ionizable lipids can also be the compounds disclosed in International Publication No. WO 2015/199952 A1, hereby incorporated by reference in its entirety. For example, the ionizable amino lipids include, but not limited to:
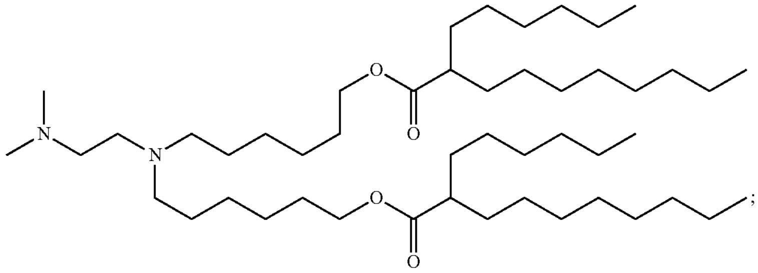
;
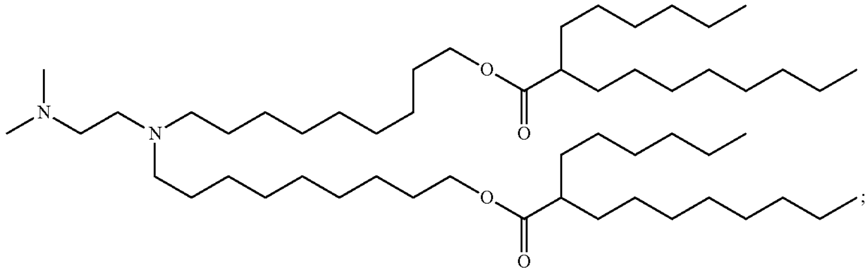
;
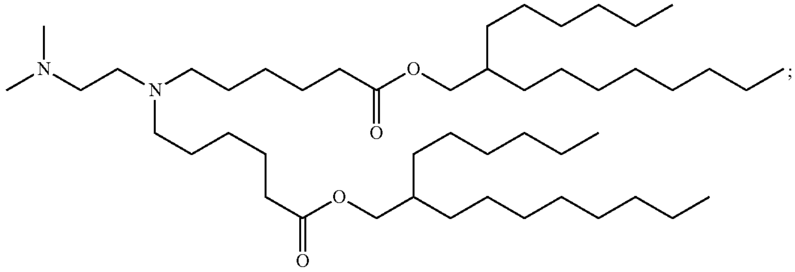
;
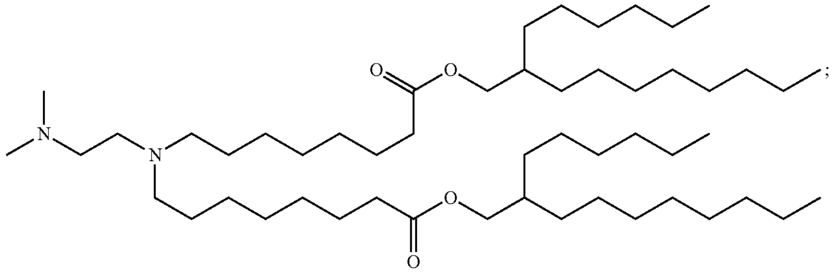
;
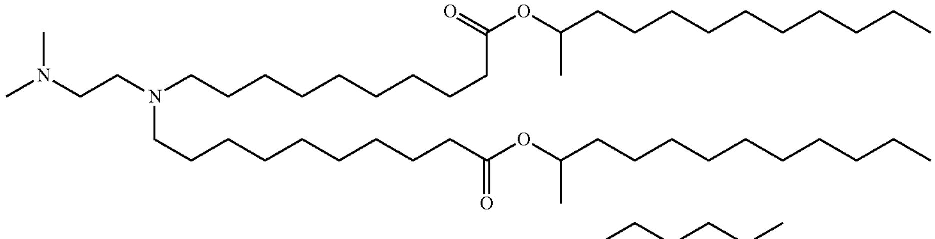
;
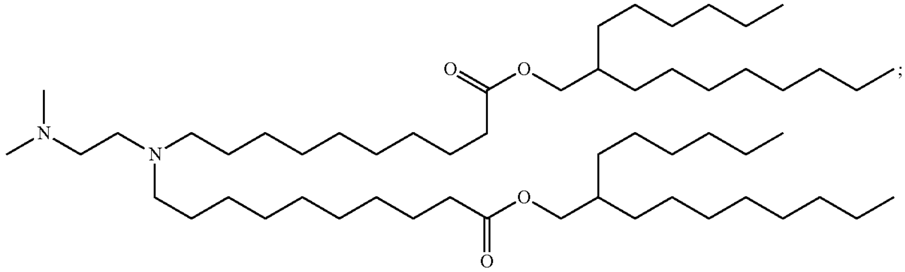

-continued

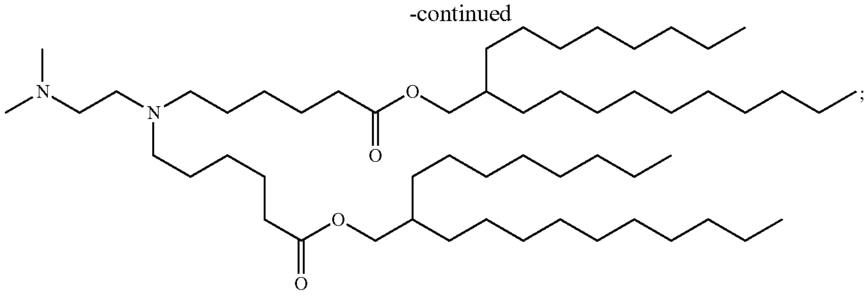

;

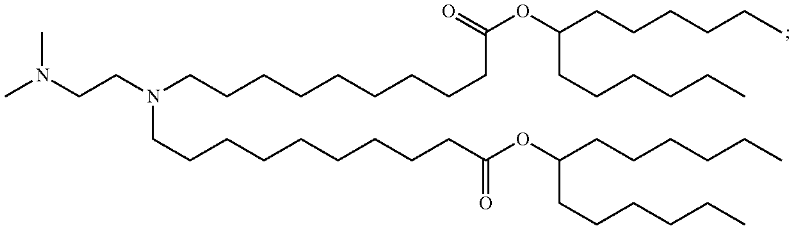

;

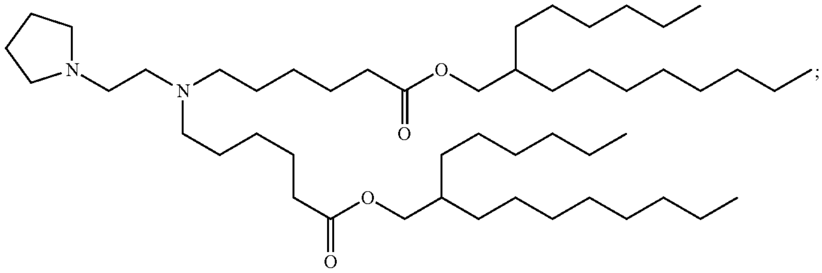

;

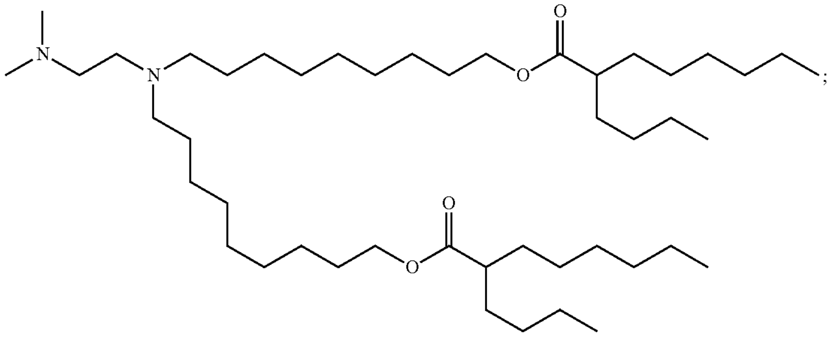

;

and any combination thereof.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety. In another embodiment, the lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In some embodiments, the ionizable lipid may be a compound of Formula (I):

(I)

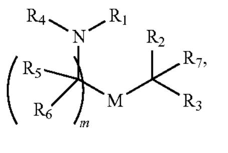

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, —N(R)S(O)$_2$R, —N(R)C(O)N(R)$_2$, —N(R)C(S)N(R)$_2$, —N(R)R, —O(CH$_2$)$_n$OR, —N(R)C(═NR$_9$)N(R)$_2$, —N(R)C(═CHR)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═NR$_9$)N(R)$_2$, —N(OR)C(═CHR$_9$)N(R)$_2$, —C(═NR$_9$)N(R)$_2$, —C(═NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(═NR$_9$)N(R)$_2$, —N(R)C(═CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═NR$_9$)N(R)$_2$, —N(OR)C(═CHR$_9$)N(R)$_2$, —C(═NR$_9$)N(R)$_2$, —C(═NR$_9$)R, —C(O)N(R)OR, and a 5- to 14-membered heterocycloalkyl having one or more heteroatoms selected from N, O, and S which is substituted with one or more substituents selected from oxo (═O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(═NR$_9$)N(R)$_2$, —N(R)C(═CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═NR$_9$)N(R)$_2$, —N(OR)C(═CHR$_9$)N(R)$_2$, —C(═NR$_9$)R, —C(O)N(R)OR, and —C(═NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii)

$R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$, is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl. $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)R$, —C(O)N(R)OR, and —$C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ is alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)CHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

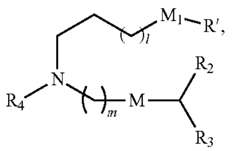

or a salt or isomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —$NHC(S)N(R)_2$, —$NHC(O)N(R)_2$, —N(R)C(O)R, —$N(R)S(O)_2R$, —$N(R)R_8$, —$NHC(=NR_9)N(R)_2$, —$NHC(=CHR_9)N(R)_2$, —$OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

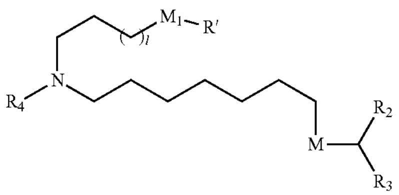

or a salt or isomer thereof, wherein l is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —$NHC(S)N(R)_2$, —$NHC(O)N(R)_2$, —N(R)C(O)R, —$N(R)S(O)_2R$, —$N(R)R_8$, —$NHC(=NR_9)N(R)_2$, —$NHC(=CHR_9)N(R)_2$, —$OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (He):

(IIa)

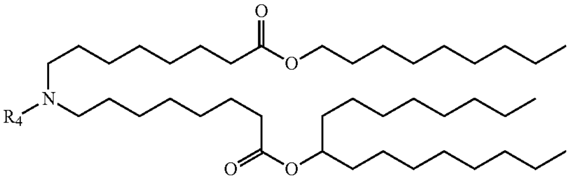

, (IIb)

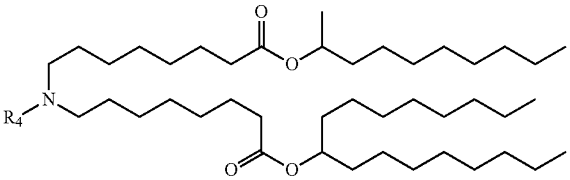

, (IIc)

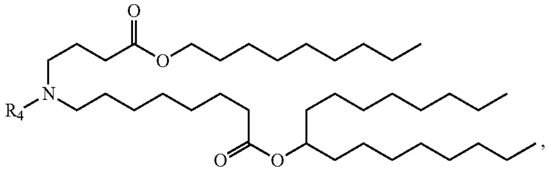

, or (IIe)

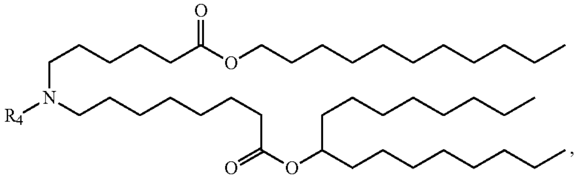

, or a salt or isomer thereof, wherein $R_4$ is as described herein.

In some embodiments, a subset of compounds of Formula (I) includes those of Formula (IId):

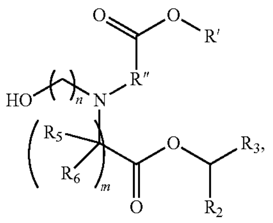

(IId)

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)

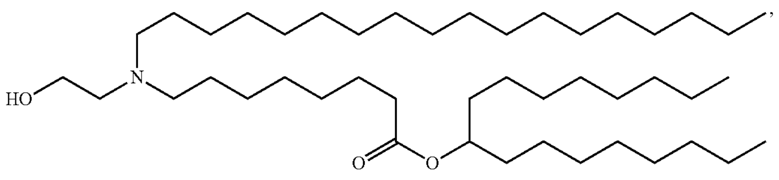

(Compound 2)

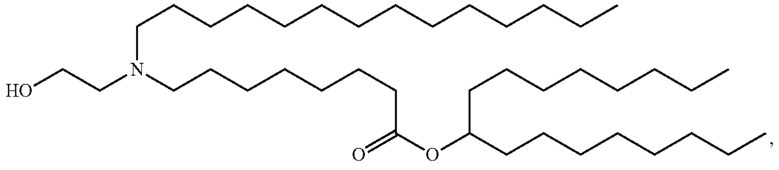

(Compound 3)

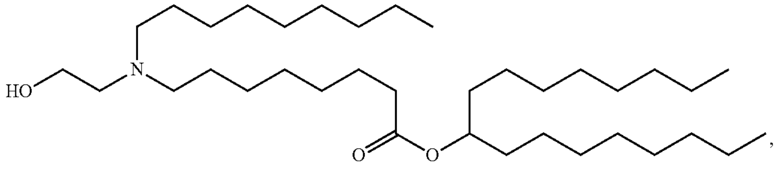

(Compound 4)

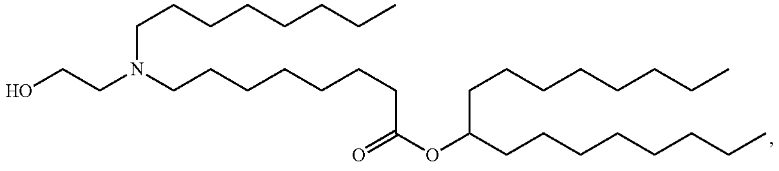

(Compound 5)

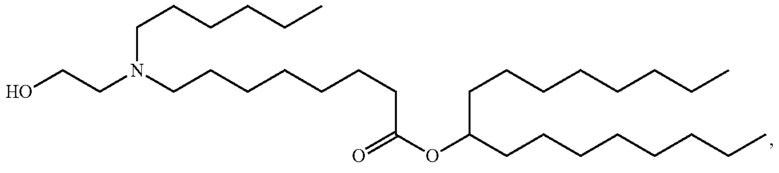

(Compound 6)

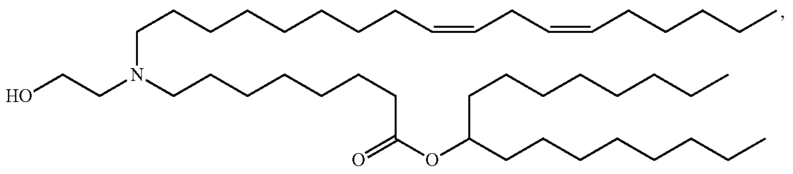

(Compound 7)

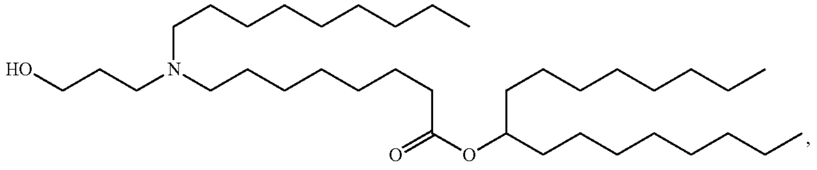

-continued
(Compound 8)
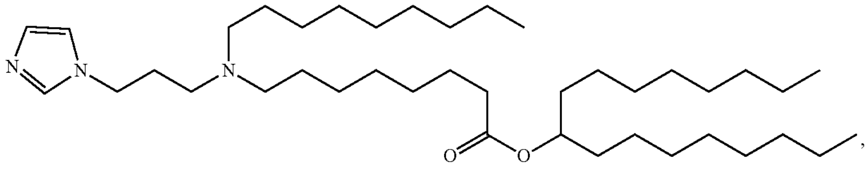
,
(Compound 9)
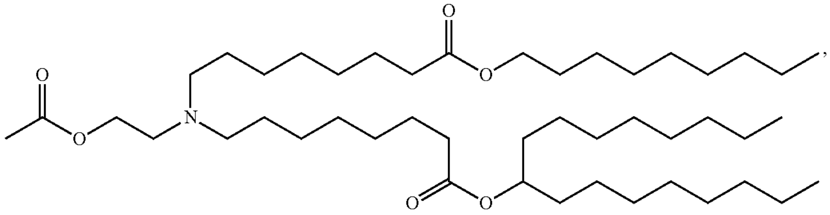
,
(Compound 10)
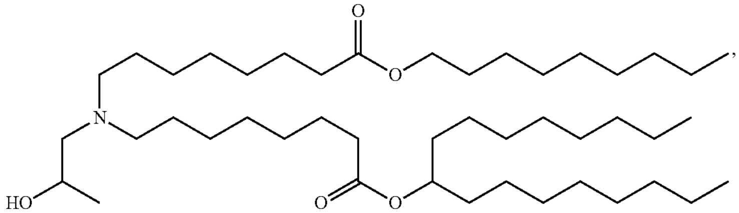
,
(Compound 11)
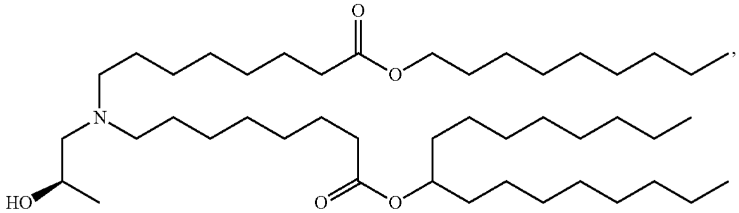
,
(Compound 12)
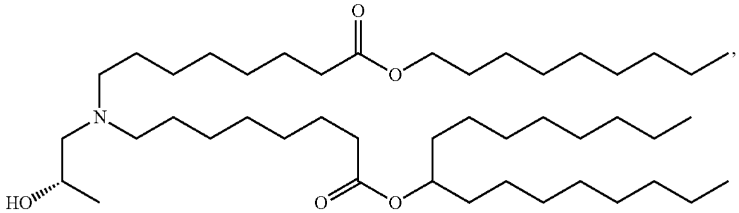
,
(Compound 13)
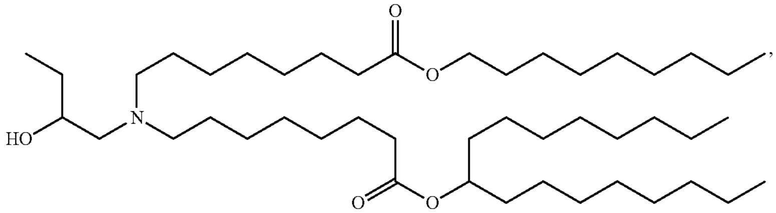
,
(Compound 14)
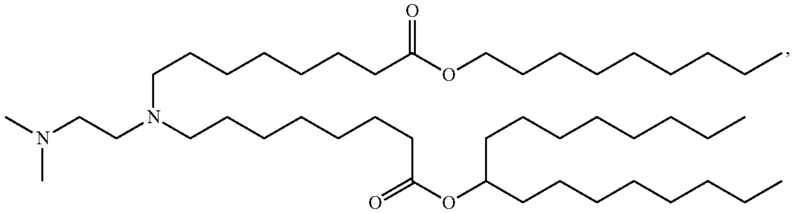
, -continued
(Compound 15)
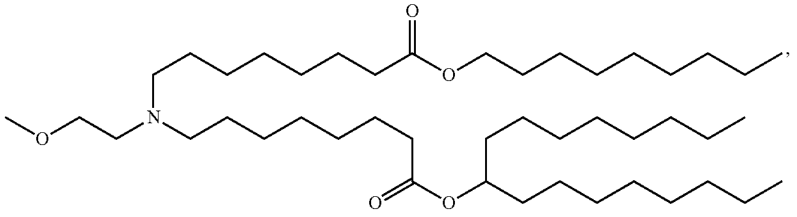
(Compound 16)
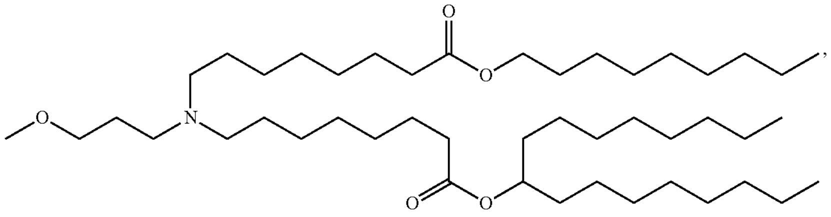
(Compound 17)
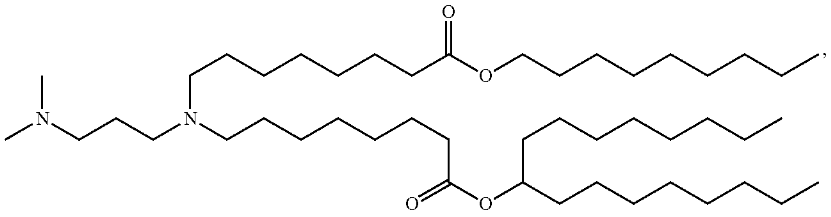
(Compound 230)
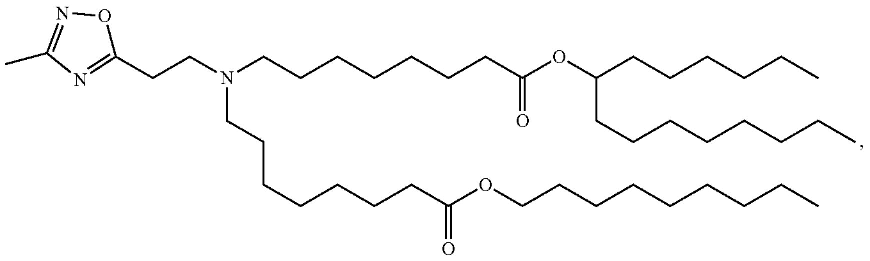
(Compound 231)
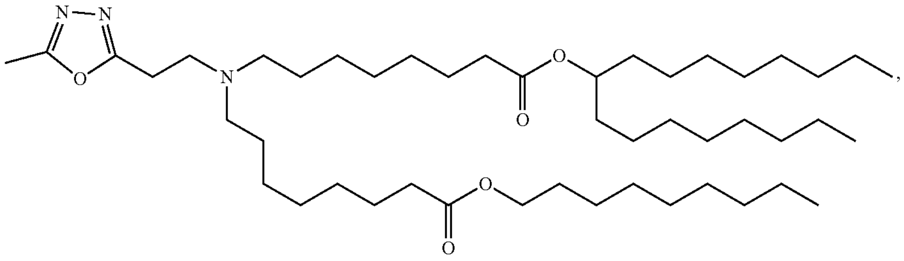
(Compound 18)
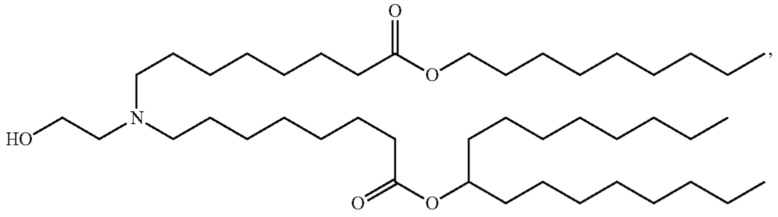

-continued
(Compound 19)
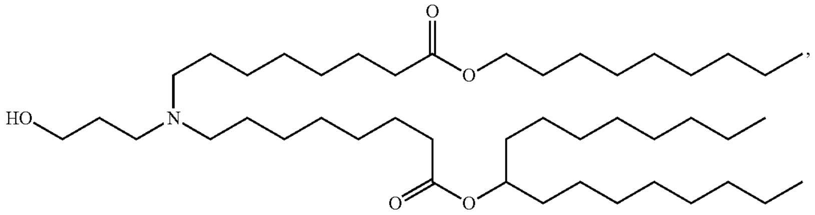
(Compound 20)
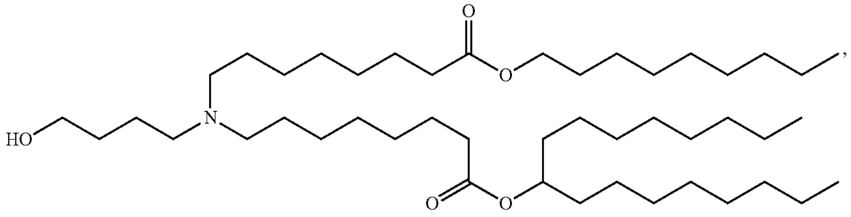
(Compound 21)
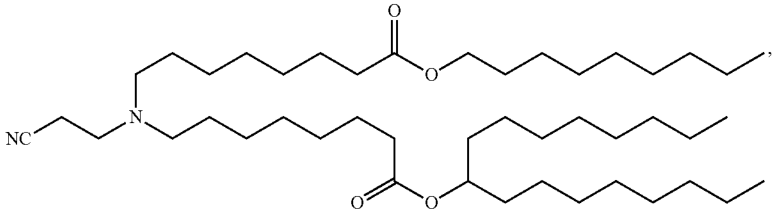
(Compound 22)
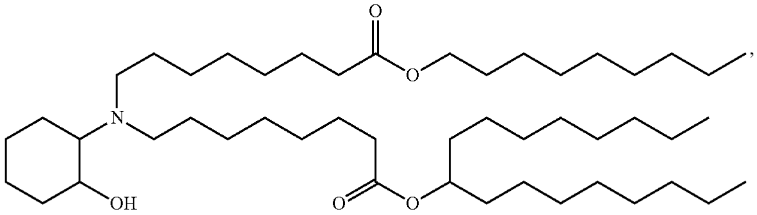
(Compound 23)
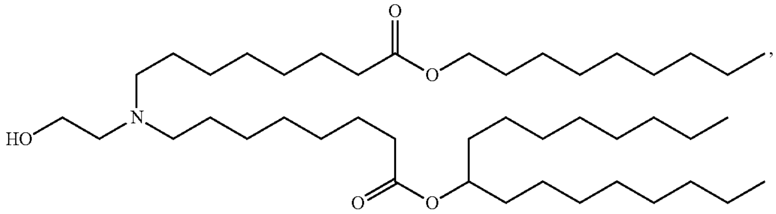
(Compound 24)
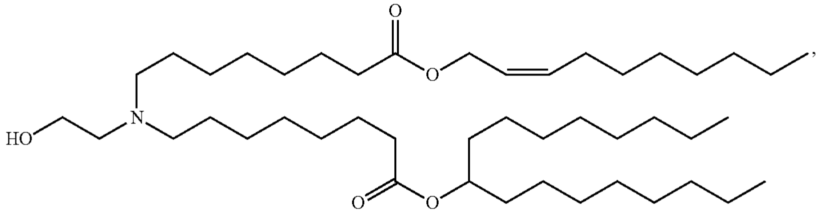
(Compound 25)
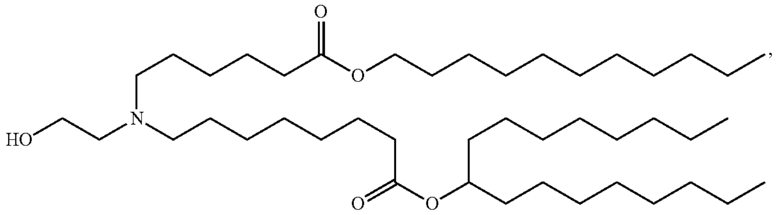

-continued
(Compound 26)
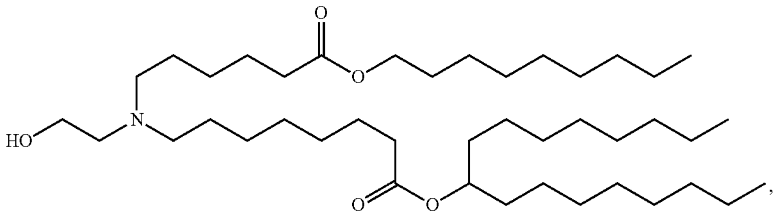
,
(Compound 27)
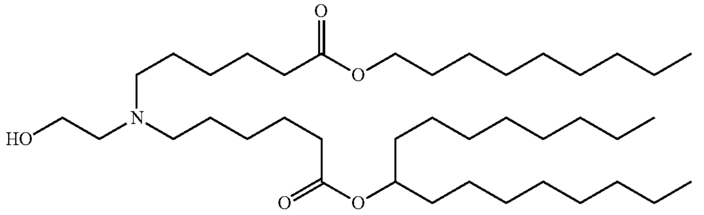
,
(Compound 28)
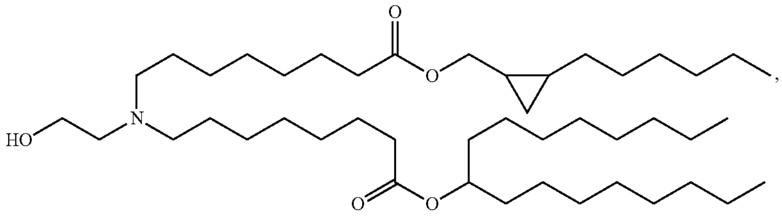
,
(Compound 29)
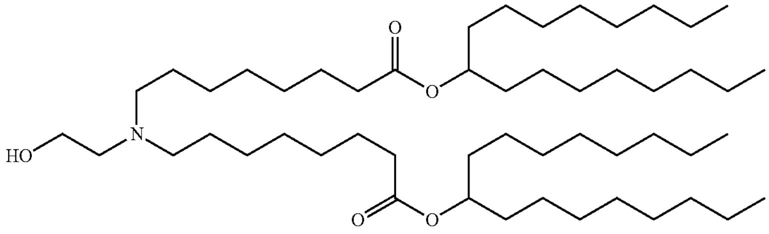
,
(Compound 30)
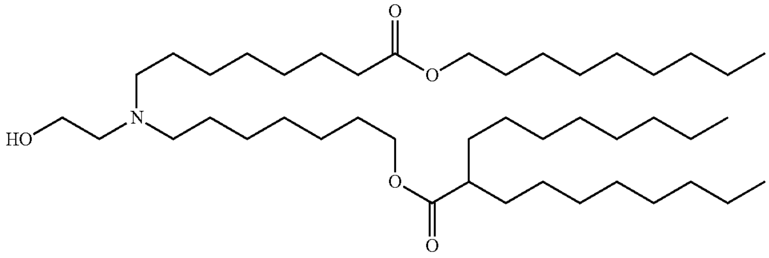
,
(Compound 31)
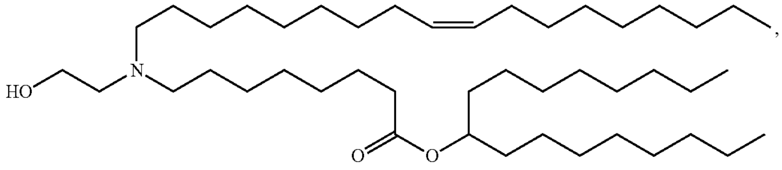
,
(Compound 32)
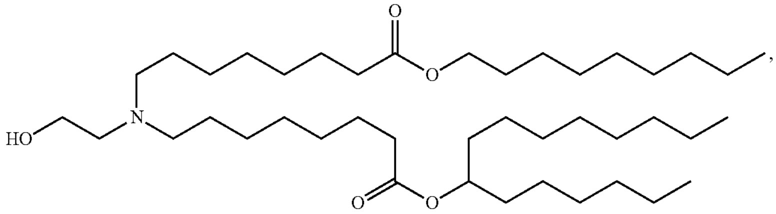
, -continued
(Compound 33)
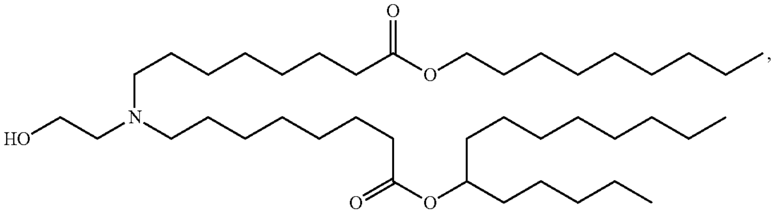
(Compound 34)
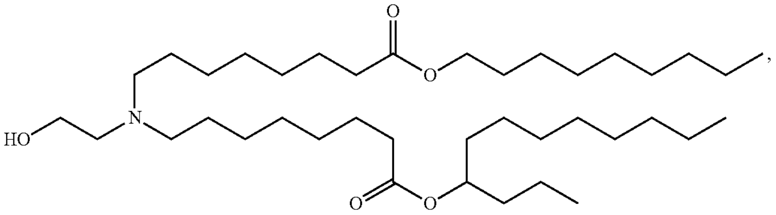
(Compound 35)
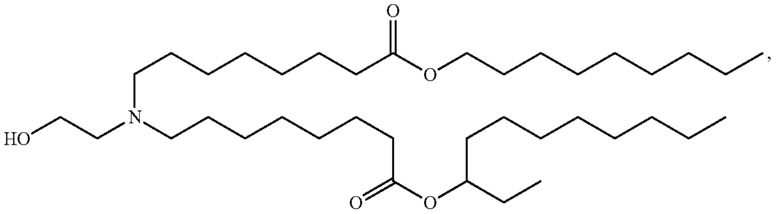
(Compound 36)
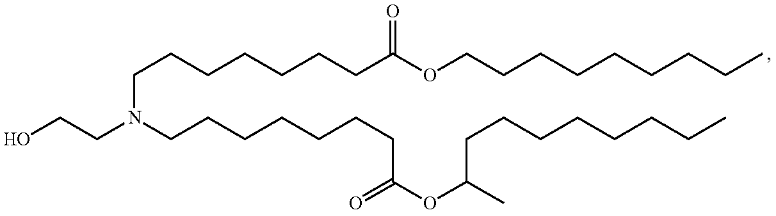
(Compound 37)
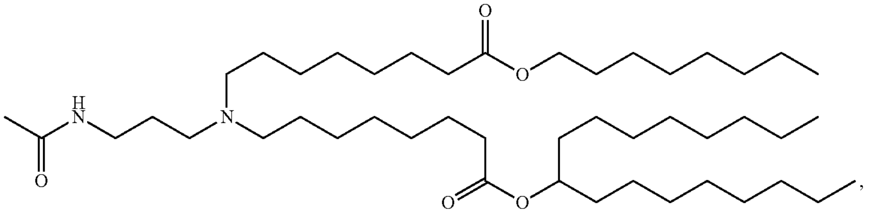
(Compound 38)
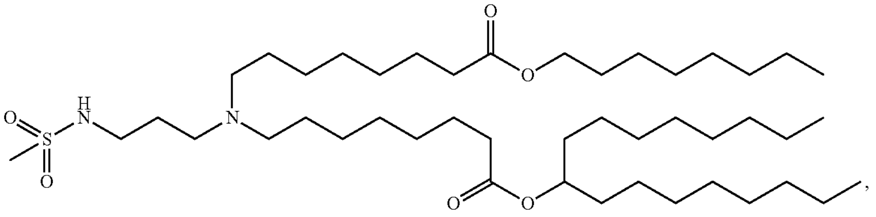
(Compound 39)
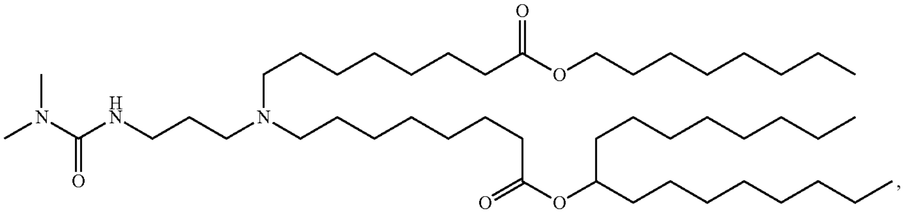

-continued
(Compound 40)
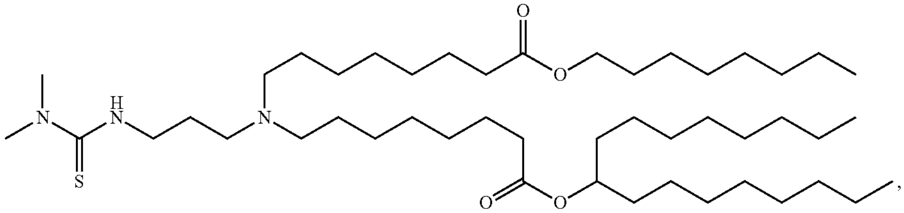
,
(Compound 41)
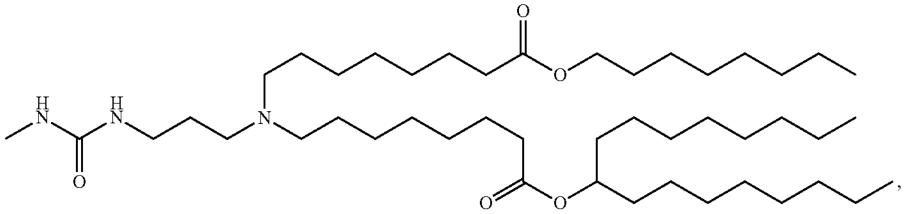
,
(Compound 42)
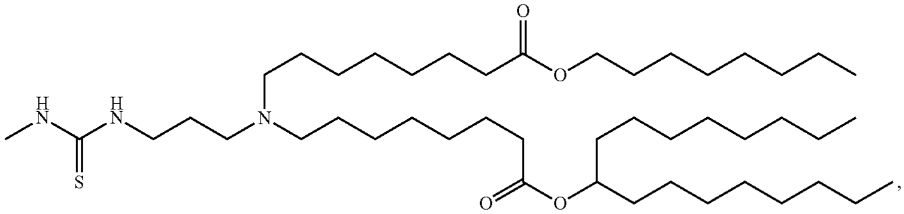
,
(Compound 43)
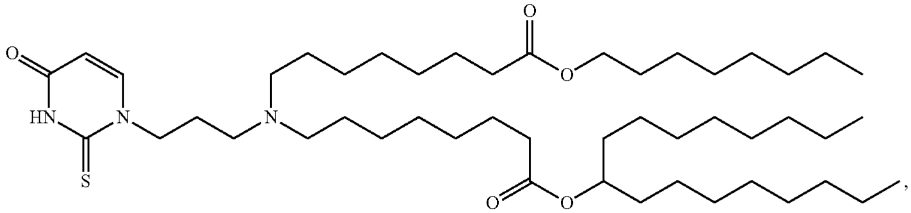
,
(Compound 44)
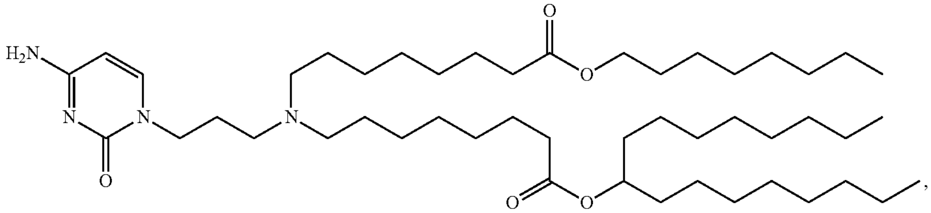
,
(Compound 45)
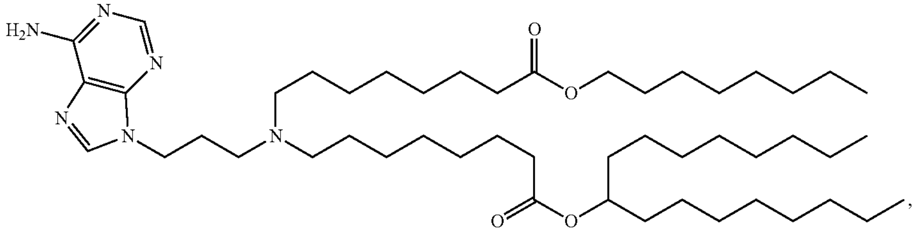
,
(Compound 46)
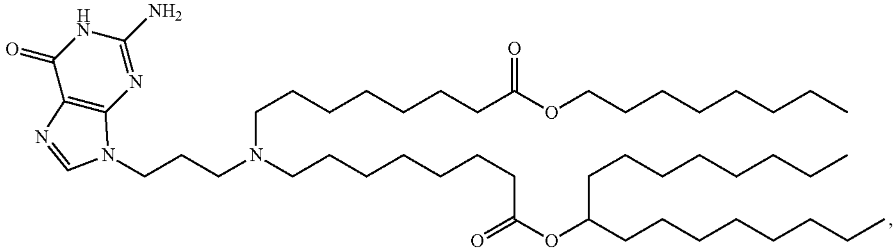
, -continued
(Compound 47)
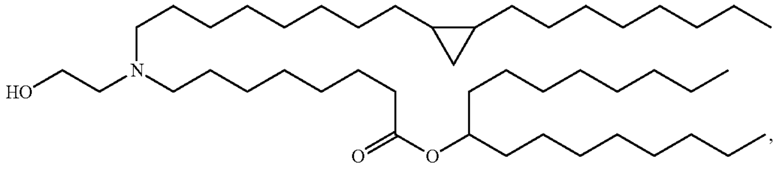
,
(Compound 48)
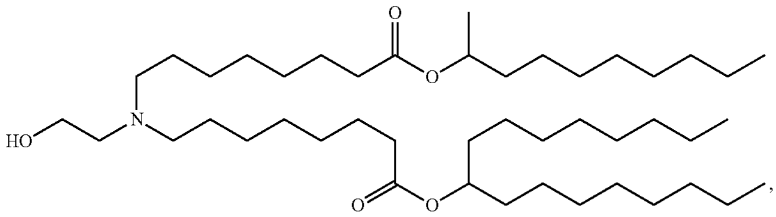
,
(Compound 49)
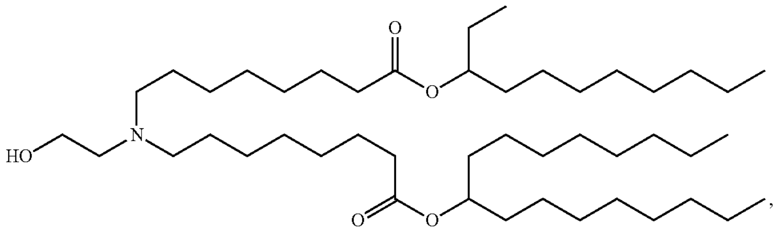
,
(Compound 50)
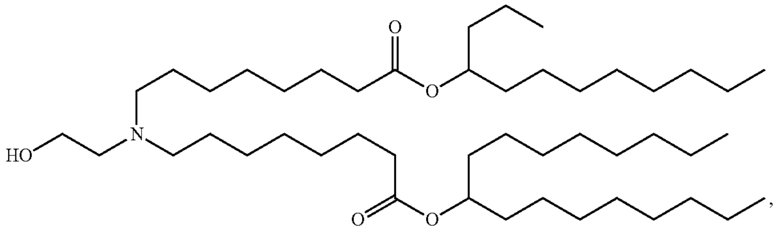
,
(Compound 51)
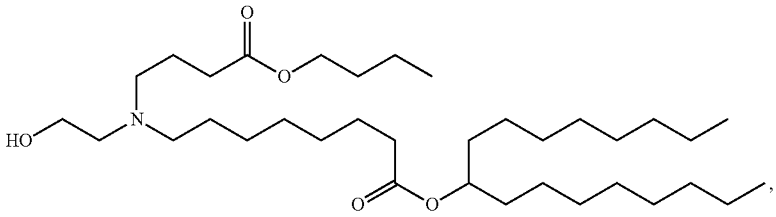
,
(Compound 52)
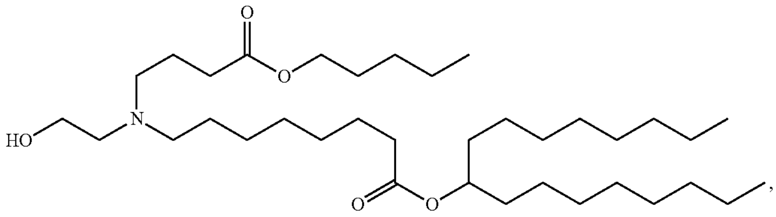
,
(Compound 53)
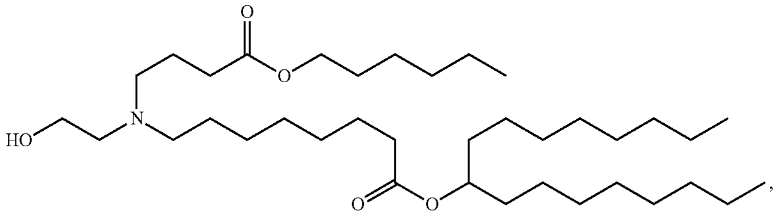
, -continued
(Compound 54)
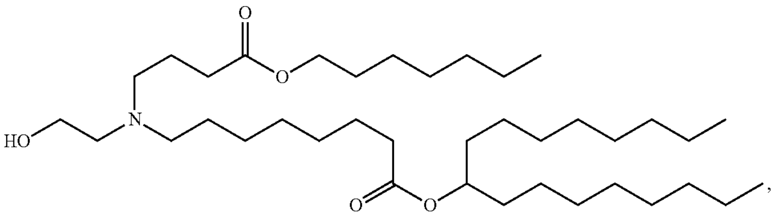
(Compound 55)
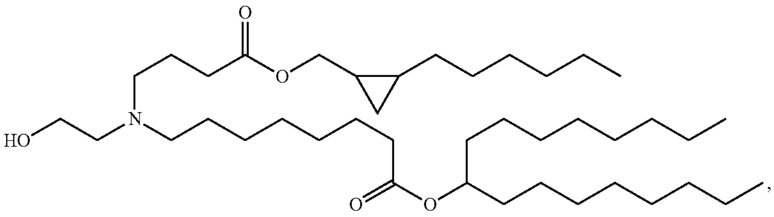
(Compound 56)
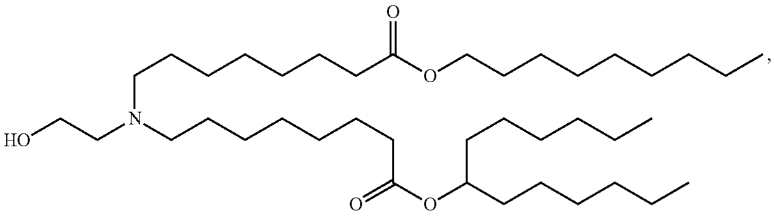
(Compound 57)
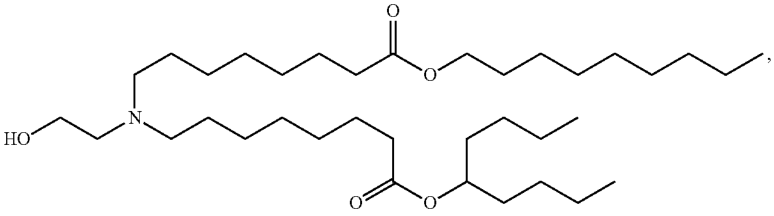
(Compound 58)
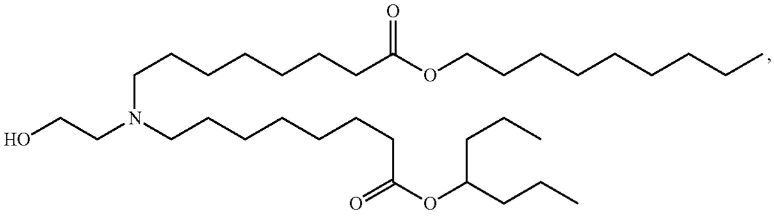
(Compound 59)
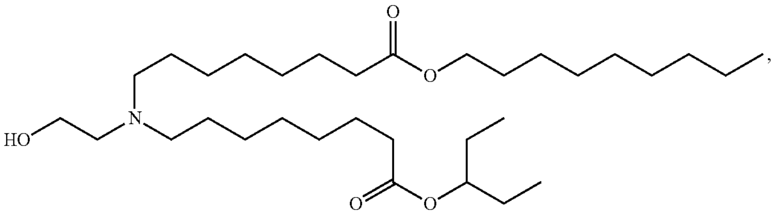
(Compound 60)
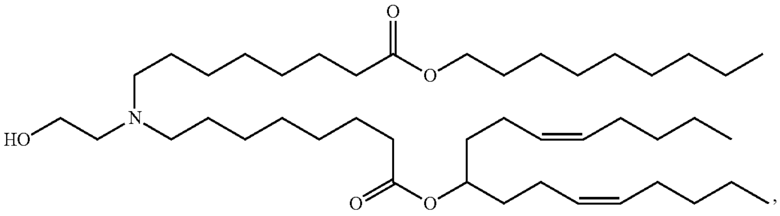
and -continued
(Compound 61)
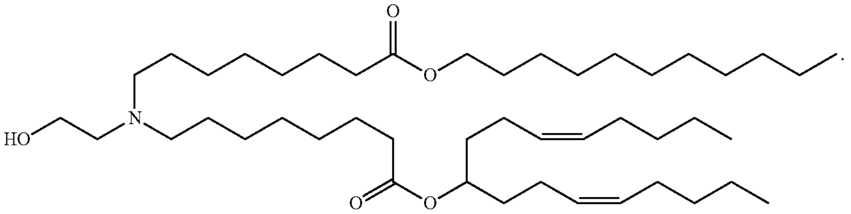
In further embodiments, the compound of Formula (I) is selected from the group consisting of:
(Compound 62)
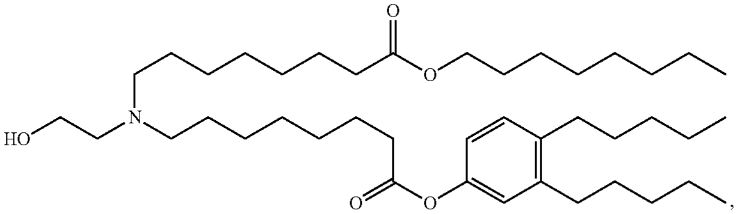
(Compound 63)
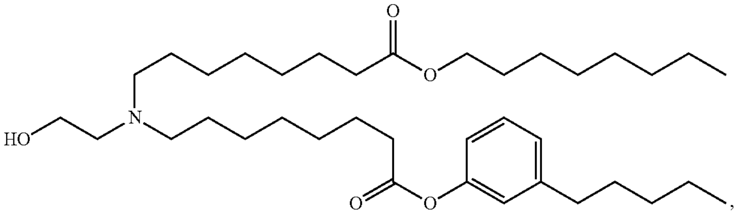
and
(Compound 64)
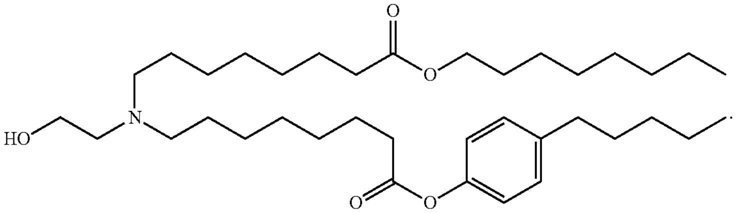
In some embodiments, the compound of Formula (I) is selected from the group consisting of:
(Compound 65)
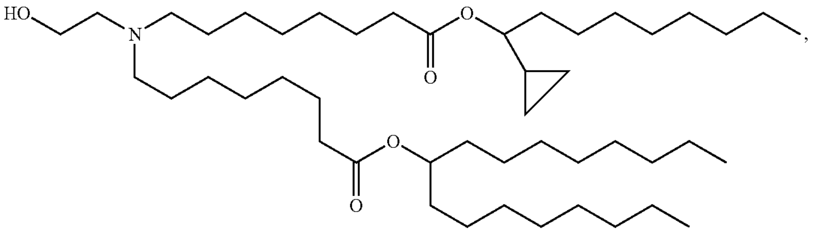

-continued
(Compound 66)
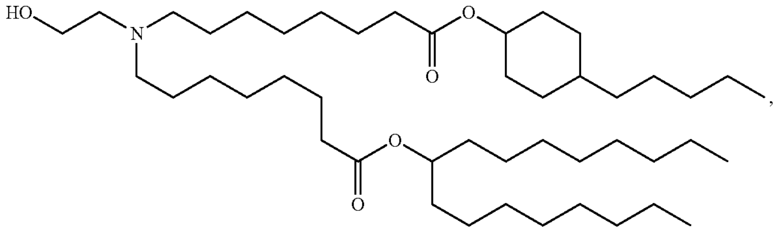
,
(Compound 67)
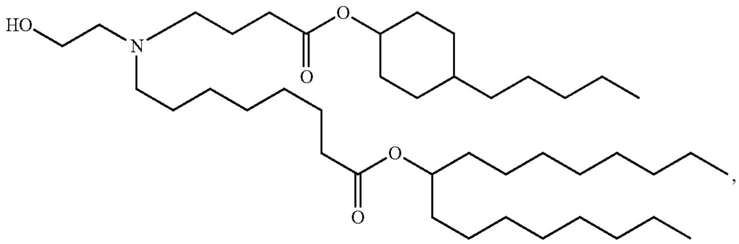
,
(Compound 68)
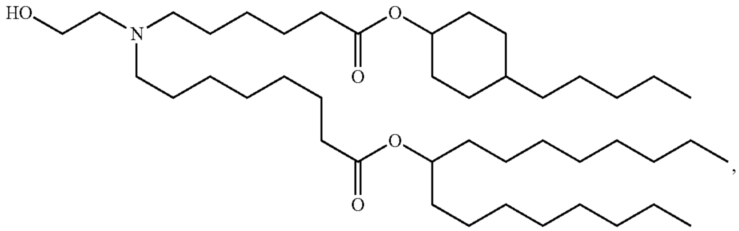
,
(Compound 69)
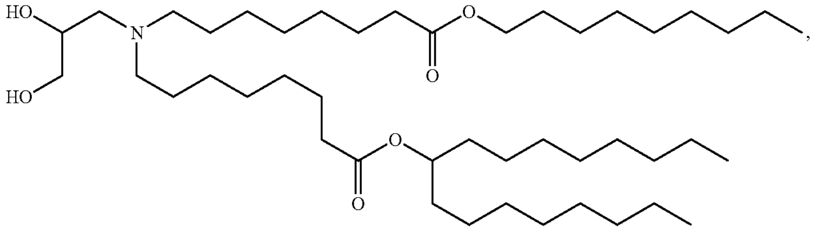
,
(Compound 70)
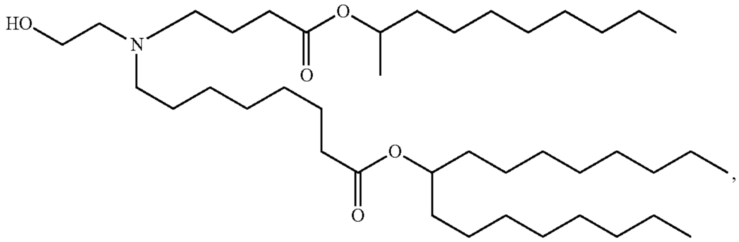
,
(Compound 71)
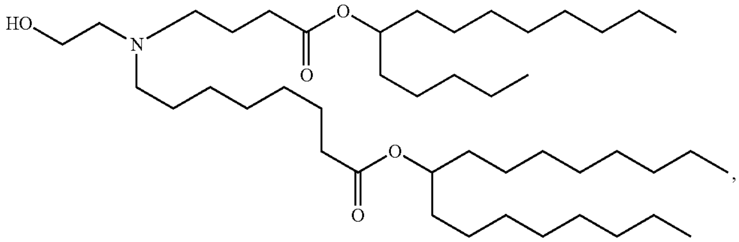
, -continued
(Compound 72)
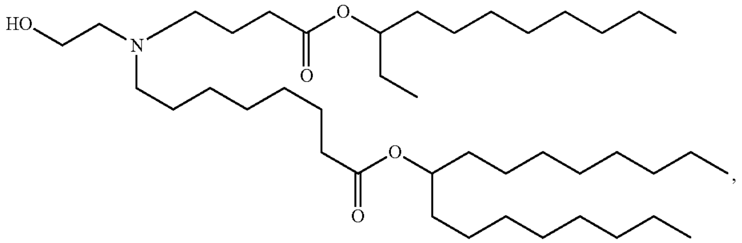
(Compound 73)
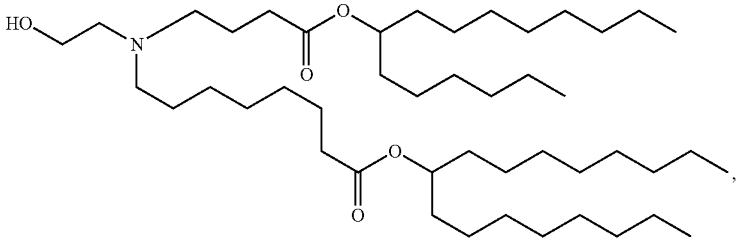
(Compound 74)
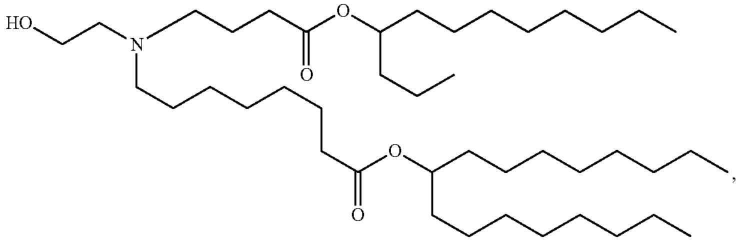
(Compound 75)
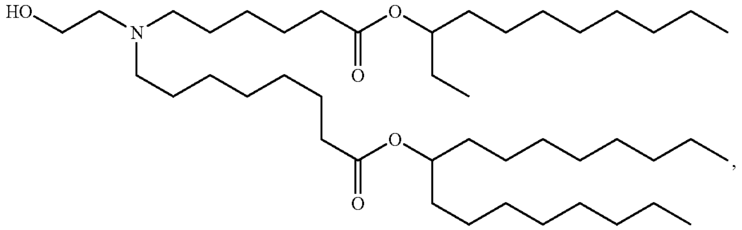
(Compound 76)
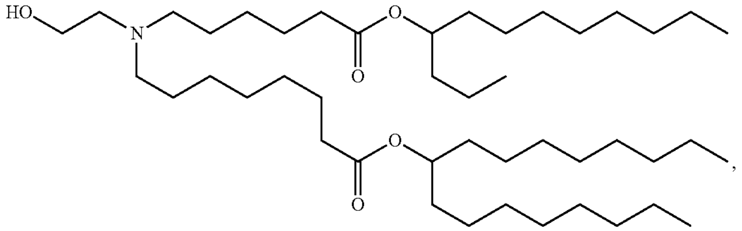
(Compound 77)
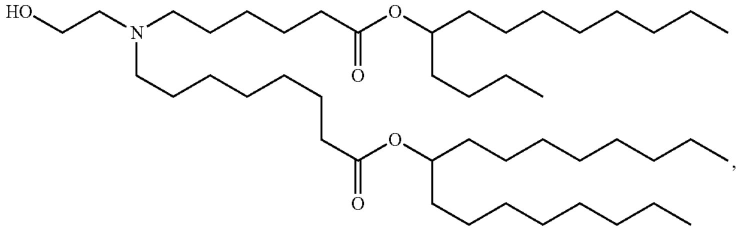

-continued
(Compound 78)
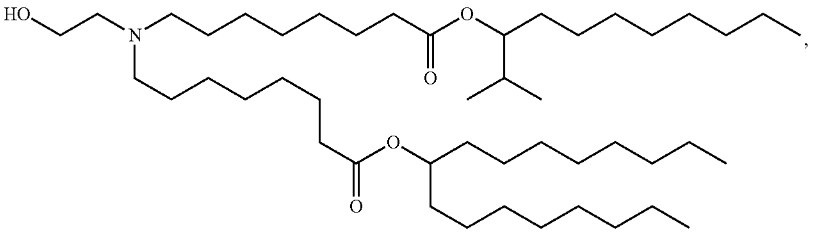
(Compound 79)
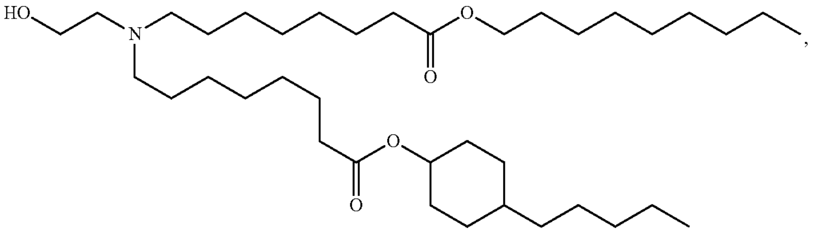
(Compound 80)
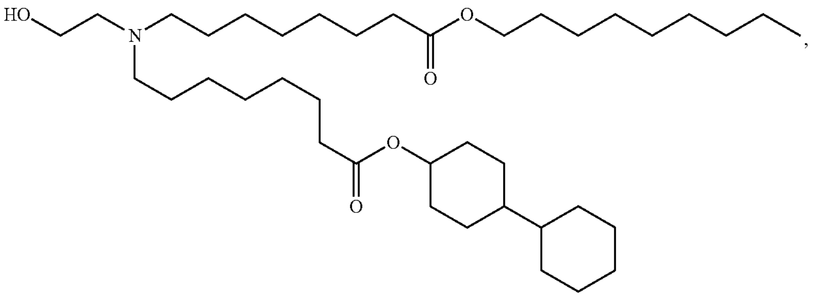
(Compound 81)
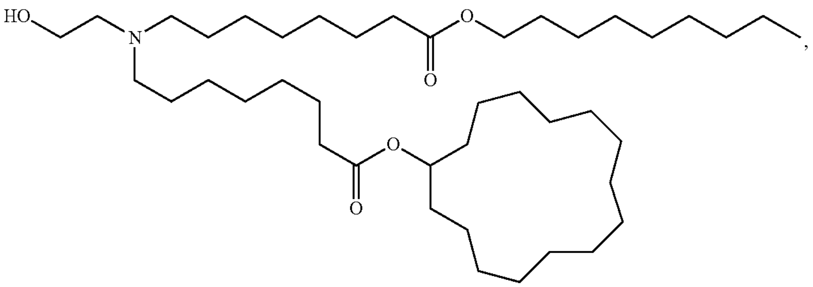
(Compound 82)
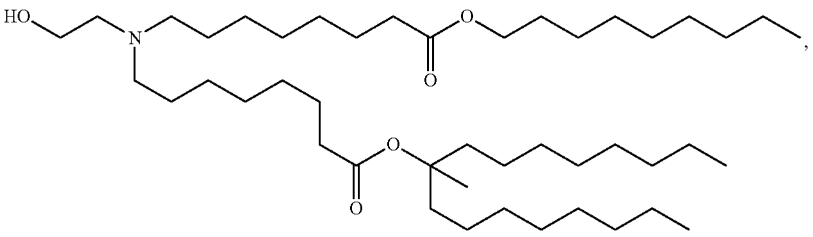
(Compound 83)
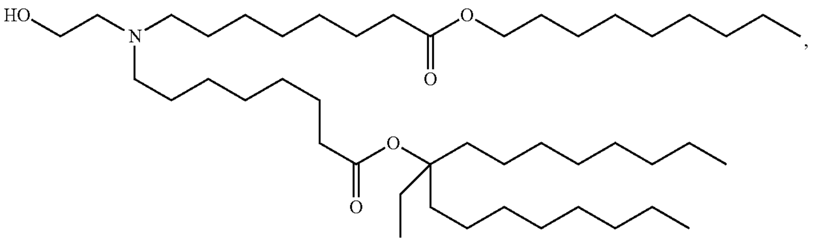

-continued
(Compound 84)
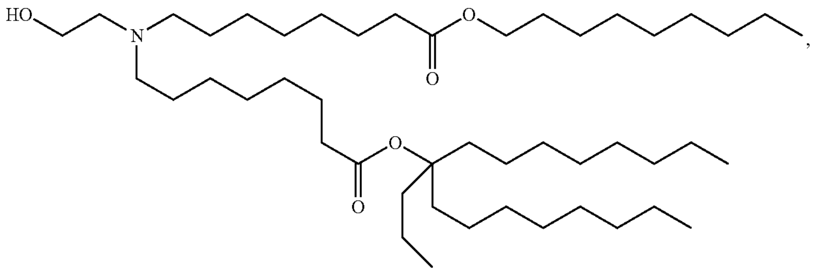
,
(Compound 85)
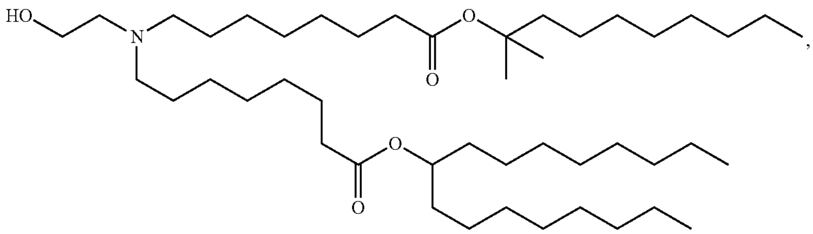
,
(Compound 86)
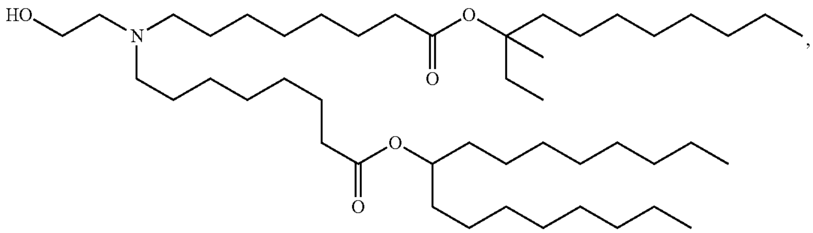
,
(Compound 87)
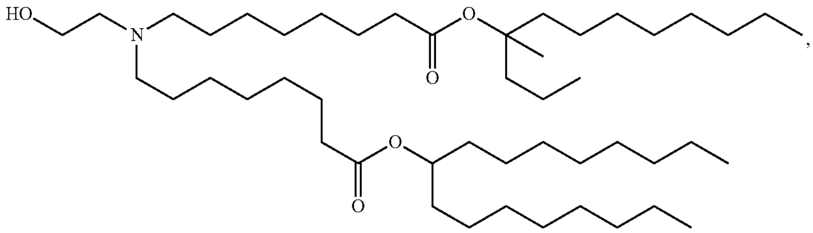
,
(Compound 88)
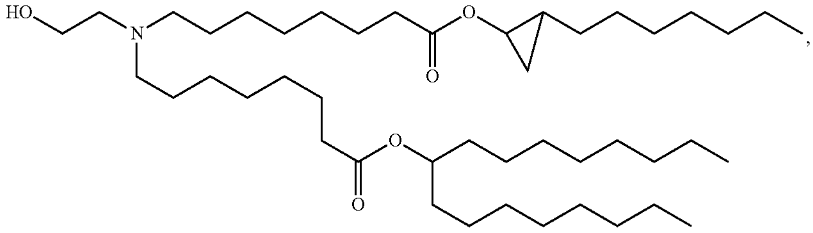
, -continued
(Compound 89)
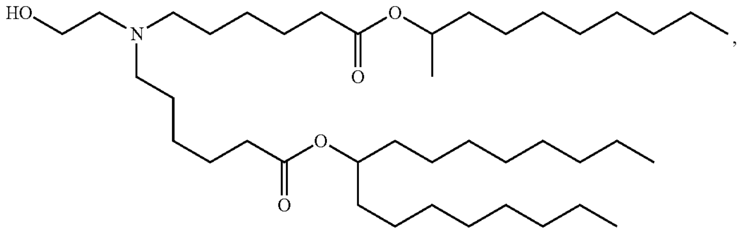
(Compound 90)
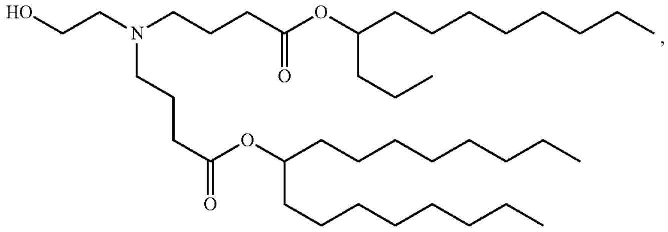
(Compound 91)
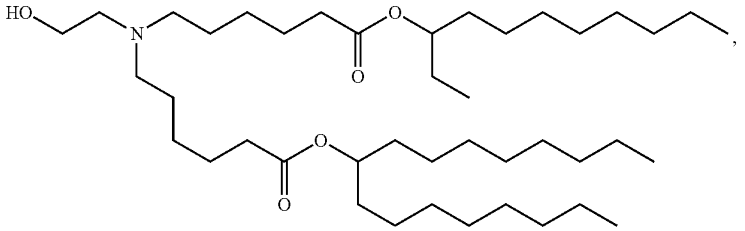
(Compound 92)
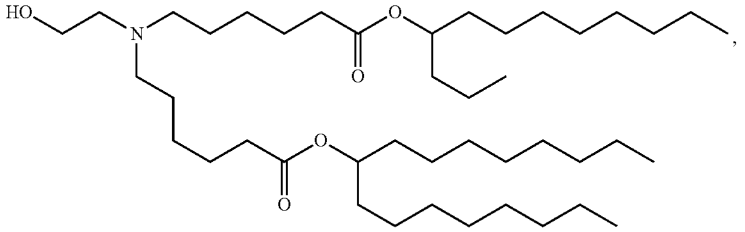
(Compound 93)
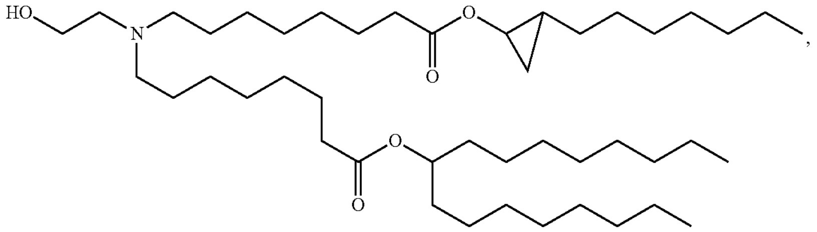
(Compound 94)
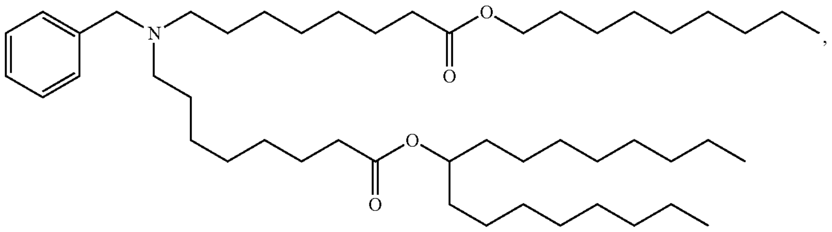

-continued
(Compound 95)
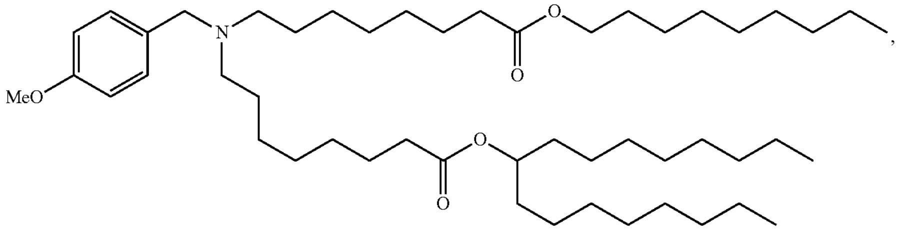
,
(Compound 96)
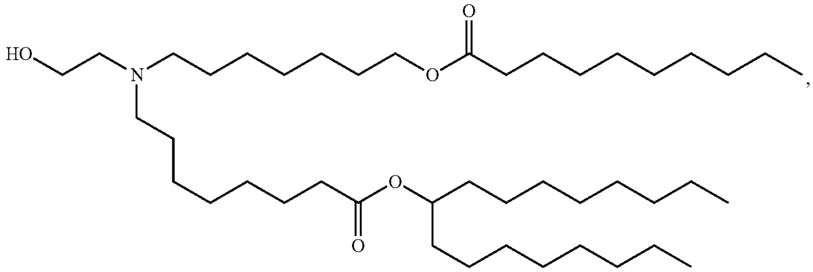
,
(Compound 97)
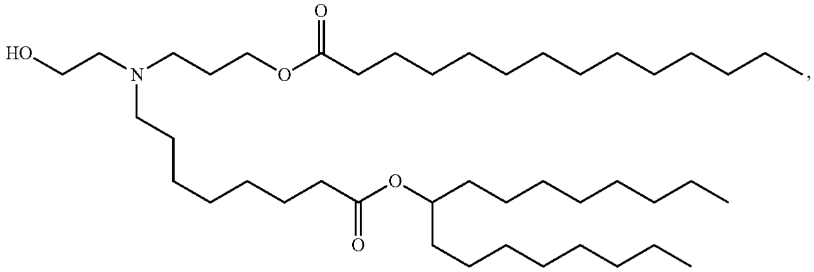
,
(Compound 98)
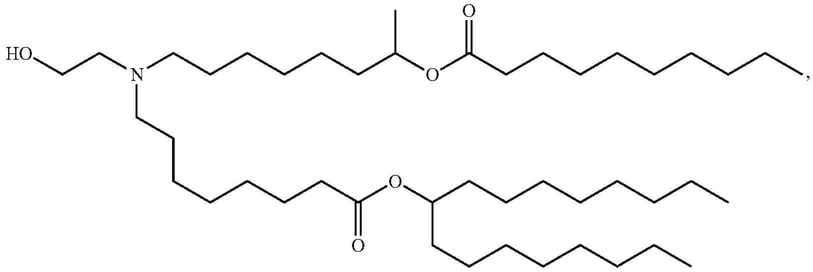
,
(Compound 99)
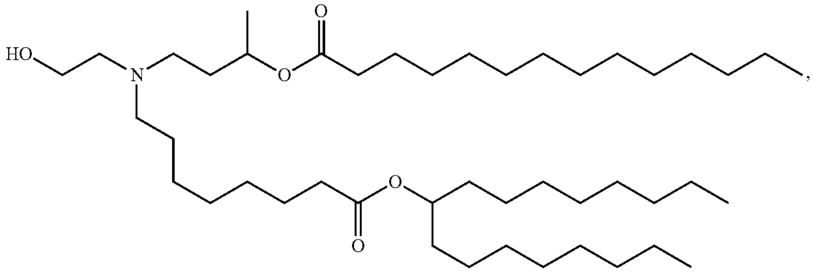
, -continued
(Compound 100)
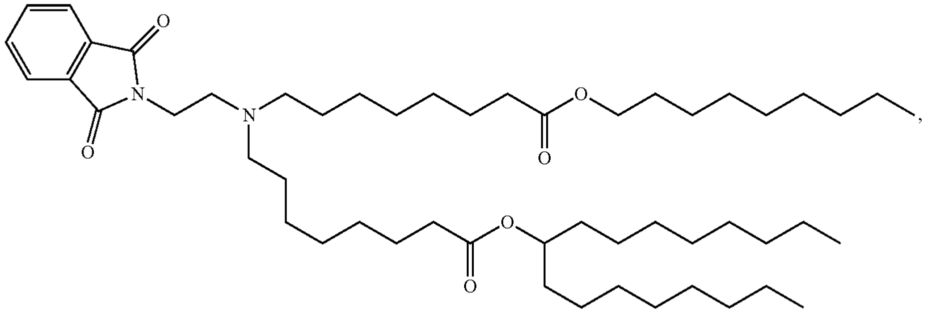
(Compound 101)
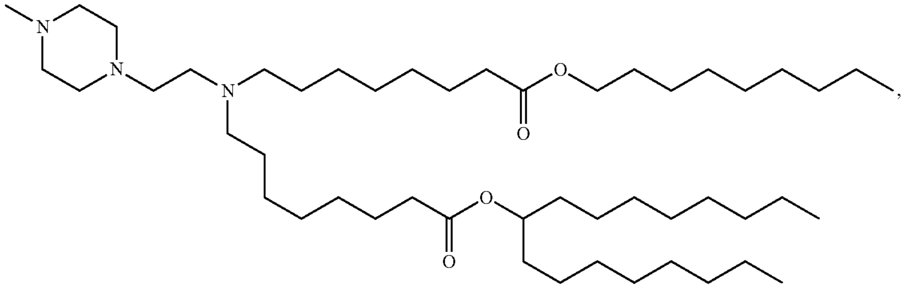
(Compound 102)
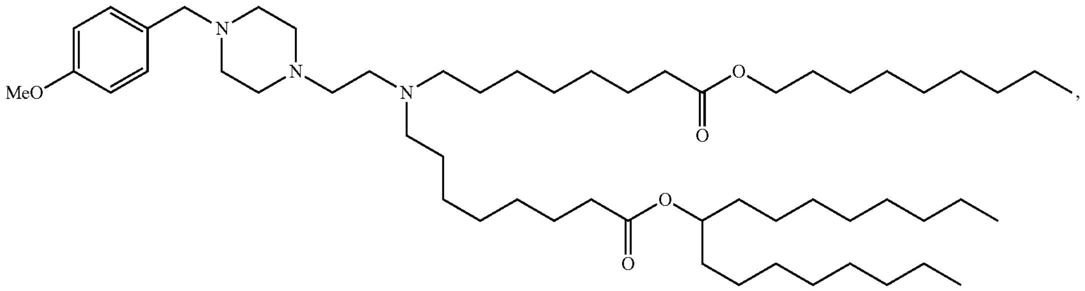
(Compound 103)
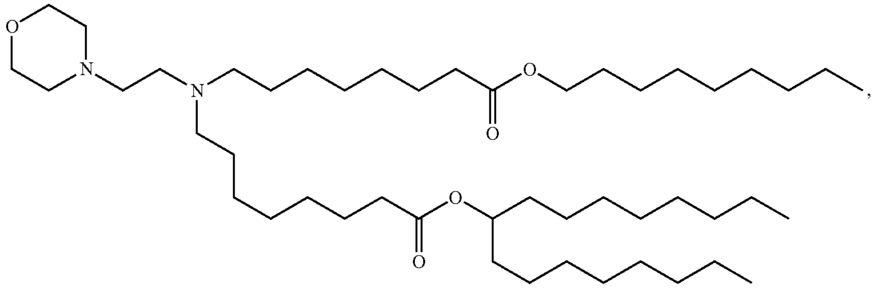
(Compound 104)
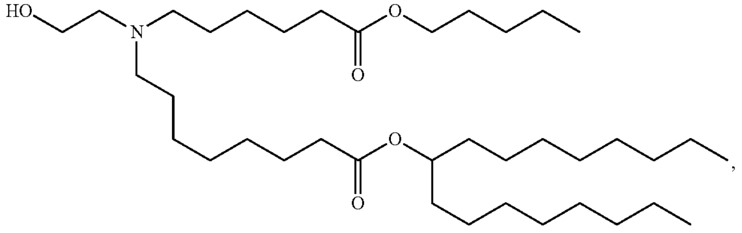

-continued
(Compound 105)
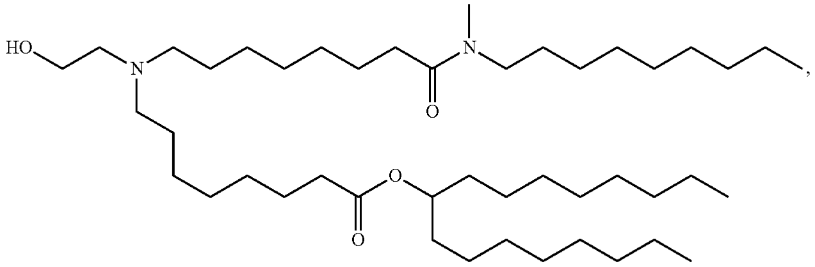
(Compound 106)
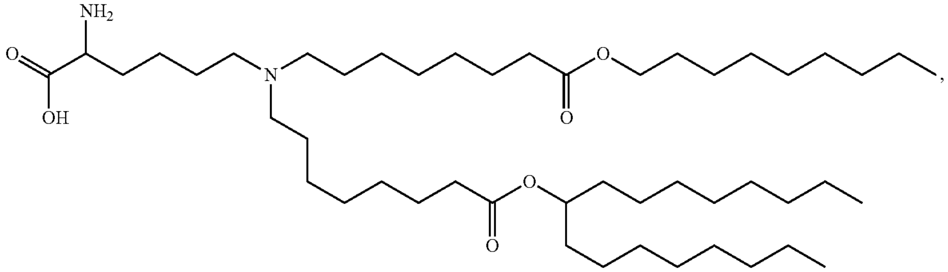
(Compound 107)
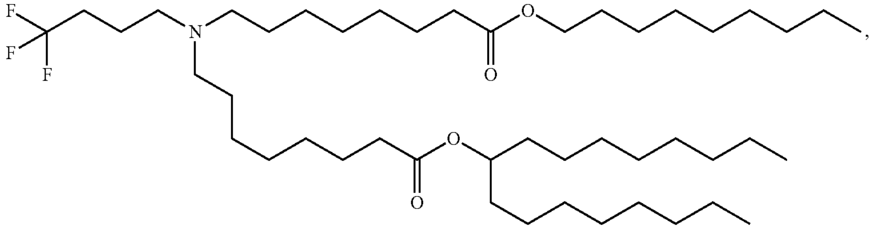
(Compound 108)
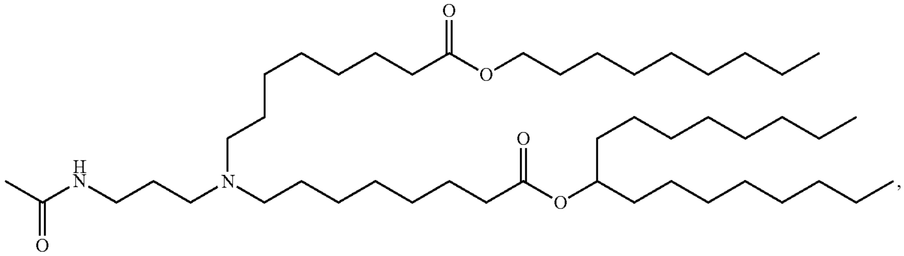
(Compound 109)
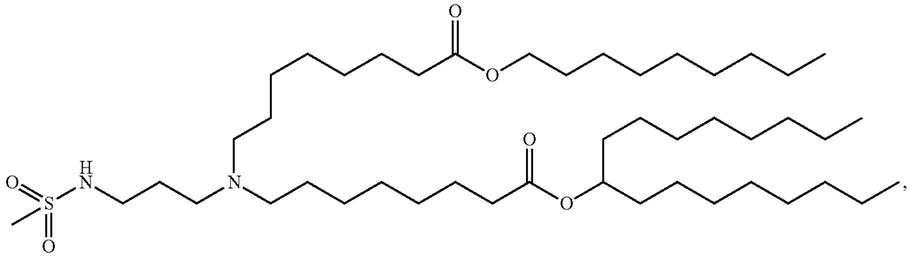

-continued
(Compound 110)
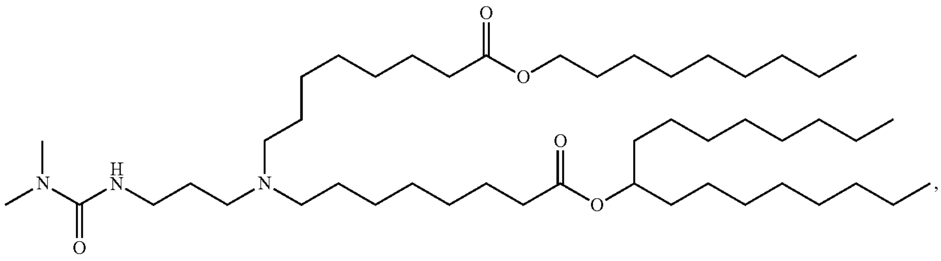,
(Compound 111)
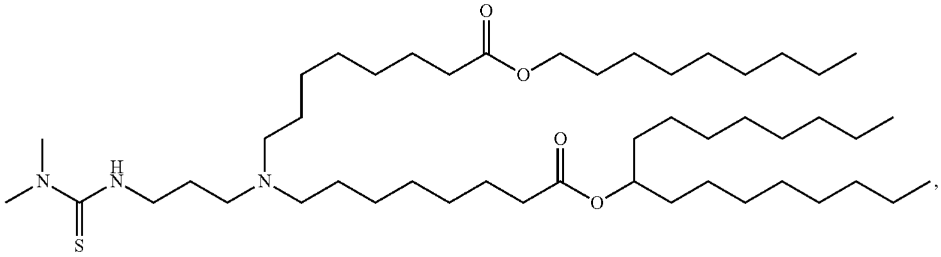,
(Compound 112)
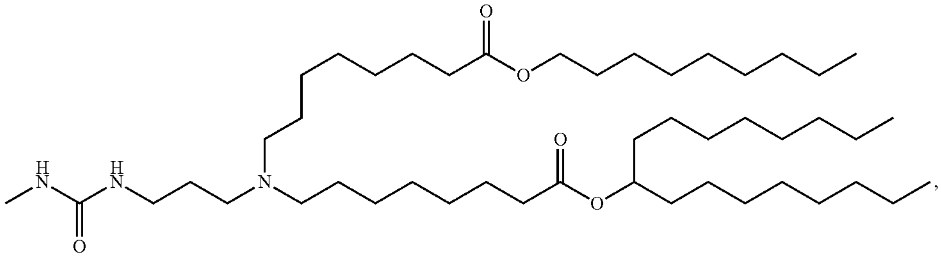,
(Compound 113)
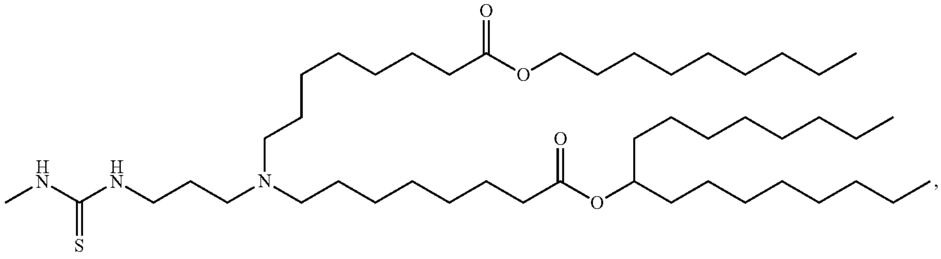,
(Compound 114)
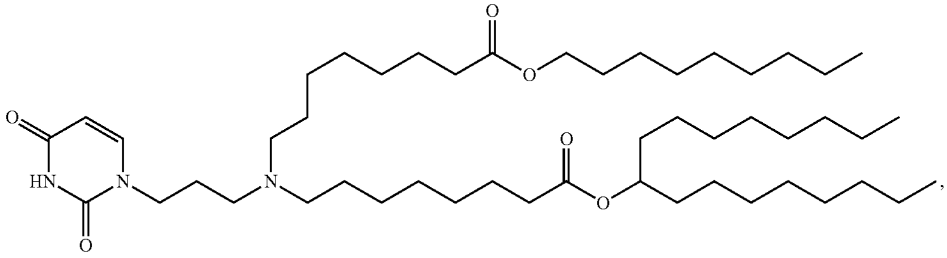, -continued
(Compound 115)
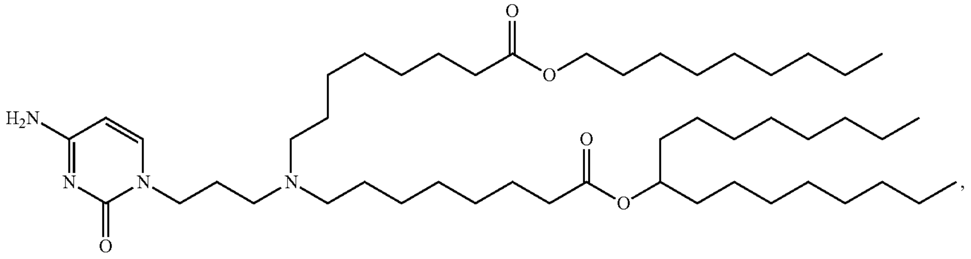
(Compound 116)
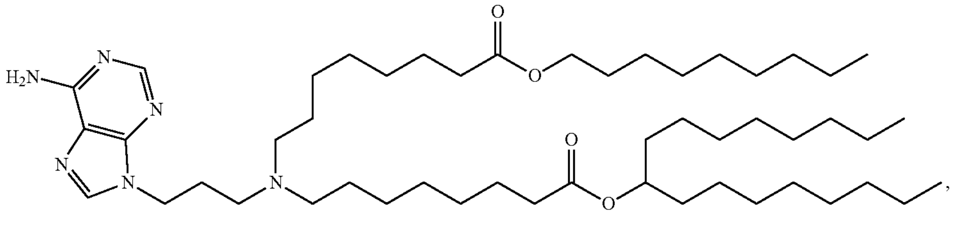
(Compound 117)
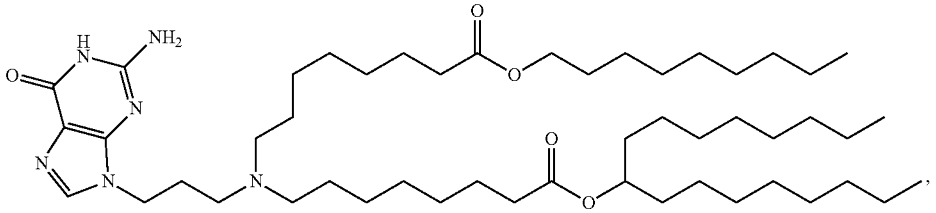
(Compound 118)
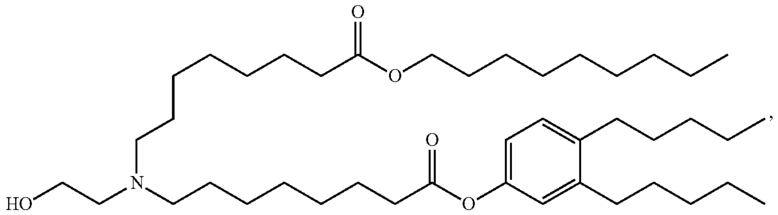
(Compound 119)
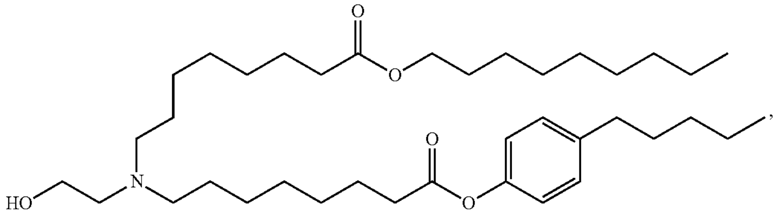
(Compound 120)
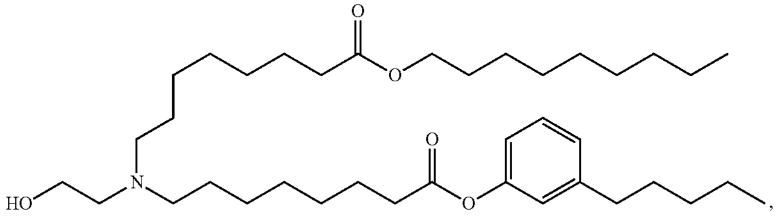

-continued
(Compound 121)
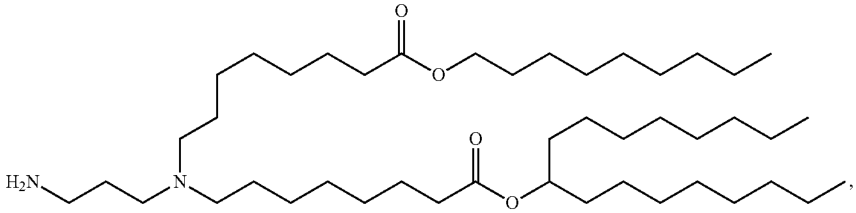
,
(Compound 122)
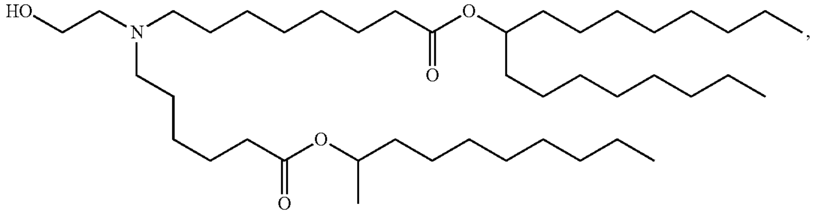
,
(Compound 123)
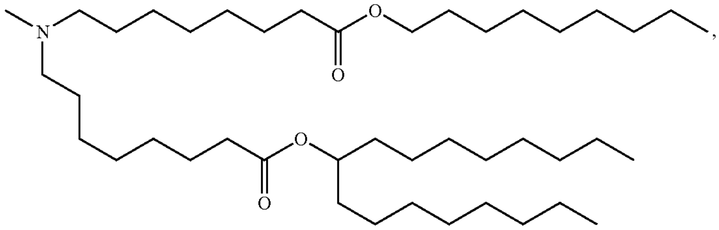
,
(Compound 124)
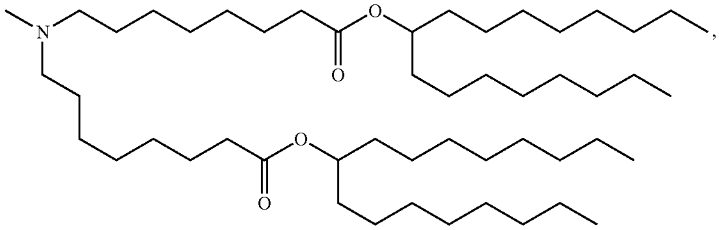
,
(Compound 125)
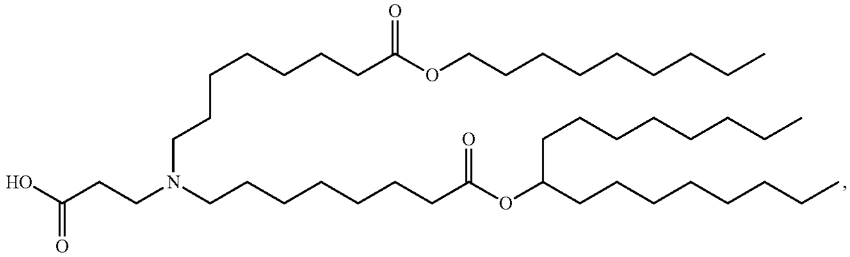
,
(Compound 126)
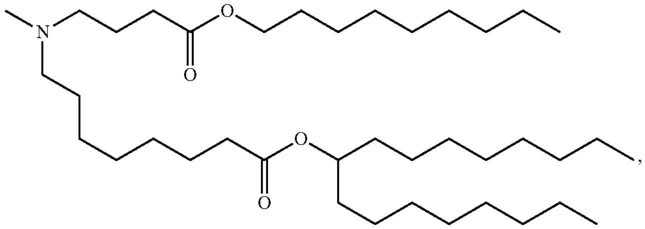
, -continued
(Compound 127)
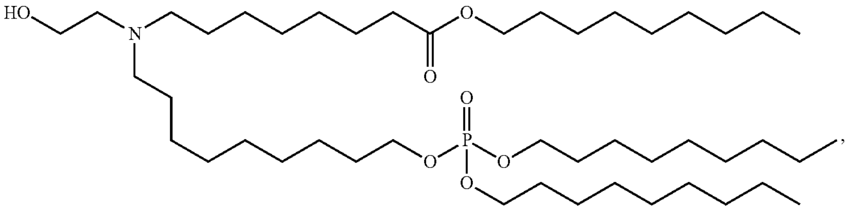
,
(Compound 128)
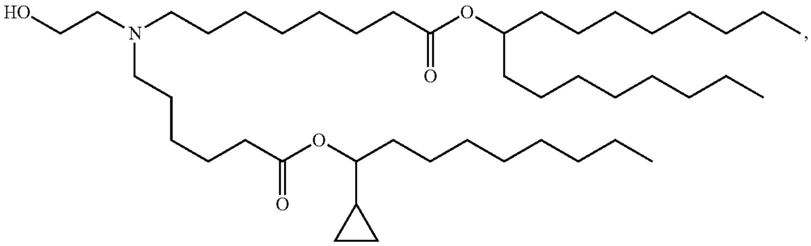
,
(Compound 129)
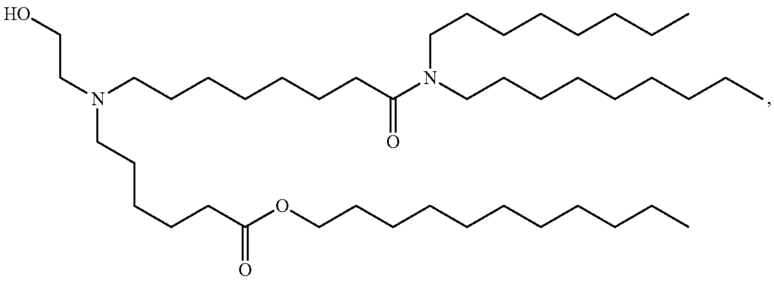
,
(Compound 130)
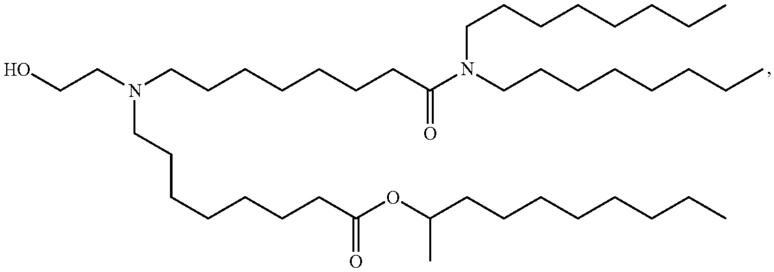
,
(Compound 131)
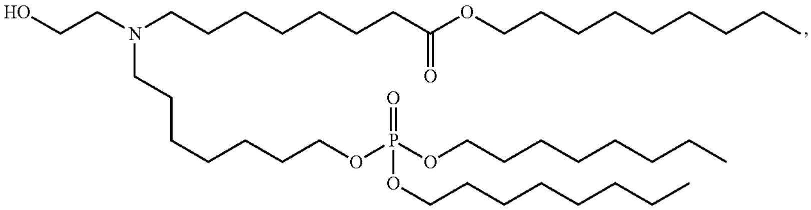
,
(Compound 132)
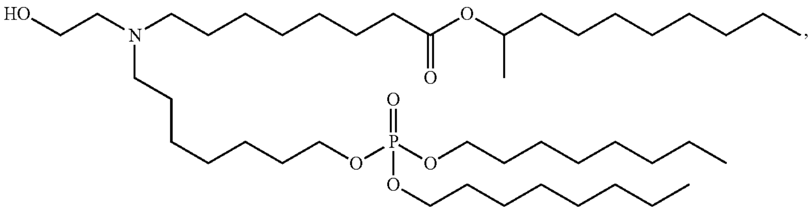
, -continued
(Compound 133)
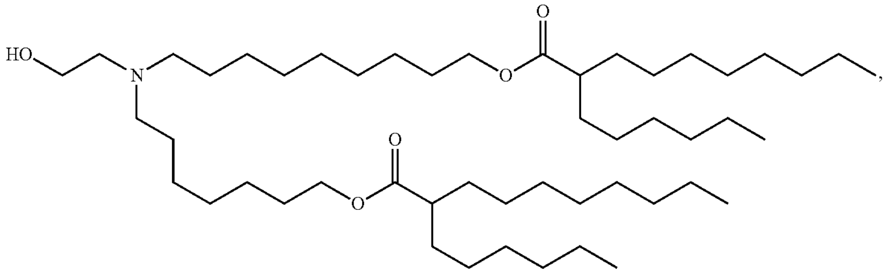
(Compound 134)
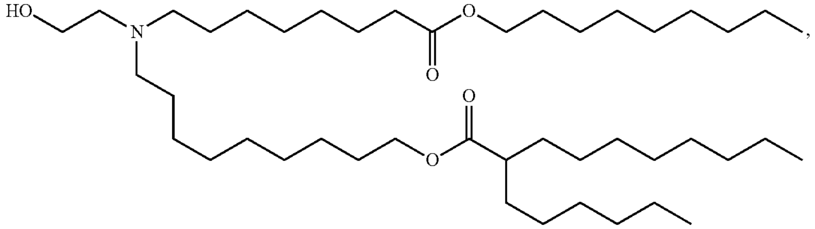
(Compound 135)
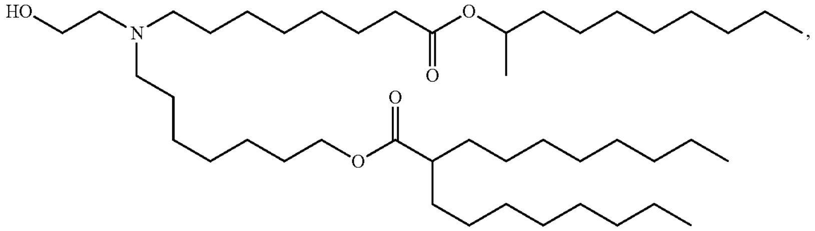
(Compound 136)
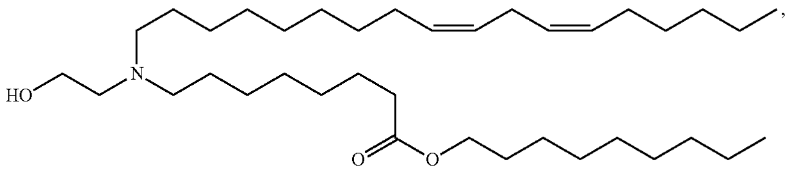
(Compound 137)
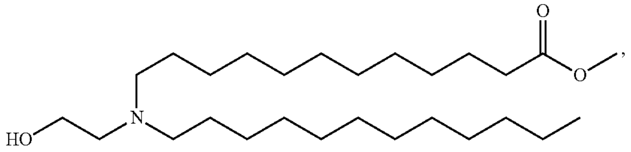
(Compound 138)
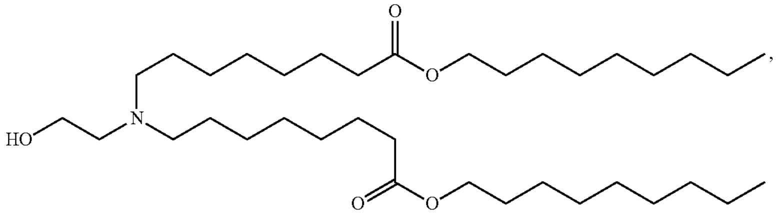
(Compound 139)
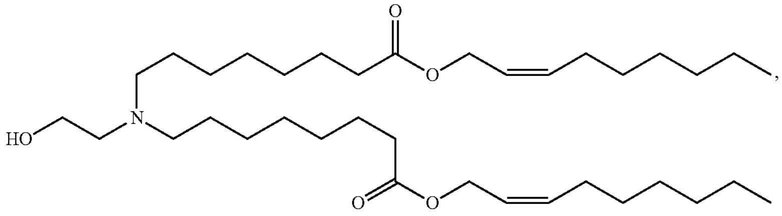

-continued
(Compound 140)
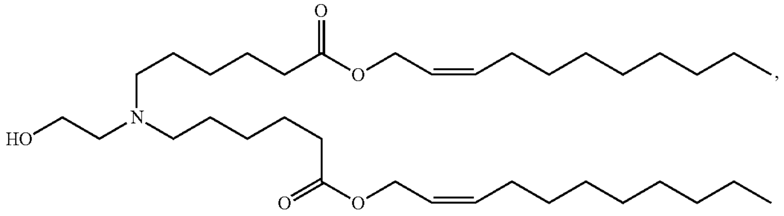
(Compound 141)
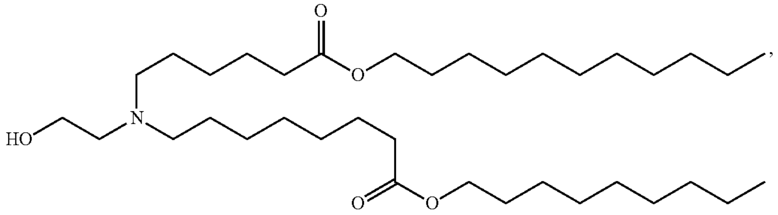
(Compound 142)
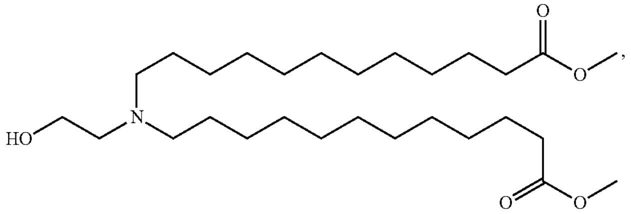
(Compound 143)
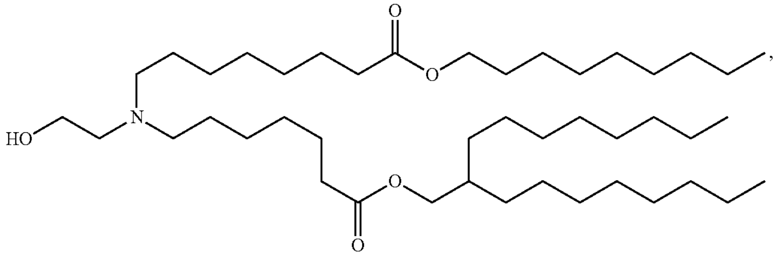
(Compound 144)
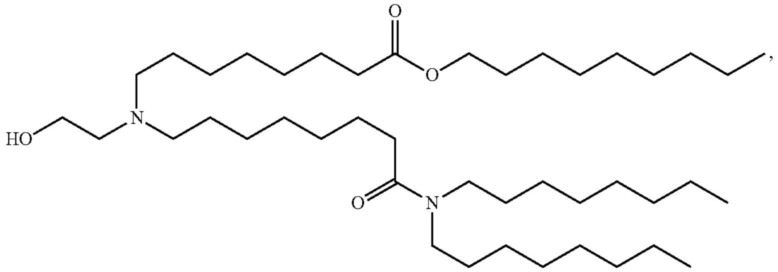
(Compound 145)
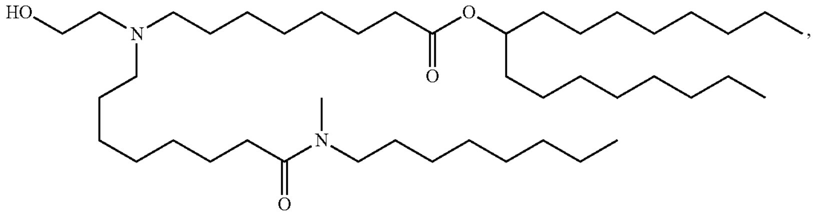

-continued
(Compound 146)
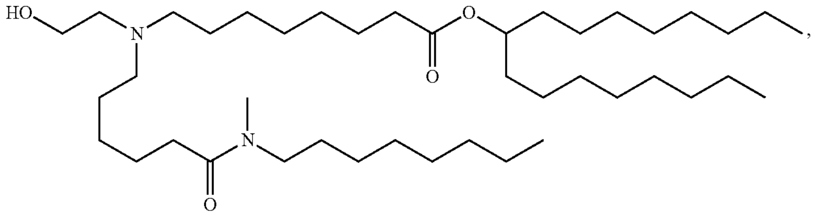
(Compound 147)
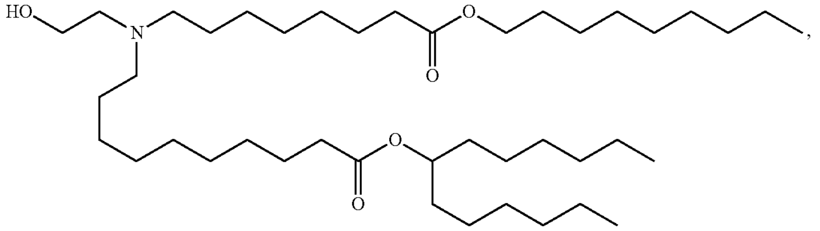
(Compound 148)
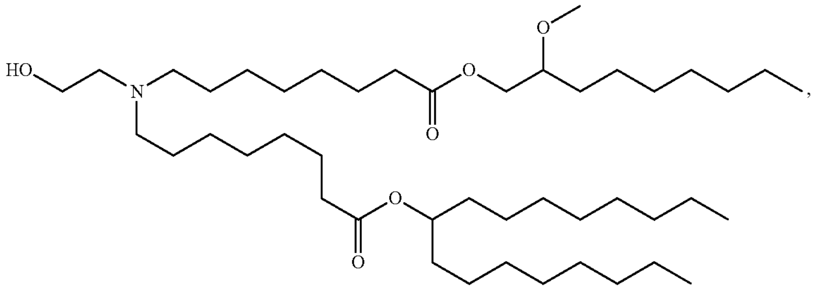
(Compound 149)
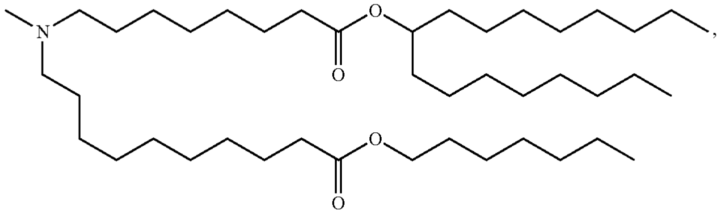
(Compound 150)
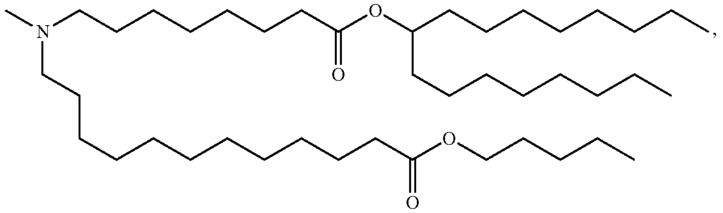
(Compound 151)
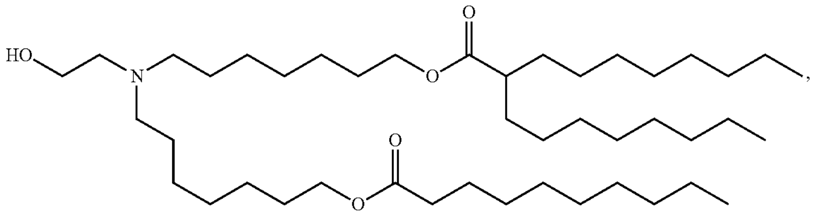

-continued
(Compound 152)
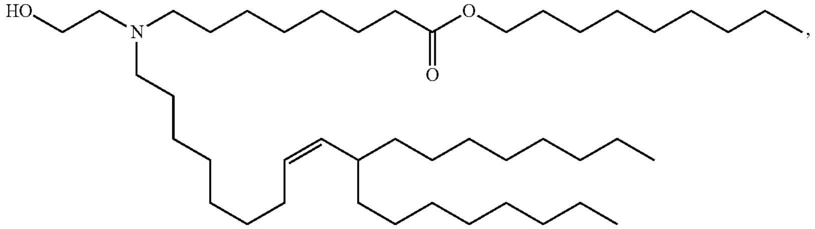
(Compound 153)
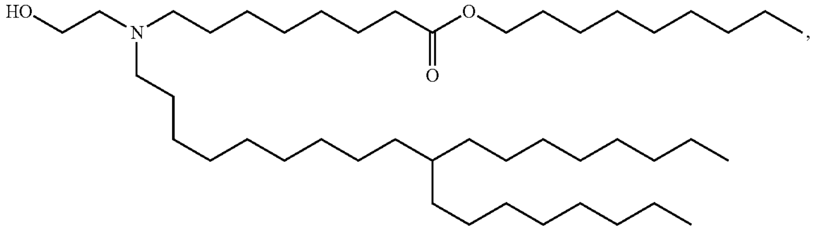
(Compound 154)
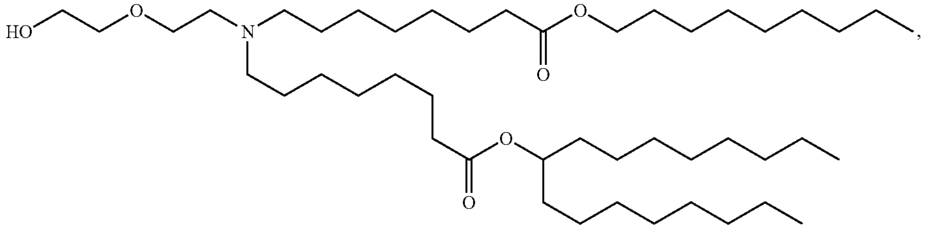
(Compound 155)
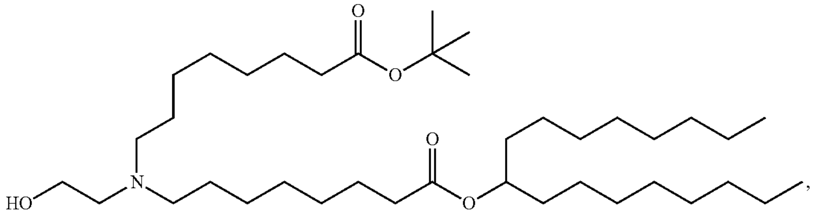
(Compound 156)
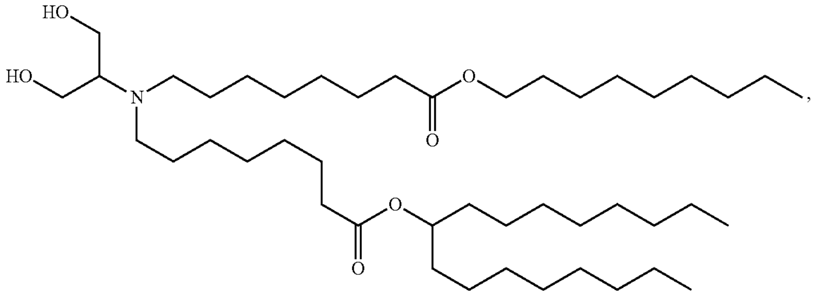
(Compound 157)
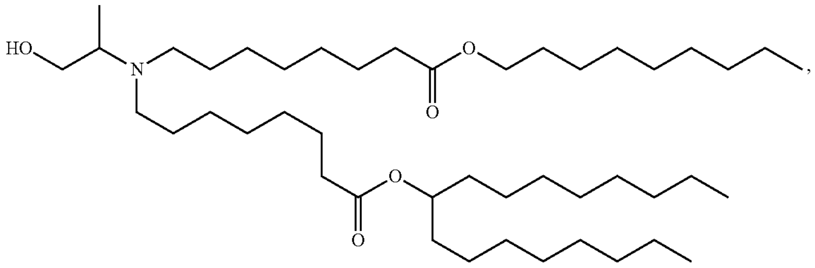

-continued
(Compound 158)
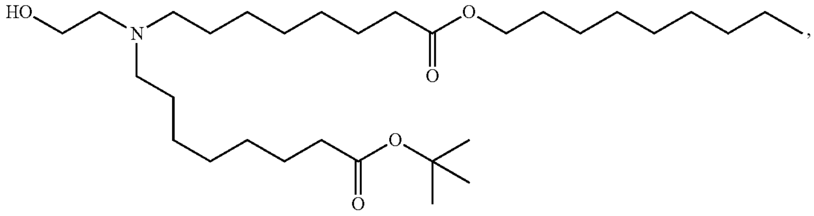
,
(Compound 159)
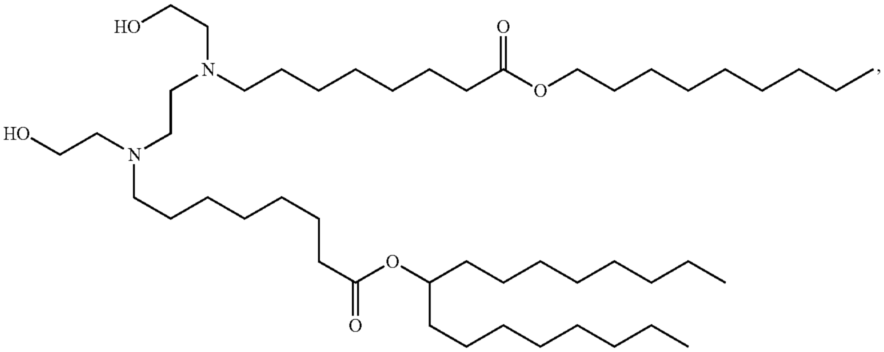
,
(Compound 160)
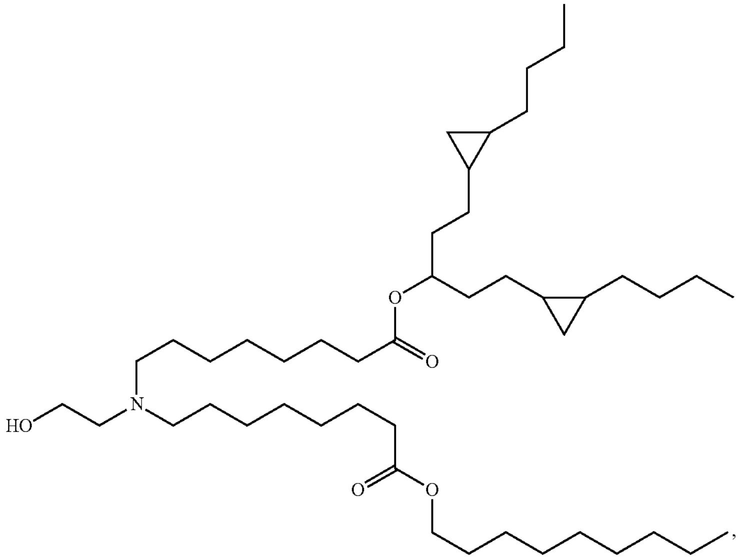
,
(Compound 161)
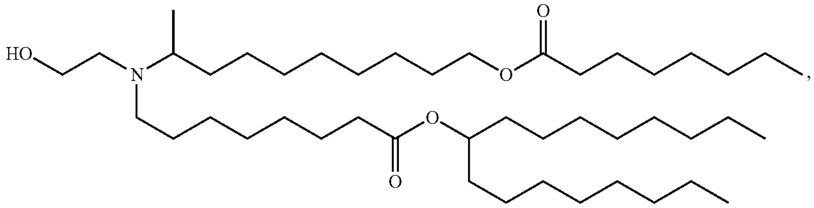
, -continued
(Compound 162)
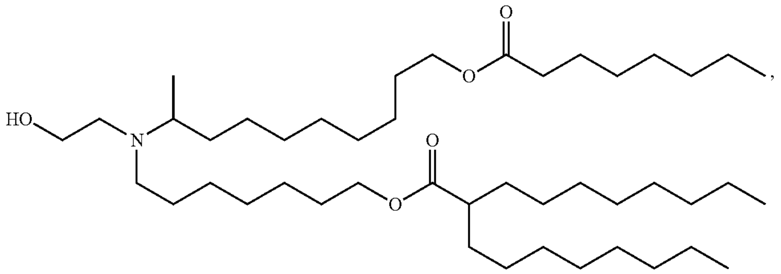
,
(Compound 163)
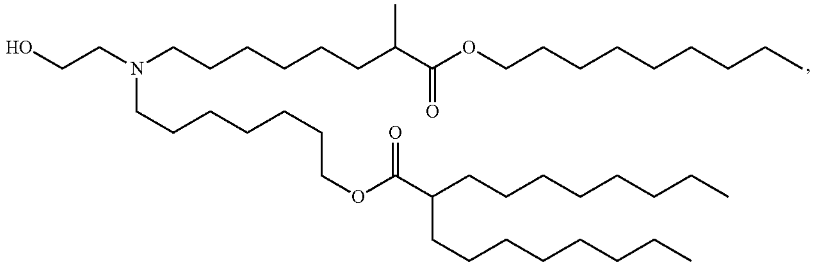
,
(Compound 164)
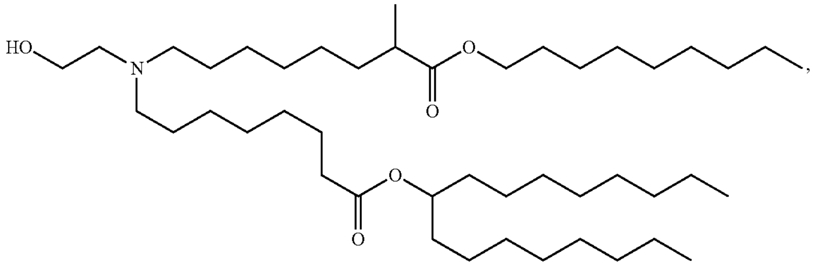
,
(Compound 165)
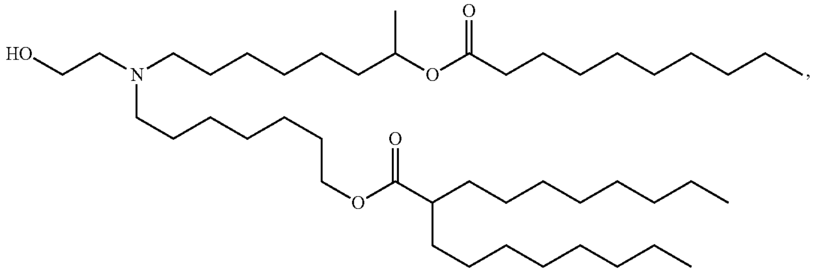
,
(Compound 166)
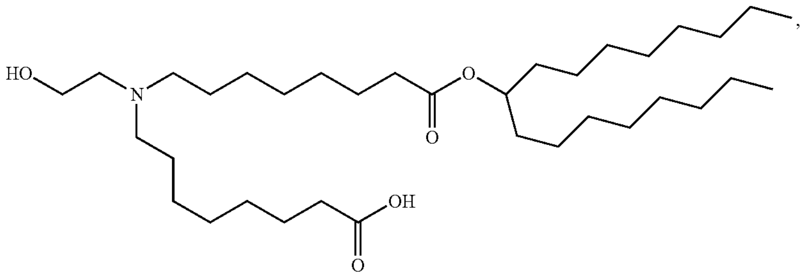
, -continued
(Compound 167)
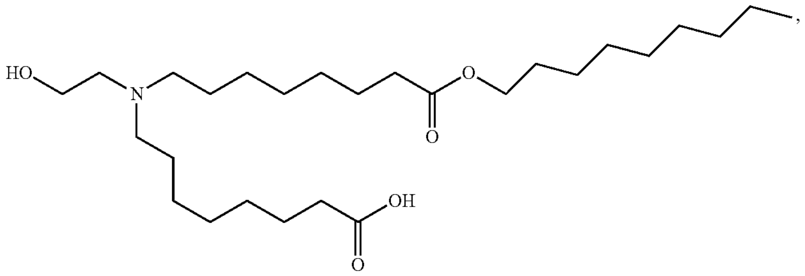
(Compound 168)
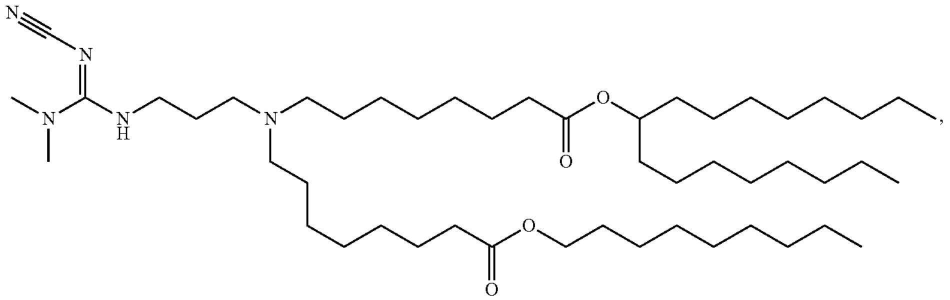
(Compound 169)
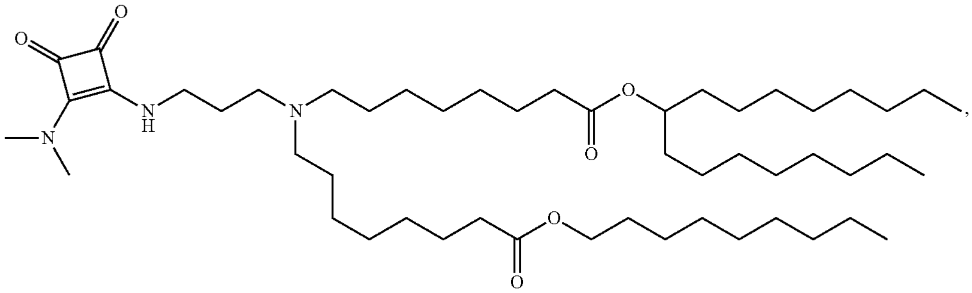
(Compound 170)
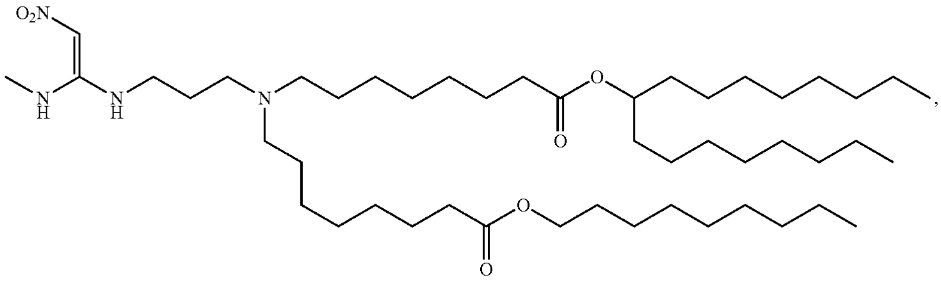
(Compound 171)
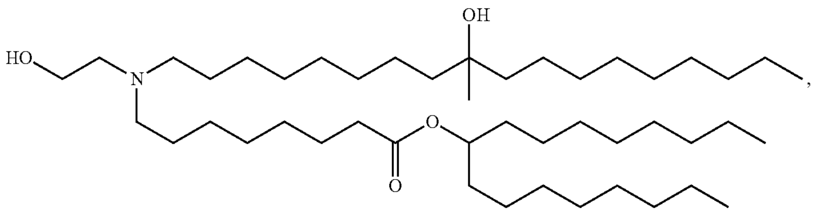

-continued
(Compound 172)
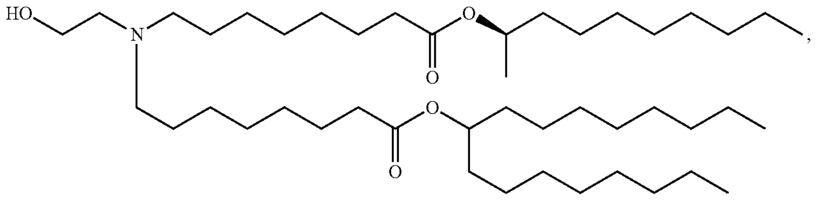
(Compound 173)
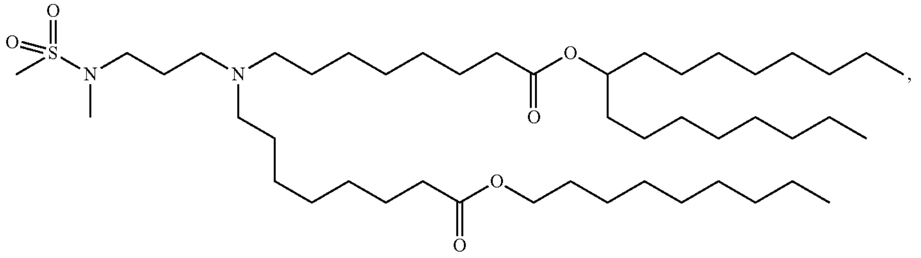
(Compound 174)
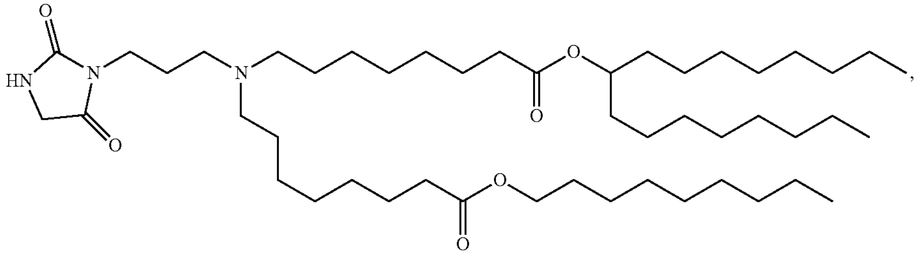
(Compound 175)
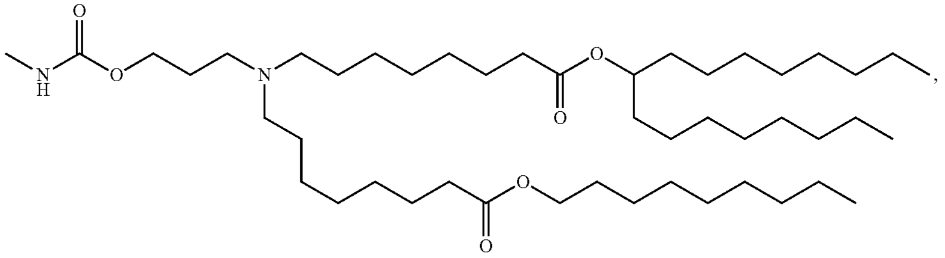
(Compound 176)
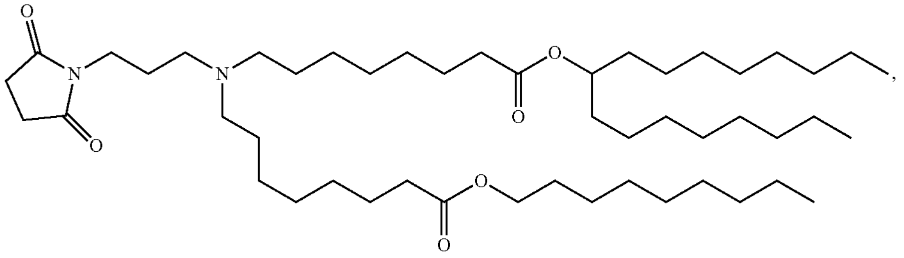
(Compound 177)
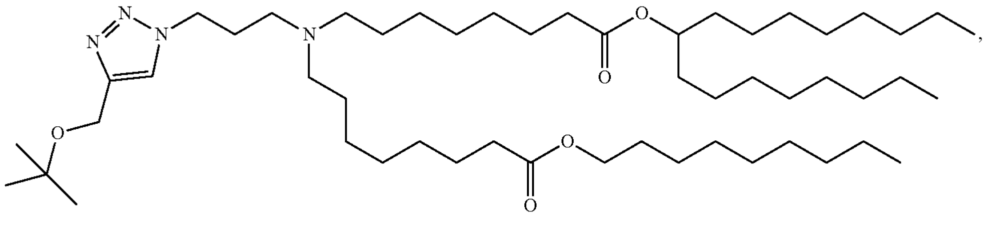

-continued
(Compound 178)
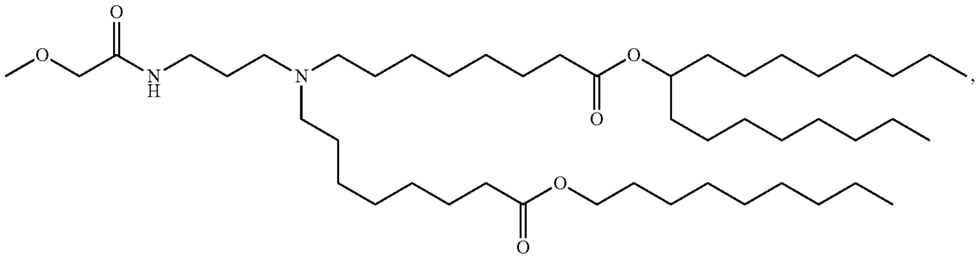
,
(Compound 179)
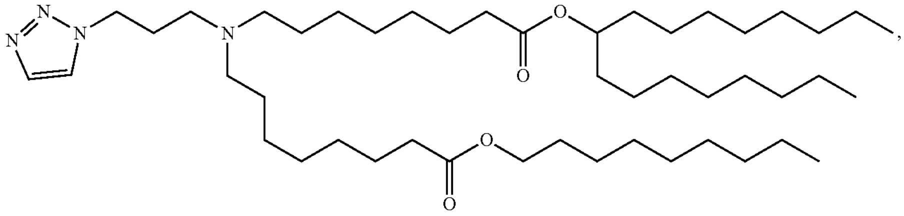
,
(Compound 180)
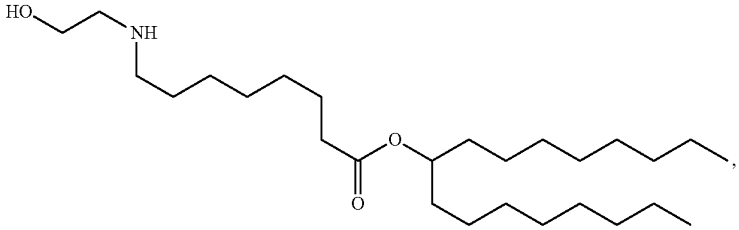
,
(Compound 181)
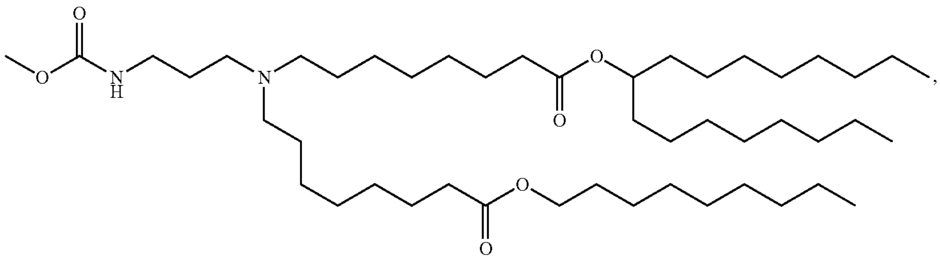
,
(Compound 182)
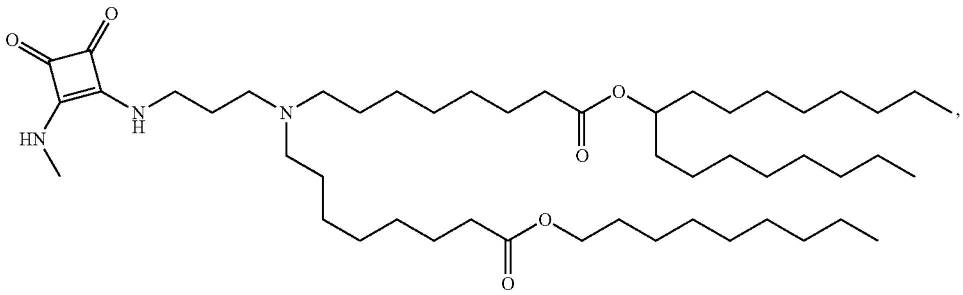
, -continued
(Compound 183)
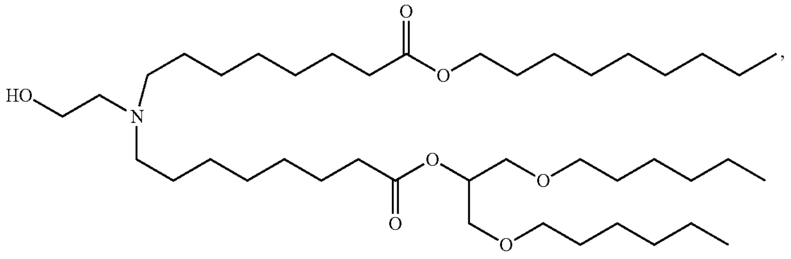
(Compound 184)
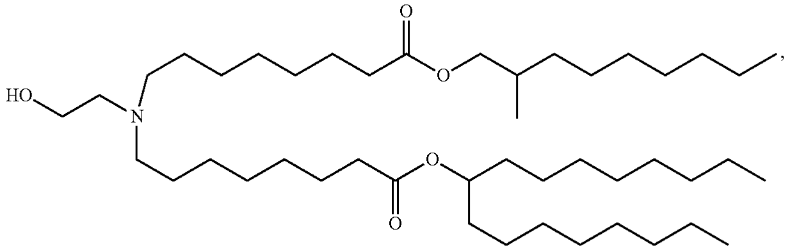
(Compound 185)
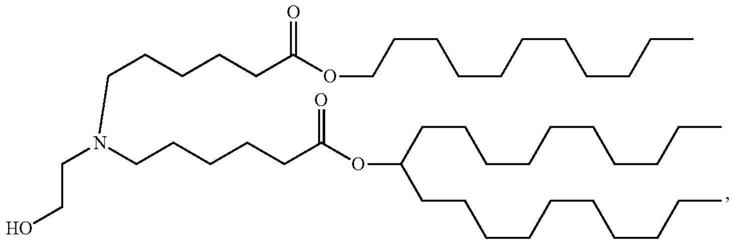
(Compound 186)
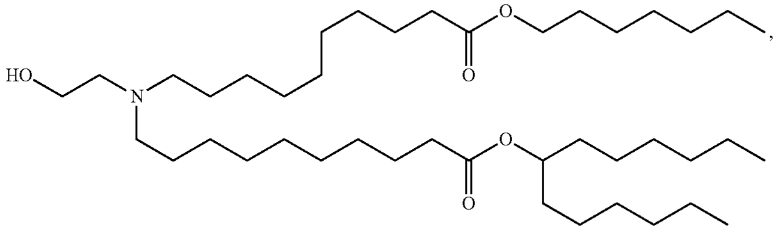
(Compound 187)
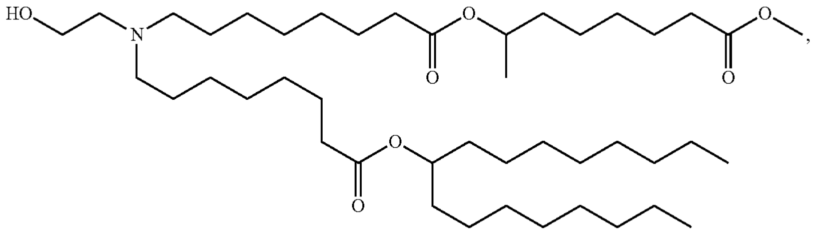
(Compound 188)
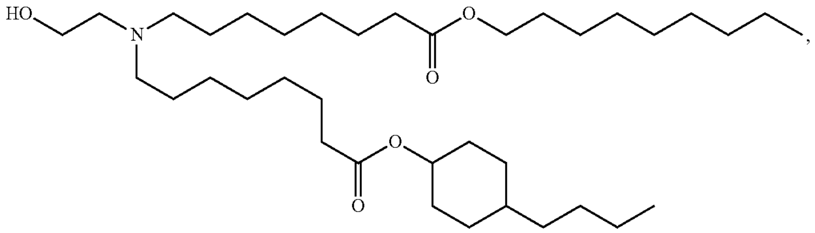

-continued
(Compound 189)
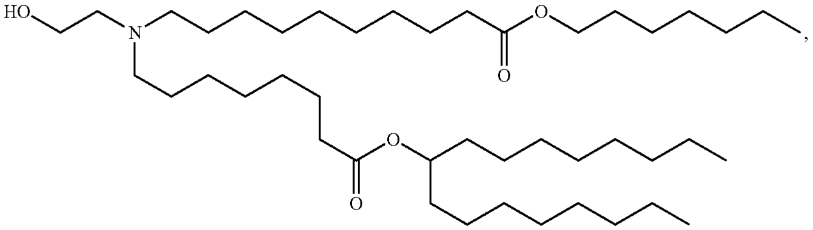
(Compound 190)
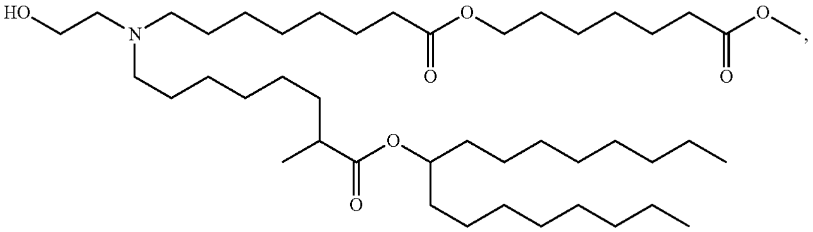
(Compound 191)
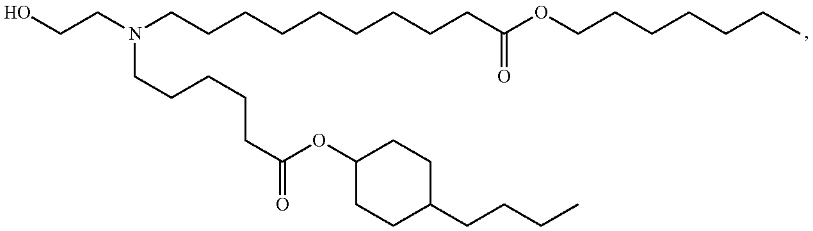
(Compound 192)
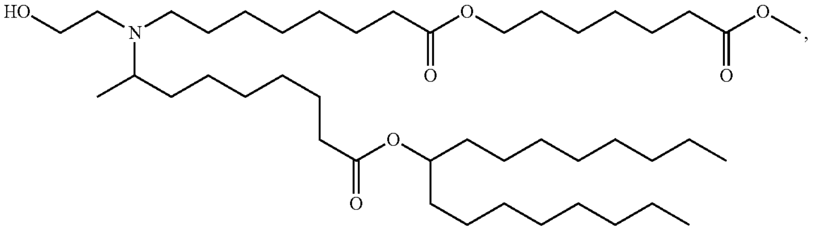
(Compound 193)
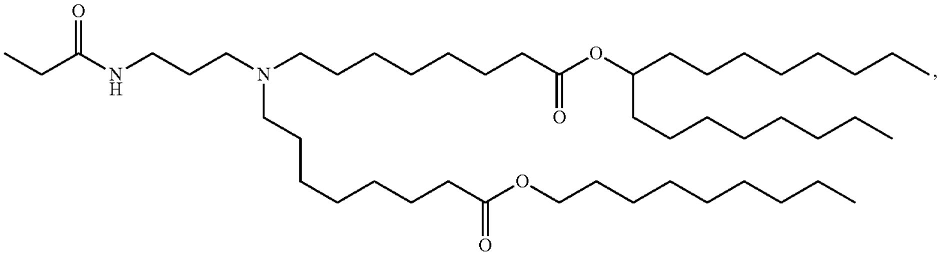
(Compound 194)
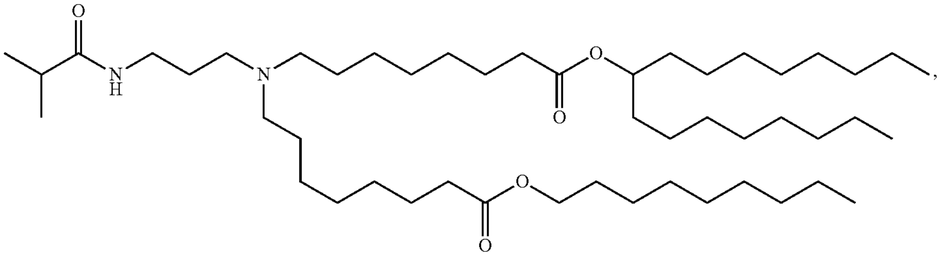

-continued
(Compound 195)
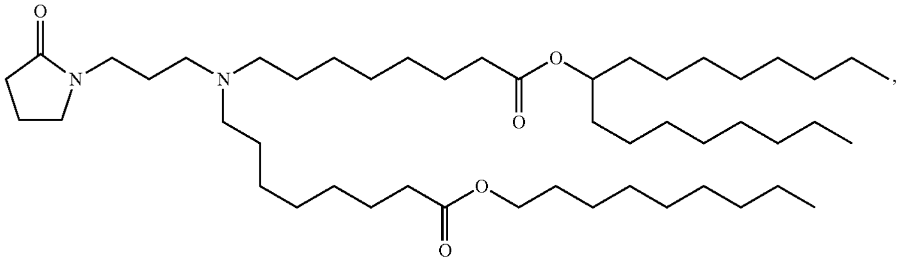
(Compound 196)
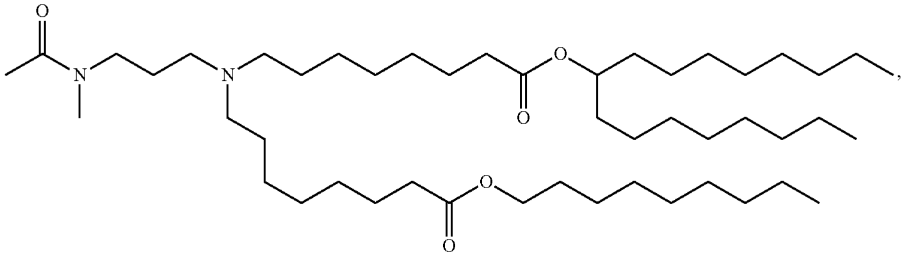
(Compound 197)
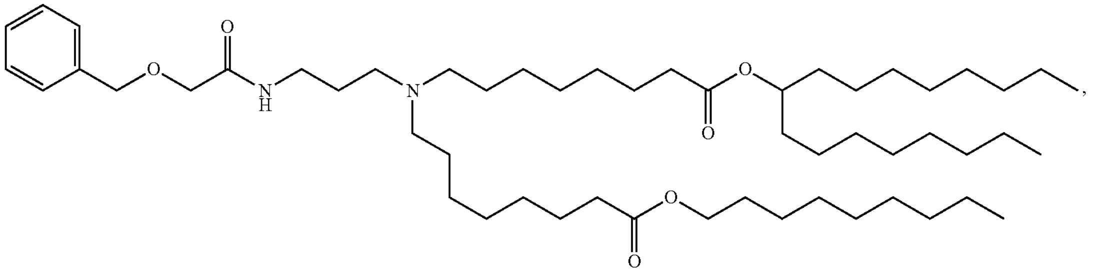
(Compound 198)
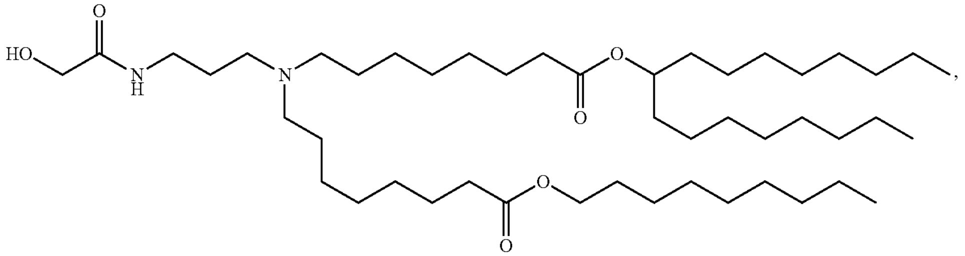
(Compound 199)
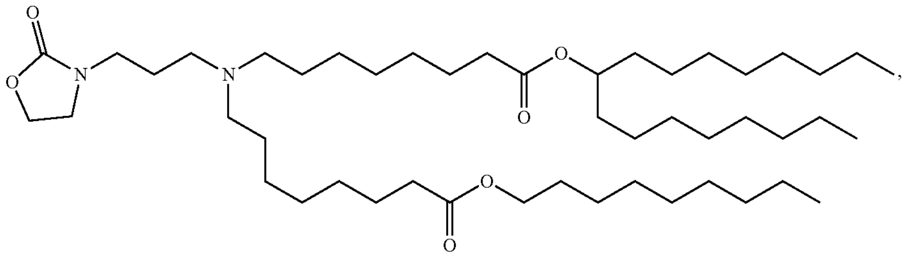
(Compound 200)
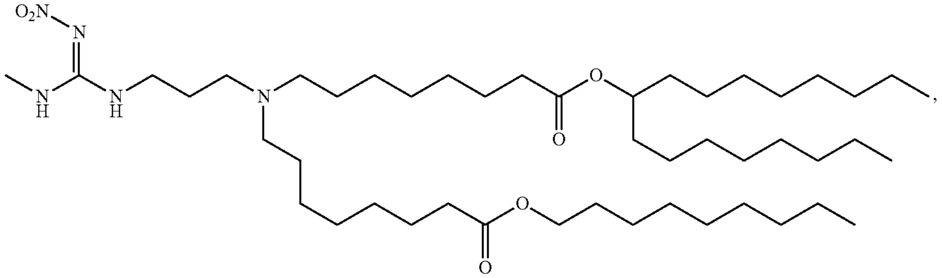

-continued
(Compound 201)
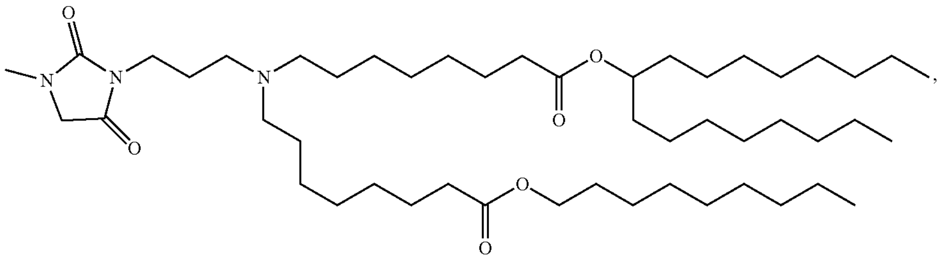
(Compound 202)
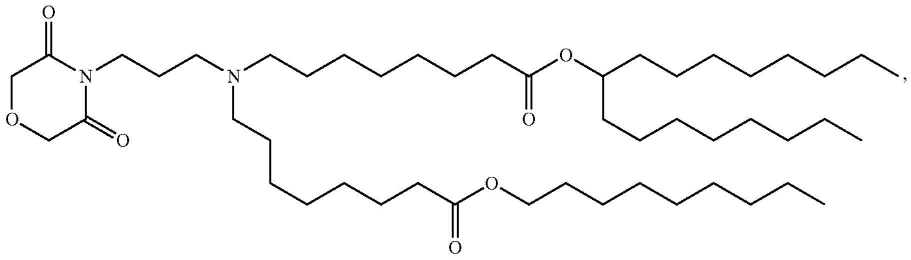
(Compound 203)
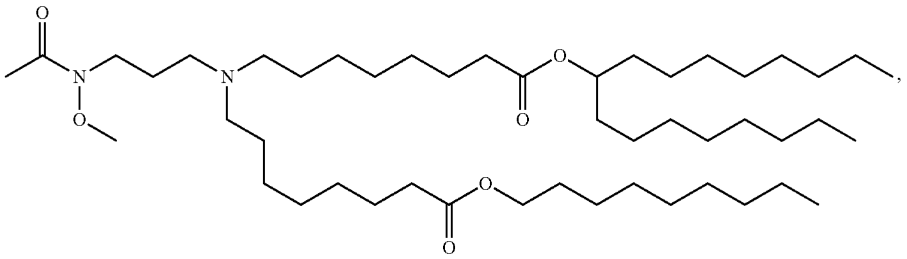
(Compound 204)
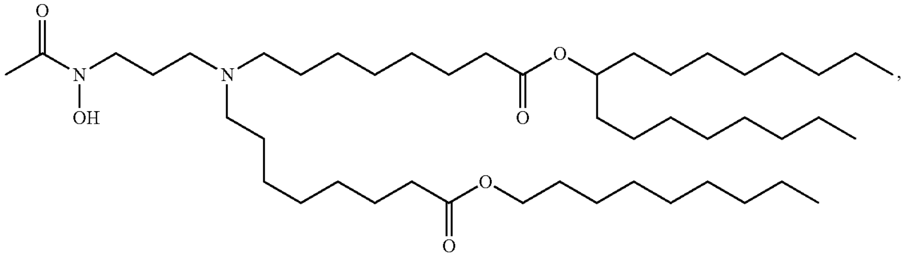
(Compound 205)
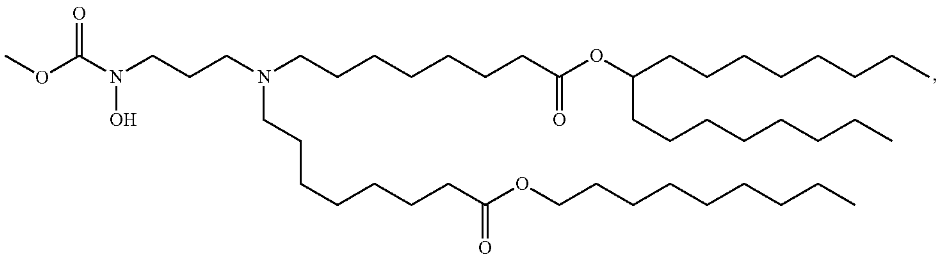

-continued
(Compound 206)
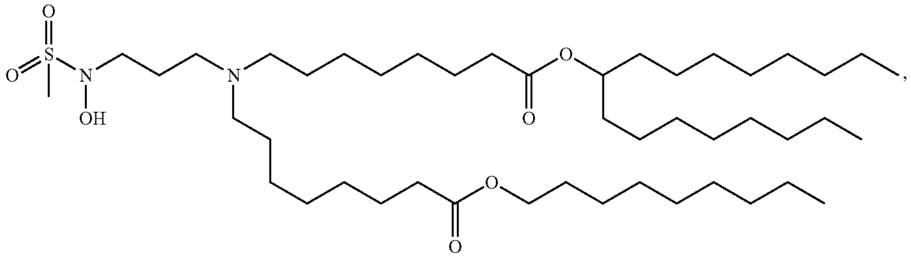
(Compound 207)
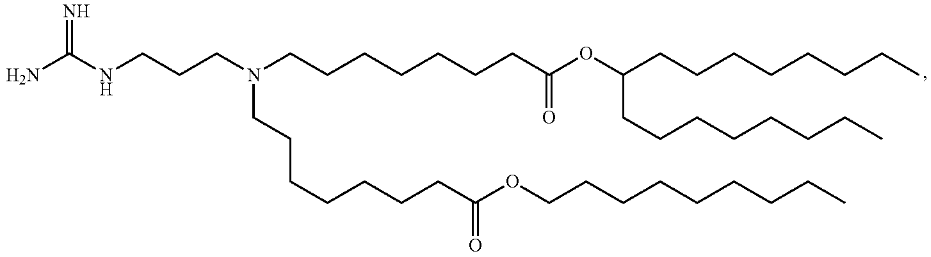
(Compound 208)
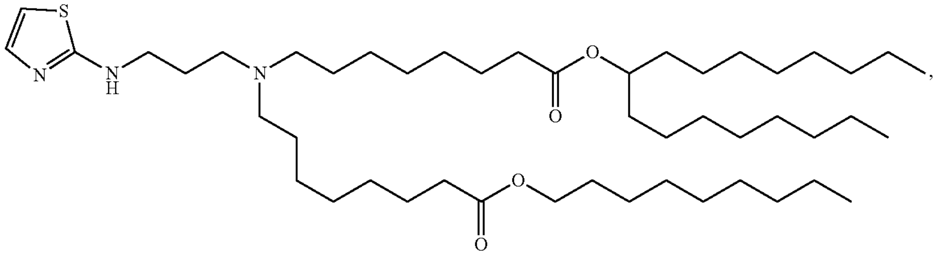
(Compound 209)
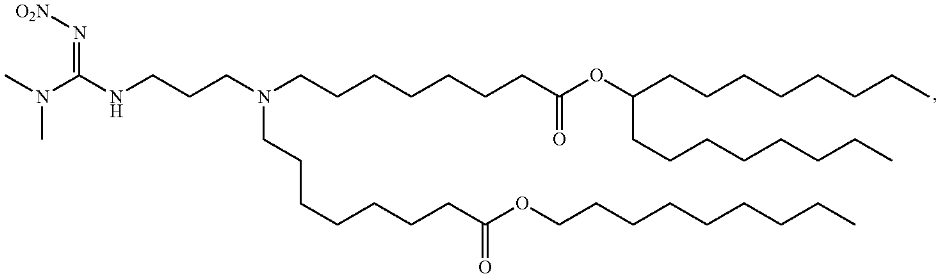
(Compound 210)
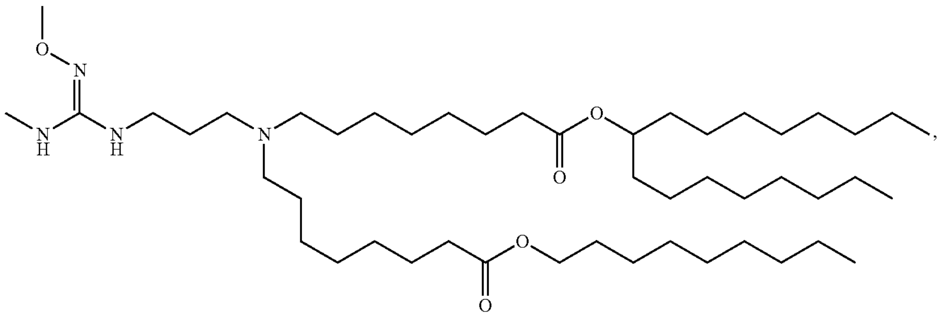

-continued
(Compound 211)
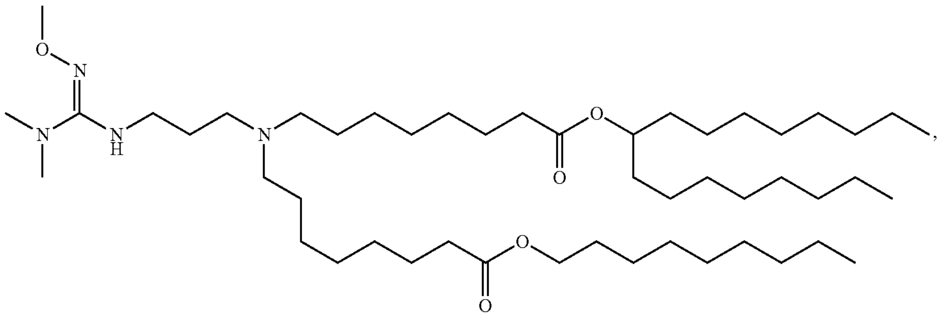
(Compound 212)
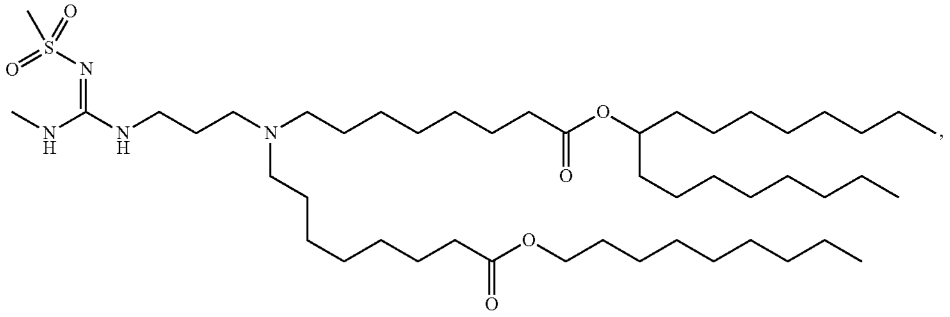
(Compound 213)
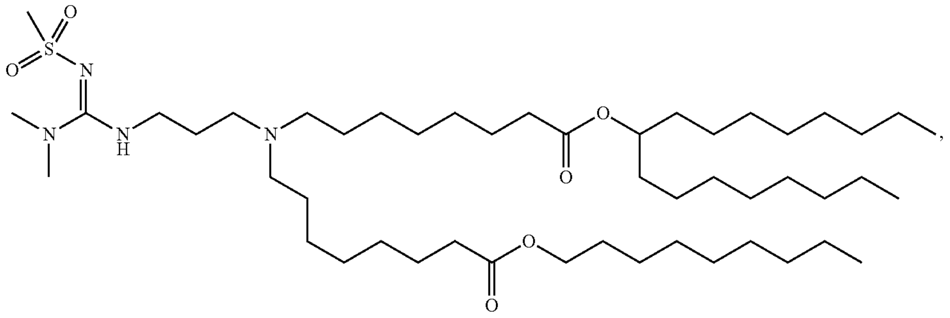
(Compound 214)
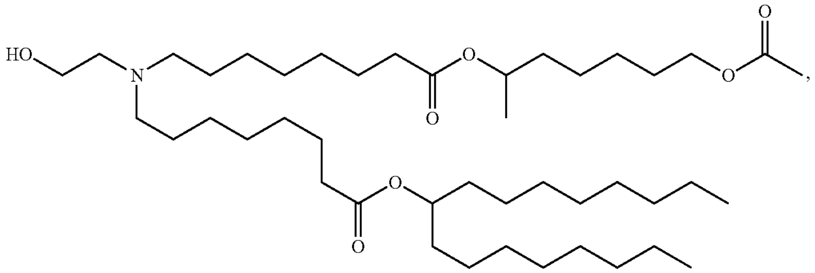
(Compound 215)
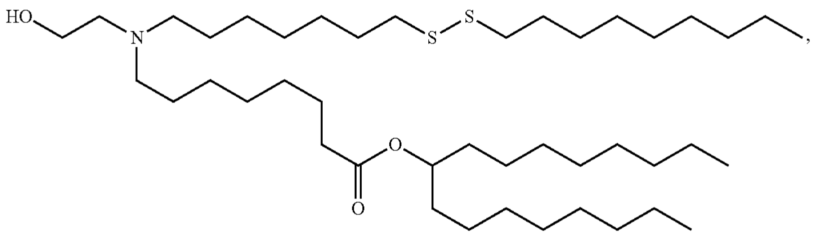

-continued
(Compound 216)
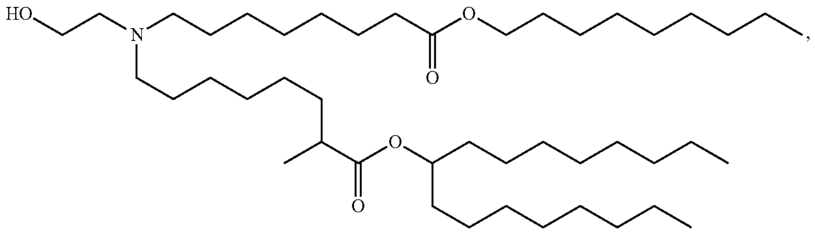
(Compound 217)
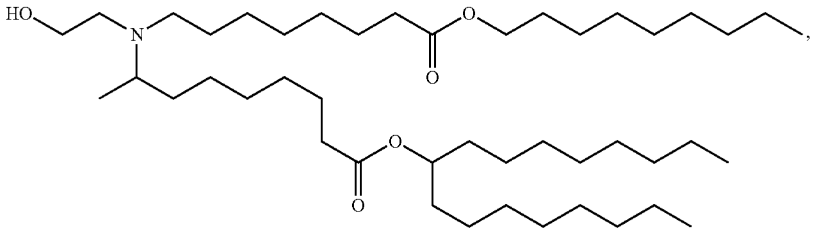
(Compound 218)
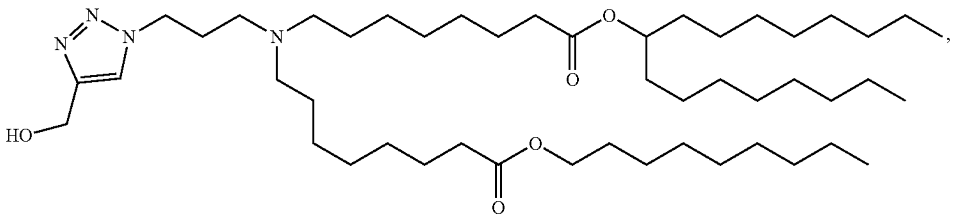
(Compound 219)
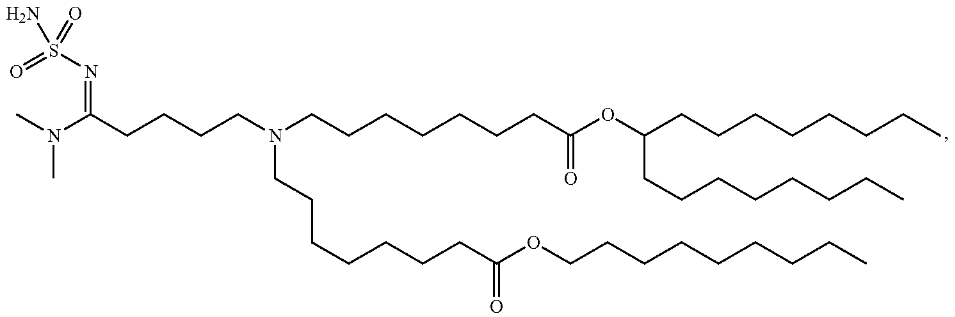
(Compound 220)
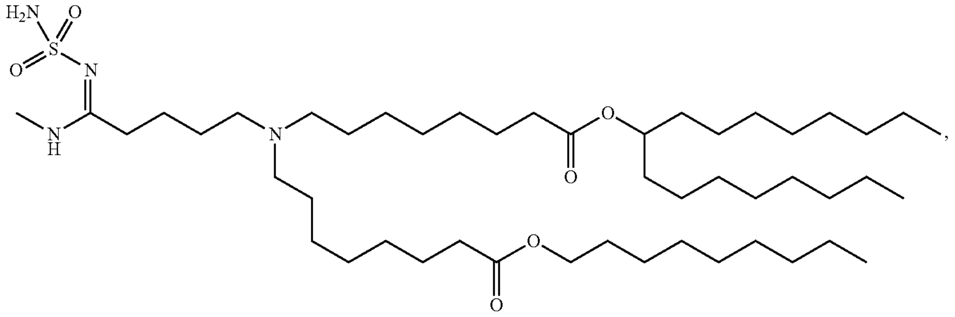

-continued
(Compound 221)
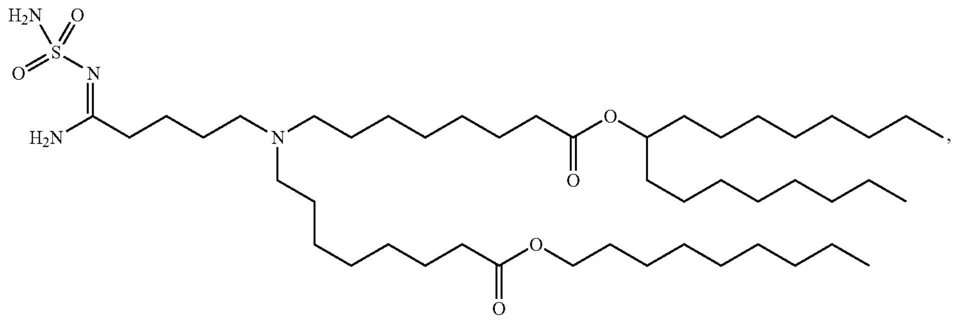
,
(Compound 222)
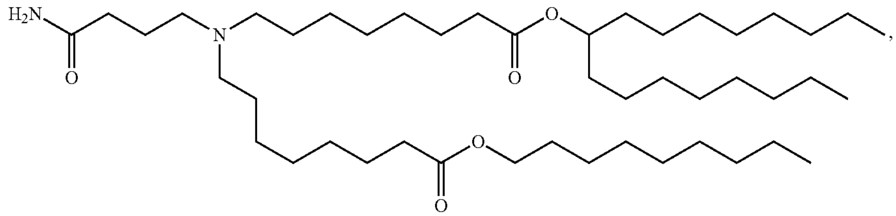
,
(Compound 223)
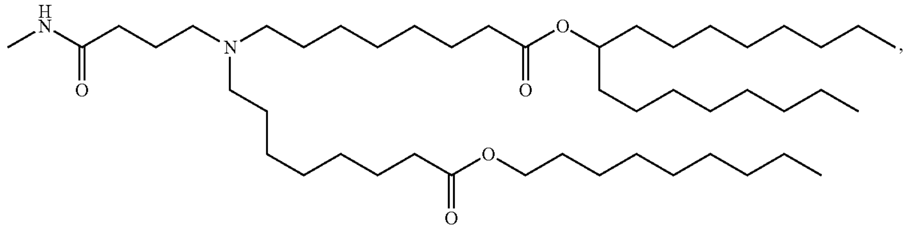
,
(Compound 224)
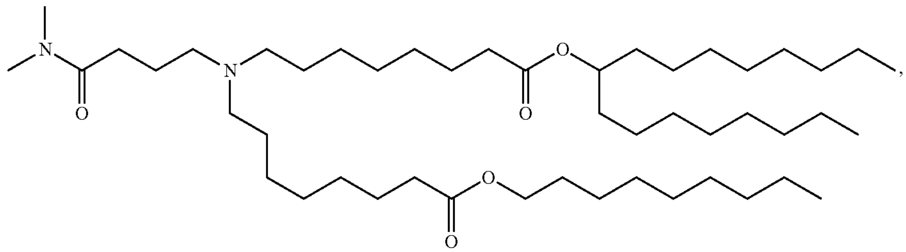
,
(Compound 225)
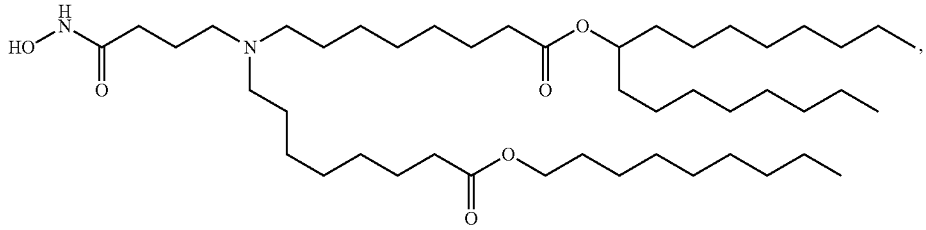
,
(Compound 226)
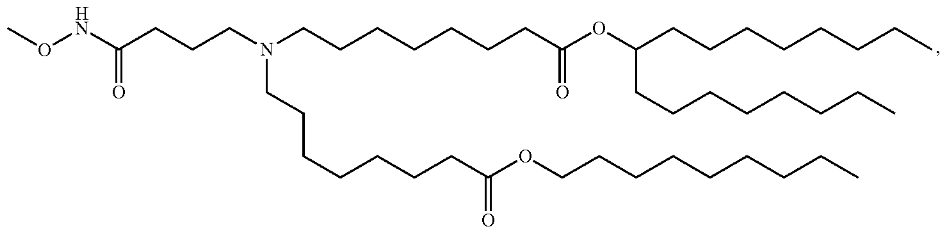
, -continued
(Compound 227)
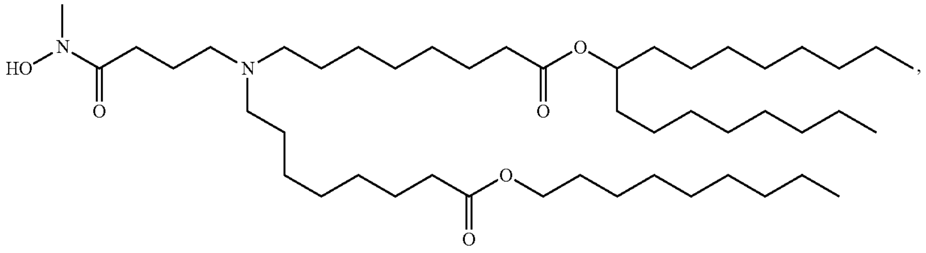
(Compound 228)
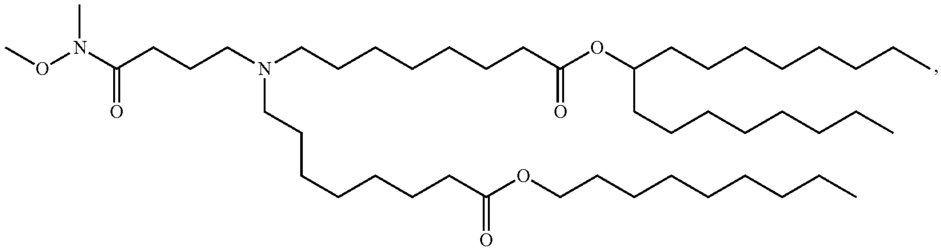
(Compound 229)
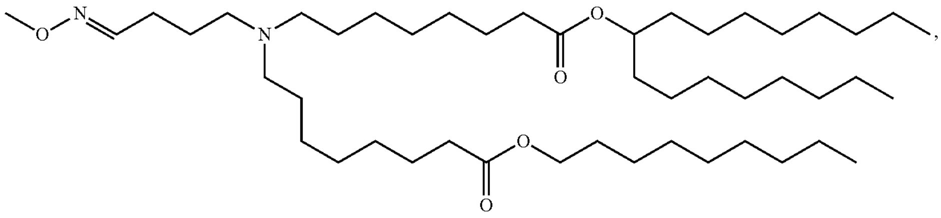
(Compound 232)
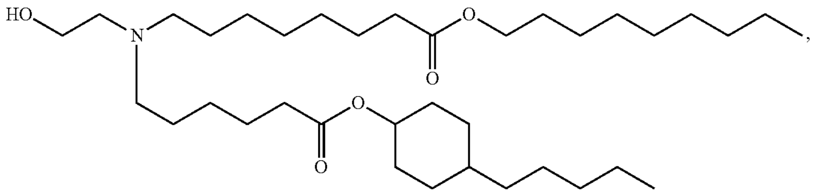
and salts and isomers thereof.

In some embodiments, a nanoparticle comprises the following compound:

(Compound 429)

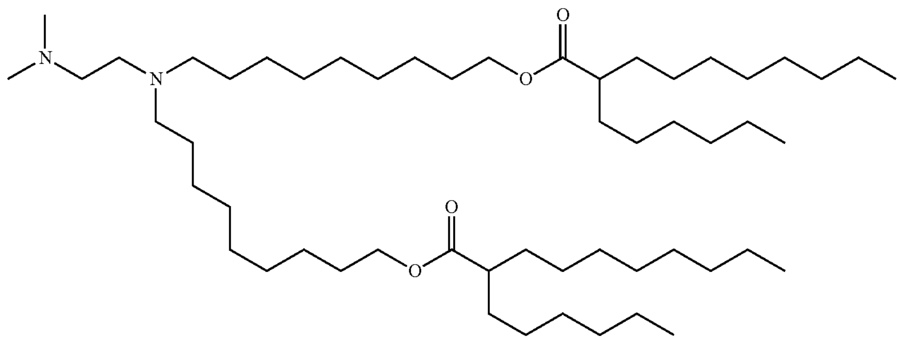

or salts and isomers thereof.

In some embodiments, a lipid nanoparticle composition includes a lipid component comprising a compound as described herein (e.g., a compound according to Formula (I), (IA), (II), (IIa), (IIb), (IIc), (IId) or (lie)).

In some embodiments LNPs may be comprised of ionizable lipids including a central piperazine moiety. Such LNPs advantageously may be composed of an ionizable lipid, a phospholipid and a PEG lipid and may optionally include a structural lipid or may lack a structural lipid. In some embodiments the phospholipid is a DSPC or DOP.

The ionizable lipids including a central piperazine moiety described herein may be advantageously used in lipid nanoparticle compositions for the delivery of therapeutic and/or prophylactic agents to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent.

Lipids may be compounds of Formula (III), (III)

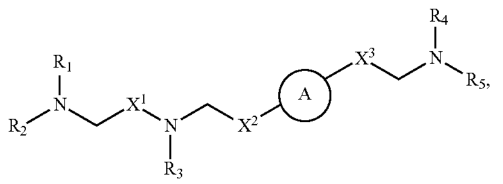

or salts or isomers thereof, wherein ring A is A

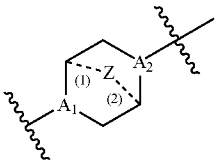

or

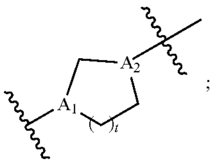

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl, each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is,

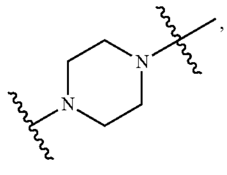 [SMILES: *N1CCN(*)CC1]

, then i) at least one of $X^1$, $X^2$, and $X^3$ is not —$CH_2$—; and/or ii) at least one of $R_1$, $R_2$, $R_3$, $R_4$, and $R_5$ is —R"MR'.

In some embodiments, the compound is of any of formulae (IIIa1)-(IIIa6):

(IIIa1)

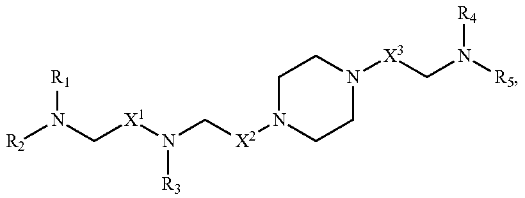

(IIIa2)

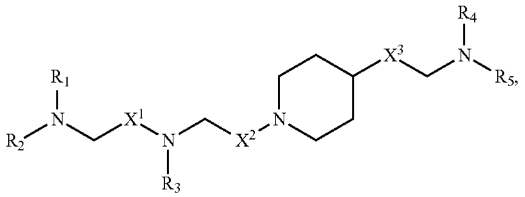

(IIIa3)

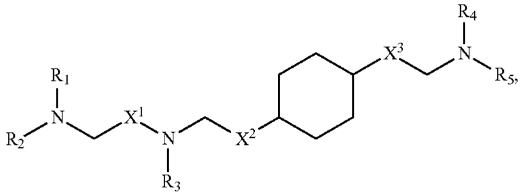

(IIIa4)

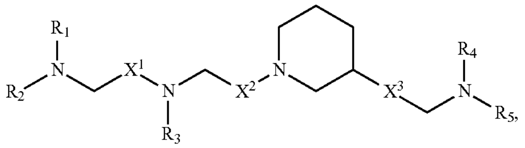

(IIIa5)

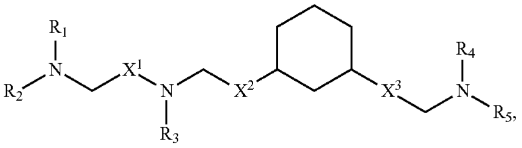

or (IIIa6)

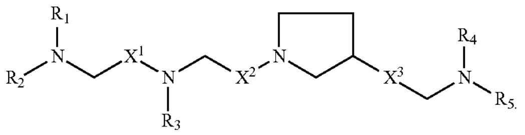

The compounds of Formula (III) or any of (IIIa1)-(IIIa6) include one or more of the following features when applicable.

In some embodiments, ring A is

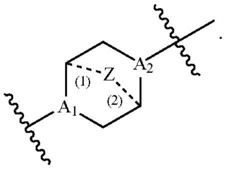

In some embodiments, ring A is

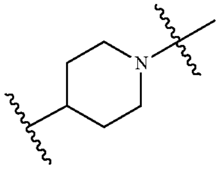

or

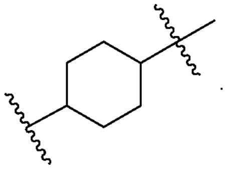

In some embodiments, ring A is

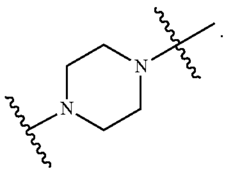 [SMILES: *N1CCN(*)CC1]

In some embodiments, ring A is

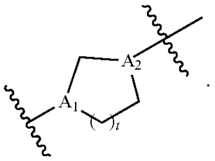

In some embodiments, ring A is

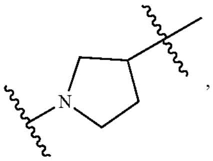

,

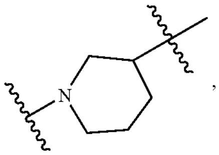

, or

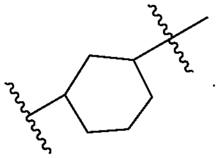

In some embodiments, ring A is

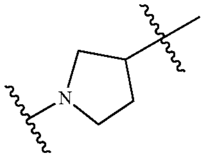

or

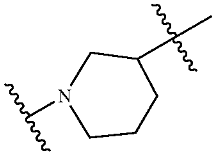

wherein ring, in which the N atom is connected with $X^2$.

In some embodiments, Z is CH2.

In some embodiments, Z is absent.

In some embodiments, at least one of A1 and A2 is N.

In some embodiments, each of A1 and A2 is N.

In some embodiments, each of A1 and A2 is CH.

In some embodiments, A1 is N and A2 is CH.

In some embodiments, A1 is CH and A2 is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—CH2-, —CH2-C(O)—, —C(O)O—CH2-, —OC(O)—CH2-, —CH2-C(O)O—, or —CH2-OC(O)—. In other embodiments, $X^3$ is —CH2-.

In some embodiments, $X^3$ is a bond or —(CH2)2-.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is C, alkyl. In certain embodiments, each R" is $C_8$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_8$ alkyl. In certain embodiments, each R' is $C_8$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In certain embodiments, the compound is selected from the group consisting of:

(Compound 233)

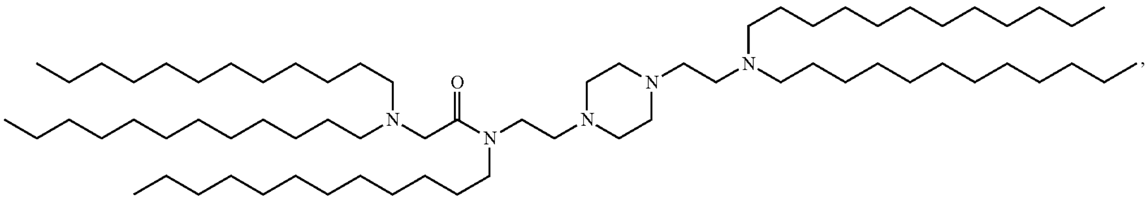

, (Compound 234)

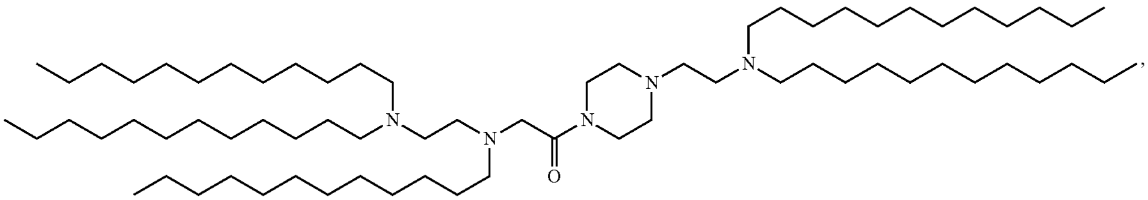

, (Compound 235)

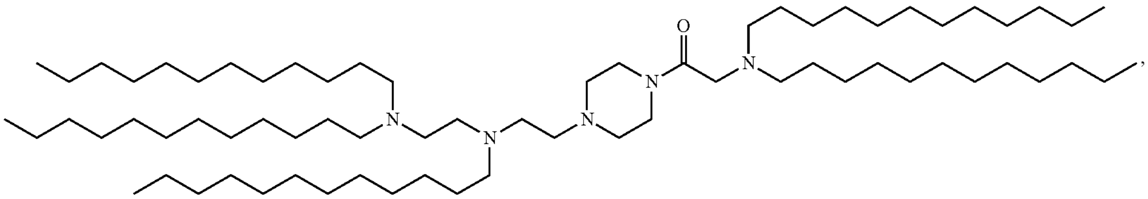

, (Compound 236)

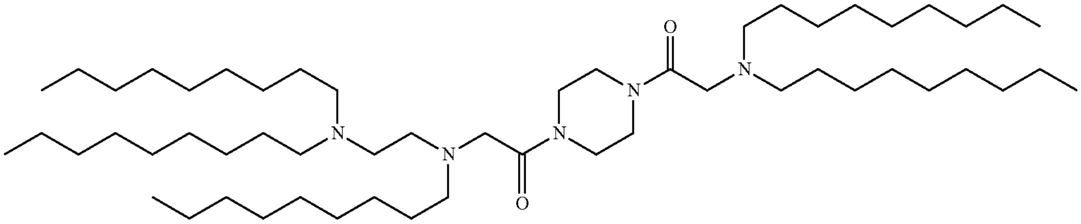

,

-continued
(Compound 237)
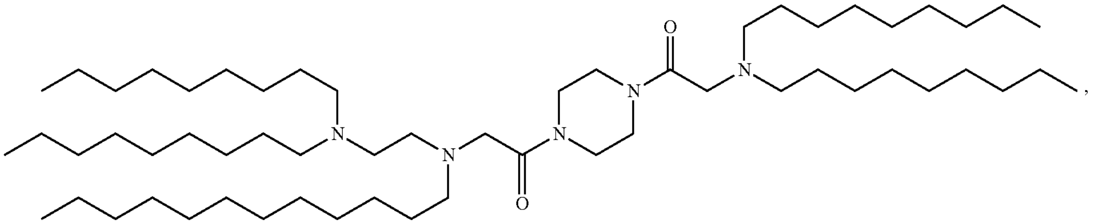
(Compound 238)
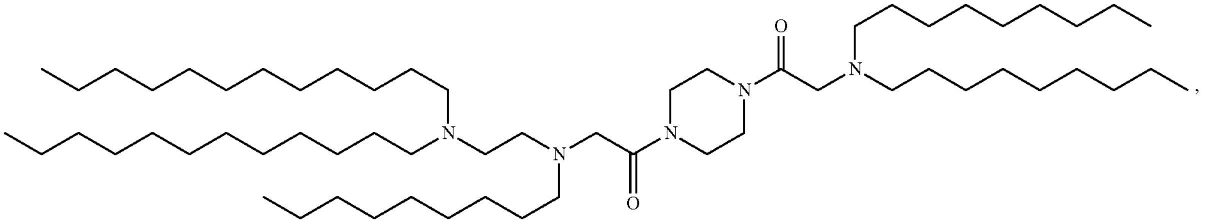
(Compound 239)
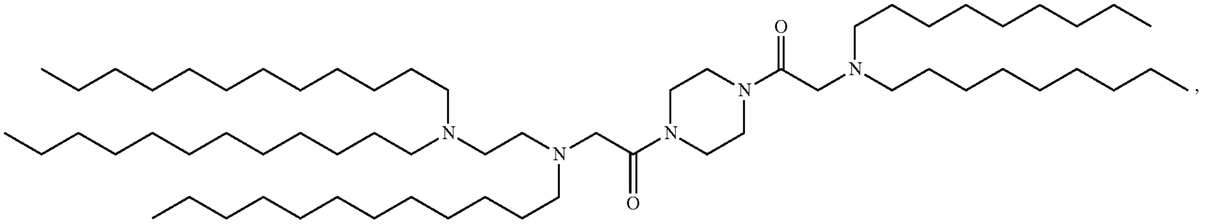
(Compound 240)
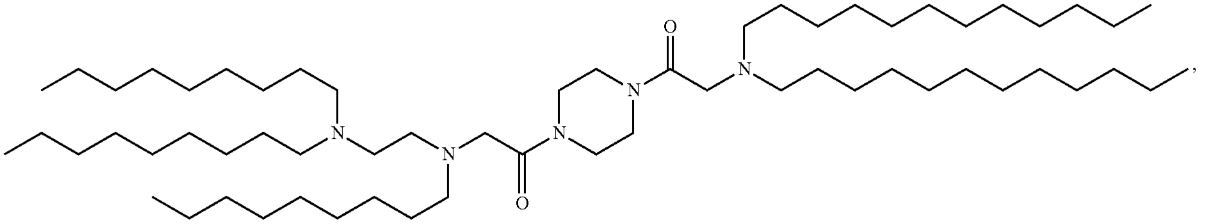
(Compound 241)
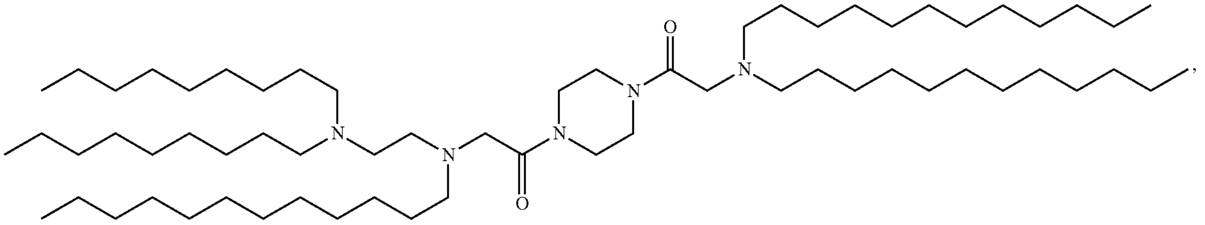
(Compound 242)
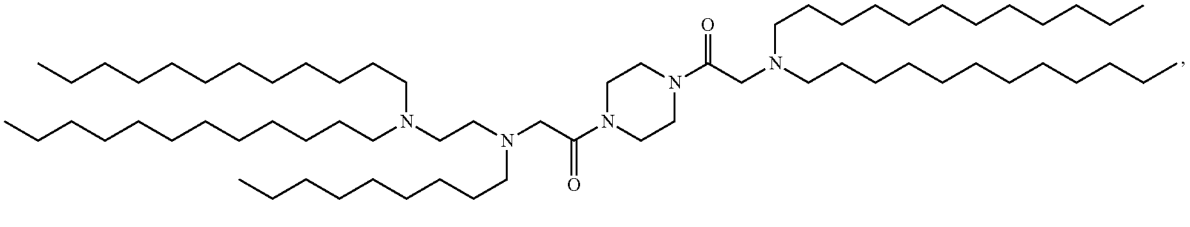

-continued
(Compound 243)
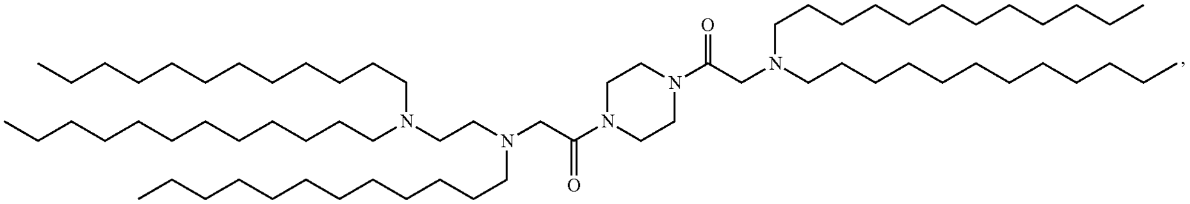
(Compound 244)
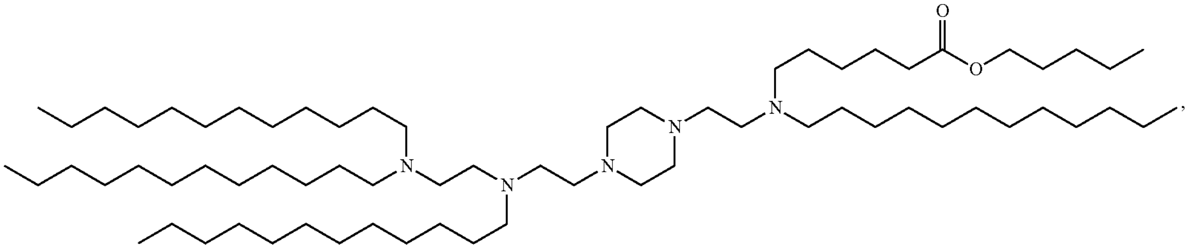
(Compound 245)
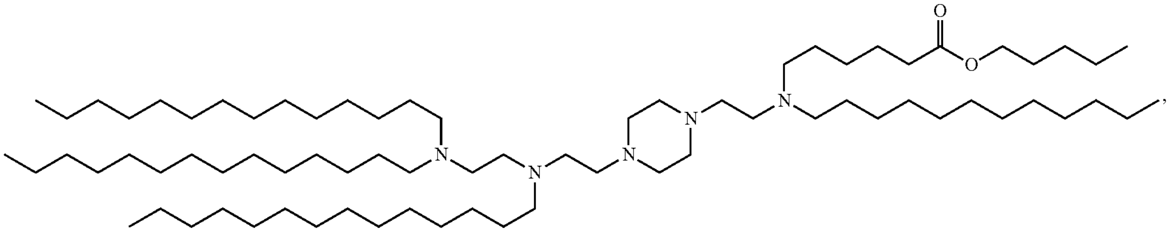
(Compound 246)
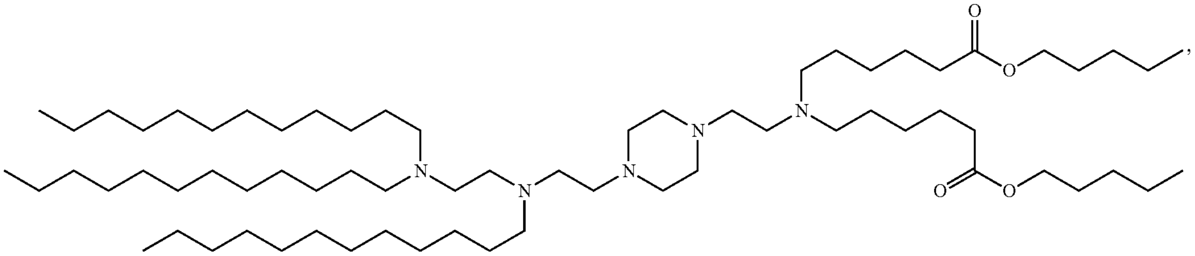
(Compound 247)
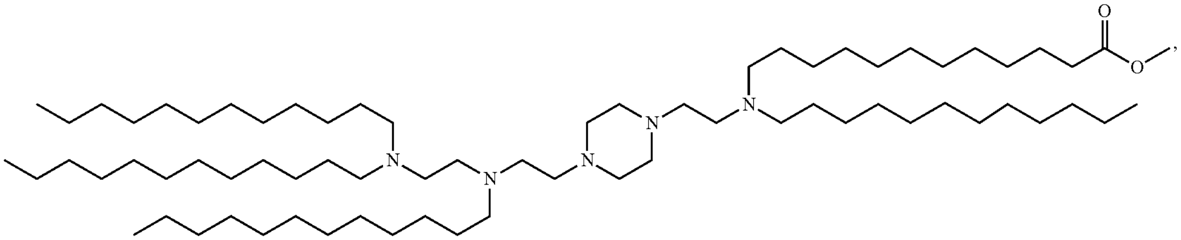
(Compound 248)
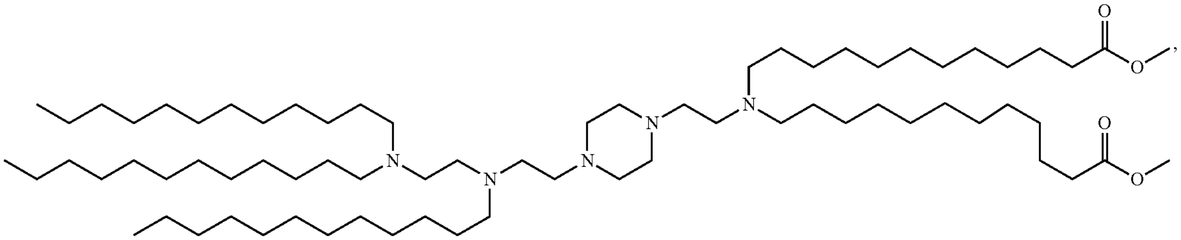

-continued
(Compound 274)
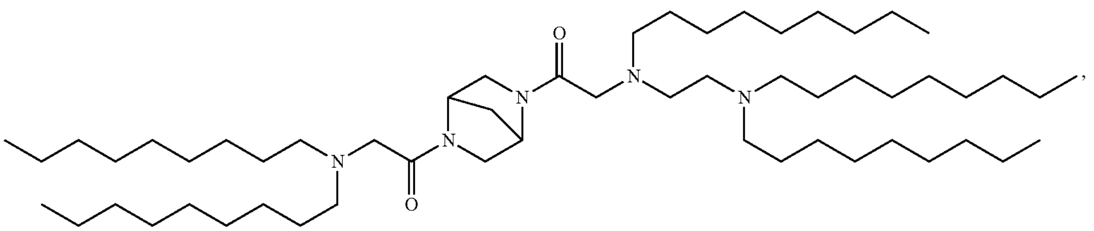
(Compound 275)
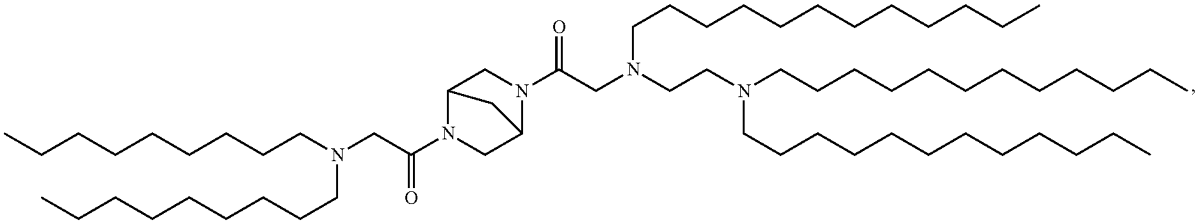
(Compound 276)
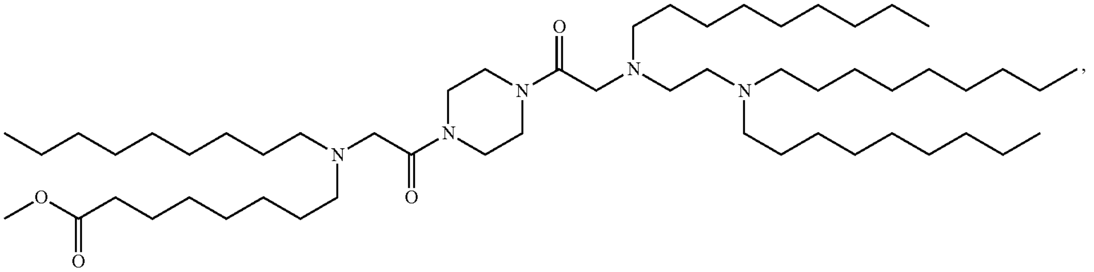
(Compound 277)
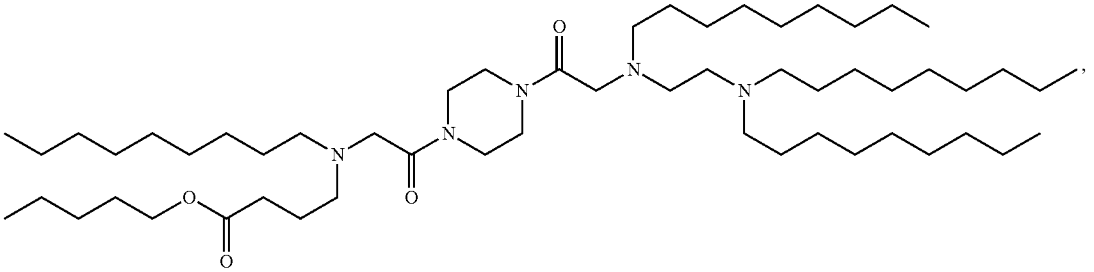
(Compound 278)
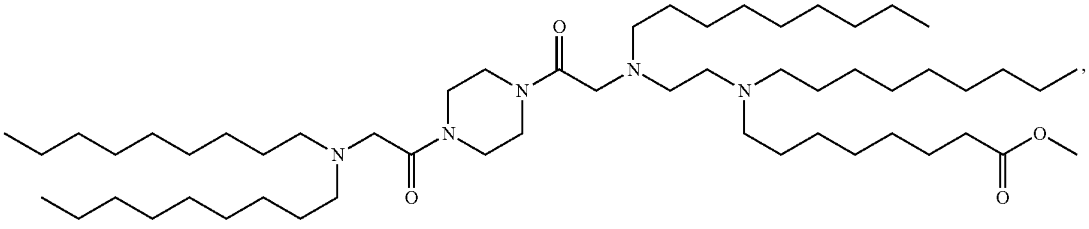
(Compound 279)
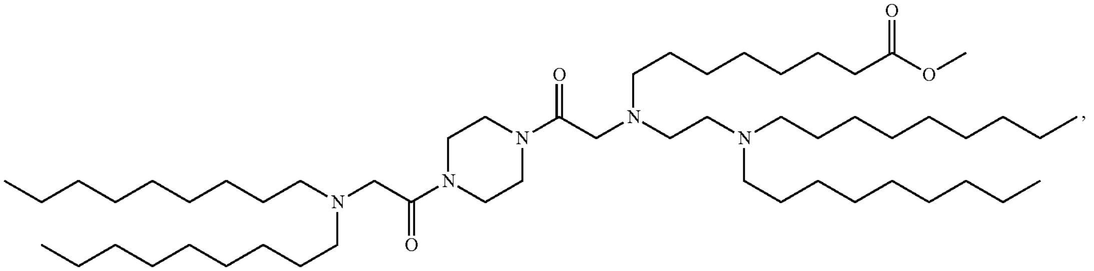

-continued
(Compound 280)
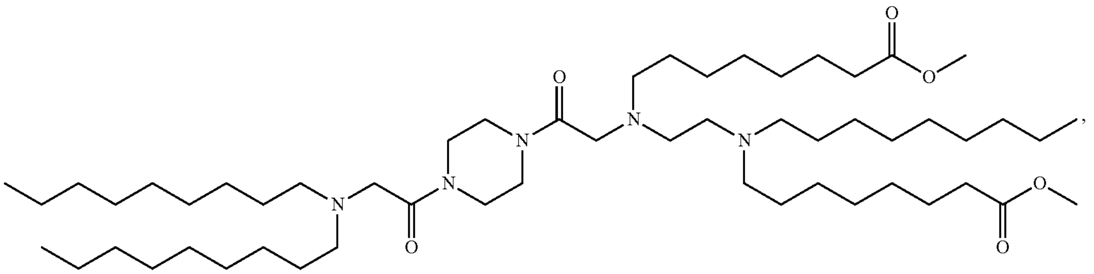
(Compound 281)
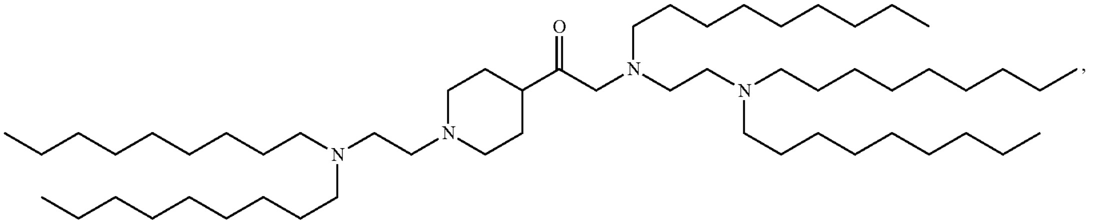
(Compound 282)
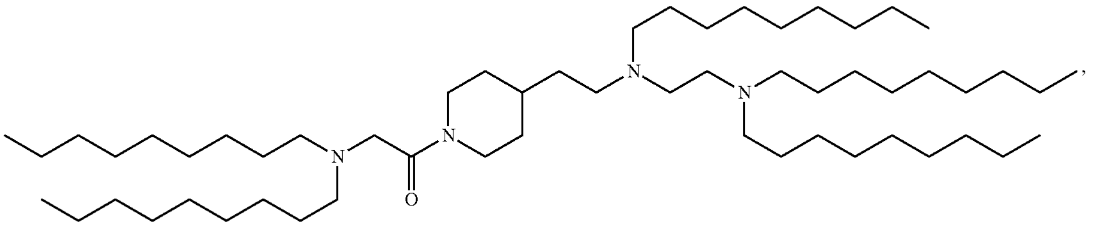
(Compound 283)
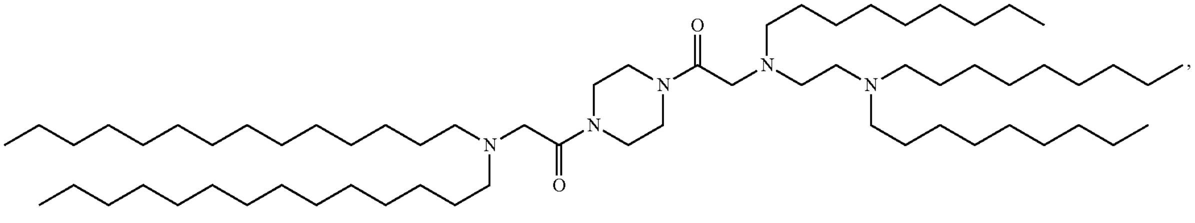
(Compound 284)
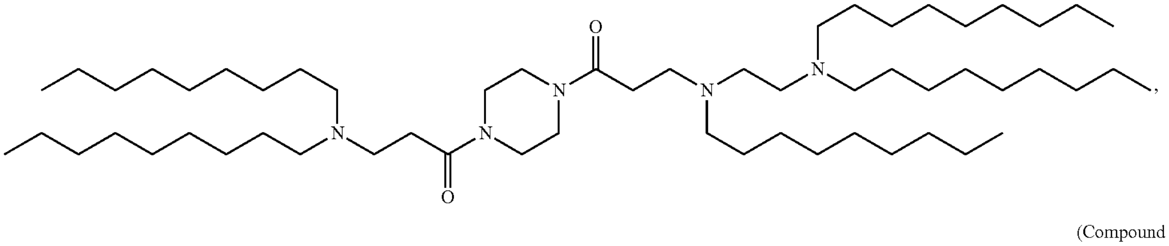
(Compound 285)
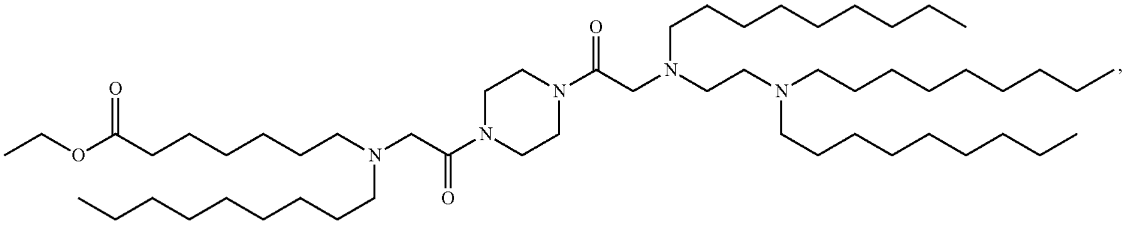

-continued
(Compound 286)
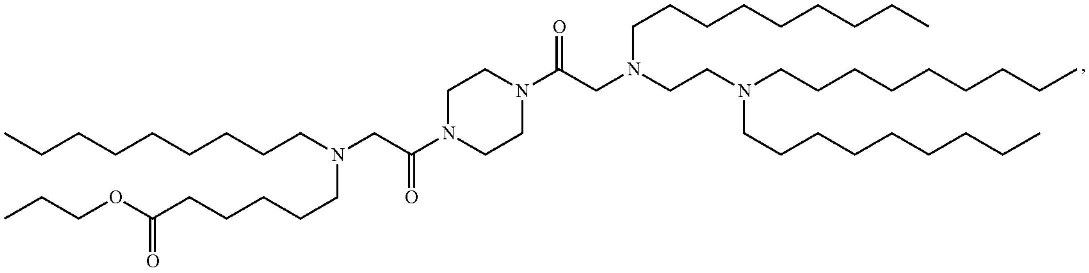
,
(Compound 287)
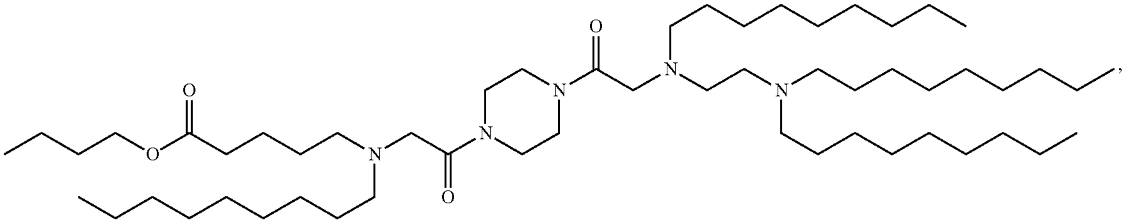
,
(Compound 288)
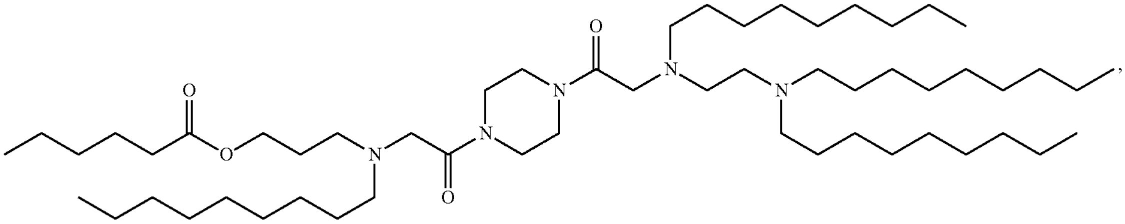
,
(Compound 289)
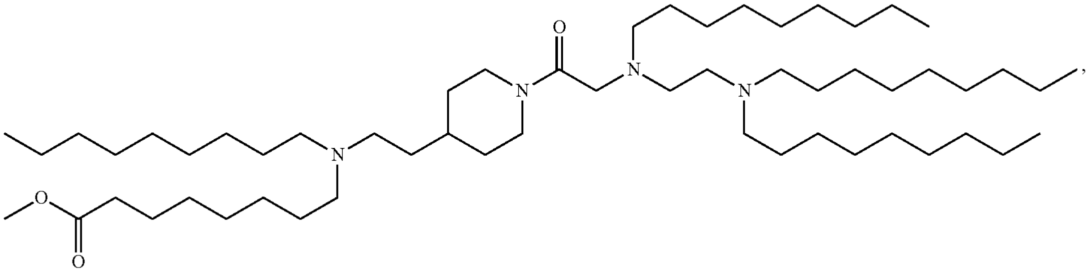
,
(Compound 290)
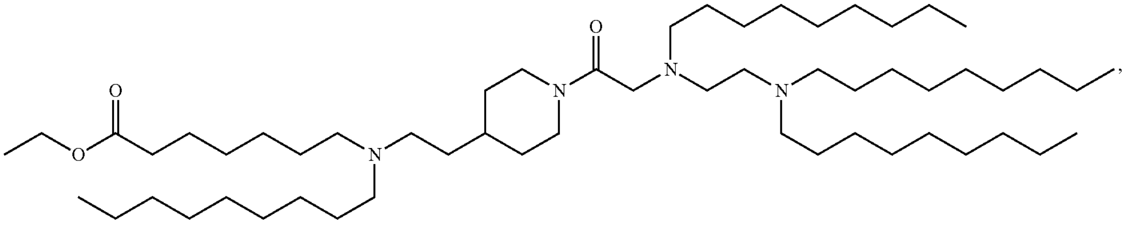
, -continued
(Compound 291)
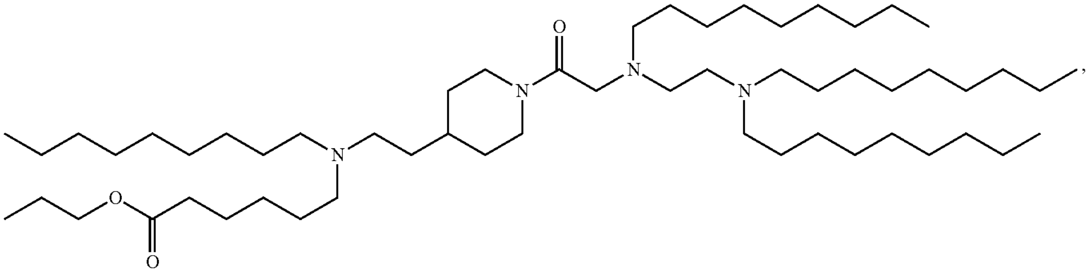
(Compound 292)
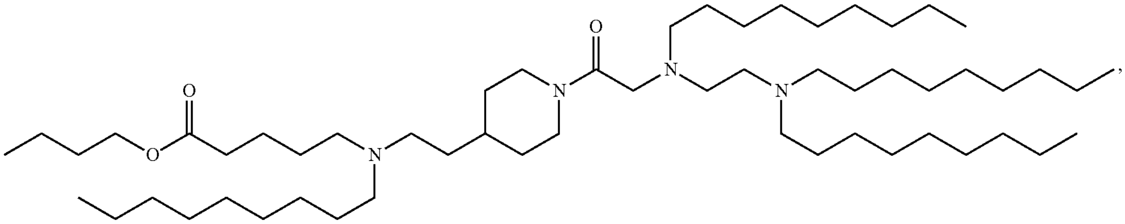
(Compound 293)
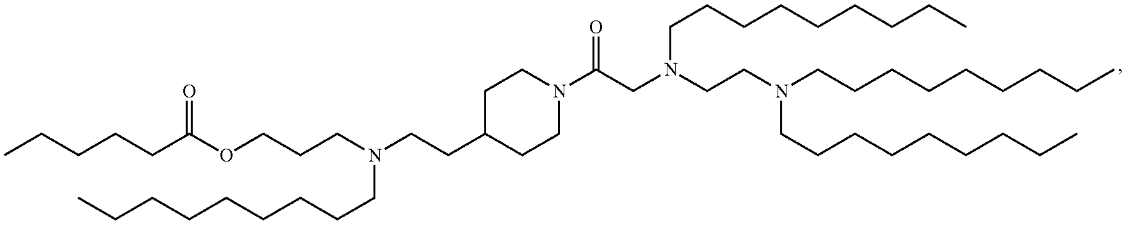
(Compound 294)
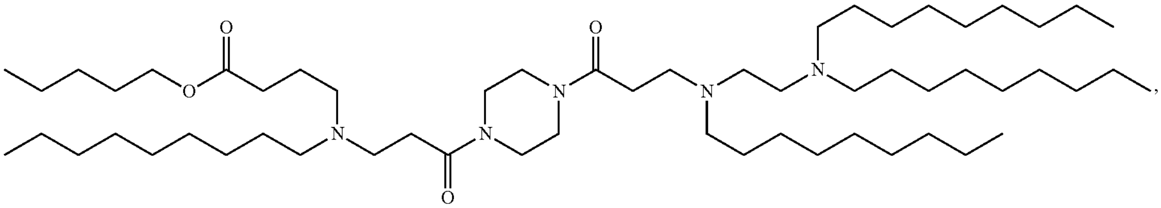
(Compound 295)
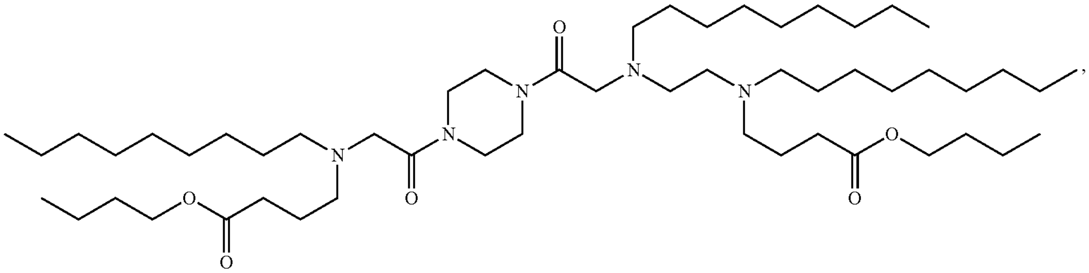
(Compound 296)
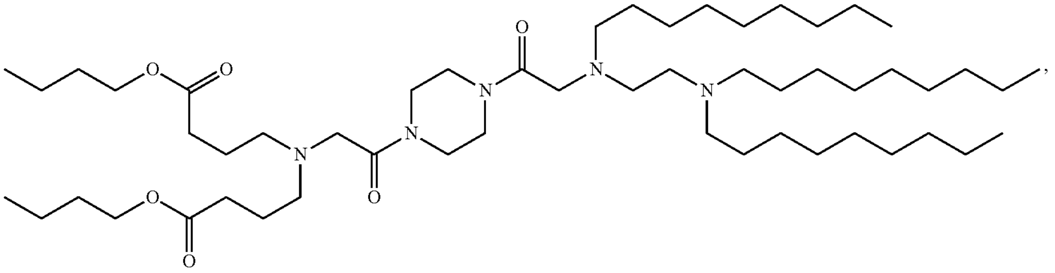

-continued
(Compound 297)
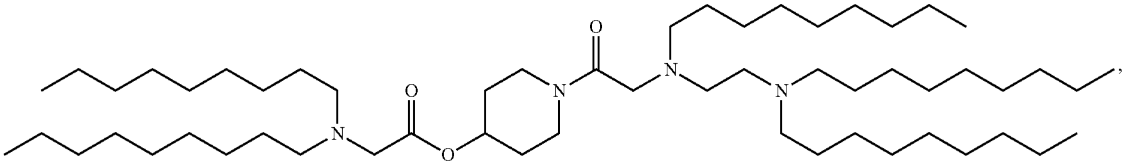
,
(Compound 298)
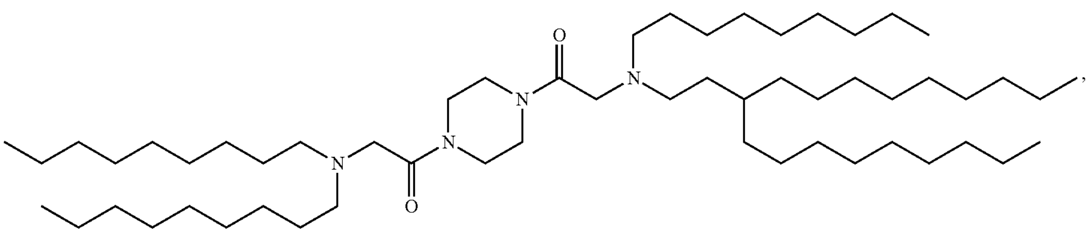
,
(Compound 300)
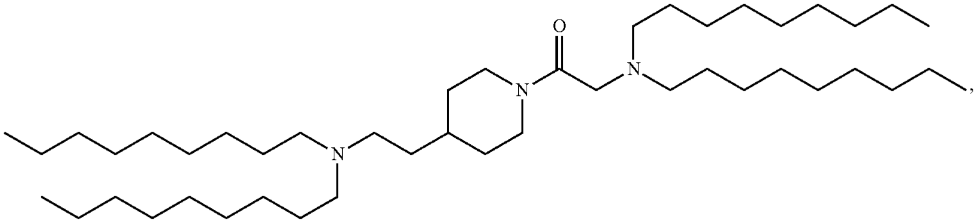
,
(Compound 301)
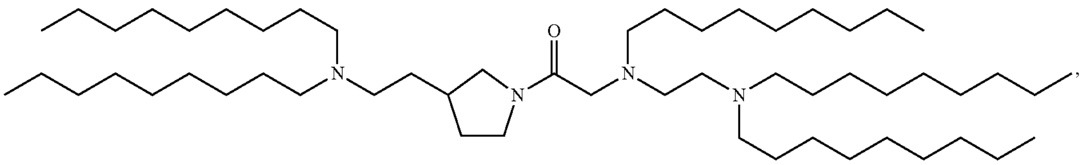
,
(Compound 302)
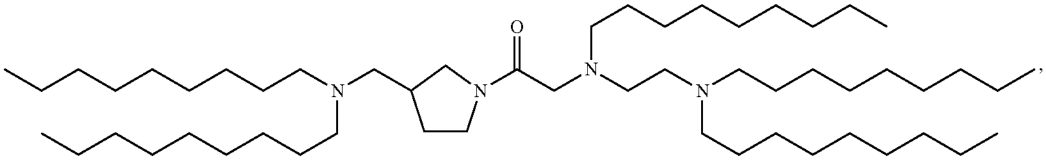
,
(Compound 303)
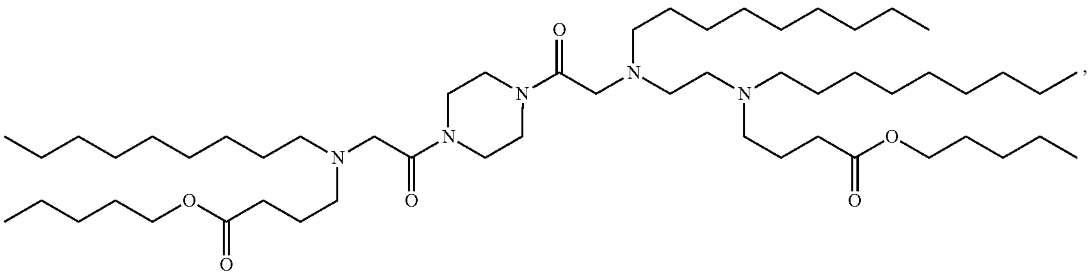
,
(Compound 304)
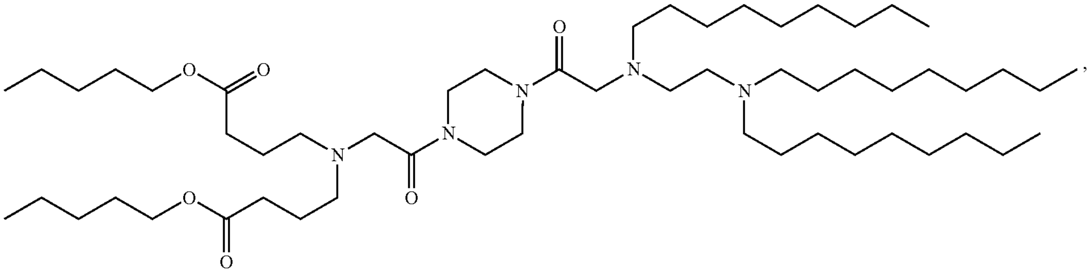
, -continued
(Compound 305)
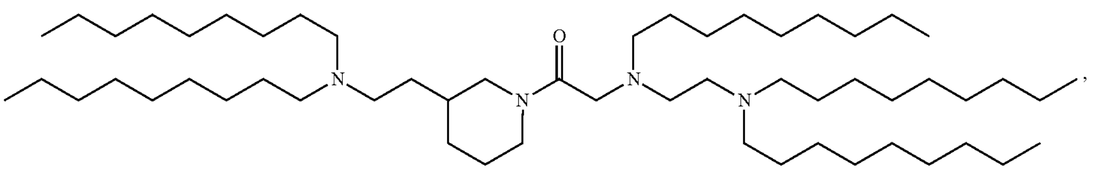
(Compound 306)
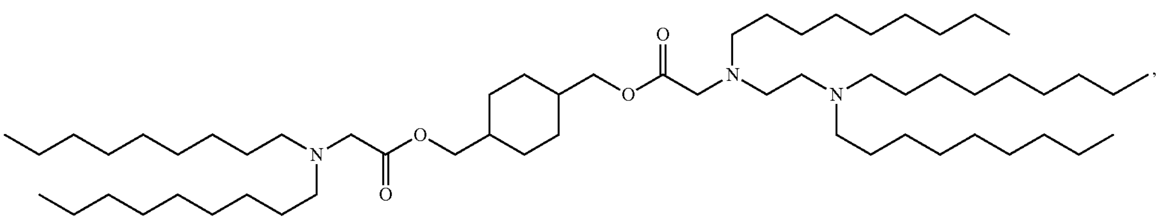
(Compound 307)
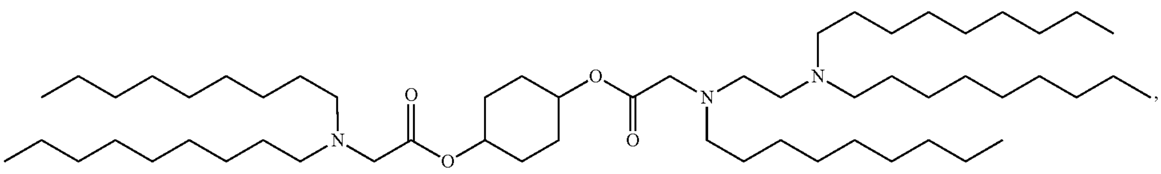
(Compound 308)
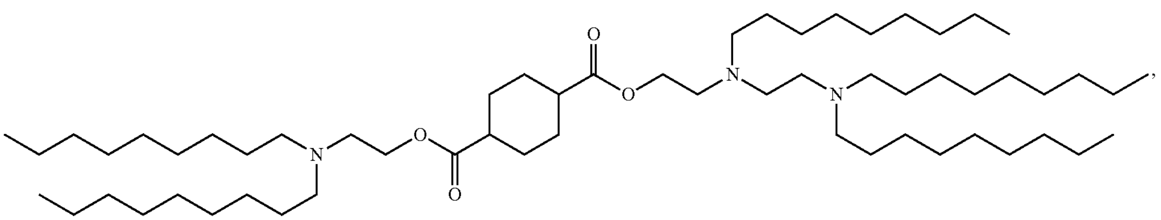
(Compound 310)
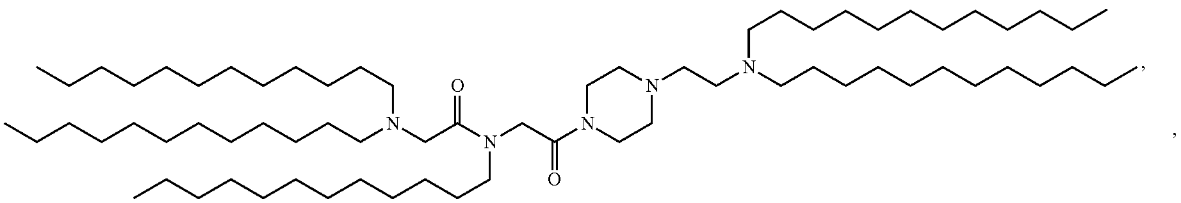
(Compound 311)
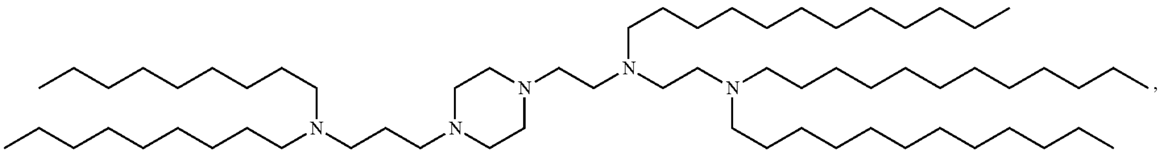
(Compound 312)
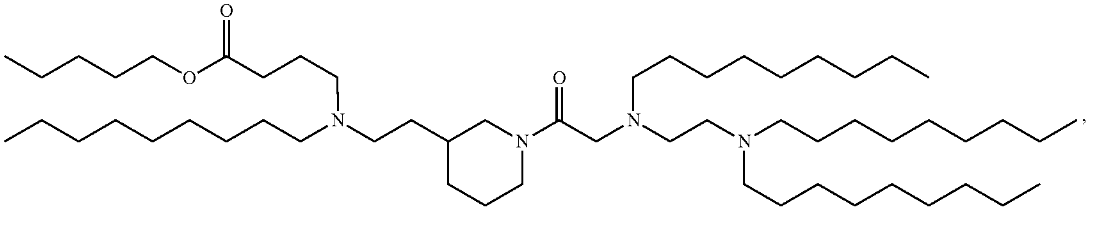

-continued
(Compound 313)
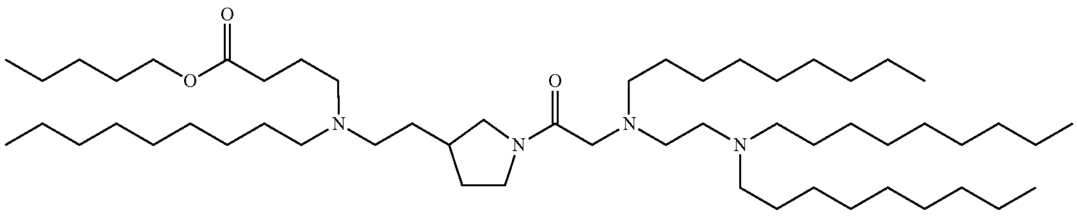,
(Compound 314)
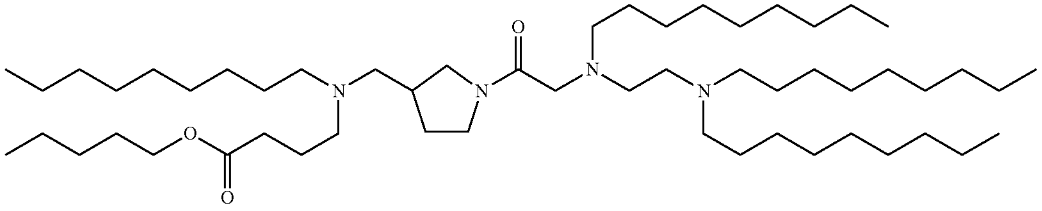,
(Compound 315)
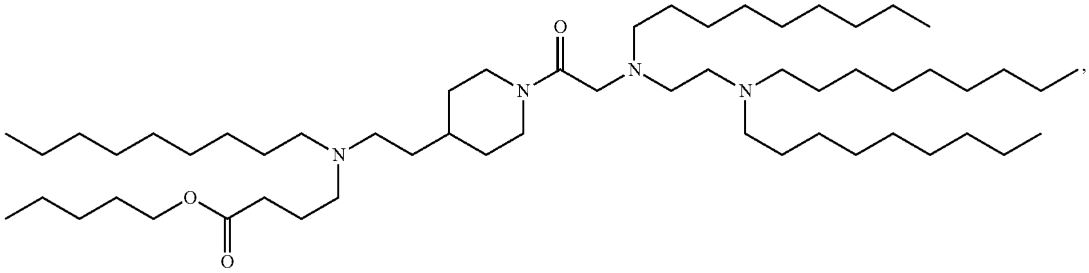,
(Compound 316)
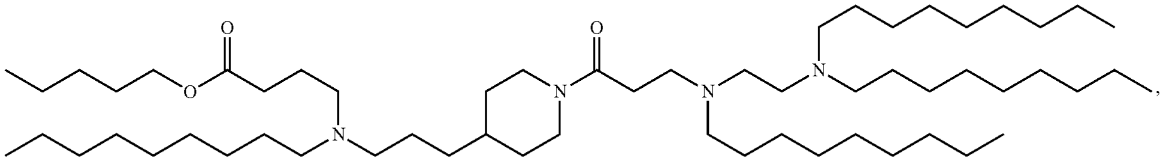,
(Compound 317)
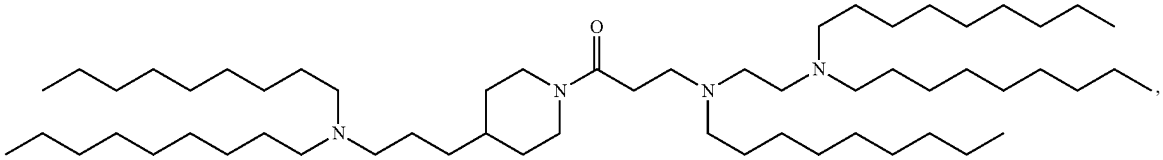,
(Compound 318)
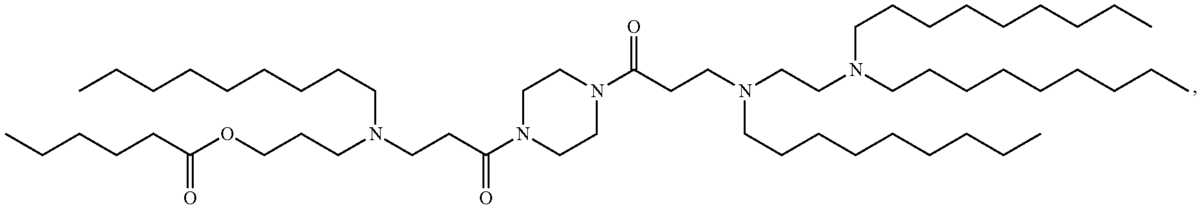,
(Compound 319)
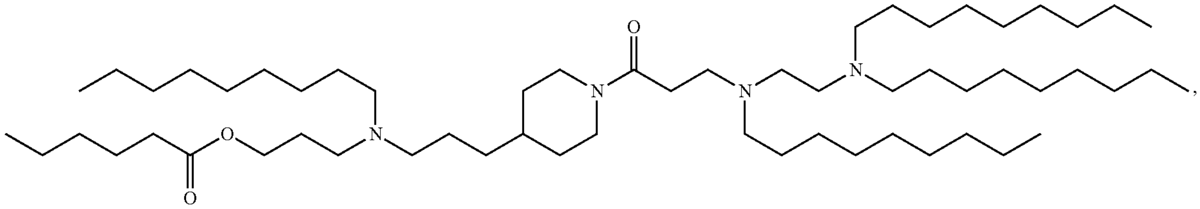, -continued
(Compound 320)
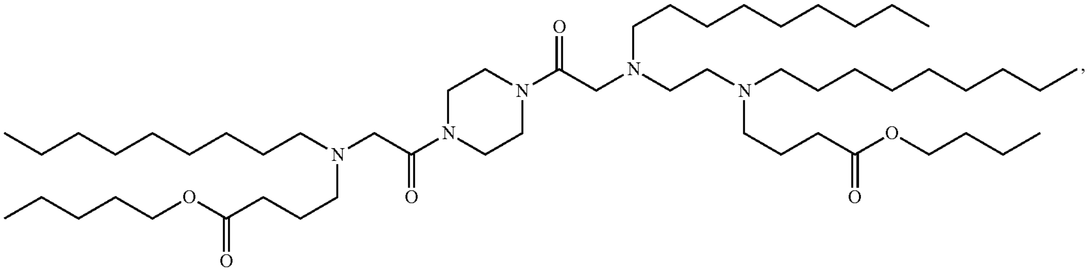
(Compound 321)
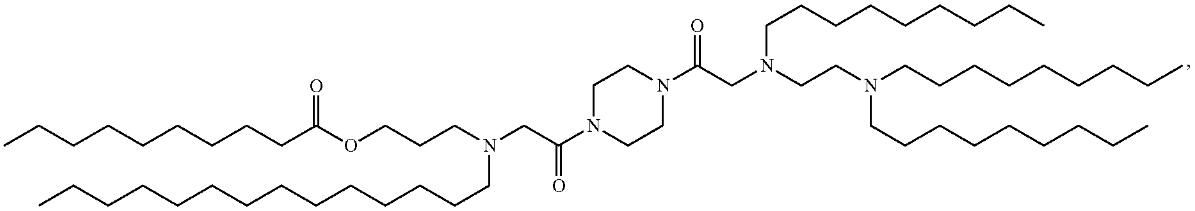
(Compound 322)
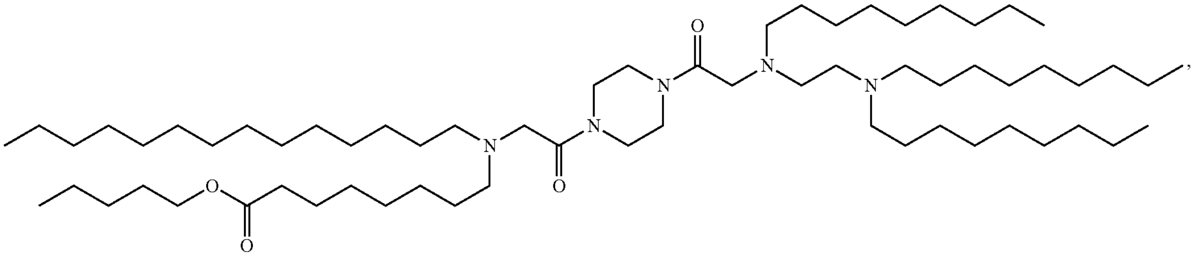
(Compound 323)
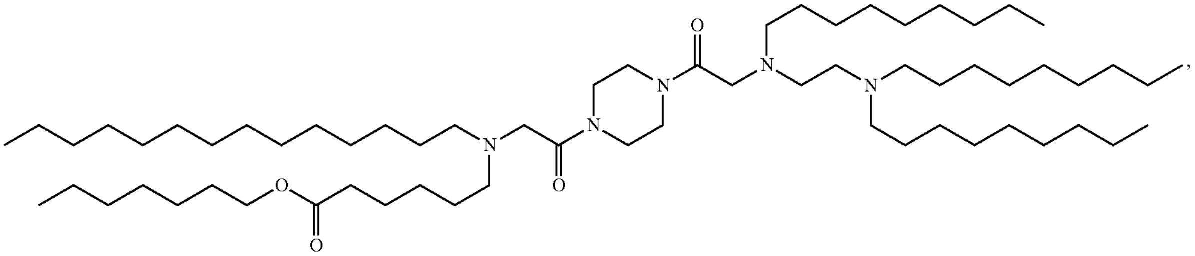
(Compound 324)
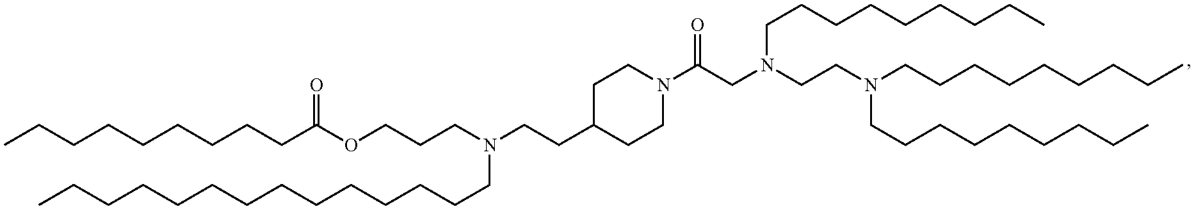
(Compound 325)
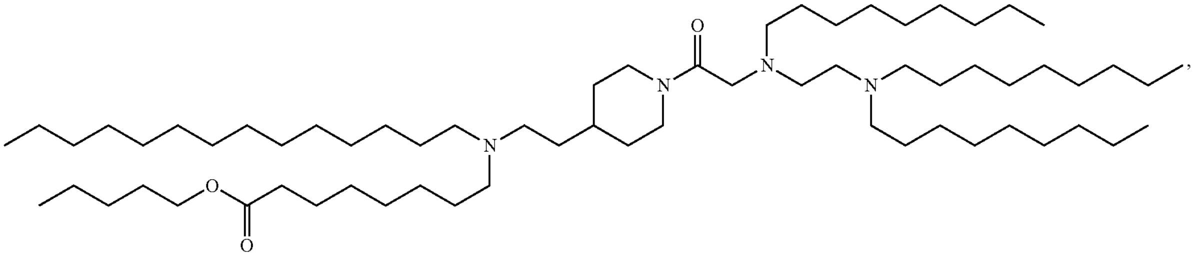

-continued
(Compound 326)
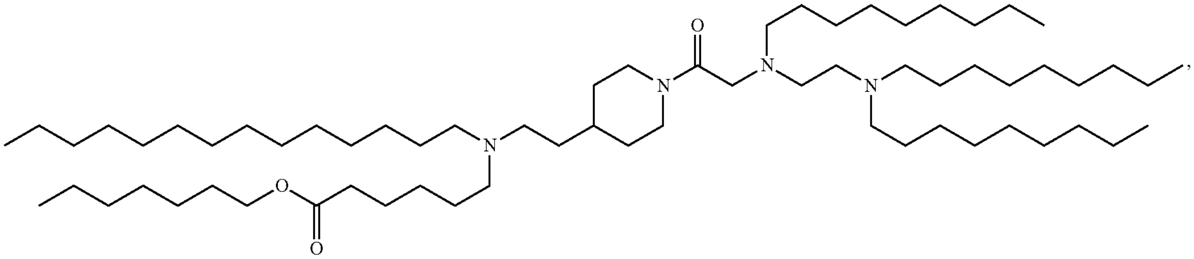
,
(Compound 327)
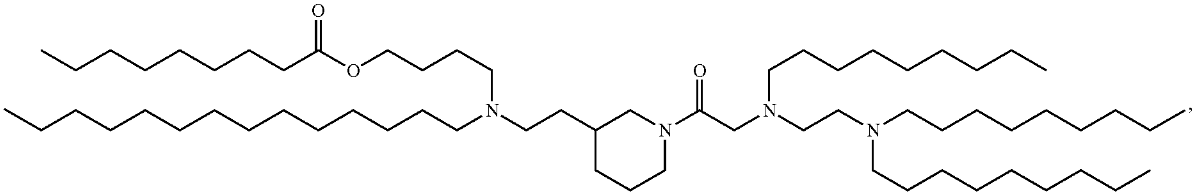
,
(Compound 328)
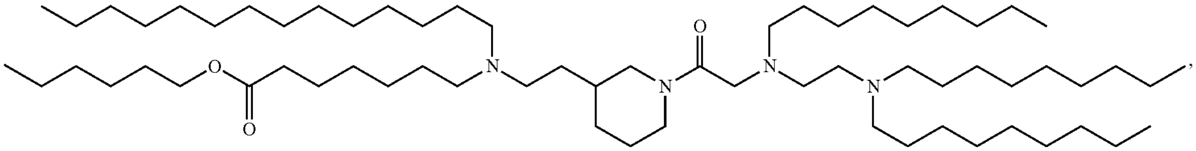
,
(Compound 329)
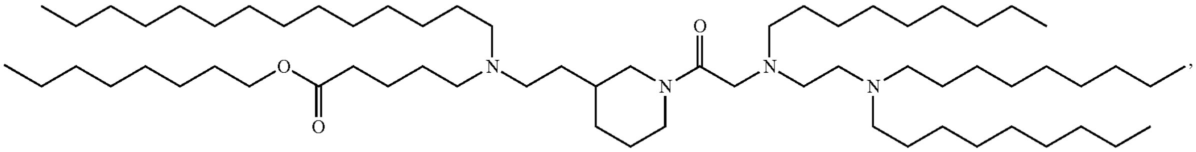
,
(Compound 330)
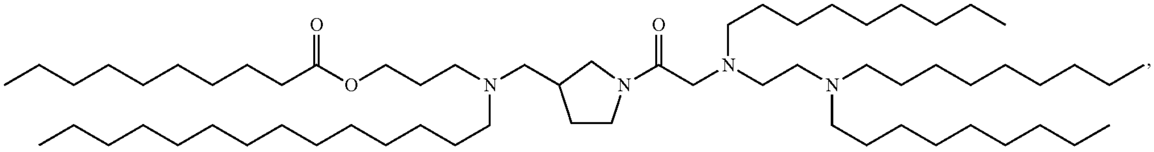
,
(Compound 331)
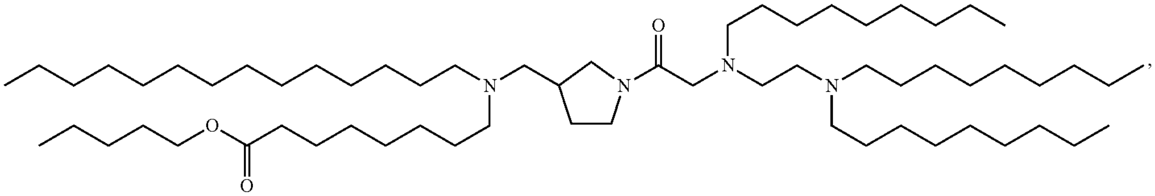
,
(Compound 332)
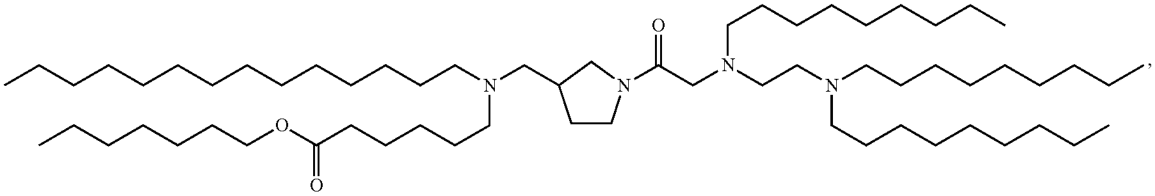
, -continued
(Compound 333)
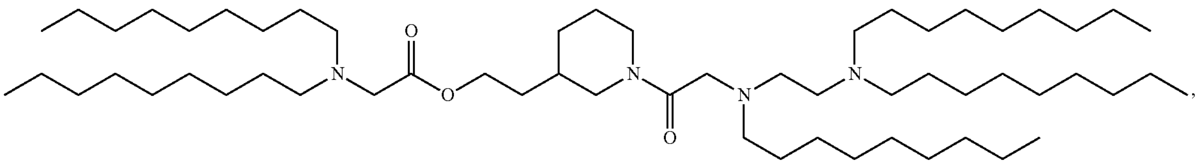
(Compound 334)
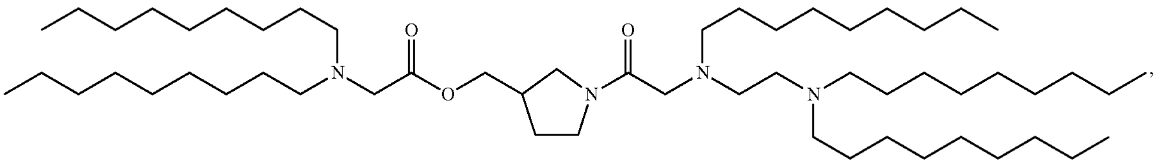
(Compound 335)
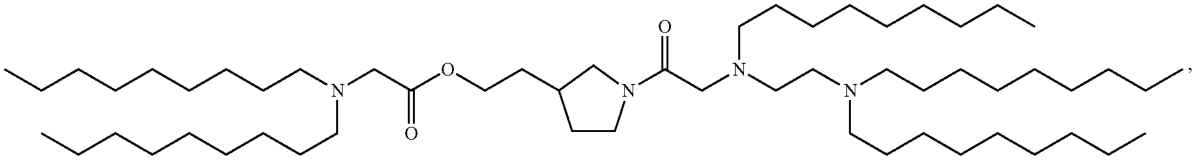
(Compound 336)
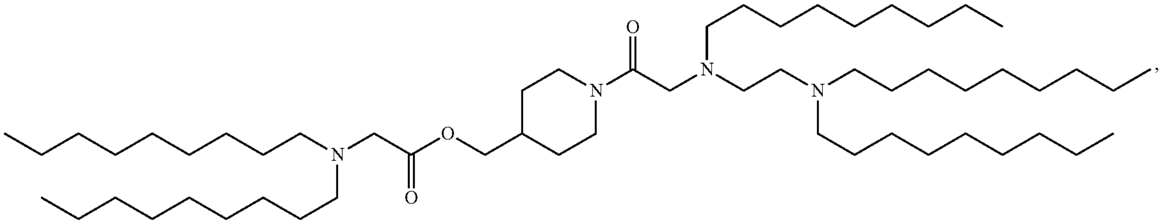
(Compound 337)
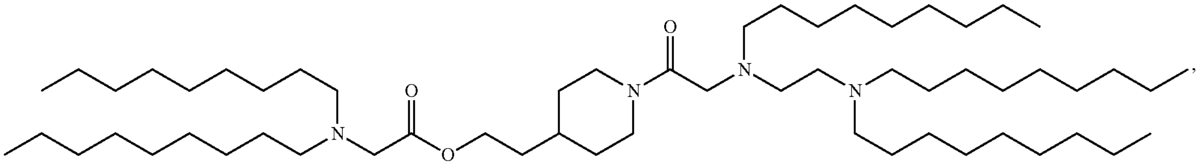
(Compound 338)
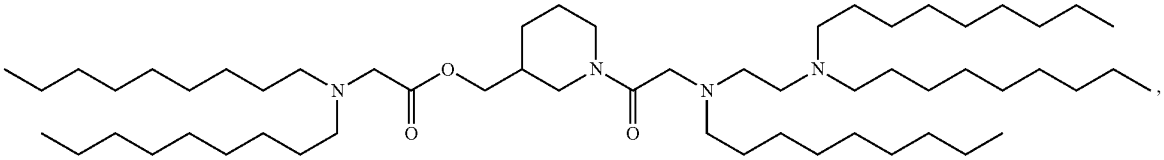
(Compound 339)
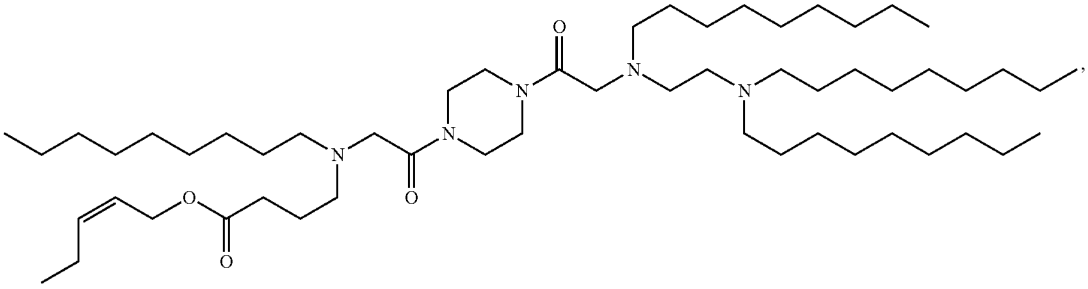

-continued (Compound 340)

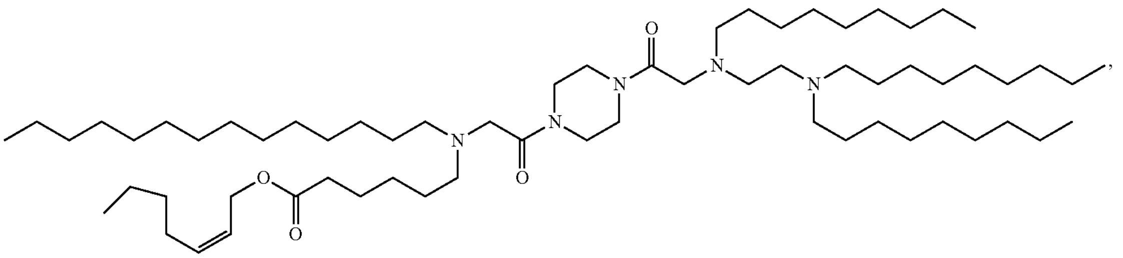

and (Compound 341)

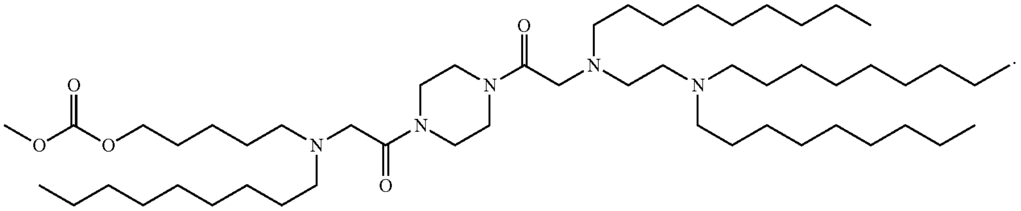

In other embodiments, a lipid has the Formula (IV)

(IV)

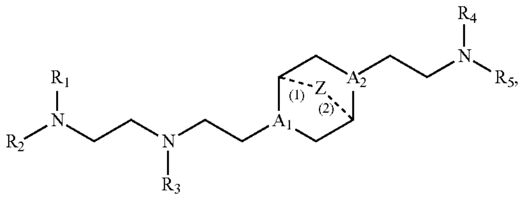

or a salt or isomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is

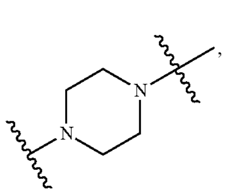 [SMILES: *N1CCN(*)CC1]

then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

(IVa)

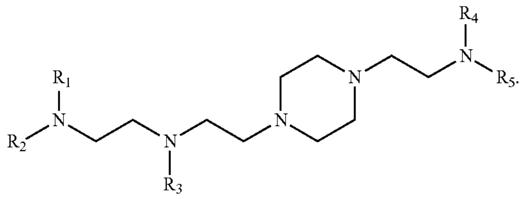

The compounds of Formula (IV) or (IVa) include one or more of the following features when applicable.

In some embodiments, Z is CH2.

In some embodiments, Z is absent.

In some embodiments, at least one of A1 and A2 is N.

In some embodiments, each of A1 and A2 is N.

In some embodiments, each of A1 and A2 is CH.

In some embodiments, A1 is N and A2 is CH.

In some embodiments, A1 is CH and A2 is N.

In some embodiments, R1, R2, R3, R4, and R5 are the same, and are not C12 alkyl, C18 alkyl, or C18 alkenyl. In some embodiments, R1, R2, R3, R4, and R5 are the same and are C9 alkyl or C14 alkyl.

In some embodiments, only one of R1, R2, R3, R4, and R5 is selected from C6-20 alkenyl. In certain such embodiments, R1, R2, R3, R4, and R5 have the same number of carbon atoms. In some embodiments, R4 is selected from C5-20 alkenyl. For example, R4 may be C12 alkenyl or C18 alkenyl.

In some embodiments, at least one of R1, R2, R3, R4, and R5 have a different number of carbon atoms than at least one other of R1, R2, R3, R4, and R5.

In certain embodiments, R1, R2, and R3 are selected from C6-20 alkenyl, and R4 and R5 are selected from C6-20 alkyl. In other embodiments, R1, R2, and R3 are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, R1, R2, and R3, or R4 and R5, are C18 alkenyl (e.g., linoleyl). In some embodiments, R1, R2, and R3, or R4 and R5, are alkyl groups including 6, 8, 9, 12, or 14 carbon atoms.

In some embodiments, R1 has a different number of carbon atoms than R2, R3, R4, and R5. In other embodiments, R3 has a different number of carbon atoms than R1, R2, R4, and R5. In further embodiments, R4 has a different number of carbon atoms than R1, R2, R3, and R5.

In some embodiments, the compound is selected from the group consisting of:

(Compound 249)

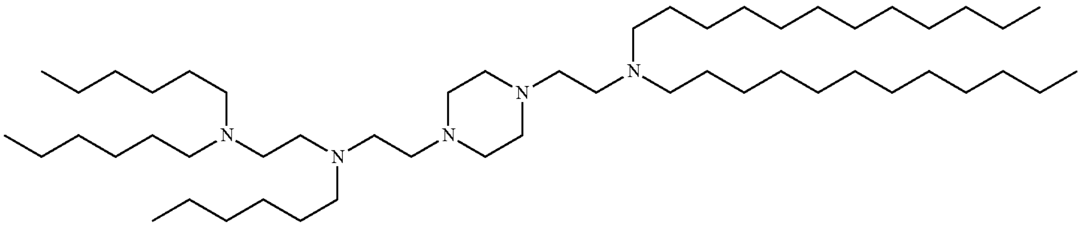

, (Compound 250)

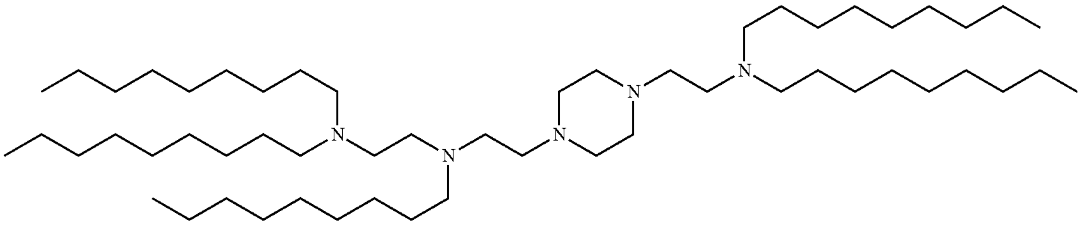

, (Compound 251)

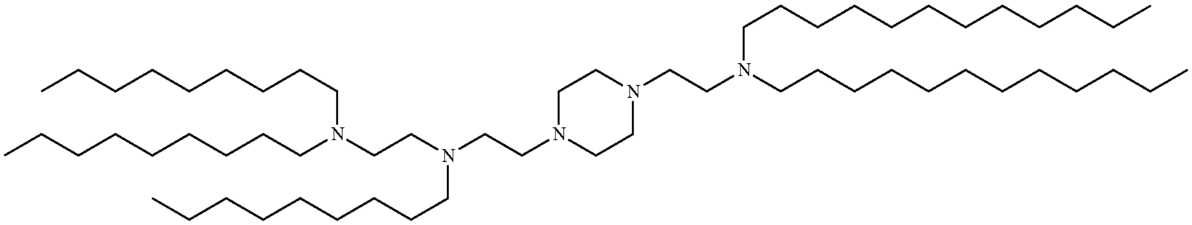

, (Compound 252)

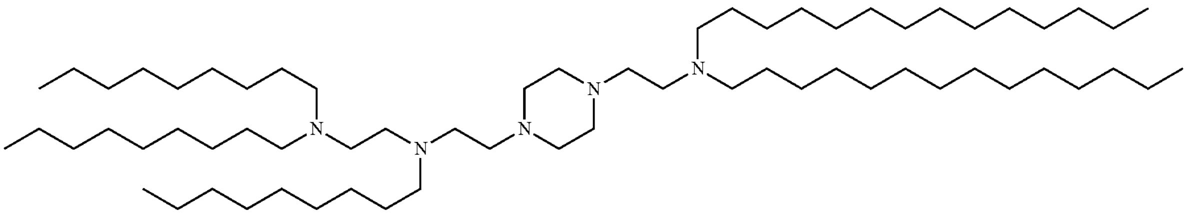

, (Compound 253)

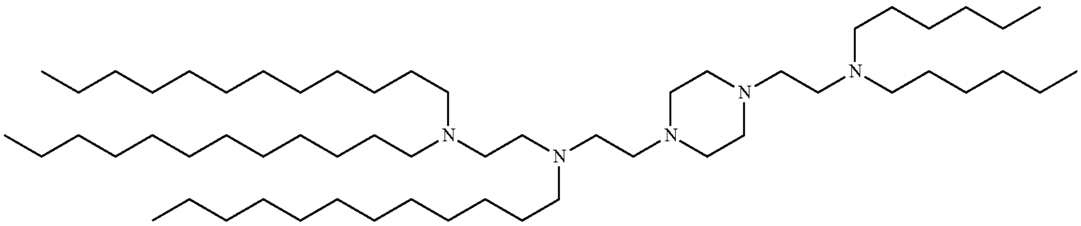

,

-continued
(Compound 254)
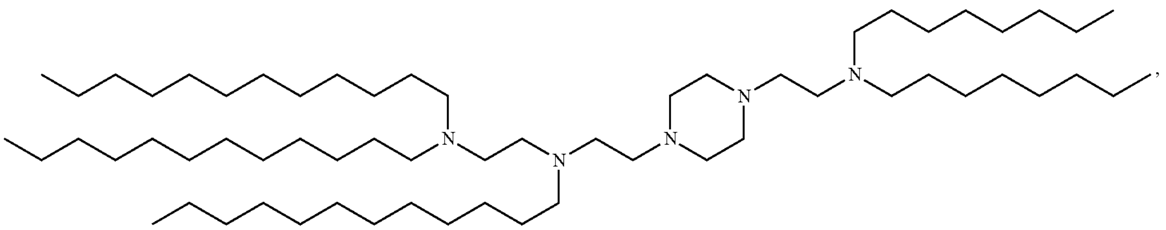
(Compound 255)
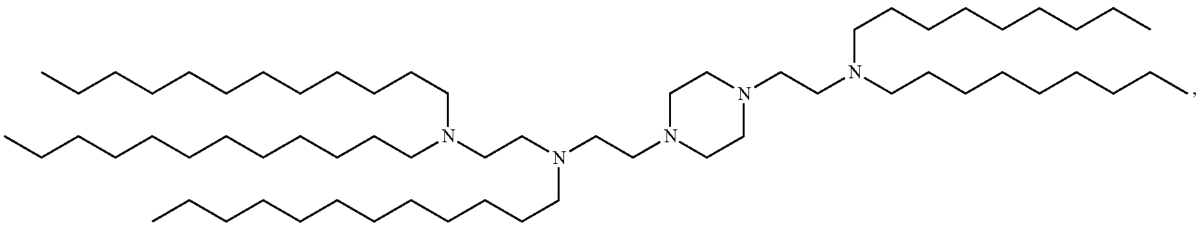
(Compound 256)
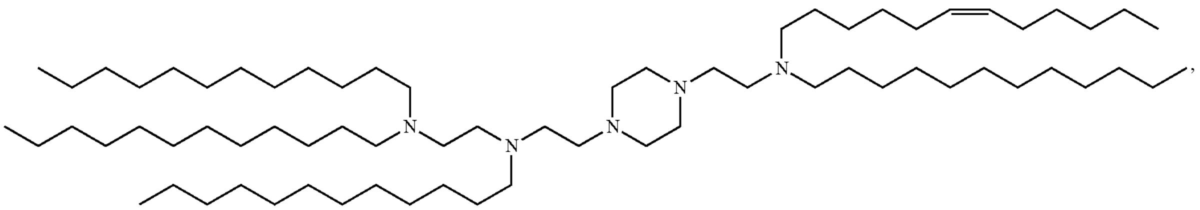
(Compound 257)
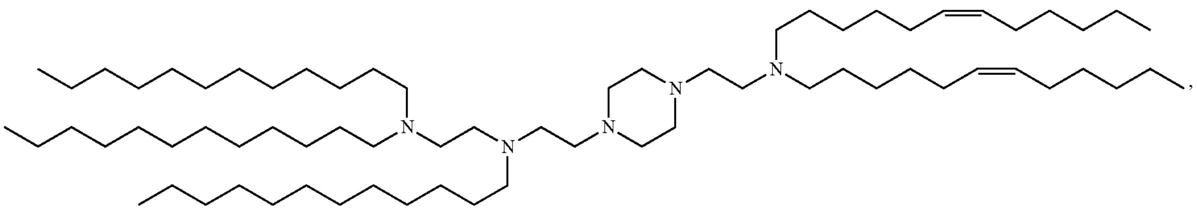
(Compound 258)
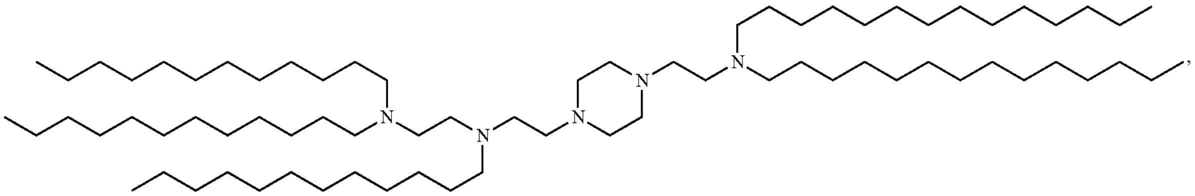
(Compound 259)
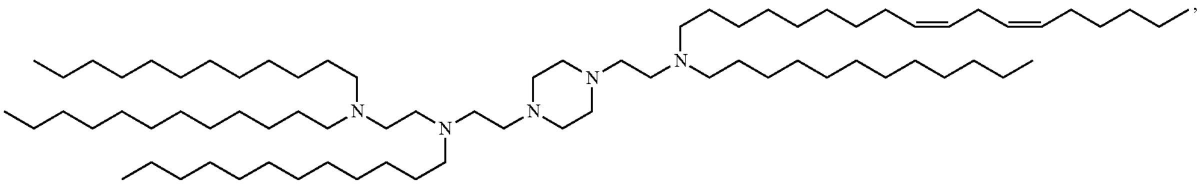
(Compound 260)
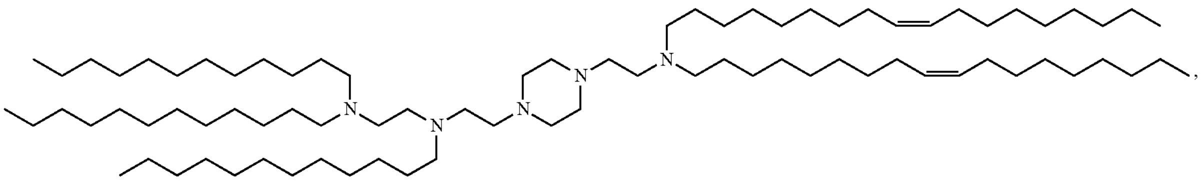

-continued (Compound 261)

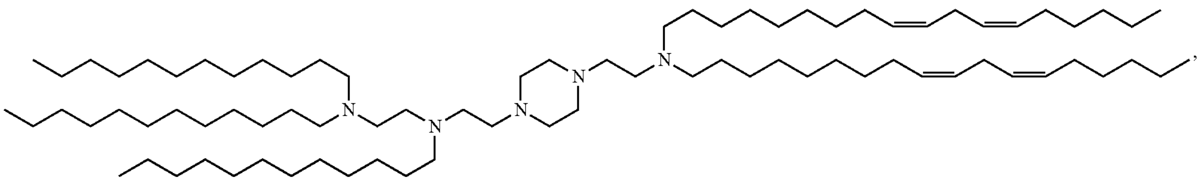

(Compound 262)

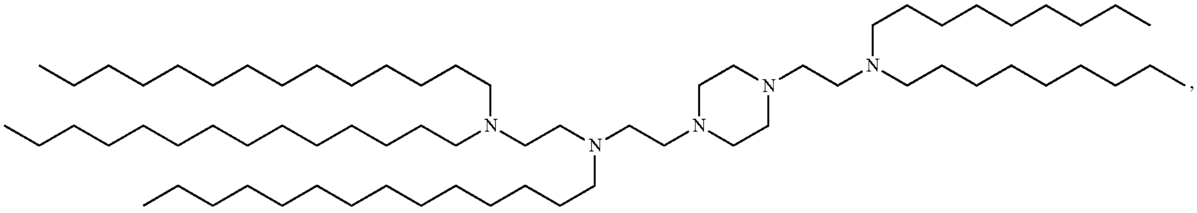

(Compound 263)

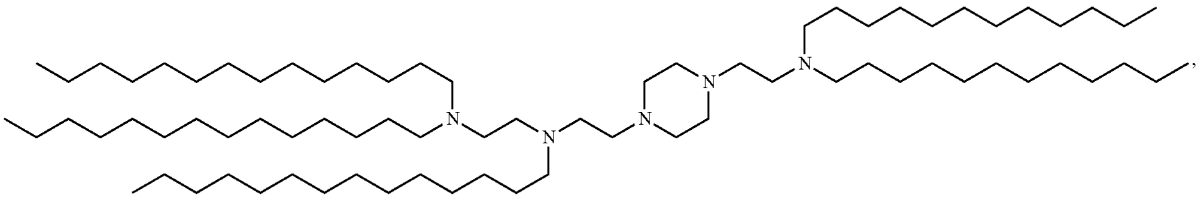

(Compound 264)

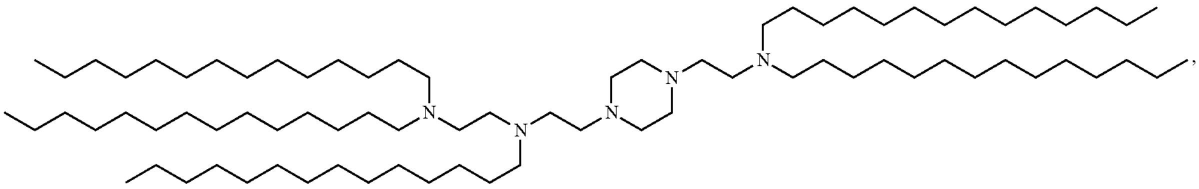

(Compound 265)

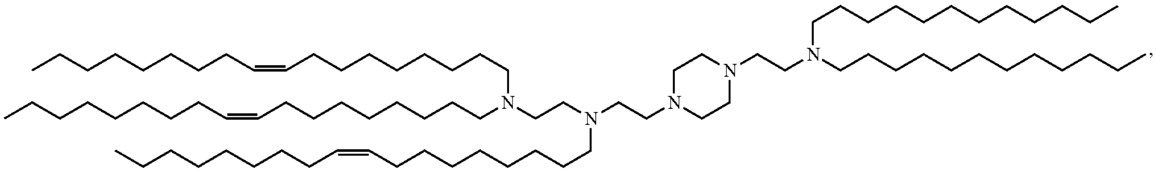

, and (Compound 266)

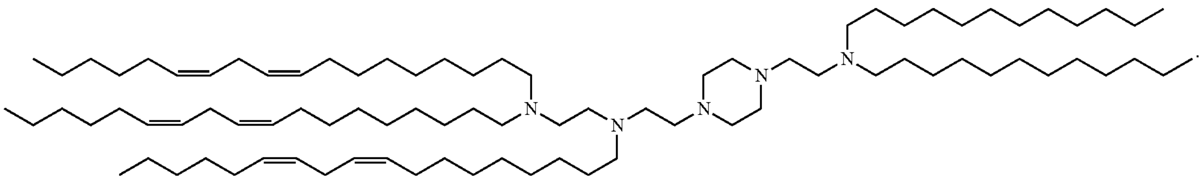

In other embodiments, the compound has the Formula (V)

(V)

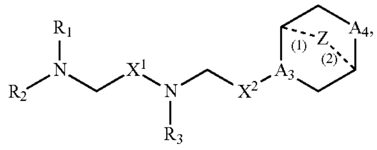

or a salt or isomer thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

$X^1$ and $X^2$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, the compound is of Formula (Va):

(Va)

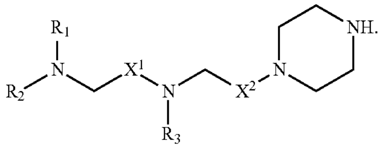

The compounds of Formula (V) or (Va) include one or more of the following features when applicable.

In some embodiments, Z is CH2.

In some embodiments, Z is absent.

In some embodiments, at least one of A3 and A4 is N or NH.

In some embodiments, A3 is N and A4 is NH.

In some embodiments, A3 is N and A4 is CH2.

In some embodiments, A3 is CH and A4 is NH.

In some embodiments, at least one of X1 and X2 is not —CH2-. For example, in certain embodiments, X1 is not —CH2-. In some embodiments, at least one of X1 and X2 is —C(O)—.

In some embodiments, X2 is —C(O)—, —C(O)O—, —OC(O)—, —C(O)—CH2-, —CH2-C(O)—, —C(O)O—CH2-, —OC(O)—CH2-, —CH2-C(O)O—, or —CH2-OC(O)—.

In some embodiments, R1, R2, and R3 are independently selected from the group consisting of C5-20 alkyl and C5-20 alkenyl. In some embodiments, R1, R2, and R3 are the same. In certain embodiments, R1, R2, and R3 are C6, C9, C12, or C14 alkyl. In other embodiments, R1, R2, and R3 are C18 alkenyl. For example, R1, R2, and R3 may be linoleyl.

In some embodiments, the compound is selected from the group consisting of:

(Compound 267)

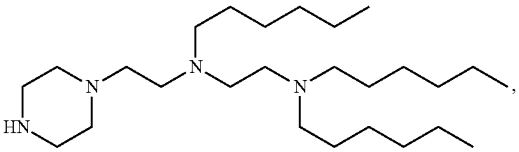

, (Compound 268)

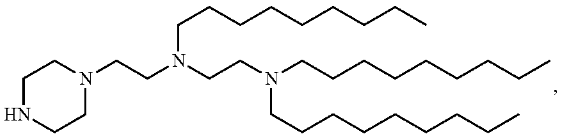

, (Compound 269)

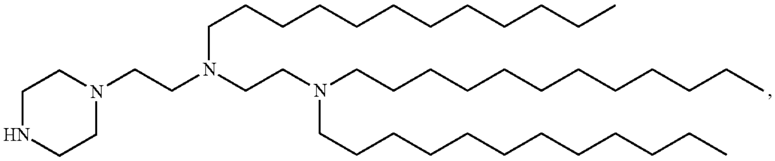

, (Compound 270)

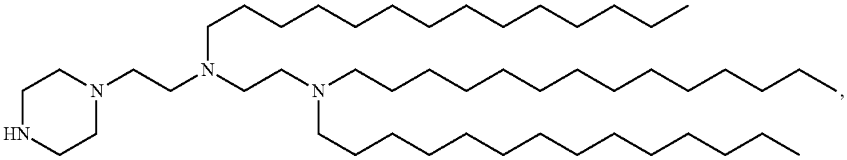

, (Compound 271)

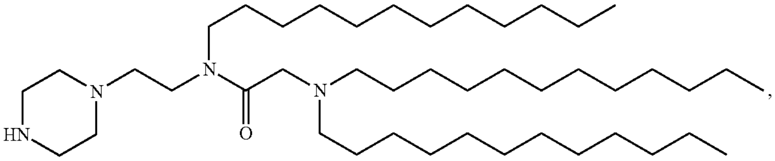

, (Compound 272)

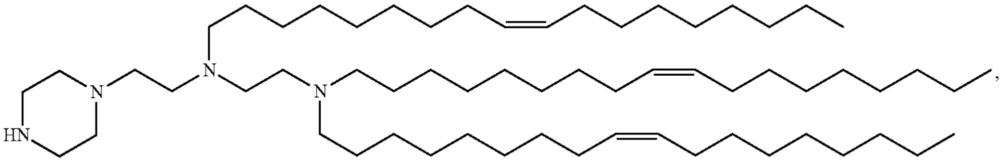

,

-continued (Compound 273)

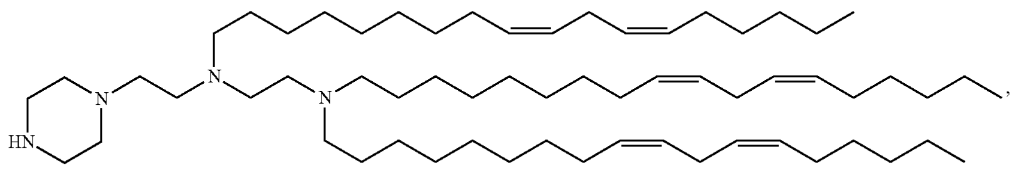

, and (Compound 309)

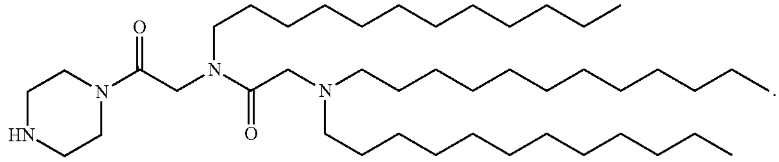

.

In another aspect, the disclosure provides a compound according to Formula (VI):

(VI)

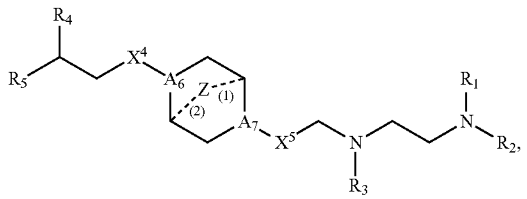

or a salt or isomer thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

$R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, R1, R2, R3, R4, and R5 each are independently selected from the group consisting of C6-20 alkyl and C6-20 alkenyl.

In some embodiments, R1 and R2 are the same. In certain embodiments, R1, R2, and R3 are the same. In some embodiments, R4 and R5 are the same. In certain embodiments, R1, R2, R3, R4, and R5 are the same.

In some embodiments, at least one of R1, R2, R3, R4, and R5 is C9-12 alkyl. In certain embodiments, each of R1, R2, R3, R4, and R5 independently is C9, C12 or C14 alkyl. In certain embodiments, each of R1, R2, R3, R4, and R5 is C9 alkyl.

In some embodiments, A6 is N and A7 is N. In some embodiments, A6 is CH and A7 is N.

In some embodiments, X4 is —CH2- and X5 is —C(O)—. In some embodiments, X4 and X5 are —C(O)—.

In some embodiments, when A6 is N and A7 is N, at least one of X4 and X5 is not —CH2-, e.g., at least one of X4 and X5 is —C(O)—. In some embodiments, when A6 is N and A7 is N, at least one of R1, R2, R3, R4, and R5 is —R"MR'.

In some embodiments, at least one of R1, R2, R3, R4, and R5 is not —R"MR'.

In some embodiments, the compound is (Compound 299)

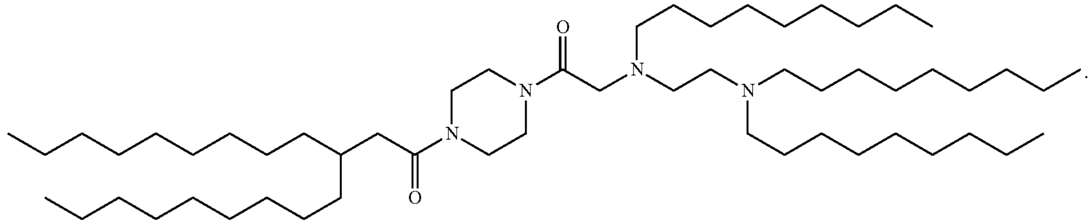

.

In an embodiment, the compound has the following formula:

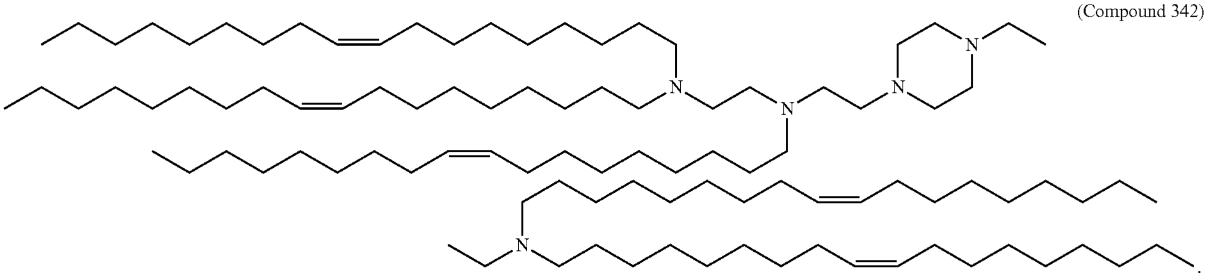

(Compound 342)

possibility represents a separate embodiment of the present invention.

PEG and PEG-Modified Lipids

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments, the PEG-modified lipids are a modified form of PEG DMG. PEG-DMG has the following structure:

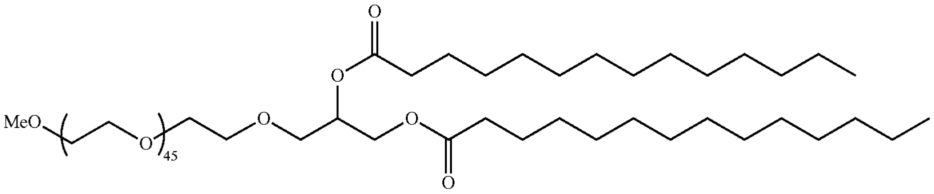

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each In certain embodiments, a PEG lipid useful in the present invention is a compound of Formula (VII). Provided herein are compounds of Formula (VII):

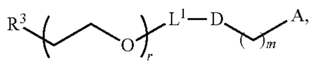

(VII)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —$N(R^N)$—, —S—, —C(O)—, —C(O)N$(R^N)$—, —$NR^NC(O)$—, —C(O)O—, —OC(O)—, —OC(O)O—, —OC(O)N$(R^N)$—, —$NR^NC(O)O$—, or —$NR^NC(O)N(R^N)$—;

D is a moiety obtained by click chemistry or a moiety cleavable under physiological conditions;

m is 0, 1, 2, 3, 4, 5, 6, 7, 8, 9, or 10;

A is of the formula:

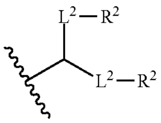

or

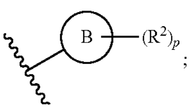

;

each instance of $L^2$ is independently a bond or optionally substituted $C_{1-6}$ alkylene, wherein one methylene unit of the optionally substituted $C_{1-6}$ alkylene is optionally replaced with —O—, —$N(R^N)$—, —S—, —C(O)—, —$C(O)N(R^N)$—, —$NR^NC(O)$—, —C(O)O—, —OC(O)—, —OC(O)O—, —$OC(O)N(R^N)$—, —$NR^NC(O)O$—, or —$NR^NC(O)N(R^N)$—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —$N(R^N)$—, —O—, —S—, —C(O)—, —$C(O)N(R^N)$, —$NR^NC(O)$—, —$NR^NC(O)N(R^N)$—, —C(O)O—, —OC(O)—, —OC(O)O—, —$OC(O)N(R^N)$—, —$NR^NC(O)O$—, —C(O)S—, —SC(O)—, —$C(=NR^N)$—, —$(=NR^N)N(R^N)$—, —$NR^NC(=NR^N)$—, —$NR^NC(=NR^N)N(R^N)$—, —C(S)—, —$C(S)N(R^N)$—, —$NR^NC(S)$—, —$NR^NC(S)N(R^N)$—, —S(O)—, —OS(O)—, —S(O)O—, —OS(O)O—, —$OS(O)_2$—, —$S(O)_2O$—, —$OS(O)_2O$—, —$N(R^N)S(O)$—, —$S(O)N(R^N)$—, —$N(R^N)S(O)N(R^N)$—, —$OS(O)N(R^N)$—, —$N(R^N)S(O)O$—, —$S(O)_2$—, —$N(R^N)S(O)_2$—, —$S(O)_2N(R^N)$—, —$N(R^N)S(O)_2N(R^N)$—, —$OS(O)_2N(R^N)$—, or —$N(R^N)S(O)_2O$—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (VII) is a PEG-OH lipid (i.e., $R^3$ is —$OR^O$, and $R^O$ is hydrogen). In certain embodiments, the compound of Formula (VII) is of Formula (VII-OH):

(VII-OH)

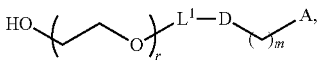

or a salt thereof.

In certain embodiments, D is a moiety obtained by click chemistry (e.g., triazole). In certain embodiments, the compound of Formula (Vii) is of Formula (VII-a-1) or (VII-a-2):

(VII-a-1)

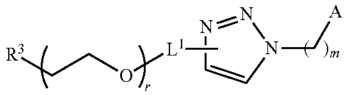

or (VII-a-2)

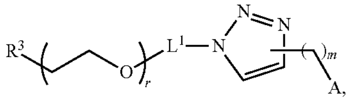

or a salt thereof.

In certain embodiments, the compound of Formula (VII) is of one of the following formulae:

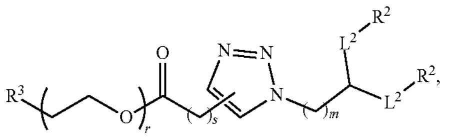

-continued

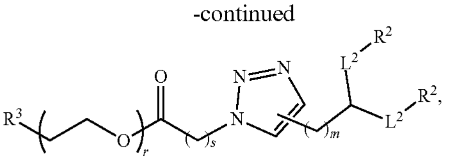

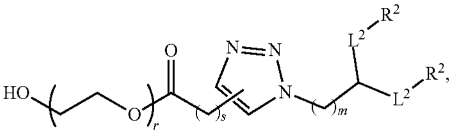

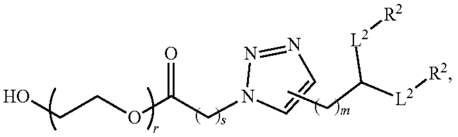

or a salt thereof, wherein s is 0, 1, 2, 3, 4, 5, 6, 7, 8, 9, or 10.

In certain embodiments, the compound of Formula (VII) is of one of the following formulae:

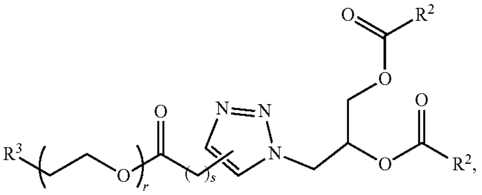

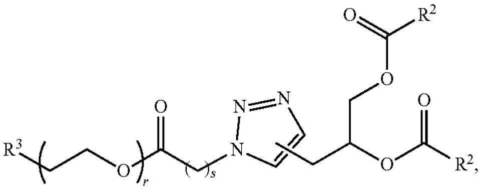

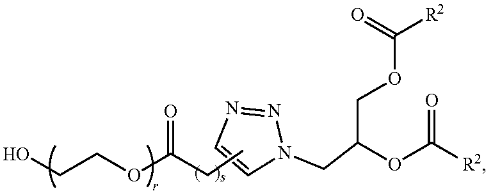

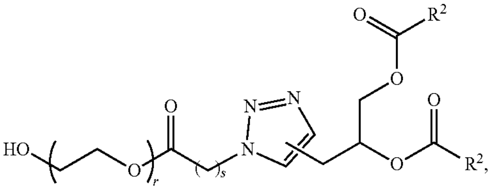

or a salt thereof.

In certain embodiments, a compound of Formula (VII) is of one of the following formulae:

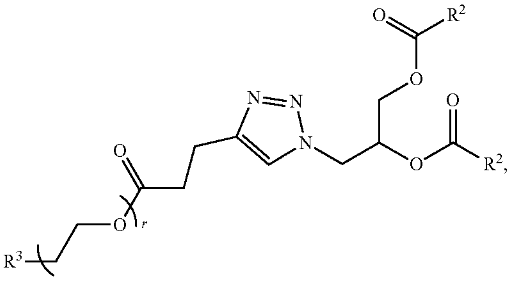

-continued
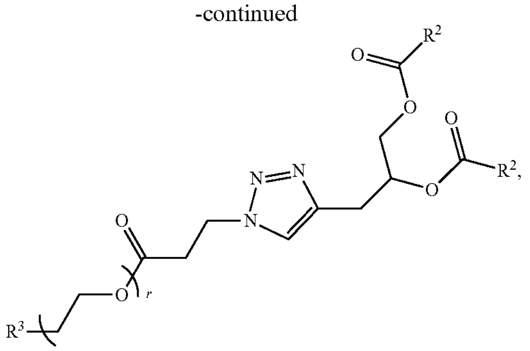
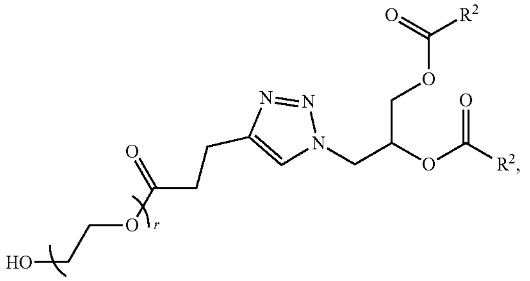
-continued
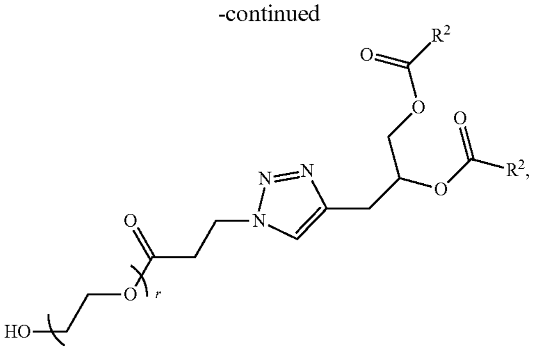
or a salt thereof.
In certain embodiments, a compound of Formula (VII) is of one of the following formulae, wherein r is 1-100:
(Compound 415)
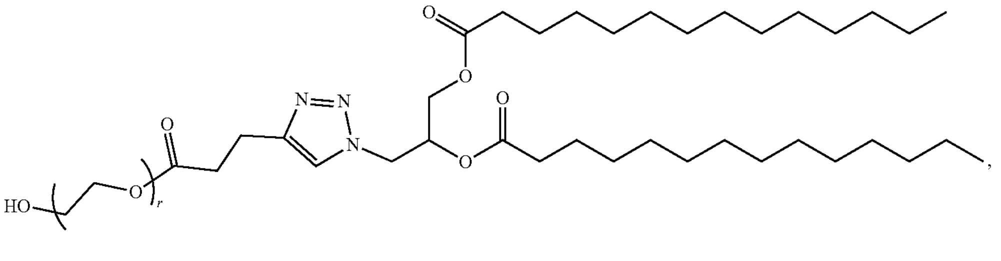
(Compound 416)
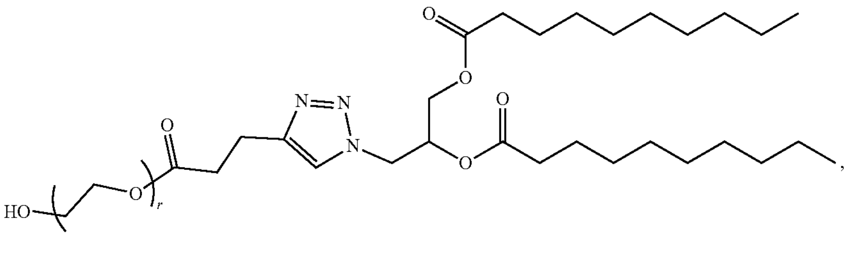
(Compound 417)
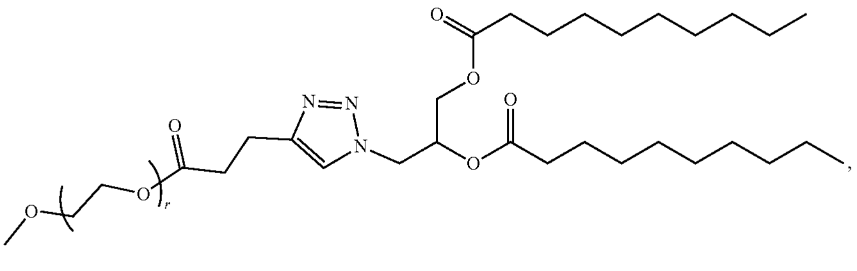

-continued (Compound 418)

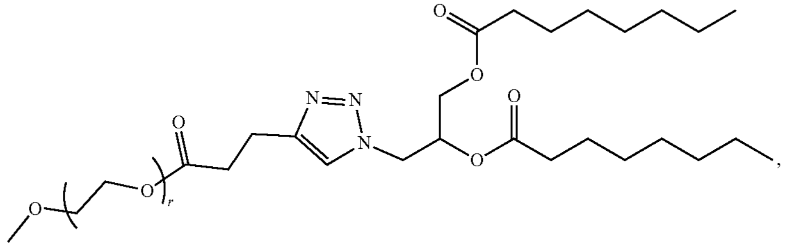

or a salt thereof.

In certain embodiments, D is a moiety cleavable under physiological conditions (e.g., ester, amide, carbonate, carbamate, urea). In certain embodiments, a compound of Formula (VII) is of Formula (VI-b-1) or (VII-b-2):

(VII-b-1)

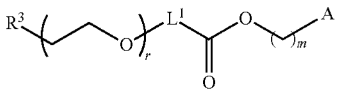

(VII-b-2)

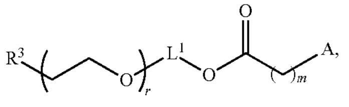

or a salt thereof.

In certain embodiments, a compound of Formula (VII) is of Formula (VII-b-1-OH) or (VII-b-2-OH):

(VII-b-1-OH)

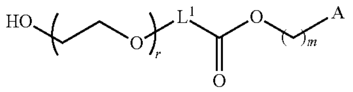

(VII-b-2-OH)

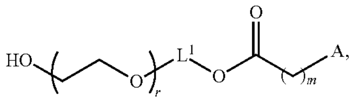

or a salt thereof.

In certain embodiments, the compound of Formula (VII) is of one of the following formulae:

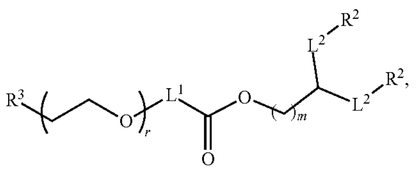

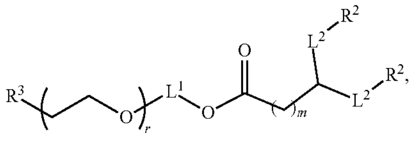

-continued

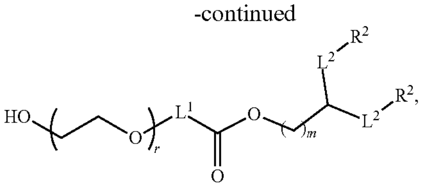

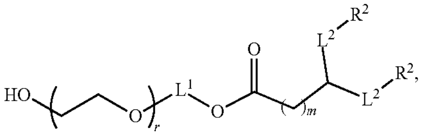

or a salt thereof.

In certain embodiments, a compound of Formula (VII) is of one of the following formulae:

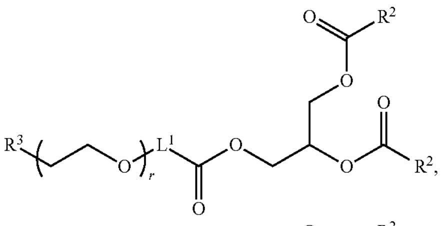

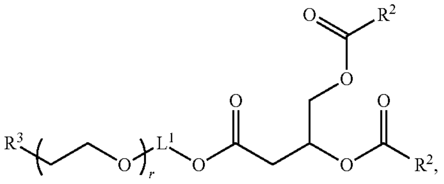

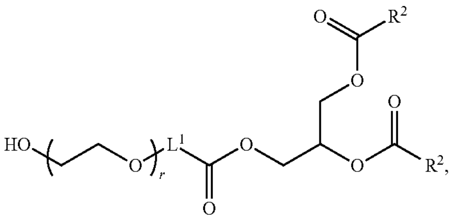

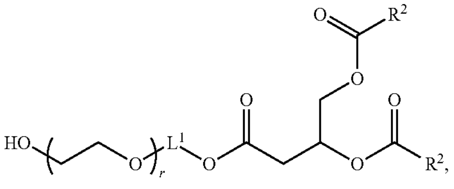

or a salt thereof.

In certain embodiments, a compound of Formula (VII) is of one of the following formulae:

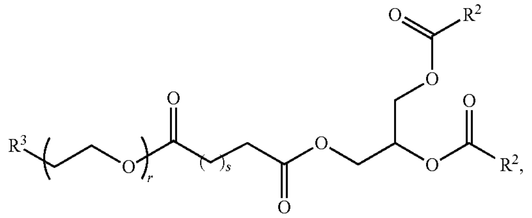

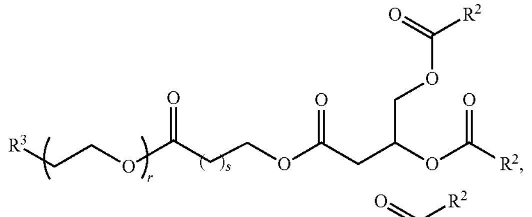

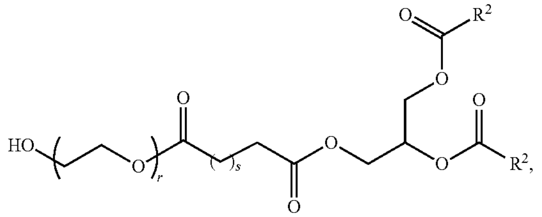

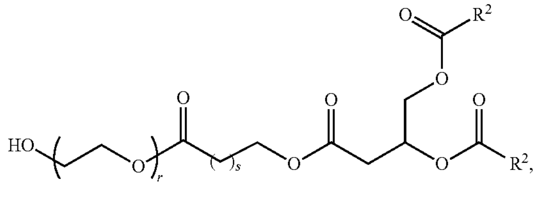

or a salt thereof.

In certain embodiments, a compound of Formula (VII) is of one of the following formulae:

(VIII)

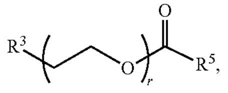

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —$N(R^N)$—, —O—, —S—, —C(O)—, —$C(O)N(R^N)$—, —$NR^NC(O)$—, —$NR^NC(O)N(R^N)$—, —C(O)O—, —OC(O)—, —OC(O)O—, —$OC(O)N(R^N)$—, —$NR^NC(O)O$—, —C(O)S—, —SC(O)—, —$C(=NR^N)$—, —$C(=NR^N)N(R^N)$—, —$NR^NC(=NR)$—, —$NR^NC(=NR^N)N(R^N)$—, —C(S)—, —$C(S)N(R^N)$—, —$NR^NC(S)$—, —$NR^NC(S)N(R^N)$—, —S(O)—, —OS(O)—, —S(O)O—, —OS(O)O—, —$OS(O)_2$—, —$S(O)_2O$—, —$OS(O)_2O$—, —$N(R^N)S(O)$—, —$S(O)N(R^N)$—, —$N(R^N)S(O)N(R^N)$—, —$OS(O)N(R^N)$—, —$N(R^N)S(O)O$—, —$S(O)_2$—, —$N(R^N)S(O)_2$-, —$S(O)_2N(R^N)$—, —$N(R^N)S(O)_2N(R^N)$—, —$OS(O)_2N(R^N)$—, or —$N(R^N)S(O)_2O$—; and each instance of $R^N$ is independently hydrogen, optionally substituted alkyl, or a nitrogen protecting group.

(Compound 430)

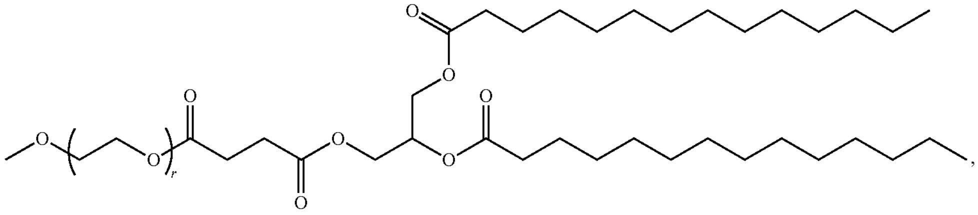

(Compound 431)

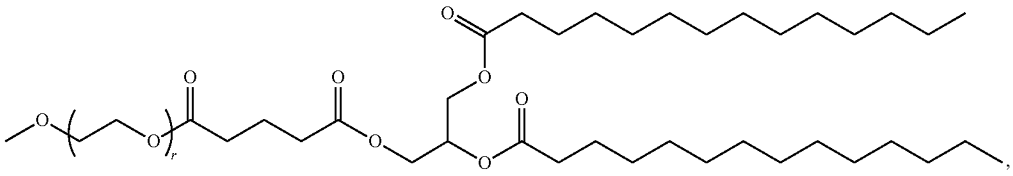

or salts thereof.

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

In certain embodiments, the compound of Formula (VIII) is of Formula (VIII-OH):

(VIII-OH)

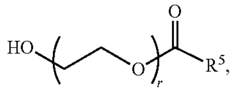

or a salt thereof.

In certain embodiments, a compound of Formula (VIII) is of one of the following formulae:

(Compound 419)

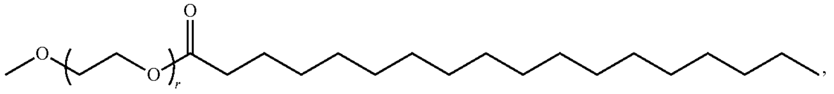

(Compound 420)

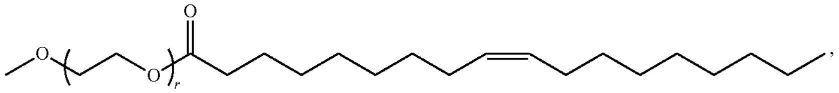

(Compound 421)

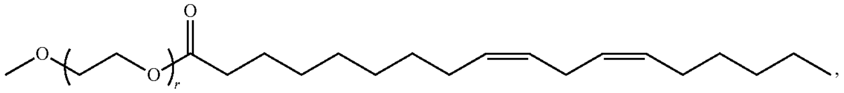

(Compound 422)

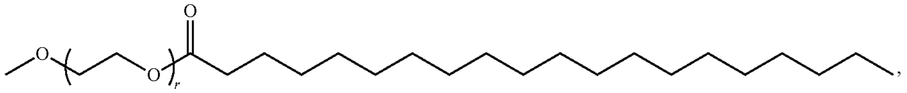

(Compound 423)

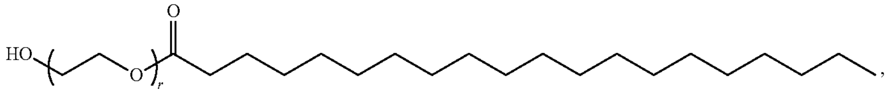

(Compound 424)

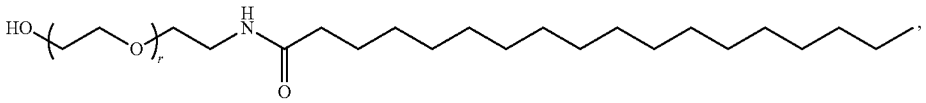

(Compound 425)

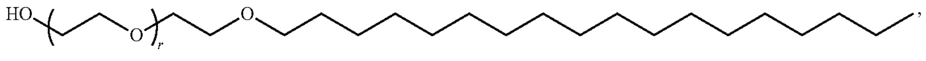

or a salt thereof. In some embodiments, r is 45.

In yet other embodiments the compound of Formula (VIII) is:

(Compound 427)

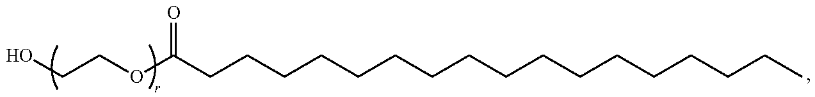

or a salt thereof.

In some embodiments, the compound of Formula (VIII) is (Compound 427)

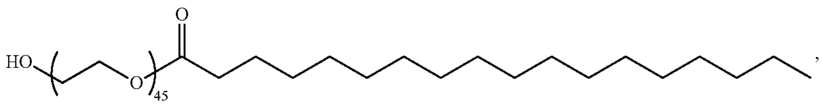

, or (Compound 403)

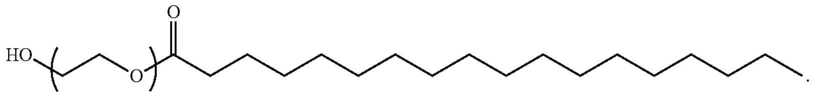

Phospholipids

Phospholipids, as defined herein, are any lipids that comprise a phosphate group. Phospholipids are a subset of non-cationic lipids. The lipid component of a lipid nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids useful or potentially useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), I-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-di stearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. Each possibility represents a separate embodiment of the present invention.

In some embodiments, a lipid nanoparticle composition includes DSPC. In certain embodiments, a lipid nanoparticle composition includes DOPE. In some embodiments, a lipid nanoparticle composition includes both DSPC and DOPE. Examples of phospholipids include, but are not limited to, the following:

(Compound 432)

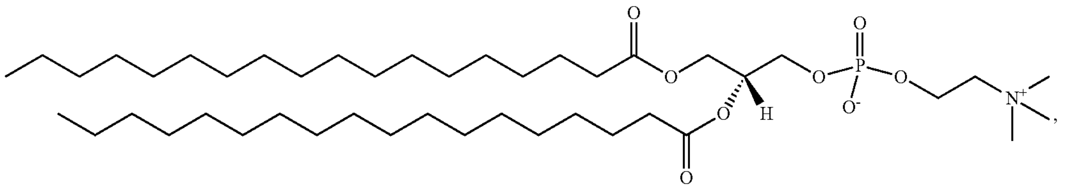

(Compound 433)

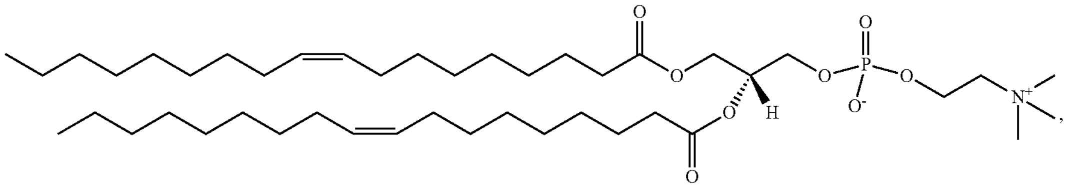

(Compound 434)

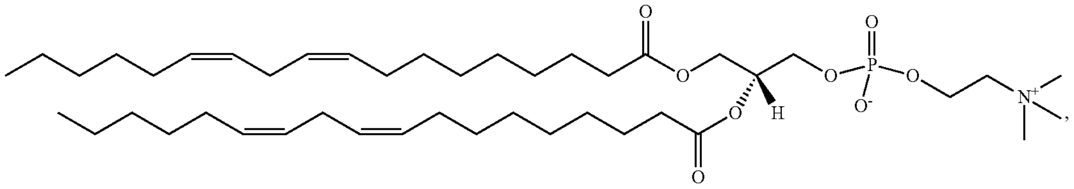

(Compound 435)

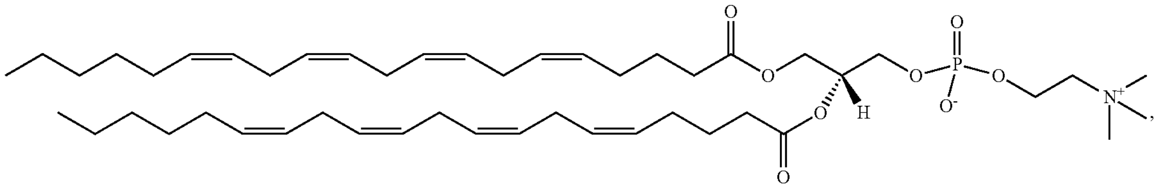

-continued
(Compound 436)
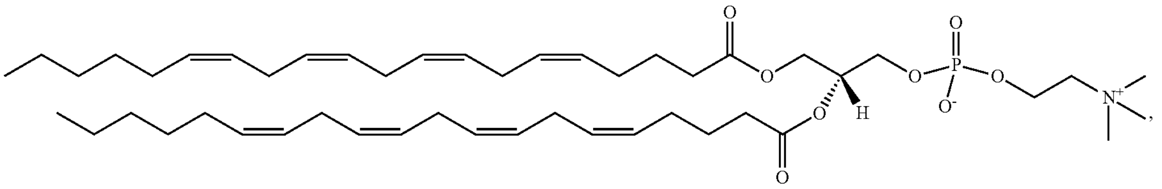
(Compound 437)
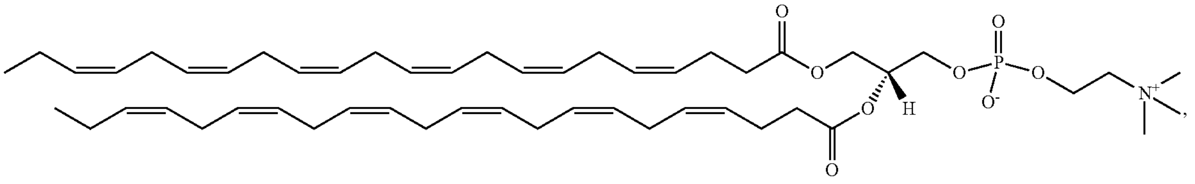
(Compound 438)
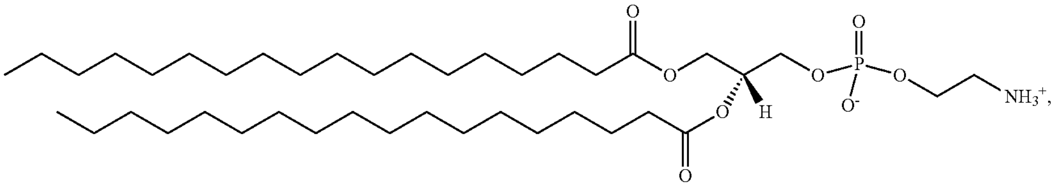
(Compound 439)
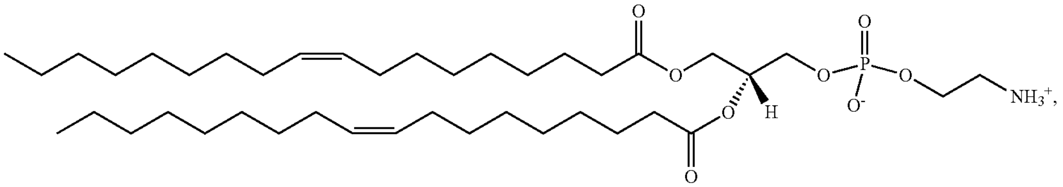
(Compound 440)
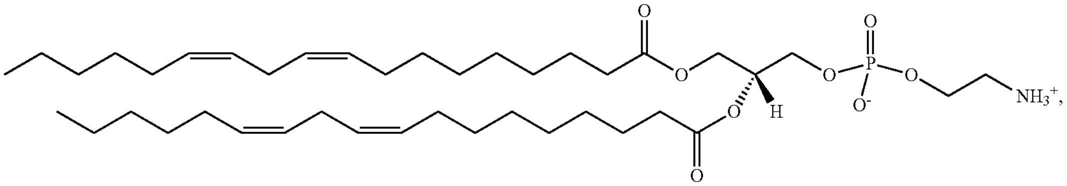
(Compound 441)
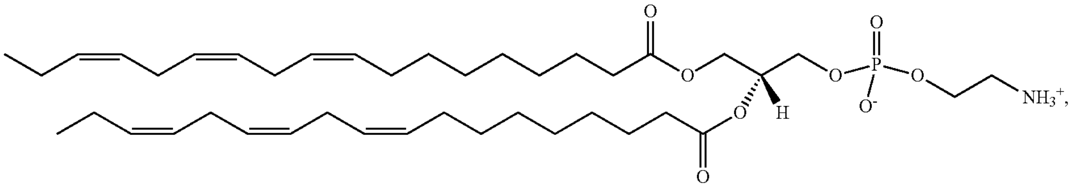
(Compound 442)
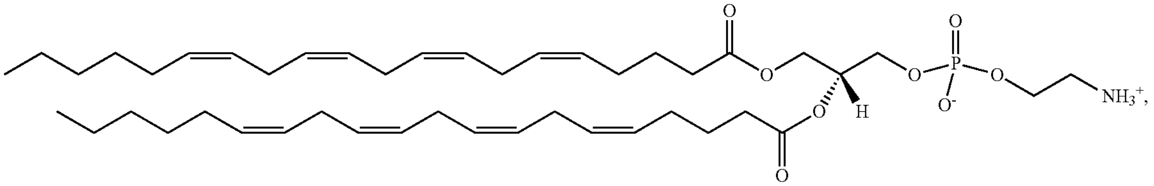

-continued (Compound 443)

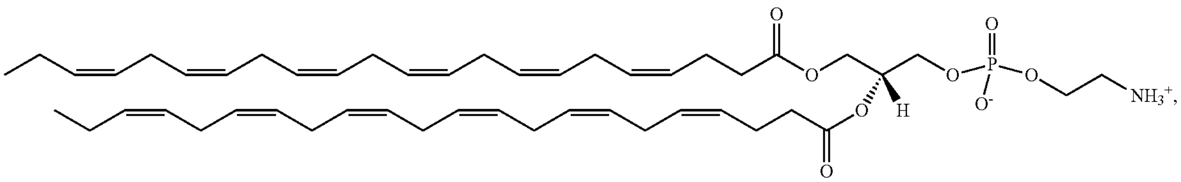

(Compound 444)

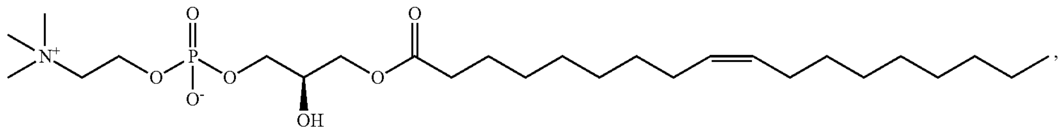

(Compound 445)

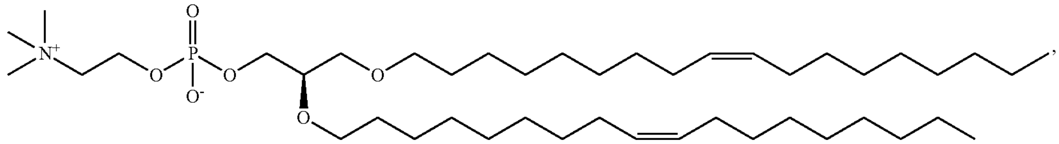

(Compound 446)

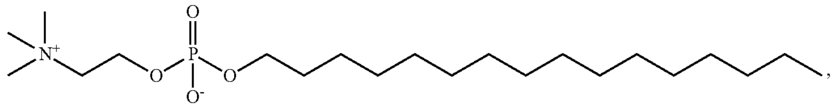

(Compound 447)

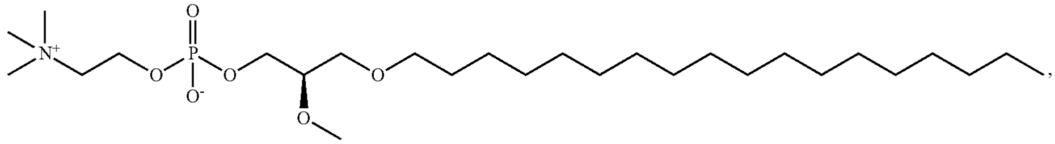

, and (Compound 448)

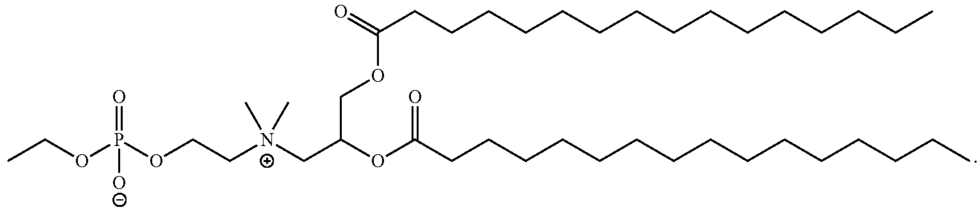

In certain embodiments, a phospholipid useful or potentially useful in the present invention is an analog or variant of DSPC. In certain embodiments, a phospholipid useful or potentially useful in the present invention is a compound of Formula (IX):

(IX)

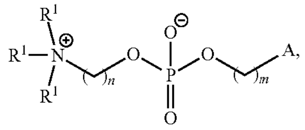

or a salt thereof, wherein:

each R' is independently optionally substituted alkyl; or optionally two $R^1$ are joined together with the intervening atoms to form optionally substituted monocyclic carbocyclyl or optionally substituted monocyclic heterocyclyl; or optionally three R' are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

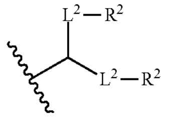

or

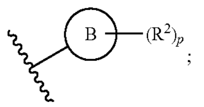

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $—N(R^N)—$, $—O—$, $—S—$, $—C(O)—$, $—C(O)N(R^N)—$, $—NR^NC(O)—$, $—NR^NC(O)N(R^N)—$, $—C(O)O—$, $—OC(O)—$, $—OC(O)O—$, $—OC(O)N(R^N)—$, $—NR^NC(O)O—$, $—C(O)S—$, $—SC(O)—$, $—C(=NR^N)—$, $—(=NR^N)N(R^N)—$, $—NR^NC(=NR^N)—$, $—NR^NC(=NR^N)N(R^N)—$, $—C(S)—$, $—C(S)N(R^N)—$, $—NR^NC(S)—$, $—NR^NC(S)N(R^N)—$, $—S(O)—$, $—OS(O)—$, $—S(O)O—$, $—OS(O)O—$, $—OS(O)_2—$, $—S(O)_2O—$, $—OS(O)_2O—$, $—N(R^N)S(O)—$, $—S(O)N(R^N)—$, $—N(R^N)S(O)N(R^N)—$, $—OS(O)N(R^N)—$, $—N(R^N)S(O)O—$, $—S(O)_2—$, $—N(R^N)S(O)_2—$, $—S(O)_2N(R^N)—$, $—N(R^N)S(O)_2N(R^N)—$, $—OS(O)_2N(R^N)—$, or $—N(R^N)S(O)_2O—$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

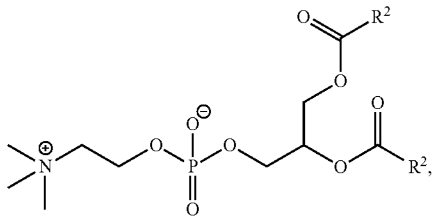

wherein each instance of $R^2$ is independently unsubstituted alkyl, unsubstituted alkenyl, or unsubstituted alkynyl.

Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

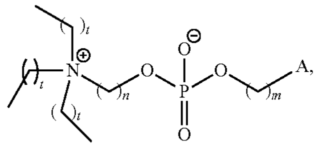

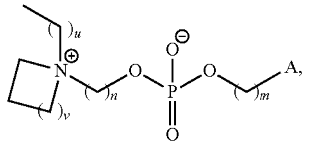

-continued

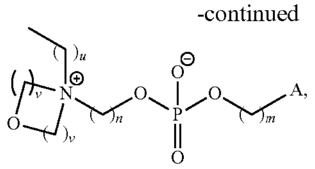

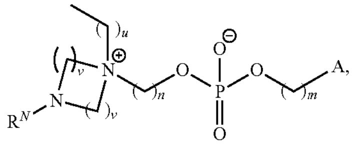

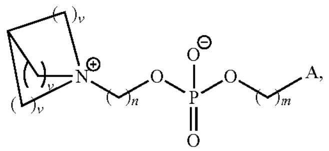

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, the compound of Formula (IX) is of one of the following formulae:

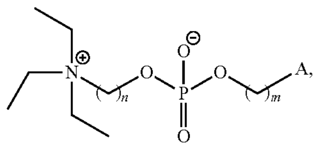

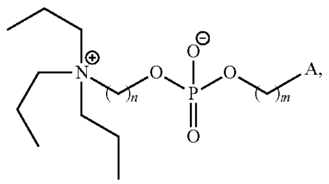

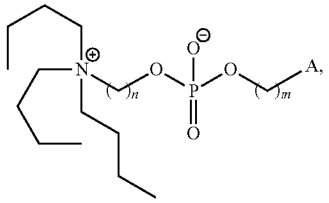

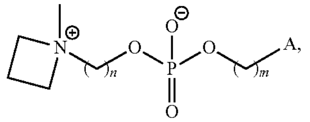

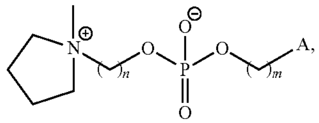

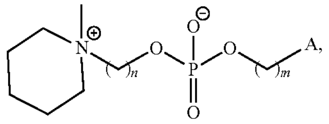

-continued
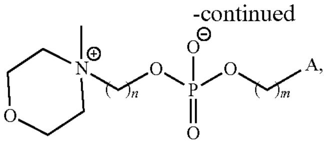
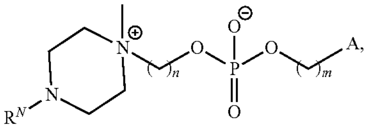
-continued
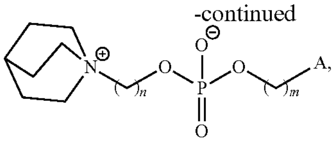
or a salt thereof.
In certain embodiments, the compound of Formula (IX) is of one of the following:
(Compound 400)
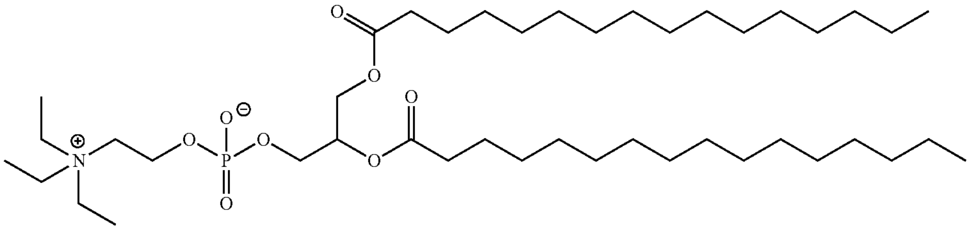
(Compound 401)
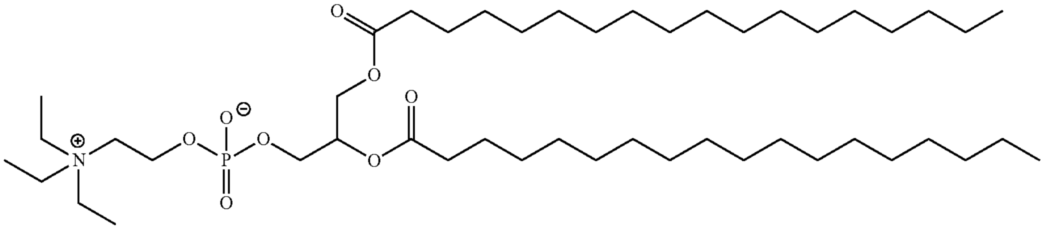
(Compound 402)
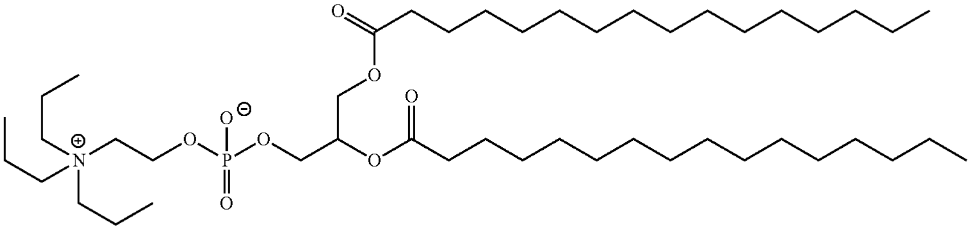
(Compound 403)
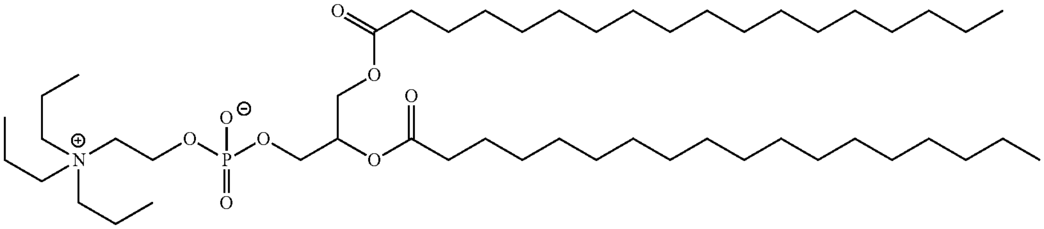
(Compound 404)
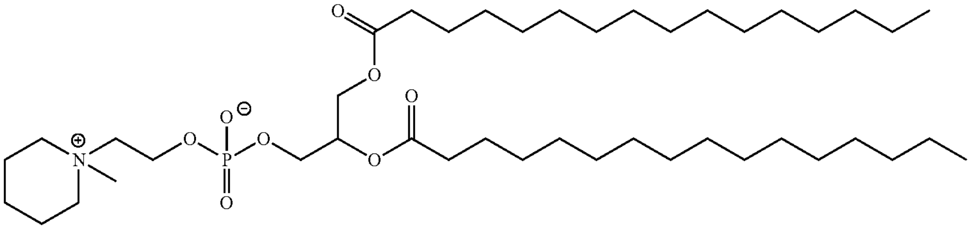

-continued
(Compound 405)
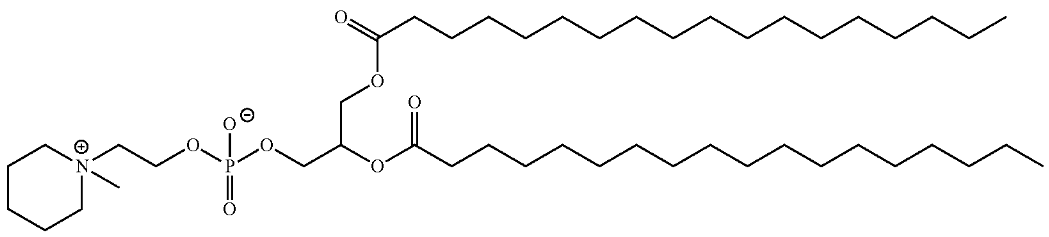
(Compound 406)
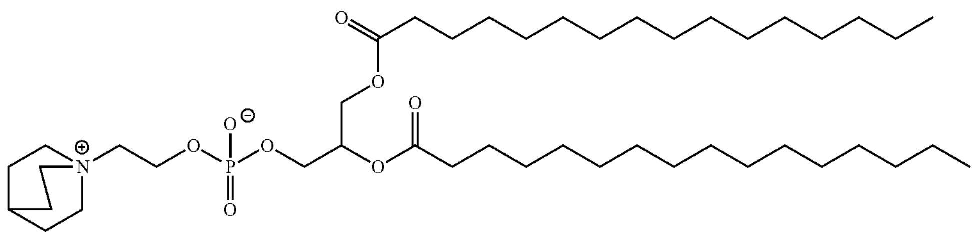
(Compound 407)
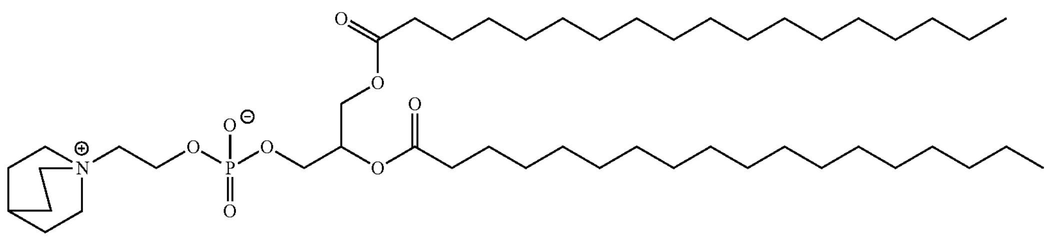
(Compound 408)
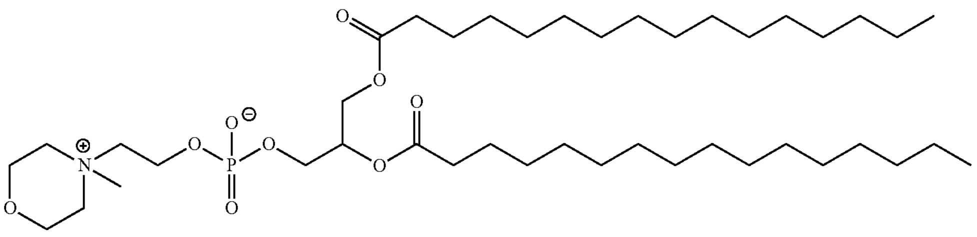

-continued (Compound 409)

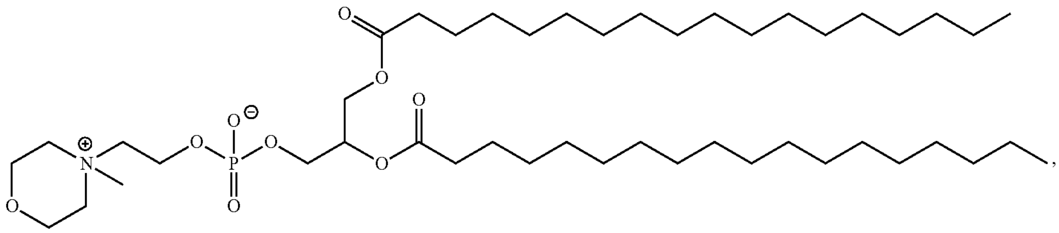

or a salt thereof.

In certain embodiments, a compound of Formula (IX) is of Formula (IX-a):

(IX-a)

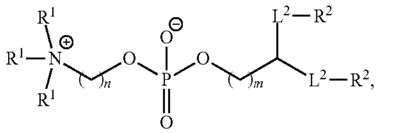

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

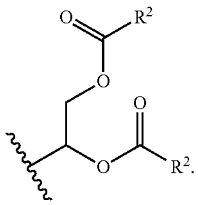

In certain embodiments, the compound of Formula (IX-b-4) is of one of the following formulae:

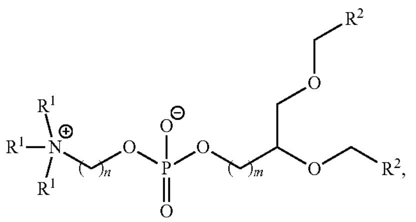

-continued

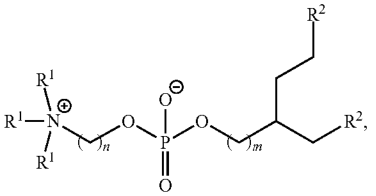

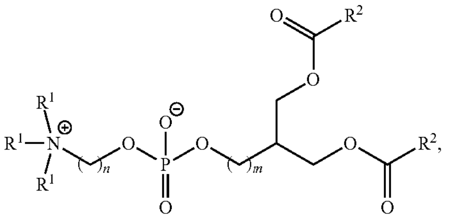

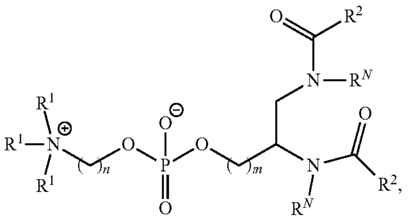

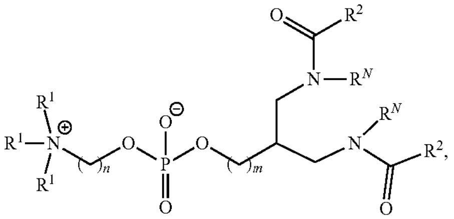

or a salt thereof.

In certain embodiments, a compound of Formula (IX) is one of the following:

(Compound 449)

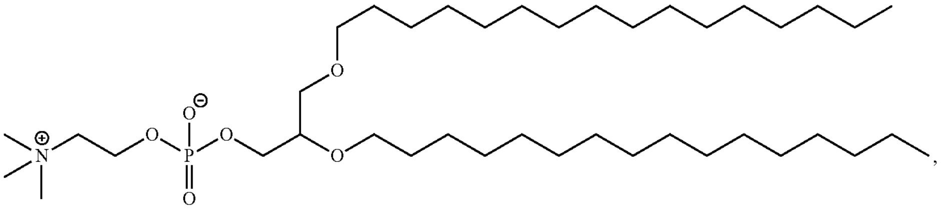

-continued (Compound 450)

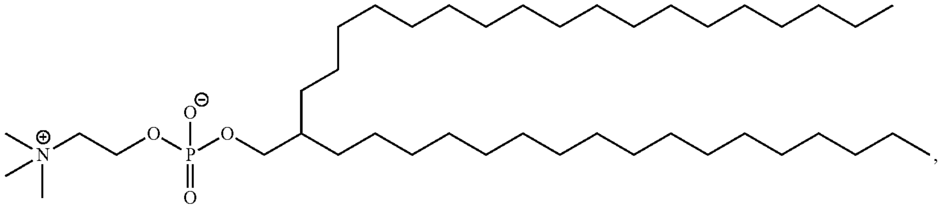

(Compound 451)

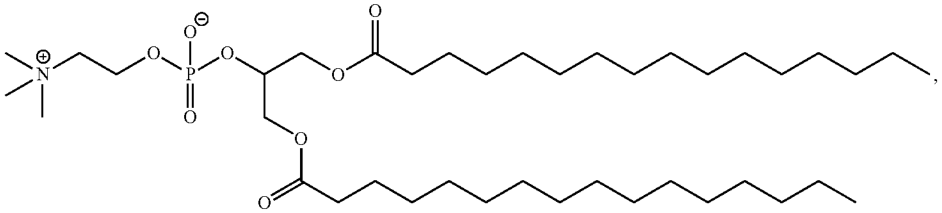

(Compound 452)

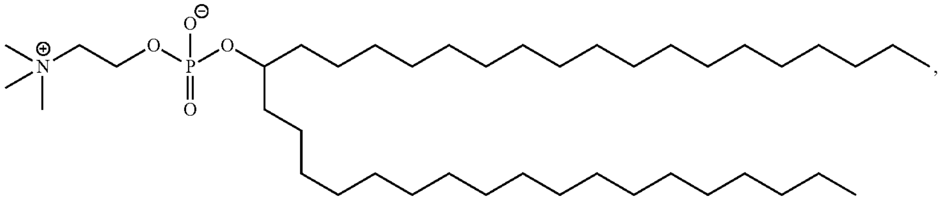

(Compound 453)

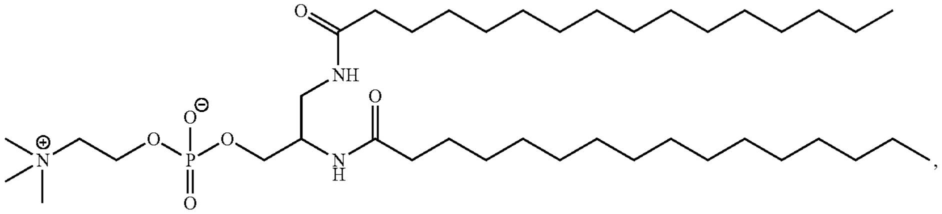

or salts thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IX) is of Formula (IX-b):

(IX-b)

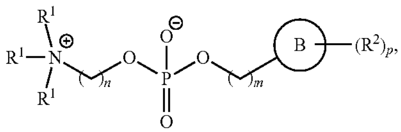

or a salt thereof.

In certain embodiments, the compound of Formula (IX-b) is of Formula (IX-b-1):

(IX-b-1)

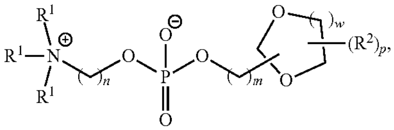

or a salt thereof, wherein:

w is 0, 1, 2, or 3.

In certain embodiments, the compound of Formula (IX-b) is of Formula (IX-b-2):

(IX-b-2)

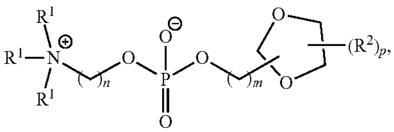

or a salt thereof.

In certain embodiments, the compound of Formula (IX-b) is of Formula (IX-b-3):

(IX-b-3)

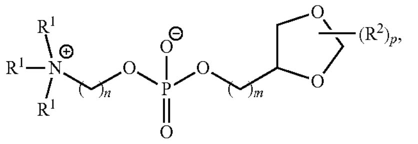

or a salt thereof.

In certain embodiments, the compound of Formula (I-b) is of Formula (I-b-4):

(IX-b-4)

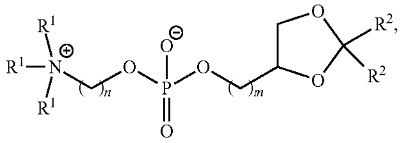

or a salt thereof.

In certain embodiments, the compound of Formula (IX-b) is one of the following:

(Compound 454)

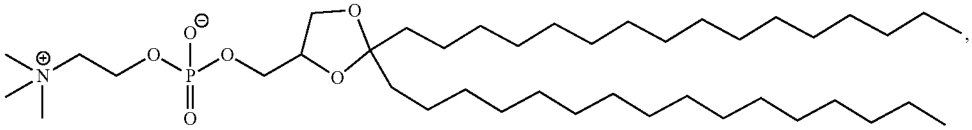

, (Compound 455)

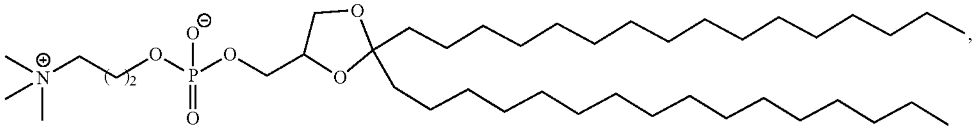

, (Compound 456)

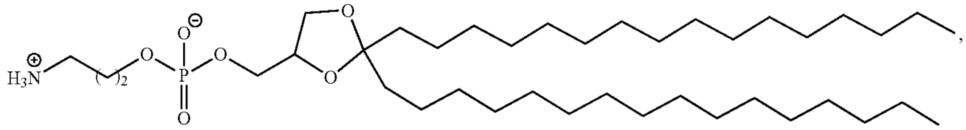

, or salts thereof.

Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$), —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$), —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —$OS(O)_2$—, —$S(O)_2O$—, —$OS(O)_2O$—, —N($R^N$)S(O)—, —S(O)N($R^N$)—, —N($R^N$)S(O)N($R^N$)—, —OS(O)N($R^N$)—, —N($R^N$)S(O)O—, —$S(O)_2$—, —N($R^N$)$S(O)_2$—, —$S(O)_2$N($R^N$)—, —N($R^N$)$S(O)_2$N($R^N$)—, —$OS(O)_2$N($R^N$)—, or —N($R^N$)$S(O)_2O$—.

In certain embodiments, the compound of Formula (IX) is of Formula (IX-c):

(IX-c)

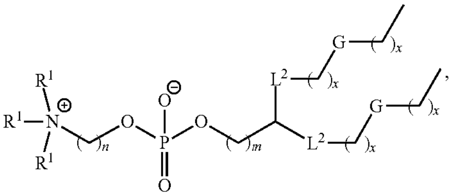

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=NR)N(R)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —$OS(O)_2$—, —$S(O)_2O$—, —$OS(O)_2O$—, —N($R^N$)S(O)—, —S(O)N($R^N$)—, —N($R^N$)S(O)N($R^N$)—, —OS(O)N($R^N$)—, —N($R^N$)S(O)O—, —$S(O)_2$—, —N(R^N)S(O)_2-, —S(O)_2N(R^N)—, —N(R^N)S(O)_2N(R^N)—, —OS(O)_2N(R^N)—, or —N(R^N)S(O)_2O—. Each possibility represents a separate embodiment of the present invention.

In certain embodiments, the compound of Formula (IX-c) is of Formula (IX-c-1):

(IX-c-1)

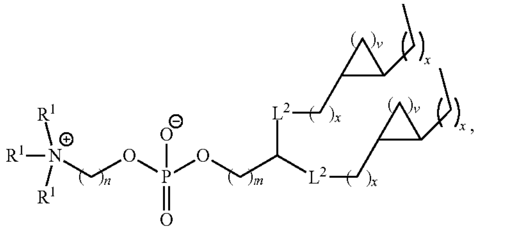

or salt thereof, wherein:

each instance of v is independently 1, 2, or 3.

In certain embodiments, the compound of Formula (IX-c) is of Formula (IX-c-2):

(IX-c-2)

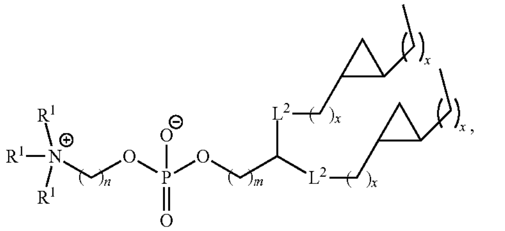

or a salt thereof.

In certain embodiments, the compound of Formula (IX-c) is of the following formula:

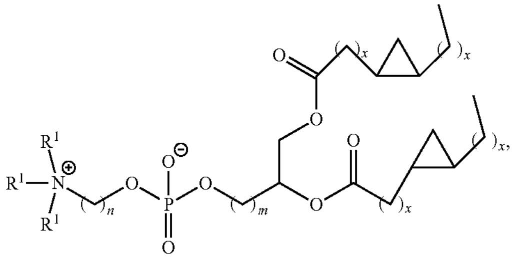

or a salt thereof.

In certain embodiments, the compound of Formula (IX-c) is the following:

In certain embodiments, the compound of Formula (IX-c) is of Formula (IX-c-3):

(IX -c-3)

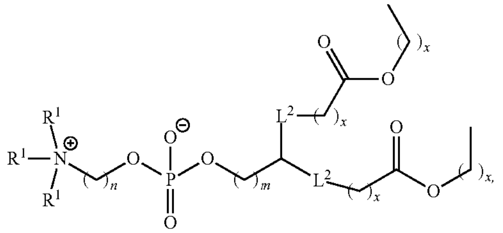

or a salt thereof.

In certain embodiments, the compound of Formula (IX-c) is of the following formulae:

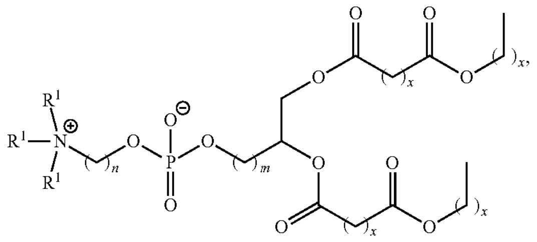

or a salt thereof.

In certain embodiments, the compound of Formula (IX-c) is the following:

(Compound 457)

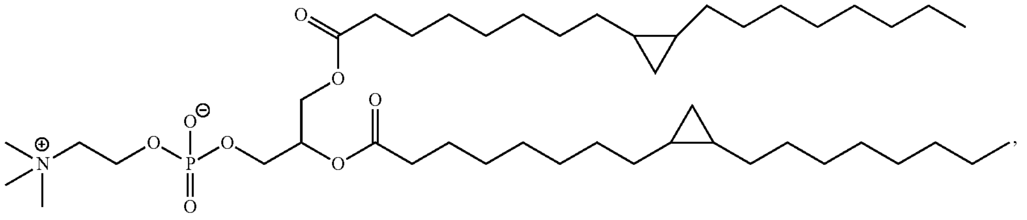

or a salt thereof.

(Compound 458)

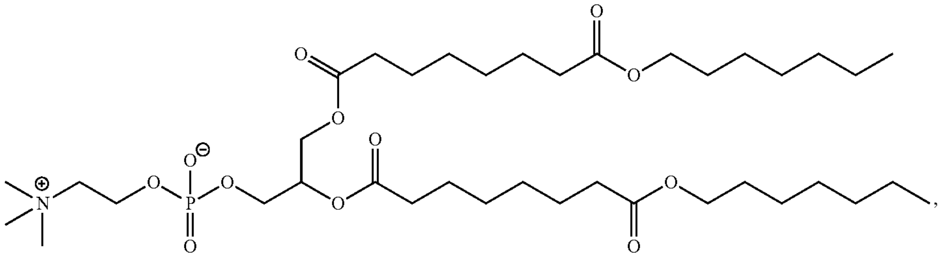

or a salt thereof.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:

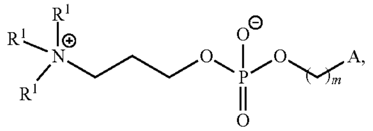

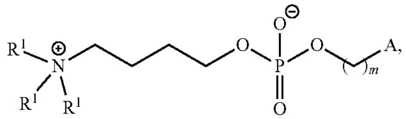

or a salt thereof.

In certain embodiments, a compound of Formula (LX) is one of the following:

(Compound 459)

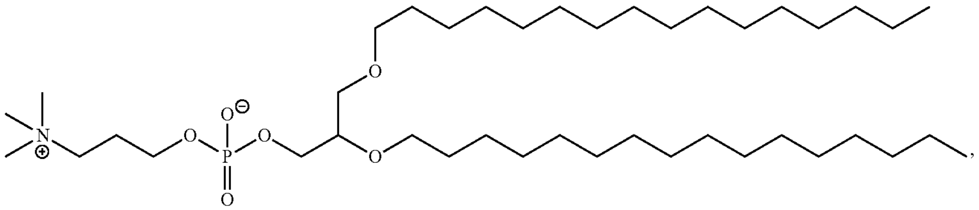

(Compound 460)

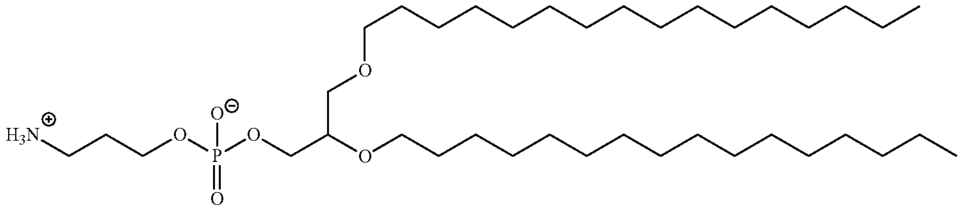

(Compound 461)

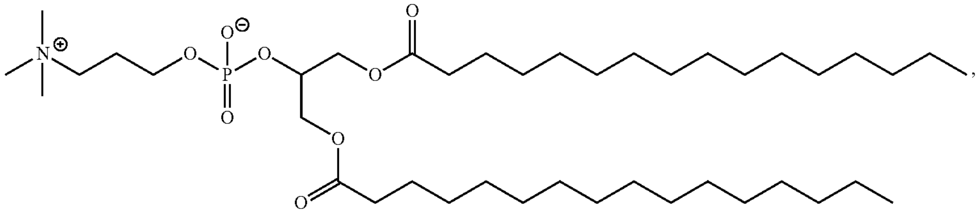

-continued
(Compound 462)
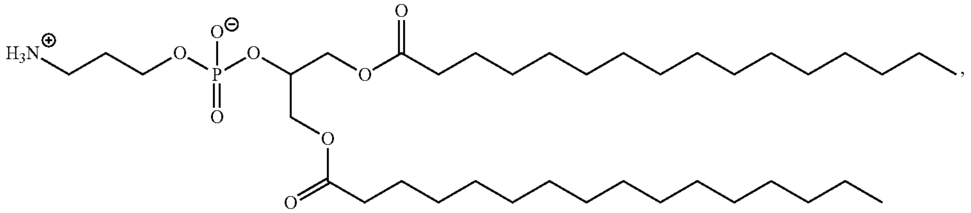
(Compound 463)
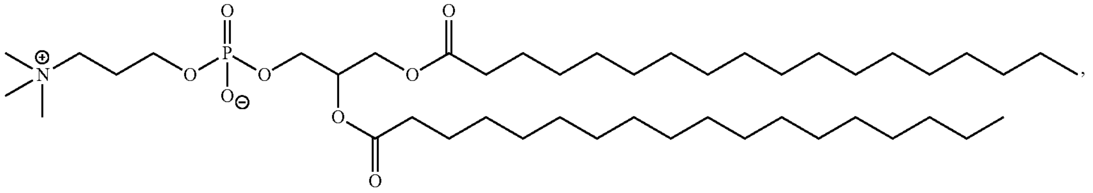
(Compound 464)
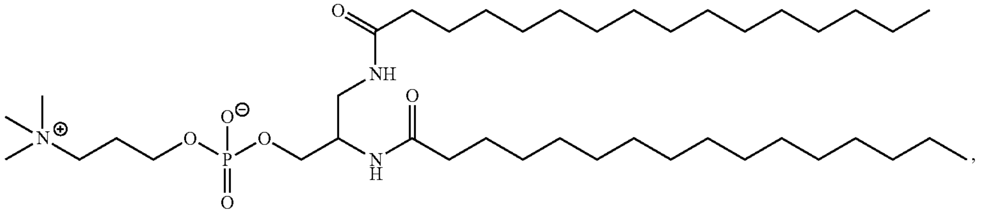
(Compound 463)
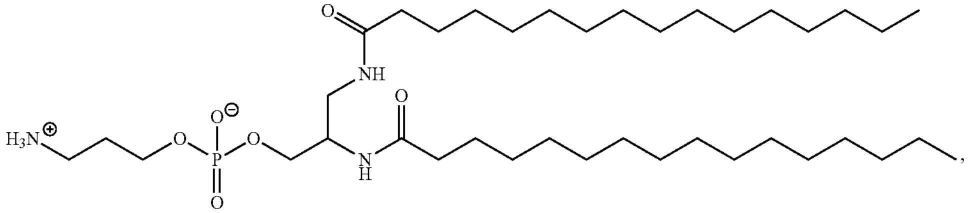
(Compound 412)
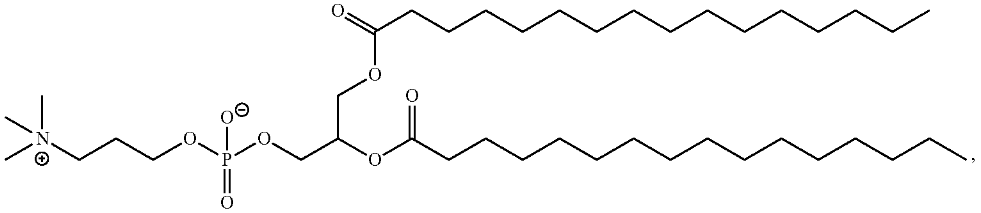
(Compound 413)
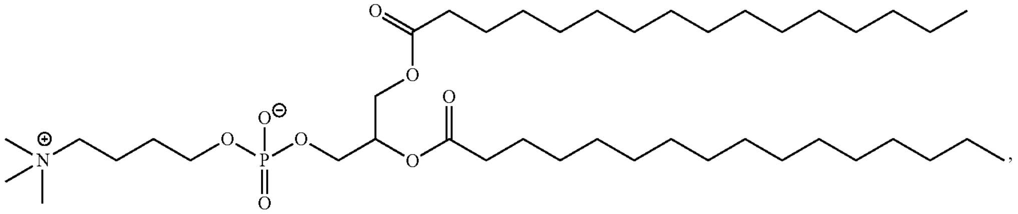
(Compound 414)
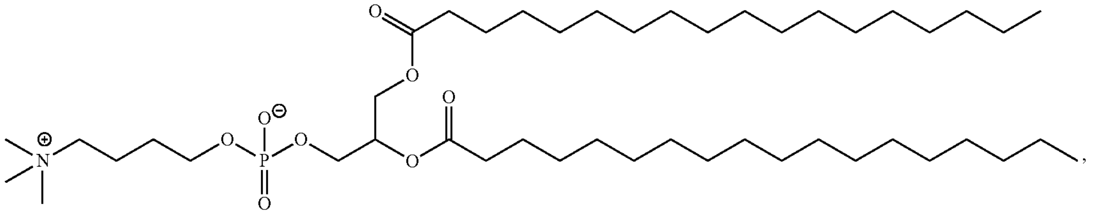
or salts thereof.

Alternative Lipids
In certain embodiments, an alternative lipid is used in place of a phospholipid of the invention. Non-limiting examples of such alternative lipids include the following:
Compound 457
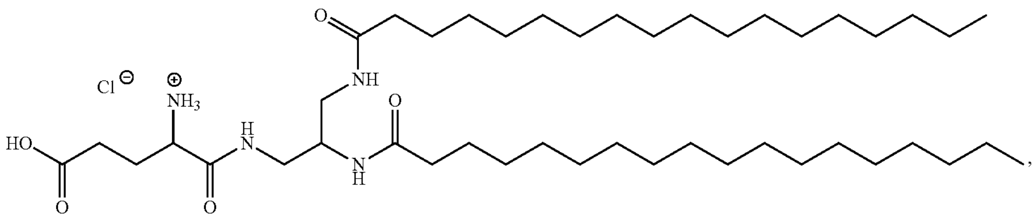
,
Compound 458
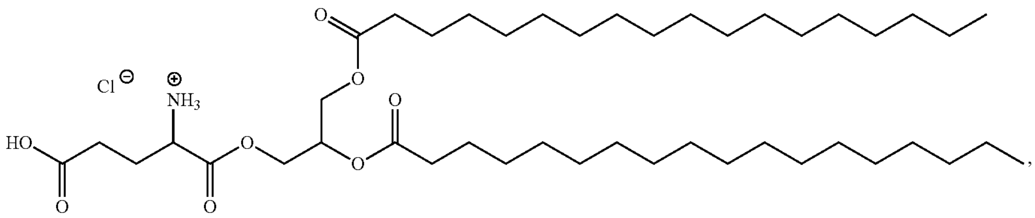
,
Compound 459
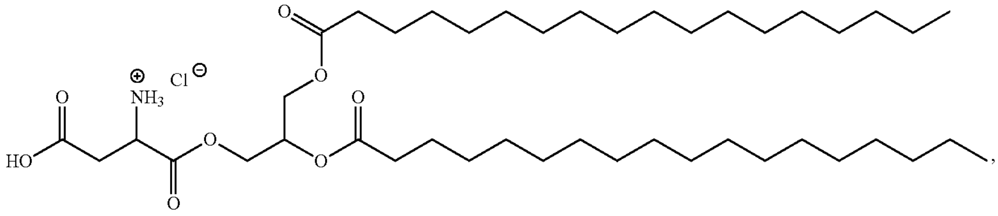
,
Compound 460
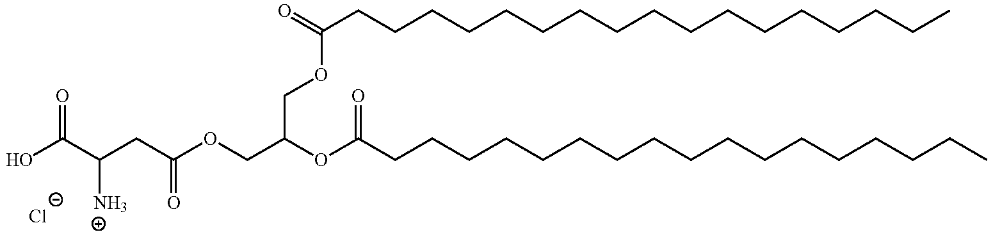
,
Compound 461
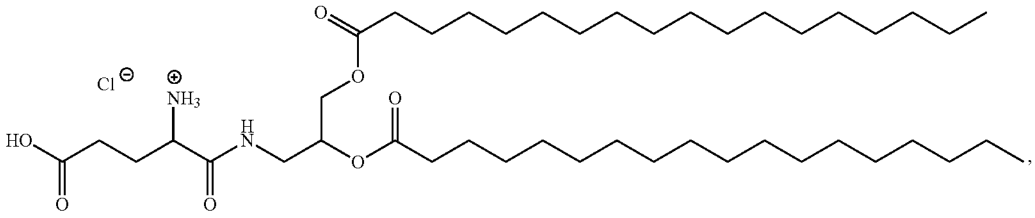
,
Compound 461
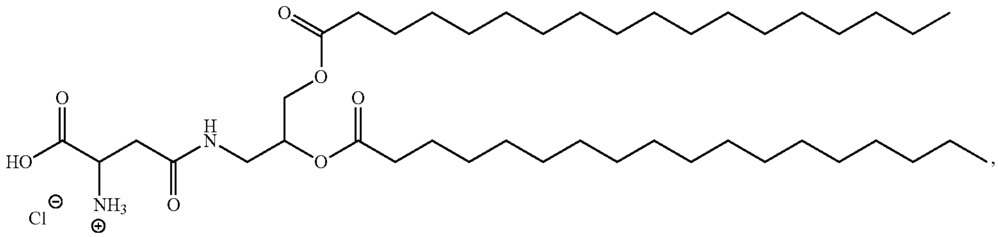
, and -continued Compound 463

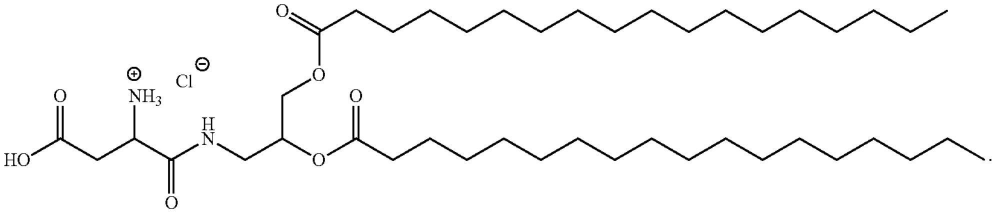

The lipid component of a lipid nanoparticle composition may include one or more structural lipids. Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

(Compound 464)

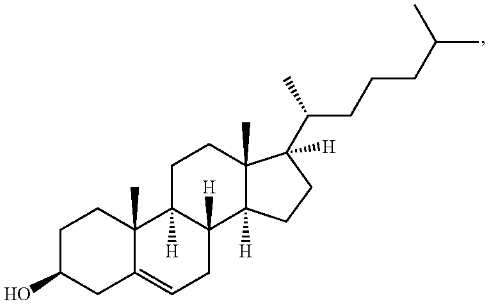

, (Compound 465)

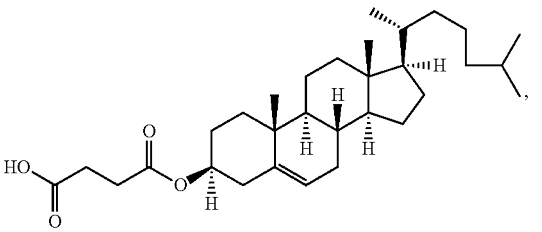

, and (Compound 466)

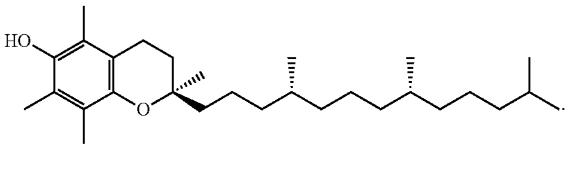

.

Lipid nanoparticles typically comprise one or more of the following components: lipids (which may include ionizable amino lipids, phospholipids, helper lipids which may be neutral lipids, zwitterionic lipid, anionic lipids, and the like), structural lipids such as cholesterol or cholesterol analogs, fatty acids, polymers, stabilizers, salts, buffers, solvent, and the like.

Certain of the LNPs provided herein comprise an ionizable lipid, such as an ionizable lipid, e.g., an ionizable amino lipid, a phospholipid, a structural lipid, and optionally a stabilizer (e.g., a molecule comprising polyethylene glycol) which may or may not be provided conjugated to another lipid.

The ionizable lipid may be but is not limited to DLin-DMA, DLin-D-DMA, DLin-MC3-DMA, DLin-KC2-DMA and DODMA. The ionizable lipid may be an ionizable amino lipid as described in more detail below. In some embodiments, the ionizable lipid is not DLin-MC3-DMA.

The structural lipid may be but is not limited to a sterol such as for example cholesterol.

The helper lipid is a non-cationic lipid. The helper lipid may comprise at least one fatty acid chain of at least 8C and at least one polar headgroup moiety.

When a molecule comprising polyethylene glycol (i.e. PEG) is used, it may be used as a stabilizer In some embodiments, the molecule comprising polyethylene glycol may be polyethylene glycol conjugated to a lipid and thus may be provided as PEG-c-DOMG or PEG-DMG, for example. Certain of the LNPs provided herein comprise no or low levels of PEGylated lipids, including no or low levels of alkyl-PEGylated lipids, and may be referred to herein as being free of PEG or PEGylated lipid. Thus, some LNPs comprise less than 0.5 mol % PEGylated lipid. In some instances, PEG may be an alkyl-PEG such as methoxy-PEG. Still other LNPs comprise non-alkyl-PEG such as hydroxy-PEG, and/or non-alkyl-PEGylated lipids such as hydroxy-PEGylated lipids.

In some embodiments, a nanoparticle composition can have the formulation of Compound 18:Phospholipid:Chol:Compound 781 with a mole ratio of 50:10:38.5:1.5. In some embodiments, a nanoparticle composition can have the formulation of Compound 18:DSPC:Chol:Compound 428 with a mole ratio of 50:10:38.5:1.5.

Compound 428

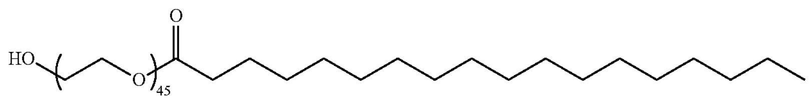

In some embodiments the LNP comprises a miR binding site. In other embodiments the miR binding site is selected from miR 126, miR 155, and miR 142 3p. The miR binding site is incorporated into a mRNA in some embodiments. In other embodiments the miR binding site is separate from the mRNA.

In various embodiments, the mRNA comprises 1-4, one, two, three or four miR binding sites, wherein at least one of the miR binding sites is a miR-126 binding site. In one embodiment, the mRNA, comprises at least two microRNA binding sites, wherein at least one of the microRNA binding sites is a miR-126 binding site. In one embodiment, the mRNA, e.g., mmRNA, comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27. In another embodiment, the mRNA, comprises a miR-126 (e.g., miR-126-3p) binding site and a miR-142 (e.g., miR-142-3p) binding site. It has now been discovered that incorporation of at least one microRNA binding site for a microRNA expressed in immune cells (e.g., miR-126, miR-142, miR-155 and combinations thereof) into an mRNA construct can reduce or inhibit ABC when the lipid-comprising compound or composition comprising the mRNA is administered to a subject. In one embodiment, the mechanism of action of the miRNA binding site(s) is a microRNA "sponge", wherein the miRNA binding site(s) in the construct or LNP "soaks up" microRNAs that bind to the binding site(s).

It has been discovered according to the invention that delivery of a miR binding site will inhibit an immune response, avoiding the production of ADA and can be used to provide repeated dosing of a subject with an LNP without susceptibility to accelerated blood clearance (ABC). The miR binding site may be incorporated into a therapeutic nucleic acid that is being delivered in the LNP. Alternatively the miR binding site may separately be incorporated into the same LNP that incorporates the therapeutic nucleic acid or into a different LNP. The miR binding site may be administered to the subject in a separate vehicle at the same or different time as the LNP and may or may not be incorporated into an LNP. In some embodiments the miR binding site may be a miR sponge.

Although Applicant is not bound by mechanism, it is believed that the miR binding site act to soak up endogenous, targeted miRNA of interest, preventing that miRNA from functioning in the cell. It is possible to target miRNA that play a positive role in regulation of immune cell function. By inhibiting the function of endogenous miRNA the miR binding site acts as an inhibitor to block the miRNA function and other downstream effects resulting from this targeting inhibition. The miRNA binding agent may also or alternatively be functioning by preventing protein translation in specific tissues or cells, such as the spleen or immune cells. By preventing translation of, for instance, an mRNA therapeutic encapsulated in the LNP, in specific tissues that are high in immune cells, the immune response in those tissues will be decreased, while not having an impact on mRNA expression in other tissues.

It has been demonstrated that introduction of miR binding sites such as miR 126 (highly abundant in pDC) results in a reduction in B cell activation, a reduction in pDC activation, a reduction in cytokine expression, such as IL6 and IFN-gamma, and a reduction in IgM relative to the response delivered by a corresponding LNP without the miR binding site.

In some embodiments the miR binding site is a miR 126, miR 155, and/or miR 142.3p binding site. In some embodiments, the mRNA can comprise at least one miR binding site to thereby reduce or inhibit an immune response. The miR binding site may be found in, for instance, the 3' UTR of the mRNA.

It has been demonstrated that introduction of miR binding sites such as miR 126 (highly abundant in pDC) results in a reduction in B cell activation, a reduction in pDC activation, a reduction in cytokine expression, such as IL6 and IFN-gamma, and a reduction in IgM relative to the response delivered by a corresponding LNP without the miR binding site.

Nanoparticle compositions of the present disclosure comprise at least one compound according to Formula (I). For example, the nanoparticle composition can include one or more of Compounds 1-232. Nanoparticle compositions can also include a variety of other components. For example, the nanoparticle composition can include one or more other lipids in addition to a lipid according to Formula (I) or (II), for example (i) at least one phospholipid, (ii) at least one structural lipid, (iii) at least one PEG-lipid, or (iv) any combination thereof.

In some embodiments, the nanoparticle composition comprises a compound of Formula (I), (e.g., Compounds 18, 25, 26 or 48). In some embodiments, the nanoparticle composition comprises a compound of Formula (I) (e.g., Compounds 18, 25, 26 or 48) and a phospholipid (e.g., DSPC, DOP, or MSPC).

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof). The lipid composition can include a buffer such as, but not limited to, citrate or phosphate at a pH of 7, salt and/or sugar. Salt and/or sugar can be included in the formulations described herein for isotonicity.

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

In one embodiment, formulations comprising the polynucleotides and lipid nanoparticles described herein can comprise 0.15 mg/ml to 2 mg/ml of the polynucleotide described herein (e.g., mRNA). In some embodiments, the formulation can further comprise 10 mM of citrate buffer and the formulation can additionally comprise up to 10% w/w of sucrose (e.g., at least 1% w/w, at least 20% w/w/, at least 3% w/w, at least 4% w/w, at least 5% w/w, at least 6% w/w, at least 7% w/w, at least 8% w/w, at least 9% w/w or 10% w/w).

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a compound of Formula (I) as described herein, and (ii) a polynucleotide encoding a JAG1 polypeptide. In such nanoparticle composition, the lipid composition disclosed herein can encapsulate the polynucleotide encoding a JAG1 polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

Nanoparticle compositions of the present disclosure comprise at least one compound according to Formula (X). For example, the nanoparticle composition can include one or more of Compounds 1-232. Nanoparticle compositions can also include a variety of other components. For example, the nanoparticle composition can include one or more other lipids in addition to a lipid according to Formula (X) or (XI), for example (i) at least one phospholipid, (ii) at least one structural lipid, (iii) at least one PEG-lipid, or (iv) any combination thereof.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a JAG1 polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a JAG1 polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide, and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is a cationic or an ionizable lipid. In some embodiments, lipid nanoparticle formulations further comprise other components, including a phospholipid, a structural lipid, a quaternary amine compound, and a molecule capable of reducing particle aggregation, for example a PEG or PEG-modified lipid.

Cationic and ionizable lipids can include those as described in, e.g., Intl. Pub. Nos. WO2015199952, WO 2015130584, WO 2015011633, and WO2012040184 WO2013126803, WO2011153120, WO2011149733, WO2011090965, WO2011043913, WO2011022460, WO2012061259, WO2012054365, WO2012044638, WO2010080724, WO201021865, WO2008103276, and WO2013086373; U.S. Pat. Nos. 7,893,302, 7,404,969, 8,283,333, and 8,466,122; and U.S. Pub. Nos. US20110224447, US20120295832, US20150315112, US20100036115, US20120202871, US20130064894, US20130129785, US20130150625, US20130178541, US20130123338 and US20130225836, each of which is herein incorporated by reference in its entirety. In some embodiments, the amount of the cationic and ionizable lipids in the lipid composition ranges from about 0.01 mol % to about 99 mol %.

Exemplary ionizable lipids include, but not limited to, any one of Compounds 1-232 disclosed herein, DLin-MC3-DMA (MC3), DLin-DMA, DLenDMA, DLin-D-DMA, DLin-K-DMA, DLin-M-C2-DMA, DLin-K-DMA, DLin- KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl]heptadecan-8-amine, 1-[(1S,2R)-2-hexylcyclopropyl]-N,N-dimethylnonadecan-10-amine, N,N-dimethyl-1-[(1 S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-([(1R,2R)-2-pentylcyclopropyl]methyl)cyclopropyl]nonadecan-10-amine, N,N-dimethyl-1-[(1 S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl})pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z. 12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(1 Z, 14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-methyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1 S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g.,) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0.1 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present disclosure in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin 134 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the present disclosure, encapsulation can be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the present disclosure can be enclosed, surrounded or encased within the delivery agent. "Partially encapsulation" means that less than 10, 10, 20, 30, 40 50 or less of the pharmaceutical composition or compound of the present disclosure can be enclosed, surrounded or encased within the delivery agent.

Advantageously, encapsulation can be determined by measuring the escape or the activity of the pharmaceutical composition or compound of the present disclosure using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the present disclosure are encapsulated in the delivery agent.

In some embodiments, the polynucleotide controlled release formulation can include at least one controlled release coating (e.g., OPADRY®, EUDRAGIT RL®, EUDRAGIT RS® and cellulose derivatives such as ethylcellulose aqueous dispersions (AQUACOAT® and SURELEASE®)). In some embodiments, the polynucleotide controlled release formulation can comprise a polymer system as described in U.S. Pub. No. US20130130348, or a PEG and/or PEG related polymer derivative as described in U.S. Pat. No. 8,404,222, each of which is incorporated by reference in its entirety.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigitial micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (UMM) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 μm, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a JAG1 polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-5LAP; also known as 98N12-5, see Murugaiah et al., Analytical Biochemistry, 401:61 (2010)), C12-200 (including derivatives and variants), and MD1, can be tested for in vivo activity. The lipidoid “98N12-5” is disclosed by Akinc et al., Mol Ther. 2009 17:872-879. The lipidoid “C12-200” is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a JAG1 polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, intratumorally, or subcutaneously.

d. Nanoparticle Mimics

In some embodiments, the polynucleotides described herein (e.g., a polynucleotide comprising a nucleotide sequence encoding a JAG1 polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Nanotubes

In some embodiments, the compositions or formulations of the present disclosure comprise the polynucleotides described herein (e.g., a polynucleotide comprising a nucleotide sequence encoding a JAG1 polypeptide) attached or otherwise bound to (e.g., through steric, ionic, covalent and/or other forces) at least one nanotube, such as, but not limited to, rosette nanotubes, rosette nanotubes having twin bases with a linker, carbon nanotubes and/or single-walled carbon nanotubes. Nanotubes and nanotube formulations comprising a polynucleotide are described in, e.g., Intl. Pub. No. WO2014152211, herein incorporated by reference in its entirety.

f. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a JAG1 polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

g. Inorganic Nanoparticles, Semi-Conductive and Metallic Nanoparticles

In some embodiments, the compositions or formulations of the present disclosure comprise the polynucleotides described herein (e.g., a polynucleotide comprising a nucleotide sequence encoding a JAG1 polypeptide) in inorganic nanoparticles, or water-dispersible nanoparticles comprising a semiconductive or metallic material. The inorganic nanoparticles can include, but are not limited to, clay substances that are water swellable. The water-dispersible nanoparticles can be hydrophobic or hydrophilic nanoparticles. As a non-limiting example, the inorganic, semi-conductive and metallic nanoparticles are described in, e.g., U.S. Pat. Nos. 5,585,108 and 8,257,745; and U.S. Pub. Nos. US20120228565, US 20120265001 and US 20120283503, each of which is herein incorporated by reference in their entirety.

h. Surgical Sealants: Gels and Hydrogels

In some embodiments, the compositions or formulations of the present disclosure comprise the polynucleotides described herein (e.g., a polynucleotide comprising a nucleotide sequence encoding a JAG1 polypeptide) in a surgical sealant. Surgical sealants such as gels and hydrogels are described in Intl. Appl. No. PCT/US2014/027077, herein incorporated by reference in its entirety.

i. Suspension Formulations

In some embodiments, the compositions or formulations of the present disclosure comprise the polynucleotides described herein (e.g., a polynucleotide comprising a nucleotide sequence encoding a JAG1 polypeptide) in suspensions. In some embodiments, suspensions comprise a polynucleotide, water immiscible oil depots, surfactants and/or co-surfactants and/or co-solvents. Suspensions can be formed by first preparing an aqueous solution of a polynucleotide and an oil-based phase comprising one or more surfactants, and then mixing the two phases (aqueous and oil-based).

Exemplary oils for suspension formulations can include, but are not limited to, sesame oil and Miglyol (comprising esters of saturated coconut and palmkernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, Capmul®, labrasol, isopropyl myristate, and/or Span 80. In some embodiments, suspensions can comprise co-solvents including, but not limited to ethanol, glycerol and/or propylene glycol.

In some embodiments, suspensions can provide modulation of the release of the polynucleotides into the surrounding environment by diffusion from a water immiscible depot followed by resolubilization into a surrounding environment (e.g., an aqueous environment).

In some embodiments, the polynucleotides can be formulated such that upon injection, an emulsion forms spontaneously (e.g., when delivered to an aqueous phase), which can provide a high surface area to volume ratio for release of polynucleotides from an oil phase to an aqueous phase. In some embodiments, the polynucleotide is formulated in a nanoemulsion, which can comprise a liquid hydrophobic core surrounded by or coated with a lipid or surfactant layer. Exemplary nanoemulsions and their preparations are described in, e.g., U.S. Pat. No. 8,496,945, herein incorporated by reference in its entirety.

j. Cations and Anions

In some embodiments, the compositions or formulations of the present disclosure comprise the polynucleotides described herein (e.g., a polynucleotide comprising a nucleotide sequence encoding a JAG1 polypeptide) and a cation or anion, such as Zn2+, Ca2+, Cu2+, Mg2+ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

k. Molded Nanoparticles and Microparticles

In some embodiments, the compositions or formulations of the present disclosure comprise the polynucleotides described herein (e.g., a polynucleotide comprising a nucleotide sequence encoding a JAG1 polypeptide) in molded nanoparticles in various sizes, shapes and chemistry. For example, the nanoparticles and/or microparticles can be made using the PRINT® technology by LIQUIDA TECHNOLOGIES® (Morrisville, NC) (e.g., International Pub. No. WO2007024323, herein incorporated by reference in its entirety).

In some embodiments, the polynucleotides described herein (e.g., a polynucleotide comprising a nucleotide sequence encoding a JAG1 polypeptide) is formulated in microparticles. The microparticles can contain a core of the polynucleotide and a cortex of a biocompatible and/or biodegradable polymer, including but not limited to, poly (a-hydroxy acid), a polyhydroxy butyric acid, a polycaprolactone, a polyorthoester and a polyanhydride. The microparticle can have adsorbent surfaces to adsorb polynucleotides. The microparticles can have a diameter of from at least 1 micron to at least 100 microns (e.g., at least 1 micron, at least 10 micron, at least 20 micron, at least 30 micron, at least 50 micron, at least 75 micron, at least 95 micron, and at least 100 micron). In some embodiment, the compositions or formulations of the present disclosure are microemulsions comprising microparticles and polynucleotides. Exemplary microparticles, microemulsions and their preparations are described in, e.g., U.S. Pat. Nos. 8,460,709, 8,309,139 and 8,206,749; U.S. Pub. Nos. US20130129830, US2013195923 and US20130195898; and Intl. Pub. No. WO2013075068, each of which is herein incorporated by reference in its entirety.

l. NanoJackets and NanoLiposomes

In some embodiments, the compositions or formulations of the present disclosure comprise the polynucleotides described herein (e.g., a polynucleotide comprising a nucleotide sequence encoding a JAG1 polypeptide) in NanoJackets and NanoLiposomes by Keystone Nano (State College, PA). NanoJackets are made of materials that are naturally found in the body including calcium, phosphate and can also include a small amount of silicates. Nanojackets can have a size ranging from 5 to 50 nm.

NanoLiposomes are made of lipids such as, but not limited to, lipids that naturally occur in the body. NanoLiposomes can have a size ranging from 60-80 nm. In some embodiments, the polynucleotides disclosed herein are formulated in a NanoLiposome such as, but not limited to, Ceramide NanoLiposomes.

m. Cells or Minicells

In some embodiments, the compositions or formulations of the present disclosure comprise the polynucleotides described herein (e.g., a polynucleotide comprising a nucleotide sequence encoding a JAG1 polypeptide) that is transfected ex vivo into cells, which are subsequently transplanted into a subject. Cell-based formulations of the polynucleotide disclosed herein can be used to ensure cell transfection (e.g., in the cellular carrier), alter the biodistribution of the polynucleotide (e.g., by targeting the cell carrier to specific tissues or cell types), and/or increase the translation of encoded protein.

Exemplary cells include, but are not limited to, red blood cells, virosomes, and electroporated cells (see e.g., Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety).

A variety of methods are known in the art and are suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In some embodiments, the polynucleotides described herein can be delivered in synthetic virus-like particles (VLPs) synthesized by the methods as described in Intl. Pub Nos. WO2011085231 and WO2013116656; and U.S. Pub. No. 20110171248, each of which is herein incorporated by reference in its entirety.

The technique of sonoporation, or cellular sonication, is the use of sound (e.g., ultrasonic frequencies) for modifying the permeability of the cell plasma membrane. Sonoporation methods are known to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; U.S. Pub. Nos. US20100196983 and US20100009424; all herein incorporated by reference in their entirety).

In some embodiments, the polynucleotides described herein can be delivered by electroporation. Electroporation techniques are known to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). Electroporation devices are sold by many companies worldwide including, but not limited to BTX® Instruments (Holliston, MA) (e.g., the AgilePulse In Vivo System) and Inovio (Blue Bell, PA) (e.g., Inovio SP-5P intramuscular delivery device or the CELLECTRA® 3000 intradermal delivery device).

In some embodiments, the cells are selected from the group consisting of mammalian cells, bacterial cells, plant, microbial, algal and fungal cells. In some embodiments, the cells are mammalian cells, such as, but not limited to, human, mouse, rat, goat, horse, rabbit, hamster or cow cells. In a further embodiment, the cells can be from an established cell line, including, but not limited to, HeLa, NS0, SP2/0, KEK 293T, Vero, Caco, Caco-2, MDCK, CO5-1, CO5-7, K562, Jurkat, CHO-K1, DG44, CHOK1SV, CHO-S, Huvec, CV-1, Huh-7, NIH3T3, HEK293, 293, A549, HepG2, IMR-90, MCF-7, U-20S, Per.C6, SF9, SF21 or Chinese Hamster Ovary (CHO) cells.

In certain embodiments, the cells are fungal cells, such as, but not limited to, *Chrysosporium* cells, *Aspergillus* cells, *Trichoderma* cells, *Dictyostelium* cells, *Candida* cells, *Saccharomyces* cells, *Schizosaccharomyces* cells, and *Penicillium* cells.

In certain embodiments, the cells are bacterial cells such as, but not limited to, *E. coli*, *B. subtilis*, or BL21 cells. Primary and secondary cells to be transfected by the methods of the present disclosure can be obtained from a variety of tissues and include, but are not limited to, all cell types that can be maintained in culture. The primary and secondary cells include, but are not limited to, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells can also be obtained from a donor of the same species or from another species (e.g., mouse, rat, rabbit, cat, dog, pig, cow, bird, sheep, goat, horse).

In some embodiments, the compositions or formulations of the present disclosure comprise the polynucleotides described herein in bacterial minicells. As a non-limiting example, bacterial minicells can be those described in Intl. Pub. No. WO2013088250 or U.S. Pub. No. US20130177499, each of which is herein incorporated by reference in its entirety.

n. Semi-Solid Compositions

In some embodiments, the compositions or formulations of the present disclosure comprise the polynucleotides described herein (e.g., a polynucleotide comprising a nucleotide sequence encoding a JAG1 polypeptide) in a hydrophobic matrix to form a semi-solid or paste-like composition. As a non-limiting example, the semi-solid or paste-like composition can be made by the methods described in Intl. Pub. No. WO201307604, herein incorporated by reference in its entirety.

o. Exosomes

In some embodiments, the compositions or formulations of the present disclosure comprise the polynucleotides described herein (e.g., a polynucleotide comprising a nucleotide sequence encoding a JAG1 polypeptide) in exosomes, which can be loaded with at least one polynucleotide and delivered to cells, tissues and/or organisms. As a non-limiting example, the polynucleotides can be loaded in the exosomes as described in Intl. Pub. No. WO2013084000, herein incorporated by reference in its entirety.

p. Silk-Based Delivery

In some embodiments, the compositions or formulations of the present disclosure comprise the polynucleotides described herein (e.g., a polynucleotide comprising a nucleotide sequence encoding a JAG1 polypeptide) that is formulated for silk-based delivery. The silk-based delivery system can be formed by contacting a silk fibroin solution with a polynucleotide described herein. As a non-limiting example, a sustained release silk-based delivery system and methods of making such system are described in U.S. Pub. No. US20130177611, herein incorporated by reference in its entirety.

q. Amino Acid Lipids

In some embodiments, the compositions or formulations of the present disclosure comprise the polynucleotides described herein (e.g., a polynucleotide comprising a nucleotide sequence encoding a JAG1 polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

r. Microvesicles

In some embodiments, the compositions or formulations of the present disclosure comprise the polynucleotides described herein (e.g., a polynucleotide comprising a nucleotide sequence encoding a JAG1 polypeptide) in a microvesicle formulation. Exemplary microvesicles include those described in U.S. Pub. No. US20130209544 (herein incorporated by reference in its entirety). In some embodiments, the microvesicle is an ARRDC 1-mediated microvesicles (ARMMs) as described in Intl. Pub. No. WO2013119602 (herein incorporated by reference in its entirety).

s. Interpolyelectrolyte Complexes

In some embodiments, the compositions or formulations of the present disclosure comprise the polynucleotides described herein (e.g., a polynucleotide comprising a nucleotide sequence encoding a JAG1 polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

t. Crystalline Polymeric Systems

In some embodiments, the compositions or formulations of the present disclosure comprise the polynucleotides described herein (e.g., a polynucleotide comprising a nucleotide sequence encoding a JAG1 polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

a. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a JAG1 polypeptide) and a natural and/or synthetic polymer. The polymers include, but not limited to, polyethenes, polyethylene glycol (PEG), poly(1-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multiblock copolymers, polycarbonates, polyanhydrides, polyhydroxyacids, polypropylfumerates, polycaprolactones, polyamides, polyacetals, polyethers, polyesters, poly (orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUS® Bio (Madison, WI) and Roche Madison (Madison, WI), PHASERX™ polymer formulations such as, without limitation, SMARTT POLYMER TECHNOLOGY™ (PHASERX®, Seattle, WA), DMRI/DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art, the polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

v. Peptides and Proteins

In some embodiments, the compositions or formulations of the present disclosure comprise the polynucleotides described herein (e.g., a polynucleotide comprising a nucleotide sequence encoding a JAG1 polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

w. Conjugates

In some embodiments, the compositions or formulations of the present disclosure comprise the polynucleotides described herein (e.g., a polynucleotide comprising a nucleotide sequence encoding a JAG1 polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fructose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835,393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

x. Micro-Organs

In some embodiments, the compositions or formulations of the present disclosure comprise the polynucleotides described herein (e.g., a polynucleotide comprising a nucleotide sequence encoding a JAG1 polypeptide) in a micro-organ that can then express an encoded polypeptide of interest in a long-lasting therapeutic formulation. Exemplary micro-organs and formulations are described in Intl. Pub. No. WO2014152211 (herein incorporated by reference in its entirety).

y. Pseudovirions

In some embodiments, the compositions or formulations of the present disclosure comprise the polynucleotides described herein (e.g., a polynucleotide comprising a nucleotide sequence encoding a JAG1 polypeptide) in pseudovirions (e.g., pseudovirions developed by Aura Biosciences, Cambridge, MA).

In some embodiments, the pseudovirion used for delivering the polynucleotides can be derived from viruses such as, but not limited to, herpes and papillomaviruses as described in, e.g., U.S. Pub. Nos. US20130012450, US20130012566, US21030012426 and US20120207840; and Intl. Pub. No. WO2013009717, each of which is herein incorporated by reference in its entirety.

The pseudovirion can be a virus-like particle (VLP) prepared by the methods described in U.S. Pub. Nos. US20120015899 and US20130177587, and Intl. Pub. Nos. WO2010047839, WO2013116656, WO2013106525 and WO2013122262. In one aspect, the VLP can be bacteriophages MS, Qβ, R17, fr, GA, Sp, MI, I, MXI, NL95, AP205, f2, PP7, and the plant viruses Turnip crinkle virus (TCV), Tomato bushy stunt virus (TBSV), Southern bean mosaic virus (SBMV) and members of the genus *Bromovirus* including Broad bean mottle virus, Brome mosaic virus, Cassia yellow blotch virus, Cowpea chlorotic mottle virus (CCMV), Melandrium yellow fleck virus, and Spring beauty latent virus. In another aspect, the VLP can be derived from the influenza virus as described in U.S. Pub. No. US20130177587 and U.S. Pat. No. 8,506,967. In one aspect, the VLP can comprise a B7-1 and/or B7-2 molecule anchored to a lipid membrane or the exterior of the particle such as described in Intl. Pub. No. WO2013116656. In one aspect, the VLP can be derived from norovirus, rotavirus recombinant VP6 protein or double layered VP2/VP6 such as the VLP as described in Intl. Pub. No. WO2012049366. Each of the references is herein incorporated by reference in its entirety.

In some embodiments, the pseudovirion can be a human papilloma virus-like particle as described in Intl. Pub. No. WO2010120266 and U.S. Pub. No. US20120171290. In some embodiments, the virus-like particle (VLP) can be a self-assembled particle. In one aspect, the pseudovirions can be virion derived nanoparticles as described in U.S. Pub. Nos. US20130116408 and US20130115247; and Intl. Pub. No. WO2013119877. Each of the references is herein incorporated by reference in their entirety.

Non-limiting examples of formulations and methods for formulating the polynucleotides described herein are also provided in Intl. Pub. No WO2013090648 (incorporated herein by reference in their entirety).

Methods of Use

The polynucleotides, pharmaceutical compositions and formulations described above are used in the preparation, manufacture and therapeutic use of to treat and/or prevent JAG1-related diseases, disorders or conditions. In some embodiments, the polynucleotides, compositions and formulations of the present disclosure are used to treat and/or prevent ALGS.

In some embodiments, the polynucleotides, pharmaceutical compositions and formulations of the present disclosure are used in methods for activating the Notch signaling pathway in a subject in need thereof. For instance, one aspect of the present disclosure provides a method of alleviating the signs and symptoms of ALGS in a subject comprising the administration of a composition or formulation comprising a polynucleotide encoding JAG1 to that subject (e.g, an mRNA encoding a JAG1 polypeptide).

In some embodiments, the administration of an effective amount of a polynucleotide, pharmaceutical composition or formulation of the present disclosure reduces the levels of a biomarker of ALGS. In some embodiments, the administration of the polynucleotide, pharmaceutical composition or formulation of the present disclosure results in reduction in the level of one or more biomarkers of ALGS, within a short period of time after administration of the polynucleotide, pharmaceutical composition or formulation of the present disclosure.

Replacement therapy is a potential treatment for ALGS. Thus, in certain aspects of the present disclosure, the polynucleotides, e.g., mRNA, disclosed herein comprise one or more sequences encoding a JAG1 polypeptide that is suitable for use in gene replacement therapy for ALGS. In some embodiments, the present disclosure treats a lack of JAG1 or JAG1 activity, or decreased or abnormal JAG1 activity in a subject by providing a polynucleotide, e.g., mRNA, that encodes a JAG1 polypeptide to the subject. In some embodiments, the polynucleotide is sequence-optimized. In some embodiments, the polynucleotide (e.g., an mRNA) comprises a nucleic acid sequence (e.g., an ORF) encoding a JAG1 polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142.

In some embodiments, the administration of a composition or formulation comprising polynucleotide, pharmaceutical composition or formulation of the present disclosure to a subject results in an increase in Notch signaling in cells to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the polynucleotide, pharmaceutical composition or formulation of the present disclosure results in expression of JAG1 in cells of the subject. In some embodiments, administering the polynucleotide, pharmaceutical composition or formulation of the present disclosure results in an increase of NOTCH receptor ligand activity in the subject. For example, in some embodiments, the polynucleotides of the present disclosure are used in methods of administering a composition or formulation comprising an mRNA encoding a JAG1 polypeptide to a subject, wherein the method results in an increase of NOTCH receptor ligand activity in at least some cells of a subject.

In some embodiments, the administration of a composition or formulation comprising an mRNA encoding a JAG1 polypeptide to a subject results in an increase of NOTCH receptor ligand activity in cells subject to a level at least 100%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the activity level expected in a normal subject, e.g., a human not suffering from ALGS.

In some embodiments, the administration of the polynucleotide, pharmaceutical composition or formulation of the present disclosure results in expression of JAG1 protein in at least some of the cells of a subject that persists for a period of time sufficient to allow significant Notch signaling to occur.

In some embodiments, the expression of the encoded polypeptide is increased. In some embodiments, the polynucleotide increases JAG1 expression levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 800, at least 85%, at least 90%, at least 95%, or to 100% with respect to the JAG1 expression level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 11 to 35 (See Table 2; FIG. 13), wherein the polynucleotide encodes an JAG1 polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

Compositions and Formulations for Use

Certain aspects of the present disclosure are directed to compositions or formulations comprising any of the polynucleotides disclosed above.

In some embodiments, the composition or formulation comprises:

(i) a polynucleotide (e.g., a RNA, e.g., an mRNA) comprising a sequence-optimized nucleotide sequence (e.g., an ORF) encoding a JAG1 polypeptide (e.g., the wild-type sequence, functional fragment, or variant thereof), wherein the polynucleotide comprises at least one chemically modified nucleobase, e.g., 5-methoxyuracil (e.g., wherein at least about 25%, at least about 30%, at least about 400, at least about 50%, at least about 60%, at least about 70%, at least about 80%, at least about 90%, at least about 95%, at least about 99%, or 100% of the uracils are 5-methoxyuracils), and wherein the polynucleotide further comprises a miRNA binding site, e.g., a miRNA binding site that binds to miR-142 (e.g., a miR-142-3p or miR-142-5p binding site); and (ii) a delivery agent comprising a compound having Formula (X), e.g., any of Compounds 1-232 (e.g., Compound 18, 25, 26 or 48).

In some embodiments, the uracil or thymine content of the ORF relative to the theoretical minimum uracil or thymine content of a nucleotide sequence encoding the JAG1 polypeptide (% $U_{TM}$ or % $T_{TM}$), is between about 100% and about 150%.

In some embodiments, the polynucleotides, compositions or formulations above are used to treat and/or prevent a JAG1-related diseases, disorders or conditions, e.g., ALGS.

Forms of Administration

The polynucleotides, pharmaceutical compositions and formulations of the present disclosure described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present disclosure (e.g., a polynucleotide comprising a nucleotide sequence encoding a JAG1 polypeptide or a functional fragment or variant thereof) can be delivered to a cell naked. As used herein in, “naked” refers to delivering polynucleotides free from agents that promote transfection. The naked polynucleotides can be delivered to the cell using routes of administration known in the art and described herein.

The polynucleotides of the present disclosure (e.g., a polynucleotide comprising a nucleotide sequence encoding a JAG1 polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions that are compatible with body tissues.

Kits and Devices a. Kits

The present disclosure provides a variety of kits for conveniently and/or effectively using the claimed nucleotides of the present disclosure. Typically kits will comprise sufficient amounts and/or numbers of components to allow a user to perform multiple treatments of a subject(s) and/or to perform multiple experiments.

In one aspect, the present disclosure provides kits comprising the molecules (polynucleotides) of the present disclosure.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present disclosure provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present disclosure provides kits for protein production, comprising a polynucleotide comprising a translatable region, wherein the polynucleotide exhibits reduced degradation by a cellular nuclease, and packaging and instructions.

In one aspect, the present disclosure provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present disclosure provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present disclosure according to single, multi- or split-dosing regimens taught herein. Such devices are taught in, for example, International Application Publ. No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present disclosure. These include, for example, those methods and devices having multiple needles, hybrid devices employing for example lumens or catheters as well as devices utilizing heat, electric current or radiation driven mechanisms.

According to the present disclosure, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present disclosure on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present disclosure according to the single, multi- or split dosing regimens taught herein. Such methods and devices are described in International Application Publication No. WO2013151666, the contents of which are incorporated herein by reference in their entirety.

Definitions

In order that the present disclosure can be more readily understood, certain terms are first defined. As used in this application, except as otherwise expressly provided herein, each of the following terms shall have the meaning set forth below. Additional definitions are set forth throughout the application.

The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the present disclosure. Where a value is explicitly recited, it is to be understood that values which are about the same quantity or amount as the recited value are also within the scope of the present disclosure. Where a combination is disclosed, each subcombination of the elements of that combination is also specifically disclosed and is within the scope of the present disclosure. Conversely, where different elements or groups of elements are individually disclosed, combinations thereof are also disclosed. Where any element of an present disclosure is disclosed as having a plurality of alternatives, examples of that present disclosure in which each alternative is excluded singly or in any combination with the other alternatives are also hereby disclosed; more than one element of an present disclosure can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art. Such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the present disclosure, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type JAG1 sequence) with another amino acid residue. An amino acid can be substituted in a parent or reference sequence (e.g., a wild type JAG1 polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue, i.e., In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, signs and symptoms, sequelae, or any effects causing a decrease in the quality of life of a patient of ALGS are considered associated with ALGS and in some embodiments of the present disclosure can be treated, ameliorated, or prevented by administering the polynucleotides of the present disclosure to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present disclosure can encode a JAG1 peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunction modified mRNA can be a chimeric or quimeric molecule comprising, for example, an RNA encoding a JAG1 peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present disclosure can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a JAG1 polypeptide, and a second part (e.g., genetically fused to the first part) comprising a second therapeutic protein (e.g., a protein with a distinct enzymatic activity, an antigen binding moiety, or a moiety capable of extending the plasma half life of JAG1, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereometric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, lie, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80%° identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present disclosure can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a JAG1 deficiency), an effective amount of an agent is, for example, an amount of mRNA expressing sufficient JAG1 to ameliorate, reduce, eliminate, or prevent the signs and symptoms associated with the JAG1 deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the present disclosure, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the present disclosure are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present disclosure include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., JAG1) wherein N-terminal, and/or C-terminal, and/or internal subsequences have been deleted. In some preferred aspects of the present disclosure, the fragments of a protein of the present disclosure are functional fragments.

Functional: As used herein, a "functional" biological molecule is a biological molecule in a form in which it exhibits a property and/or activity by which it is characterized. Thus, a functional fragment of a polynucleotide of the present disclosure is a polynucleotide capable of expressing a functional JAG1 fragment. As used herein, a functional fragment of JAG1 refers to a fragment of wild type JAG1 (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present disclosure, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99%0 of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 400, at least 50%, at least 60%, at least 700, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1, also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,165Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated.

Isolated substances and/or entities can be separated from at least about 10%, about 20%, about 30%, about 40%, about 50%, about 60%, about 700%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the present disclosure. It is recognized that the compounds of the present disclosure can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the present disclosure, the chemical structures depicted herein, and therefore the compounds of the present disclosure, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the present disclosure can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the present disclosure. Molecules can be modified in many ways including chemically, structurally, and functionally. In some embodiments, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the present disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition.

JAG1 Associated Disease: As use herein the terms "JAG1-associated disease" or "JAG1-associated disorder" refer to diseases or disorders, respectively, which result from aberrant JAG1 activity (e.g., decreased activity or increased activity). As a non-limiting example, Alagille syndrome is a JAG1 associated disease. Numerous clinical variants of Alagille syndrome are know in the art. See, e.g., www.omim.org/entry/118450.

The terms "JAG1 binding activity," "JAG1 activity," and "NOTCH receptor ligand activity" are used interchangeably in the present disclosure and refer to JAG1's ability to bind as a ligand to NOTCH receptors. Accordingly, a fragment or variant retaining or having JAG1 activity or JAG1 activity refers to a fragment or variant that has measurable ability to activate signaling of a NOTCH receptor.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two, generally, nonaqueous media like ether, ethyl acetate, ethanol, isopropanol, or acetonitrile are used. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

Pharmaceutically acceptable solvate: The term "pharmaceutically acceptable solvate," as used herein, means a compound of the present disclosure wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA)

comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 600 identity, at least about 70% identity, at least about 800 identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more signs and symptoms, features, or clinical manifestations of a particular infection, disease, disorder, and/or condition; partially or completely delaying onset of one or more signs and symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine (ψ) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine (ψm).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Salts: In some aspects, the pharmaceutical composition for intratumoral delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present disclosure can exist in different tautomeric forms, all of the latter being included within the scope of the present disclosure.

Subject: By "subject" or "individual" or "animal" or "patient" or "mammal," is meant any subject, particularly a mammalian subject, for whom diagnosis, prognosis, or therapy is desired.

Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more signs and symptoms of the disease, disorder, and/or condition.

Susceptible to: An individual who is "susceptible to" a disease, disorder, and/or condition has not been diagnosed with and/or can not exhibit signs and symptoms of the disease, disorder, and/or condition but harbors a propensity to develop a disease or its signs and symptoms. In some embodiments, an individual who is susceptible to a disease, disorder, and/or condition (for example, cancer) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present disclosure can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a kidney, a lung, a spleen, vascular endothelium in vessels. An "off-target tissue" refers to any one or more tissue types in which the expression of the encoded protein does not result in a desired biological and/or pharmacological effect. In particular applications, off-target tissues can include the liver and the spleen.

The presence of a therapeutic agent in an off-target issue can be the result of: (i) leakage of a polynucleotide from the administration site to peripheral tissue or distant off-target tissue (e.g., liver) via diffusion or through the bloodstream (e.g., a polynucleotide intended to express a polypeptide in a certain tissue would reach the liver and the polypeptide would be expressed in the liver); or (ii) leakage of an polypeptide after administration of a polynucleotide encoding such polypeptide to peripheral tissue or distant off-target tissue (e.g., liver) via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the present disclosure can be characterized as having both an N-terminus (terminated by an amino acid with a free amino group ($NH_2$)) and a C-terminus (terminated by an amino acid with a free carboxyl group (COOH)). Proteins of the present disclosure are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a JAG1 polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve signs and symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve signs and symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence).

Transfection: As used herein, "transfection" refers to the introduction of a polynucleotide into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more signs and symptoms or features of a disease, e.g., Alagille syndrome. For example, "treating" Alagille syndrome can refer to diminishing signs and symptoms associated with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a β-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g, polymorphisms, isoforms, etc) and artificial variants in which at least one amino acid residue in a native or starting sequence (e.g., a wild type sequence) has been removed and a different amino acid inserted in its place at the same position. These variants can de described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

EQUIVALENTS AND SCOPE

Those skilled in the art will recognize, or be able to ascertain using no more than routine experimentation, many equivalents to the specific embodiments in accordance with the present disclosure described herein. The scope of the present disclosure is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the present disclosure, to the tenth of the unit of the lower limit of the range, unless the context clearly dictates otherwise.

In addition, it is to be understood that any particular embodiment of the present disclosure that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the present disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Chimeric Polynucleotide Synthesis

Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

Synthetic Route

The chimeric polynucleotide can be made using a series of starting segments. Such segments include:

(a) Capped and protected 5' segment comprising a normal 3'OH (SEG. 1)

(b) 5' triphosphate segment which can include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG. 2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5'UTR (SEG. 1), open reading frame or ORF (SEG. 2) and 3'UTR+PolyA (SEG. 3).

The yields of each step can be as much as 90-95%.

Example 2

PCR for cDNA Production

PCR procedures for the preparation of cDNA can be performed using 2×KAPA HIFI™ HotStart ReadyMix by Kapa Biosystems (Woburn, MA). This system includes 2×KAPA ReadyMix12.5 μl; Forward Primer (10 μM) 0.75 μl; Reverse Primer (10 μM) 0.75 μl; Template cDNA −100 ng; and $dH_2O$ diluted to 25.0 μl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the present disclosure can incorporate a poly-$T_{120}$ for a poly-$A_{120}$ in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, CA) per manufacturer's instructions (up to 5 pg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3

In Vitro Transcription (IVT)

The in vitro transcription reactions can generate polynucleotides containing uniformly modified polynucleotides. Such uniformly modified polynucleotides can comprise a region or part of the polynucleotides of the present disclosure. The input nucleotide triphosphate (NTP) mix can be made using natural and un-natural NTPs.

A typical in vitro transcription reaction can include the following:

Template cDNA—1.0 μg

10× transcription buffer (400 mM Tris-HCl pH 8.0, 190 mM $MgCl_2$, 50 mM DTT, 10 mM Spermidine)—2.0 μl Custom NTPs (25 mM each)—7.2 μl RNase Inhibitor—20 U T7 RNA polymerase—3000 U $dH_2O$—Up to 20.0 μl. and Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 μg of RNA. Following the cleanup, the RNA can be quantified using the NanoDrop and analyzed by agarose gel electrophoresis to confirm the RNA is the proper size and that no degradation of the RNA has occurred.

Example 4

Enzymatic Capping

Capping of a polynucleotide can be performed with a mixture includes: IVT RNA 60 μg-180 μg and $dH_2O$ up to 72 μl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5

PolyA Tailing Reaction

Without a poly-T in the cDNA, a poly-A tailing reaction must be performed before cleaning the final product. This can be done by mixing Capped IVT RNA (100 μl); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubating at 37° C. for 30 min. If the poly-A tail is already in the transcript, then the tailing reaction can be skipped and proceed directly to cleanup with Ambion's MEGACLEAR™ kit (Austin, TX) (up to 500 μg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 6

Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England BioLabs. Ipswich, MA). Cap 1 structure can be generated using both Vaccinia Virus Capping Enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7

Capping Assays

Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8

Agarose Gel Electrophoresis of Modified RNA or RT PCR Products

Individual polynucleotides (200-400 ng in a 20 µl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 9

Nanodrop Modified RNA Quantification and UV Spectral Data

Modified polynucleotides in TE buffer (1 µl) can be used for Nanodrop UV absorbance readings to quantitate the yield of each polynucleotide from an chemical synthesis or in vitro transcription reaction.

Example 10

Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11

Method of Screening for Protein Expression

Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI).

Patterns of protein fragments, or whole proteins, can be compared to known controls for a given protein and identity can be determined by comparison.

Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest, more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 12

Synthesis of mRNA Encoding JAG1

Sequence optimized polynucleotides encoding JAG1 polypeptides, i.e., SEQ ID NOs: 1, 3 or 5, are synthesized and characterized as described in Examples 1 to 11. mRNA's encoding both human JAG1 are prepared for Examples 13-19 described below, and are synthesized and characterized as described in Examples 1 to 11.

An mRNA encoding human JAG1 is constructed, e.g., by using the ORF sequence provided in SEQ ID NO: 2. The mRNA sequence includes both 5' and 3' UTR regions (see, e.g., SEQ ID NOs: 84 and 85, respectively). In a construct, the 5'UTR and 3'UTR sequences are:

```
5'UTR
                                        (SEQ ID NO: 84)
TCAAGCTTTTGGACCCTCGTACAGAAGCTAATACGACTCACTATAGGGAA

ATAAGAGAGAAAAGAAGAGTAAGAAGAAATATAAGAGCCACC

3'UTR
                                        (SEQ ID NO: 85)
TGATAATAGGCTGGAGCCTCGGTGGCCATGCTTCTTGCCCCTTGGGCCTC

CCCCCAGCCCCTCCTCCCCTTCCTGCACCCGTACCCCCGTGGTCTTTGAA

TAAAGTCTGAGTGGGCGGC
```

The JAG1 mRNA sequence is prepared as modified mRNA. Specifically, during in vitro translation, modified mRNA is generated using 5-methoxy-UTP to ensure that the mRNAs contain 100% 5-methoxy-uridine instead of uridine. Further, JAG1-mRNA is synthesized with a primer that introduces a polyA-tail, and a Cap 1 structure is generated on both mRNAs using Vaccinia Virus Capping Enzyme and a 2'-0 methyl-transferase to generate: m7G(5')ppp(5')G-2'-O-methyl.

Example 13

Detecting Endogenous JAG1 Expression In Vitro

JAG1 expression is characterized in a variety of cell lines derived from both mice and human sources. Cell are cultured in standard conditions and cell extracts are obtained by placing the cells in lysis buffer. For comparison purposes, appropriate controls are also prepared. To analyze JAG1 expression, lysate samples are prepared from the tested cells and mixed with lithium dodecyl sulfate sample loading buffer and subjected to standard Western blot analysis. For detection of JAG1, the antibody used is a commercial anti-JAG1 antibody. For detection of a load control, the antibody used is anti-citrase synthase (rabbit polyclonal; PA5-22126; Thermo-Fisher Scientific®). To examine the localization of endogenous JAG1, immunofluorescence analysis is performed on cells. JAG1 expression is detected using a commercial anti-JAG1. The location of specific organelles can be detected with existing commercial products. For example, mitochondria can be detected using Mitotracker, and the nucleus can be stained with DAPI. Image analysis is performed on a Zeiss ELYRA imaging system.

Endogenous JAG1 expression can be used as a base line to determine changes in JAG1 expression resulting from transfection with mRNAs comprising nucleic acids encoding JAG1.

Example 14

In Vitro Expression of JAG1 in HeLa Cells

To measure in vitro expression of human JAG1 in HeLa cells, those cells are seeded on 12-well plates (BD Biosciences, San Jose, USA) one day prior to transfection. mRNA formulations comprising human JAG1 or a GFP control are transfected using 800 ng mRNA and 2 μL Lipofectamin 2000 in 60 μL OPTI-MEM per well and incubated.

After 24 hours, the cells in each well are lysed using a consistent amount of lysis buffer. Appropriate controls are used. Protein concentrations of each are determined using a BCA assay according to manufacturer's instructions. To analyze JAG1 expression, equal loads of each lysate (24 μg) are prepared in a loading buffer and subjected to standard Western blot analysis. For detection of JAG1, a commercial anti-JAG1 antibody is used according to the manufacturer's instructions.

Example 15

In Vitro JAG1 Activity in HeLa Cells

An in vitro JAG1 activity assay is performed to determine whether JAG1 exogenously-expressed after introduction of mRNA comprising a JAG1 sequence is active.

Expression Assay

HeLa cells are transfected with mRNA formulations comprising human JAG1 or a GFP control. Cells are transfected with Lipofectamin 2000 and lysed as described in Example 14 above. Appropriate controls are also prepared.

Activity Assay

To assess whether exogenous JAG1 can function, an in vitro activity assay is performed using transfected HeLa cell lysates as the source of enzymatic activity. To begin, lysate is mixed JAG1 substrate. The reaction is stopped by adding 100 g/L TCA and vortexing. The reaction tubes are then centrifuged at 13,000 g for 1 min, and the supernatant is analyzed for the presence of labeled enzymatic products resulting from the activity of JAG1 using HPLC-based separation and quantification. Specifically, 20 μL of each activity reaction supernatant are analyzed using a HPLC system equipped with a Quaternary-Pump, a Multi-sampler, a Thermostated Column-Compartment, a Poroshell EC-C18 120 HPLC-column and a Radiometric Detector controlled by OpenLAB Chromatography Data System, all used according to the manufacturers' recommendations.

Example 16

Measuring In Vitro Expression of JAG1 in Cells

Cells from normal subjects and Alagille syndrome patients are examined for their capacity to express exogenous JAG1. Cells are transfected with mRNA formulations comprising human JAG1, mouse JAG1, or a GFP control via electroporation using a standard protocol. Each construct is tested separately. After incubation, cells are lysed and protein concentration in each lysate is measured using a suitable assay, e.g., by BCA assay. To analyze JAG1 expression, equal loads of each lysate are prepared in a loading buffer and subjected to standard Western blot analysis. For detection of JAG1, an anti-JAG1 is used. For detection of a load control, the antibody used is anti-citrase synthase (rabbit polyclonal; MA5-17625; Pierce®).

Example 17

Measuring In Vitro JAG1 Activity in Lysates Expression

Cells from normal human subjects and Alagille syndrome patients are cultured. Cells are transfected with mRNA formulations comprising human JAG1, mouse JAG1, or a GFP control via electroporation using a standard protocol.

Activity Assay

To assess whether exogenous JAG1 function, an in vitro activity assay is performed using transfected cell lysates as the source of enzymatic activity. Lysate containing expressed JAG1 protein is incubated with labeled JAG1 substrate, and the activity of JAG1 is quantified by measuring the levels of labeled products resulting from the enzymatic activity of JAG1.

Example 18

In Vivo JAG1 Expression in Animal Models

To assess the ability of JAG1-containing mRNA's to facilitate JAG1 expression in vivo, mRNA encoding human JAG1 is introduced into C57B/L6 mice. C57B/L6 mice are injected intravenously with either control mRNA (NT-FIX) or human JAG1 mRNA. The mRNA is formulated in lipid nanoparticles for delivery into the mice. Mice are sacrificed after 24 or 48 hrs. and JAG1 protein levels in liver lysates are determined by capillary electrophoresis (CE). Citrate synthase expression is examined for use as a load control. For control NT-FIX injections, 4 mice are tested for each time point. For human JAG1 mRNA injections, 6 mice are tested for each time point. Treatment with mRNA encoding JAG1 is expected to reliably induce expression of JAG1.

Example 19

Human JAG1 Mutant and Chimeric Constructs

A polynucleotide of the present disclosure can comprise at least a first region of linked nucleosides encoding human JAG1, which can be constructed, expressed, and characterized according to the examples above. Similarly, the polynucleotide sequence can contain one or more mutations that results in the expression of a JAG1 with increased or decreased activity. Furthermore, the polynucleotide sequence encoding JAG1 can be part of a construct encoding a chimeric fusion protein.

Example 20

Synthesis of Compounds According to Formula (X)

A. General Considerations

All solvents and reagents used were obtained commercially and used as such unless noted otherwise. $^1H$ NMR spectra were recorded in $CDCl_3$, at 300 K using a Bruker Ultrashield 300 MHz instrument. Chemical shifts are reported as parts per million (ppm) relative to TMS (0.00) for $^1H$. Silica gel chromatographies were performed on ISCO CombiFlash Rf+ Lumen Instruments using ISCO RediSep Rf Gold Flash Cartridges (particle size: 20-40 microns). Reverse phase chromatographies were performed on ISCO CombiFlash Rf+ Lumen Instruments using RediSep Rf Gold C18 High Performance columns. All final compounds were determined to be greater than 85% pure via analysis by reverse phase UPLC-MS (retention times, RT, in minutes) using Waters Acquity UPLC instrument with DAD and ELSD and a ZORBAX Rapid Resolution High Definition (RRHD) SB-C18 LC column, 2.1 mm, 50 mm, 1.8 μm, and a gradient of 65 to 100% acetonitrile in water with 0.1% TFA over 5 minutes at 1.2 mL/min. Injection volume was 5 μL and the column temperature was 80° C. Detection was based on electrospray ionization (ESI) in positive mode using Waters SQD mass spectrometer (Milford, MA, USA) and evaporative light scattering detector.

The representative procedures described below are useful in the synthesis of Compounds 1-232.

The following abbreviations are employed herein:

THF: Tetrahydrofuran
DMAP: 4-Dimethylaminopyridine
LDA: Lithium Diisopropylamide
rt: Room Temperature
DME: 1,2-Dimethoxyethane
n-BuLi: n-Butyllithium

B. Compound 2: Heptadecan-9-yl 8-((2-hydroxyethyl)(tetradecyl)amino) octanoate Representative Procedure 1

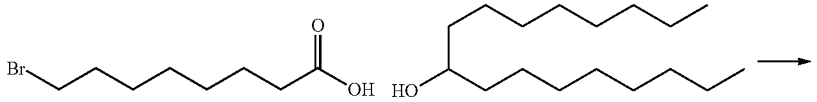

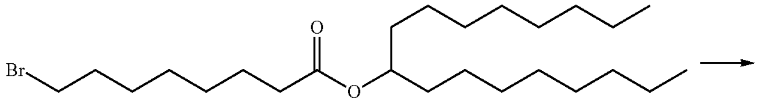

heptadecan-9-yl 8-bromooctanoate

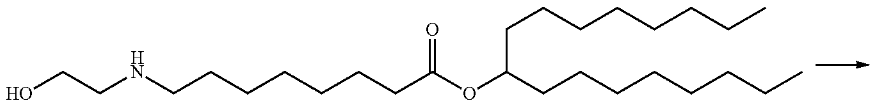

heptadecan-9-yl 8-((2-hydroxyethyl)amino)octanoate

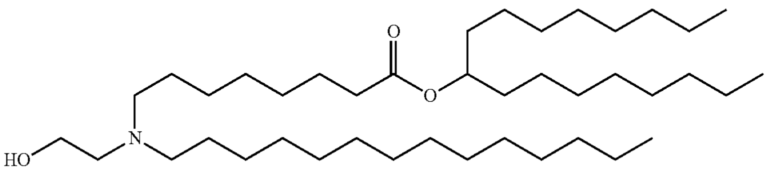

heptadecan-9-yl 8-((2-hydroxyethyl)(tetradecyl)amino)octanoate

Heptadecan-9-yl 8-bromooctanoate (Method A)

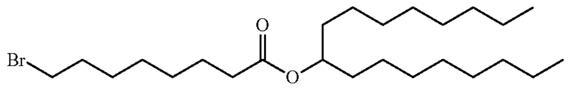 [SMILES: CCCCCCCCC(CCCCCCCC)OC(=O)CCCCCCCBr]

To a solution of 8-bromooctanoic acid (1.04 g, 4.6 mmol) and heptadecan-9-ol (1.5 g, 5.8 mmol) in dichloromethane (20 mL) was added N-(3-dimethylaminopropyl)-N'-ethylcarbodiimide hydrochloride (1.1 g, 5.8 mmol), N,N-diisopropylethylamine (3.3 mL, 18.7 mmol) and DMAP (114 mg, 0.9 mmol). The reaction was allowed to stir at rt for 18 h. The reaction was diluted with dichloromethane and washed with saturated sodium bicarbonate. The organic layer was separated and washed with brine, and dried over $MgSO_4$. The organic layer was filtered and evaporated in vacuo. The residue was purified by silica gel chromatography (0-10% ethyl acetate in hexanes) to obtain heptadecan-9-yl 8-bromooctanoate (875 mg, 1.9 mmol, 41%).

$^1$H NMR (300 MHz, $CDCl_3$) δ: ppm 4.89 (m, 1H); 3.42 (m, 2H); 2.31 (m, 2H); 1.89 (m, 2H); 1.73-1.18 (br. m, 36H); 0.88 (m, 6H).

Heptadecan-9-yl 8-((2-hydroxyethyl)amino)octanoate (Method B)

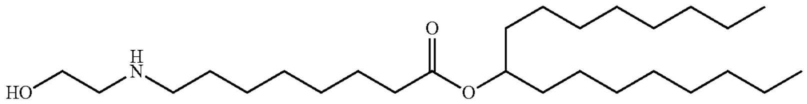 [SMILES: CCCCCCCCC(CCCCCCCC)OC(=O)CCCCCCCNCCO]

A solution of heptadecan-9-yl 8-bromooctanoate (3.8 g, 8.2 mmol) and 2-aminoethan-1-ol (15 mL, 248 mmol) in ethanol (3 mL) was allowed to stir at 62° C. for 18 h. The reaction mixture was concentrated in vacuo and the residue was taken-up in ethyl acetate and water. The organic layer was separated and washed with water, brine and dried over $Na_2SO_4$. The mixture was filtered and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)amino)octanoate (3.1 g, 7 mmol, 85%). UPLC/ELSD: RT=2.67 min. MS (ES): m/z ($MH^+$) 442.68 for $C_{27}H_{55}NO_3$ $^1$H NMR (300 MHz, $CDCl_3$) δ: ppm 4.89 (p, 1H); 3.67 (t, 2H); 2.81 (t, 2H); 2.65 (t, 2H); 2.30 (t, 2H); 2.05 (br. m, 2H); 1.72-1.41 (br. m, 8H); 1.40-1.20 (br. m, 30H); 0.88 (m, 6H).

Heptadecan-9-yl 8-((2-hydroxyethyl)tetradecyl) amino)octanoate (Method C)

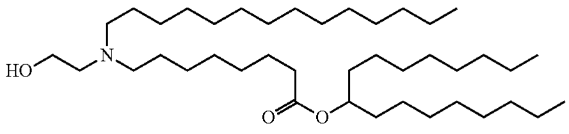

Chemical Formula: $C_{41}H_{83}NO_3$
Molecular Weight: 638.12

A solution of heptadecan-9-yl 8-((2-hydroxyethyl)amino) octanoate (125 mg, 0.28 mmol), 1-bromotetradecane (94 mg, 0.34 mmol) and N,N-diisopropylethylamine (44 mg, 0.34 mmol) in ethanol was allowed to stir at 65° C. for 18 h. The reaction was cooled to rt and solvents were evaporated in vacuo. The residue was taken-up in ethyl acetate and saturated sodium bicarbonate. The organic layer was separated, dried over $Na_2SO_4$ and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)(tetradecyl)amino)octanoate (89 mg, 0.14 mmol, 50%). UPLC/ELSD: RT=3.61 min. MS (ES): m/z ($MH^+$) 638.91 for $C_{41}H_{83}NO_3$. $^1$H NMR (300 MHz, $CDCl_3$) δ: ppm 4.86 (p, 1H); 3.72-3.47 (br. m, 2H); 2.78-2.40 (br. m, 5H); 2.28 (t, 2H); 1.70-1.40 (m, 10H); 1.38-1.17 (br. m, 54H); 0.88 (m, 9H).

Synthesis of Intermediates

Intermediate A: 2-Octyldecanoic acid

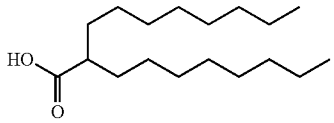 [SMILES: CCCCCCCCC(CCCCCCCC)C(=O)O]

A solution of diisopropylamine (2.92 mL, 20.8 mmol) in THF (10 mL) was cooled to −78° C. and a solution of n-BuLi (7.5 mL, 18.9 mmol, 2.5 M in hexanes) was added. The reaction was allowed to warm to 0° C. To a solution of decanoic acid (2.96 g, 17.2 mmol) and NaH (754 mg, 18.9 mmol, 60% w/w) in THF (20 mL) at 0° C. was added the solution of LDA and the mixture was allowed to stir at rt for 30 min. After this time 1-iodooctane (5 g, 20.8 mmol) was added and the reaction mixture was heated at 45° C. for 6 h. The reaction was quenched with 1N HCl (10 mL). The organic layer was dried over $MgSO_4$, filtered and evaporated in vacuo. The residue was purified by silica gel chromatography (0-20% ethyl acetate in hexanes) to yield 2-octyldecanoic acid (1.9 g, 6.6 mmol, 38%). $^1$H NMR (300 MHz, $CDCl_3$) δ: ppm 2.38 (br. m, 1H); 1.74-1.03 (br. m, 28H); 0.91 (m, 6H).

Intermediate B: 7-Bromoheptyl 2-octyldecanoate

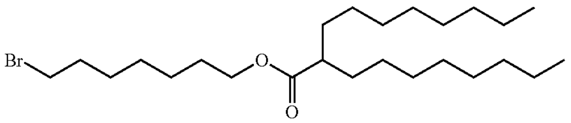 [SMILES: CCCCCCCCC(CCCCCCCC)C(=O)OCCCCCCCBr]

7-bromoheptyl 2-octyldecanoate was synthesized using Method A from 2-octyldecanoic acid and 7-bromoheptan-1-ol. $^1$H NMR (300 MHz, $CDCl_3$) δ: ppm 4.09 (br. m, 2H); 3.43 (br. m, 2H); 2.48-2.25 (br. m, 1H); 1.89 (br. m, 2H); 1.74-1.16 (br. m, 36H); 0.90 (m, 6H).

Intermediate C: (2-Hexylcyclopropyl)methanol

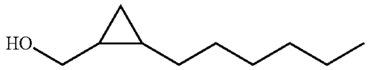

A solution of diethyl zinc (20 mL, 20 mmol, 1 M in hexanes), in dichloromethane (20 mL) was allowed to cool to −40° C. for 5 min. Then a solution of diiodomethane (3.22 mL, 40 mmol) in dichloromethane (10 mL) was added dropwise. After the reaction was allowed to stir for 1 h at −40 OC, a solution of trichloro-acetic acid (327 mg, 2 mmol) and DME (I mL, 9.6 mmol) in dichloromethane (10 mL) was added. The reaction was allowed to warm to −15° C. and stir at this temperature for 1 h. A solution of (Z)-non-2-en-1-ol (1.42 g, 10 mmol) in dichloromethane (10 mL) was then added to the −15° C. solution. The reaction was then slowly allowed to warm to rt and stir for 18 h. After this time saturated $NH_4Cl$ (200 mL) was added and the reaction was extracted with dichloromethane (3×), washed with brine, and dried over $Na_2SO_4$. The organic layer was filtered, evaporated in vacuo and the residue was purified by silica gel chromatography (0-50% ethyl acetate in hexanes) to yield (2-hexylcyclopropyl)methanol (1.43 g, 9.2 mmol, 92%). $^1$H NMR (300 MHz, $CDCl_3$) δ: ppm 3.64 (m, 2H); 1.57-1.02 (m, 12H); 0.99-0.80 (m, 4H); 0.72 (m, 1H), 0.00 (m, 1H).

C. Compound 18: Heptadecan-9-yl 8-((2-hydroxyethyl)(8-(nonyloxy)-8-oxooctyl)amino) octanoate

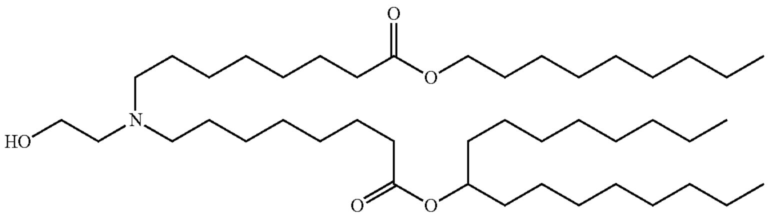

Chemical Formula: $C_{44}H_{87}NO_5$
Molecular Weight: 710.18

Compound 18 was synthesized according to the general procedure and Representative Procedure 1 described above.

UPLC/ELSD: RT=3.59 min. MS (ES): m/z ($MH^+$) 710.89 for $C_{44}H_{87}NO_5$. $^1$H NMR (300 MHz, $CDCl_3$) δ: ppm 4.86 (m, 1H) 4.05 (t, 2H); 3.53 (br. m, 2H); 2.83-2.36 (br. m, 5H); 2.29 (m, 4H); 0.96-1.71 (m, 64H); 0.88 (m, 9H).

D. Compound 136: Nonyl 8-((2-hydroxyethyl)(9Z, 12Z)-octadeca-9,12-dien-1-yl)amino)octanoate Representative Procedure 2

Nonyl 8-bromooctanoate (Method A)

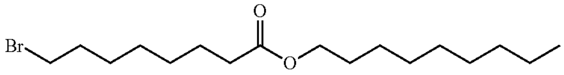 [SMILES: CCCCCCCCCOC(=O)CCCCCCCBr]

To a solution of 8-bromooctanoic acid (5 g, 22 mmol) and nonan-1-ol (6.46 g, 45 mmol) in dichloromethane (100 mL) were added N-(3-Dimethylaminopropyl)-N'-ethylcarbodiimide hydrochloride (4.3 g, 22 mmol) and DMAP (547 mg, 4.5 mmol). The reaction was allowed to stir at rt for 18 h. The reaction was diluted with dichloromethane and washed with saturated sodium bicarbonate. The organic layer was separated and washed with brine, dried over $MgSO_4$. The organic layer was filtered and evaporated under vacuum. The residue was purified by silica gel chromatography (0-10% ethyl acetate in hexanes) to obtain nonyl 8-bromooctanoate (6.1 g, 17 mmol, 77%).

$^1$H NMR (300 MHz, $CDCl_3$) δ: ppm 4.06 (t, 2H); 3.40 (t, 2H); 2.29 (t, 2H); 1.85 (m, 2H); 1.72-0.97 (m, 22H); 0.88 (m, 3H).

Nonyl 8-((2-hydroxyethyl)amino)octanoate

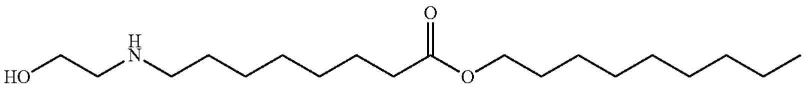 [SMILES: CCCCCCCCCOC(=O)CCCCCCCNCCO]

A solution of nonyl 8-bromooctanoate (1.2 g, 3.4 mmol) and 2-aminoethan-1-ol (5 mL, 83 mmol) in ethanol (2 mL) was allowed to stir at 62° C. for 18 h. The reaction mixture was concentrated in vacuum and the residue was extracted with ethyl acetate and water. The organic layer was separated and washed with water, brine and dried over $Na_2SO_4$. The organic layer was filtered and evaporated in vacuo. The residue was purified by silica gel chromatography (0-100% (mixture of 1% $NH_4OH$, 20% MeOH in dichloromethane) in dichloromethane) to obtain nonyl 8-((2-hydroxyethyl) amino)octanoate (295 mg, 0.9 mmol, 26%).

UPLC/ELSD: RT=1.29 min. MS (ES): m/z ($MH^+$) 330.42 for $C_{19}H_{39}NO_3$ $^1$H NMR (300 MHz, $CDCl_3$) δ: ppm 4.07 (t, 2H); 3.65 (t, 2H); 2.78 (t, 2H); 2.63 (t, 2H); 2.32-2.19 (m, 4H); 1.73-1.20 (m, 24H); 0.89 (m, 3H)

Nonyl 8-((2-hydroxyethyl)((9Z,12Z)-octadeca-9,12-dien-1-yl)amino)octanoate

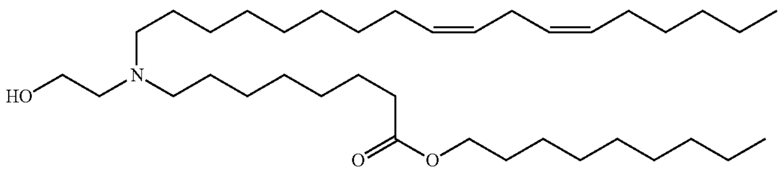

Chemical Formula: $C_{37}H_{71}NO_3$
Molecular Weight: 577.98

A solution of nonyl 8-((2-hydroxyethyl)amino)octanoate (150 mg, 0.46 mmol), (6Z,9Z)-18-bromooctadeca-6,9-diene (165 mg, 0.5 mmol) and N,N-diisopropylethylamine (65 mg, 0.5 mmol) in ethanol (2 mL) was allowed to stir at reflux for 48 h. The reaction was allowed to cool to rt and solvents were evaporated under vacuum. The residue was purified by silica gel chromatography (0-10% MeOH in dichloromethane) to obtain nonyl 8-((2-hydroxyethyl)((9Z,12Z)-octadeca-9,12-dien-1-yl)amino)octanoate (81 mg, 0.14 mmol, 30%) as a HBr salt.

UPLC/ELSD: RT=3.24 min. MS (ES): m/z ($MH^+$) 578.64 for $C_{37}H_{71}NO_3$ $^1$H NMR (300 MHz, $CDCl_3$) δ: ppm 10.71 (br., 1H); 5.36 (br. m, 4H); 4.04 (m, 4H); 3.22-2.96 (br. m, 5H); 2.77 (m, 2H); 2.29 (m, 2H); 2.04 (br. m, 4H); 1.86 (br. m, 4H); 1.66-1.17 (br. m, 40H); 0.89 (m, 6H)

E. Compound 138: Dinonyl 8,8'-((2-hydroxyethyl)azanediyl)dioctanoate

Representative Procedure 3

Dinonyl 8,8'-((2-hydroxyethyl)azanediyl)dioctanoate

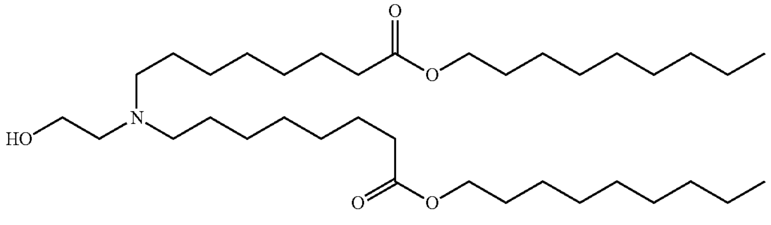

Chemical Formula: $C_{36}H_{71}NO_5$
Molecular Weight: 597.97

A solution of nonyl 8-bromooctanoate (200 mg, 0.6 mmol) and 2-aminoethan-1-ol (16 mg, 0.3 mmol) and N,N-diisopropylethylamine (74 mg, 0.6 mmol) in THF/$CH_3CN$ (1:1) (3 mL) was allowed to stir at 63° C. for 72 h. The reaction was cooled to rt and solvents were evaporated under vacuum. The residue was extracted with ethyl acetate and saturated sodium bicarbonate. The organic layer was separated, dried over $Na_2SO_4$ and evaporated under vacuum. The residue was purified by silica gel chromatography (0-10% MeOH in dichloromethane) to obtain dinonyl 8,8'-((2-hydroxyethyl)azanediyl)dioctanoate (80 mg, 0.13 mmol, 43%).

UPLC/ELSD: RT=3.09 min. MS (ES): m/z ($MH^+$) 598.85 for $C_{36}H_{71}NO_5$ $^1$H NMR (300 MHz, $CDCl_3$) δ: ppm 4.05 (m, 4H); 3.57 (br. m, 2H); 2.71-2.38 (br. m, 6H); 2.29 (m, 4H), 1.71-1.01 (br. m, 49H), 0.88 (m, 6H).

All other compounds of Formula (X) of this disclosure can be obtained by a method analogous to Representative Procedures 1-3 as described above.

Example 21

Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining a lipid according to Formula (X), a phospholipid (such as DOPE or DSPC, obtainable from Avanti Polar Lipids, Alabaster, AL), a PEG lipid (such as 1,2-dimyristoyl-sn-glycerol methoxy-polyethylene glycol, also known as PEG-DMG, obtainable from Avanti Polar Lipids, Alabaster, AL), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilabel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the Table 4 below.

TABLE 4

Exemplary Formulations of Nanoparticles

| Composition (mol %) | Components |
|---|---|
| 40:20:38.5:1.5 | Compound:Phospholipid:Chol:PEG-DMG |
| 45:15:38.5:1.5 | Compound:Phospholipid:Chol:PEG-DMG |
| 50:10:38.5:1.5 | Compound:Phospholipid:Chol:PEG-DMG |
| 55:5:38.5:1.5 | Compound:Phospholipid:Chol:PEG-DMG |
| 60:5:33.5:1.5 | Compound:Phospholipid:Chol:PEG-DMG |
| 45:20:33.5:1.5 | Compound:Phospholipid:Chol:PEG-DMG |
| 50:20:28.5:1.5 | Compound:Phospholipid:Chol:PEG-DMG |
| 55:20:23.5:1.5 | Compound:Phospholipid:Chol:PEG-DMG |
| 60:20:18.5:1.5 | Compound:Phospholipid:Chol:PEG-DMG |
| 40:15:43.5:1.5 | Compound:Phospholipid:Chol:PEG-DMG |
| 50:15:33.5:1.5 | Compound:Phospholipid:Chol:PEG-DMG |
| 55:15:28.5:1.5 | Compound:Phospholipid:Chol:PEG-DMG |
| 60:15:23.5:1.5 | Compound:Phospholipid:Chol:PEG-DMG |
| 40:10:48.5:1.5 | Compound:Phospholipid:Chol:PEG-DMG |
| 45:10:43.5:1.5 | Compound:Phospholipid:Chol:PEG-DMG |
| 55:10:33.5:1.5 | Compound:Phospholipid:Chol:PEG-DMG |
| 60:10:28.5:1.5 | Compound:Phospholipid:Chol:PEG-DMG |
| 40:5:53.5:1.5 | Compound:Phospholipid:Chol:PEG-DMG |
| 45:5:48.5:1.5 | Compound:Phospholipid:Chol:PEG-DMG |
| 50:5:43.5:1.5 | Compound:Phospholipid:Chol:PEG-DMG |
| 40:20:40:0 | Compound:Phospholipid:Chol:PEG-DMG |
| 45:20:35:0 | Compound:Phospholipid:Chol:PEG-DMG |
| 50:20:30:0 | Compound:Phospholipid:Chol:PEG-DMG |
| 55:20:25:0 | Compound:Phospholipid:Chol:PEG-DMG |
| 60:20:20:0 | Compound:Phospholipid:Chol:PEG-DMG |
| 40:15:45:0 | Compound:Phospholipid:Chol:PEG-DMG |
| 45:15:40:0 | Compound:Phospholipid:Chol:PEG-DMG |
| 50:15:35:0 | Compound:Phospholipid:Chol:PEG-DMG |
| 55:15:30:0 | Compound:Phospholipid:Chol:PEG-DMG |
| 60:15:25:0 | Compound:Phospholipid:Chol:PEG-DMG |
| 40:10:50:0 | Compound:Phospholipid:Chol:PEG-DMG |
| 45:10:45:0 | Compound:Phospholipid:Chol:PEG-DMG |
| 50:10:40:0 | Compound:Phospholipid:Chol:PEG-DMG |
| 55:10:35:0 | Compound:Phospholipid:Chol:PEG-DMG |
| 60:10:30:0 | Compound:Phospholipid:Chol:PEG-DMG |

Example 22 Expression and Activity of Wild Type JAG1 and Secreted JAG1 mRNA constructs encoding the wild-type human JAG1 or mouse JAG1 or secreted JAG1 were tested in Hela cells and HEK293 cells for their expression in vitro. Both wild-type human JAG1 and wild-type mouse JAG1 were expressed in Hela cells and in HEK293 cells (FIG. 14A). The secreted form of JAG1 (JAG1-08), engineered to include a JAG1 peptide fused to an antibody Fc domain, and its expression was detected in cell lysate and in culture media, indicating that it is successfully secreted after expression (FIG. 14B). The activity of the wild-type JAG1 and secreted JAG1 in embryonic cells were confirmed. Both the wild type JAG1 and secreted JAG1 induced cell branching in embryonic cells (FIG. 15A, quantification shown in FIG. 15B).

Next, the expression of mRNA constructs encoding wild-type human JAG1 or mouse JAG1, or the secreted form of JAG1, were tested in the liver of C56BL6 mice. The results show that the expression level of all mRNA constructs tested increased when the dose of mRNA administered to mice increased (0.3 mg/kg, 0.5 mg/kg, or 1 mg/kg) (FIG. 16A and FIG. 17A). Further, the wild-type human JAG1 or mouse JAG1 had a relatively short half-life in the liver of C56BL6 mice (FIG. 16B), while the secreted JAG1 had a long half-life in the liver of C56BL6 mice and was detectable 7 days after the administration of the mRNA constructs to mice (FIG. 17B).

TABLE 5

Additional JAG1 Sequences

| Name | mRNA Sequence | Amino Acid Sequence |
|---|---|---|
| human jagged-1 FLAG | AUGCGUUCCCCACGGACGCG<br>CGGCCGGUCCGGGCGCCCCCUAAG<br>CCUCCUGCUCGCCCUGCUCUGUGC<br>CCUGCGAGCCAAGGUGUGUGGGGC<br>CUCGGGUCAGUUCGAGUUGGAGAU<br>CCUGUCCAUGCAGAACGUGAACGG<br>GGAGCUGCAGAACGGGAACUGCUG<br>CGGCGGCGCCCGGAACCCGGGAGA<br>CCGCAAGUGCACCCGCGACGAGUG<br>UGACACAUACUUCAAAGUGUGCCU<br>CAAGGAGUAUCAGUCCCGCGUCAC<br>GGCCGGGGGGCCCUGCAGCUUCGG<br>CUCAGGGUCCACGCCUGUCAUCGG<br>GGGCAACACCUUCAACCUCAAGGC<br>CAGCCGCGGCAACGACCGCAACCG<br>CAUCGUGCUGCCUUUCAGUUUCGC<br>CUGGCCGAGGUCCUAUACGUUGCU<br>UGUGGAGGCGUGGGAUUCCAGUAA<br>UGACACCGUUCAACCUGACAGUAU<br>UAUUGAAAAGGCUUCUCACUCGGG<br>CAUGAUCAACCCCAGCCGGCAGUG<br>GCAGACGCUGAAGCAGAACACGGG<br>CGUUGCCCACUUUGAGUAUCAGAU<br>CCGCGUGACCUGUGAUGACUACUA<br>CUAUGGCUUUGGCUGCAAUAAGUU<br>CUGCCGCCCCAGAGAUGACUUCUU<br>UGGACACUAUGCCUGUGACCAGAA<br>UGGCAACAAAACUUGCAUGGAAGG<br>CUGGAUGGGCCCCGAAUGUAACAG<br>AGCUAUUUGCCGACAAGGCUGCAG<br>UCCUAAGCAUGGGUCUUGCAAACU<br>CCCAGGUGACUGCAGGUGCCAGUA<br>CGGCUGGCAAGGCCUGUACUGUGA<br>UAAGUGCAUCCCACACCCGGGAUG<br>CGUCCACGGCAUCUGUAAUGAGCC<br>CUGGCAGUGCCUCUGUGAGACCAA<br>CUGGGGCGGCCAGCUCUGUGACAA<br>AGAUCUCAAUUACUGUGGGACUCA<br>UCAGCCGUGUCUCAACGGGGGAAC<br>UUGUAGCAACACAGGCCCUGACAA<br>AUAUCAGUGUUCCUGCCCUGAGGG<br>GUAUUCAGGACCCAACUGUGAAAU<br>UGCUGAGCACGCCUGCCUCUCUGA<br>UCCCUGUCACAACAGAGGCAGCUG<br>UAAGGAGACCUCCCUGGGCUUUGA<br>GUGUGAGUGUUCCCCAGGCUGGAC<br>CGGCCCCACAUGCUCTTACAAACAU<br>UGAUGACUGUUCUCCUAAUAACUG<br>UUCCCACGGGGGCACCUGCCAGGA<br>CCUGGUUAACGGAUUUAAGUGUGU<br>GUGCCCCCCACAGUGGACUGGGAA<br>AACGUGCCAGUUAGAUGCAAAUGA<br>AUGUGAGGCCAAACCUUGUGUAAA<br>CGCCAAAUCCUGUAAGAAUCUCAU<br>UGCCAGCUACUACUGCGACUGUCU<br>UCCCGGCUGGAUGGGUCAGAAUUG<br>UGACAUAAAUAUUAAUGACUGCCU<br>UGGCCAGUGUCAGAAUGACGCCUC<br>CUGUCGGGAUUUGGUUAAUGGUUA<br>UCGCUGUAUCUGUCCACCUGGCUA<br>UGCAGGCGAUCACUGUGAGAGAGA<br>CAUCGAUGAAUGUGCCAGCAACCC<br>CUGUUUGAAUGGGGGUCACUGUCA<br>GAAUGAAAUCAACAGAUUCCAGUG<br>UCUGUGUCCCACUGGUUUCUCUGG<br>AAACCUCUGUCAGCUGGACAUCGA<br>UUAUUGUGAGCCUAAUCCCUGCCA<br>GAACGGUGCCCAGUGCUACAACCG | |

TABLE 5-continued

| Additional JAG1 Sequences | | |
|---|---|---|
| Name | mRNA Sequence | Amino Acid Sequence |
| | UGCCAGUGACUAUUUCUGCAAGUG<br>CCCCGAGGACUAUGAGGGCAAGAA<br>CUGCUCACACCUGAAAGACCACUG<br>CCGCACGACCCCCUGUGAAGUGAU<br>UGACAGCUGCACAGUGGCCAUGGC<br>UUCCAACGACACACCUGAAGGGGU<br>GCGGUAUAUUUCCUCCAACGUCUG<br>UGGUCCUCACGGGAAGUGCAAGAG<br>UCAGUCGGGAGGCAAAUUCACCUG<br>UGACUGUAACAAAGGCUUCACGGG<br>AACAUACUGCCAUGAAAAUAUUAA<br>UGACUGUGAGAGCAACCCUUGUAG<br>AAACGGUGGCACUUGCAUCGAUGG<br>UGUCAACUCCUACAAGUGCAUCUG<br>UAGUGACGGCUGGGAGGGGGCCUA<br>CUGUGAAACCAAUAUUAAUGACUG<br>CAGCCAGAACCCCUGCCACAAUGG<br>GGGCACGUGUCGCGACCUGGUCAA<br>UGACUUCUACUGUGACUGUAAAAA<br>UGGGUGGAAAGGAAAGACCUGCCA<br>CUCACGUGACAGUCAGUGUGAUGA<br>GGCCACGUGCAACAACGGUGGCAC<br>CUGCUAUGAUGAGGGGGAUGCUUU<br>UAAGUGCAUGUGUCCUGGCGGCUG<br>GGAAGGAACAACCUGUAACAUAGC<br>CCGAAACAGUAGCUGCCUGCCCAA<br>CCCCUGCCAUAAUGGGGGCACAUG<br>UGUGGUCAACGGCGAGUCCUUUAC<br>GUGCGUCUGCAAGGAAGGCUGGGA<br>GGGGCCCAUCUGUGCUCAGAAUAC<br>CAAUGACUGCAGCCCUCAUCCCUG<br>UUACAACAGCGGCACCUGUGUGGA<br>UGGAGACAACUGGUACCGGUGCGA<br>AUGUGCCCCGGGUUUUGCUGGGCC<br>CGACUGCAGAAUAAACAUCAAUGA<br>AUGCCAGUCUUCACCUUGUGCCUU<br>UGGAGCGACCUGUGUGGAUGAGAU<br>CAAUGGCUACCGGUGUGUCUGCCC<br>UCCAGGGCACAGUGGUGCCAAGUG<br>CCAGGAAGUUUCAGGGAGACCUUG<br>CAUCACCAUGGGGAGUGUGAUACC<br>AGAUGGGGCCAAAUGGGAUGAUGA<br>CUGUAAUACCUGCCAGUGCCUGAA<br>UGGACGGAUCGCCUGCUCAAAGGU<br>CUGGUGUGGCCCUCGACCUUGCCU<br>GCUCCACAAAGGGCACAGCGAGUG<br>CCCCAGCGGGCAGAGCUGCAUCCC<br>CAUCCUGGACGACCAGUGCUUCGU<br>CCACCCCUGCACUGGUGUGGGCGA<br>GUGUCGGUCUUCCAGUCUCCAGCC<br>GGUGAAGACAAAGUGCACCUCUGA<br>CUCCUAUUACCAGGAUAACUGUGC<br>GAACAUCACAUUUACCUUUAACAA<br>GGAGAUGAUGUCACCAGGUCUUAC<br>UACGGAGCACAUUUGCAGUGAAUU<br>GAGGAAUUUGAAUAUUUUGAAGA<br>AUGUUUCCGCUGAAUAUUCAAUCU<br>ACAUCGCUUGCGAGCCUUCCCCUU<br>CAGCGAACAAUGAAAUACAUGUGG<br>CCAUUUCUGCUGAAGAUAUACGGG<br>AUGAUGGGAACCCGAUCAAGGAAA<br>UCACUGACAAAAUAAUCGAUCUUG<br>UUAGUAAACGUGAUGGAAACAGCU<br>CGCUGAUUGCUGCCGUUGCAGAAG<br>UAAGAGUUCAGAGGCGGCCUCUGA<br>AGAACAGAACAGAUUUCCUUGUUC<br>CCUUGCUGAGCUCUGUCUUAACUG<br>UGGCUUGGAUCUGUUGCUUGGUGA<br>CGGCCUUCUACUGGUGCCUGCGGA<br>AGCGGCGGAAGCCGGGCAGCCACA<br>CACACUCAGCCUCUGAGGACAACA<br>CCACCAACAACGUGCGGGAGCAGC<br>UGAACCAGAUCAAAAACCCCAUUG<br>AGAAACAUGGGGCCAACACGGUCC<br>CCAUCAAGGAUUAUGAGAACAAGA<br>ACUCCAAAAUGUCUAAAAUAAGGA | |

TABLE 5-continued

| Additional JAG1 Sequences | | |
|---|---|---|
| Name | mRNA Sequence | Amino Acid Sequence |
| | CACACAAUUCUGAAGUAGAAGAGG<br>ACGACAUGGACAAACACCAGCAGA<br>AAGCCCGGUUUGCCAAGCAGCCGG<br>CGUACACGCUGGUAGACAGAGAAG<br>AGAAGCCCCCCAACGGCACGCCGA<br>CAAAACACCCAAACUGGACAAACA<br>AACAGGACAACAGAGACUUGGAAA<br>GUGCCCAGAGCUUAAACCGAAUGG<br>AGUACAUCGUAGACUACAAAGACG<br>AUGACGACAAG (SEQ ID NO: 125) | |
| mouse jagged-1 | AUGCGGUCCCCACGGACGCG<br>CGGCCGGCCCGGGCGCCCCCUGAG<br>UCUUCUGCUCGCCCUGCUCUGUGC<br>CCUGCGAGCCAAGGUGUGCGGGGC<br>CUCGGGUCAGUUUGAGCUGGAGAU<br>CCUGUCCAUGCAGAACGUGAAUGG<br>AGAGCUACAGAAUGGGAACUGUUG<br>UGGUGGAGUCCGGAACCCUGGCGA<br>CCGCAAGUGCACCCGCGACGAGUG<br>UGAUACGUACUUCAAAGUGUGCCU<br>CAAGGAGUAUCAGUCCCGCGUCAC<br>UGCCGGGGGACCCUGCAGCUUCGG<br>CUCAGGGUCUACGCCUGUCAUCGG<br>GGGUAACACCUUCAAUCUCAAGGC<br>CAGCCGUGGCAACGACCGUAAUCG<br>CAUCGUACUGCCUUUCAGUUUCGC<br>CUGGCCGAGGUCCUACACUUUGCU<br>GGUGGAGGCCUGGGAUUCCAGUAA<br>UGACACUAUUCAACCUGAUAGCAU<br>AAUUGAAAAGGCUUCUCACUCAGG<br>CAUGAUAAACCCUAGCCGGCAAUG<br>GCAGACACUGAAACAAAACACAGG<br>GAUUGCCCACUUCGAGUAUCAGAU<br>CCGAGUGACCUGUGAUGACCACUA<br>CUAUGGCUUUGGCUGCAAUAAGUU<br>CUGUCGUCCCAGAGAUGACUUCUU<br>UGGACAUUAUGCCUGUGACCAGAA<br>CGGCAACAAAACUUGCAUGGAAGG<br>CUGGAUGGGUCCUGAUUGCAACAA<br>AGCUAUCUGCCGACAGGGCUGCAG<br>UCCCAAGCAUGGGUCUUGUAAACU<br>UCCAGGUGACUGCAGGUGCCAGUA<br>CGGUUGGCAGGGCCUGUACUGCGA<br>CAAGUGCAUCCCGCACCCAGGAUG<br>UGUCCACGGCACCUGCAAUGAACC<br>CUGGCAGUGCCUCUGUGAGACCAA<br>CUGGGGUGGACAGCUCUGUGACAA<br>AGAUCUGAAUUACUGUGGGACUCA<br>UCAGCCCUGUCUCAACCGGGGAAC<br>AUGUAGCAACACUGGGCCUGACAA<br>AUACCAGUGCUCCUGCCCAGAGGG<br>CUACUCGGGCCCCAACUGUGAAAU<br>UGCUGAGCAUGCUUGUCUCUCUGA<br>CCCCUGCCAUAACCGAGGCAGCUG<br>CAAGGAGACCUCCUCAGGCUUUGA<br>GUGUGAGUGUUCUCCAGGCUGGAC<br>UGGCCCCACGUGUUCCACAAACAU<br>CGAUGACUGUUCUCCAAAUAACUG<br>UUCCCAUGGGGGCACCUGCCAGGA<br>UCUGGUGAAUGGAUUCAAGUGUGU<br>GUGCCCGCCCCAGUGGACUGGCAA<br>GACUUGUCAGUUAGAUGCAAAUGA<br>GUGCGAGGCCAAACCUUGUGUAAA<br>UGCCAGAUCCUGUAAGAAUCUGAU<br>UGCCAGCUACUACUGUGAUUGCCU<br>UCCUGGCUGGAUGGGUCAGAACUG<br>UGACAUAAAUAUCAAUGACUGCCU<br>UGGCCAGUGUCAGAAUGACGCCUC<br>CUGUCGGGAUUUGGUUAAUGGUUA<br>UCGCUGUAUCUGUCCACCUGGCUA<br>UGCAGGCGAUCACUGUGAGAGAGA<br>CAUCGAUGAGUGUGCUAGCAACCC<br>CUGCUUGAAUGGGGGUCACUGUCA<br>GAAUGAAAUCAACAGAUUCCAGUG<br>UCUCUGUCCCACUGGUUUCUCUGG | MRSPRTRGRPGRPLSLLL<br>ALLCALRAKVCGASGQFELEILS<br>MQNVNGELQNGNCCGGVRNPG<br>DRKCTRDECDTYFKVCLKEYQS<br>RVTAGGPCSFGSGSTPVIGGNTF<br>NLKASRGNDRNRIVLPFSFAWPR<br>SYTLLVEAWDSSNDTIQPDSIIEK<br>ASHSGMINPSRQWQTLKQNTGI<br>AHFEYQIRVTCDDHYYGFGCNK<br>FCRPRDDFFGHYACDQNGNKTC<br>MEGWMGPDCNKAICRQGCSPK<br>HGSCKLPGDCRCQYGWQGLYC<br>DKCIPHPGCVHGTCNEPWQCLC<br>ETNWGGQLCDKDLNYCGTHQP<br>CLNRGTCSNTGPDKYQCSCPEG<br>YSGPNCEIAEHACLSDPCHNRGS<br>CKETSSGFECECSPGWTGPTCST<br>NIDDCSPNNCSHGGTCQDLVNG<br>FKCVCPPQWTGKTCQLDANECE<br>AKPCVNARSCKNLIASYYCDCLP<br>GWMGQNCDININDCLGQCQND<br>ASCRDLVNGYRCICPPGYAGDH<br>CERDIDECASNPCLNGGHCQNEI<br>NRFQCLCPTGFSGNLCQLDIDYC<br>EPNPCQNGAQCYNRASDYFCKC<br>PEDYEGKNCSHLKDHCRTTTCE<br>VIDSCTVAMASNDTPEGVRYISS<br>NVCGPHGKCKSQSGGKFTCDCN<br>KGFTGTYCHENINDCESNPCKNG<br>GTCIDGVNSYKCICSDGWEGAH<br>CENNINDCSQNPCHYGGTCRDL<br>VNDFYCDCKNGWKGKTCHSRD<br>SQCDEATCNNGGTCYDEVDTFK<br>CMCPGGWEGTTCNIARNSSCLP<br>NPCHNGGTCVVNGDSFTCVCKE<br>GWEGPICTQNTNDCSPHPCYNSG<br>TCVDGDNWYRCECAPGFAGPDC<br>RININECQSSPCAFGATCVDEING<br>YQCICPPGHSGAKCHEVSGRSCI<br>TMGRVILDGAKWDDDCNTCQC<br>LNGRVACSKVWCGPRPCRLHKS<br>HNECPSGQSCIPVLDDQCFVRPC<br>TGVGECRSSSLQPVKTKCTSDSY<br>YQDNCANITFTFNKEMMSPGLT<br>TEHICSELRNLNILKNVSAEYSIYI<br>ACEPSLSANNEIHVAISAEDIRDD<br>GNPVKEITDKIIDLVSKRDGNSSL<br>IAAVAEVRVQRRPLKNRTDFLVP<br>LLSSVLTVAWVCCLVTAFYWCV<br>RKRRKPSSHTHSAPEDNTTNNVR<br>EQLNQIKNPIEKHGANTVPIKDY<br>ENKNSKMSKIRTHNSEVEEDDM<br>DKHQQKVRFAKQPVYTLVDREE<br>KAPSGTPTKHPNWTNKQDNRDL<br>ESAQSLNRMEYIV (SEQ ID NO:<br>131) |

TABLE 5-continued

Additional JAG1 Sequences

| Name | mRNA Sequence | Amino Acid Sequence |
|---|---|---|
| | AAACCUCUGUCAGCUGGACAUCGA<br>UUACUGCGAGCCCAACCCUUGCCA<br>GAAUGGCGCCCAGUGCUACAAUCG<br>UGCCAGUGACUAUUUCUGCAAGUG<br>CCCCGAGGACUAUGAGGGCAAGAA<br>CUGCUCACACCUGAAAGACCACUG<br>CCGUACCACCACCUGCGAAGUGAU<br>UGACAGCUGCACUGUGGCCAUGGC<br>CUCCAACGACACGCCUGAAGGGGU<br>GCGGUAUAUCUCUUCUAACGUCUG<br>UGGUCCCCAUGGGAAGUGCAAGAG<br>CCAGUCGGGAGGCAAAUUCACCUG<br>UGACUGUAACAAAGGCUUCACCGG<br>CACCUACUGCCAUGAAAAUAUCAA<br>CGACUGCGAGAGCAACCCCUGUAA<br>AAACGGUGGCACCUGCAUCGAUGG<br>CGUUAACUCCUACAAGUGUAUCUG<br>UAGUGACGGCUGGGAGGGAGCGCA<br>CUGUGAGAACAACAUAAAUGACUG<br>UAGCCAGAACCCUUGUCACUACGG<br>GGGUACAUGUCGAGACCUGGUCAA<br>UGACUUUUACUGUGACUGCAAAAA<br>UGGCUGGAAAGGAAAGACUUGCCA<br>UUCCCGUGACAGCCAGUGUGACGA<br>AGCCACGUGUAAUAAUGGUGGUAC<br>CUGCUAUGAUGAAGUGGACACGUU<br>UAAGUGCAUGUGUCCCGGUGGCUG<br>GGAAGGAACAACCUGUAAUAUAGC<br>UAGAAACAGUAGCUGCCUGCCGAA<br>CCCCUGUCAUAAUGGAGGUACCUG<br>CGUGGUCAAUGGAGACUCCUUCAC<br>CUGUGUCUGCAAAGAAGGCUGGGA<br>GGGGCCUAUUUGUACUCAAAAUAC<br>CAACGACUGCAGUCCCCAUCCUUG<br>UUACAAUAGCGGGACCUGUGUGGA<br>CGGAGACAACUGGUAUCGGUGCGA<br>AUGUGCCCCGGGUUUUGCUGGGCC<br>AGACUGCAGGAUAAACAUCAAUGA<br>GUGCCAGUCUUCCCCUUGUGCCUU<br>UGGGGCCACCUGUGUGGAUGAGAU<br>CAAUGGCUACCAGUGUAUCUGCCC<br>UCCAGGACAUAGUGGUGCCAAGUG<br>CCAUGAAGUUUCAGGGCGAUCUUG<br>CAUCACCAUGGGGAGAGUGAUACU<br>UGAUGGGGCCAAGUGGGAUGAUGA<br>CUGUAACACCUGCCAGUGCCUGAA<br>UGGACGGGUGGCCUGCUCCAAGGU<br>CUGGUGUGGCCCGAGACCUUGCAG<br>GCUCCACAAAAGCCACAAUGAGUG<br>CCCCAGUGGGCAGAGCUGCAUCCC<br>GGUCCUGGAUGACCAGUGUUUCGU<br>GCGCCCCUGCACUGGUGUUGGCGA<br>GUGUCGGUCCUCCAGCCUCCAGCC<br>AGUGAAGACCAAGUGCACAUCUGA<br>CUCCUAUUACCAGGAUAACUGUGC<br>AAACAUCACUUUCACCUUUAACAA<br>AGAGAUGAUGUCUCCAGGUCUUAC<br>CACCGAACACAUUUGCAGCGAAUU<br>GAGGAAUUUGAAUAUCCUGAAGAA<br>UGUUUCUGCUGAAUAUUCGAUCUA<br>CAUAGCCUGUGAGCCUUCCCUGUC<br>AGCAAACAAUGAAAUACACGUGGC<br>CAUCUCUGCAGAAGACAUCCGGGA<br>UGAUGGGAACCCUGUCAAGGAAAU<br>UACCGAUAAAAUAAUAGAUCUCGU<br>UAGUAAACGGGAUGGAAACAGCUC<br>ACUUAUUGCUGCGGUUGCAGAAGU<br>CAGAGUUCAGAGGCGUCCUCUGAA<br>AAACAGAACAGAUUUCCUGGUUCC<br>UCUGCUGAGCUCUGUCUUAACAGU<br>GGCUUGGGUCUGUUGCUUGGUGAC<br>AGCCUUCUACUGGUGUGUAAGGAA<br>GCGGCGGAAGCCCAGCAGCCACAC<br>UCACUCCGCCCCCGAGGACAACAC<br>CACCAACAAUGUGCGGGAGCAGCU<br>GAACCAAAUCAAAAACCCCAUCGA | |

TABLE 5-continued

Additional JAG1 Sequences

| Name | mRNA Sequence | Amino Acid Sequence |
|---|---|---|
| | GAAACACGGAGCCAACACGGUCCC | |
| | CAUUAAGGAUUACGAGAACAAAAA | |
| | CUCGAAAAUGUCAAAAAUCAGGAC | |
| | ACACAACUCGGAAGUGGAGGAGGA | |
| | UGACAUGGAUAAACACCAGCAGAA | |
| | AGUCCGCUUUGCCAAACAGCCAGU | |
| | GUAUACGCUGGUAGACAGAGAGGA | |
| | GAAGGCCCCCAGCGGCACGCCGAC | |
| | AAAACACCCGAACUGGACAAAUAA | |
| | ACAGGACAACAGAGACUUGGAAAG | |
| | UGCCCAGAGCUUGAACCGGAUGGA | |
| | AUACAUCGUA (SEQ ID NO: 126) | |
| mJAG1, | AUGCGGUCCCCACGGACGCG | MRSPRTRGRPGRPLSLLLAL |
| 1- | CGGCCGGCCCGGGCGCCCCCUGAG | LCALRAKVCGASGQFELEILSMQN |
| 1054 | UCUUCUGCUCGCCCUGCUCUGUGC | VNGELQNGNCCGGVRNPGDRKCT |
| | CCUGCGAGCCAAGGUGUGCGGGGC | RDECDTYFKVCLKEYQSRVTAGG |
| | CUCGGGUCAGUUUGAGCUGGAGAU | PCSFGSGSTPVIGGNTFNLKASRG |
| | CCUGUCCAUGCAGAACGUGAAUGG | NDRNRIVLPFSFAWPRSYTLLVEA |
| | AGAGCUACAGAAUGGGAACUGUUG | WDSSNDTIQPDSIIEKASHSGMINP |
| | UGGUGGAGUCCGGAACCCUGGCGA | SRQWQTLKQNTGIAHFEYQIRVTC |
| | CCGCAAGUGCACCCGCGACGAGUG | DDHYYGFGCNKFCRPRDDFFGHY |
| | UGAUACGUACUUCAAAGUGUGCCU | ACDQNGNKTCMEGWMGPDCNK |
| | CAAGGAGUAUCAGUCCCGCGUCAC | AICRQGCSPKHGSCKLPGDCRCQY |
| | UGCCGGGGGACCCUGCAGCUUCGG | GWQGLYCDKCIPHPGCVHGTCNE |
| | CUCAGGGUCUACGCCUGUCAUCGG | PWQCLCETNWGGQLCDKDLNYC |
| | GGGUAACACCUUCAAUCUCAAGGC | GTHQPCLNRGTCSNTGPDKYQCS |
| | CAGCCGUGGCAACGACCGUAAUCG | CPEGYSGPNCEIAEHACLSDPCHN |
| | CAUCGUACUGCCUUUCAGUUUCGC | RGSCKETSSGFECECSPGWTGPTC |
| | CUGGCCGAGGUCCUACACUUUGCU | STNIDDCSPNNCSHGGTCQDLVNG |
| | GGUGGAGGCCUGGGAUUCCAGUAA | FKCVCPPQWTGKTCQLDANECEA |
| | UGACACUAUUCAACCUGAUAGCAU | KPCVNARSCKNLIASYYCDCLPG |
| | AAUUGAAAAGGCUUCUCACUCAGG | WMGQNCDININDCLGQCQNDASC |
| | CAUGAUAAACCCUAGCCGGCAAUG | RDLVNGYRCICPPGYAGDHCERDI |
| | GCAGACACUGAAACAAAACACAGG | DECASNPCLNGGHCQNEINRFQCL |
| | GAUUGCCCACUUCGAGUAUCAGAU | CPTGFSGNLCQLDIDYCEPNPCQN |
| | CCGAGUGACCUGUGAUGACCACUA | GAQCYNRASDYFCKCPEDYEGKN |
| | CUAUGGCUUUGGCUGCAAUAAGUU | CSHLKDHCRTTTCEVIDSCTVAMA |
| | CUGUCGUCCCAGAGAUGACUUCUU | SNDTPEGVRYISSNVCGPHGKCKS |
| | UGGACAUUAUGCCUGUGACCAGAA | QSGGKFTCDCNKGFTGTYCHENIN |
| | CGGCAACAAAACUUGCAUGGAAGG | DCESNPCKNGGTCIDGVNSYKCIC |
| | CUGGAUGGGUCCUGAUUGCAACAA | SDGWEGAHCENNINDCSQNPCHY |
| | AGCUAUCUGCCGACAGGGCUGCAG | GGTCRDLVNDFYCDCKNGWKGK |
| | UCCCAAGCAUGGGUCUUGUAAACU | TCHSRDSQCDEATCNNGGTCYDE |
| | UCCAGGUGACUGCAGGUGCCAGUA | VDTFKCMCPGGWEGTTCNIARNS |
| | CGGUUGGCAGGGCCUGUACUGCGA | SCLPNPCHNGGTCVVNGDSFTCV |
| | CAAGUGCAUCCCGCACCCAGGAUG | CKEGWEGPICTQNTNDCSPHPCYN |
| | UGUCCACGGCACCUGCAAUGAACC | SGTCVDGDNWYRCECAPGFAGPD |
| | CUGGCAGUGCCUCUGUGAGACCAA | CRININECQSSPCAFGATCVDEING |
| | CUGGGGUGGACAGCUCUGUGACAA | YQCICPPGHSGAKCHEVSGRSCIT |
| | AGAUCUGAAUUACUGUGGGACUCA | MGRVILDGAKWDDDCNTCQCLN |
| | UCAGCCCUGUCUCAACCGGGGAAC | GRVACSKVWCGPRPCRLHKSHNE |
| | AUGUAGCAACACUGGGCCUGACAA | CPSGQSCIPVLDDQCFVRPCTGVG |
| | AUACCAGUGCUCCUGCCCAGAGGG | ECRSSSLQPVKTKCTSDSYYQDNC |
| | CUACUCGGGCCCCAACUGUGAAAU | ANITFTFNKEMMSPGLTTEHICSEL |
| | UGCUGAGCAUGCUUGUCUCUCUGA | RNLNILKNVSAEYSIYIACEPSLSA |
| | CCCCUGCCAUAACCGAGGCAGCUG | NNEIHVAISAEDIRDDGNPVKEITD |
| | CAAGGAGACCUCCUCAGGCUUUGA | KIIDLVSKRDGNSSLIAAVAE (SEQ |
| | GUGUGAGUGUUCUCCAGGCUGGAC | ID NO: 132) |
| | UGGCCCCACGUGUUCCACAAACAU | |
| | CGAUGACUGUUCUCCAAAUAACUG | |
| | UUCCCAUGGGGGCACCUGCCAGGA | |
| | UCUGGUGAAUGGAUUCAAGUGUGU | |
| | GUGCCCGCCCCAGUGGACUGGCAA | |
| | GACUUGUCAGUUAGAUGCAAAUGA | |
| | GUGCGAGGCCAAACCUUGUGUAAA | |
| | UGCCAGAUCCUGUAAGAAUCUGAU | |
| | UGCCAGCUACUACUGUGAUUGCCU | |
| | UCCUGGCUGGAUGGGUCAGAACUG | |
| | UGACAUAAAUAUCAAUGACUGCCU | |
| | UGGCCAGUGUCAGAAUGACGCCUC | |
| | CUGUCGGGAUUUGGUUAAUGGUUA | |
| | UCGCUGUAUCUGUCCACCUGGCUA | |
| | UGCAGGCGAUCACUGUGAGAGAGA | |
| | CAUCGAUGAGUGUGCUAGCAACCC | |
| | CUGCUUGAAUGGGGGUCACUGUCA | |

TABLE 5-continued

| Additional JAG1 Sequences | | |
|---|---|---|
| Name | mRNA Sequence | Amino Acid Sequence |
| | GAAUGAAAUCAACAGAUUCCAGUG UCUCUGUCCCACUGGUUUCUCUGG AAACCUCUGUCAGCUGGACAUCGA UUACUGCGAGCCCAACCCUUGCCA GAAUGGCGCCCAGUGCUACAAUCG UGCCAGUGACUAUUUCUGCAAGUG CCCCGAGGACUAUGAGGGCAAGAA CUGCUCACACCUGAAAGACCACUG CCGUACCACCACCUGCGAAGUGAU UGACAGCUGCACUGUGGCCAUGGC CUCCAACGACACGCCUGAAGGGGU GCGGUAUAUCUCUUCUAACGUCUG UGGUCCCCAUGGGAAGUGCAAGAG CCAGUCGGGAGGCAAAUUCACCUG UGACUGUAACAAAGGCUUCACCGG CACCUACUGCCAUGAAAAUAUCAA CGACUGCGAGAGCAACCCCUGUAA AAACGGUGGCACCUGCAUCGAUGG CGUUAACUCCUACAAGUGUAUCUG UAGUGACGGCUGGGAGGGAGCGCA CUGUGAGAACAACAUAAAUGACUG UAGCCAGAACCCUUGUCACUACGG GGGUACAUGUCGAGACCUGGUCAA UGACUUUUACUGUGACUGCAAAAA UGGCUGGAAAGGAAAGACUUGCCA UUCCCGUGACAGCCAGUGUGACGA AGCCACGUGUAAUAAUGGUGGUAC CUGCUAUGAUGAAGUGGACACGUU UAAGUGCAUGUGUCCCGGUGGCUG GGAAGGAACAACCUGUAAUAUAGC UAGAAACAGUAGCUGCCUGCCGAA CCCCUGUCAUAAUGGAGGUACCUG CGUGGUCAAUGGAGACUCCUUCAC CUGUGUCUGCAAAGAAGGCUGGGA GGGGCCUAUUUGUACUCAAAAUAC CAACGACUGCAGUCCCCAUCCUUG UUACAAUAGCGGGACCUGUGUGGA CGGAGACAACUGGUAUCGGUGCGA AUGUGCCCCGGGUUUUGCUGGGCC AGACUGCAGGAUAAACAUCAAUGA GUGCCAGUCUUCCCCUUGUGCCUU UGGGGCCACCUGUGUGGAUGAGAU CAAUGGCUACCAGUGUAUCUGCCC UCCAGGACAUAGUGGUGCCAAGUG CCAUGAAGUUUCAGGGCGAUCUUG CAUCACCAUGGGGAGAGUGAUACU UGAUGGGGCCAAGUGGGAUGAUGA CUGUAACACCUGCCAGUGCCUGAA UGGACGGGUGGCCUGCUCCAAGGU CUGGUGUGGCCCGAGACCUUGCAG GCUCCACAAAAGCCACAAUGAGUG CCCCAGUGGGCAGAGCUGCAUCCC GGUCCUGGAUGACCAGUGUUUCGU GCGCCCCUGCACUGGUGUUGGCGA GUGUCGGUCCUCCAGCCUCCAGCC AGUGAAGACCAAGUGCACAUCUGA CUCCUAUUACCAGGAUAACUGUGC AAACAUCACUUUCACCUUUAACAA AGAGAUGAUGUCUCCAGGUCUUAC CACCGAACACAUUUGCAGCGAAUU GAGGAAUUUGAAUAUCCUGAAGAA UGUUUCUGCUGAAUAUUCGAUCUA CAUAGCCUGUGAGCCUUCCCUGUC AGCAAACAAUGAAAUACACGUGGC CAUCUCUGCAGAAGACAUCCGGGA UGAUGGGAACCCUGUCAAGGAAAU UACCGAUAAAAUAAUAGAUCUCGU UAGUAAACGGGAUGGAAACAGCUC ACUUAUUGCUGCGGUUGCAGAA (SEQ ID NO: 127) | |
| mJAG1, 1-1046 | AUGCGGUCCCCACGGACGCG CGGCCGGCCCGGGCGCCCCCUGAG UCUUCUGCUCGCCCUGCUCUGUGC CCUGCGAGCCAAGGUGUGCGGGGC CUCGGGUCAGUUUGAGCUGGAGAU | MRSPRTRGRPGRPLSLLLAL LCALRAKVCGASGQFELEILSMQN VNGELQNGNCCGGVRNPGDRKCT RDECDTYFKVCLKEYQSRVTAGG PCSFGSGSTPVIGGNTFNLKASRG |

TABLE 5-continued

Additional JAG1 Sequences

| Name | mRNA Sequence | Amino Acid Sequence |
|---|---|---|
| | CCUGUCCAUGCAGAACGUGAAUGG | NDRNRTVLPFSFAWPRSYTLLVEA |
| | AGAGCUACAGAAUGGGAACUGUUG | WDSSNDTIQPDSIIEKASHSGMINP |
| | UGGUGGAGUCCGGAACCCUGGCGA | SRQWQTLKQNTGIAHFEYQIRVTC |
| | CCGCAAGUGCACCCGCGACGAGUG | DDHYYGFGCNKFCRPRDDFFGHY |
| | UGAUACGUACUUCAAAGUGUGCCU | ACDQNGNKTCMEGWMGPDCNK |
| | CAAGGAGUAUCAGUCCCGCGUCAC | AICRQGCSPKHGSCKLPGDCRCQY |
| | UGCCGGGGGACCCUGCAGCUUCGG | GWQGLYCDKCIPHPGCVHGTCNE |
| | CUCAGGGUCUACGCCUGUCAUCGG | PWQCLCETNWGGQLCDKDLNYC |
| | GGGUAACACCUUCAAUCUCAAGGC | GTHQPCLNRGTCSNTGPDKYQCS |
| | CAGCCGUGGCAACGACCGUAAUCG | CPEGYSGPNCEIAEHACLSDPCHN |
| | CAUCGUACUGCCUUUCAGUUUCGC | RGSCKETSSGFECECSPGWTGPTC |
| | CUGGCCGAGGUCCUACACUUUGCU | STNIDDCSPNNCSHGGTCQDLVNG |
| | GGUGGAGGCCUGGGAUUCCAGUAA | FKCVCPPQWTGKTCQLDANECEA |
| | UGACACUAUUCAACCUGAUAGCAU | KPCVNARSCKNLIASYYCDCLPG |
| | AAUUGAAAAGGCUUCUCACUCAGG | WMGQNCDININDCLGQCQNDASC |
| | CAUGAUAAACCCUAGCCGGCAAUG | RDLVNGYRCICPPGYAGDHCERDI |
| | GCAGACACUGAAACAAAACACAGG | DECASNPCLNGGHCQNEINRFQCL |
| | GAUUGCCCACUUCGAGUAUCAGAU | CPTGFSGNLCQLDIDYCEPNPCQN |
| | CCGAGUGACCUGUGAUGACCACUA | GAQCYNRASDYFCKCPEDYEGKN |
| | CUAUGGCUUUGGCUGCAAUAAGUU | CSHLKDHCRTTTCEVIDSCTVAMA |
| | CUGUCGUCCCAGAGAUGACUUCUU | SNDTPEGVRYISSNVCGPHGKCKS |
| | UGGACAUUAUGCCUGUGACCAGAA | QSGGKFTCDCNKGFTGTYCHENIN |
| | CGGCAACAAAACUUGCAUGGAAGG | DCESNPCKNGGTCIDGVNSYKCIC |
| | CUGGAUGGGUCCUGAUUGCAACAA | SDGWEGAHCENNINDCSQNPCHY |
| | AGCUAUCUGCCGACAGGGCUGCAG | GGTCRDLVNDFYCDCKNGWKGK |
| | UCCCAAGCAUGGGUCUUGUAAACU | TCHSRDSQCDEATCNNGGTCYDE |
| | UCCAGGUGACUGCAGGUGCCAGUA | VDTFKCMCPGGWEGTTCNIARNS |
| | CGGUUGGCAGGGCCUGUACUGCGA | SCLPNPCHNGGTCVVNGDSFTCV |
| | CAAGUGCAUCCCGCACCCAGGAUG | CKEGWEGPICTQNTNDCSPHPCYN |
| | UGUCCACGGCACCUGCAAUGAACC | SGTCVDGDNWYRCECAPGFAGPD |
| | CUGGCAGUGCCUCUGUGAGACCAA | CRININECQSSPCAFGATCVDEING |
| | CUGGGGUGGACAGCUCUGUGACAA | YQCICPPGHSGAKCHEVSGRSCIT |
| | AGAUCUGAAUUACUGUGGGACUCA | MGRVILDGAKWDDDCNTCQCLN |
| | UCAGCCCUGUCUCAACCGGGGAAC | GRVACSKVWCGPRPCRLHKSHNE |
| | AUGUAGCAACACUGGGCCUGACAA | CPSGQSCIPVLDDQCFVRPCTGVG |
| | AUACCAGUGCUCCUGCCCAGAGGG | ECRSSSLQPVKTKCTSDSYYQDNC |
| | CUACUCGGGCCCCAACUGUGAAAU | ANITFTFNKEMMSPGLTTEHICSEL |
| | UGCUGAGCAUGCUUGUCUCUCUGA | RNLNILKNVSAEYSIYIACEPSLSA |
| | CCCCUGCCAUAACCGAGGCAGCUG | NNEIHVAISAEDIRDDGNPVKEITD |
| | CAAGGAGACCUCCUCAGGCUUUGA | KIIDLVSKRDGNS (SEQ ID NO: |
| | GUGUGAGUGUUCUCCAGGCUGGAC | 133) |
| | UGGCCCCACGUGUUCCACAAACAU | |
| | CGAUGACUGUUCUCCAAAUAACUG | |
| | UUCCCAUGGGGGCACCUGCCAGGA | |
| | UCUGGUGAAUGGAUUCAAGUGUGU | |
| | GUGCCCGCCCCAGUGGACUGGCAA | |
| | GACUUGUCAGUUAGAUGCAAAUGA | |
| | GUGCGAGGCCAAACCUUGUGUAAA | |
| | UGCCAGAUCCUGUAAGAAUCUGAU | |
| | UGCCAGCUACUACUGUGAUUGCCU | |
| | UCCUGGCUGGAUGGGUCAGAACUG | |
| | UGACAUAAAUAUCAAUGACUGCCU | |
| | UGGCCAGUGUCAGAAUGACGCCUC | |
| | CUGUCGGGAUUUGGUUAAUGGUUA | |
| | UCGCUGUAUCUGUCCACCUGGCUA | |
| | UGCAGGCGAUCACUGUGAGAGAGA | |
| | CAUCGAUGAGUGUGCUAGCAACCC | |
| | CUGCUUGAAUGGGGGUCACUGUCA | |
| | GAAUGAAAUCAACAGAUUCCAGUG | |
| | UCUCUGUCCCACUGGUUUCUCUGG | |
| | AAACCUCUGUCAGCUGGACAUCGA | |
| | UUACUGCGAGCCCAACCCUUGCCA | |
| | GAAUGGCGCCCAGUGCUACAAUCG | |
| | UGCCAGUGACUAUUUCUGCAAGUG | |
| | CCCCGAGGACUAUGAGGGCAAGAA | |
| | CUGCUCACACCUGAAAGACCACUG | |
| | CCGUACCACCACCUGCGAAGUGAU | |
| | UGACAGCUGCACUGUGGCCAUGGC | |
| | CUCCAACGACACGCCUGAAGGGGU | |
| | GCGGUAUAUCUCUUCUAACGUCUG | |
| | UGGUCCCCAUGGGAAGUGCAAGAG | |
| | CCAGUCGGGAGGCAAAUUCACCUG | |
| | UGACUGUAACAAAGGCUUCACCGG | |
| | CACCUACUGCCAUGAAAAUAUCAA | |
| | CGACUGCGAGAGCAACCCCUGUAA | |
| | AAACGGUGGCACCUGCAUCGAUGG | |

TABLE 5-continued

| Additional JAG1 Sequences | | |
|---|---|---|
| Name | mRNA Sequence | Amino Acid Sequence |
| | CGUUAACUCCUACAAGUGUAUCUG<br>UAGUGACGGCUGGGAGGGAGCGCA<br>CUGUGAGAACAACAUAAAUGACUG<br>UAGCCAGAACCCUUGUCACUACGG<br>GGGUACAUGUCGAGACCUGGUCAA<br>UGACUUUUACUGUGACUGCAAAAA<br>UGGCUGGAAAGGAAAGACUUGCCA<br>UUCCCGUGACAGCCAGUGUGACGA<br>AGCCACGUGUAAUAAUGGUGGUAC<br>CUGCUAUGAUGAAGUGGACACGUU<br>UAAGUGCAUGUGUCCCGGUGGCUG<br>GGAAGGAACAACCUGUAAUAUAGC<br>UAGAAACAGUAGCUGCCUGCCGAA<br>CCCCUGUCAUAAUGGAGGUACCUG<br>CGUGGUCAAUGGAGACUCCUUCAC<br>CUGUGUCUGCAAAGAAGGCUGGGA<br>GGGGCCUAUUUGUACUCAAAAUAC<br>CAACGACUGCAGUCCCCAUCCUUG<br>UUACAAUAGCGGGACCUGUGUGGA<br>CGGAGACAACUGGUAUCGGUGCGA<br>AUGUGCCCCGGGUUUUGCUGGGCC<br>AGACUGCAGGAUAAACAUCAAUGA<br>GUGCCAGUCUUCCCCUUGUGCCUU<br>UGGGGCCACCUGUGUGGAUGAGAU<br>CAAUGGCUACCAGUGUAUCUGCCC<br>UCCAGGACAUAGUGGUGCCAAGUG<br>CCAUGAAGUUUCAGGGCGAUCUUG<br>CAUCACCAUGGGGAGAGUGAUACU<br>UGAUGGGGCCAAGUGGGAUGAUGA<br>CUGUAACACCUGCCAGUGCCUGAA<br>UGGACGGGUGGCCUGCUCCAAGGU<br>CUGGUGUGGCCCGAGACCUUGCAG<br>GCUCCACAAAAGCCACAAUGAGUG<br>CCCCAGUGGGCAGAGCUGCAUCCC<br>GGUCCUGGAUGACCAGUGUUUCGU<br>GCGCCCCUGCACUGGUGUUGGCGA<br>GUGUCGGUCCUCCAGCCUCCAGCC<br>AGUGAAGACCAAGUGCACAUCUGA<br>CUCCUAUUACCAGGAUAACUGUGC<br>AAACAUCACUUUCACCUUUAACAA<br>AGAGAUGAUGUCUCCAGGUCUUAC<br>CACCGAACACAUUUGCAGCGAAUU<br>GAGGAAUUUGAAUAUCCUGAAGAA<br>UGUUUCUGCUGAAUAUUCGAUCUA<br>CAUAGCCUGUGAGCCUUCCCUGUC<br>AGCAAACAAUGAAAUACACGUGGC<br>CAUCUCUGCAGAAGACAUCCGGGA<br>UGAUGGGAACCCUGUCAAGGAAAU<br>UACCGAUAAAAUAAUAGAUCUCGU<br>UAGUAAACGGGAUGGAAACAGC<br>(SEQ ID NO: 128) | |

Additional Embodiments

The present disclosure encompasses the following embodiments, represented by numbered paragraphs.

A polynucleotide comprising an open reading frame (ORF) encoding a Jagged-1 (JAG1) polypeptide, wherein the uracil or thymine content of the ORF relative to the theoretical minimum uracil or thymine content of a nucleotide sequence encoding the JAG1 polypeptide (% $U_{TM}$ or % $T_{TM}$) is between about 175% and about 225%.

The polynucleotide of paragraph 1, wherein the % $U_{TM}$ or % $T_{TM}$ is between about 180% and about 220%, about 184% and about 220%, about 184% and about 215%, about 180% and about 215%, about 180% and about 210%, about 184% and about 210%, about 180% and about 200%, about 184% and about 200%, or about 184% and about 198%.

The polynucleotide of paragraph 2, wherein the % $U_{TM}$ or % $T_{TM}$ is between (i) 174%, 175%, 176%, 177%, 178%, 179%, 180%, 181%, 182%, 183%, or 184%, and (ii) 198%, 199%, 200%, 201%, 202%, 203%, 204%, 205%, 206%, 207%, or 208%.

The polynucleotide of any one of paragraphs 1 to 3, wherein the uracil or thymine content of the ORF relative to the uracil or thymine content of the corresponding wild-type ORF (% $U_{WT}$ or % $T_{WT}$) is less than 100%.

The polynucleotide of paragraph 4, wherein the % $U_{WT}$ or % $T_{WT}$ is less than about 95%, less than about 90%, less than about 85%, less than about 80%, less than about 75%, or less than 74%.

The polynucleotide of paragraph 4, wherein the $U_{WT}$ or % $T_{WT}$ is between 68% and 74%.

The polynucleotide of any one of paragraphs 1 to 6, wherein the uracil or thymine content in the ORF relative to the total nucleotide content in the ORF (% $U_{TL}$ or % $T_{TL}$) is less than about 50%, less than about 40%, less than about 30%, or less than about 21%.

The polynucleotide of paragraph 7, wherein the % $U_T$ or % $T_{TL}$ is less than about 21%.

The polynucleotide of any one of paragraphs 1 to 8, wherein the % $U_{TL}$ or % $T_{TL}$ is between about 14% and about 16%.

The polynucleotide of any one of paragraphs 1 to 9, wherein the guanine content of the ORF with respect to the theoretical maximum guanine content of a nucleotide sequence encoding the JAG1 polypeptide (% $G_{TMX}$) is at least 71%, at least 72%, at least about 75%, at least about 80%, at least about 85%, at least about 90%, at least about 95%, or about 100%.

The polynucleotide of paragraph 10, wherein the % $G_{TMX}$ is between about 72% and about 80%, between about 72% and about 79%, between about 73% and about 78%, or between about 74% and about 77%.

The polynucleotide of any one of paragraphs 1 to 11, wherein the cytosine content of the ORF relative to the theoretical maximum cytosine content of a nucleotide sequence encoding the JAG1 polypeptide (% $G_{TMX}$) is at least 63%, at least 64%, at least about 65%, at least about 70%, at least about 75%, at least about 80%, at least about 85%, at least about 90%, or about 100%.

The polynucleotide of paragraph 12, wherein the % $C_{TMX}$ is between about 65% and about 80%, between about 65% and about 79%, between about 65% and about 78%, or between about 72% and about 77%.

The polynucleotide of any one of paragraphs 1 to 13, wherein the guanine and cytosine content (G/C) of the ORF relative to the theoretical maximum G/C content in a nucleotide sequence encoding the JAG1 polypeptide (% $G/C_{TMX}$) is at least about 81%, at least about 82%, at least about 85%, at least about 90%, at least about 95%, or about 100%.

The polynucleotide of any one of paragraphs 1 to 13, wherein the % $G/C_{TMX}$ is between about 80% and about 100%, between about 85% and about 99%, between about 90% and about 97%, or between about 90% and about 93%.

The polynucleotide of any one of paragraphs 1 to 15, wherein the G/C content in the ORF relative to the G/C content in the corresponding wild-type ORF (% $G/C_{TMX}$) is at least 102%, at least 103%, at least 104%, at least 105%, at least 106%, at least 107%, or at least about 110%.

The polynucleotide of any one of paragraphs 1 to 15, wherein the average G/C content in the $3^{rd}$ codon position in the ORF is at least 20%, at least 21%, at least 22%, at least 23%, or at least 24% higher than the average G/C content in the $3^{rd}$ codon position in the corresponding wild-type ORF.

The polynucleotide of any one of paragraphs 1 to 17, wherein the ORF further comprises at least one low-frequency codon.

The polynucleotide of any one of paragraphs 1 to 18, (i) wherein the ORF is at least 91%, at least 92%, at least 93%, at least 94%, at least 95%, at least 96%, at least 97%, at least 98%, at least 99%, or 100% identical to JAG1-CO21, JAG1-CO17, JAG1-CO7, JAG1-CO2, JAG1-C018, JAG1-CO1, JAG1-CO16, JAG1-C012, JAG1-CO4, JAG1-CO24, JAG1-CO15, JAG1-CO5, JAG1-CO25, or JAG1-CO23;

(ii) wherein the ORF is at least 90%, at least 91%, at least 92%, at least 93%, at least 94%, at least 95%, at least 96%, at least 97%, at least 98%, at least 99%, or 100% identical to JAG1-CO14, JAG1-CO11, JAG1-CO13, JAG1-CO10, JAG1-CO22, JAG1-CO8, JAG1-CO9, JAG1-CO19, JAG1-CO3, or JAG1-C020; or (iii) wherein the ORF is at least 890%, at least 90%, at least 91%, at least 92%, at least 93%, at least 94%, at least 95%, at least 96%, at least 97%, at least 98%, at least 99%, or 100% identical to JAG1-CO6.

A polynucleotide comprising an ORF, (i) wherein the ORF is at least 91%, at least 92%, at least 93%, at least 94%, at least 95%, at least 96%, at least 97%, at least 98%, at least 99%, or 100% identical to JAG CO21, JAG1-CO17, JAG1-CO7, JAG1-CO2, JAG1-CO18, JAG1-CO1, JAG1-CO16, JAG1-CO12, JAG1-CO4, JAG1-CO24, JAG1-CO15, JAG1-CO55, JAG1-CO25, or JAG1-CO23;

(ii) wherein the ORF is at least 90%, at least 91%, at least 92%, at least 93%, at least 94%, at least 95%, at least 96%, at least 97%, at least 98%, at least 99%, or 100% identical to JAG1-CO14, JAG1-CO11, JAG1-CO13, JAG1-CO10, JAG1-CO22, JAG1-CO8, JAG1-CO9, JAG1-CO19, JAG1-CO3, or JAG1-CO20; or (iii) wherein the ORF is at least 89%, at least 90%, at least 91%, at least 92%, at least 93%, at least 94%, at least 95%, at least 96%, at least 97%, at least 98%, at least 99%, or 100%, identical to JAG1-CO6.

The polynucleotide of any one of paragraphs 1 to 20, wherein the ORF has at least 890%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 11 to 35.

The polynucleotide of any one of paragraphs 1 to 21, wherein the JAG1 polypeptide comprises an amino acid sequence at least about 95%, at least about 96%, at least about 97%, at least about 98%, at least about 99%, or about 100% identical to the polypeptide sequence of wild type JAG1 (SEQ ID NO: 1), and wherein the JAG1 polypeptide has NOTCH receptor ligand activity.

The polynucleotide of paragraph 22, wherein the JAG1 polypeptide is a variant, derivative, or mutant having an NOTCH receptor ligand activity.

The polynucleotide of any one of paragraphs 1 to 23, wherein the polynucleotide sequence further comprises a nucleotide sequence encoding a transit peptide.

The polynucleotide of any one of paragraphs 1 to 24, wherein the polynucleotide is single stranded.

The polynucleotide of any one of paragraphs 1 to 24, wherein the polynucleotide is double stranded.

The polynucleotide of any one of paragraphs 1 to 26, wherein the polynucleotide is DNA.

The polynucleotide of any one of paragraphs 1 to 26, wherein the polynucleotide is RNA.

The polynucleotide of paragraph 28, wherein the polynucleotide is mRNA.

The polynucleotide of any one of paragraphs 1 to 29, wherein the polynucleotide comprises at least one chemically modified nucleobase, sugar, backbone, or any combination thereof.

The polynucleotide of paragraph 30, wherein the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combination thereof.

The polynucleotide of paragraph 30, wherein the at least one chemically modified nucleobase is 5-methoxyuracil.

The polynucleotide of paragraph 32, wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils.

The polynucleotide of any one of paragraphs 1 to 33, wherein the polynucleotide further comprises a miRNA binding site.

The polynucleotide of paragraph 34, wherein the miRNA binding site comprises one or more nucleotide sequences selected from Table 3.

The polynucleotide of paragraph 34, wherein the miRNA binding site binds to miR-142.

The polynucleotide of paragraph 35 or 36, wherein the miRNA binding site binds to miR-142-3p or miR-142-5p.

The polynucleotide of paragraph 36 or 37, wherein the miR-142 comprises SEQ ID NO: 79.

The polynucleotide of any one of paragraphs 1 to 38, wherein the polynucleotide further comprises a 5' UTR.

The polynucleotide of paragraph 39, wherein the 5' UTR comprises a nucleic acid sequence at least 90%, at least about 95%, at least about 96%, at least about 97%, at least about 98%, at least about 99%, or about 100% identical to a sequence selected from the group consisting of SEQ ID NOs:36-78.

The polynucleotide of any one of paragraphs 1 to 40, wherein the polynucleotide further comprises a 3' UTR.

The polynucleotide of paragraph 41, wherein the 3' UTR comprises a nucleic acid sequence at least about 90%, at least about 95%, at least about 96%, at least about 97%, at least about 98%, at least about 99%, or about 100% identical to a sequence selected from the group consisting of SEQ ID NOs:36-78.

The polynucleotide of paragraph 41 or 42, wherein the miRNA binding site is located within the 3' UTR.

The polynucleotide of any one of paragraphs 1 to 43, wherein the polynucleotide further comprises a 5' terminal cap.

The polynucleotide of paragraph 44, wherein the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

The polynucleotide of any one of paragraphs 1 to 45, wherein the polynucleotide further comprises a poly-A region.

The polynucleotide of paragraph 46, wherein the poly-A region is at least about 10, at least about 20, at least about 30, at least about 40, at least about 50, at least about 60, at least about 70, at least about 80, or at least about 90 nucleotides in length.

The polynucleotide of paragraph 47, wherein the poly-A region has about 10 to about 200, about 20 to about 180, about 50 to about 160, about 70 to about 140, or about 80 to about 120 nucleotides in length.

The polynucleotide of any one of paragraphs 1 to 46, wherein the polynucleotide encodes a JAG1 polypeptide that is fused to one or more heterologous polypeptides.

The polynucleotide of paragraph 49, wherein the one or more heterologous polypeptides increase a pharmacokinetic property of the JAG1 polypeptide.

The polynucleotide of any one of paragraphs 1 to 50, wherein upon administration to a subject, the polynucleotide has:

(i) a longer plasma half-life;

(ii) increased expression of a JAG1polypeptide encoded by the ORF;

(iii) a lower frequency of arrested translation resulting in an expression fragment;

(iv) greater structural stability; or (v) any combination thereof, relative to a corresponding polynucleotide comprising SEQ ID NO: 2.

The polynucleotide of any one of paragraphs 1 to 51, wherein the polynucleotide comprises:

(i) a 5'-terminal cap;

(ii) a 5'-UTR;

(iii) an ORF encoding a JAG1 polypeptide;

(iv) a 3'-UTR; and (v) a poly-A region.

The polynucleotide of paragraph 52, wherein the 3'-UTR comprises a miRNA binding site.

A method of producing the polynucleotide of any one of paragraphs 1 to 52, the method comprising modifying an ORF encoding a JAG1 polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions.

The method of paragraph 54, wherein the method further comprises replacing at least about 90%, at least about 95%, at least about 99%, or about 100% of uracils with 5-methoxyuracils.

A composition comprising the polynucleotide of any one of paragraphs 1 to 53; and a delivery agent.

The composition of paragraph 56, wherein the delivery agent comprises a lipidoid, a liposome, a lipoplex, a lipid nanoparticle, a polymeric compound, a peptide, a protein, a cell, a nanoparticle mimic, a nanotube, or a conjugate.

The composition of paragraph 56, wherein the delivery agent comprises a lipid nanoparticle.

The composition of paragraph 58, wherein the lipid nanoparticle comprises a lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,165Z)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-dien-1-yl oxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)), and any combination thereof.

The composition of any one of paragraphs 56 to 59, wherein the delivery agent comprises a compound having the Formula (I)

(I)

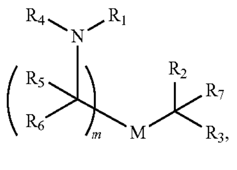

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

A composition comprising a nucleotide sequence encoding a JAG1 polypeptide and a delivery agent, wherein the delivery agent comprises a compound having the Formula (I)

(I)

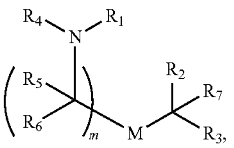

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

The composition of paragraph 60 or 61, wherein the compound is of Formula (IA):

(IA)

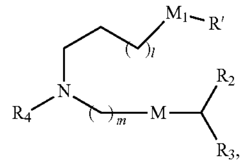

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or —$(CH_2)_n$Q, in which n is 1, 2, 3, 4, or 5 and Q is OH, —NHC(S)N$(R)_2$, or —NHC(O)N$(R)_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

The composition of any one of paragraphs 60 to 62, wherein m is 5, 7, or 9.

The composition of any one of paragraphs 60 to 63, wherein the compound is of Formula (II):

(II)

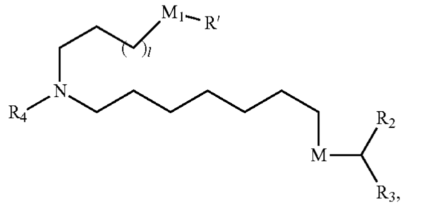

or a salt or stereoisomer thereof, wherein l is selected from 1, 2, 3, 4, and 5;

$M_1$ is a bond or M';

$R_4$ is unsubstituted $C_{1-3}$ alkyl, or $—(CH_2)_nQ$, in which n is 2, 3, or 4 and Q is OH, $—NHC(S)N(R)_2$, or $—NHC(O)N(R)_2$;

M and M' are independently selected from $—C(O)O—$, $—OC(O)—$, $—C(O)N(R')—$, $—P(O)(OR')O—$, an aryl group, and a heteroaryl group, and $R_2$ and $R_3$ are independently selected from the group consisting of H, $C_{1-14}$ alkyl, and $C_{2-14}$ alkenyl.

The composition of any one of paragraphs 62 to 64, wherein $M_1$ is M'.

The composition of paragraph 65, wherein M and M' are independently $—C(O)O—$ or $—OC(O)—$.

The composition of any one of paragraphs 62 to 66, wherein l is 1, 3, or 5.

The composition of paragraph 60 or 61, wherein the compound is selected from the group consisting of Compound 1 to Compound 147, salts and stereoisomers thereof, and any combination thereof.

The composition of paragraph 60 or 61, wherein the compound is of the Formula (IIa), (IIa)

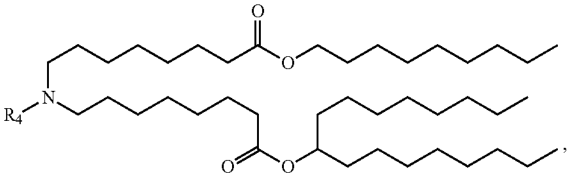

or a salt or stereoisomer thereof.

The composition of paragraph 60 or 61, wherein the compound is of the Formula (IIb), (IIb)

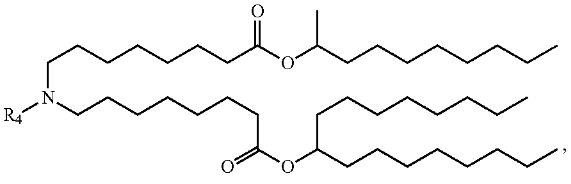

or a salt or stereoisomer thereof.

The composition of paragraph 60 or 61, wherein the compound is of the Formula (IIc) or (IIe), (IIc)

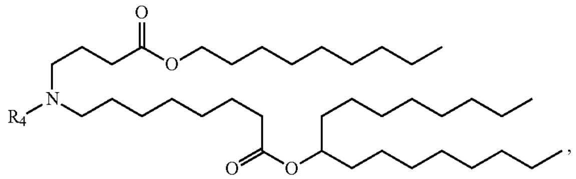

(IIe)

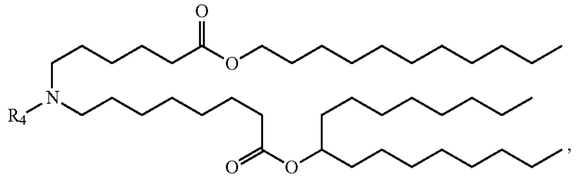

or a salt or stereoisomer thereof.

The composition of any one of paragraphs 69 to 71, wherein $R_4$ is selected from $—(CH_2)_nQ$ and $—(CH_2)_nCHQR$.

The composition of paragraph 60 or 61, wherein the compound is of the Formula (IId), (IId)

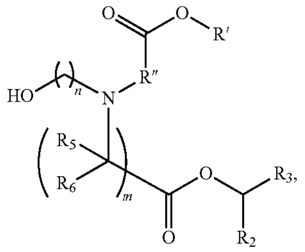

or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R'', $R_5$, $R_6$ and m are as defined in paragraph 61 or 62.

The composition of paragraph 73, wherein $R_2$ is $C_8$ alkyl.

The composition of paragraph 74, wherein $R_3$ is $C_5$ alkyl, $C_6$ alkyl, $C_7$ alkyl, $C_8$ alkyl, or $C_9$ alkyl.

The composition of any one of paragraphs 73 to 75, wherein m is 5, 7, or 9.

The composition of any one of paragraphs 73 to 76, wherein each $R_5$ is H.

The composition of paragraph 77, wherein each $R_6$ is H.

The composition of any one of paragraphs 60 to 78, which is a nanoparticle composition.

The composition of paragraph 79, wherein the delivery agent further comprises a phospholipid.

The composition of paragraph 80, wherein the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

The composition of any one of paragraphs 60 to 81, wherein the delivery agent further comprises a structural lipid.

The composition of paragraph 82, wherein the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

The composition of any one of paragraphs 60 to 83, wherein the delivery agent further comprises a PEG lipid.

The composition of paragraph 84, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof.

The composition of any one of paragraphs 60 to 85, wherein the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yl oxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

The composition of any one of paragraphs 60 to 86, wherein the delivery agent further comprises a phospholipid, a structural lipid, a PEG lipid, or any combination thereof.

The composition of any one of paragraphs 60 to 87, wherein the composition is formulated for in vivo delivery.

The composition according any one of paragraphs 60 to 88, which is formulated for intramuscular, subcutaneous, or intradermal delivery.

A host cell comprising the polynucleotide of any one of paragraphs 1 to 53.

The host cell of paragraph 90, wherein the host cell is a eukaryotic cell.

A vector comprising the polynucleotide of any one of paragraphs 1 to 53.

A method of making a polynucleotide comprising enzymatically or chemically synthesizing the polynucleotide of any one of paragraphs 1 to 53.

A polypeptide encoded by the polynucleotide of any one of paragraphs 1 to 53, the composition of any one of paragraphs 56 to 89, the host cell of paragraph 90 or 91, or the vector of paragraph 92 or produced by the method of paragraph 93.

A method of expressing in vivo an active JAG1 polypeptide in a subject in need thereof comprising administering to the subject an effective amount of the polynucleotide of any one of paragraphs 1 to 53, the composition of any one of paragraphs 56 to 89, the host cell of paragraph 90 or 91, or the vector of paragraph 92.

A method of treating Alagille syndrome in a subject in need thereof comprising administering to the subject a therapeutically effective amount of the polynucleotide of any one of paragraphs 1 to 53, the composition of any one of paragraphs 56 to 89, the host cell of paragraph 90 or 91, or the vector of paragraph 92, wherein the administration alleviates the signs or symptoms of Alagille syndrome in the subject.

A method to prevent or delay the onset of Alagille syndrome signs or symptoms in a subject in need thereof comprising administering to the subject a prophylactically effective amount of the polynucleotide of any one of paragraphs 1 to 53, the composition of any one of paragraphs 56 to 89, the host cell of paragraph 90 or 91, or the vector of paragraph 92 before Alagille syndrome signs or symptoms manifest, wherein the administration prevents or delays the onset of Alagille syndrome signs or symptoms in the subject.

A method to ameliorate the signs or symptoms of Alagille syndrome in a subject in need thereof comprising administering to the subject a therapeutically effective amount of the polynucleotide of any one of paragraphs 1 to 53, the composition of any one of paragraphs 56 to 89, the host cell of paragraph 90 or 91, or the vector of paragraph 92 before Alagille syndrome or symptoms manifest, wherein the administration ameliorates Alagille syndrome signs or symptoms in the subject.

It is to be appreciated that the Detailed Description section, and not the Summary and Abstract sections, is intended to be used to interpret the claims. The Summary and Abstract sections can set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

What is claimed is:

1. A composition comprising:

a lipid nanoparticle and a messenger ribonucleic acid (mRNA) comprising an open reading frame (ORF) encoding a human Jagged1 (JAG1) polypeptide, wherein the lipid nanoparticle comprises an ionizable lipid, and wherein the ionizable lipid comprises a compound of Formula (IIa), (IIc), or (IIe):

(IIa)

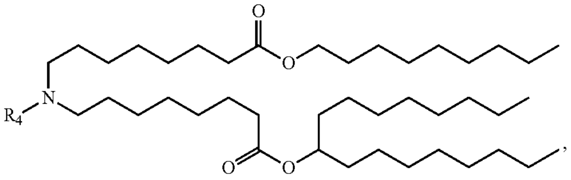

, (IIc)

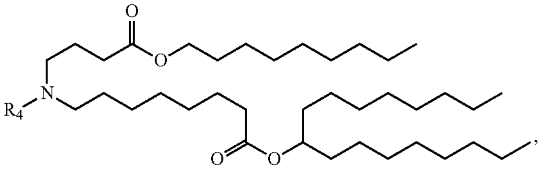

, or

-continued (IIe)

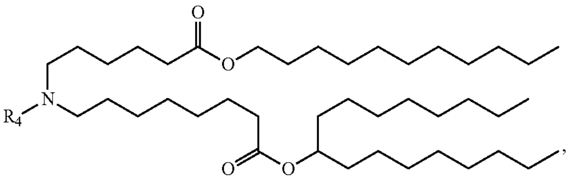

, or a salt or stereoisomer thereof, wherein $R_4$ is unsubstituted $C_{1-3}$ alkyl, or $—(CH_2)_nQ$, in which n is 1, 2, 3, 4 or 5 and Q is OH, $—NHC(S)N(R)_2$, or $—NHC(O)N(R)_2$; and each R is independently selected from the group consisting of $C_{1-3}$ alkyl, $C_{2-3}$ alkenyl, and H.

2. The composition of claim 1, wherein n is 2.

3. The composition of claim 1, wherein the ionizable lipid comprises the compound of the formula:

(Compound 18)

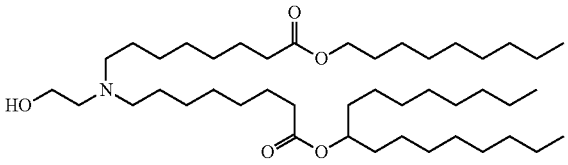

or a salt thereof.

4. The composition of claim 1, wherein the lipid nanoparticle further comprises a phospholipid, a structural lipid, and a PEG lipid.

5. The composition of claim 4, wherein the phospholipid is selected from the group consisting of:

1,2-dilinoleoyl-sn-glycero-3-phosphocholine (DLPC);
1,2-dimyristoyl-sn-glycero-phosphocholine (DMPC);
1,2-dioleoyl-sn-glycero-3-phosphocholine (DOPC);
1,2-dipalmitoyl-sn-glycero-3-phosphocholine (DPPC);
1,2-distearoyl-sn-glycero-3-phosphocholine (DSPC);
1,2-diundecanoyl-sn-glycero-phosphocholine (DUPC);
1-palmitoyl-2-oleoyl-sn-glycero-3-phosphocholine (POPC);
1,2-di-O-octadecenyl-sn-glycero-3-phosphocholine (18:0 Diether PC);
1-oleoyl-2-cholesterylhemisuccinoyl-sn-glycero-3-phosphocholine (OChemsPC);
1-hexadecyl-sn-glycero-3-phosphocholine (C16 Lyso PC);
1,2-dilinolenoyl-sn-glycero-3-phosphocholine;
1,2-diarachidonoyl-sn-glycero-3-phosphocholine;
1,2-didocosahexaenoyl-sn-glycero-3-phosphocholine;
1,2-dioleoyl-sn-glycero-3-phosphoethanolamine (DOPE);

1,2-diphytanoyl-sn-glycero-3-phosphoethanolamine (ME 16.0 PE);
1,2-distearoyl-sn-glycero-3-phosphoethanolamine;
1,2-dilinoleoyl-sn-glycero-3-phosphoethanolamine;
1,2-dilinolenoyl-sn-glycero-3-phosphoethanolamine;
1,2-diarachidonoyl-sn-glycero-3-phosphoethanolamine;
1,2-didocosahexaenoyl-sn-glycero-3-phosphoethanolamine;
1,2-dioleoyl-sn-glycero-3-phospho-rac-(1-glycerol) sodium salt (DOPG);
sphingomyelin; and
mixtures thereof.

6. The composition of claim 1, wherein the mRNA further comprises a microRNA (miRNA) binding site.

7. A pharmaceutical composition comprising a lipid nanoparticle and an mRNA comprising an ORF encoding a human JAG1 polypeptide, wherein the lipid nanoparticle comprises an ionizable lipid, and wherein the ionizable lipid comprises a compound selected from the group consisting of (Compound 1)

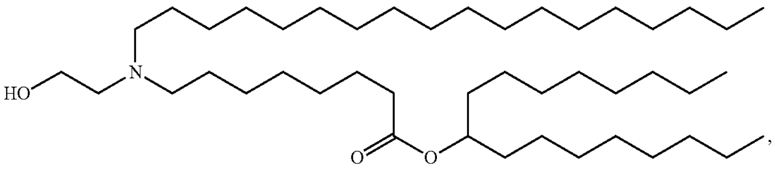
, (Compound 2)

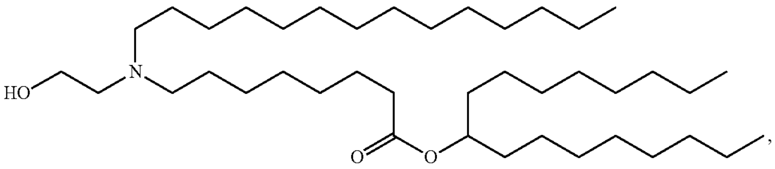
, (Compound 3)

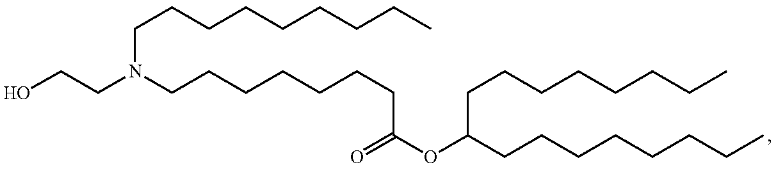
, (Compound 4)

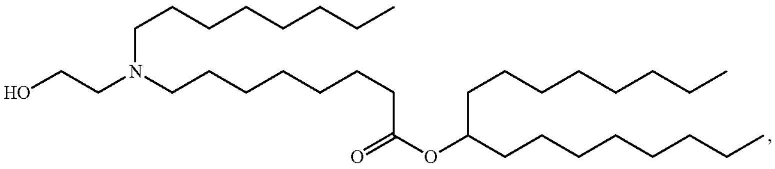
, (Compound 5)

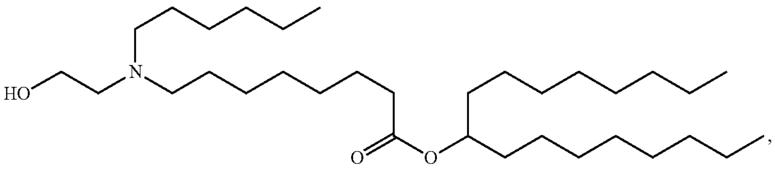
, (Compound 7)

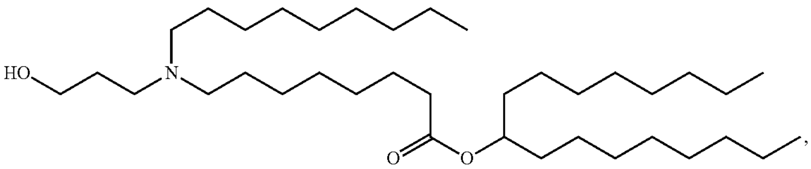
,

-continued
(Compound 18)
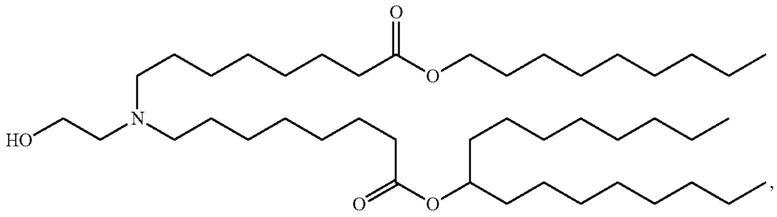,
(Compound 19)
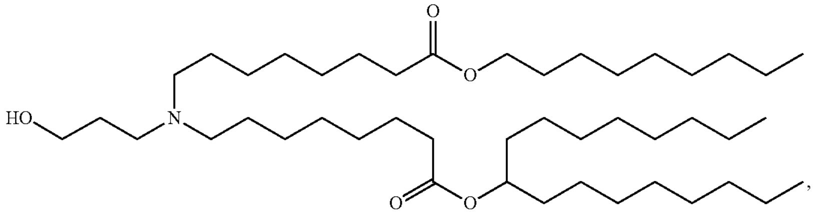,
(Compound 20)
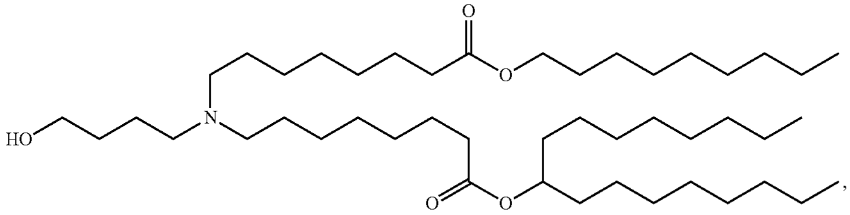,
(Compound 23)
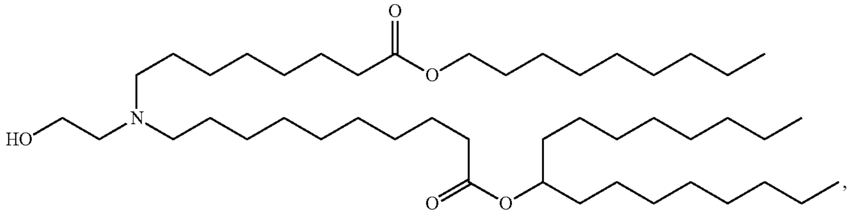,
(Compound 25)
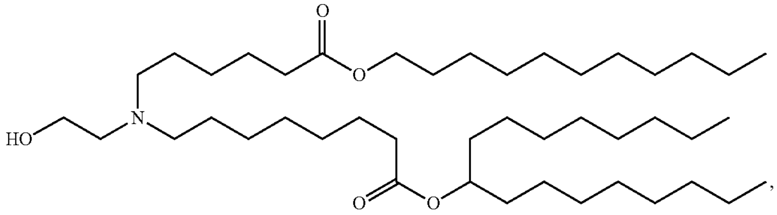,
(Compound 26)
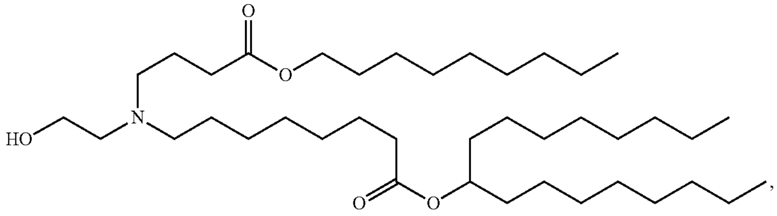,
(Compound 27)
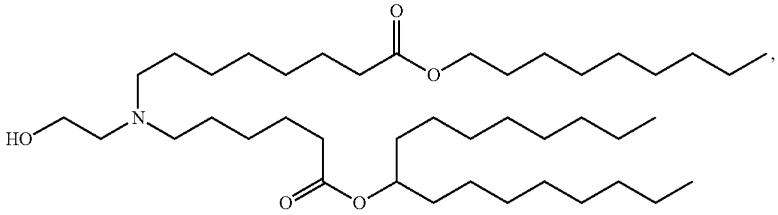

-continued
(Compound 30)
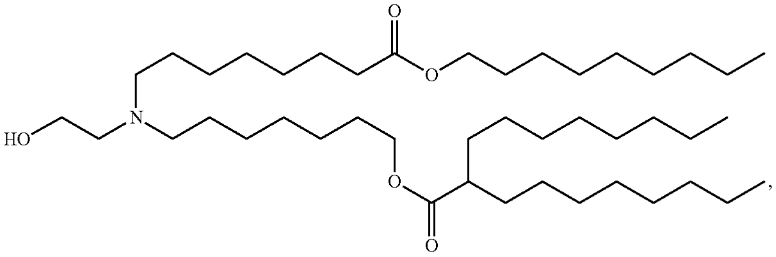
(Compound 32)
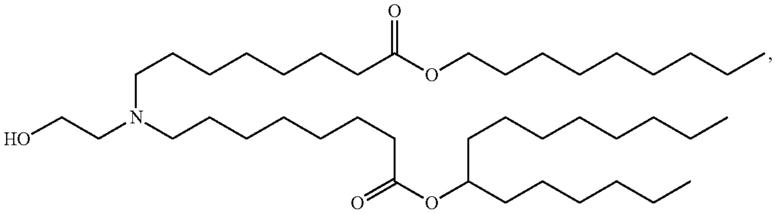
(Compound 33)
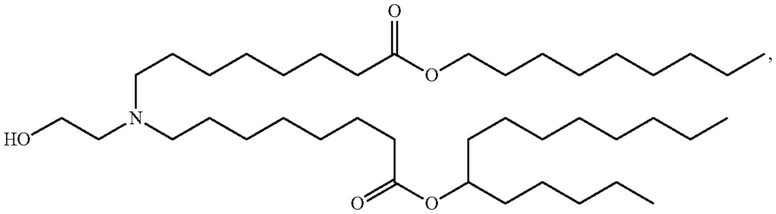
(Compound 34)
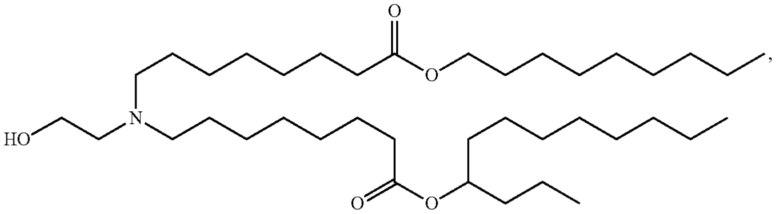
(Compound 35)
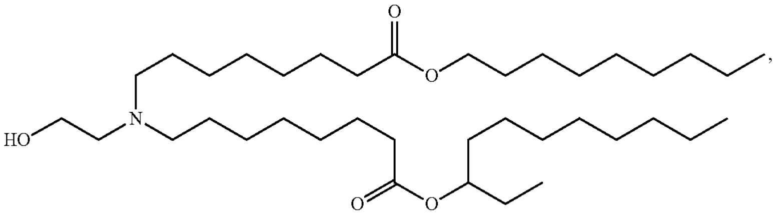
(Compound 36)
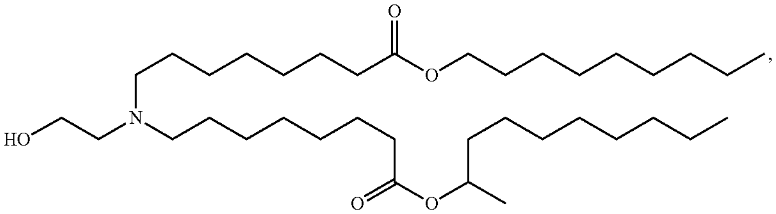
(Compound 39)
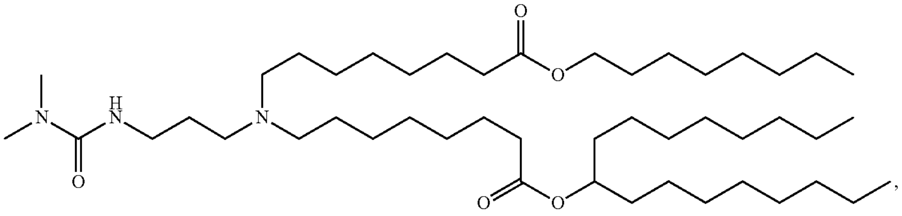

-continued
(Compound 40)
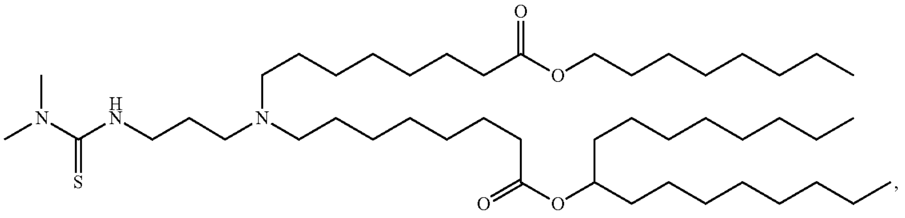
(Compound 41)
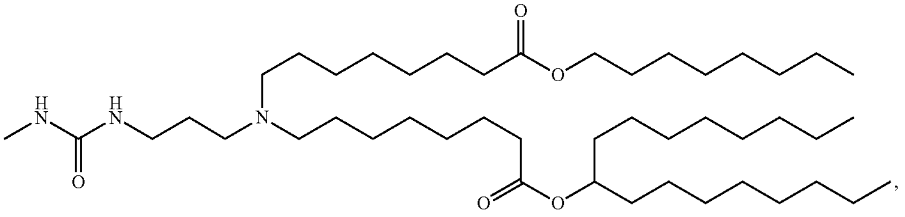
(Compound 42)
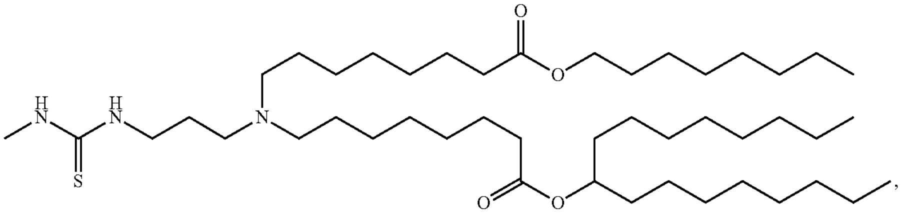
(Compound 51)
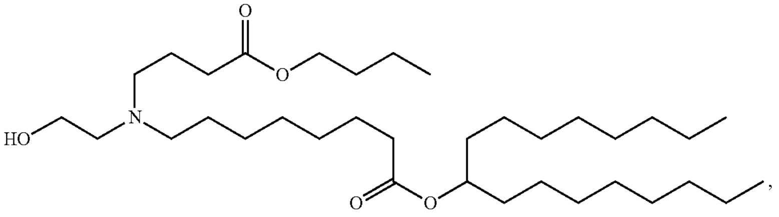
(Compound 52)
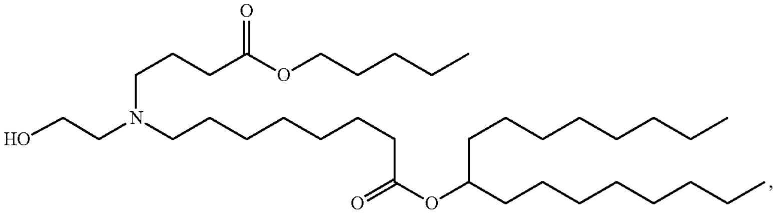
(Compound 53)
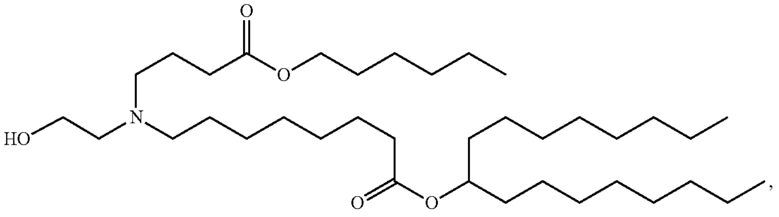
(Compound 54)
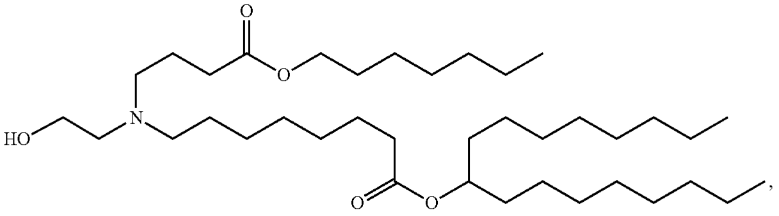

-continued
(Compound 56)
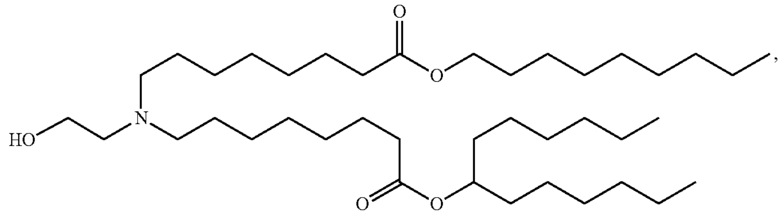
(Compound 57)
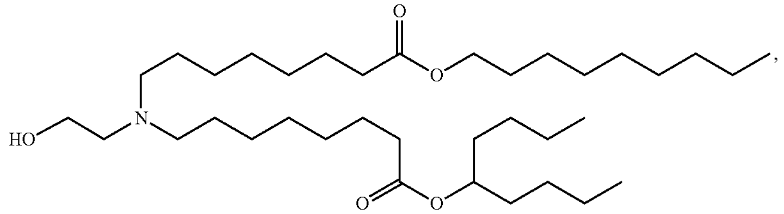
(Compound 58)
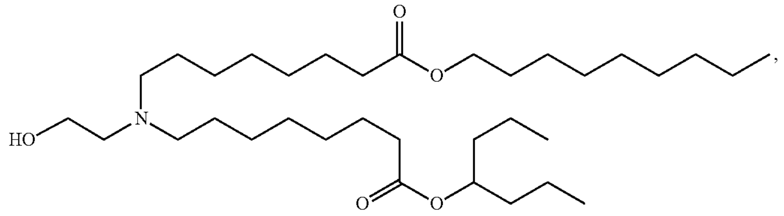
(Compound 59)
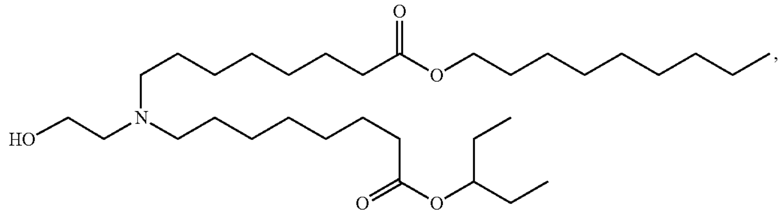
(Compound 60)
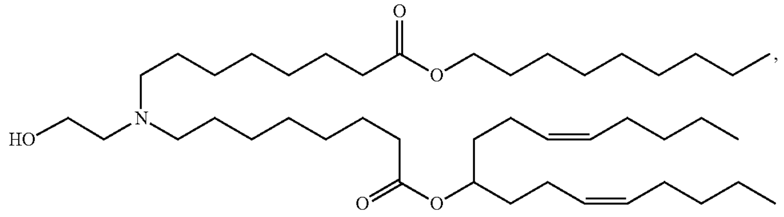
(Compound 61)
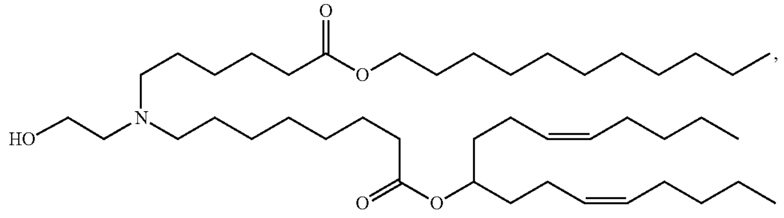
(Compound 63)
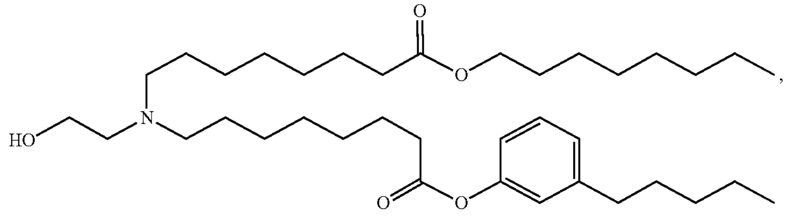

-continued
(Compound 64)
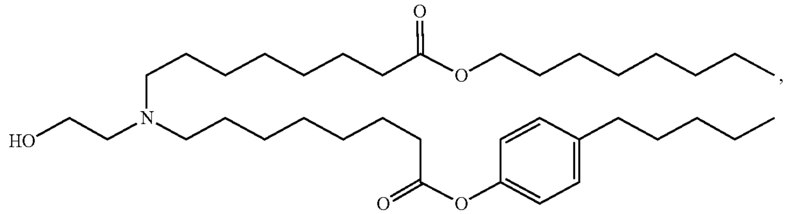
(Compound 70)
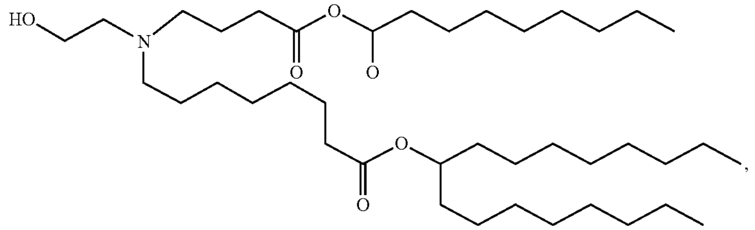
(Compound 79)
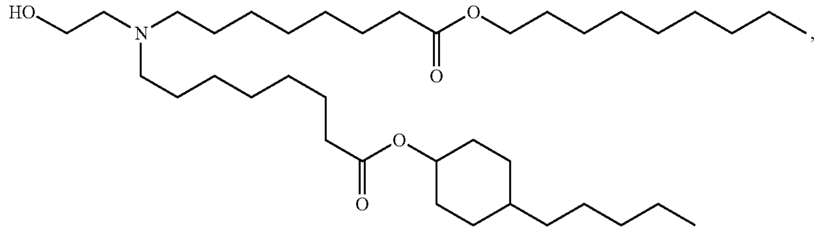
(Compound 82)
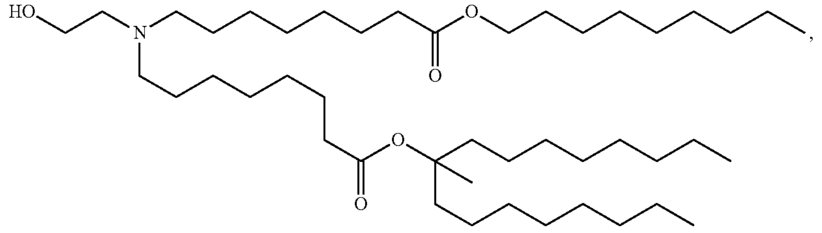
(Compound 96)
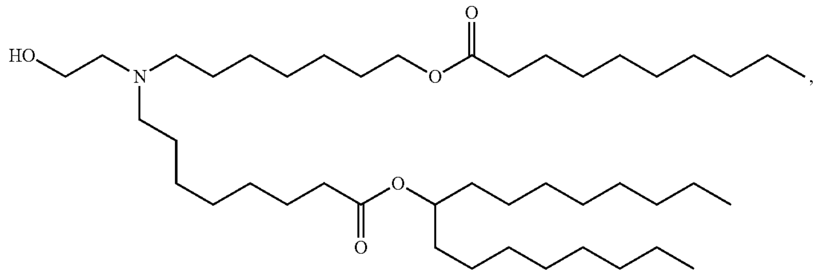
(Compound 97)
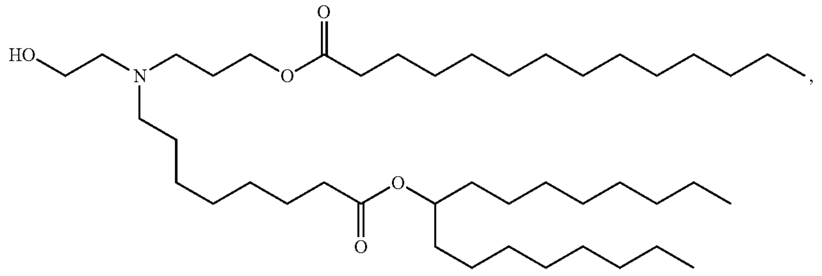

-continued
(Compound 104)
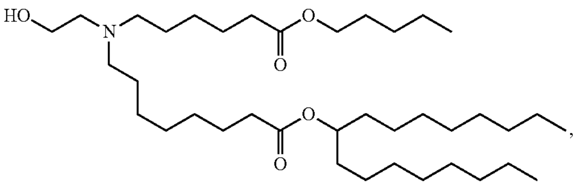
(Compound 105)
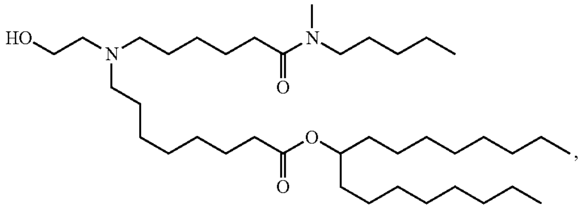
(Compound 110)
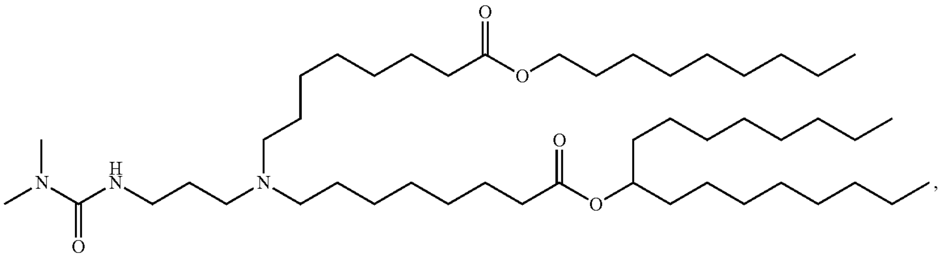
(Compound 111)
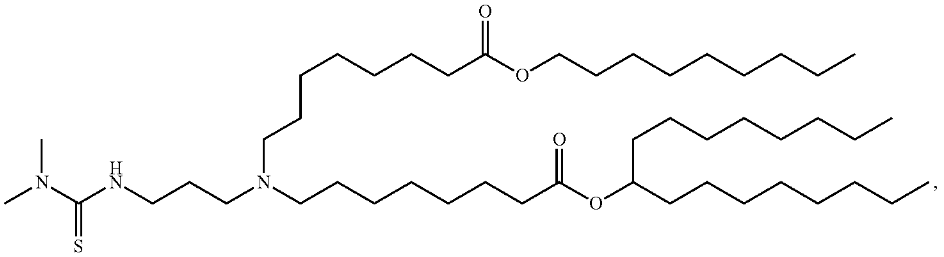
(Compound 112)
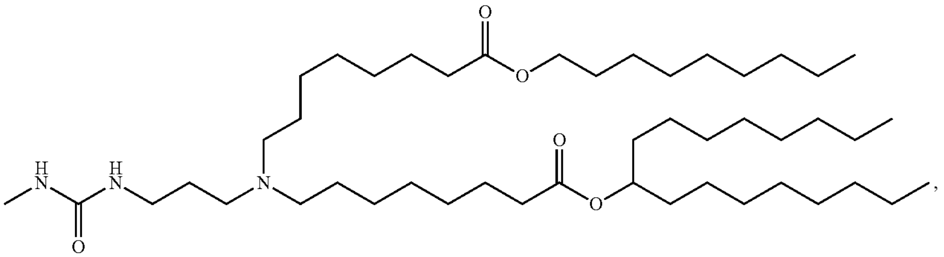
(Compound 113)
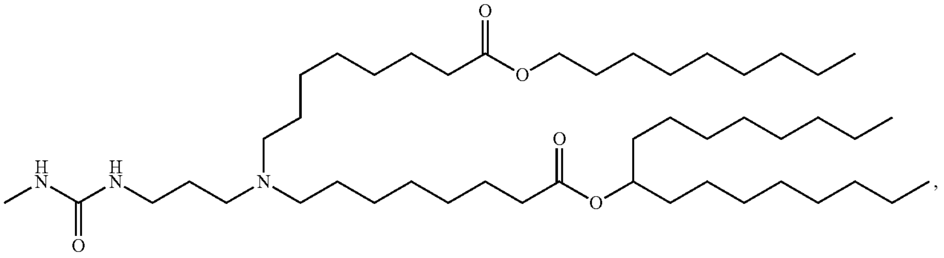
(Compound 119)
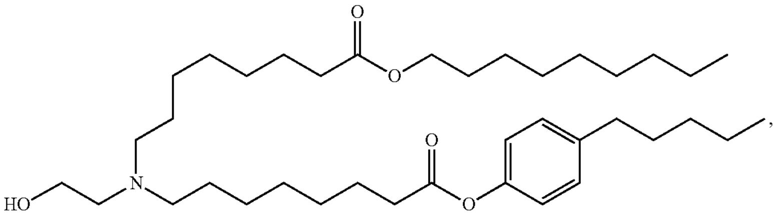

-continued
(Compound 120)
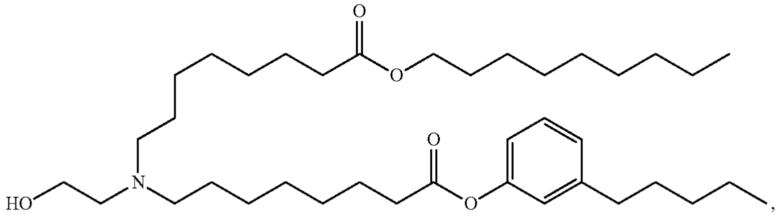
(Compound 121)
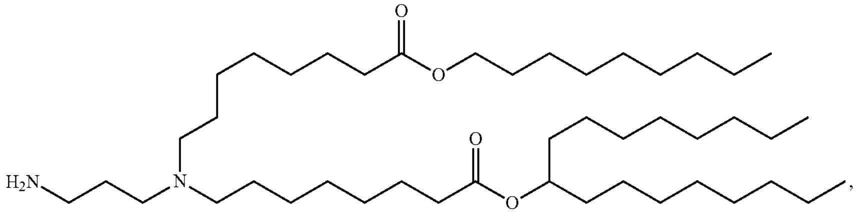
(Compound 123)
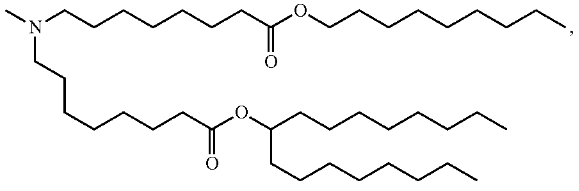
(Compound 126)
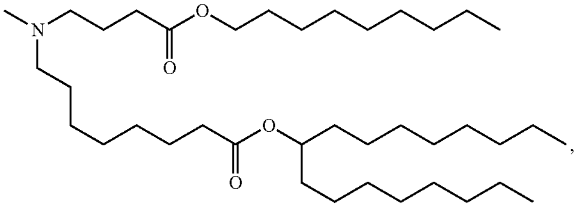
(Compound 127)
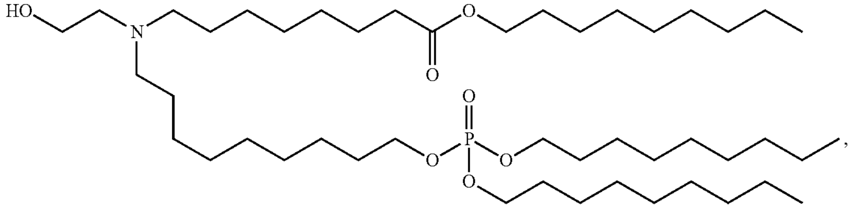
(Compound 129
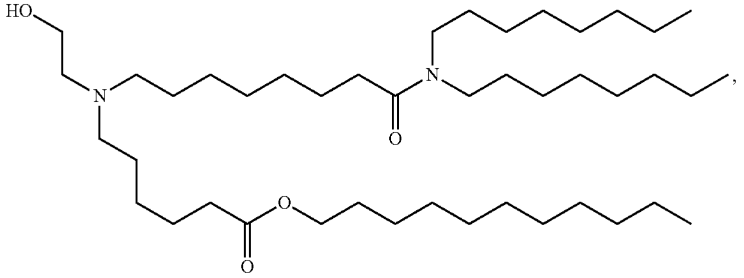
(Compound 131)
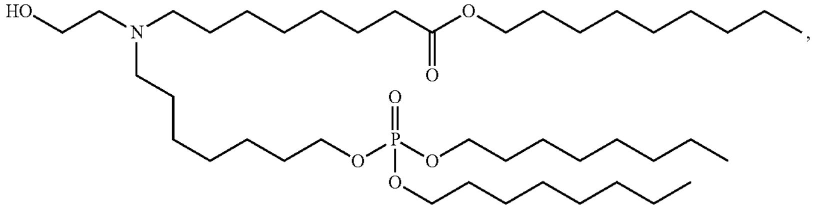
(Compound 134)
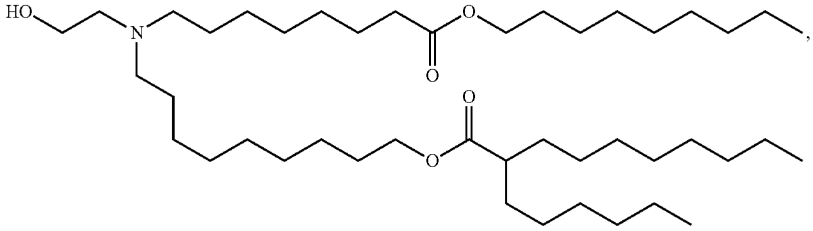

-continued
(Compound 137)
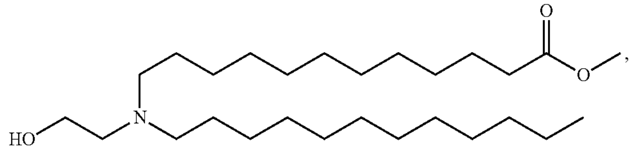
(Compound 138)
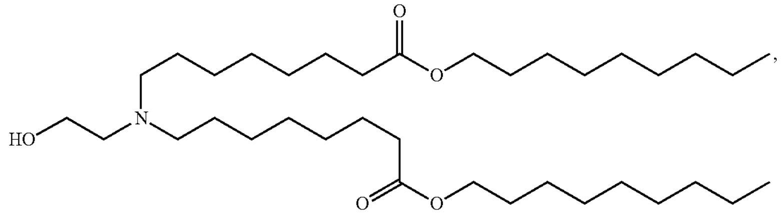
(Compound 141)
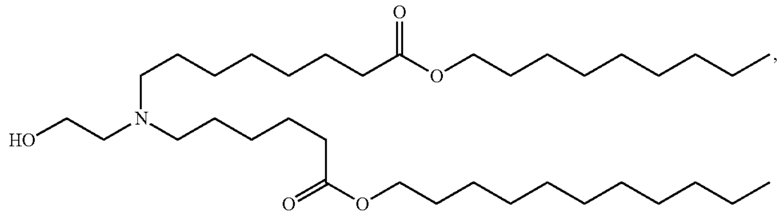
(Compound 142)
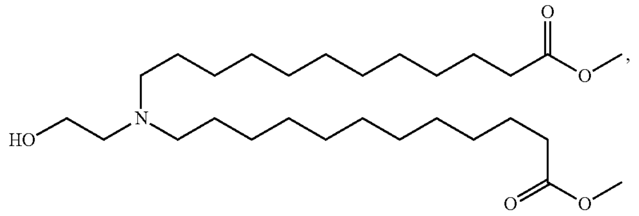
(Compondu 143)
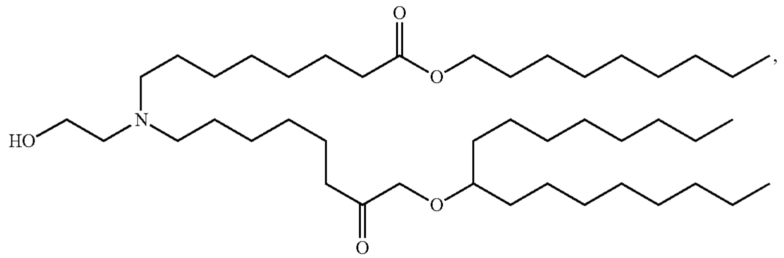
(Compound 144)
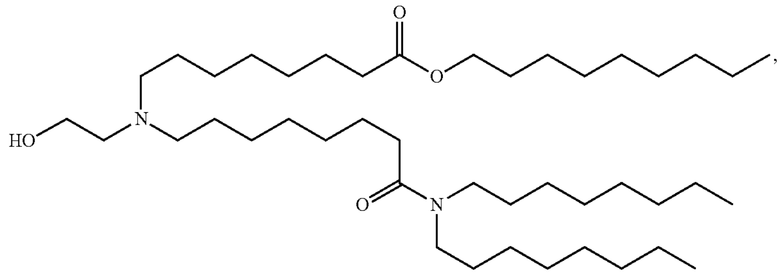
(Compound 145)
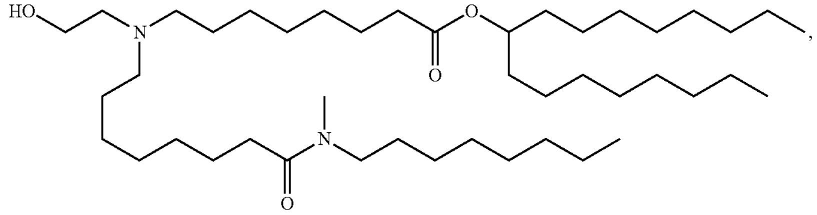

-continued (Compound 146)

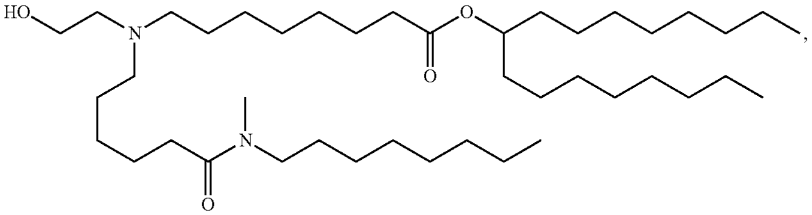

and (Compound 147)

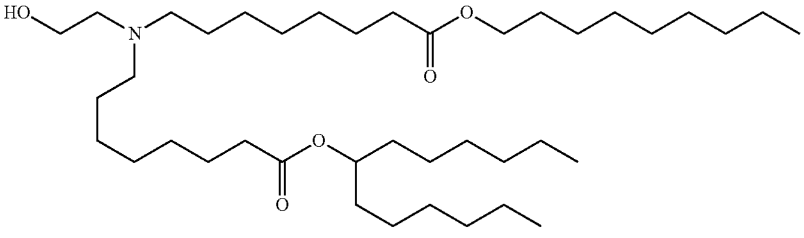

or salts and stereoisomers thereof, and any combination thereof.

8. The composition of claim 4, wherein the structural lipid is selected from the group consisting of: cholesterol, fecosterol, sitosterol, ergosterol, campesterol, stigmasterol, brassicasterol, tomatidine, ursolic acid, alpha-tocopherol, and mixtures thereof.

9. The composition of claim 4, wherein the PEG lipid is selected from the group consisting of: a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

10. The composition of claim 4, wherein the PEG lipid is (Compound 428).

(Compound 428)

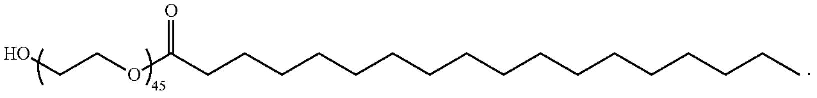

11. A composition comprising:

(a) a lipid nanoparticle; and (b) a messenger ribonucleic acid (mRNA) comprising an open reading frame (ORF) encoding a human Jagged1 (JAG1) polypeptide, wherein the lipid nanoparticle comprises (i) the ionizable lipid of the formula (Compound 18)

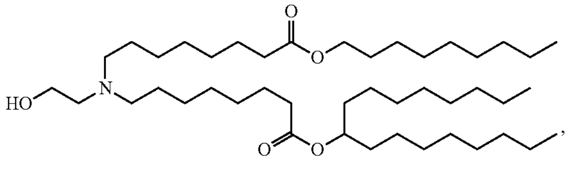

(ii) 1,2-distearoyl-sn-glycero-3-phosphocholine (DSPC), (iii) cholesterol, and (iv) a PEG lipid of the formula (Compound 428)

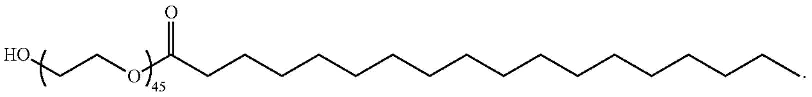

12. The composition of claim 1, wherein the ORF comprises at least one chemically modified nucleobase, sugar, backbone, or any combination thereof.

13. The composition of claim 12, wherein the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

14. The composition of claim 12, wherein the at least one chemically modified nucleobase is N1-methylpseudouracil (m1ψ).

15. The composition of claim 3, wherein the lipid nanoparticle further comprises a phospholipid, a structural lipid, and a PEG lipid.

16. The composition of claim 15, wherein the phospholipid is selected from the group consisting of:

1,2-dilinoleoyl-sn-glycero-3-phosphocholine (DLPC);
1,2-dimyristoyl-sn-glycero-phosphocholine (DMPC);
1,2-dioleoyl-sn-glycero-3-phosphocholine (DOPC);
1,2-dipalmitoyl-sn-glycero-3-phosphocholine (DPPC);
1,2-distearoyl-sn-glycero-3-phosphocholine (DSPC);
1,2-diundecanoyl-sn-glycero-phosphocholine (DUPC);
1-palmitoyl-2-oleoyl-sn-glycero-3-phosphocholine (POPC);
1,2-di-O-octadecenyl-sn-glycero-3-phosphocholine (18:0 Diether PC);
1-oleoyl-2-cholesterylhemisuccinoyl-sn-glycero-3-phosphocholine (OChemsPC);
1-hexadecyl-sn-glycero-3-phosphocholine (C16 Lyso PC);
1,2-dilinolenoyl-sn-glycero-3-phosphocholine;
1,2-diarachidonoyl-sn-glycero-3-phosphocholine;
1,2-didocosahexaenoyl-sn-glycero-3-phosphocholine;
1,2-dioleoyl-sn-glycero-3-phosphoethanolamine (DOPE);
1,2-diphytanoyl-sn-glycero-3-phosphoethanolamine (ME 16:0 PE);
1,2-distearoyl-sn-glycero-3-phosphoethanolamine;
1,2-dilinoleoyl-sn-glycero-3-phosphoethanolamine;
1,2-dilinolenoyl-sn-glycero-3-phosphoethanolamine;
1,2-diarachidonoyl-sn-glycero-3-phosphoethanolamine;
1,2-didocosahexaenoyl-sn-glycero-3-phosphoethanolamine;
1,2-dioleoyl-sn-glycero-3-phospho-rac-(1-glycerol) sodium salt (DOPG);
sphingomyelin; and
mixtures thereof.

17. The composition of claim 3, wherein the mRNA further comprises a microRNA (miRNA) binding site.

18. The composition of claim 15, wherein the structural lipid is selected from the group consisting of: cholesterol, fecosterol, sitosterol, ergosterol, campesterol, stigmasterol, brassicasterol, tomatidine, ursolic acid, alpha-tocopherol, and mixtures thereof.

19. The composition of claim 15, wherein the PEG lipid is selected from the group consisting of: a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

20. The composition of claim 15, wherein the PEG lipid is (Compound 428)

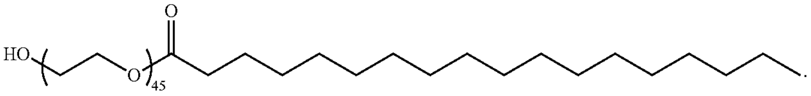

21. The composition of claim 3, wherein the ORF comprises at least one chemically modified nucleobase, sugar, backbone, or any combination thereof.

22. The composition of claim 12, wherein the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

23. The composition of claim 22, wherein the at least one chemically modified nucleobase is N1-methylpseudouracil (m1ψ).

24. The composition of claim 7, wherein the lipid nanoparticle further comprises a phospholipid, a structural lipid, and a PEG lipid.

25. The composition of claim 24, wherein the phospholipid is selected from the group consisting of:

1,2-dilinoleoyl-sn-glycero-3-phosphocholine (DLPC);
1,2-dimyristoyl-sn-glycero-phosphocholine (DMPC);
1,2-dioleoyl-sn-glycero-3-phosphocholine (DOPC);
1,2-dipalmitoyl-sn-glycero-3-phosphocholine (DPPC);
1,2-distearoyl-sn-glycero-3-phosphocholine (DSPC);
1,2-diundecanoyl-sn-glycero-phosphocholine (DUPC);
1-palmitoyl-2-oleoyl-sn-glycero-3-phosphocholine (POPC);
1,2-di-O-octadecenyl-sn-glycero-3-phosphocholine (18:0 Diether PC);
1-oleoyl-2-cholesterylhemisuccinoyl-sn-glycero-3-phosphocholine (OChemsPC);
1-hexadecyl-sn-glycero-3-phosphocholine (C16 Lyso PC);
1,2-dilinolenoyl-sn-glycero-3-phosphocholine;
1,2-diarachidonoyl-sn-glycero-3-phosphocholine;
1,2-didocosahexaenoyl-sn-glycero-3-phosphocholine;

1,2-dioleoyl-sn-glycero-3-phosphoethanolamine (DOPE);

1,2-diphytanoyl-sn-glycero-3-phosphoethanolamine (ME 16:0 PE);

1,2-distearoyl-sn-glycero-3-phosphoethanolamine;

1,2-dilinoleoyl-sn-glycero-3-phosphoethanolamine;

1,2-dilinolenoyl-sn-glycero-3-phosphoethanolamine;

1,2-diarachidonoyl-sn-glycero-3-phosphoethanolamine;

1,2-didocosahexaenoyl-sn-glycero-3-phosphoethanolamine;

1,2-dioleoyl-sn-glycero-3-phospho-rac-(1-glycerol) sodium salt (DOPG);

sphingomyelin; and mixtures thereof.

26. The composition of claim 7, wherein the mRNA further comprises a microRNA (miRNA) binding site.

27. The composition of claim 24, wherein the structural lipid is selected from the group consisting of: cholesterol, fecosterol, sitosterol, ergosterol, campesterol, stigmasterol, brassicasterol, tomatidine, ursolic acid, alpha-tocopherol, and mixtures thereof.

28. The composition of claim 24, wherein the PEG lipid is selected from the group consisting of: a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

29. The composition of claim 24, wherein the PEG lipid is (Compound 428)

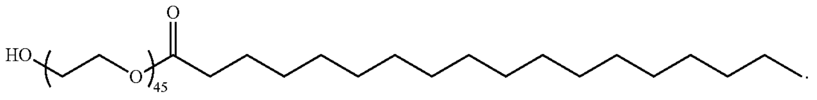

-

30. The composition of claim 7, wherein the ORF comprises at least one chemically modified nucleobase, sugar, backbone, or any combination thereof.

31. The composition of claim 30, wherein the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

32. The composition of claim 30, wherein the at least one chemically modified nucleobase is N1-methylpseudouracil (m1ψ).

* * * * *